US012624053B2

(12) United States Patent
Liu et al.

(10) Patent No.: US 12,624,053 B2
(45) Date of Patent: May 12, 2026

(54) RAS INHIBITORS

(71) Applicant: Revolution Medicines, Inc., Redwood City, CA (US)

(72) Inventors: Yang Liu, Foster City, CA (US); James Cregg, Belmont, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 19/308,863

(22) Filed: Aug. 25, 2025

(65) Prior Publication Data

US 2025/0388608 A1 Dec. 25, 2025

Related U.S. Application Data

(63) Continuation of application No. 18/762,805, filed on Jul. 3, 2024, which is a continuation of application No. 18/516,457, filed on Nov. 21, 2023, now abandoned, which is a continuation of application No. 17/737,131, filed on May 5, 2022, now abandoned.

(60) Provisional application No. 63/184,599, filed on May 5, 2021.

(51) Int. Cl.

| | |
|---|---|
| ***C07F 5/02*** | (2006.01) |
| ***C07D 213/55*** | (2006.01) |
| ***C07D 213/61*** | (2006.01) |
| ***C07D 513/22*** | (2006.01) |
| ***C07D 519/00*** | (2006.01) |

(52) U.S. Cl.

CPC ......... *C07D 519/00* (2013.01); *C07D 213/55* (2013.01); *C07D 213/61* (2013.01); *C07D 513/22* (2013.01); *C07F 5/02* (2013.01); *C07F 5/025* (2013.01)

(58) Field of Classification Search

None

See application file for complete search history.

(56) References Cited

U.S. PATENT DOCUMENTS

| | | | |
|---|---|---|---|
| 9,119,853 | B2 | 9/2015 | Moss et al. |
| 11,566,007 | B2 | 1/2023 | Koltun et al. |
| 11,608,346 | B2 | 3/2023 | Koltun et al. |
| 11,690,915 | B2 | 7/2023 | Aay et al. |
| 11,739,074 | B2 | 8/2023 | Aggen et al. |
| 11,952,352 | B2 | 4/2024 | Gill et al. |
| 12,202,845 | B2 | 1/2025 | Knox et al. |
| 12,252,497 | B2 | 3/2025 | Burnett et al. |
| 12,280,113 | B2 | 4/2025 | Koltun et al. |
| 12,384,750 | B2 | 8/2025 | Gill et al. |
| 12,403,196 | B2 | 9/2025 | Koltun et al. |
| 12,409,225 | B2 | 9/2025 | Koltun et al. |
| 2013/0344030 | A1 | 12/2013 | Steadman et al. |
| 2016/0083373 | A1 | 3/2016 | Xu |
| 2017/0190734 | A1 | 7/2017 | Aciro et al. |
| 2021/0130303 | A1* | 5/2021 | Koltun .................... A61P 35/00 |
| 2021/0130326 | A1* | 5/2021 | Aggen ................. C07D 487/04 |
| 2021/0130369 | A1* | 5/2021 | Koltun ............... C07K 5/06191 |
| 2023/0374035 | A1 | 11/2023 | Koltun et al. |
| 2025/0051306 | A1 | 2/2025 | Aggen et al. |
| 2025/0074923 | A1 | 3/2025 | Knox et al. |
| 2025/0129097 | A1 | 4/2025 | Cregg et al. |
| 2025/0145643 | A1 | 5/2025 | Koltun et al. |
| 2025/0154171 | A1 | 5/2025 | Knox et al. |
| 2025/0197423 | A1 | 6/2025 | Koltun et al. |
| 2025/0242029 | A1 | 7/2025 | Koltun et al. |
| 2025/0255964 | A1 | 8/2025 | Cregg et al. |
| 2025/0269037 | A1 | 8/2025 | Burnett et al. |

FOREIGN PATENT DOCUMENTS

| | | | |
|---|---|---|---|
| WO | WO-98/07743 | A1 | 2/1998 |
| WO | WO-2012/131371 | A1 | 10/2012 |
| WO | WO-2013/185103 | A1 | 12/2013 |
| WO | WO-2018/081592 | A2 | 5/2018 |
| WO | WO-2018/091634 | A1 | 5/2018 |
| WO | WO-2022/060583 | A1 | 3/2022 |
| WO | WO-2022/060836 | A1 | 3/2022 |
| WO | WO-2022/217053 | A1 | 10/2022 |
| WO | WO-2022/235870 | A1 | 11/2022 |
| WO | WO-2023/015559 | A1 | 2/2023 |
| WO | WO-2023/025832 | A1 | 3/2023 |
| WO | WO-2023/086341 | A1 | 5/2023 |
| WO | WO-2023/208005 | A1 | 11/2023 |
| WO | WO-2023/232776 | A1 | 12/2023 |
| WO | WO-2024/008610 | A1 | 1/2024 |
| WO | WO-2024/008834 | A1 | 1/2024 |
| WO | WO-2024/067857 | A1 | 4/2024 |

OTHER PUBLICATIONS

U.S. Appl. No. 19/388,266, Liu et al.

Banteli et al., "A synthesis of the C1—N12 tripeptide fragment of sanglifehrin A," Tetrahedron Letters. 40(11):2109-2112 (Mar. 12, 1999).

Doak et al., "Cyclophilin Succumbs to a Macrocyclic Chameleon," J Med Chem. 61(21):9469-9472 (Nov. 2018).

Nakamura et al., "Asymmetric reduction of ketones by Geotrichum candidum in the presence of AmberliteTM XAD, a solid organic solvent," J Chem Soc., Perkin Trans 1:3205-3211 (2000).

PubChem CID 130196149, <https://pubchem.ncbi.nlm.nih.gov/compound/130196149>, retrieved on Apr. 1, 2020 (10 pages).

* cited by examiner

*Primary Examiner* — Noble E Jarrell

(74) *Attorney, Agent, or Firm* — Clark & Elbing LLP

(57) ABSTRACT

The disclosure features macrocyclic compounds, and pharmaceutical compositions and protein complexes thereof, capable of inhibiting Ras proteins, and their uses in the treatment of cancers.

6 Claims, 5 Drawing Sheets wherein A is or

Formula AA wherein A is or

Formula BB wherein A is
or

Formula AA wherein A is
or

Formula BB

RAS INHIBITORS

BACKGROUND

The vast majority of small molecule drugs act by binding a functionally important pocket on a target protein, thereby modulating the activity of that protein. For example, cholesterol-lowering drugs known as statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18: 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras(ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, a drug directly targeting Ras is still not approved. Additional efforts are needed to uncover additional medicines for cancers driven by the various Ras mutations.

SUMMARY

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF and PI3K, which are required for propagating the oncogenic signal.

As such, in some embodiments, the disclosure features a compound, or pharmaceutically acceptable salt thereof, of structural Formula I:

Formula I

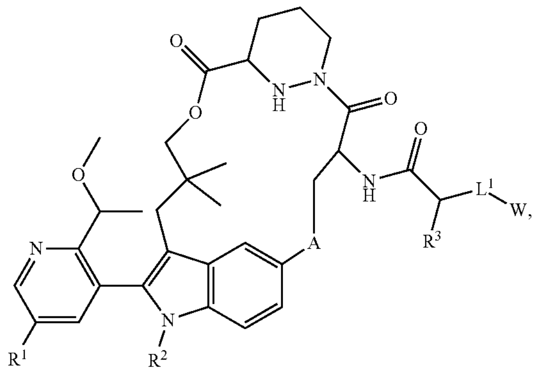

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$L^1$ is absent or a linker;

W is a cross-linking group comprising a vinyl ketone, vinyl sulfone, ynone, or an alkynyl sulfone;

$R^1$ is hydrogen, optionally substituted 3 to 10-membered heterocycloalkyl, or optionally substituted $C_1$-$C_6$ heteroalkyl;

$R^2$ is optionally substituted $C_1$-$C_6$ alkyl; and $R^3$ is optionally substituted $C_1$-$C_6$ alkyl or optionally substituted $C_1$-$C_3$ heteroalkyl.

Also provided are pharmaceutical compositions comprising a compound of Formula I, or a pharmaceutically acceptable salt thereof, and a pharmaceutically acceptable excipient. Also provided are pharmaceutical compositions comprising a compound of Table 1, or a pharmaceutically acceptable salt thereof, and a pharmaceutically acceptable excipient.

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

Definitions and Chemical Terms

In this application, unless otherwise clear from context, (i) the term "a" means "one or more"; (ii) the term "or" is used to mean "and/or" unless explicitly indicated to refer to alternatives only or the alternative are mutually exclusive, although the disclosure supports a definition that refers to only alternatives and "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of Formula I and subformula thereof, for example, a compound of Table 1, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc) state- or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H—, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}p$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Non-limiting examples of moieties that may contain one or more deuterium substitutions in compounds of the present invention, where any position "R" may be deuterium (D), include

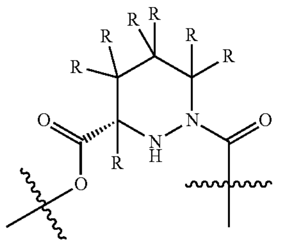

-continued

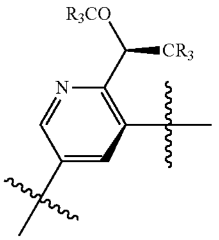

and

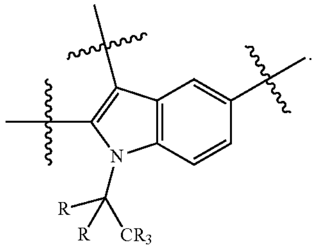

Additional examples include moieties such as

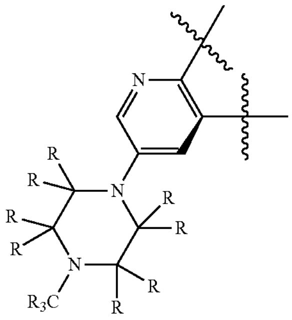

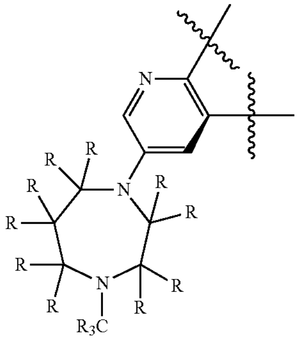

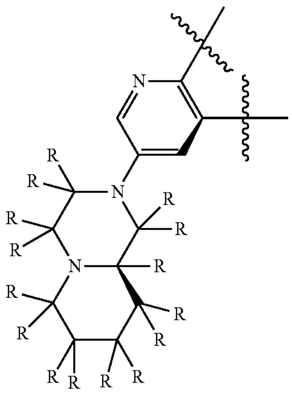

and

-continued

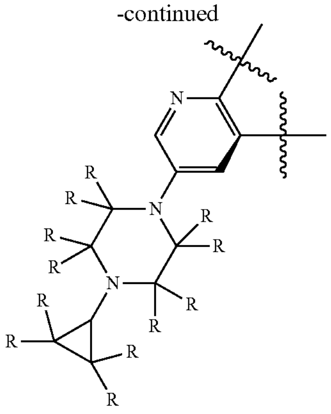

and deuteration of similar R[1]-type moieties, wherein the definition of R[1] is found herein (e.g., in compounds of Formula I, Ia, II-5, II-5a, II-6, II-6a, II-6b, and II-6c). Deuteration of moieties within substituent W in compounds of the present invention are also contemplated, where W is defined herein (see, e.g., generic Formulas I and II and subformulas thereof as well as specific examples of W described herein, such as

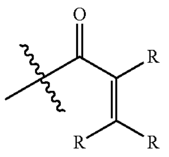

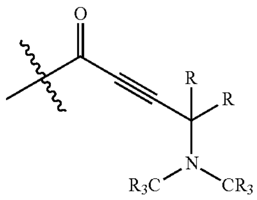

and

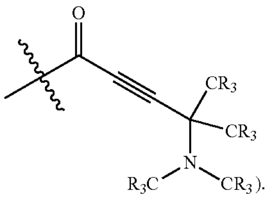

Moreover, deuteration of available positions in any A moiety of compounds of the Formulas described herein is also contemplated, such as

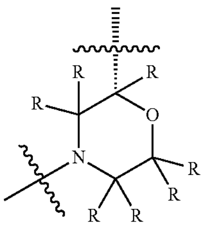

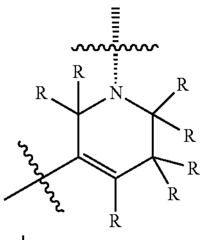

and

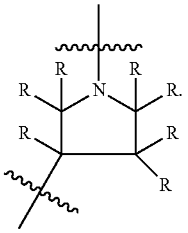

Further, deuterium substitution may also take place in compounds of the present invention at the linker position, such as

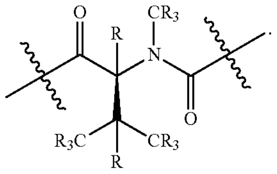

In a further embodiment, silylation substitution is also contemplated, such as in the linker as follows:

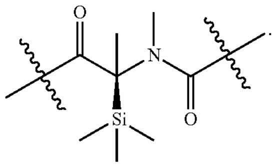 [SMILES: *C(=O)N(C)[C@@](C)(C(*)=O)[Si](C)(C)C]

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present disclosure is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; $-(CH_2)_{0-4}R^\circ$; $-(CH_2)_{0-4}OR^\circ$; $-O(CH_2)_{0-4}R^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH{=}CHPh$, which may be substituted with $R^\circ$; $-(CH_2)_{0-4}O(CH_2)_{0-1}$-pyridyl which may be substituted with $R^\circ$; 4-8 membered saturated or unsaturated heterocycloalkyl (e.g., pyridyl); 3-8 membered saturated or unsaturated cycloalkyl (e.g., cyclopropyl, cyclobutyl, or cyclopentyl); $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}-C(O)-N(R^\circ)_2$; $-(CH_2)_{0-4}-C(O)-N(R^0)-S(O)_2-R^\circ$; $-C(NCN)NR^\circ_2$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$; $-SC(S)SR^\circ$; $-(CH_2)_{0-4}SC(O)R^\circ$; $-(CH_2)_{0-4}C(O)NR^0_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NOR^\circ)NR^\circ_2$; $-C(NH)NR^\circ_2$; $-P(O)_2R^\circ$; $-P(O)R^\circ_2$; $-P(O)(OR^\circ)_2$; $-OP(O)R^\circ_2$; $-OP(O)(OR^\circ)_2$; $-OP(O)(OR^\circ)R^\circ$, $-SiR^0_3$; $-(C_{1-4}$ straight or branched alkylene$)O-N(R^\circ)_2$; or $-(C_{1-4}$ straight or branched alkylene$)C(O)O-N(R^\circ)_2$, wherein each $R^\circ$ may be substituted as defined below and is independently hydrogen, $-C_{1-6}$ aliphatic, $-CH_2Ph$, $-O(CH_2)_{0-1}Ph$, $-CH_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), may be, independently, halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O$(halo$R^\bullet$), $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene$)C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: =O, =S, =NNR*2, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*2)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —O$R^\bullet$, —O(halo$R^\bullet$), —CN, —C(O)OH, —C(O)O$R^\bullet$, —$NH_2$, —NH$R^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)O$R^\dagger$, —C(O)C(O)$R^\dagger$, —C(O)$CH_2$C(O)$R^\dagger$, —S(O)$_2R^\dagger$, —S(O)$_2NR^\dagger_2$, —C(S)$NR^\dagger_2$, —C(NH)$NR^\dagger_2$, or —N($R^\dagger$)S(O)$_2R^\dagger$; wherein each $R^\dagger$ is independently hydrogen, $C_{1-6}$ aliphatic which may be substituted as defined below, unsubstituted —OPh, or an unsubstituted 3-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of $R^\dagger$ are independently halogen, —$R^\bullet$, -(halo$R^\bullet$), —OH, —O$R^\bullet$, —O(halo$R^\bullet$), —CN, —C(O)OH, —C(O)O$R^\bullet$, —$NH_2$, —NH$R^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\dagger$ include =O and =S.

The term "acetyl," as used herein, refers to the group —C(O)$CH_3$.

The term "alkoxy," as used herein, refers to a —O—$C_1$-$C_2$H alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "$C_x$-$C_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_1$-$C_6$, $C_1$-$C_{10}$, $C_2$-$C_{20}$, $C_2$-$C_6$, $C_2$-$C_{10}$, or $C_2$-$C_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "alkynyl sulfone," as used herein, represents a group comprising the structure

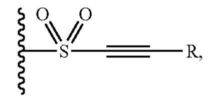

wherein R is any chemically feasible substituent described herein.

The term "amino," as used herein, represents —N($R^\dagger$)$_2$, e.g., —$NH_2$ and —N($CH_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —$CO_2$H or —$SO_3$H), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure $H_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "$C_0$," as used herein, represents a bond. For example, part of the term —N(C(O)—($C_0$-$C_5$ alkylene-H)— includes —N(C(O)—($C_0$ alkylene-H)—, which is also represented by —N(C(O)—H)—.

The terms "carbocyclic" and "carbocyclyl," as used herein, refer to a monovalent, optionally substituted $C_3$-$C_{12}$ monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C═O.

The term "carboxyl," as used herein, means —$CO_2$H, (C═O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "guanidinyl," refers to a group having the structure:

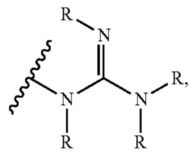

wherein each R is, independently, any chemically feasible substituent described herein.

The term "guanidinoalkyl alkyl," as used herein, represents an alkyl moiety substituted on one or more carbon atoms with one or more guanidinyl moieties.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl," as used herein, refers to an "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzooxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent monocyclic, bicyclic or polycyclic ring system, which may be bridged, fused or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "isomer," as used herein, means any tautomer, stereoisomer, atropiosmer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein, the term "linker" refers to a divalent organic moiety connecting a first moiety (e.g., a macrocyclic moiety) to a second moiety (e.g., a cross-linking group). In some embodiments, the linker results in a compound capable of achieving an IC50 of 2 uM or less in the Ras-RAF disruption assay protocol provided in the Examples below, and provided here:

The purpose of this biochemical assay is to measure the ability of test compounds to facilitate ternary complex formation between a nucleotide-loaded Ras isoform and cyclophilin A; the resulting ternary complex disrupts binding to a $BRAF^{RBD}$ construct, inhibiting Ras signaling through a RAF effector.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP (or other Ras variant), and GST-$BRAF^{RBD}$ are combined in a 384-well assay plate at final concentrations of 25 μM, 12.5 nM and 50 nM, respectively. Compound is present in plate wells as a 10-point 3-fold dilution series starting at a final concentration of 30 μM. After incubation at 25° C. for 3 hours, a mixture of Anti-His Eu—W1024 and anti-GST allophycocyanin is then added to assay sample wells at final concentrations of 10 nM and 50 nM, respectively, and the reaction incubated for an additional 1.5 hours. TR-FRET signal is read on a microplate reader (Ex 320 nm, Em 665/615 nm). Compounds that facilitate disruption of a Ras:RAF complex are identified as those eliciting a decrease in the TR-FRET ratio relative to DMSO control wells.

In some embodiments, the linker comprises 20 or fewer linear atoms. In some embodiments, the linker comprises 15 or fewer linear atoms. In some embodiments, the linker comprises 10 or fewer linear atoms. In some embodiments, the linker has a molecular weight of under 500 g/mol. In some embodiments, the linker has a molecular weight of under 400 g/mol. In some embodiments, the linker has a molecular weight of under 300 g/mol. In some embodiments, the linker has a molecular weight of under 200 g/mol. In some embodiments, the linker has a molecular weight of under 100 g/mol. In some embodiments, the linker has a molecular weight of under 50 g/mol.

As used herein, a "monovalent organic moiety" is less than 500 kDa. In some embodiments, a "monovalent organic moiety" is less than 400 kDa. In some embodiments, a "monovalent organic moiety" is less than 300 kDa. In some embodiments, a "monovalent organic moiety" is less than 200 kDa. In some embodiments, a "monovalent organic moiety" is less than 100 kDa. In some embodiments, a "monovalent organic moiety" is less than 50 kDa. In some embodiments, a "monovalent organic moiety" is less than 25 kDa. In some embodiments, a "monovalent organic moiety" is less than 20 kDa. In some embodiments, a "monovalent organic moiety" is less than 15 kDa. In some embodiments, a "monovalent organic moiety" is less than 10 kDa. In some embodiments, a "monovalent organic moiety" is less than 1 kDa. In some embodiments, a "monovalent organic moiety" is less than 500 g/mol. In some embodiments, a "monovalent organic moiety" ranges between 500 g/mol and 500 kDa.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an $—S(O)_2—$ group.

The term "thiocarbonyl," as used herein, refers to a —C(S)— group.

The term "vinyl ketone," as used herein, refers to a group comprising a carbonyl group directly connected to a carbon-carbon double bond.

The term "vinyl sulfone," as used herein, refers to a group comprising a sulfonyl group directed connected to a carbon-carbon double bond.

The term "ynone," as used herein, refers to a group comprising the structure

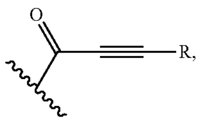

wherein R is any chemically feasible substituent described herein.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

DETAILED DESCRIPTION

Compounds

Figure 1A:
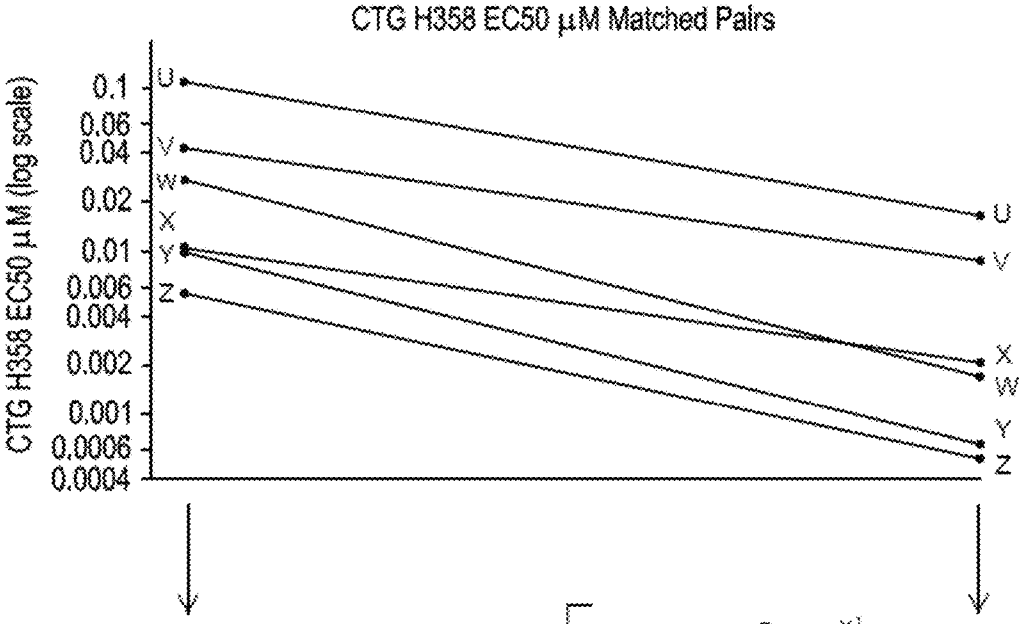
FIGS. 1A and 1B: Matched pair analysis of potencies of certain compounds of the present invention (Formula BB) (points on the right) and corresponding compounds of Formula AA (points on the left) wherein a H is replaced with (S)Me in the context of two different cell-based assays. The y axes represent pERK EC50 (FIG. 1A) or CTG IC50 (FIG. 1B) as measured in an H358 cell line.
Figure 1A:
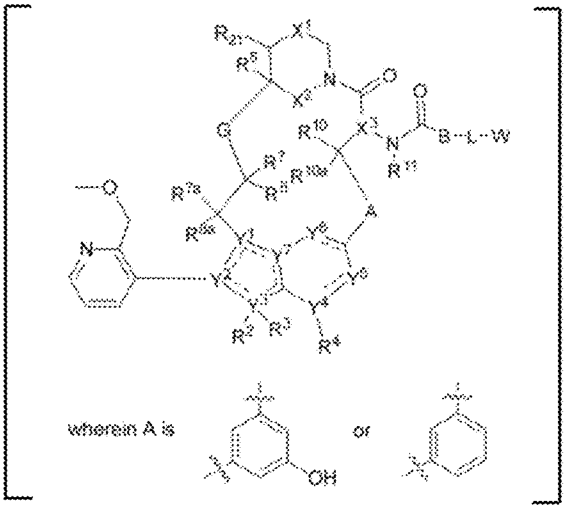
Figure 1A:
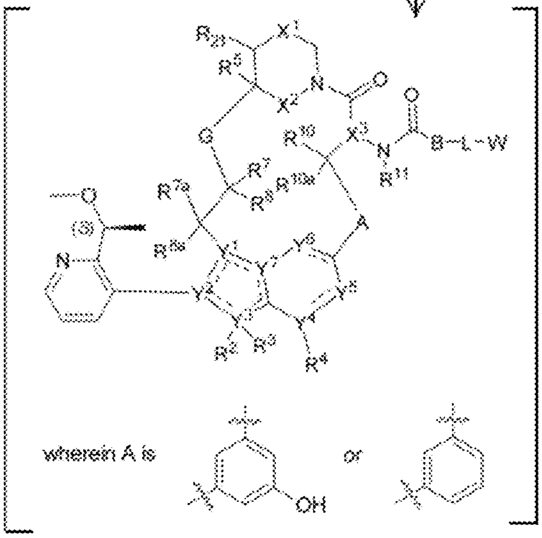

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF, which are required for propagating the oncogenic signal.

Without being bound by theory, the inventors postulate that both covalent and non-covalent interactions of a compound of the present invention with Ras and the chaperone protein (e.g., cyclophilin A) may contribute to the inhibition of Ras activity. In some embodiments, a compound of the present invention forms a covalent adduct with a side chain of a Ras protein (e.g., a sulfhydryl side chain of the cysteine at position 12 or 13 of a mutant Ras protein). Covalent adducts may also be formed with other side chains of Ras. In addition, or alternatively, non-covalent interactions may be at play: for example, van der Waals, hydrophobic, hydrophilic and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., K-Ras, N-Ras, H-Ras, and mutants thereof at positions 12, 13 and 61, such as G12C, G12D, G12V, G12S, G13C, G13D, and Q61L, and others described herein).

Methods of determining covalent adduct formation are known in the art. One method of determining covalent adduct formation is to perform a "cross-linking" assay, such as under these conditions (Note—the following protocol describes a procedure for monitoring cross-linking of K-Ras G12C (GMP-PNP) to a compound of the invention. This protocol may also be executed substituting other Ras proteins or nucleotides).

The purpose of this biochemical assay is to measure the ability of test compounds to covalently label nucleotide-loaded K-Ras isoforms. In assay buffer containing 12.5 mM HEPES pH 7.4, 75 mM NaCl, 1 mM $MgCl_2$, 1 mM BME, 5 μM Cyclophilin A and 2 μM test compound, a 5 μM stock of GMP-PNP-loaded K-Ras (1-169) G12C is diluted 10-fold to yield a final concentration of 0.5 μM; with final sample volume being 100 μL.

The sample is incubated at 25° C. for a time period of up to 24 hours prior to quenching by the addition of 10 μL of 5% Formic Acid. Quenched samples are centrifuged at 15000 rpm for 15 minutes in a benchtop centrifuge before injecting a 10 μL aliquot onto a reverse phase C4 column and eluting into the mass spectrometer with an increasing acetonitrile gradient in the mobile phase. Analysis of raw data may be carried out using Waters MassLynx MS software, with % bound calculated from the deconvoluted protein peaks for labeled and unlabeled K-Ras.

In some embodiments, compounds of the present invention more potently inhibit K-Ras G12C versus K-Ras G13C. In some embodiments, compounds of the present invention more potently inhibit K-Ras G13C versus K-Ras G12C. In some embodiments, compounds of the present invention more potently inhibit K-Ras G13C versus compounds known in the art. In some embodiments, compounds of the present invention cross-link K-Ras G12C to a greater degree versus K-Ras G13C. In some embodiments, compounds of the present invention cross-link K-Ras G13C to a greater degree versus K-Ras G12C. For example, in some embodiments, compounds of the present invention demonstrate no G12C cross-linking while exhibiting 100% G13C cross-linking. In some embodiments, compounds of the present invention demonstrate no G13C cross-linking while exhibiting 100% G12C cross-linking. In some embodiments, compounds of the present invention cross-link K-Ras G13C to a greater degree versus compounds known in the art. Preference for targeting G13C Ras mutants versus other Ras mutants (namely, G12C) by certain compounds of the present invention are typically due, at least in part, to the nature of the linker (e.g., $L^1$), particularly the length of the linker.

Accordingly, provided herein is a compound, or pharmaceutically acceptable salt thereof, having the structure of Formula I:

Formula I

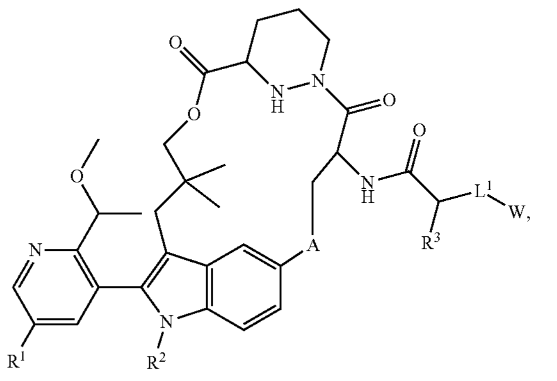

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$L^1$ is absent or a linker;

W is a cross-linking group comprising a vinyl ketone, vinyl sulfone, ynone, or an alkynyl sulfone;

$R^1$ is hydrogen, optionally substituted 3 to 10-membered heterocycloalkyl, or optionally substituted $C_1$-$C_6$ heteroalkyl;

$R^2$ is optionally substituted $C_1$-$C_6$ alkyl; and $R^3$ is optionally substituted $C_1$-$C_6$ alkyl or optionally substituted $C_1$-$C_3$ heteroalkyl.

In some embodiments, W is a cross-linking group comprising a vinyl ketone, vinyl sulfone, or an ynone.

In some embodiments, provided herein is a compound, or pharmaceutically acceptable salt thereof, having the structure of Formula Ia:

Formula Ia

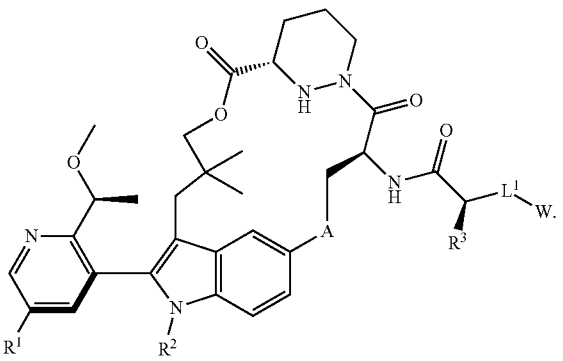

In some embodiments of compounds of the present invention, A is optionally substituted thiazole, optionally substituted oxazole, optionally substituted morpholino, optionally substituted pyrrolidinyl, optionally substituted pyridyl, optionally substituted azetidinyl, optionally substituted pyrazinyl, optionally substituted pyrimidine, optionally substituted piperidinyl, optionally substituted oxadiazole, optionally substituted thiadiazole, optionally substituted triazole, optionally substituted thiomorpholino, or optionally substituted phenyl.

In some embodiments, the disclosure features a compound, or pharmaceutically acceptable salt thereof, of structural Formula II-1:

Formula II-1

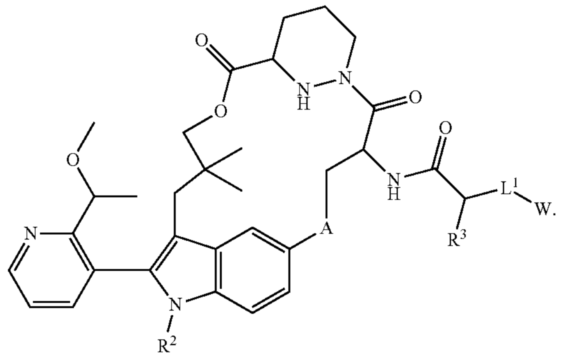

In some embodiments, a compound having the structure of Formula II-2 is provided, or a pharmaceutically acceptable salt thereof:

Formula II-2

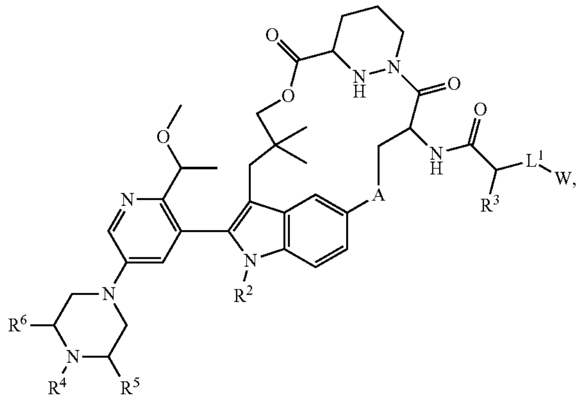

wherein $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

In some embodiments, a compound of the present invention has the structure of Formula II-3, or a pharmaceutically acceptable salt thereof:

Formula II-3

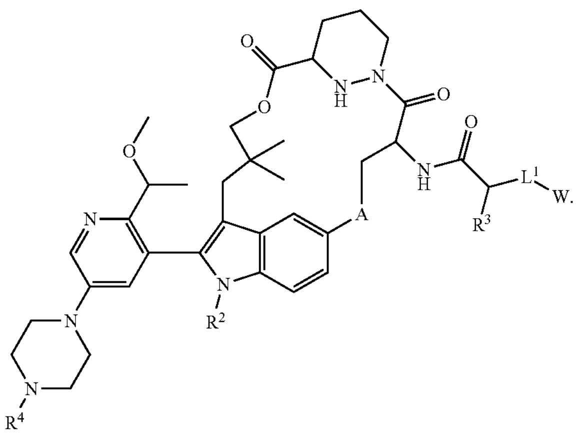

In some embodiments, a compound of the present invention has the structure of Formula II-4, or a pharmaceutically acceptable salt thereof:

Formula II-4

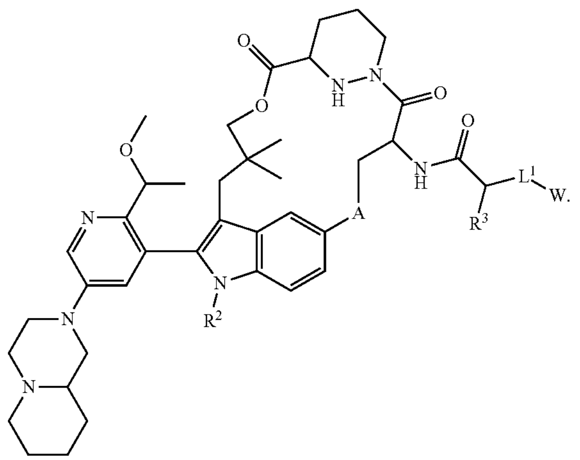

In some embodiments of a compound of the present invention, $R^2$ is:

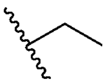 or 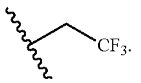

In some embodiments of a compound of the present invention, $R^3$ is optionally substituted $C_1$-$C_6$ alkyl. In some embodiments, $R^3$ is:

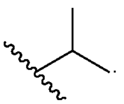 [SMILES: *C(C)C]

In some embodiments of a compound of the present invention, $R^3$ is optionally substituted $C_1$-$C_3$ heteroalkyl. In some embodiments, $R^3$ is:

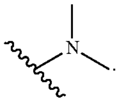 [SMILES: *N(C)C]

In some embodiments of a compound of the present invention, A is optionally substituted 5 to 10-membered heteroarylene. In some embodiments, A is:

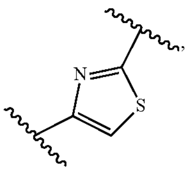, 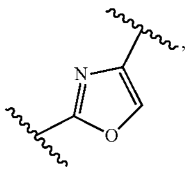,

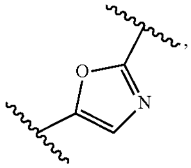, 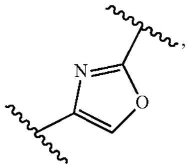,

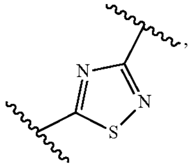, 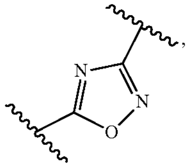,

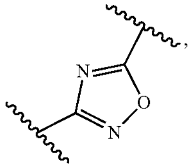, 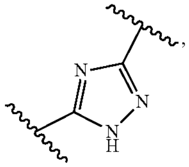,

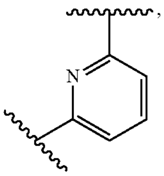, 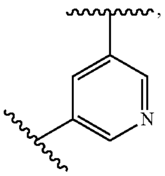,

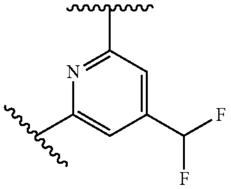, 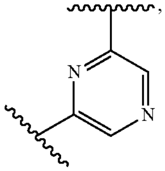, or

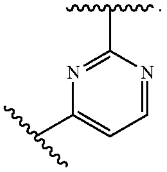.

In some embodiments of a compound of the present invention, A is optionally substituted phenyl. In some embodiments, A is:

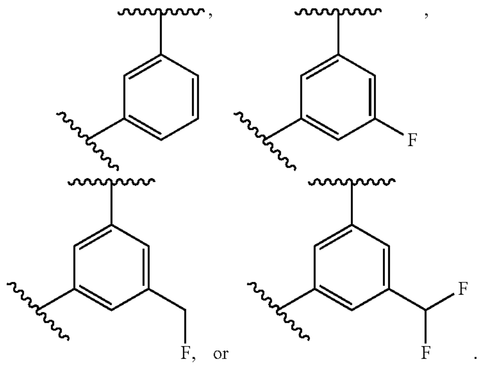

In some embodiments of a compound of the present invention, A is optionally substituted 3 to 6-membered heterocycloalkylene. In some embodiments, A is selected from the following, or a stereoisomer thereof:

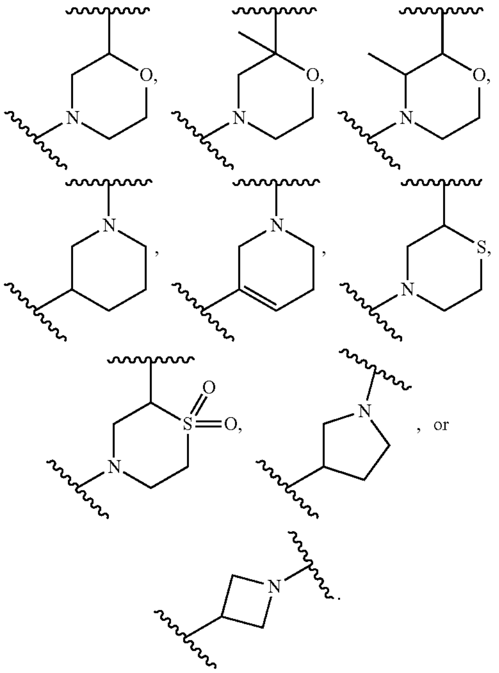

In some embodiments of a compound of the present invention, the linker is the structure of Formula III:

Formula III $$A^1—(B^1)_f—(C^1)_g—(B^2)_h—(D^1)—(B^3)_i—(C^2)_j—(B^4)_k—A^2,$$

wherein $A^1$ is a bond between the linker and $CH(R^3)$; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and $NR^N$; each $R^N$ is, independently, hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$— to —$(B^3)_i$—$(C^2)_j$—$(B^4)_k$-$A^2$.

In some embodiments of a compound of the present invention, the linker is or comprises a cyclic moiety. In some embodiments, the linker has the structure of Formula IIIa:

Formula IIIa

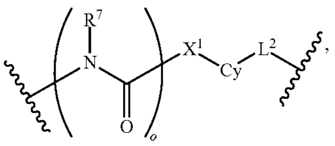

wherein o is 0 or 1;

$R^7$ is hydrogen, optionally substituted $C_1$-$C_6$ alkyl, optionally substituted 3 to 8-membered cycloalkylene, or optionally substituted 3 to 8-membered heterocycloalkylene;

$X^1$ is absent, optionally substituted $C_1$-$C_4$ alkylene, O, $NCH_3$, or optionally substituted $C_1$-$C_4$ heteroalkylene;

Cy is optionally substituted 3 to 8-membered cycloalkylene, optionally substituted 3 to 12-membered heterocycloalkylene, optionally substituted 6-10 membered arylene, or optionally substituted 5 to 10-membered heteroarylene; and $L^2$ is absent, —$SO_2$—, —NH—, optionally substituted $C_1$-$C_4$ alkylene, optionally substituted $C_1$-$C_4$ heteroalkylene, or optionally substituted 3 to 6-membered heterocycloalkylene.

In some embodiments, the linker is selected from, or a stereoisomer thereof:

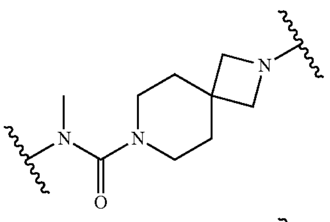

,

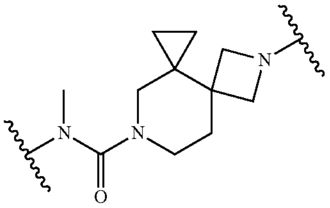

,

-continued
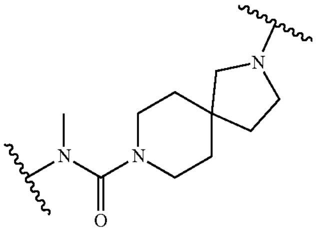
,
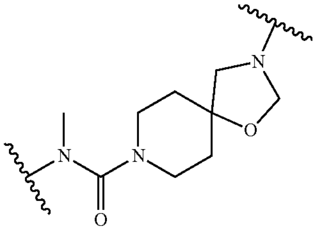
,
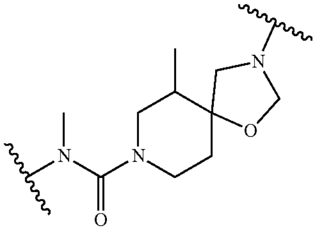
,
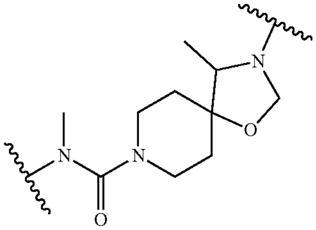
,
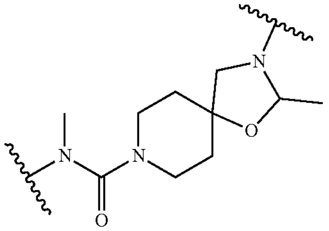
,
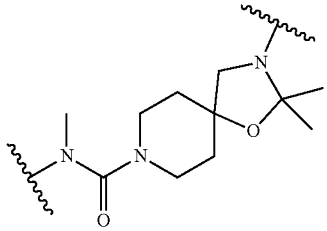
,
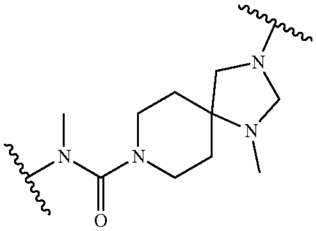
,
-continued
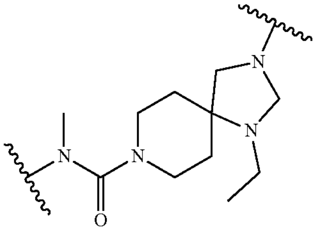
,
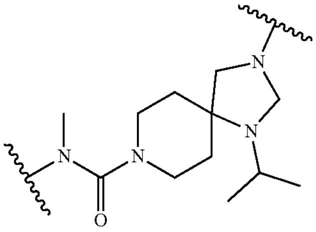
,
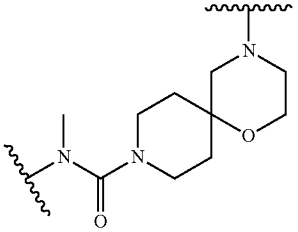
,
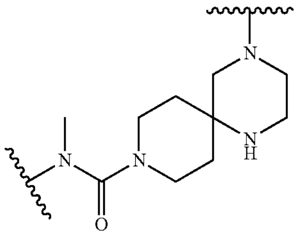
,
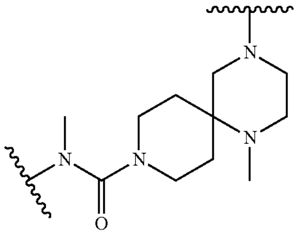
,
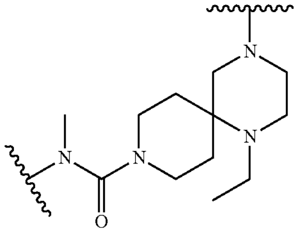
,
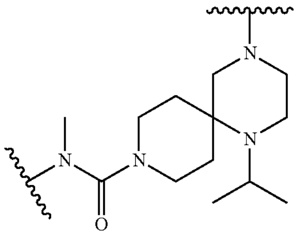
, -continued
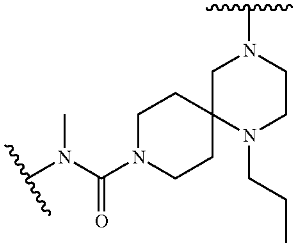
,
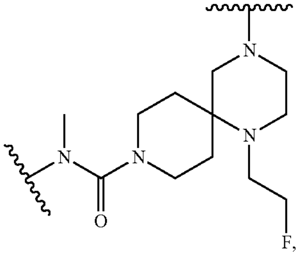
,
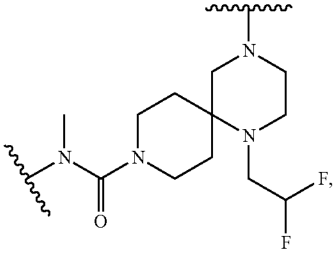
,
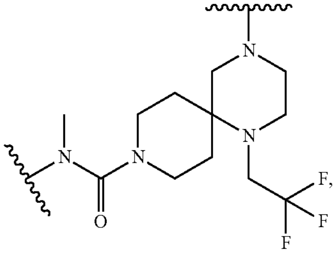
,
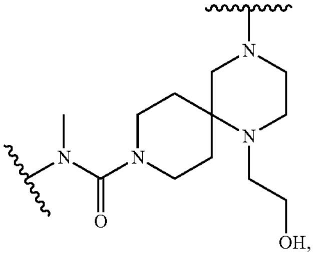
,
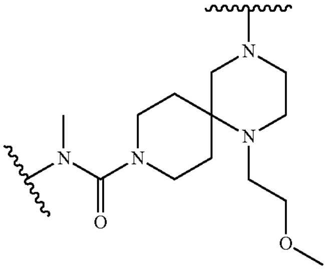
,
-continued
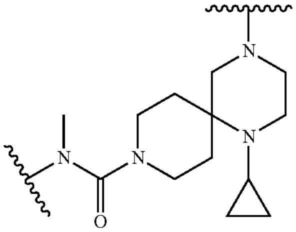
,
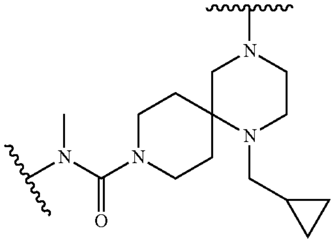
,
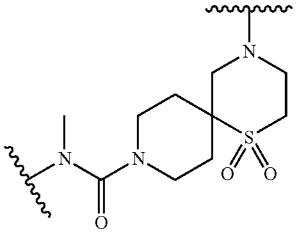
,
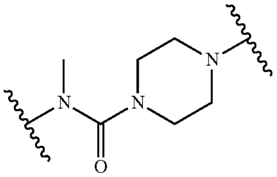
,
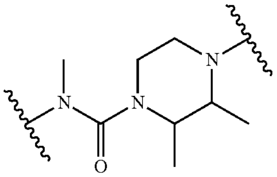
,
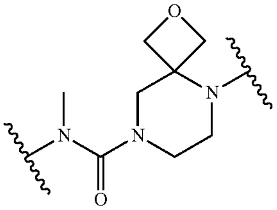
,
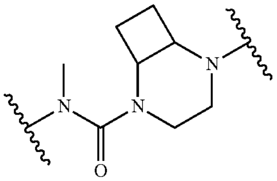
,
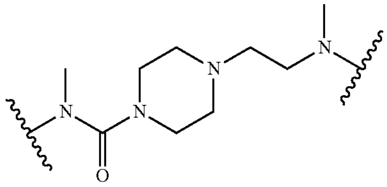
, -continued
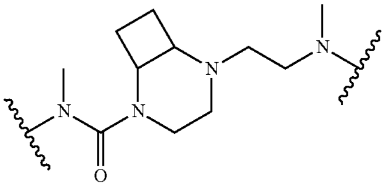
,
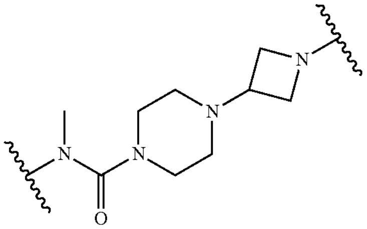
,
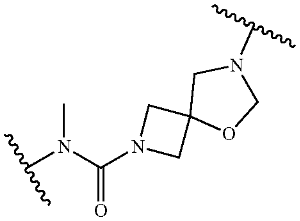
,
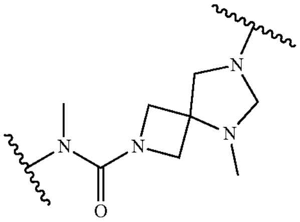
,
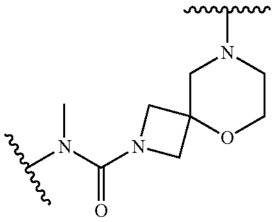
,
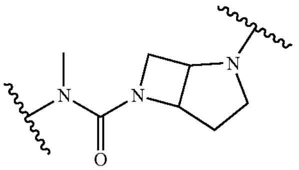
,
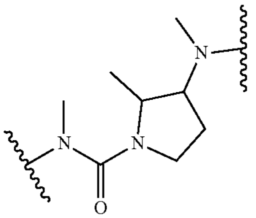
,
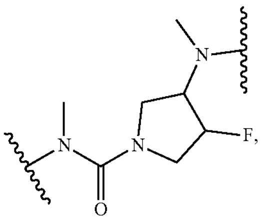
,
-continued
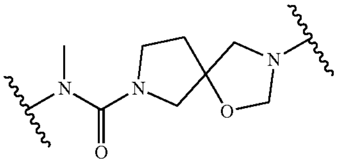
,
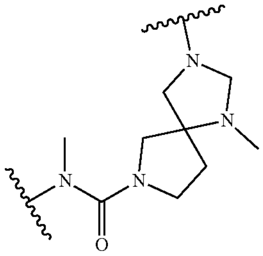
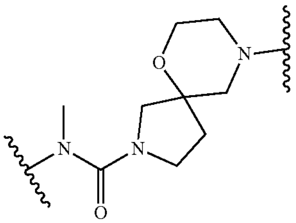
,
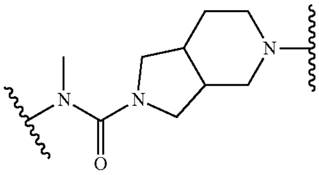
,
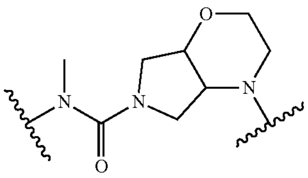
,
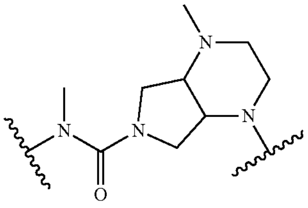
,
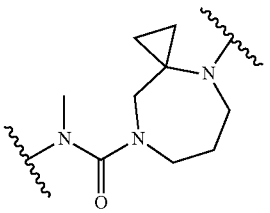
,
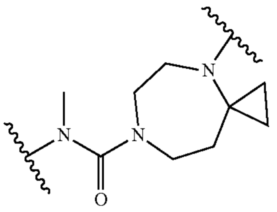
, -continued

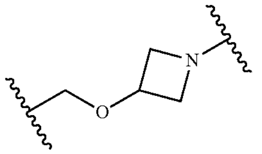

,

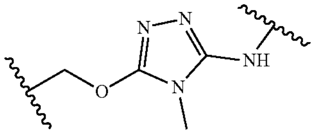

,

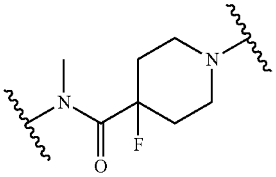

,

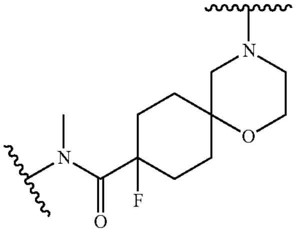

,

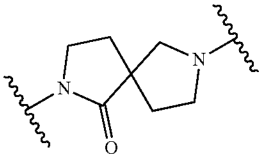

, or

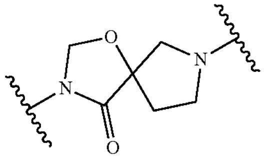

.

In some embodiments, a compound of the present invention has the structure of Formula II-5, or a pharmaceutically acceptable salt thereof:

Formula II-5

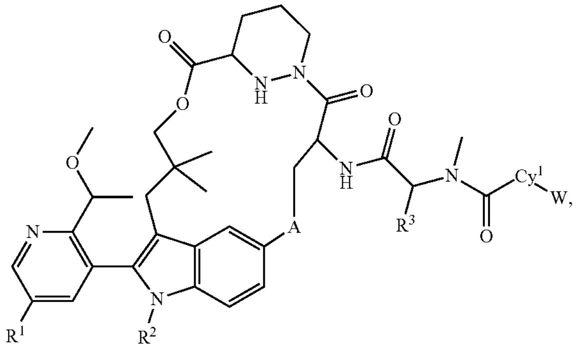

wherein $Cy^1$ is optionally substituted spirocyclic 8 to 11-membered heterocycloalkylene or optionally substituted bicyclic 7 to 9-membered heterocycloalkylene; and wherein W comprises a vinyl ketone or a vinyl sulfone.

In some embodiments, $Cy^1$ is optionally substituted spirocyclic 10 to 11-membered heterocycloalkylene.

In some embodiments, a compound of the present invention has the structure of Formula II-5a:

Formula II-5a

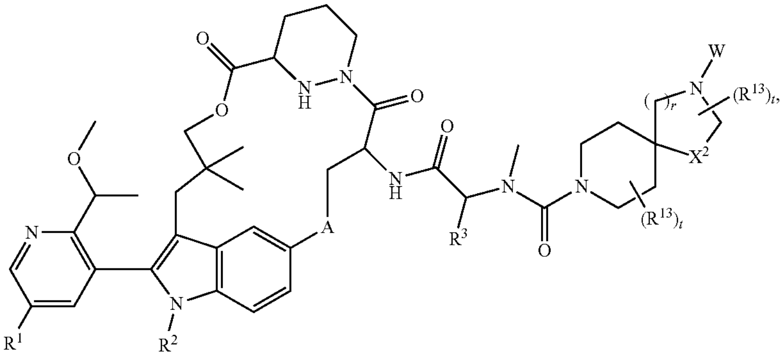

wherein $X^2$ is O, $C(R^1)_2$, $NR^{12}$, S, or $SO_2$.

r is 1 or 2;

each t is, independently, 0, 1, or 2;

$R^{11}$ and $R^{12}$ are each, independently, hydrogen, optionally substituted $C_1$-$C_4$ alkyl, optionally substituted $C_2$-$C_4$ heteroalkyl, or optionally substituted 3 to 5-membered cycloalkyl; and each $R^{13}$ is, independently, —$CH_3$.

In some embodiments, r is 1. In some embodiments, r is 2. In some embodiments, $X^2$ is O. In some embodiments, $X^2$ is S. In some embodiments, $X^2$ is $SO_2$.

In some embodiments, $X^2$ is $NR^{12}$. In some embodiments, $R^{12}$ is selected from, or a stereoisomer thereof:

—$CH_3$, 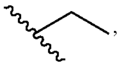, 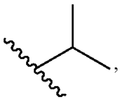, 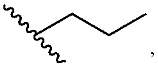,

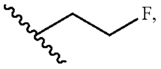 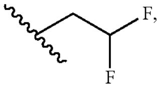 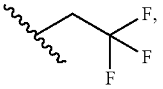

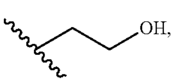 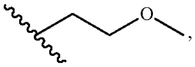,

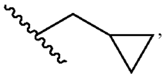, 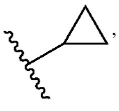, or —H.

In some embodiments, $X^2$ is $C(R^{11})_2$. In some embodiments, each $R^{11}$ is hydrogen.

In some embodiments of a compound of the present invention, W is a cross-linking group comprising a vinyl ketone. In some embodiments, W has the structure of Formula IVa:

Formula IVa

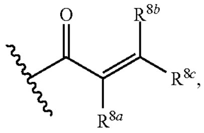

wherein $R^{8a}$, $R^{8b}$, and $R^{8c}$ are, independently, hydrogen, —CN, halogen, or —$C_1$-$C_3$ alkyl optionally substituted with one or more substituents independently selected from —OH, —O—$C_1$-$C_3$ alkyl, —$NH_2$, —$NH(C_1$-$C_3$ alkyl), —$N(C_1$-$C_3$ alkyl$)_2$, or a 4 to 7-membered saturated heterocycloalkyl. In some embodiments, W is selected from, or a stereoisomer thereof:

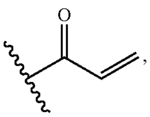, 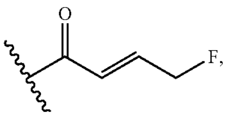

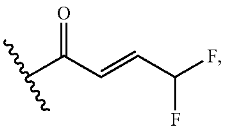 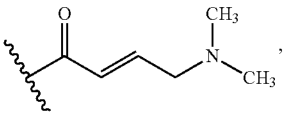,

-continued

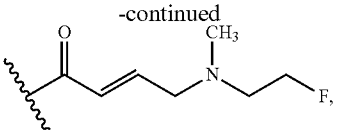

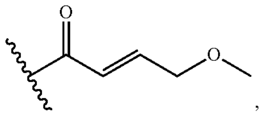, 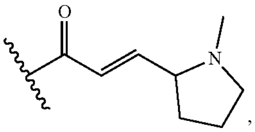, or

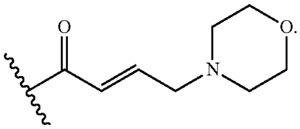

In some embodiments of a compound of the present invention, W is a cross-linking group comprising a vinyl sulfone. In some embodiments, W has the structure of Formula IVc:

Formula IVc

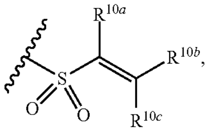

wherein $R^{10a}$, $R^{10b}$, and $R^{10c}$ are, independently, hydrogen, —CN, or —$C_1$-$C_3$ alkyl optionally substituted with one or more substituents independently selected from —OH, —O—$C_1$-$C_3$ alkyl, —$NH_2$, —$NH(C_1$-$C_3$ alkyl), —$N(C_1$-$C_3$ alkyl$)_2$, or a 4 to 7-membered saturated heterocycloalkyl. In some embodiments, W is:

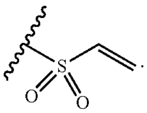 [SMILES: *S(=O)(=O)C=C]

In some embodiments of a compound of the present invention, W is a cross-linking group comprising an ynone. In some embodiments, W has the structure of Formula IVb:

Formula IVb

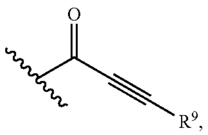

wherein $R^9$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated cycloalkyl, or a 4 to 7-membered saturated heterocycloalkyl. In some embodiments, W is selected from:

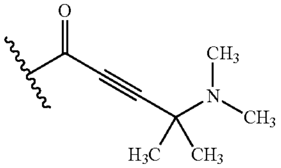
or
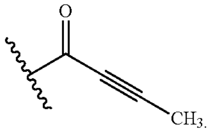

In some embodiments, a compound of the present invention has the structure of Formula II-6:

Formula II-6

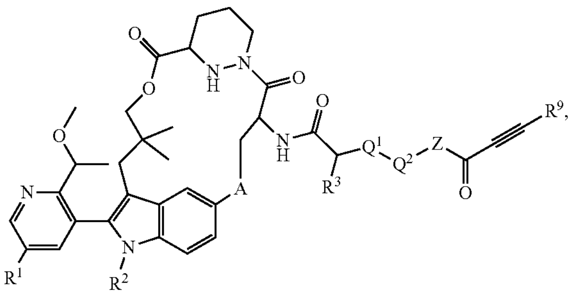

wherein $Q^1$ is $CH_2$, $NR^N$, or O;

$Q^2$ is CO, $NR^N$, or O; and

Z is optionally substituted 3 to 6-membered heterocycloalkylene or optionally substituted 5 to 10-membered heteroarylene; or wherein $Q^1$-$Q^2$-Z is an optionally substituted 9 to 10-membered spirocyclic heterocycloalkylene.

In some embodiments, a compound of the present invention has the structure of Formula II-6a:

Formula II-6a

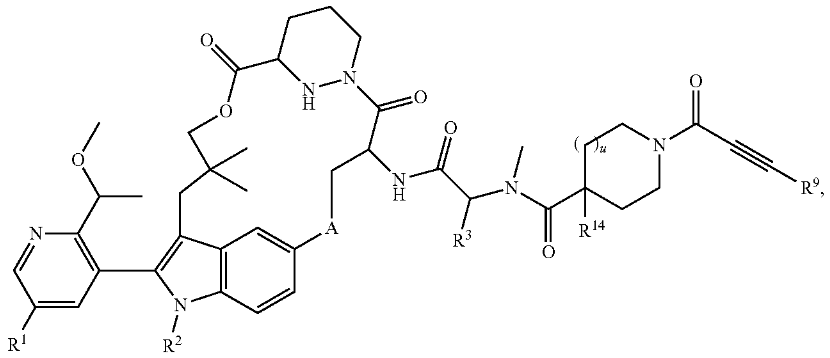

wherein $R^{14}$ is fluoro, hydrogen, or $C_1$-$C_3$ alkyl; and u is 0 or 1.

In some embodiments, $R^{14}$ is fluoro and u is 1. In some embodiments, $R^{14}$ is hydrogen and u is 0.

In some embodiments, a compound of the present invention has the structure of Formula II-6b:

Formula II-6b

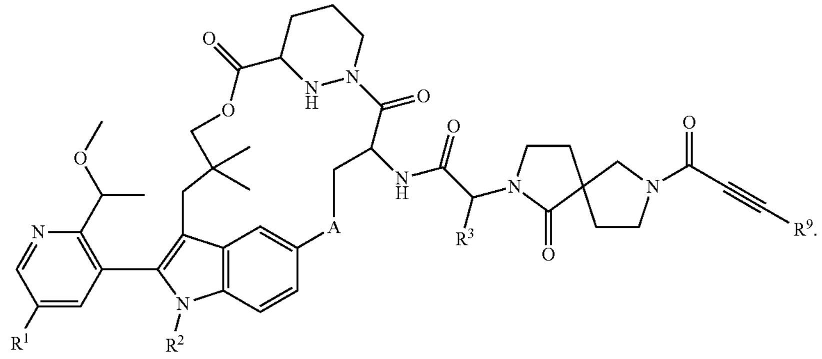

In some embodiments, a compound of the present invention has the structure of Formula II-6c:

Formula II-6c

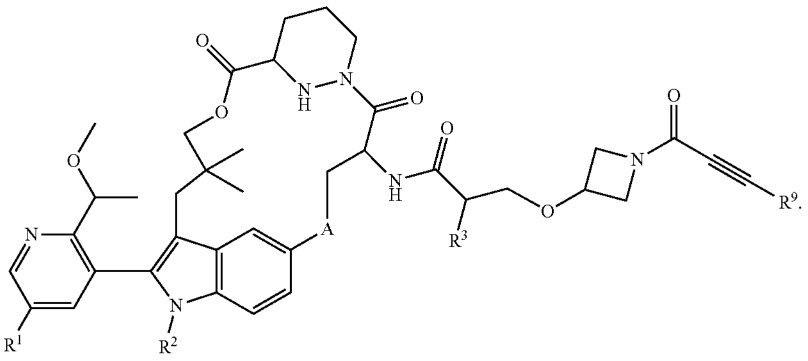

In some embodiments, a compound of the present invention is selected from Table 1, or a pharmaceutically acceptable salt or stereoisomer thereof. In some embodiments, a compound of the present invention is selected from Table 1, or a pharmaceutically acceptable salt or atropisomer thereof.

TABLE 1

| Certain Compounds of the Present Invention | |
|---|---|
| Ex# | Structure |
| A1 | 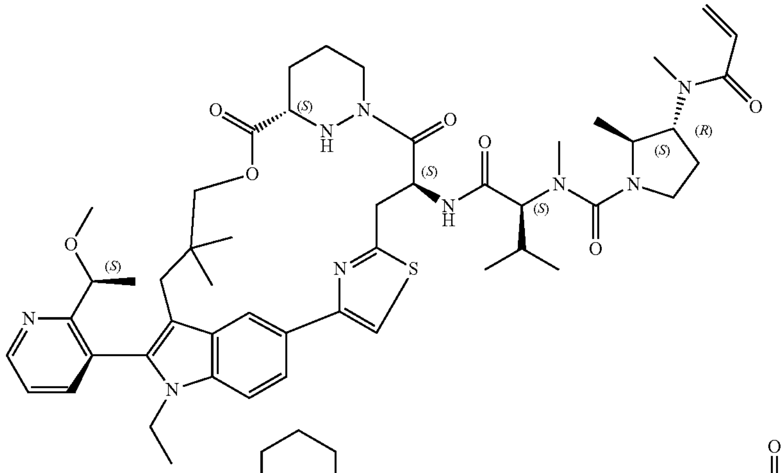 |
| A2 | 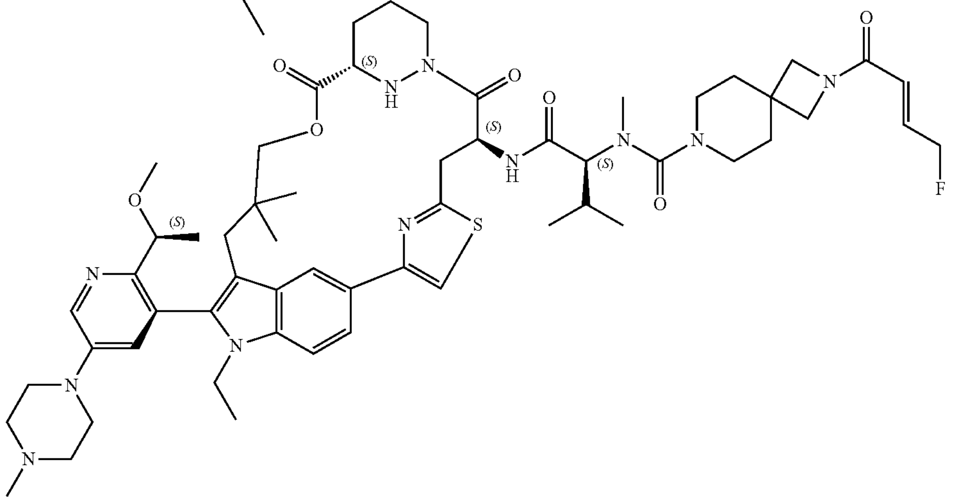 |

TABLE 1-continued
| Ex# | Structure |
| --- | --- |
| Certain Compounds of the Present Invention | |
| A3 | 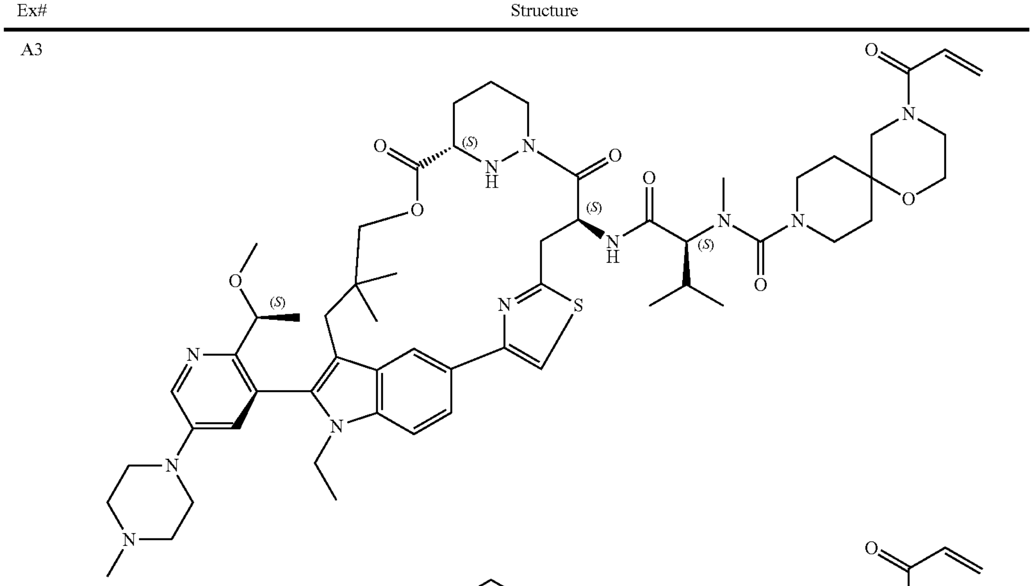 |
| A4 | 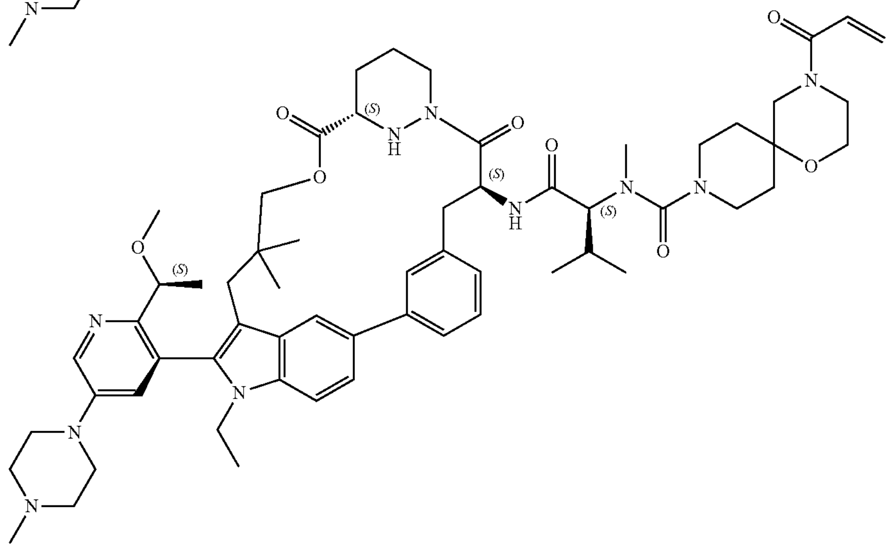 |
| A5 | 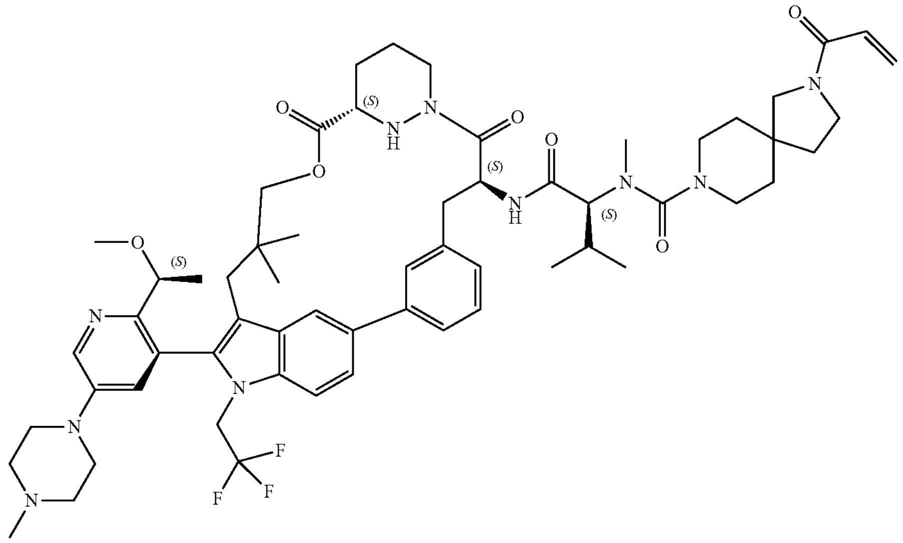 |

TABLE 1-continued
| Certain Compounds of the Present Invention | |
|---|---|
| Ex# | Structure |
| A6 | 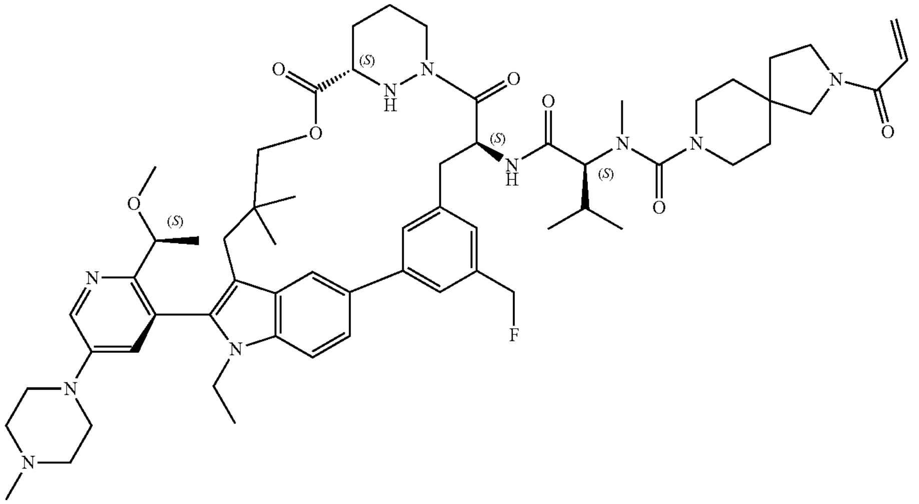 |
| A7 | 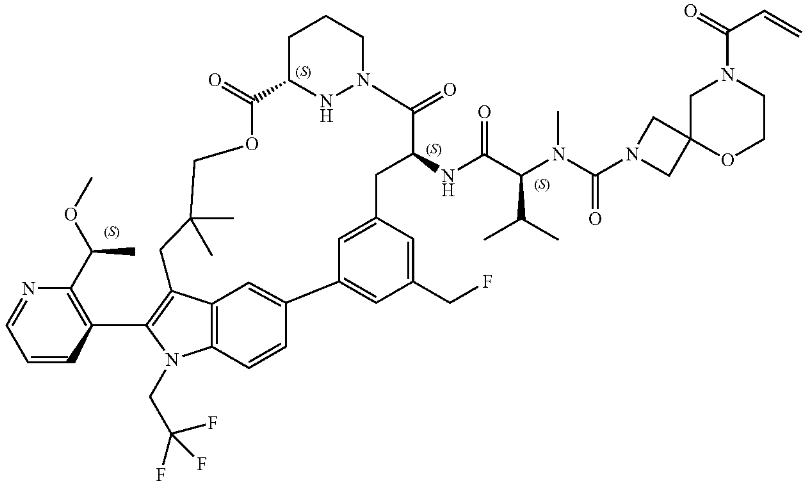 |
| A8 | 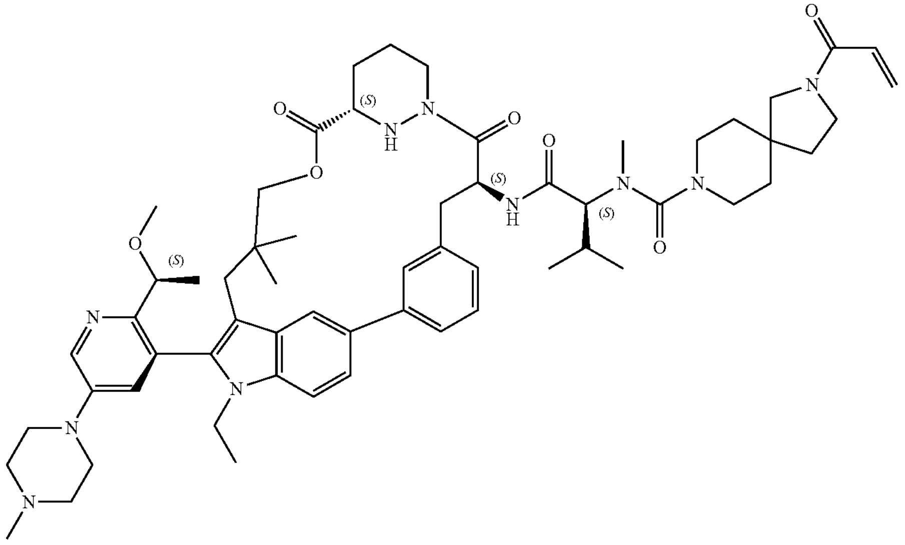 |

TABLE 1-continued
| Certain Compounds of the Present Invention | |
|---|---|
| Ex# | Structure |
| A9 | 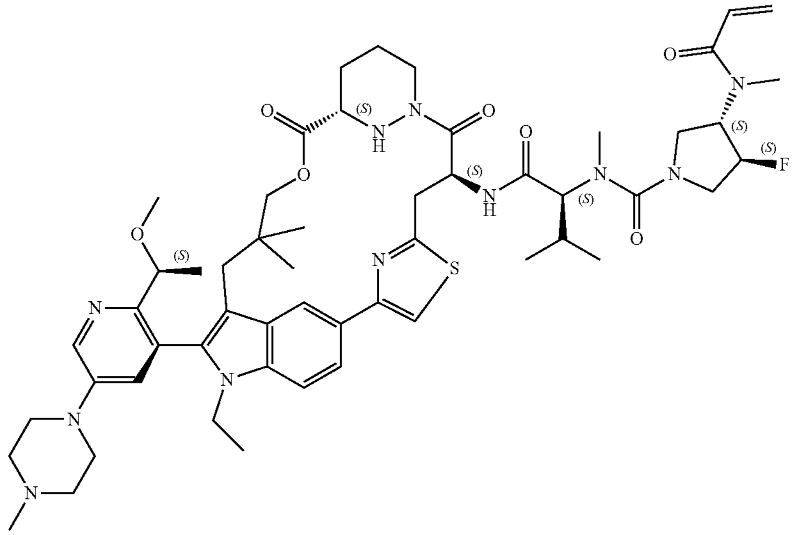 |
| A10 | 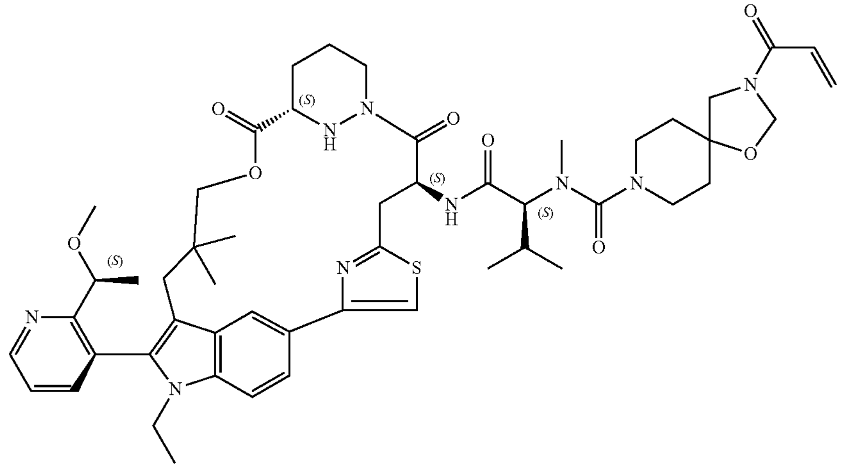 |
| A11 | 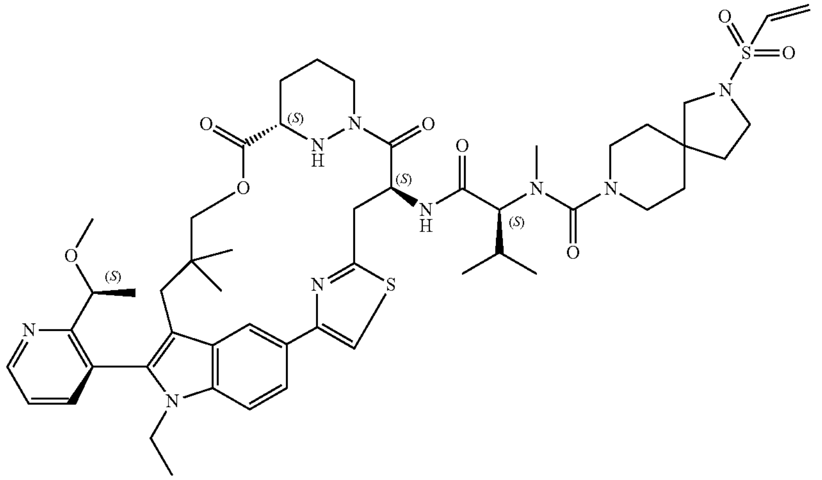 |

TABLE 1-continued
| Certain Compounds of the Present Invention | |
|---|---|
| Ex# | Structure |
| A12 | 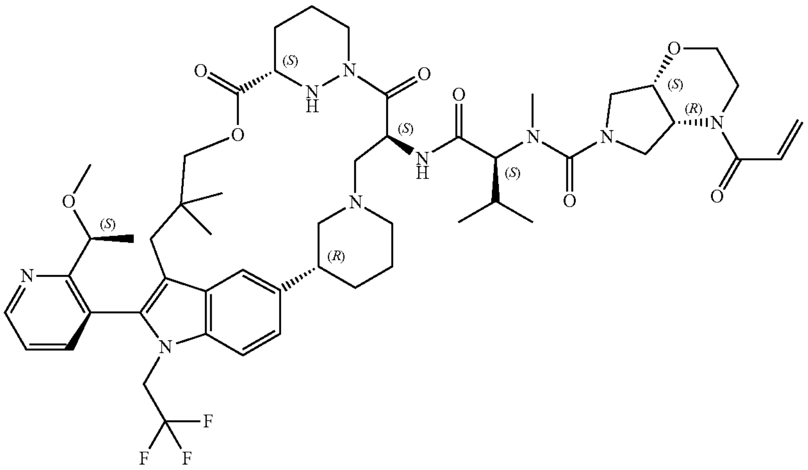 |
| A13 | 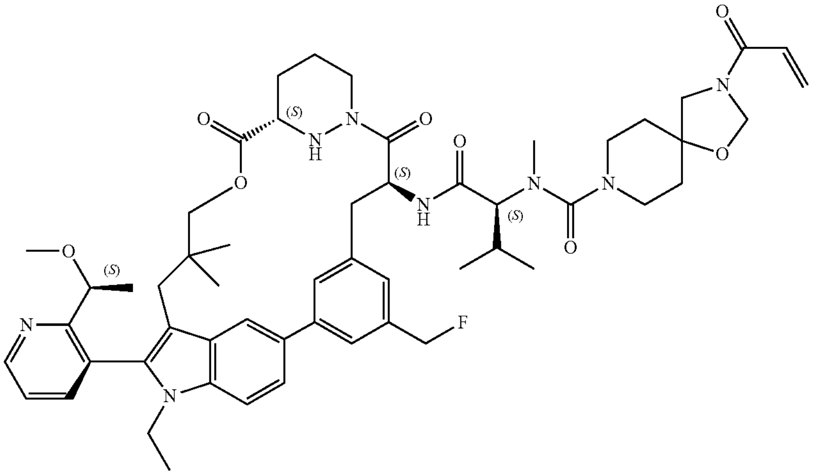 |
| A14 | 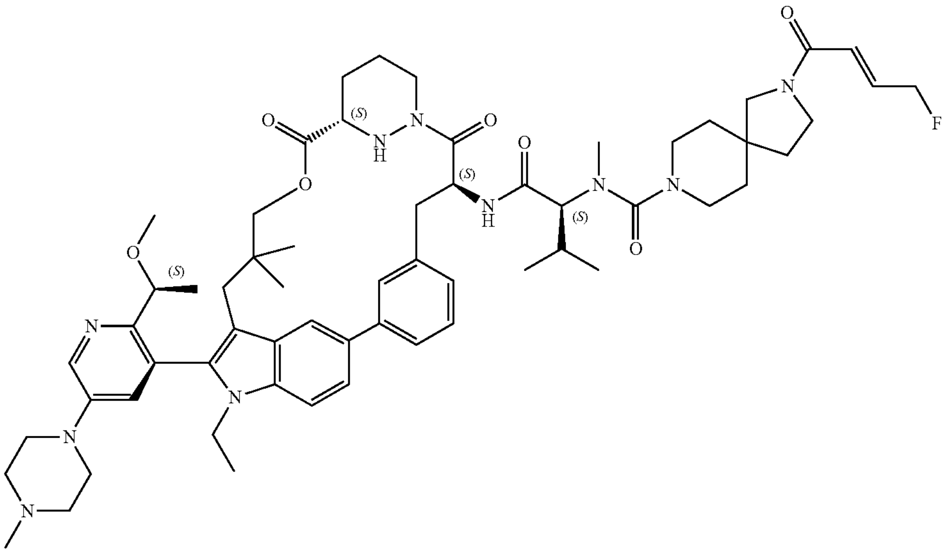 |

TABLE 1-continued
| Certain Compounds of the Present Invention | |
|---|---|
| Ex# | Structure |
| A15 | 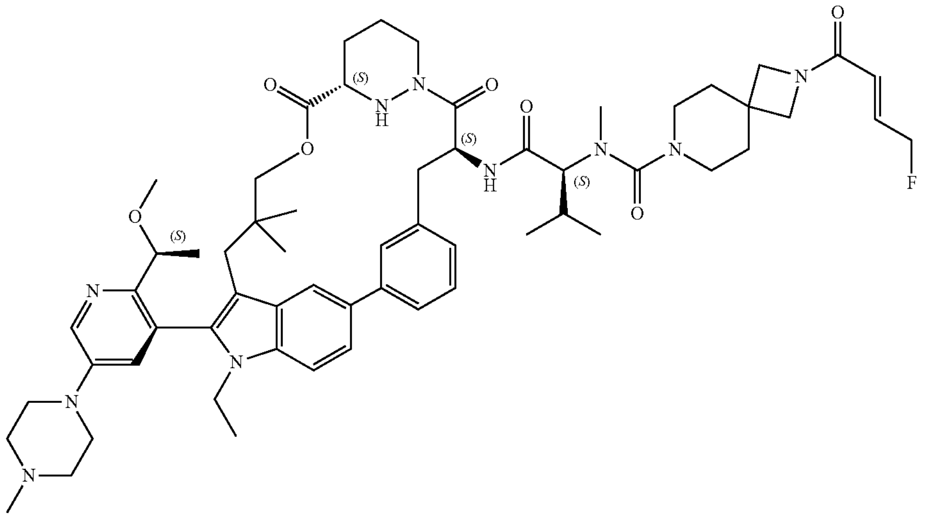 |
| A16 | 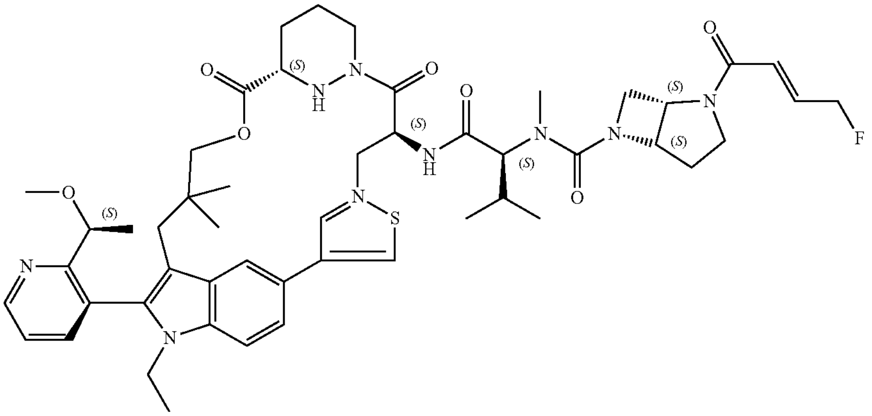 |
| A17 | 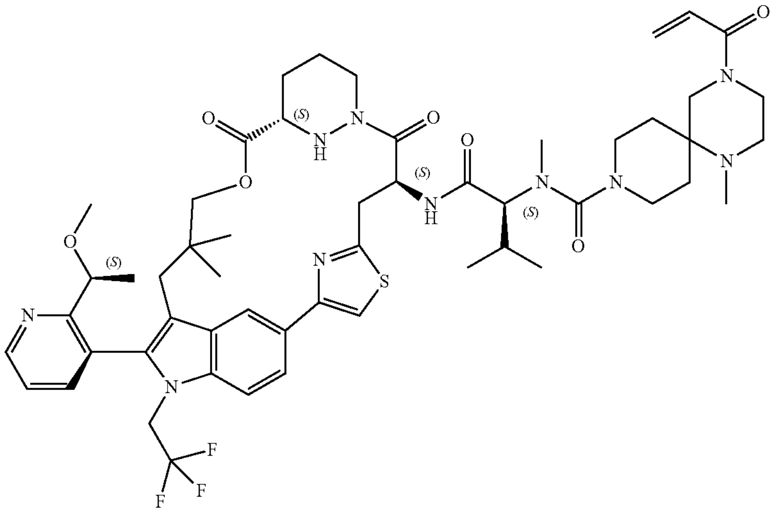 |

TABLE 1-continued
| Certain Compounds of the Present Invention | |
|---|---|
| Ex# | Structure |
| A18 | 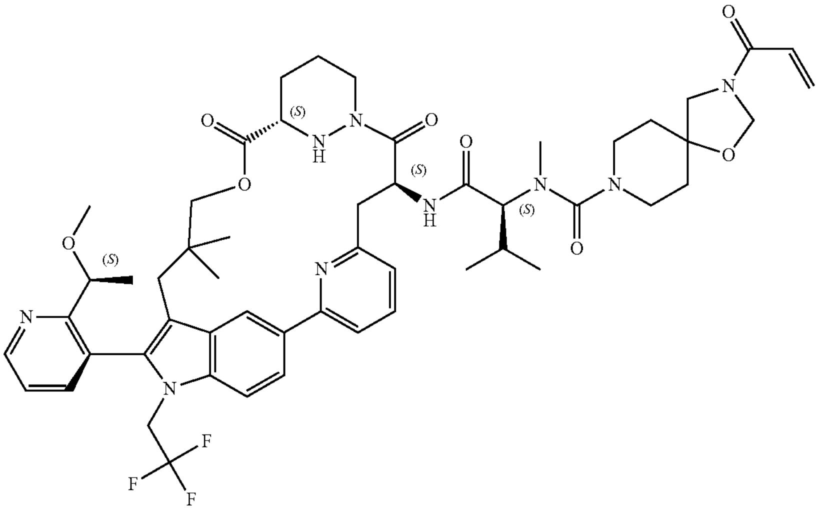 |
| A19 | 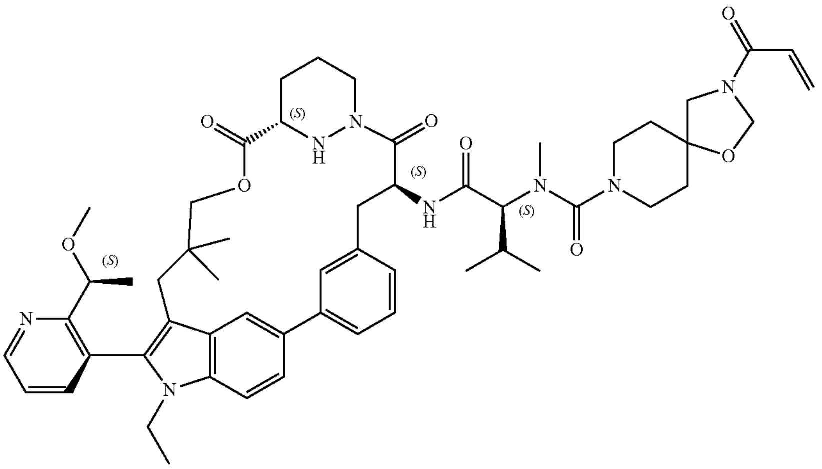 |
| A20 | 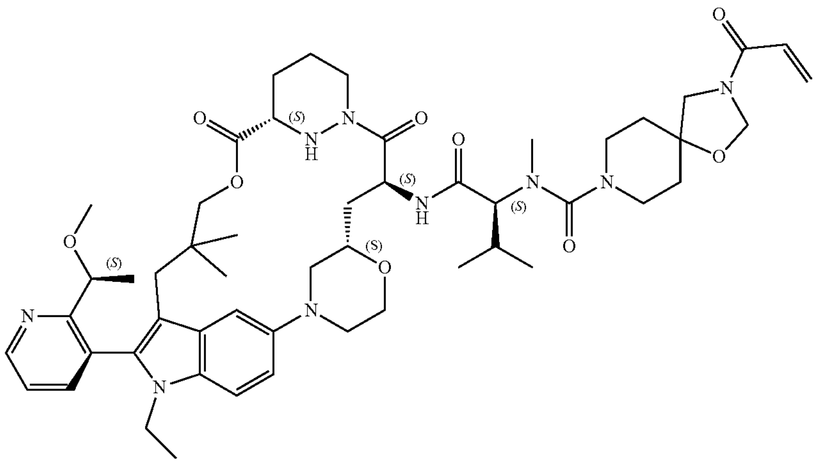 |

TABLE 1-continued
| Certain Compounds of the Present Invention | |
|---|---|
| Ex# | Structure |
| A21 | 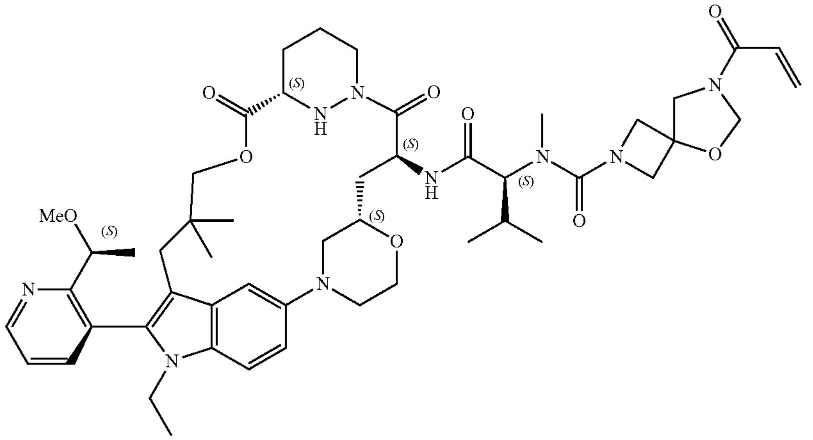 |
| A22 | 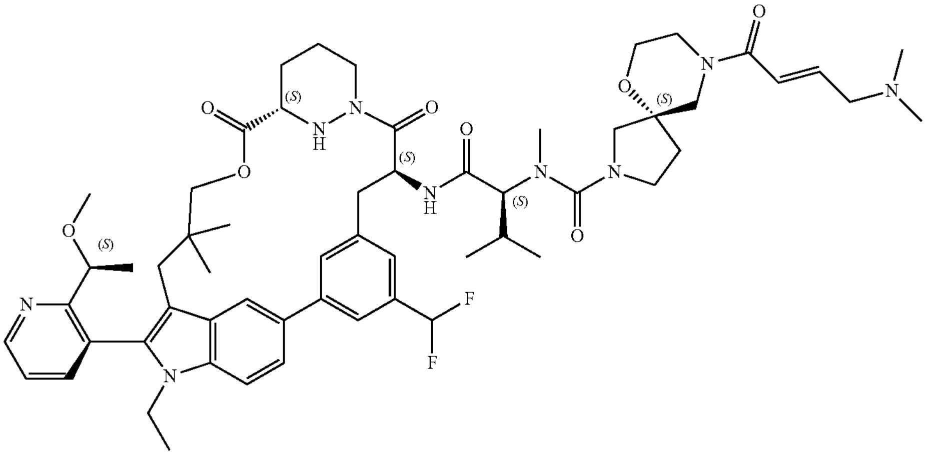 |
| A23 | 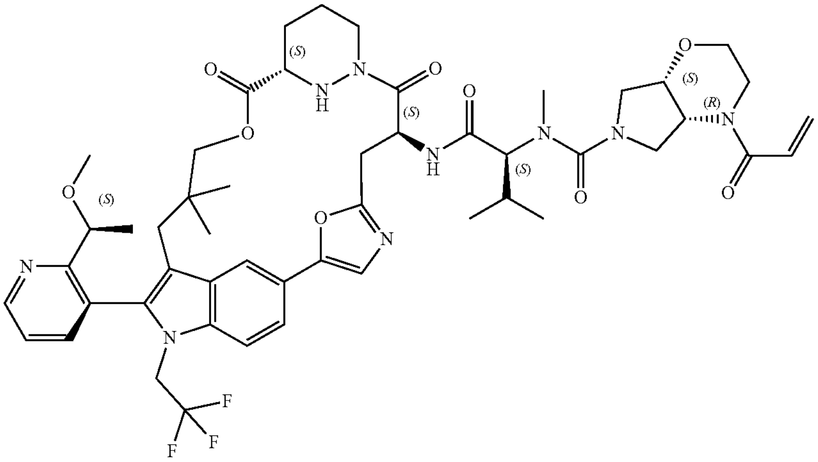 |

TABLE 1-continued
| Certain Compounds of the Present Invention | |
|---|---|
| Ex# | Structure |
| A24 | 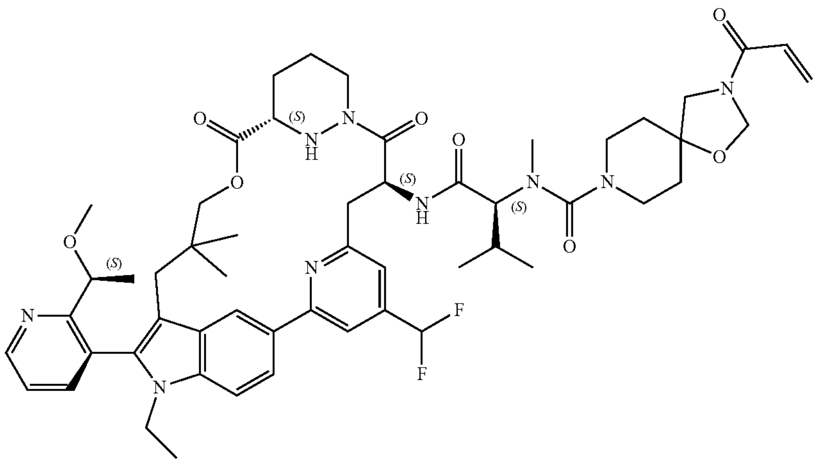 |
| A25 | 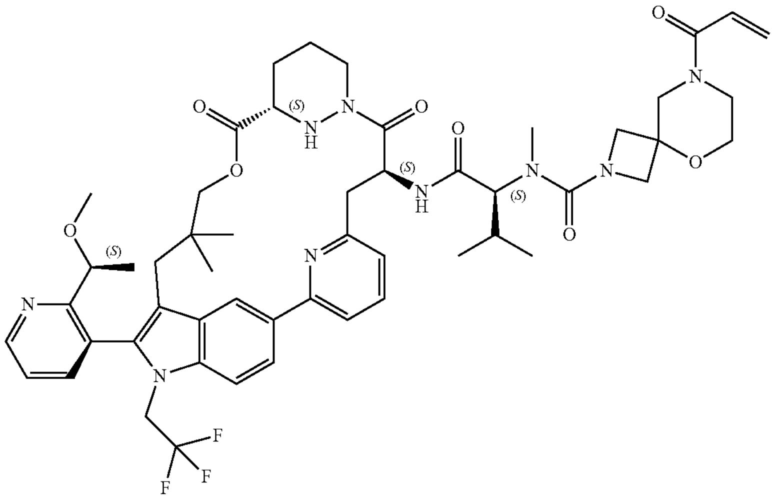 |
| A26 | 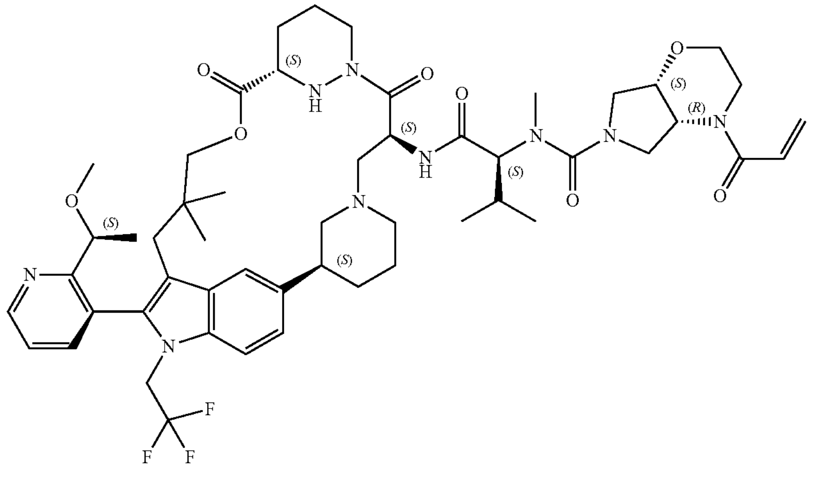 |

TABLE 1-continued
| Certain Compounds of the Present Invention | |
|---|---|
| Ex# | Structure |
| A27 | 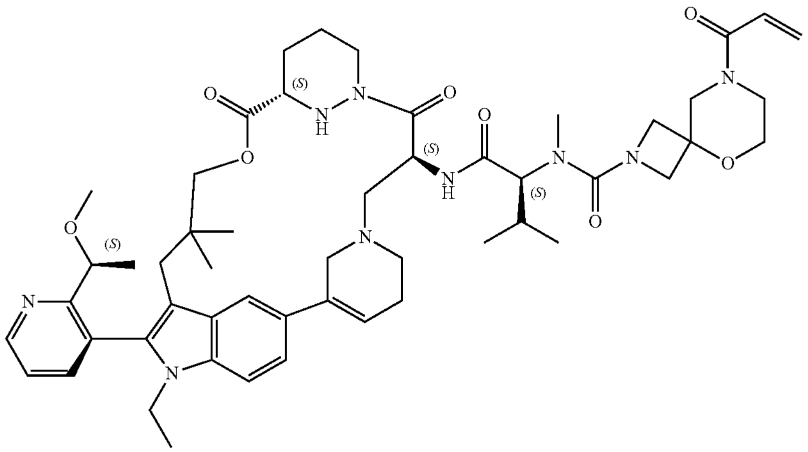 |
| A28 | 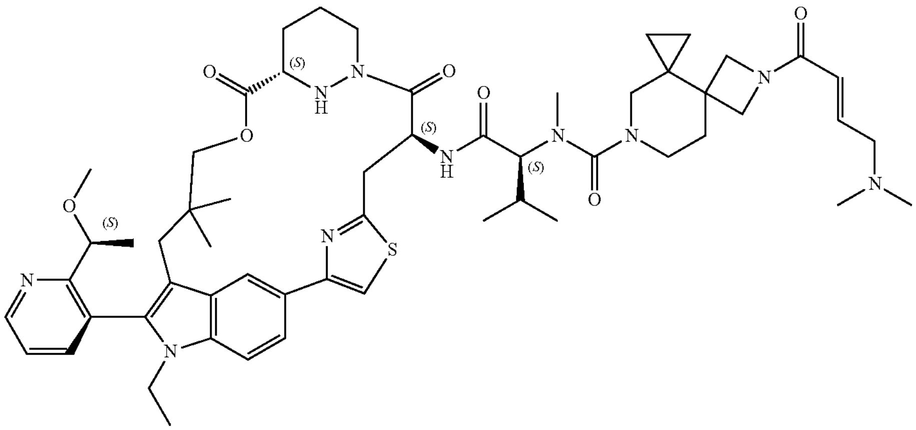 |
| A29 | 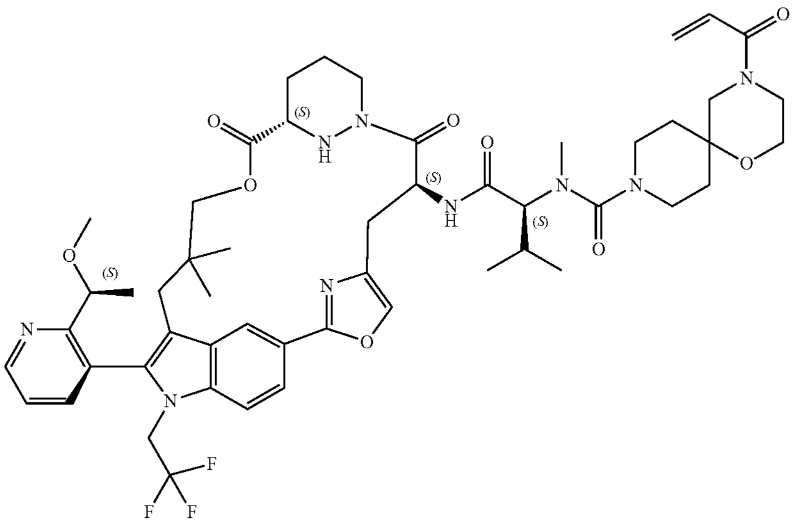 |

TABLE 1-continued
| Certain Compounds of the Present Invention | |
|---|---|
| Ex# | Structure |
| A30 | 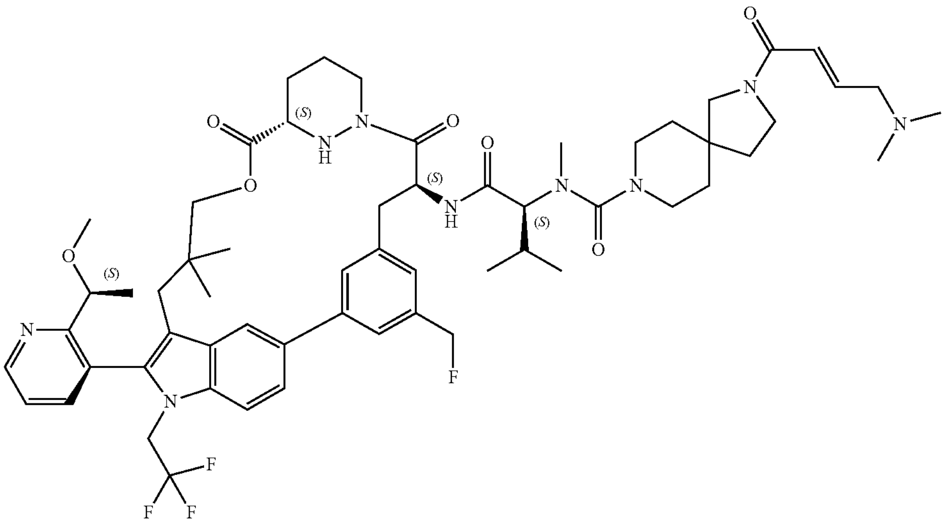 |
| A31 | 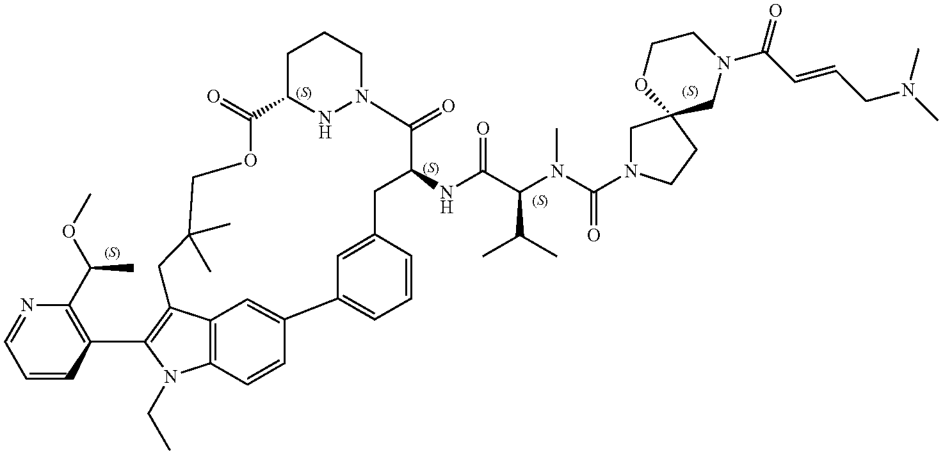 |
| A32 | 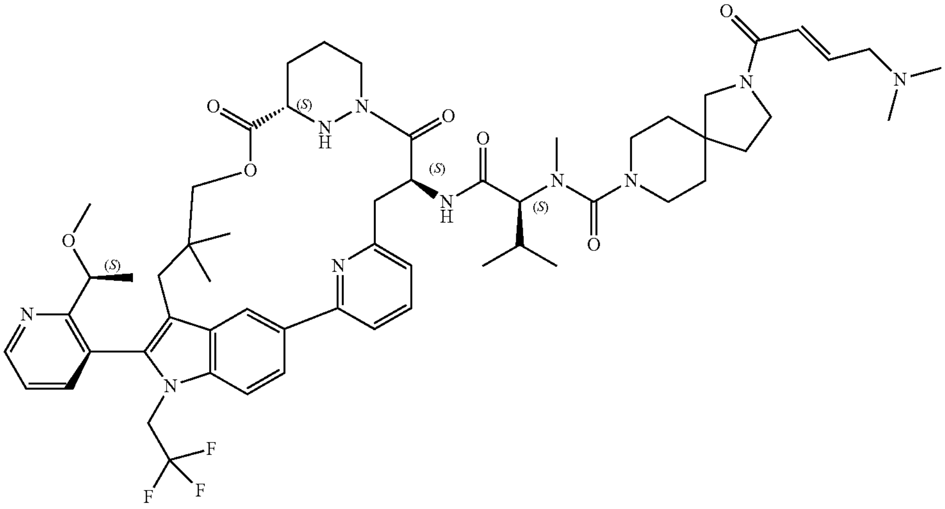 |

TABLE 1-continued
| Certain Compounds of the Present Invention | |
|---|---|
| Ex# | Structure |
| A33 | 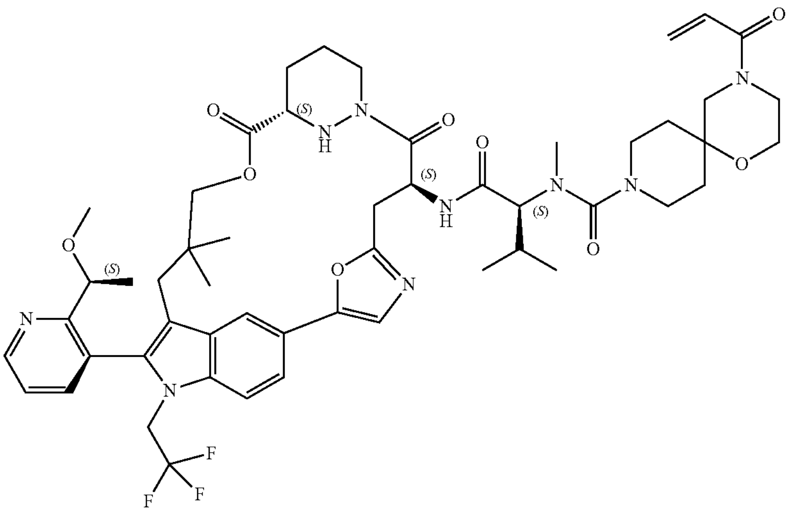 |
| A34 | 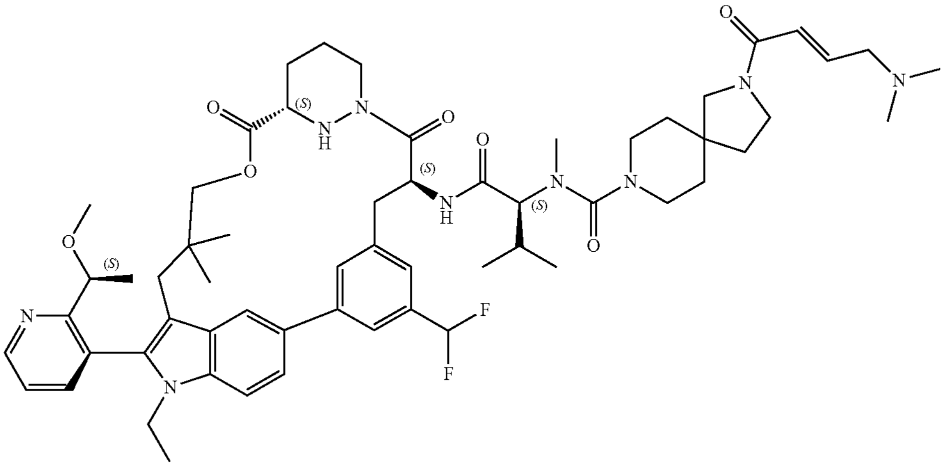 |
| A35 | 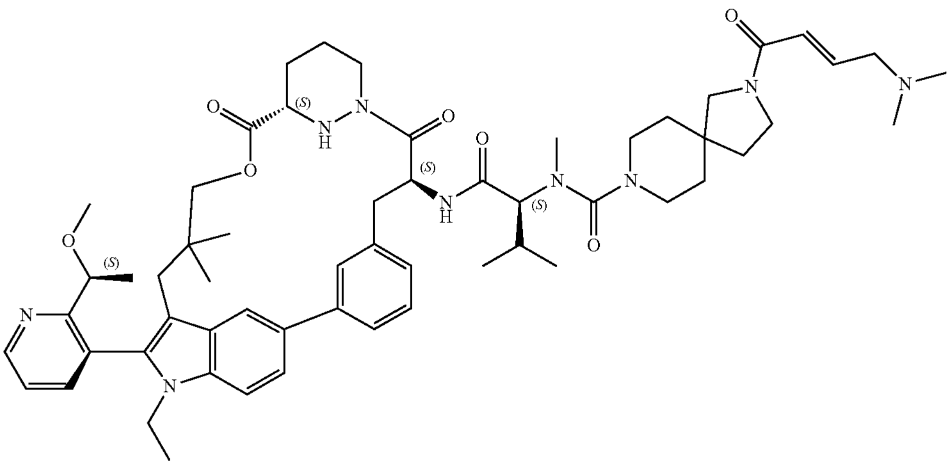 |

TABLE 1-continued
| Certain Compounds of the Present Invention | |
|---|---|
| Ex# | Structure |
| A36 | 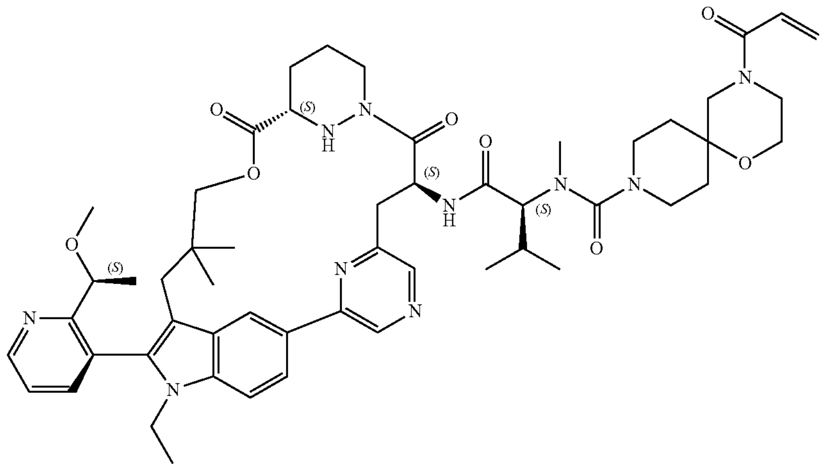 |
| A37 | 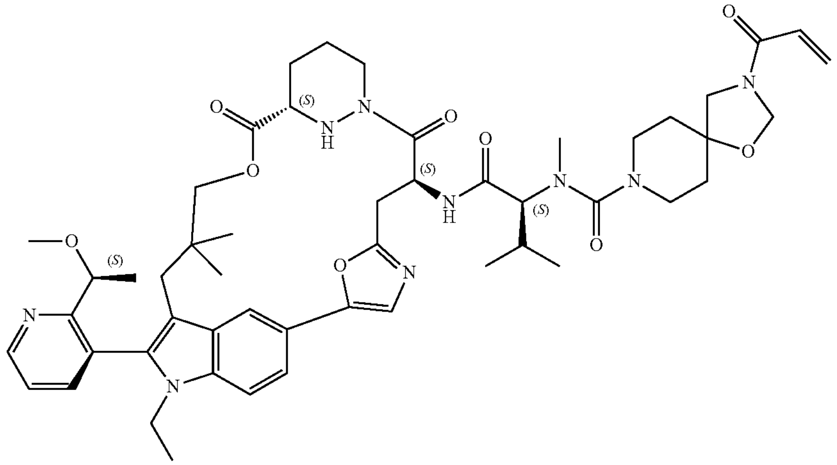 |
| A38 | 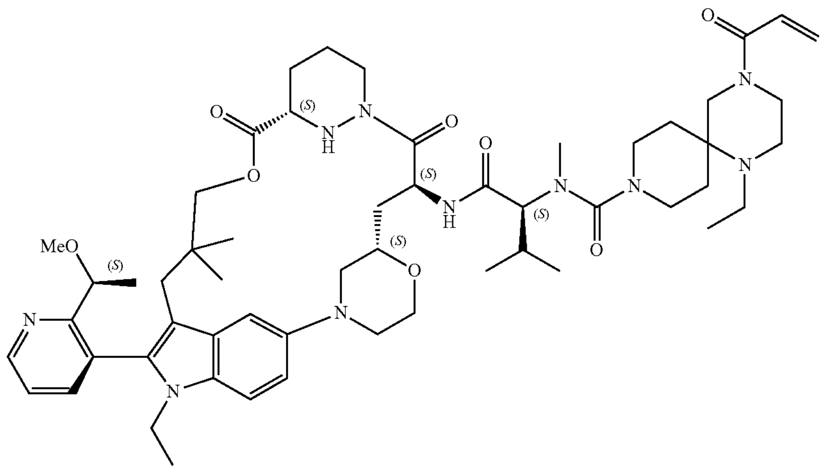 |

TABLE 1-continued
| Certain Compounds of the Present Invention | |
|---|---|
| Ex# | Structure |
| A39 | 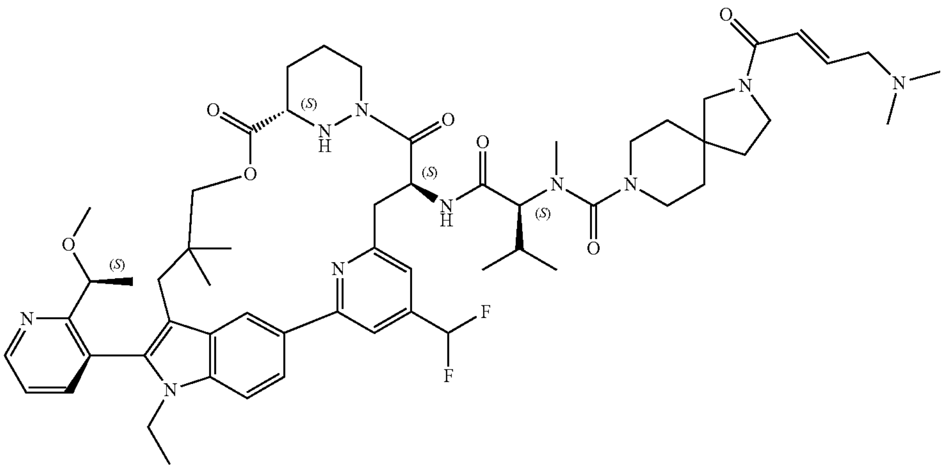 |
| A40 | 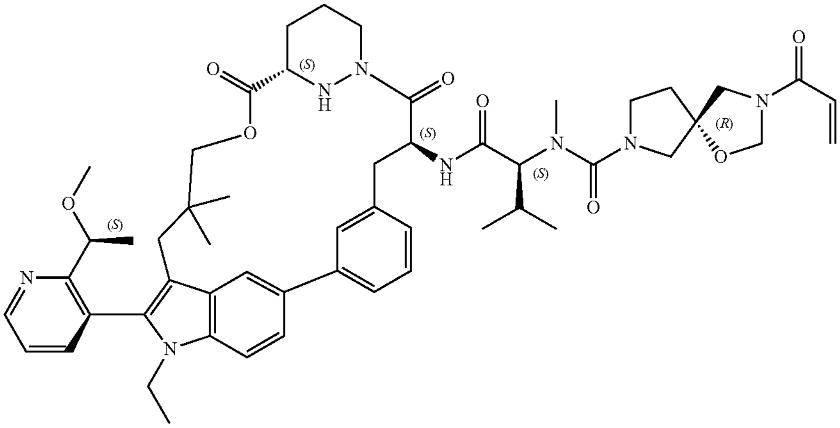 |
| A41 | 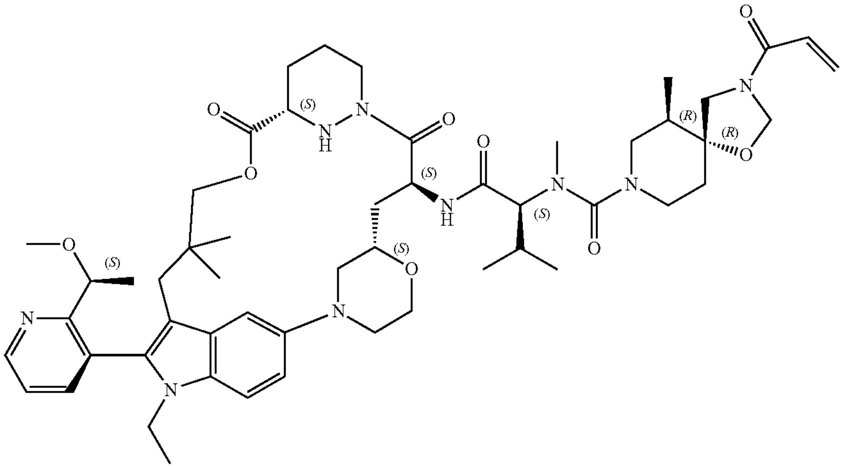 |

TABLE 1-continued
| Certain Compounds of the Present Invention | |
|---|---|
| Ex# | Structure |
| A42 | 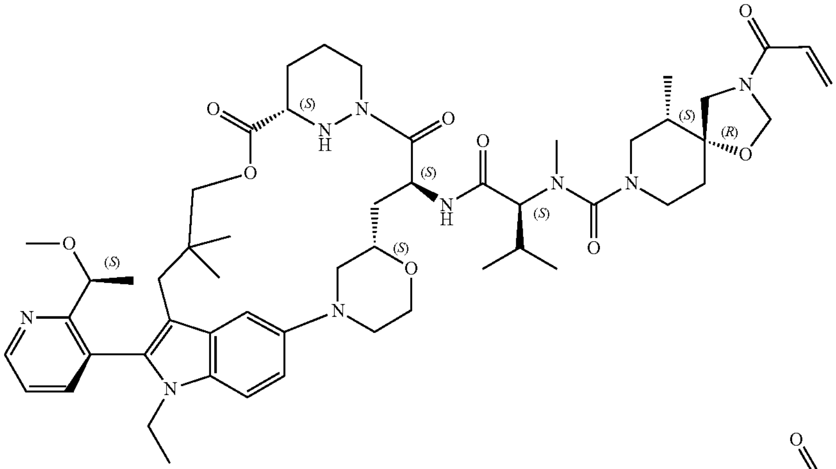 |
| A43 | 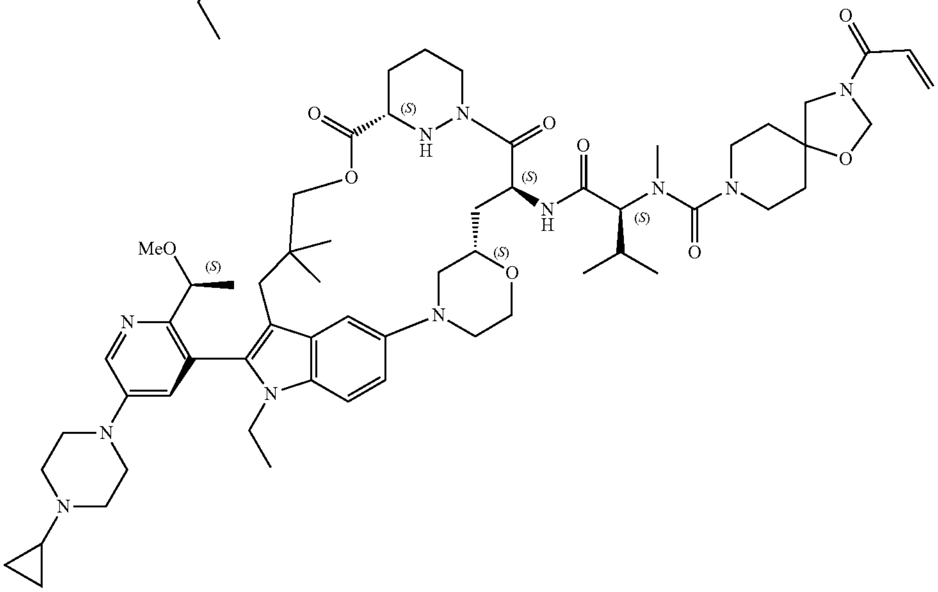 |
| A44 | 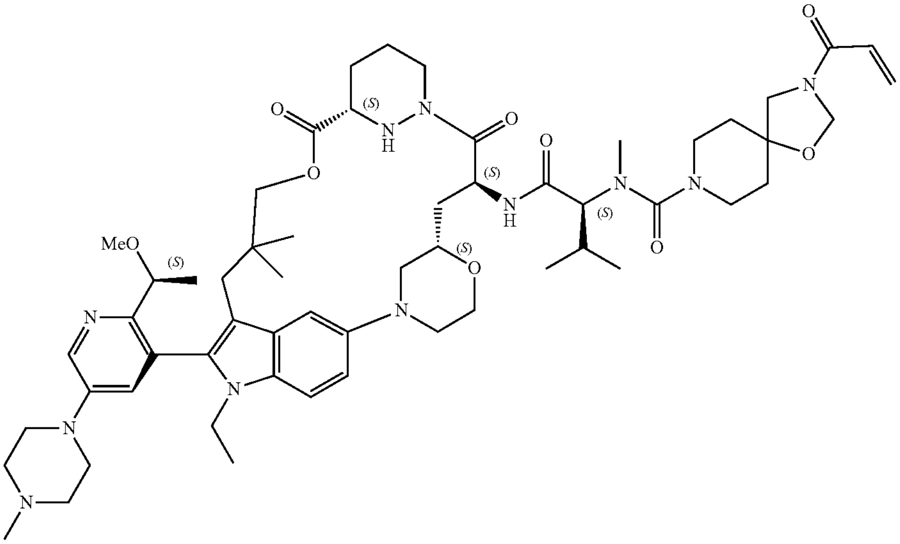 |

TABLE 1-continued
| Certain Compounds of the Present Invention | |
|---|---|
| Ex# | Structure |
| A45 | 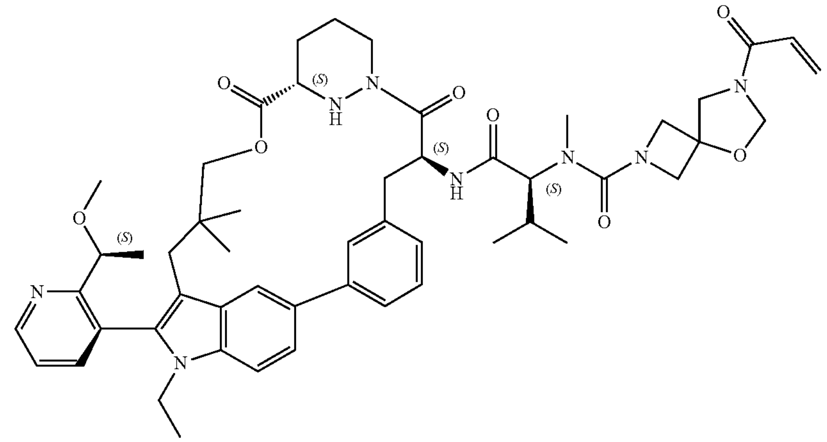 |
| A46 | 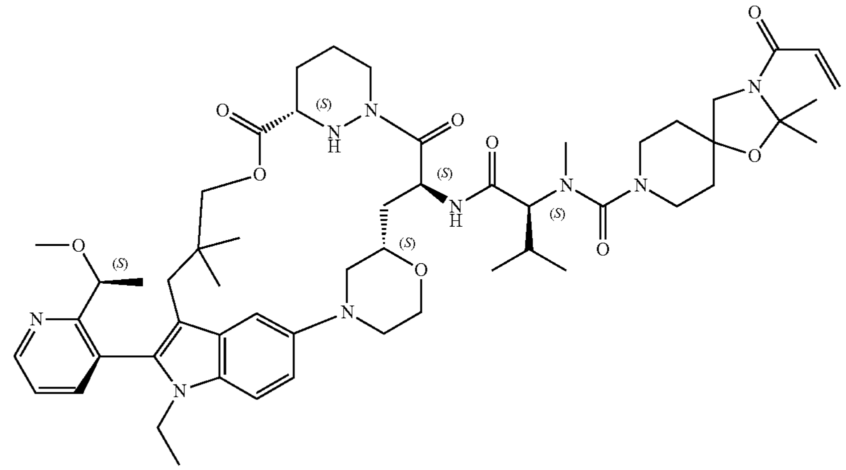 |
| A47 | 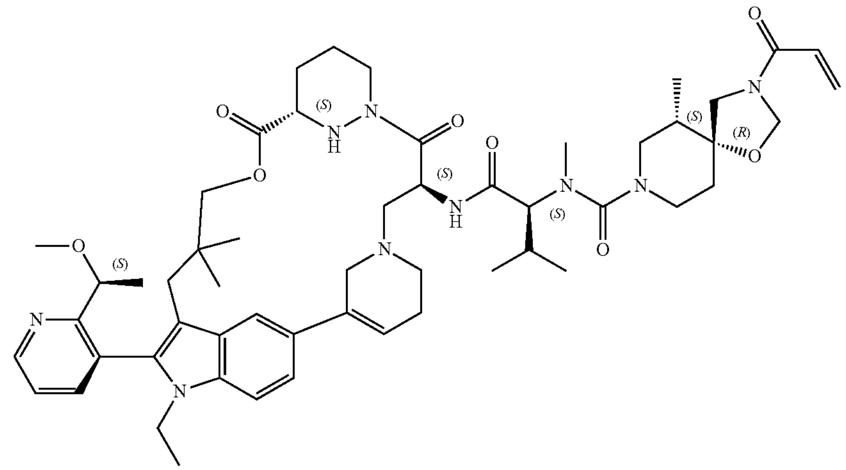 |

TABLE 1-continued
| Certain Compounds of the Present Invention | |
|---|---|
| Ex# | Structure |
| A48 | 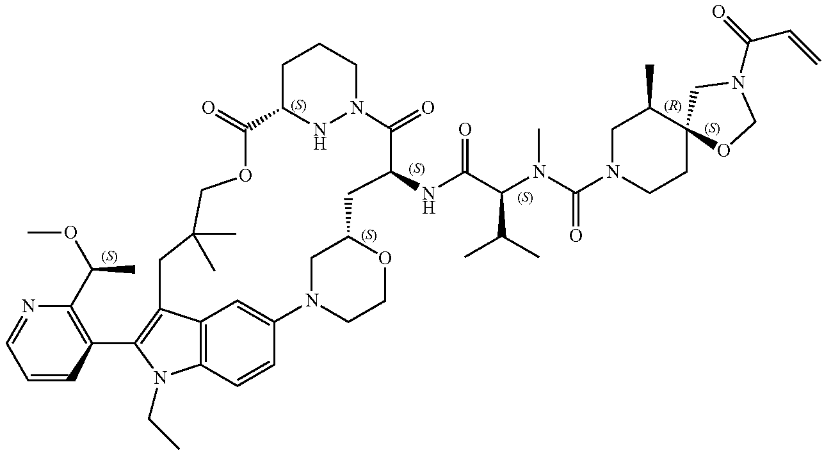 |
| A49 | 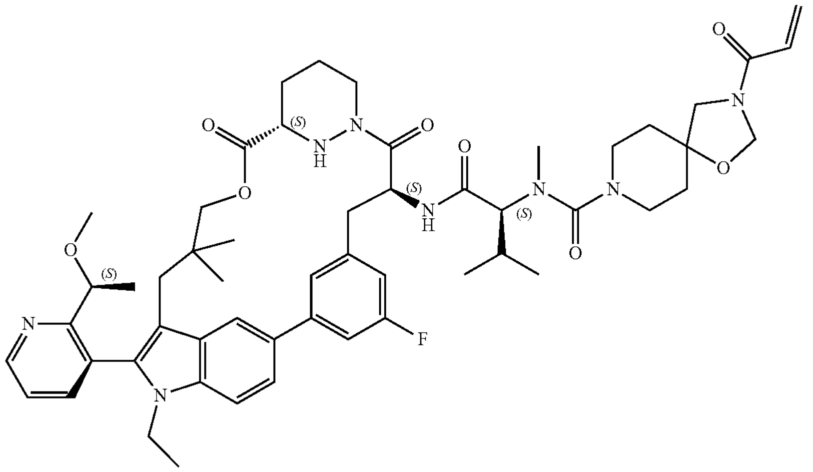 |
| A50 | 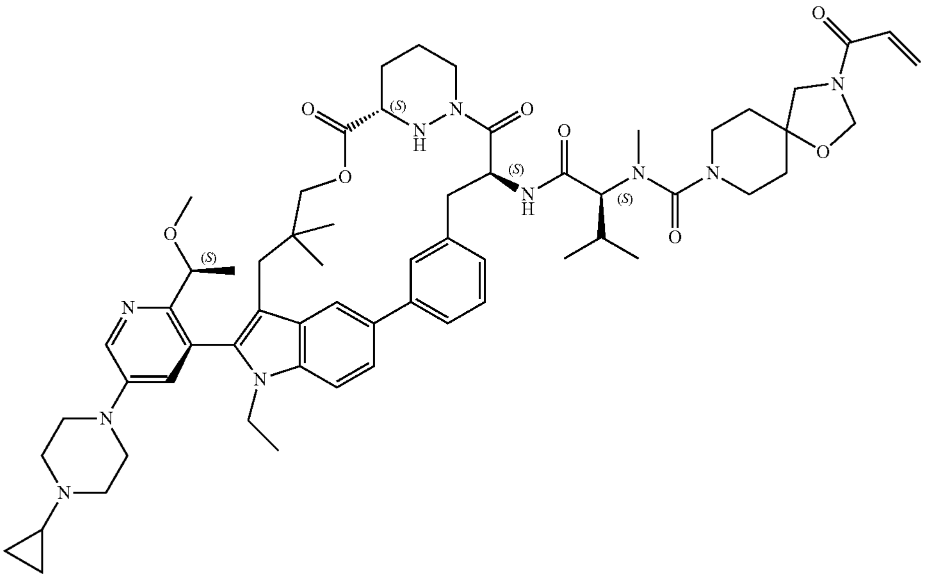 |

TABLE 1-continued
| Certain Compounds of the Present Invention | |
|---|---|
| Ex# | Structure |
| A51 | 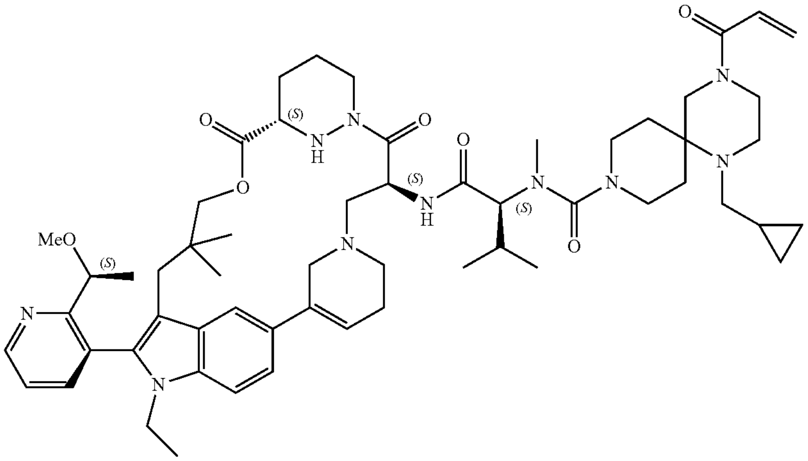 |
| A52 | 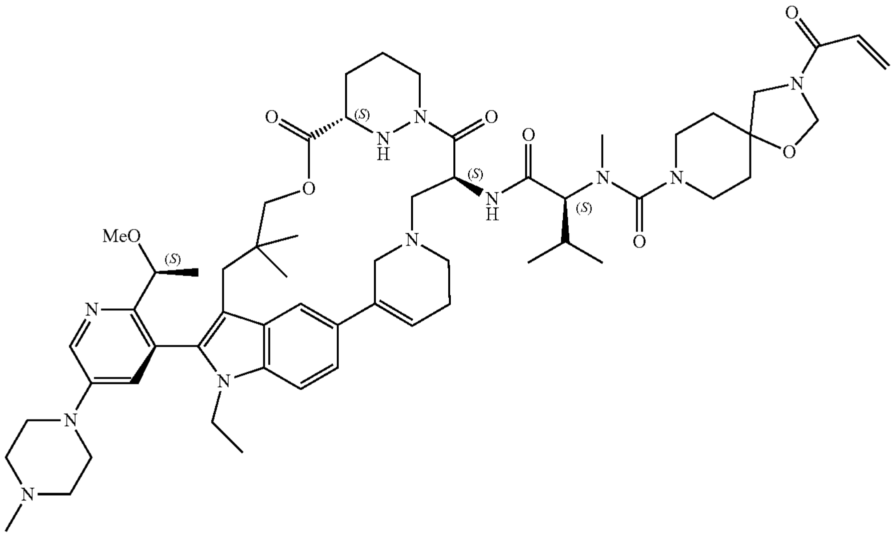 |
| A53 | 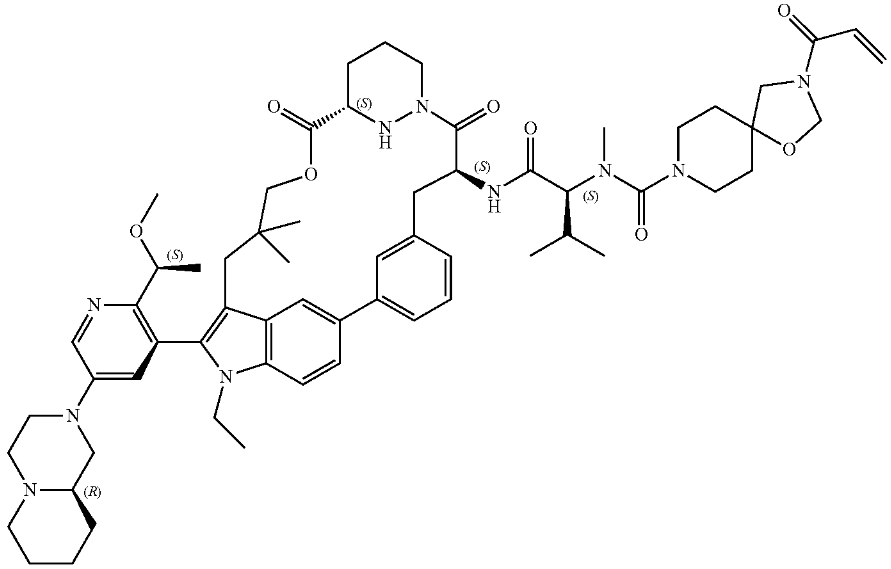 |

TABLE 1-continued
| Certain Compounds of the Present Invention | |
|---|---|
| Ex# | Structure |
| A54 | 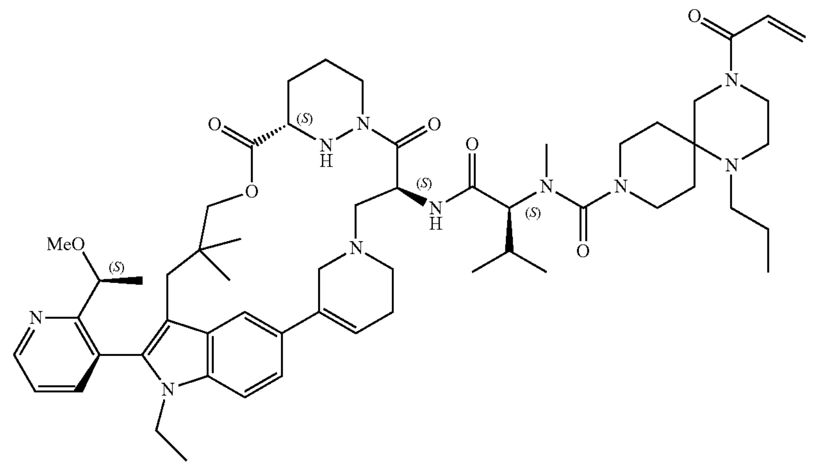 |
| A55 | 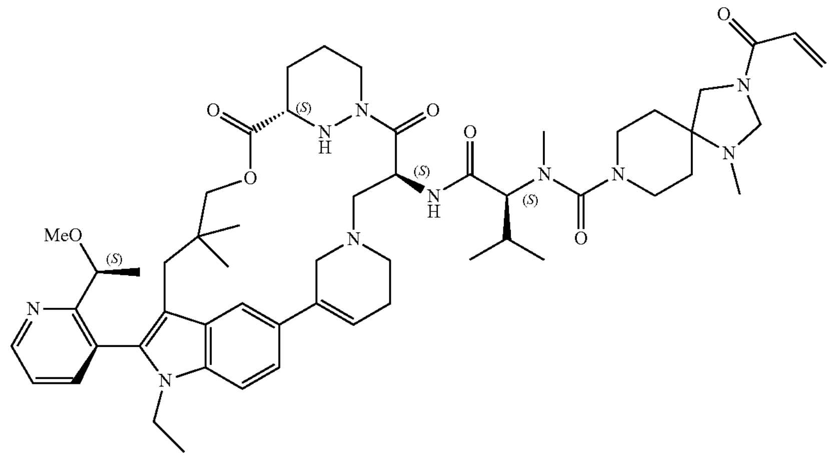 |
| A56 | 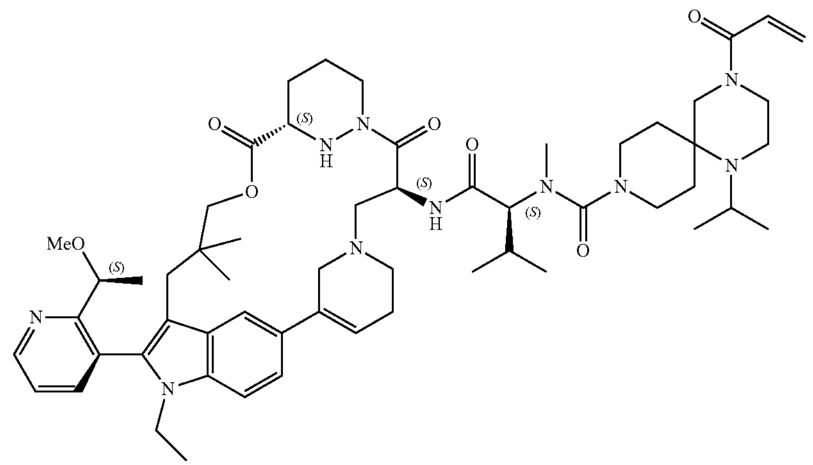 |

TABLE 1-continued
| Certain Compounds of the Present Invention | |
|---|---|
| Ex# | Structure |
| A57 | 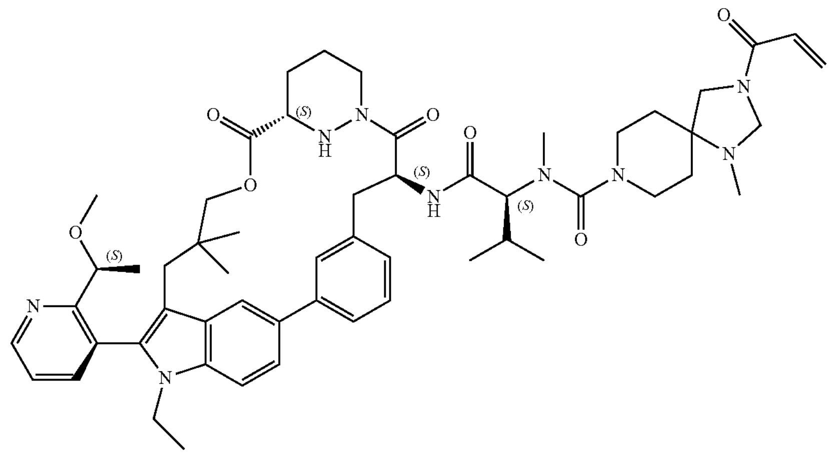 |
| A58 | 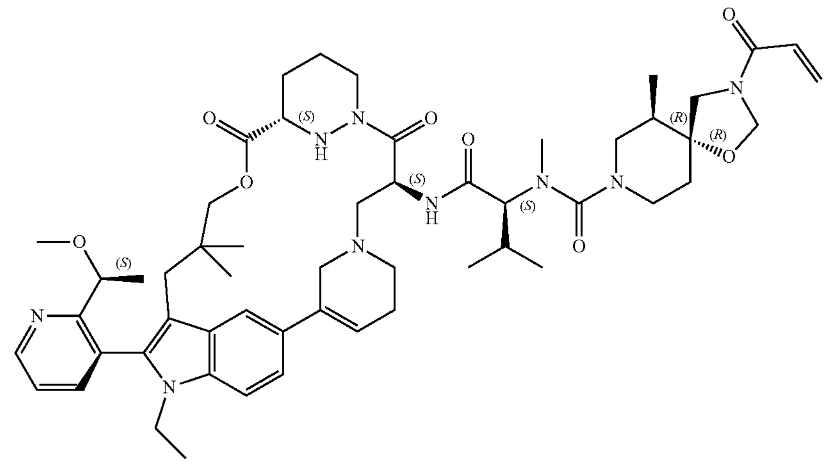 |
| A59 | 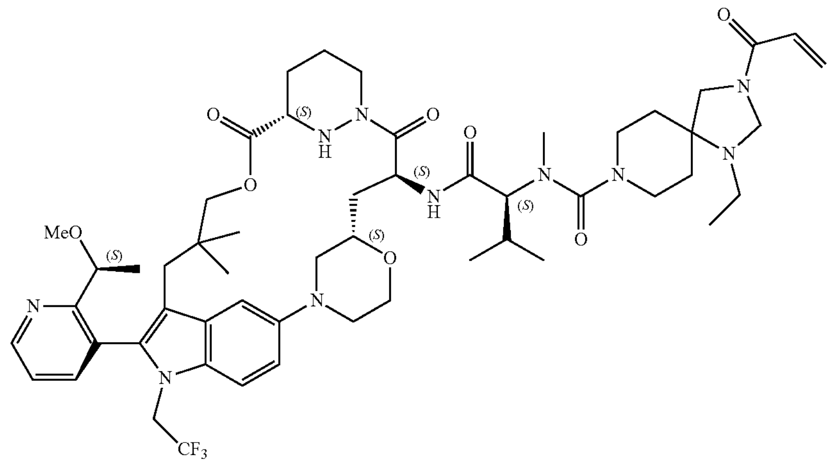 |

TABLE 1-continued
| Certain Compounds of the Present Invention | |
|---|---|
| Ex# | Structure |
| A60 | 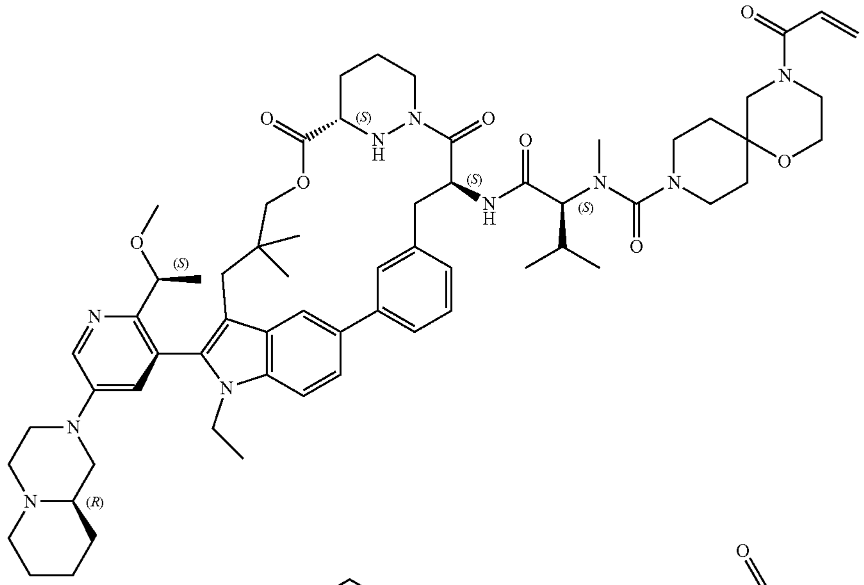 |
| A61 | 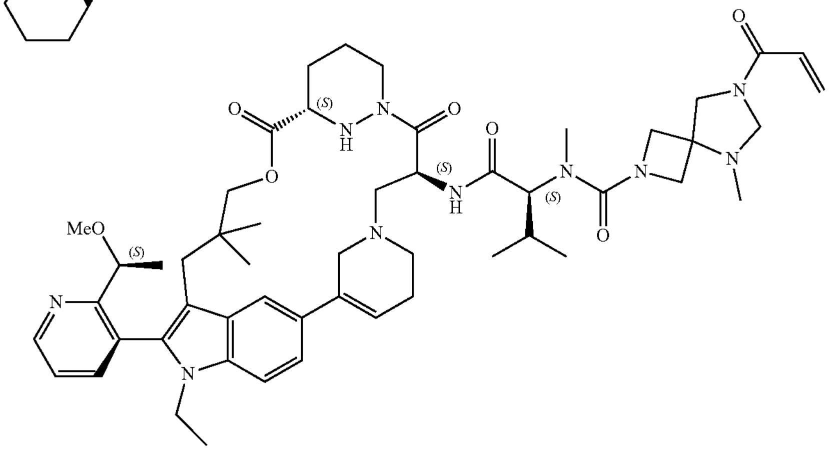 |
| A62 | 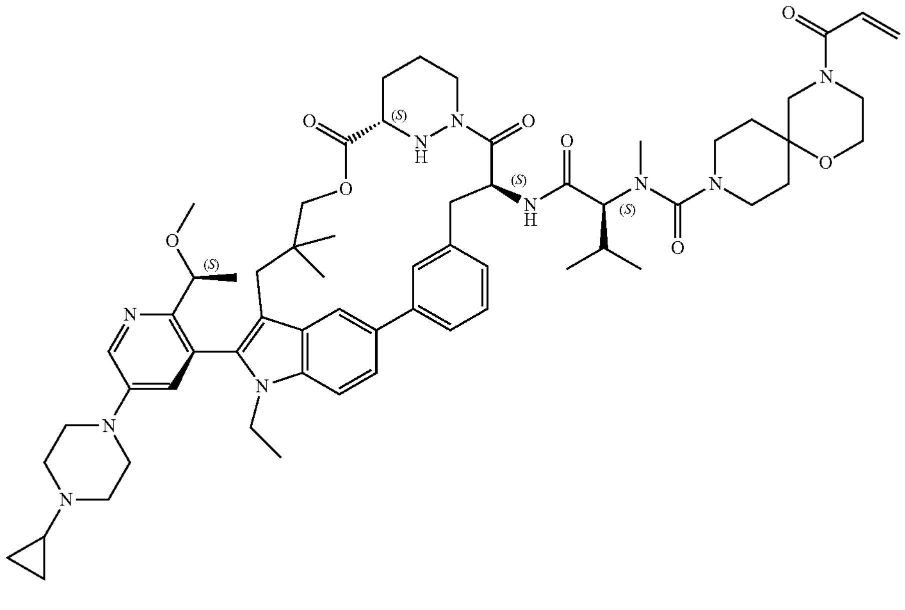 |

TABLE 1-continued
| Certain Compounds of the Present Invention | |
|---|---|
| Ex# | Structure |
| A63 | 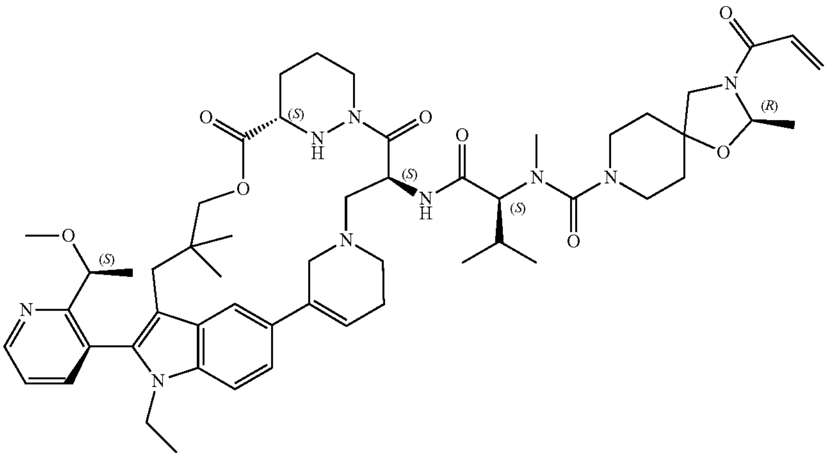 |
| A64 | 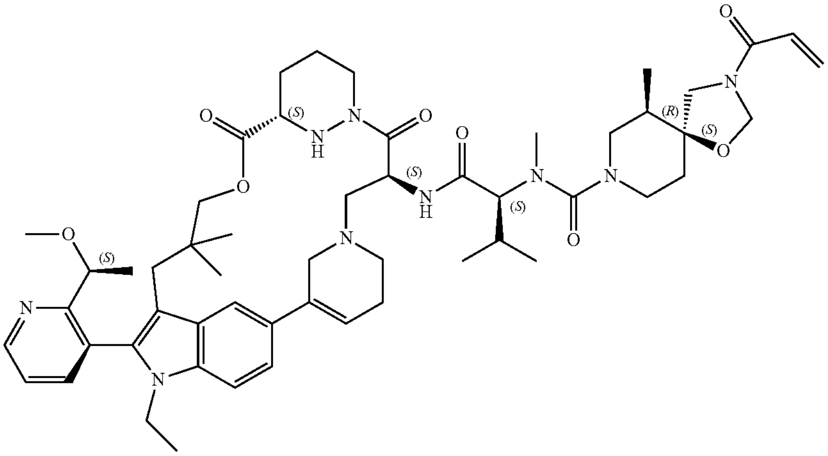 |
| A65 | 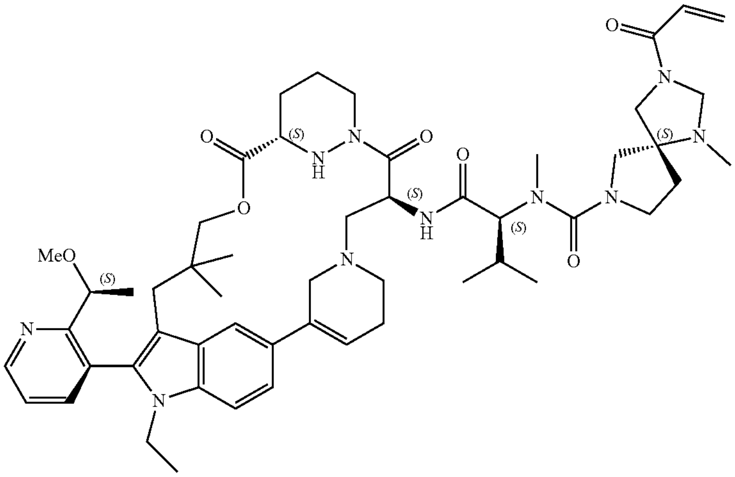 |

TABLE 1-continued
| Certain Compounds of the Present Invention | |
|---|---|
| Ex# | Structure |
| A66 | 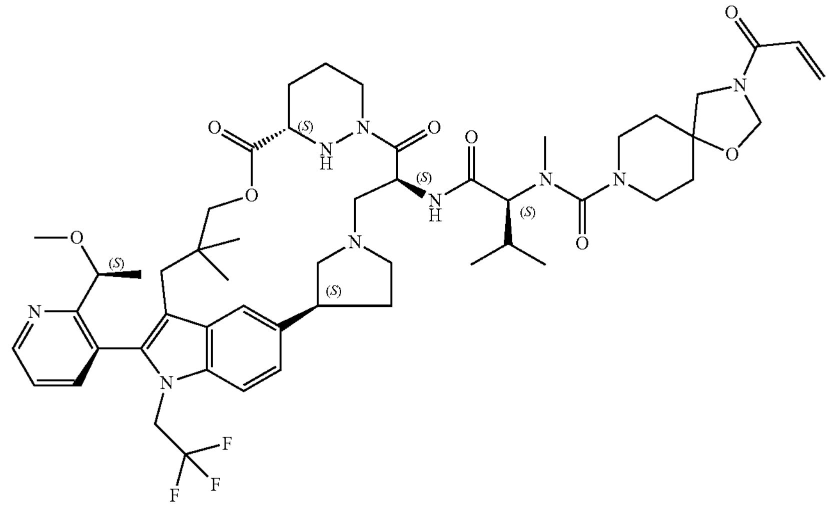 |
| A67 | 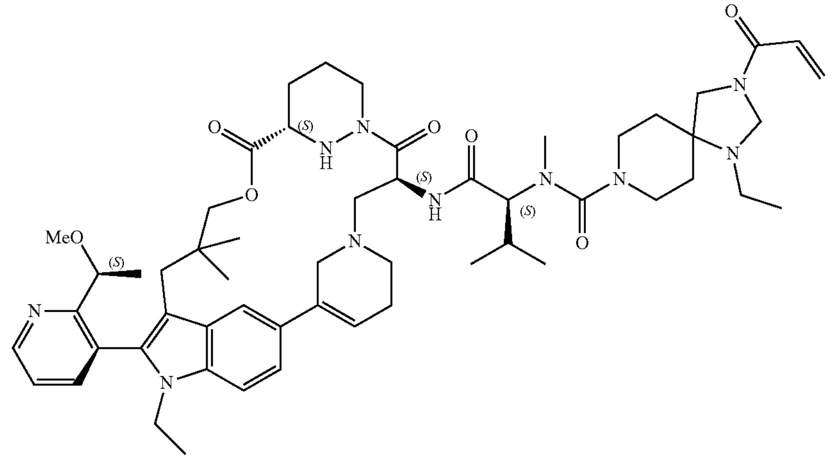 |
| A68 | 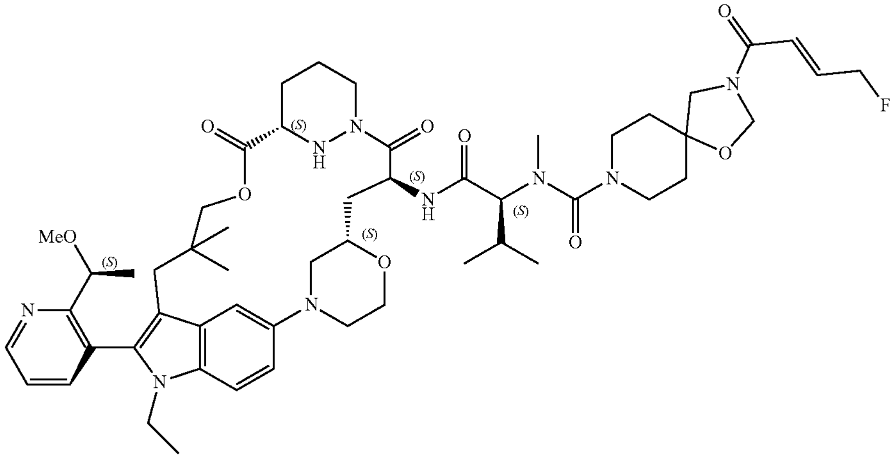 |

TABLE 1-continued
| Certain Compounds of the Present Invention | |
|---|---|
| Ex# | Structure |
| A69 | 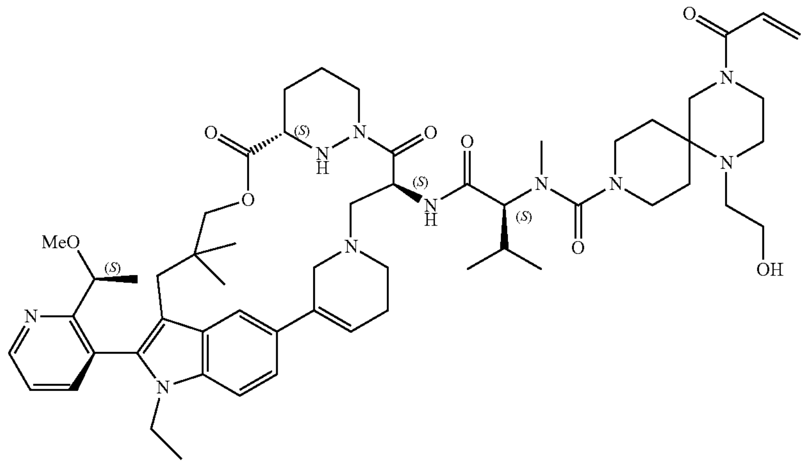 |
| A70 | 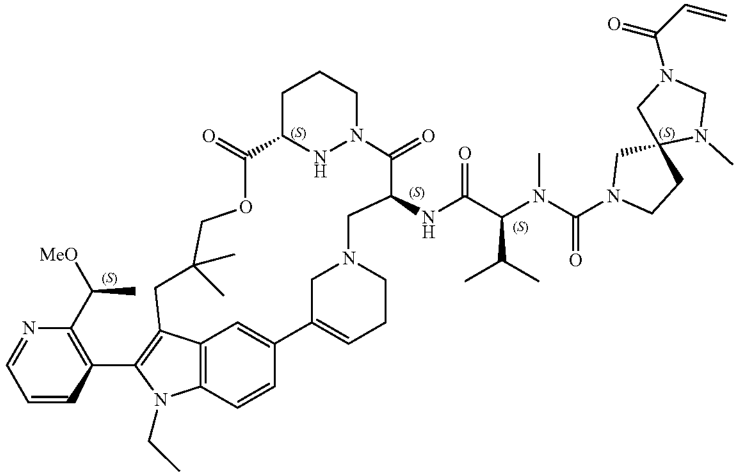 |
| A71 | 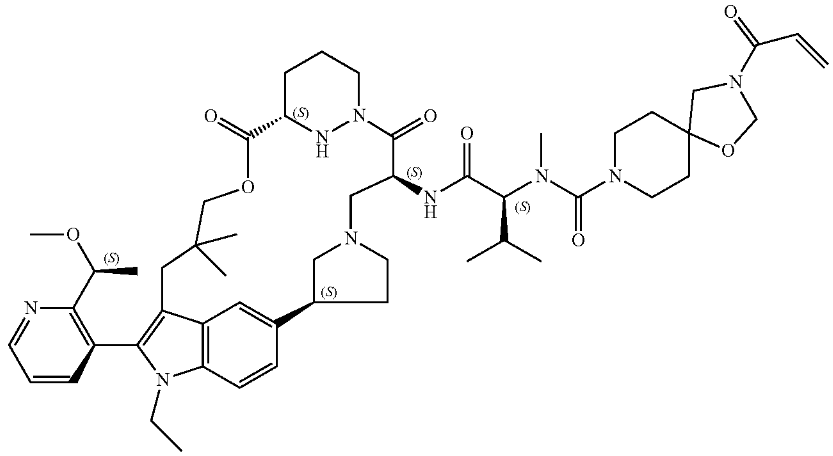 |

TABLE 1-continued
Certain Compounds of the Present Invention
| Ex# | Structure |
| --- | --- |
| A72 | 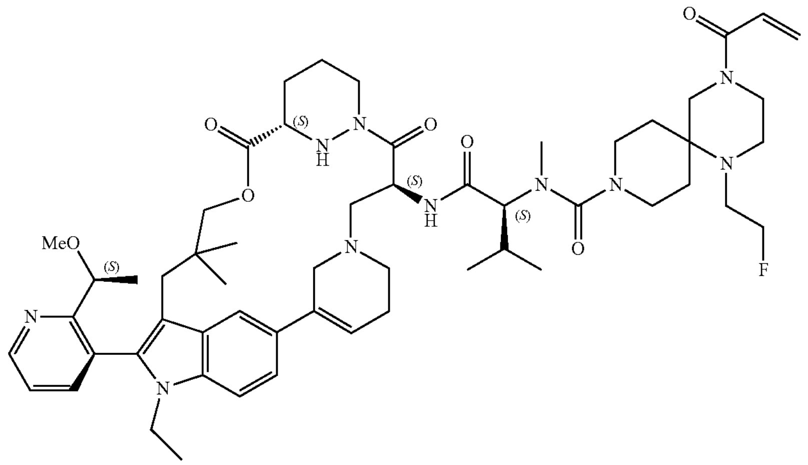 |
| A73 | 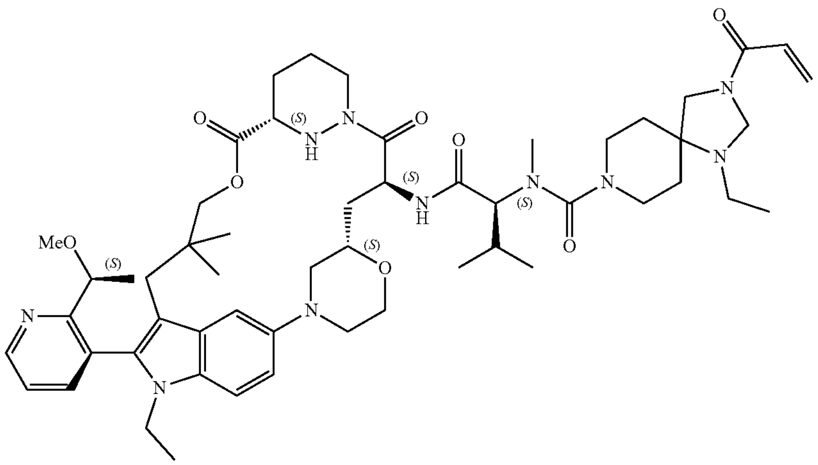 |
| A74 | 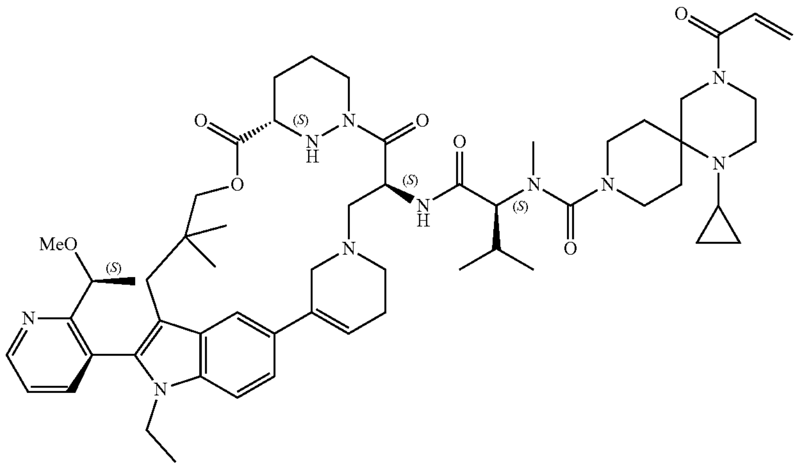 |

TABLE 1-continued
| Certain Compounds of the Present Invention | |
|---|---|
| Ex# | Structure |
| A75 | 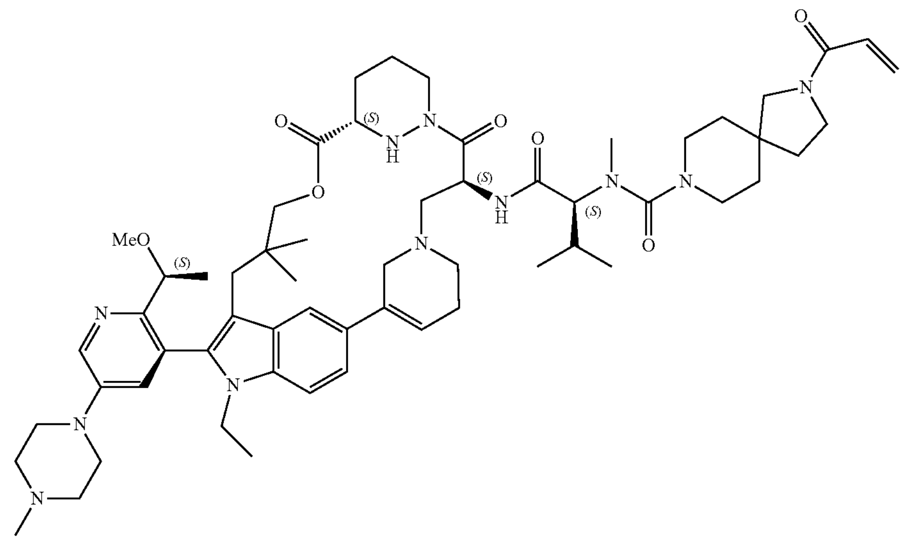 |
| A76 | 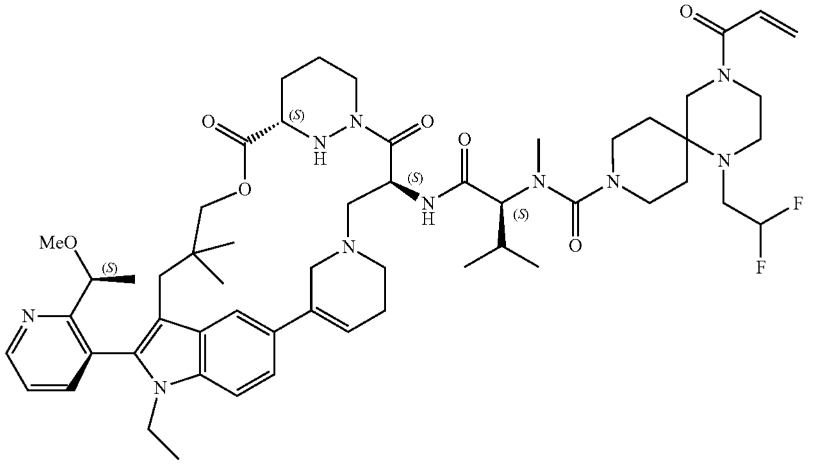 |
| A77 | 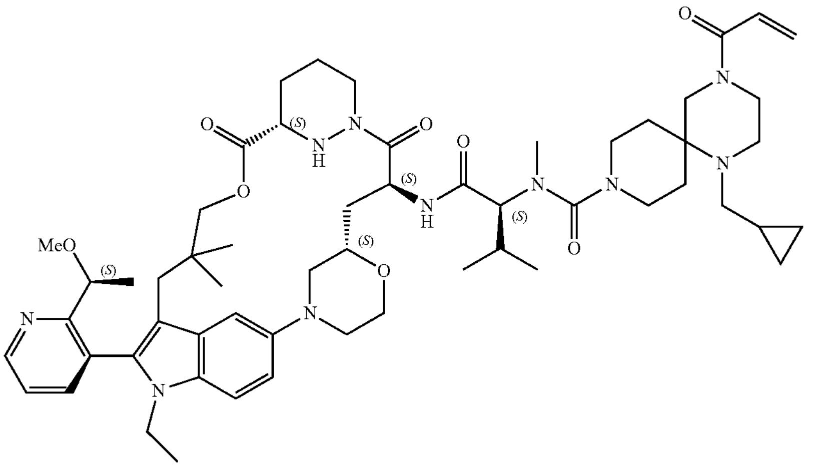 |

TABLE 1-continued
| Certain Compounds of the Present Invention | |
|---|---|
| Ex# | Structure |
| A78 | 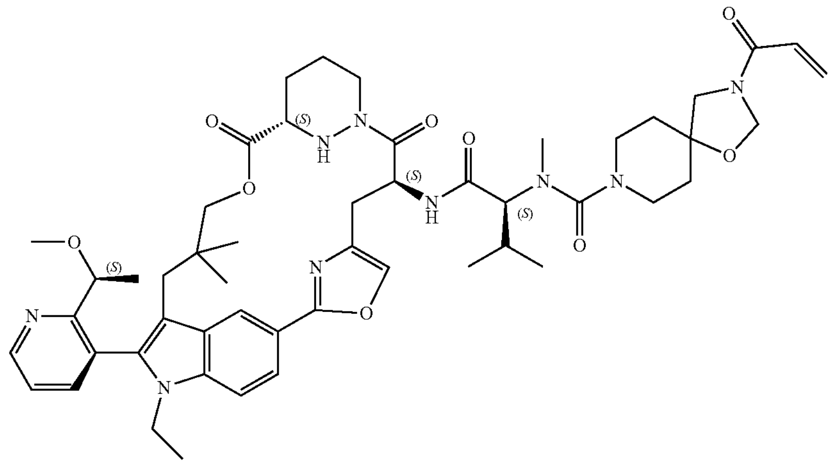 |
| A79 | 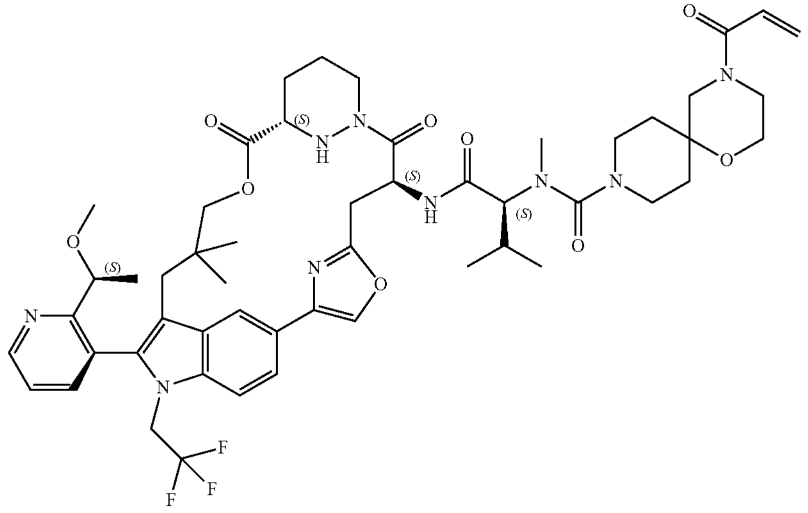 |
| A80 | 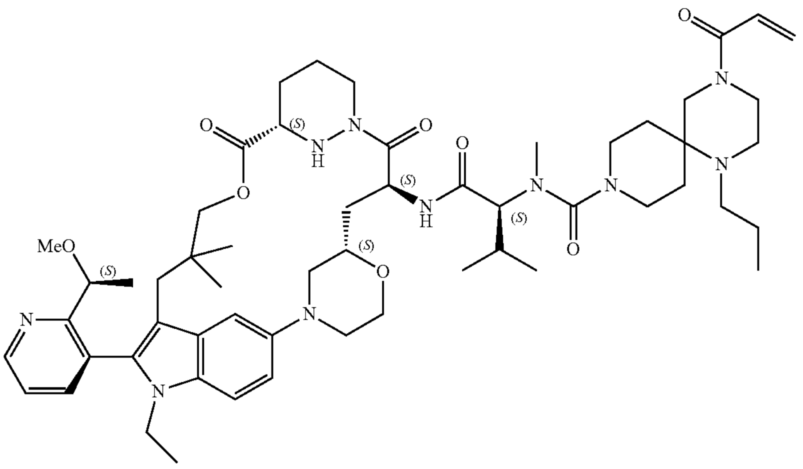 |

TABLE 1-continued
| Certain Compounds of the Present Invention | |
|---|---|
| Ex# | Structure |
| A81 | 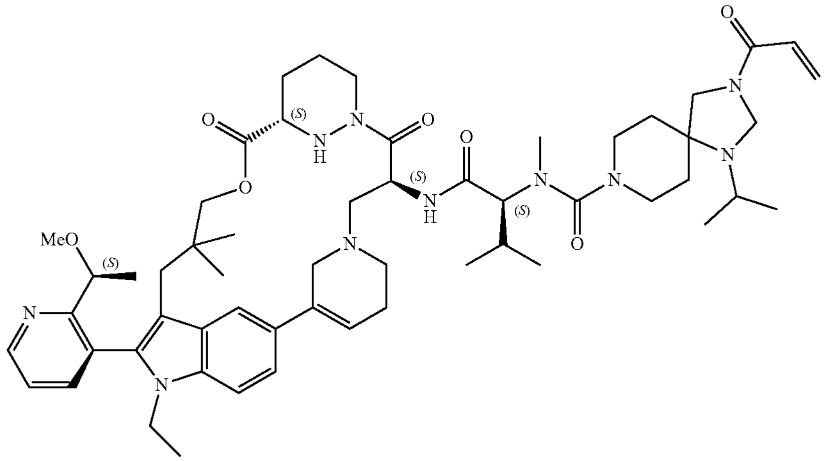 |
| A82 | 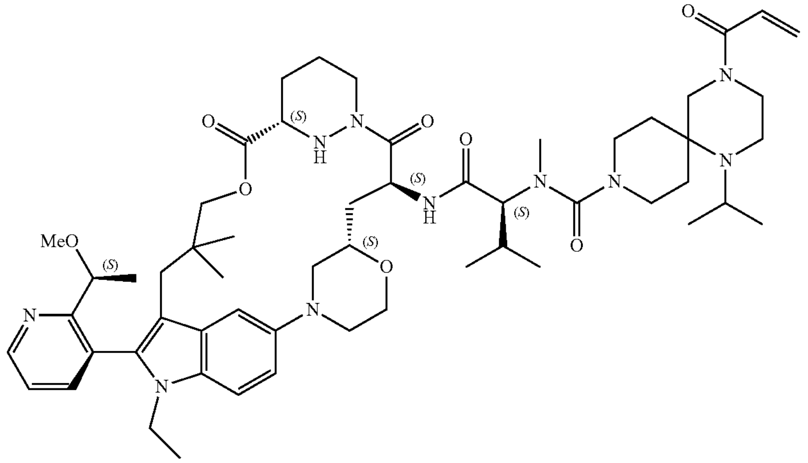 |
| A83 | 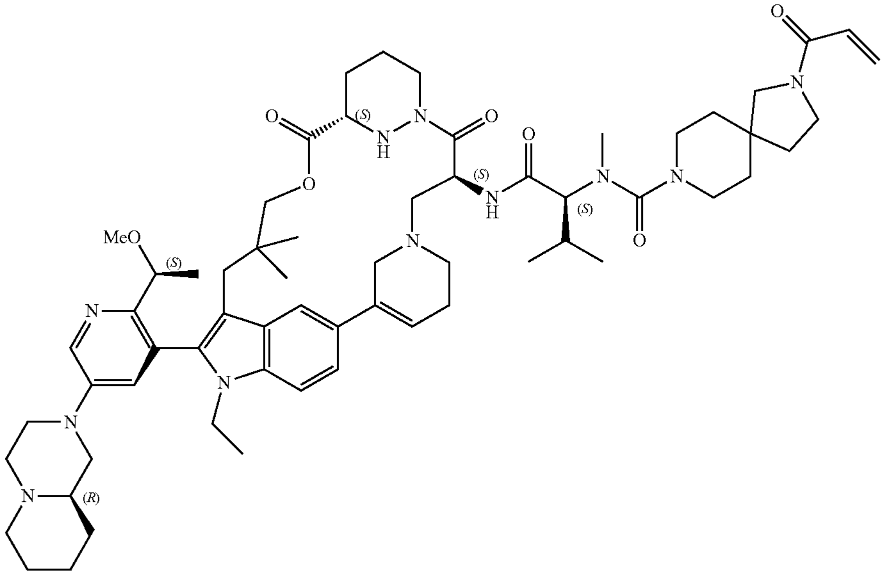 |

TABLE 1-continued
| Certain Compounds of the Present Invention | |
|---|---|
| Ex# | Structure |
| A84 | 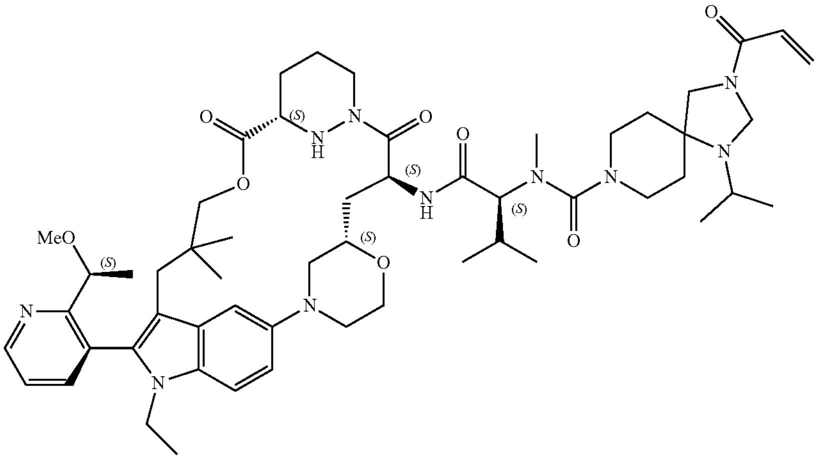 |
| A85 | 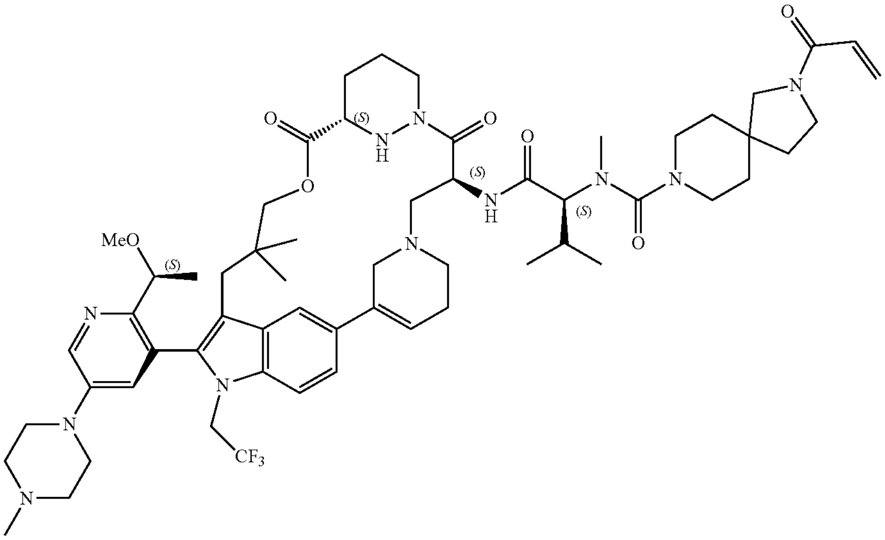 |
| A86 | 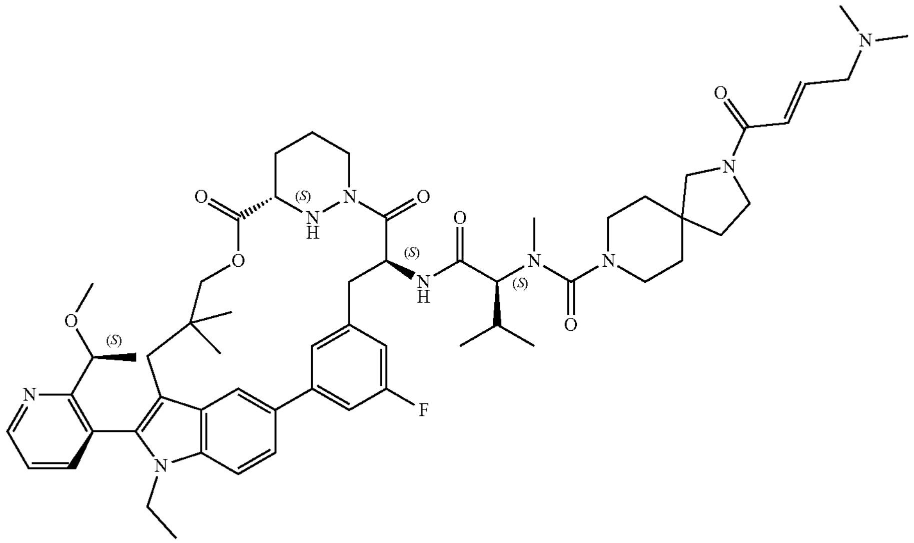 |

TABLE 1-continued
| Certain Compounds of the Present Invention | |
|---|---|
| Ex# | Structure |
| A87 | 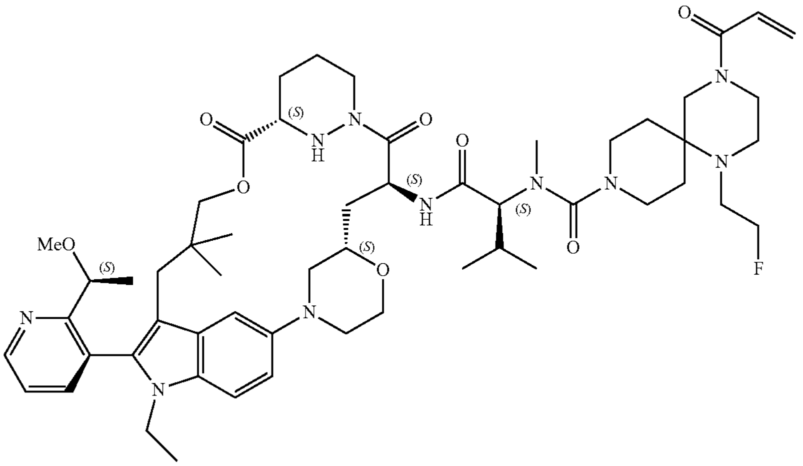 |
| A88 | 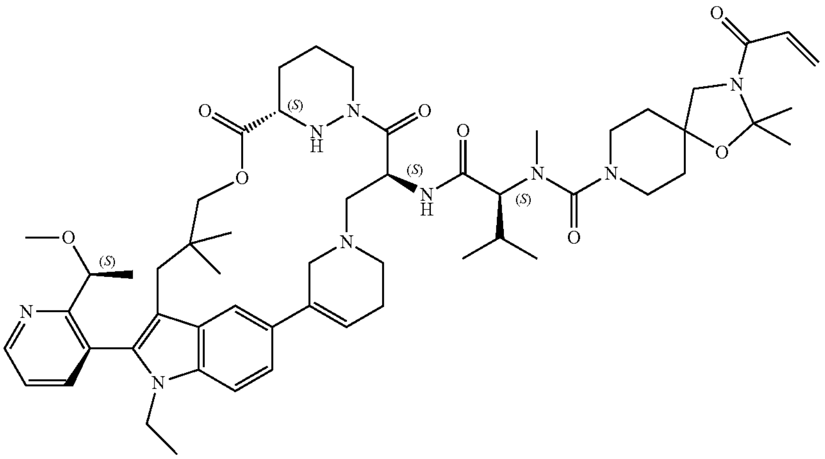 |
| A89 | 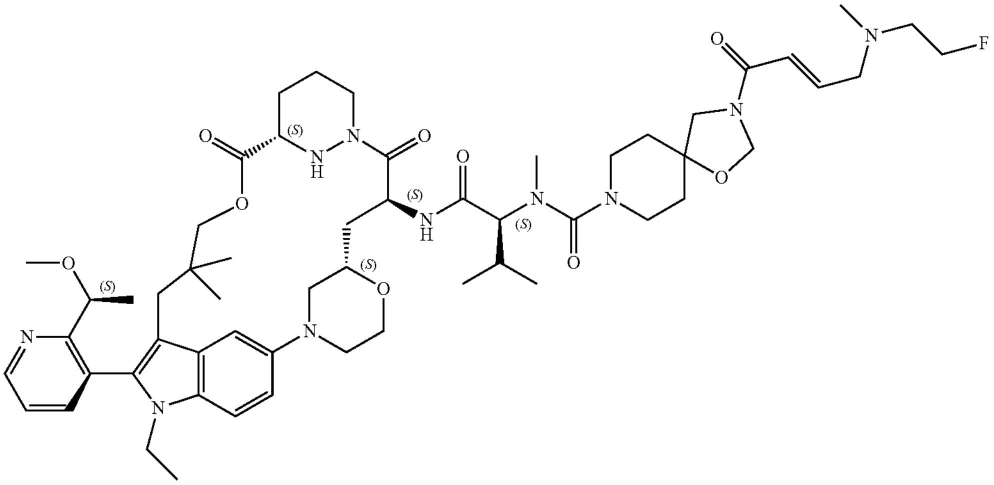 |

TABLE 1-continued
Certain Compounds of the Present Invention
| Ex# | Structure |
| --- | --- |
| A90 | 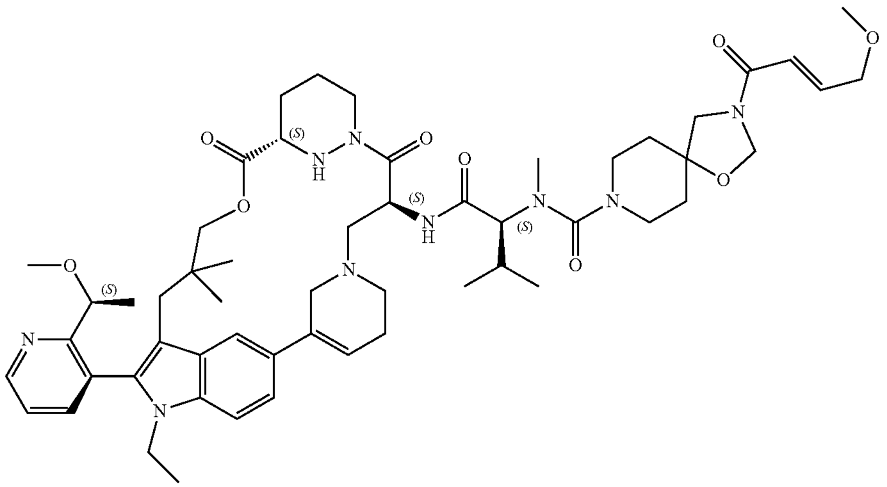 |
| A91 | 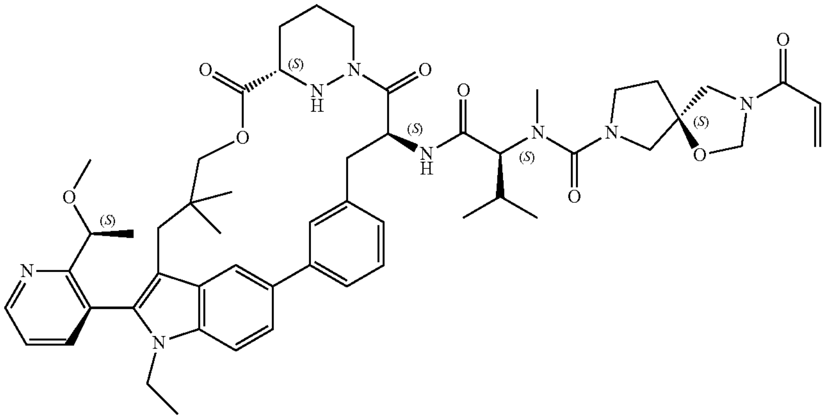 |
| A92 | 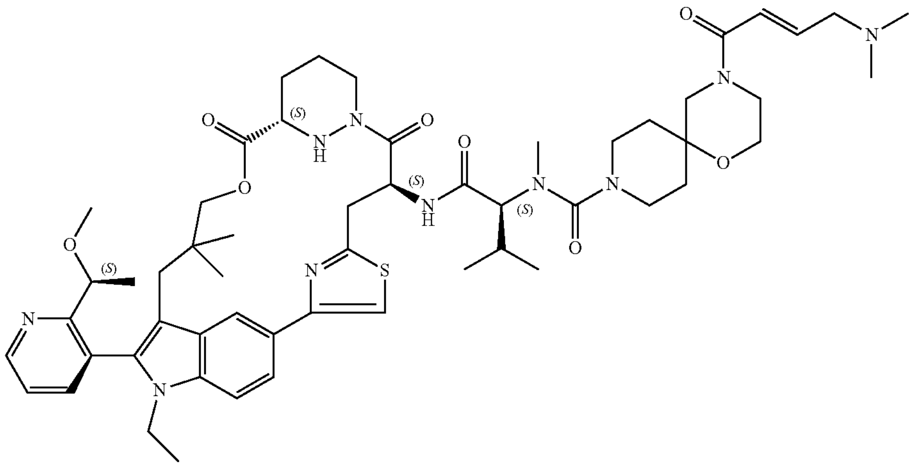 |

TABLE 1-continued
| Certain Compounds of the Present Invention | |
|---|---|
| Ex# | Structure |
| A93 | 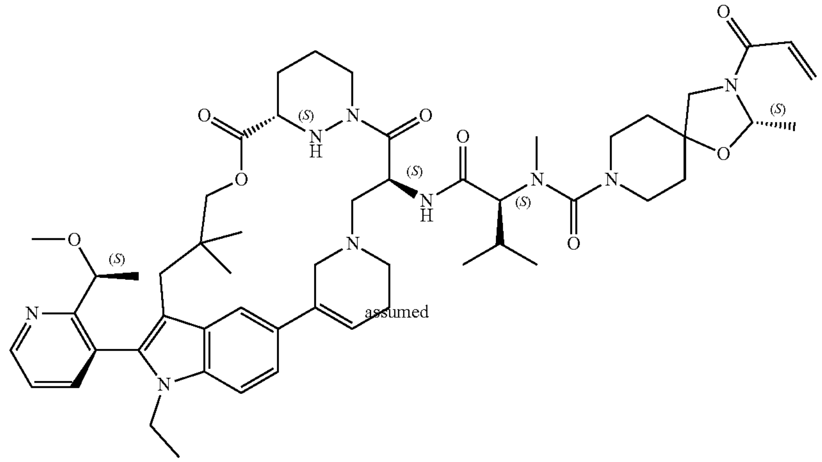 |
| A94 | 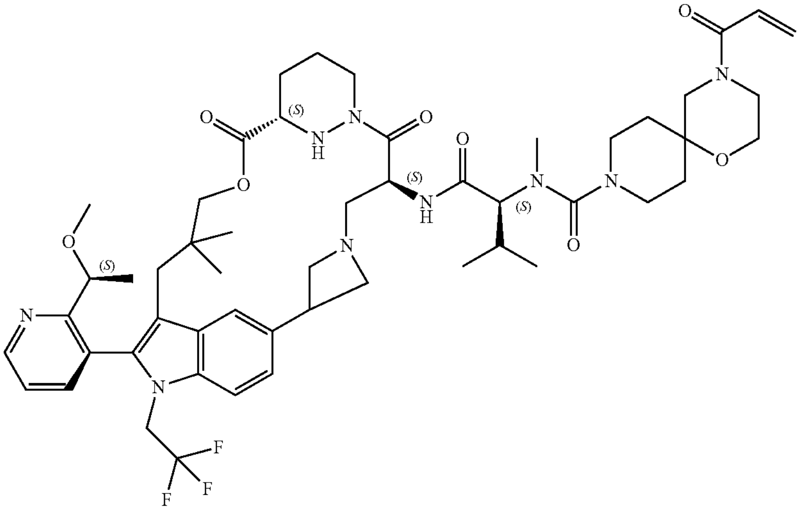 |
| A95 | 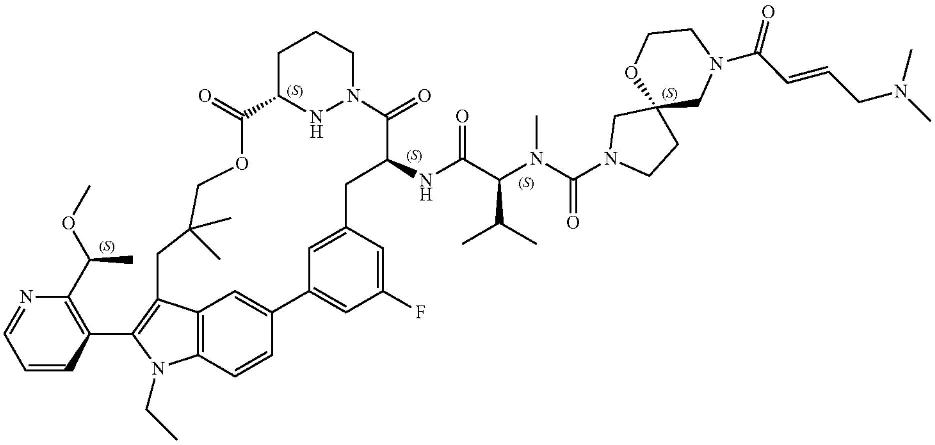 |

TABLE 1-continued
| Certain Compounds of the Present Invention | |
|---|---|
| Ex# | Structure |
| A96 | 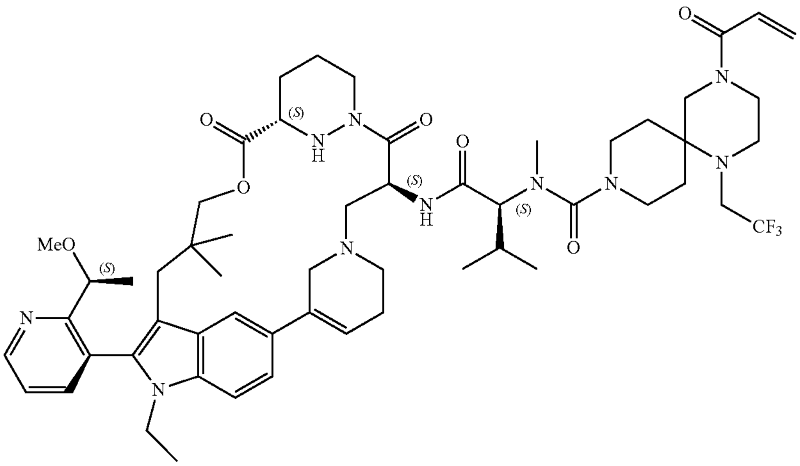 |
| A97 | 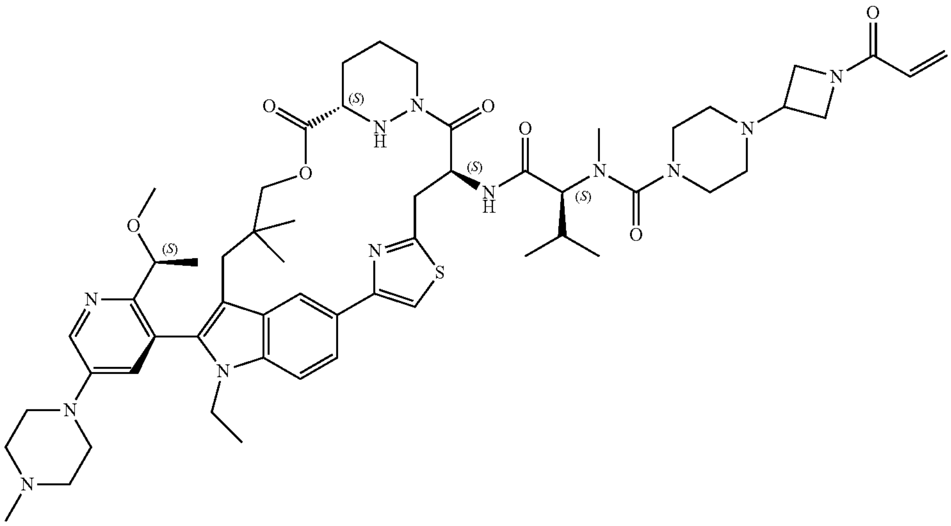 |
| A98 | 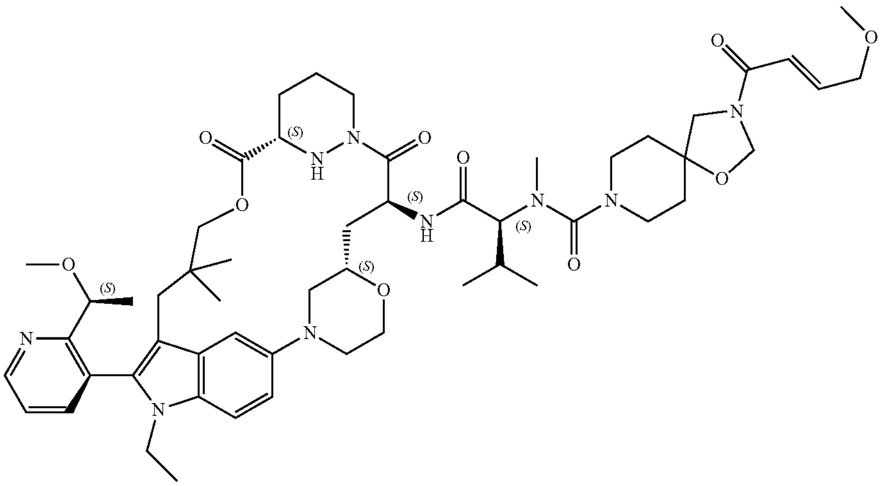 |

TABLE 1-continued
Certain Compounds of the Present Invention
| Ex# | Structure |
|---|---|
| A99 | 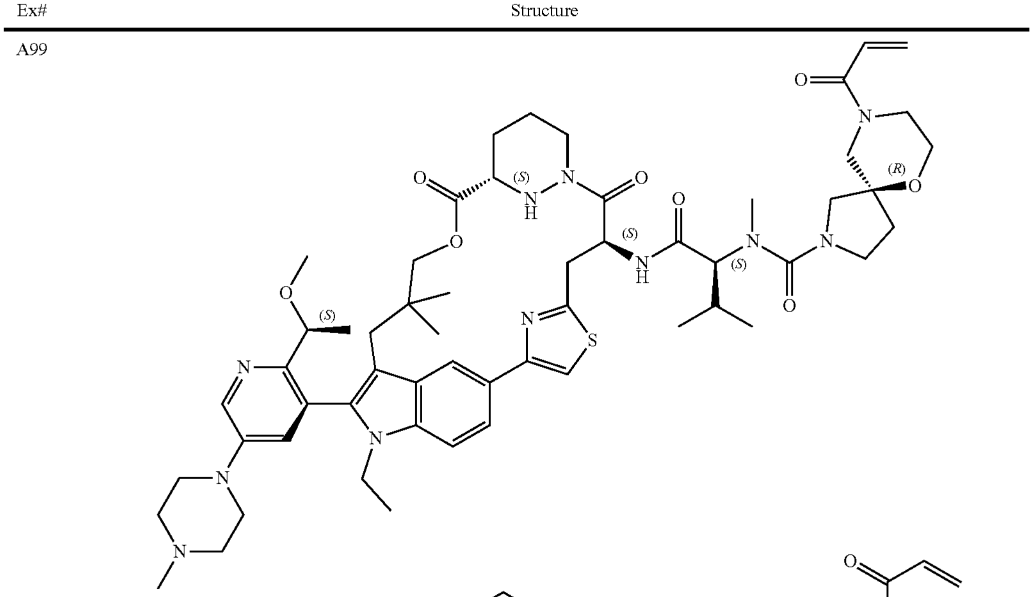 |
| A100 | 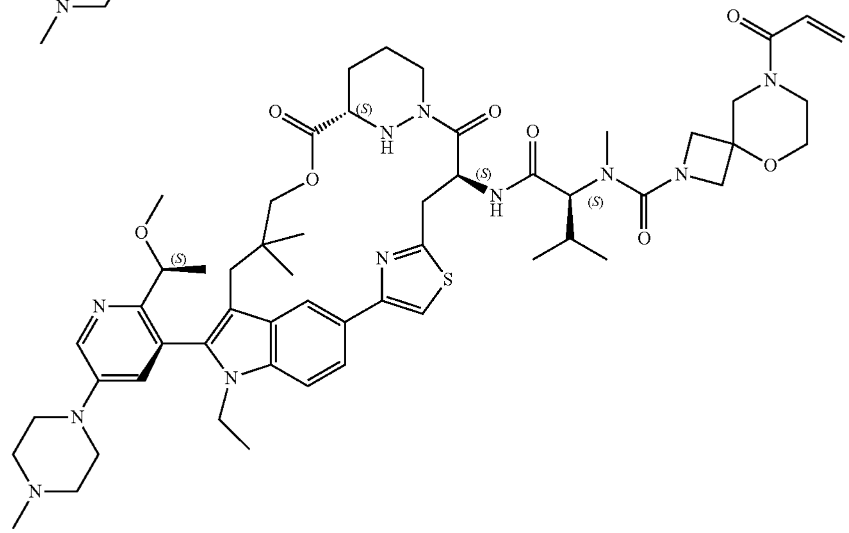 |
| A101 | 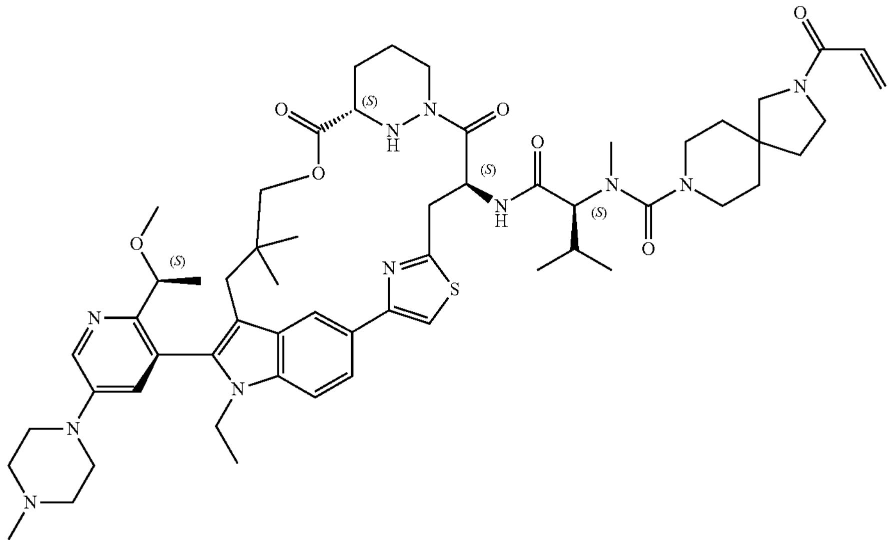 |

TABLE 1-continued
| Certain Compounds of the Present Invention | |
|---|---|
| Ex# | Structure |
| A102 | 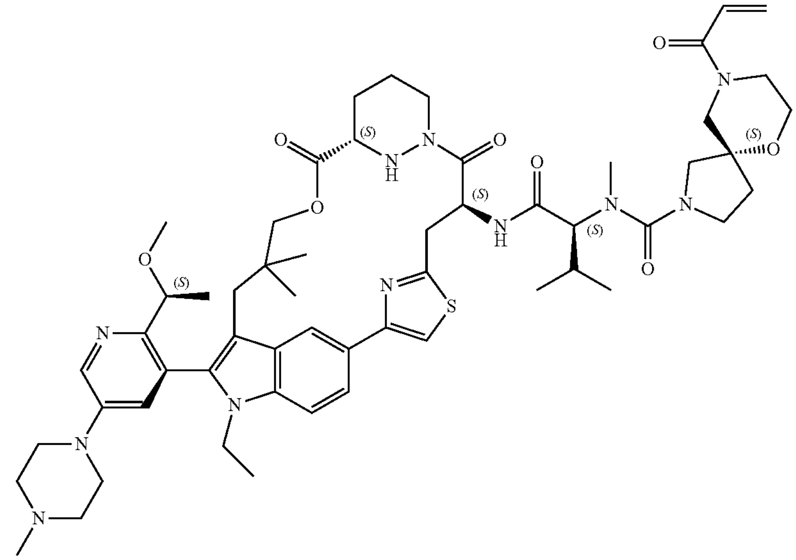 |
| A103 | 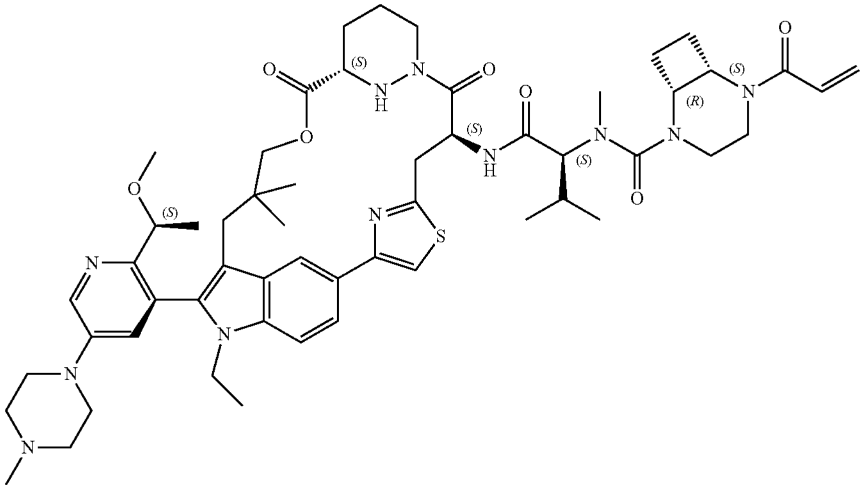 |
| A104 | 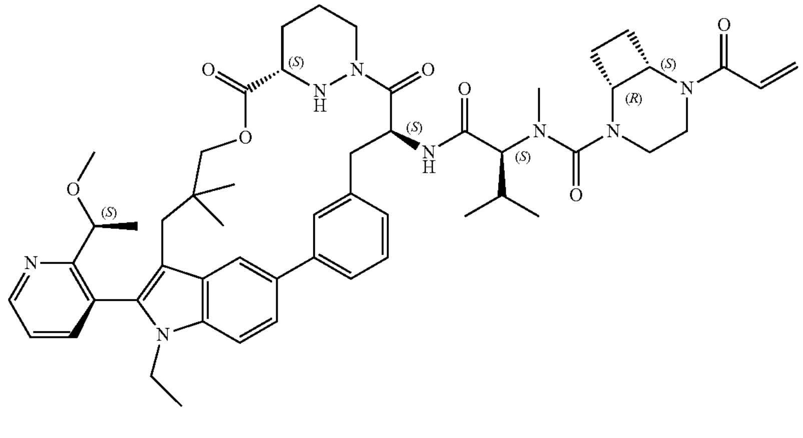 |

TABLE 1-continued
| Certain Compounds of the Present Invention | |
|---|---|
| Ex# | Structure |
| A105 | 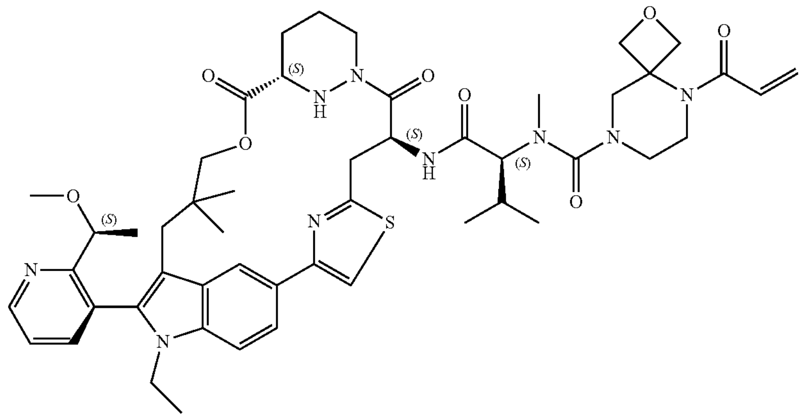 |
| A105 | 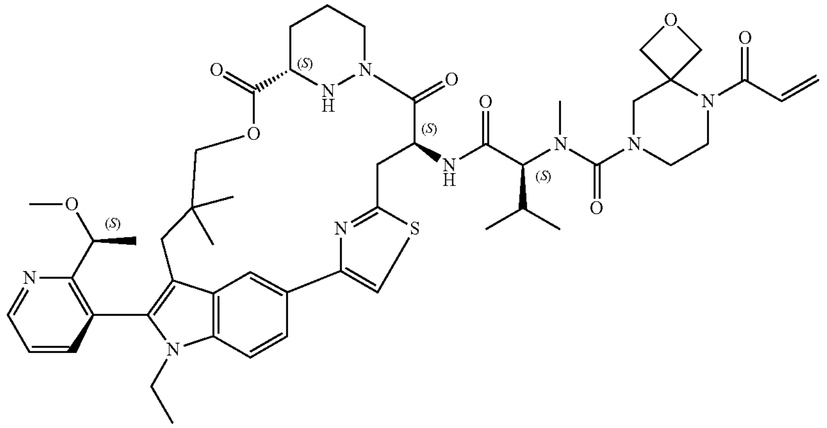 |
| A106 | 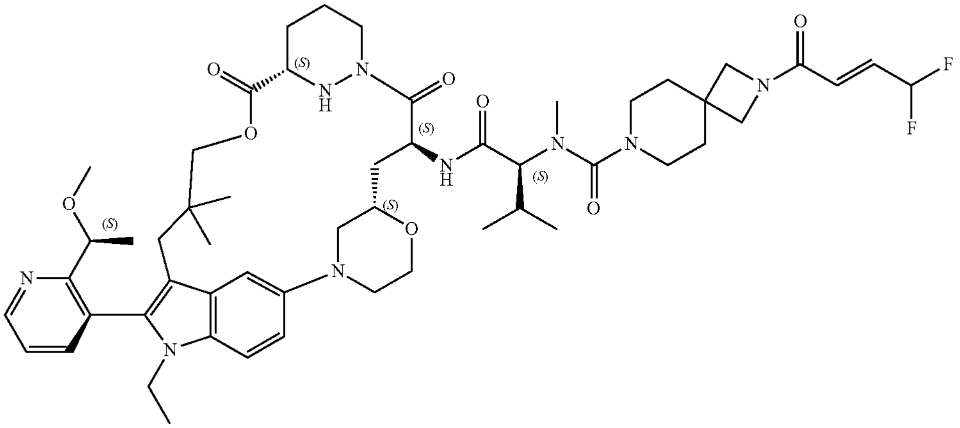 |

TABLE 1-continued
| Certain Compounds of the Present Invention | |
|---|---|
| Ex# | Structure |
| A107 | 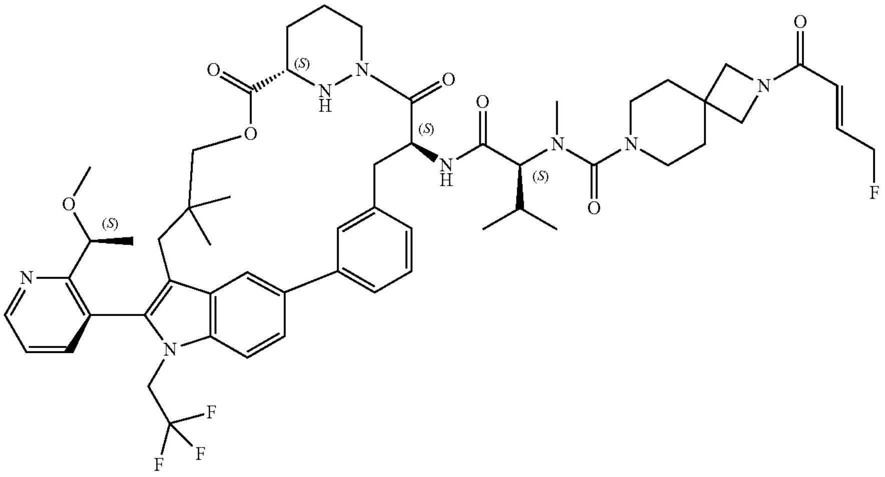 |
| A108 | 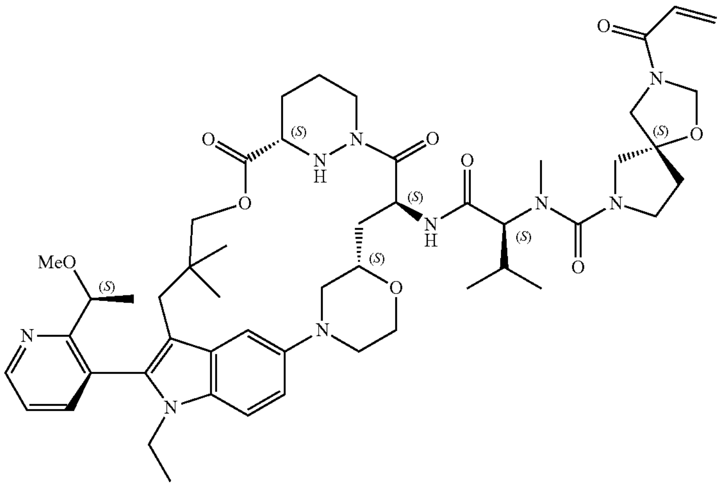 |
| A109 | 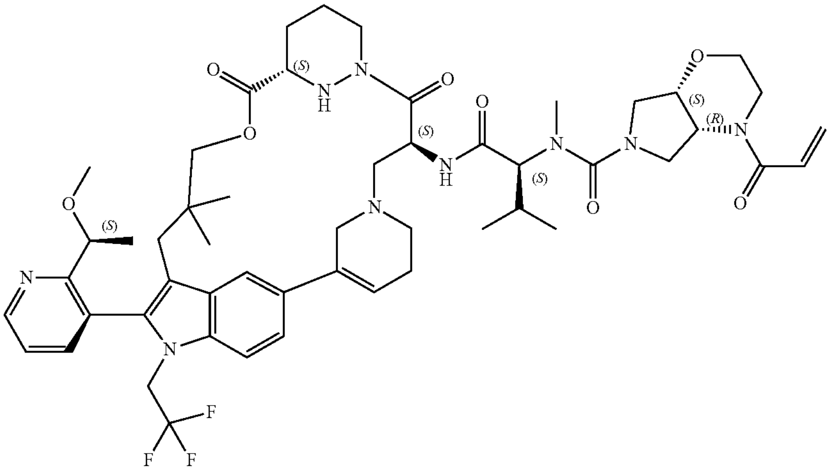 |

TABLE 1-continued
| Certain Compounds of the Present Invention | |
|---|---|
| Ex# | Structure |
| A110 | 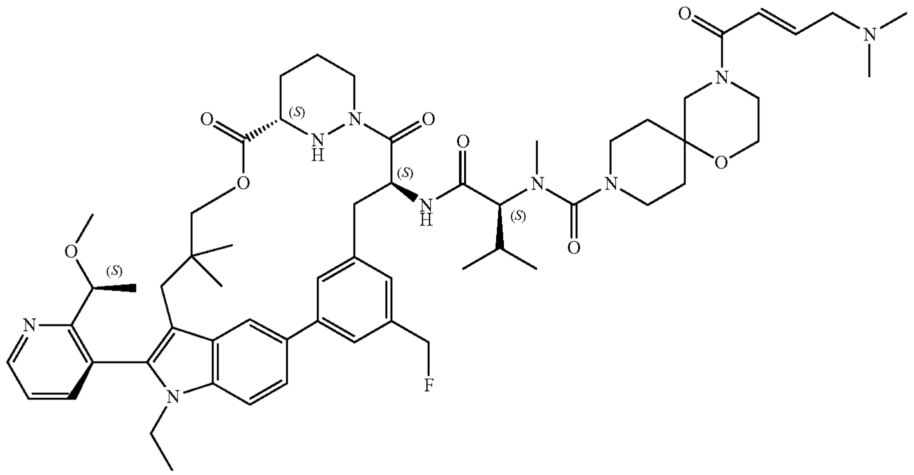 |
| A111 | 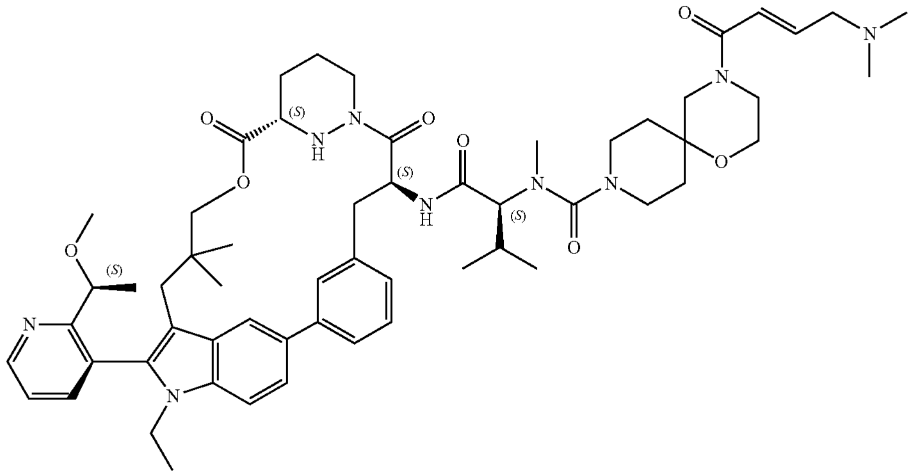 |
| A112 | 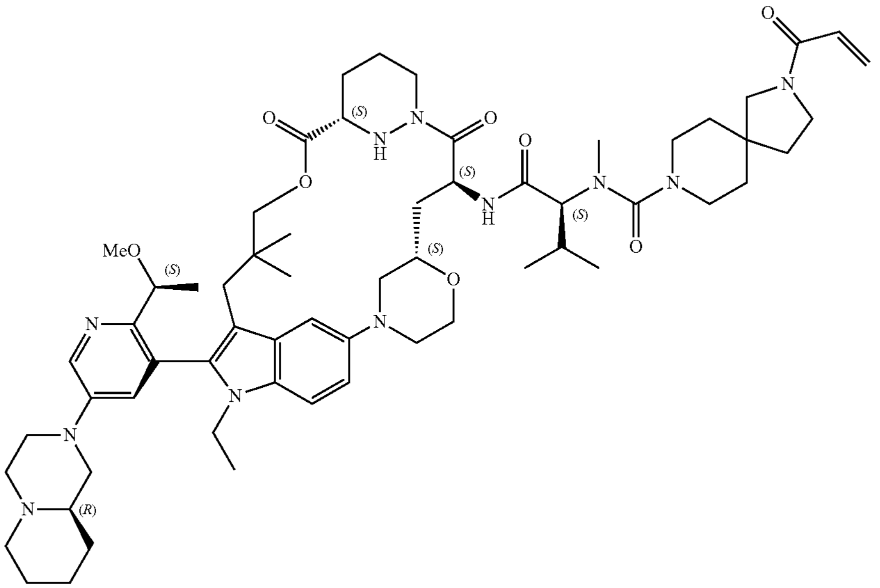 |

TABLE 1-continued
| Certain Compounds of the Present Invention | |
|---|---|
| Ex# | Structure |
| A113 | 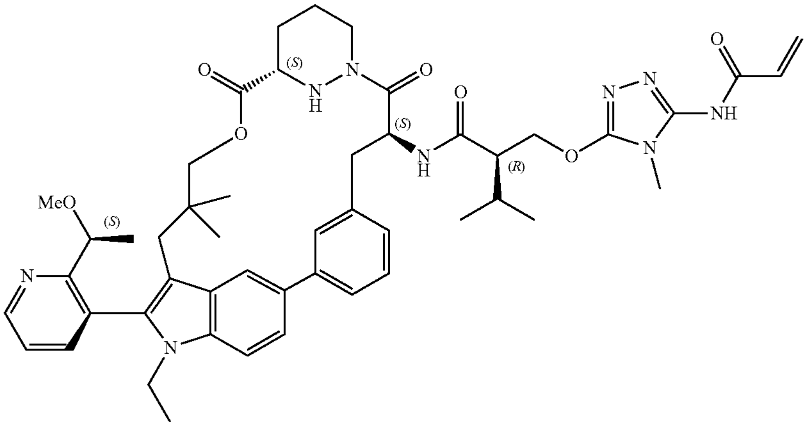 |
| A114 | 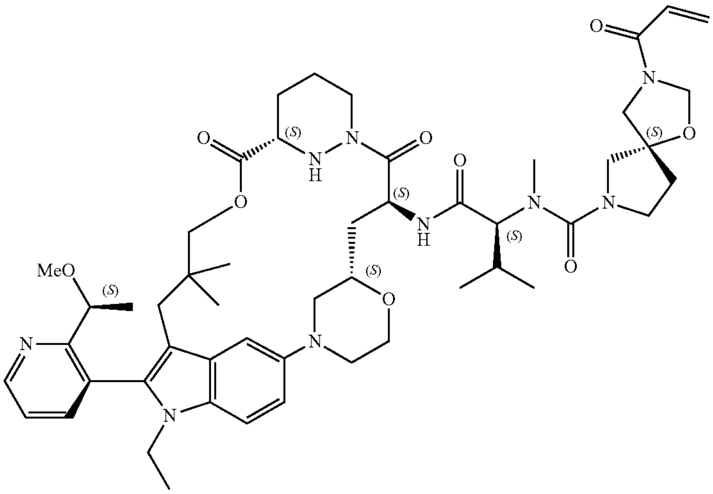 |
| A115 | 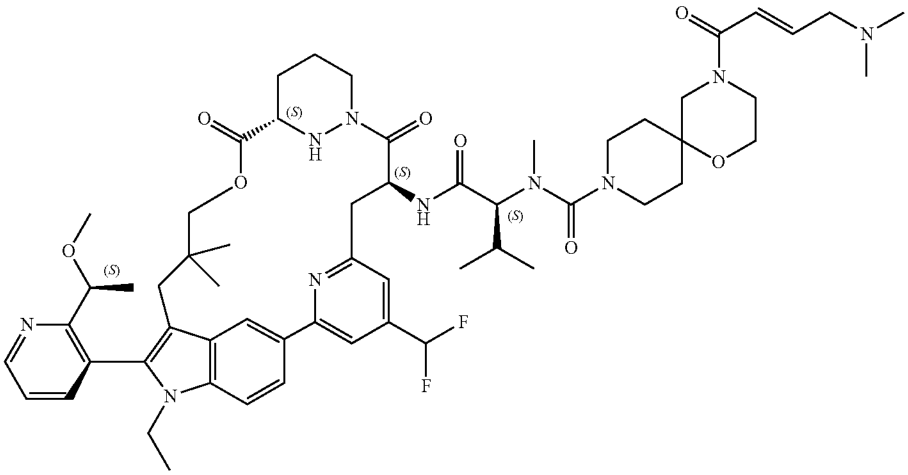 |

TABLE 1-continued
| Certain Compounds of the Present Invention | |
|---|---|
| Ex# | Structure |
| A116 | 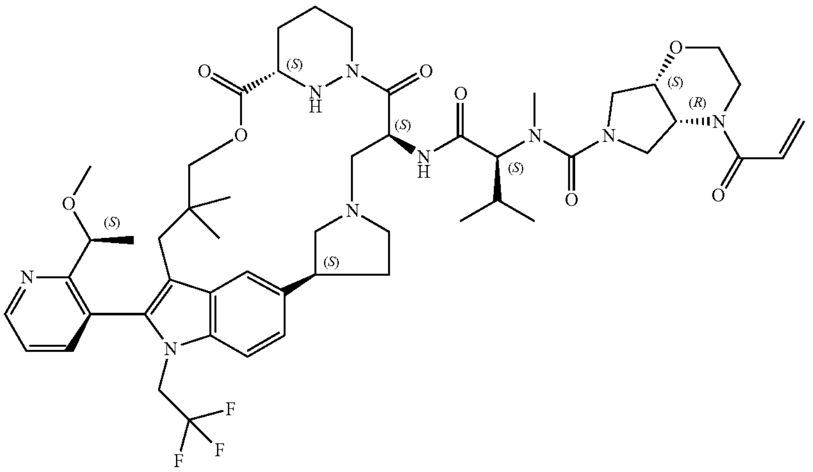 |
| A117 | 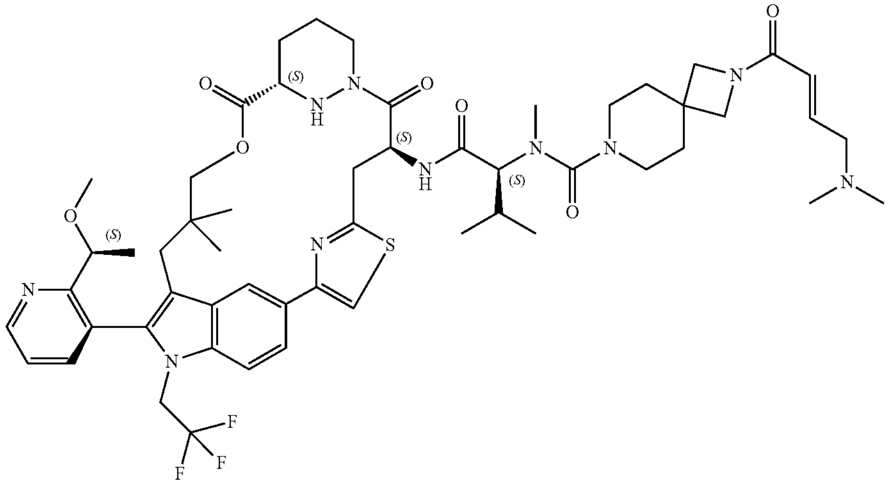 |
| A118 | 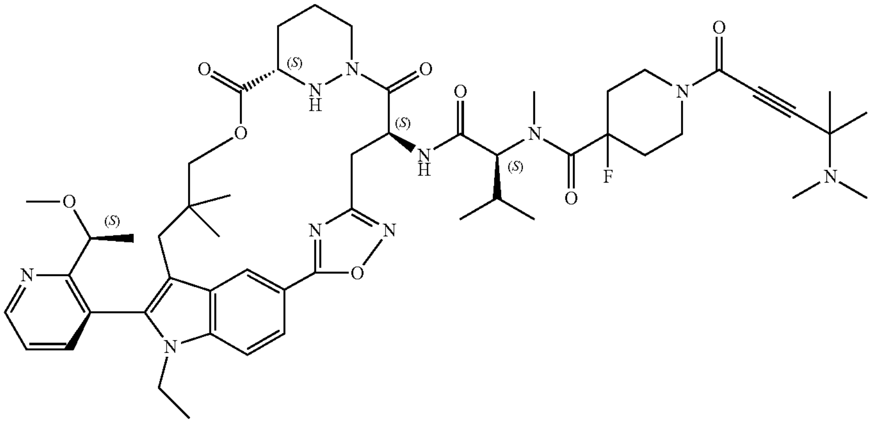 |

TABLE 1-continued
| Certain Compounds of the Present Invention | |
|---|---|
| Ex# | Structure |
| A119 | 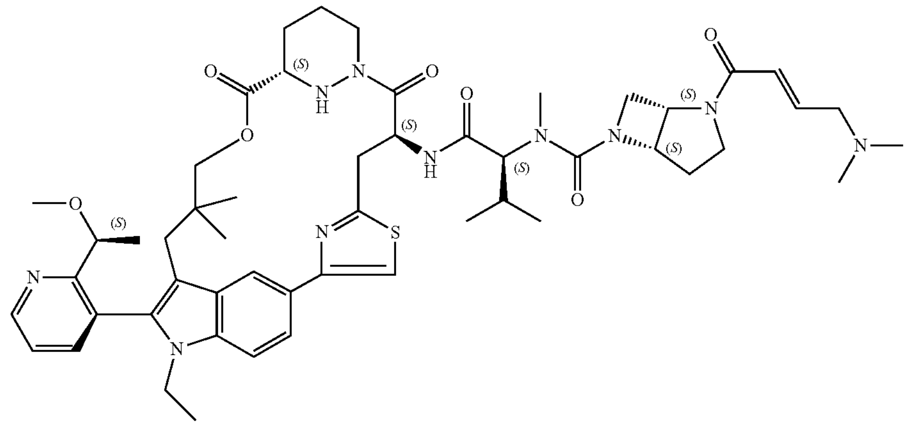 |
| A120 | 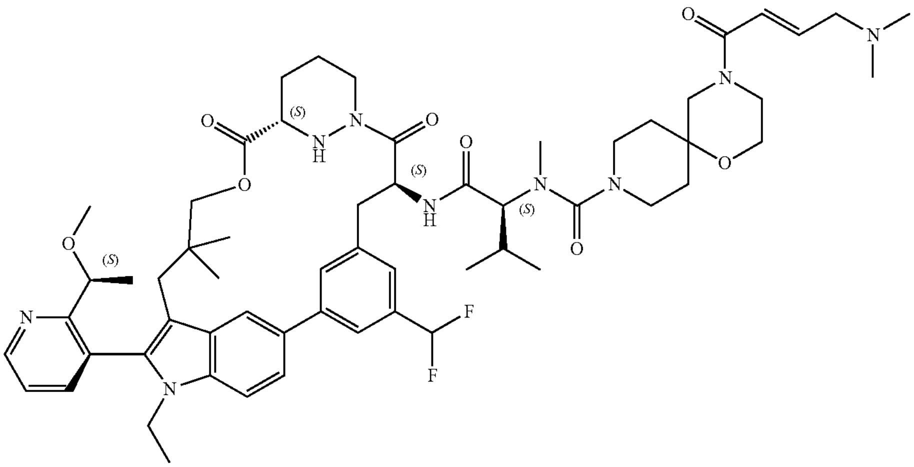 |
| A121 | 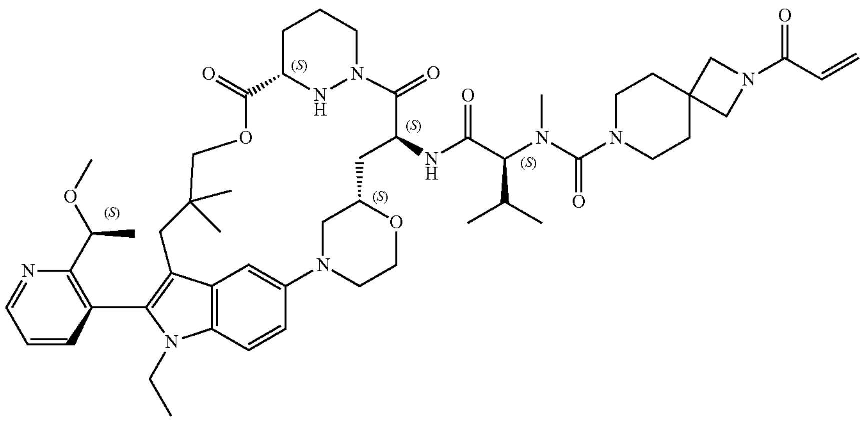 |

TABLE 1-continued
| Certain Compounds of the Present Invention | |
|---|---|
| Ex# | Structure |
| A122 | 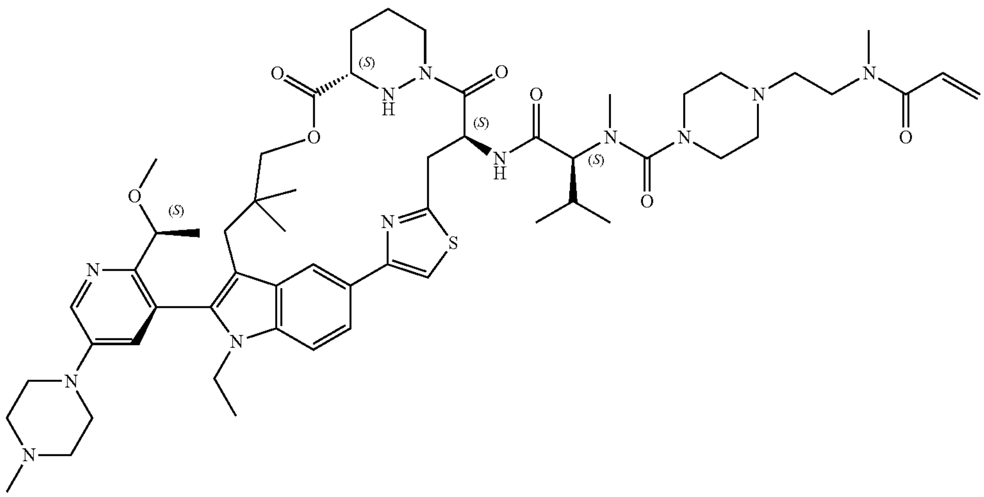 |
| A123 | 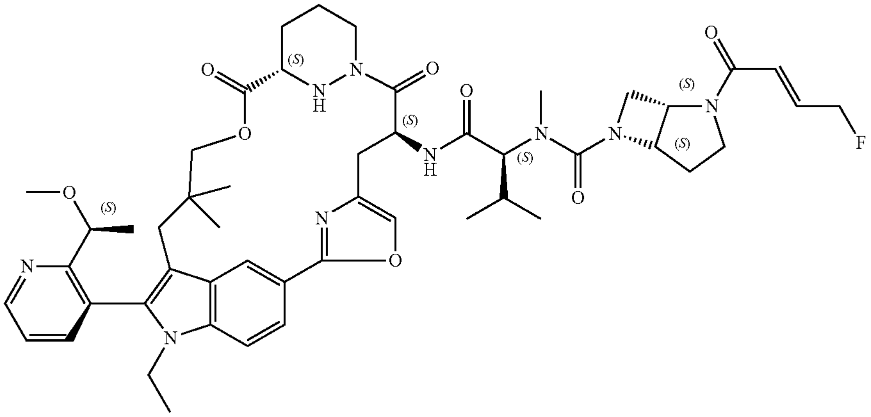 |
| A124 | 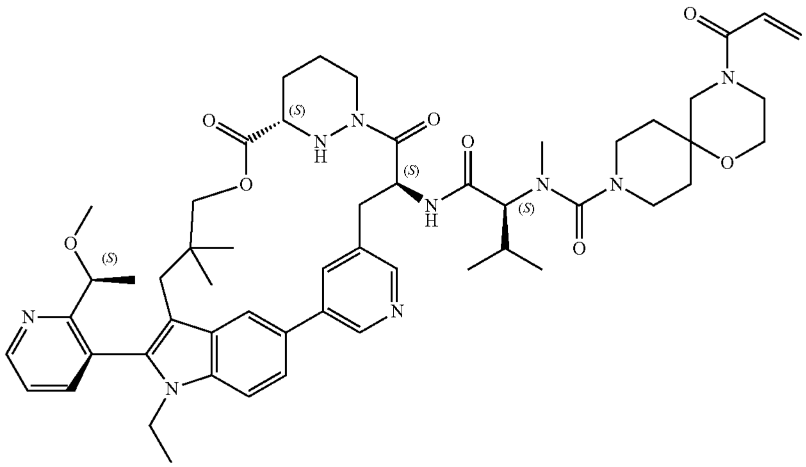 |

TABLE 1-continued
| Certain Compounds of the Present Invention | |
|---|---|
| Ex# | Structure |
| A125 | 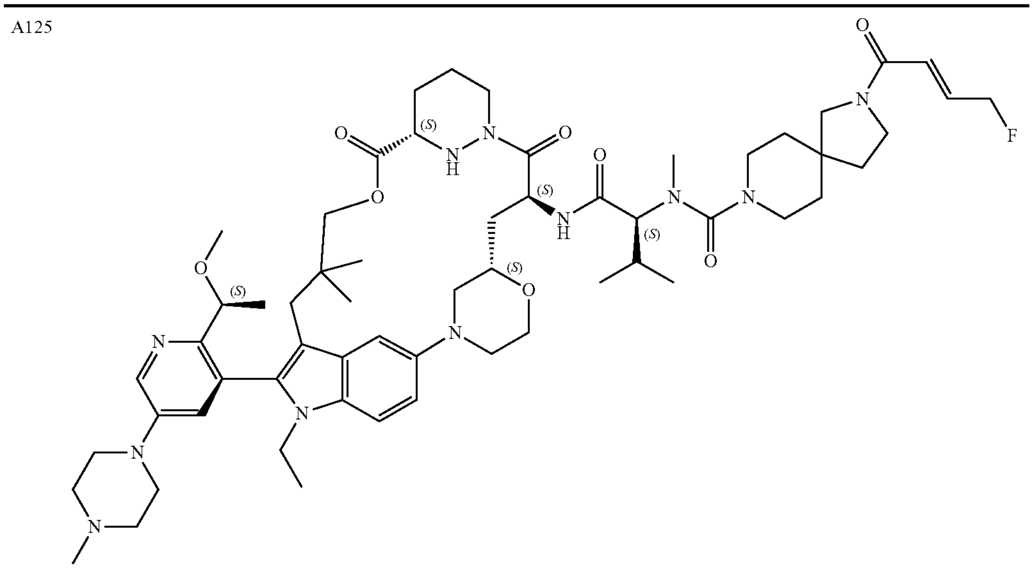 |
| A126 | 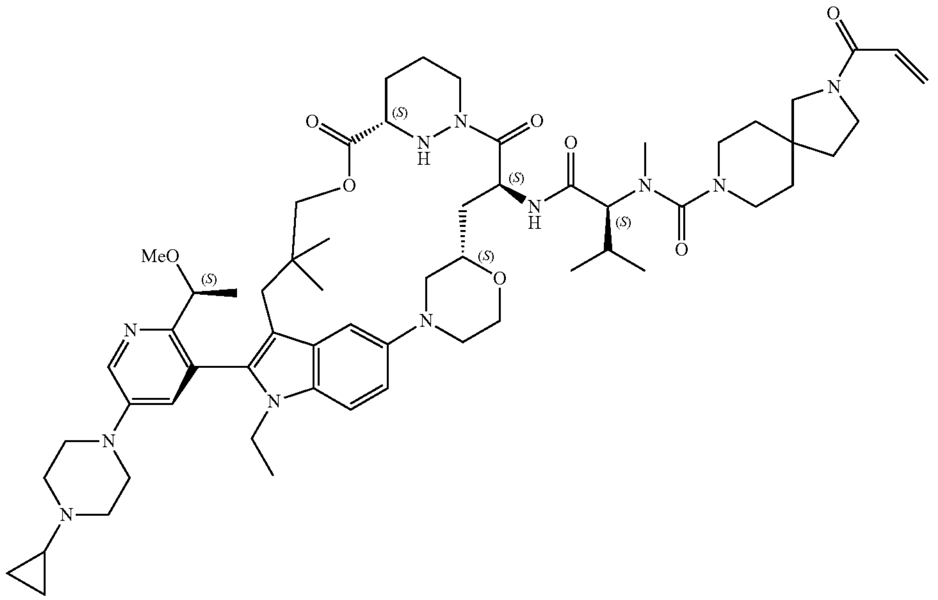 |
| A127 | 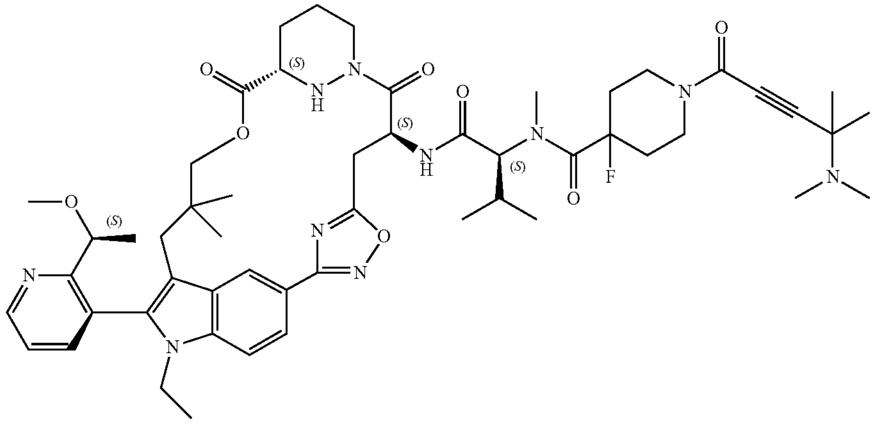 |

TABLE 1-continued
| Certain Compounds of the Present Invention | |
|---|---|
| Ex# | Structure |
| A128 | 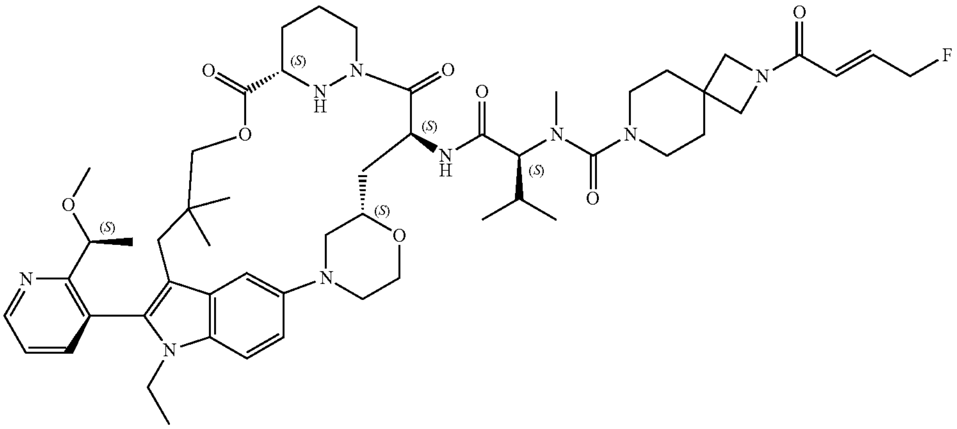 |
| A129 | 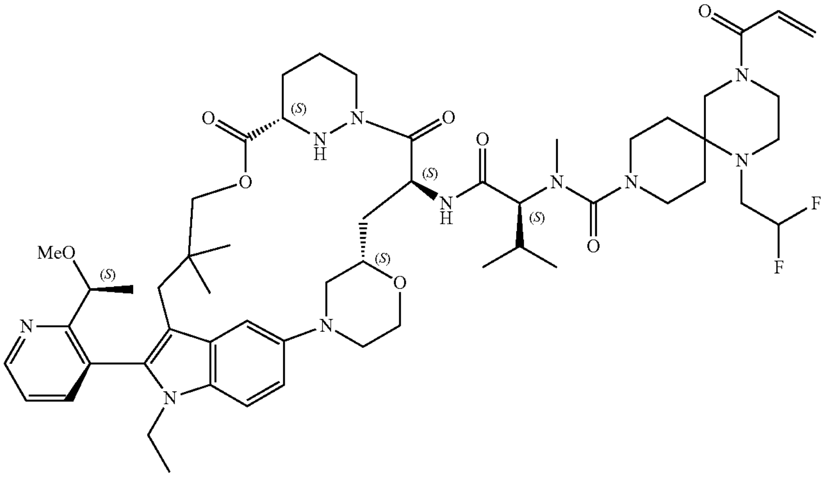 |
| A130 | 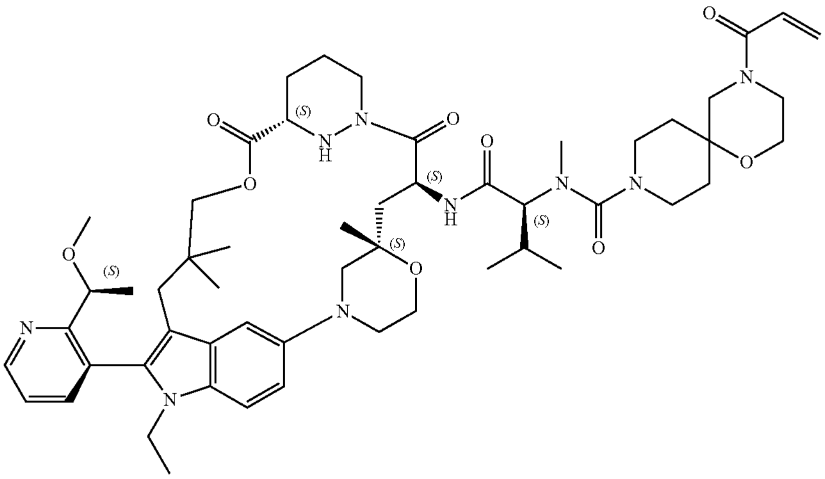 |

TABLE 1-continued
| Certain Compounds of the Present Invention | |
|---|---|
| Ex# | Structure |
| A131 | 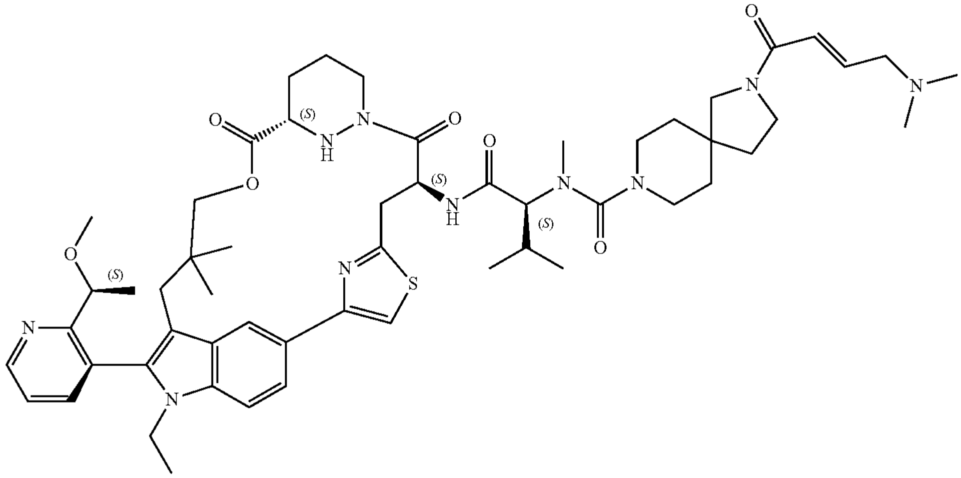 |
| A132 | 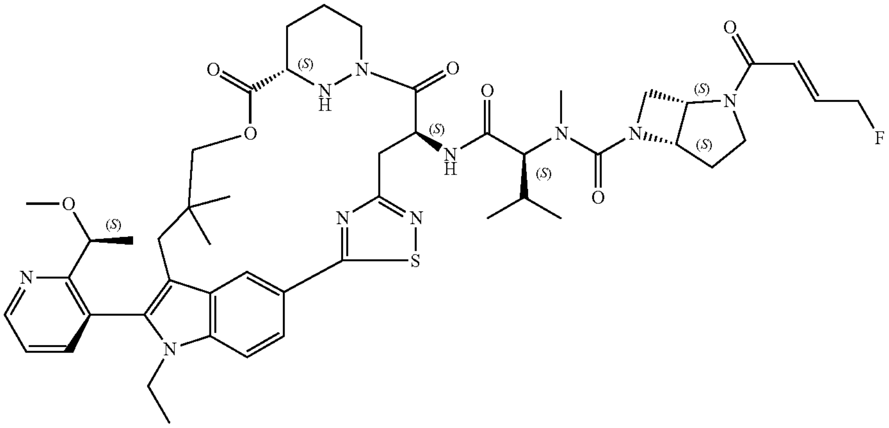 |
| A133 | 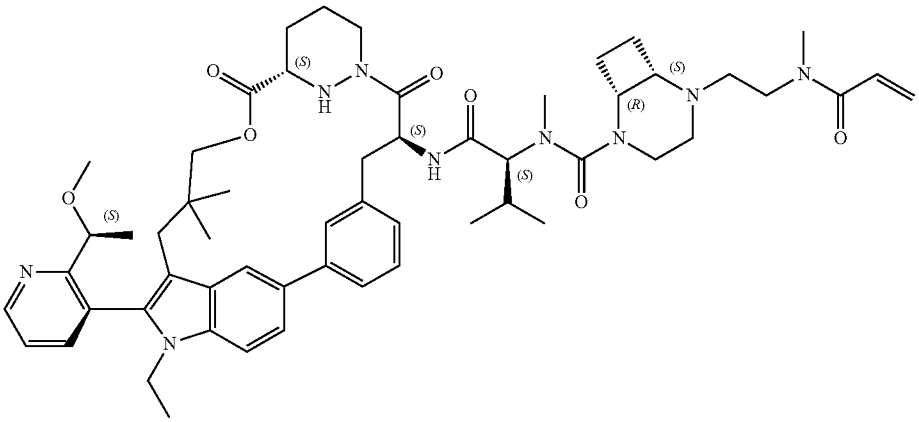 |

TABLE 1-continued
| Certain Compounds of the Present Invention | |
|---|---|
| Ex# | Structure |
| A134 | 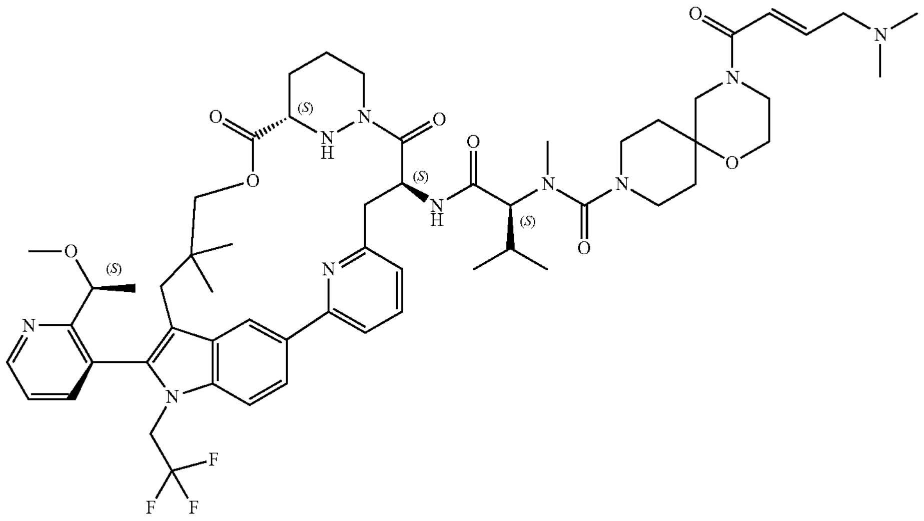 |
| A135 | 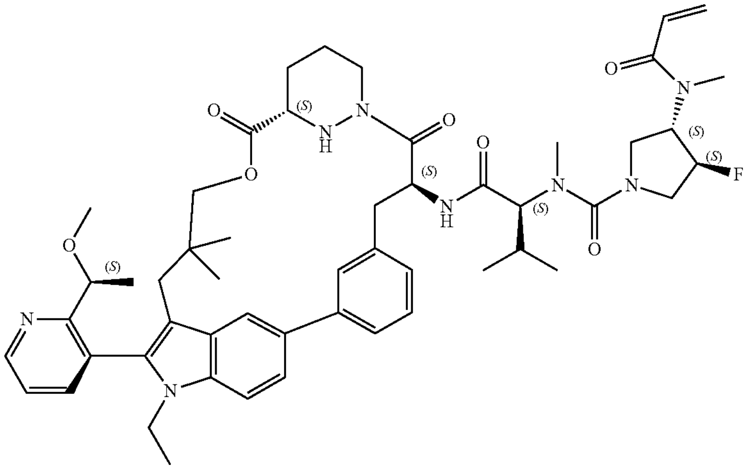 |
| A136 | 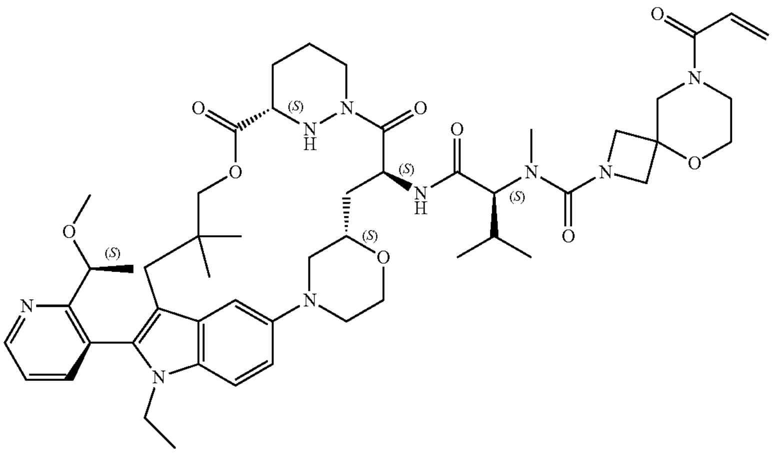 |

TABLE 1-continued
| Certain Compounds of the Present Invention | |
|---|---|
| Ex# | Structure |
| A137 | 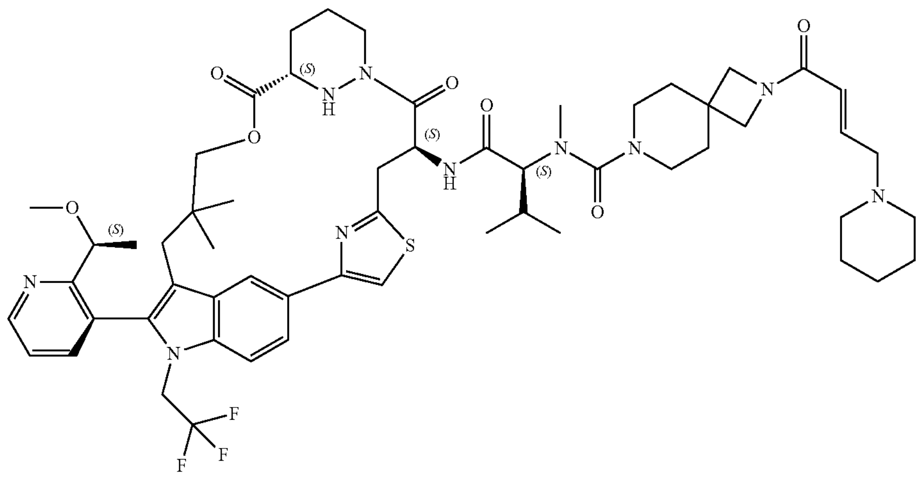 |
| A138 | 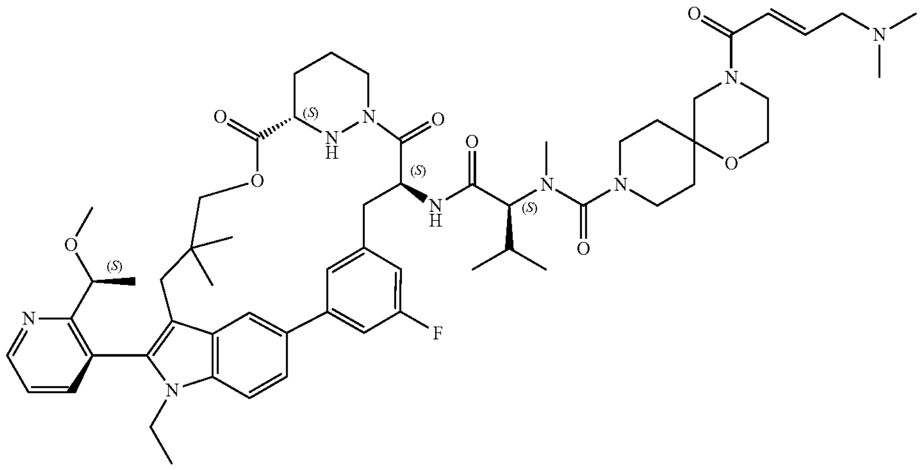 |
| A139 | 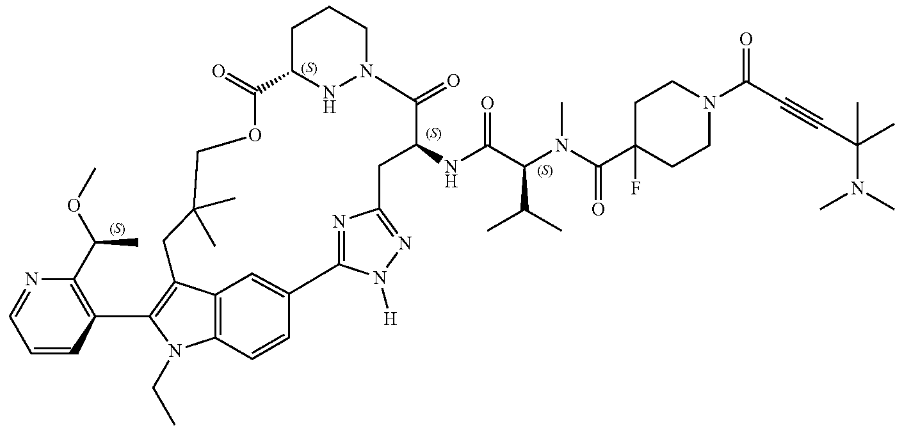 |

TABLE 1-continued
| Certain Compounds of the Present Invention | |
|---|---|
| Ex# | Structure |
| A140 | 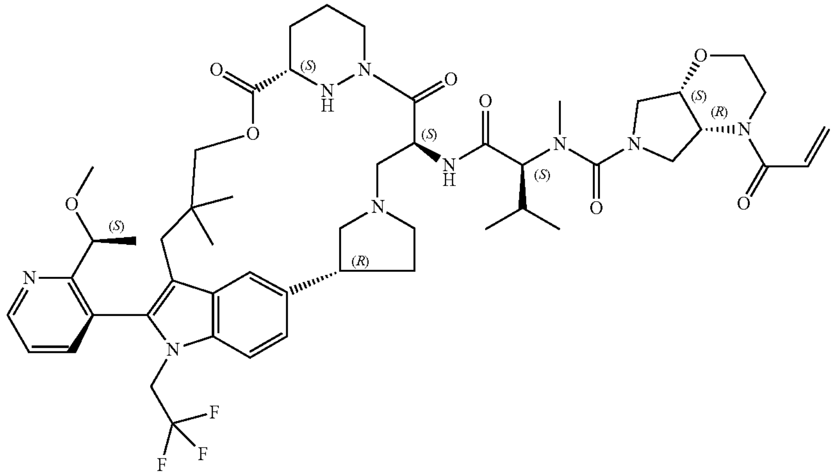 |
| A141 | 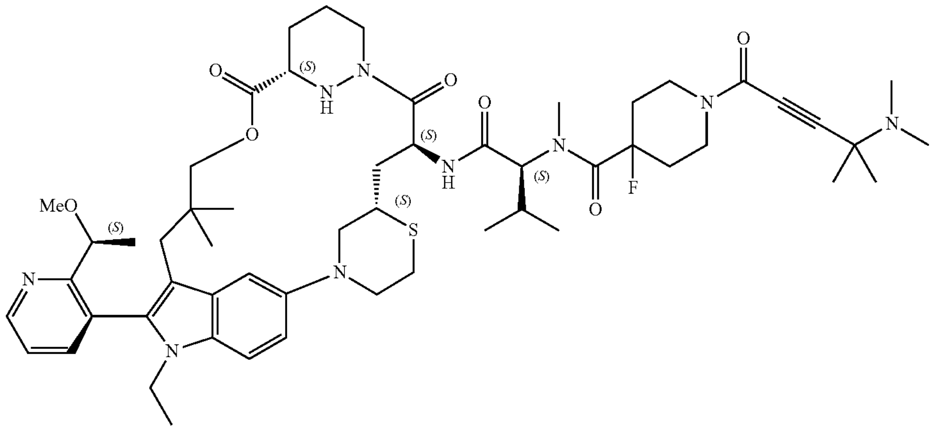 |
| A142 | 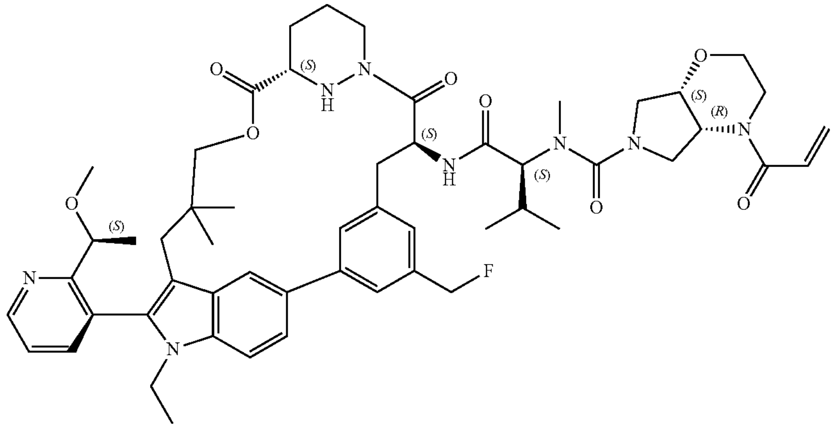 |

TABLE 1-continued
| Certain Compounds of the Present Invention | |
|---|---|
| Ex# | Structure |
| A143 | 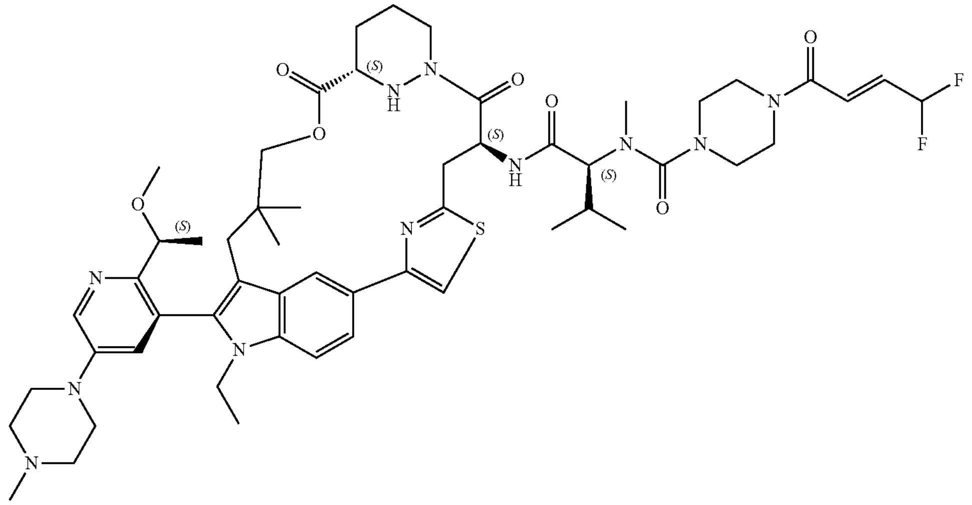 |
| A144 | 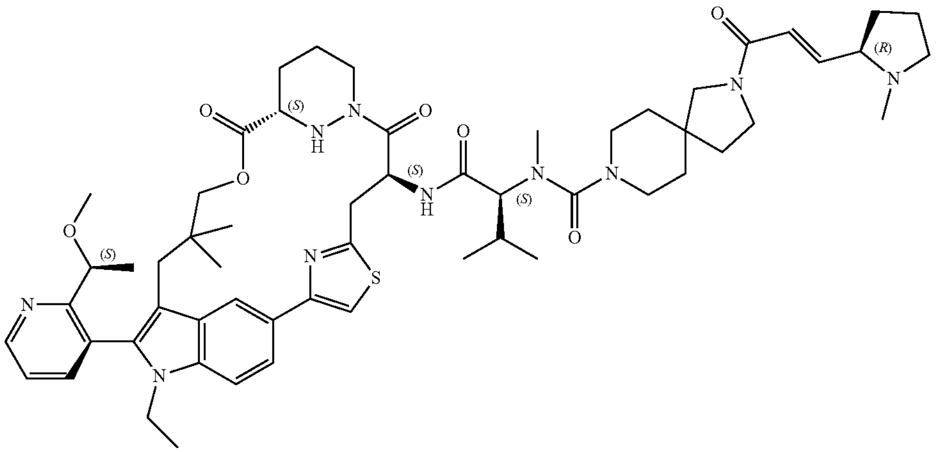 |
| A145 | 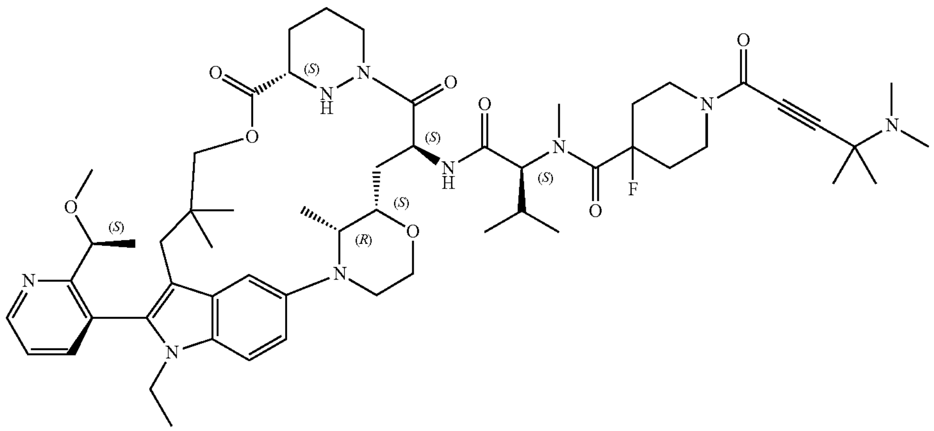 |

TABLE 1-continued
| Certain Compounds of the Present Invention | |
|---|---|
| Ex# | Structure |
| A146 | 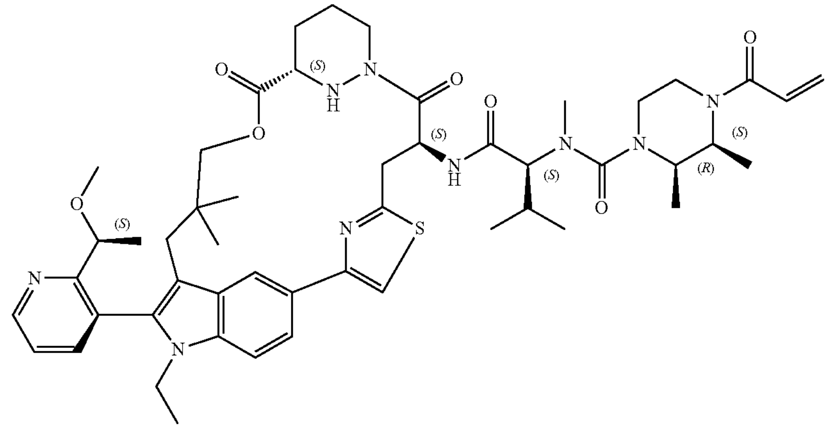 |
| A147 | 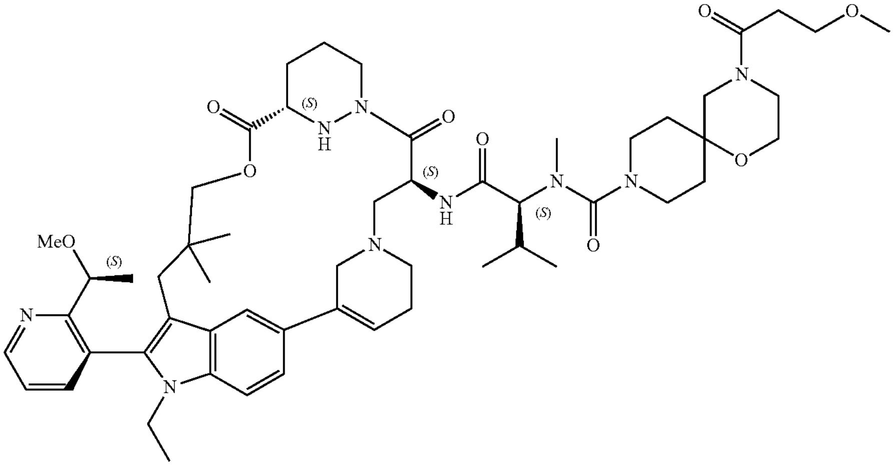 |
| A148 | 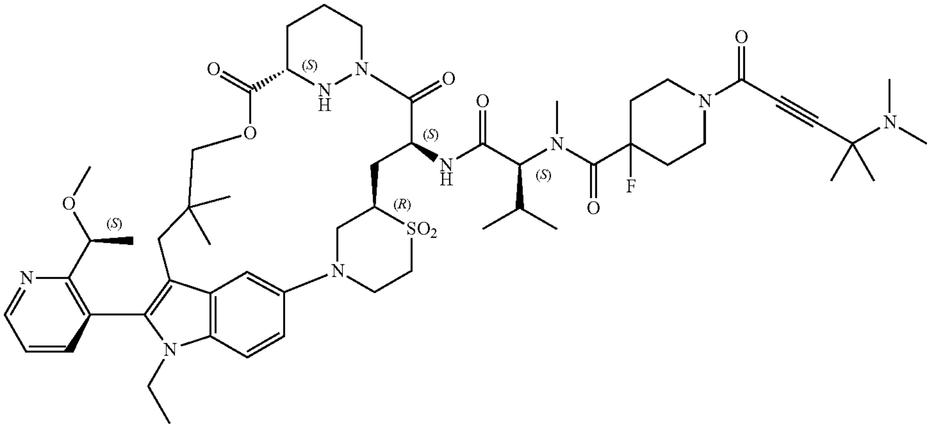 |

TABLE 1-continued
| Certain Compounds of the Present Invention | |
|---|---|
| Ex# | Structure |
| A149 | 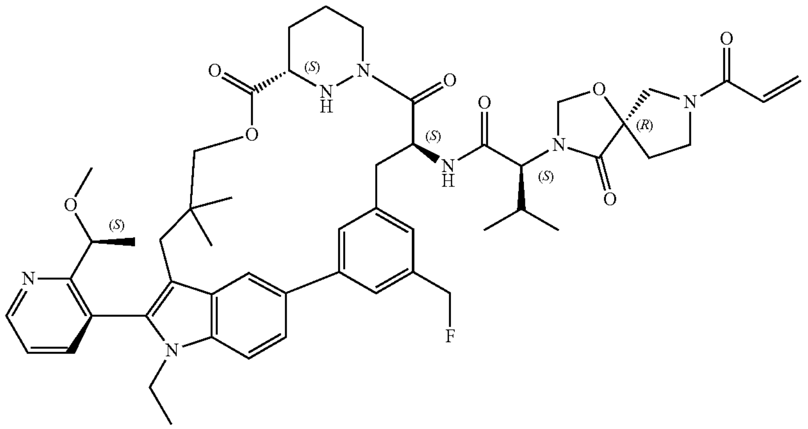 |
| A150 | 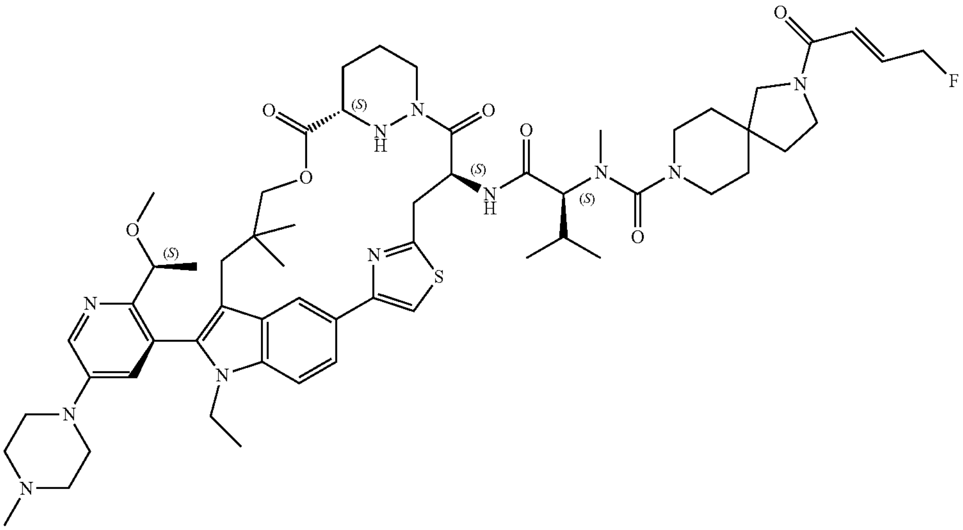 |
| A151 | 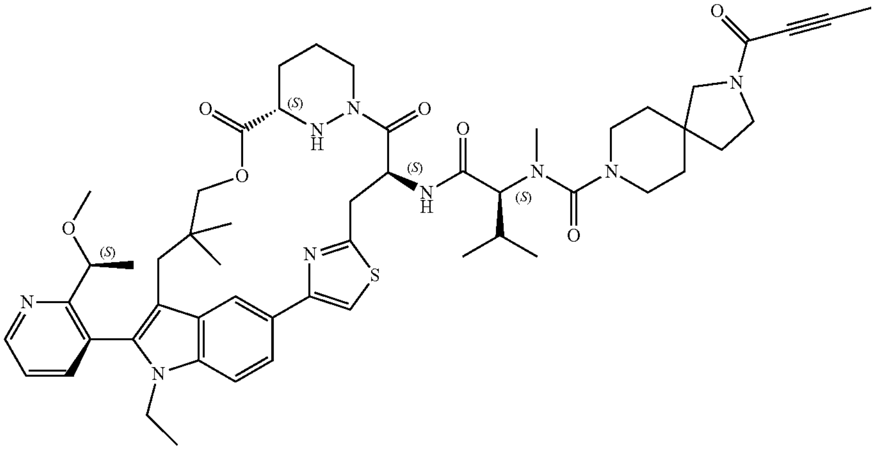 |

TABLE 1-continued
| Certain Compounds of the Present Invention | |
|---|---|
| Ex# | Structure |
| A152 | 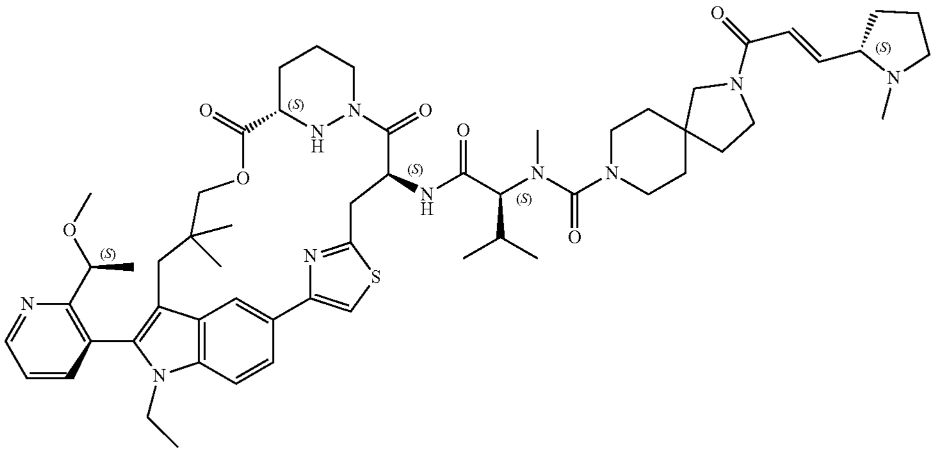 |
| A153 | 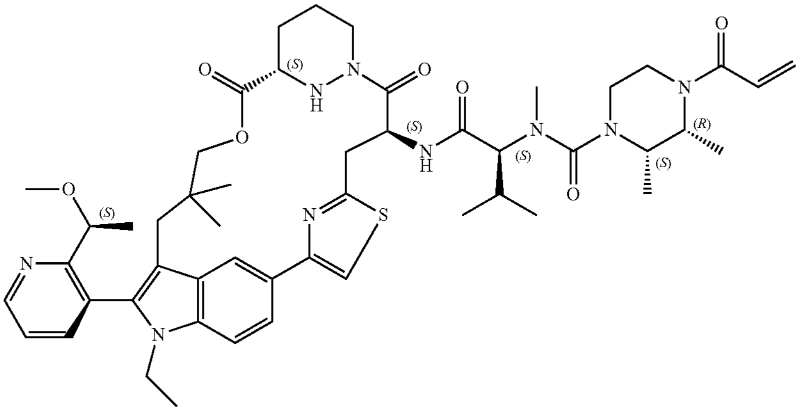 |
| A154 | 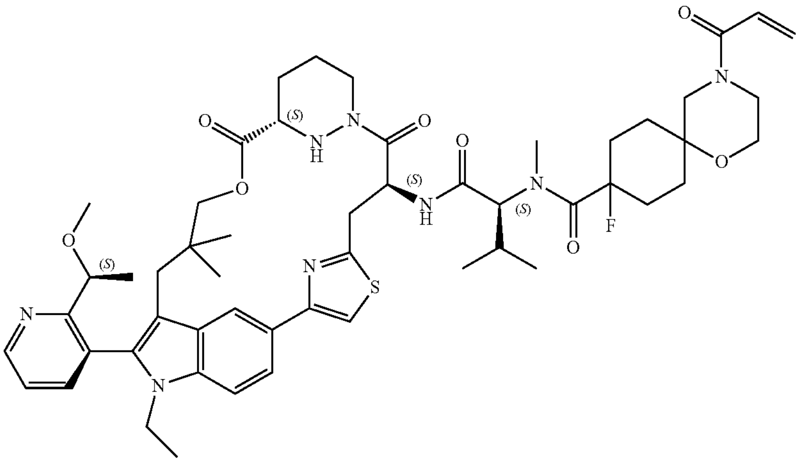 |

TABLE 1-continued
| Certain Compounds of the Present Invention | |
|---|---|
| Ex# | Structure |
| A155 | 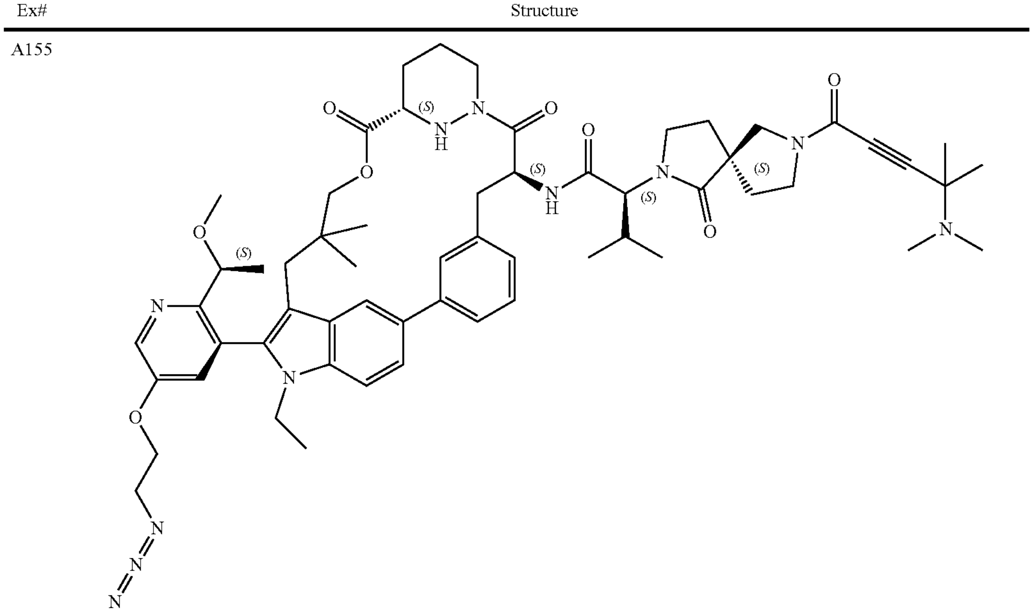 |
| A156 | 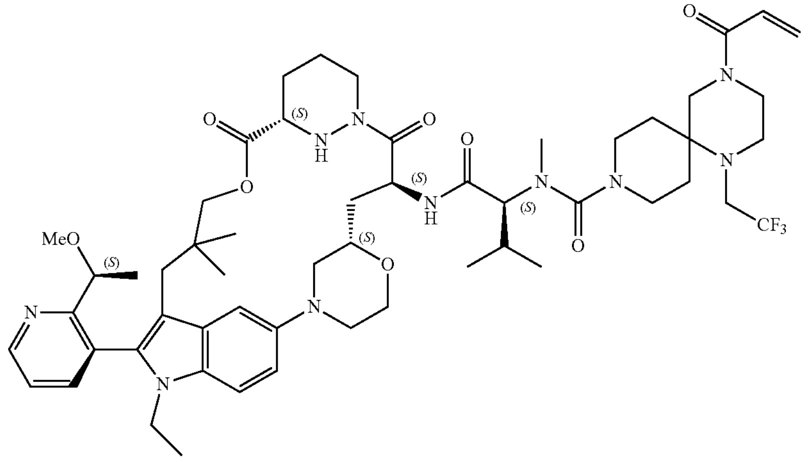 |
| A157 | 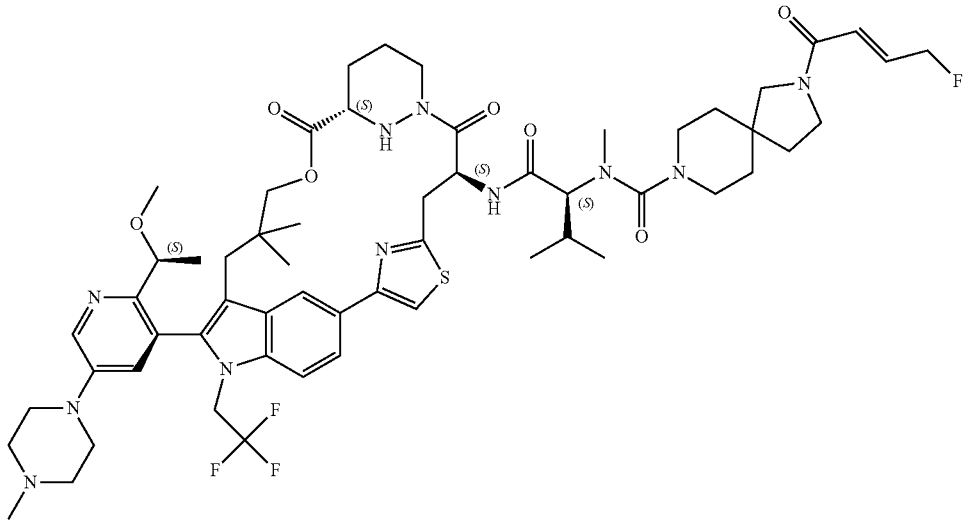 |

TABLE 1-continued
| Certain Compounds of the Present Invention | |
|---|---|
| Ex# | Structure |
| A158 | 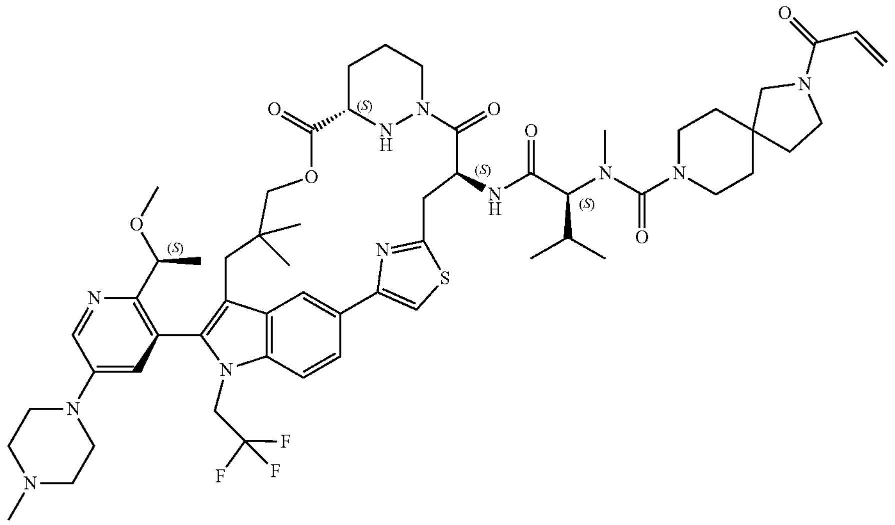 |
| A159 | 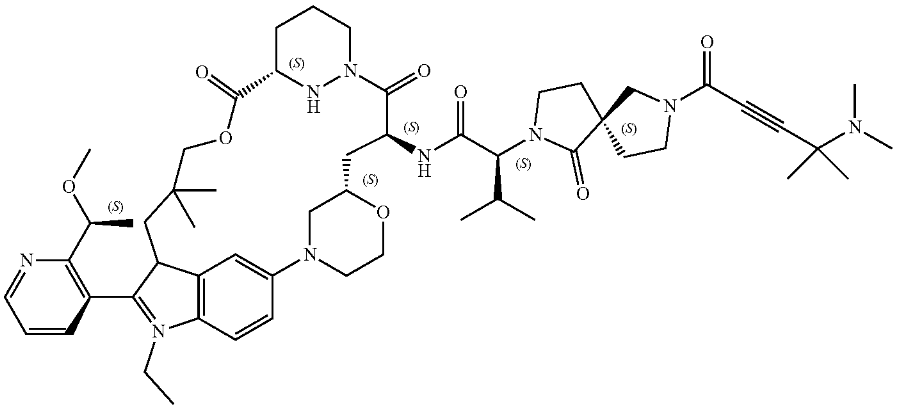 |
| A160 | 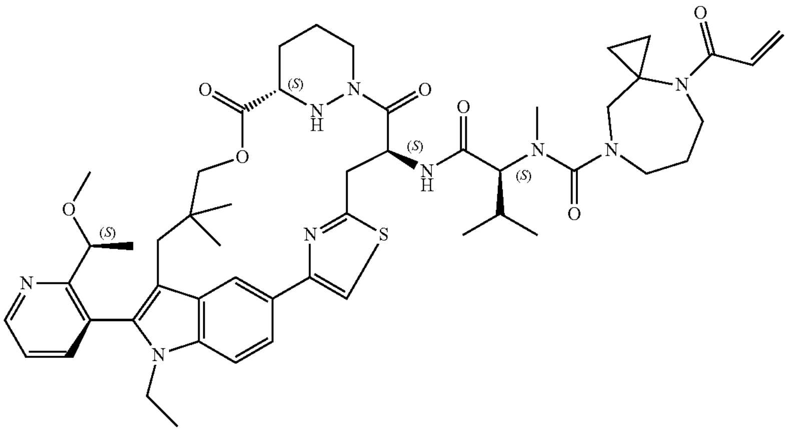 |

TABLE 1-continued
| Certain Compounds of the Present Invention | |
|---|---|
| Ex# | Structure |
| A161 | 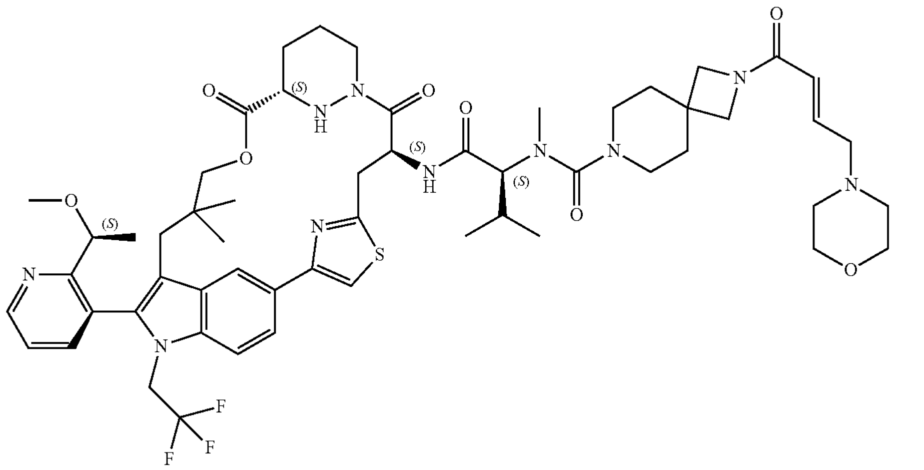 |
| A162 | 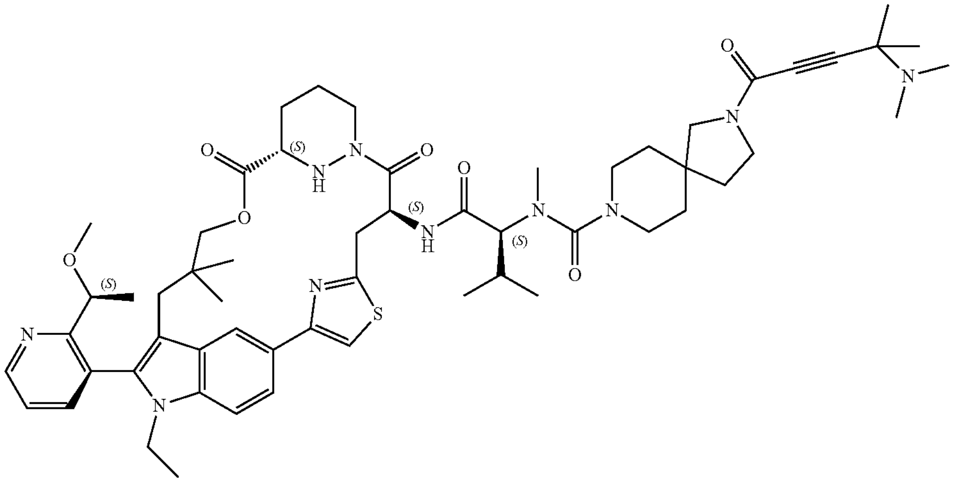 |
| A163 | 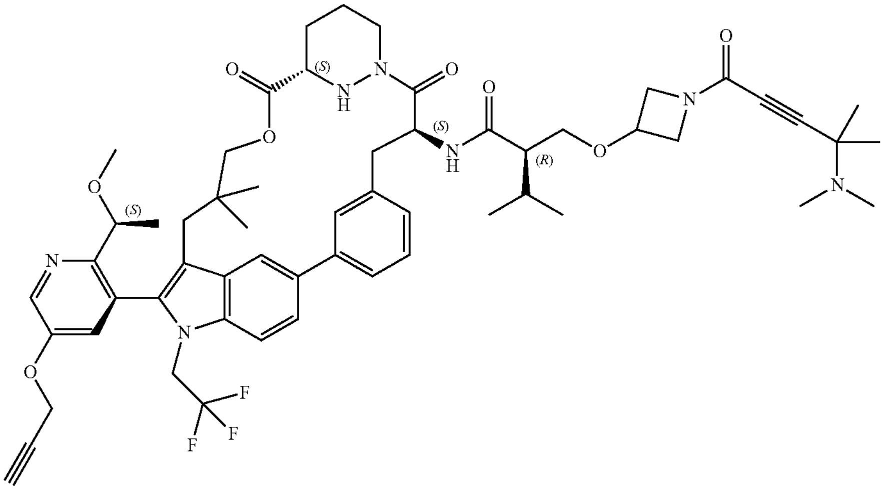 |

TABLE 1-continued
| Certain Compounds of the Present Invention | |
|---|---|
| Ex# | Structure |
| A164 | 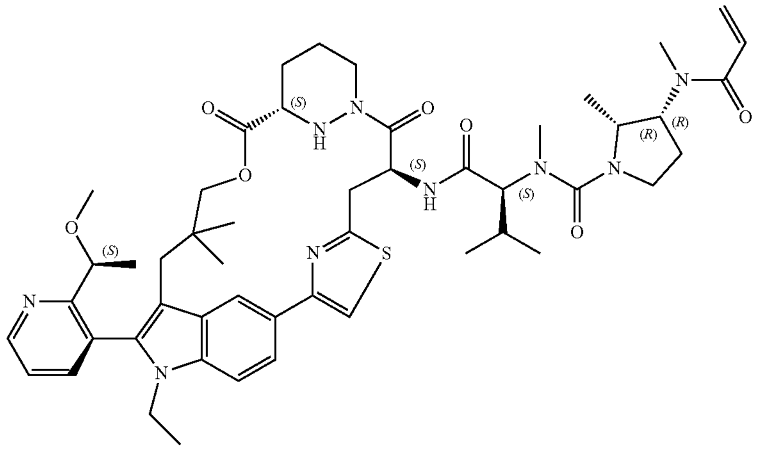 |
| A165 | 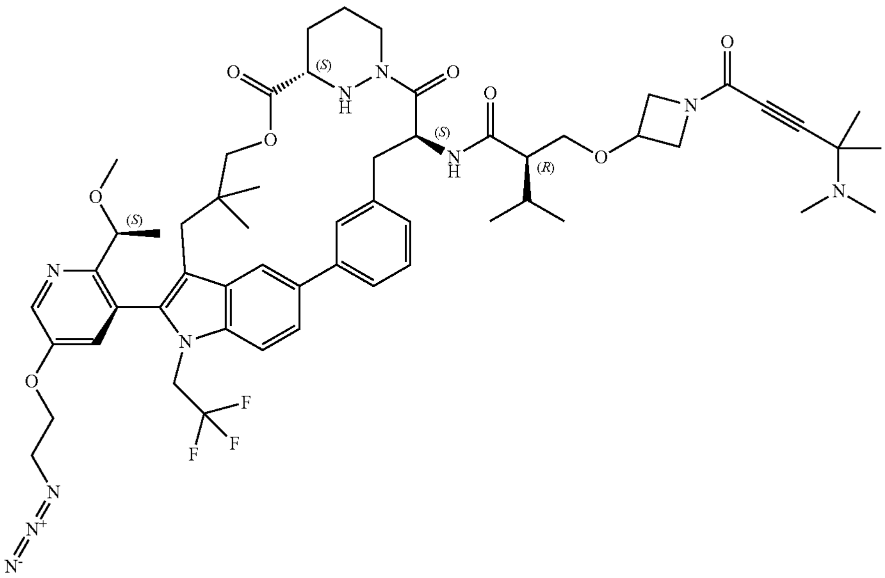 |
| A166 | 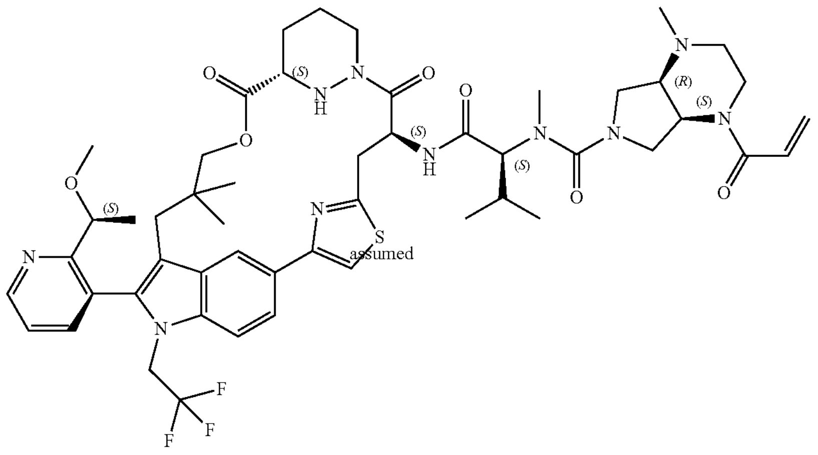 |

TABLE 1-continued
| Certain Compounds of the Present Invention | |
|---|---|
| Ex# | Structure |
| A167 | 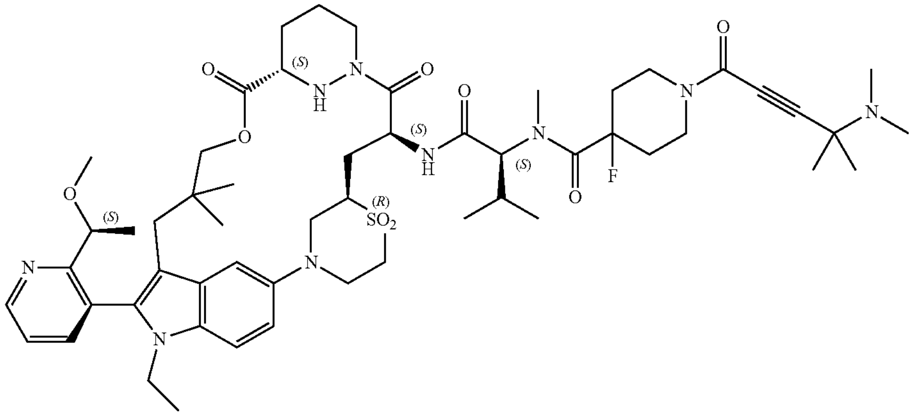 |
| A168 | 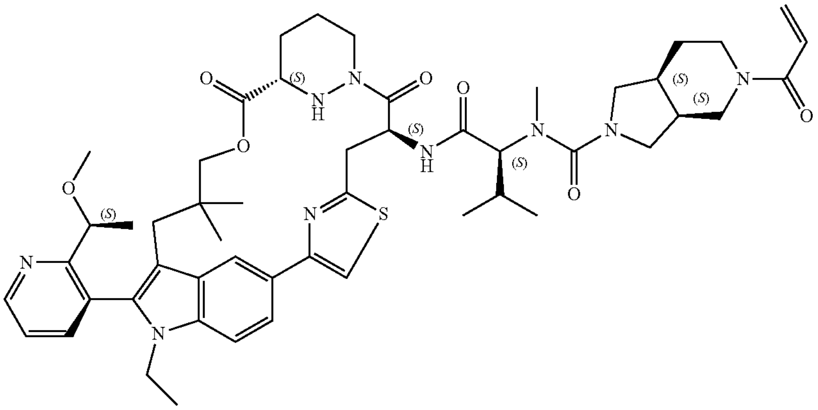 |
| A169 | 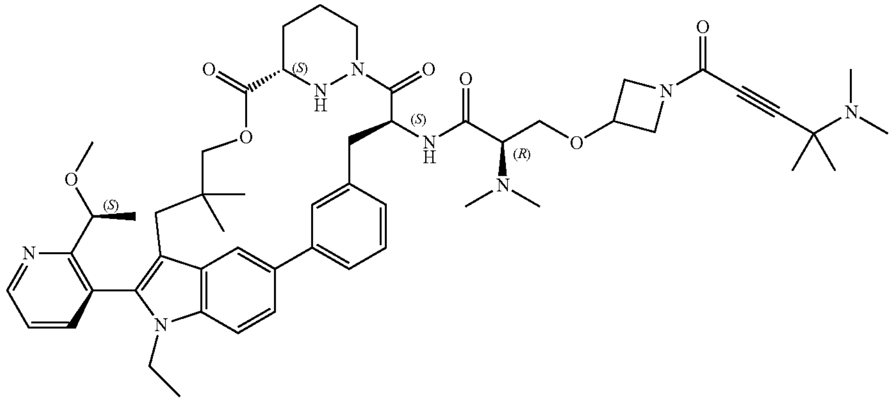 |

TABLE 1-continued
| Certain Compounds of the Present Invention | |
|---|---|
| Ex# | Structure |
| A170 | 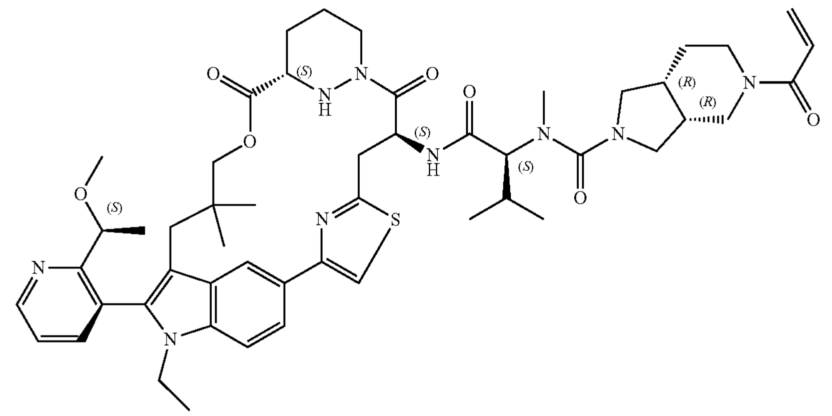 |
| A171 | 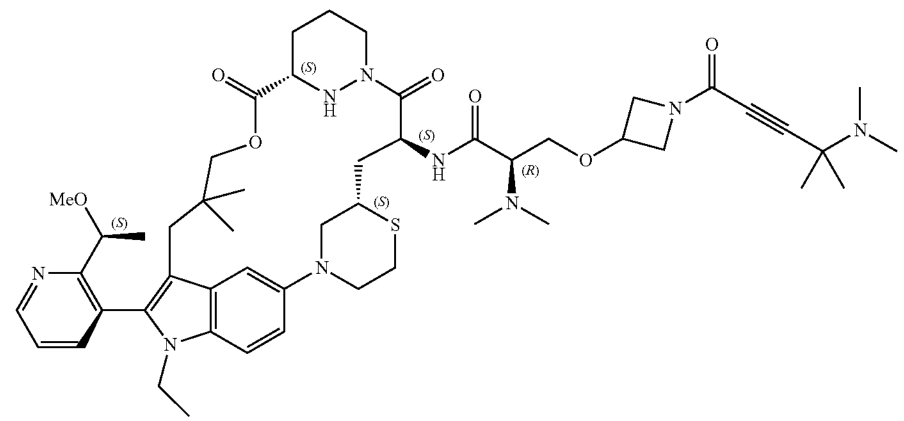 |
| A172 | 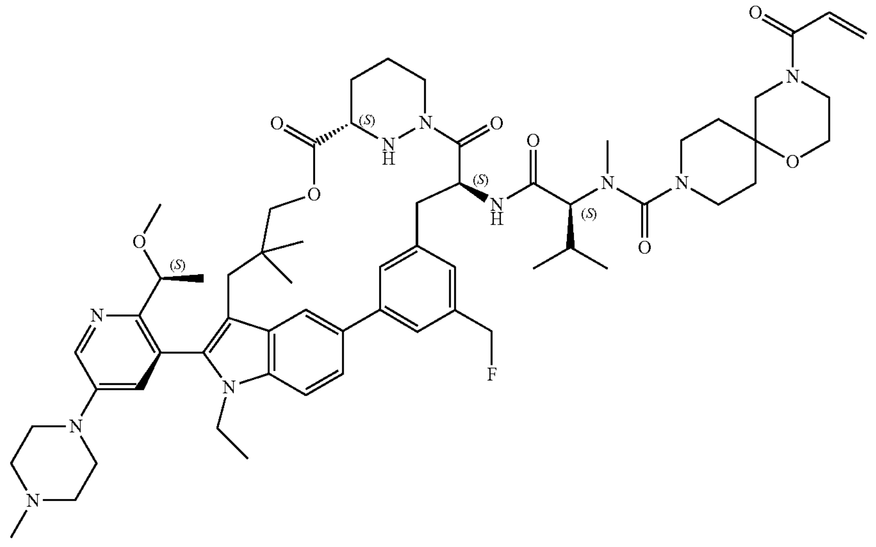 |

TABLE 1-continued
| Certain Compounds of the Present Invention | |
|---|---|
| Ex# | Structure |
| A173 | 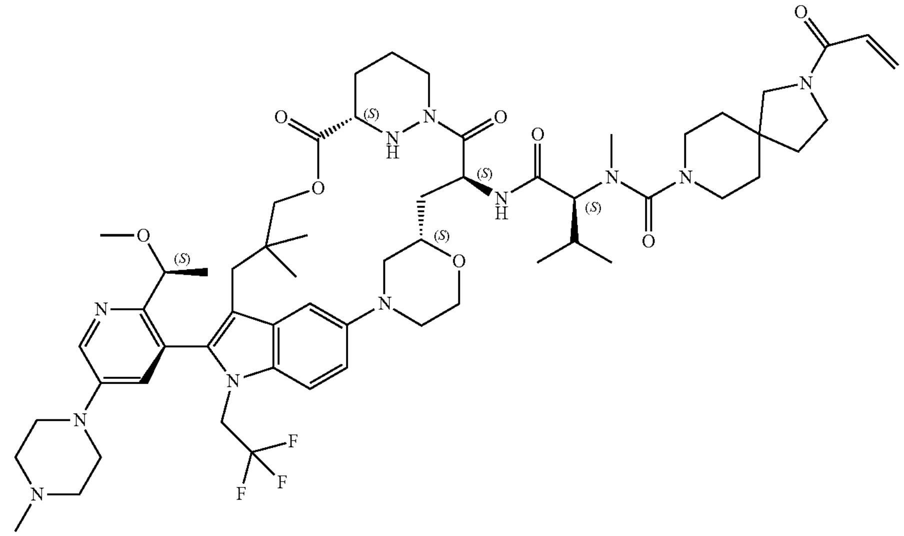 |
| A174 | 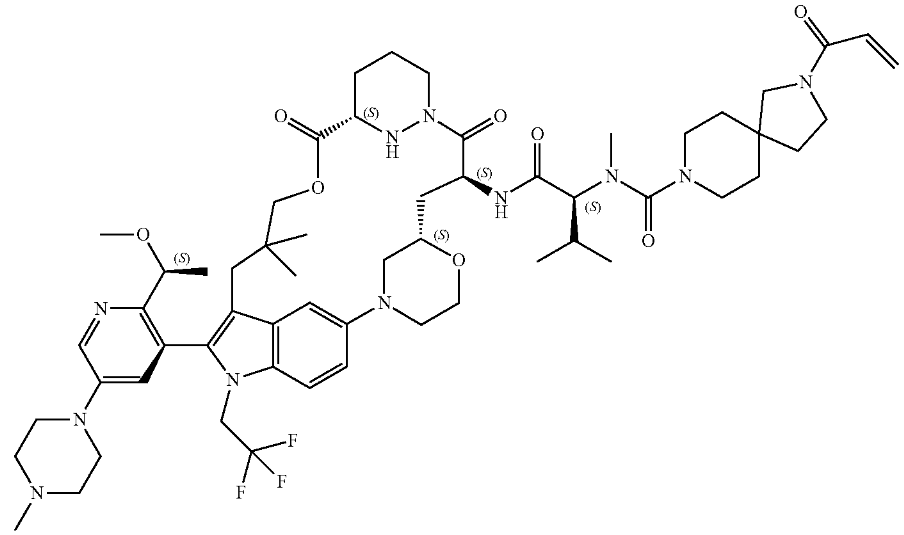 |
| A175 | 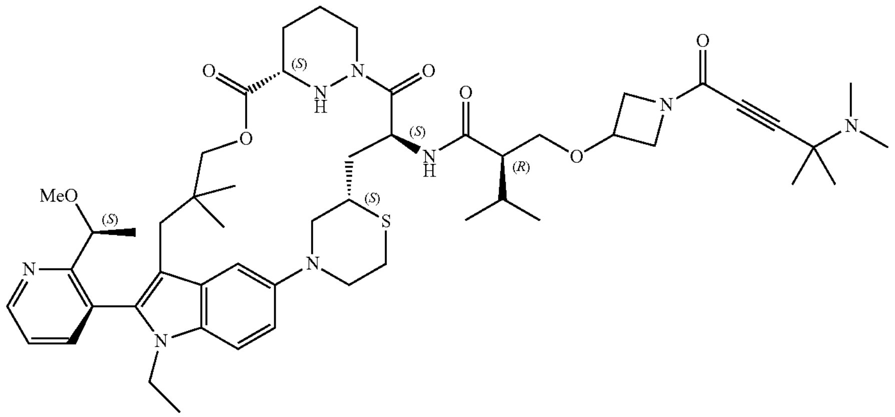 |

TABLE 1-continued
| Certain Compounds of the Present Invention | |
|---|---|
| Ex# | Structure |
| A176 | 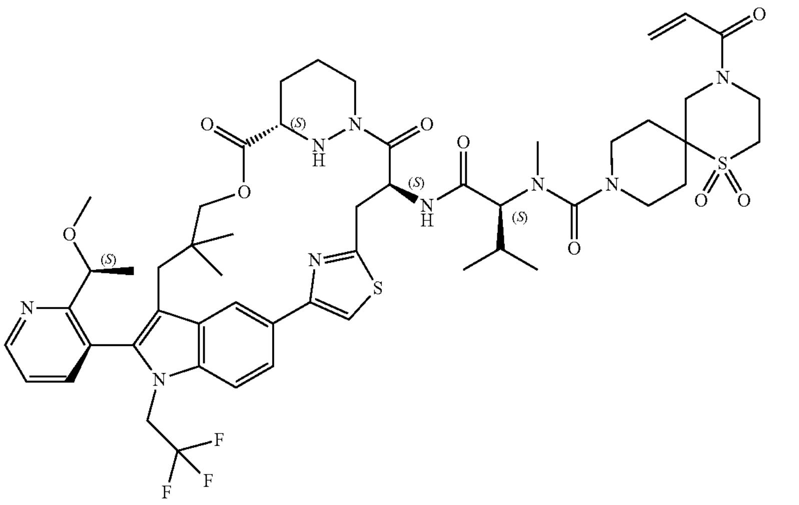 |
| A177 | 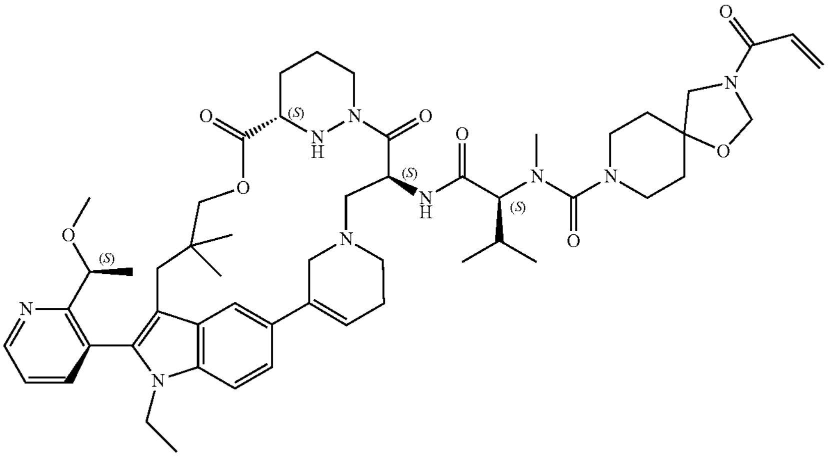 |
| A178 | 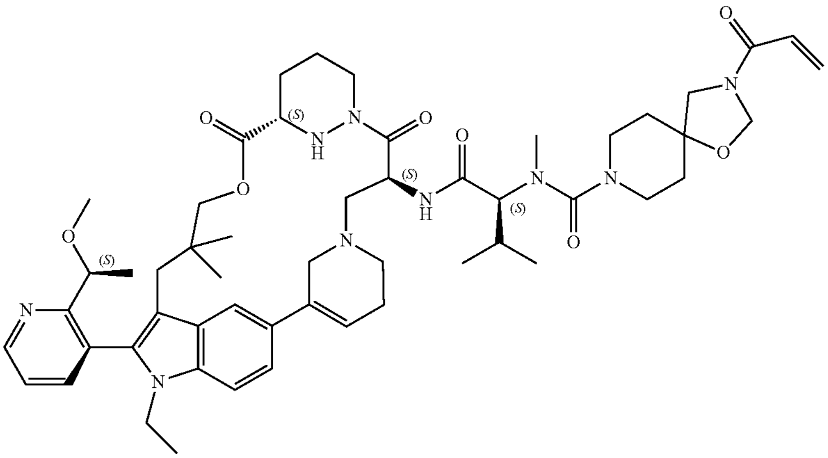 |

TABLE 1-continued
| Certain Compounds of the Present Invention | |
|---|---|
| Ex# | Structure |
| A179 | 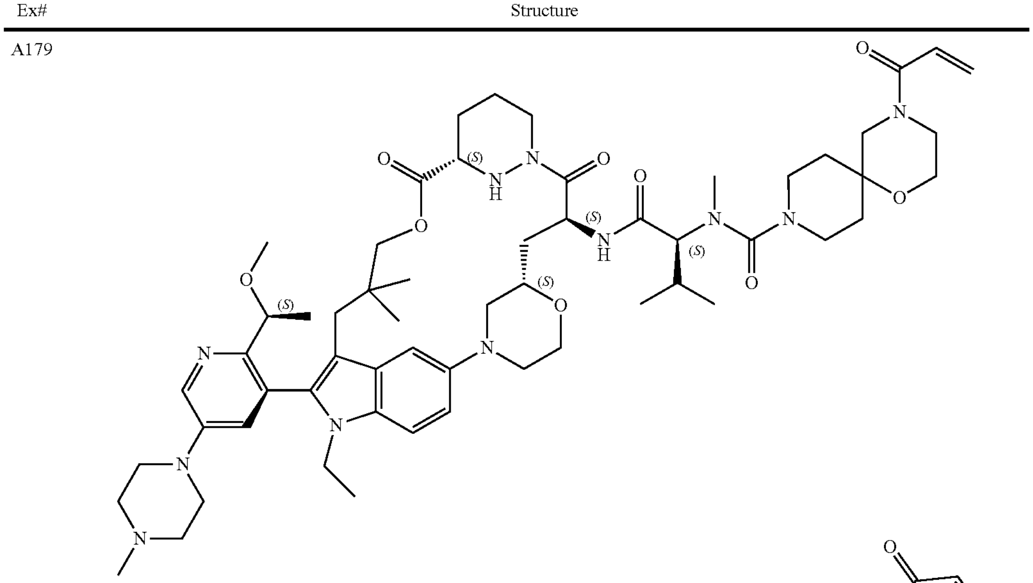 |
| A180 | 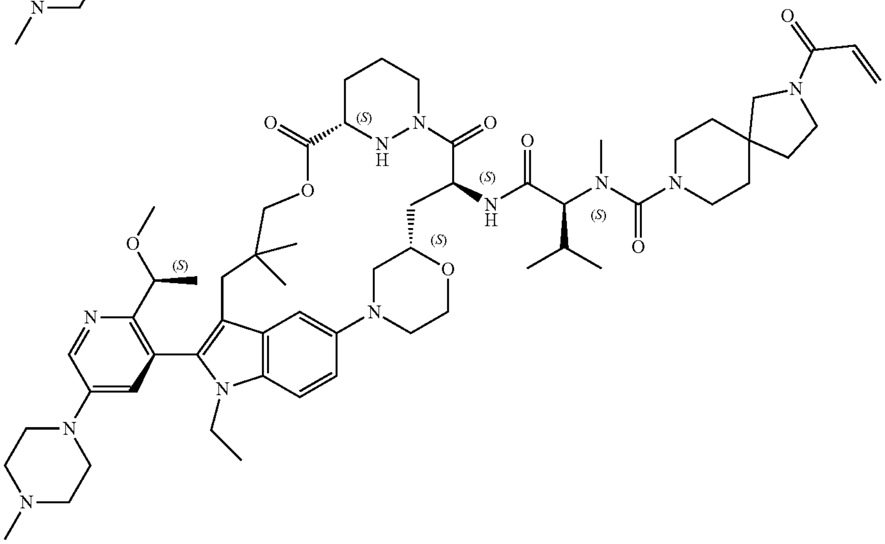 |
| A181 | 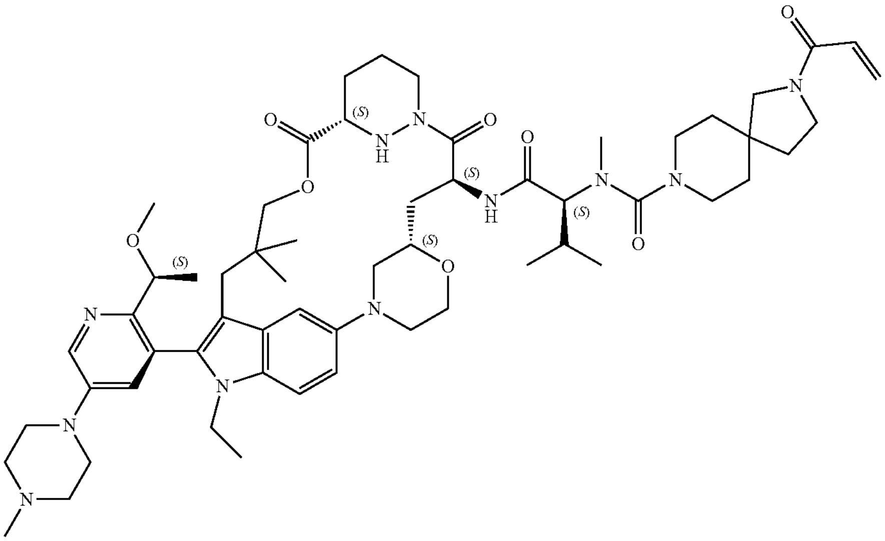 |

TABLE 1-continued
| Certain Compounds of the Present Invention | |
|---|---|
| Ex# | Structure |
| A182 | 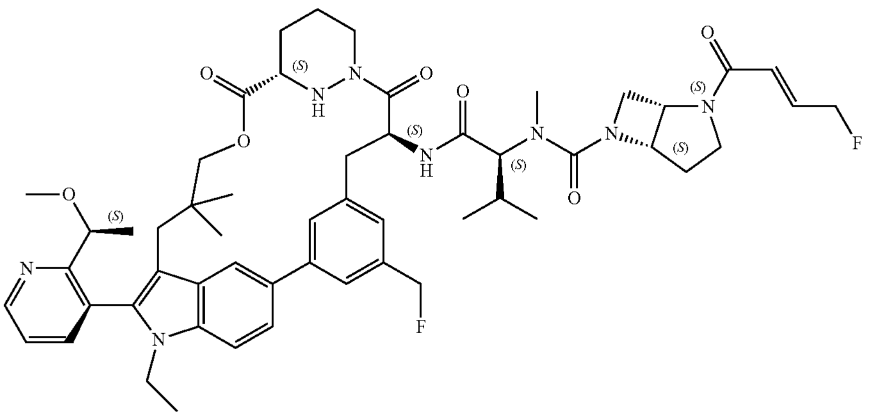 |
| A183 | 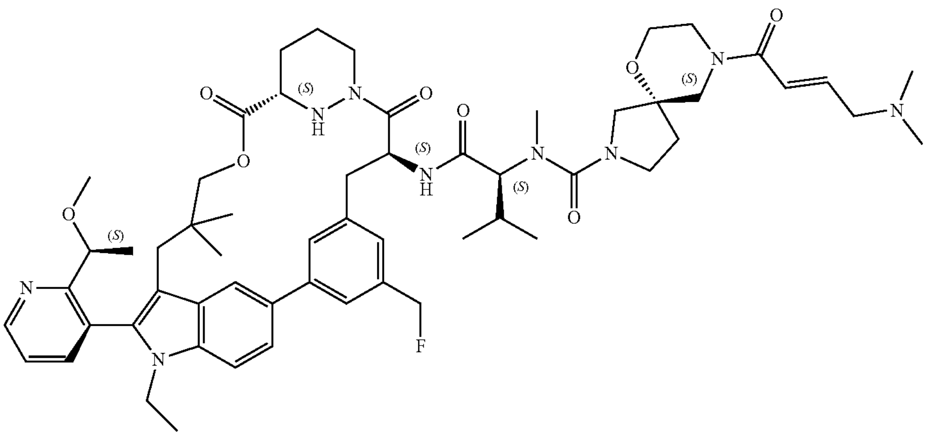 |
| A184 | 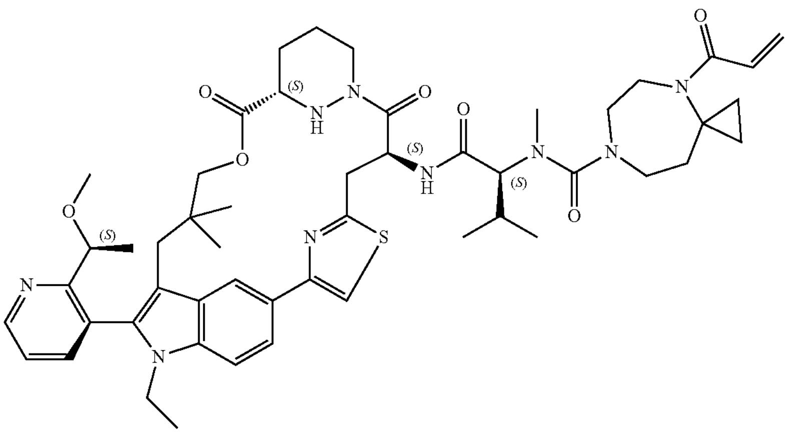 |

TABLE 1-continued
| Certain Compounds of the Present Invention | |
|---|---|
| Ex# | Structure |
| A185 | 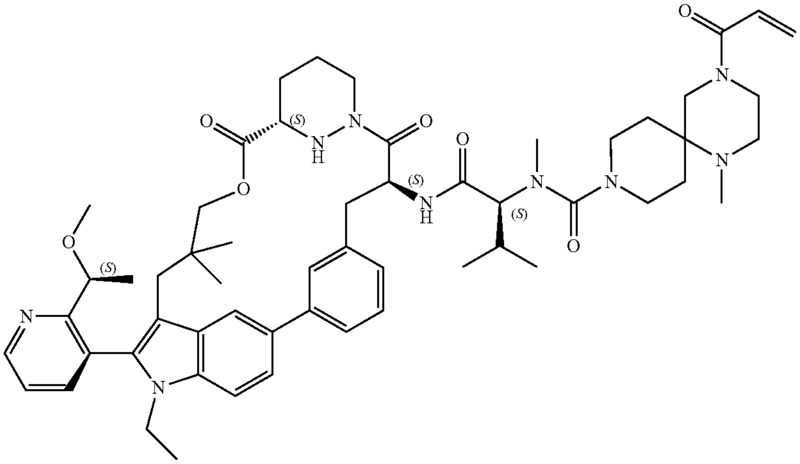 |
| A186 | 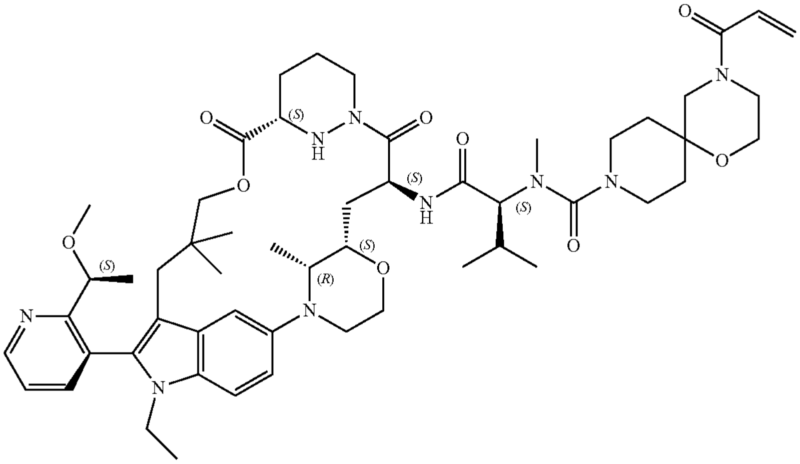 |
| A187 | 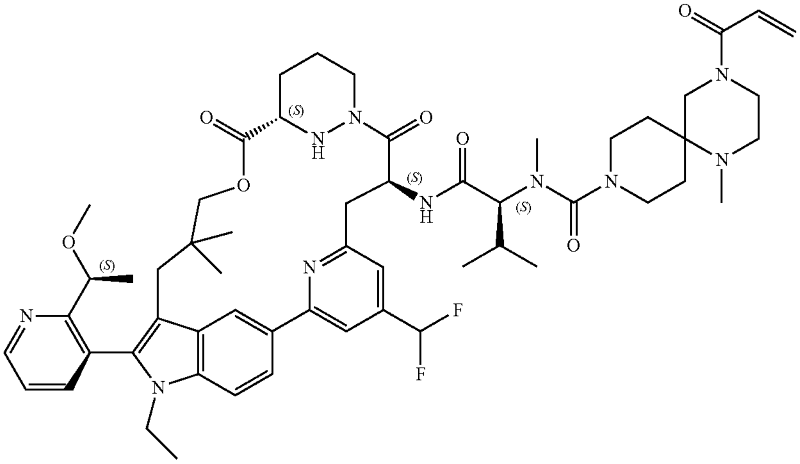 |

TABLE 1-continued
| Certain Compounds of the Present Invention | |
|---|---|
| Ex# | Structure |
| A188 | 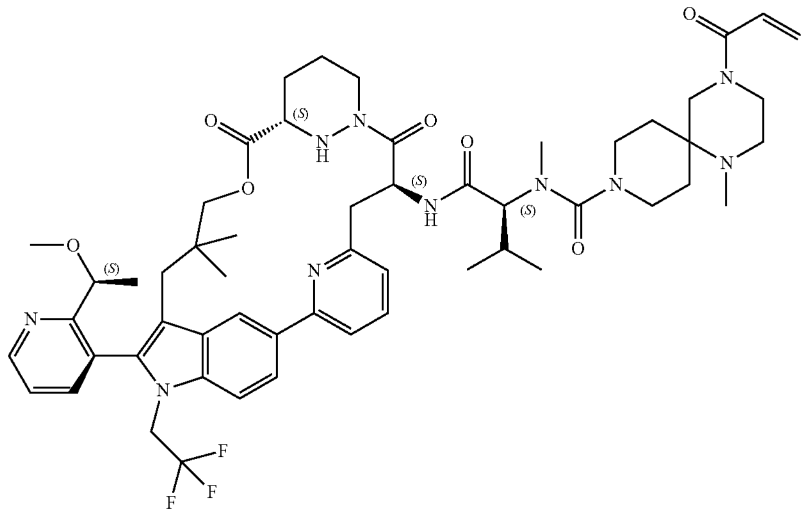 |
| A189 | 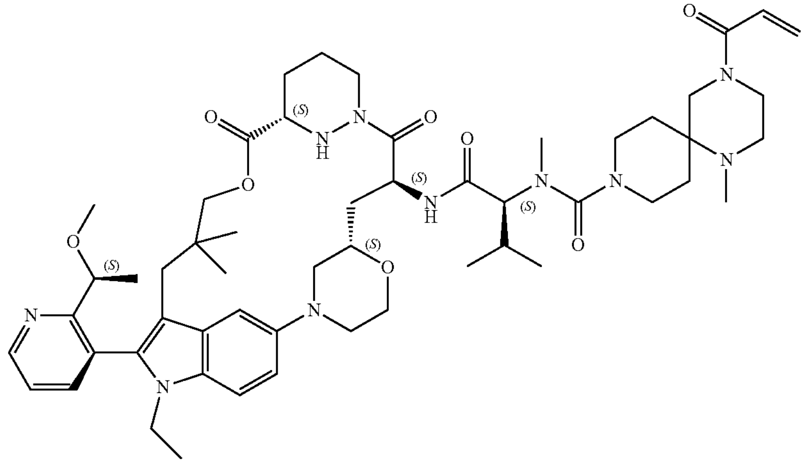 |
| A190 | 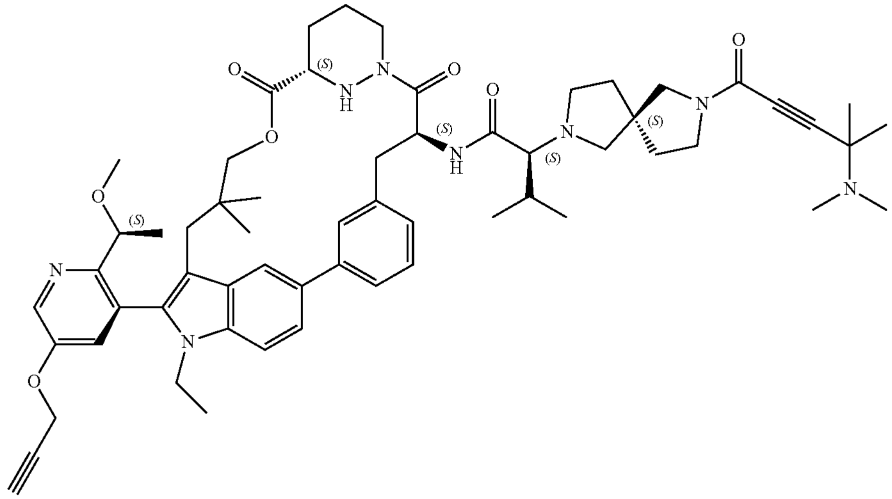 |

TABLE 1-continued
| Certain Compounds of the Present Invention | |
|---|---|
| Ex# | Structure |
| A191 | 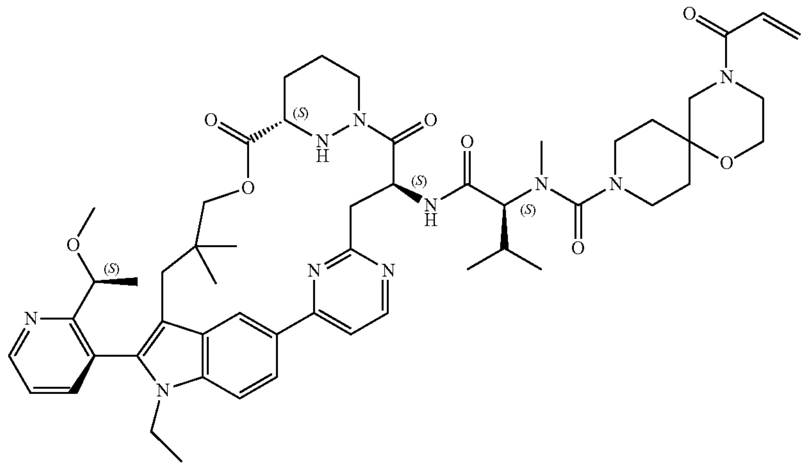 |
| A192 | 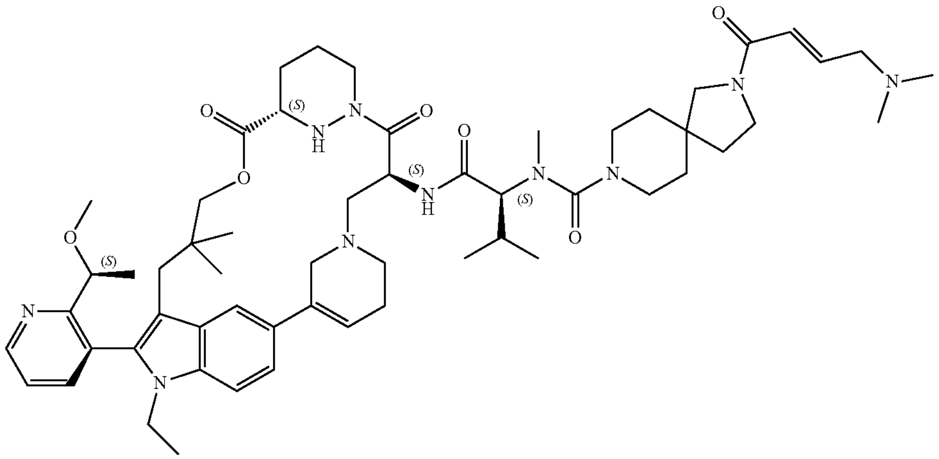 |
| A193 | 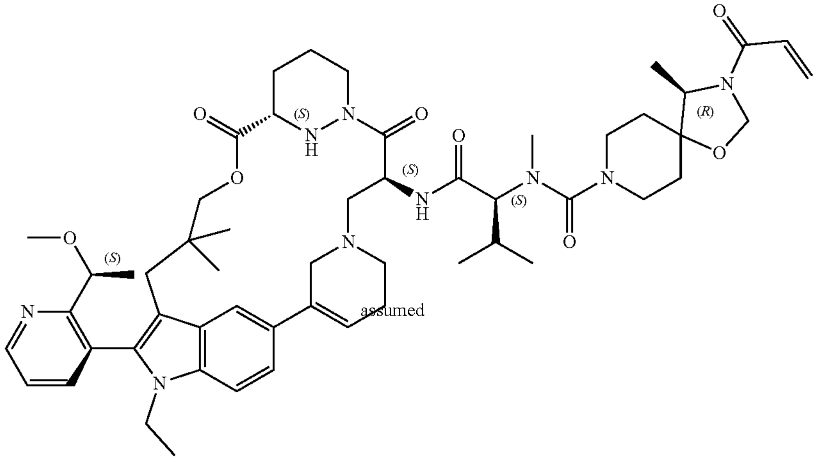 |

TABLE 1-continued
Certain Compounds of the Present Invention
| Ex# | Structure |
|---|---|
| A194 | 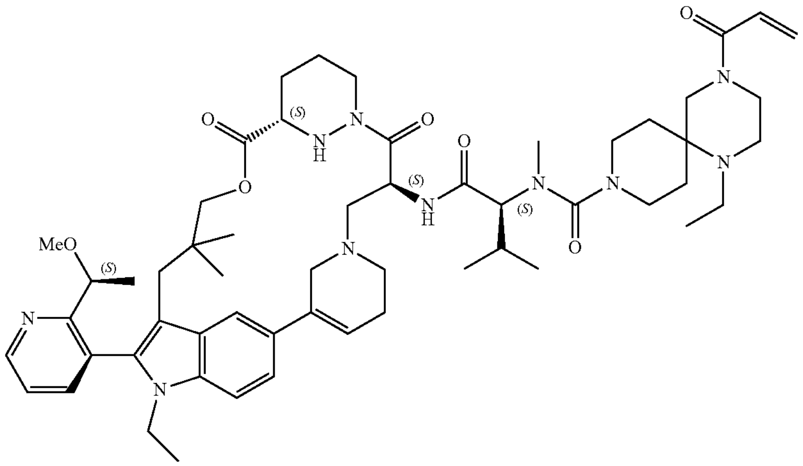 |
| A195 | 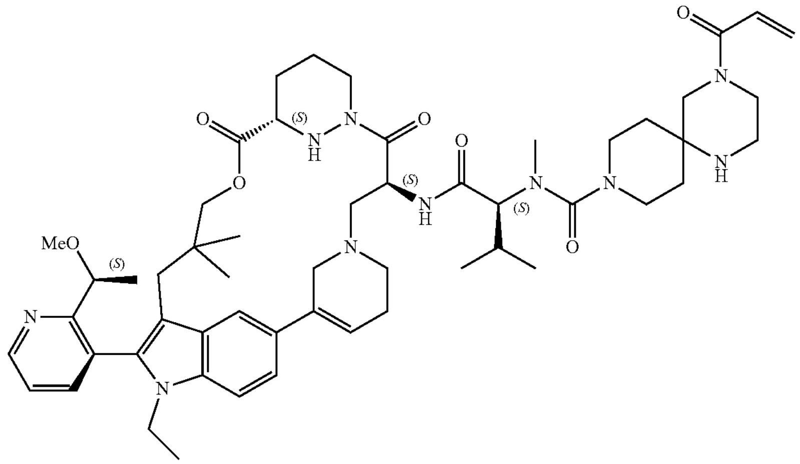 |
| A196 | 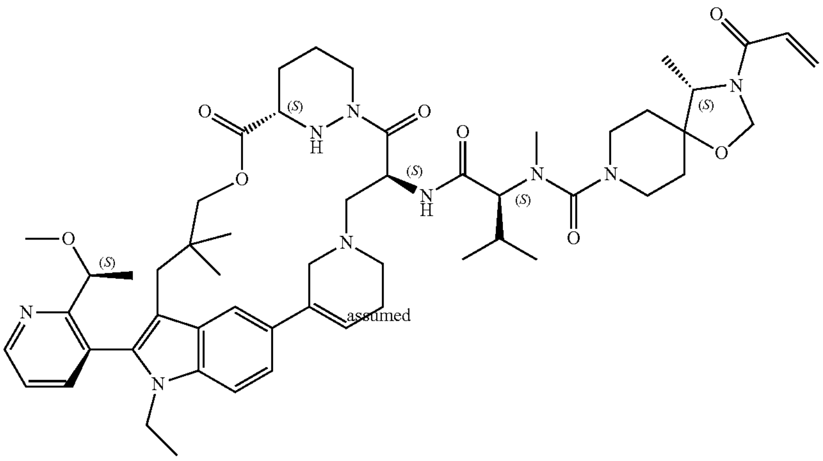 |

TABLE 1-continued
| Certain Compounds of the Present Invention | |
|---|---|
| Ex# | Structure |
| A197 | 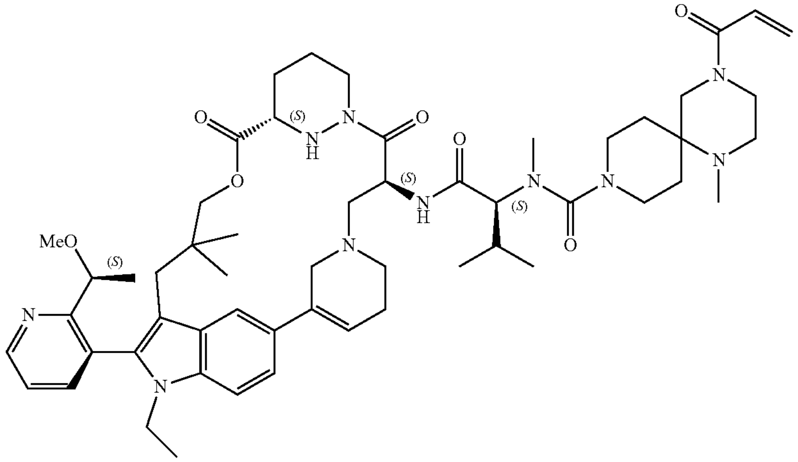 |
| A198 | 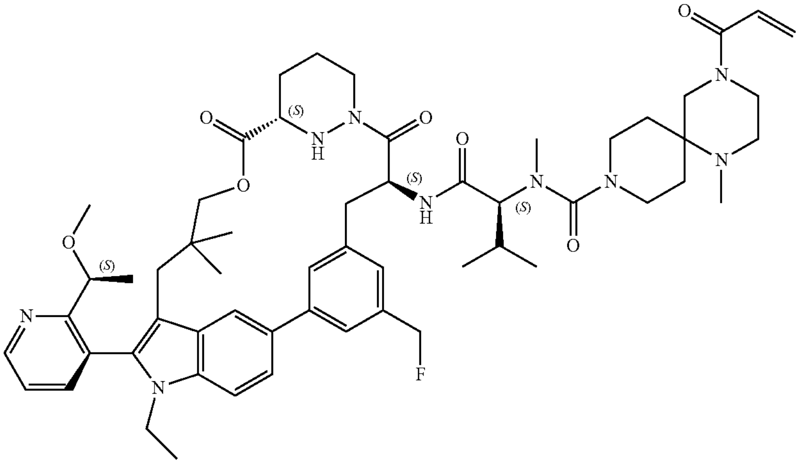 |
| A199 | 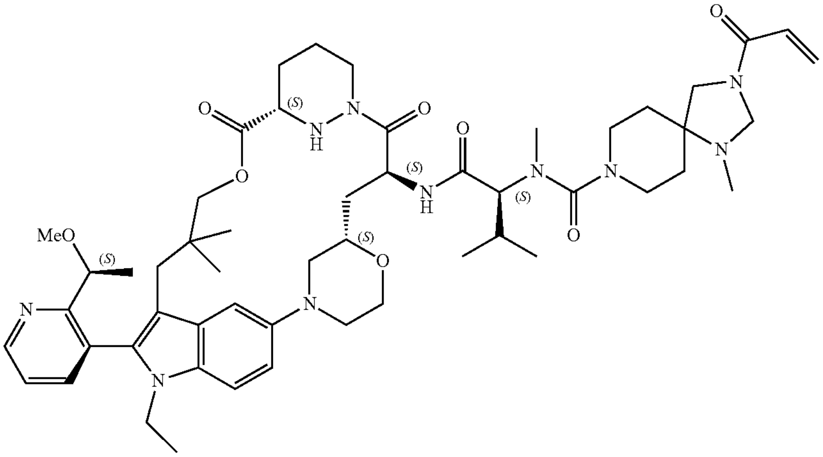 |

TABLE 1-continued
| Certain Compounds of the Present Invention | |
|---|---|
| Ex# | Structure |
| A200 | 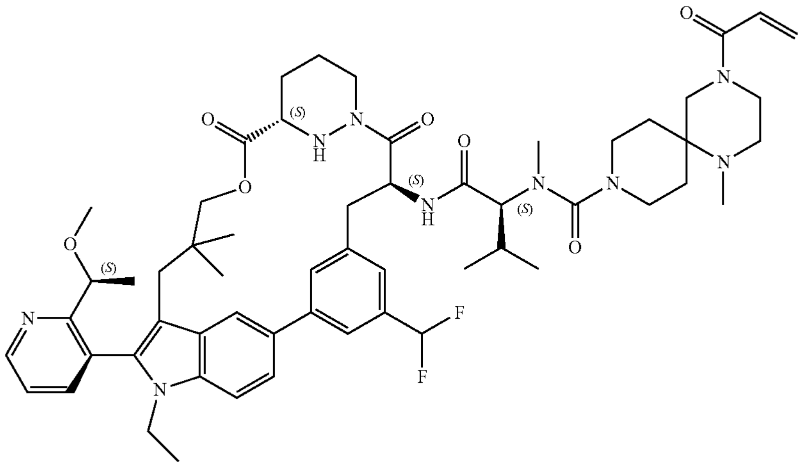 |
| A201 | 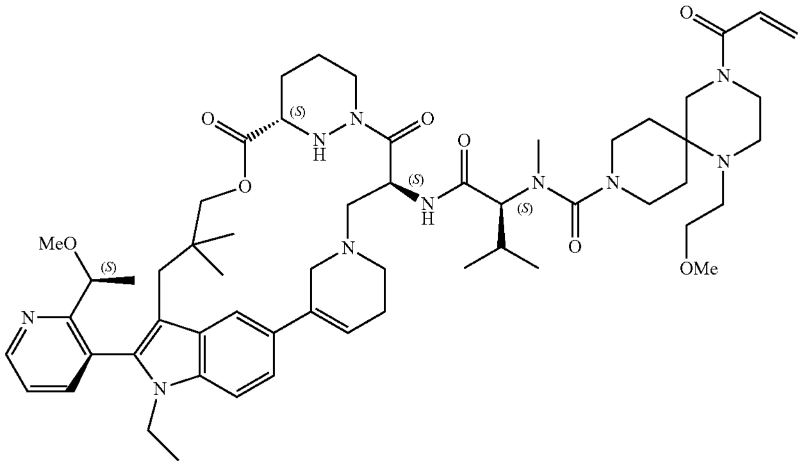 |
| A202 | 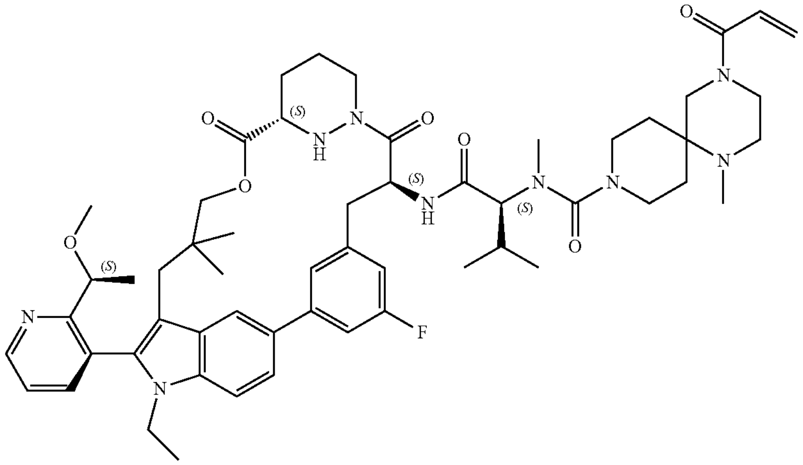 |

TABLE 1-continued
| Certain Compounds of the Present Invention | |
|---|---|
| Ex# | Structure |
| A203 | 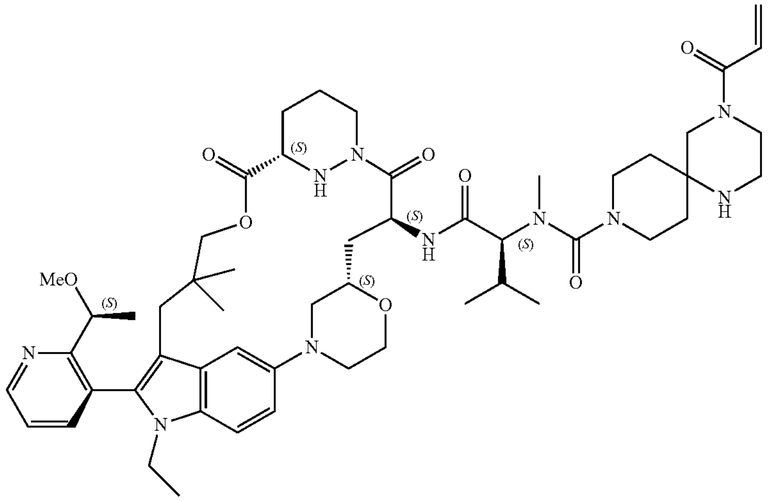 |
| A204 | 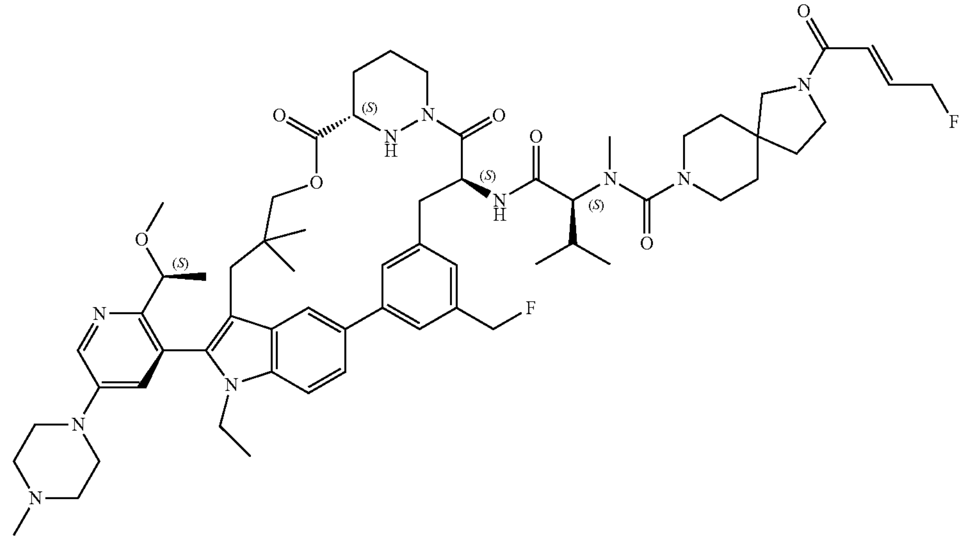 |
| A205 | 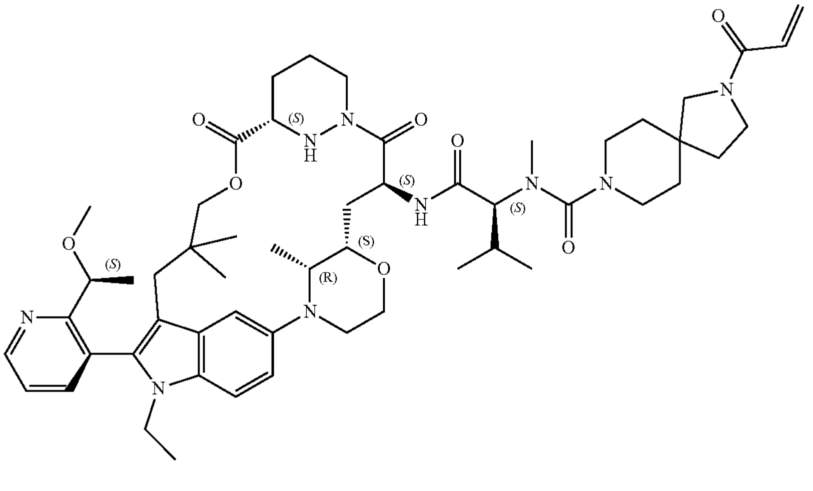 |

TABLE 1-continued
| Certain Compounds of the Present Invention | |
|---|---|
| Ex# | Structure |
| A206 | 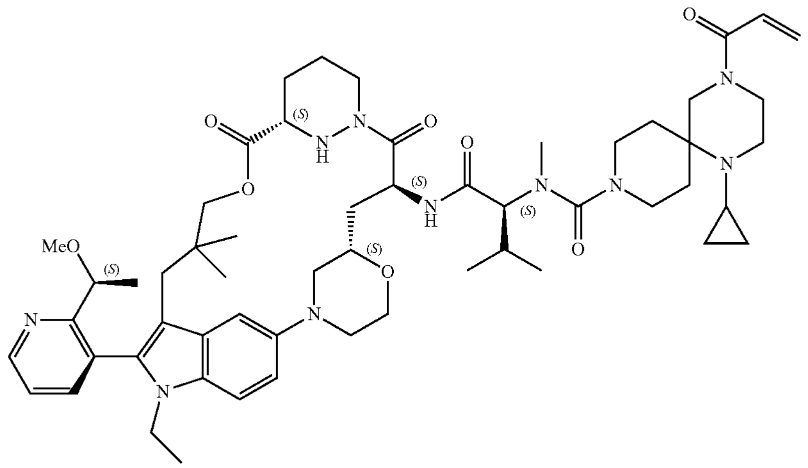 |
| A207 | 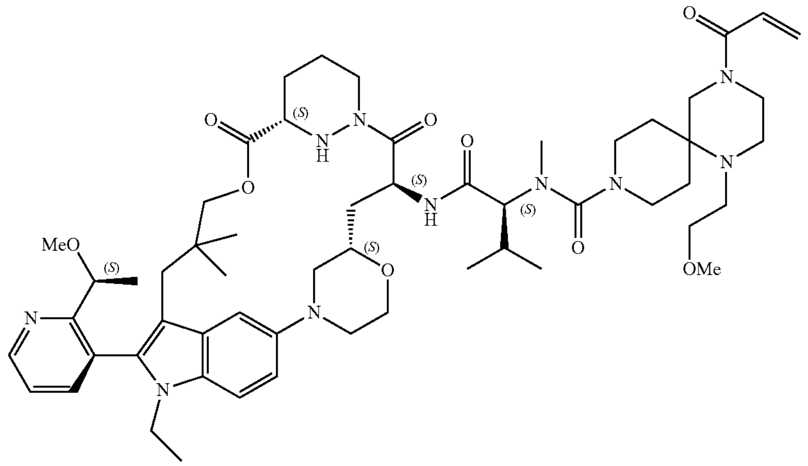 |
| A208 | 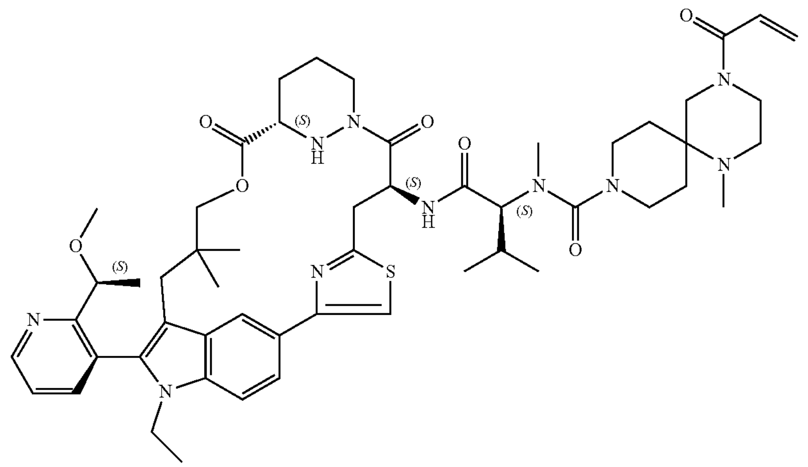 |

TABLE 1-continued

| Certain Compounds of the Present Invention | |
|---|---|
| Ex# | Structure |
| A209 | 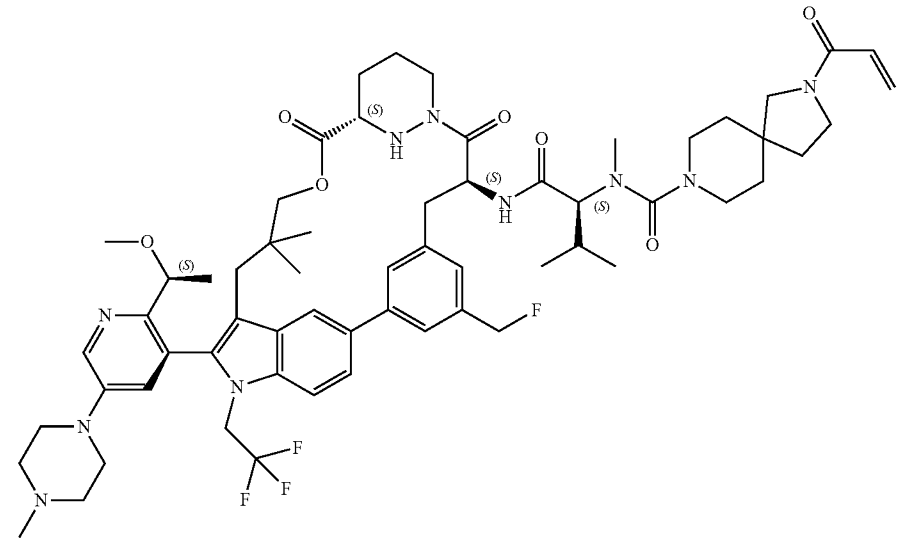 |

In some embodiments, a compound of the present invention is a compound selected from Table 2, or a pharmaceutically acceptable salt or stereoisomer thereof. In some embodiments, a compound of the present invention is a compound selected from Table 2, or a pharmaceutically acceptable salt or atropisomer thereof In some embodiments, a compound of the present invention is not a compound selected from Table 2. In some embodiments, a compound of the present invention is not a compound selected from Table 2, or a pharmaceutically acceptable salt or stereoisomer thereof. In some embodiments, a compound of the present invention is not a compound selected from Table 2, or a pharmaceutically acceptable salt or atropisomer thereof.

TABLE 2

| Certain Compounds | |
|---|---|
| Ex # | Structure |
| B1 | 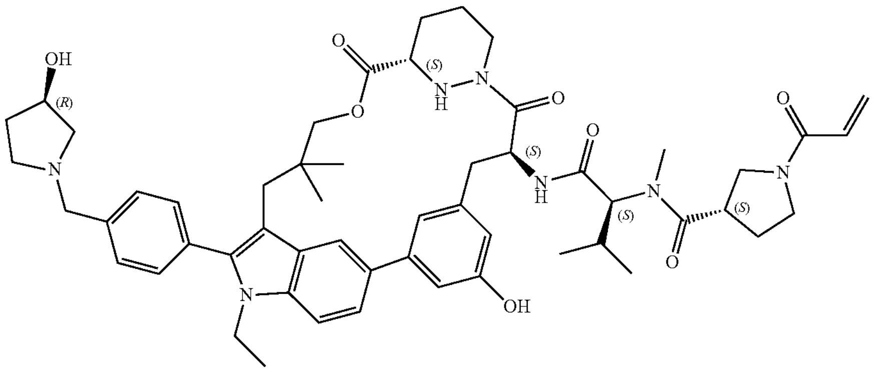 |

TABLE 2-continued
| Certain Compounds | |
|---|---|
| Ex # | Structure |
| B2 | 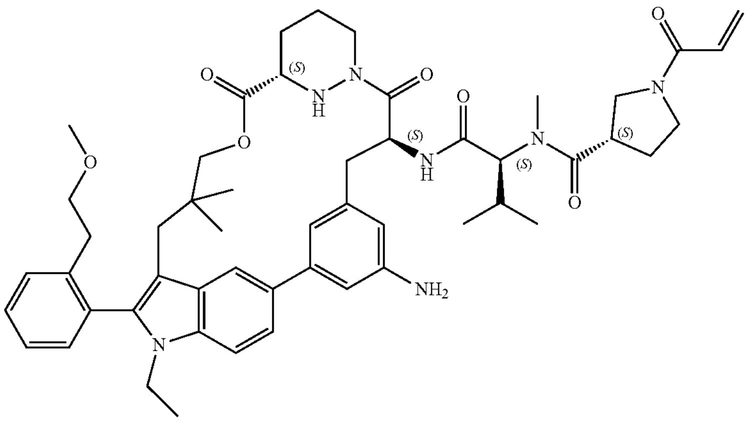 |
| B3 | 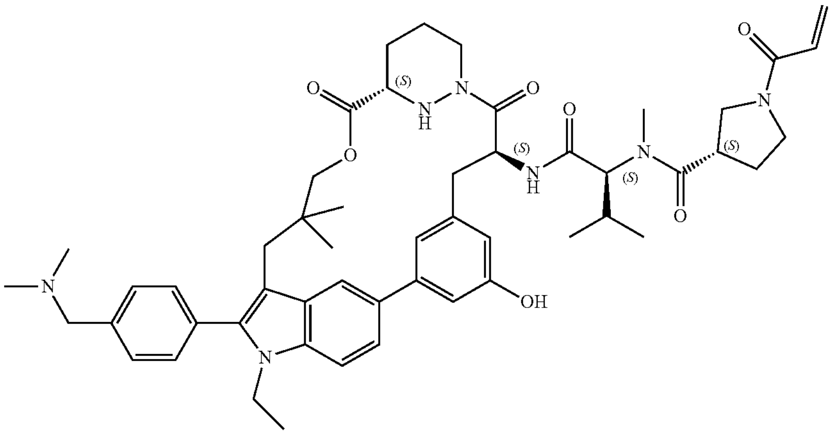 |
| B4 | 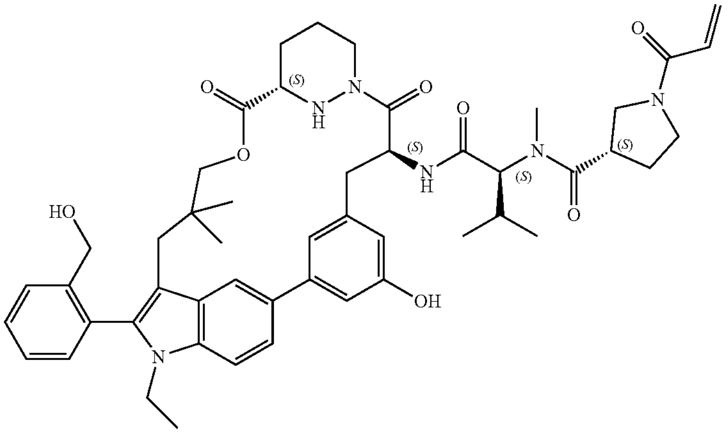 |

TABLE 2-continued
| Certain Compounds | |
|---|---|
| Ex # | Structure |
| B5 | 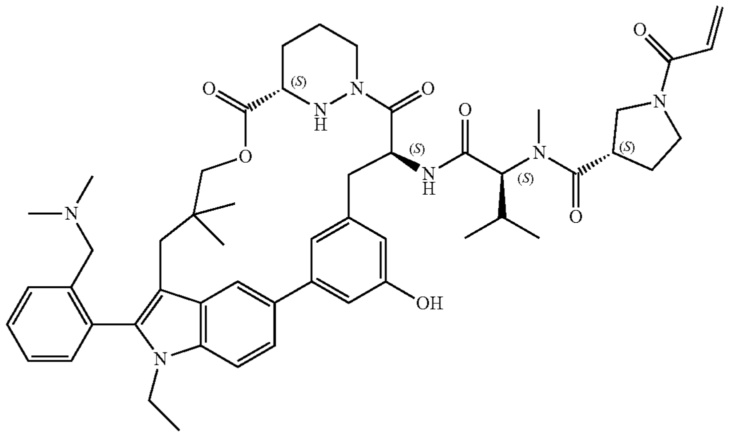 |
| B6 | 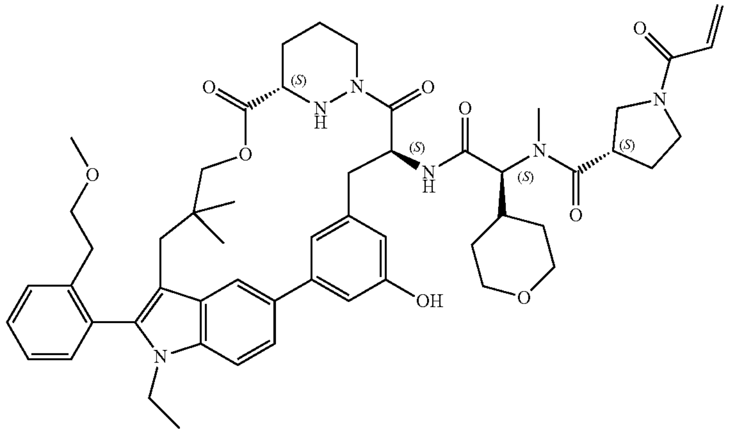 |
| B7 | 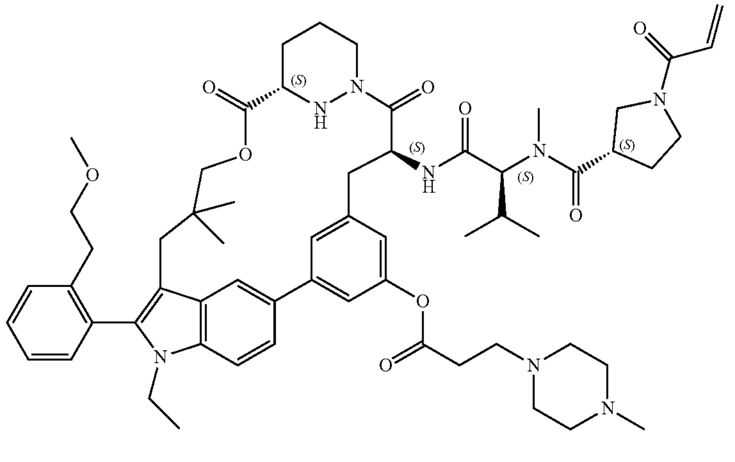 |

TABLE 2-continued
| Certain Compounds | |
|---|---|
| Ex # | Structure |
| B8 | 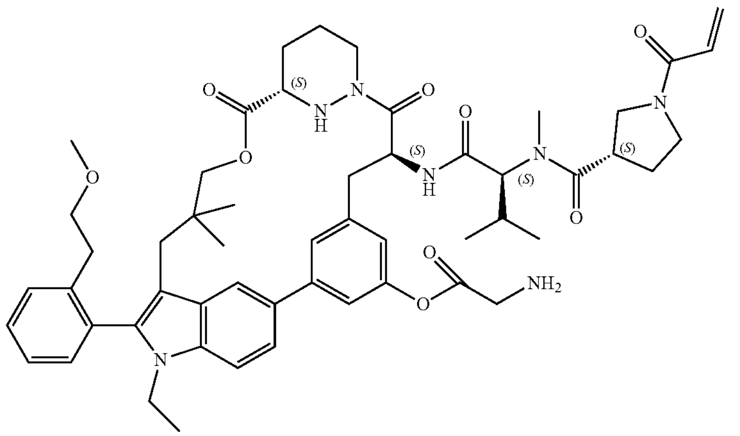 |
| B9 | 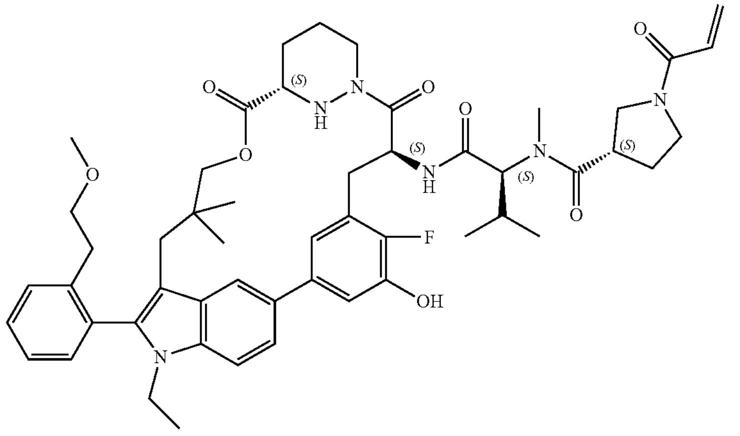 |
| B10 | 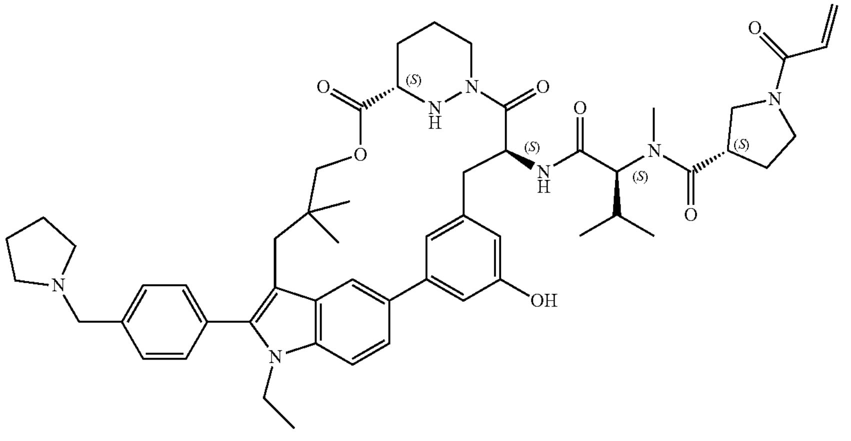 |

TABLE 2-continued
| Certain Compounds | |
|---|---|
| Ex # | Structure |
| B11 | 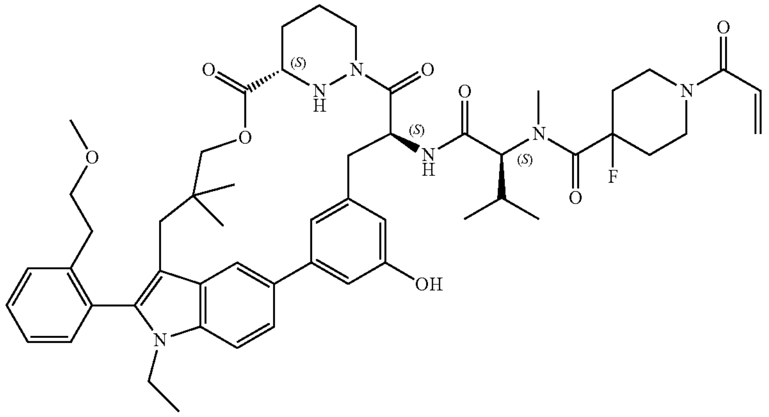 |
| B12 | 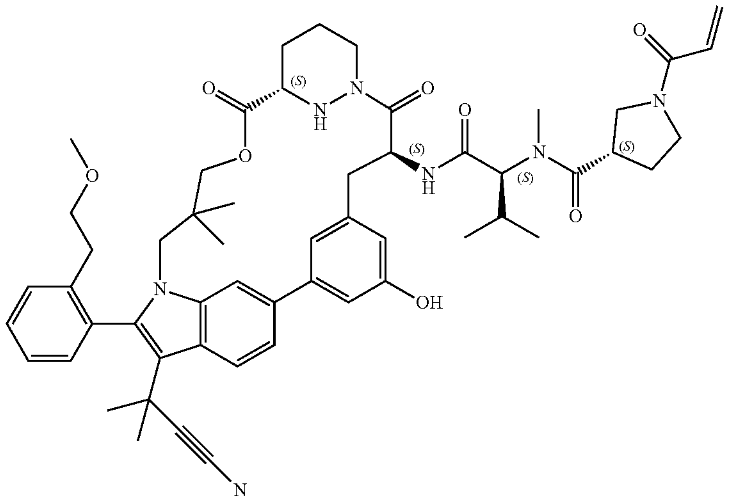 |
| B13 | 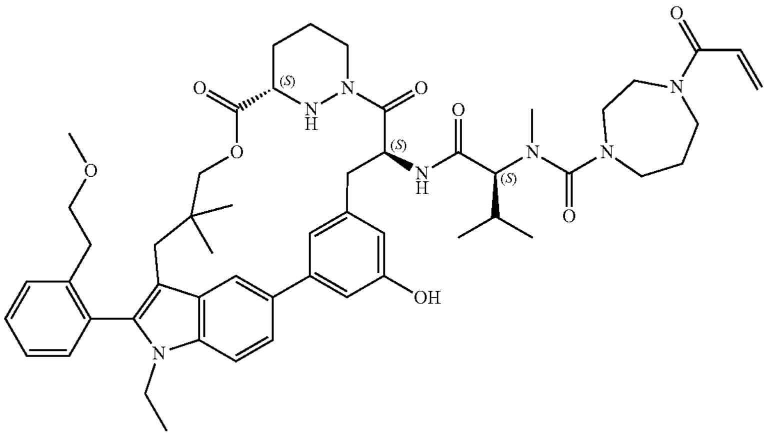 |

TABLE 2-continued
| Certain Compounds | |
|---|---|
| Ex # | Structure |
| B14 | 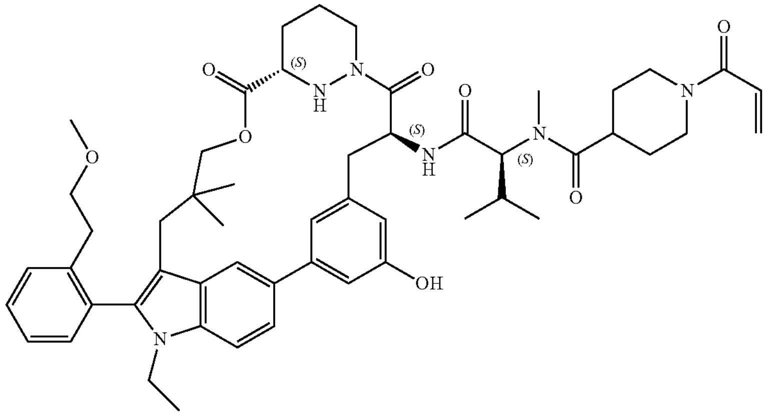 |
| B15 | 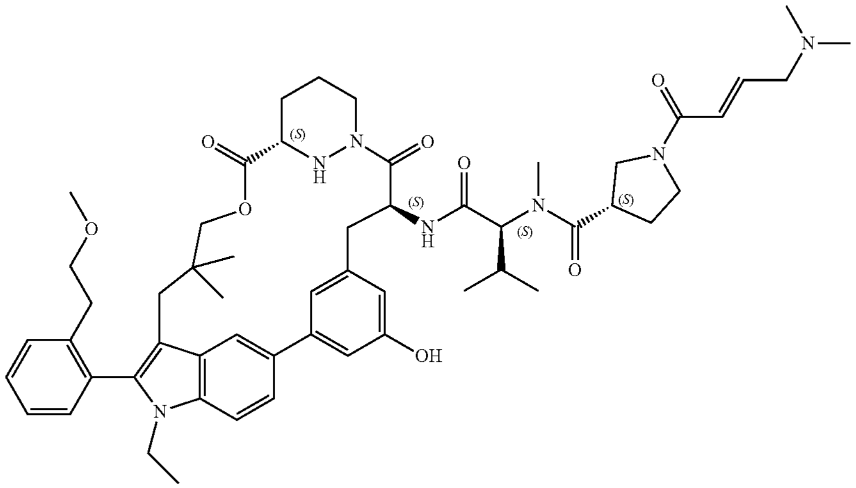 |
| B16 | 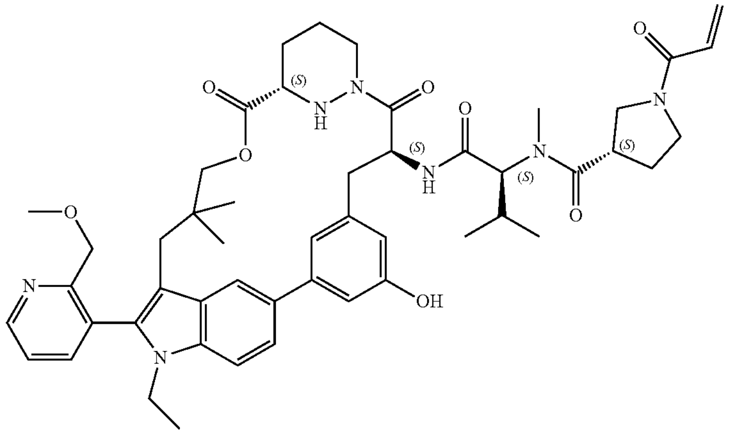 |

TABLE 2-continued
| Certain Compounds | |
|---|---|
| Ex # | Structure |
| B17 | 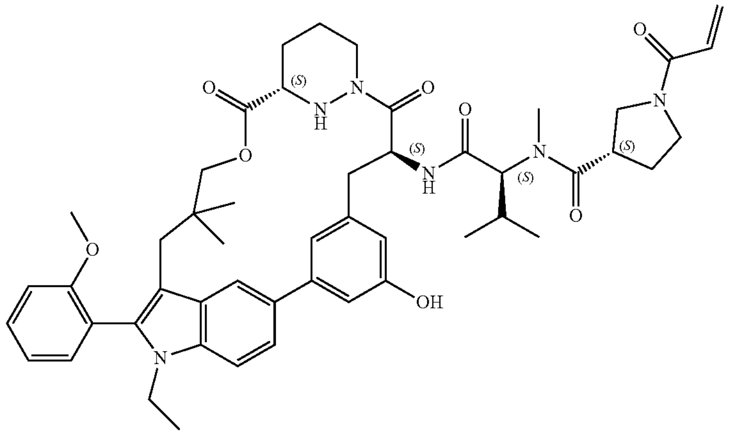 |
| B18 | 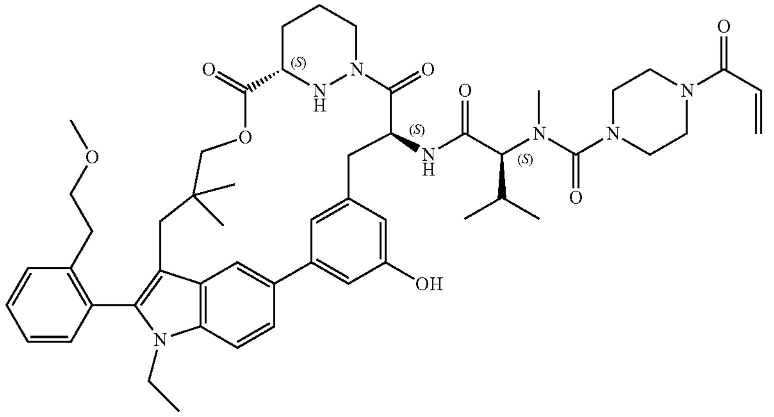 |
| B19 | 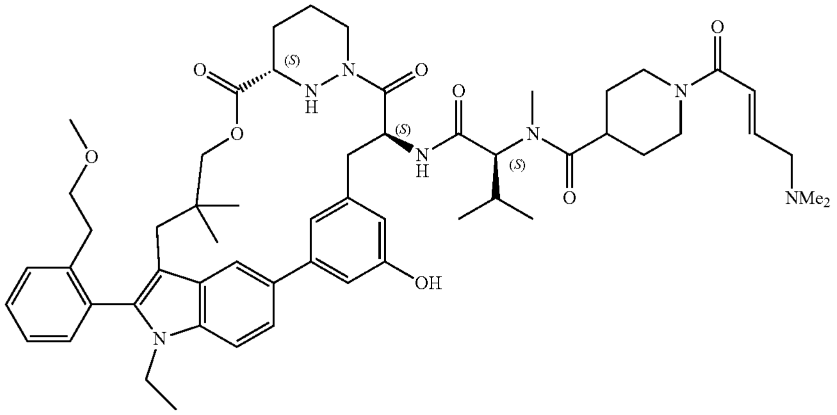 |

TABLE 2-continued
| Certain Compounds | |
|---|---|
| Ex # | Structure |
| B20 | 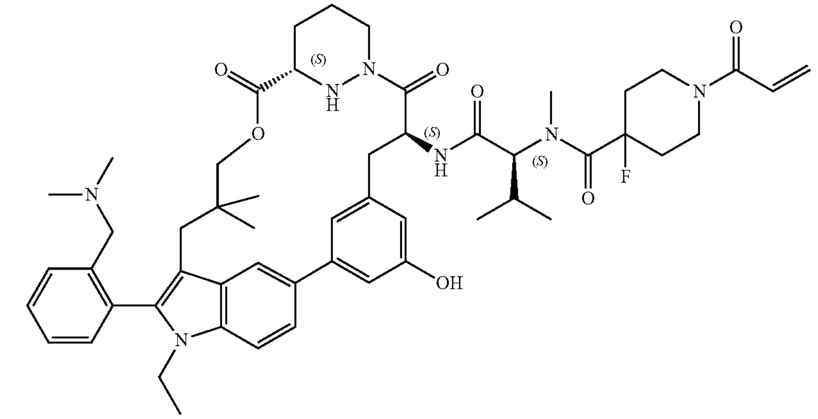 |
| B21 | 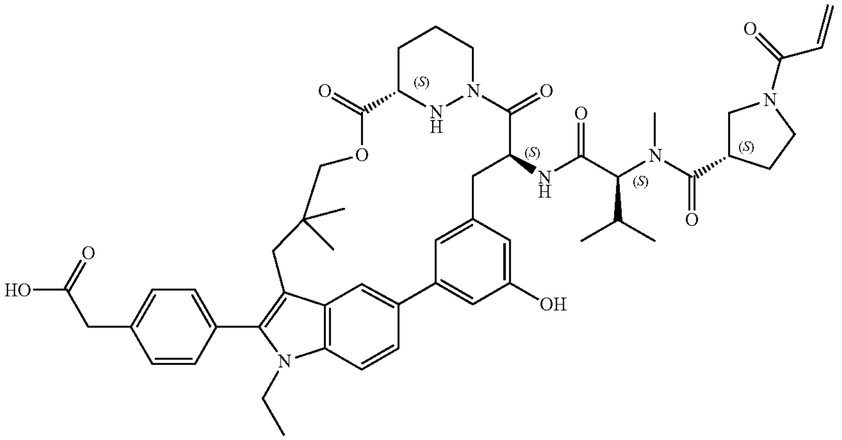 |
| B22 | 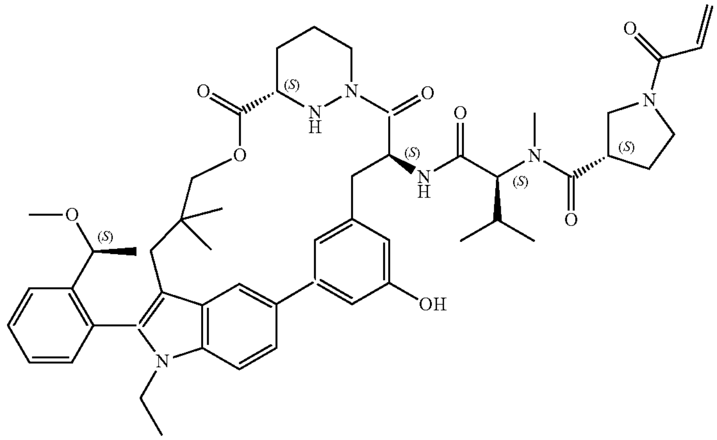 |

TABLE 2-continued
| Certain Compounds | |
|---|---|
| Ex # | Structure |
| B23 | 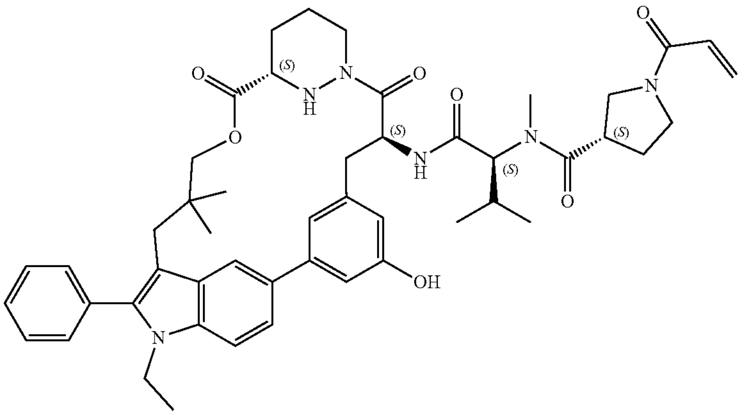 |
| B24 | 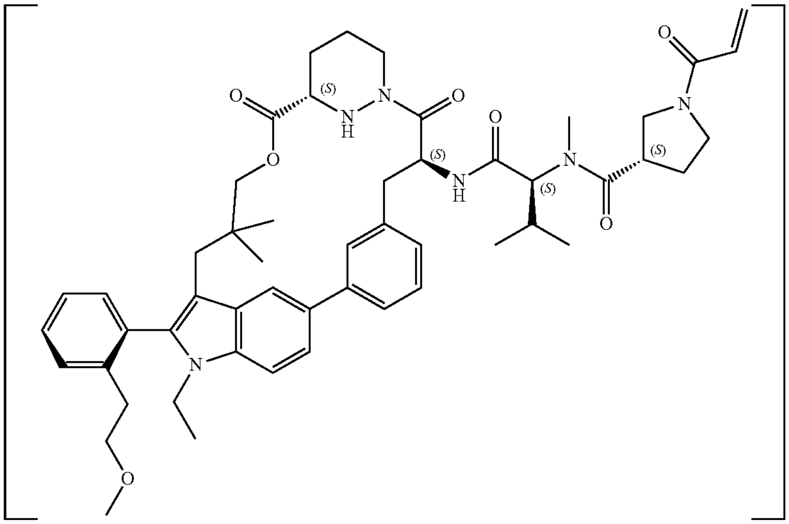 |
| B25 | 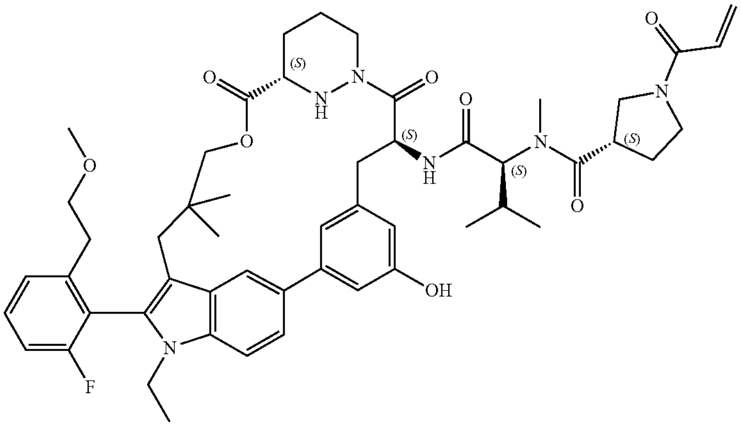 |

TABLE 2-continued
| Certain Compounds | |
|---|---|
| Ex # | Structure |
| B26 | 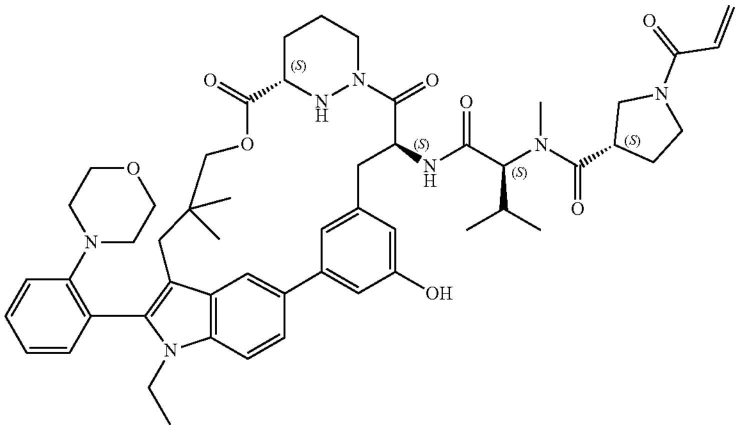 |
| B27 | 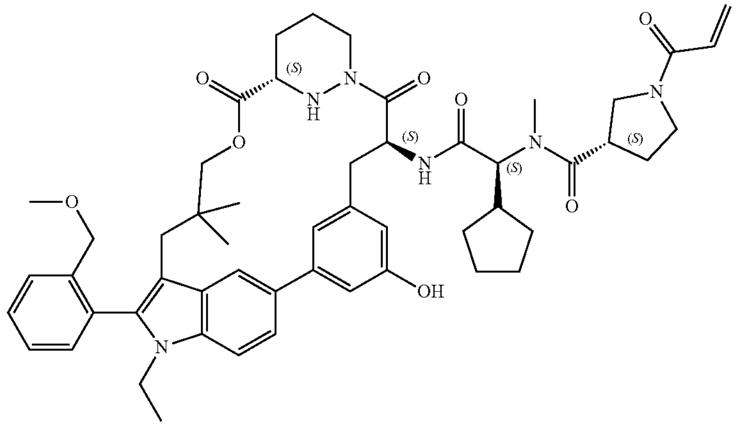 |
| B28 | 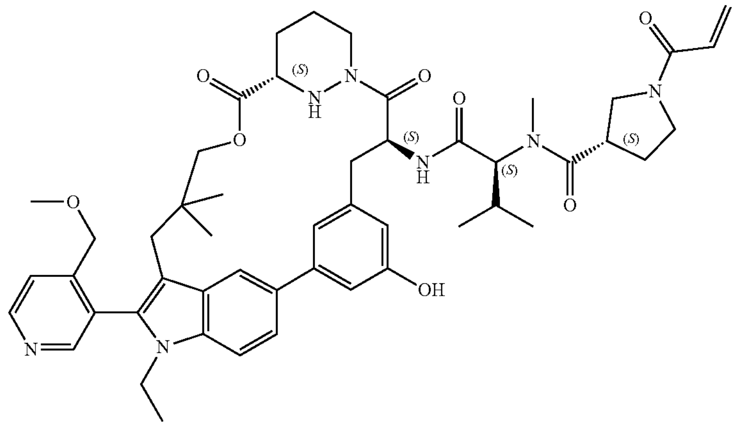 |

TABLE 2-continued
| Certain Compounds | |
|---|---|
| Ex # | Structure |
| B29 | 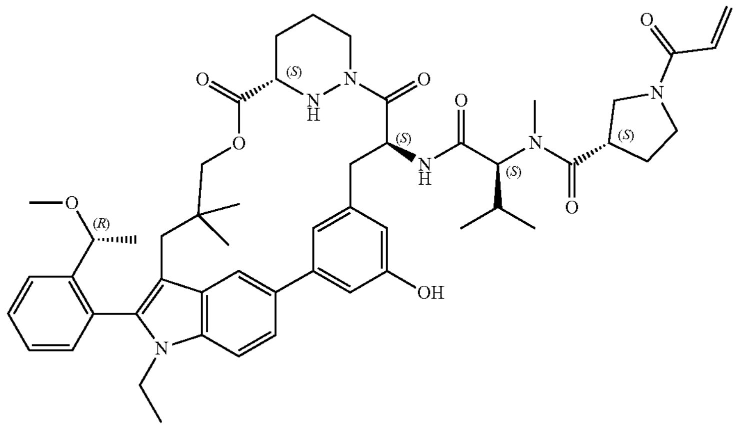 |
| B30 | 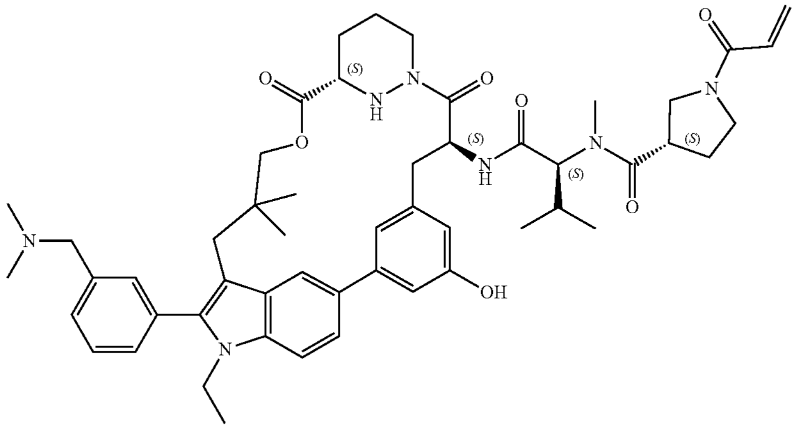 |
| B31 | 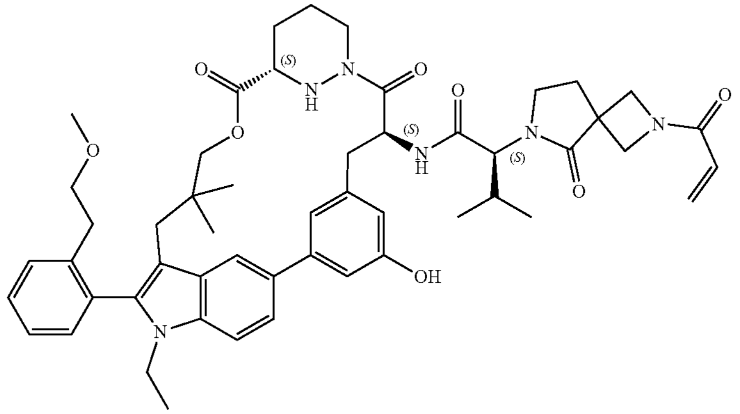 |

TABLE 2-continued
| Certain Compounds | |
|---|---|
| Ex # | Structure |
| B32 | 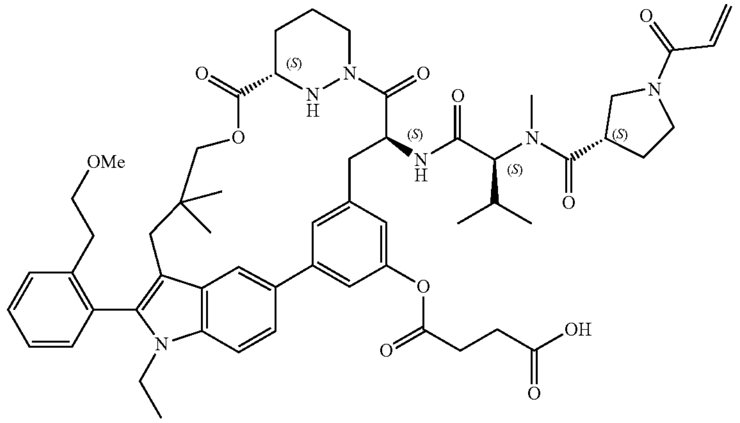 |
| B33 | 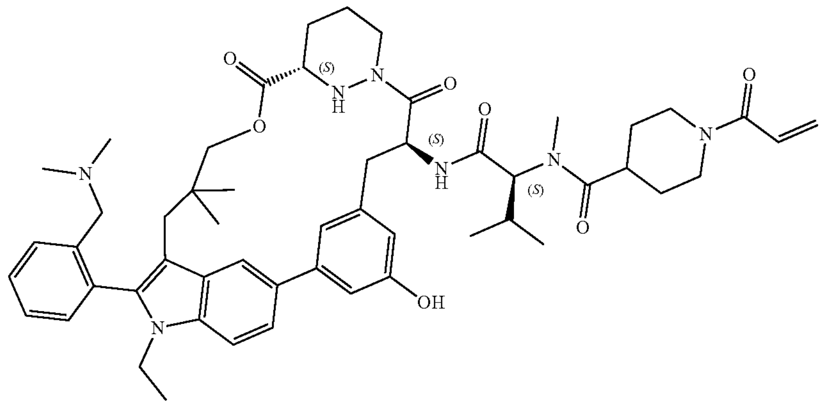 |
| B34 | 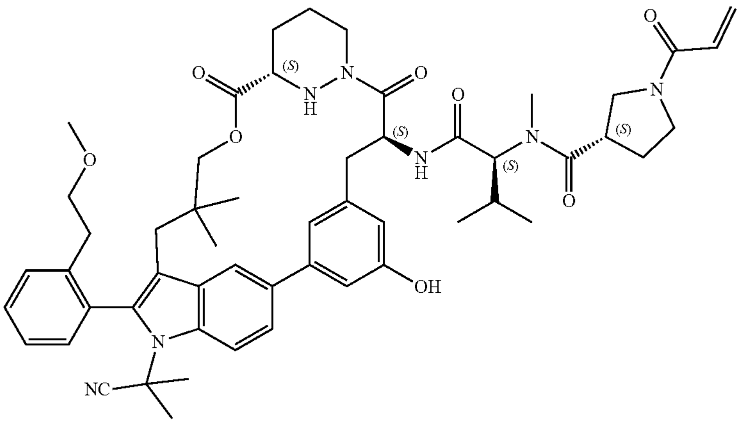 |

TABLE 2-continued
| Certain Compounds | |
|---|---|
| Ex # | Structure |
| B35 | 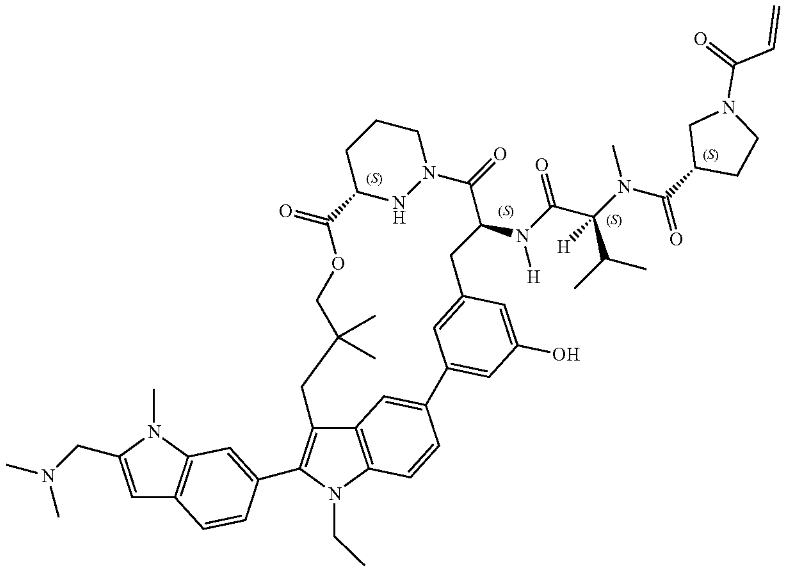 |
| B36 | 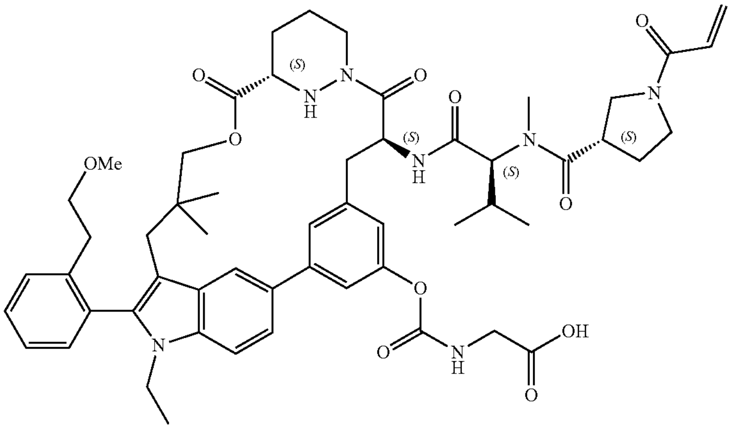 |
| B37 | 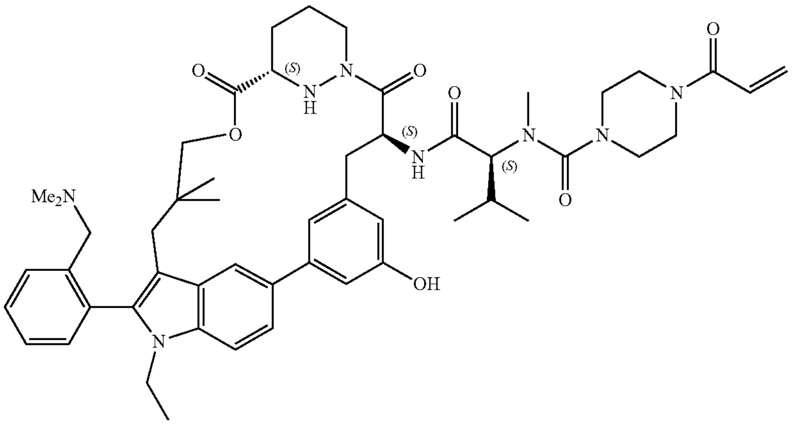 |

TABLE 2-continued
| Certain Compounds | |
|---|---|
| Ex # | Structure |
| B38 | 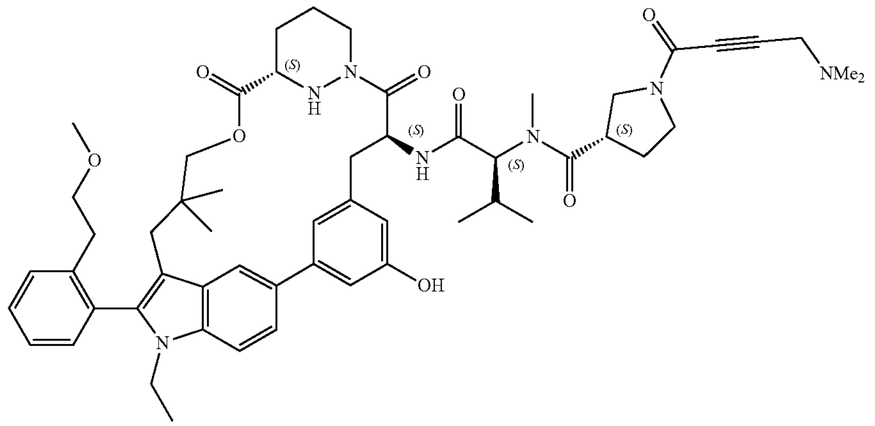 |
| B39 | 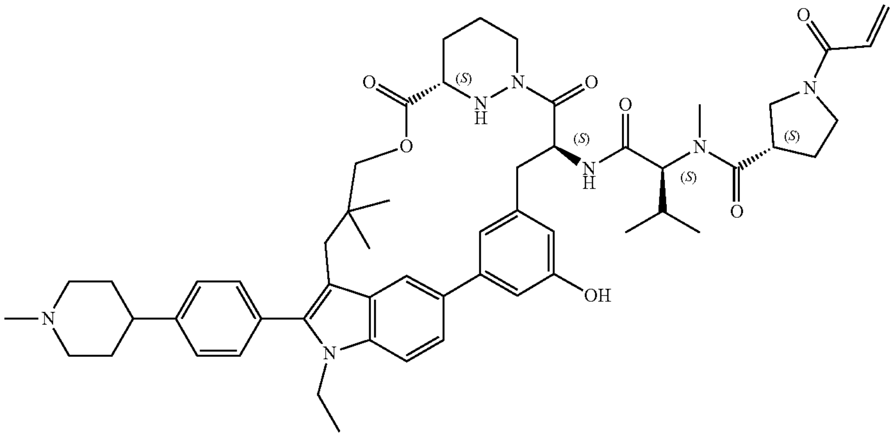 |
| B40 | 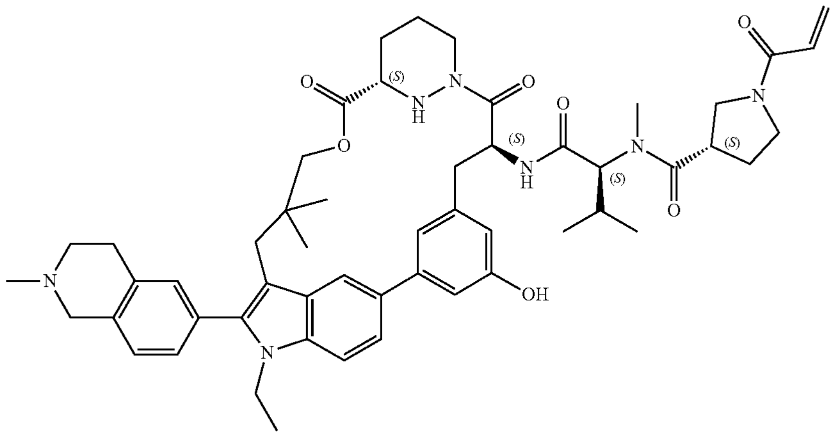 |

TABLE 2-continued
| Certain Compounds | |
|---|---|
| Ex # | Structure |
| B41 | 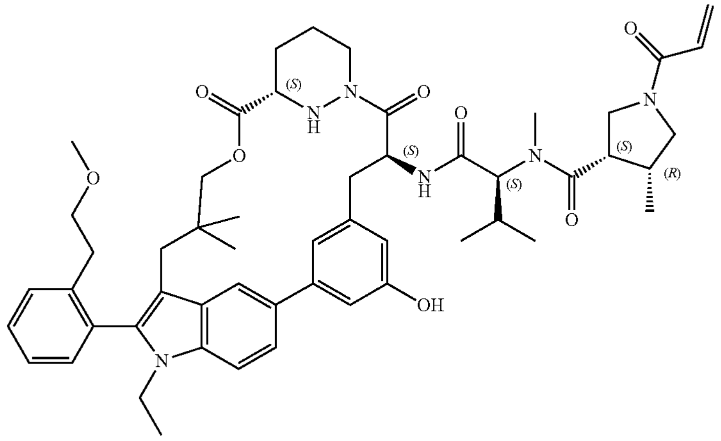 |
| B42 | 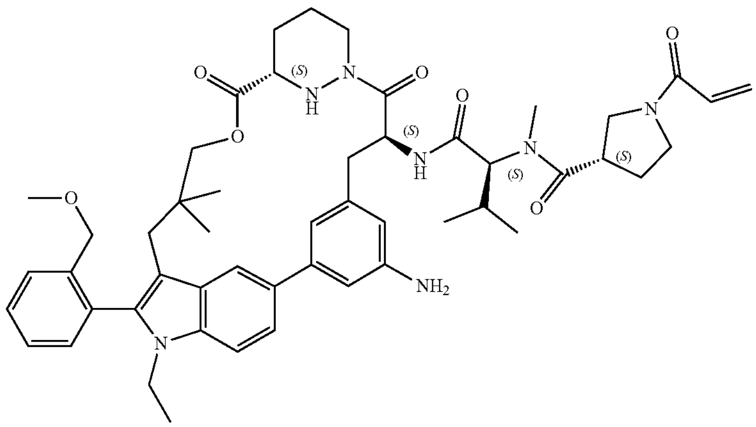 |
| B43 | 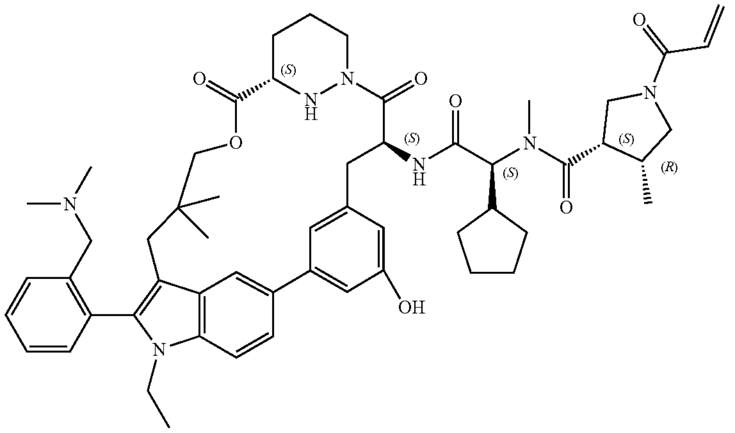 |

TABLE 2-continued
| Certain Compounds | |
|---|---|
| Ex # | Structure |
| B44 | 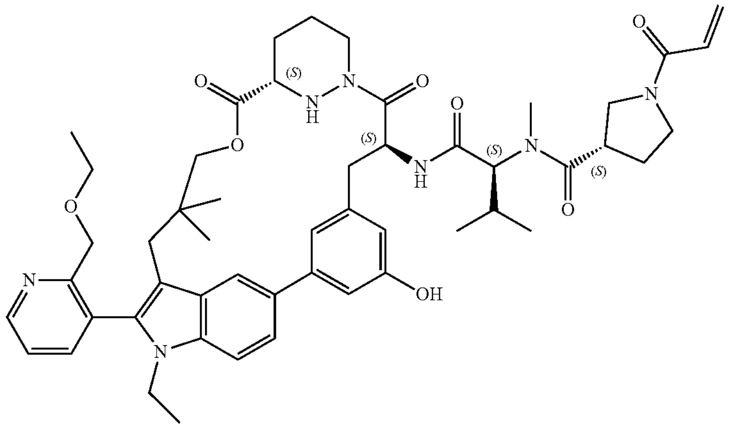 |
| B45 | 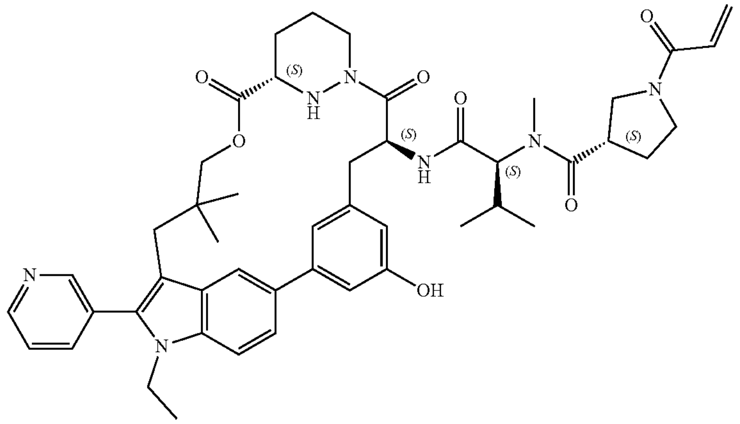 |
| B46 | 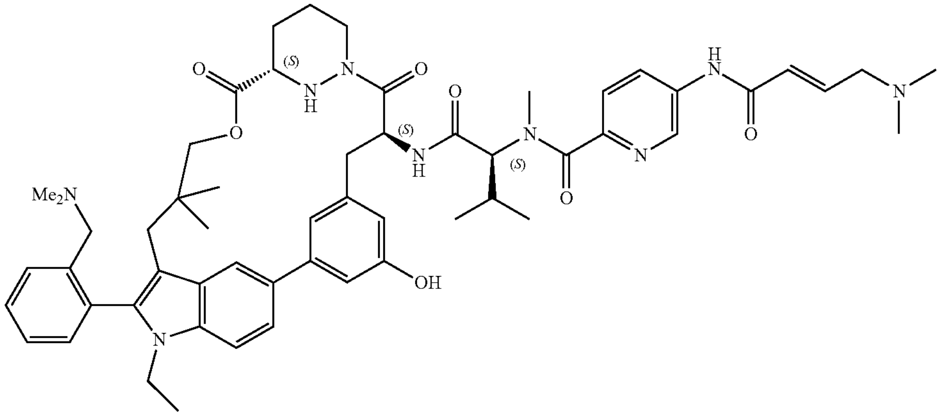 |

TABLE 2-continued
| Certain Compounds | |
|---|---|
| Ex # | Structure |
| B47 | 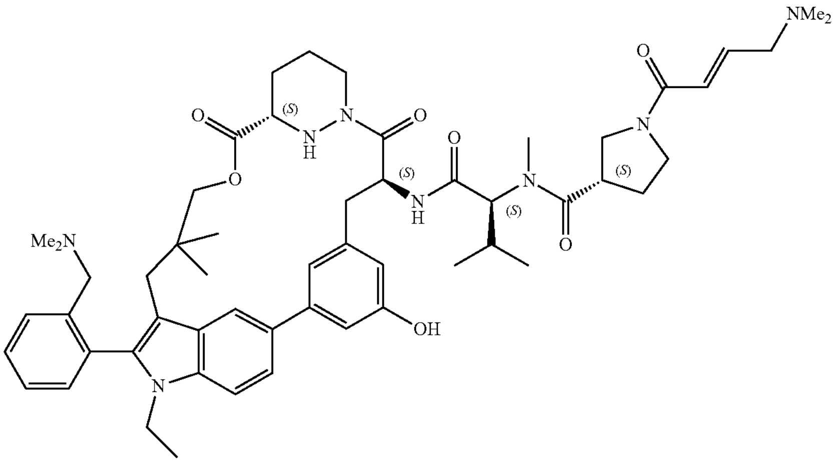 |
| B48 | 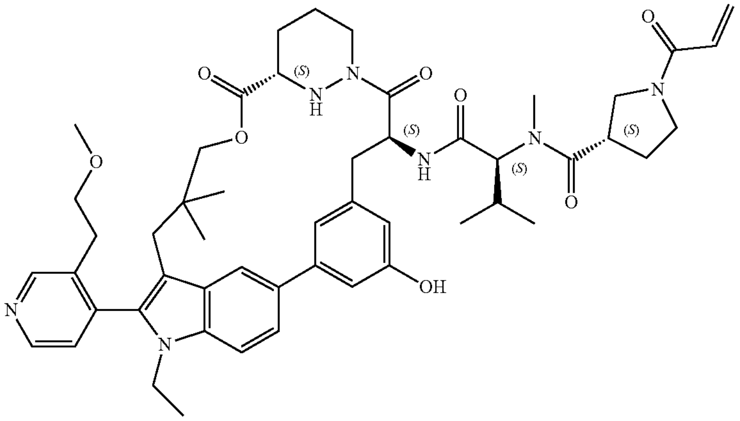 |
| B49 | 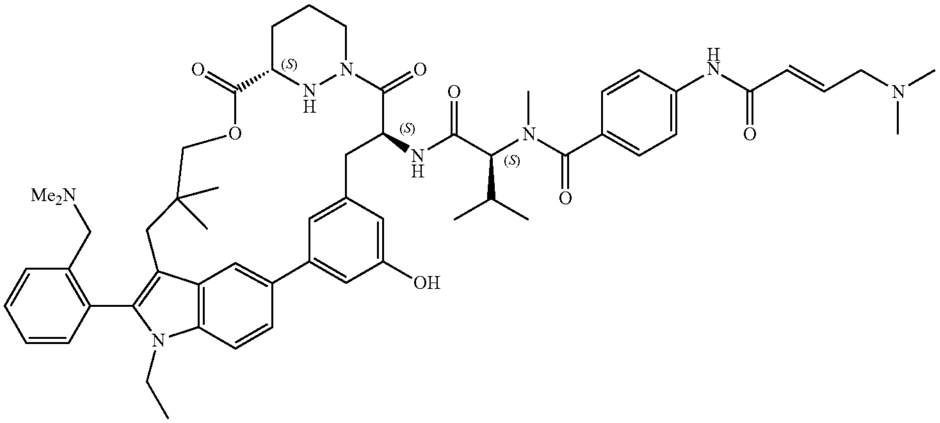 |

TABLE 2-continued
| Certain Compounds | |
|---|---|
| Ex # | Structure |
| B50 | 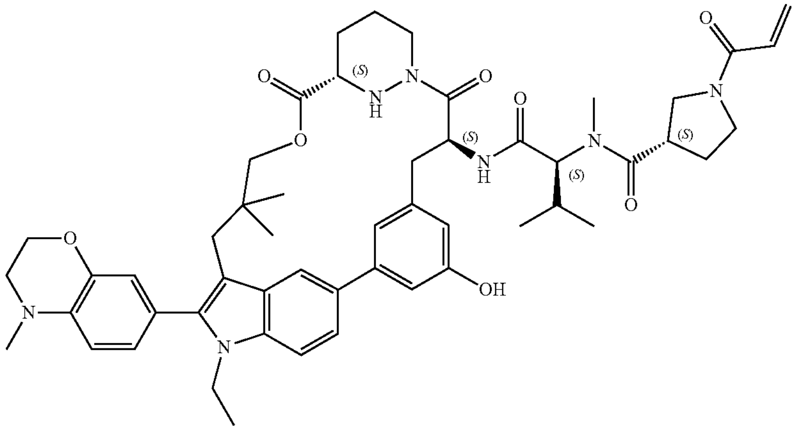 |
| B51 | 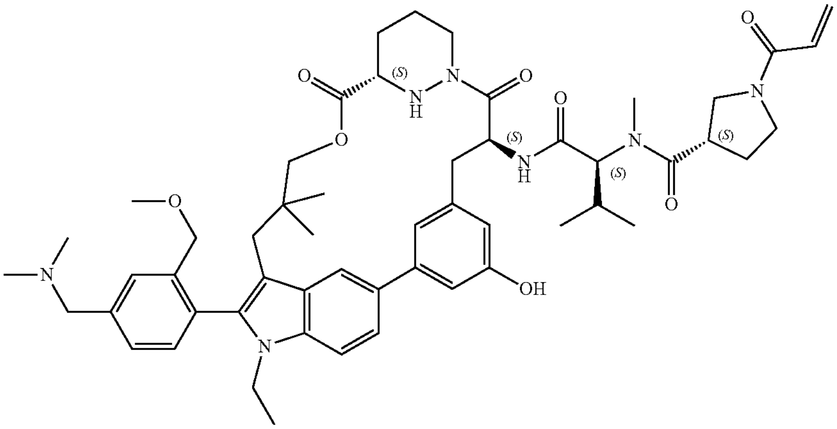 |
| B52 | 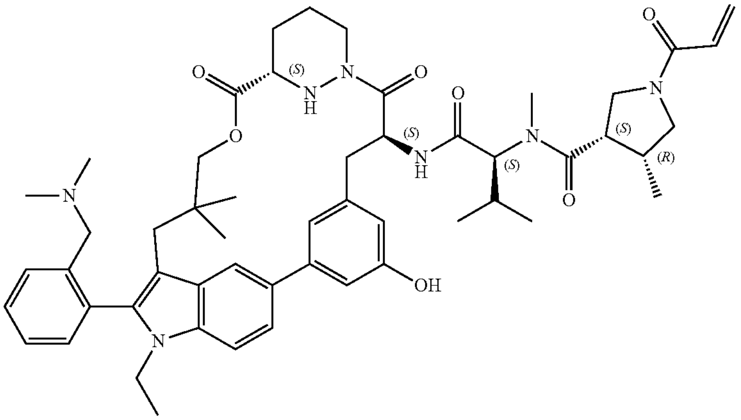 |

TABLE 2-continued
| Certain Compounds | |
|---|---|
| Ex # | Structure |
| B53 | 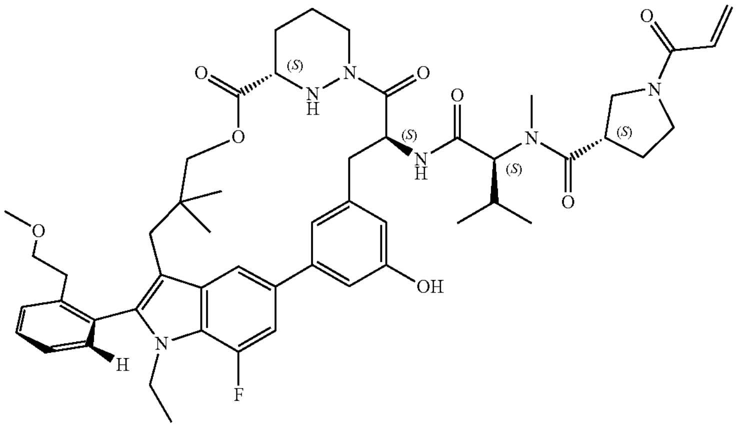 |
| B54 | 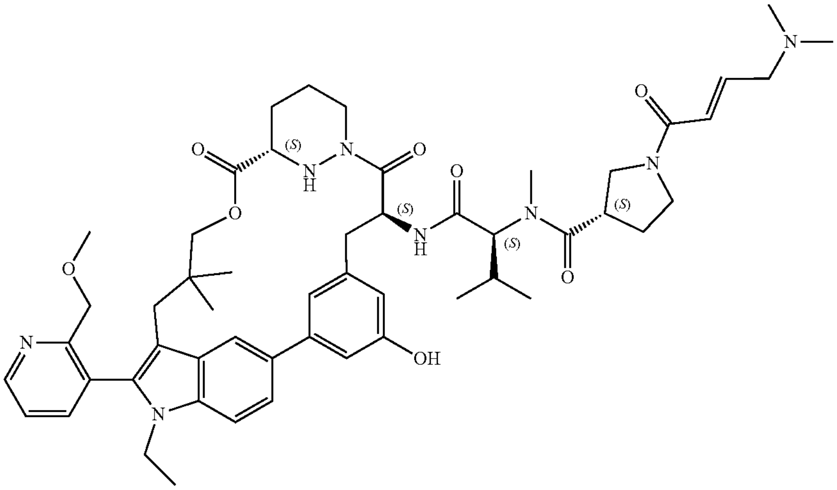 |
| B55 | 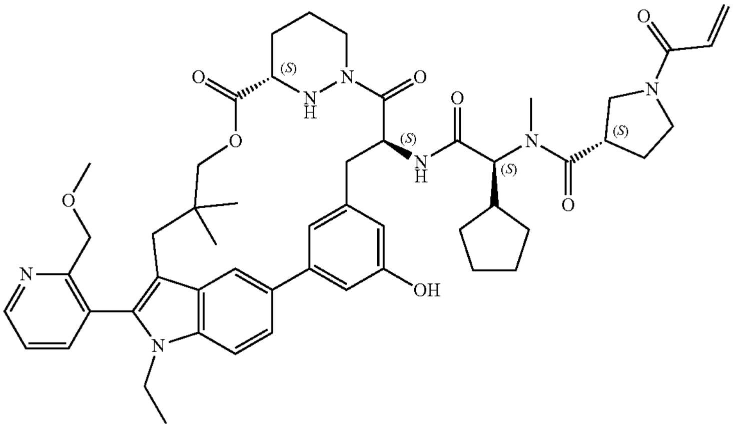 |

TABLE 2-continued
| Certain Compounds | |
|---|---|
| Ex # | Structure |
| B56 | 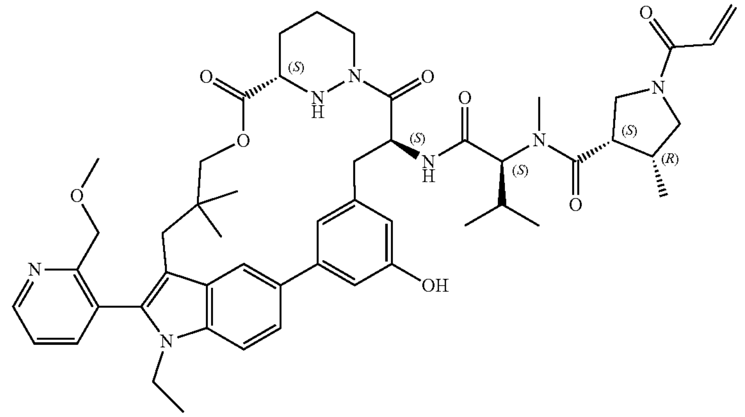 |
| B57 | 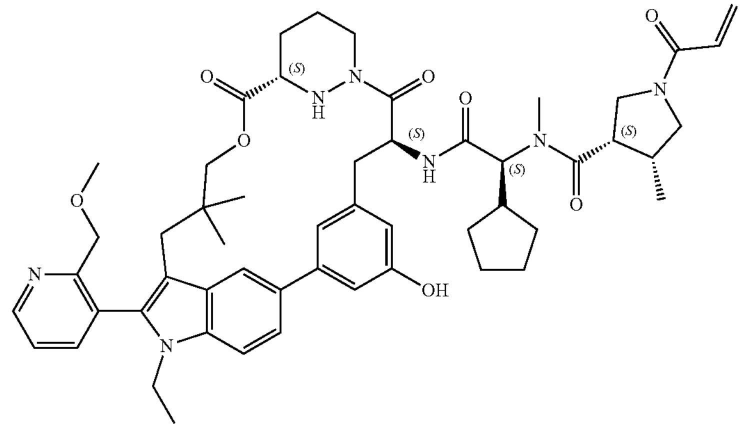 |
| B58 | 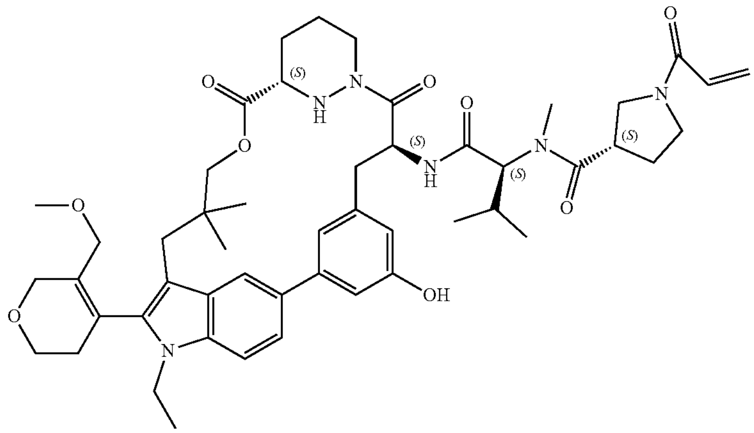 |

TABLE 2-continued
| Certain Compounds | |
|---|---|
| Ex # | Structure |
| B59 | 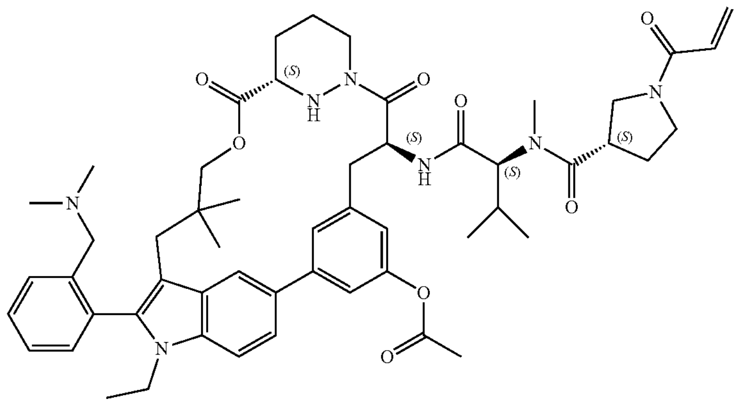 |
| B60 | 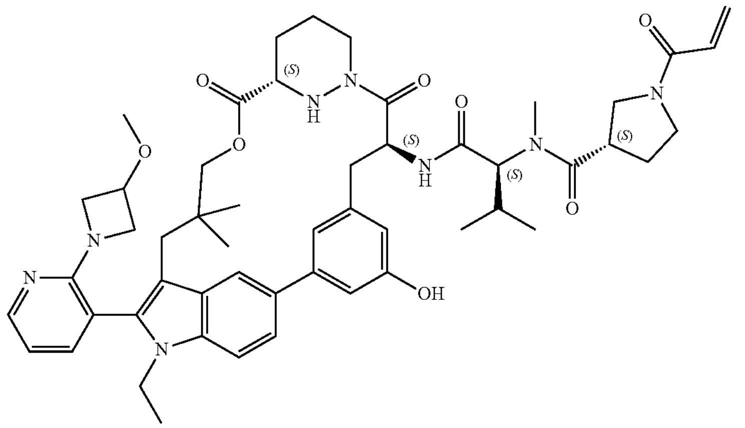 |
| B61 | 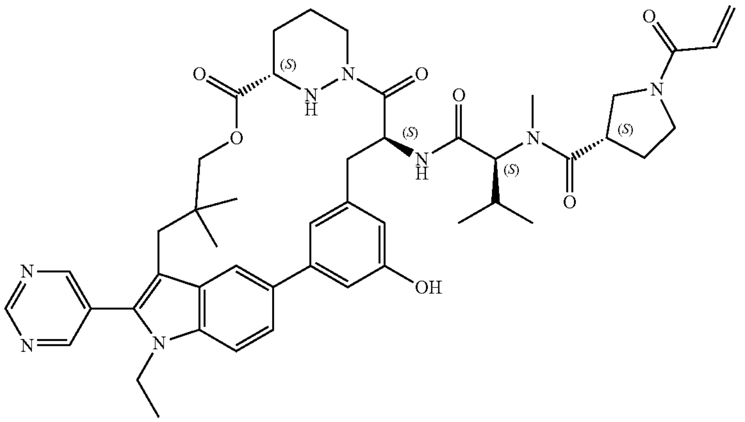 |

TABLE 2-continued
| Certain Compounds | |
|---|---|
| Ex # | Structure |
| B62 | 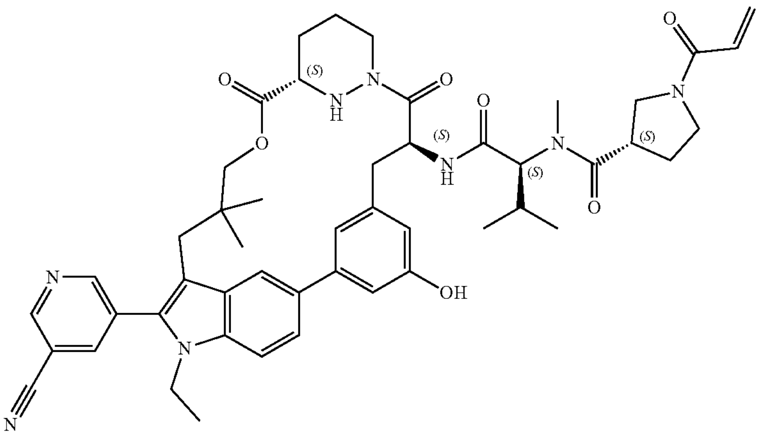 |
| B63 | 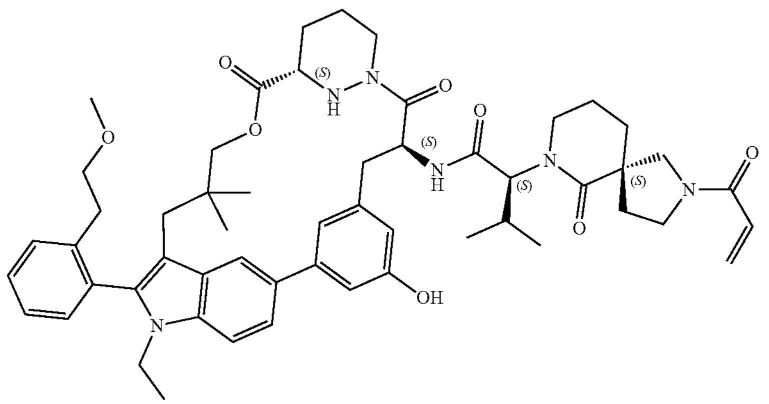 |
| B64 | 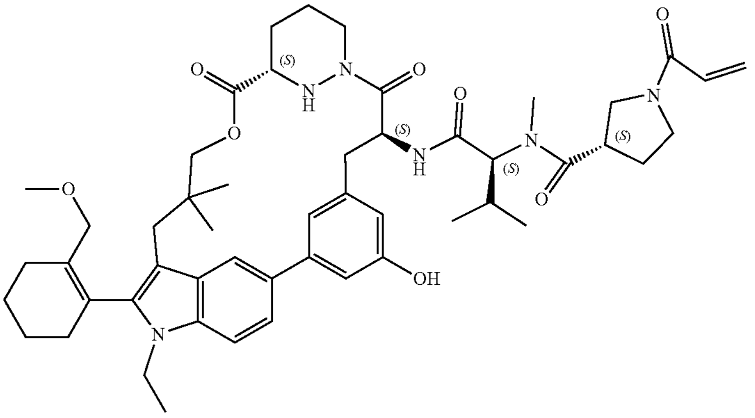 |

TABLE 2-continued
| Certain Compounds | |
|---|---|
| Ex # | Structure |
| B65 | 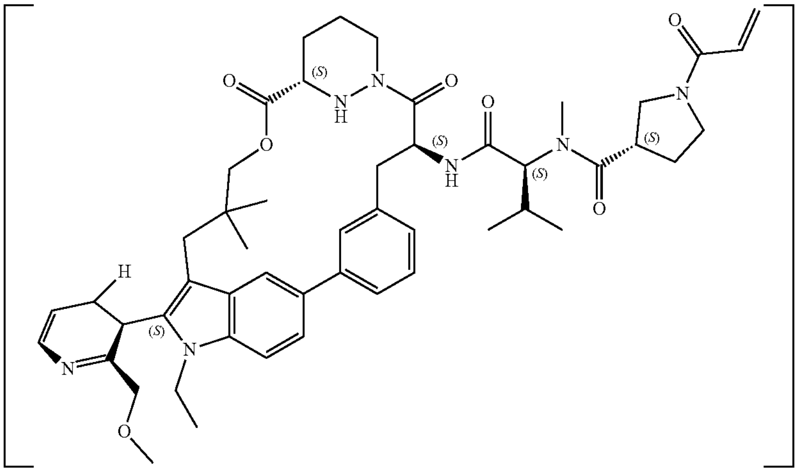 |
| B66 | 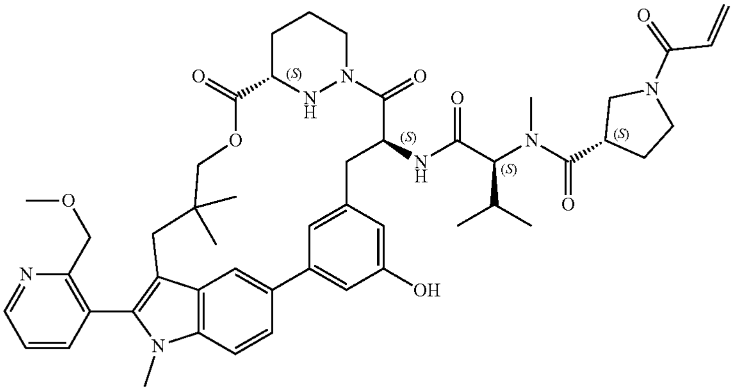 |
| B67 | 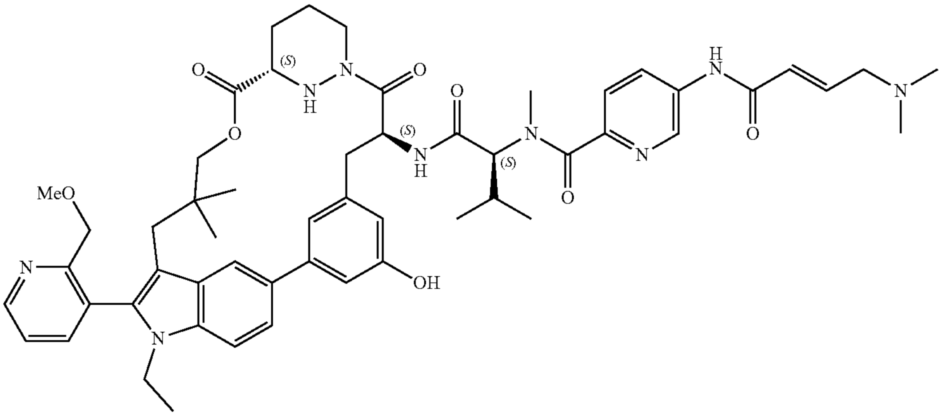 |

TABLE 2-continued
| Certain Compounds | |
|---|---|
| Ex # | Structure |
| B68 | 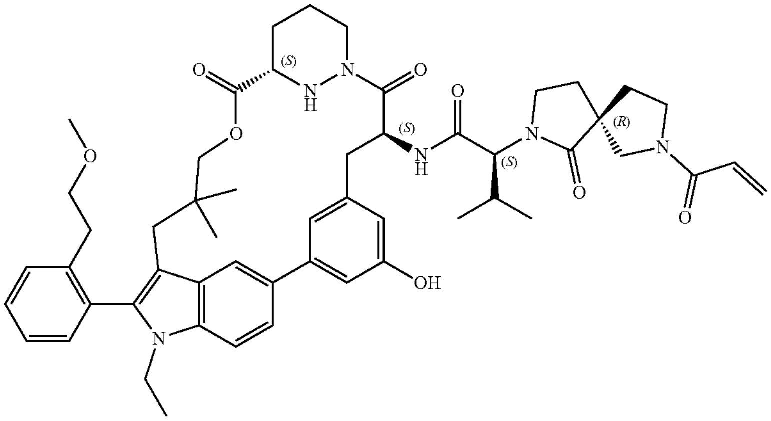 |
| B69 | 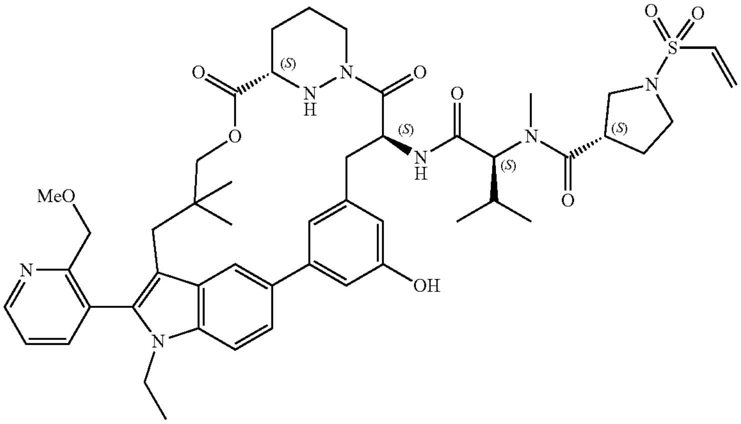 |
| B70 | 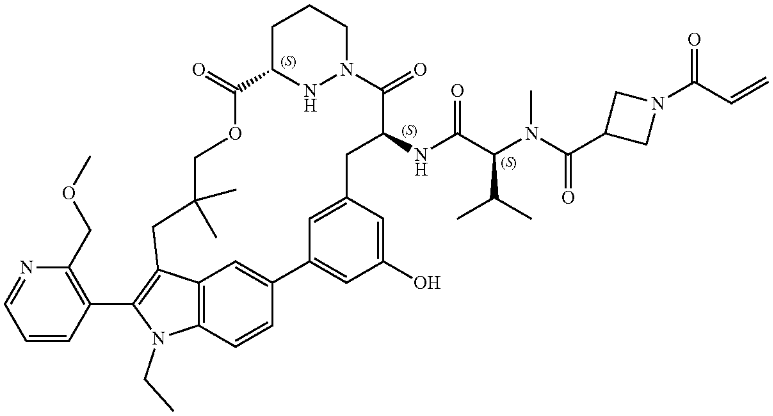 |

TABLE 2-continued
| Certain Compounds | |
|---|---|
| Ex # | Structure |
| B71 | 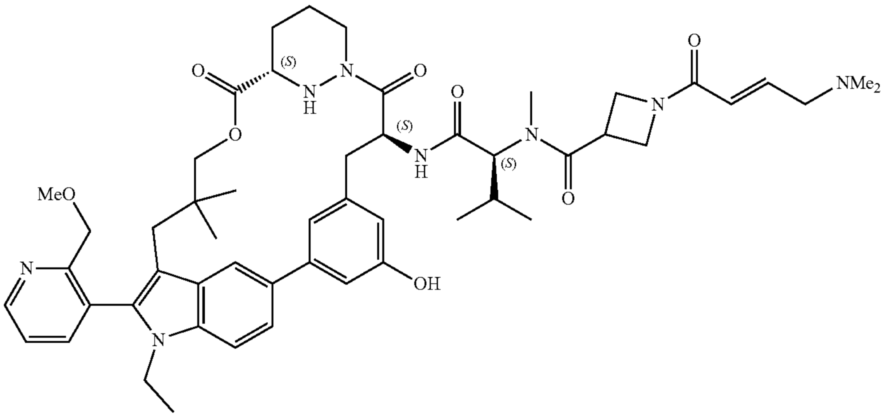 |
| B72 | 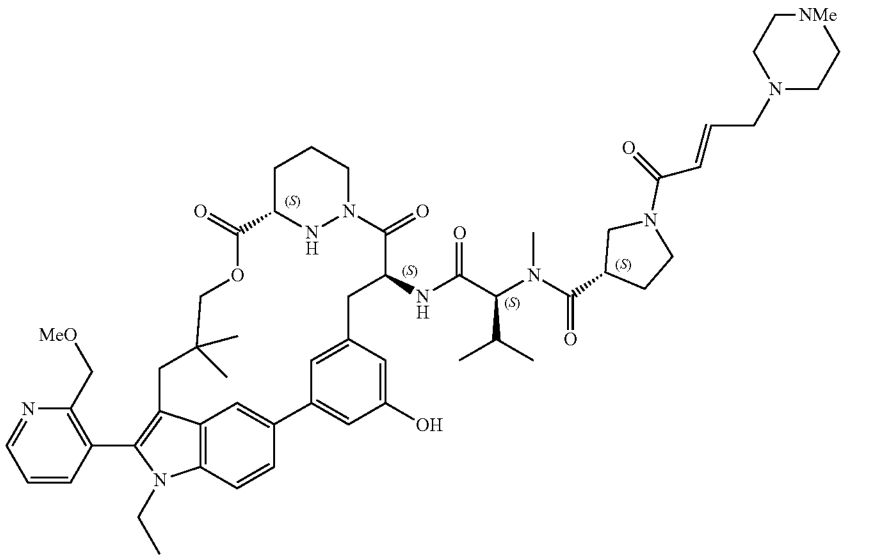 |
| B73 | 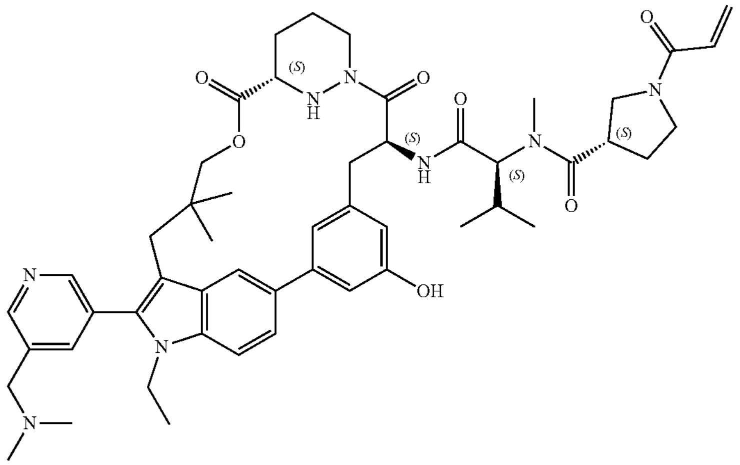 |

TABLE 2-continued
| Certain Compounds | |
|---|---|
| Ex # | Structure |
| B74 | 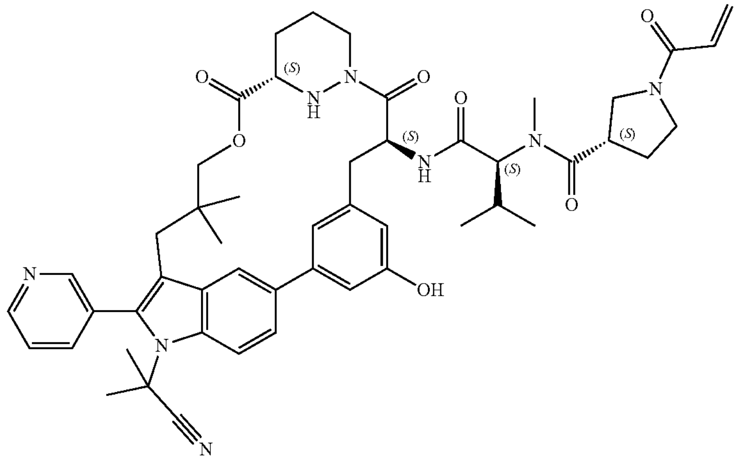 |
| B75 | 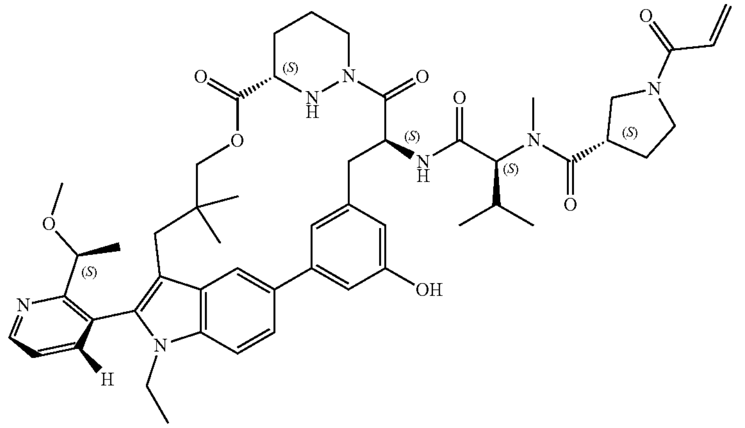 |
| B76 | 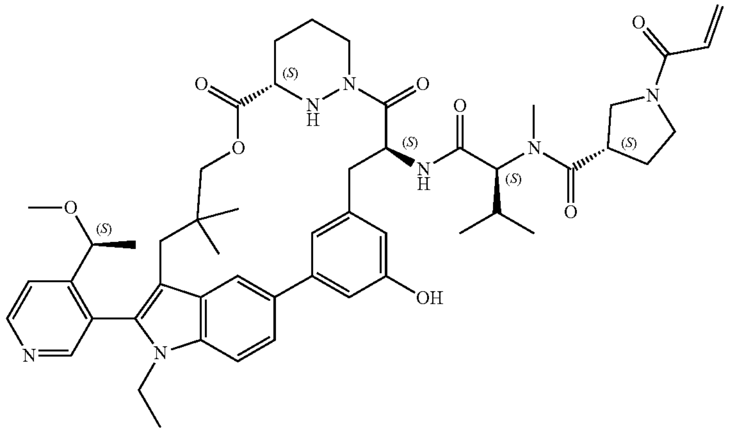 |

TABLE 2-continued
| Certain Compounds | |
|---|---|
| Ex # | Structure |
| B77 | 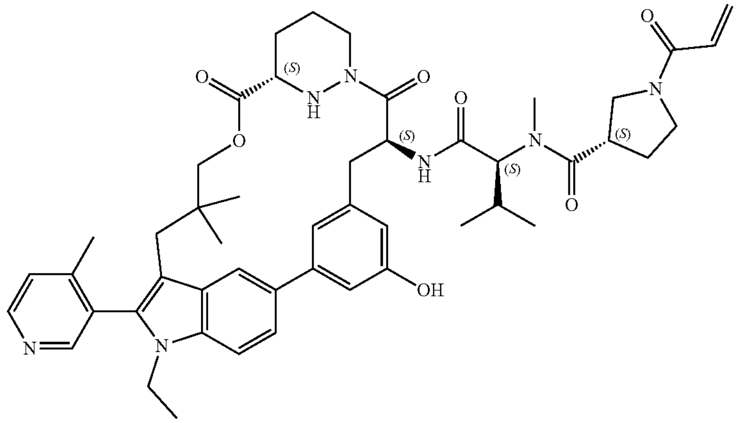 |
| B78 | 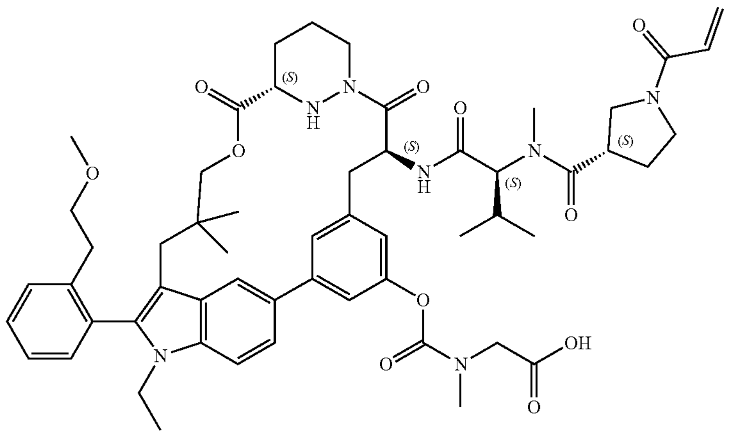 |
| B79 | 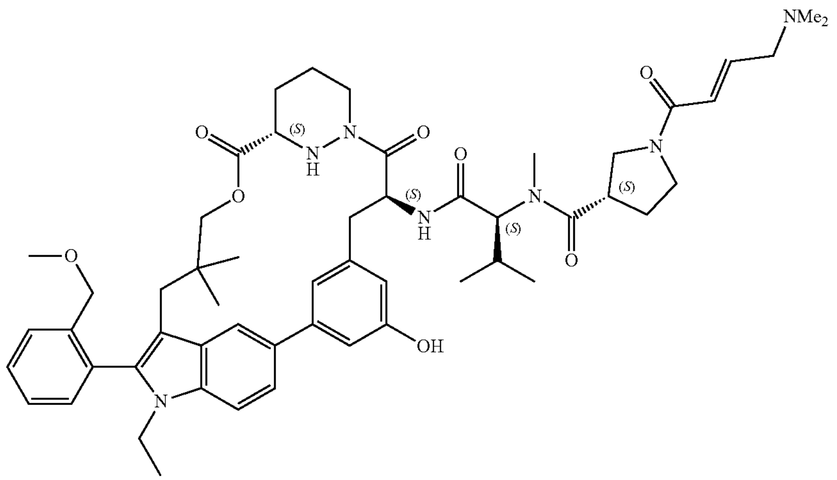 |

TABLE 2-continued
| Certain Compounds | |
|---|---|
| Ex # | Structure |
| B80 | 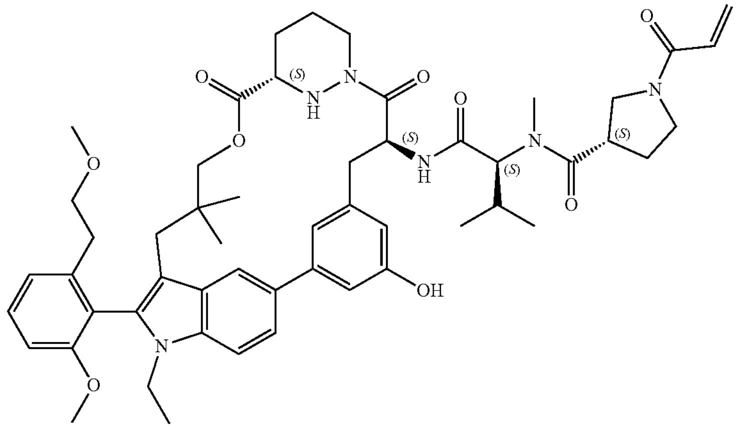 |
| B81 | 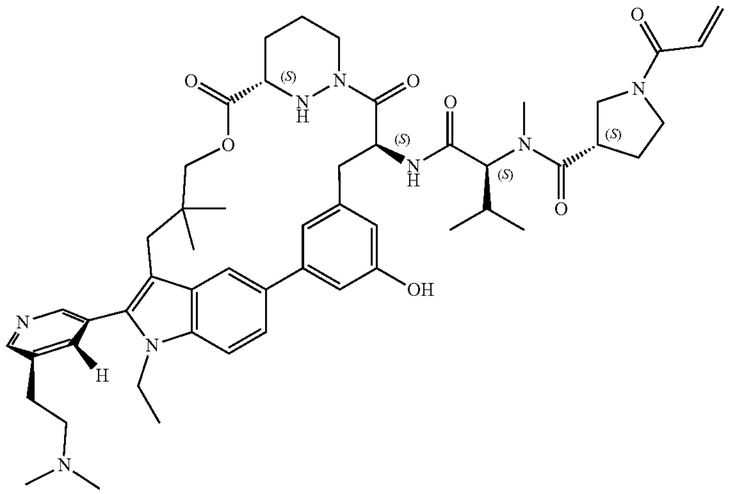 |
| B82 | 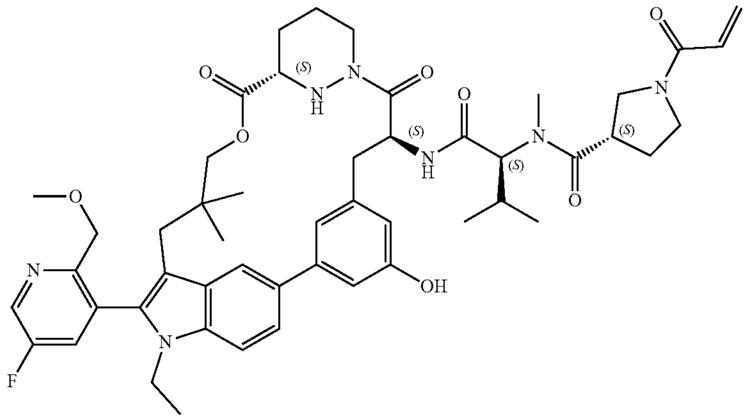 |

TABLE 2-continued
| Certain Compounds | |
|---|---|
| Ex # | Structure |
| B83 | 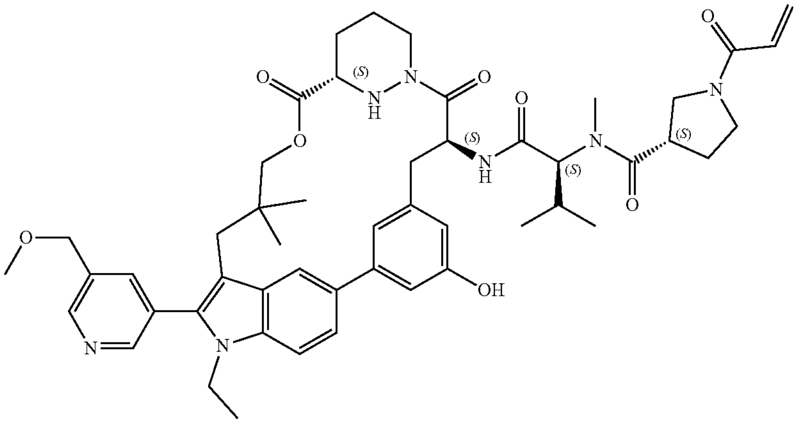 |
| B84 | 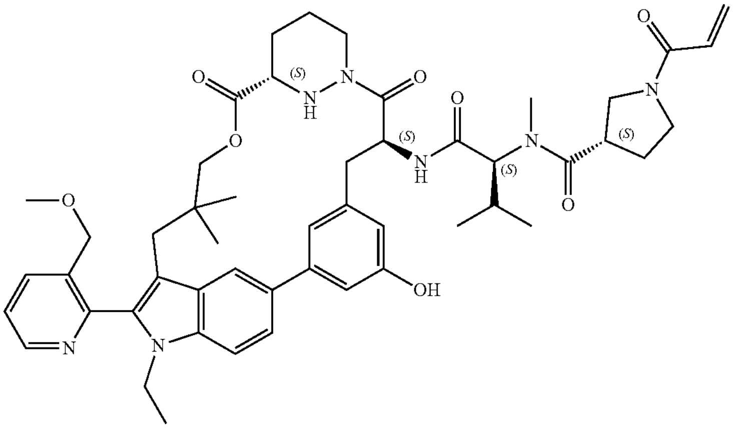 |
| B85 | 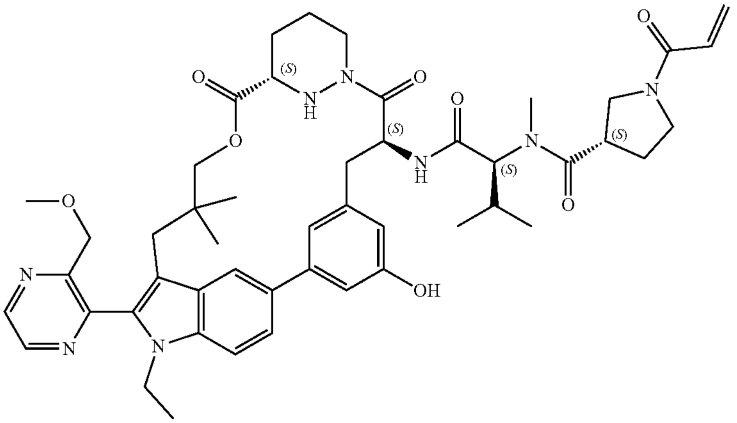 |

TABLE 2-continued
| Certain Compounds | |
|---|---|
| Ex # | Structure |
| B86 | 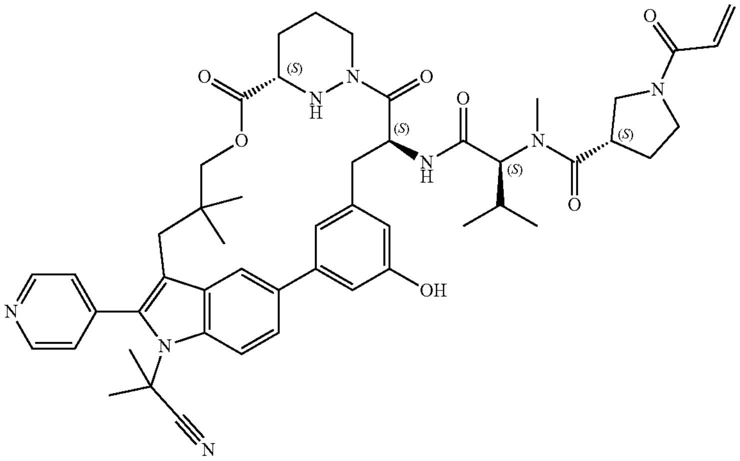 |
| B87 | 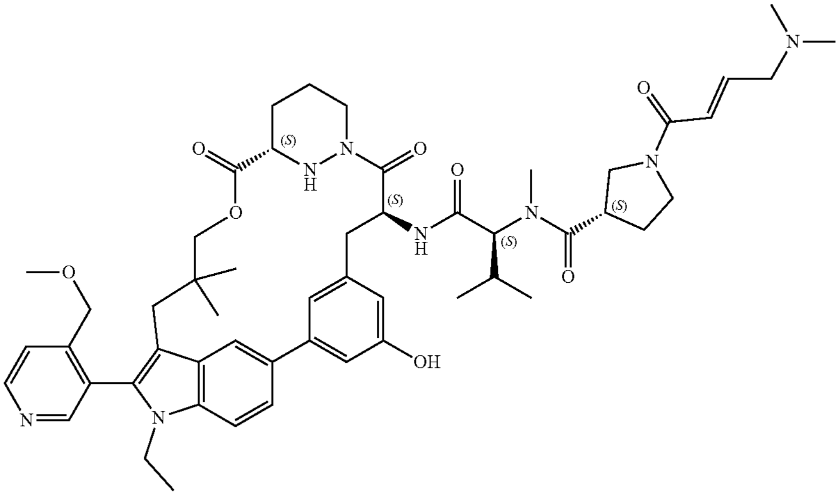 |
| B88 | 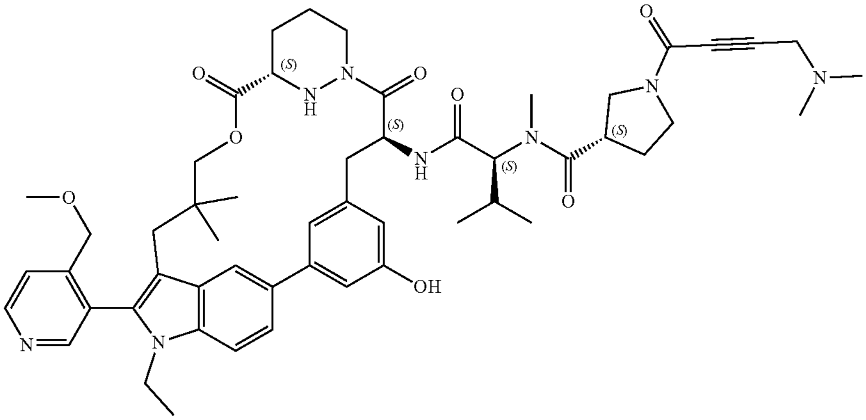 |

TABLE 2-continued
| Certain Compounds | |
|---|---|
| Ex # | Structure |
| B89 | 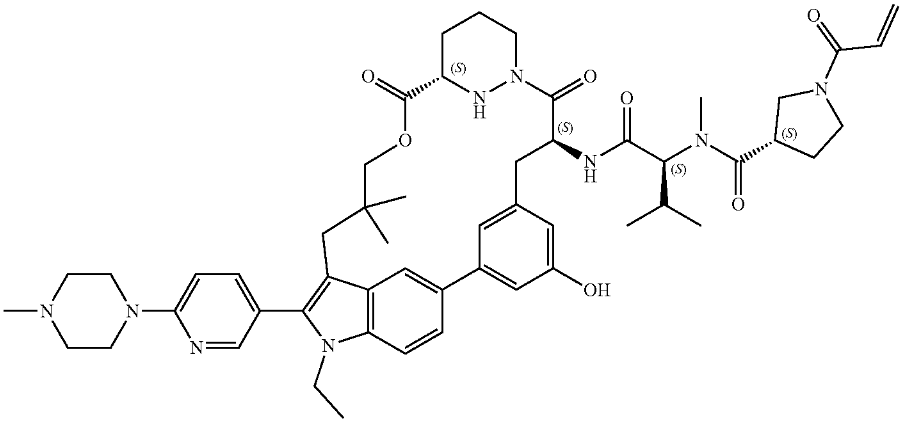 |
| B90 | 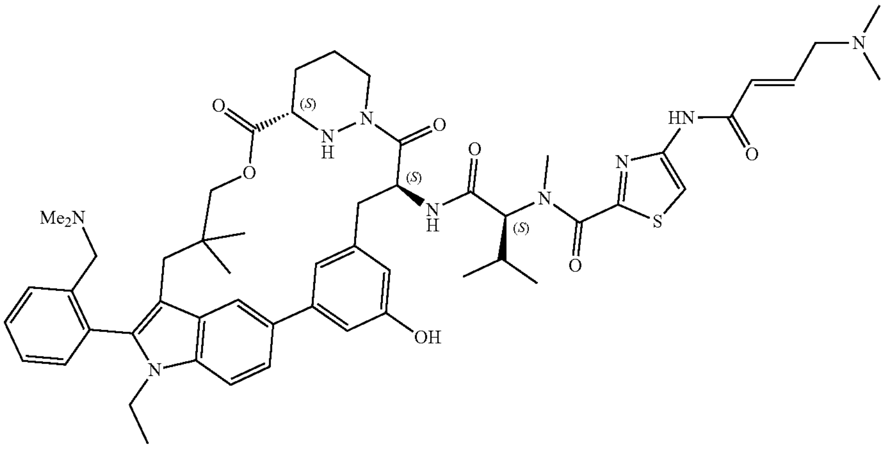 |
| B91 | 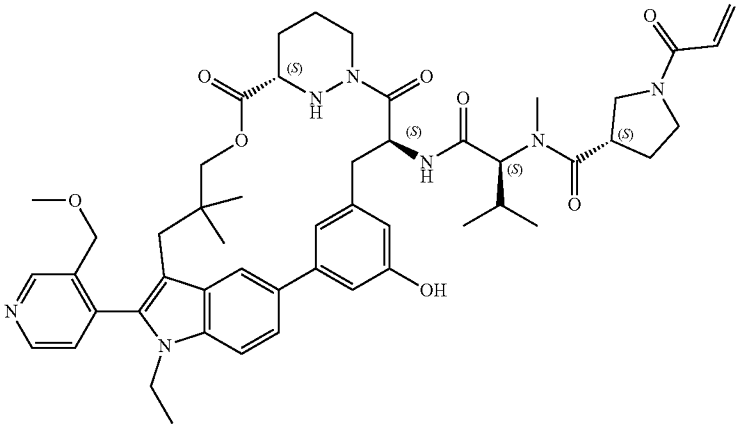 |

TABLE 2-continued
| Certain Compounds | |
|---|---|
| Ex # | Structure |
| B92 | 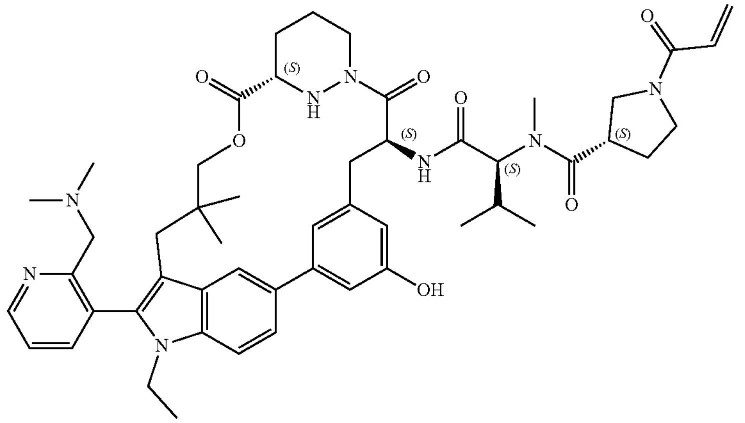 |
| B93 | 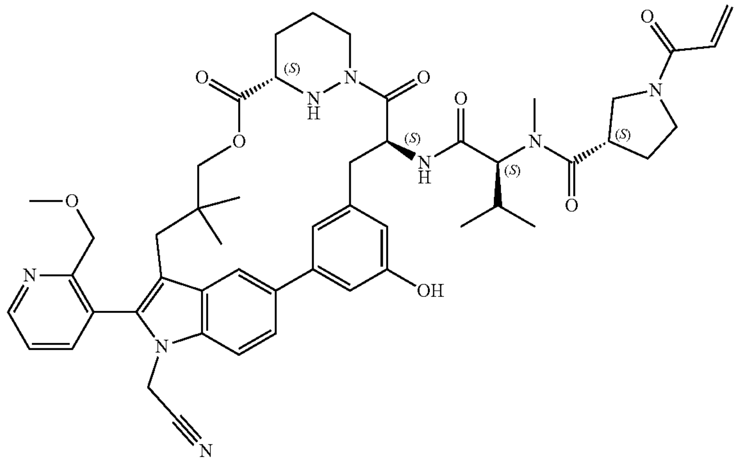 |
| B94 | 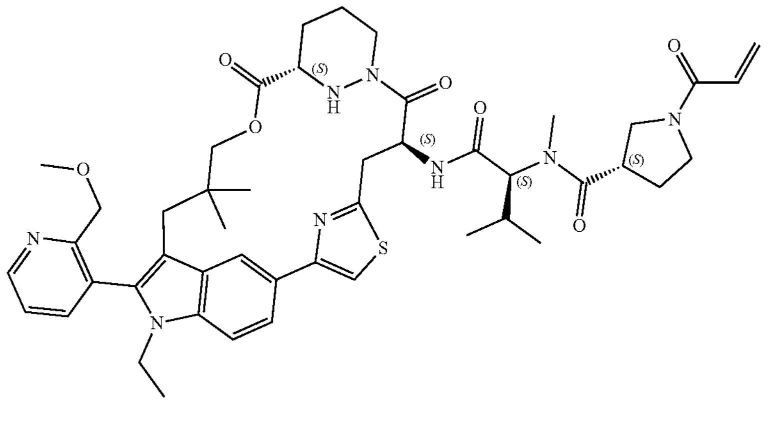 |

TABLE 2-continued
| Certain Compounds | |
|---|---|
| Ex # | Structure |
| B95 | 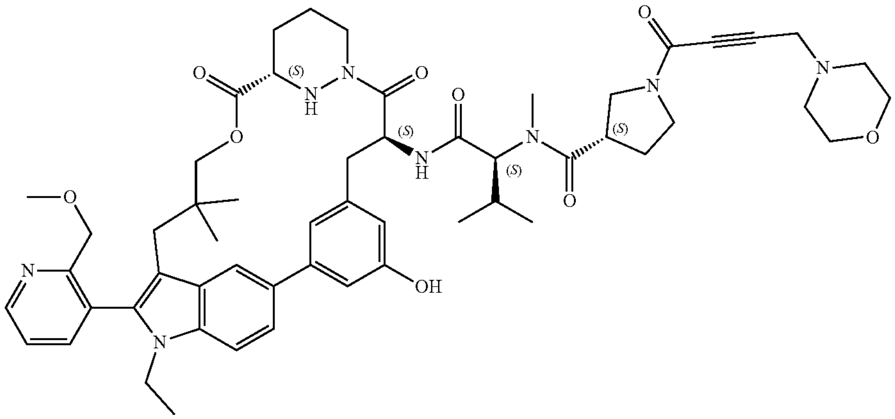 |
| B96 | 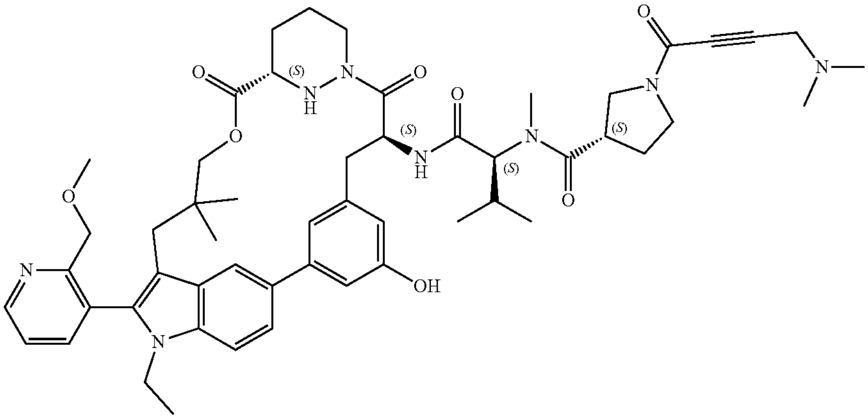 |
| B97 | 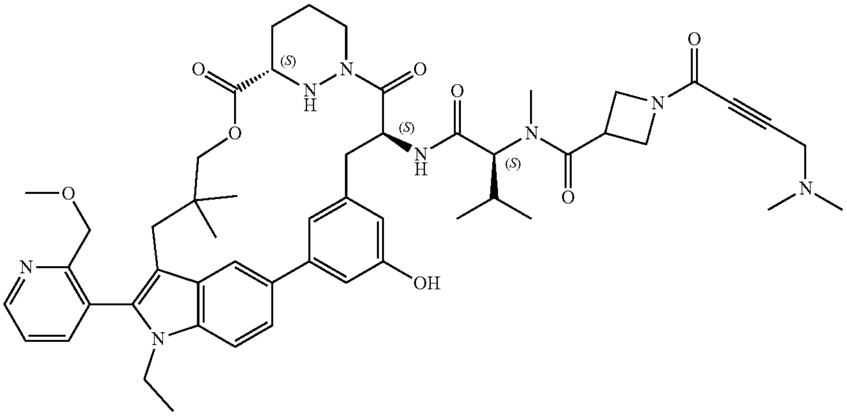 |

TABLE 2-continued
| Certain Compounds | |
|---|---|
| Ex # | Structure |
| B98 | 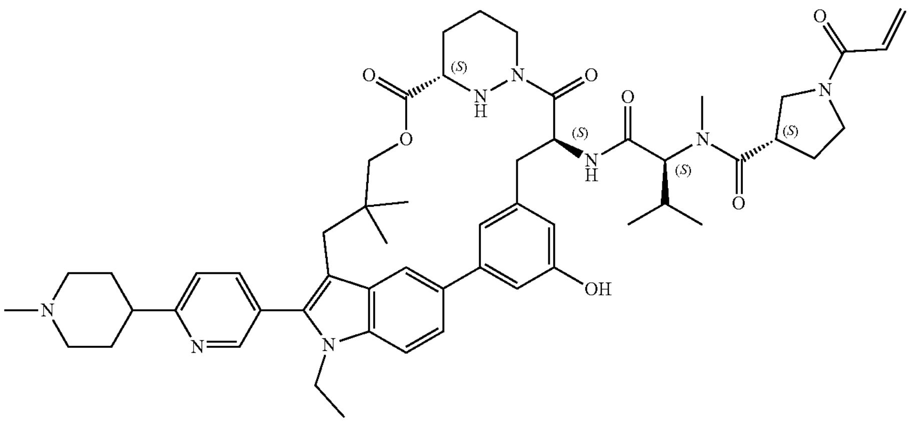 |
| B99 | 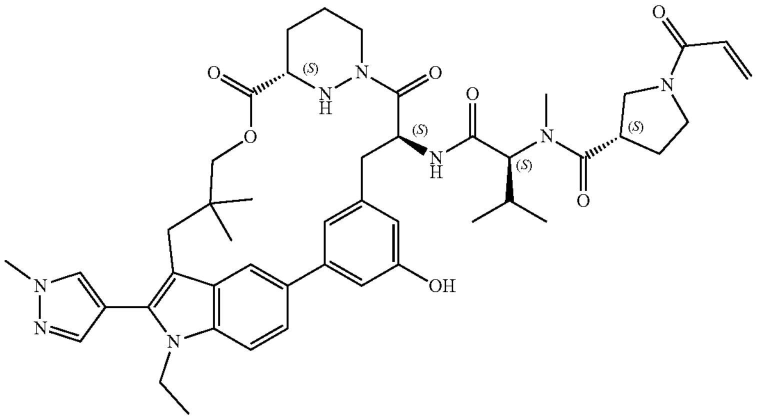 |
| B100 | 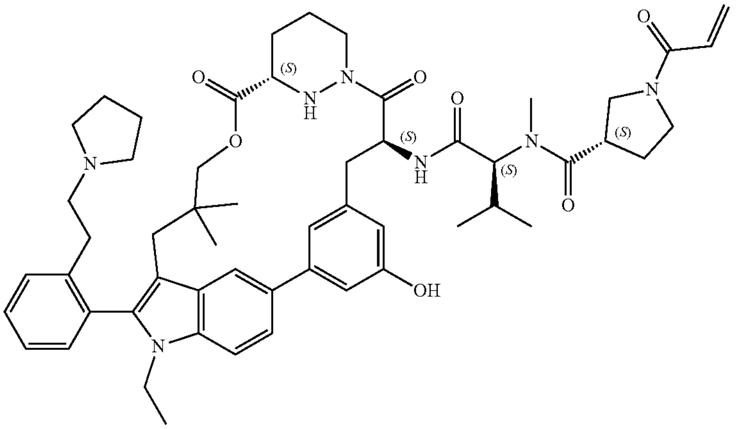 |

TABLE 2-continued
| Certain Compounds | |
|---|---|
| Ex # | Structure |
| B101 | 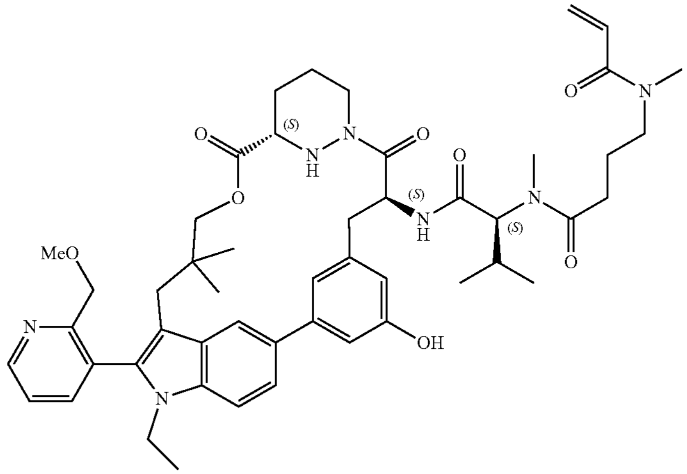 |
| B102 | 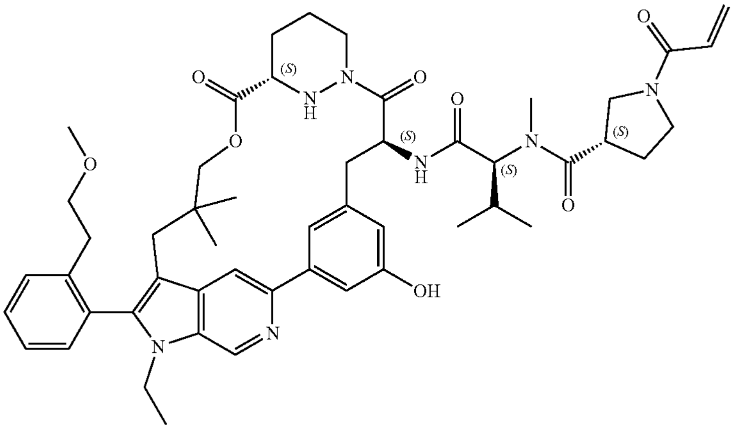 |
| B103 | 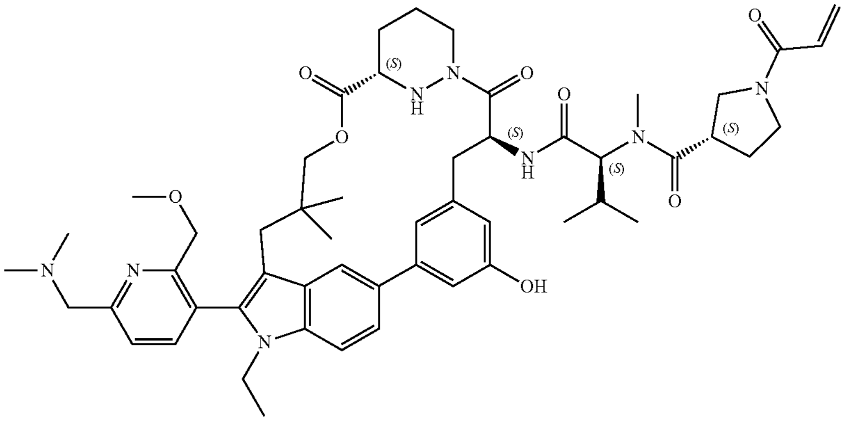 |

TABLE 2-continued
| Certain Compounds | |
|---|---|
| Ex # | Structure |
| B104 | 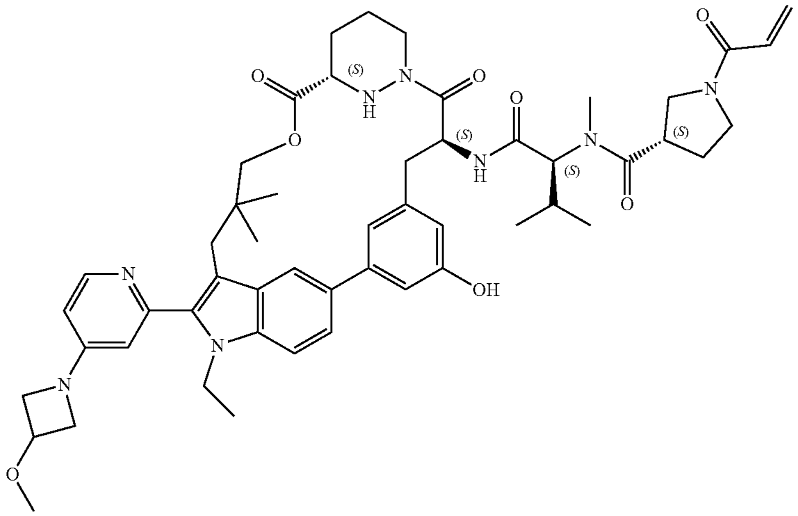 |
| B105 | 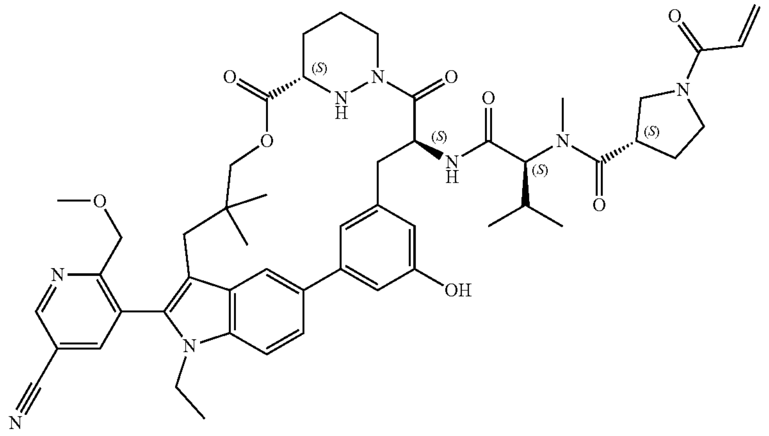 |
| B106 | 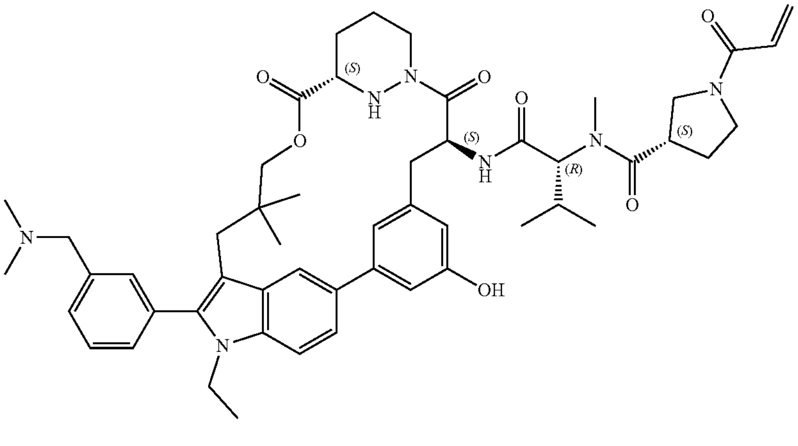 |

TABLE 2-continued
| Certain Compounds | |
|---|---|
| Ex # | Structure |
| B107 | 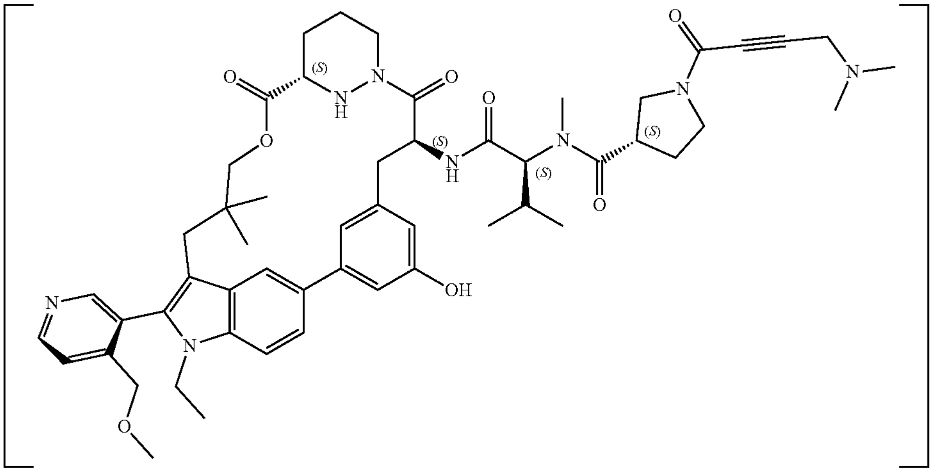 |
| B108 | 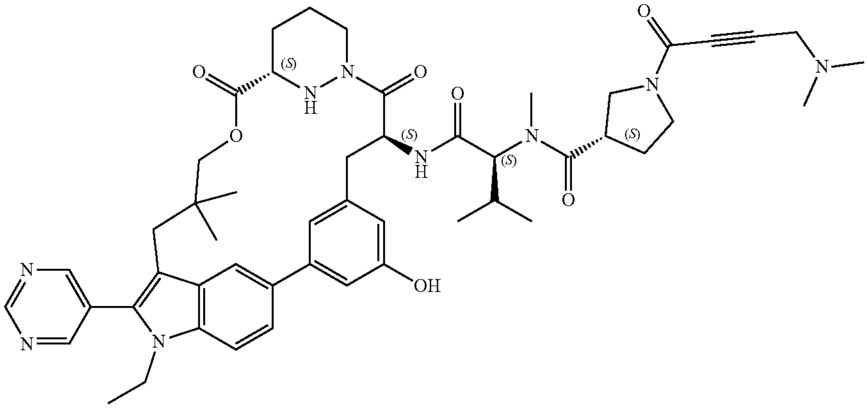 |
| B109 | 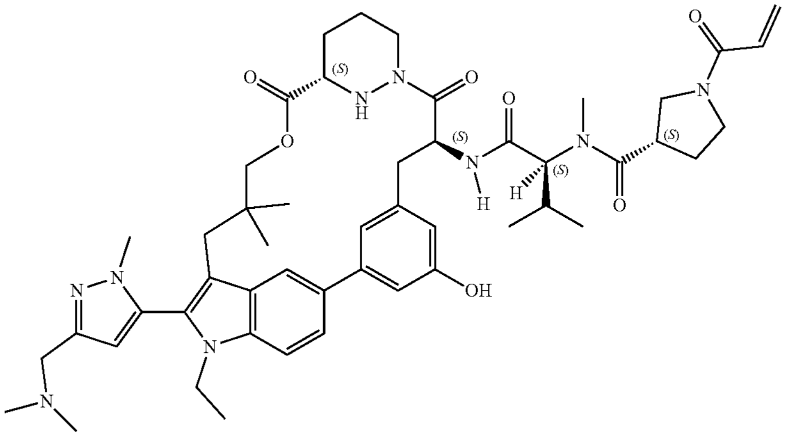 |

TABLE 2-continued
| Certain Compounds | |
|---|---|
| Ex # | Structure |
| B110 | 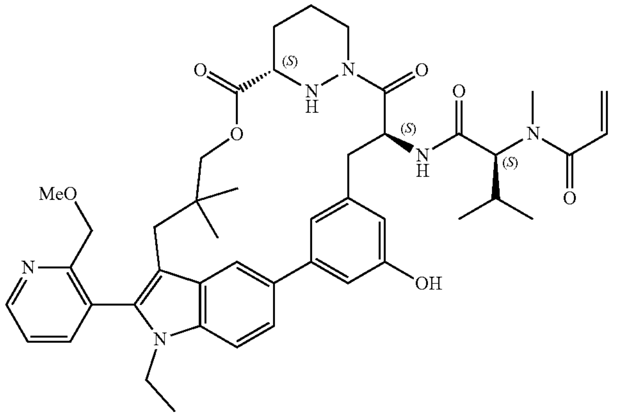 |
| B111 | 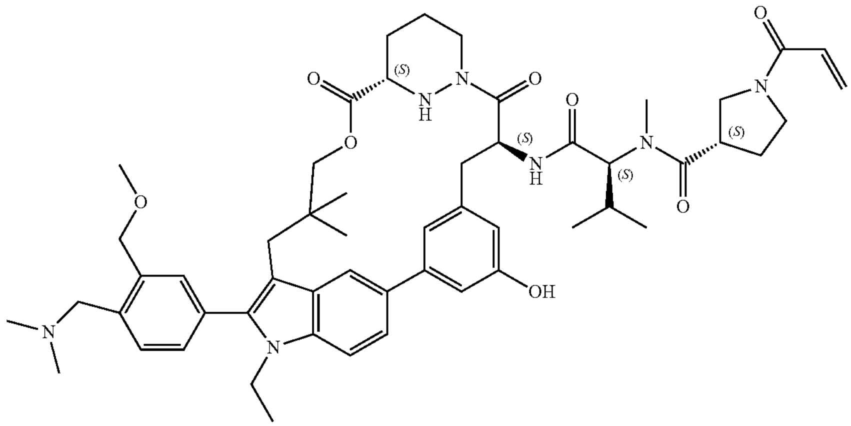 |
| B112 | 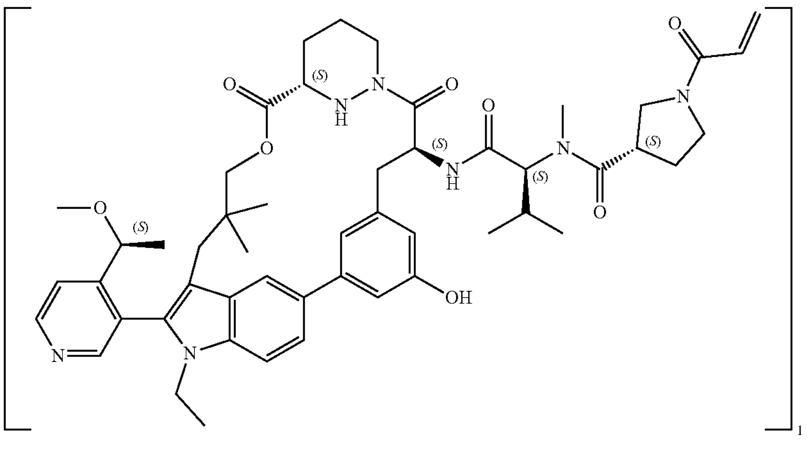 |

TABLE 2-continued
| Certain Compounds | |
|---|---|
| Ex # | Structure |
| B113 | 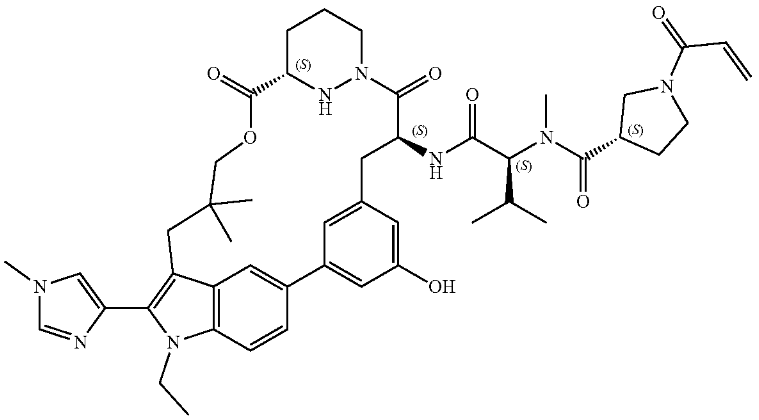 |
| B114 | 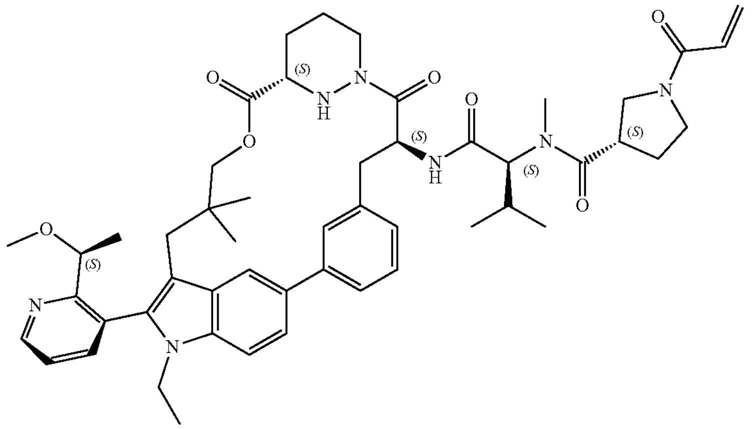 |
| B115 | 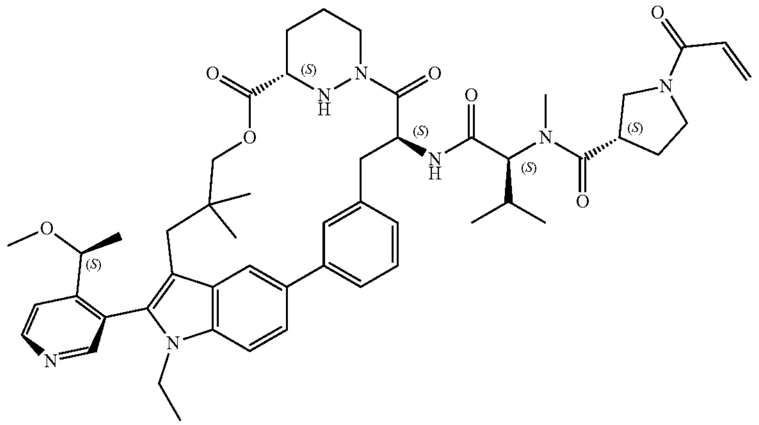 |

TABLE 2-continued
| Certain Compounds | |
|---|---|
| Ex # | Structure |
| B116 | 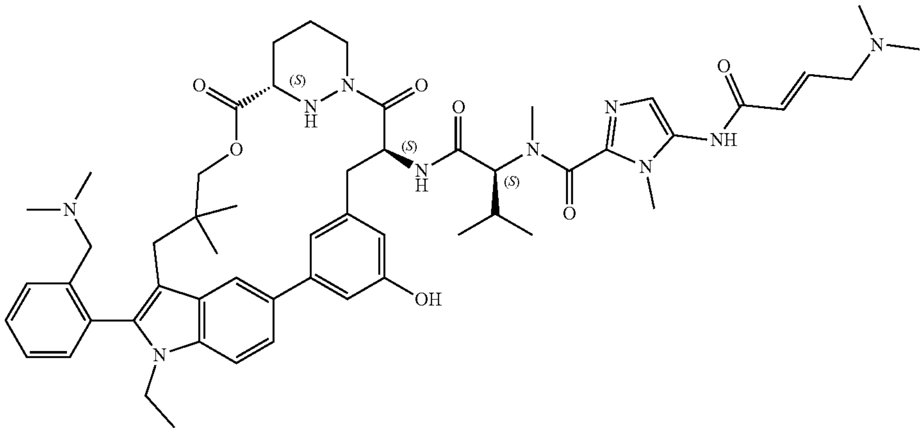 |
| B117 | 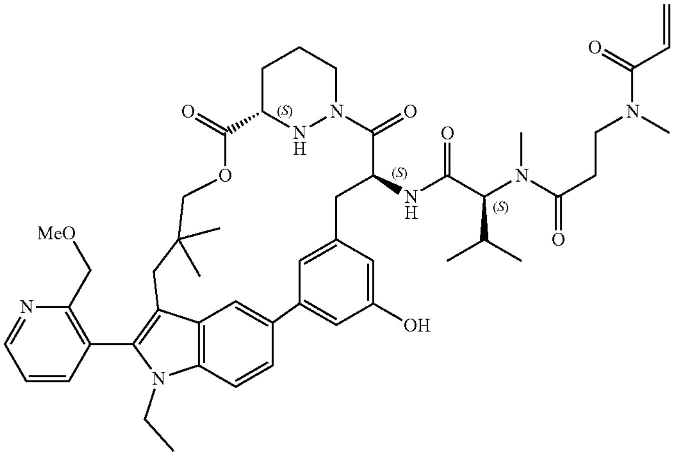 |
| B118 | 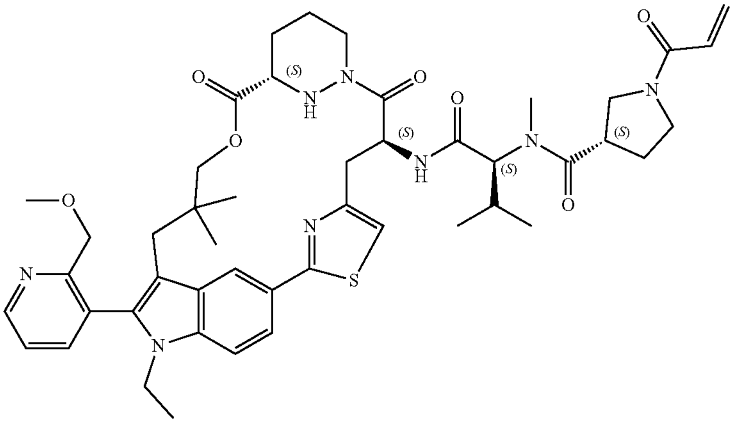 |

TABLE 2-continued
| Certain Compounds | |
|---|---|
| Ex # | Structure |
| B119 | 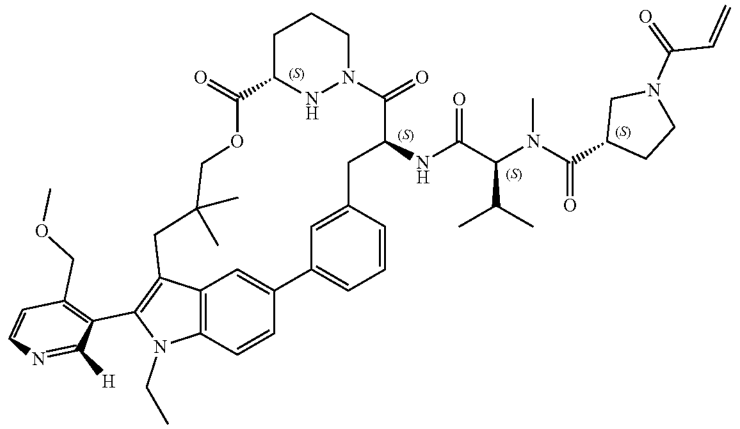 |
| B120 | 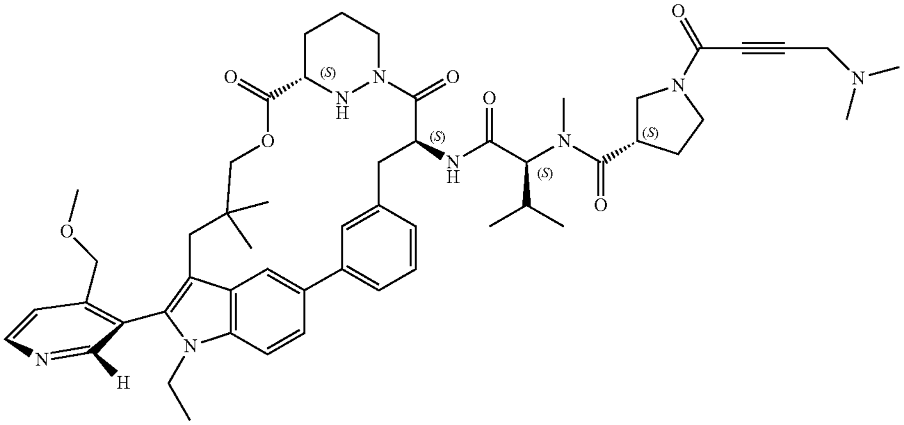 |
| B121 | 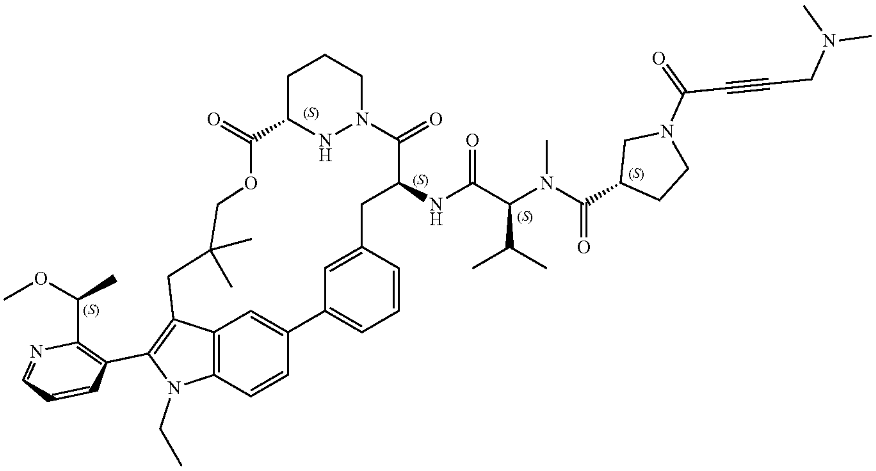 |

TABLE 2-continued
| Certain Compounds | |
|---|---|
| Ex # | Structure |
| B122 | 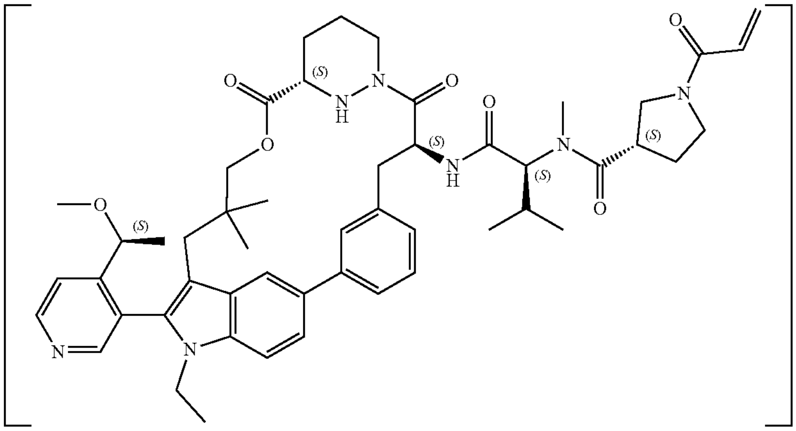 |
| B123 | 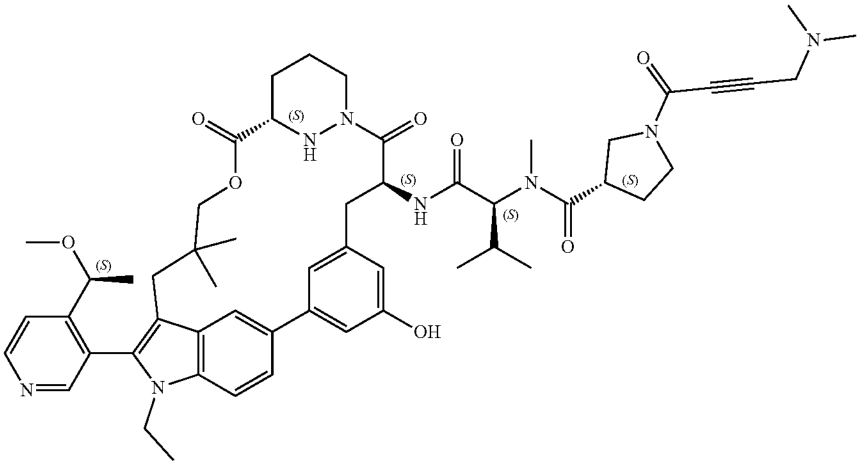 |
| B124 | 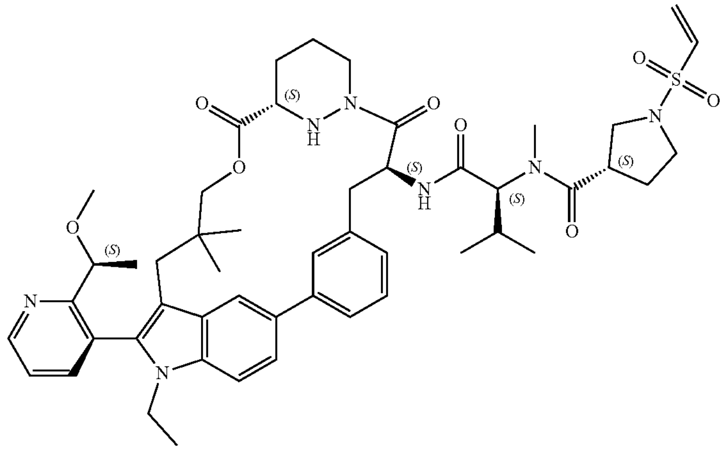 |

TABLE 2-continued
| Certain Compounds | |
|---|---|
| Ex # | Structure |
| B125 | 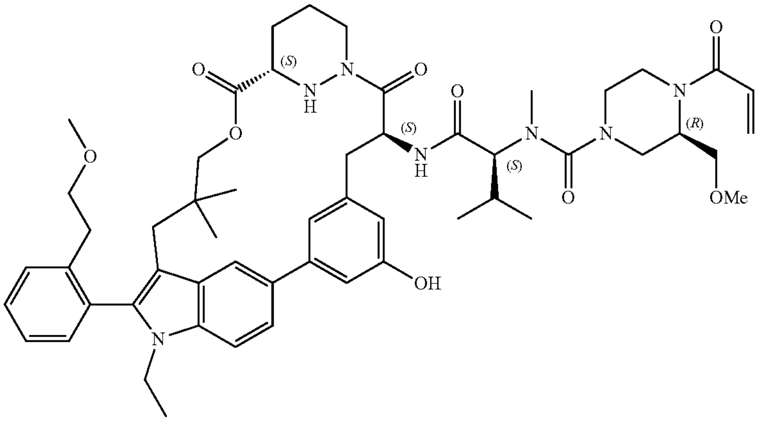 |
| B126 | 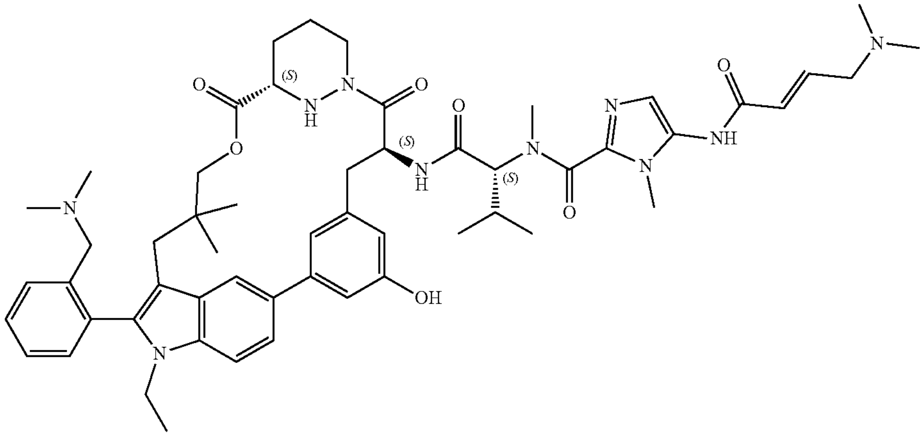 |
| B127 | 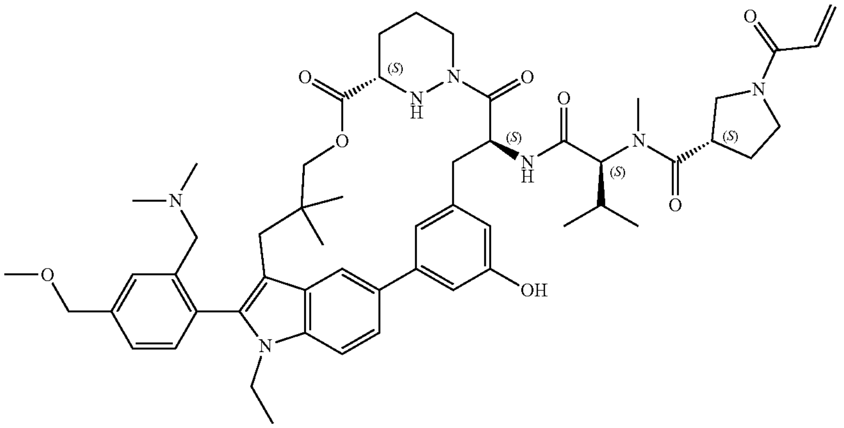 |

TABLE 2-continued
| Certain Compounds | |
|---|---|
| Ex # | Structure |
| B128 | 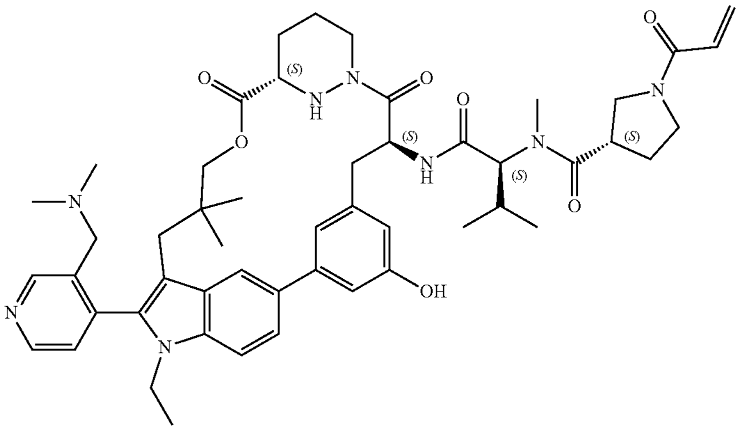 |
| B129 | 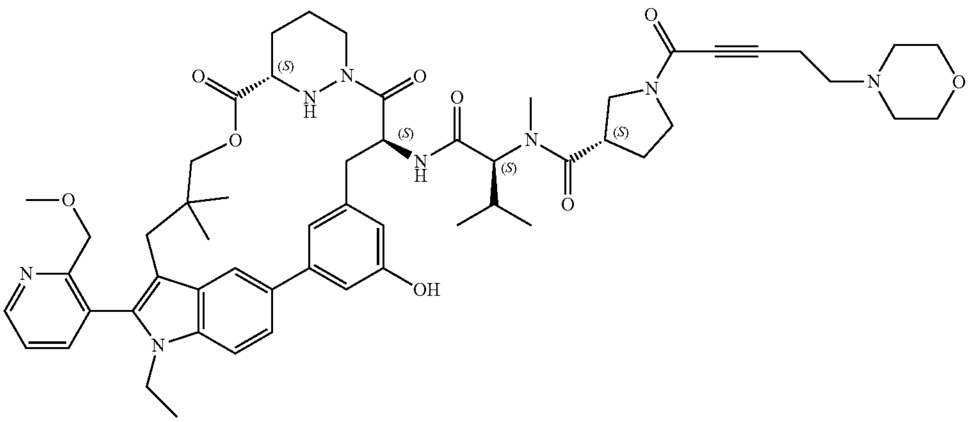 |
| B130 | 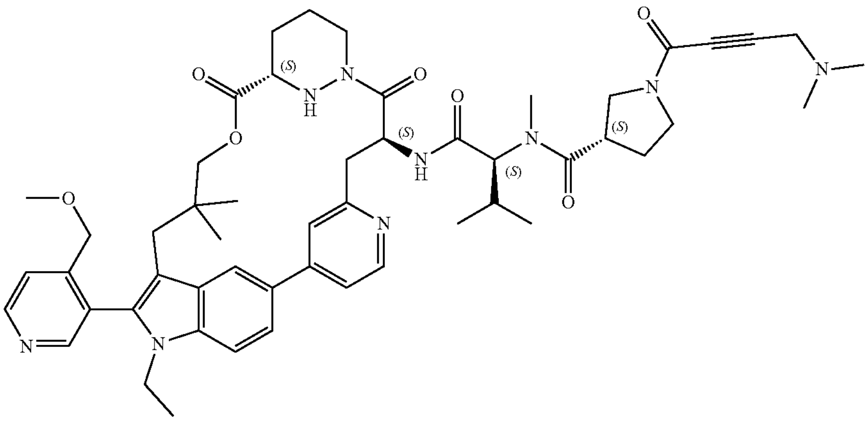 |

TABLE 2-continued
| Certain Compounds | |
|---|---|
| Ex # | Structure |
| B131 | 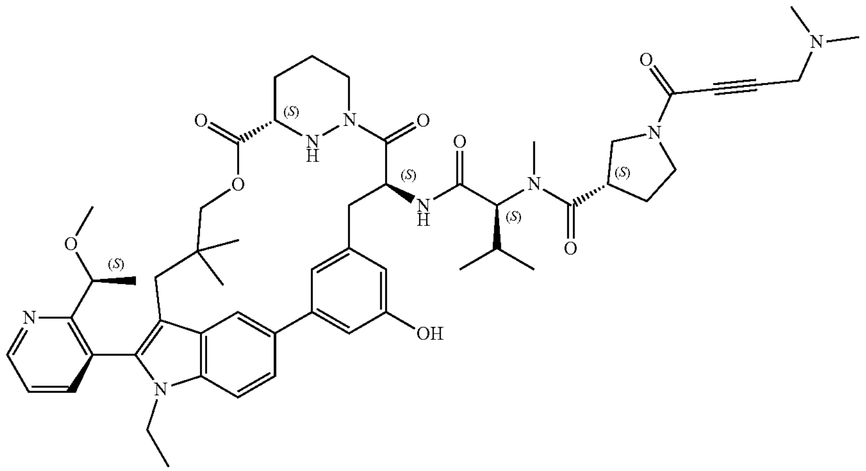 |
| B132 | 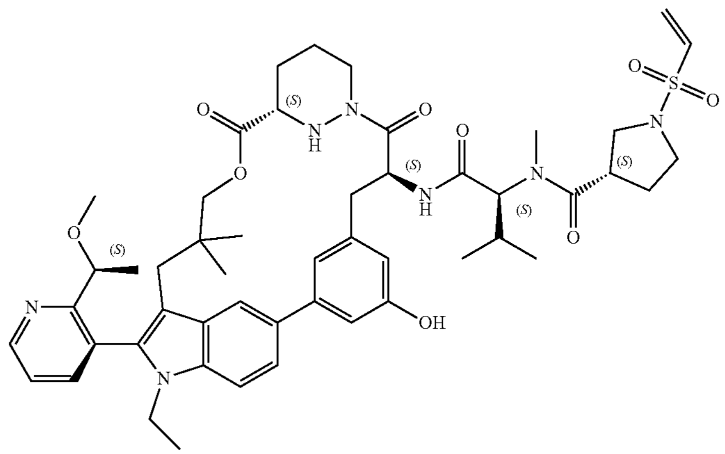 |
| B133 | 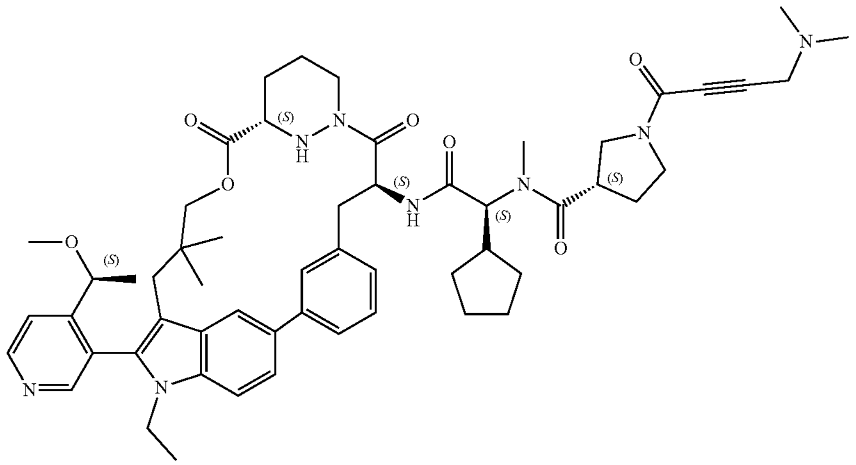 |

TABLE 2-continued
| Certain Compounds | |
|---|---|
| Ex # | Structure |
| B134 | 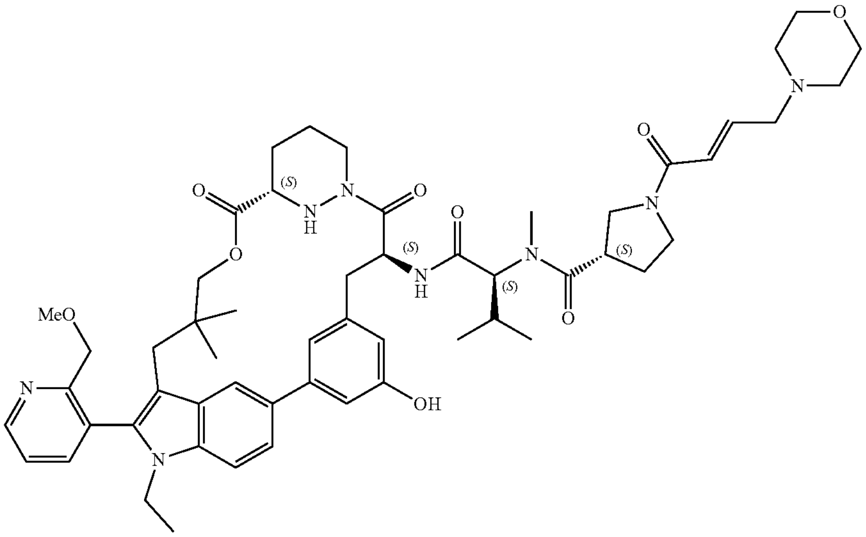 |
| B135 | 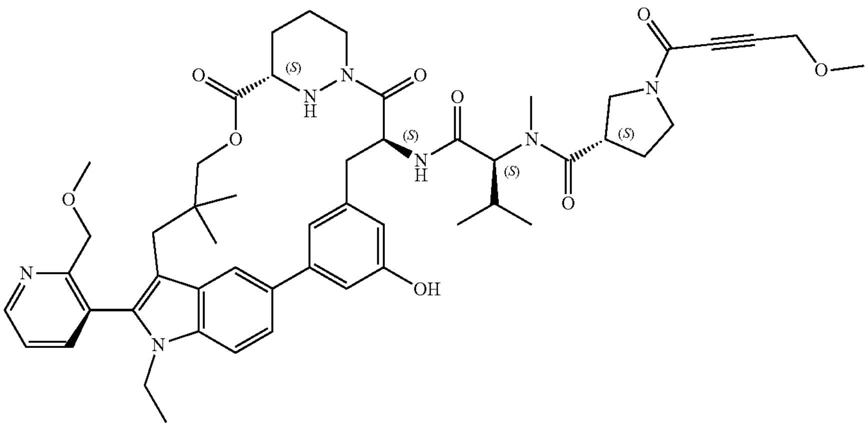 |
| B136 | 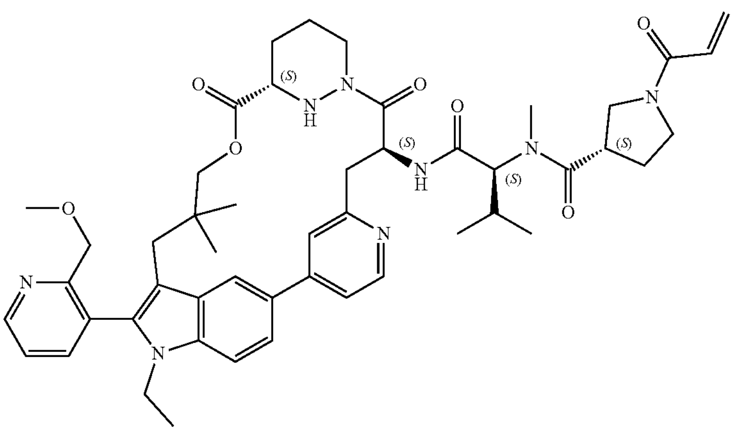 |

TABLE 2-continued
| Certain Compounds | |
|---|---|
| Ex # | Structure |
| B137 | 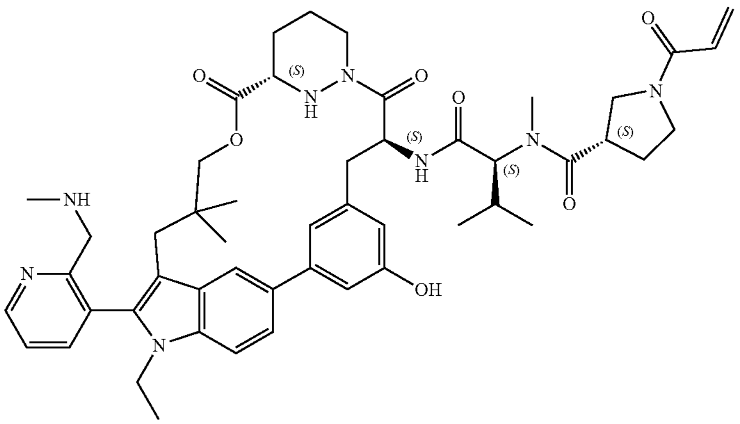 |
| B138 | 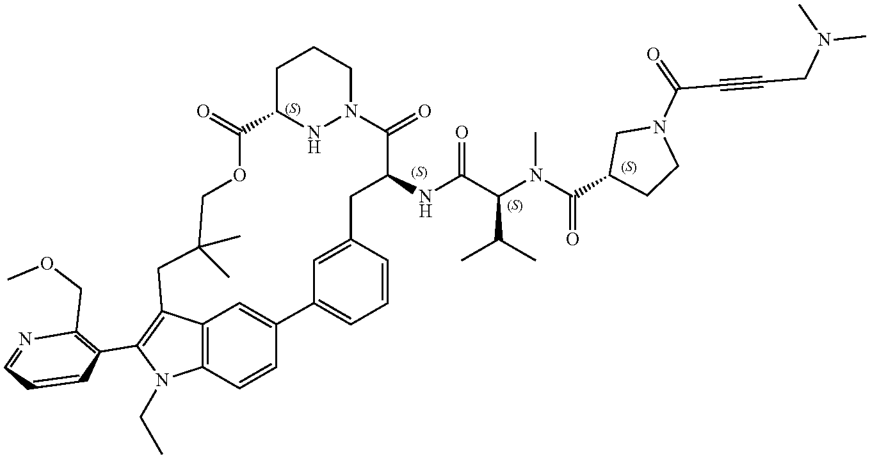 |
| B139 | 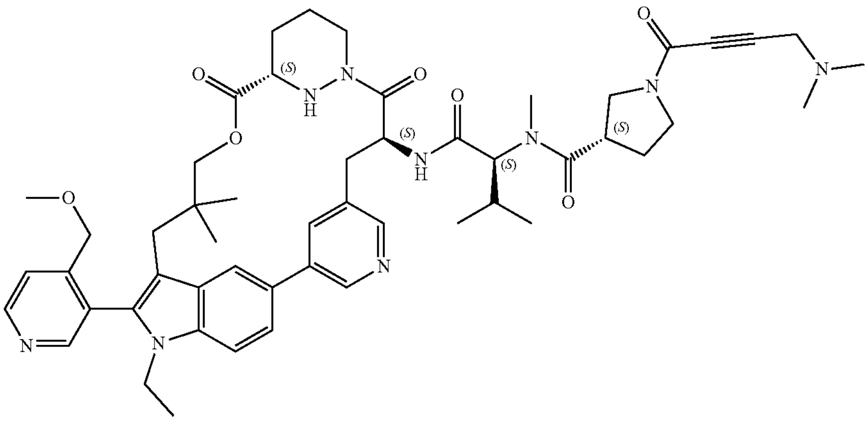 |

TABLE 2-continued
| Certain Compounds | |
|---|---|
| Ex # | Structure |
| B140 | 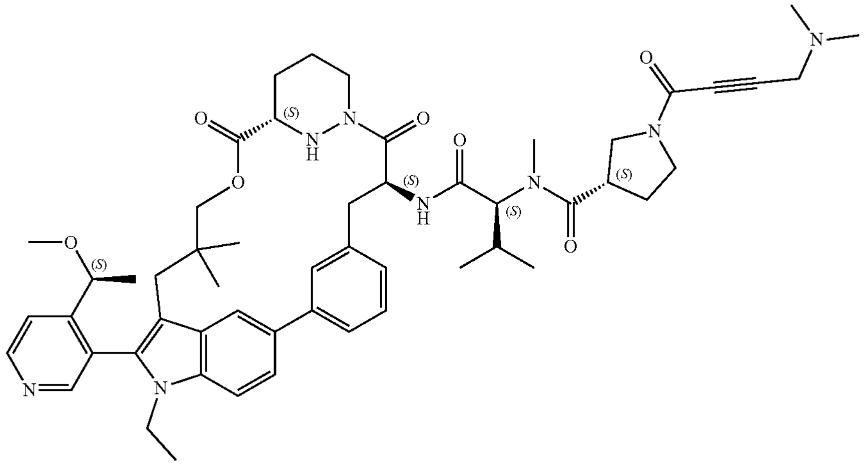 |
| B141 | 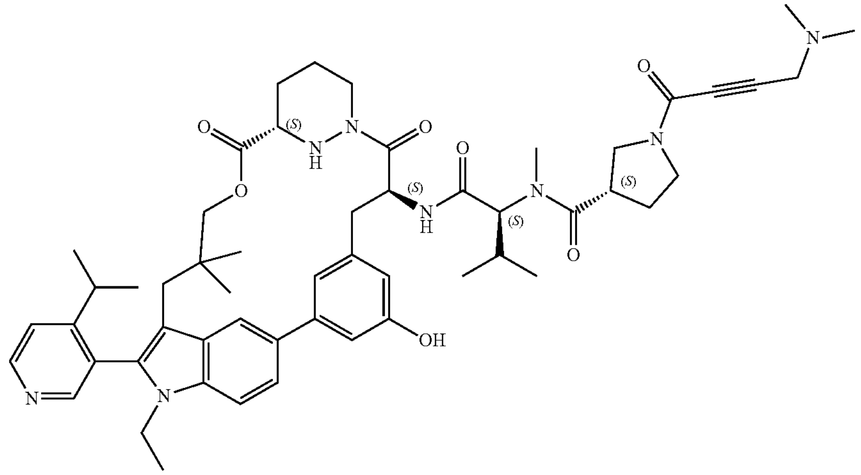 |
| B142 | 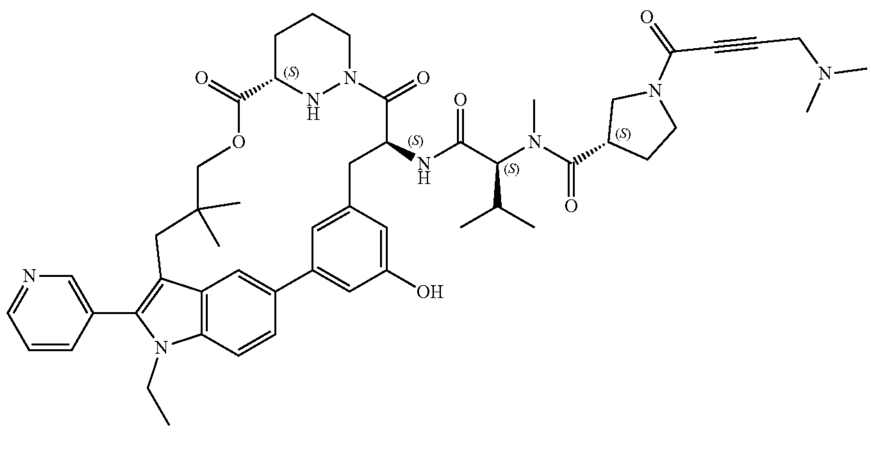 |

TABLE 2-continued
| Certain Compounds | |
|---|---|
| Ex # | Structure |
| B143 | 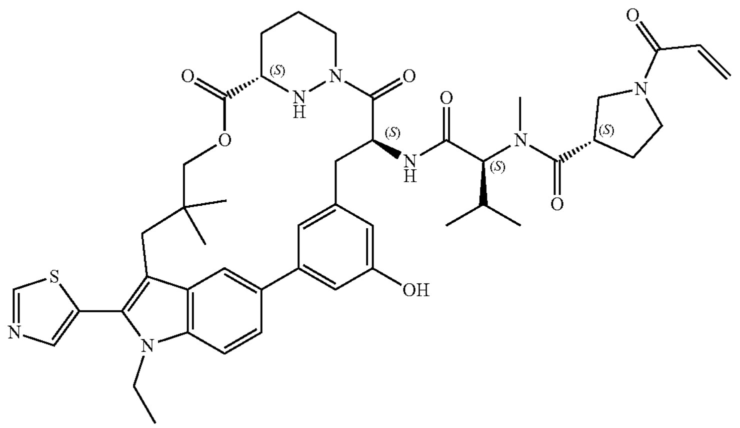 |
| B144 | 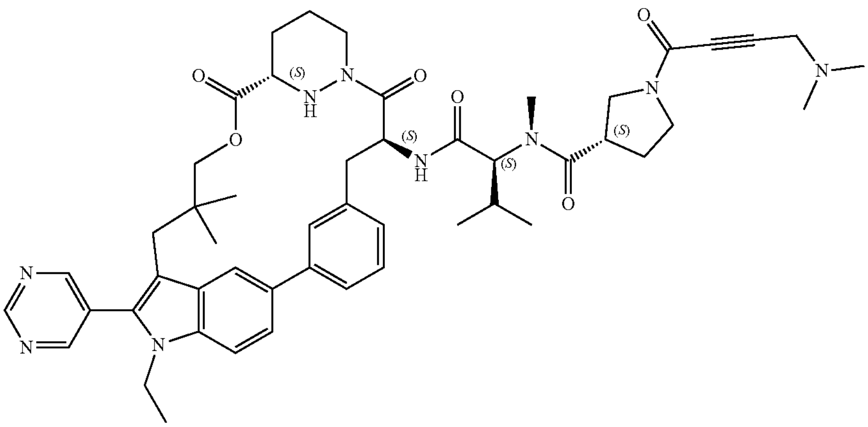 |
| B145 | 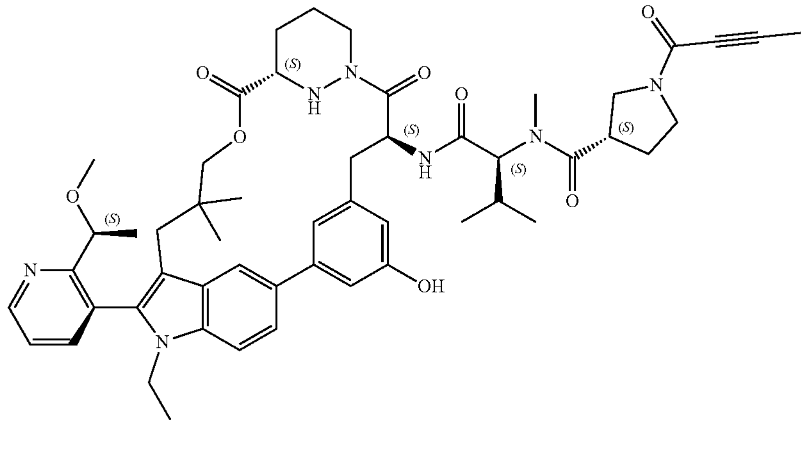 |

TABLE 2-continued
| Certain Compounds | |
|---|---|
| Ex # | Structure |
| B146 | 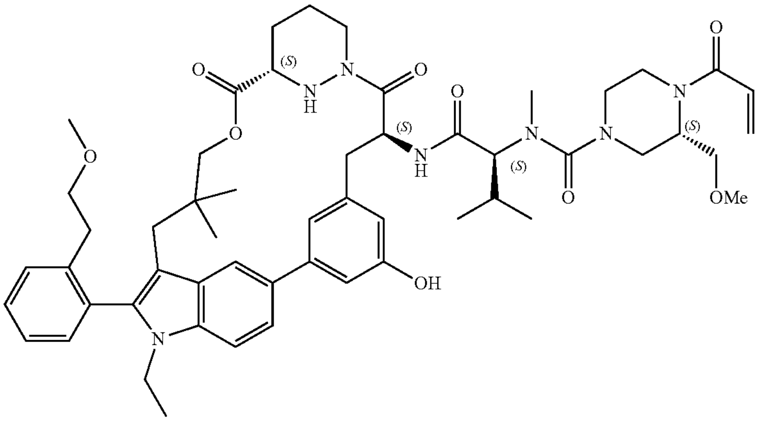 |
| B147 | 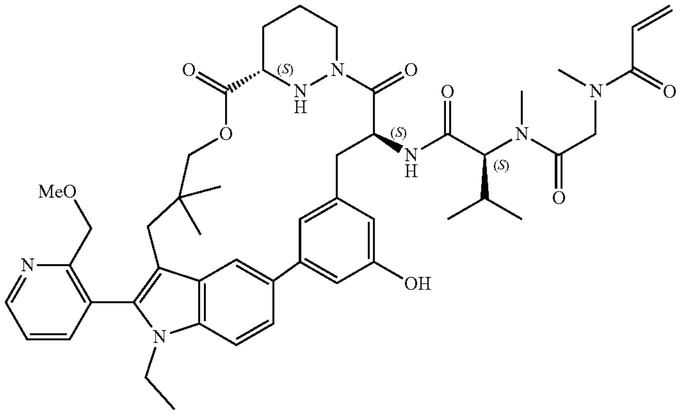 |
| B148 | 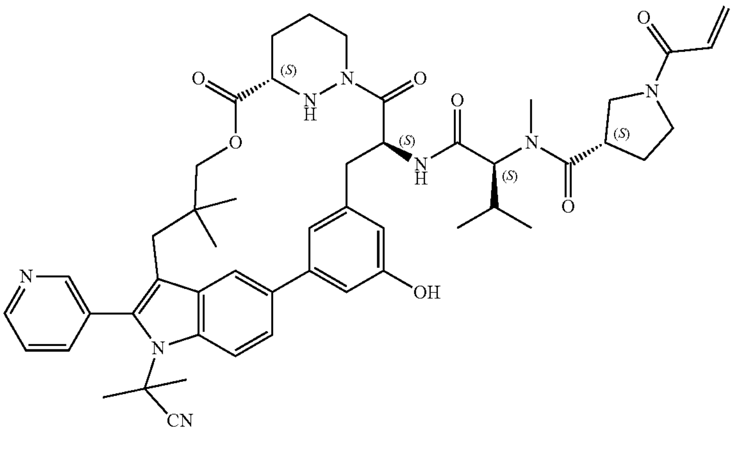 |

TABLE 2-continued
| Certain Compounds | |
|---|---|
| Ex # | Structure |
| B149 | 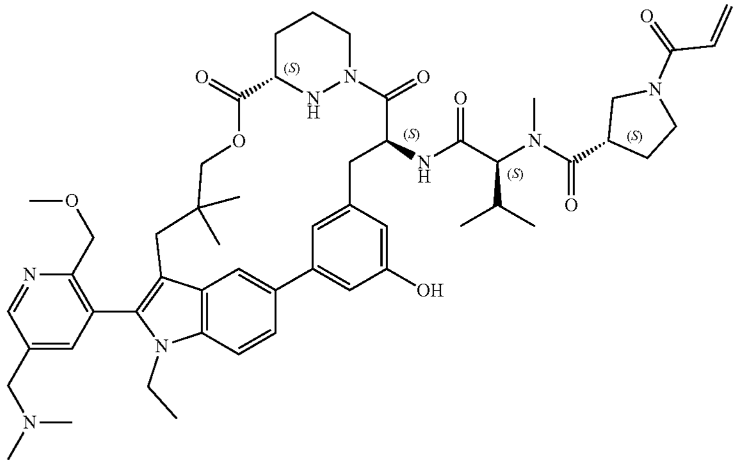 |
| B150 | 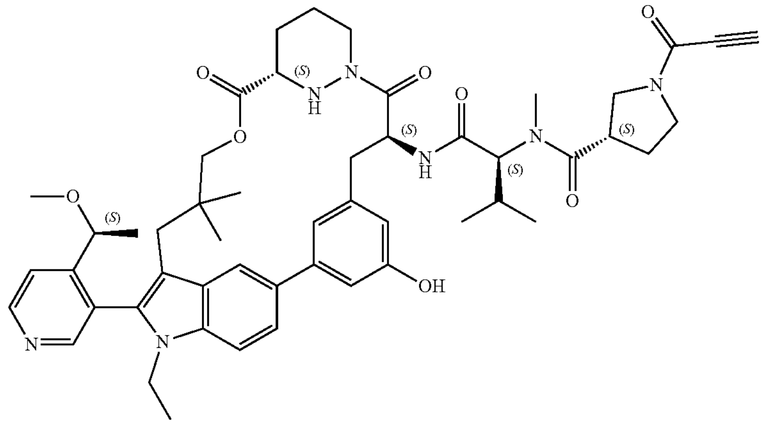 |
| B151 | 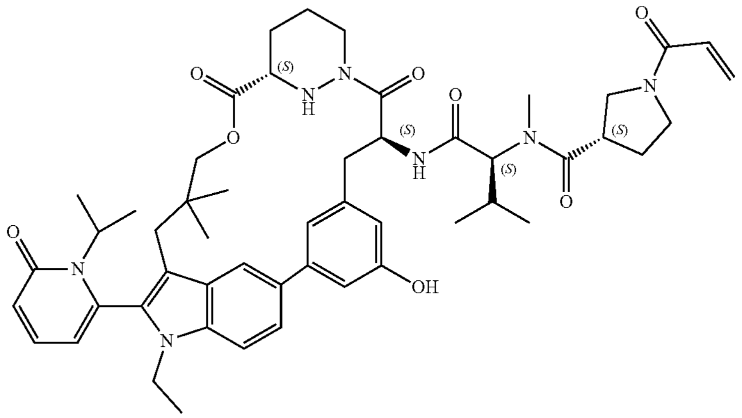 |

TABLE 2-continued
| Certain Compounds | |
|---|---|
| Ex # | Structure |
| B152 | 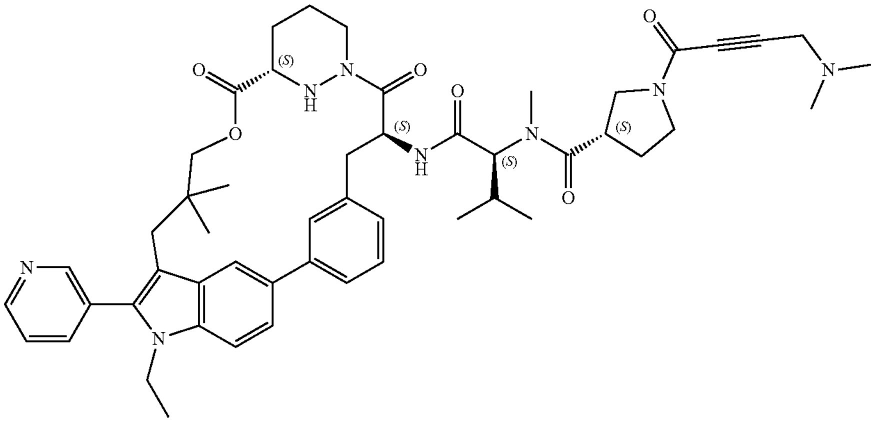 |
| B153 | 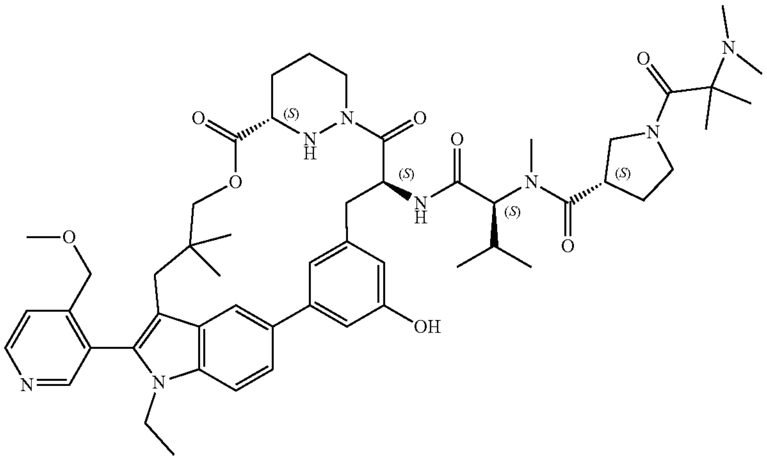 |
| B154 | 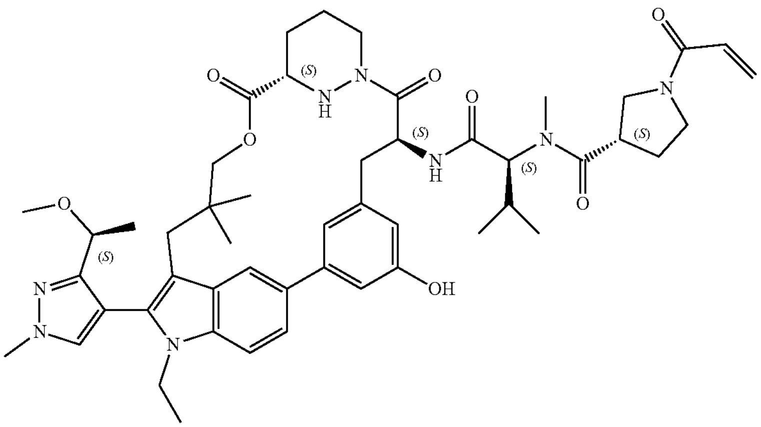 |

TABLE 2-continued
| Certain Compounds | |
|---|---|
| Ex # | Structure |
| B155 | 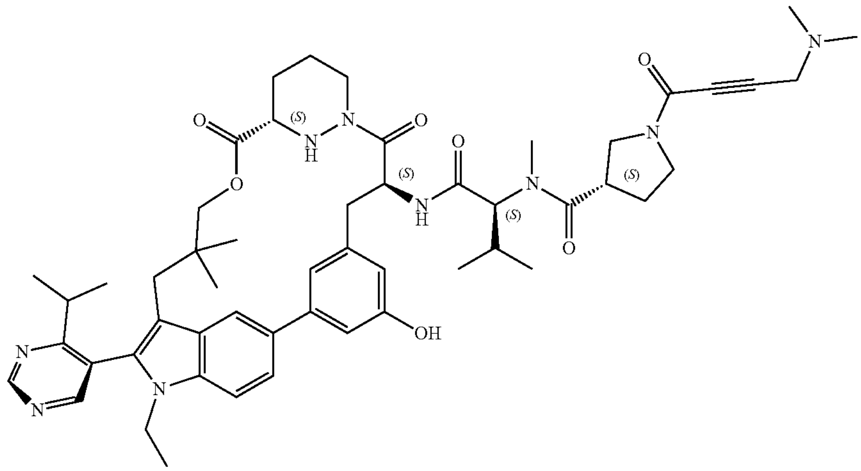 |
| B156 | 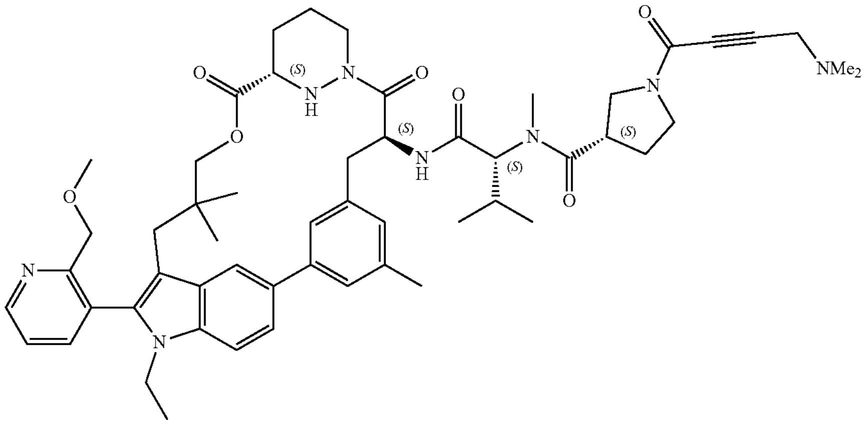 |
| B157 | 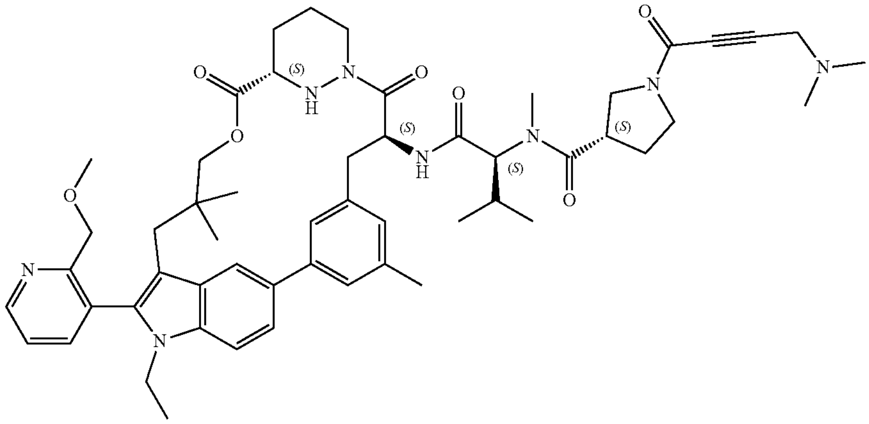 |

TABLE 2-continued
| Certain Compounds | |
|---|---|
| Ex # | Structure |
| B158 | 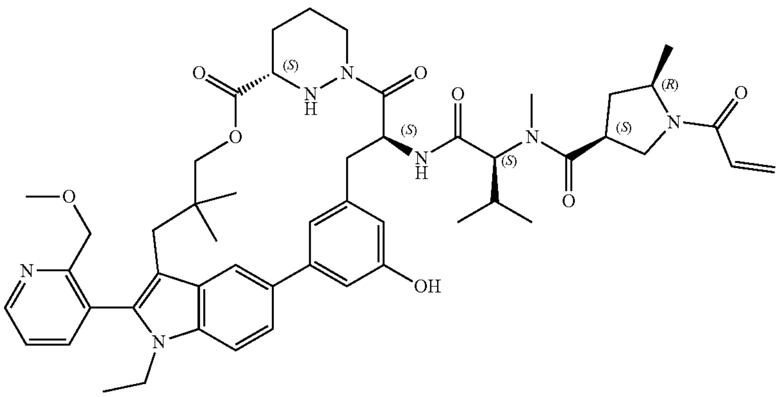 |
| B159 | 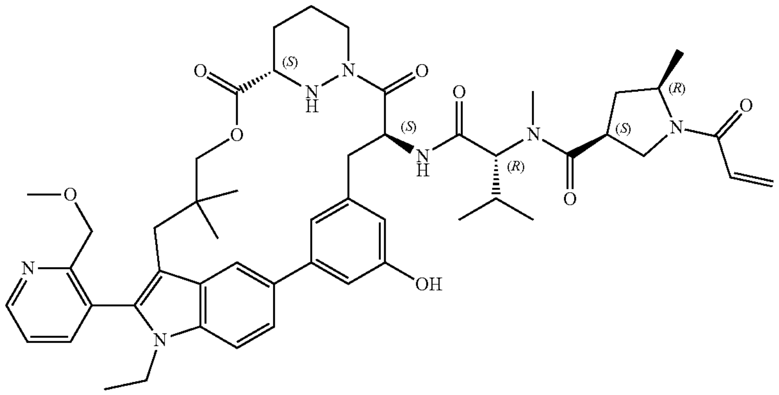 |
| B160 | 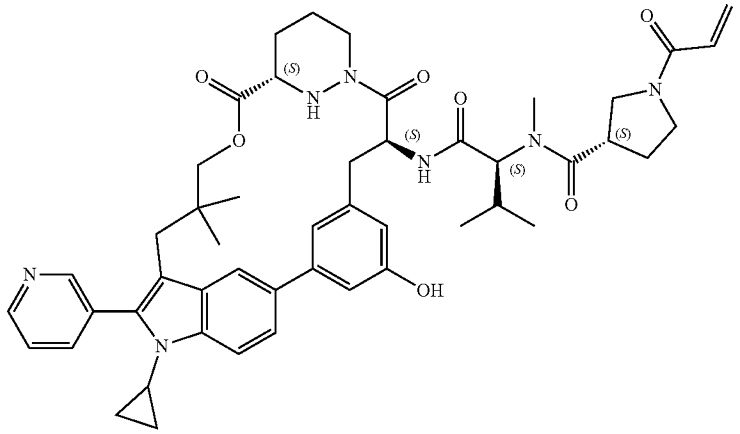 |

TABLE 2-continued
| Certain Compounds | |
|---|---|
| Ex # | Structure |
| B161 | 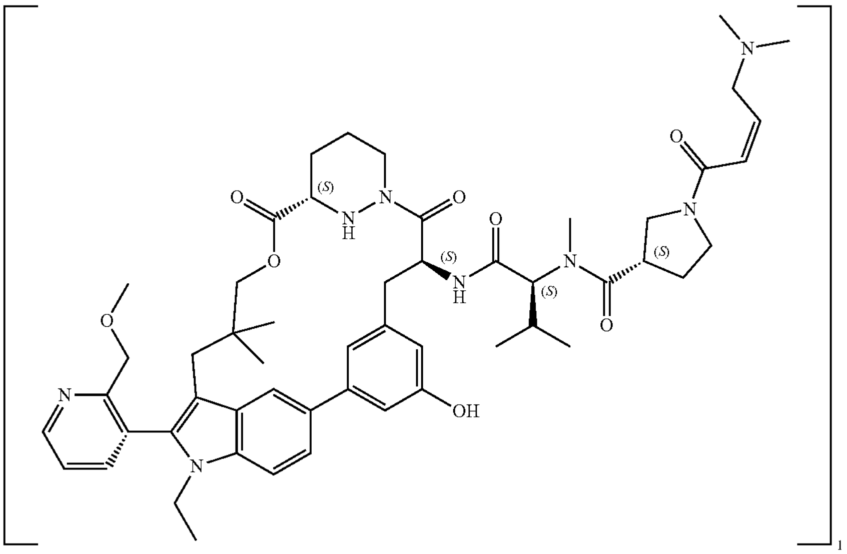 |
| B162 | 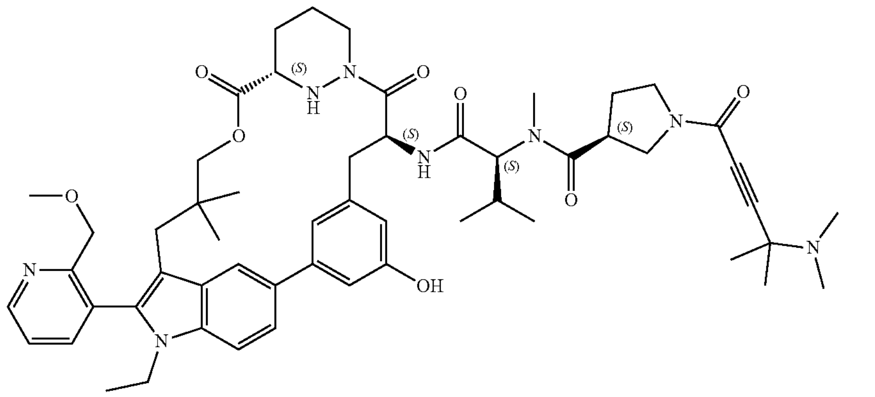 |
| B163 | 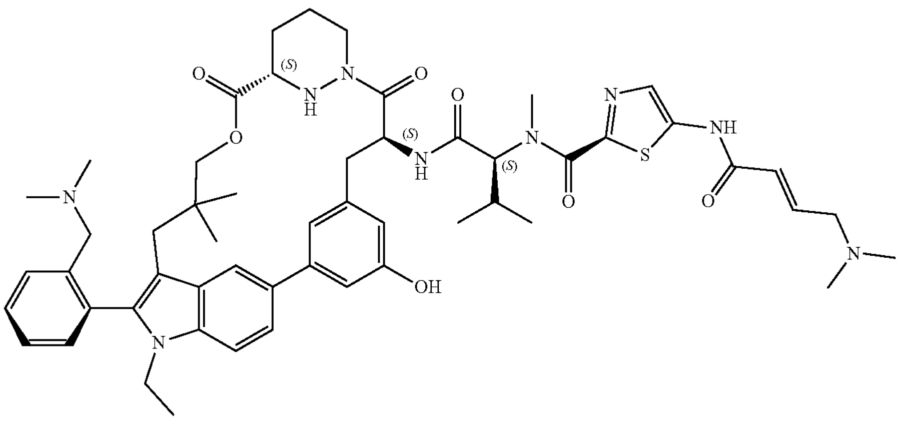 |

TABLE 2-continued
| Certain Compounds | |
|---|---|
| Ex # | Structure |
| B164 | 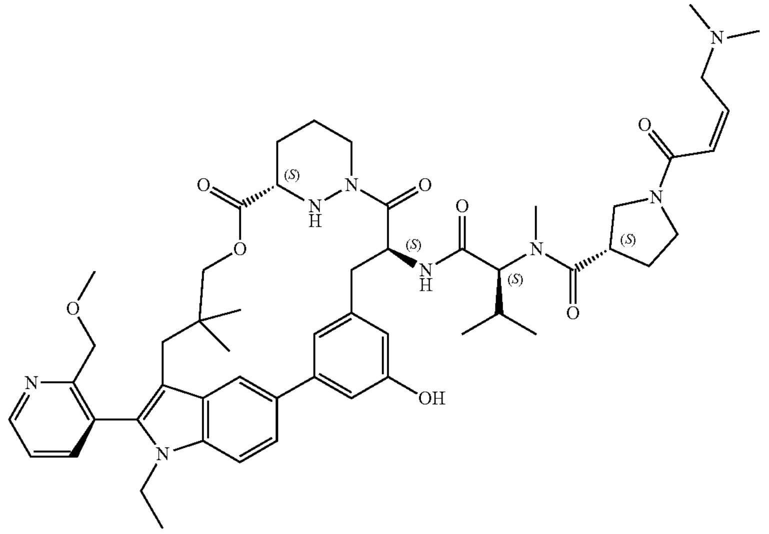 |
| B165 | 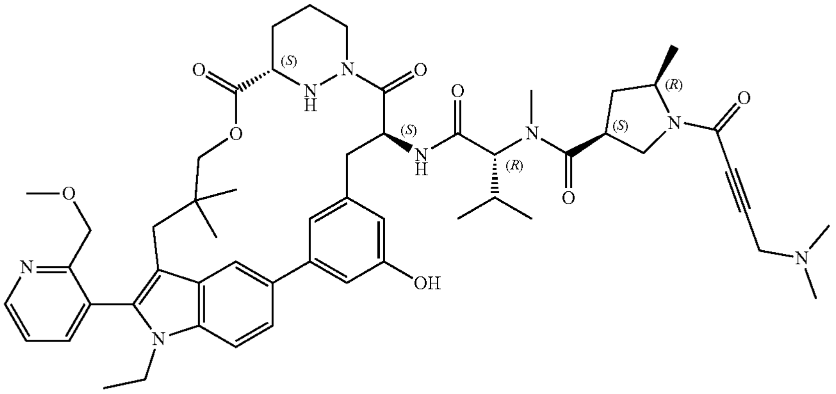 |
| B166 | 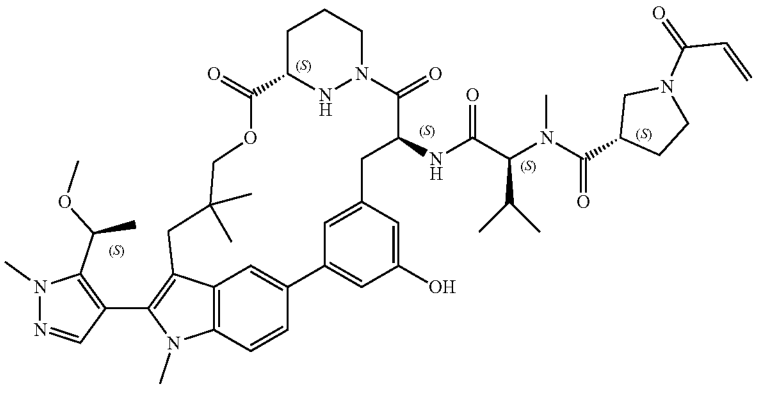 |

TABLE 2-continued
| Certain Compounds | |
|---|---|
| Ex # | Structure |
| B167 | 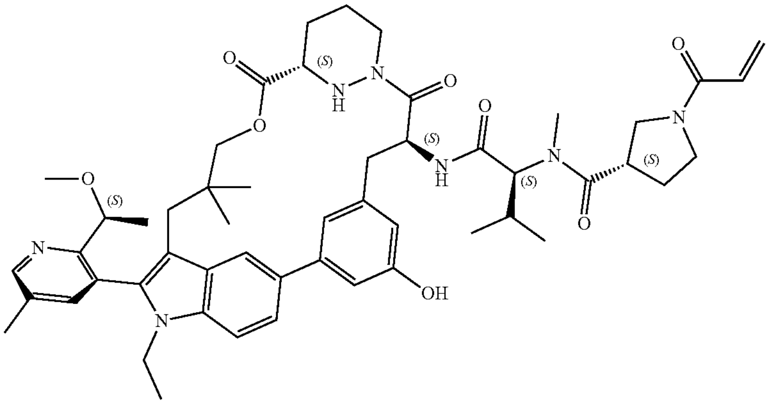 |
| B168 | 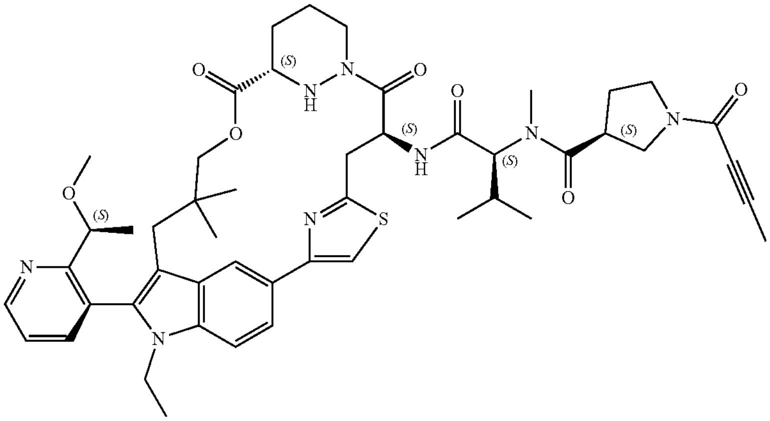 |
| B169 | 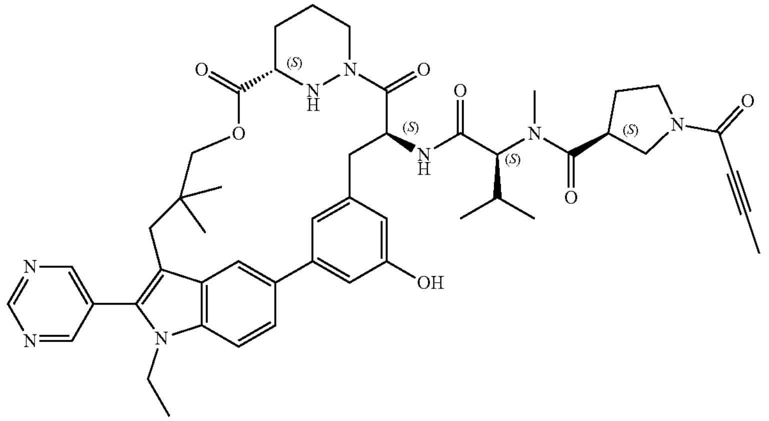 |

TABLE 2-continued
| Certain Compounds | |
|---|---|
| Ex # | Structure |
| B170 | 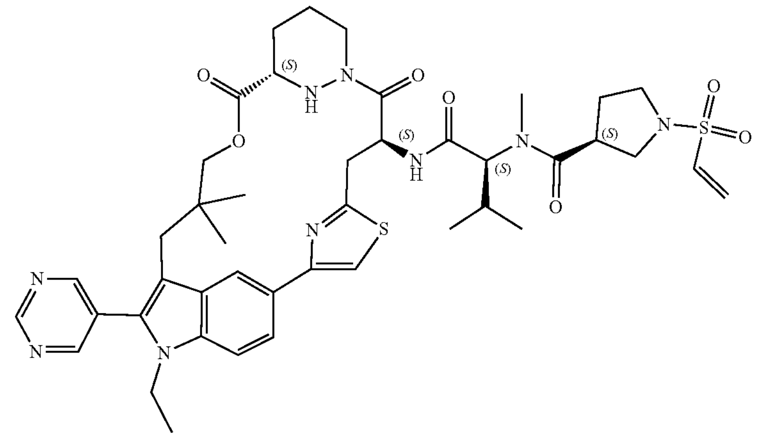 |
| B171 | 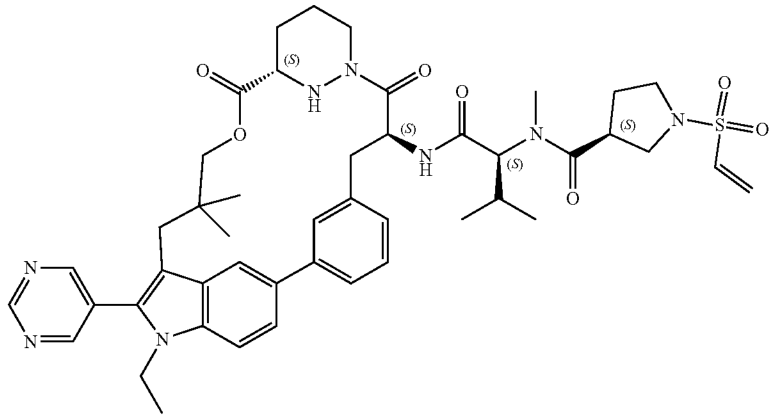 |
| B172 | 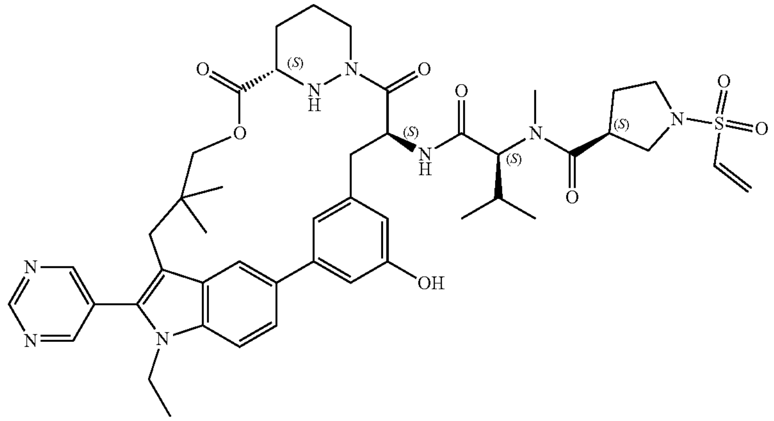 |

TABLE 2-continued
| Certain Compounds | |
|---|---|
| Ex # | Structure |
| B173 | 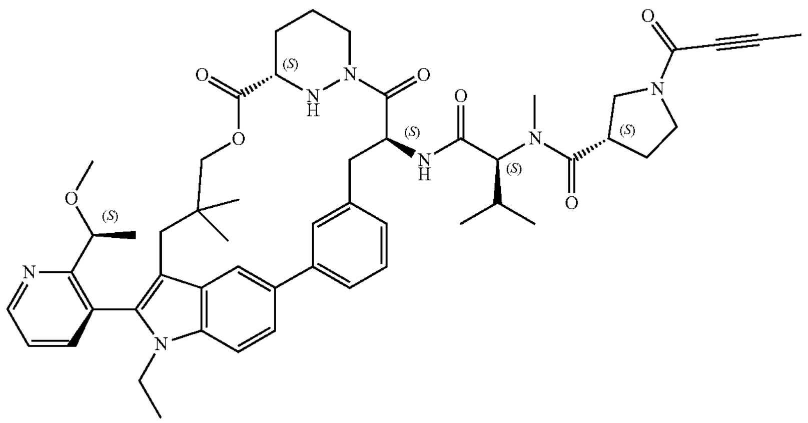 |
| B174 | 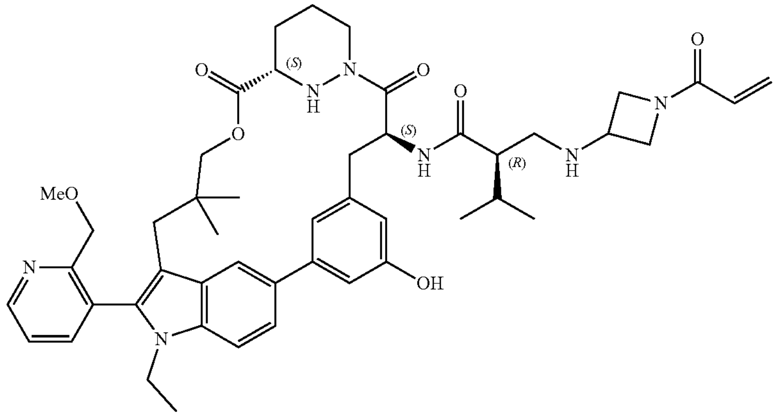 |
| B175 | 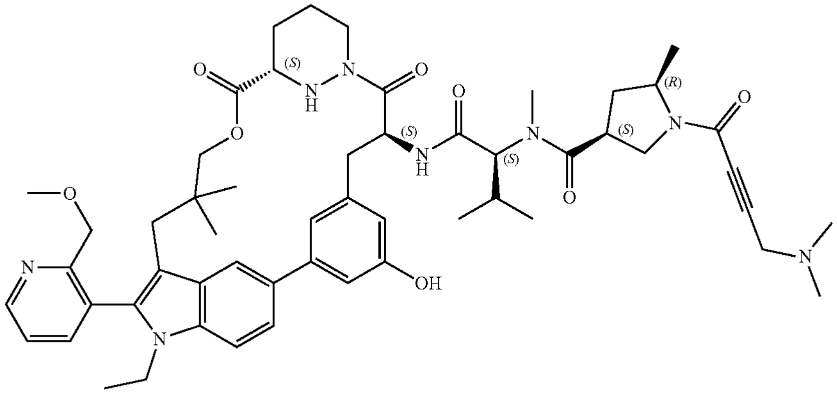 |

TABLE 2-continued
| Certain Compounds | |
|---|---|
| Ex # | Structure |
| B176 | 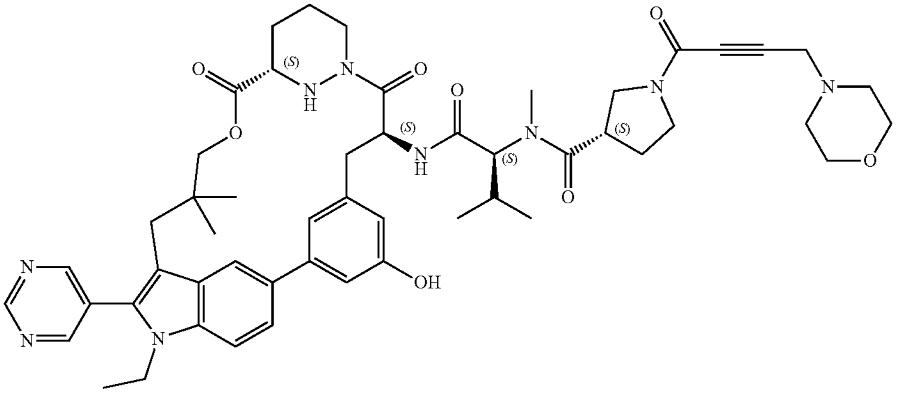 |
| B177 | 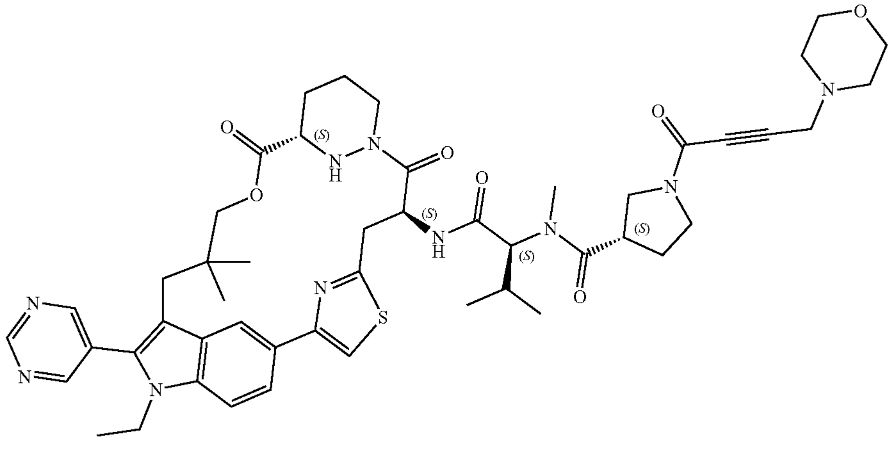 |
| B178 | 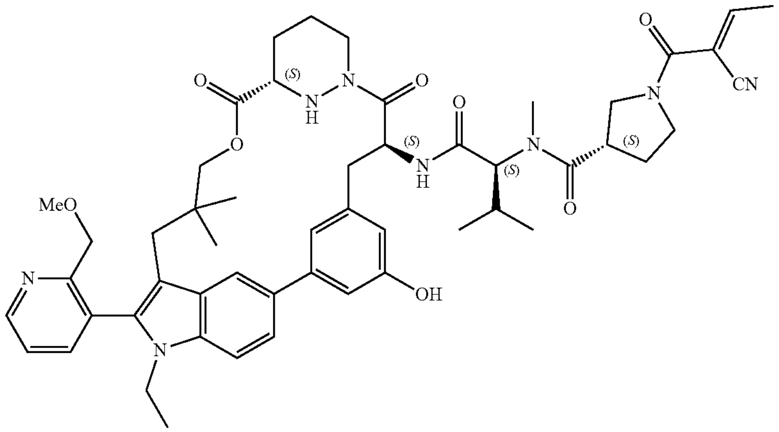 |

TABLE 2-continued
| Certain Compounds | |
|---|---|
| Ex # | Structure |
| B179 | 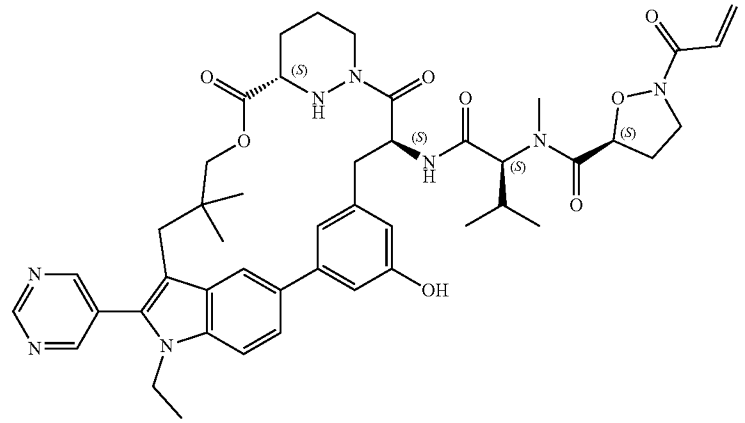 |
| B180 | 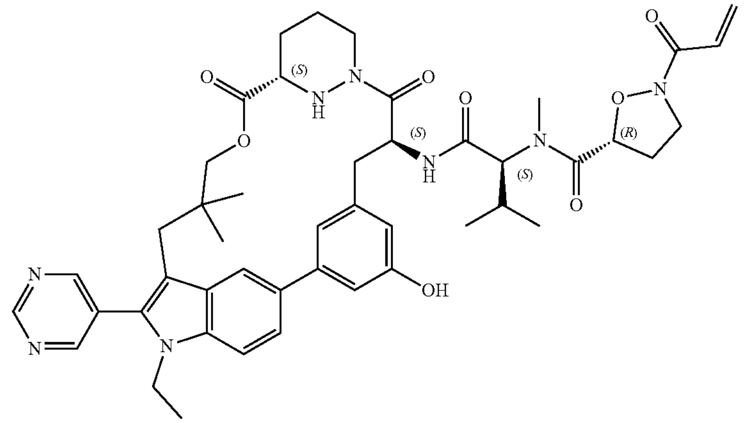 |
| B181 | 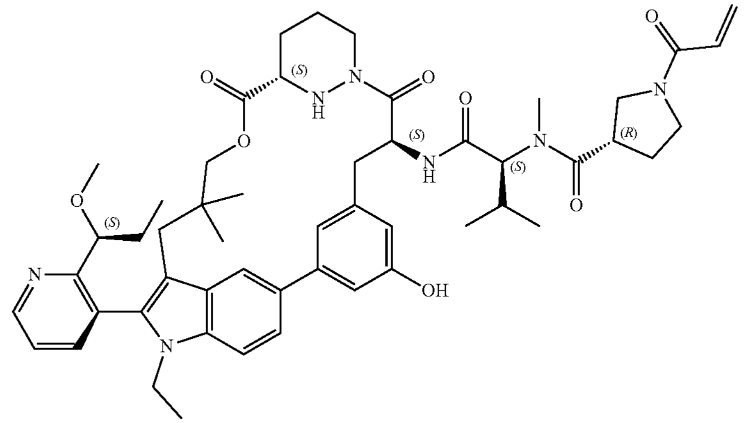 |

TABLE 2-continued
| Certain Compounds | |
|---|---|
| Ex # | Structure |
| B182 | 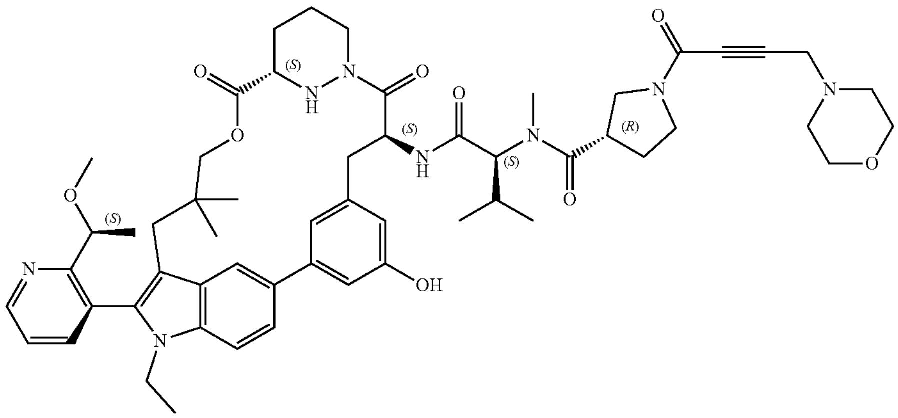 |
| B183 | 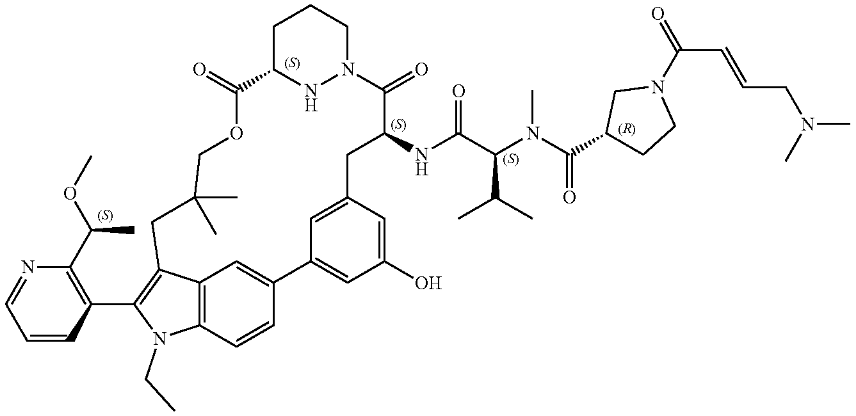 |
| B184 | 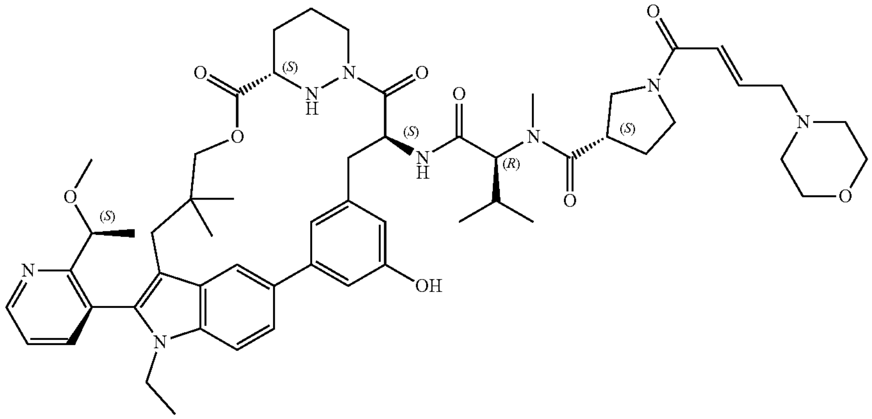 |

TABLE 2-continued
| Certain Compounds | |
|---|---|
| Ex # | Structure |
| B185 | 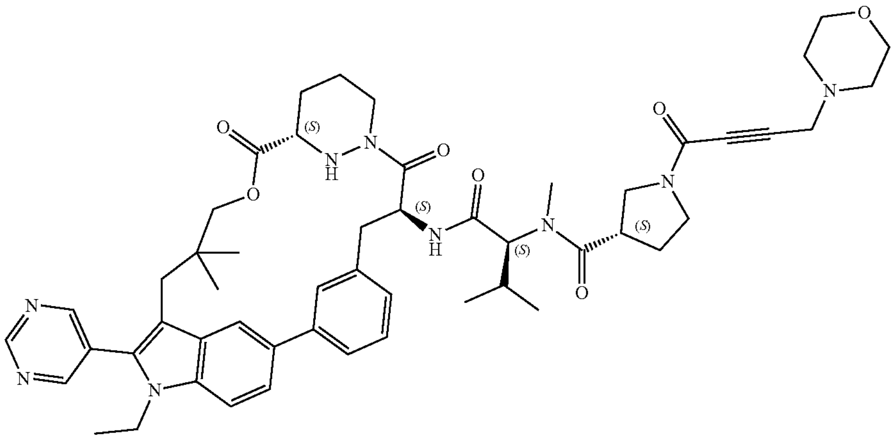 |
| B186 | 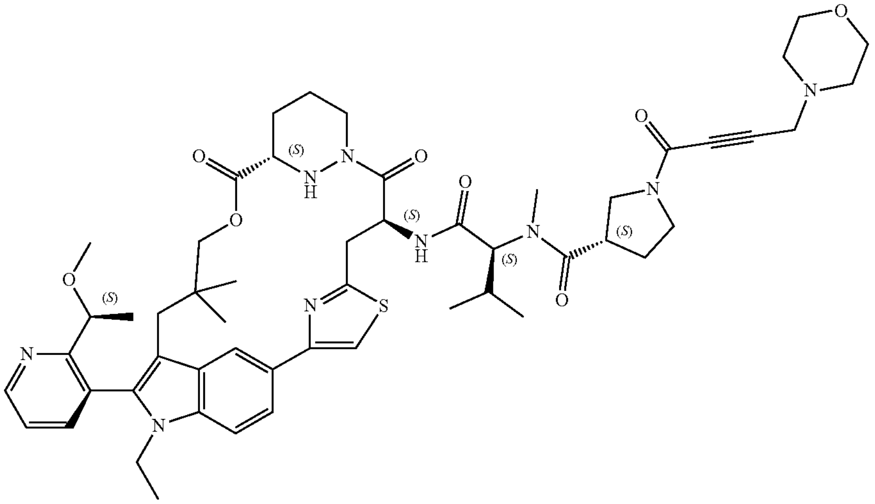 |
| B187 | 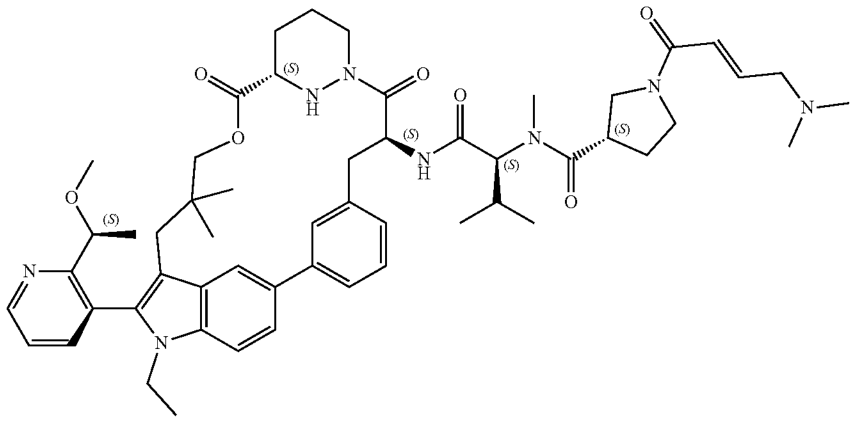 |

TABLE 2-continued
| Certain Compounds | |
|---|---|
| Ex # | Structure |
| B188 | 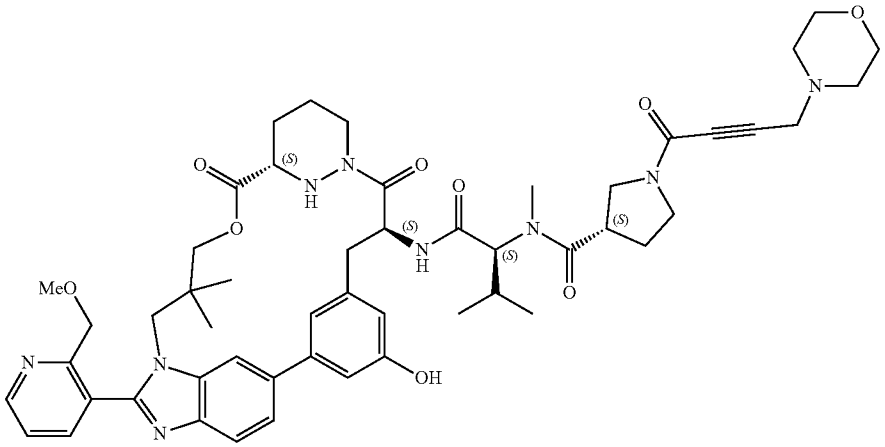 |
| B189 | 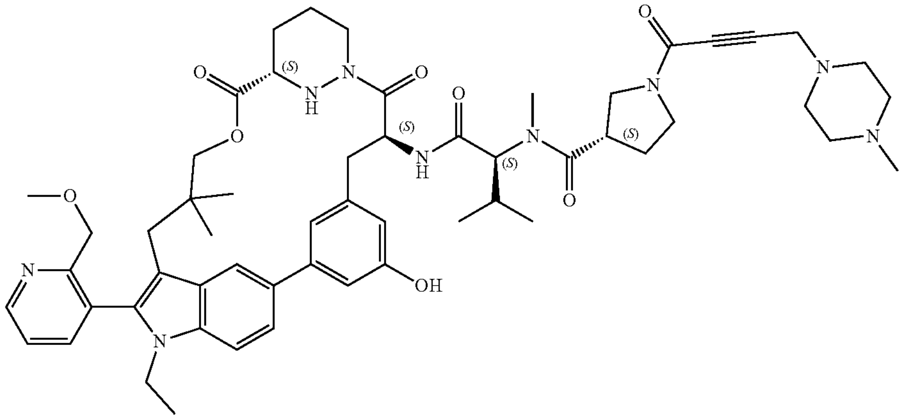 |
| B190 | 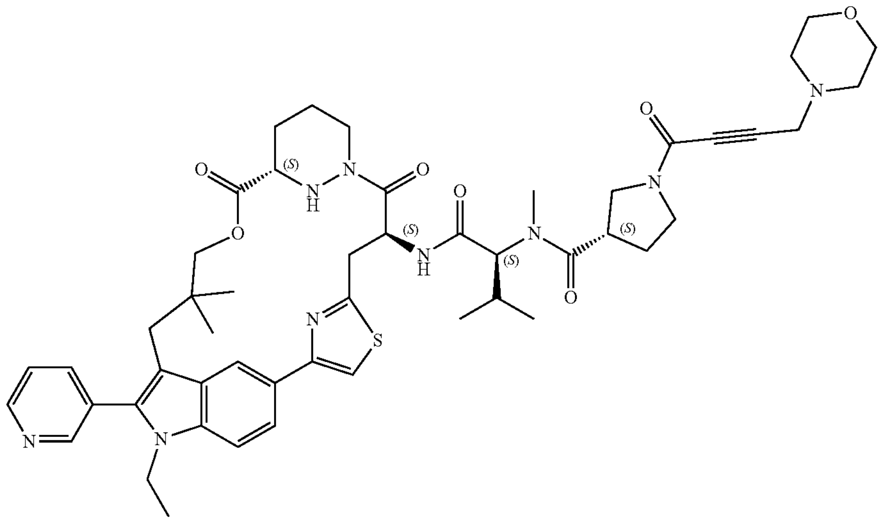 |

TABLE 2-continued
| Certain Compounds | |
|---|---|
| Ex # | Structure |
| B191 | 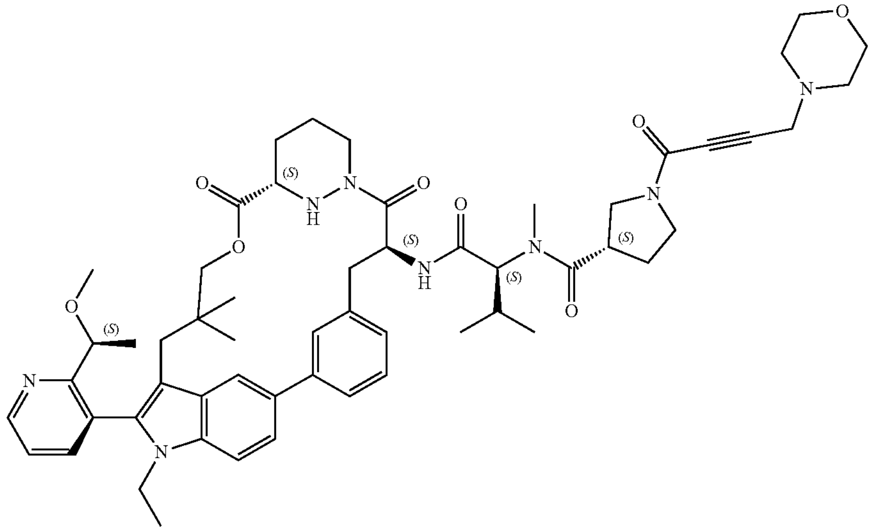 |
| B192 | 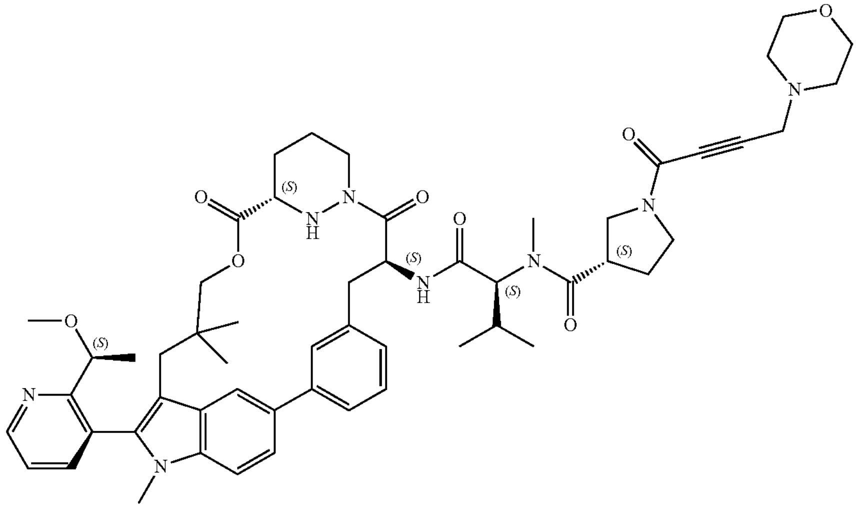 |
| B193 | 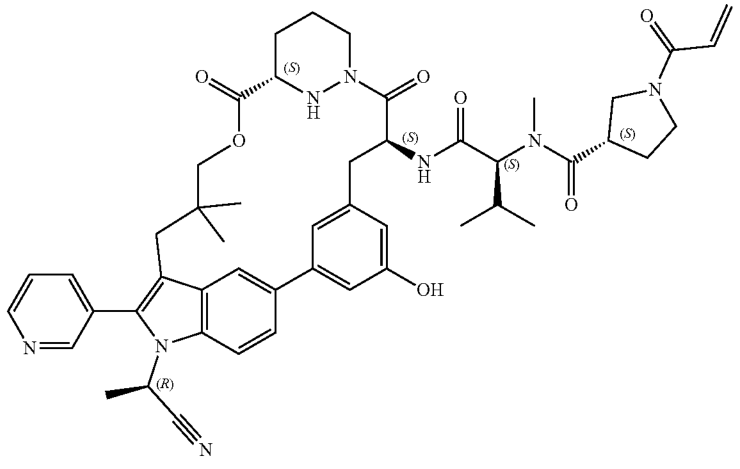 |

TABLE 2-continued
| Certain Compounds | |
|---|---|
| Ex # | Structure |
| B194 | 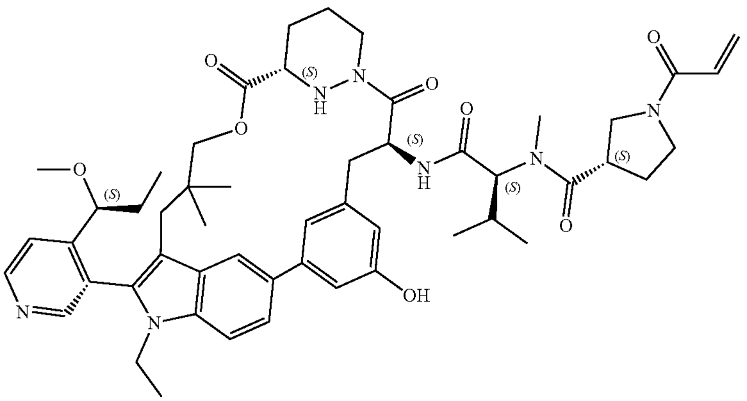 |
| B195 | 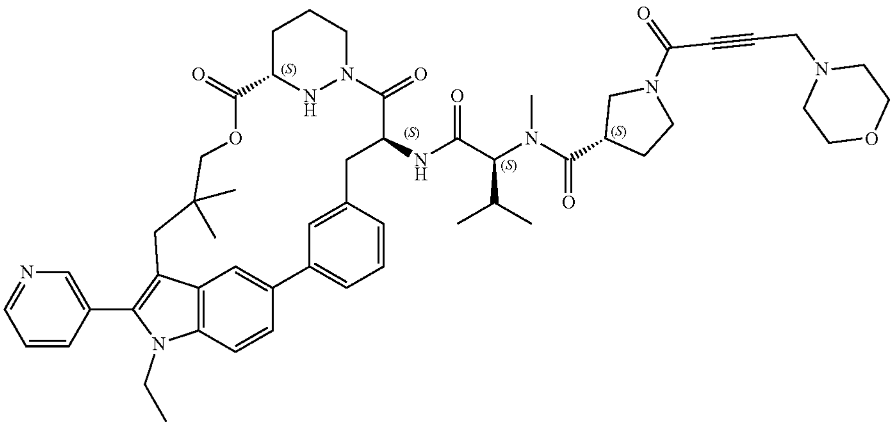 |
| B196 | 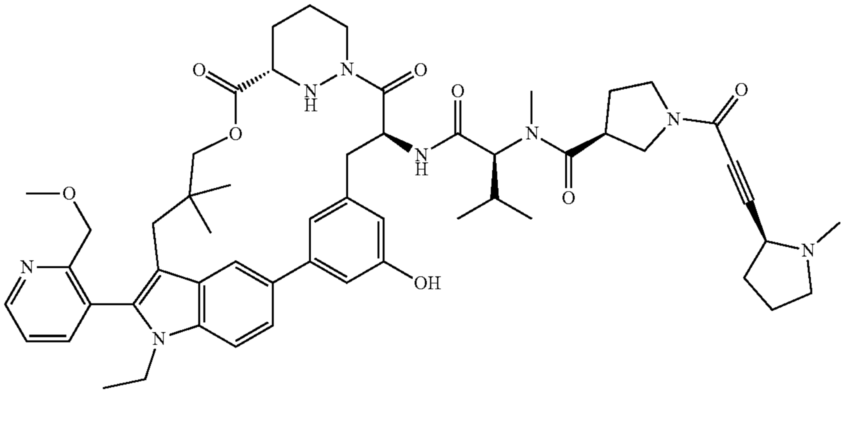 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@@H]3CCCN3C)C1)C(=O)N1CCC[C@H](N1)C(=O)OCC(C)(C)C2] |

TABLE 2-continued
| Certain Compounds | |
|---|---|
| Ex # | Structure |
| B197 | 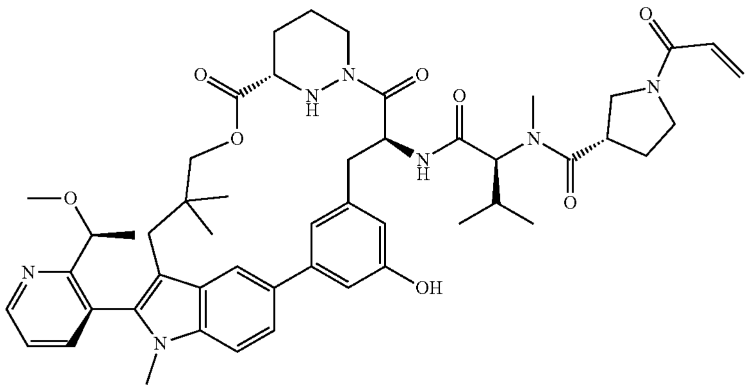 |
| B198 | 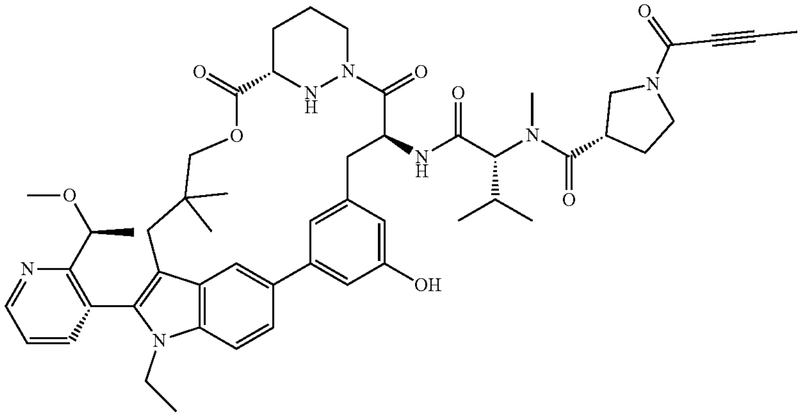 |
| B199 | 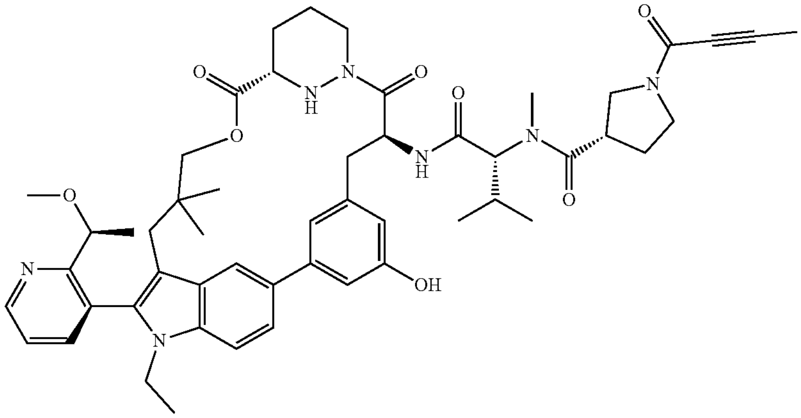 |

TABLE 2-continued
| Certain Compounds | |
|---|---|
| Ex # | Structure |
| B200 | 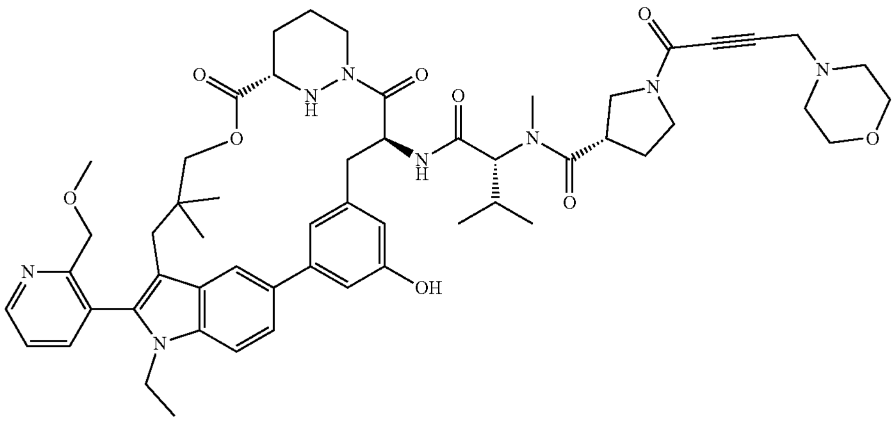 [SMILES: CCn1c(-c2cccnc2COC)c2c3cc(ccc31)-c1cc(O)cc(c1)C[C@H](NC(=O)[C@@H](C(C)C)N(C)C(=O)[C@H]1CCN(C(=O)C#CCN3CCOCC3)C1)C(=O)N1CCC[C@H](N1)C(=O)OCC(C)(C)C2] |
| B201 | 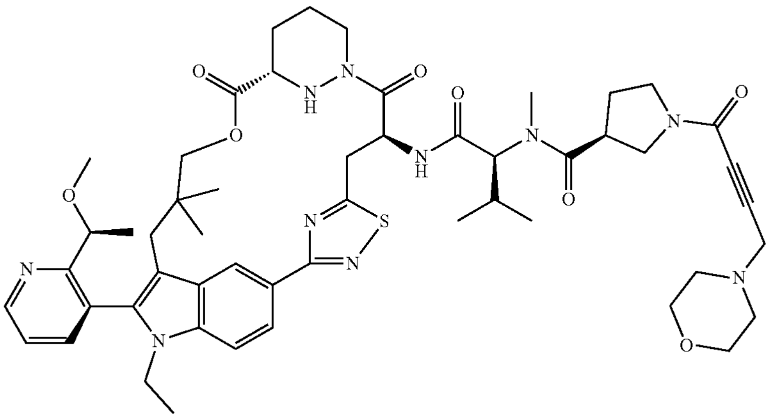 |
| B202 | 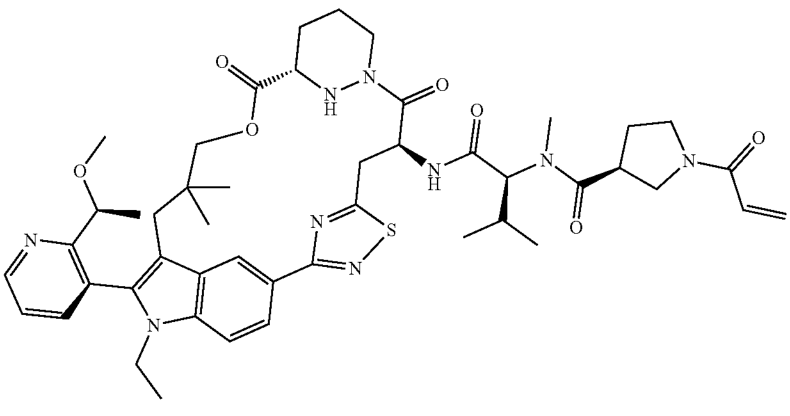 |

TABLE 2-continued
| Certain Compounds | |
|---|---|
| Ex # | Structure |
| B203 | 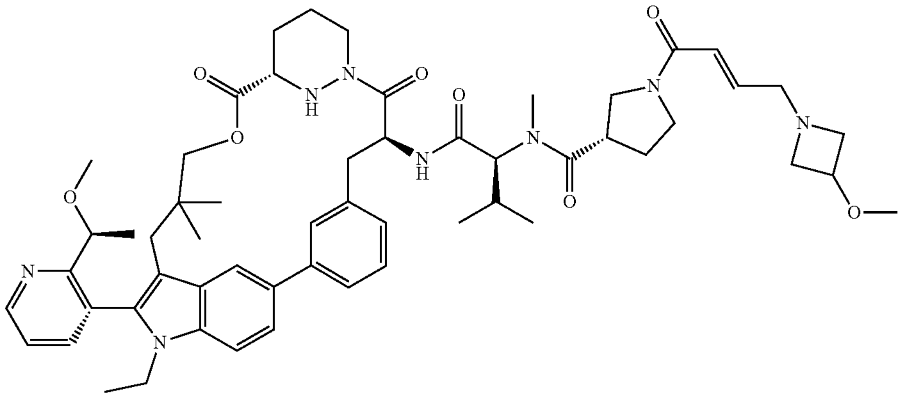 |
| B204 | 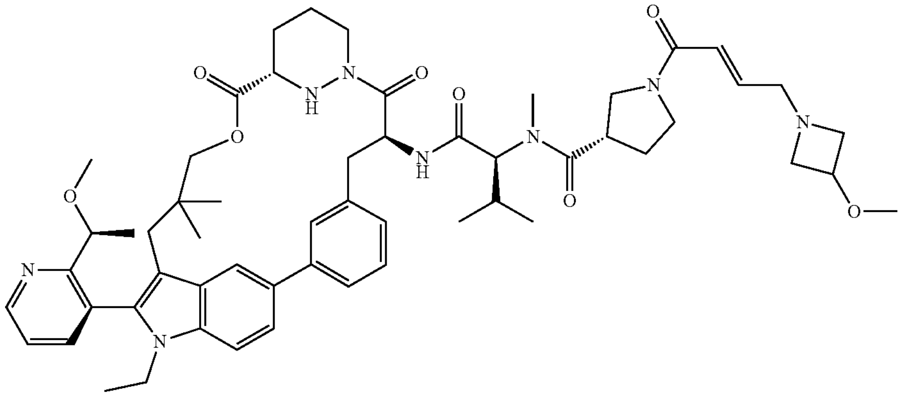 |
| B205 | 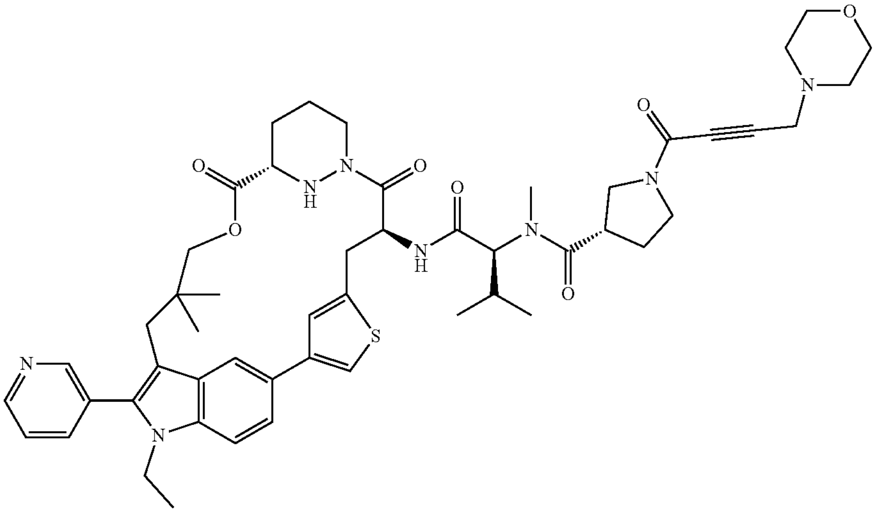 [SMILES: CCn1c(-c2cccnc2)c2c3cc(ccc31)-c1csc(c1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |

TABLE 2-continued
| Certain Compounds | |
|---|---|
| Ex # | Structure |
| B206 | 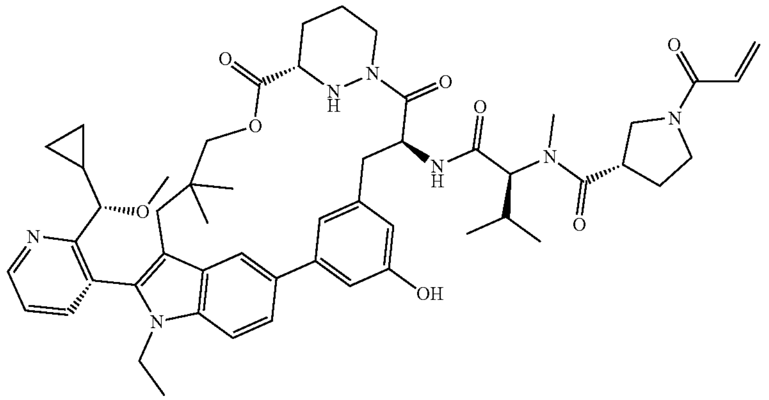 |
| B207 | 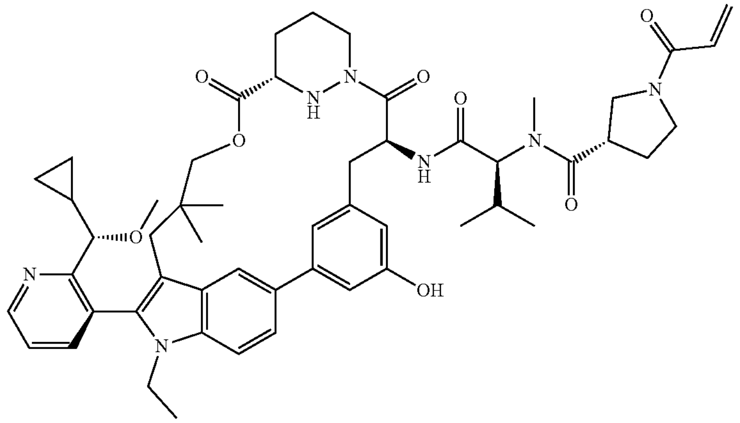 |
| B208 | 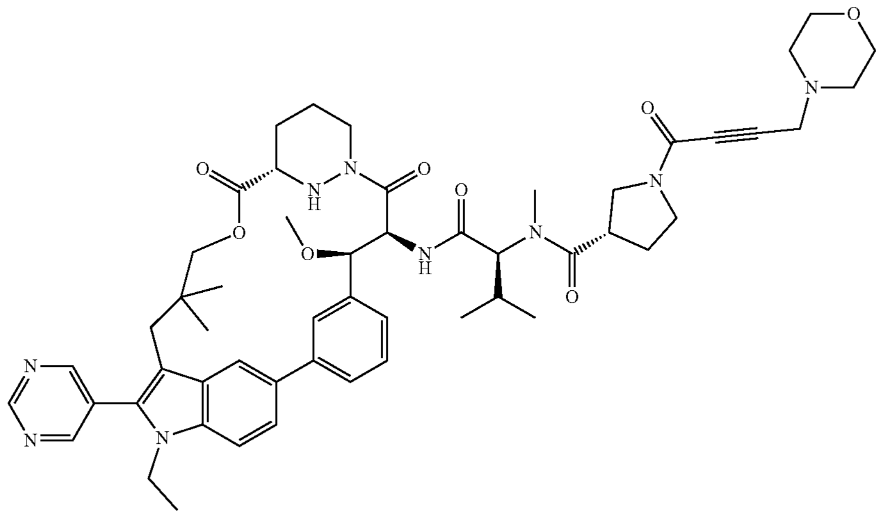 [SMILES: CCn1c(-c2cncnc2)c2c3cc(ccc31)-c1cccc(c1)[C@@H](OC)[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |

TABLE 2-continued
| Certain Compounds | |
|---|---|
| Ex # | Structure |
| B209 | 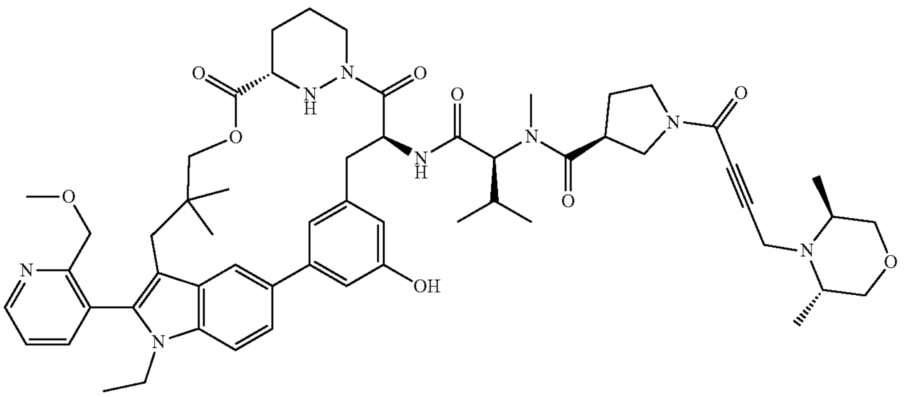 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CCN3[C@@H](C)COC[C@@H]3C)C1)C(=O)N1CCC[C@H](N1)C(=O)OCC(C)(C)C2] |
| B210 | 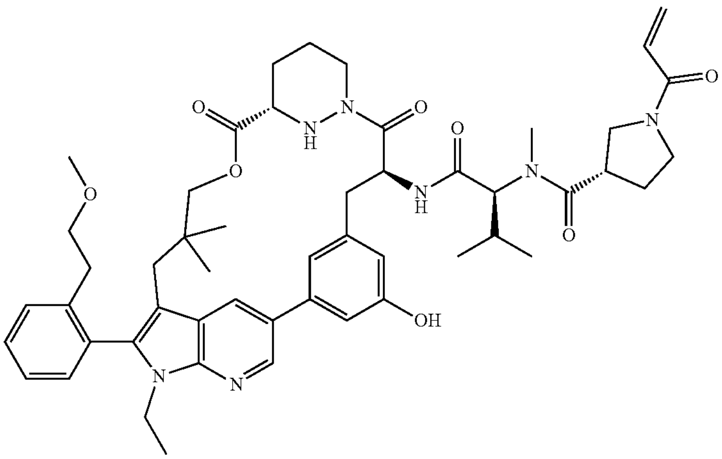 [SMILES: C=CC(=O)N1CC[C@H](C(=O)N(C)[C@H](C(=O)N[C@H]2Cc3cc(O)cc(c3)-c3cnc4c(c3)c(c(-c3ccccc3CCOC)n4CC)CC(C)(C)COC(=O)[C@@H]3CCCN(N3)C2=O)C(C)C)C1] |
| B211 | 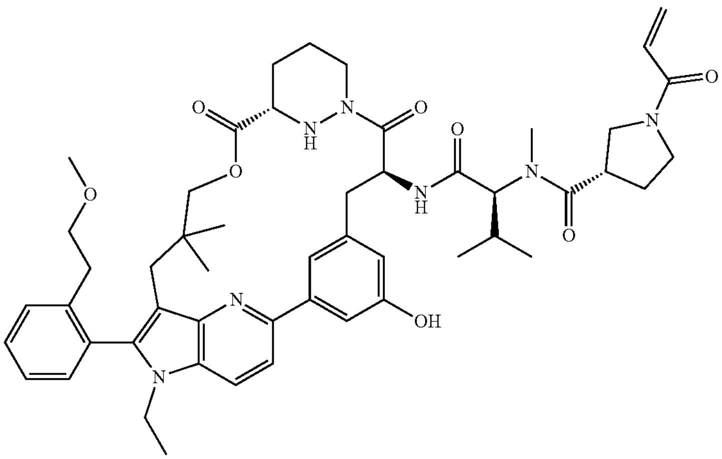 [SMILES: C=CC(=O)N1CC[C@H](C(=O)N(C)[C@H](C(=O)N[C@H]2Cc3cc(O)cc(c3)-c3ccc4c(n3)c(c(-c3ccccc3CCOC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B212 | 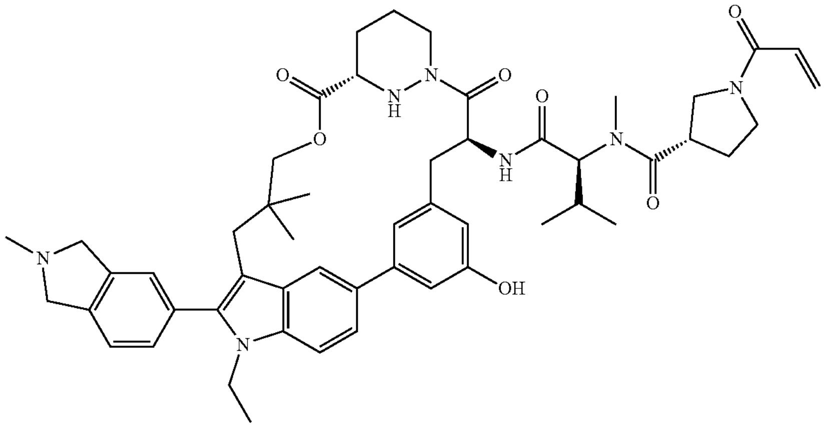 [SMILES: C=CC(=O)N1CC[C@H](C(=O)N(C)[C@H](C(=O)N[C@H]2Cc3cc(O)cc(c3)-c3ccc4c(c3)c(c(-c3ccc5c(c3)CN(C)C5)n4CC)CC(C)(C)COC(=O)[C@@H]3CCCN(N3)C2=O)C(C)C)C1] |
| B213 | 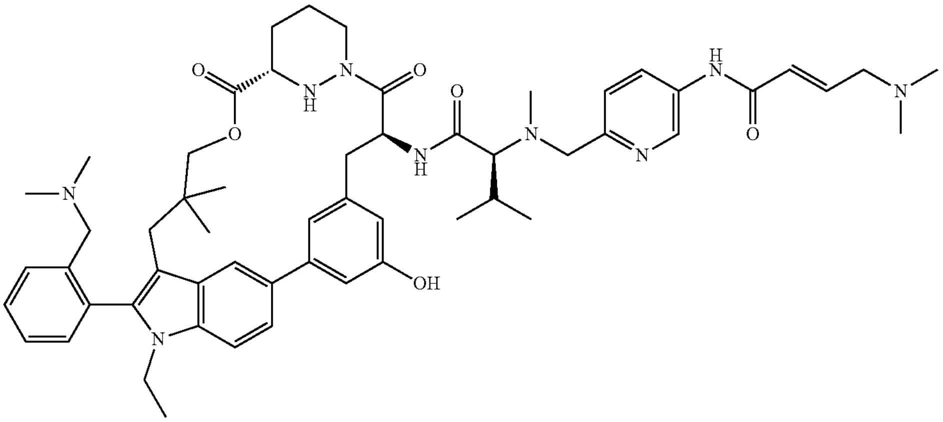 [SMILES: CCn1c(-c2ccccc2CN(C)C)c2c3cc(ccc31)-c1cc(O)cc(c1)C[C@H](NC(=O)[C@H](C(C)C)N(C)Cc1ccc(NC(=O)/C=C/CN(C)C)cn1)C(=O)N1CCC[C@H](N1)C(=O)OCC(C)(C)C2] |
| B214 | 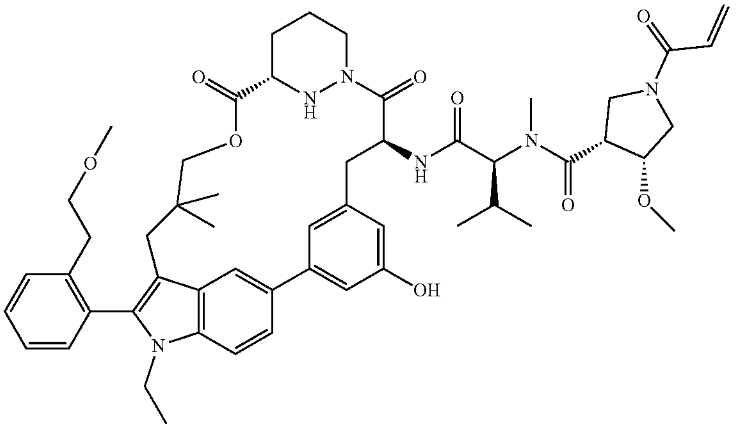 [SMILES: C=CC(=O)N1C[C@H](OC)[C@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B215 | 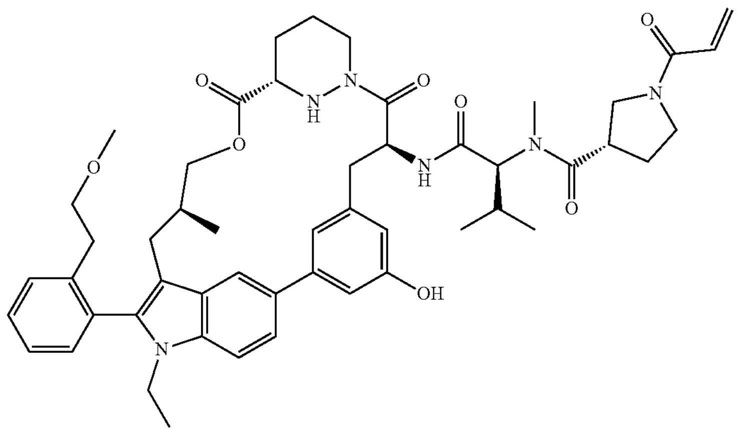 [SMILES: C=CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)C[C@H](C)COC(=O)[C@@H]3CCCN(N3)C2=O)C(C)C)C1] |
| B216 | 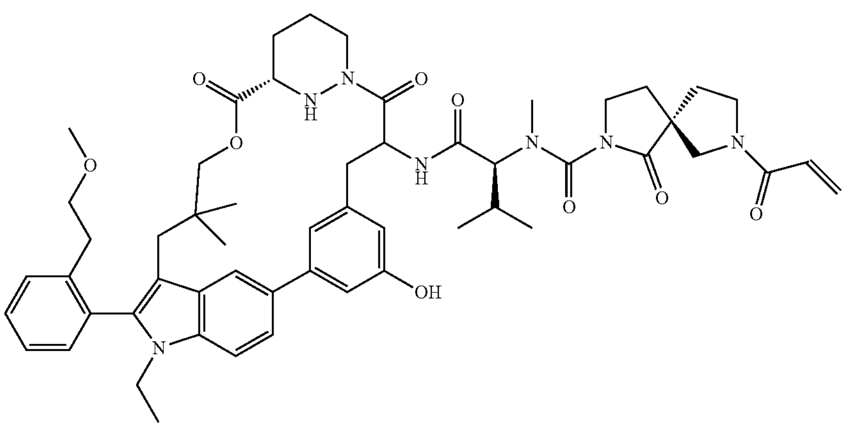 [SMILES: C=CC(=O)N1CC[C@]2(CCN(C(=O)N(C)[C@H](C(=O)NC3Cc4cc(O)cc(c4)-c4ccc5c(c4)c(c(-c4ccccc4CCOC)n5CC)CC(C)(C)COC(=O)[C@@H]4CCCN(N4)C3=O)C(C)C)C2=O)C1] |
| B217 | 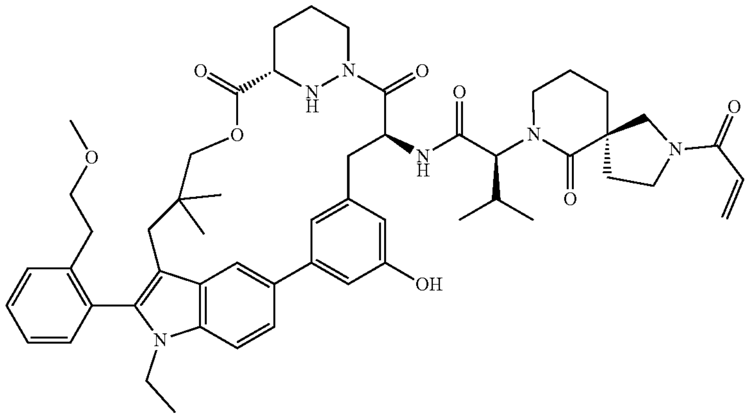 [SMILES: C=CC(=O)N1CC[C@]2(CCCN([C@H](C(=O)N[C@H]3Cc4cc(O)cc(c4)-c4ccc5c(c4)c(c(-c4ccccc4CCOC)n5CC)CC(C)(C)COC(=O)[C@@H]4CCCN(N4)C3=O)C(C)C)C2=O)C1] |

TABLE 2-continued
| Certain Compounds | |
|---|---|
| Ex # | Structure |
| B218 | 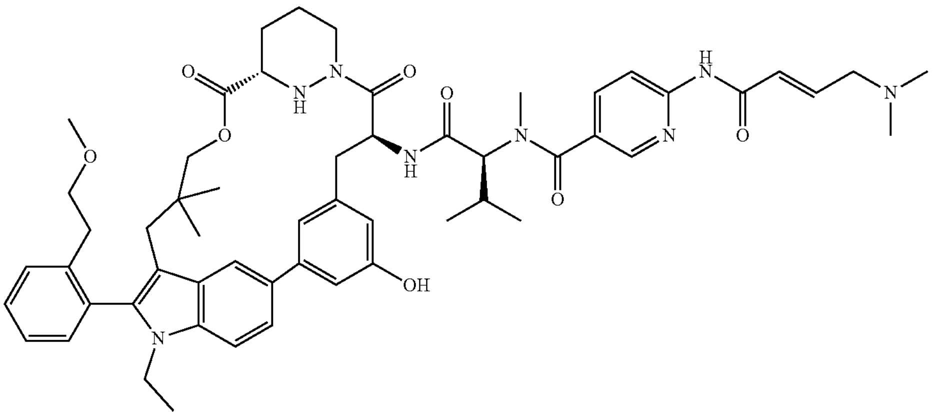 [SMILES: CCn1c(-c2ccccc2CCOC)c2c3cc(ccc31)-c1cc(O)cc(c1)C[C@H](NC(=O)[C@H](C(C)C)N(C)C(=O)c1ccc(NC(=O)/C=C/CN(C)C)nc1)C(=O)N1CCC[C@H](N1)C(=O)OCC(C)(C)C2] |
| B219 | 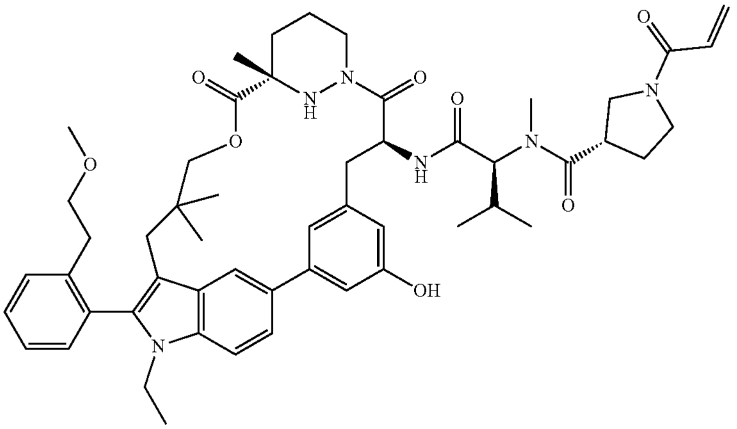 [SMILES: C=CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@]3(C)CCCN(N3)C2=O)C(C)C)C1] |
| B220 | 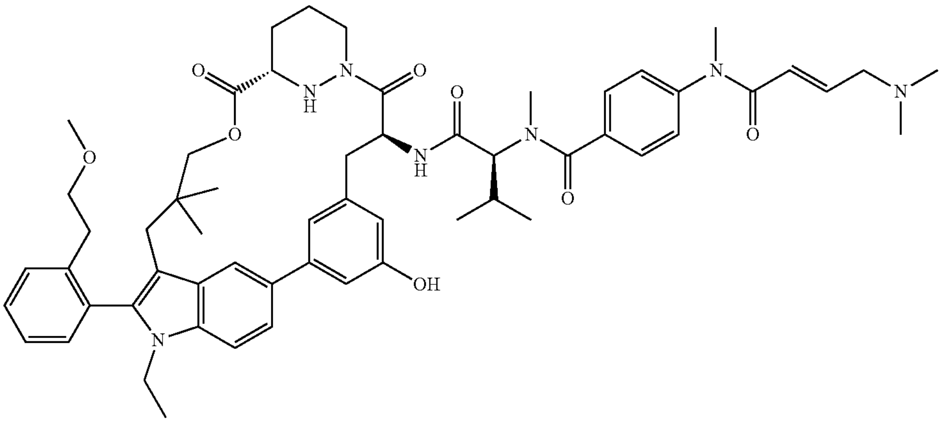 [SMILES: CCn1c(-c2ccccc2CCOC)c2c3cc(ccc31)-c1cc(O)cc(c1)C[C@H](NC(=O)[C@H](C(C)C)N(C)C(=O)c1ccc(N(C)C(=O)/C=C/CN(C)C)cc1)C(=O)N1CCC[C@H](N1)C(=O)OCC(C)(C)C2] |

TABLE 2-continued
| Certain Compounds | |
|---|---|
| Ex # | Structure |
| B221 | 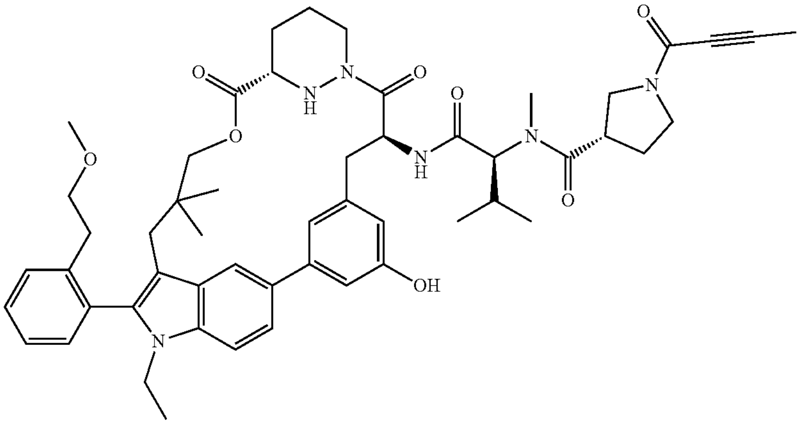 [SMILES: CC#CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@@H]3CCCN(N3)C2=O)C(C)C)C1] |
| B222 | 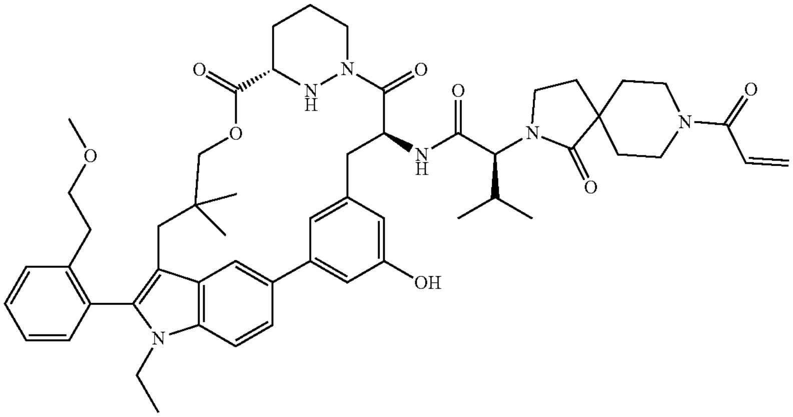 [SMILES: C=CC(=O)N1CCC2(CC1)CCN([C@H](C(=O)N[C@H]1Cc3cc(O)cc(c3)-c3ccc4c(c3)c(c(-c3ccccc3CCOC)n4CC)CC(C)(C)COC(=O)[C@@H]3CCCN(N3)C1=O)C(C)C)C2=O] |
| B223 | 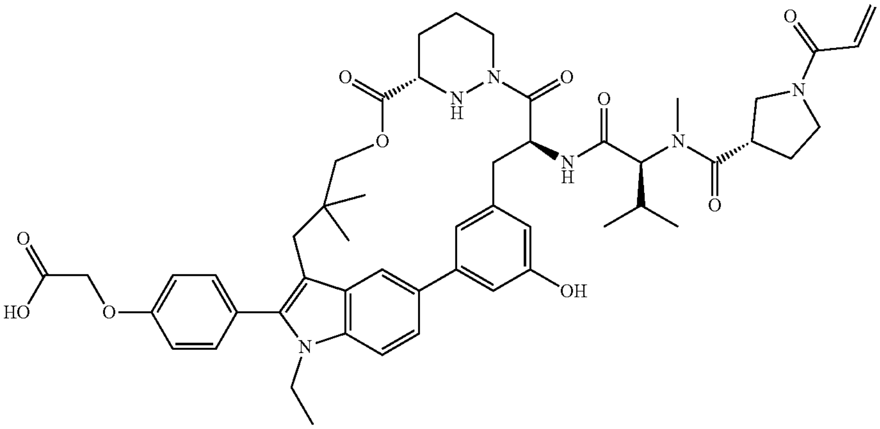 [SMILES: C=CC(=O)N1CC[C@H](C(=O)N(C)[C@H](C(=O)N[C@H]2Cc3cc(O)cc(c3)-c3ccc4c(c3)c(c(-c3ccc(OCC(=O)O)cc3)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B224 | 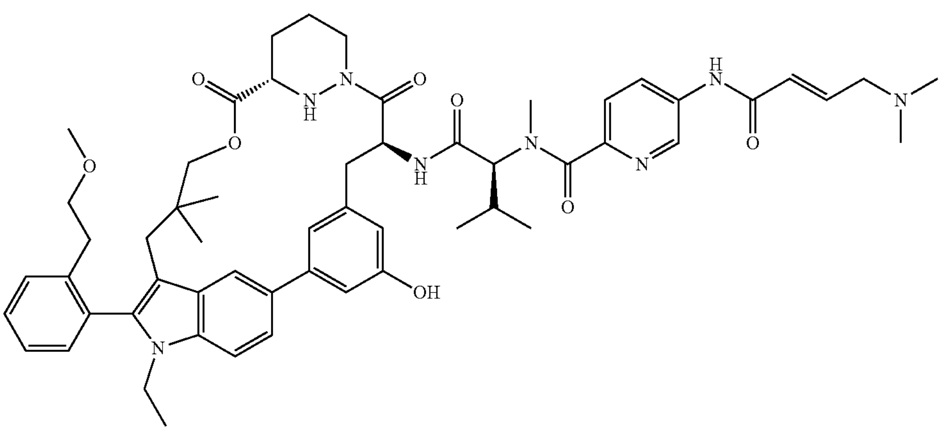 |
| B225 | 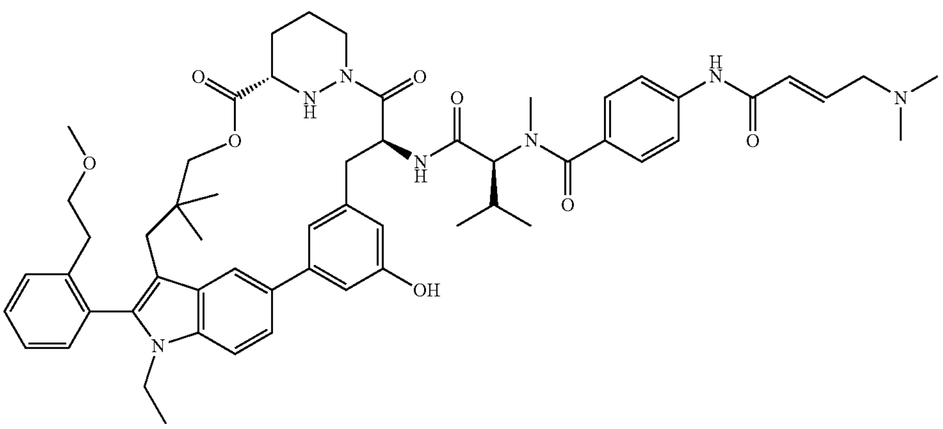 [SMILES: CCn1c(-c2ccccc2CCOC)c2c3cc(ccc31)-c1cc(O)cc(c1)C[C@H](NC(=O)[C@H](C(C)C)N(C)C(=O)c1ccc(NC(=O)/C=C/CN(C)C)cc1)C(=O)N1CCC[C@H](N1)C(=O)OCC(C)(C)C2] |
| B226 | 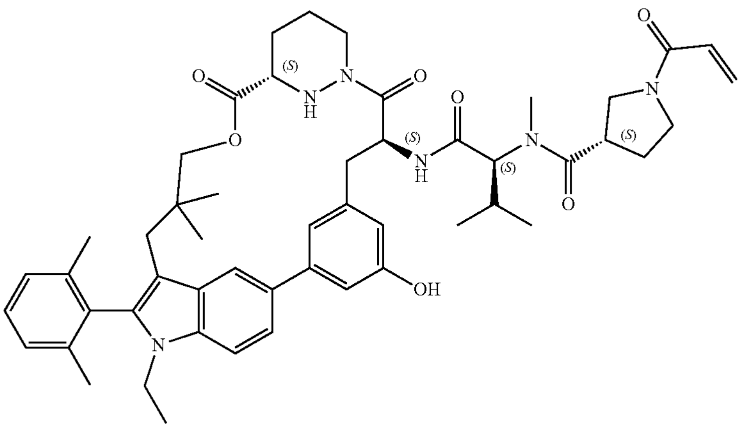 |

TABLE 2-continued
| Certain Compounds | |
|---|---|
| Ex # | Structure |
| B227 | 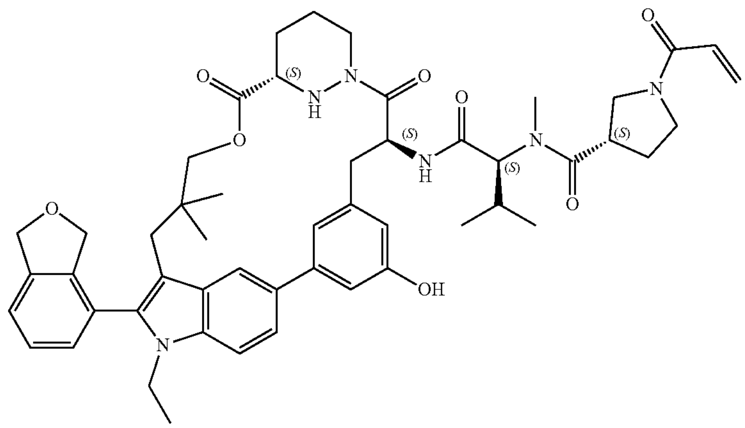 |
| B228 | 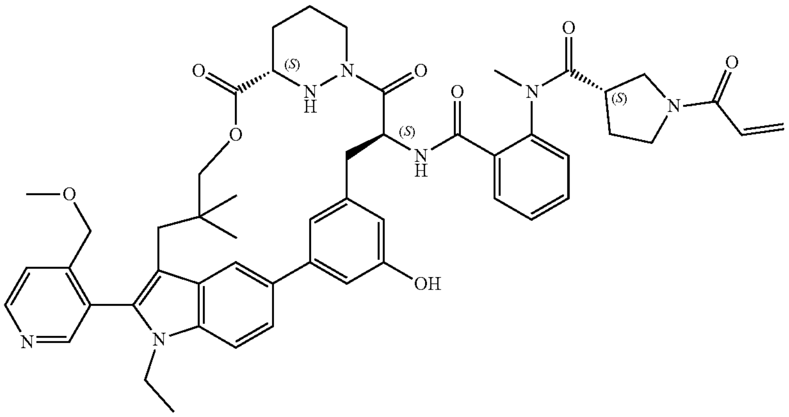 |
| B229 | 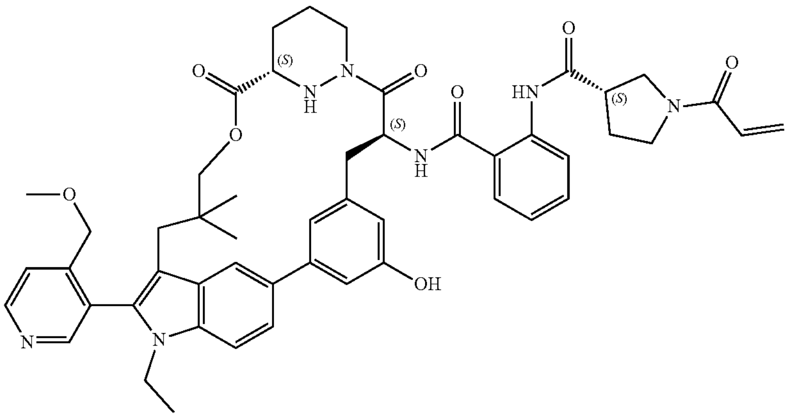 |

TABLE 2-continued
| Certain Compounds | |
|---|---|
| Ex # | Structure |
| B230 | 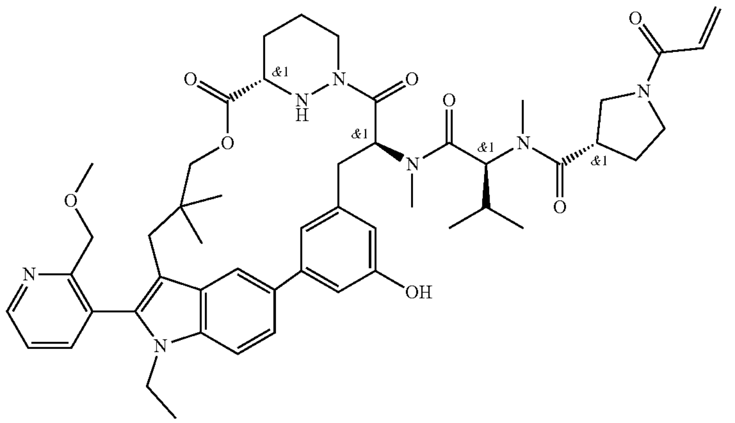 |
| B231 | 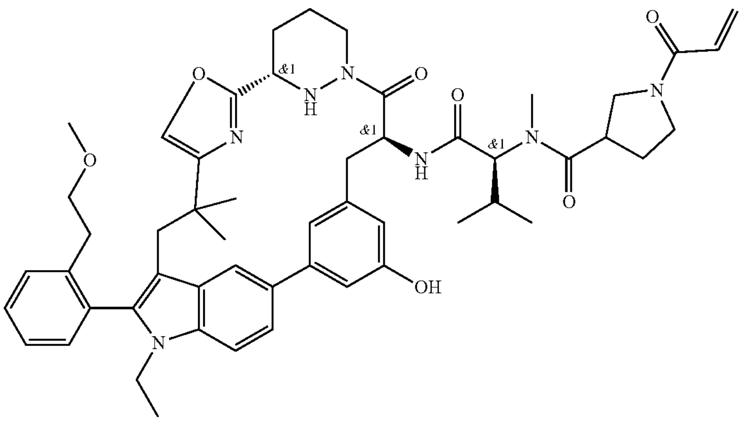 [SMILES: C=CC(=O)N1CCC(C(=O)N(C)[C@H](C(=O)N[C@H]2Cc3cc(O)cc(c3)-c3ccc4c(c3)c(c(-c3ccccc3CCOC)n4CC)CC(C)(C)c3coc(n3)[C@@H]3CCCN(N3)C2=O)C(C)C)C1] |
| B232 | 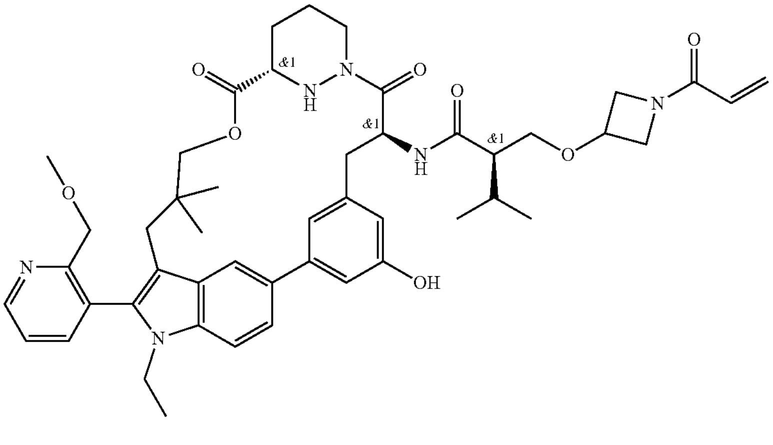 [SMILES: C=CC(=O)N1CC(OC[C@H](C(=O)N[C@H]2Cc3cc(O)cc(c3)-c3ccc4c(c3)c(c(-c3cccnc3COC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B233 | 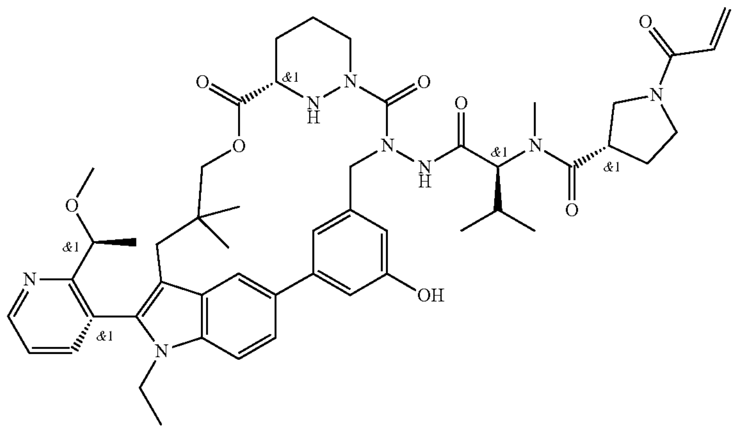 |
| B234 | 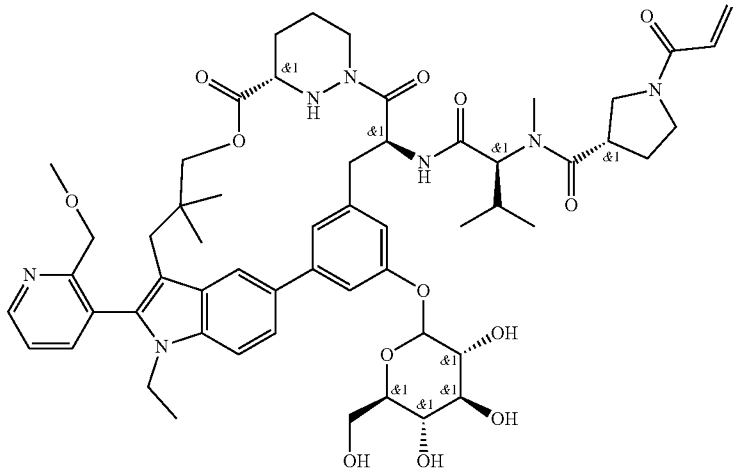 [SMILES: C=CC(=O)N1CC[C@H](C(=O)N(C)[C@H](C(=O)N[C@H]2Cc3cc(OC4O[C@H](CO)[C@@H](O)[C@H](O)[C@H]4O)cc(c3)-c3ccc4c(c3)c(c(-c3cccnc3COC)n4CC)CC(C)(C)COC(=O)[C@@H]3CCCN(N3)C2=O)C(C)C)C1] |
| B235 | 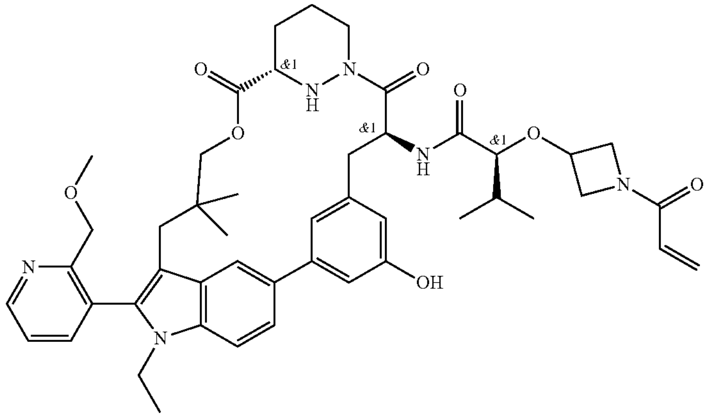 [SMILES: C=CC(=O)N1CC(O[C@H](C(=O)N[C@H]2Cc3cc(O)cc(c3)-c3ccc4c(c3)c(c(-c3cccnc3COC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B236 | 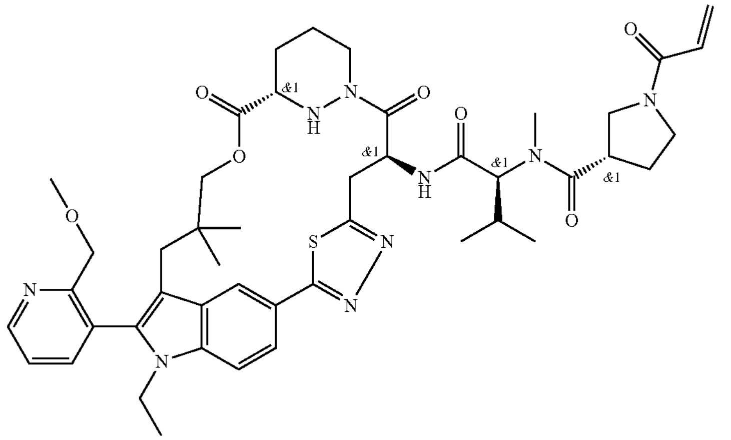 [SMILES: C=CC(=O)N1CC[C@H](C(=O)N(C)[C@H](C(=O)N[C@H]2CC3=NN=C(S3)c3ccc4c(c3)c(c(-c3cccnc3COC)n4CC)CC(C)(C)COC(=O)[C@@H]3CCCN(N3)C2=O)C(C)C)C1] |
| B237 | 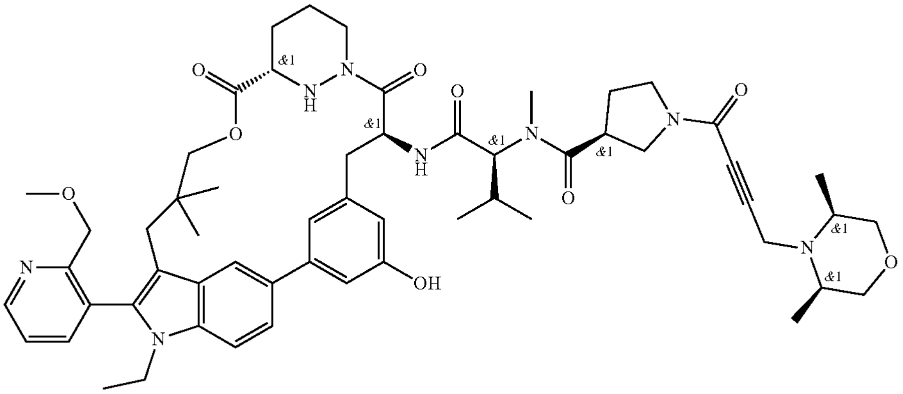 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CCN3[C@H](C)COC[C@@H]3C)C1)C(=O)N1CCC[C@H](N1)C(=O)OCC(C)(C)C2] |
| B238 | 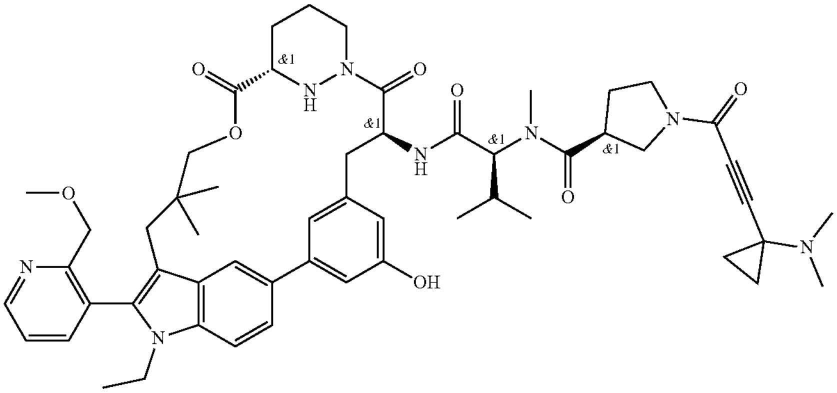 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CC3(N(C)C)CC3)C1)C(=O)N1CCC[C@H](N1)C(=O)OCC(C)(C)C2] |

TABLE 2-continued
| Certain Compounds | |
|---|---|
| Ex # | Structure |
| B239 | 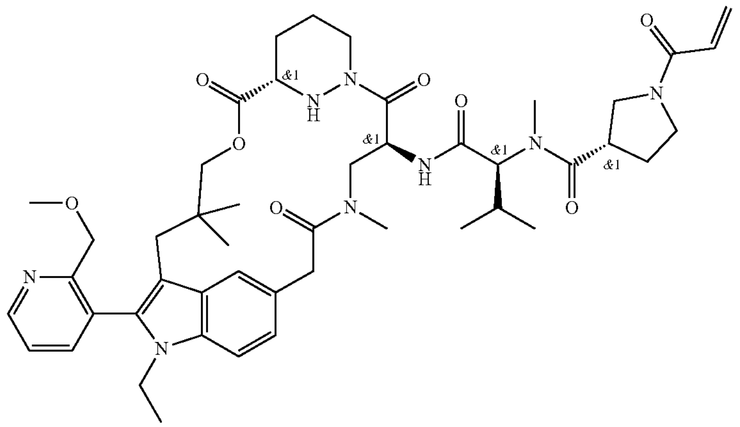 [SMILES: C=CC(=O)N1CC[C@H](C(=O)N(C)[C@H](C(=O)N[C@H]2CN(C)C(=O)Cc3ccc4c(c3)c(c(-c3cccnc3COC)n4CC)CC(C)(C)COC(=O)[C@@H]3CCCN(N3)C2=O)C(C)C)C1] |
| B240 | 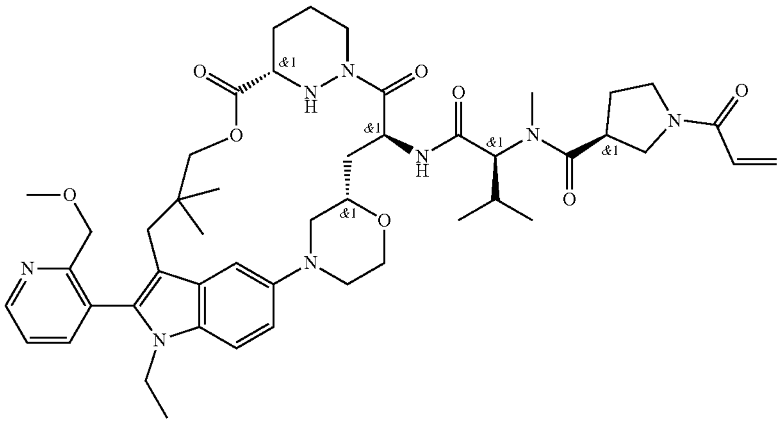 [SMILES: C=CC(=O)N1CC[C@H](C(=O)N(C)[C@H](C(=O)N[C@H]2C[C@H]3CN(CCO3)c3ccc4c(c3)c(c(-c3cccnc3COC)n4CC)CC(C)(C)COC(=O)[C@@H]3CCCN(N3)C2=O)C(C)C)C1] |
| B241 | 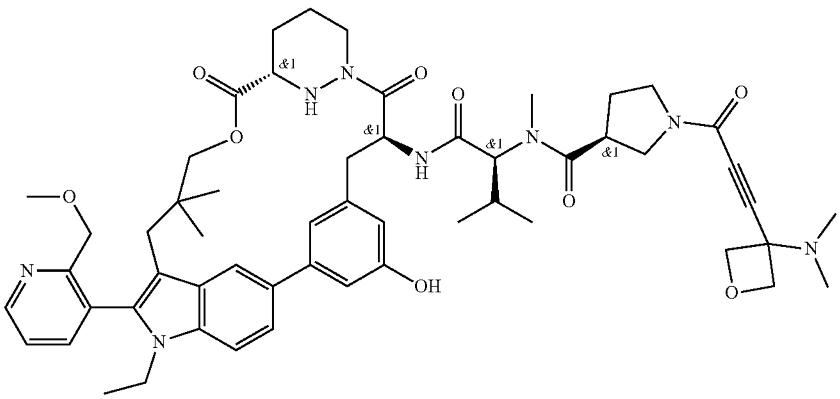 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CC3(N(C)C)COC3)C1)C(=O)N1CCC[C@H](N1)C(=O)OCC(C)(C)C2] |

TABLE 2-continued
| Certain Compounds | |
|---|---|
| Ex # | Structure |
| B242 | 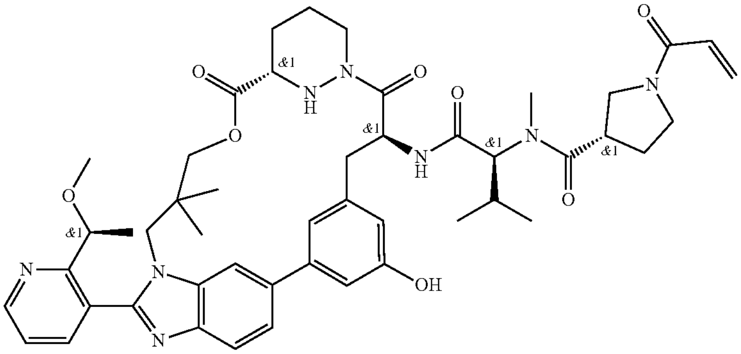 [SMILES: C=CC(=O)N1CC[C@H](C(=O)N(C)[C@H](C(=O)N[C@H]2Cc3cc(O)cc(c3)-c3ccc4nc(-c5cccnc5[C@H](C)OC)n(c4c3)CC(C)(C)COC(=O)[C@@H]3CCCN(N3)C2=O)C(C)C)C1] |
| B243 | 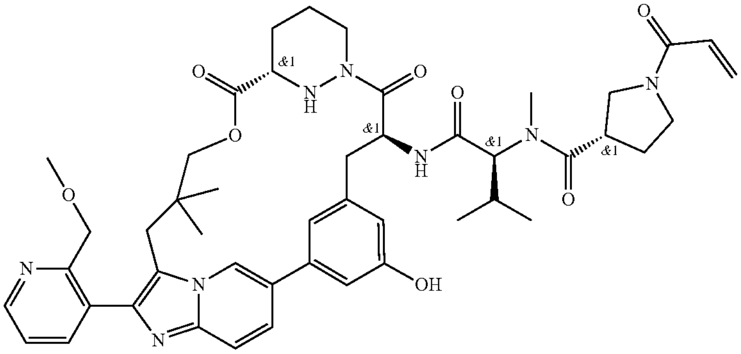 [SMILES: C=CC(=O)N1CC[C@H](C(=O)N(C)[C@H](C(=O)N[C@H]2Cc3cc(O)cc(c3)-c3ccc4nc(-c5cccnc5COC)c(n4c3)CC(C)(C)COC(=O)[C@@H]3CCCN(N3)C2=O)C(C)C)C1] |
| B244 | 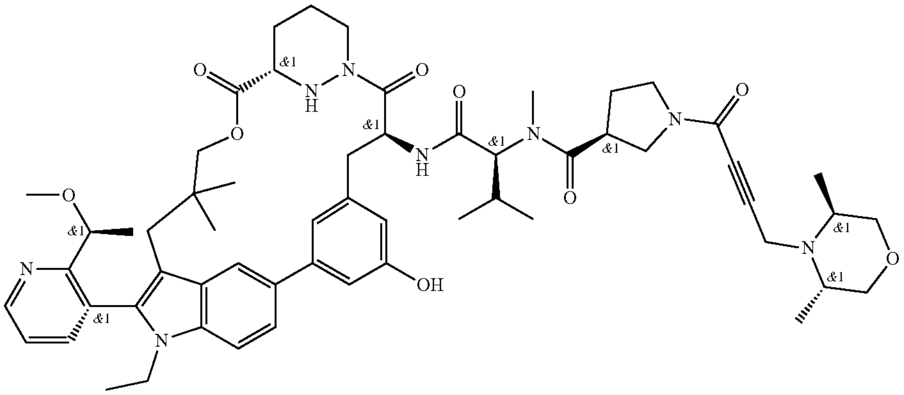 |
| B245 | 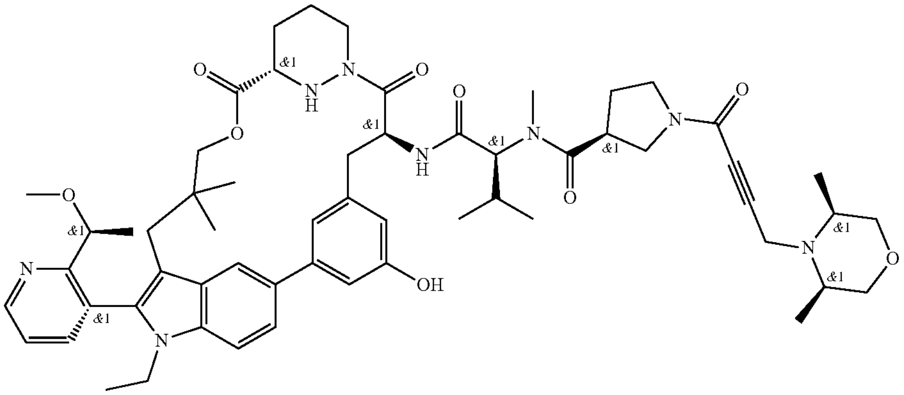 |

TABLE 2-continued
| Certain Compounds | |
|---|---|
| Ex # | Structure |
| B246 | 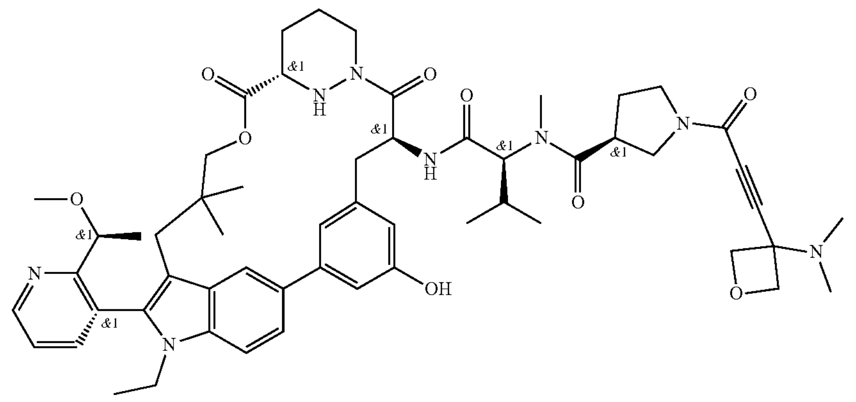 |
| B247 | 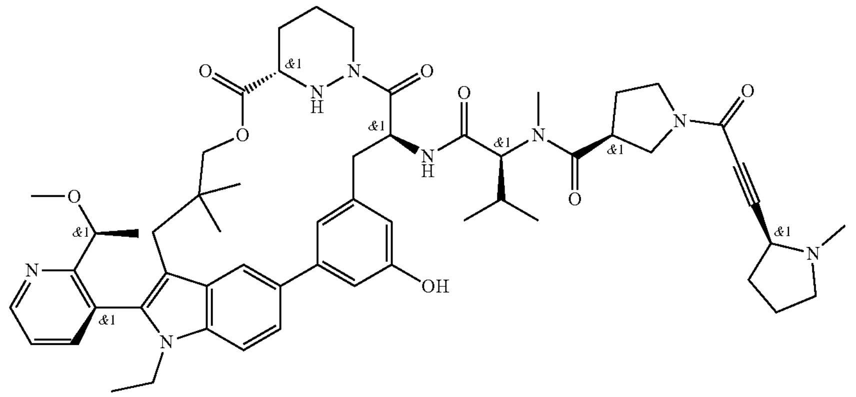 |
| B248 | 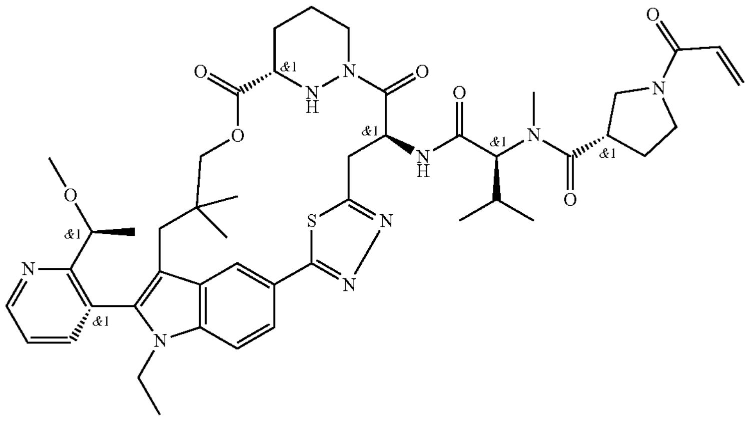 |

TABLE 2-continued
| Certain Compounds | |
|---|---|
| Ex # | Structure |
| B249 | 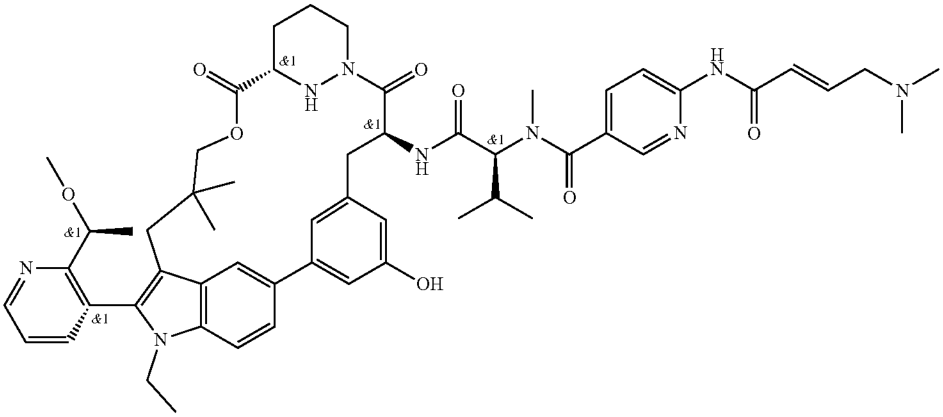 |
| B250 | 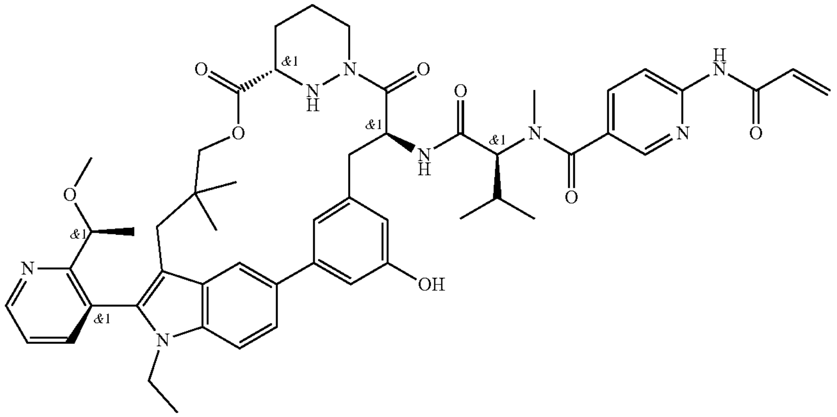 |
| B251 | 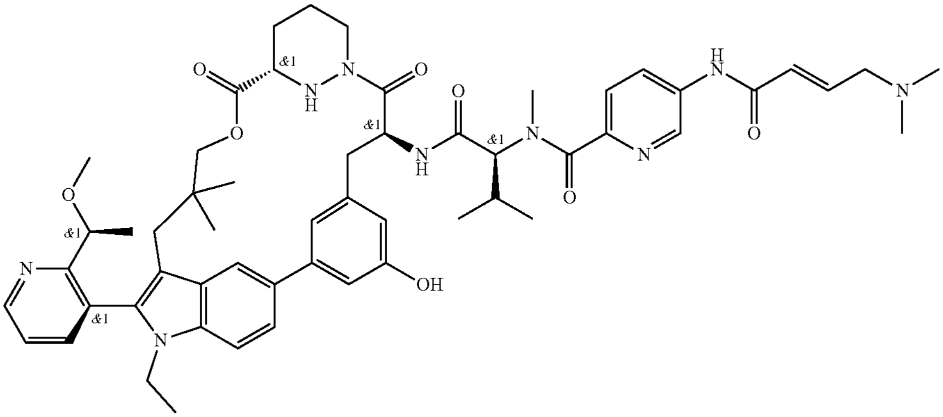 |

TABLE 2-continued
| Certain Compounds | |
|---|---|
| Ex # | Structure |
| B252 | 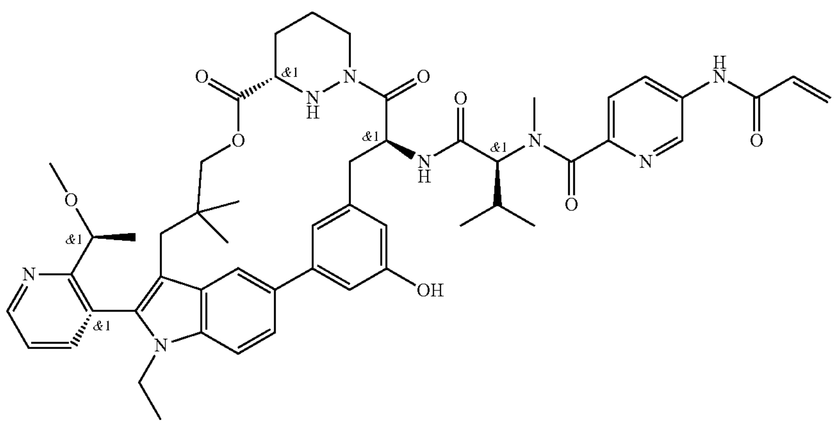 |
| B253 | 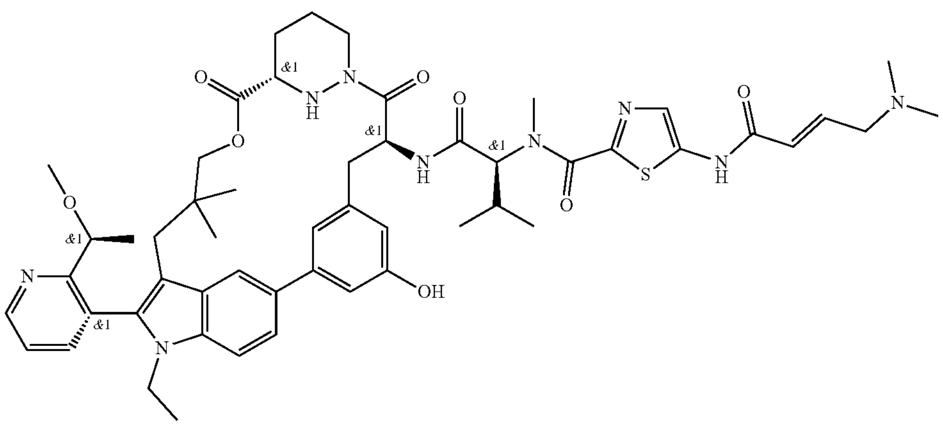 |
| B254 | 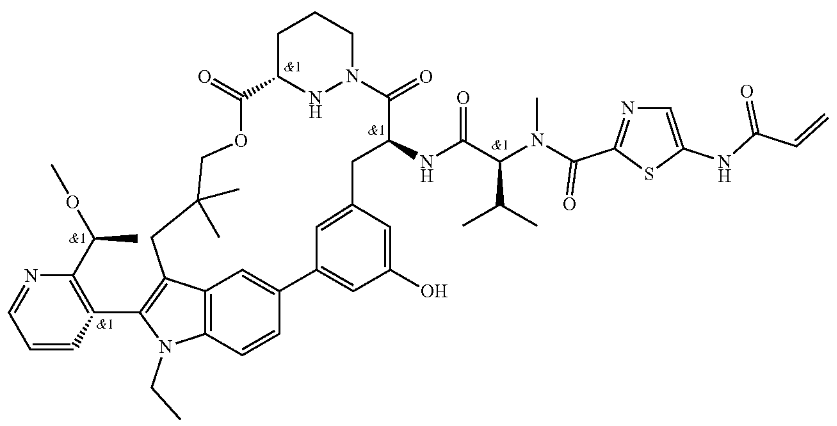 |

TABLE 2-continued
| Certain Compounds | |
|---|---|
| Ex # | Structure |
| B255 | 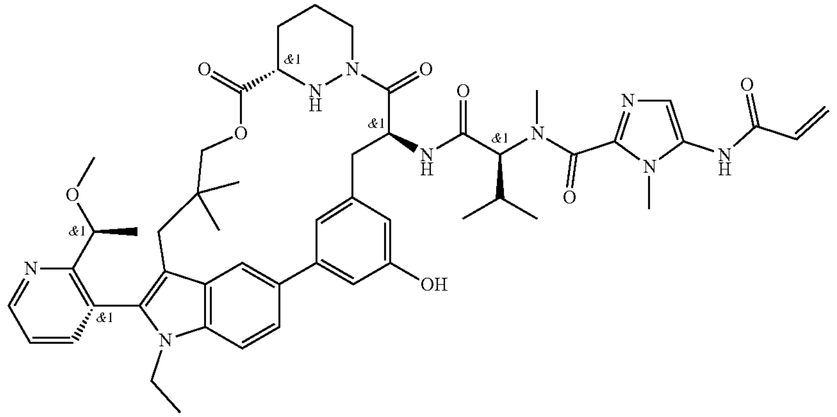 |
| B256 | 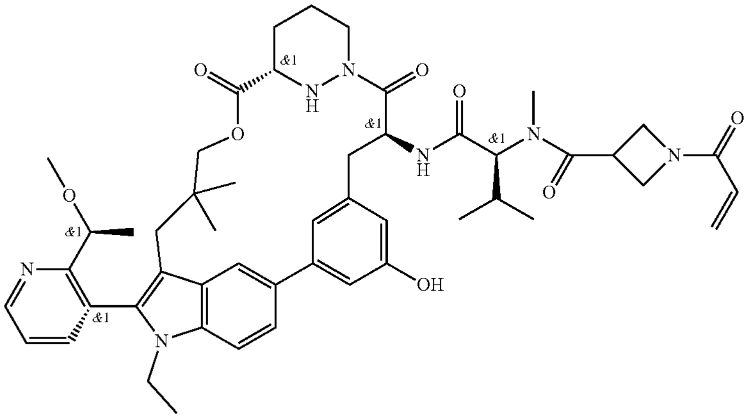 |
| B257 | 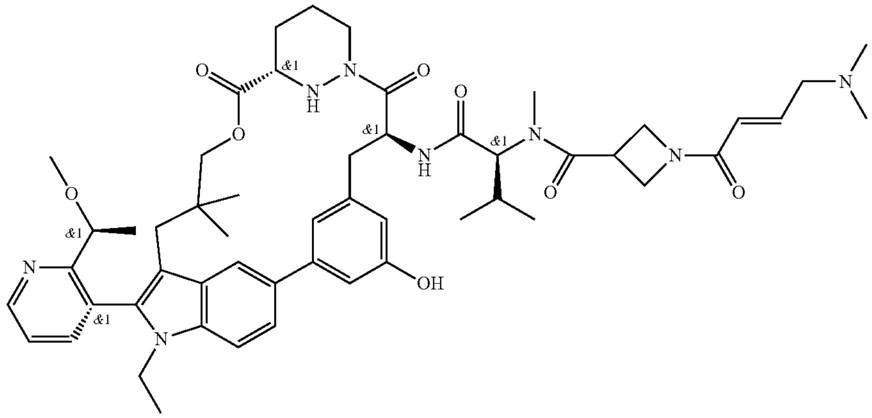 |

TABLE 2-continued
| Certain Compounds | |
|---|---|
| Ex # | Structure |
| B258 | 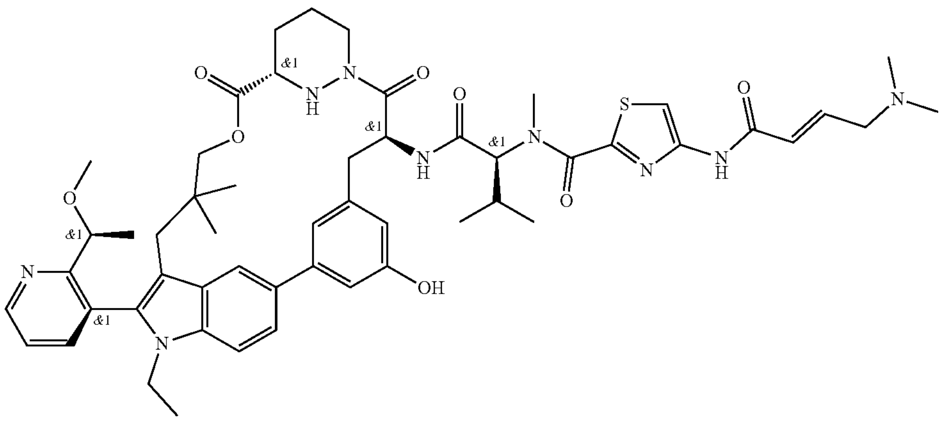 |
| B259 | 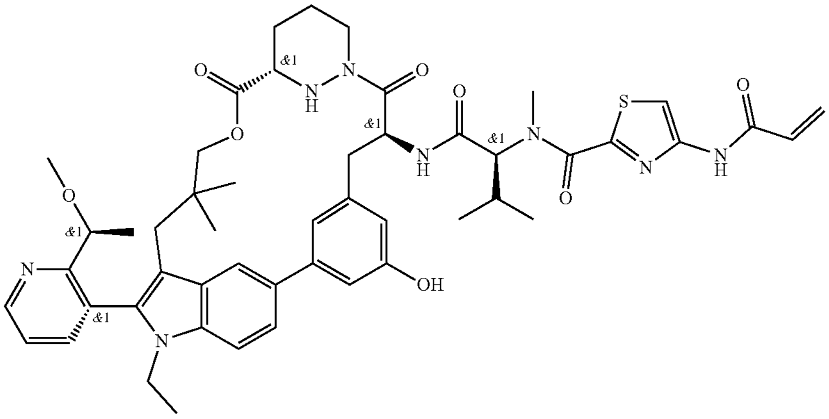 |
| B260 | 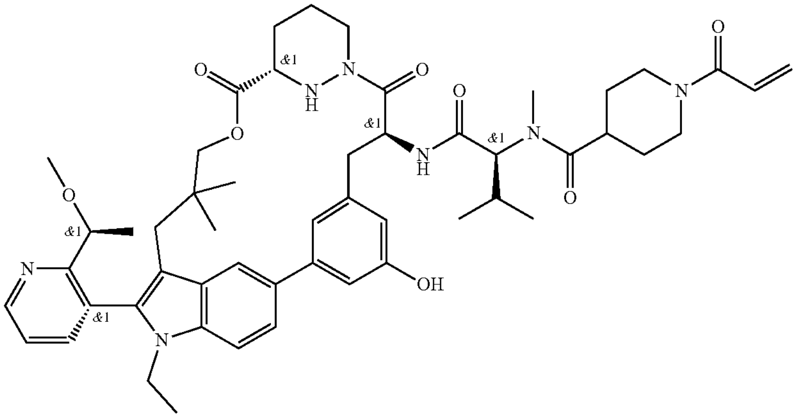 |

TABLE 2-continued
| Certain Compounds | |
|---|---|
| Ex # | Structure |
| B261 | 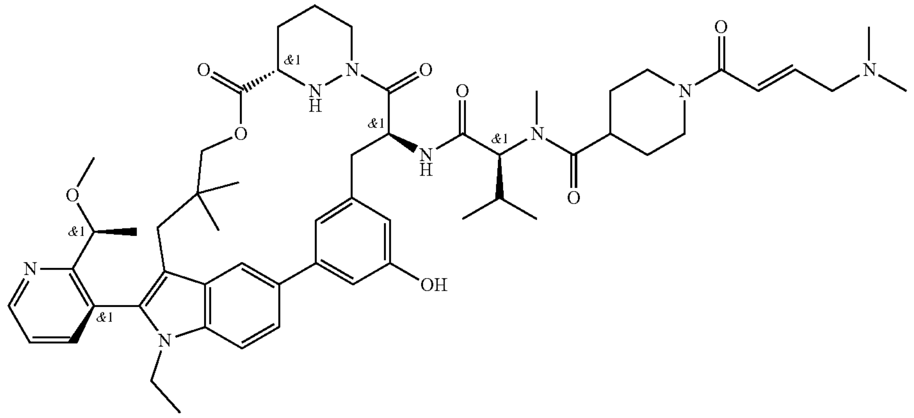 |
| B262 | 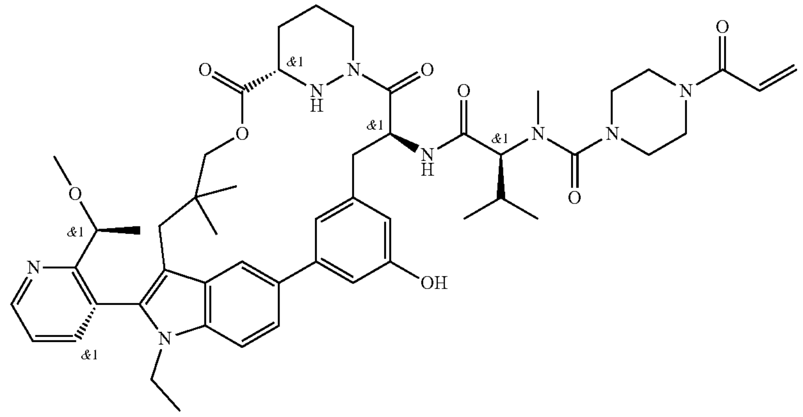 |
| B263 | 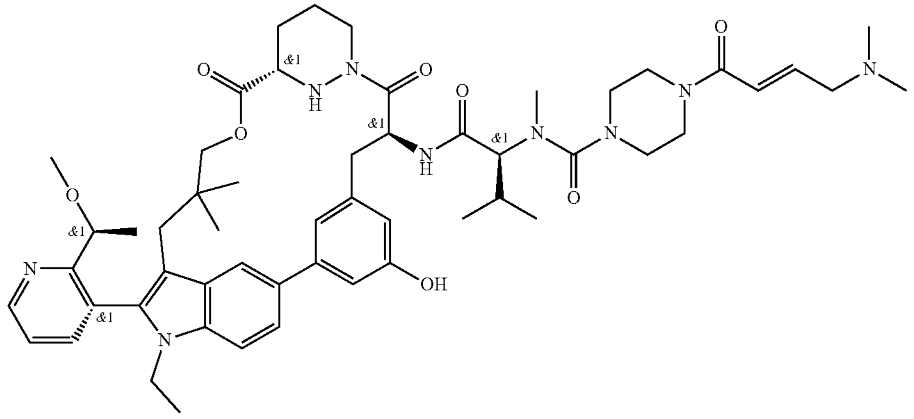 |

TABLE 2-continued
| Certain Compounds | |
|---|---|
| Ex # | Structure |
| B264 | 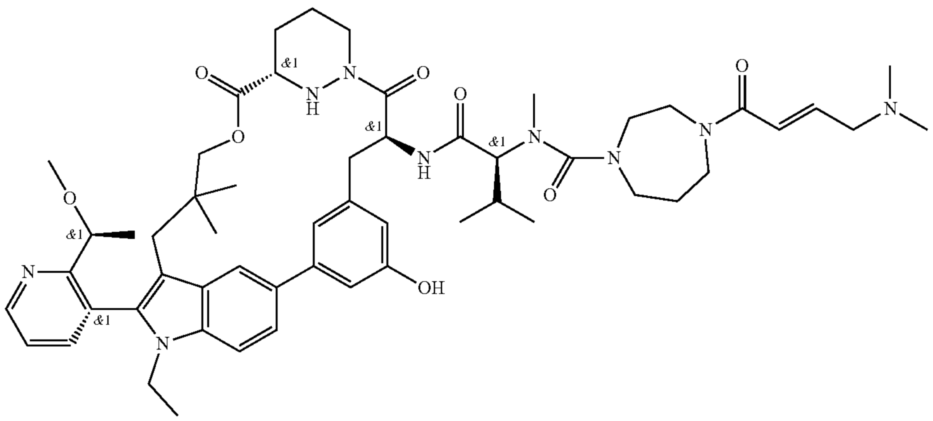 |
| B265 | 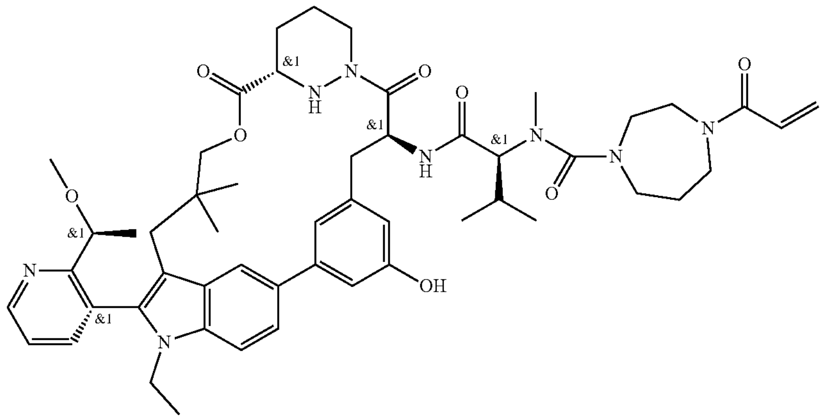 |
| B266 | 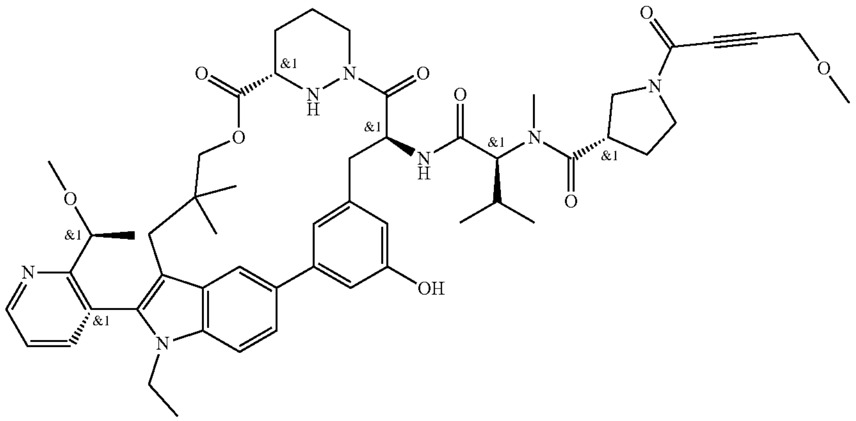 |

TABLE 2-continued
| Certain Compounds | |
|---|---|
| Ex # | Structure |
| B267 | 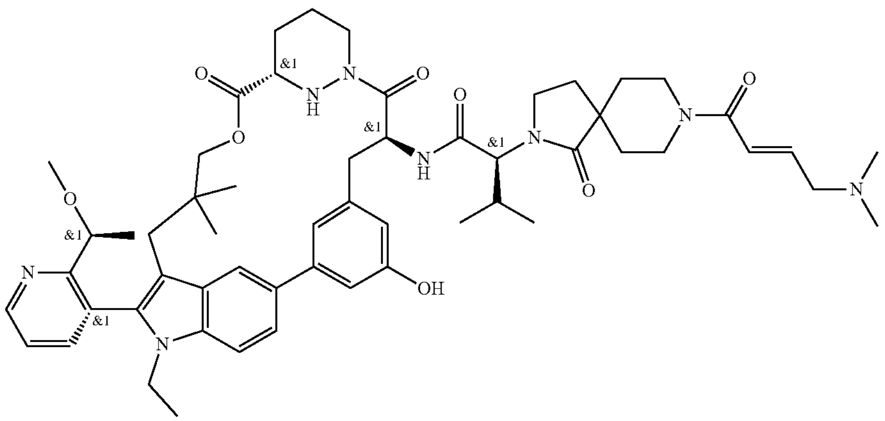 |
| B268 | 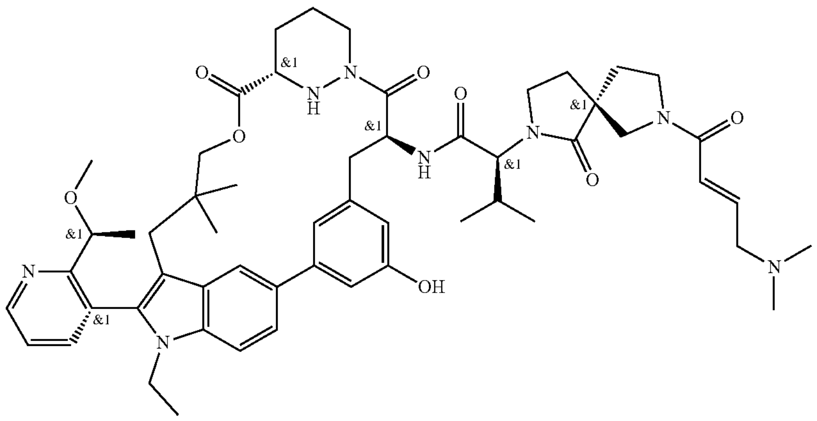 |
| B269 | 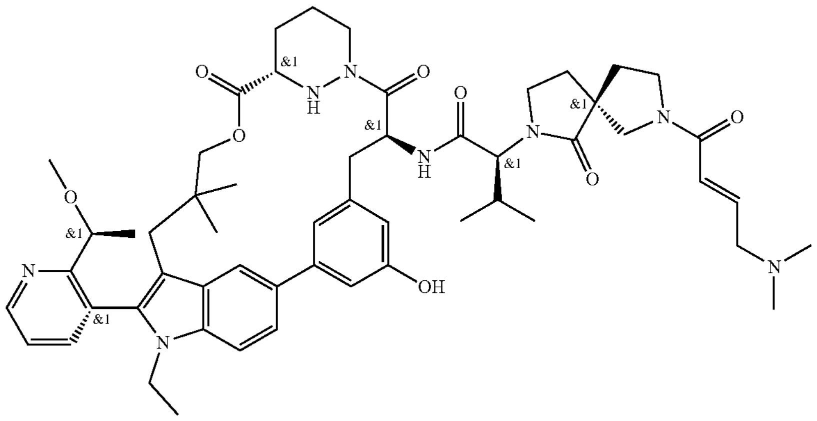 |

TABLE 2-continued
| Certain Compounds | |
|---|---|
| Ex # | Structure |
| B270 | 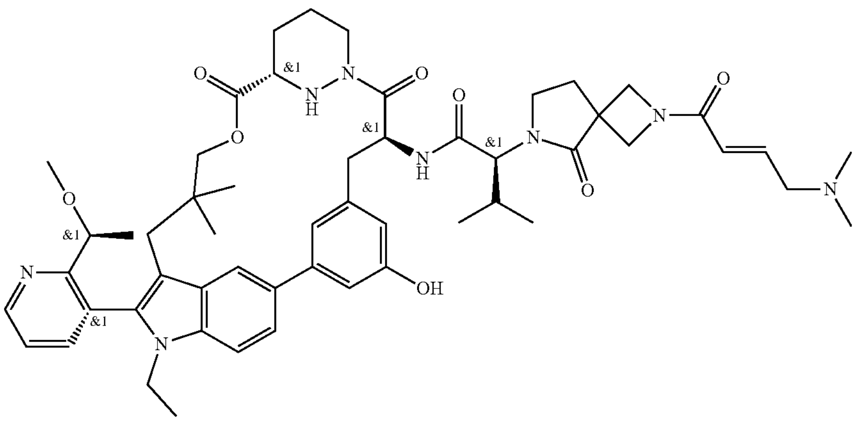 |
| B271 | 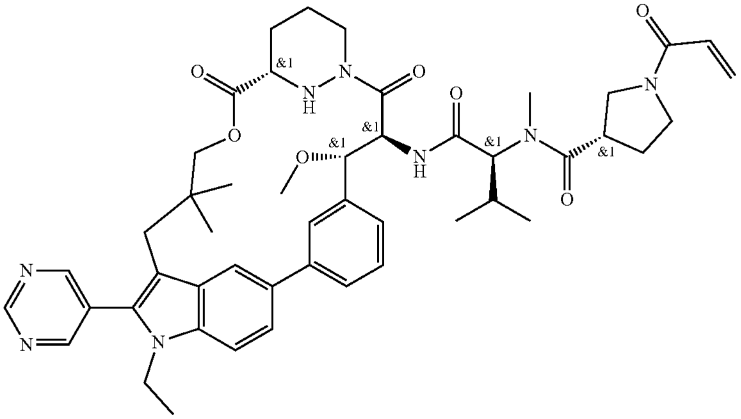 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@@H]2OC)C(C)C)C1] |
| B272 | 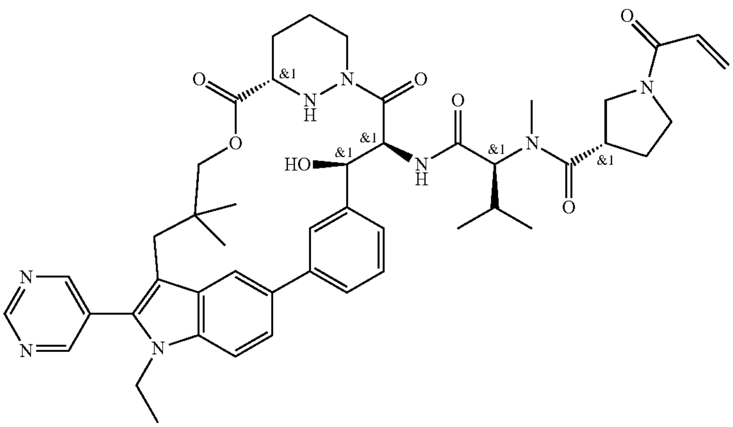 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@H]2O)C(C)C)C1] |

TABLE 2-continued
| Certain Compounds | |
|---|---|
| Ex # | Structure |
| B273 | 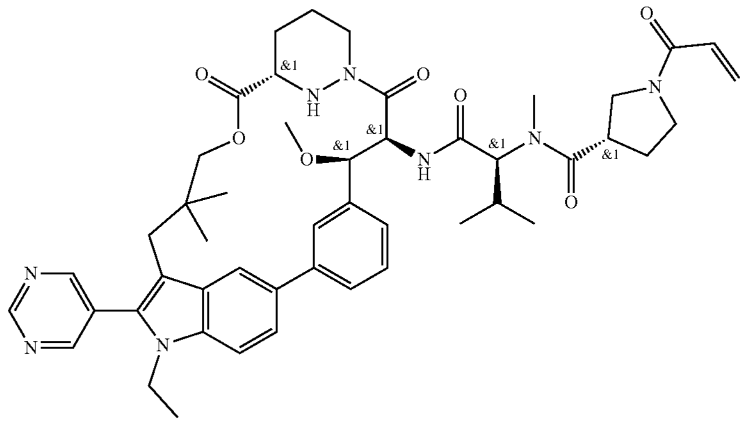 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@H]2OC)C(C)C)C1] |
| B274 | 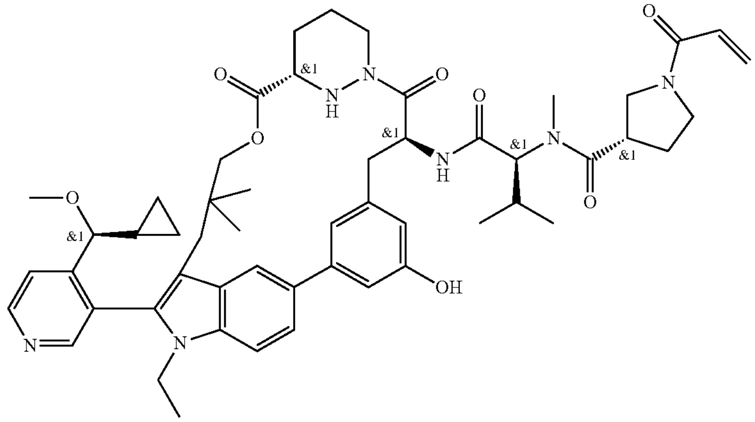 [SMILES: C=CC(=O)N1CC[C@H](C(=O)N(C)[C@H](C(=O)N[C@H]2Cc3cc(O)cc(c3)-c3ccc4c(c3)c(c(-c3cnccc3[C@@H](OC)C3CC3)n4CC)CC(C)(C)COC(=O)[C@@H]3CCCN(N3)C2=O)C(C)C)C1] |
| B275 | 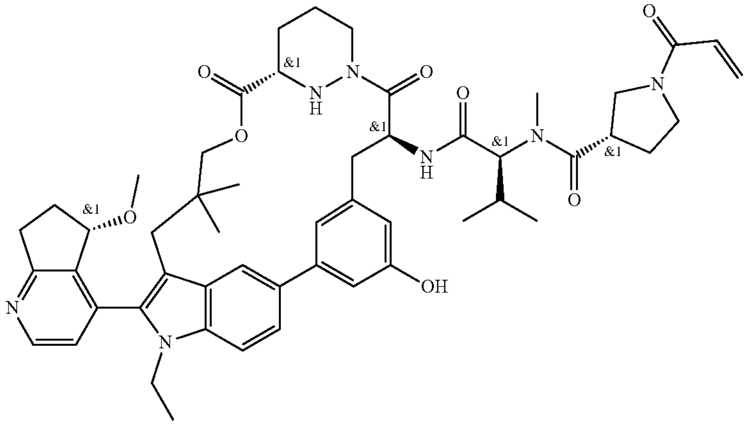 [SMILES: C=CC(=O)N1CC[C@H](C(=O)N(C)[C@H](C(=O)N[C@H]2Cc3cc(O)cc(c3)-c3ccc4c(c3)c(c(-c3ccnc5c3[C@@H](OC)CC5)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| B276 | 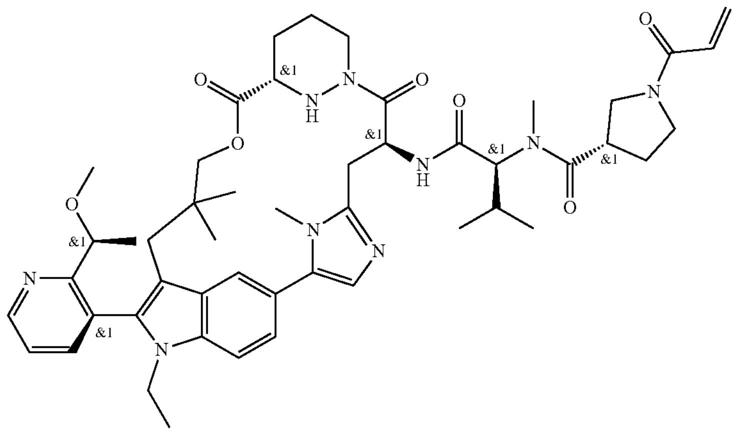 |
| B277 | 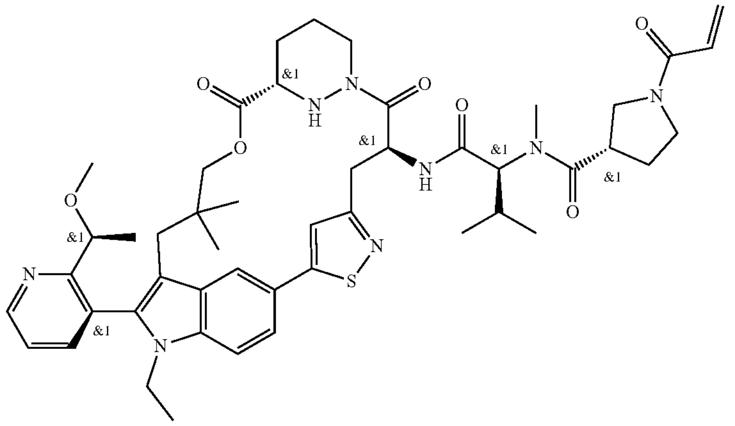 |
| B278 | 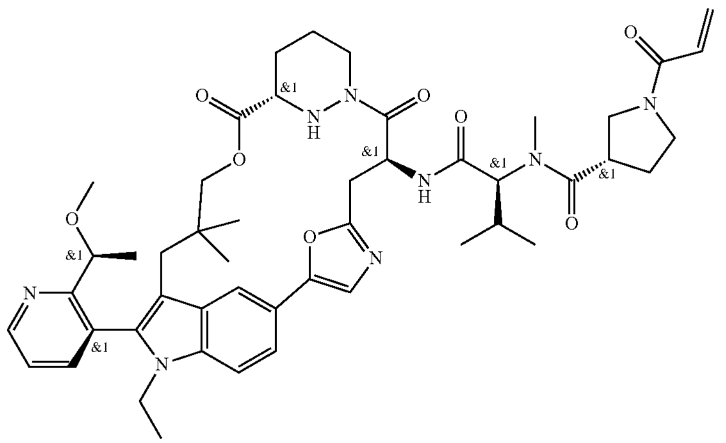 |

TABLE 2-continued
| Certain Compounds | |
|---|---|
| Ex # | Structure |
| B279 | 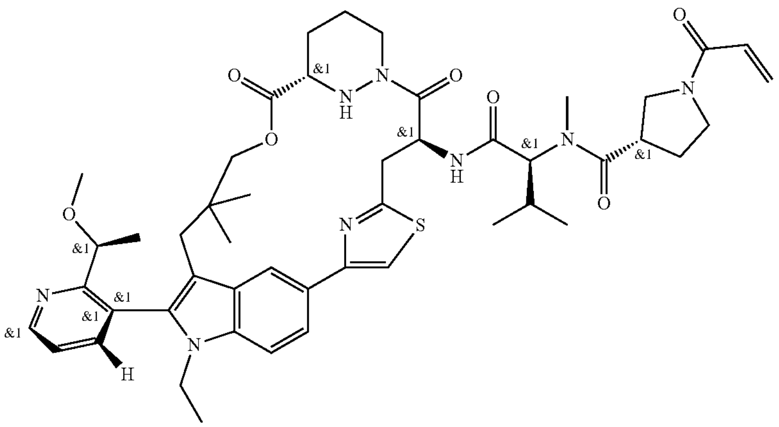 |
| B280 | 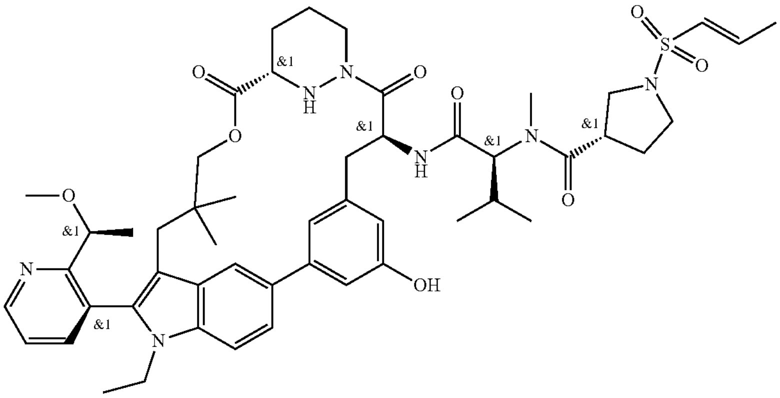 |
| B281 | 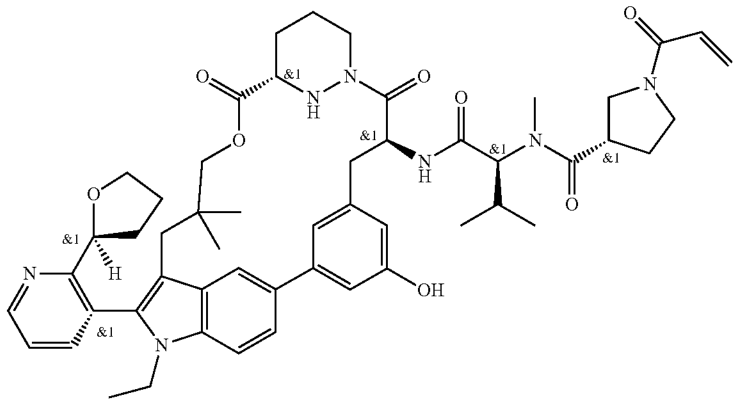 |

TABLE 2-continued
| Certain Compounds | |
|---|---|
| Ex # | Structure |
| B282 | 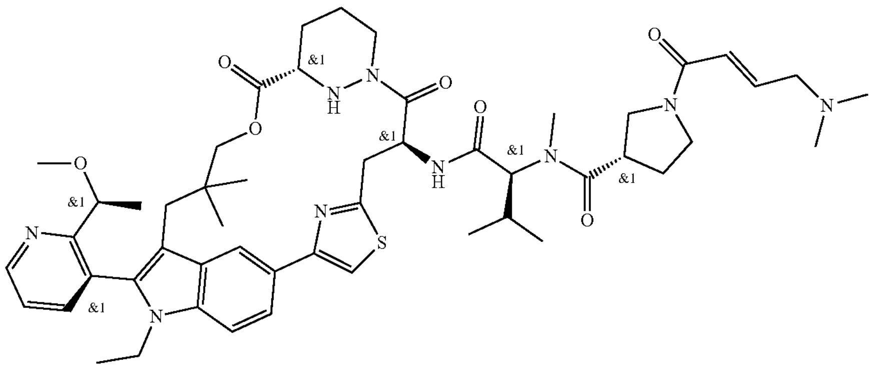 |
| B283 | 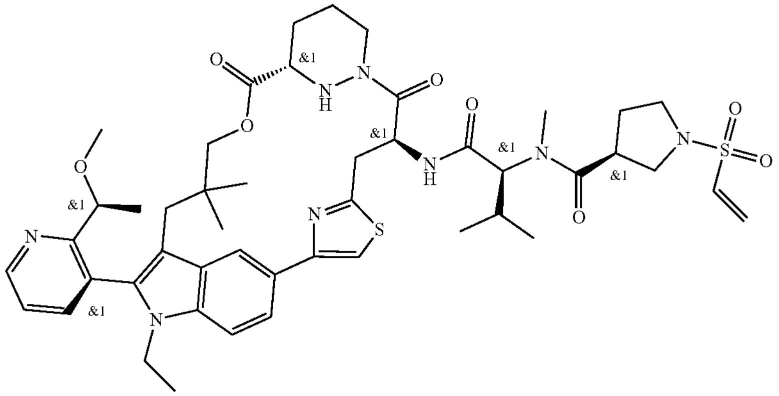 |
| B284 | 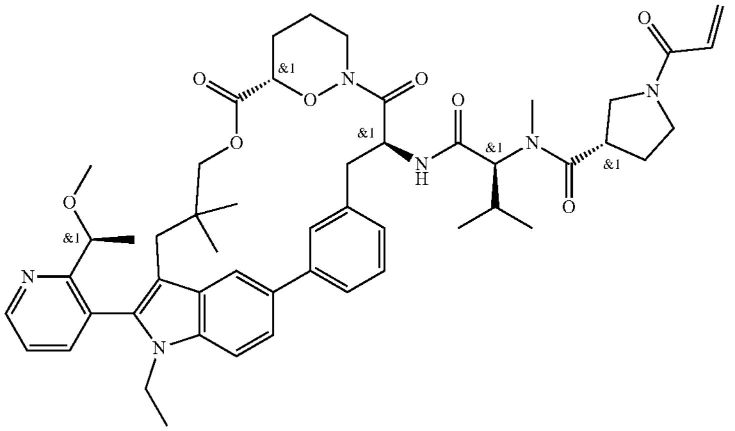 |

TABLE 2-continued
| Certain Compounds | |
|---|---|
| Ex # | Structure |
| B285 | 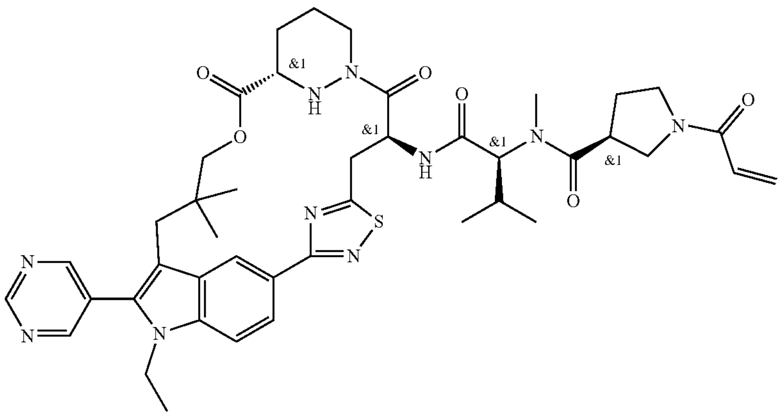 |
| B286 | 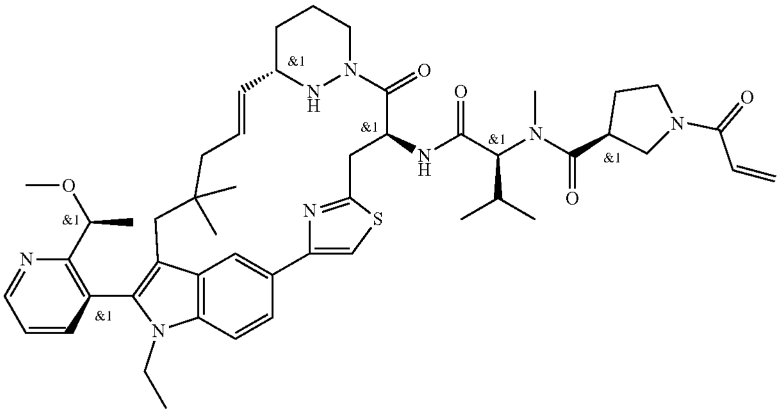 |
| B287 | 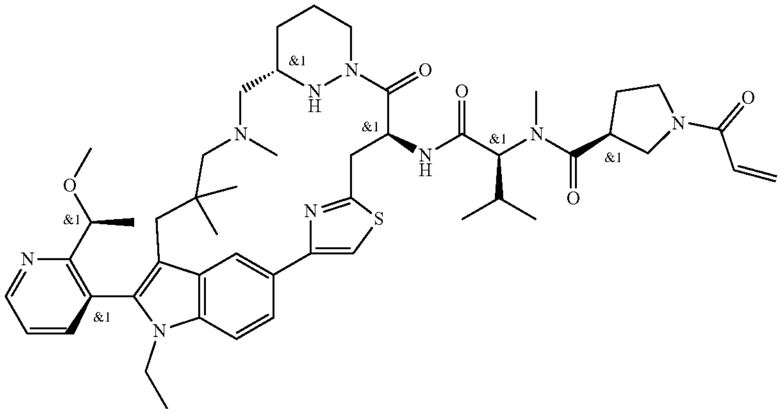 |

TABLE 2-continued
| Certain Compounds | |
|---|---|
| Ex # | Structure |
| B288 | 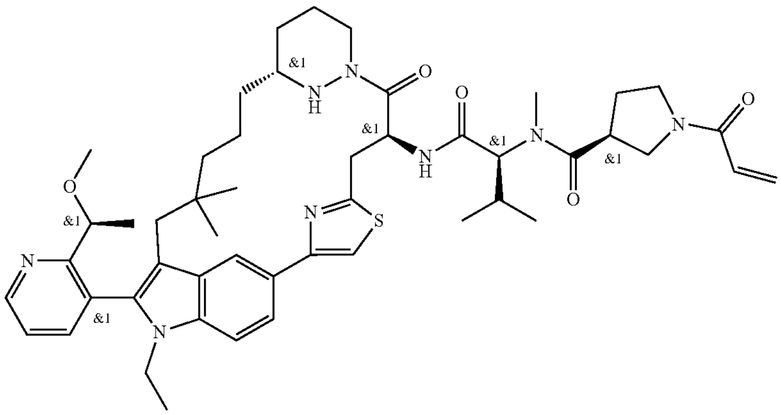 |
| B289 | 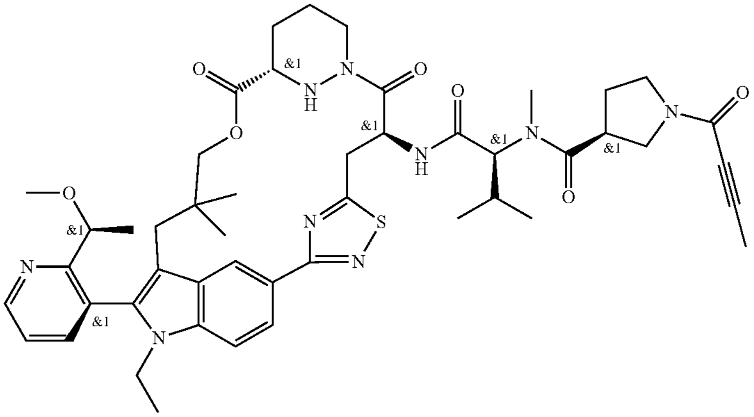 |
| B290 | 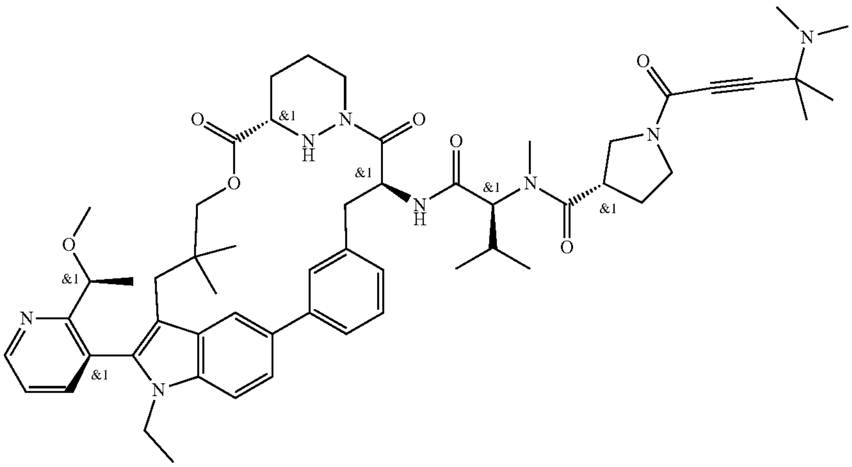 |

TABLE 2-continued
| Certain Compounds | |
|---|---|
| Ex # | Structure |
| B291 | 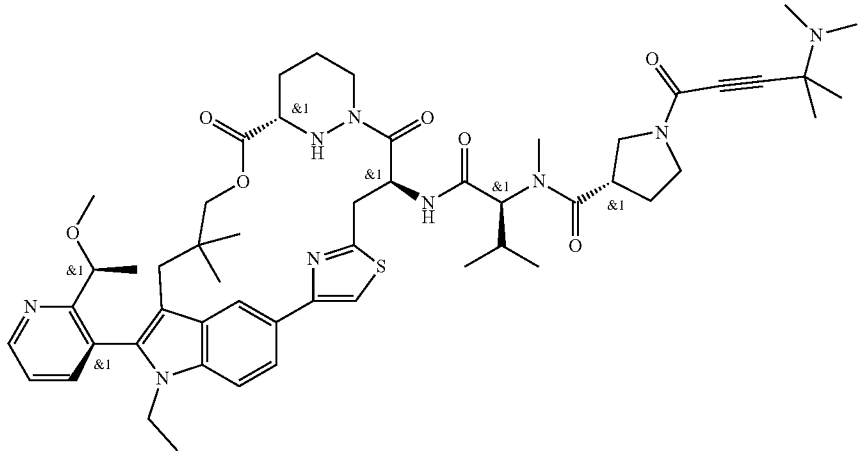 |
| B292 | 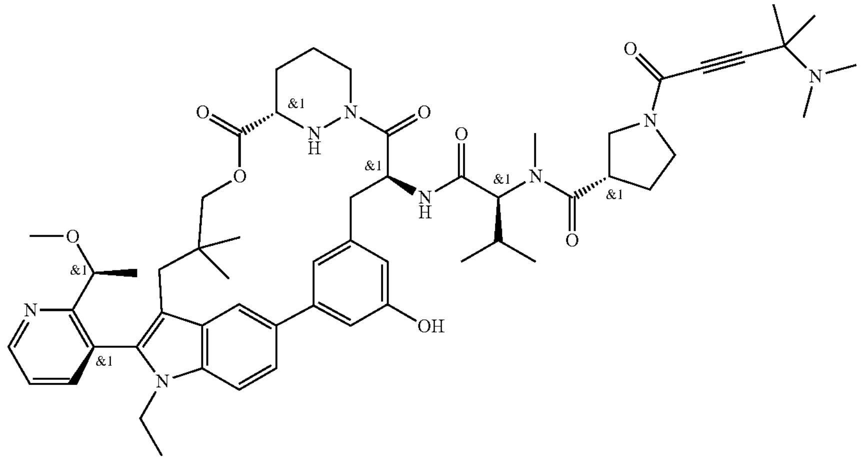 |
| B293 | 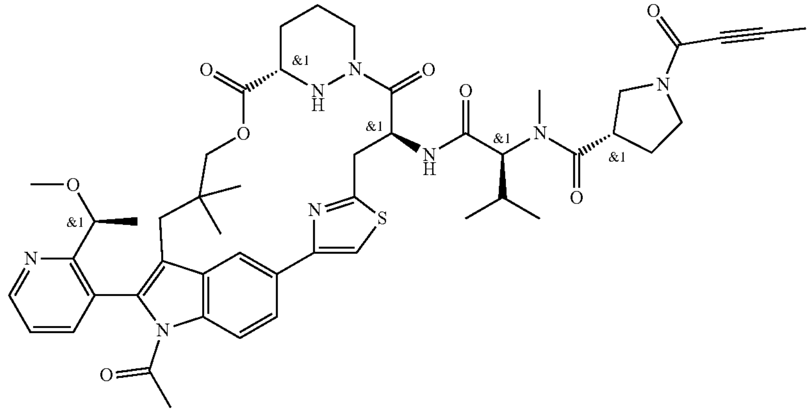 |

TABLE 2-continued
| Certain Compounds | |
|---|---|
| Ex # | Structure |
| B294 | 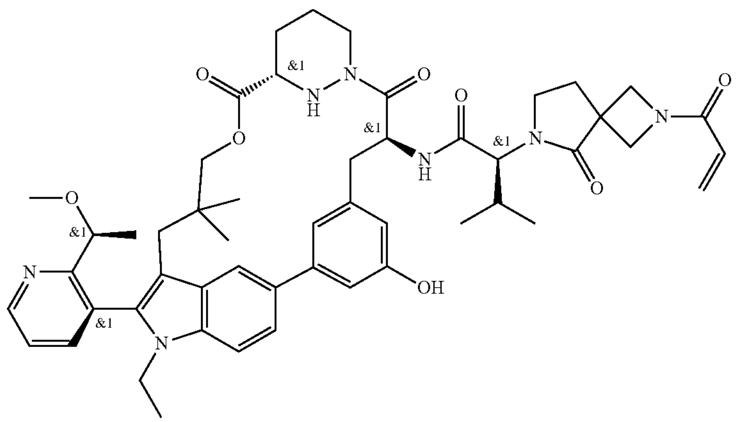 |
| B295 | 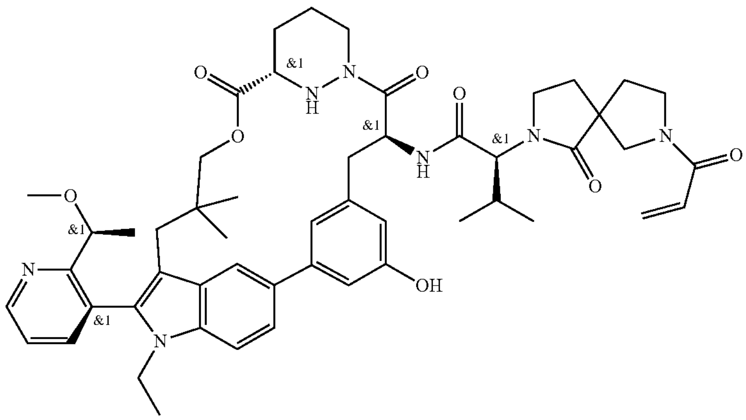 |
| B296 | 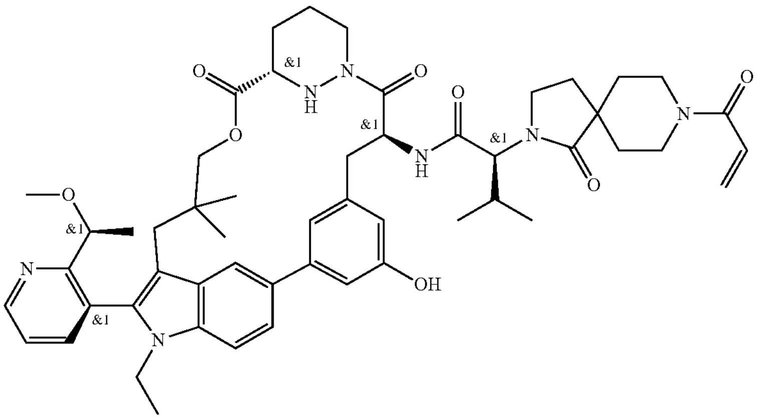 |

TABLE 2-continued
| Certain Compounds | |
|---|---|
| Ex # | Structure |
| B297 | 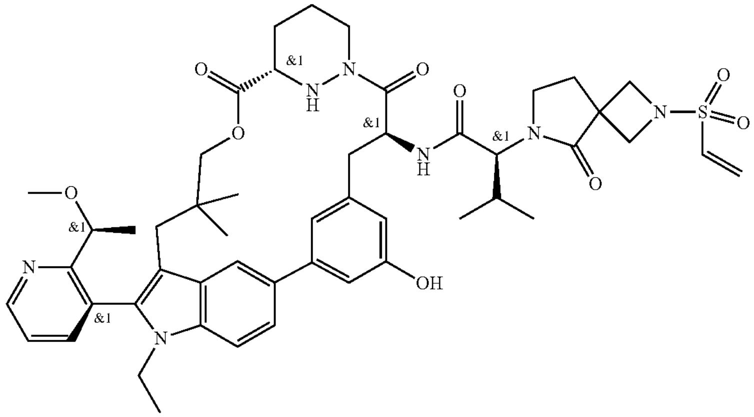 |
| B298 | 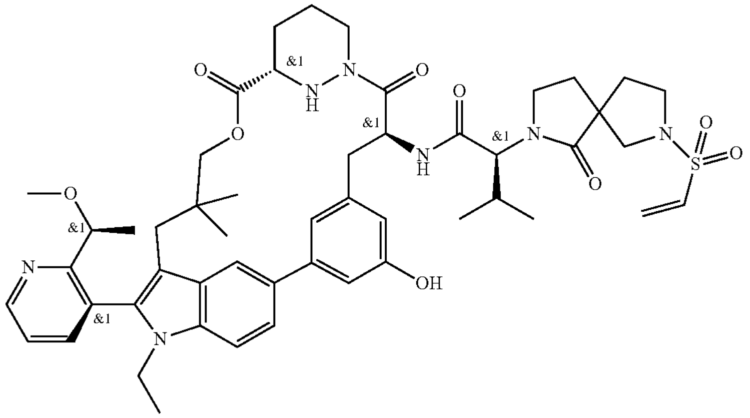 |
| B299 | 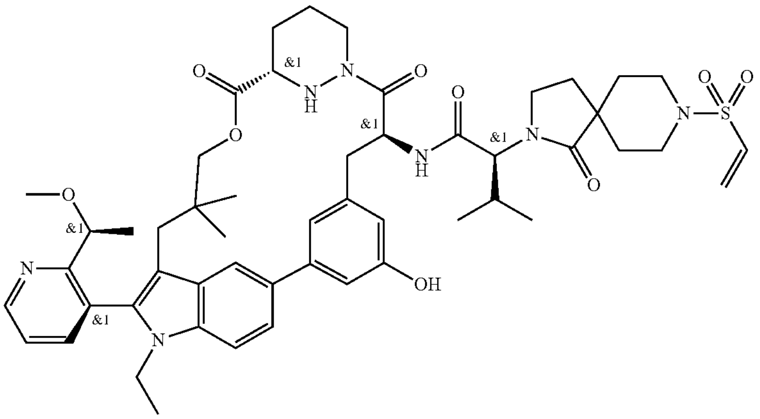 |

TABLE 2-continued
| Certain Compounds | |
|---|---|
| Ex # | Structure |
| B300 | 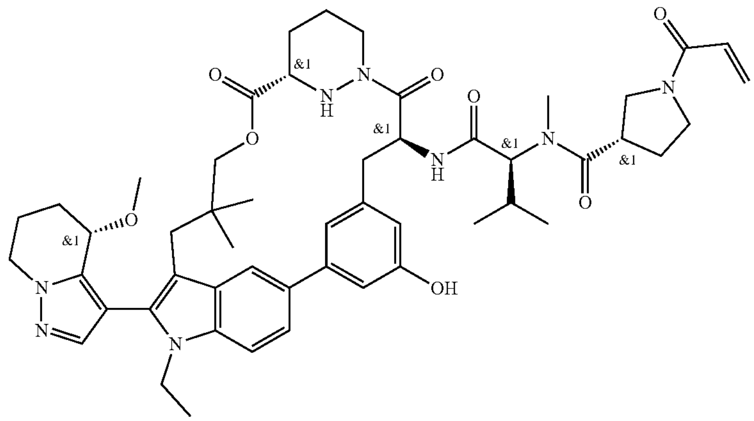 |
| B301 | 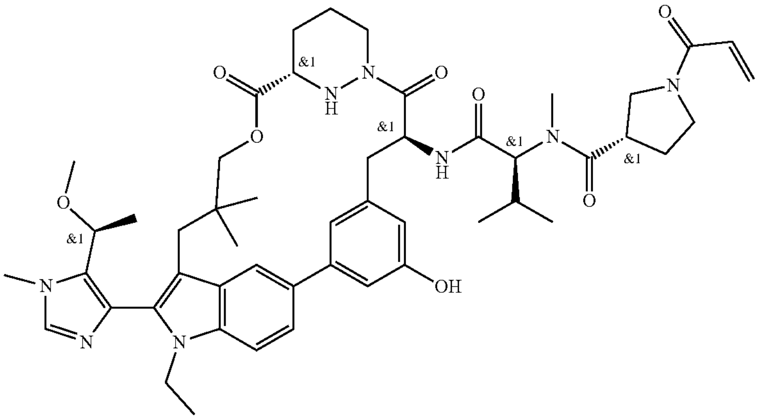 |
| B302 | 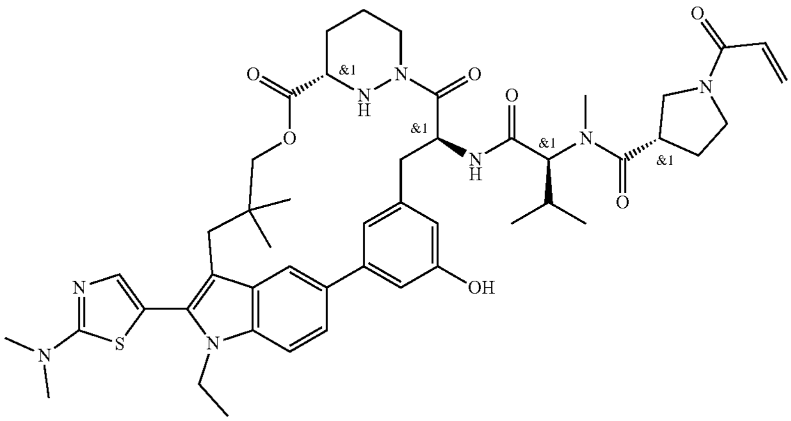 |

TABLE 2-continued
| Certain Compounds | |
|---|---|
| Ex # | Structure |
| B303 | 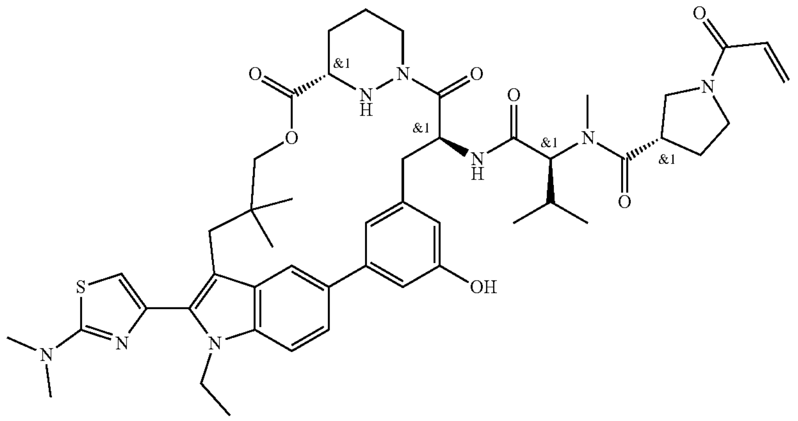 |
| B304 | 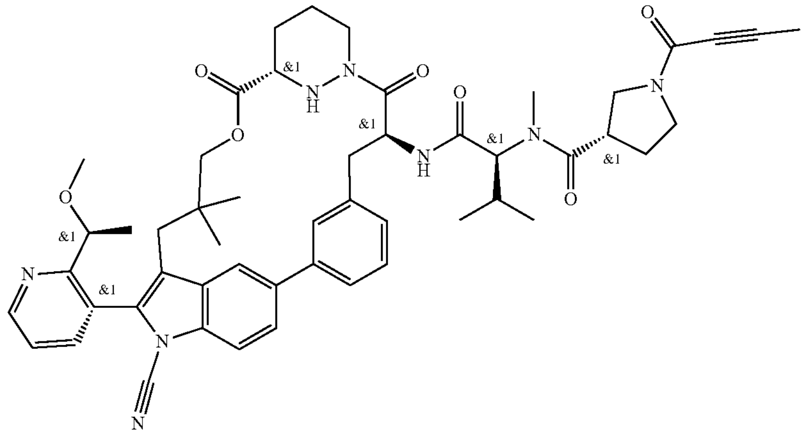 |
| B305 | 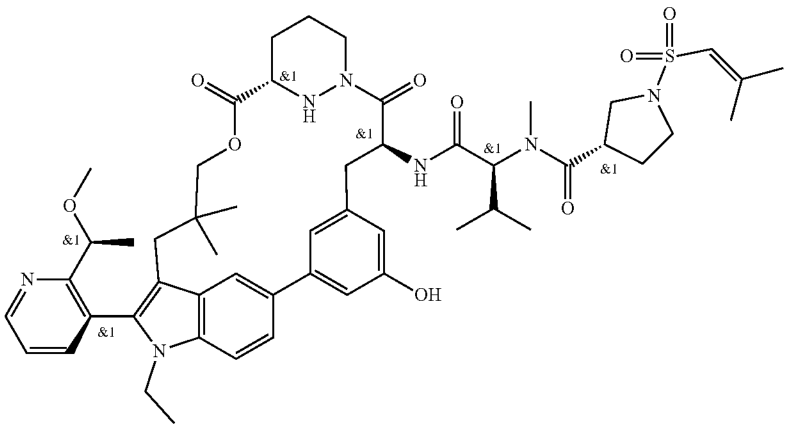 |

TABLE 2-continued
| Certain Compounds | |
|---|---|
| Ex # | Structure |
| B306 | 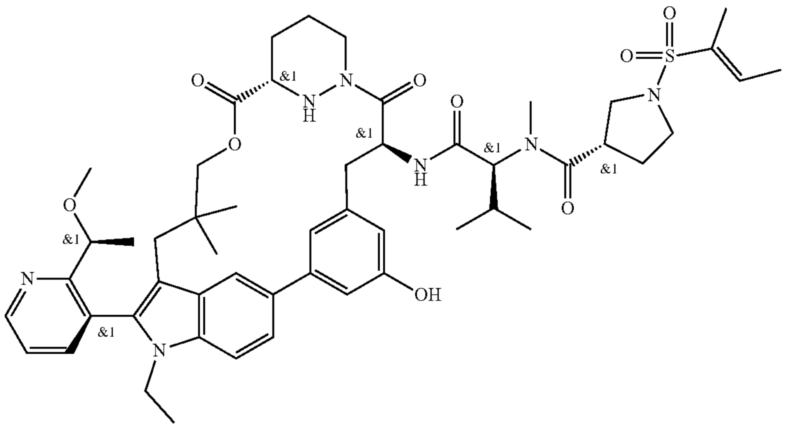 |
| B307 | 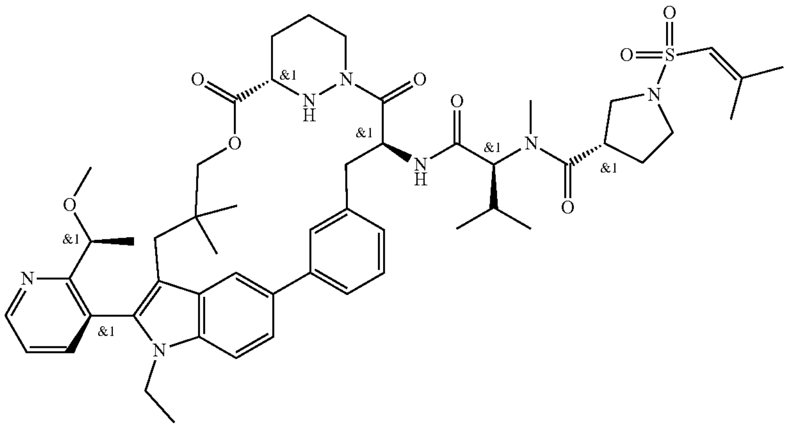 |
| B308 | 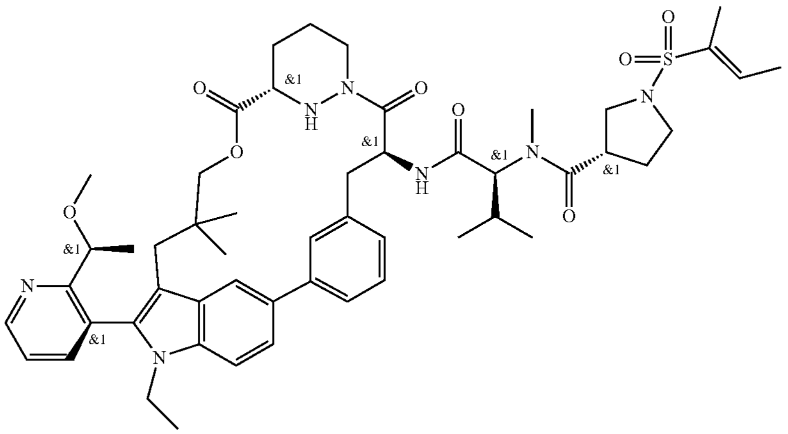 |

TABLE 2-continued
| Certain Compounds | |
|---|---|
| Ex # | Structure |
| B309 | 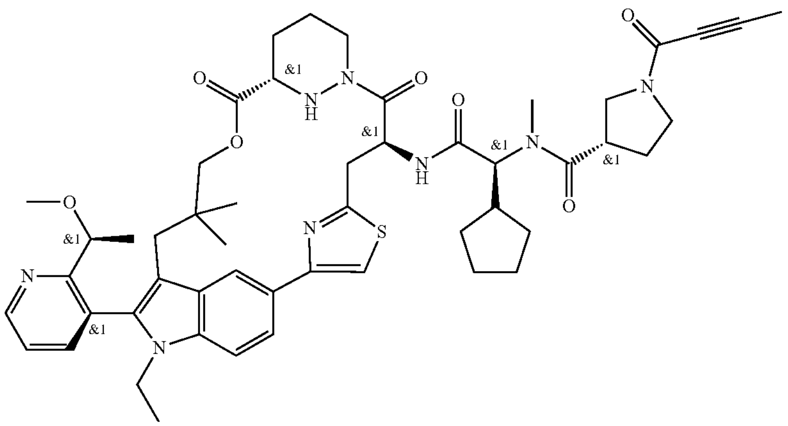 |
| B310 | 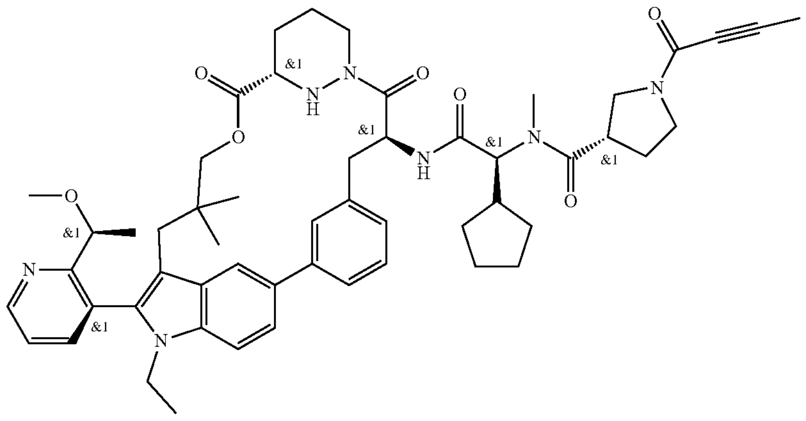 |
| B311 | 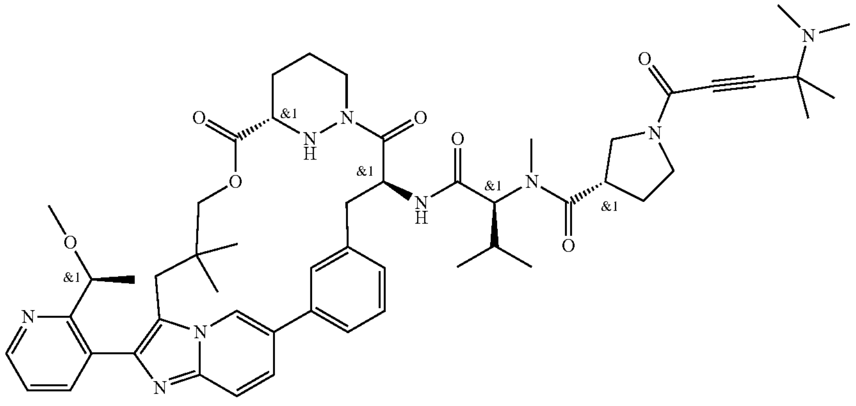 |

TABLE 2-continued
| Certain Compounds | |
|---|---|
| Ex # | Structure |
| B312 | 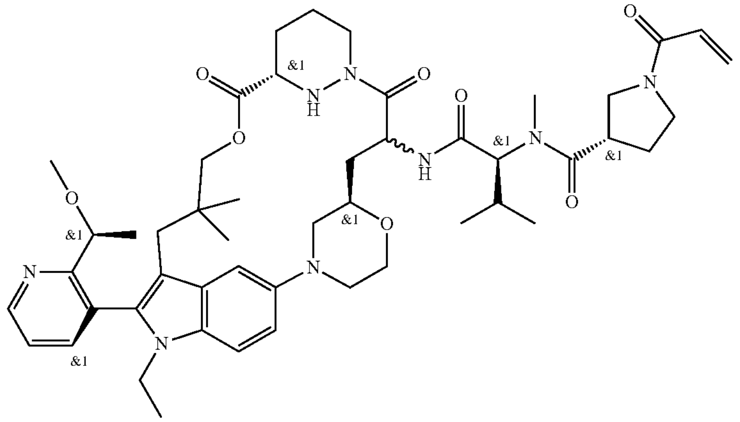 |
| B313 | 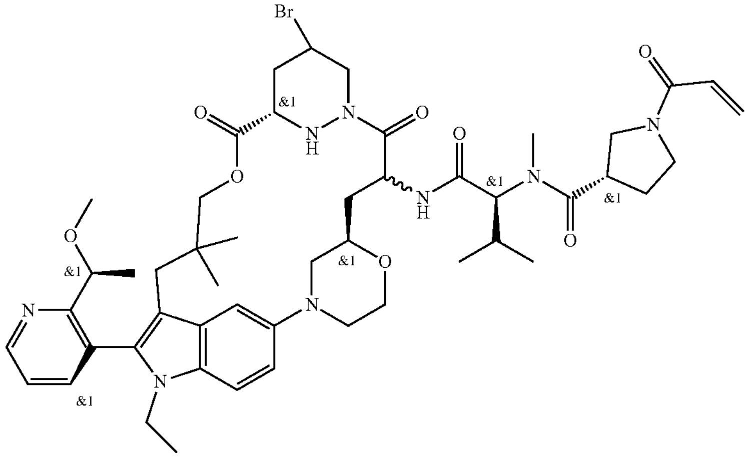 |
| B314 | 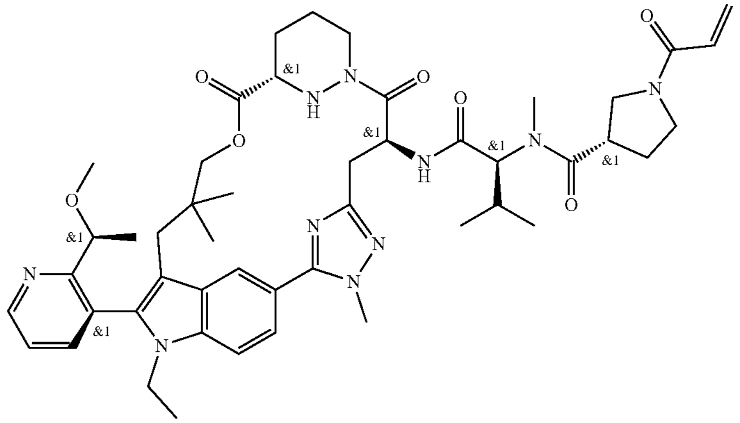 |

TABLE 2-continued
| Certain Compounds | |
|---|---|
| Ex # | Structure |
| B316 | 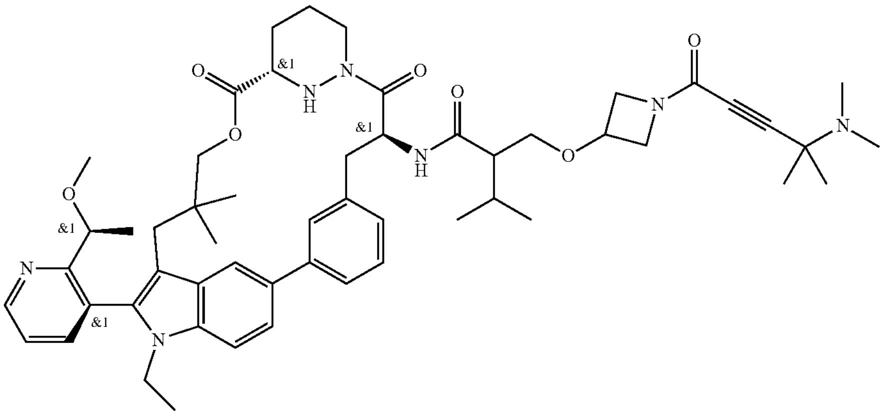 |
| B317 | 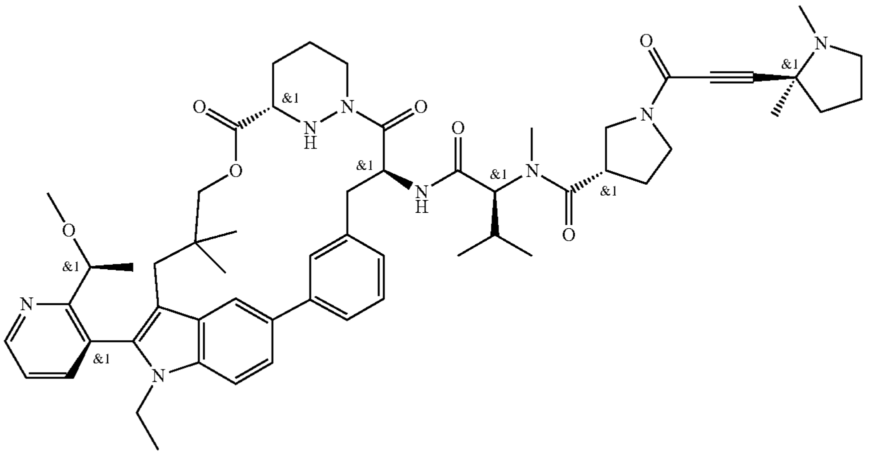 |
| B318 | 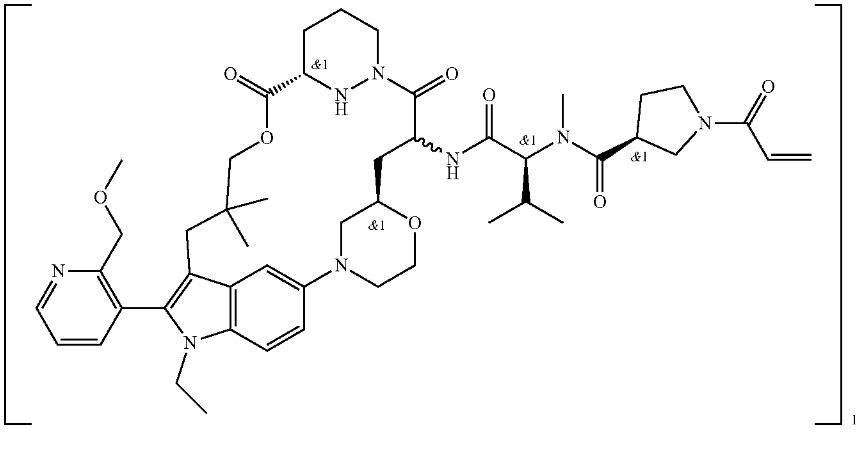 |

TABLE 2-continued
| Certain Compounds | |
|---|---|
| Ex # | Structure |
| B319 | 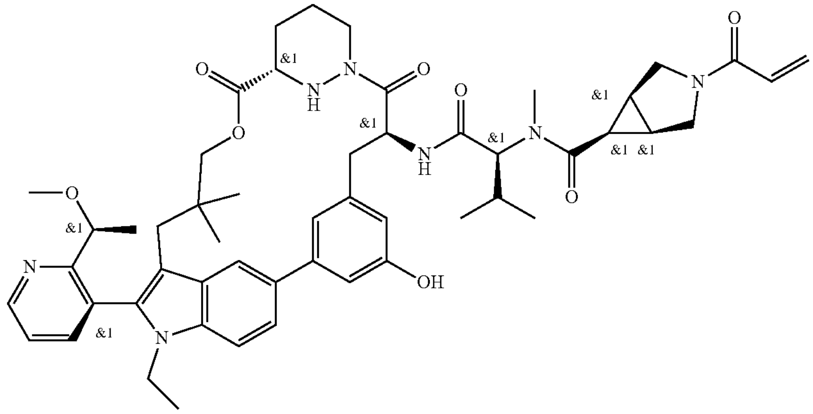 |
| B320 | 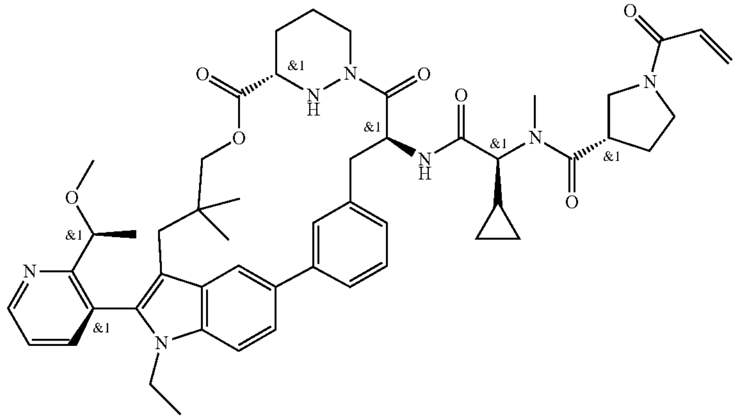 |
| B321 | 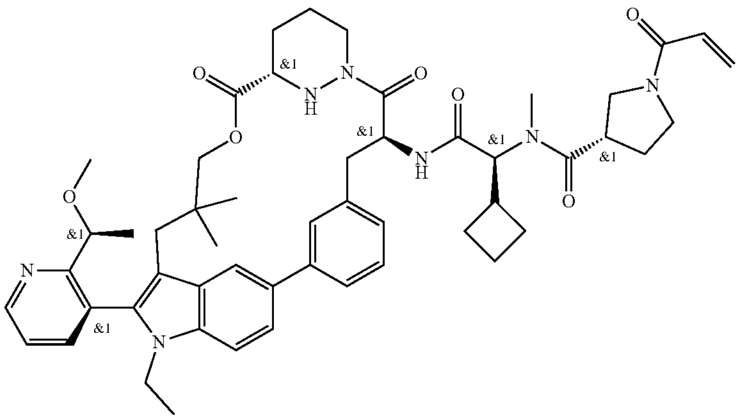 |

TABLE 2-continued
| Certain Compounds | |
|---|---|
| Ex # | Structure |
| B322 | 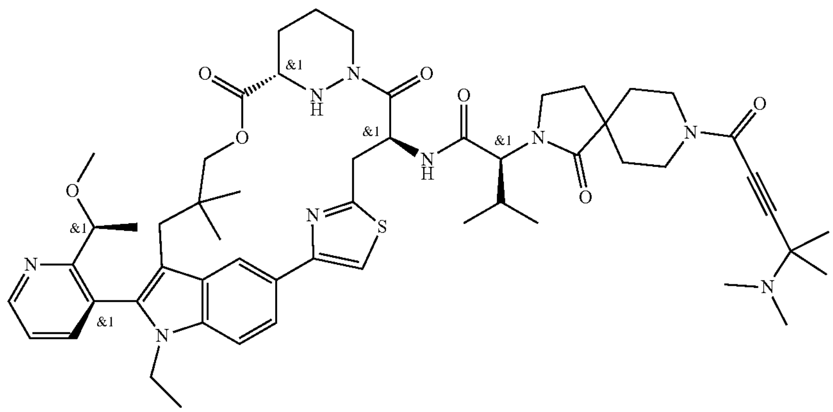 |
| B323 | 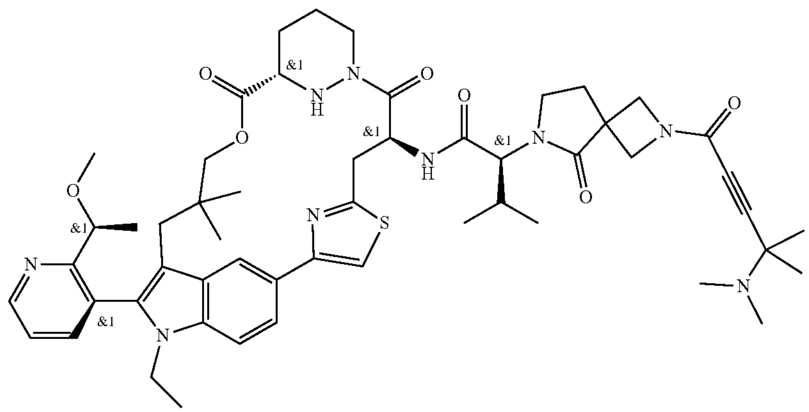 |
| B324 | 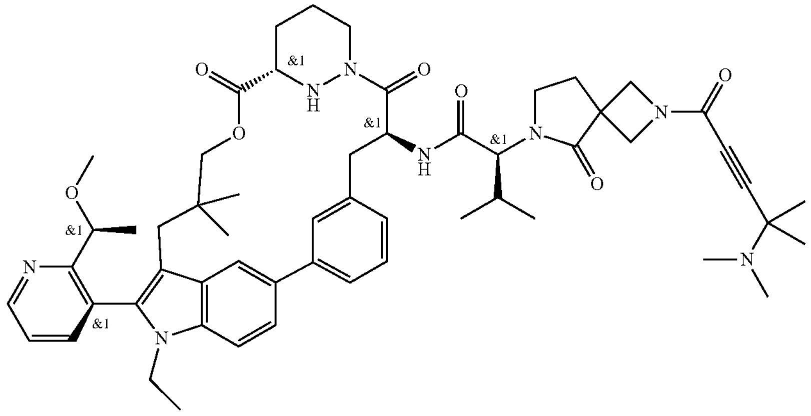 |

TABLE 2-continued
| Certain Compounds | |
|---|---|
| Ex # | Structure |
| B325 | 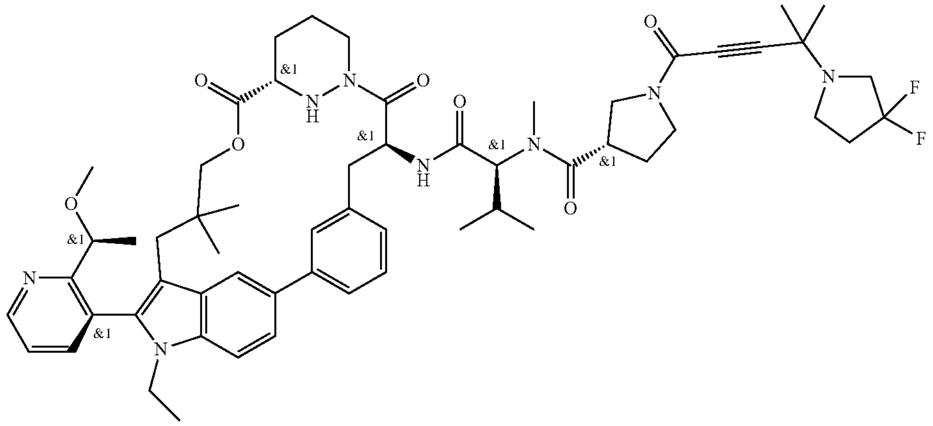 |
| B326 | 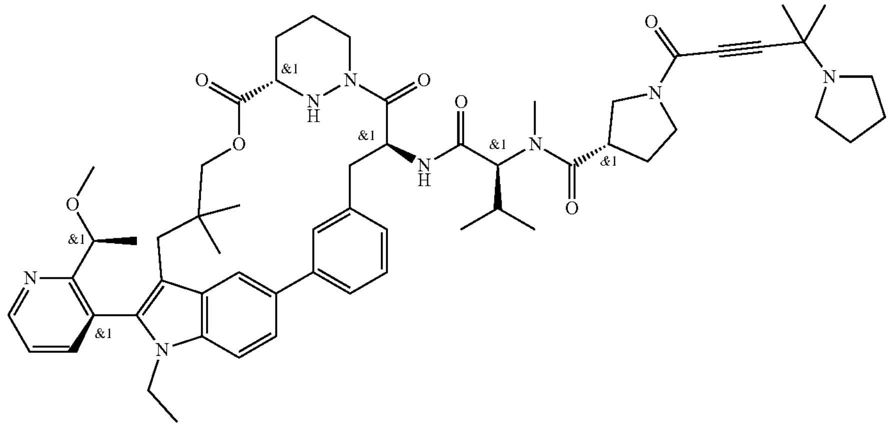 |
| B327 | 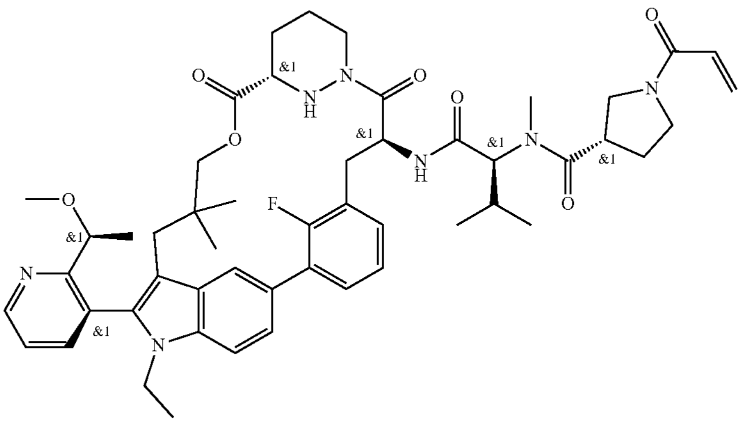 |

TABLE 2-continued
| Certain Compounds | |
|---|---|
| Ex # | Structure |
| B328 | 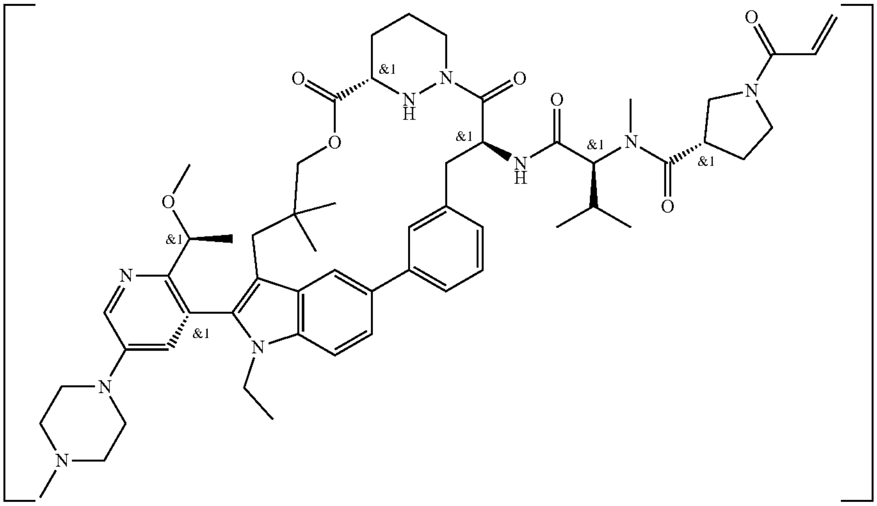 |
| B329 | 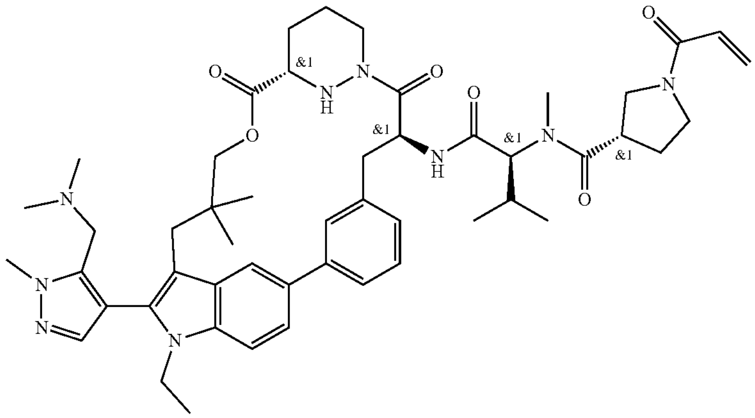 [SMILES: C=CC(=O)N1CC[C@H](C(=O)N(C)[C@H](C(=O)N[C@H]2Cc3cccc(c3)-c3ccc4c(c3)c(c(-c3cnn(C)c3CN(C)C)n4CC)CC(C)(C)COC(=O)[C@@H]3CCCN(N3)C2=O)C(C)C)C1] |
| B330 | 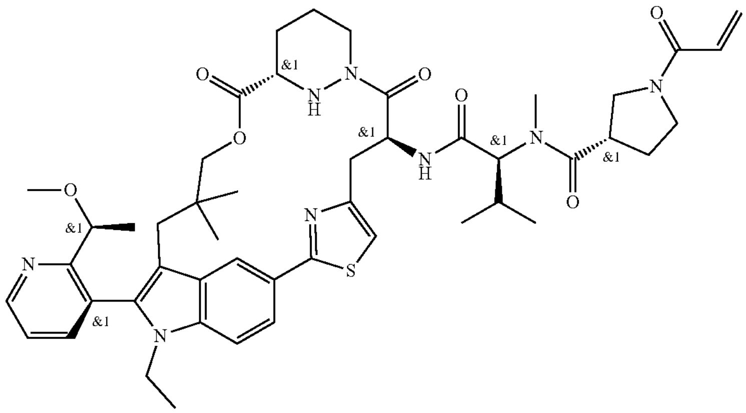 |

TABLE 2-continued
| Certain Compounds | |
|---|---|
| Ex # | Structure |
| B331 | 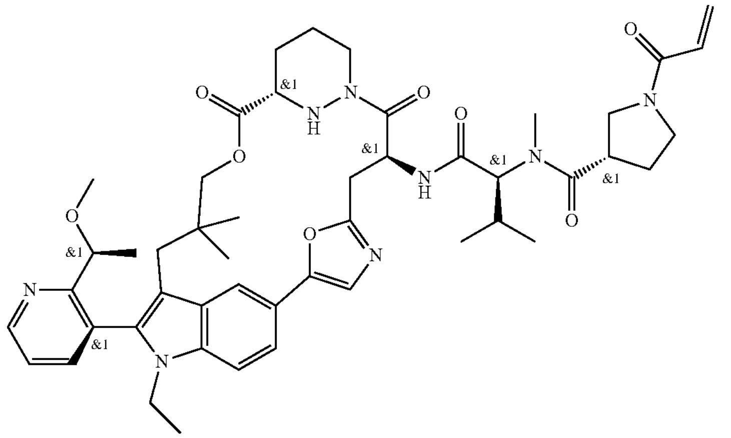 |
| B332 | 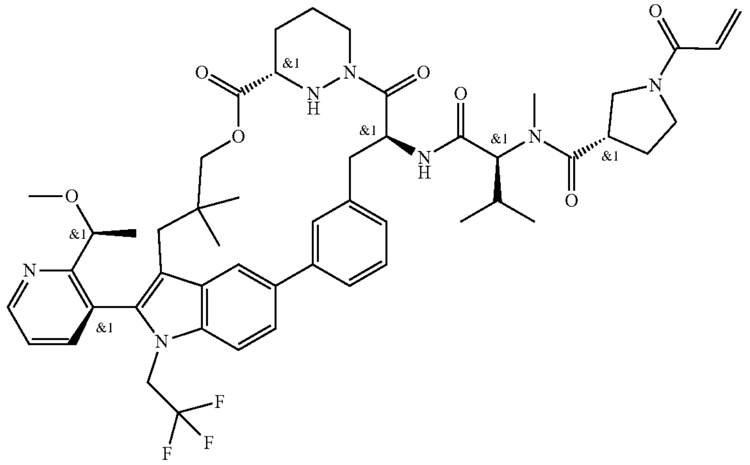 |
| B333 | 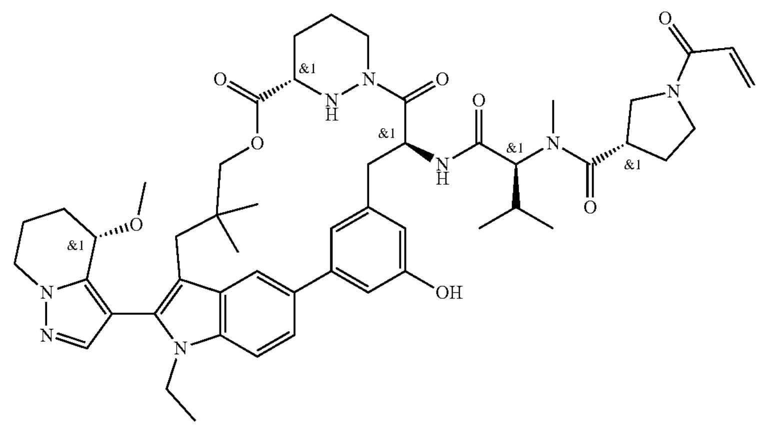 |

TABLE 2-continued
| Certain Compounds | |
|---|---|
| Ex # | Structure |
| B334 | 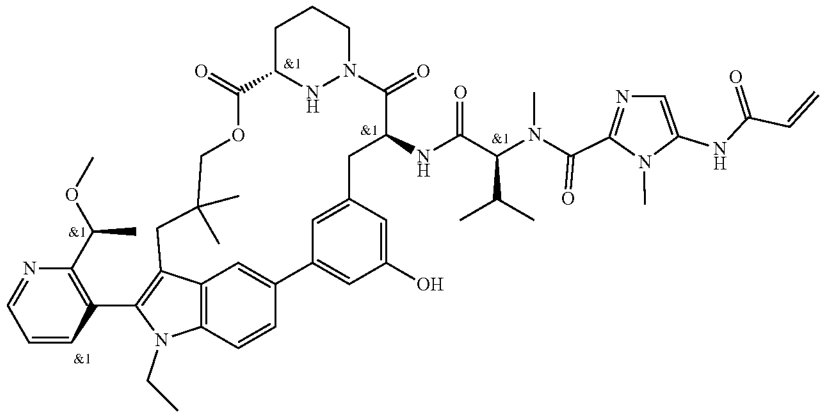 |
| B335 | 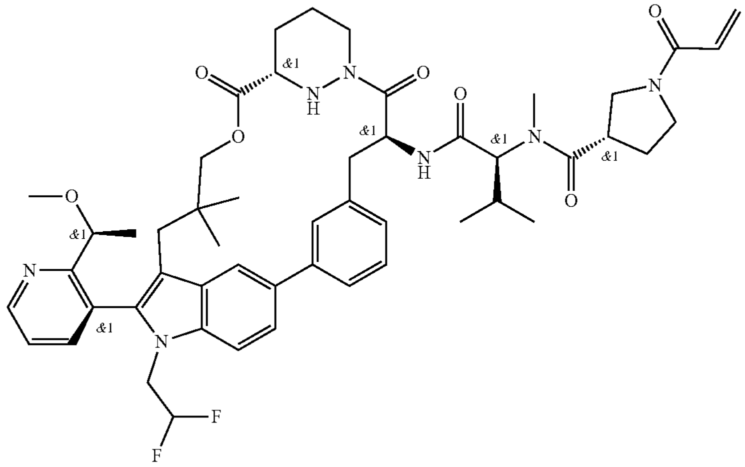 |
| B336 | 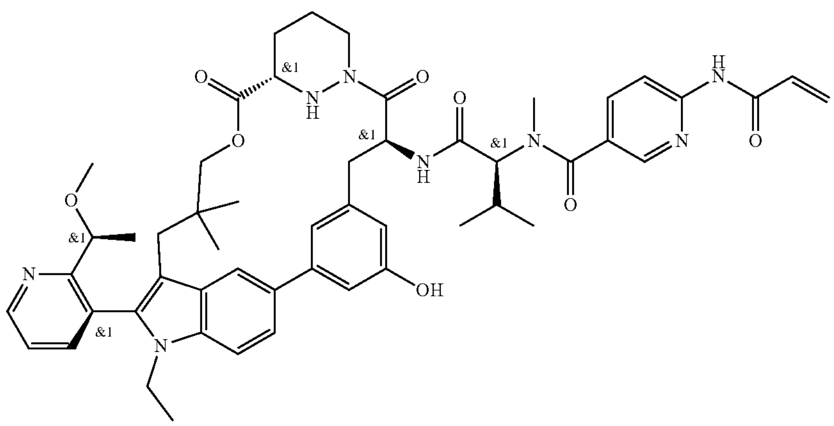 |

TABLE 2-continued
| Certain Compounds | |
|---|---|
| Ex # | Structure |
| B337 | 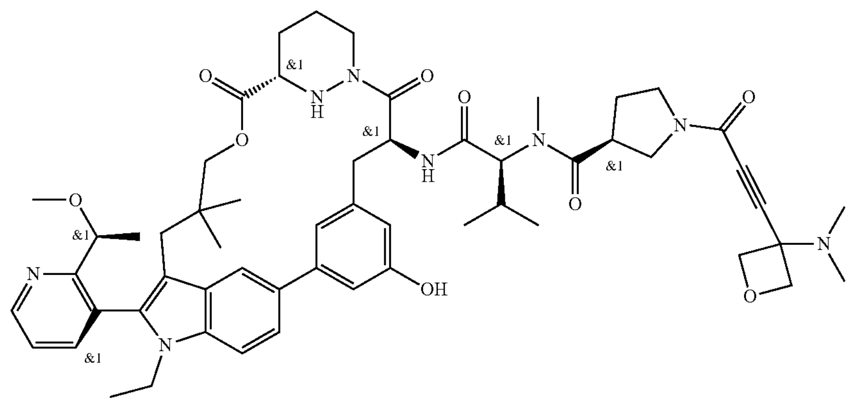 |
| B338 | 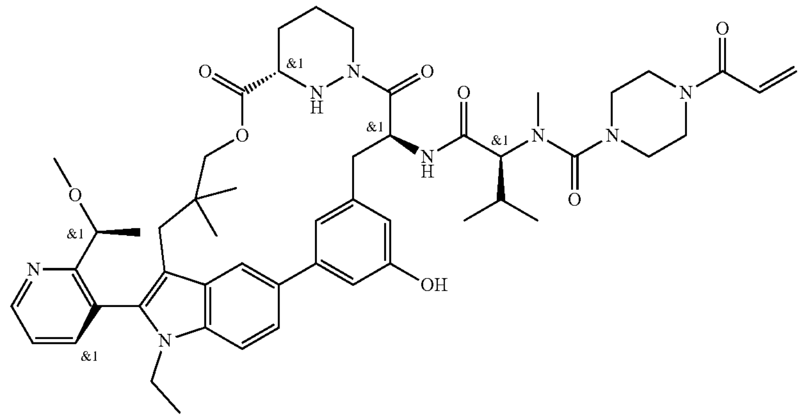 |
| B339 | 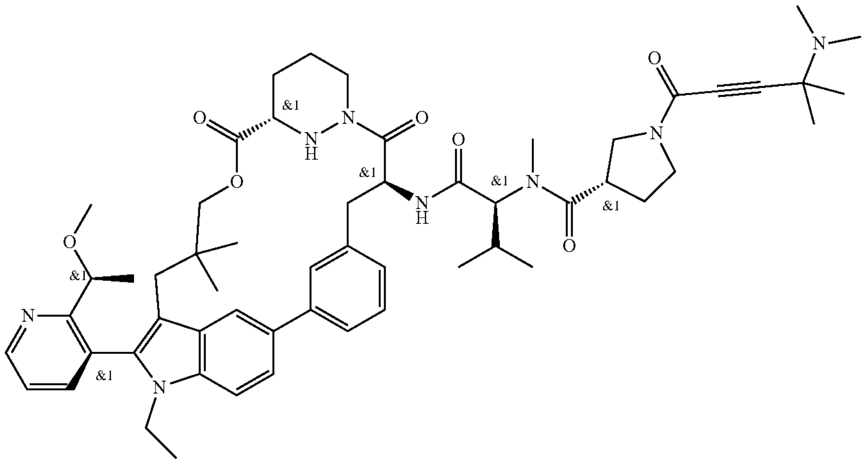 |

TABLE 2-continued
| Certain Compounds | |
|---|---|
| Ex # | Structure |
| B340 | 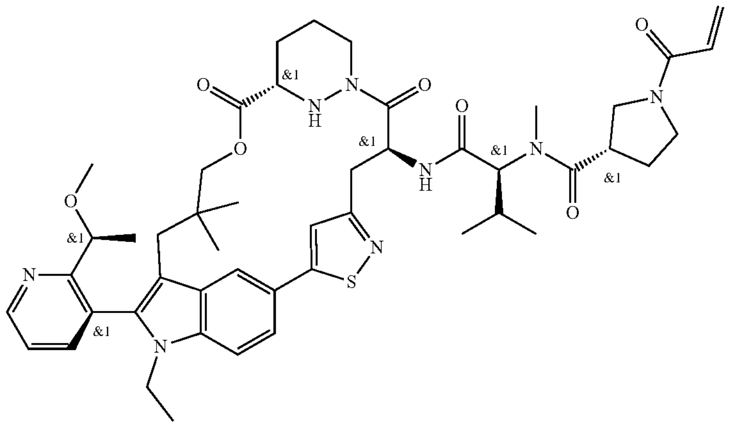 |
| B341 | 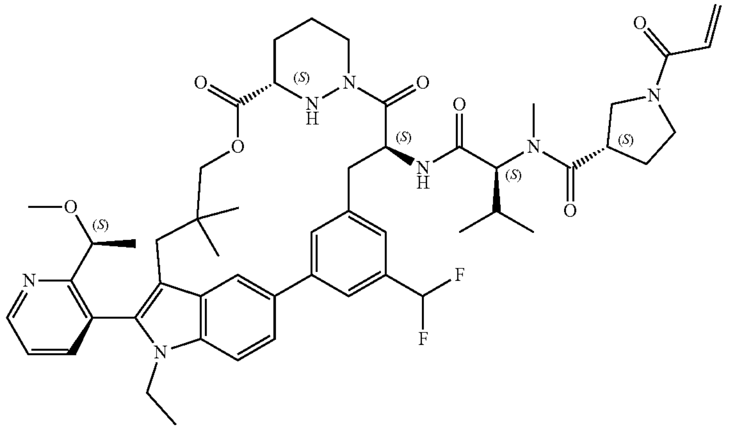 |
| B342 | 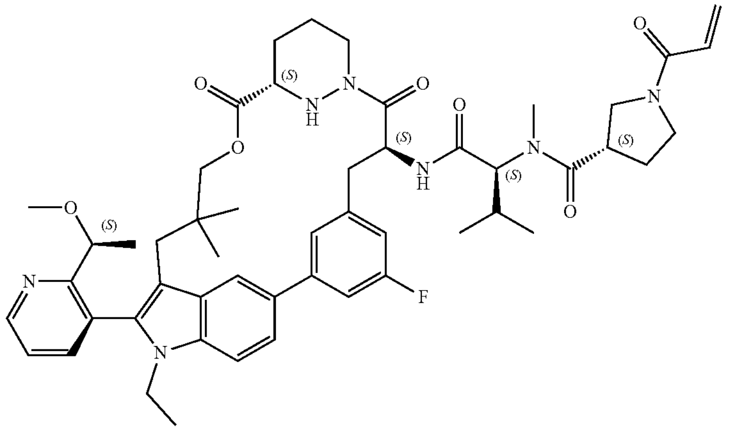 |

TABLE 2-continued
| Certain Compounds | |
|---|---|
| Ex # | Structure |
| B343 | 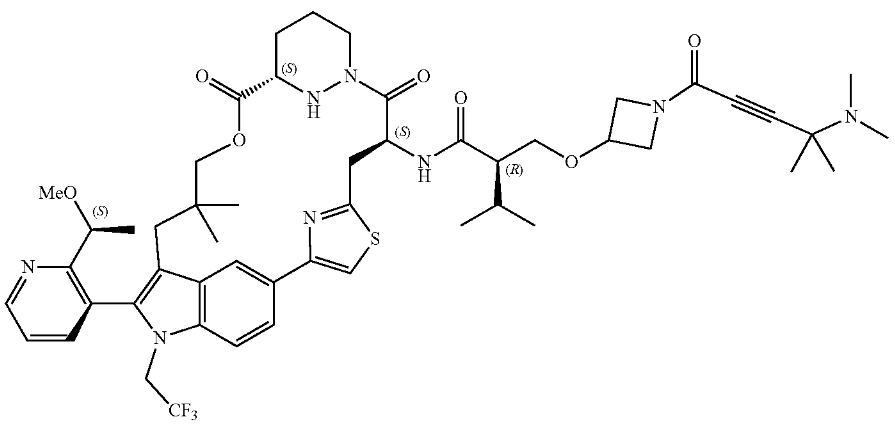 |
| B344 | 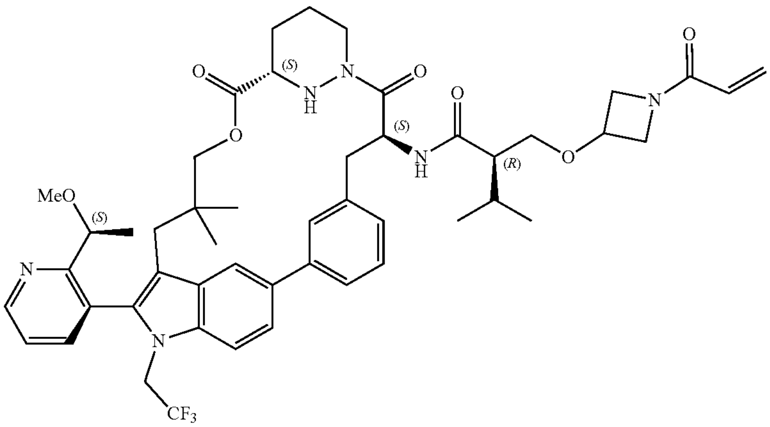 |
| B345 | 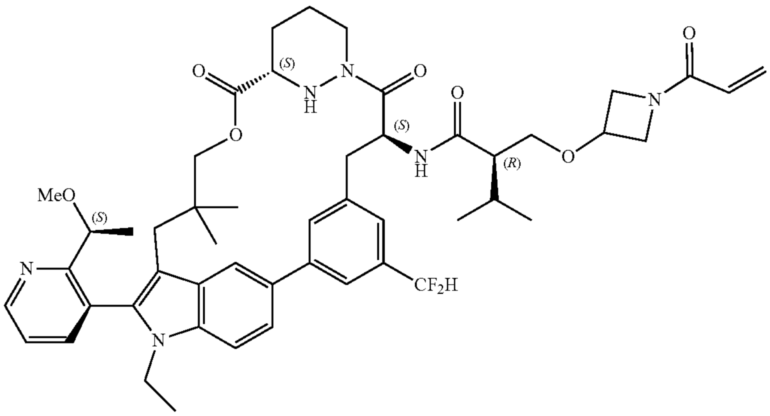 |

TABLE 2-continued
| Certain Compounds | |
|---|---|
| Ex # | Structure |
| B346 | 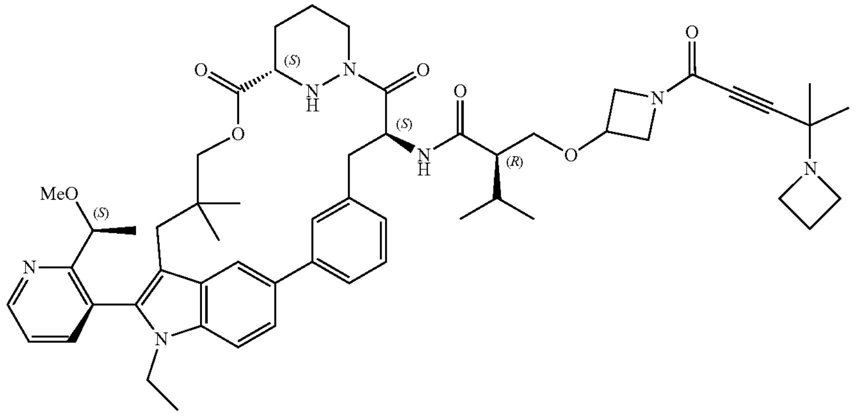 |
| B347 | 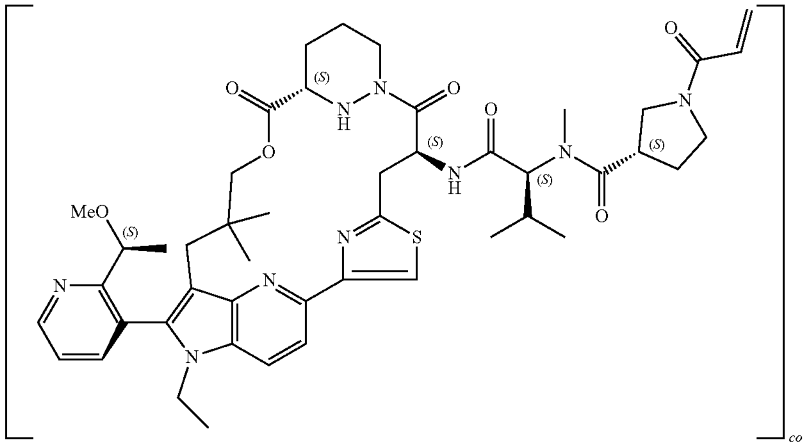 |
| B348 | 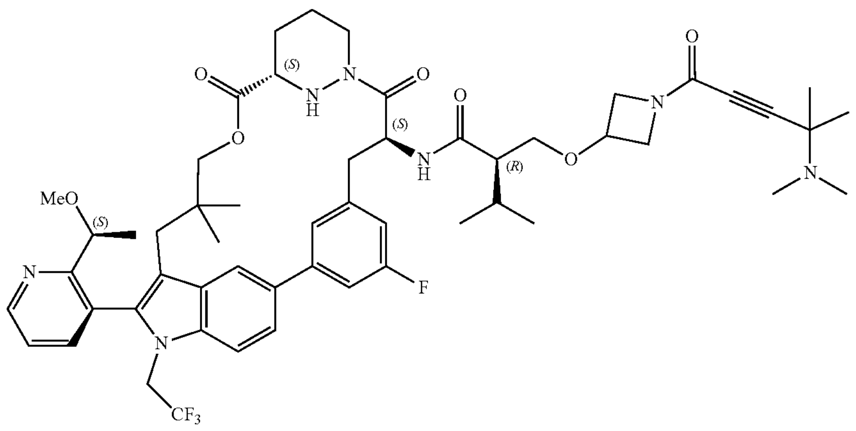 |

TABLE 2-continued
| Certain Compounds | |
|---|---|
| Ex # | Structure |
| B349 | 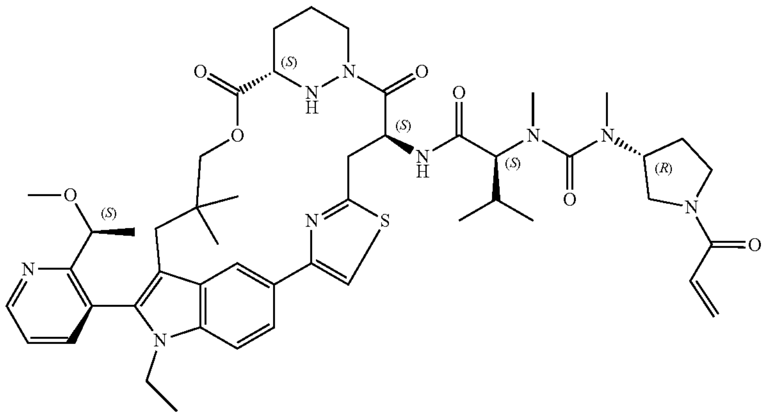 |
| B350 | 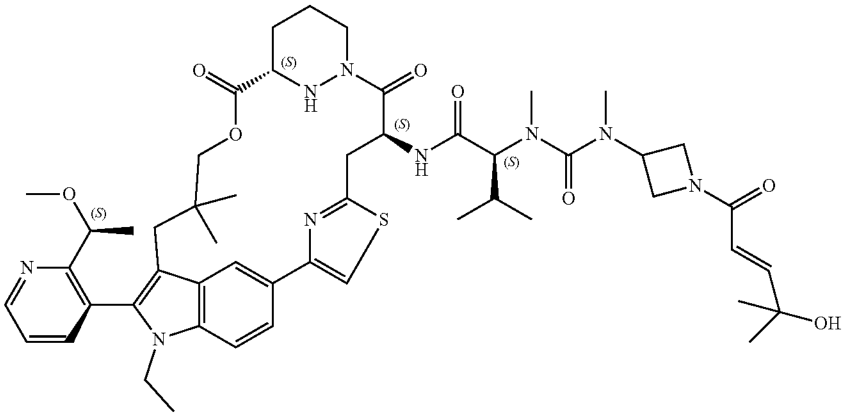 |
| B351 | 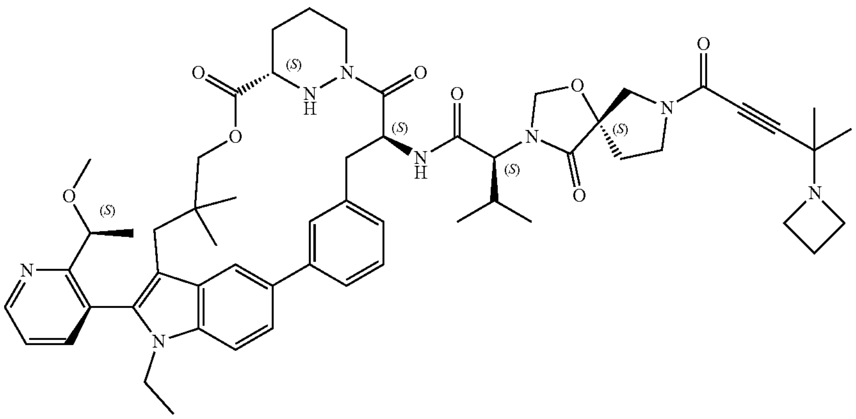 |

TABLE 2-continued
| Certain Compounds | |
|---|---|
| Ex # | Structure |
| B352 | 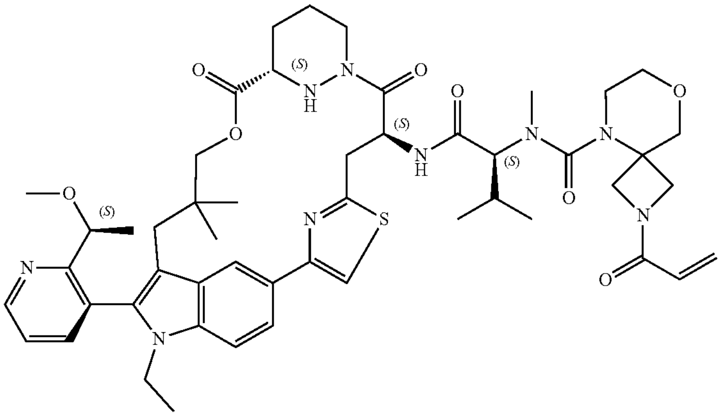 |
| B353 | assumed<br>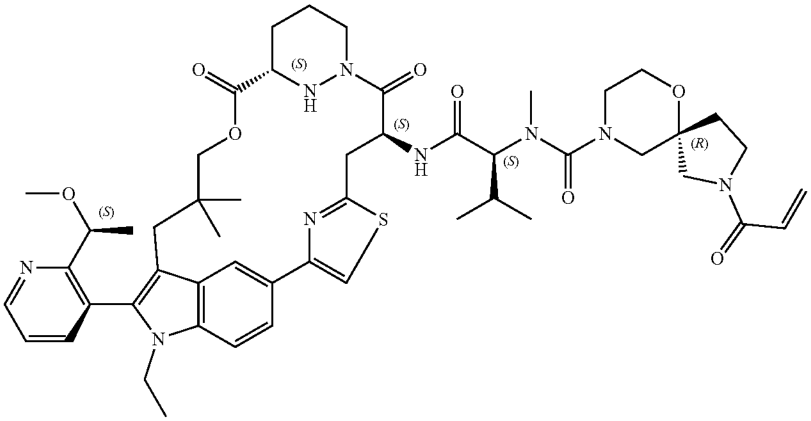 |
| B354 | assumed<br>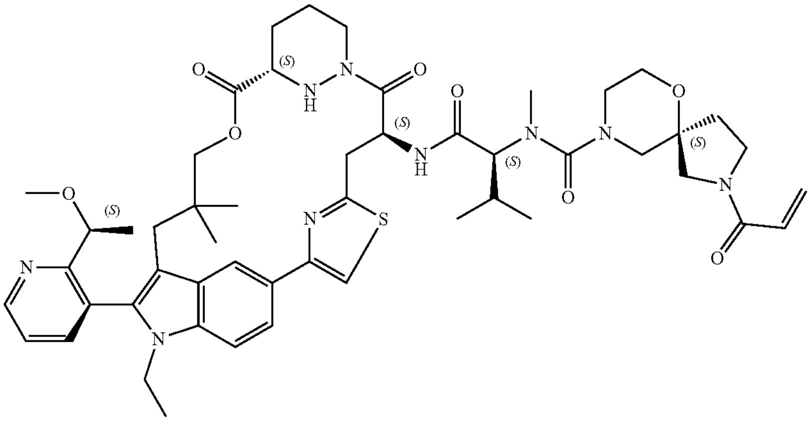 |

TABLE 2-continued
| Certain Compounds | |
|---|---|
| Ex # | Structure |
| B355 | 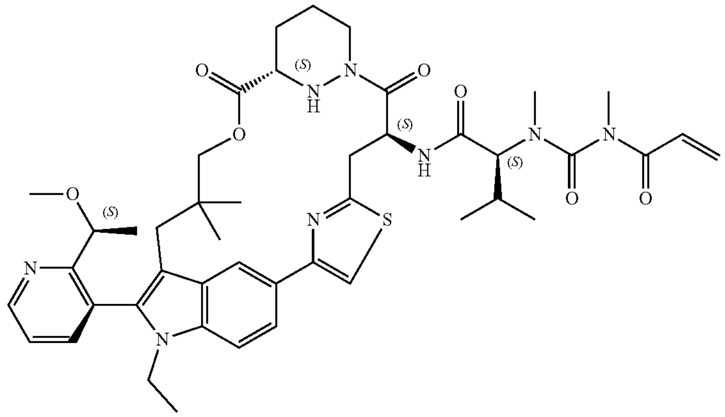 |
| B356 | 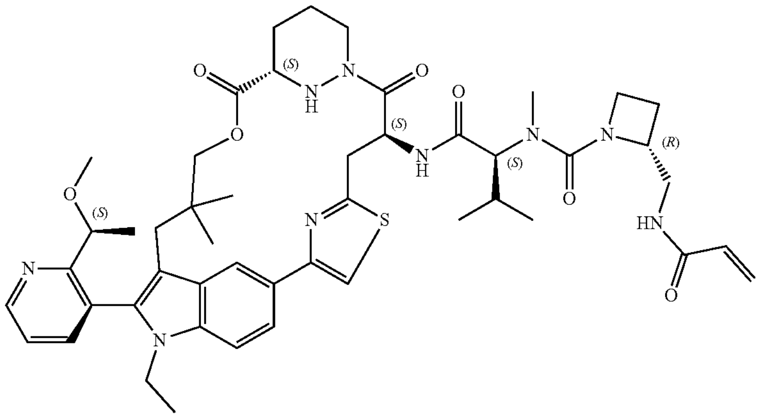 |
| B357 | 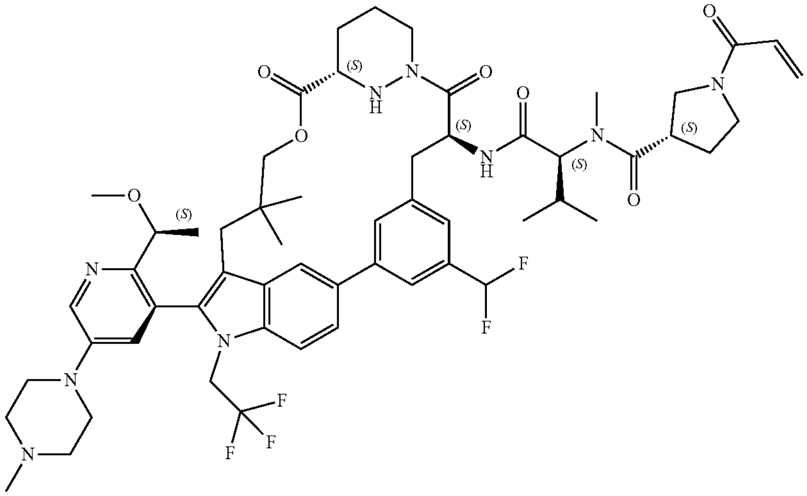 |

TABLE 2-continued
| Certain Compounds | |
|---|---|
| Ex # | Structure |
| B358 | 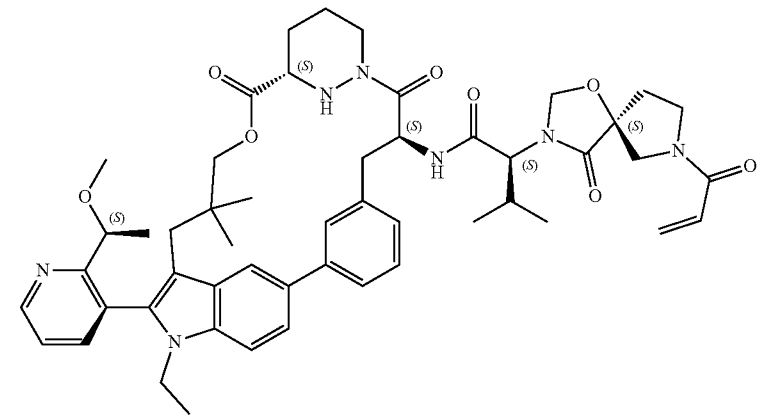 |
| B359 | 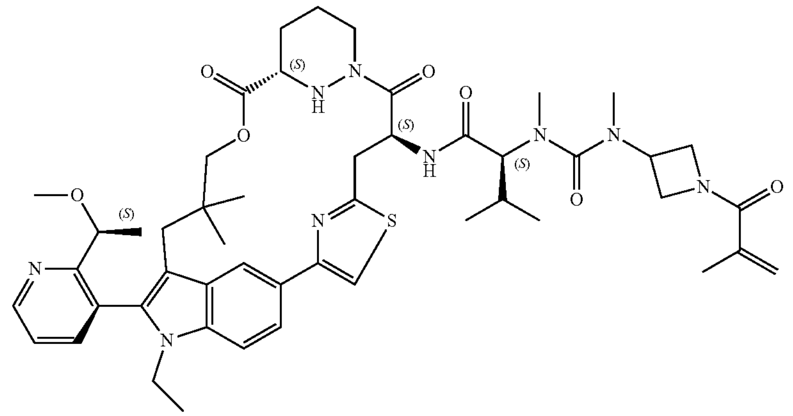 |
| B360 | 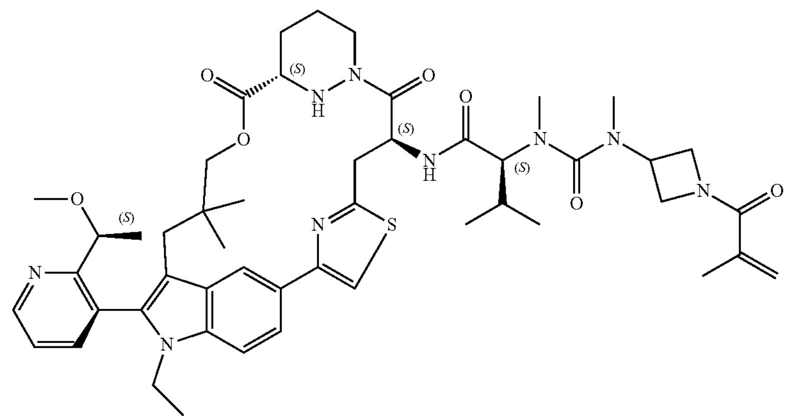 |

TABLE 2-continued
| Certain Compounds | |
|---|---|
| Ex # | Structure |
| B361 | 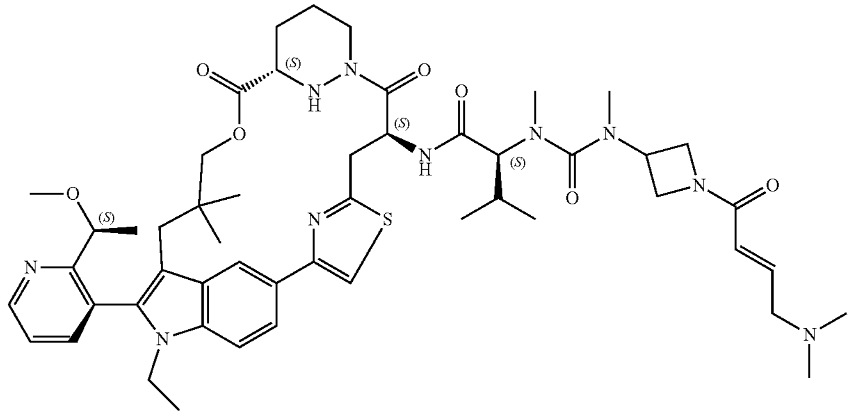 |
| B362 | 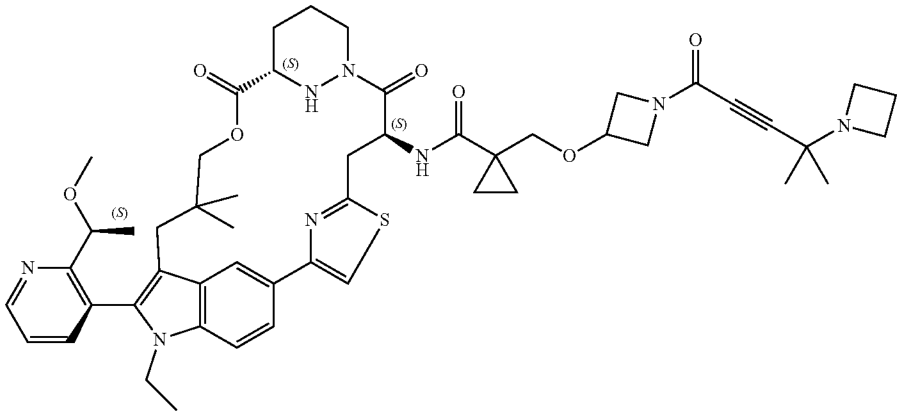 |
| B363 | 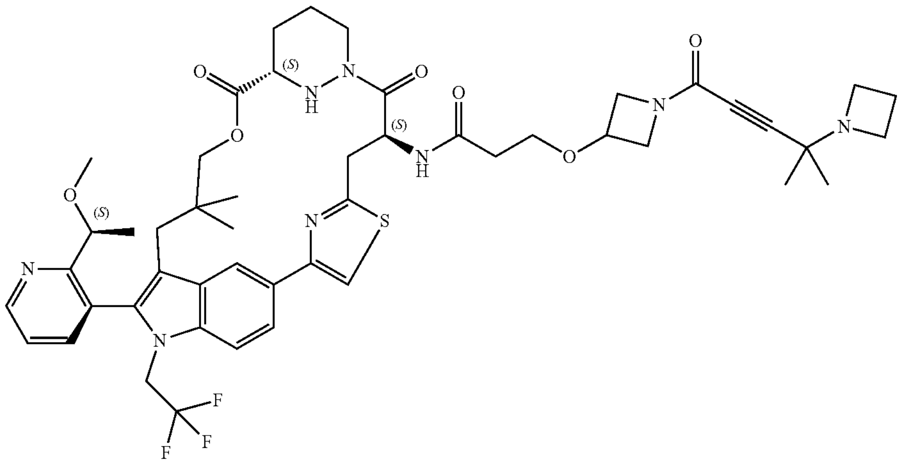 |

TABLE 2-continued
| Certain Compounds | |
|---|---|
| Ex # | Structure |
| B364 | 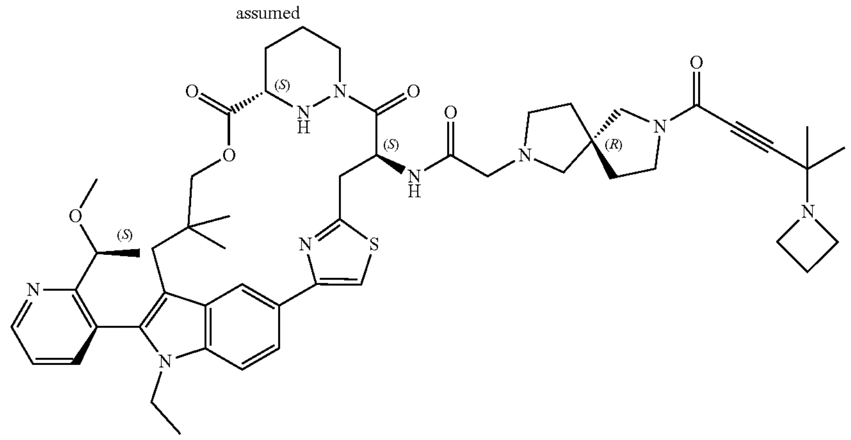 |
| B365 | 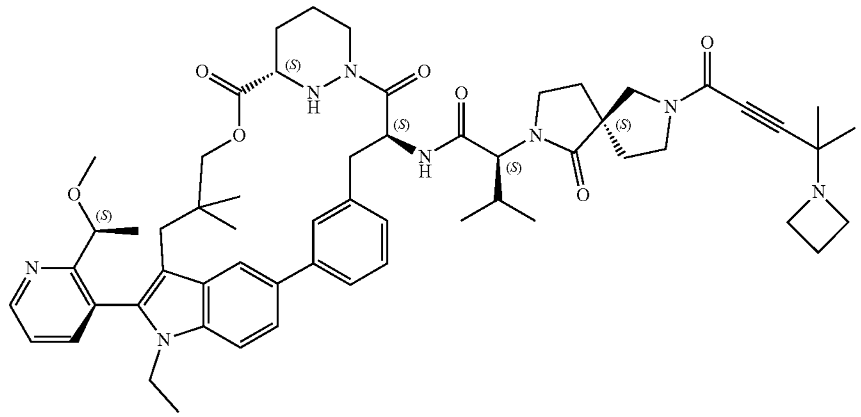 |
| B366 | 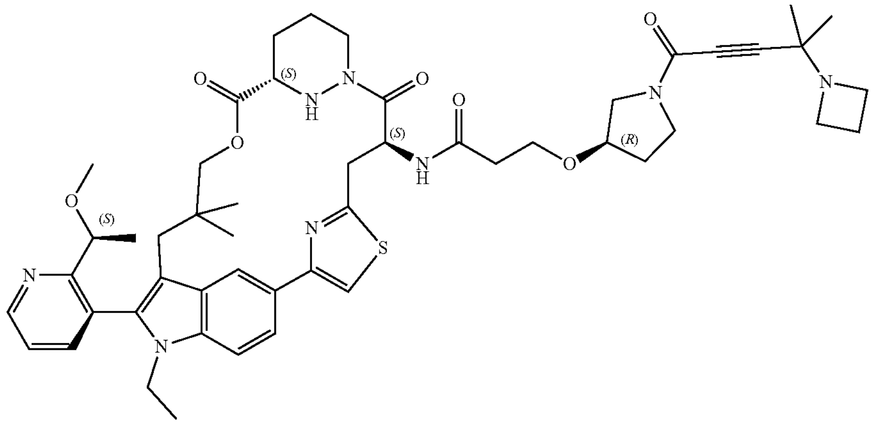 |

TABLE 2-continued
| Certain Compounds | |
|---|---|
| Ex # | Structure |
| B367 | assumed 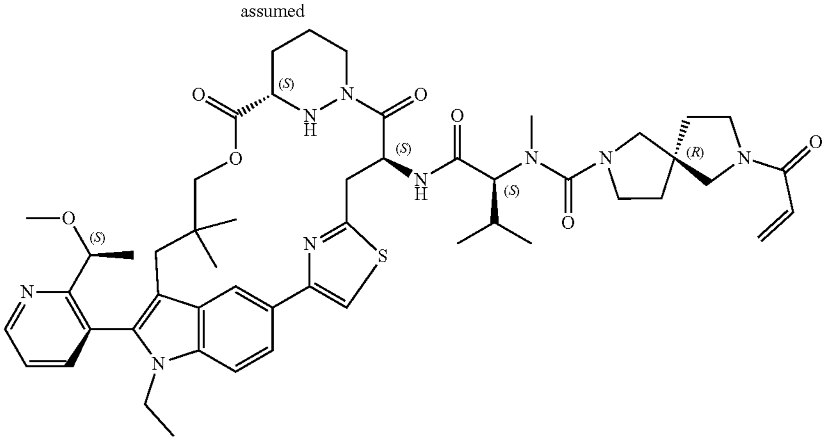 |
| B368 | 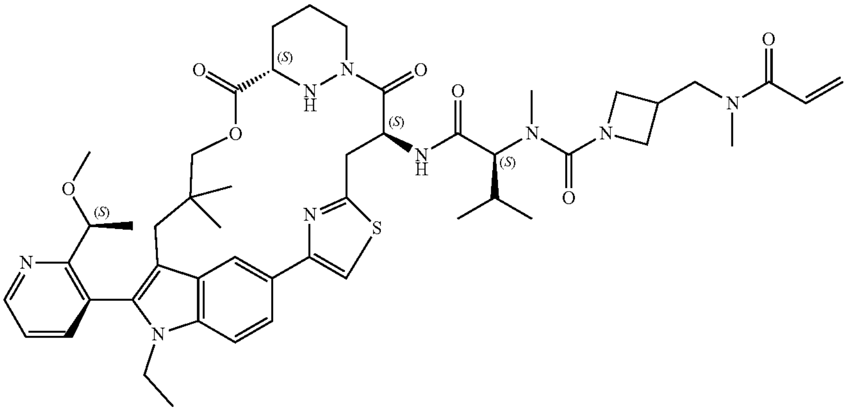 |
| B369 | 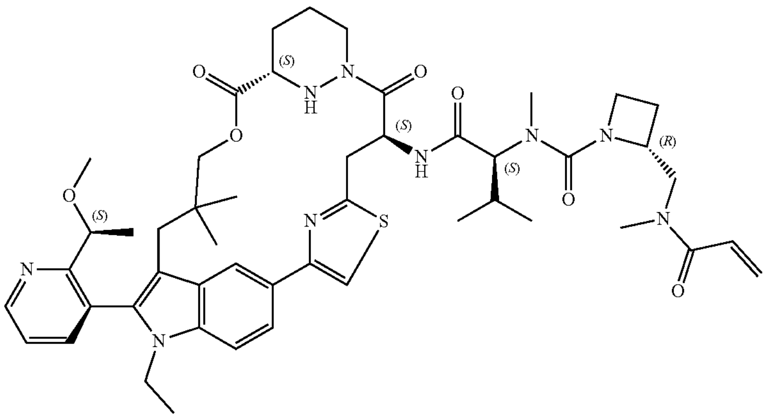 |

TABLE 2-continued
| Certain Compounds | |
|---|---|
| Ex # | Structure |
| B370 | 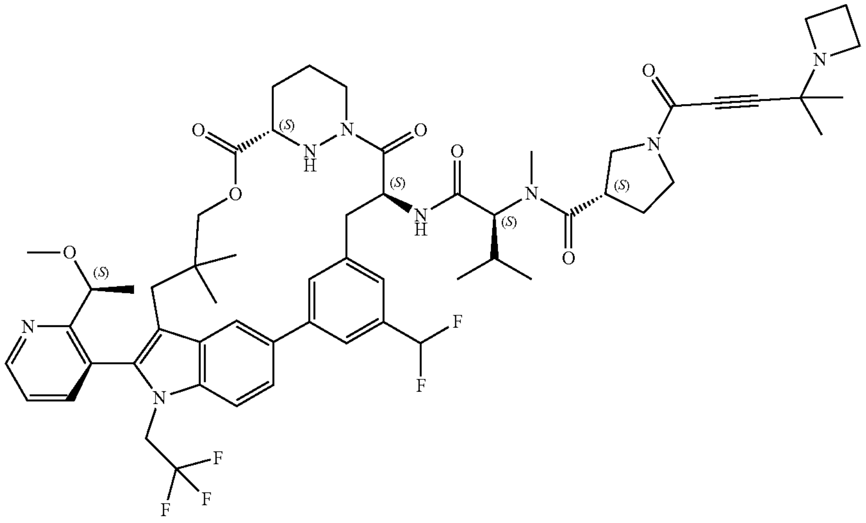 |
| B371 | 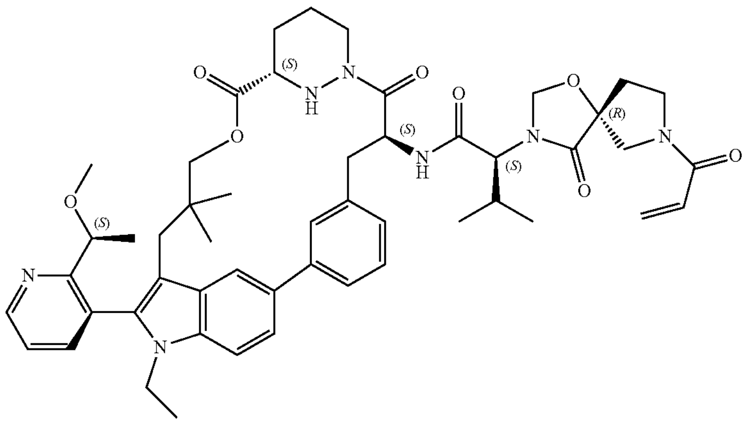 |
| B372 | 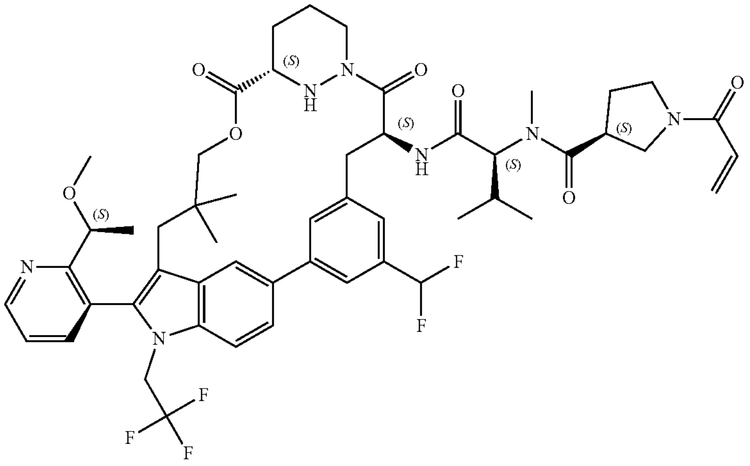 |

TABLE 2-continued
| Certain Compounds | |
|---|---|
| Ex # | Structure |
| B373 | 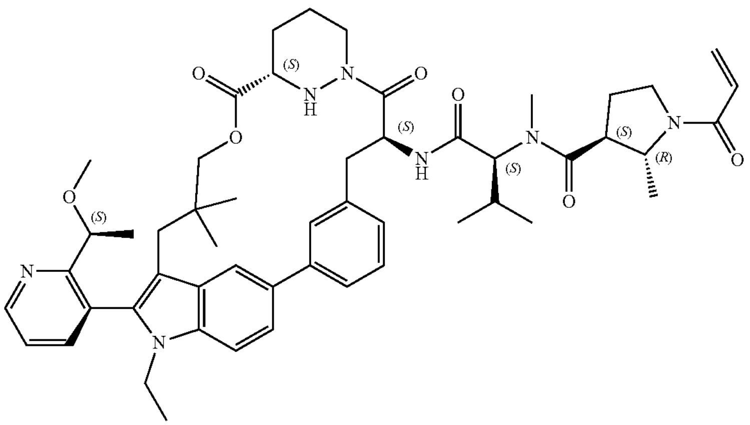 |
| B374 | 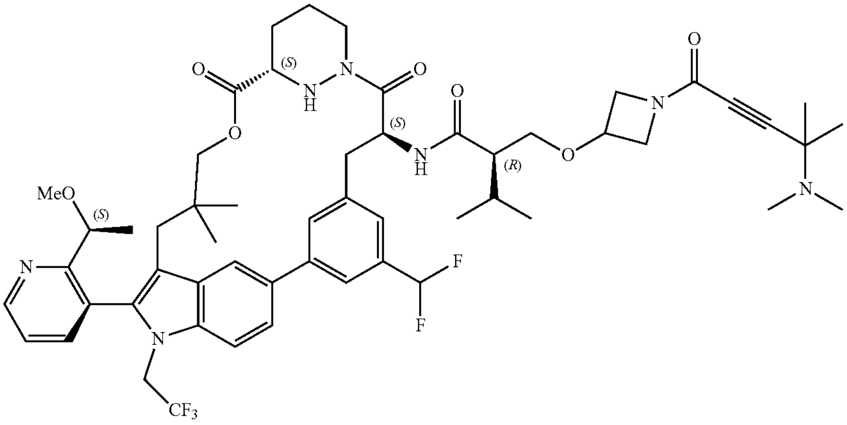 |
| B375 | 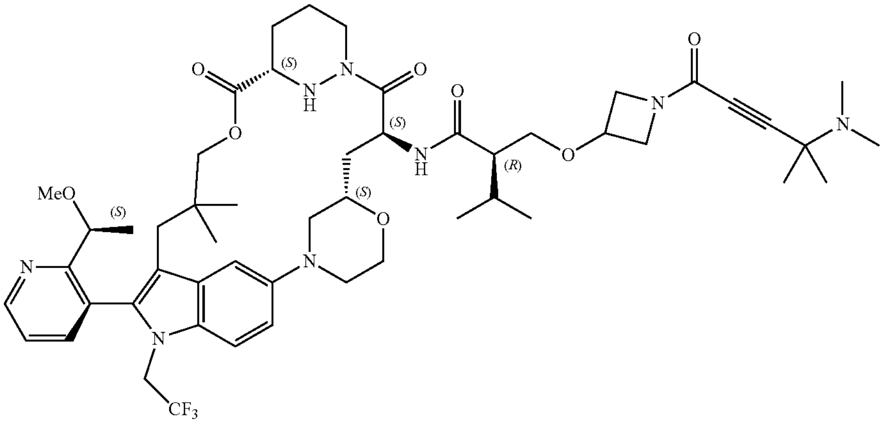 |

TABLE 2-continued
| Certain Compounds | |
|---|---|
| Ex # | Structure |
| B376 | 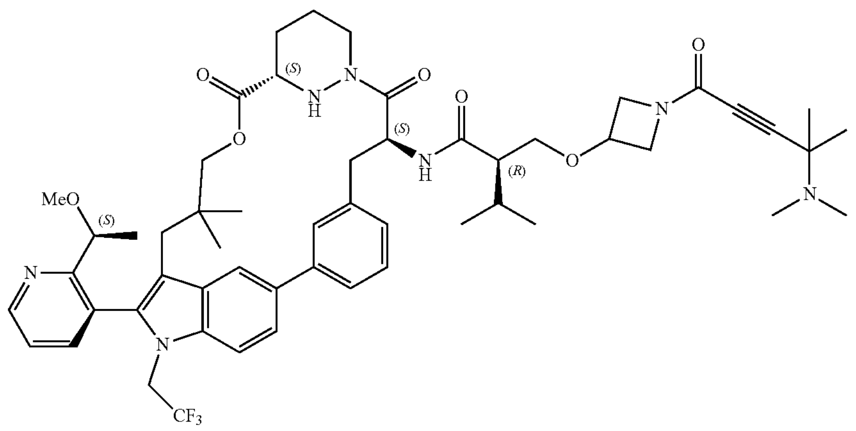 |
| B377 | 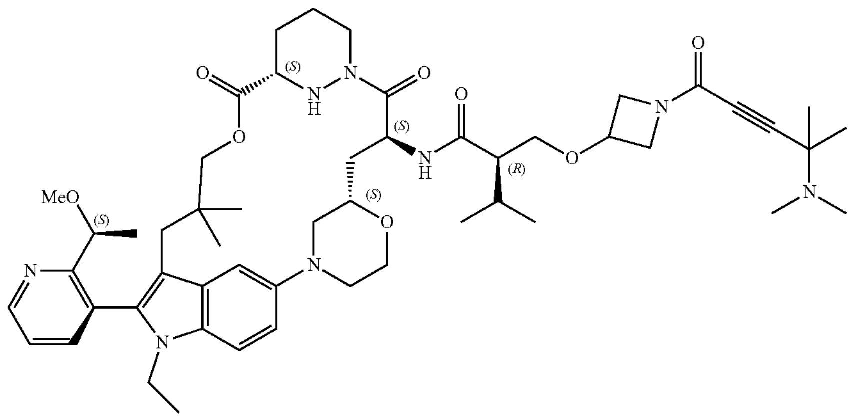 |
| B378 | 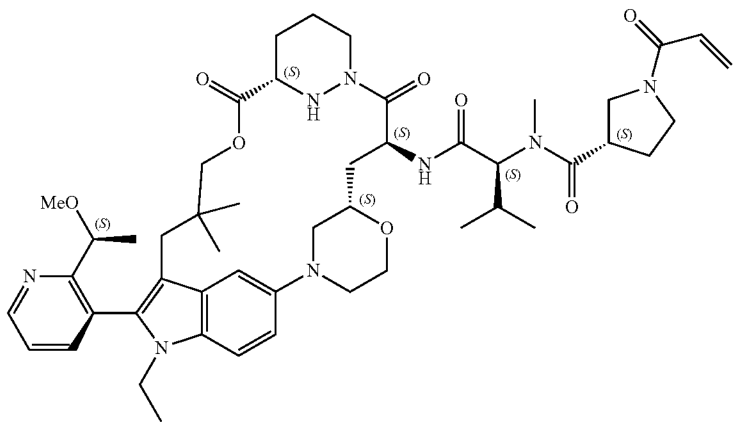 |

TABLE 2-continued
| Certain Compounds | |
|---|---|
| Ex # | Structure |
| B379 | 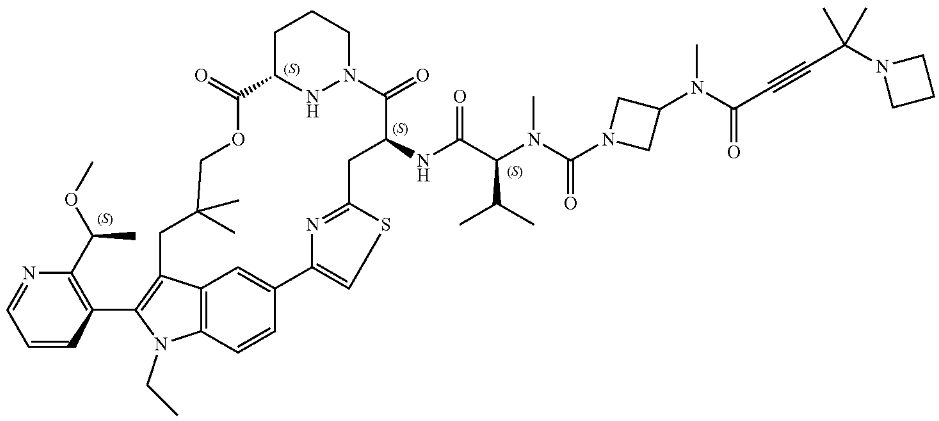 |
| B380 | 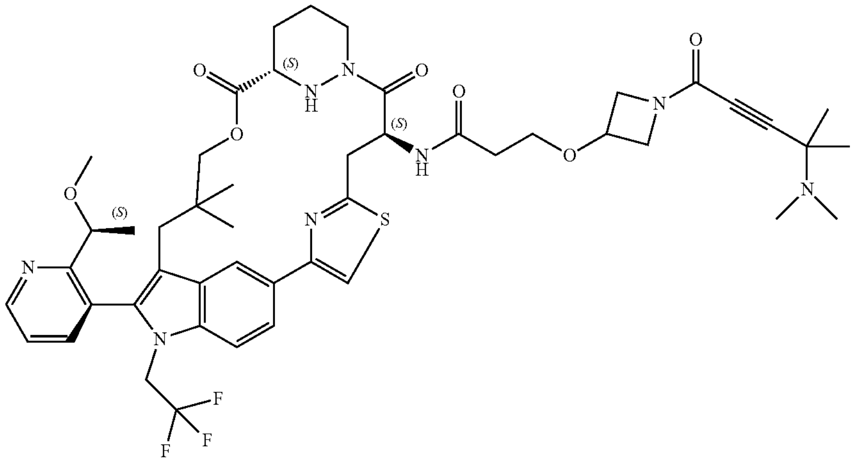 |
| B381 | 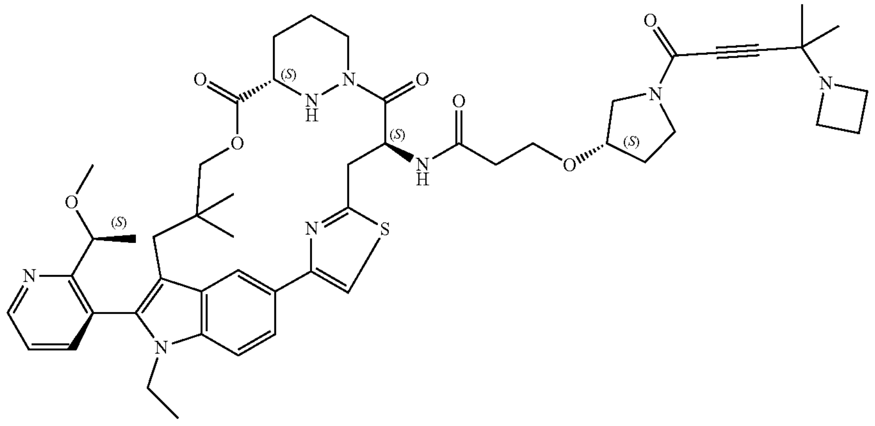 |

TABLE 2-continued
| Certain Compounds | |
|---|---|
| Ex # | Structure |
| B382 | 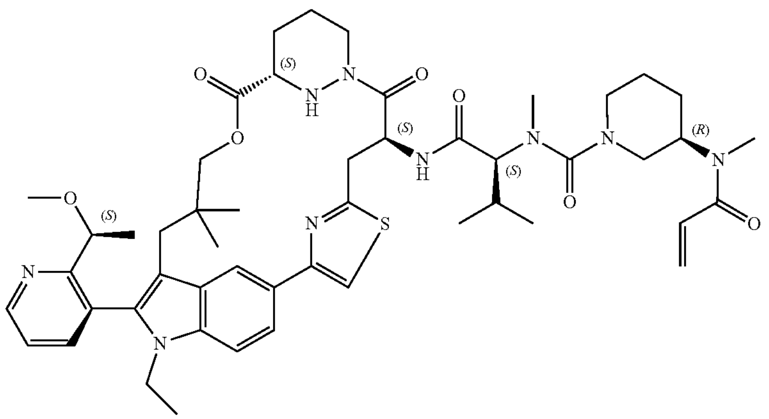 |
| B383 | 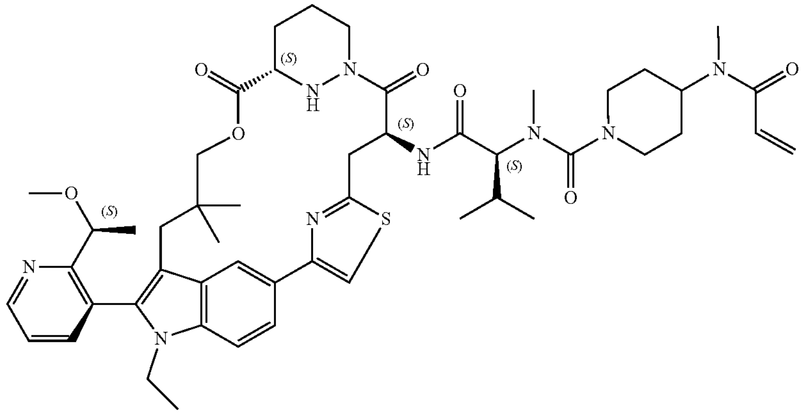 |
| B384 | 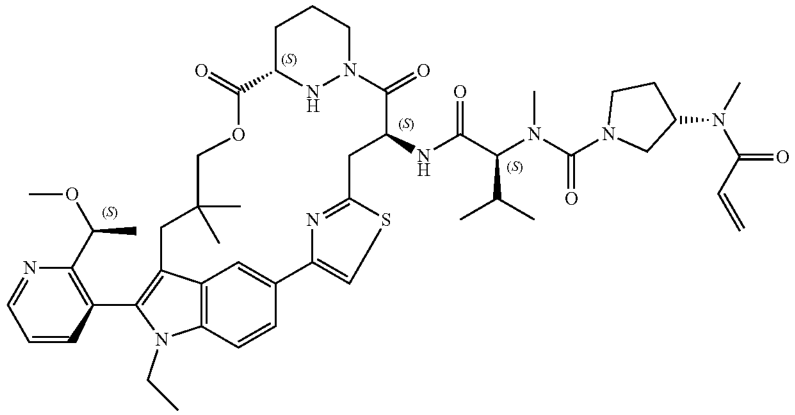 |

TABLE 2-continued
| Certain Compounds | |
|---|---|
| Ex # | Structure |
| B385 | 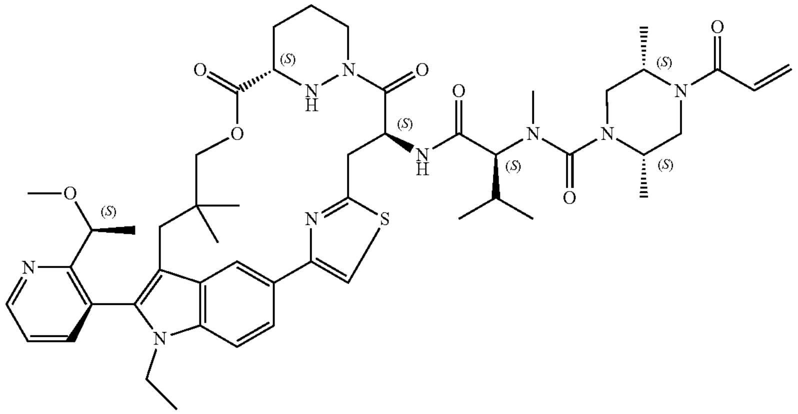 |
| B386 | 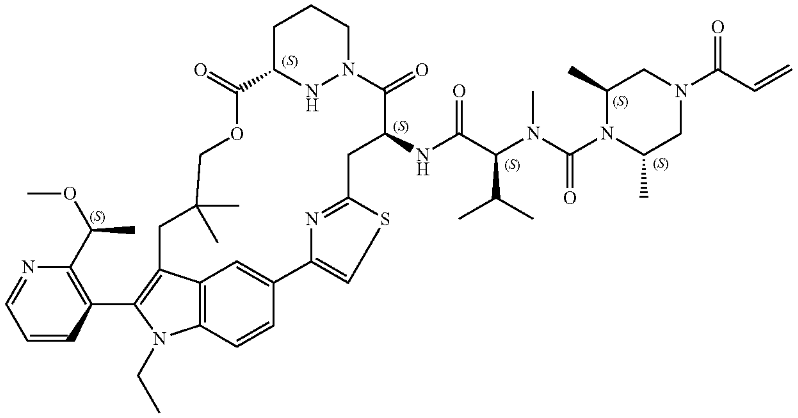 |
| B387 | 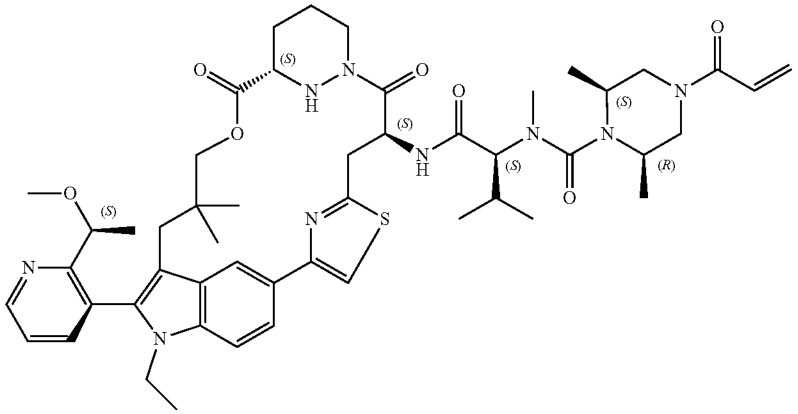 |

TABLE 2-continued
| Certain Compounds | |
|---|---|
| Ex # | Structure |
| B388 | 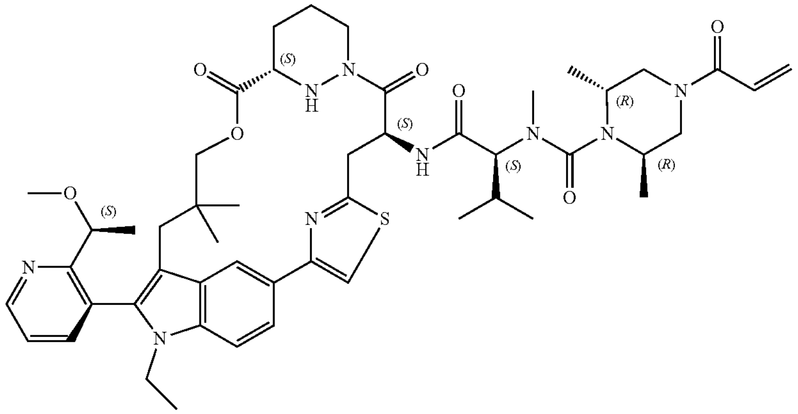 |
| B389 | 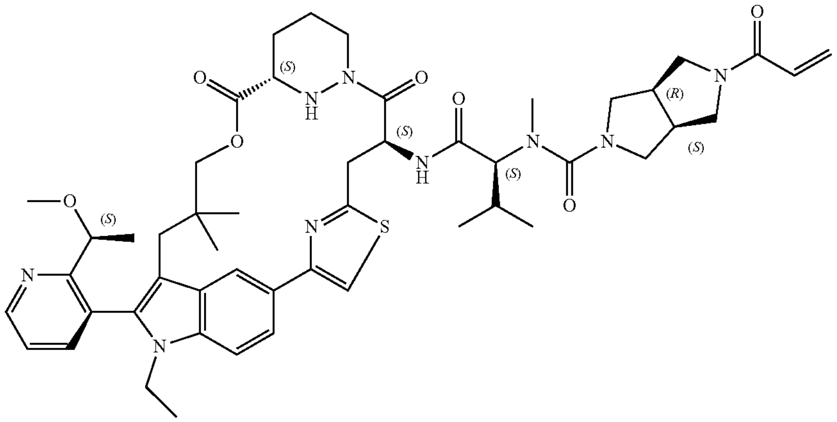 |
| B390 | 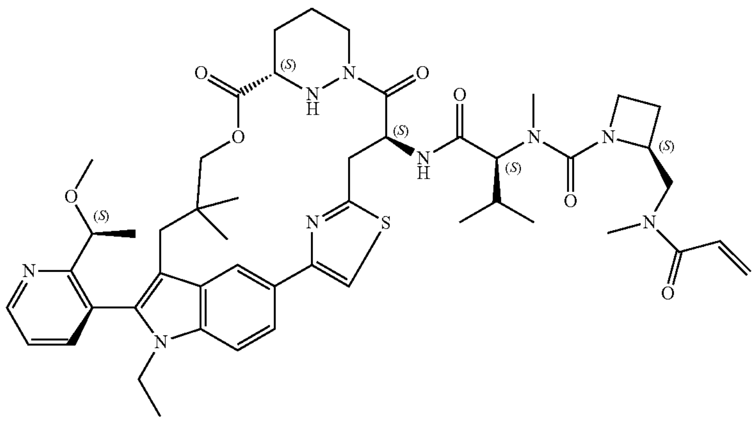 |

TABLE 2-continued
| Certain Compounds | |
|---|---|
| Ex # | Structure |
| B391 | 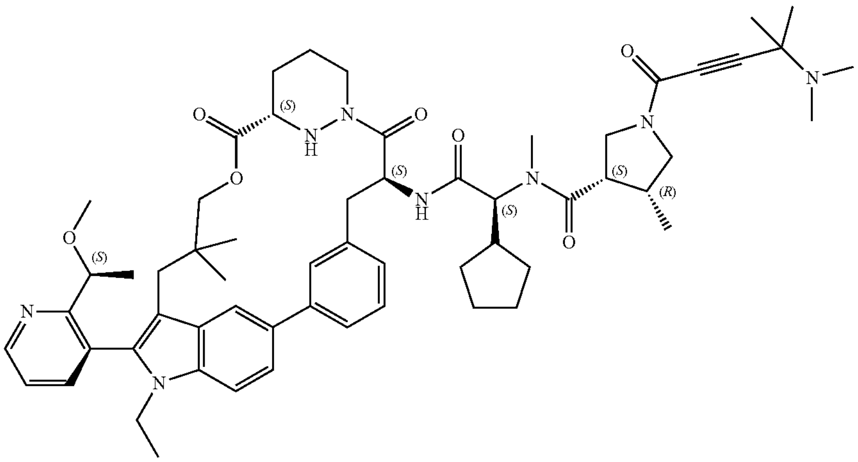 |
| B392 | 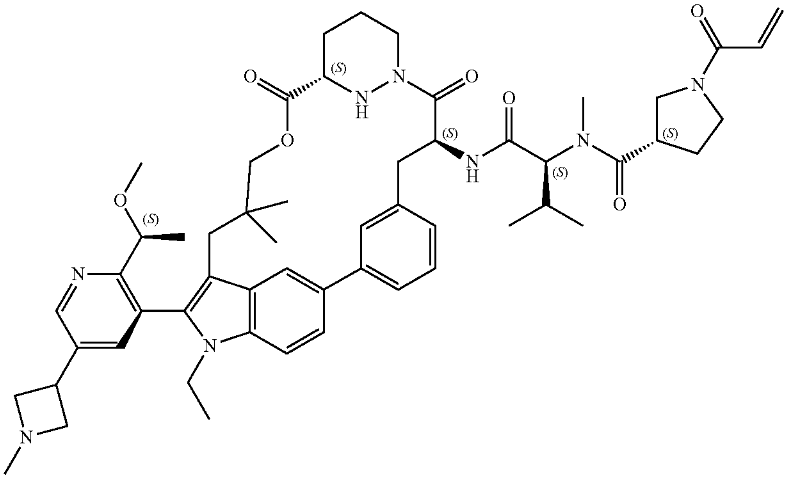 |
| B393 | 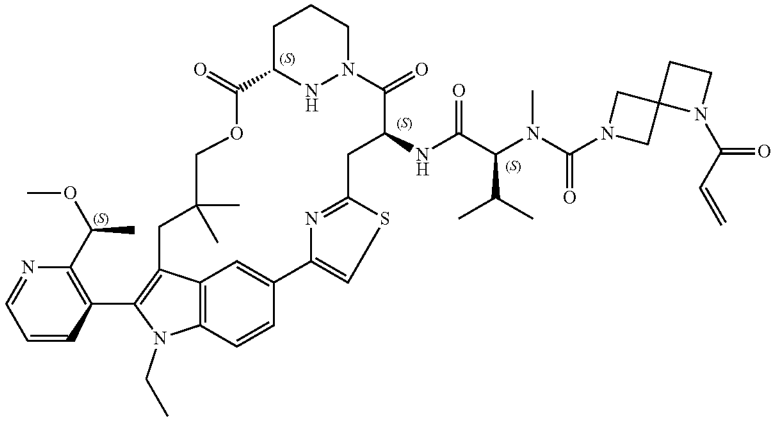 |

TABLE 2-continued
| Certain Compounds | |
|---|---|
| Ex # | Structure |
| B394 | 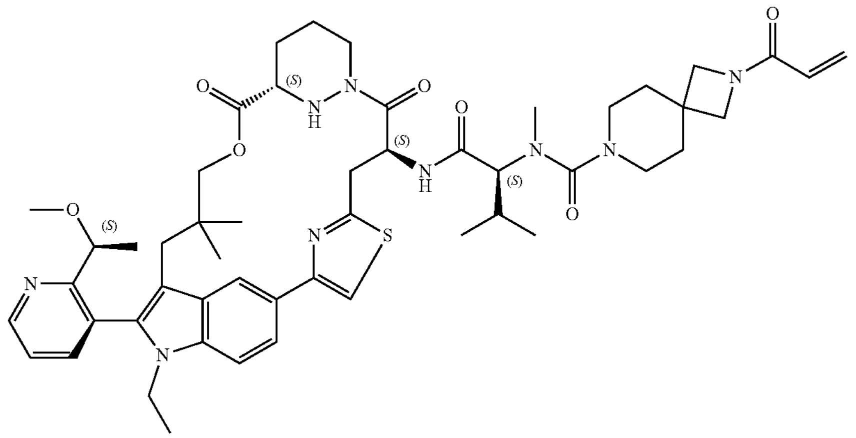 |
| B395 | 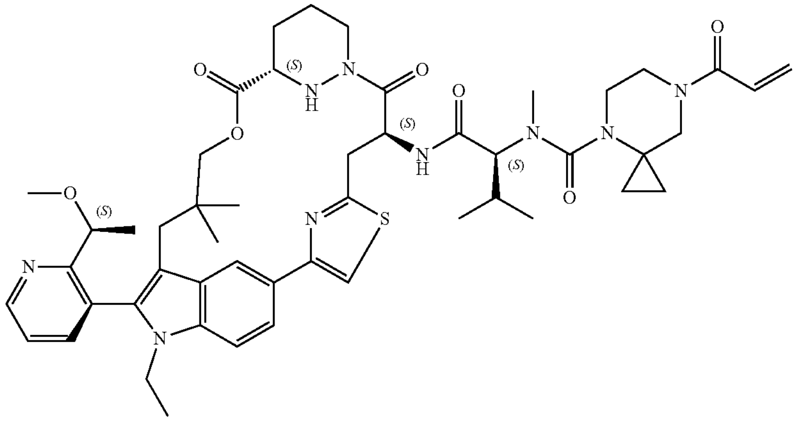 |
| B396 | 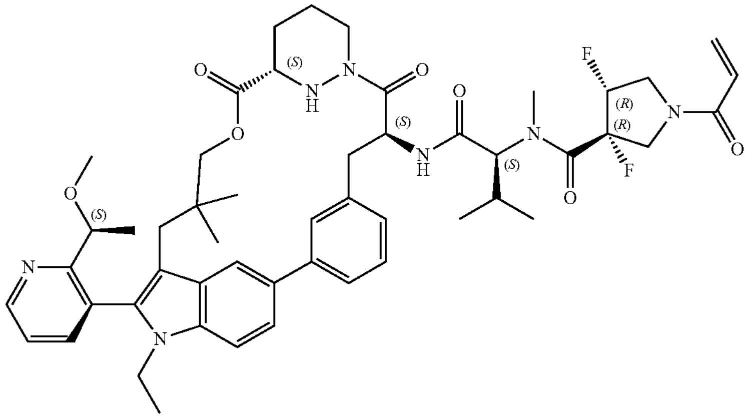 |

TABLE 2-continued
| Certain Compounds | |
|---|---|
| Ex # | Structure |
| B397 | 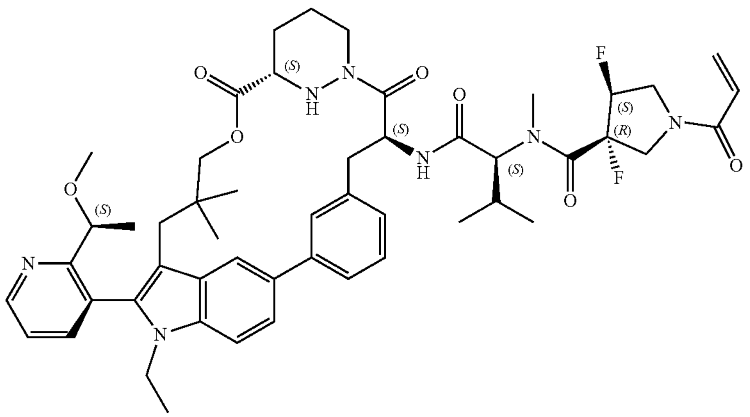 |
| B398 | 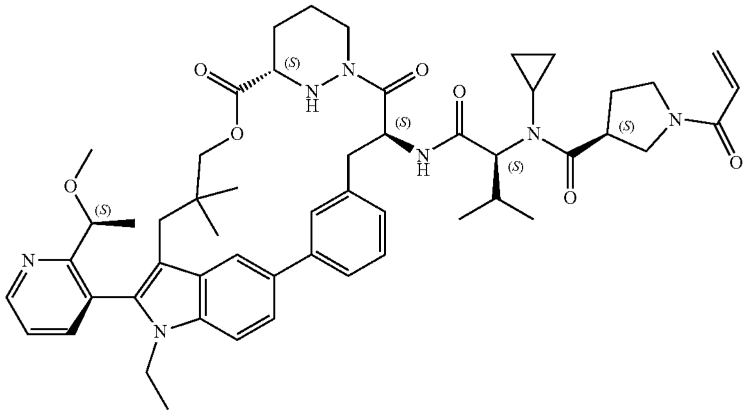 |
| B399 | 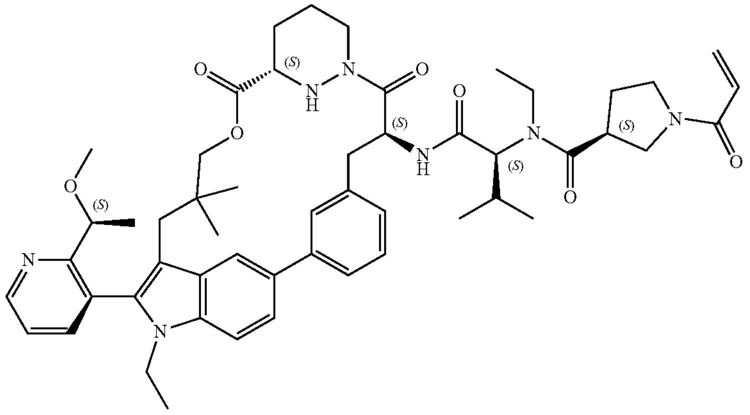 |

TABLE 2-continued
| Certain Compounds | |
|---|---|
| Ex # | Structure |
| B400 | 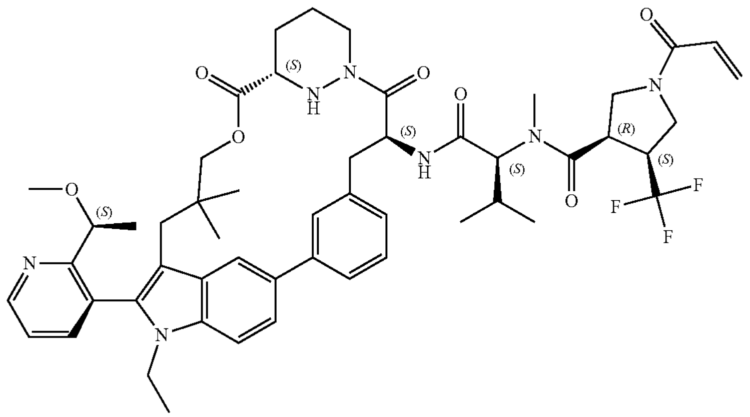 |
| B401 | 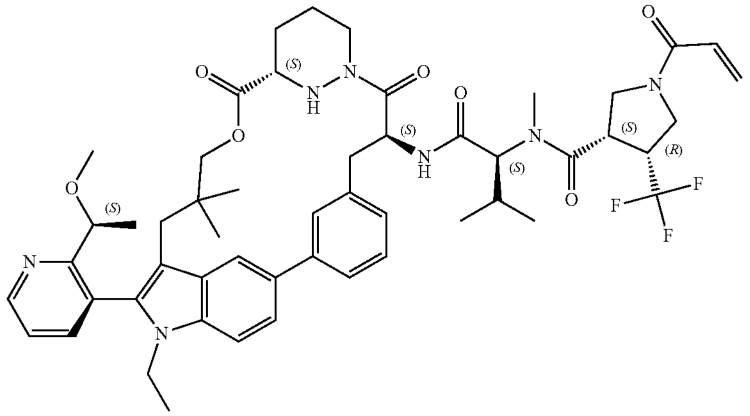 |
| B402 | 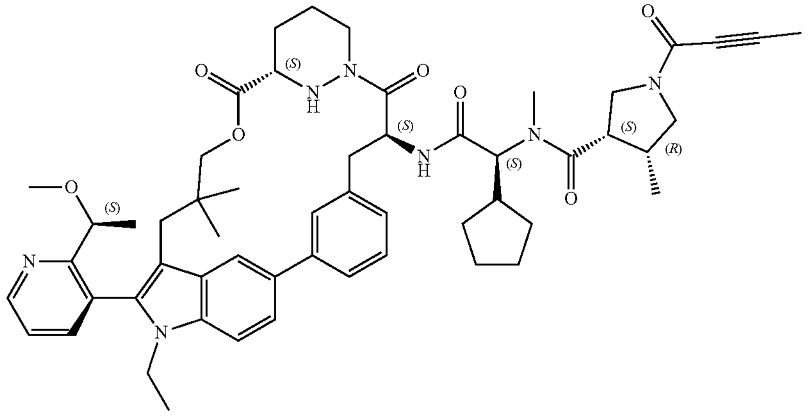 |

TABLE 2-continued
| Certain Compounds | |
|---|---|
| Ex # | Structure |
| B403 | 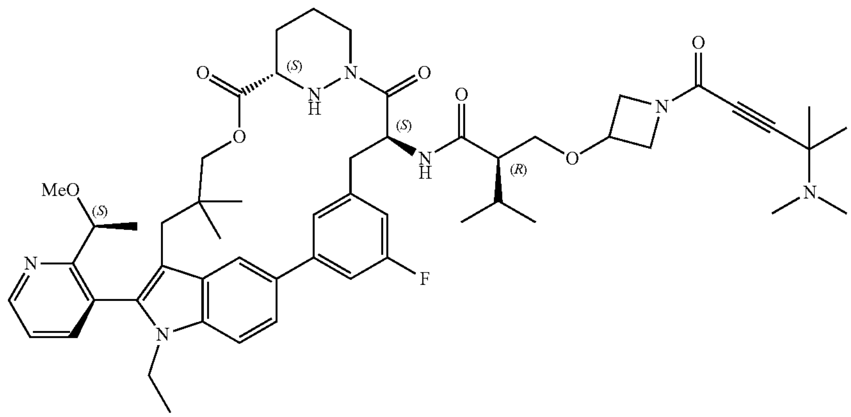 |
| B404 | 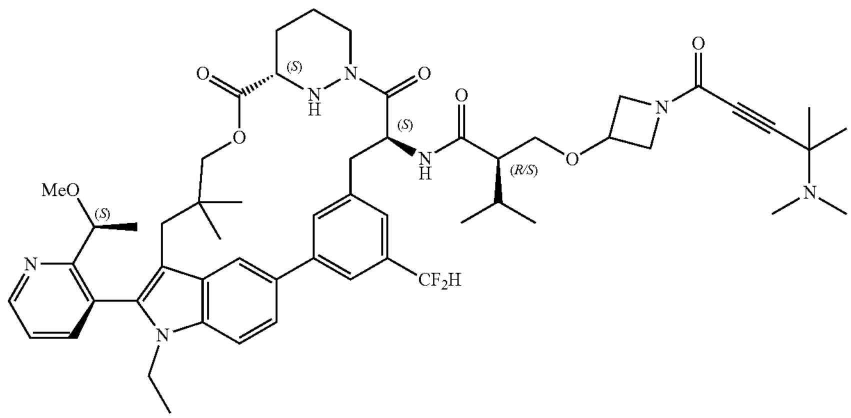 |
| B405 | 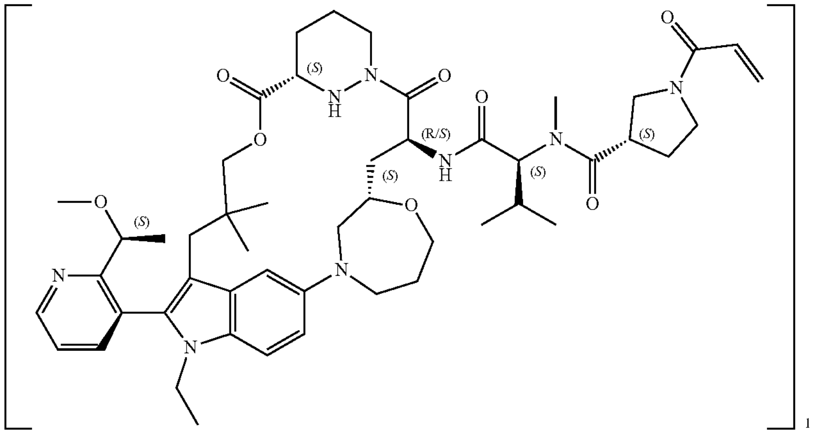 |

TABLE 2-continued
| Certain Compounds | |
|---|---|
| Ex # | Structure |
| B406 | 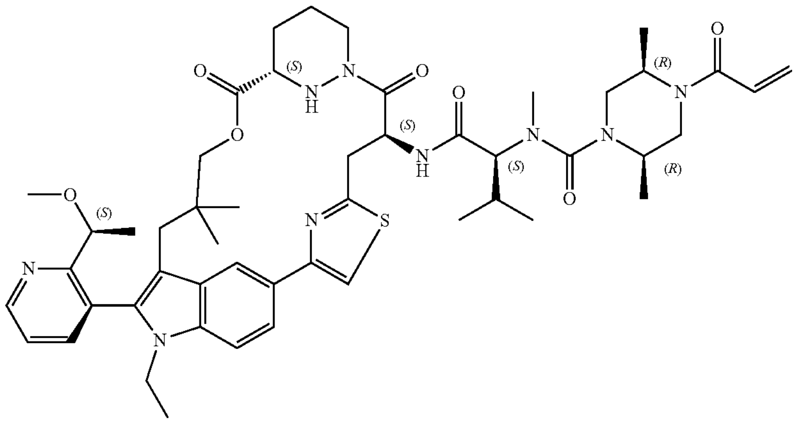 |
| B407 | 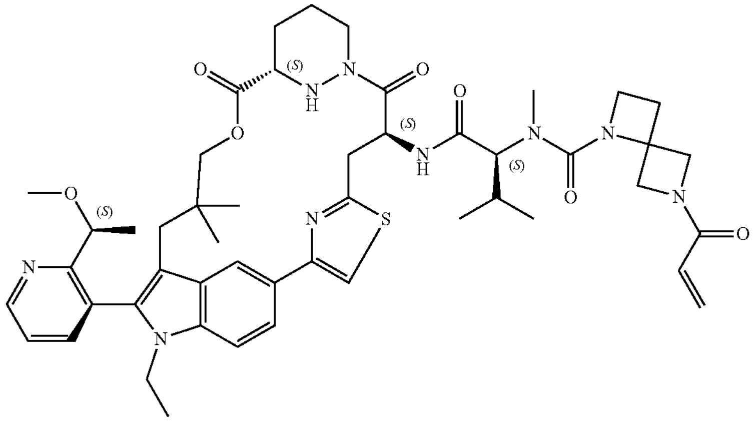 |
| B408 | 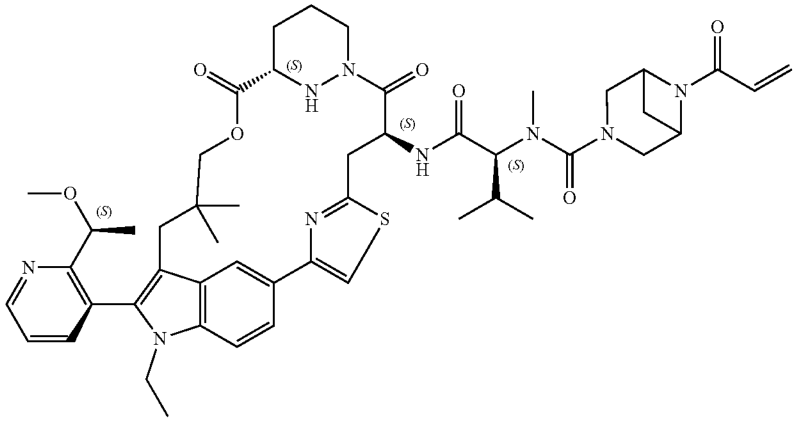 |

TABLE 2-continued
| Certain Compounds | |
|---|---|
| Ex # | Structure |
| B409 | 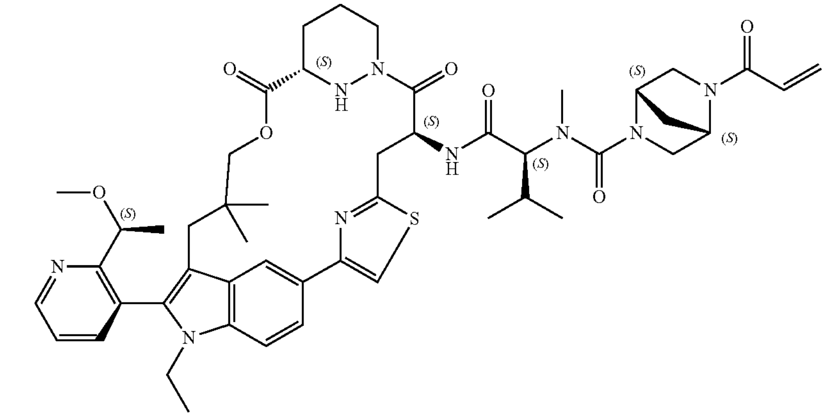 |
| B410 | 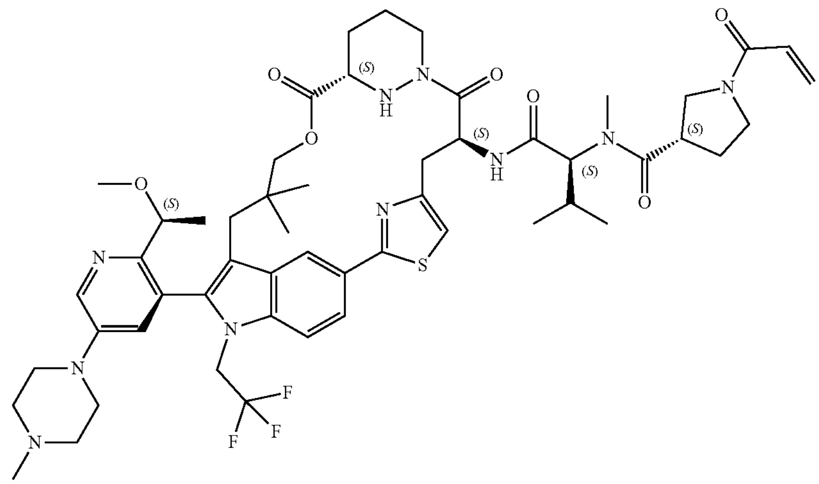 |
| B411 | assumed<br>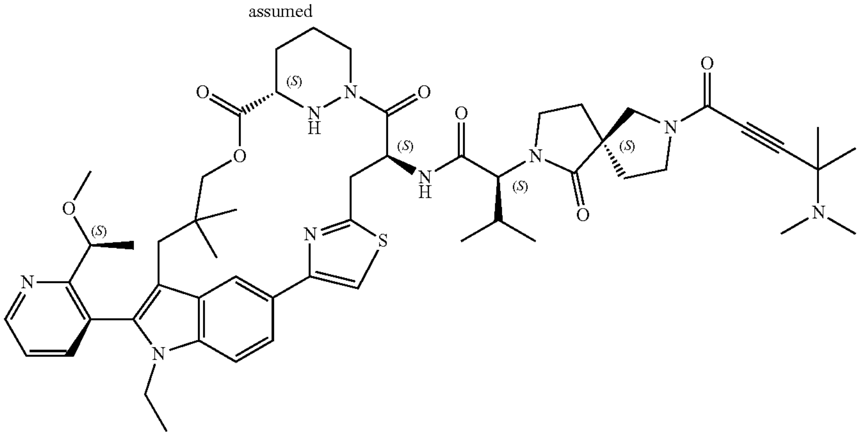 |

TABLE 2-continued
| Certain Compounds | |
|---|---|
| Ex # | Structure |
| B412 | 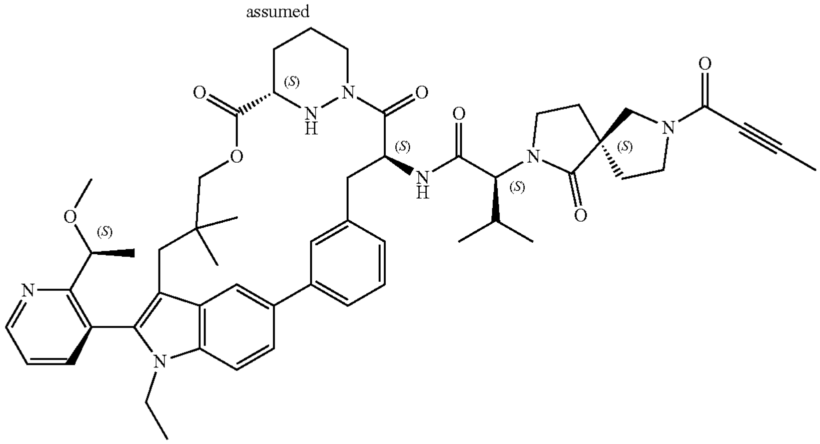 |
| B413 | 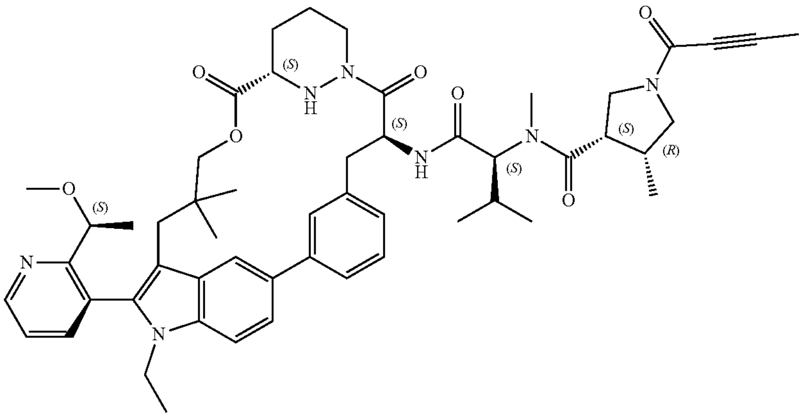 |
| B414 | 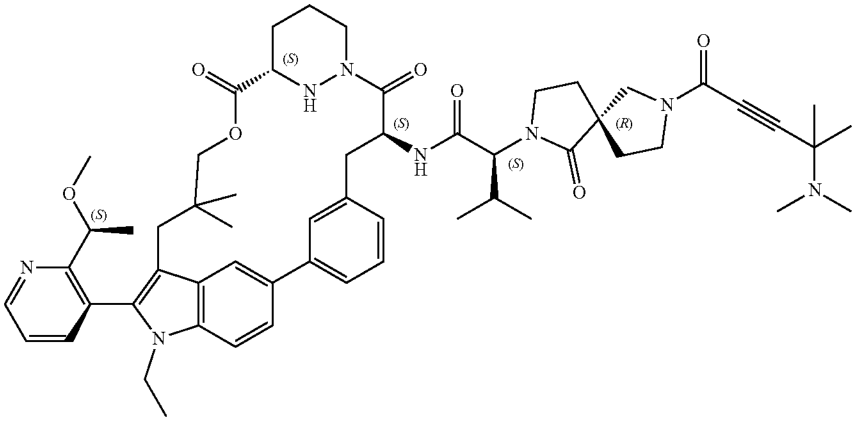 |

TABLE 2-continued
| Certain Compounds | |
|---|---|
| Ex # | Structure |
| B415 | 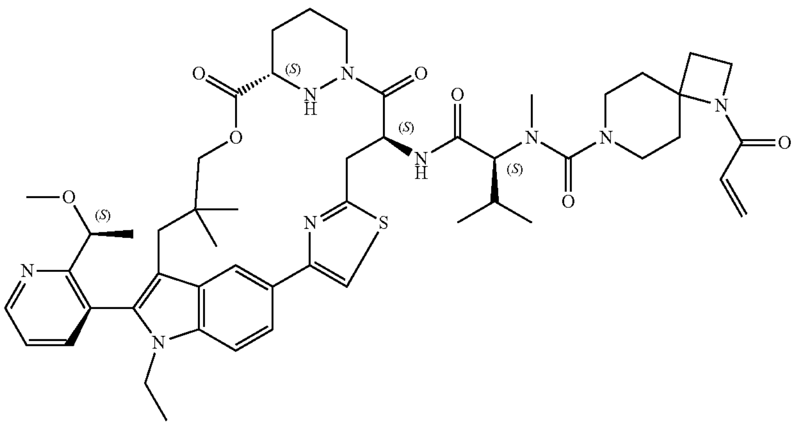 |
| B416 | 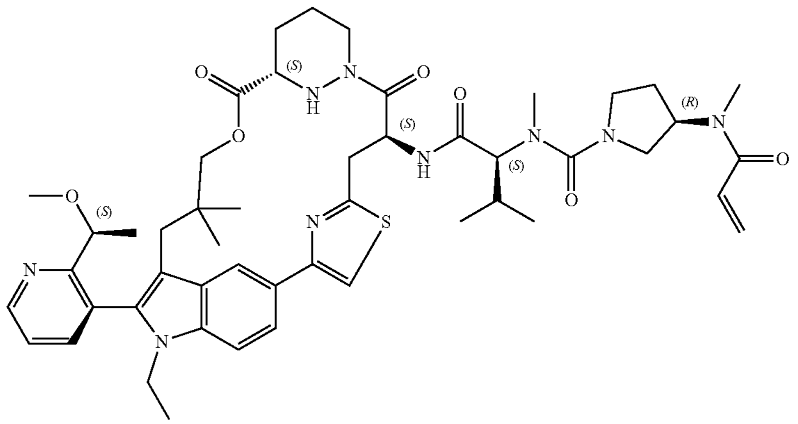 |
| B417 | 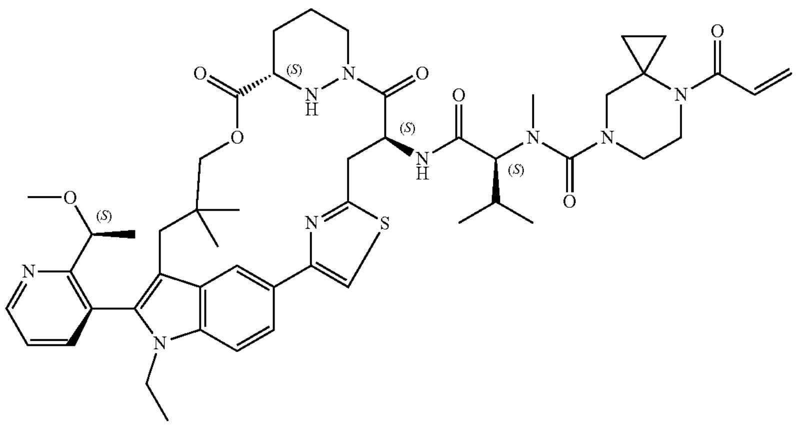 |

TABLE 2-continued
| Certain Compounds | |
|---|---|
| Ex # | Structure |
| B418 | 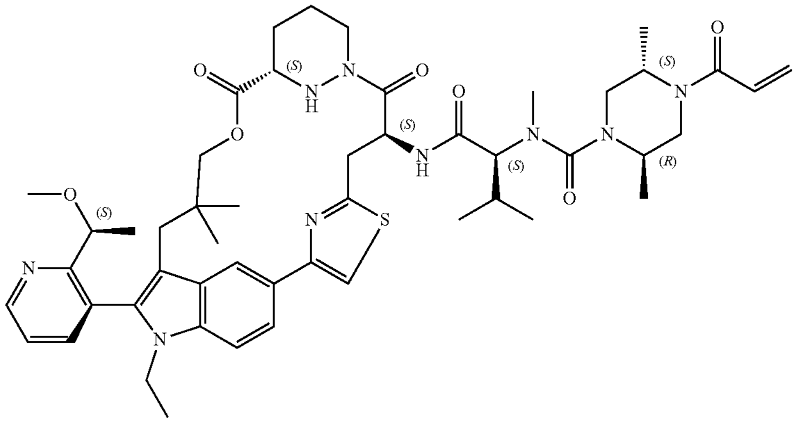 |
| B419 | 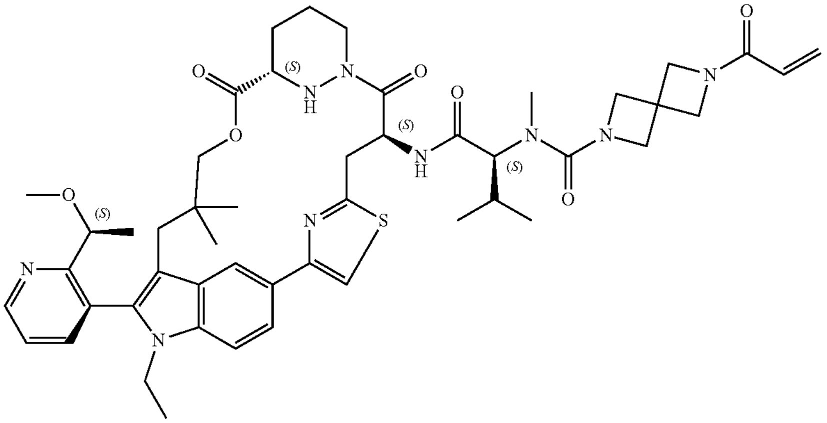 |
| B420 | 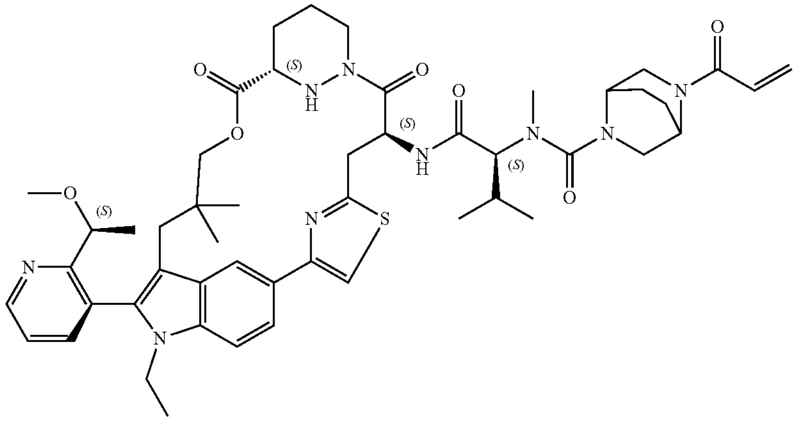 |

TABLE 2-continued
| Certain Compounds | |
|---|---|
| Ex # | Structure |
| B421 | 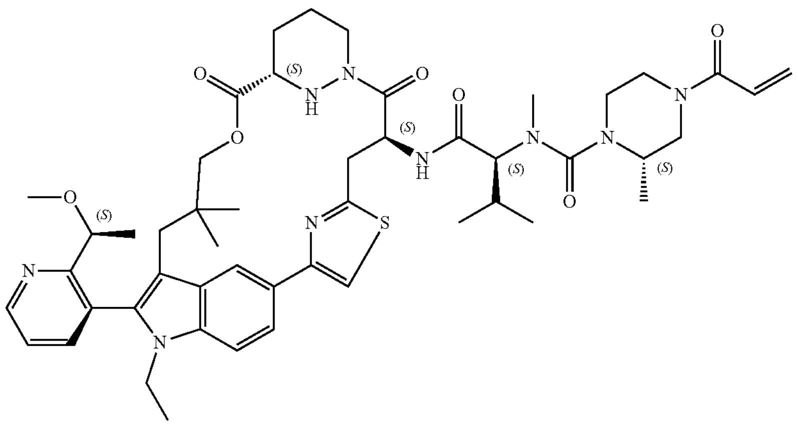 |
| B422 | 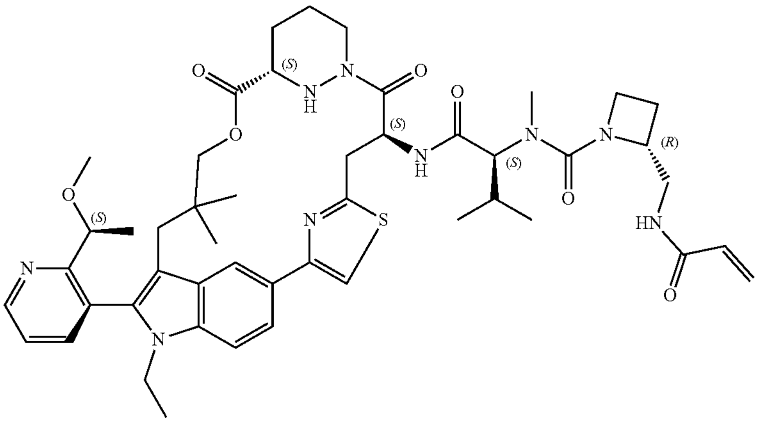 |
| B423 | 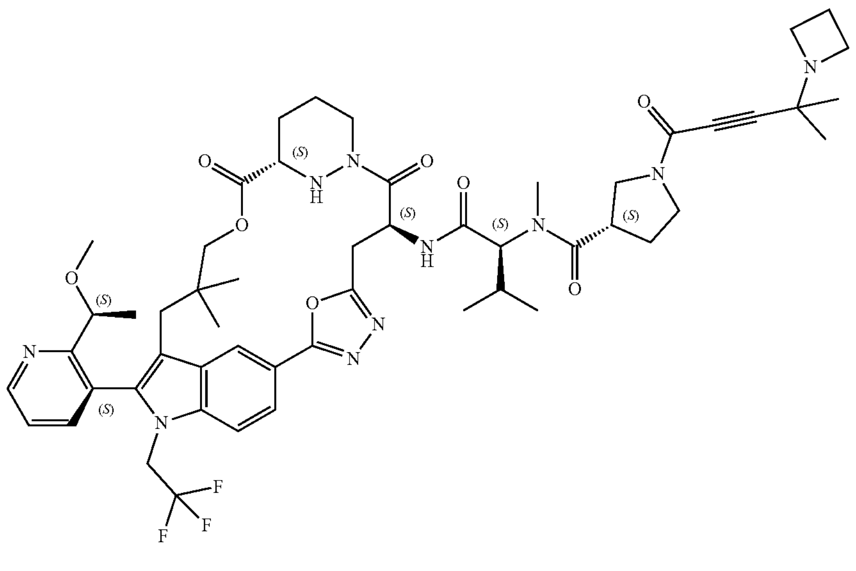 |

TABLE 2-continued
| Certain Compounds | |
|---|---|
| Ex # | Structure |
| B424 | 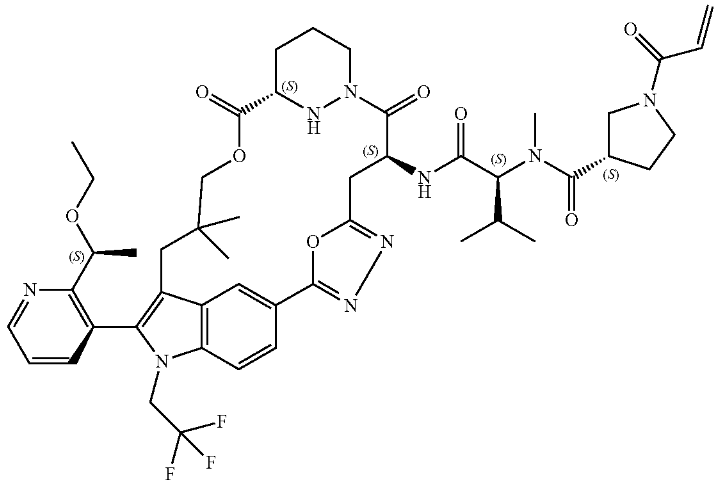 |
| B425 | 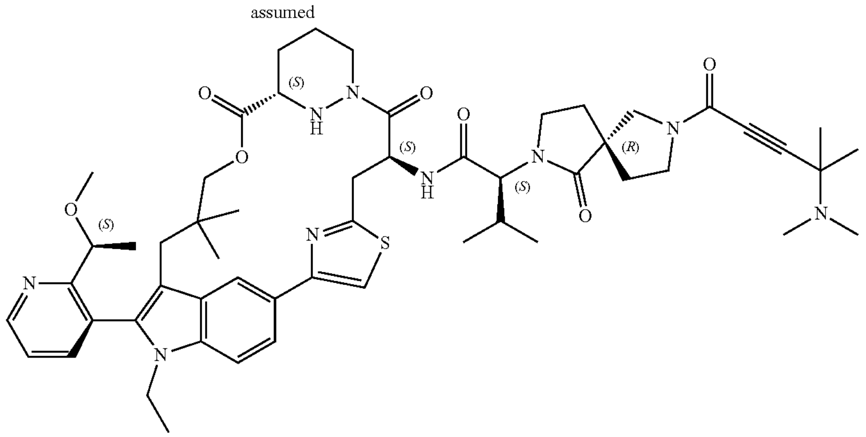 |
| B426 | 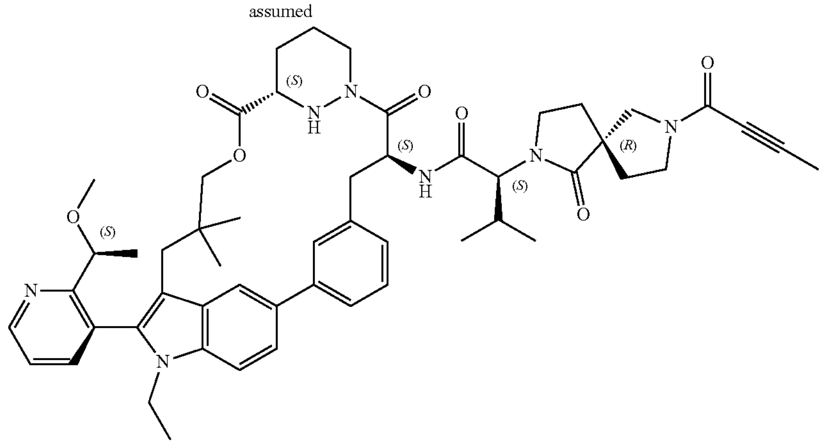 |

TABLE 2-continued
| Certain Compounds | |
|---|---|
| Ex # | Structure |
| B427 | 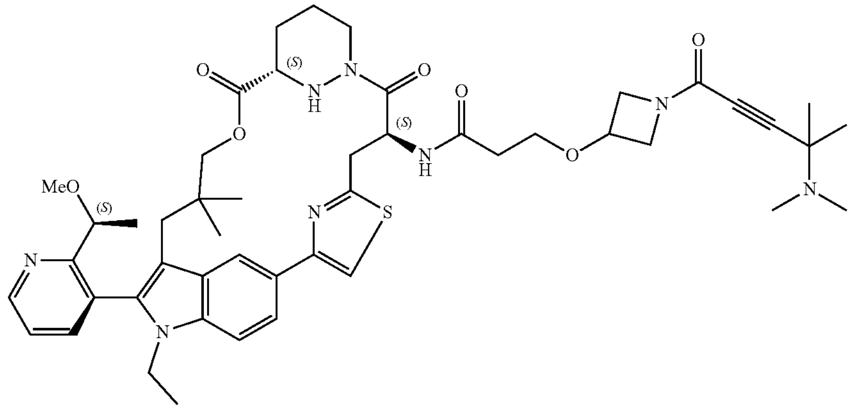 |
| B428 | 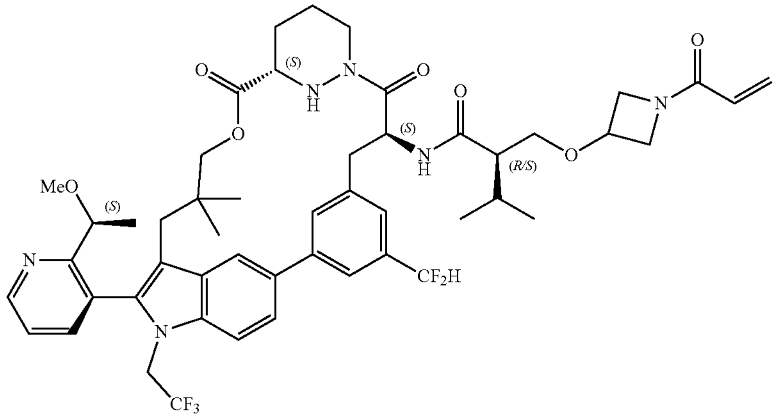 |
| B429 | 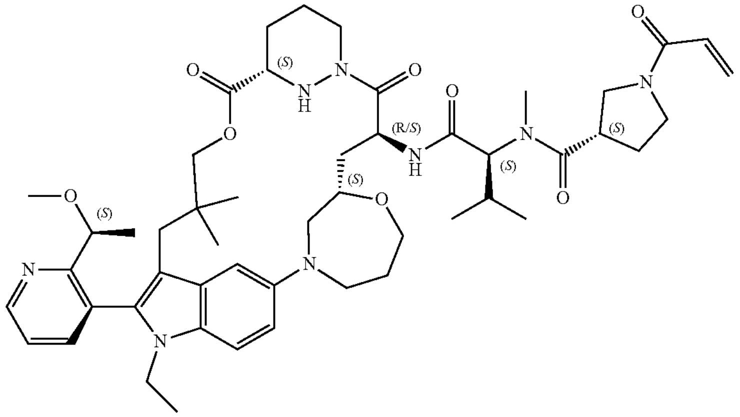 |

TABLE 2-continued
| Certain Compounds | |
|---|---|
| Ex # | Structure |
| B430 | 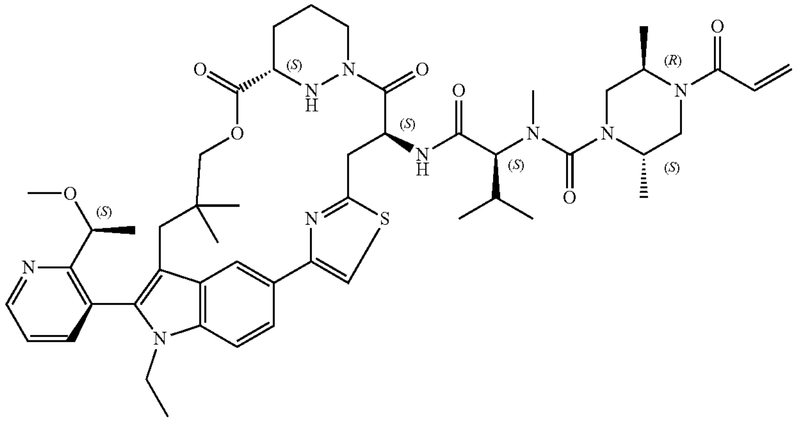 |
| B431 | 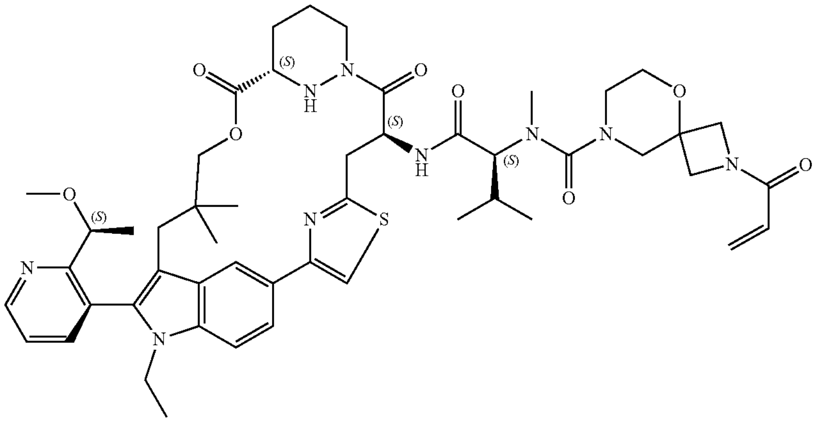 |
| B432 | 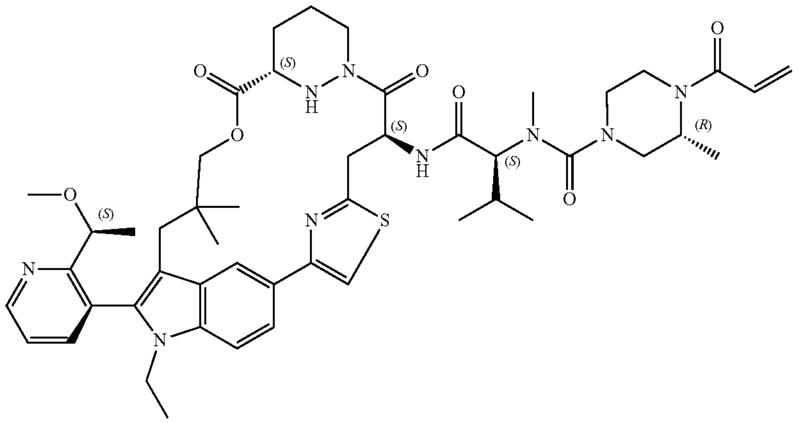 |

TABLE 2-continued
| Certain Compounds | |
|---|---|
| Ex # | Structure |
| B433 | 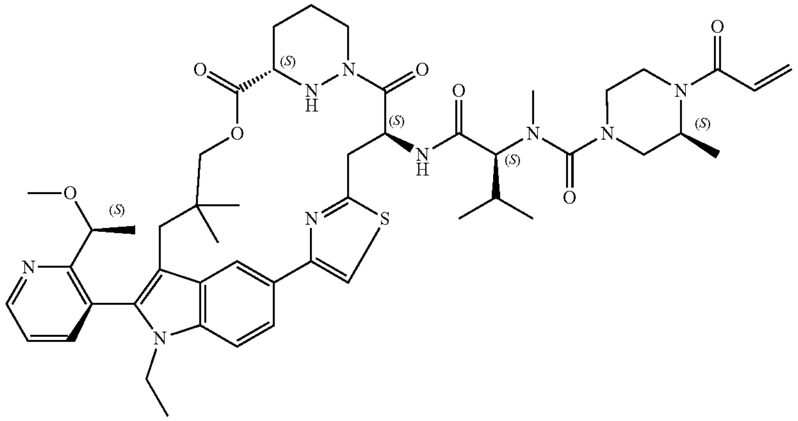 |
| B434 | 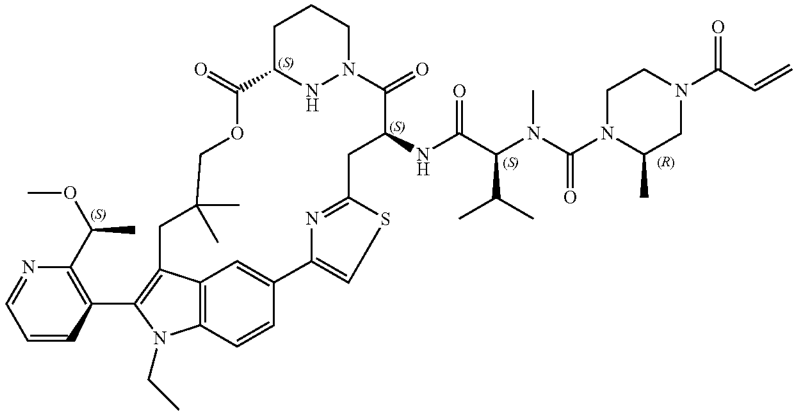 |
| B435 | 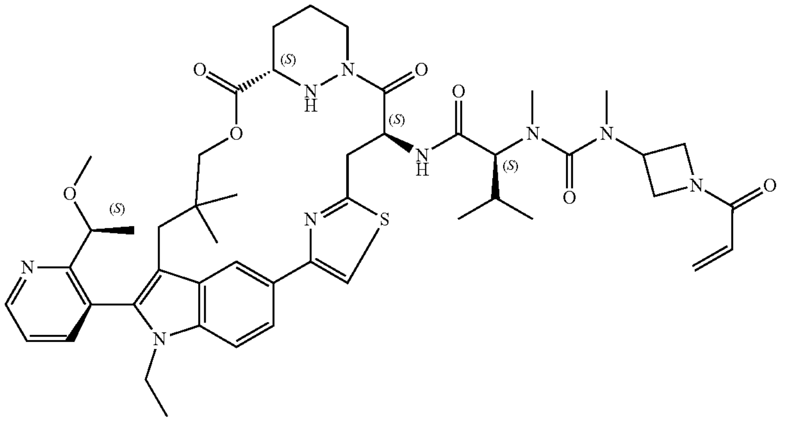 |

TABLE 2-continued
| Certain Compounds | |
|---|---|
| Ex # | Structure |
| B436 | 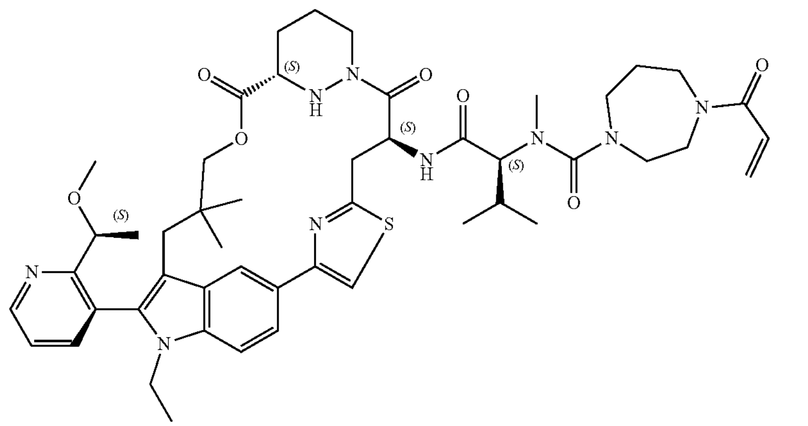 |
| B437 | 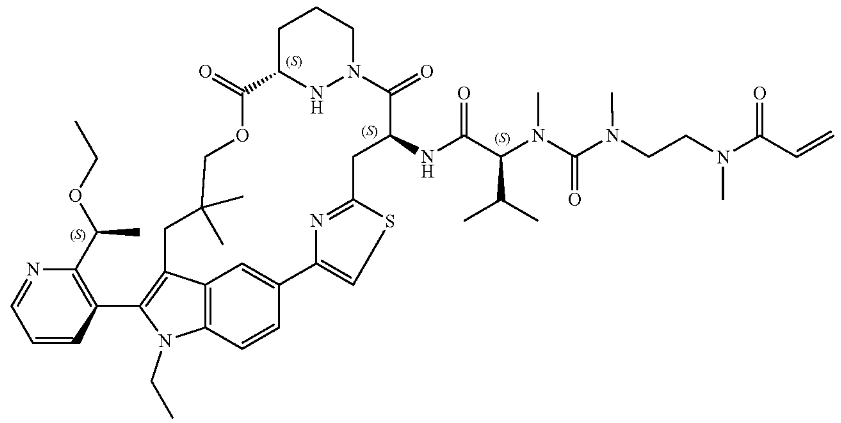 |
| B438 | 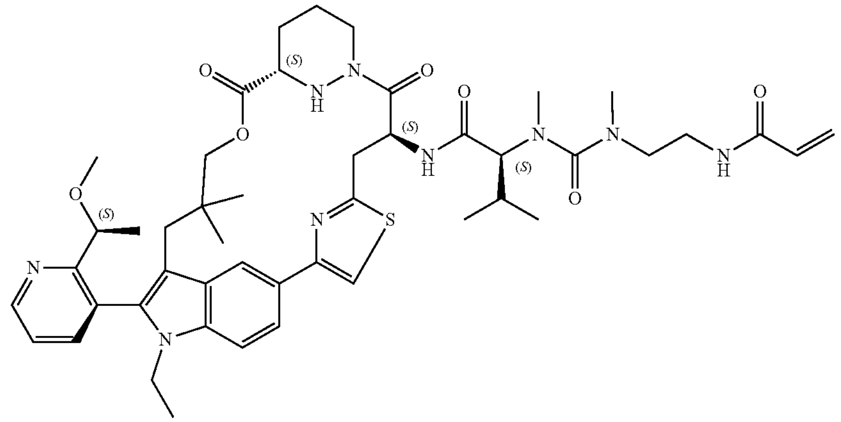 |

TABLE 2-continued
| Certain Compounds | |
|---|---|
| Ex # | Structure |
| B439 | 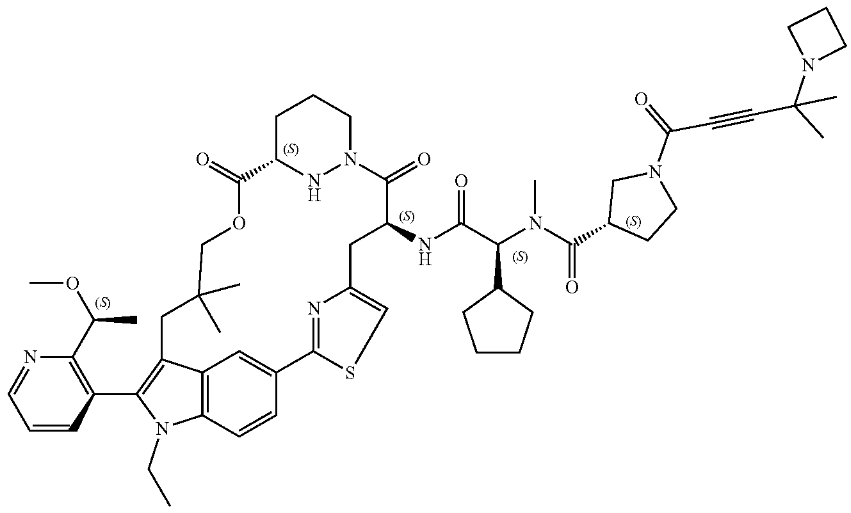 |
| B440 | 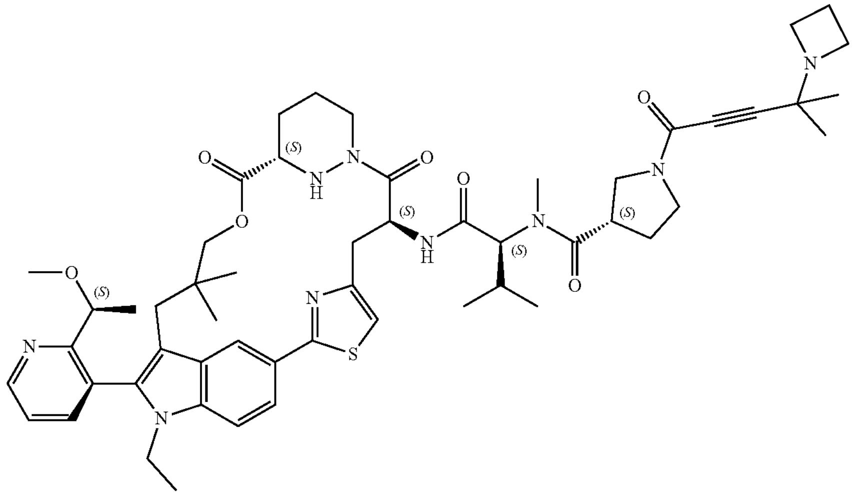 |
| B441 | 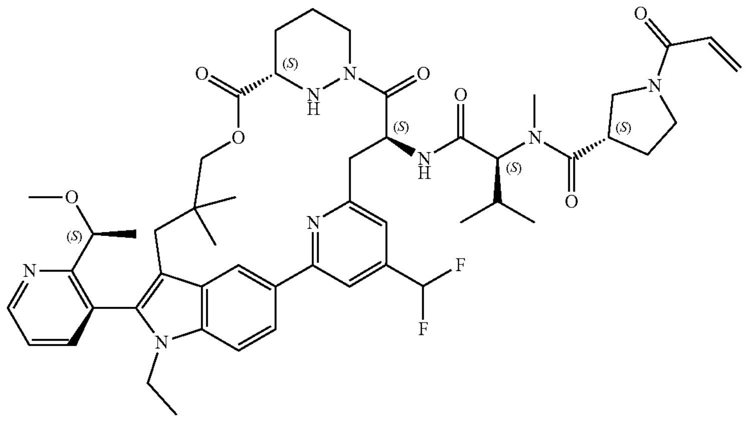 |

TABLE 2-continued
| Certain Compounds | |
|---|---|
| Ex # | Structure |
| B442 | 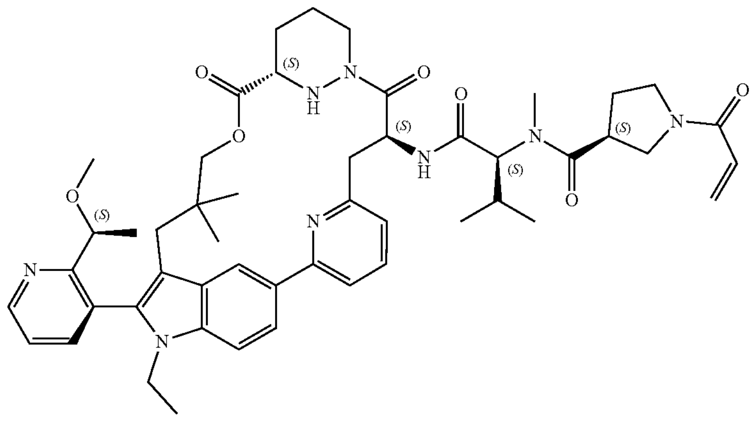 |
| B443 | 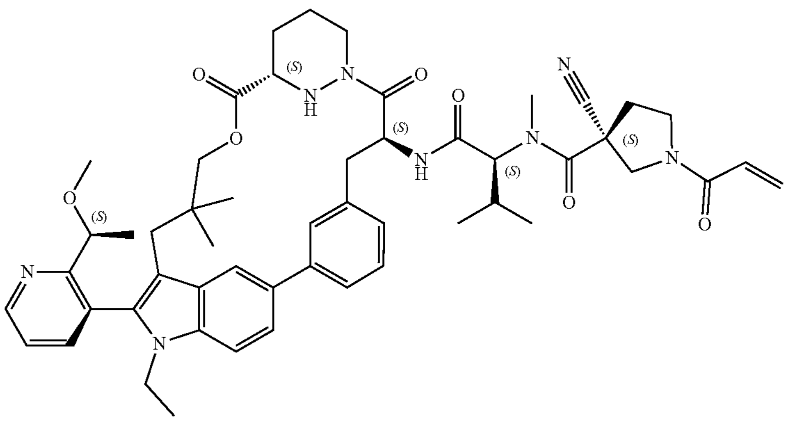 |
| B444 | 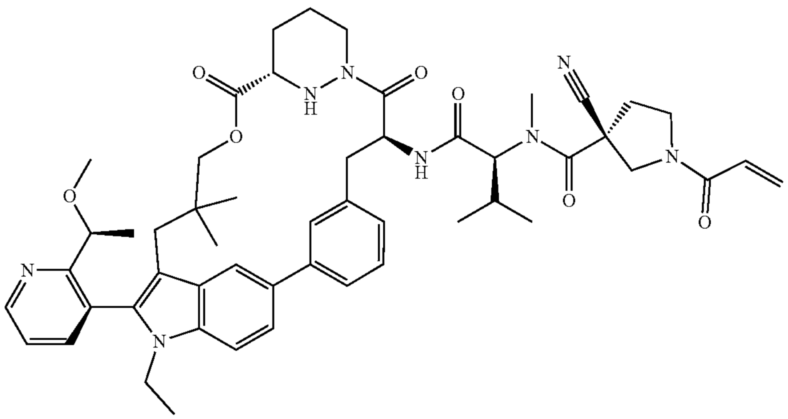 |

TABLE 2-continued
| Certain Compounds | |
|---|---|
| Ex # | Structure |
| B445 | 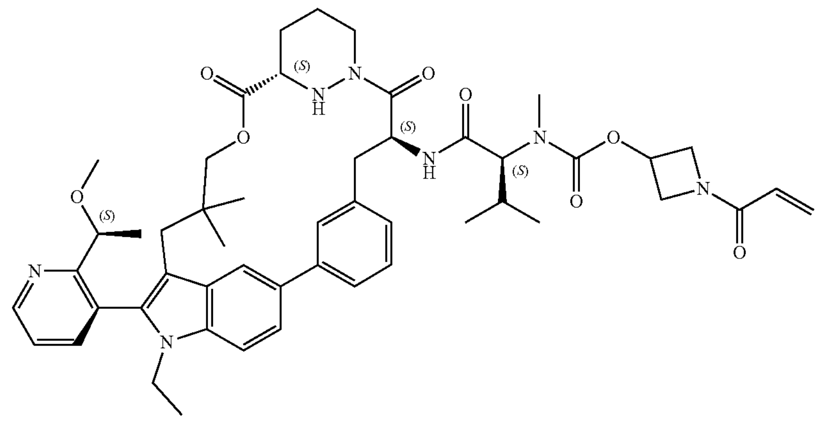 |
| B446 | 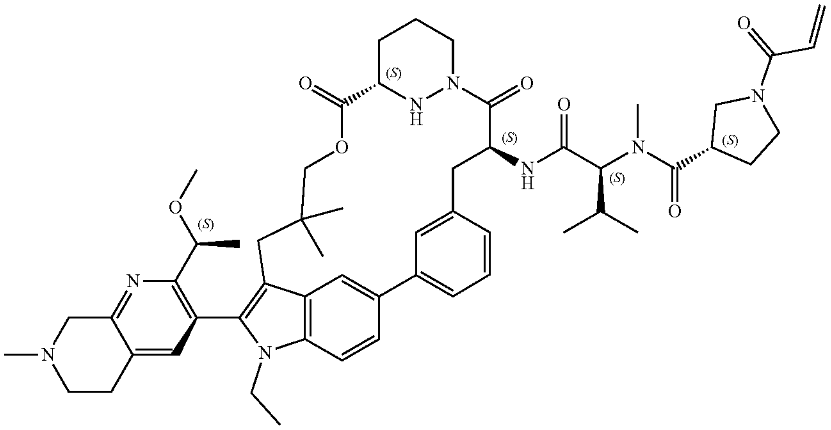 |
| B447 | 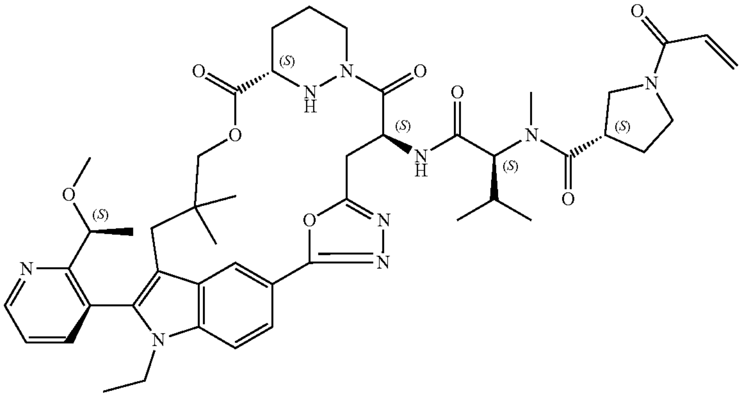 |

TABLE 2-continued
| Certain Compounds | |
|---|---|
| Ex # | Structure |
| B448 | 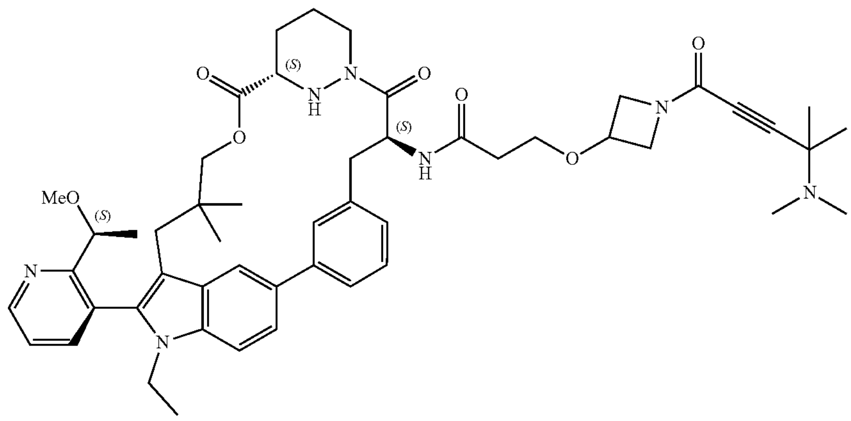 |
| B449 | 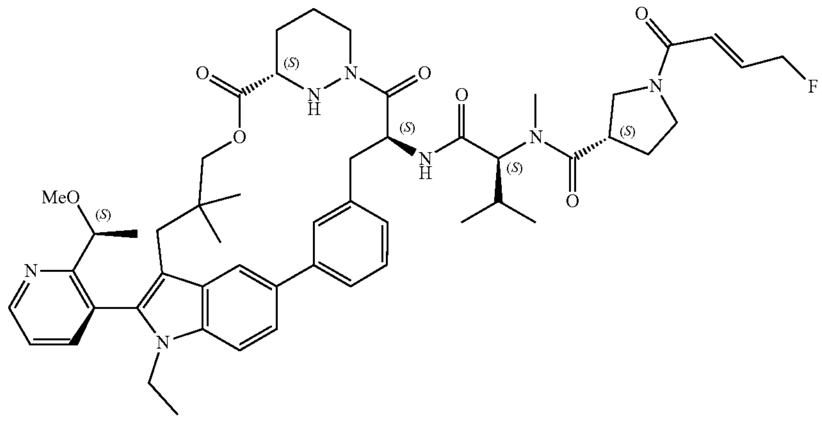 |
| B450 | 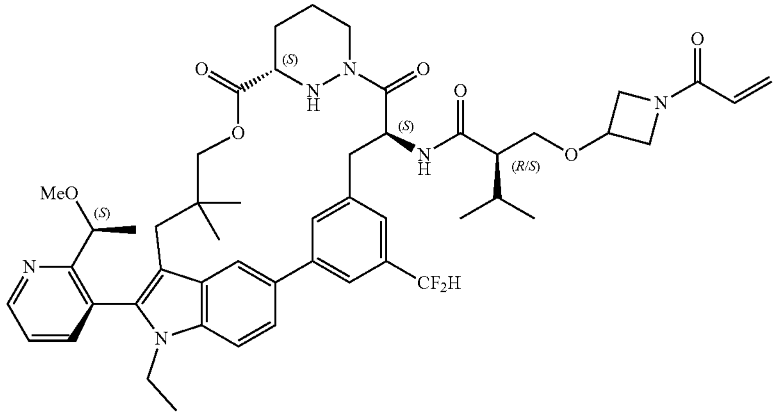 |

TABLE 2-continued
| Certain Compounds | |
|---|---|
| Ex # | Structure |
| B451 | 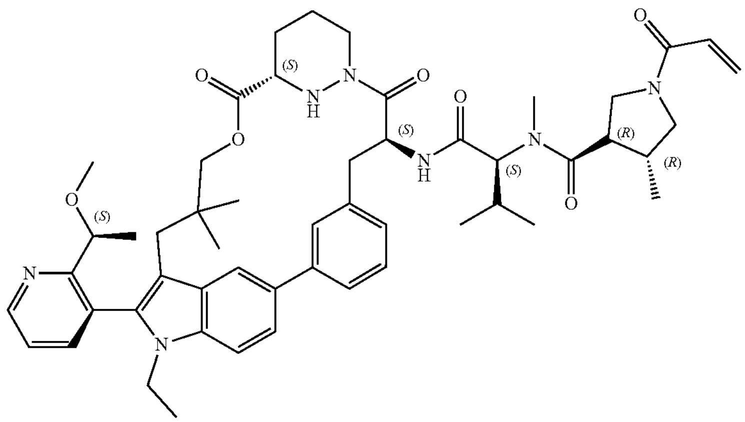 |
| B452 | 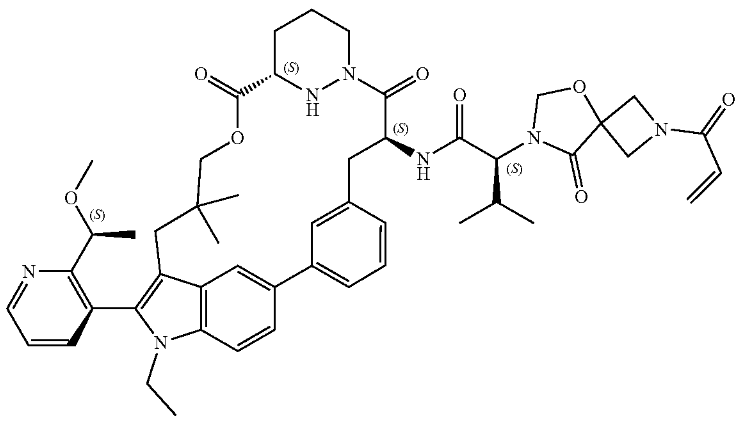 |
| B453 | 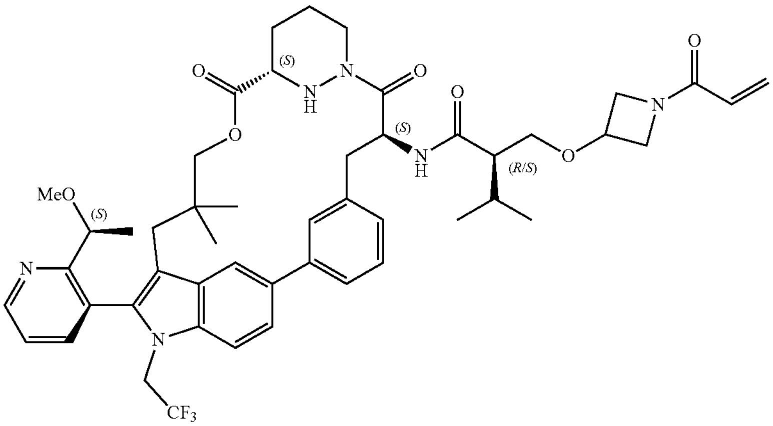 |

TABLE 2-continued
| Certain Compounds | |
|---|---|
| Ex # | Structure |
| B454 | 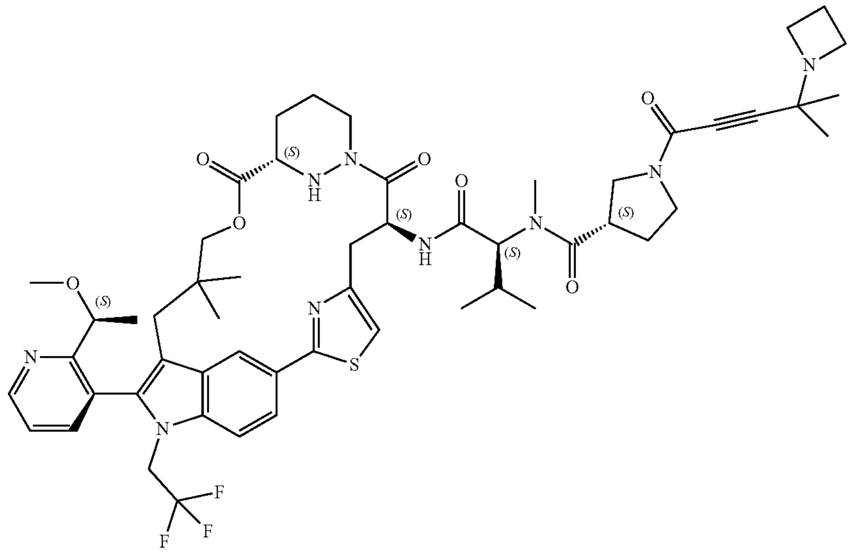 |
| B455 | 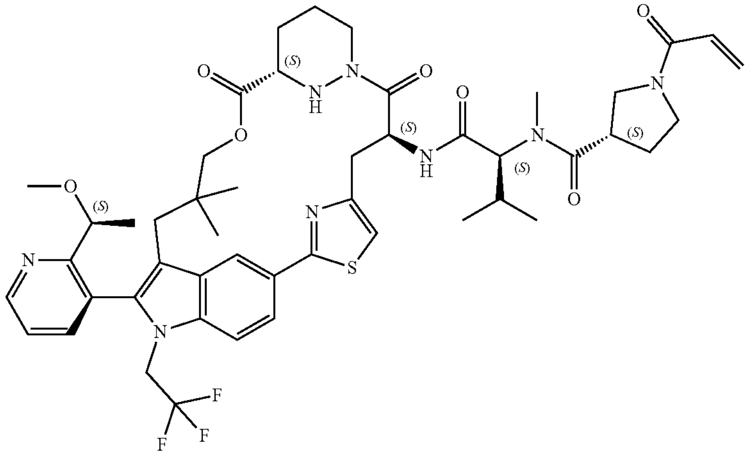 |
| B456 | 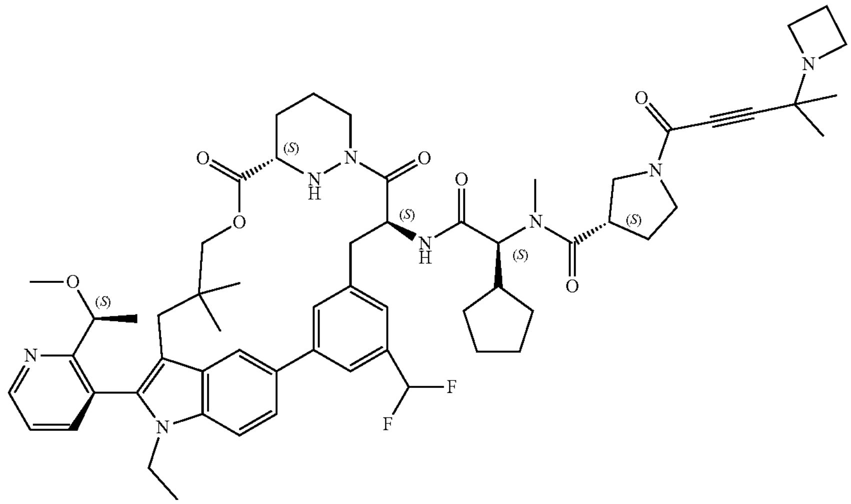 |

TABLE 2-continued
| Certain Compounds | |
|---|---|
| Ex # | Structure |
| B457 | 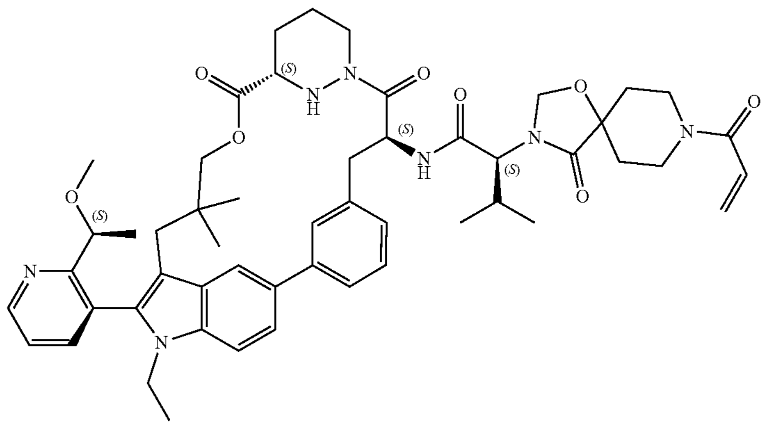 |
| B458 | 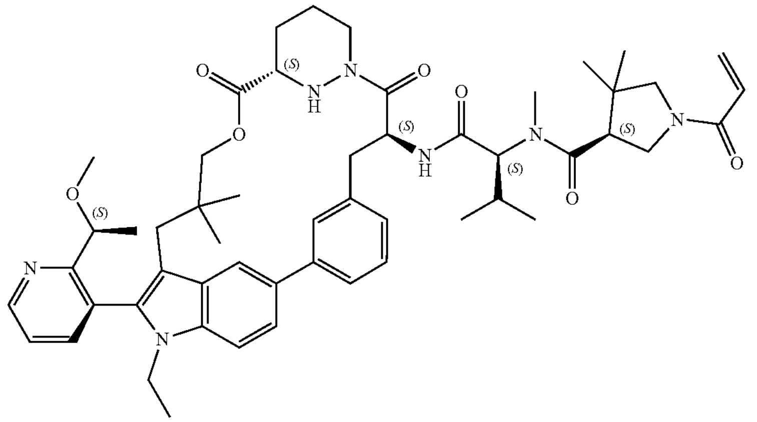 |
| B459 | 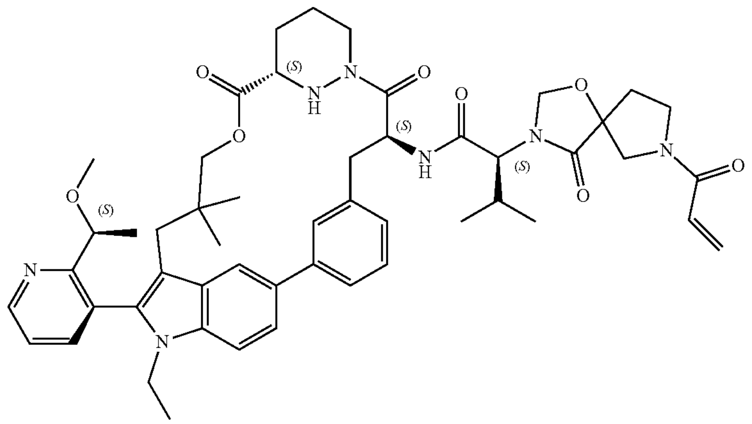 |

TABLE 2-continued
| Certain Compounds | |
|---|---|
| Ex # | Structure |
| B460 | 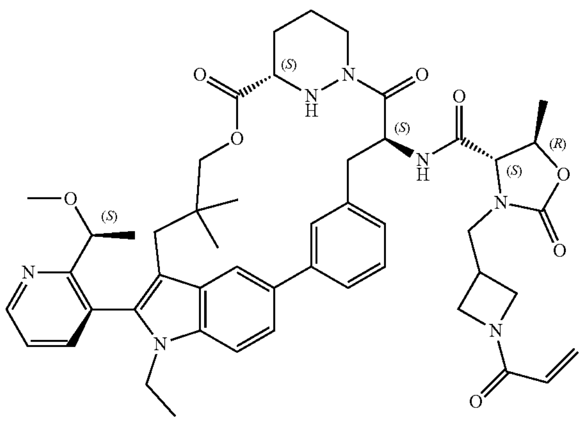 |
| B461 | 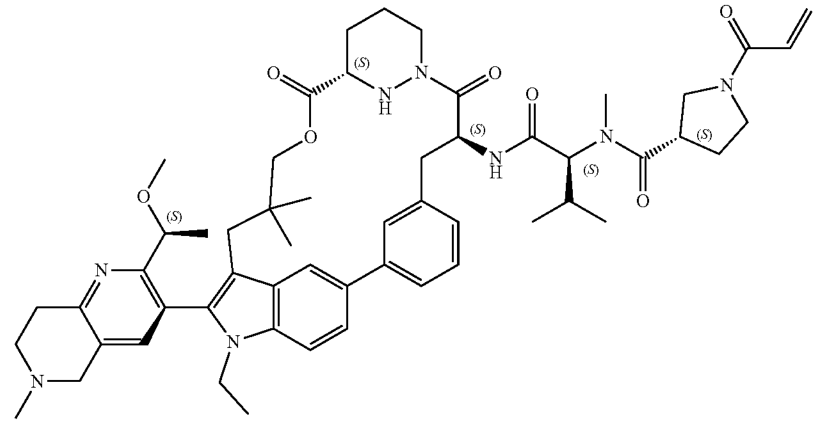 |
| B462 | 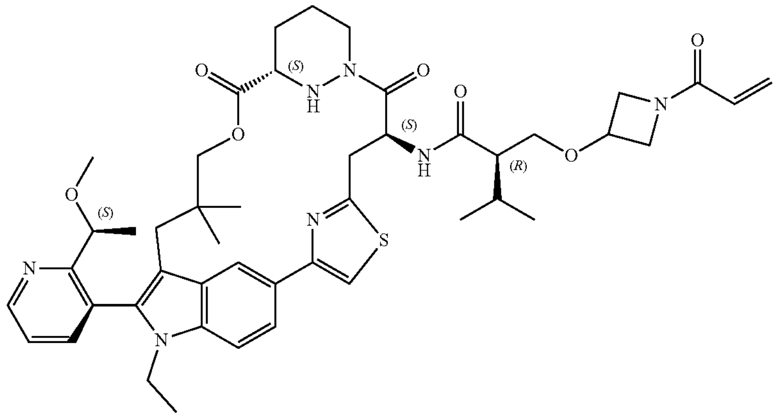 |

TABLE 2-continued
| Certain Compounds | |
|---|---|
| Ex # | Structure |
| B463 | 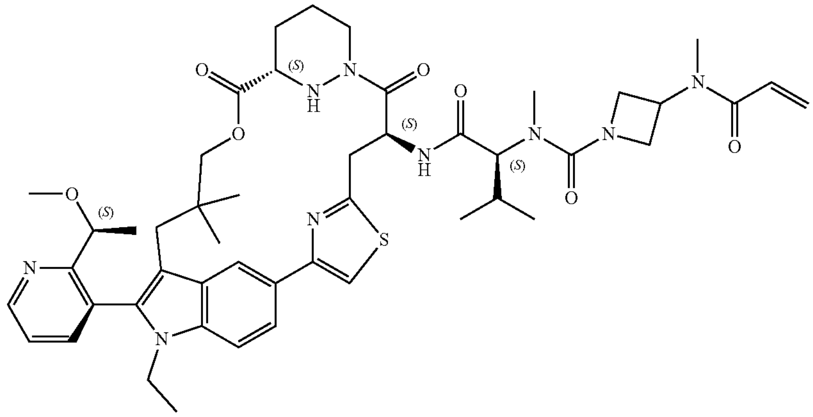 |
| B464 | 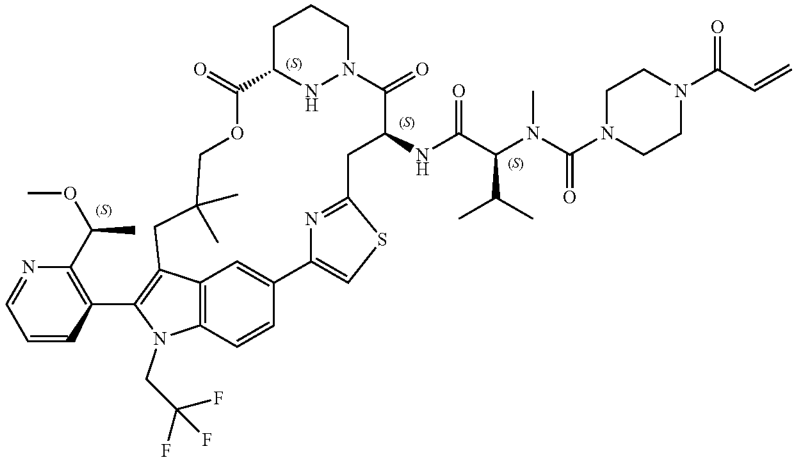 |
| B465 | 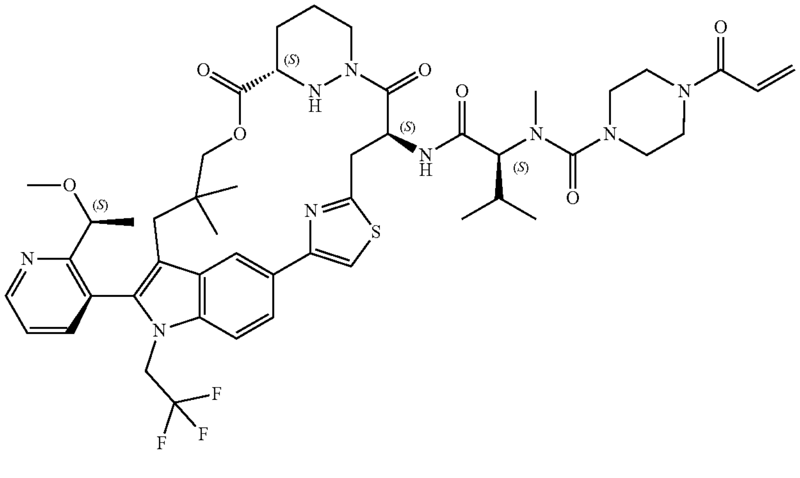 |

TABLE 2-continued
| Certain Compounds | |
|---|---|
| Ex # | Structure |
| B466 | 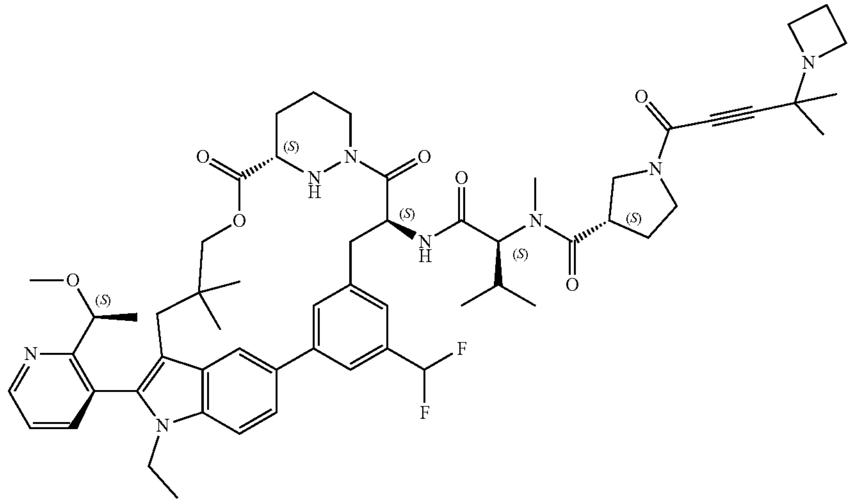 |
| B467 | 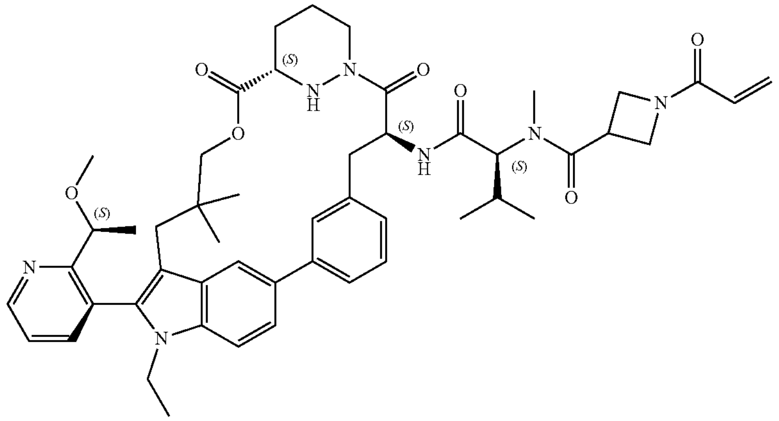 |
| B468 | 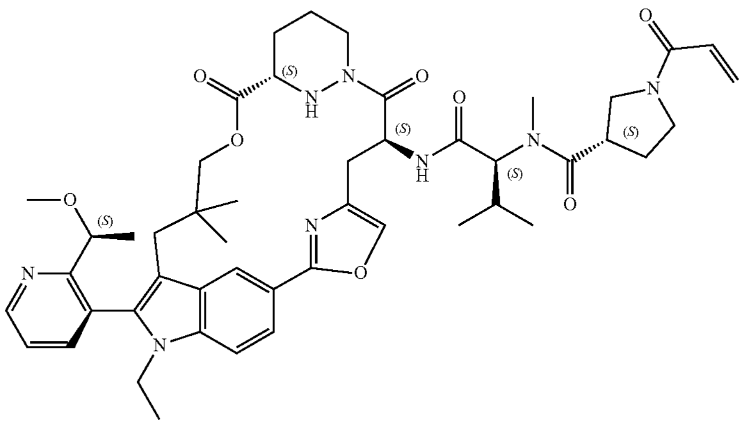 |

TABLE 2-continued
| Certain Compounds | |
|---|---|
| Ex # | Structure |
| B469 | 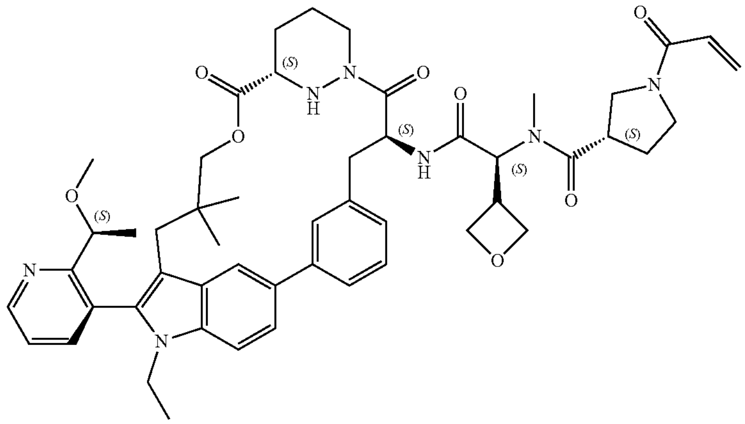 |
| B470 | assumed 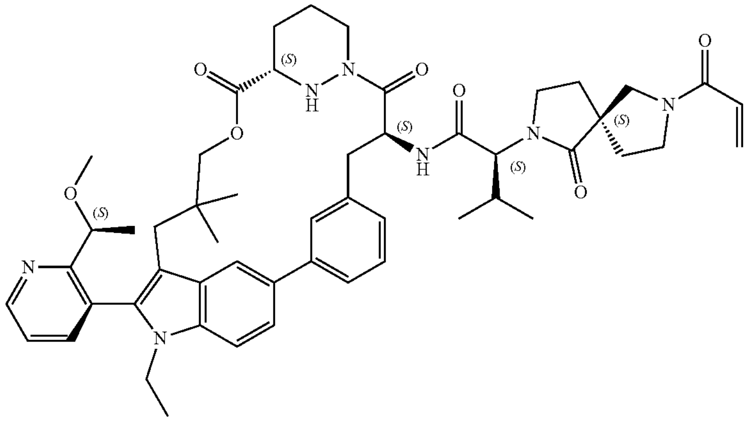 |
| B471 | assumed 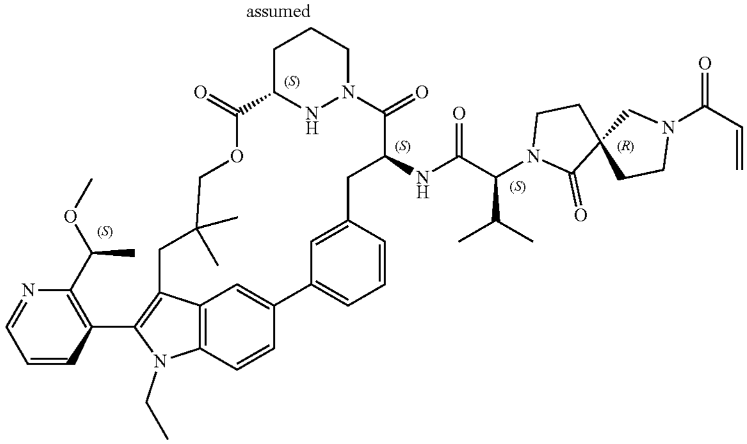 |

TABLE 2-continued
| Certain Compounds | |
|---|---|
| Ex # | Structure |
| B472 | 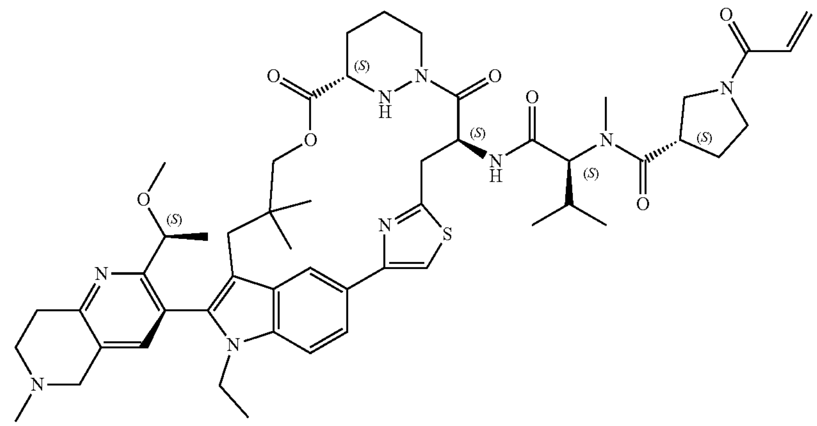 |
| B473 | 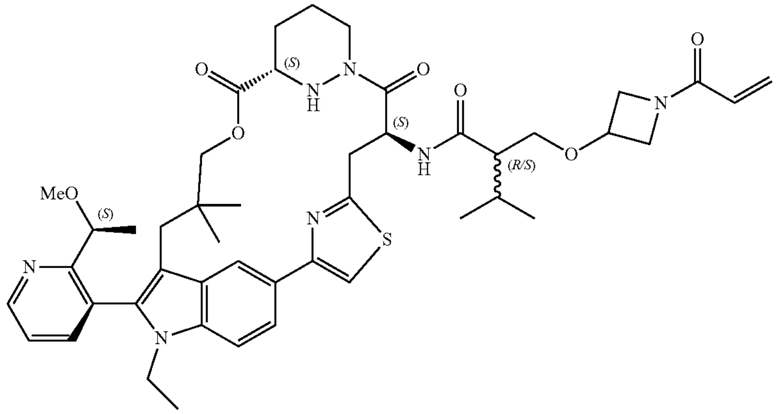 |
| B474 | 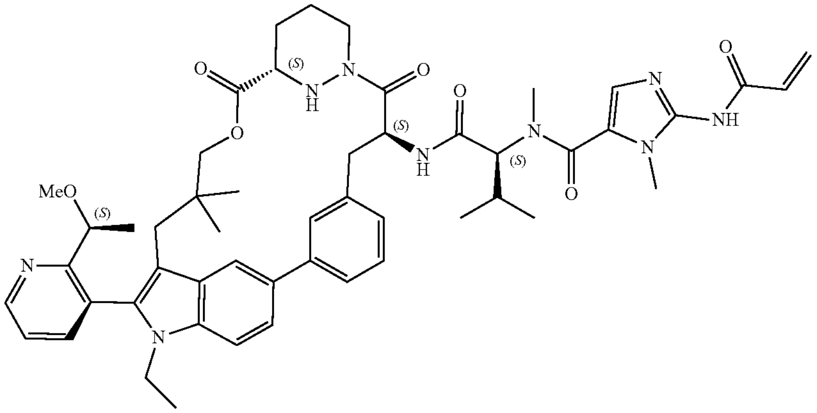 |

TABLE 2-continued
| Certain Compounds | |
|---|---|
| Ex # | Structure |
| B475 | 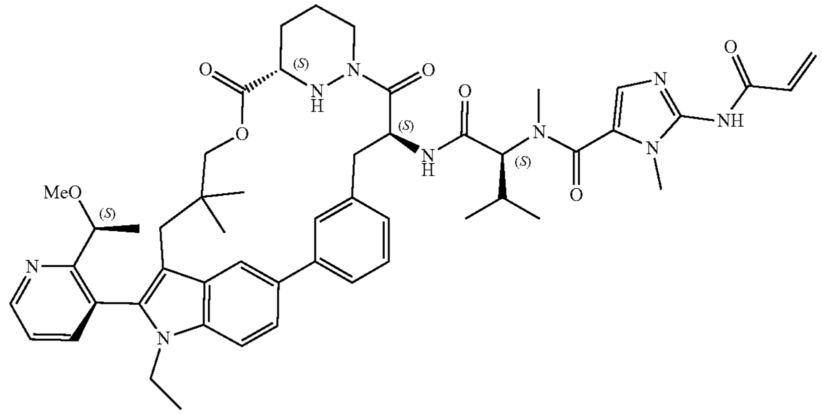 |
| B476 | 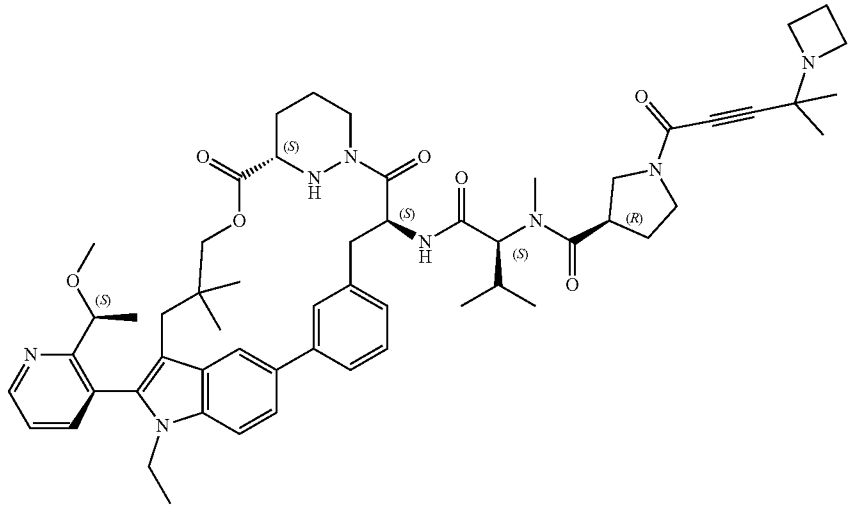 |
| B477 | 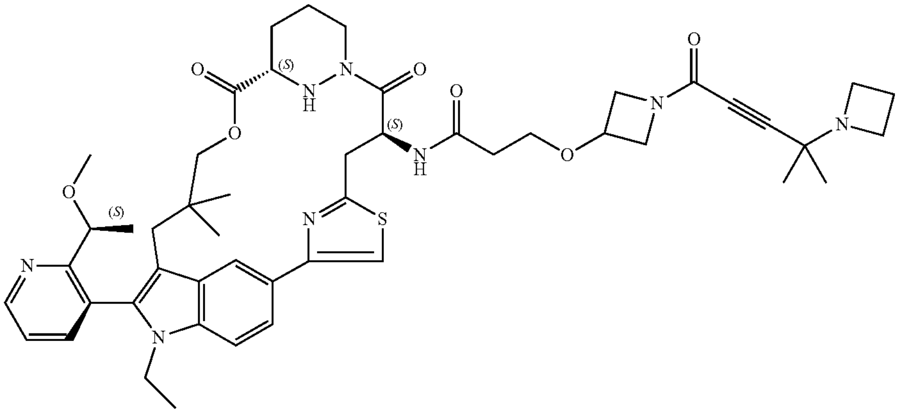 |

TABLE 2-continued
| Certain Compounds | |
|---|---|
| Ex # | Structure |
| B478 | 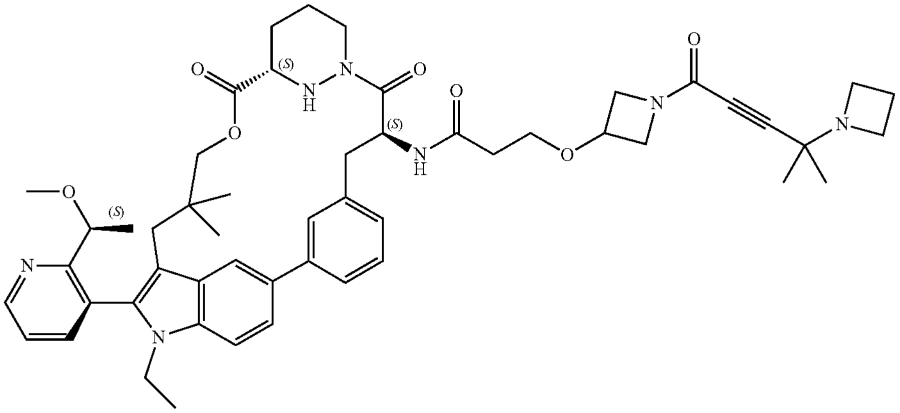 |
| B479 | 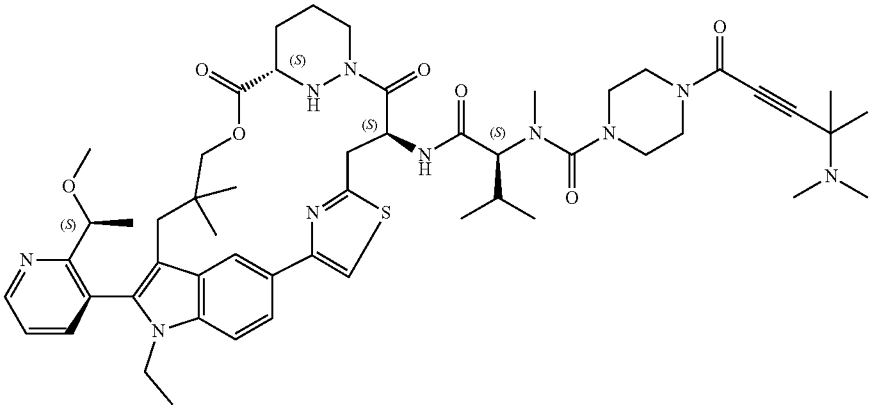 |
| B480 | 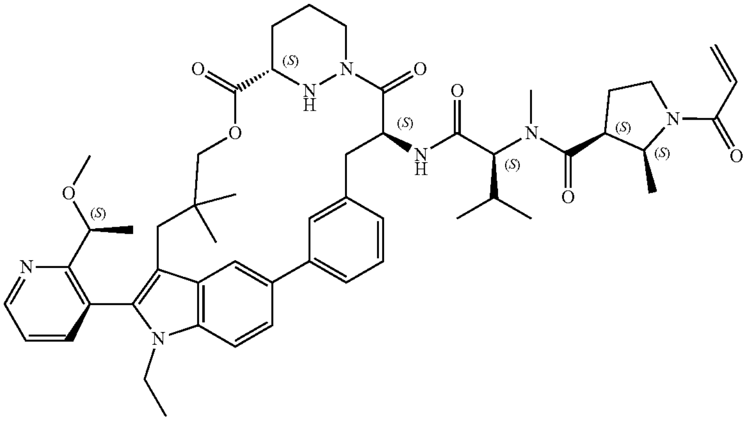 |

TABLE 2-continued
| Certain Compounds | |
|---|---|
| Ex # | Structure |
| B481 | 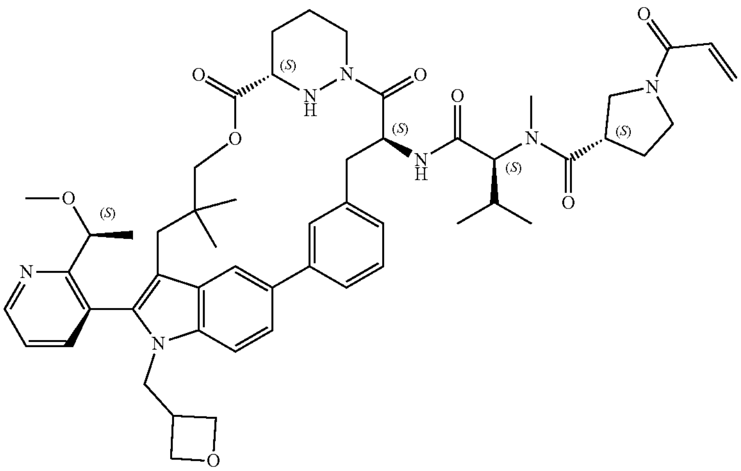 |
| B482 | 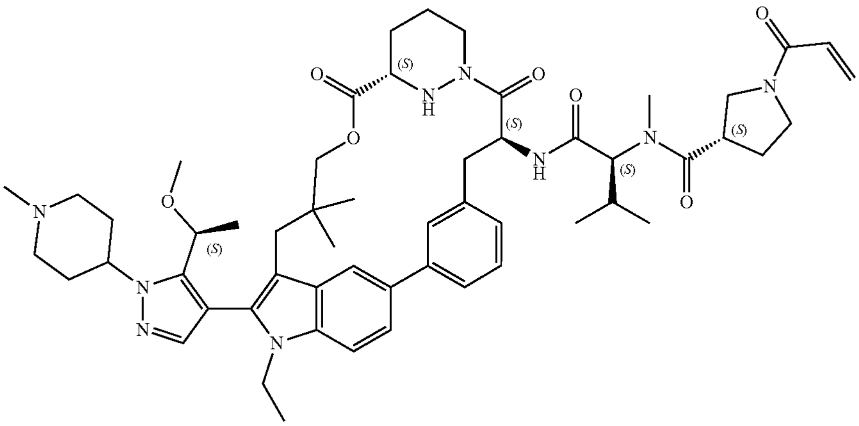 |
| B483 | 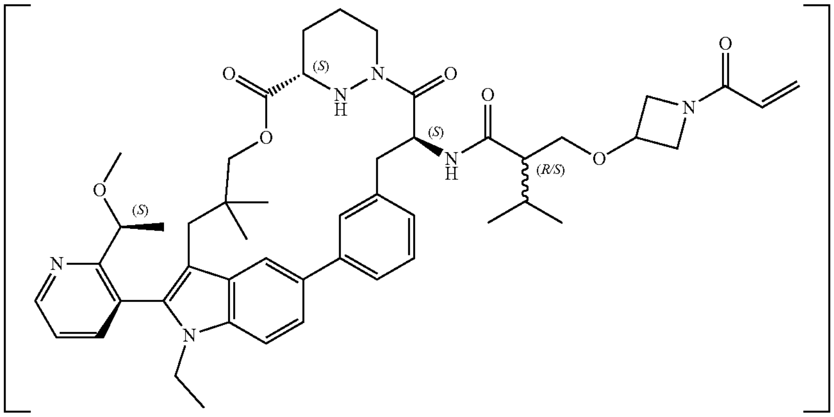 |

TABLE 2-continued
| Certain Compounds | |
|---|---|
| Ex # | Structure |
| B484 | 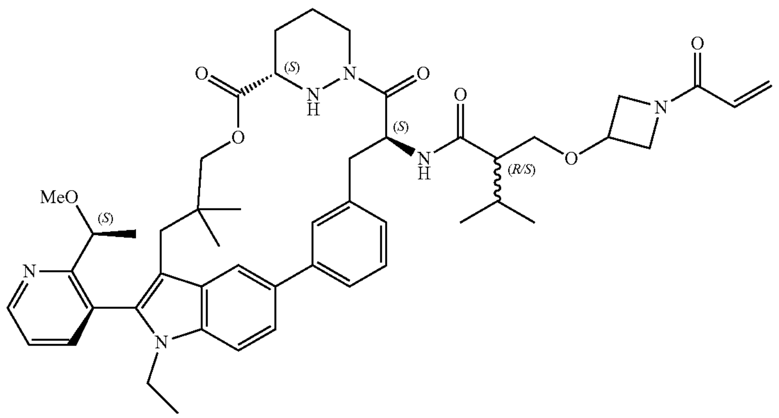 |
| B485 | 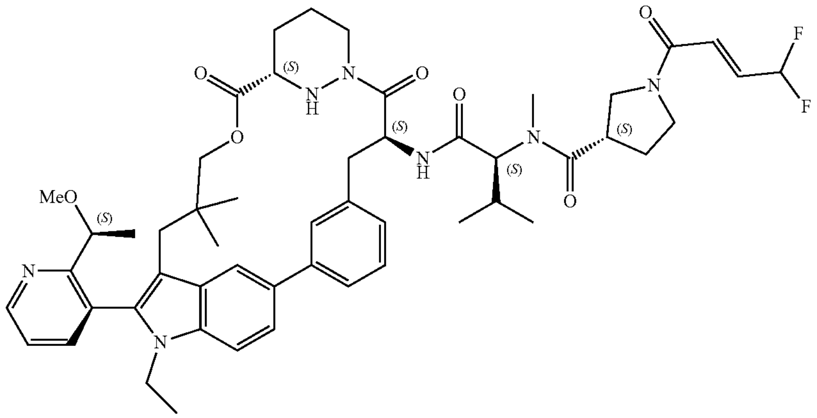 |
| B486 | 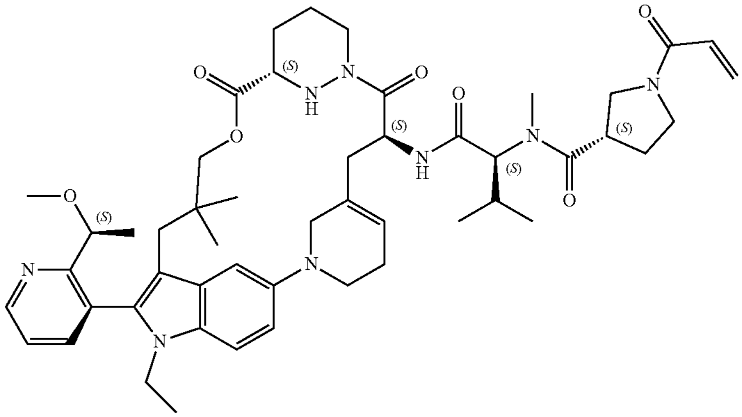 |

TABLE 2-continued
| Certain Compounds | |
|---|---|
| Ex # | Structure |
| B487 | 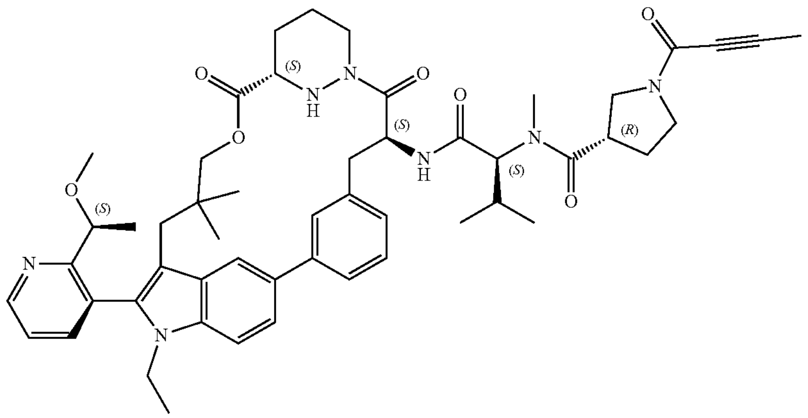 |
| B488 | 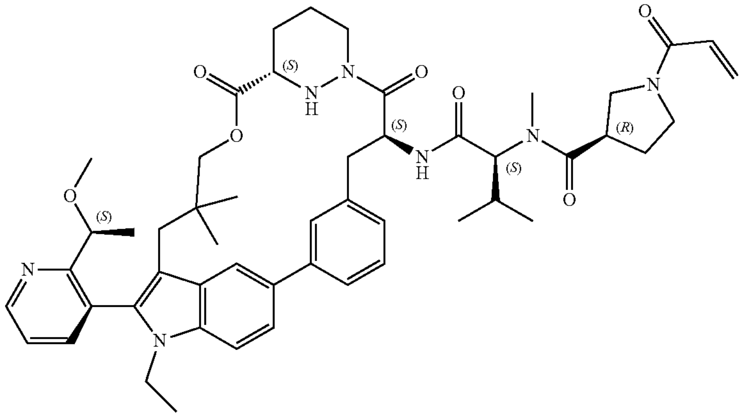 |
| B489 | 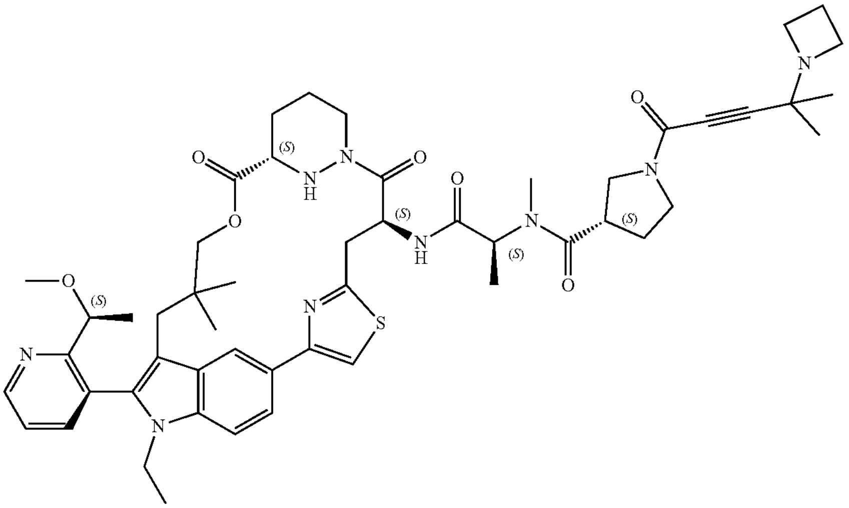 |

TABLE 2-continued
| Certain Compounds | |
|---|---|
| Ex # | Structure |
| B490 | 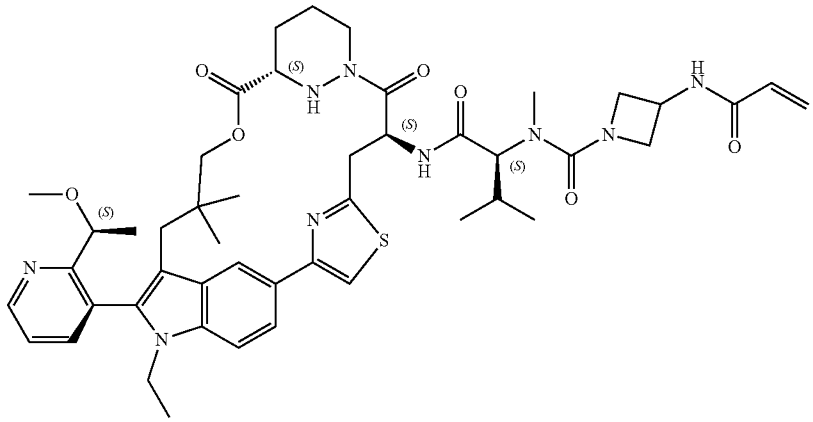 |
| B491 | 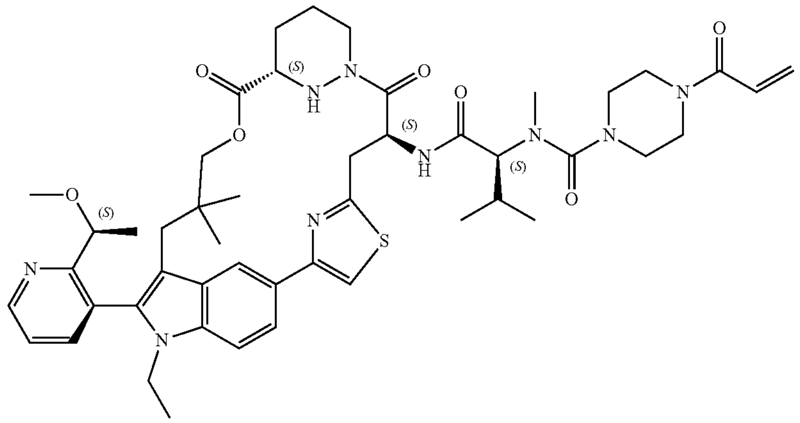 |
| B492 | 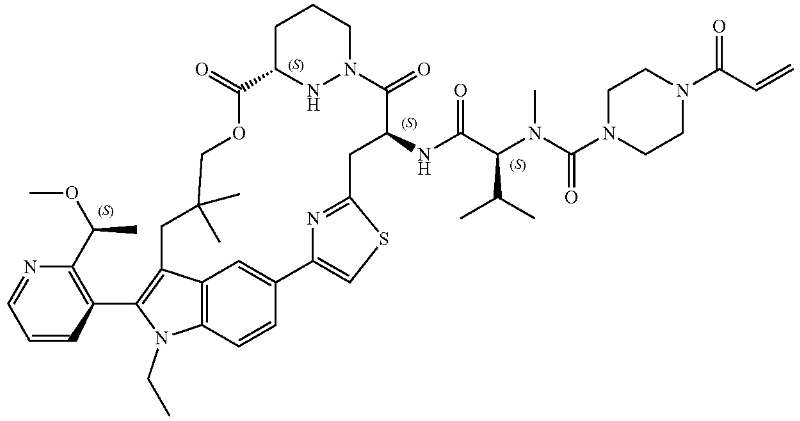 |

TABLE 2-continued
| Certain Compounds | |
|---|---|
| Ex # | Structure |
| B493 | 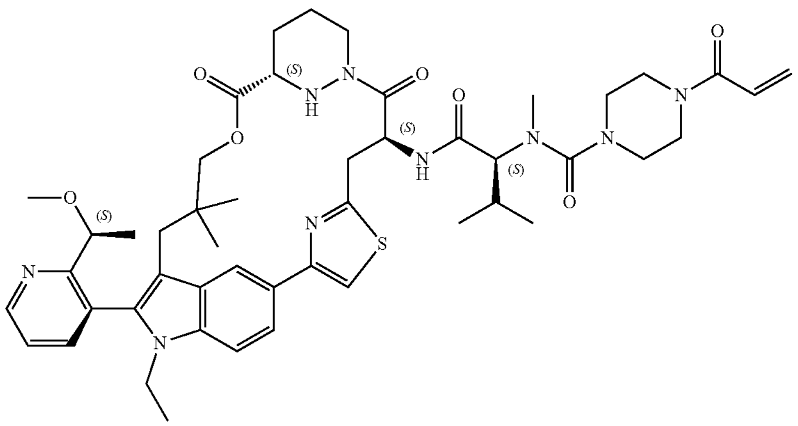 |
| B494 | 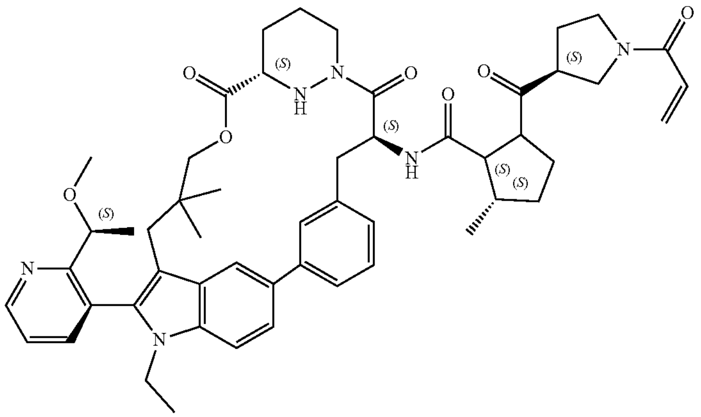 |
| B495 | 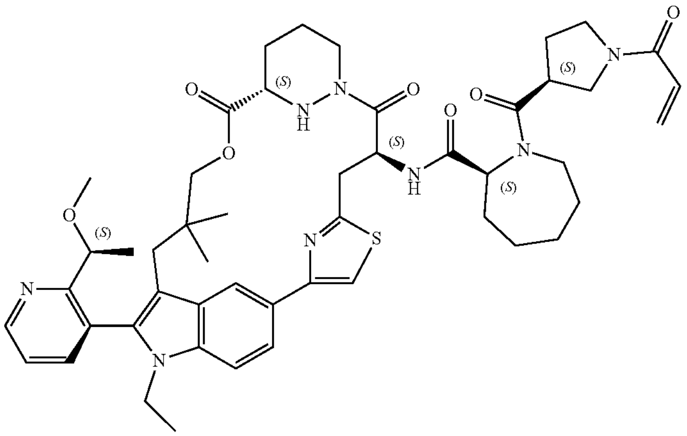 |

TABLE 2-continued
| Certain Compounds | |
|---|---|
| Ex # | Structure |
| B496 | 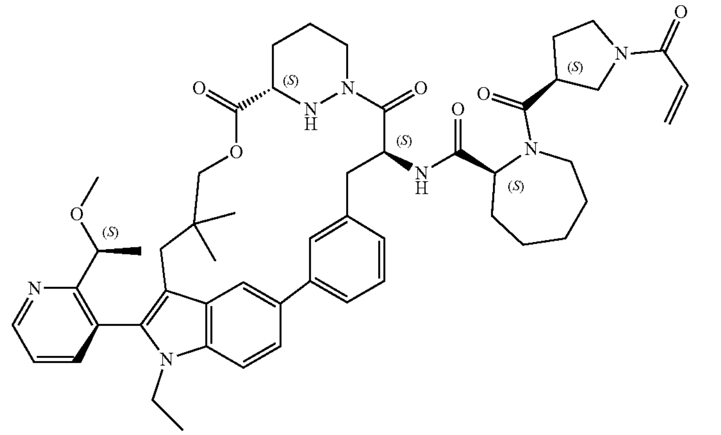 |
| B497 | 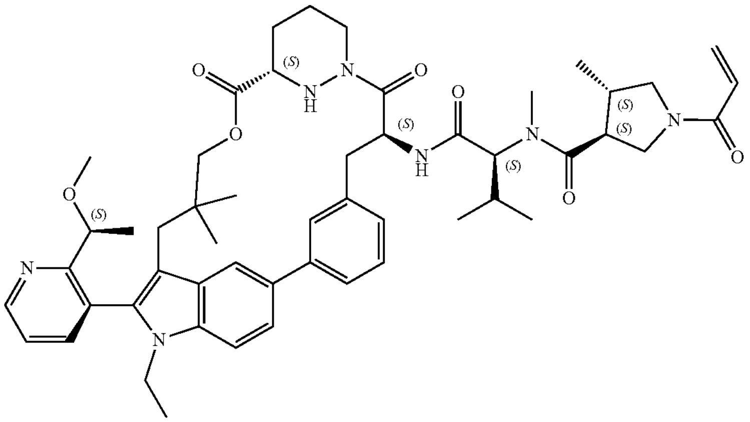 |
| B498 | 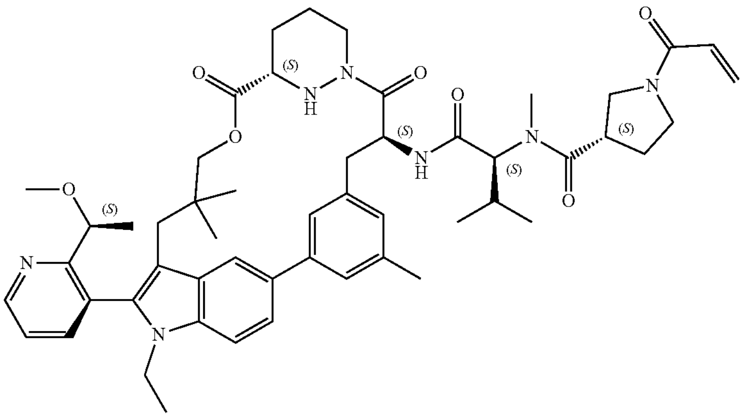 |

TABLE 2-continued
| Certain Compounds | |
|---|---|
| Ex # | Structure |
| B499 | 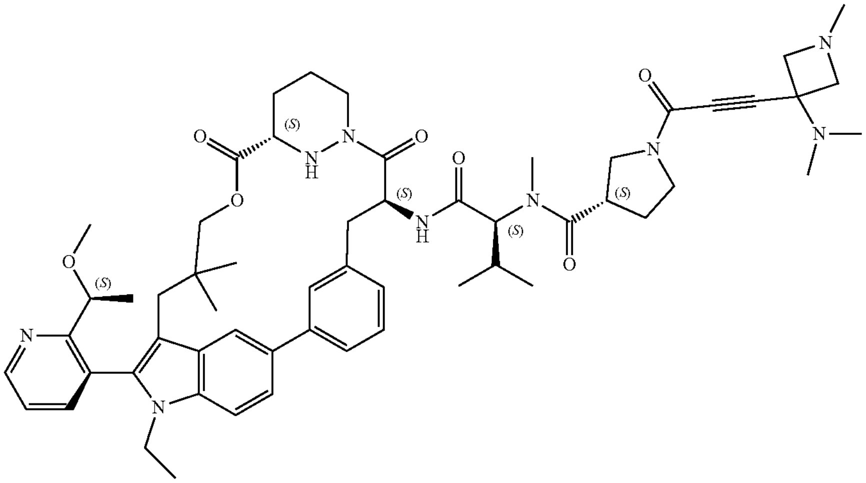 |
| B500 | 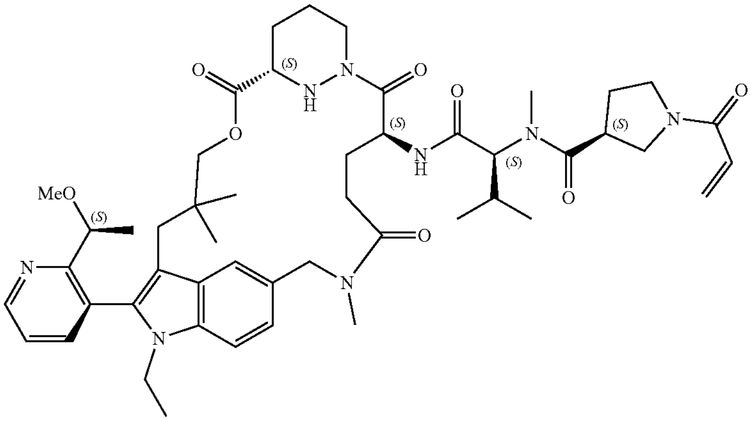 |
| B501 | 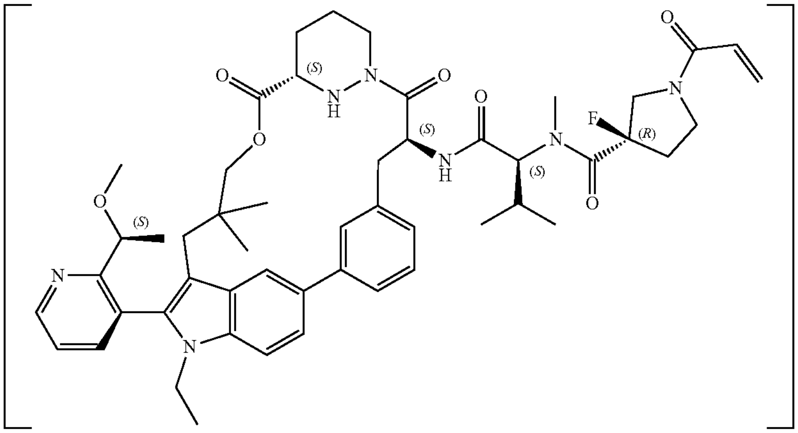 |

TABLE 2-continued
| Certain Compounds | |
|---|---|
| Ex # | Structure |
| B502 | 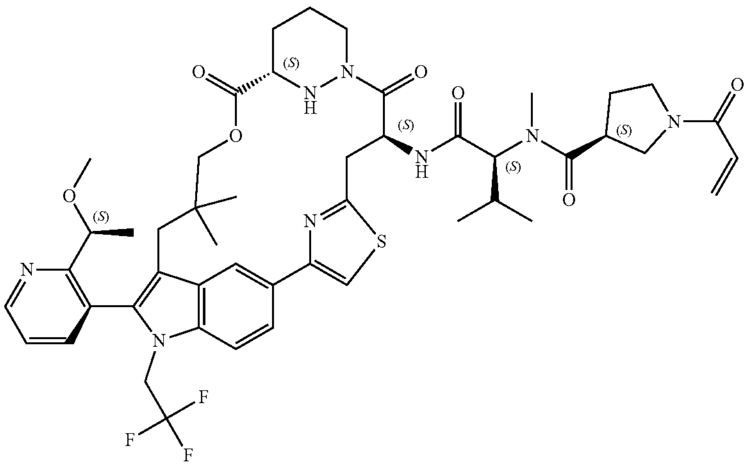 |
| B503 | 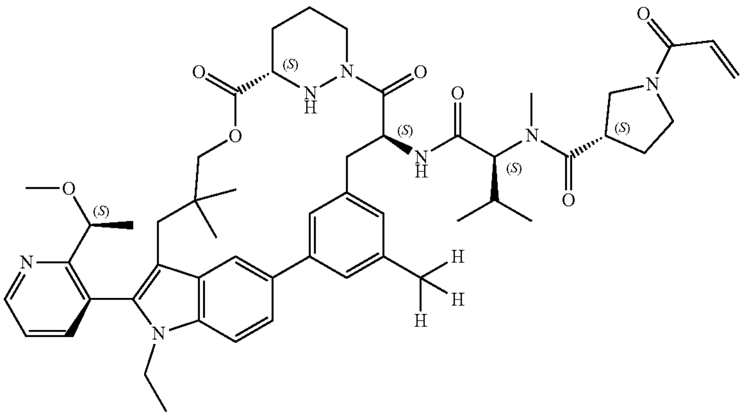 |
| B504 | 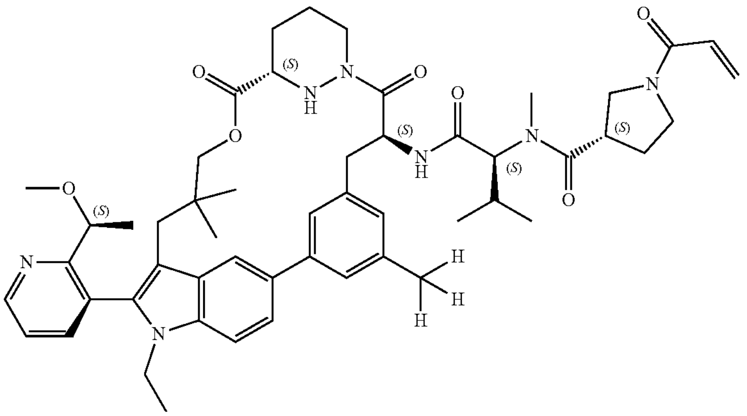 |

TABLE 2-continued
| Certain Compounds | |
|---|---|
| Ex # | Structure |
| B505 | 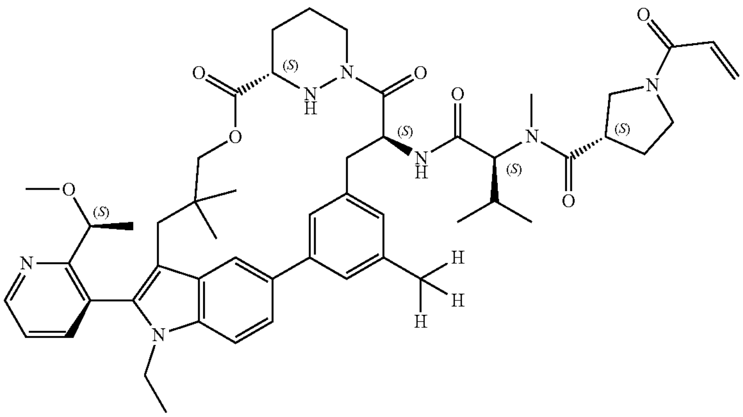 |
| B506 | 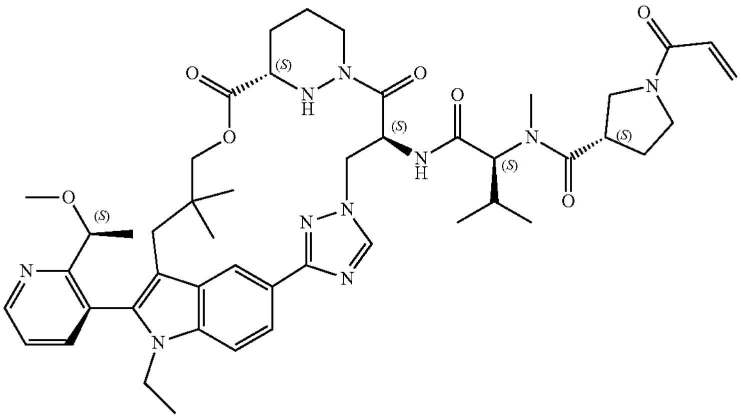 |
| B507 | 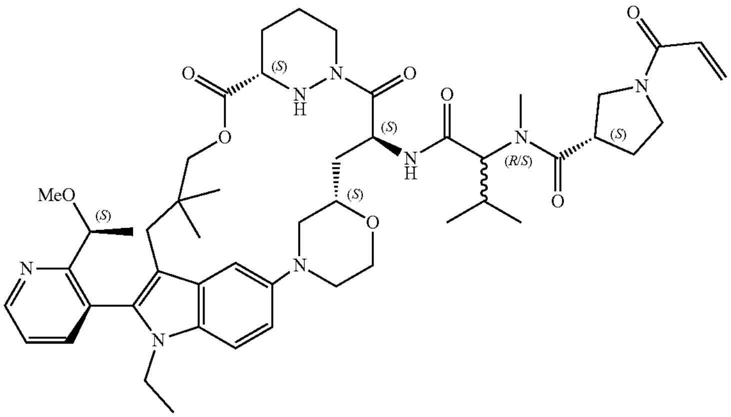 |

TABLE 2-continued
| Certain Compounds | |
|---|---|
| Ex # | Structure |
| B508 | 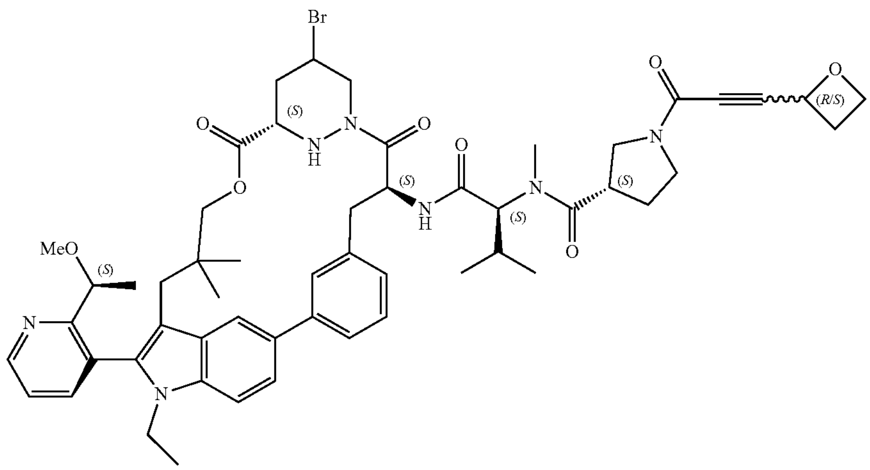 |
| B509 | 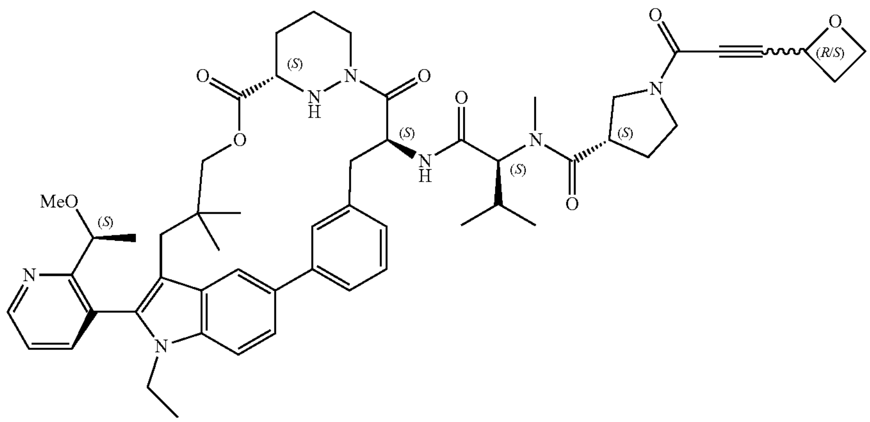 |
| B510 | 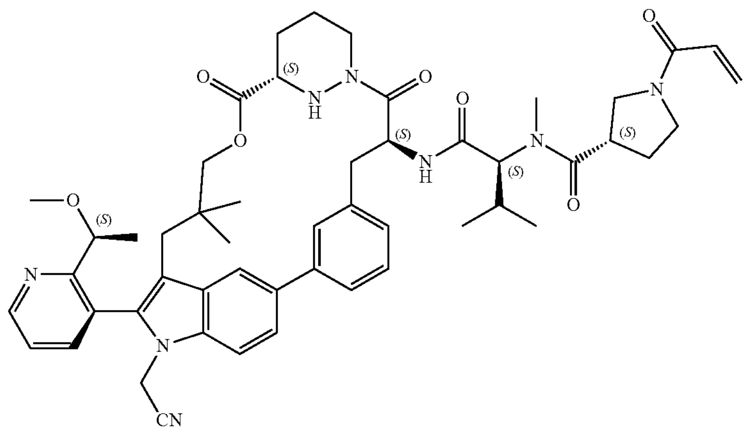 |

TABLE 2-continued
| Certain Compounds | |
|---|---|
| Ex # | Structure |
| B511 | 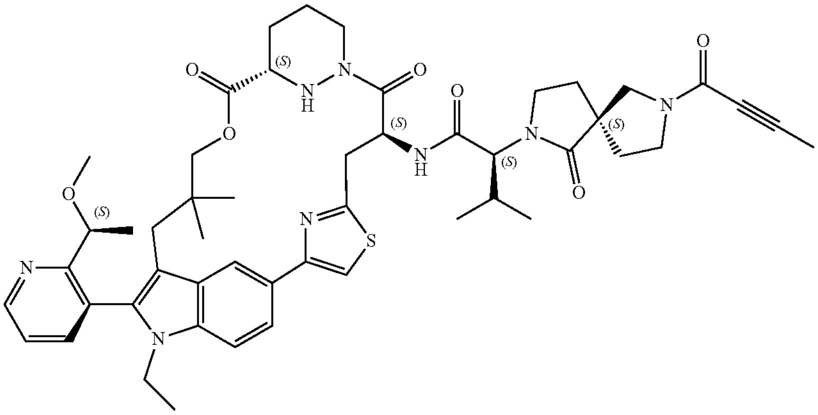 |
| B512 | 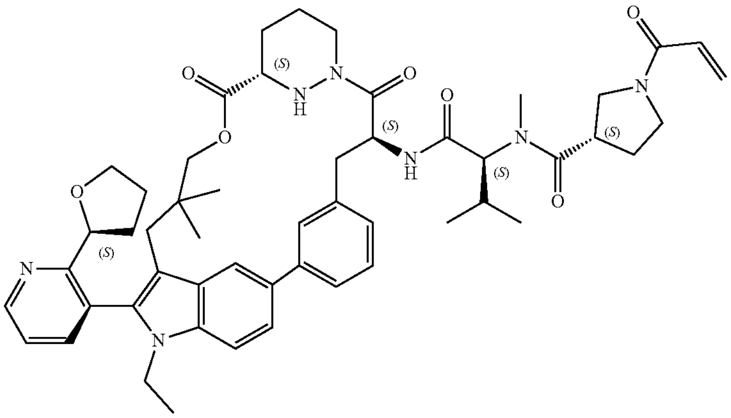 |
| B513 | 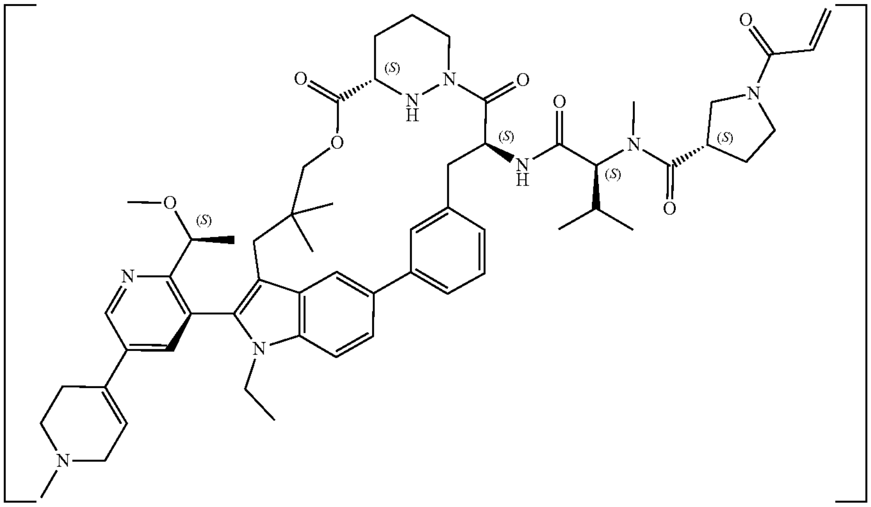 |

TABLE 2-continued
| Certain Compounds | |
|---|---|
| Ex # | Structure |
| B514 | 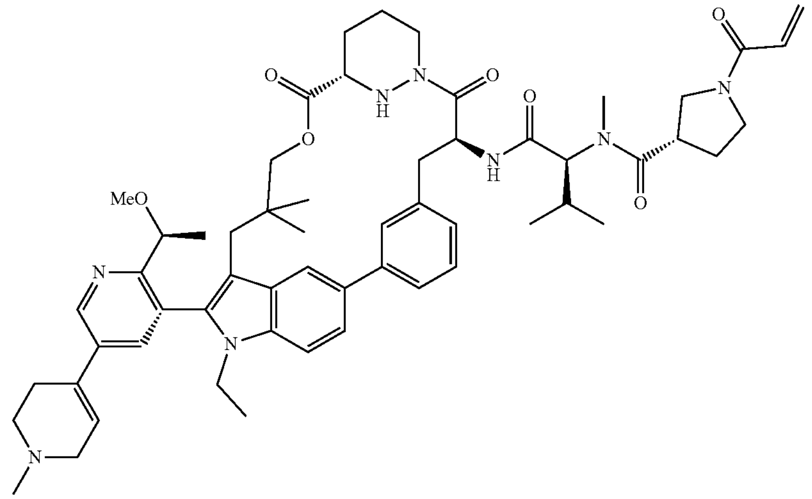 |
| B515 | 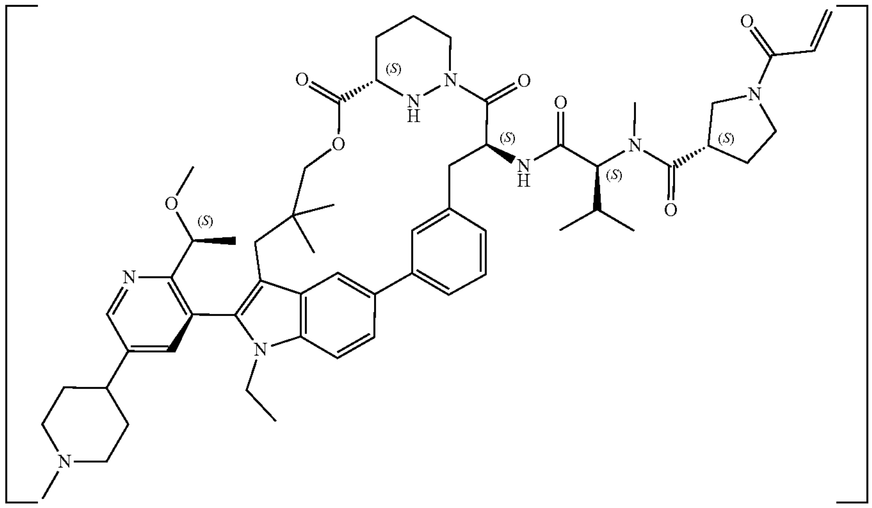 |
| B516 | 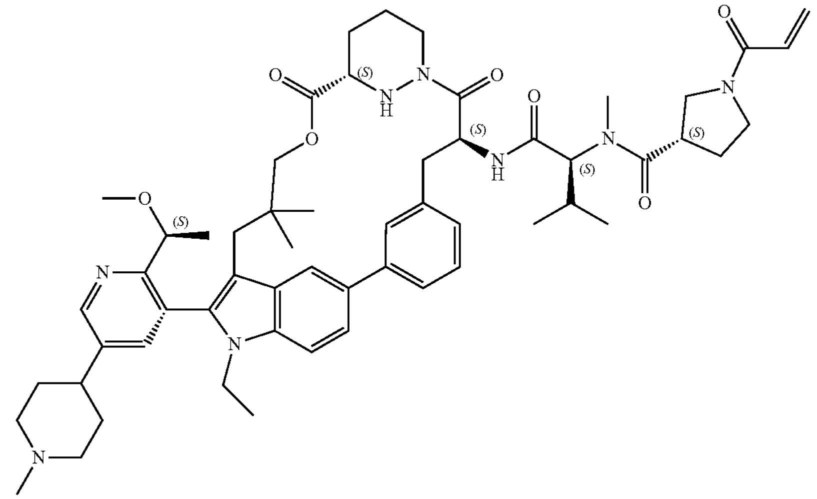 |

TABLE 2-continued
| Certain Compounds | |
|---|---|
| Ex # | Structure |
| B517 | 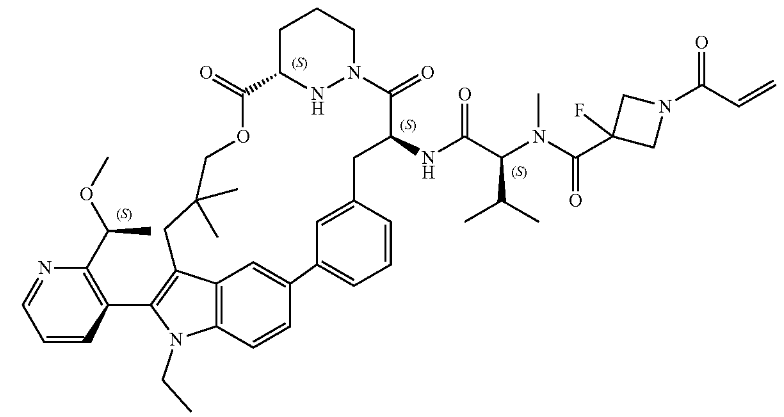 |
| B518 | 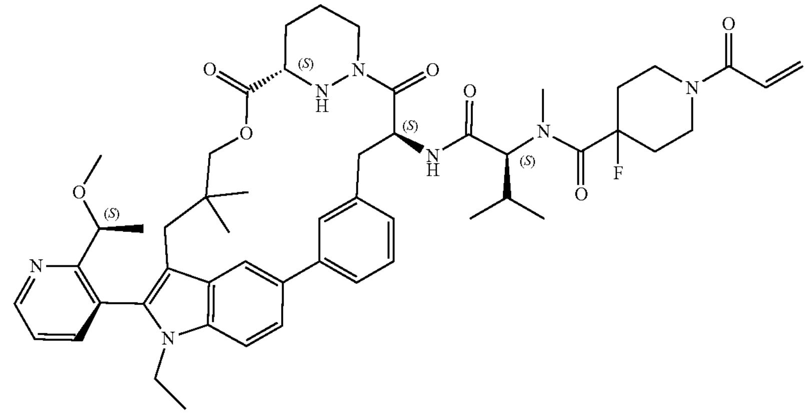 |
| B519 | 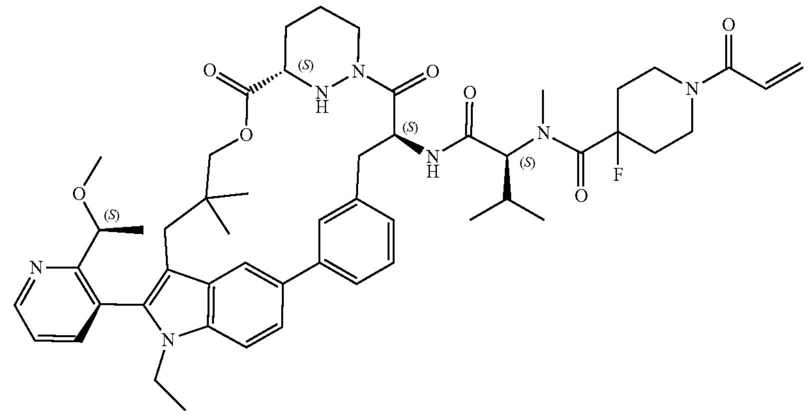 |

TABLE 2-continued
| Certain Compounds | |
|---|---|
| Ex # | Structure |
| B520 | 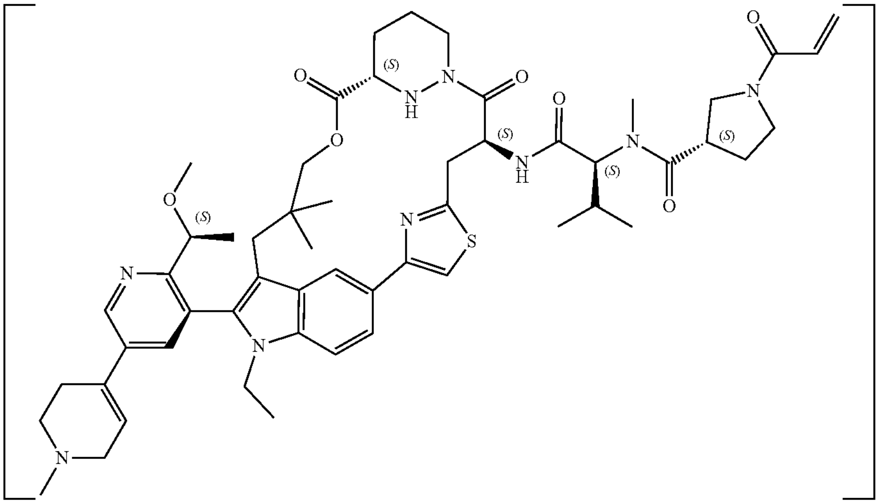 |
| B521 | 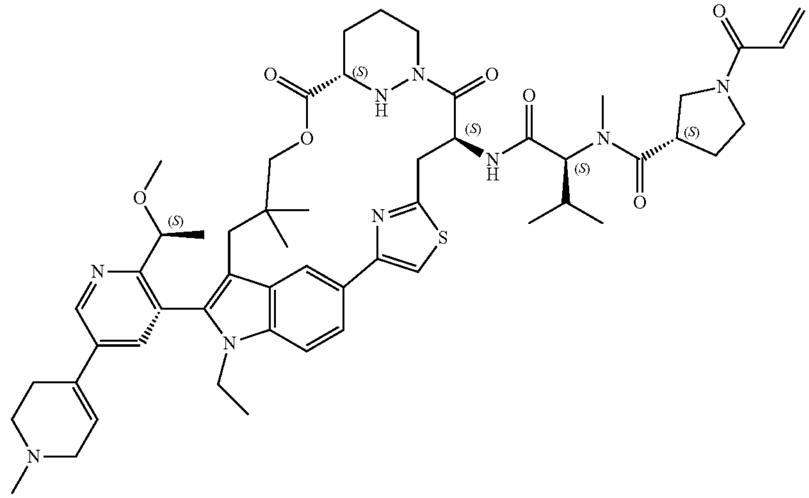 |
| B522 | 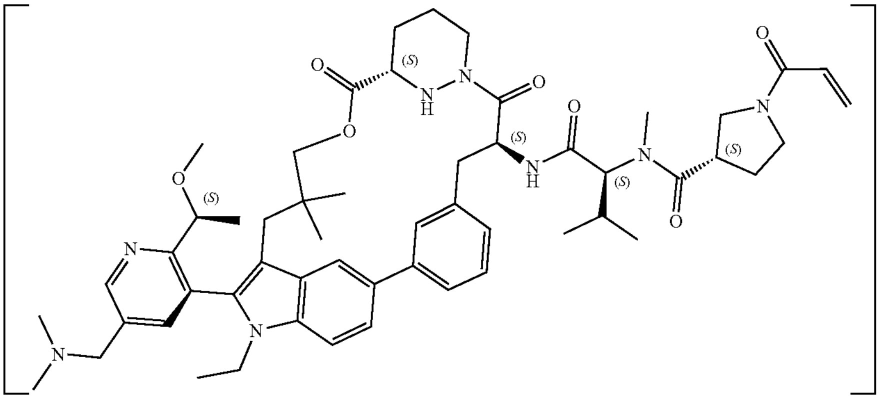 |

TABLE 2-continued
| Certain Compounds | |
|---|---|
| Ex # | Structure |
| B523 | 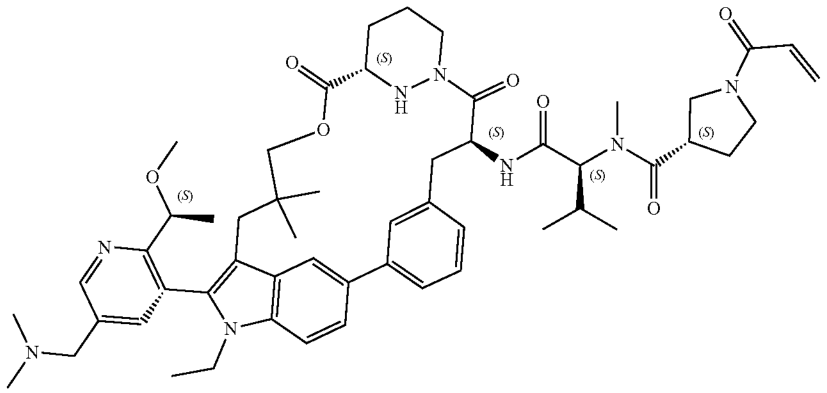 |
| B524 | 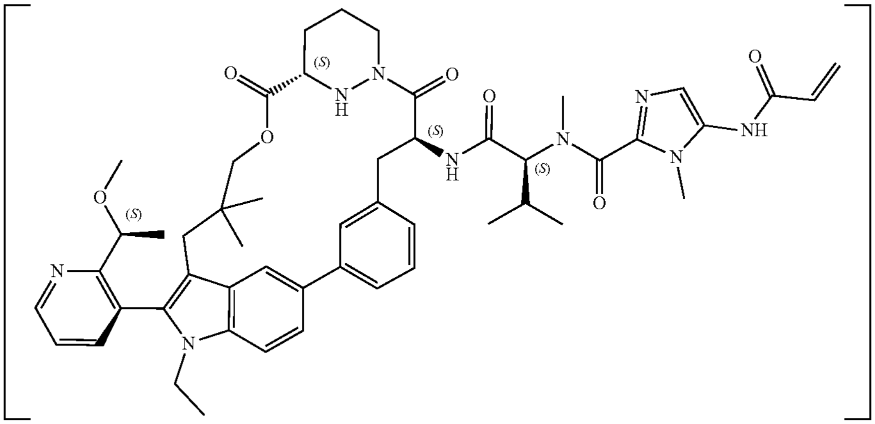 |
| B525 | 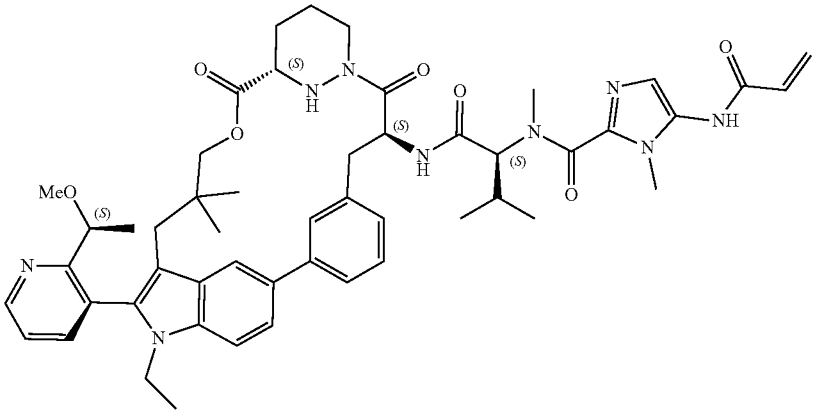 |

TABLE 2-continued
| Certain Compounds | |
|---|---|
| Ex # | Structure |
| B526 | 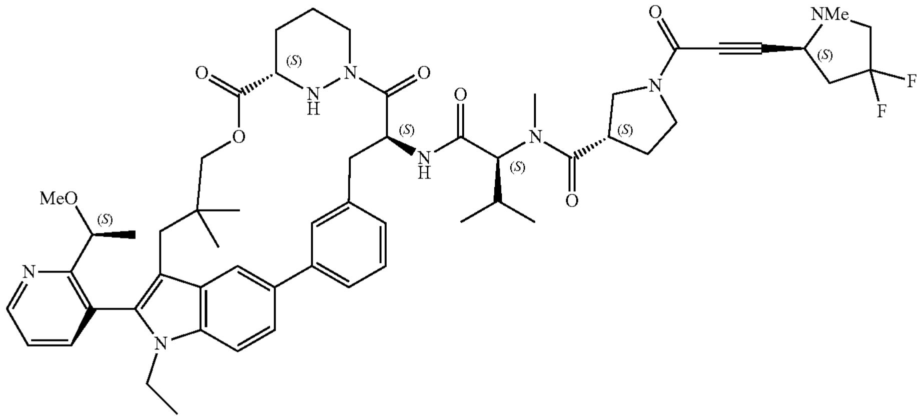 |
| B527 | 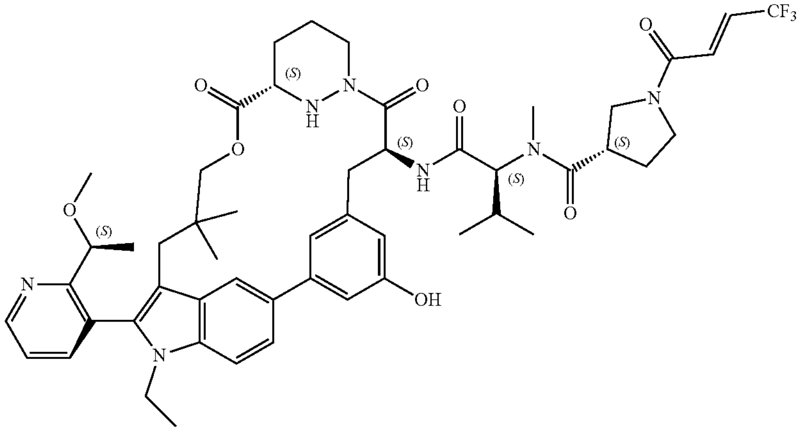 |
| B528 | 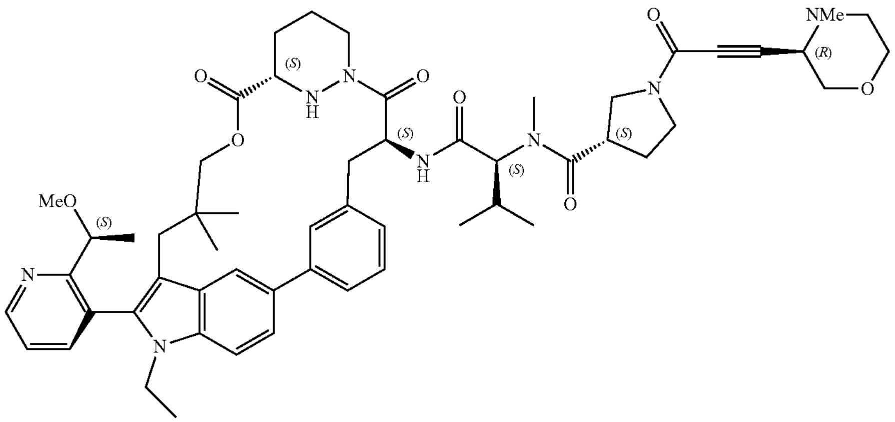 |

TABLE 2-continued
| Certain Compounds | |
|---|---|
| Ex # | Structure |
| B529 | 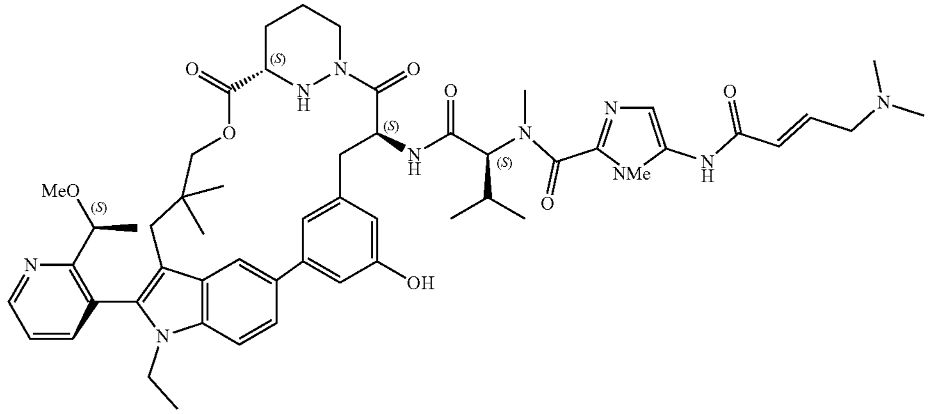 |
| B530 | 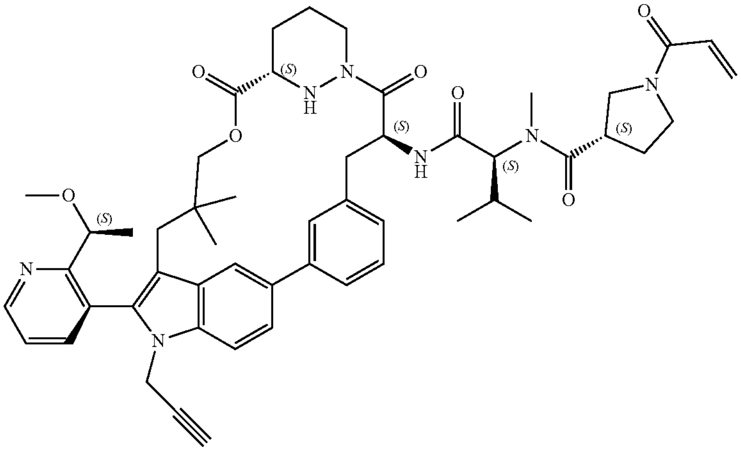 |
| B531 | 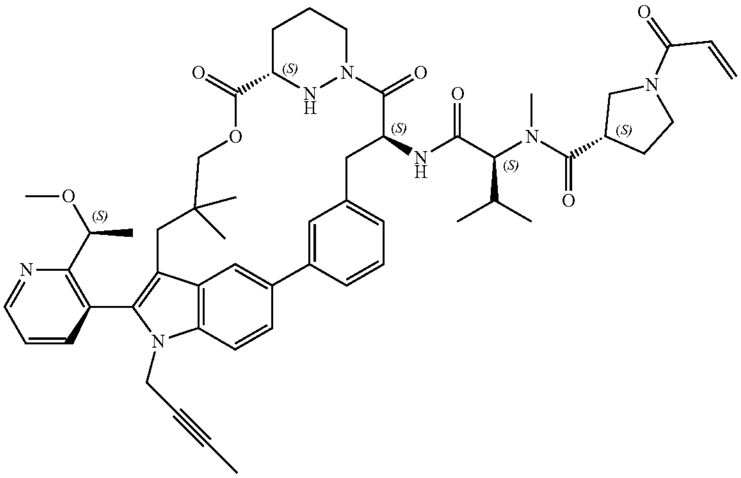 |

TABLE 2-continued
| Certain Compounds | |
|---|---|
| Ex # | Structure |
| B532 | 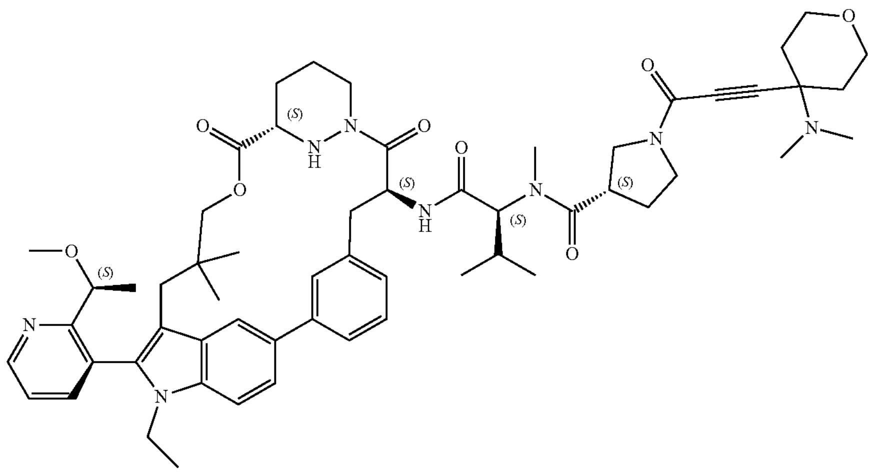 |
| B533 | 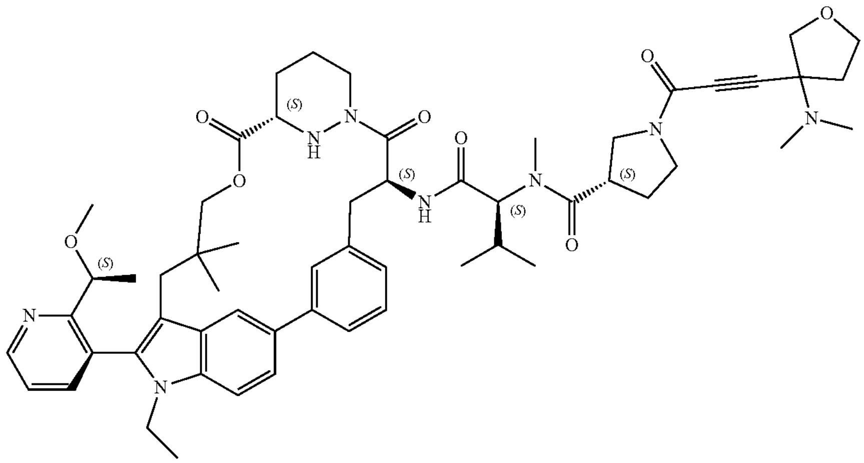 |
| B534 | 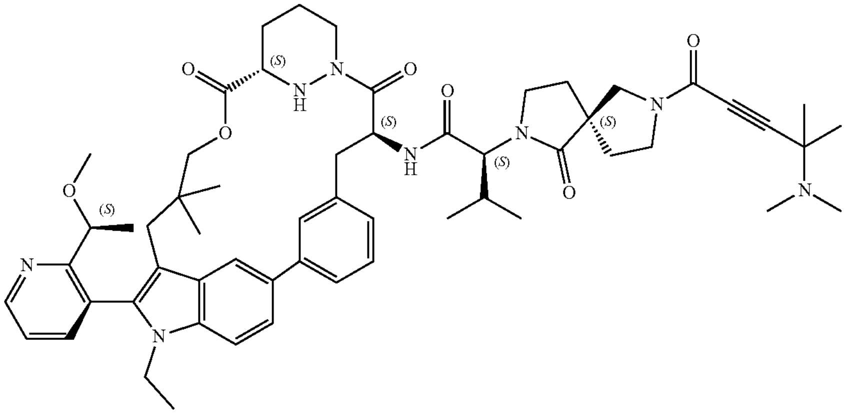 |

TABLE 2-continued
| Certain Compounds | |
|---|---|
| Ex # | Structure |
| B535 | 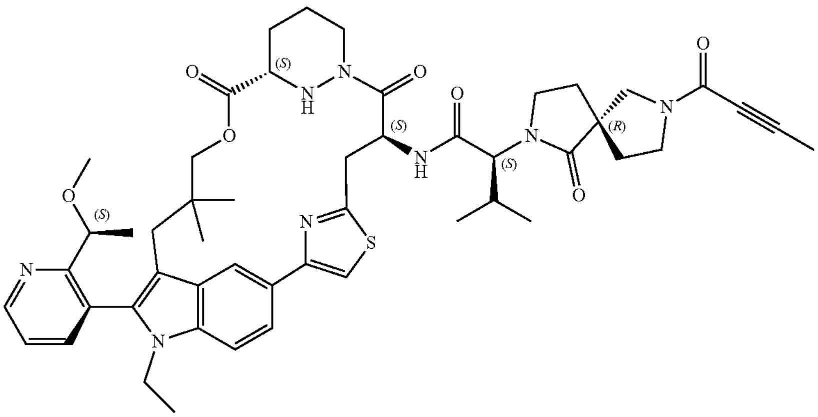 |
| B536 | 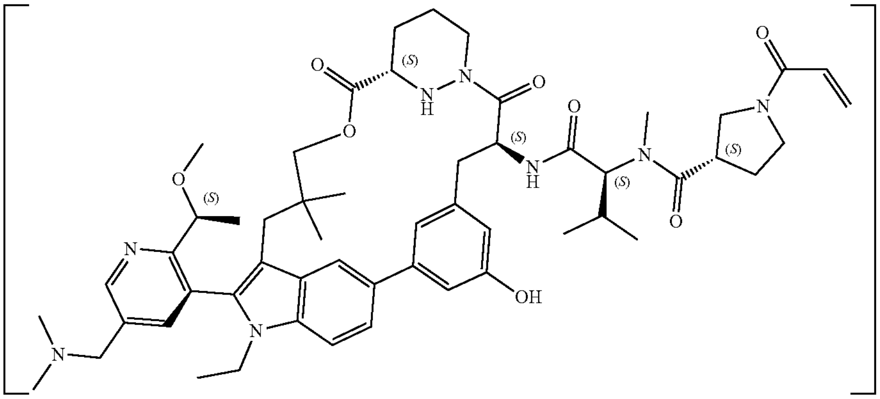 |
| B537 | 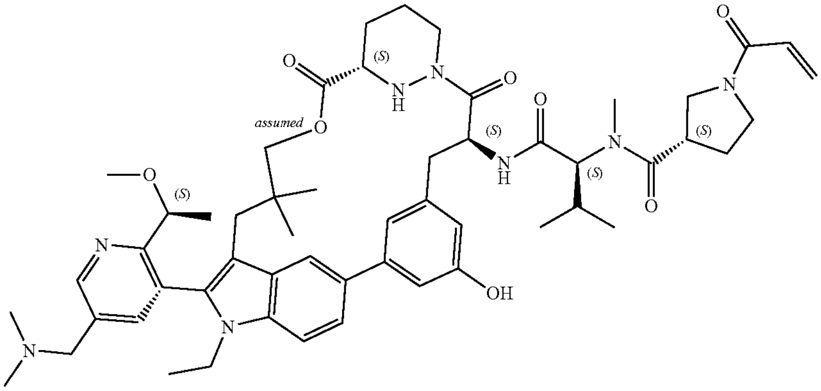 |

TABLE 2-continued
| Certain Compounds | |
|---|---|
| Ex # | Structure |
| B538 | 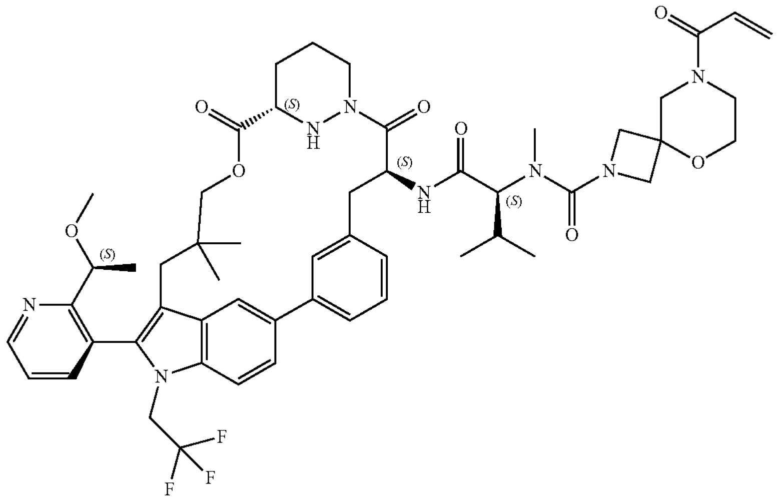 |
| B539 | 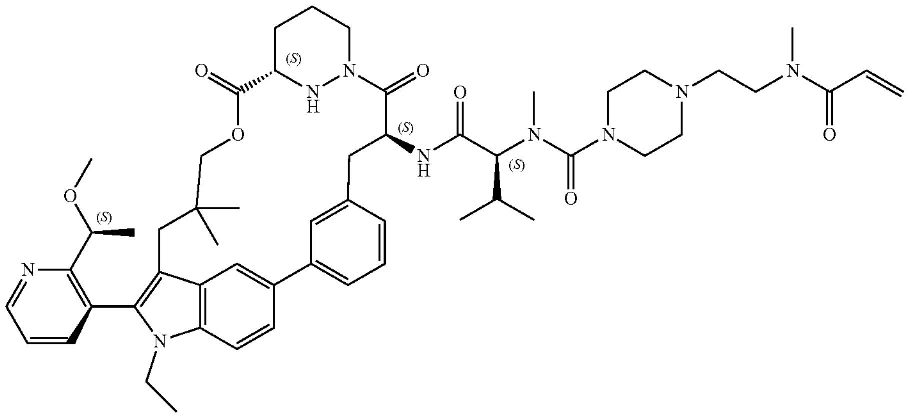 |
| B540 | 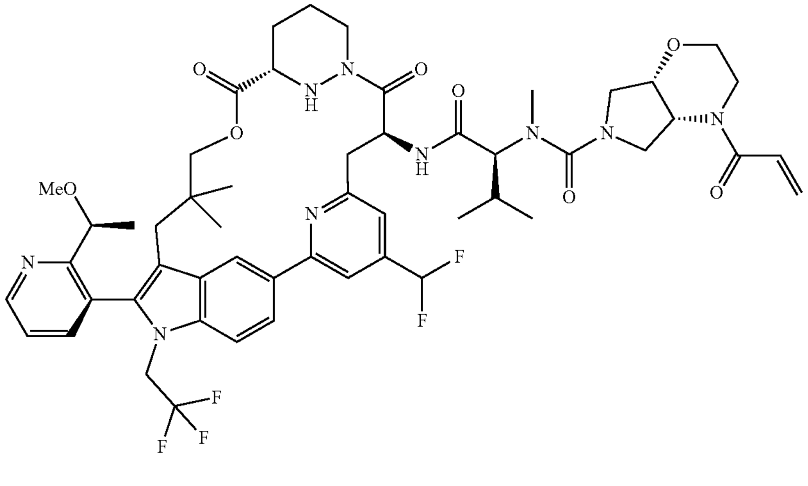 |

TABLE 2-continued
| Certain Compounds | |
|---|---|
| Ex # | Structure |
| B541 | 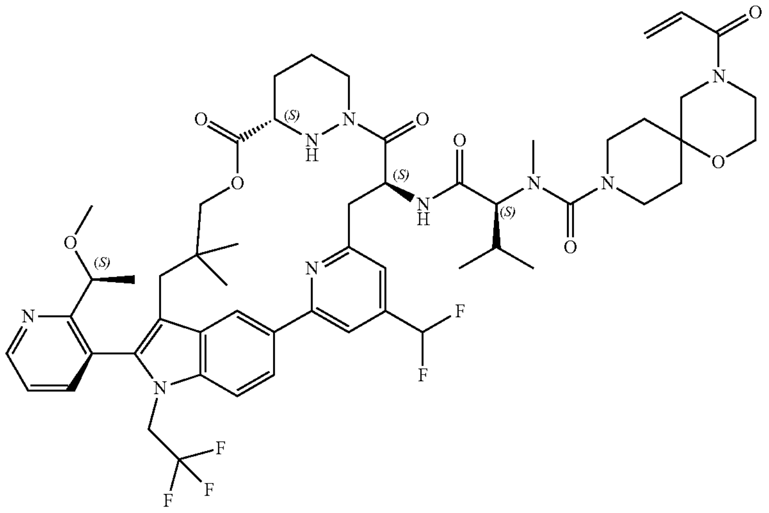 |
| B542 | 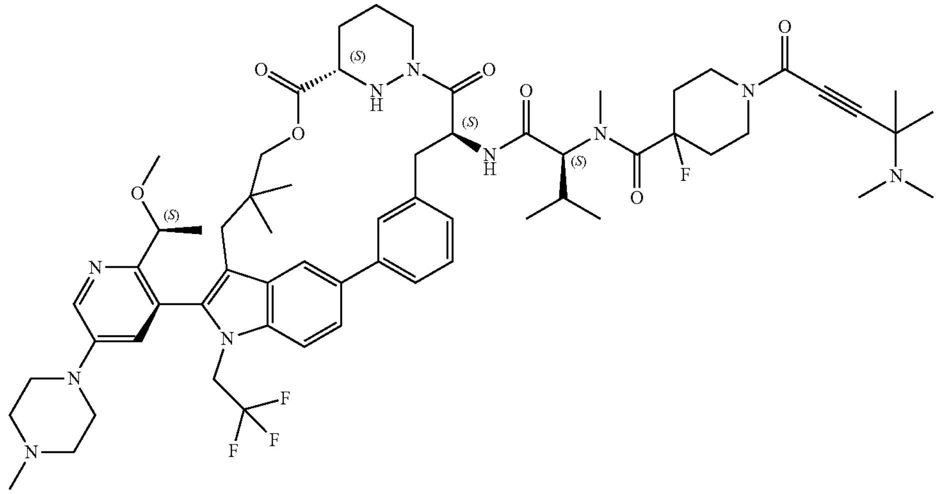 |
| B543 | 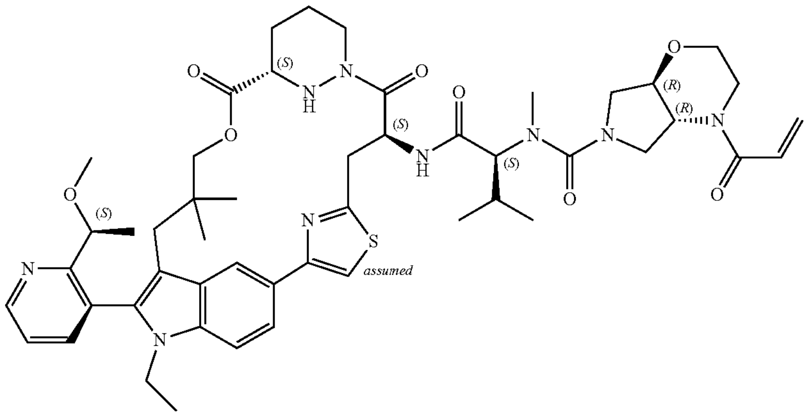 |

TABLE 2-continued
| Certain Compounds | |
|---|---|
| Ex # | Structure |
| B544 | 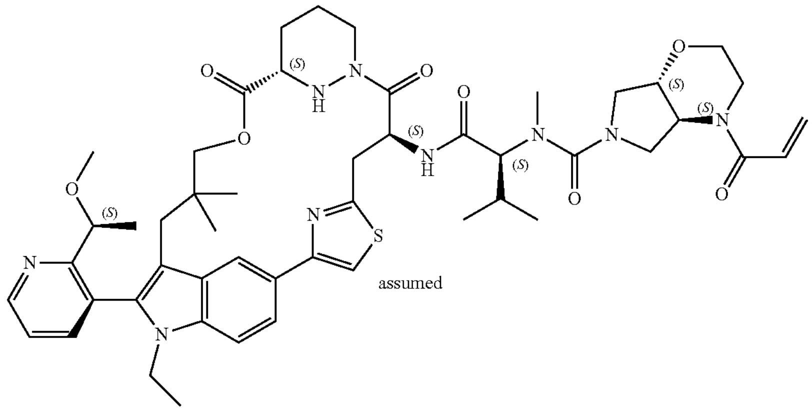 |
| B545 | 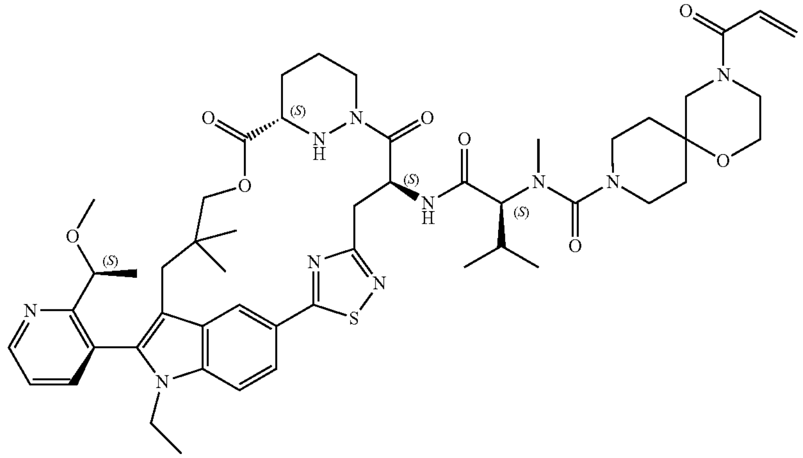 |
| B546 | 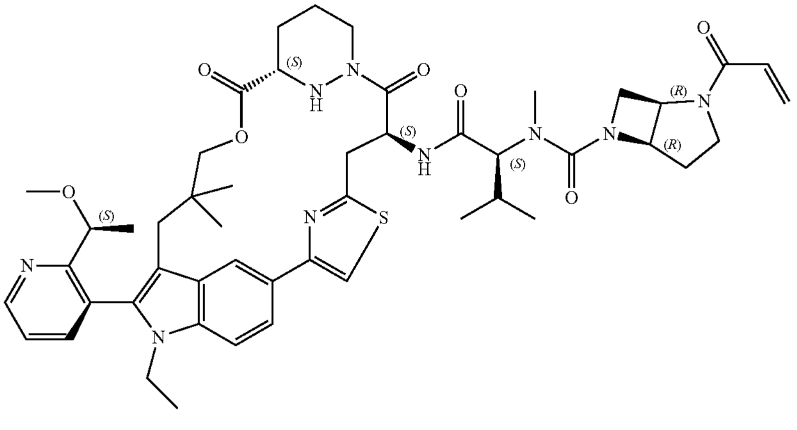 |

TABLE 2-continued
| Certain Compounds | |
|---|---|
| Ex # | Structure |
| B547 | 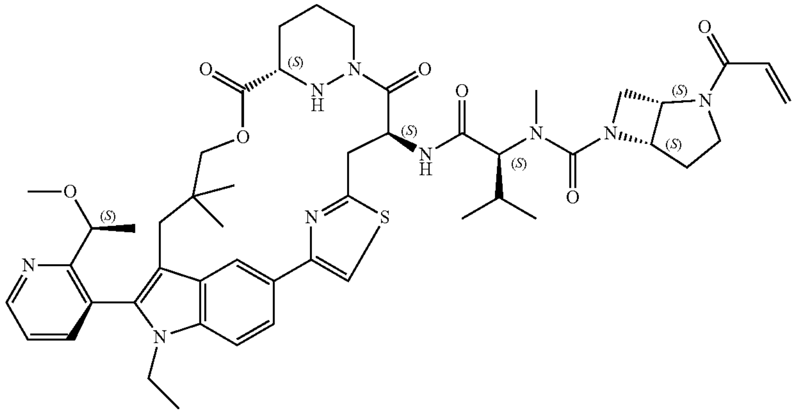 |
| B548 | 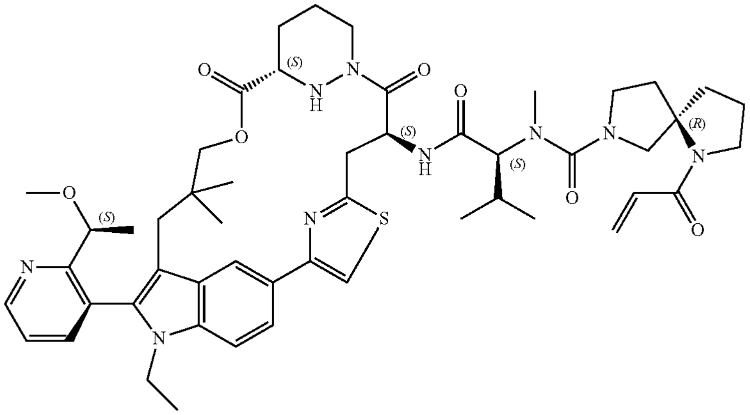 |
| B549 | 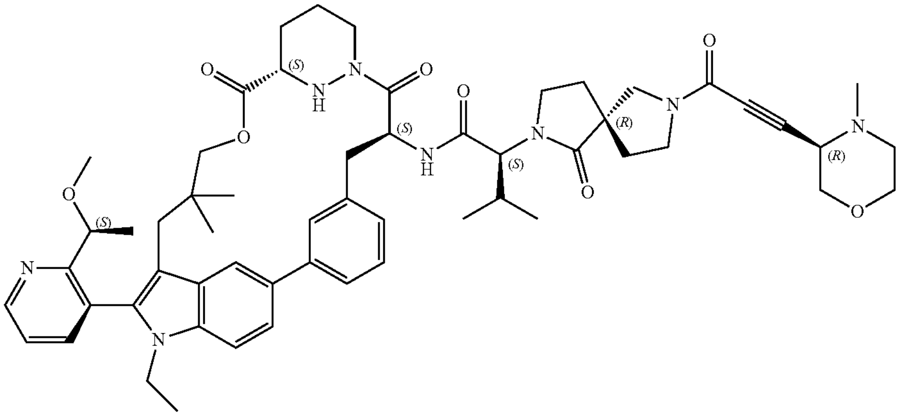 |

TABLE 2-continued
| Certain Compounds | |
|---|---|
| Ex # | Structure |
| B550 | 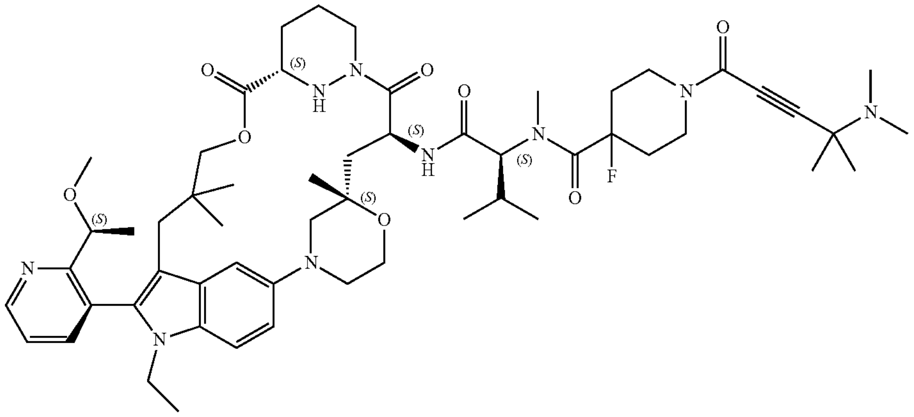 |
| B551 | 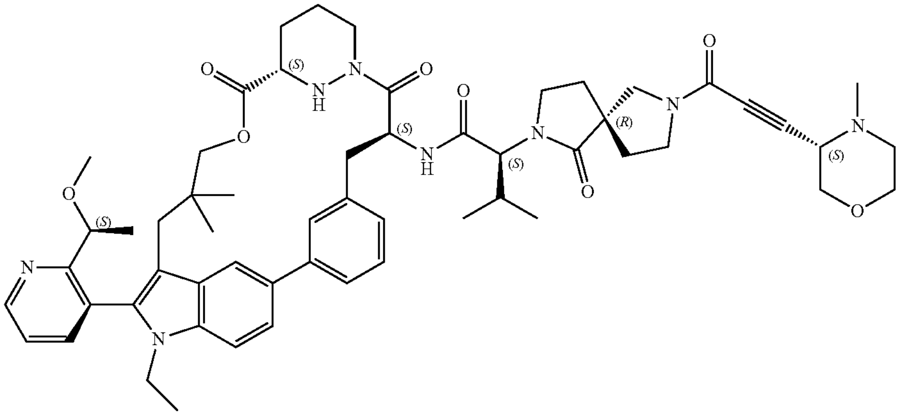 |
| B552 | 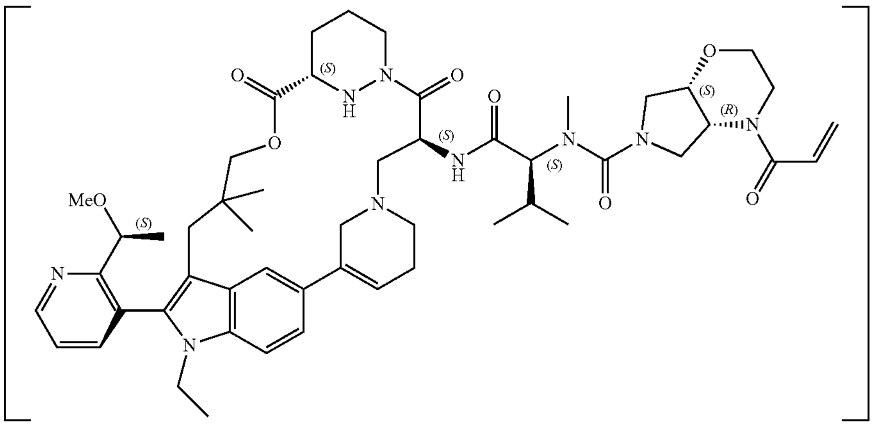 |

TABLE 2-continued
| Certain Compounds | |
|---|---|
| Ex # | Structure |
| B553 | 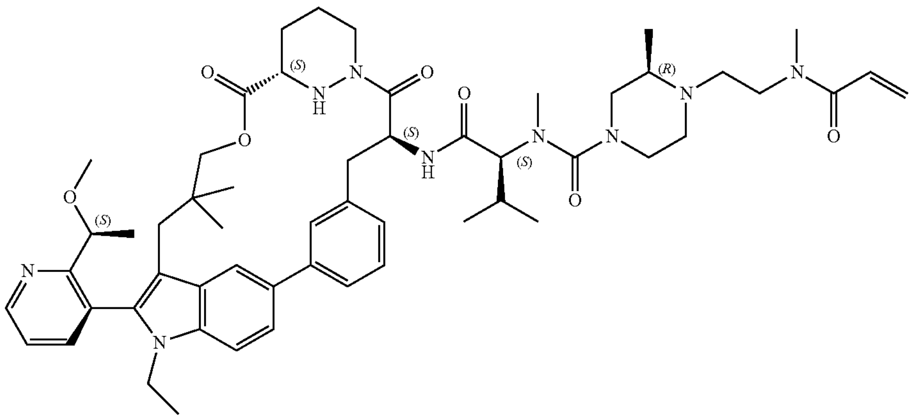 |
| B554 | 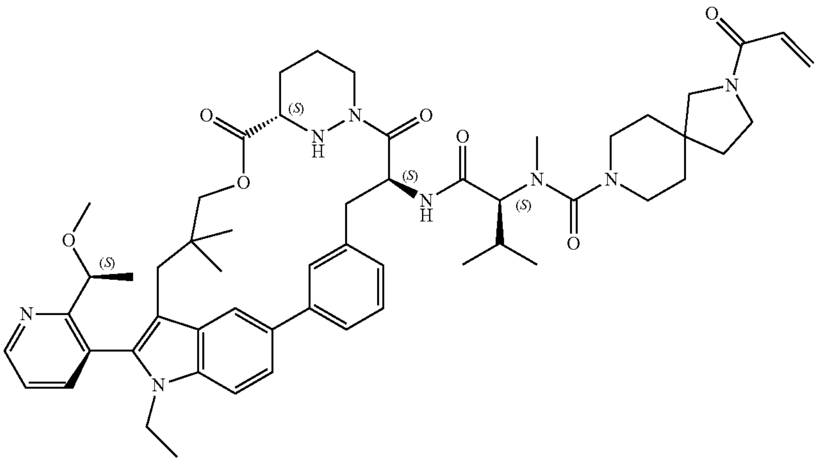 |
| B555 | 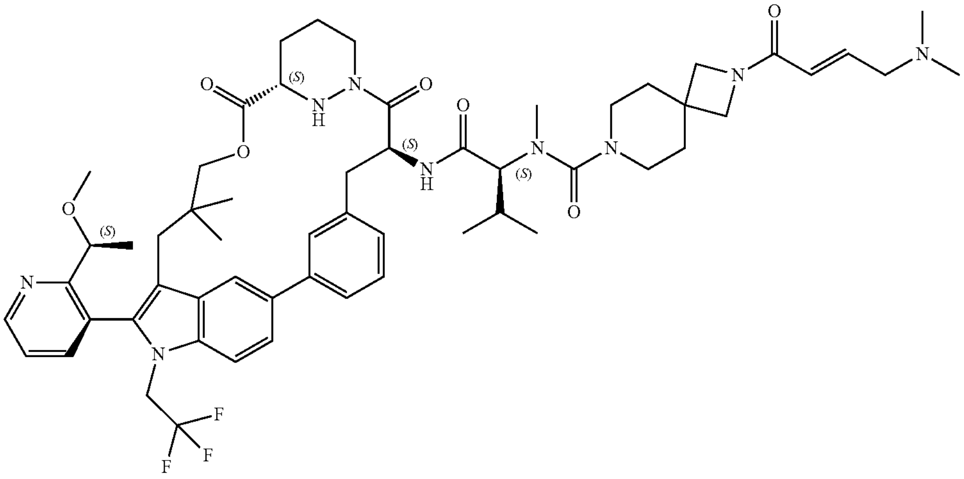 |

TABLE 2-continued
| Certain Compounds | |
|---|---|
| Ex # | Structure |
| B556 | 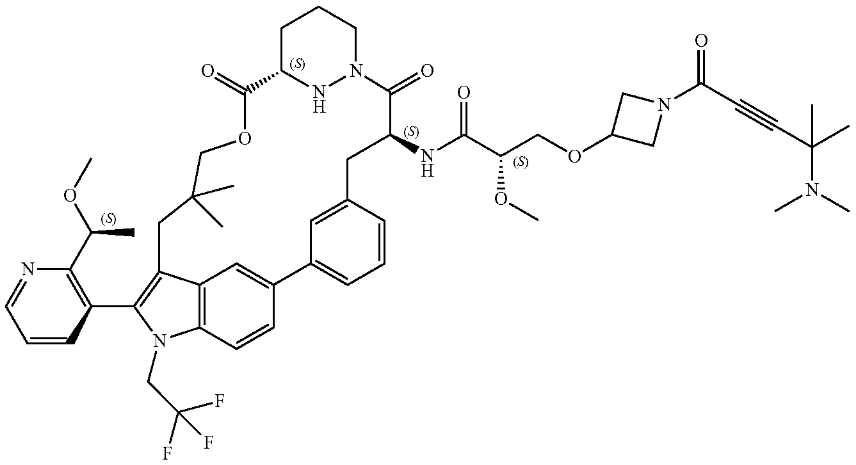 |
| B557 | 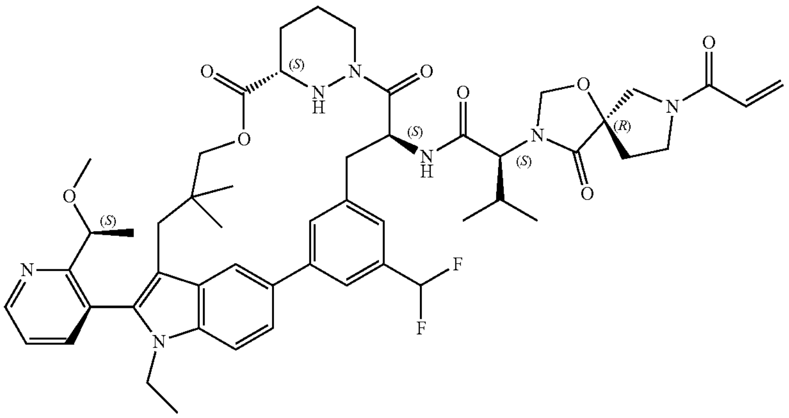 |
| B558 | 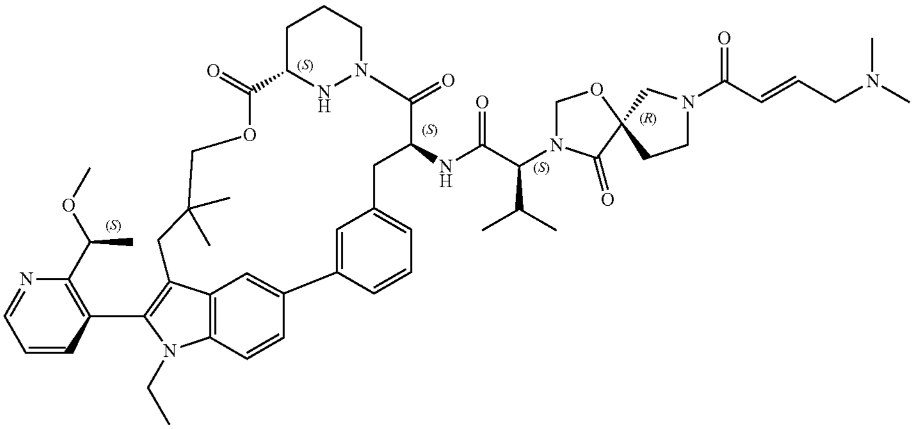 |

TABLE 2-continued
| Certain Compounds | |
|---|---|
| Ex # | Structure |
| B559 | 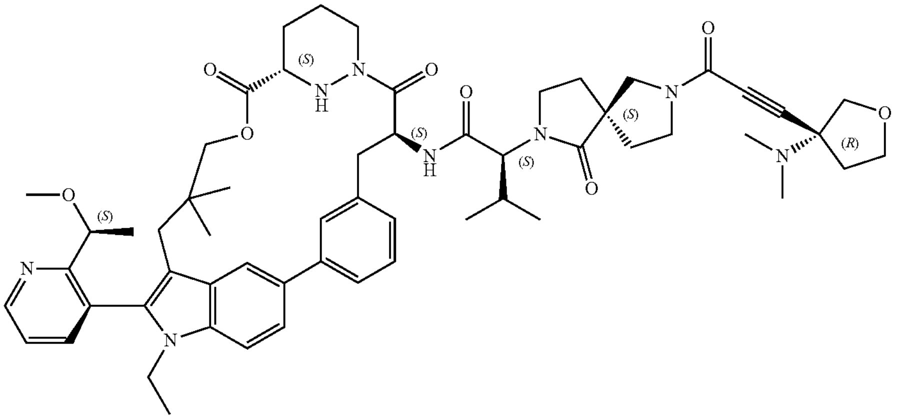 |
| B560 | 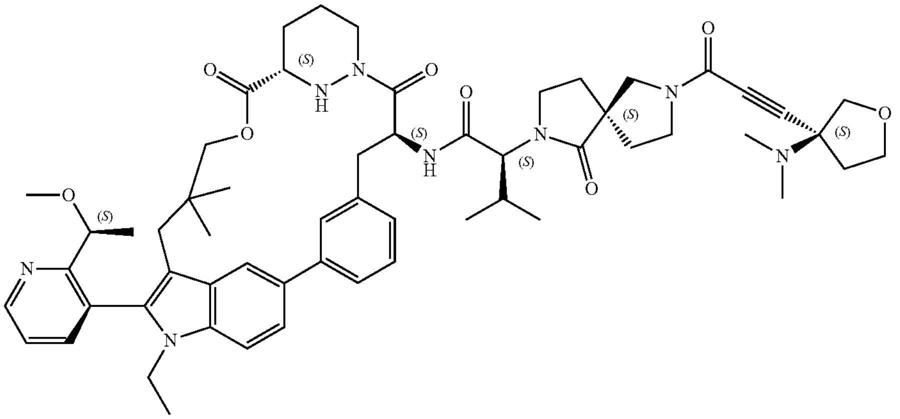 |
| B561 | 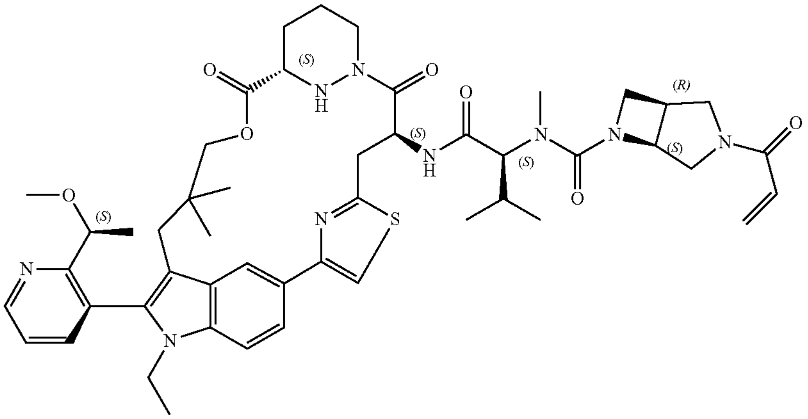 |

TABLE 2-continued
| Certain Compounds | |
|---|---|
| Ex # | Structure |
| B562 | 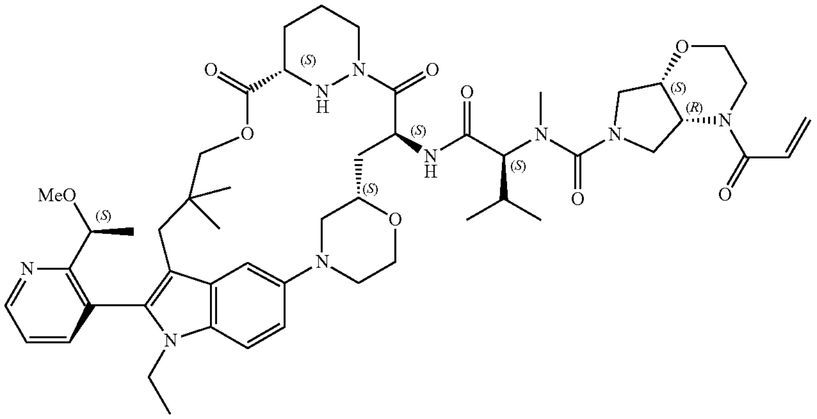 |
| B563 | 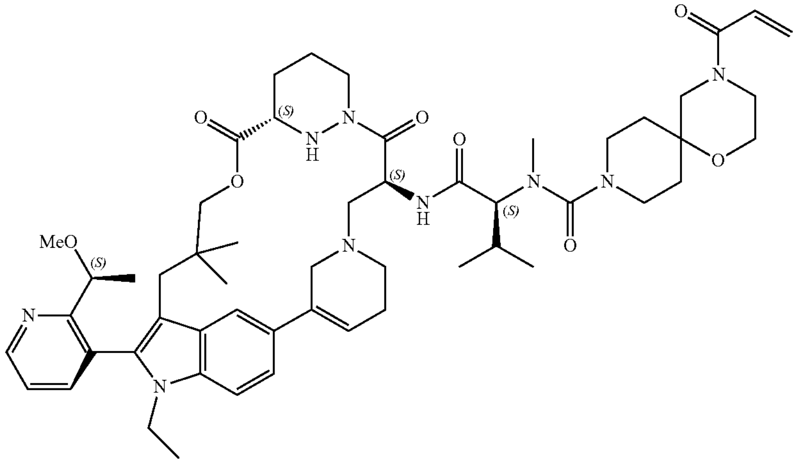 |
| B564 | 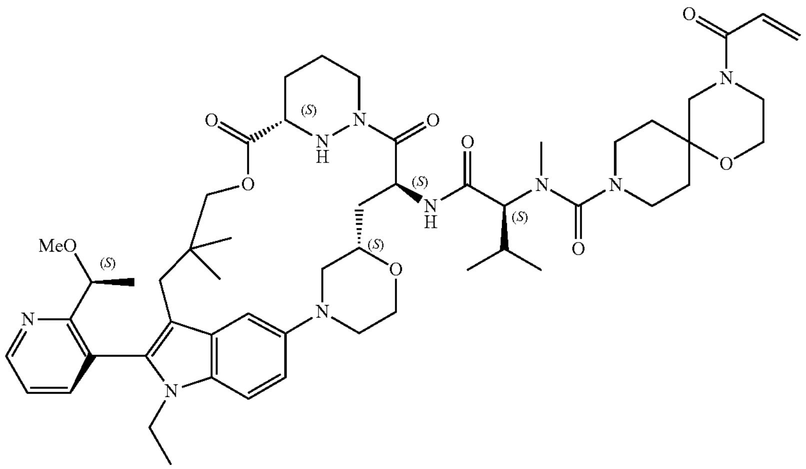 |

TABLE 2-continued
| Certain Compounds | |
|---|---|
| Ex # | Structure |
| B565 | 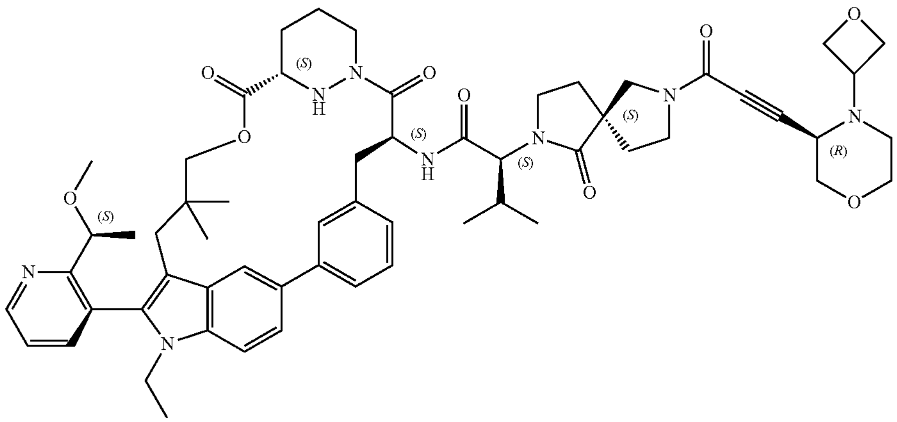 |
| B566 | 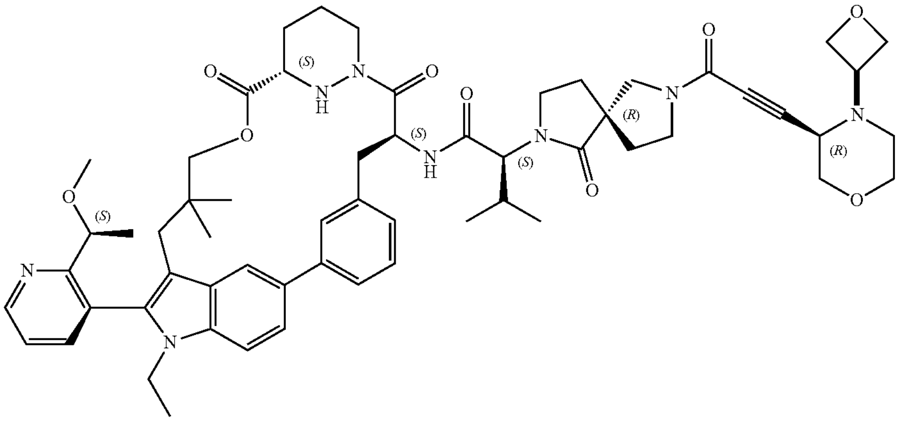 |
| B567 | 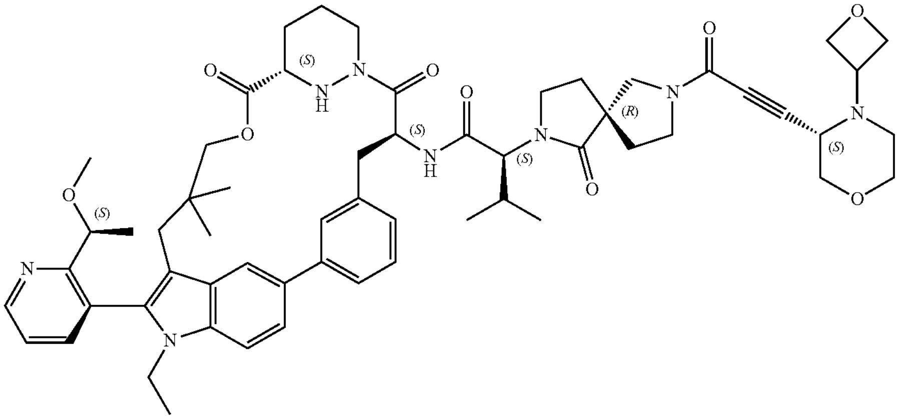 |

TABLE 2-continued
| Certain Compounds | |
|---|---|
| Ex # | Structure |
| B568 | 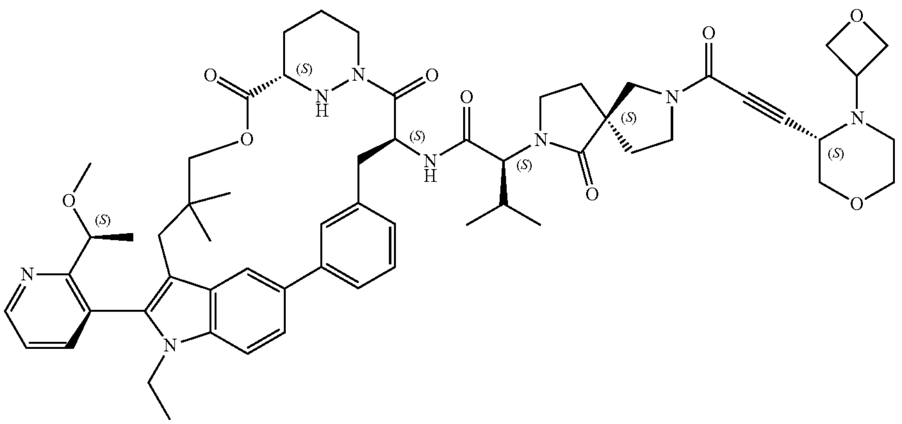 |
| B569 | 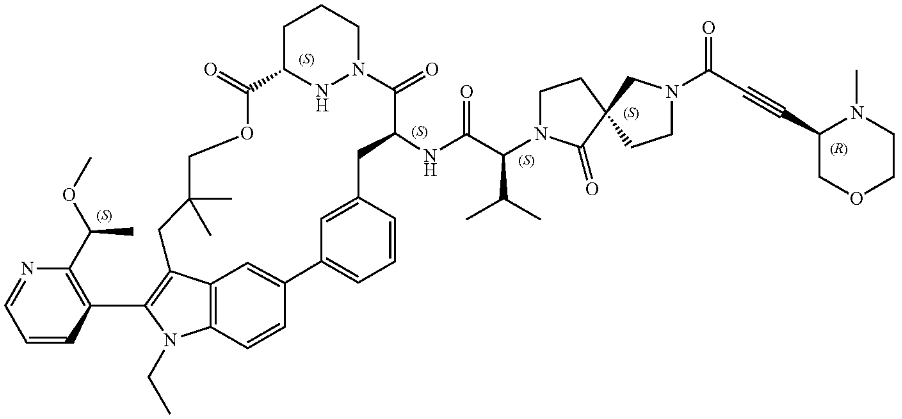 |
| B570 | 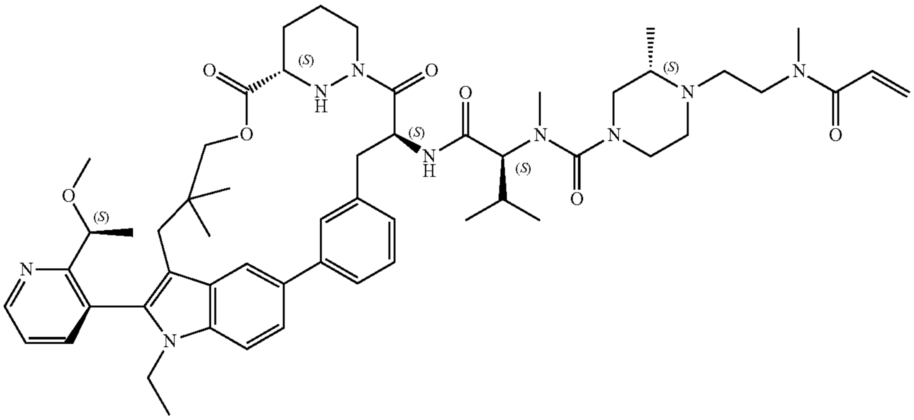 |

TABLE 2-continued
| Certain Compounds | |
|---|---|
| Ex # | Structure |
| B571 | 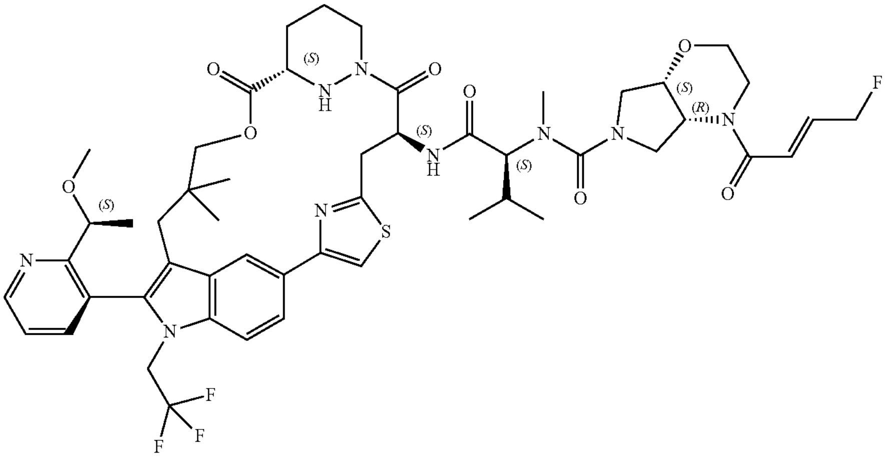 |
| B572 | 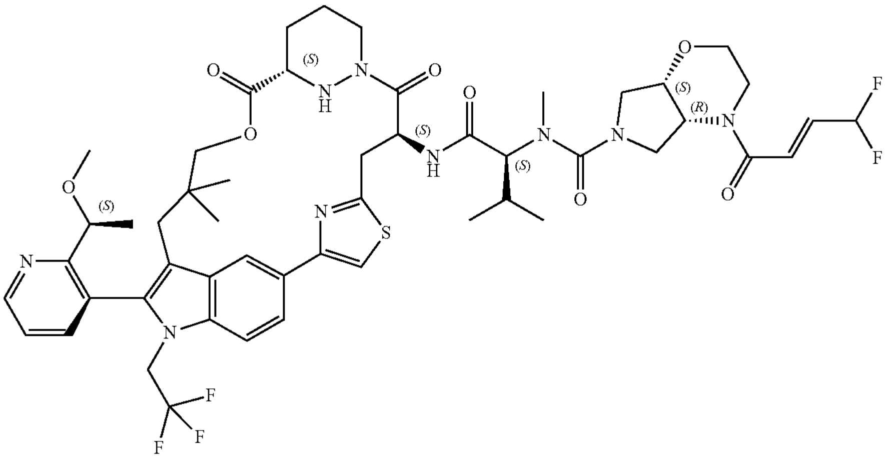 |
| B573 | 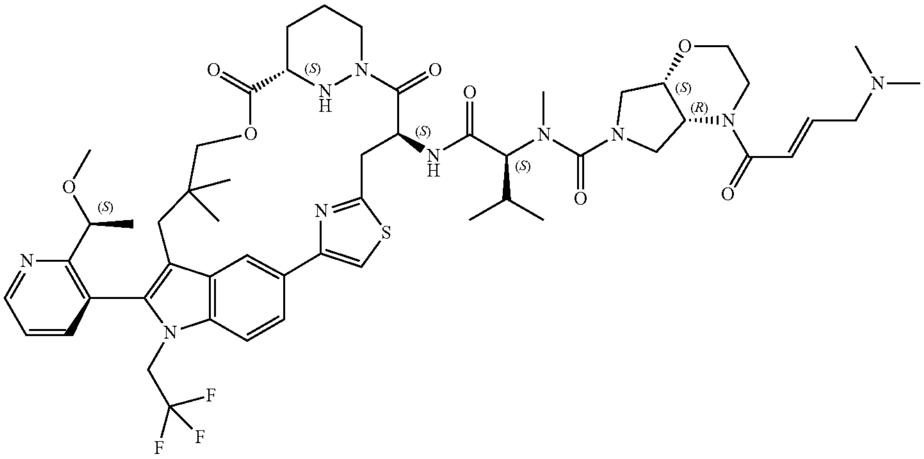 |

TABLE 2-continued
| Certain Compounds | |
|---|---|
| Ex # | Structure |
| B574 | 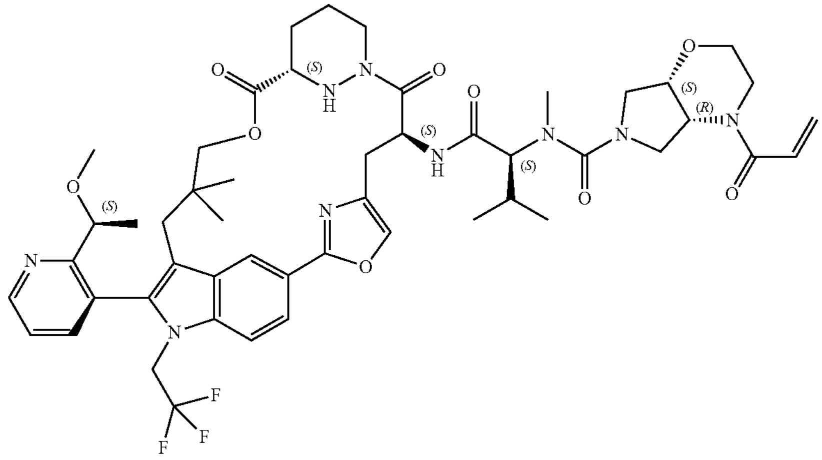 |
| B575 | 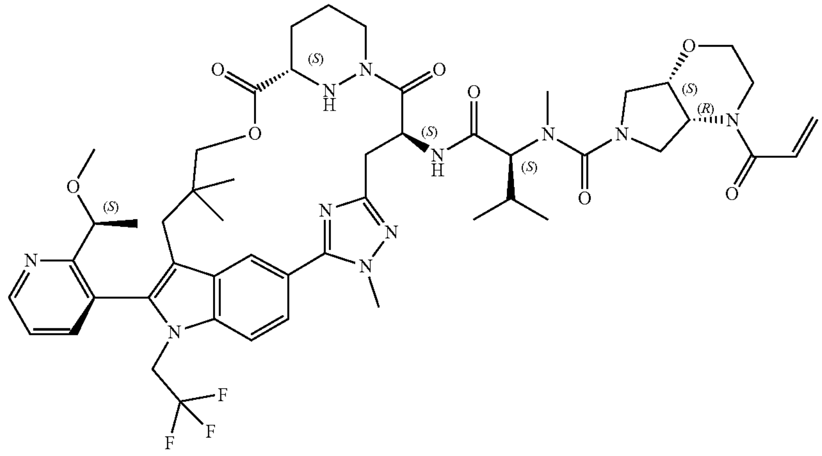 |
| B576 | 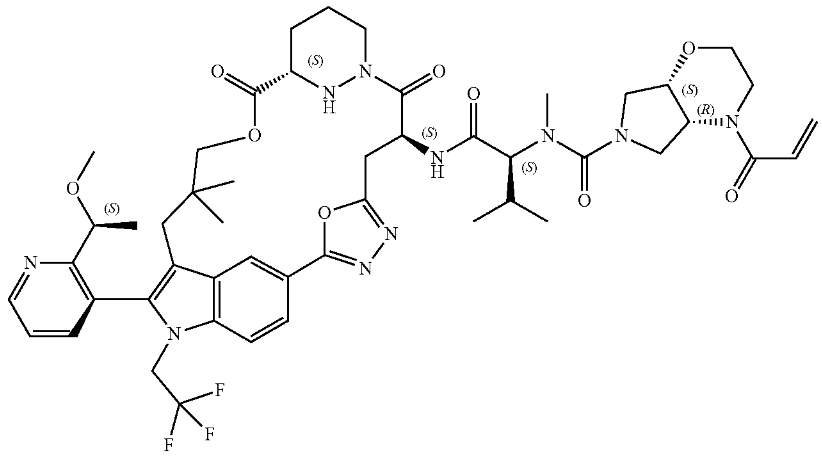 |

TABLE 2-continued
| Certain Compounds | |
|---|---|
| Ex # | Structure |
| B577 | 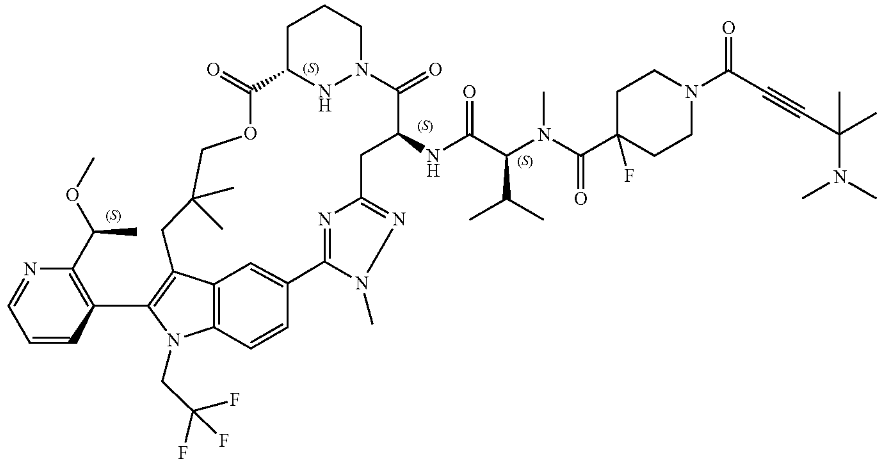 |
| B578 | 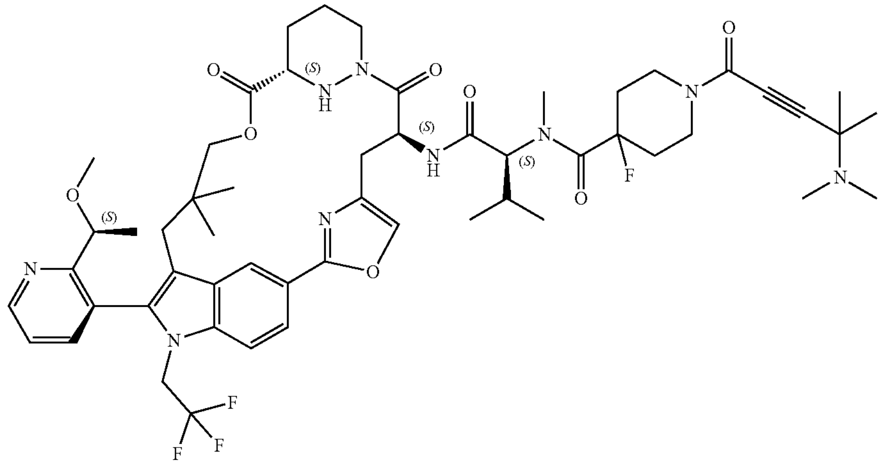 |
| B579 | 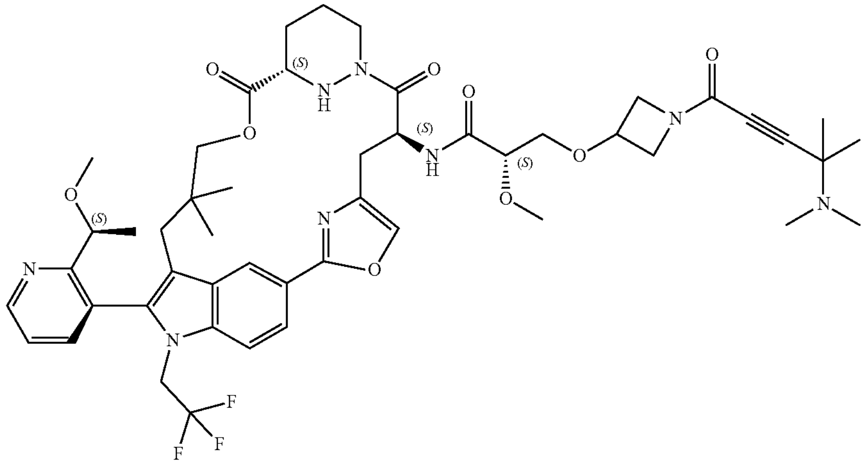 |

TABLE 2-continued
| Certain Compounds | |
|---|---|
| Ex # | Structure |
| B580 | 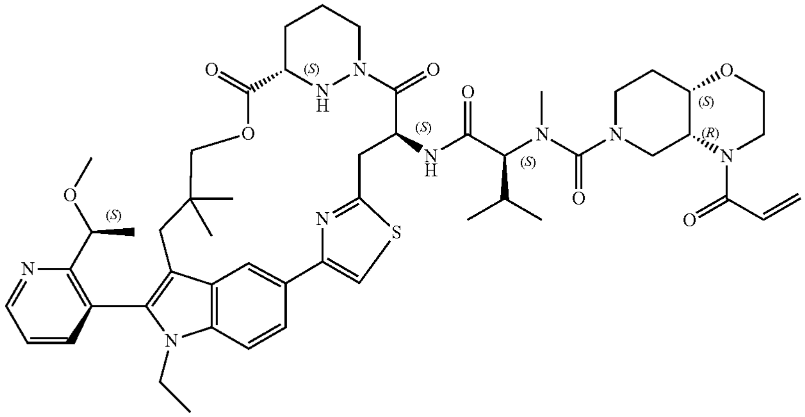 |
| B581 | 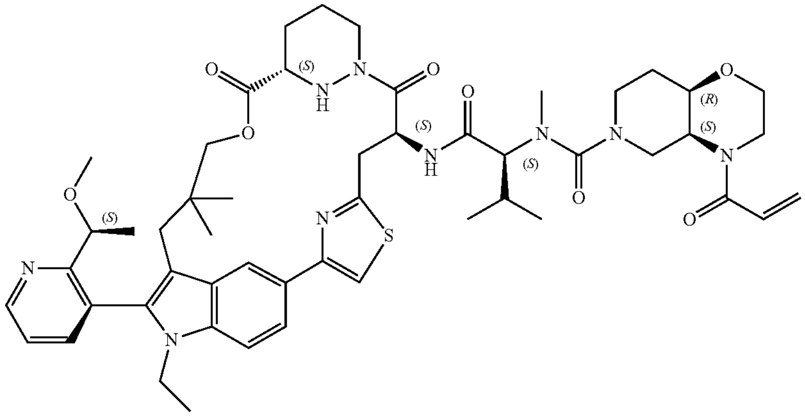 |
| B582 | 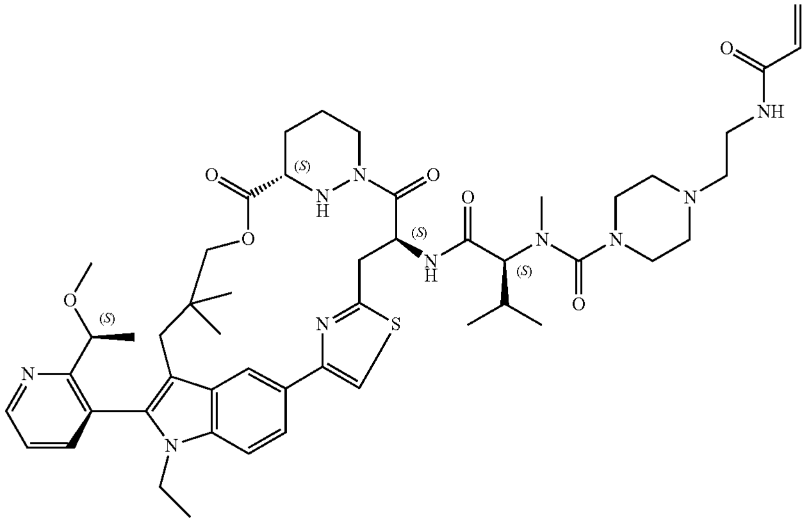 |

TABLE 2-continued
| Certain Compounds | |
|---|---|
| Ex # | Structure |
| B583 | 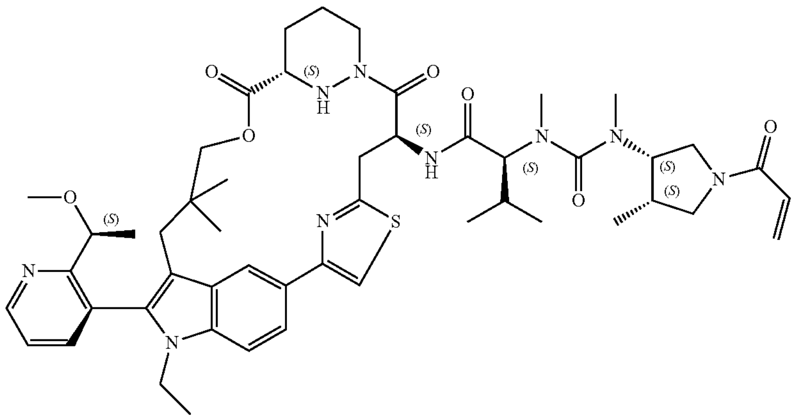 |
| B584 | 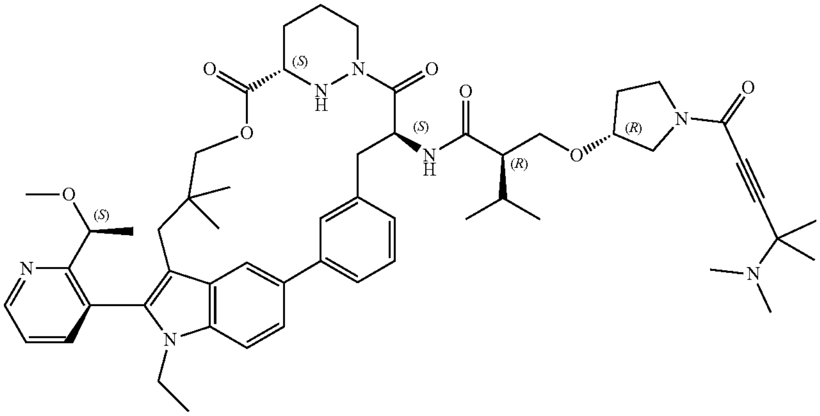 |
| B585 | 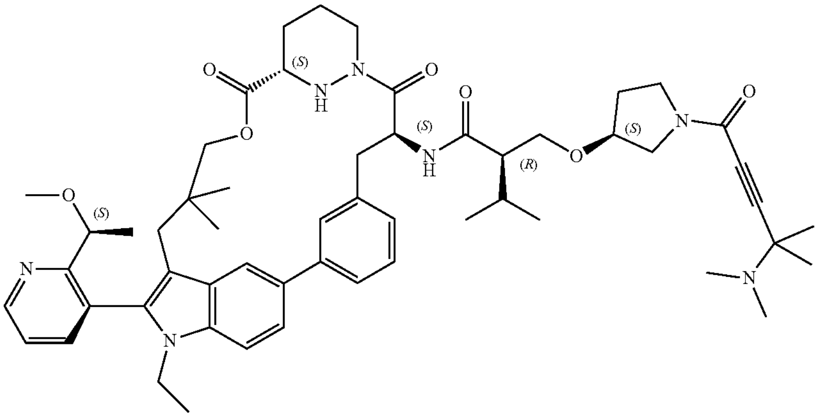 |

TABLE 2-continued
| Certain Compounds | |
|---|---|
| Ex # | Structure |
| B586 | 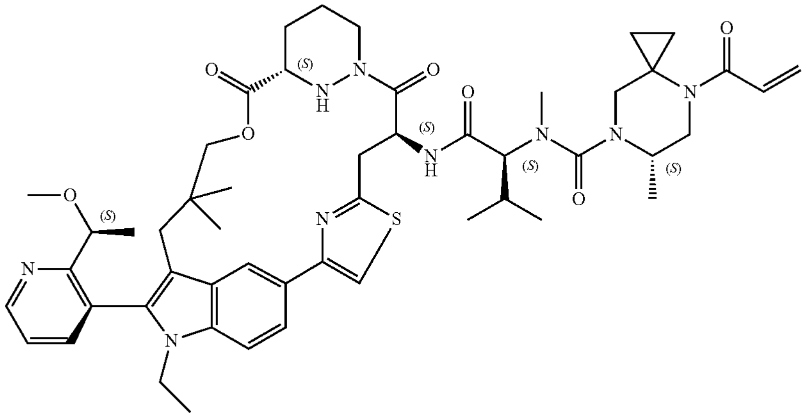 |
| B587 | 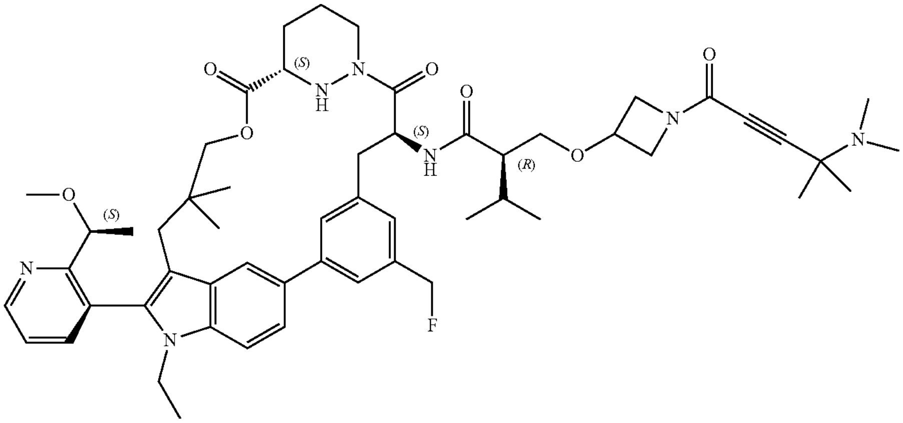 |
| B588 | 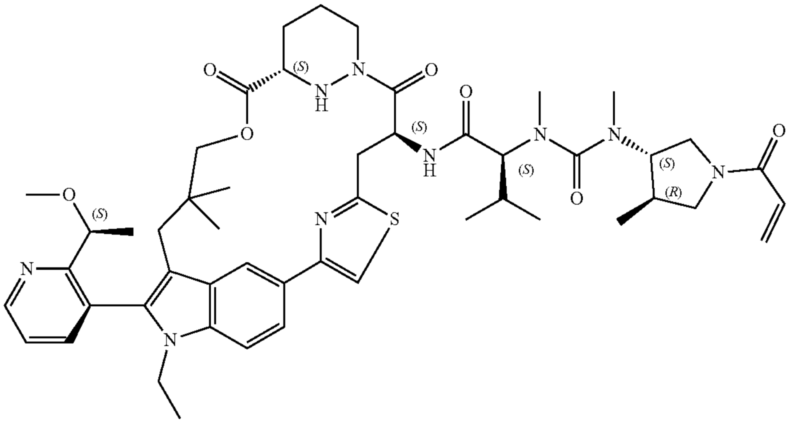 |

TABLE 2-continued
| Certain Compounds | |
|---|---|
| Ex # | Structure |
| B589 | 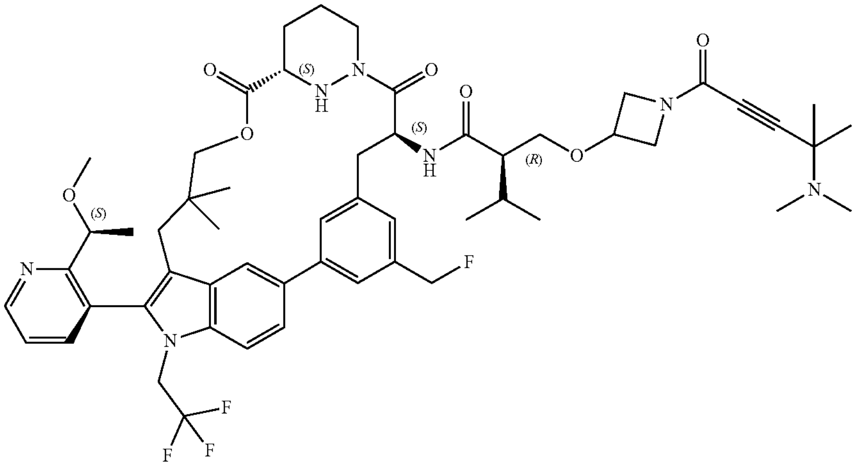 |
| B590 | 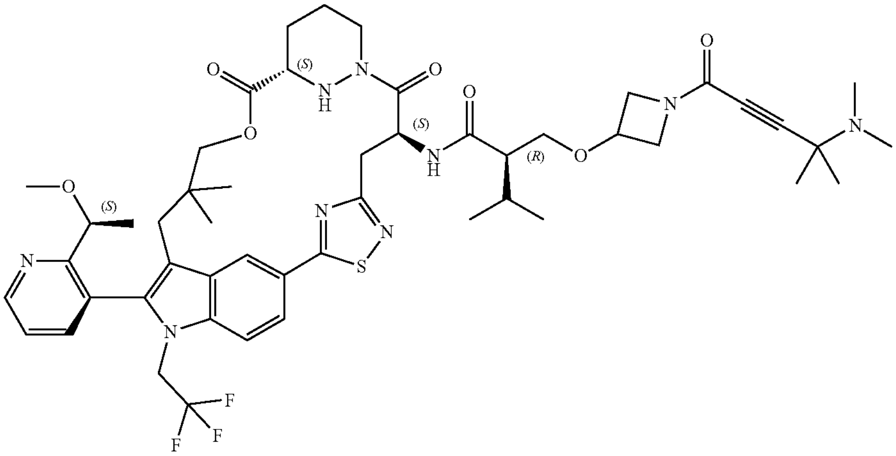 |
| B591 | 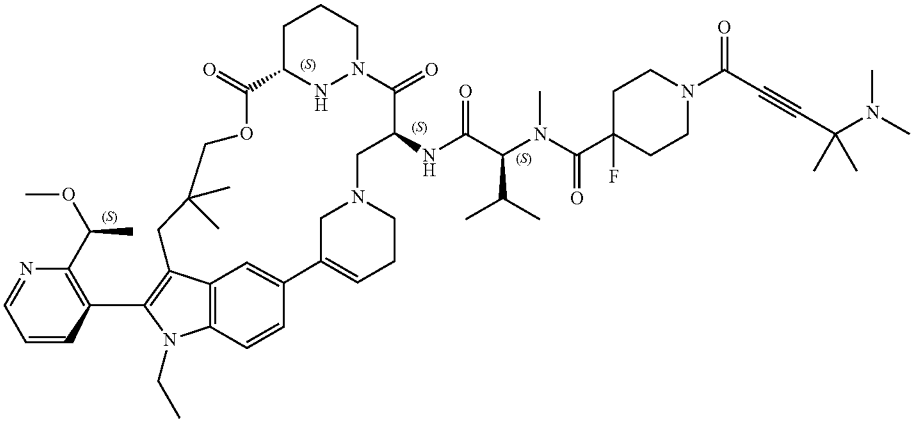 |

TABLE 2-continued
| Certain Compounds | |
|---|---|
| Ex # | Structure |
| B592 | 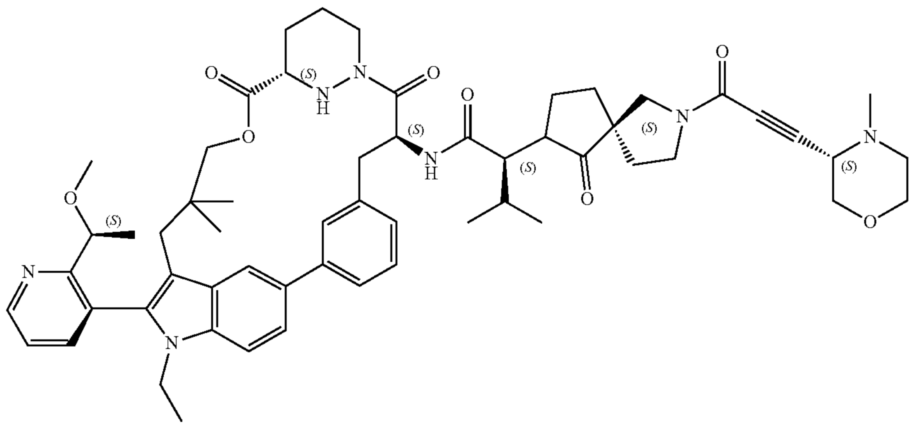 |
| B593 | 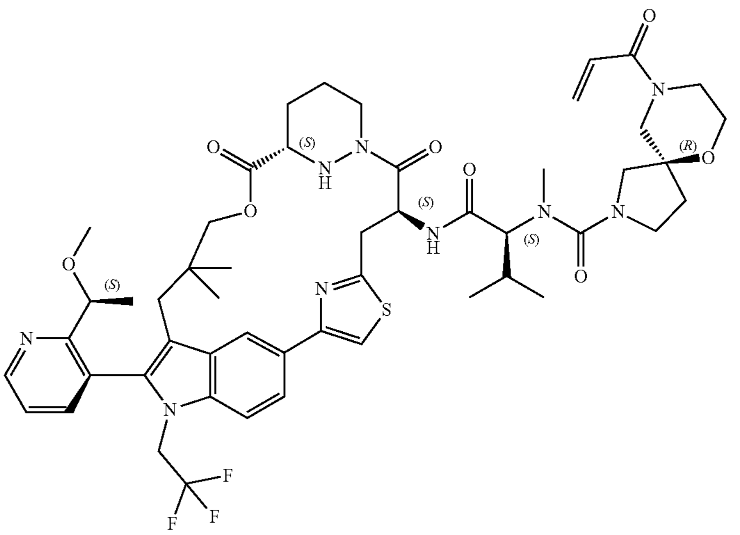 |
| B594 | 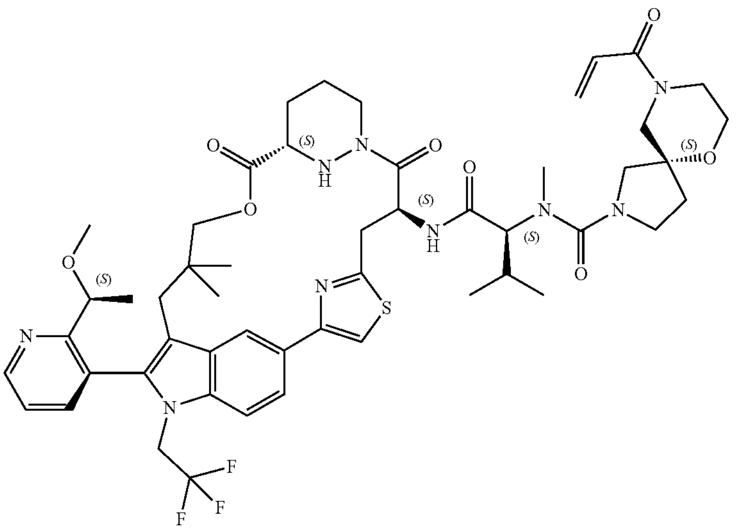 |

TABLE 2-continued
| Certain Compounds | |
|---|---|
| Ex # | Structure |
| B595 | 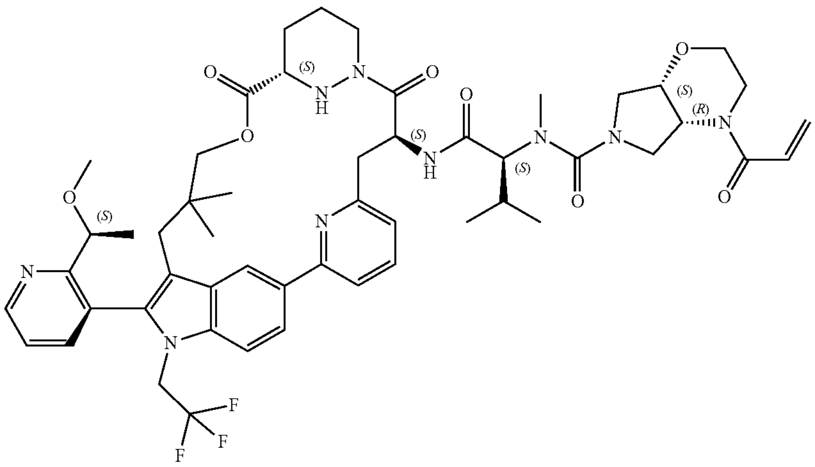 |
| B596 | 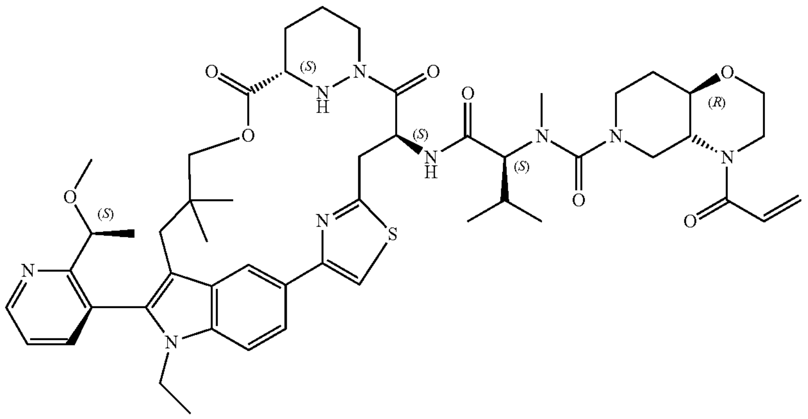 |
| B597 | 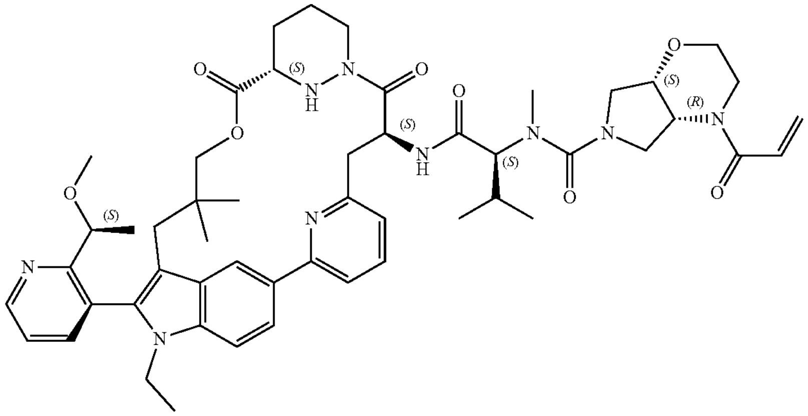 |

TABLE 2-continued
| Certain Compounds | |
|---|---|
| Ex # | Structure |
| B598 | 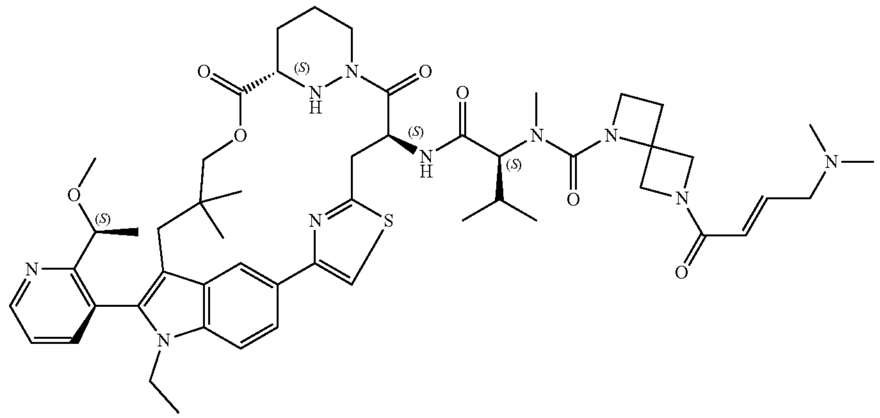 |
| B599 | 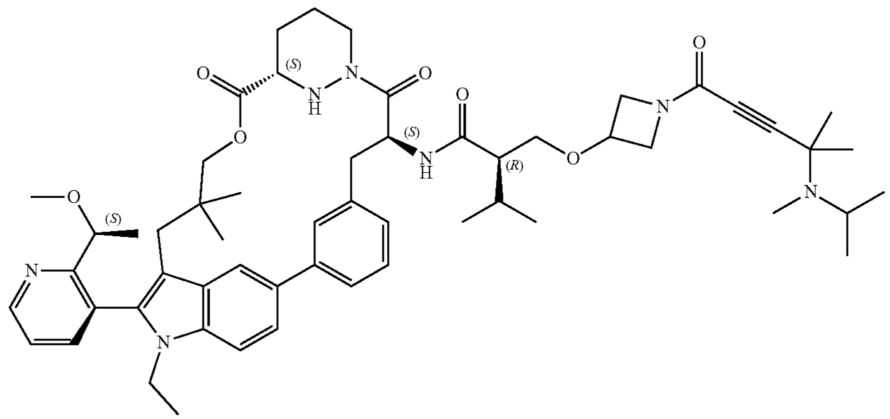 |
| B600 | 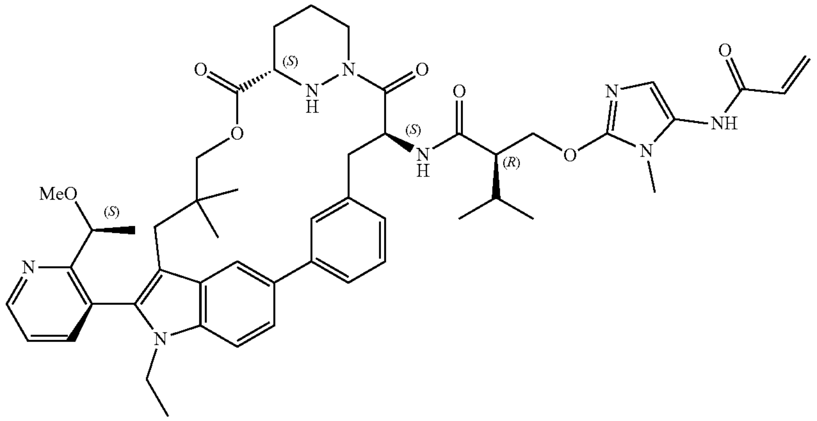 |

TABLE 2-continued
| Certain Compounds | |
|---|---|
| Ex # | Structure |
| B601 | 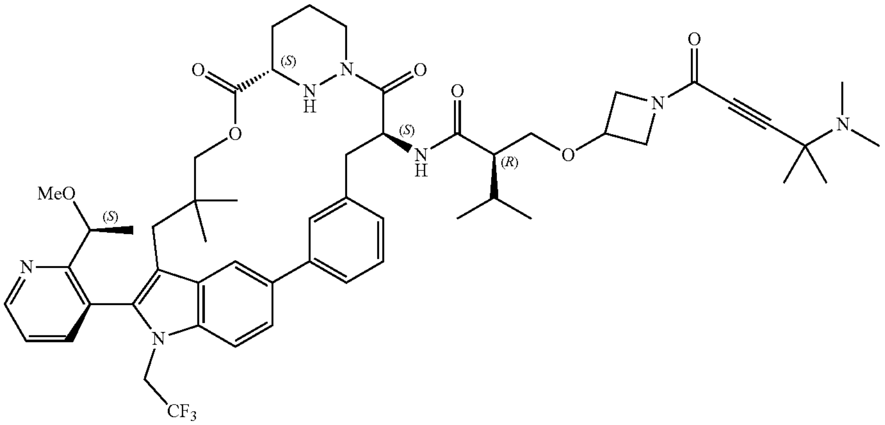 |
| B602 | 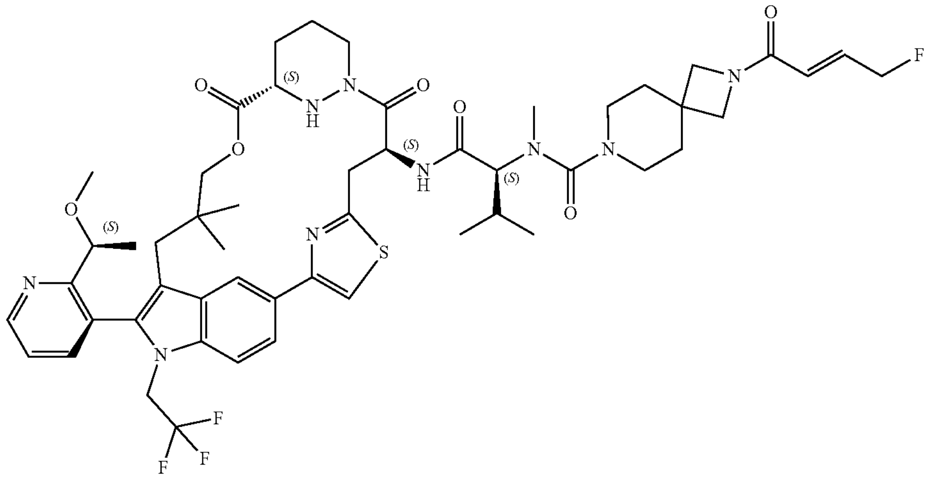 |
| B603 | 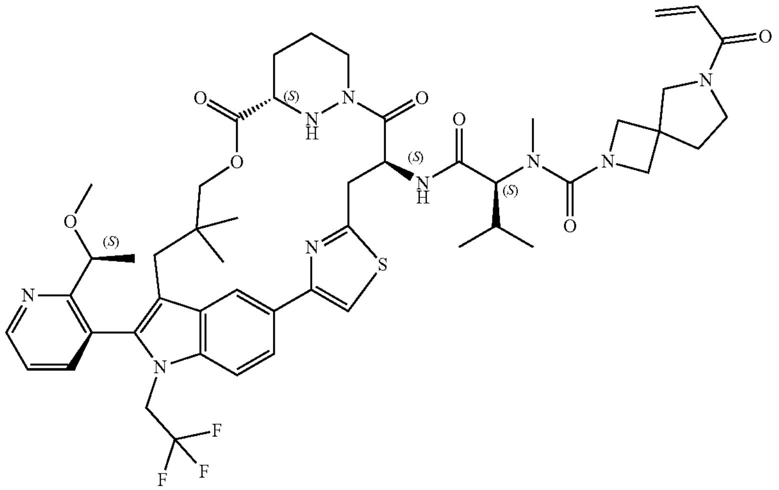 |

TABLE 2-continued
| Certain Compounds | |
|---|---|
| Ex # | Structure |
| B604 | 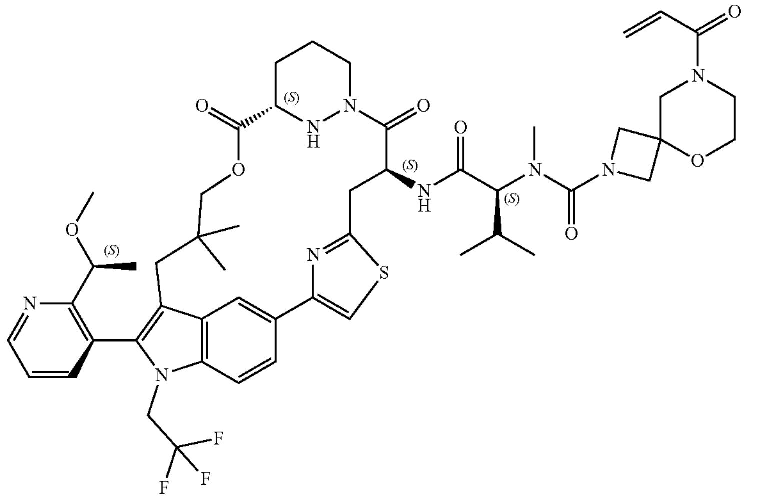 |
| B605 | 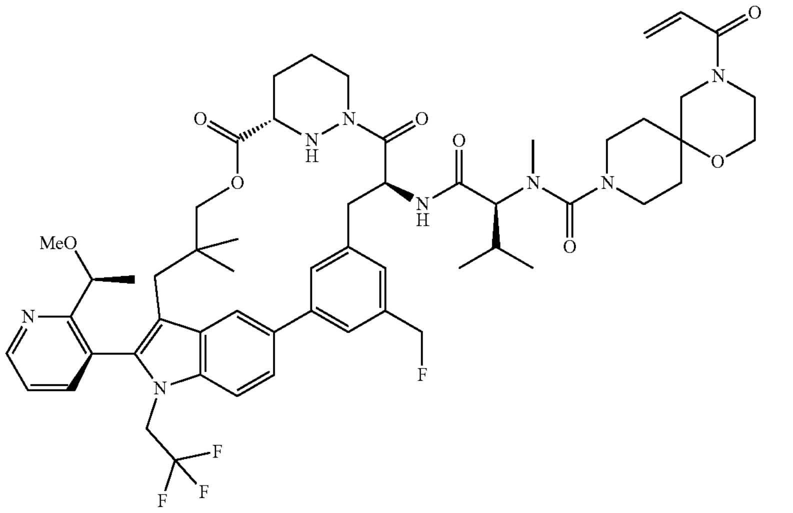 |
| B606 | 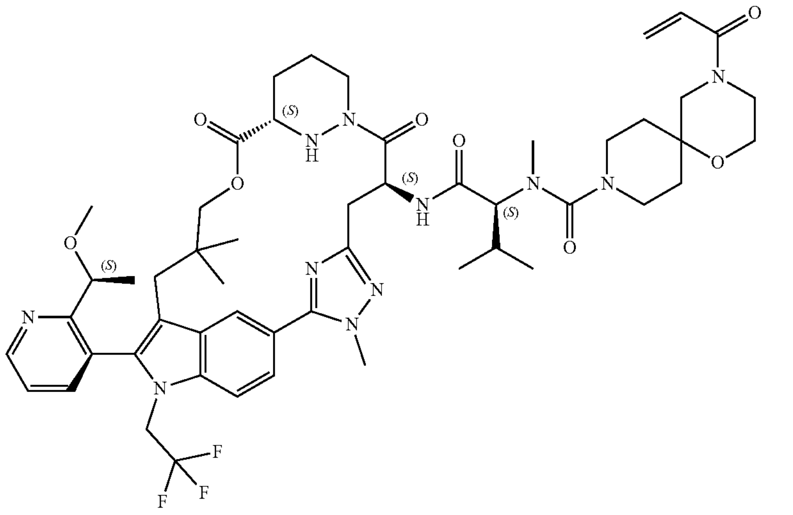 |

TABLE 2-continued
| Certain Compounds | |
|---|---|
| Ex # | Structure |
| B607 | 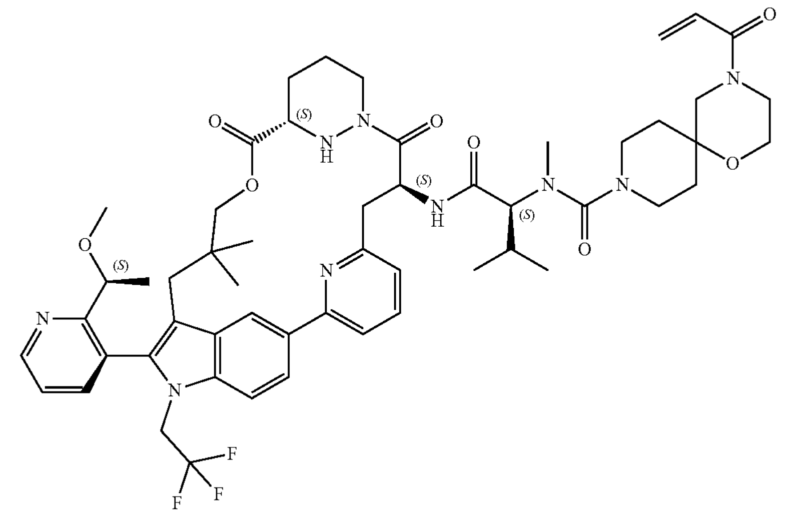 |
| B608 | 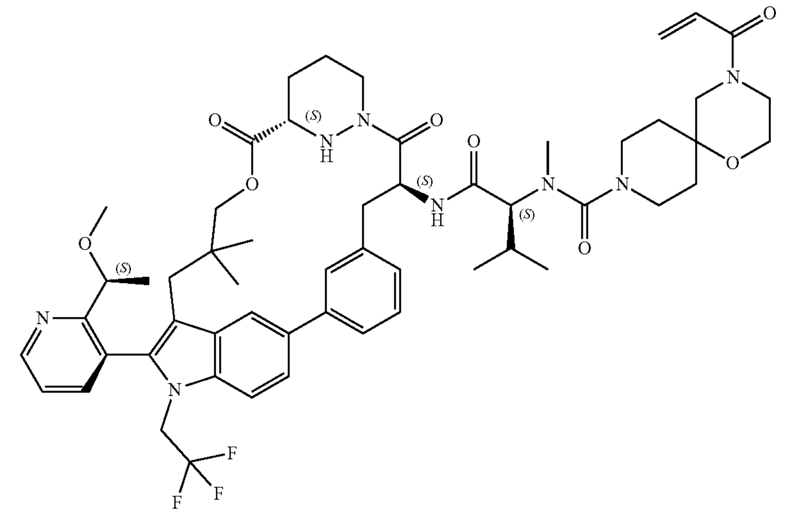 |
| B609 | 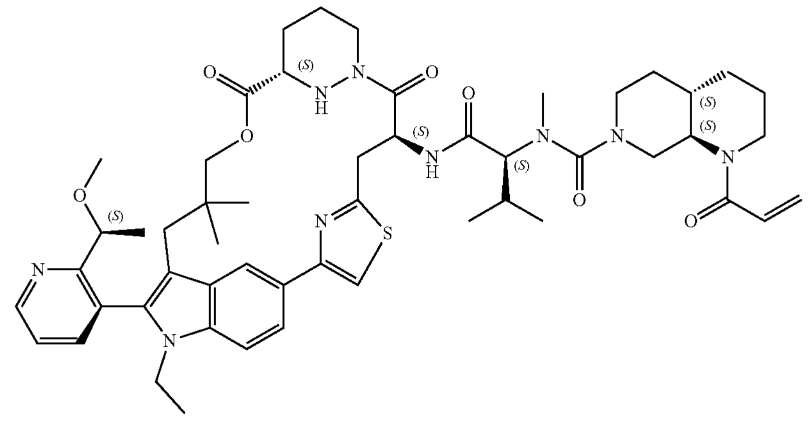 |

TABLE 2-continued
| Certain Compounds | |
|---|---|
| Ex # | Structure |
| B610 | 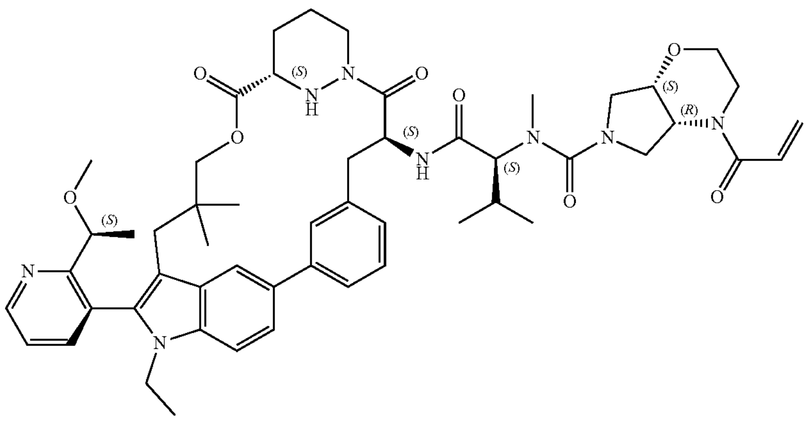 |
| B611 | 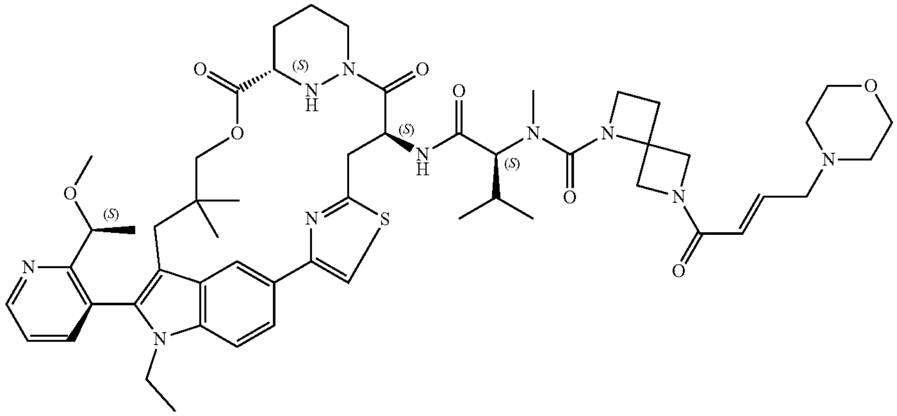 |
| B612 | 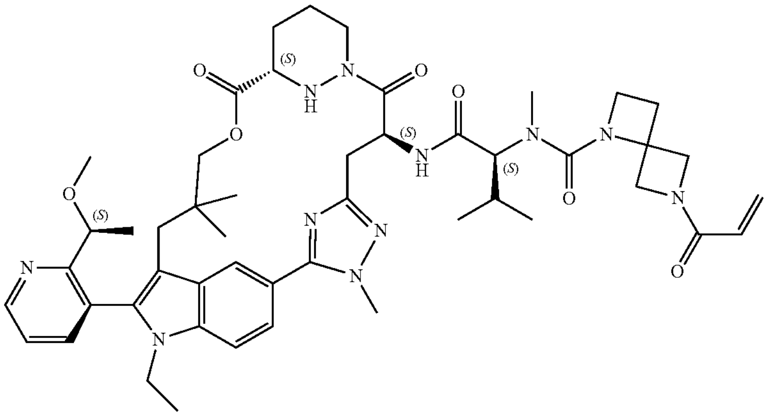 |

TABLE 2-continued
| Certain Compounds | |
|---|---|
| Ex # | Structure |
| B613 | 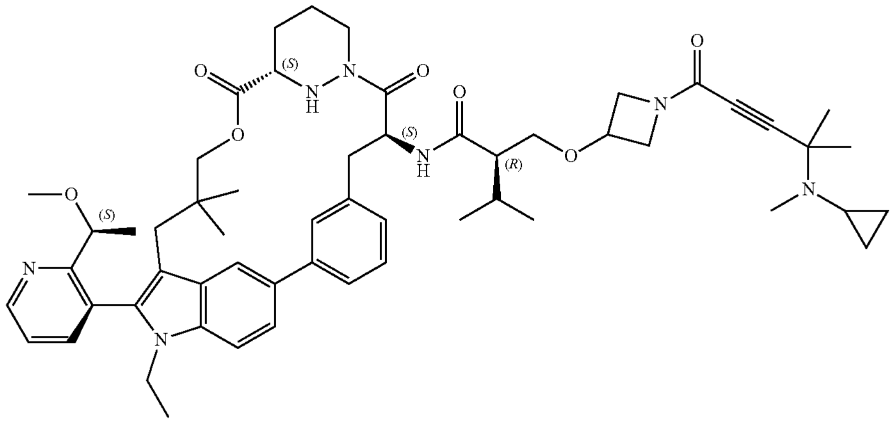 |
| B614 | 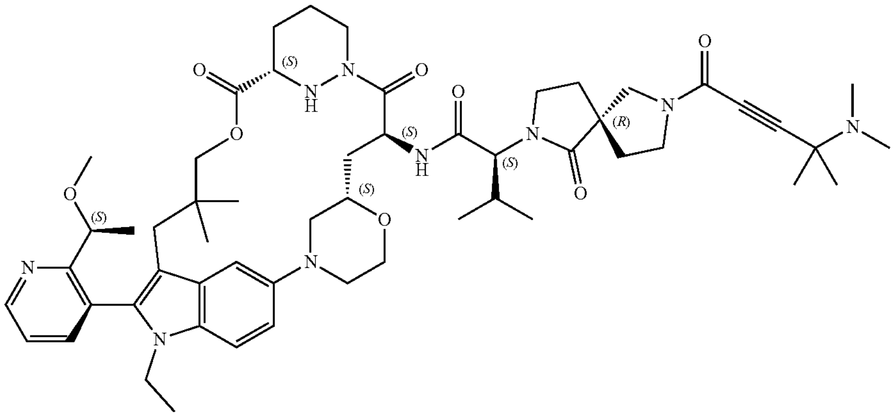 |
| B615 | 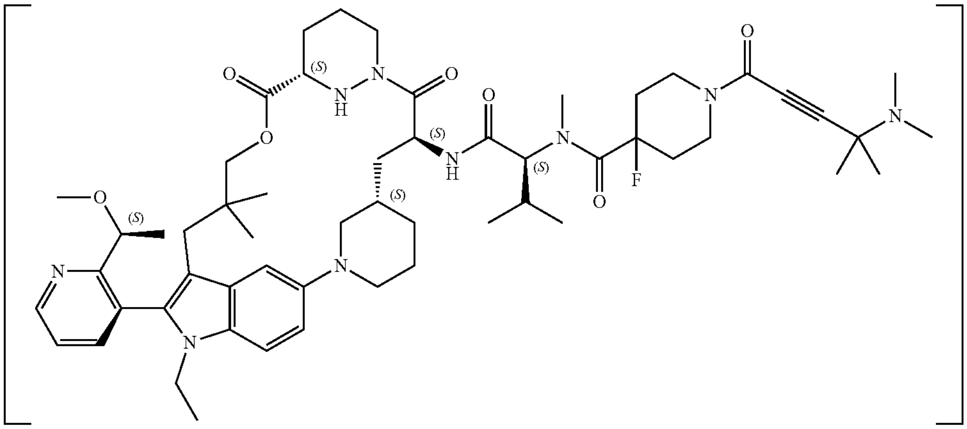 |

TABLE 2-continued
| Certain Compounds | |
|---|---|
| Ex # | Structure |
| B616 | 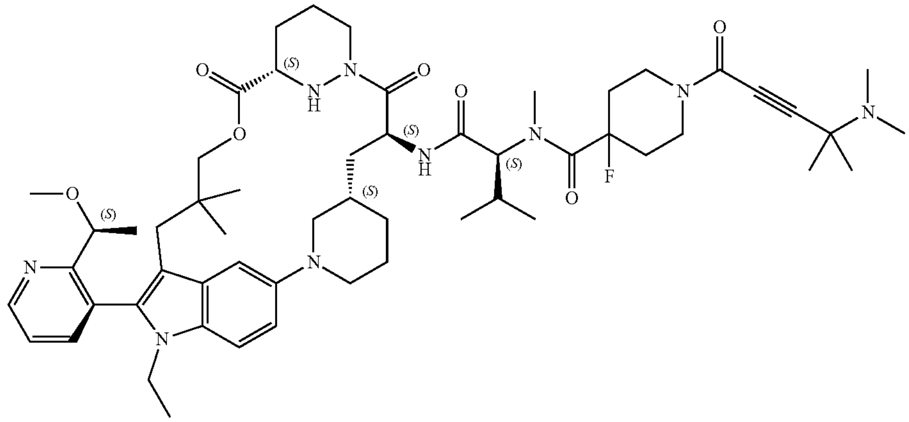 |
| B617 | 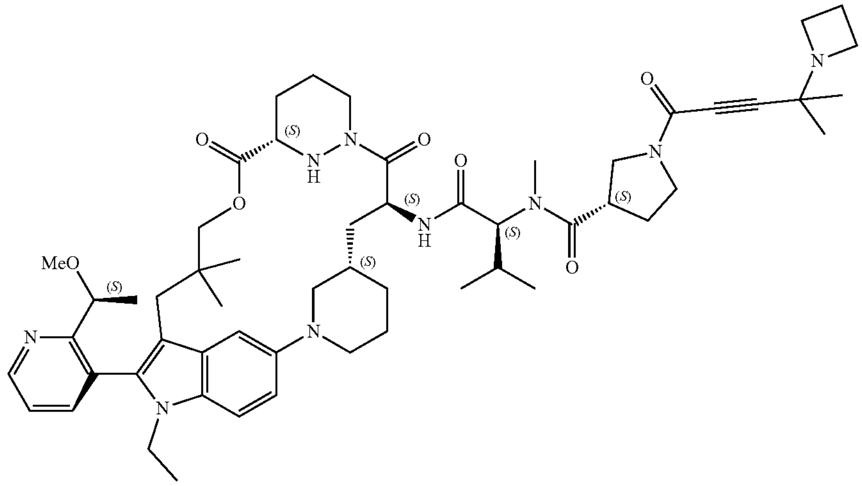 |
| B618 | 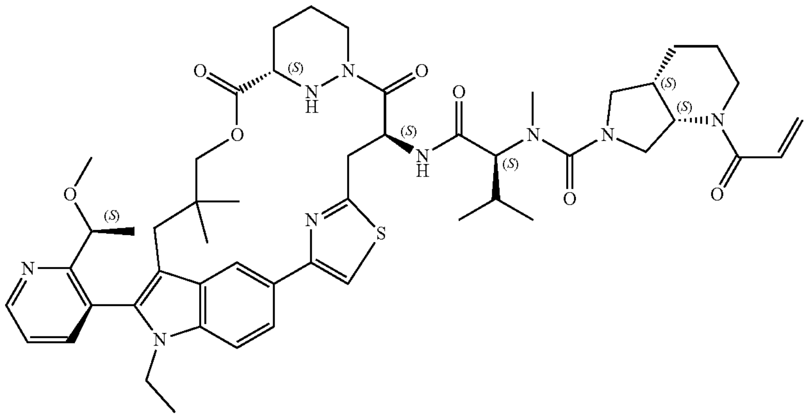 |

TABLE 2-continued
| Certain Compounds | |
|---|---|
| Ex # | Structure |
| B619 | 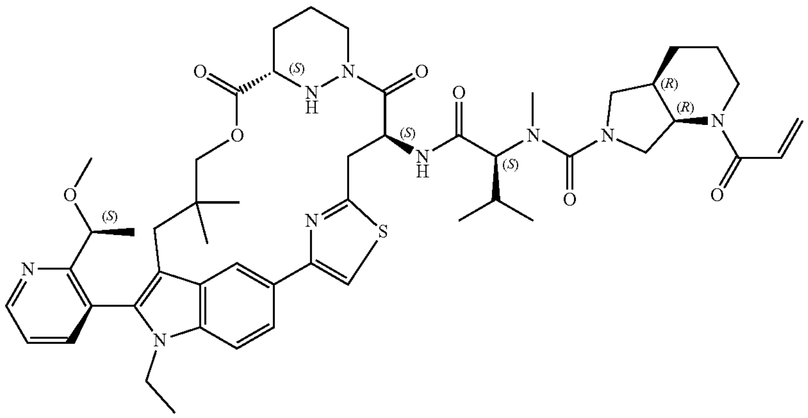 |
| B620 | 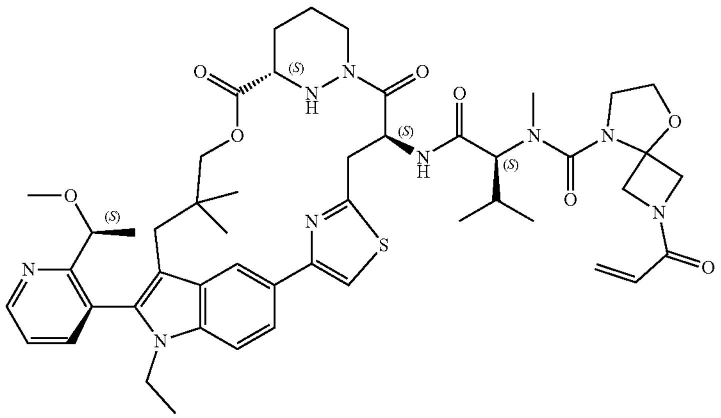 |
| B621 | 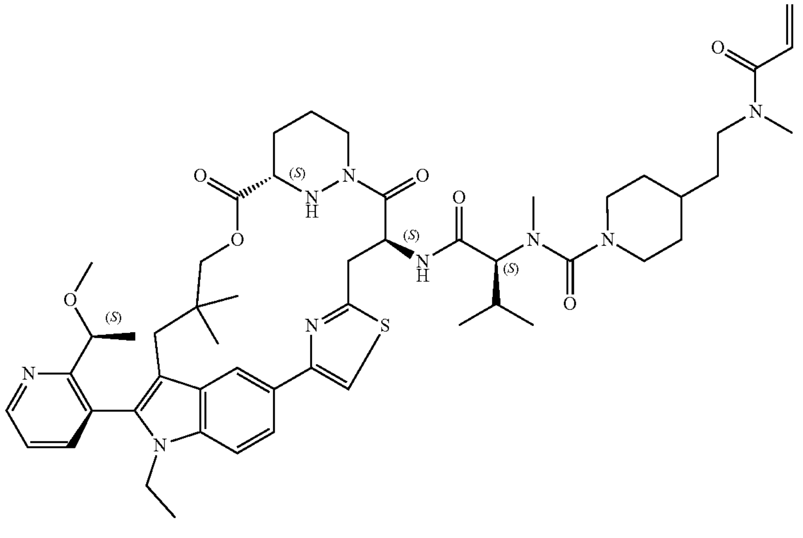 |

TABLE 2-continued
| Certain Compounds | |
|---|---|
| Ex # | Structure |
| B622 | 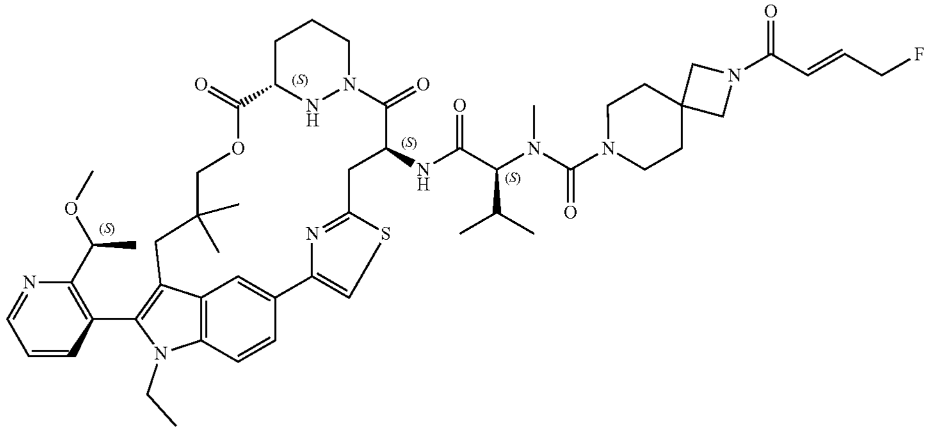 |
| B623 | 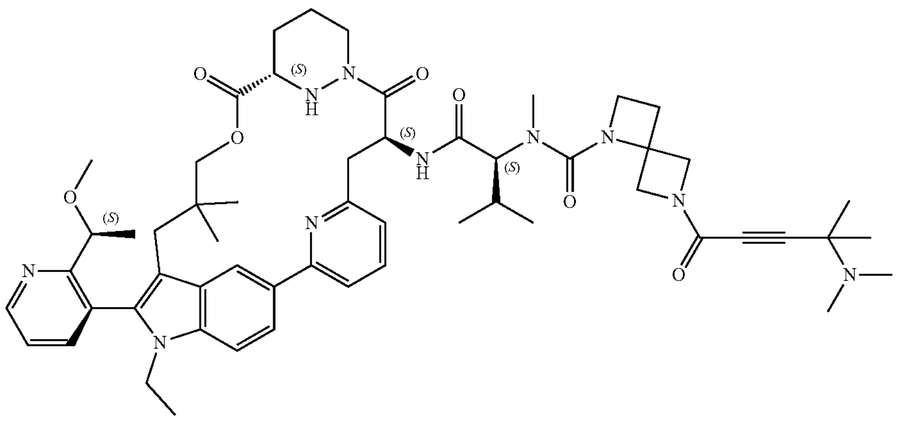 |
| B624 | 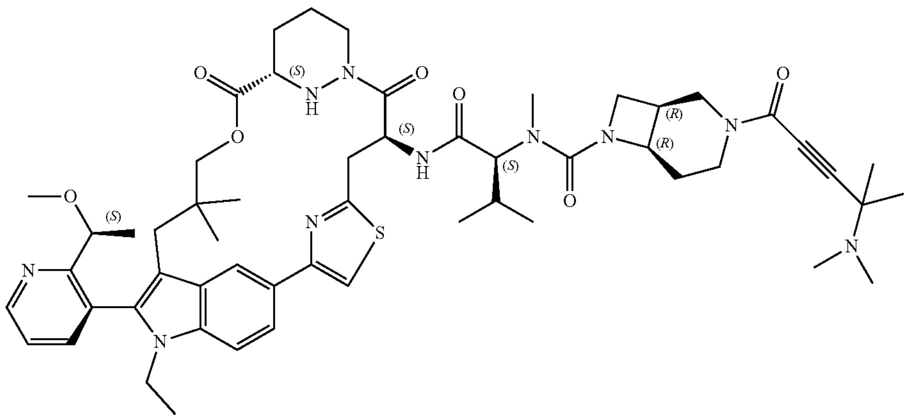 |

TABLE 2-continued
| Certain Compounds | |
|---|---|
| Ex # | Structure |
| B625 | 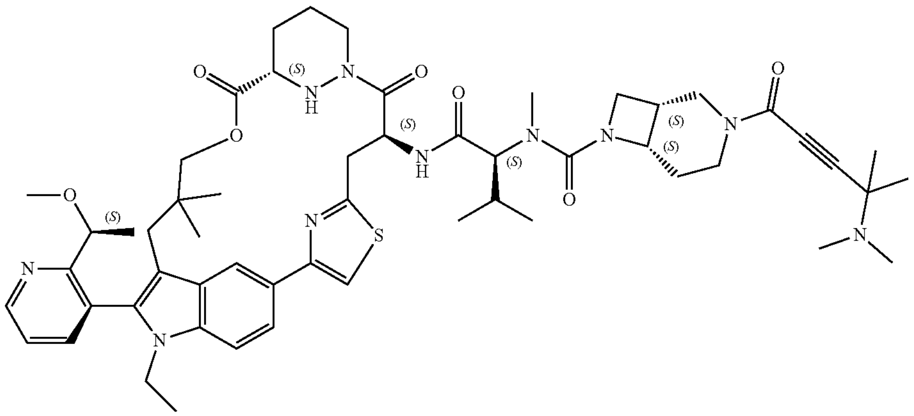 |
| B626 | 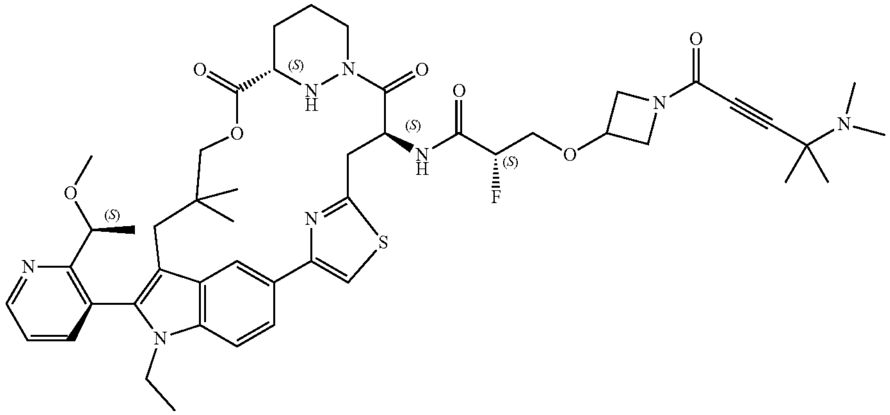 |
| B627 | 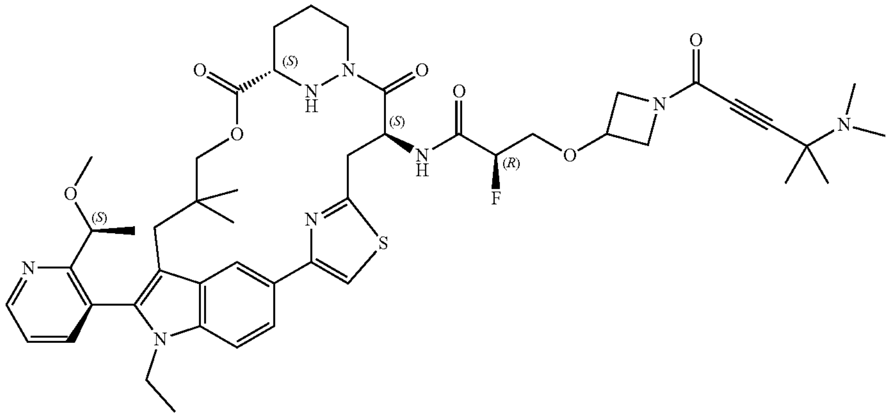 |

TABLE 2-continued
| Certain Compounds | |
|---|---|
| Ex # | Structure |
| B628 | 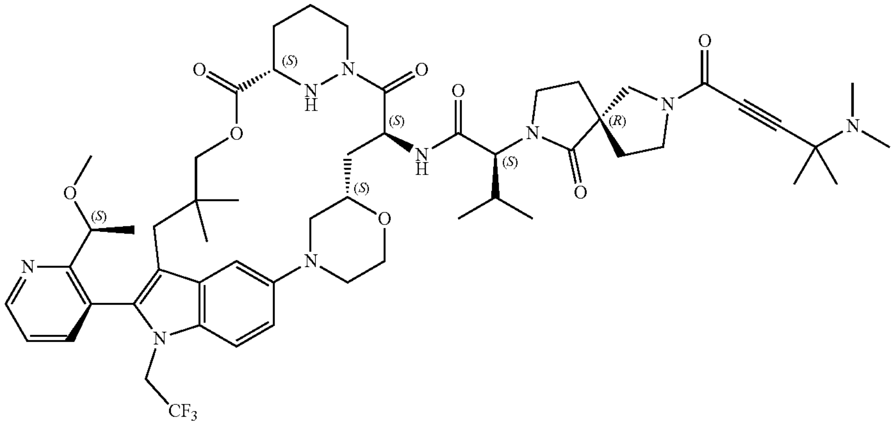 |
| B629 | 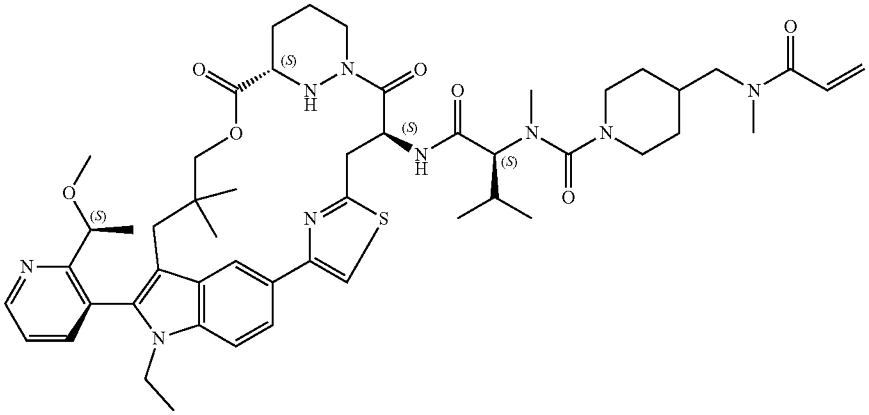 |
| B630 | 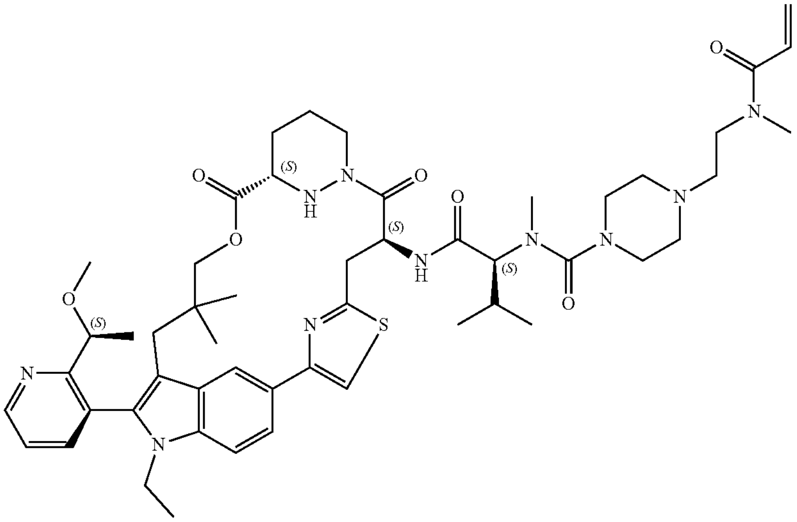 |

TABLE 2-continued
| Certain Compounds | |
|---|---|
| Ex # | Structure |
| B631 | 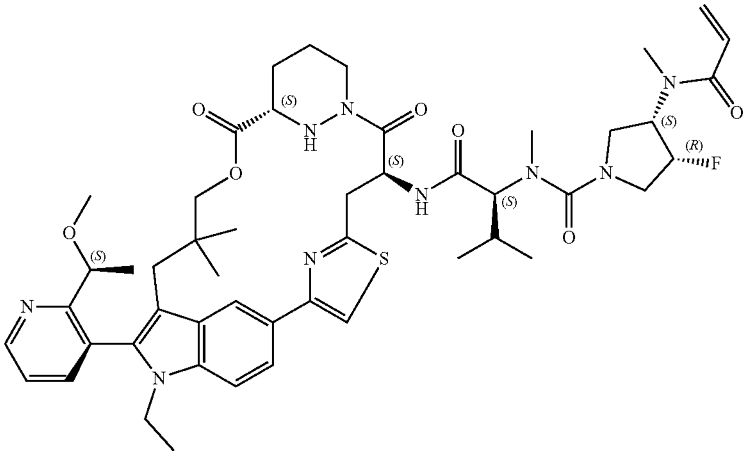 |
| B632 | 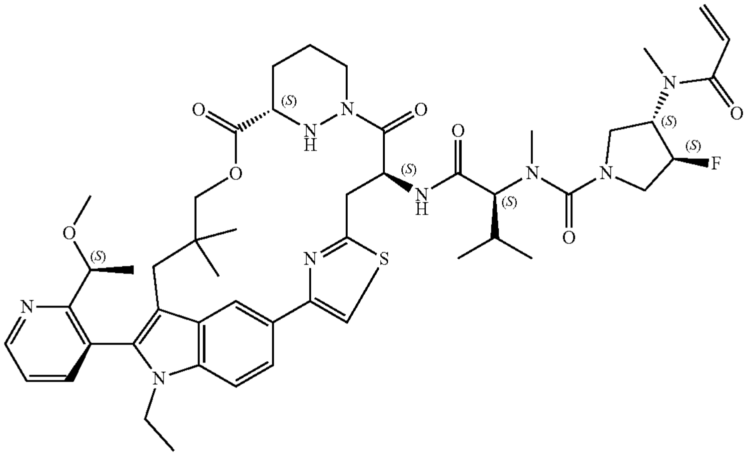 |
| B633 | 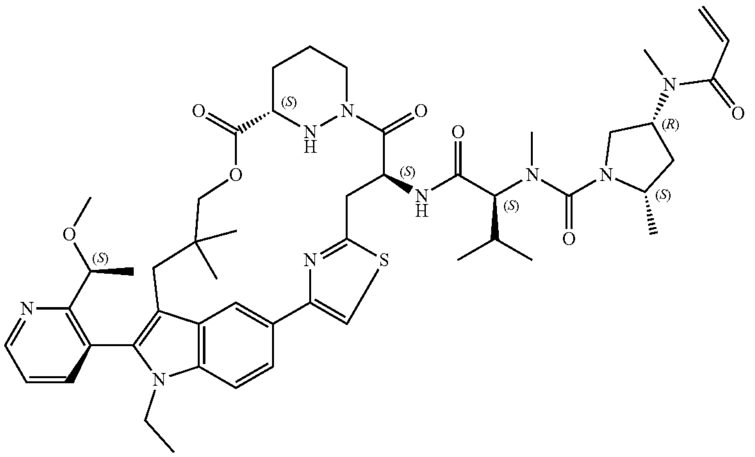 |

TABLE 2-continued
| Certain Compounds | |
|---|---|
| Ex # | Structure |
| B634 | 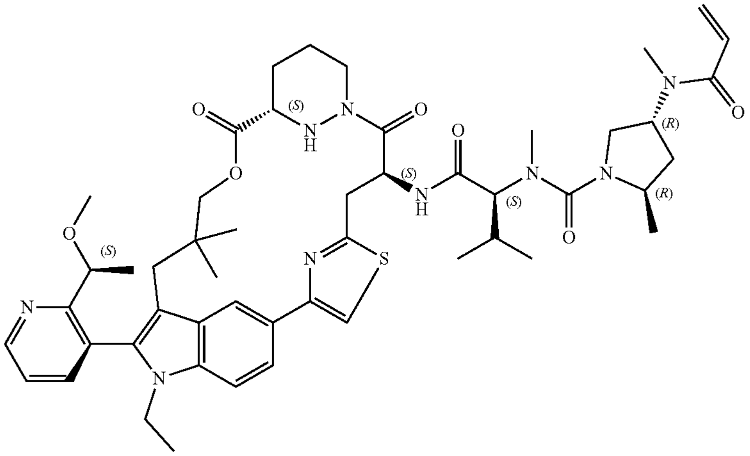 |
| B635 | 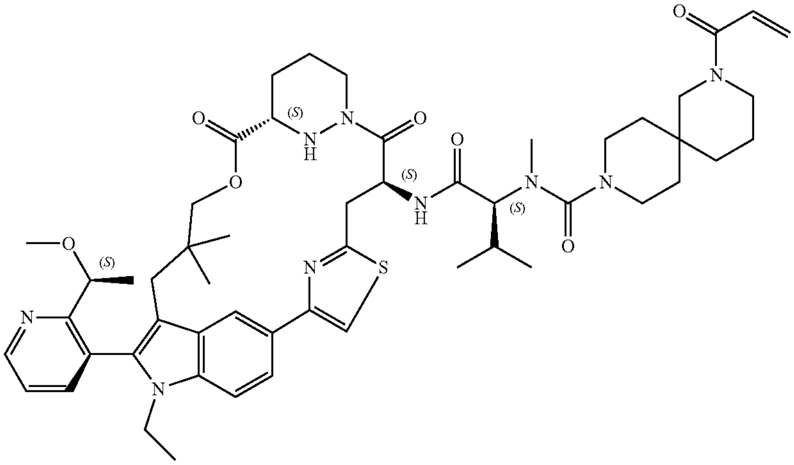 |
| B636 | 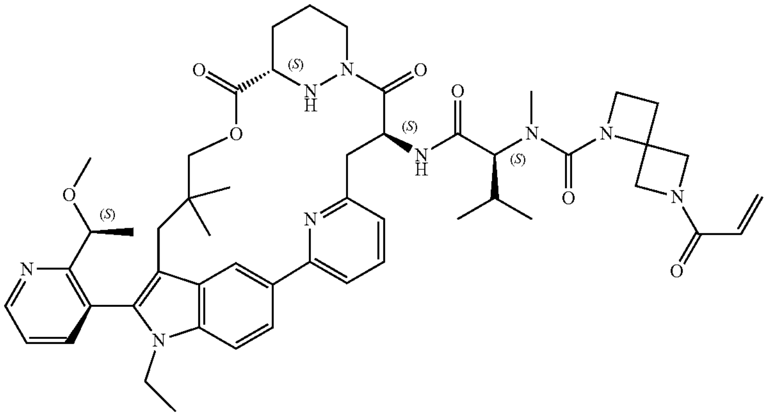 |

TABLE 2-continued
| Certain Compounds | |
|---|---|
| Ex # | Structure |
| B637 | 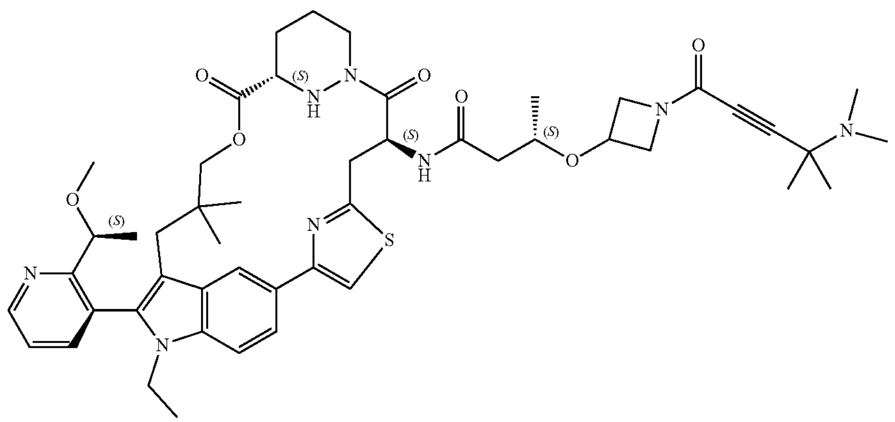 |
| B638 | 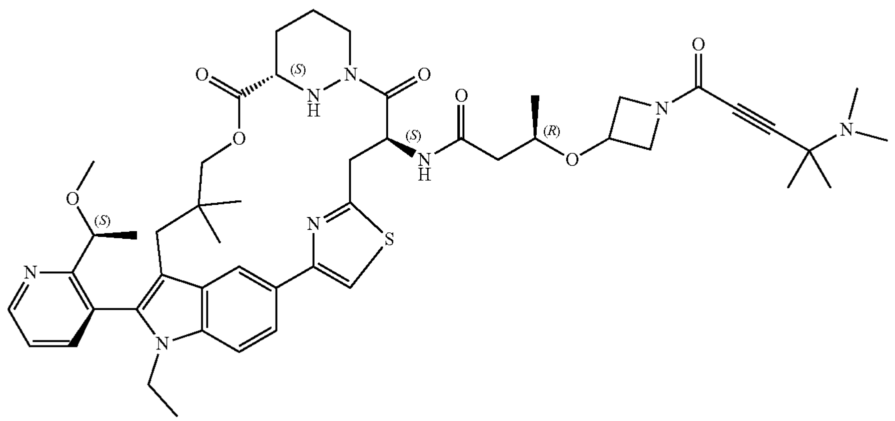 |
| B639 | 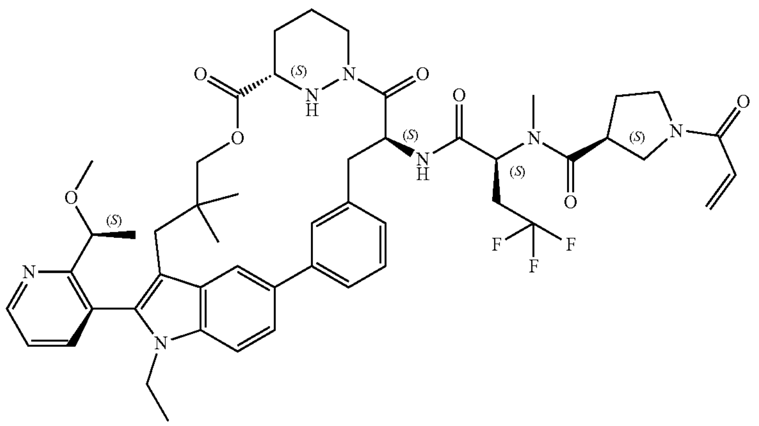 |

TABLE 2-continued
| Certain Compounds | |
|---|---|
| Ex # | Structure |
| B640 | 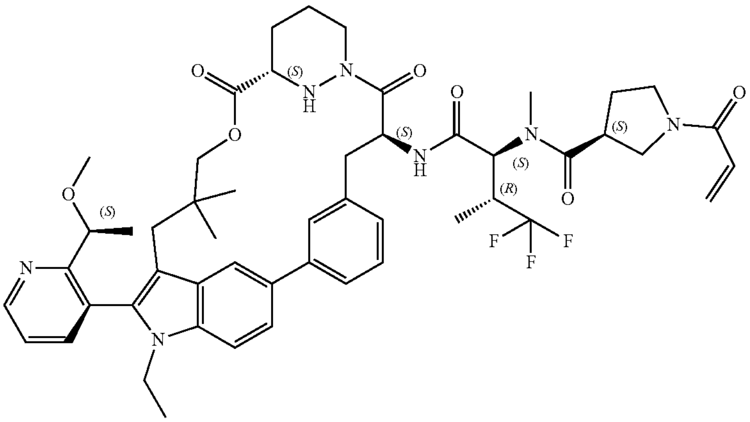 |
| B641 | 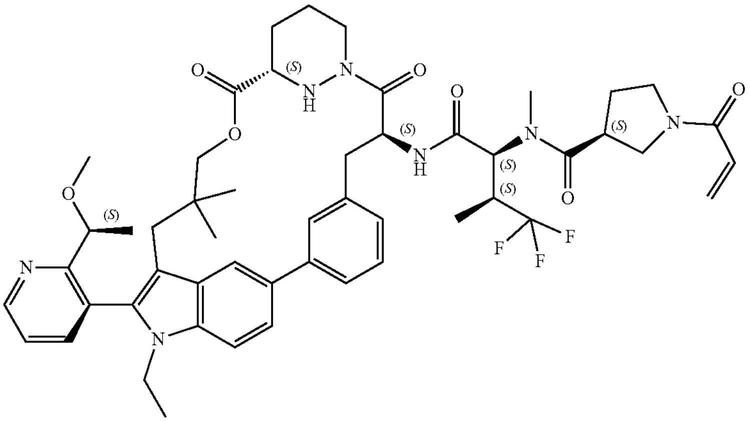 |
| B642 | 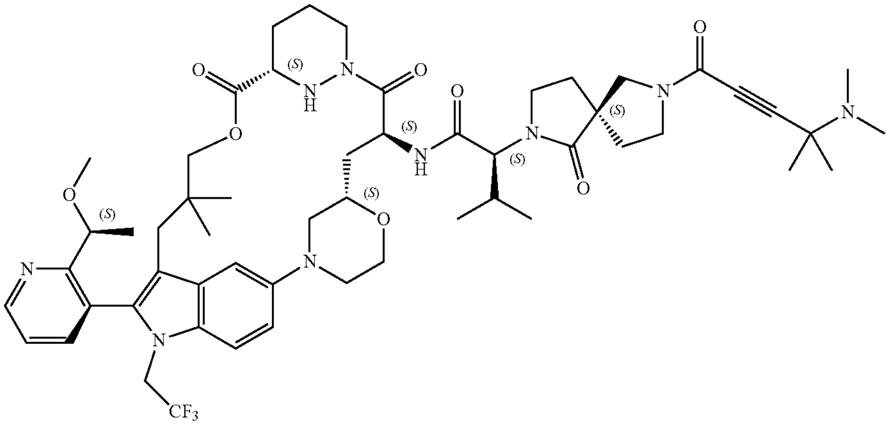 |

TABLE 2-continued
| Certain Compounds | |
|---|---|
| Ex # | Structure |
| B643 | 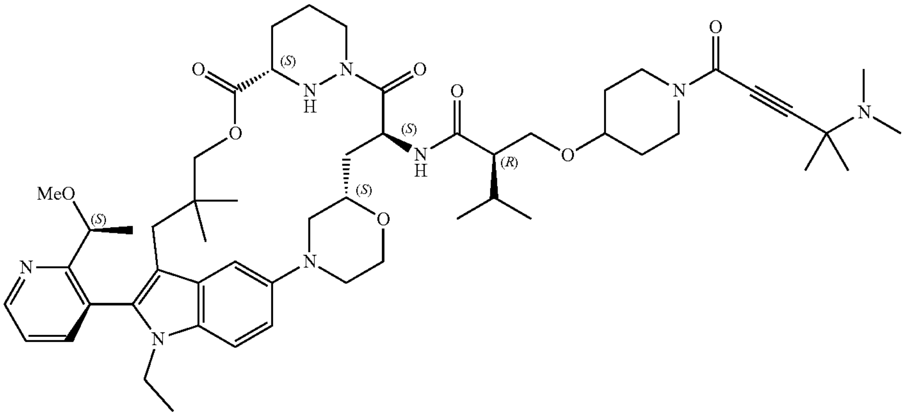 |
| B644 | 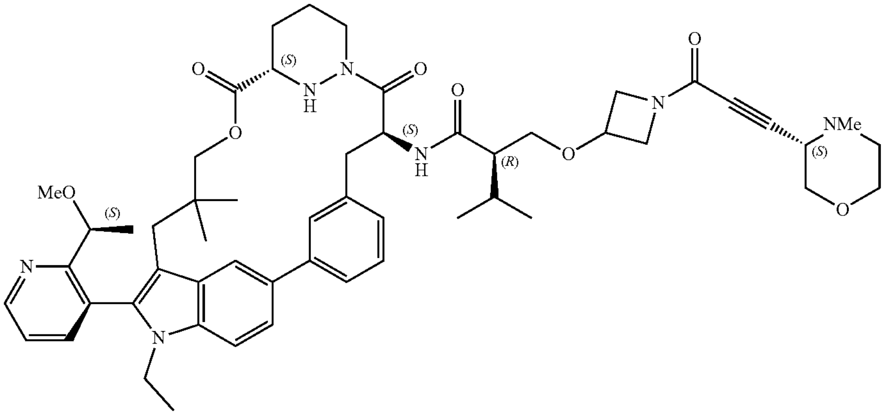 |
| B645 | 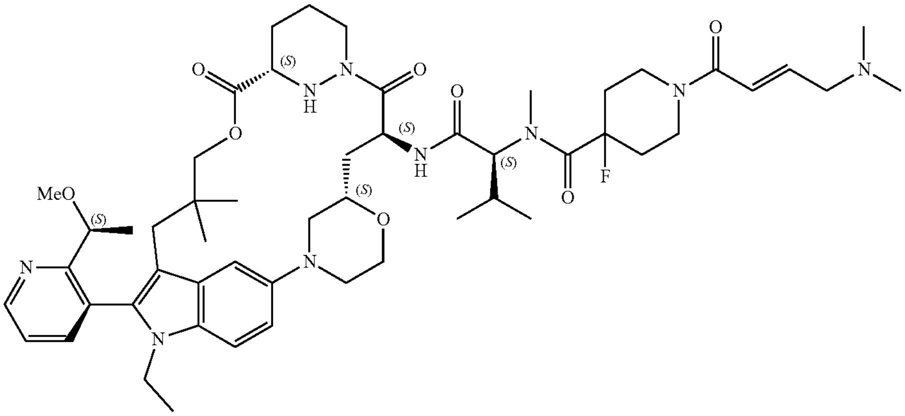 |

TABLE 2-continued
| Certain Compounds | |
|---|---|
| Ex # | Structure |
| B646 | 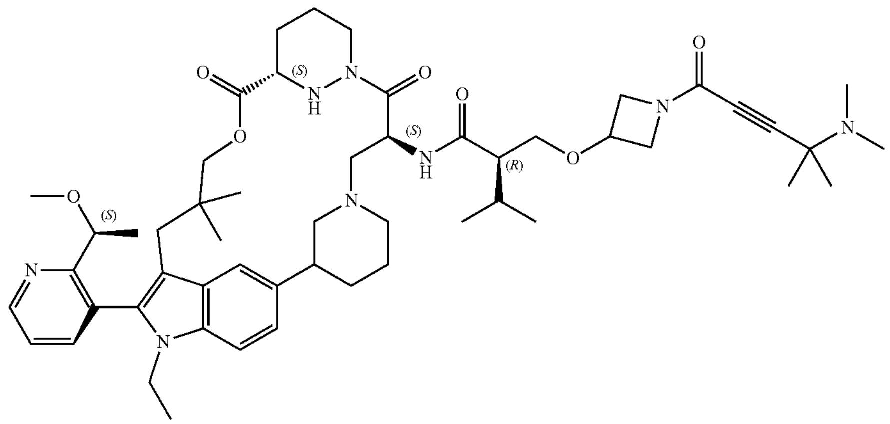 |
| B647 | 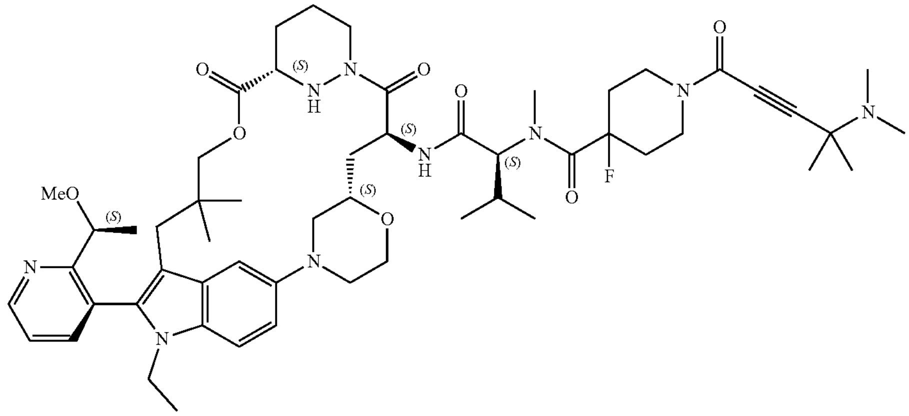 |
| B648 | 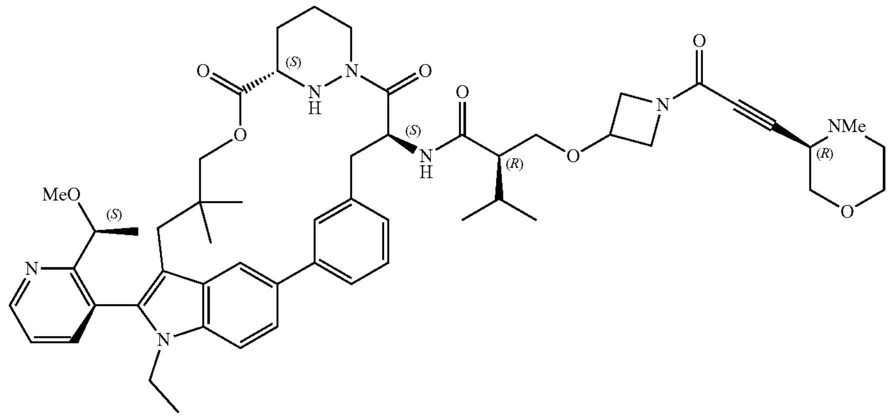 |

TABLE 2-continued
| Certain Compounds | |
|---|---|
| Ex # | Structure |
| B649 | 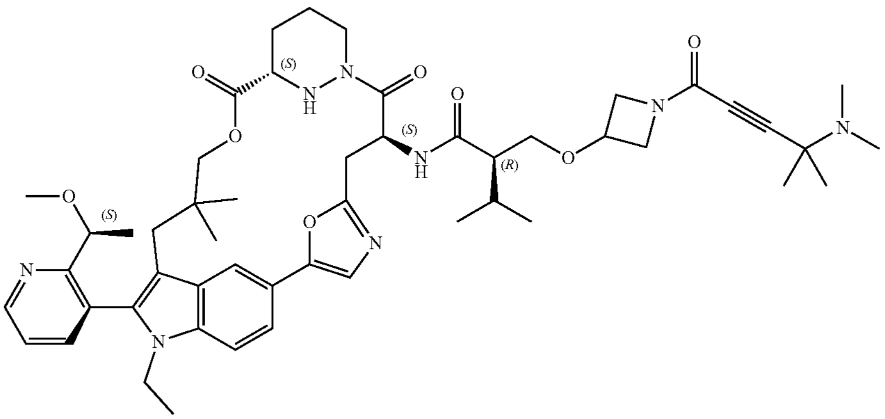 |
| B650 | 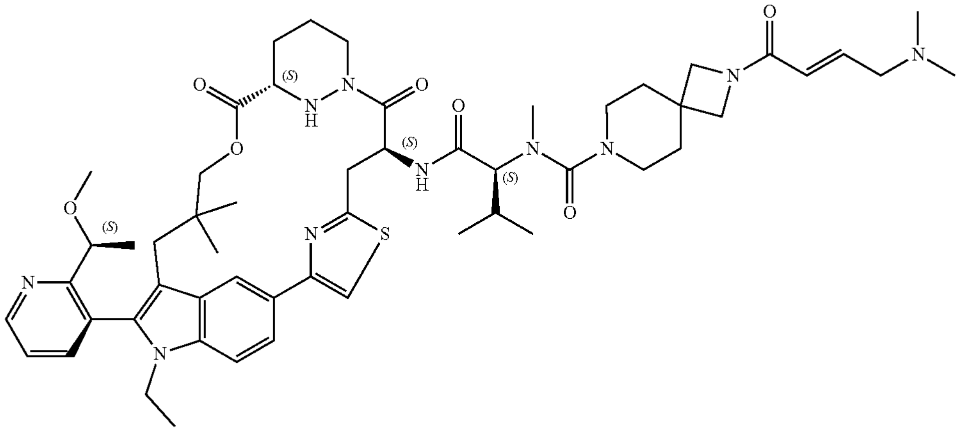 |
| B651 | 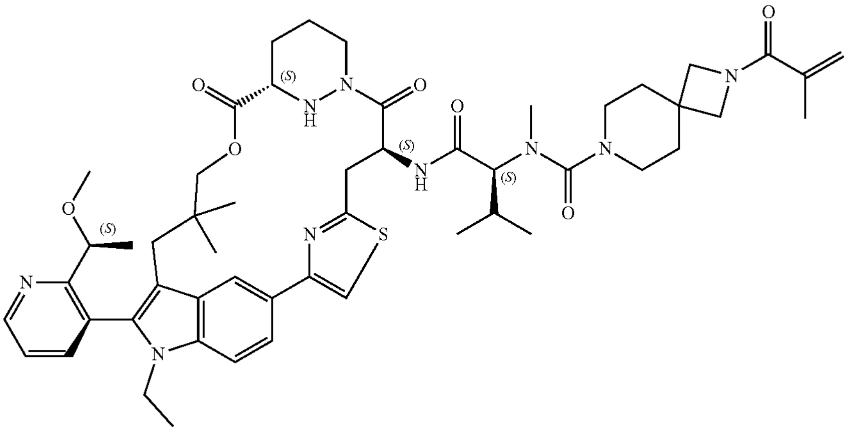 |

TABLE 2-continued
| Certain Compounds | |
|---|---|
| Ex # | Structure |
| B652 | 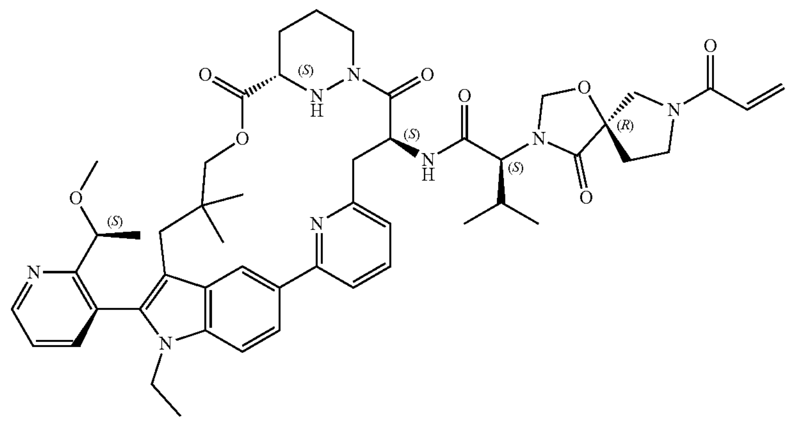 |
| B653 | 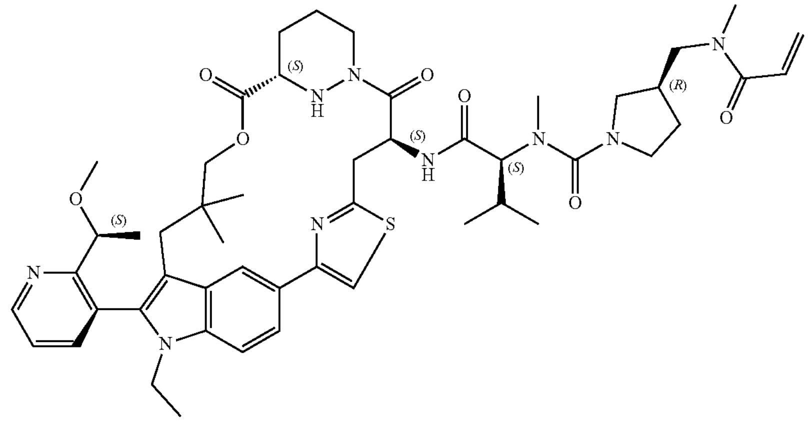 |
| B654 | 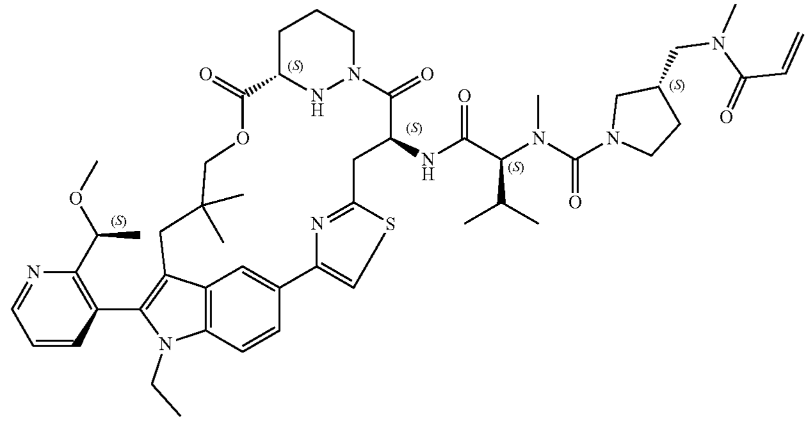 |

TABLE 2-continued
| Certain Compounds | |
|---|---|
| Ex # | Structure |
| B655 | 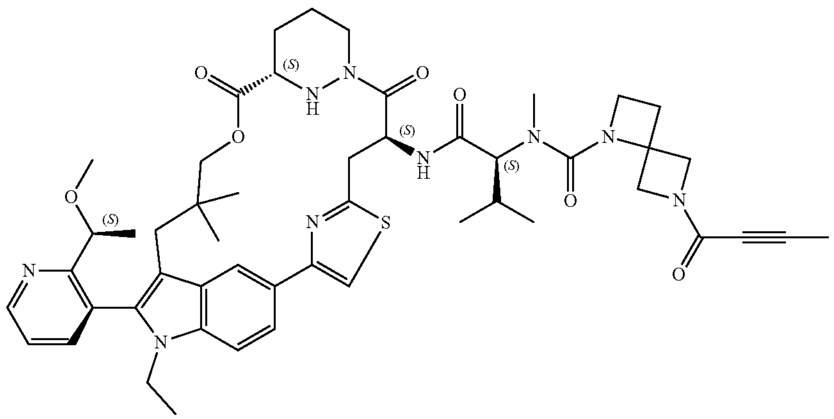 |
| B656 | 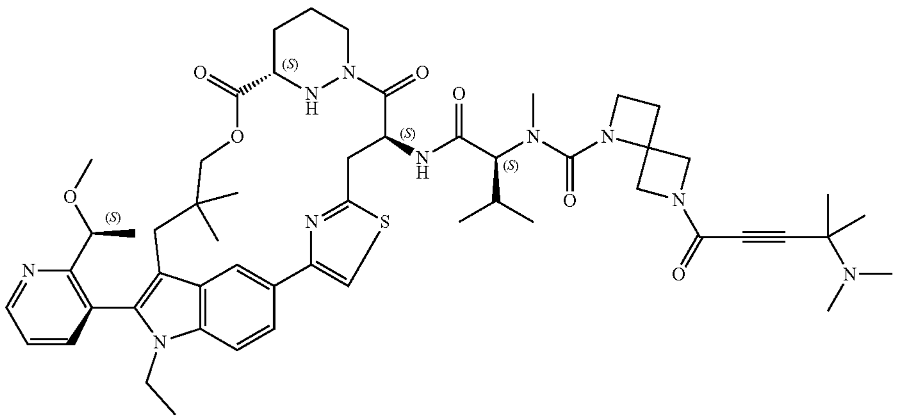 |
| B657 | 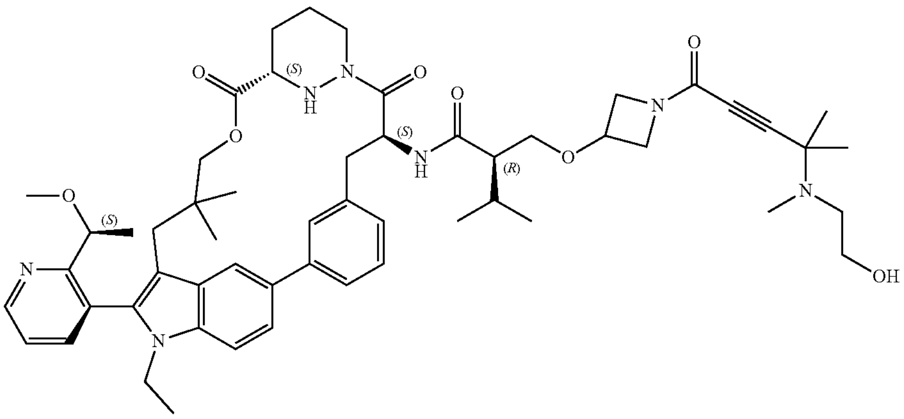 |

TABLE 2-continued
| Certain Compounds | |
|---|---|
| Ex # | Structure |
| B658 | 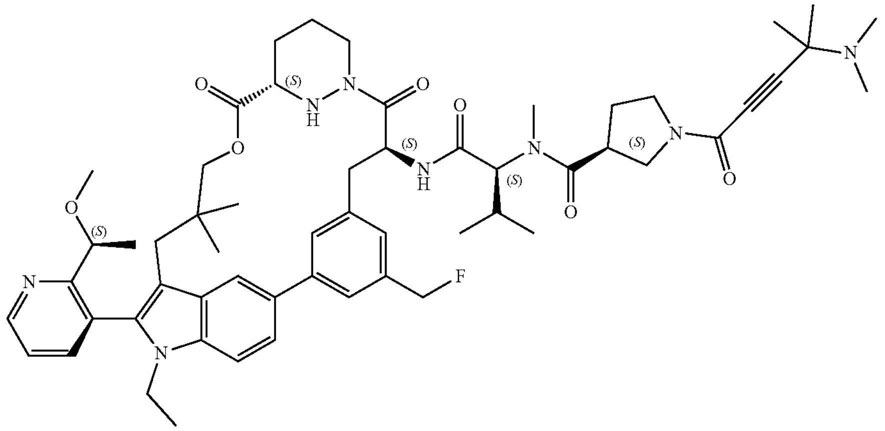 |
| B659 | 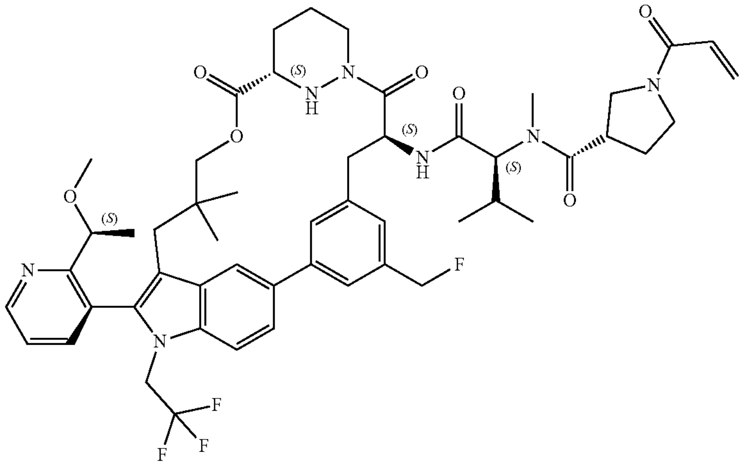 |
| B660 | 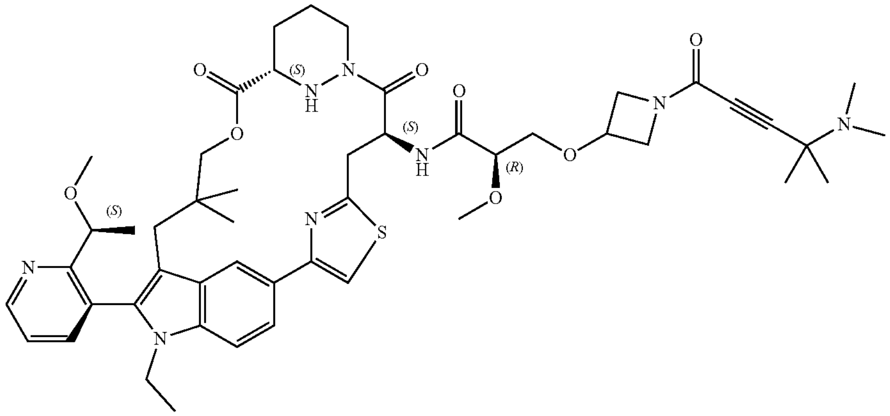 |

TABLE 2-continued
| Certain Compounds | |
|---|---|
| Ex # | Structure |
| B661 | 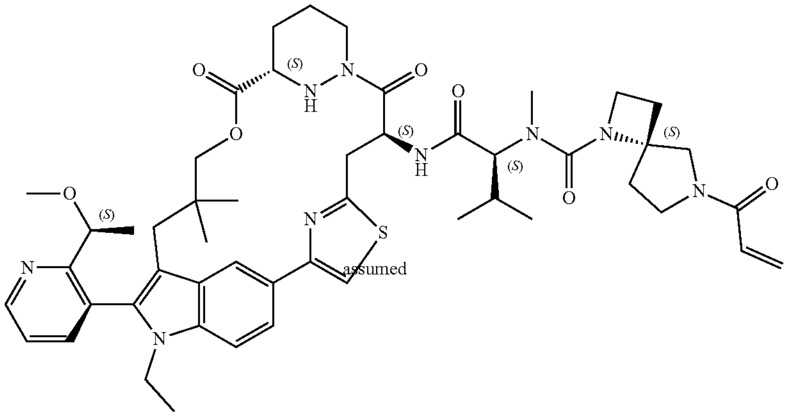 |
| B662 | 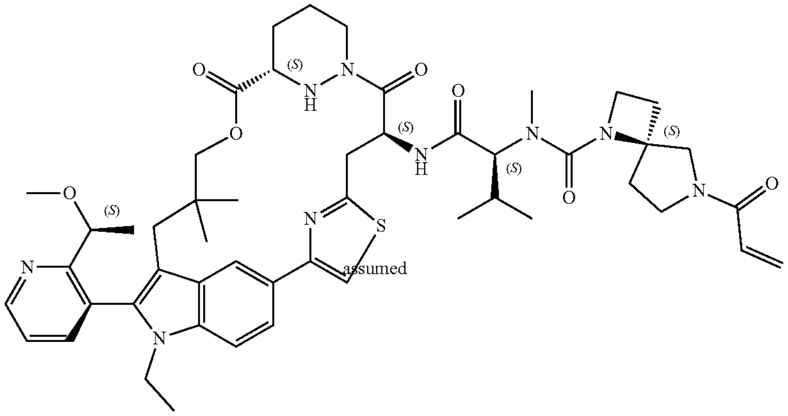 |
| B663 | 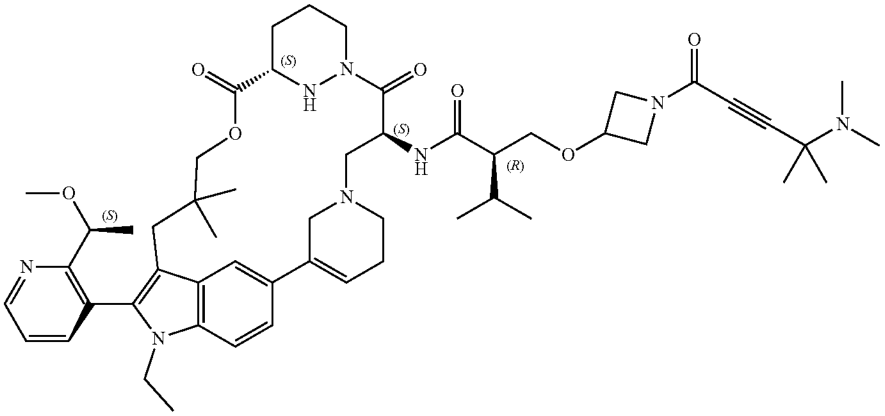 |

TABLE 2-continued
| Certain Compounds | |
|---|---|
| Ex # | Structure |
| B664 | 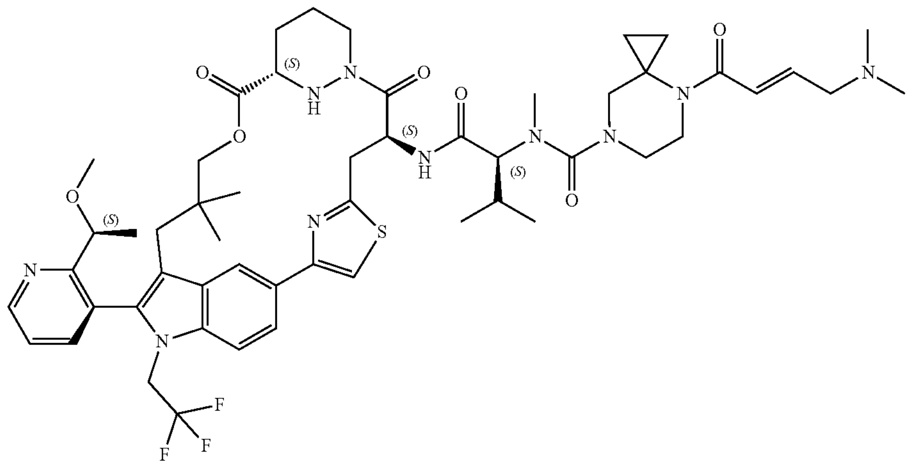 |
| B665 | 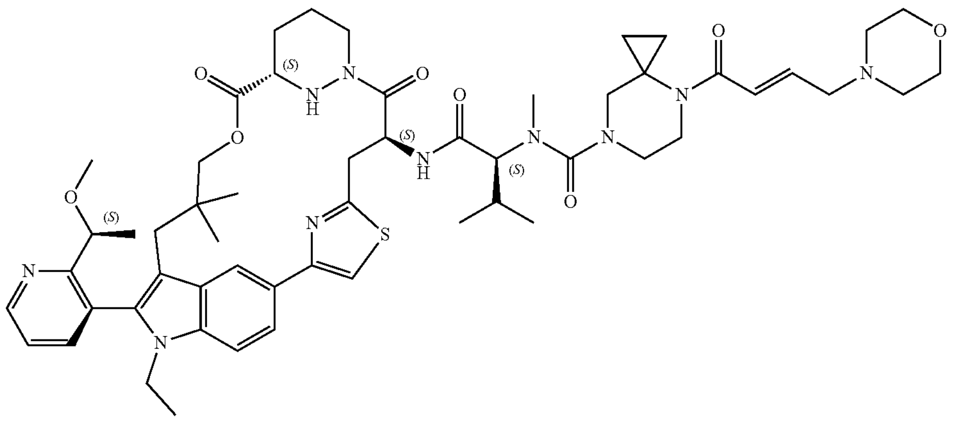 |
| B666 | 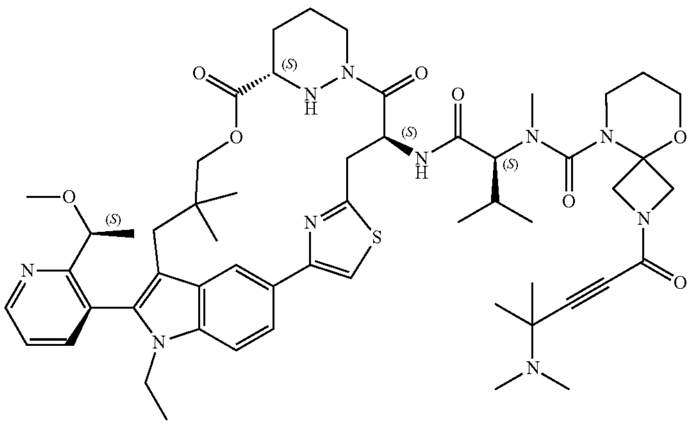 |

TABLE 2-continued
| Certain Compounds | |
|---|---|
| Ex # | Structure |
| B667 | 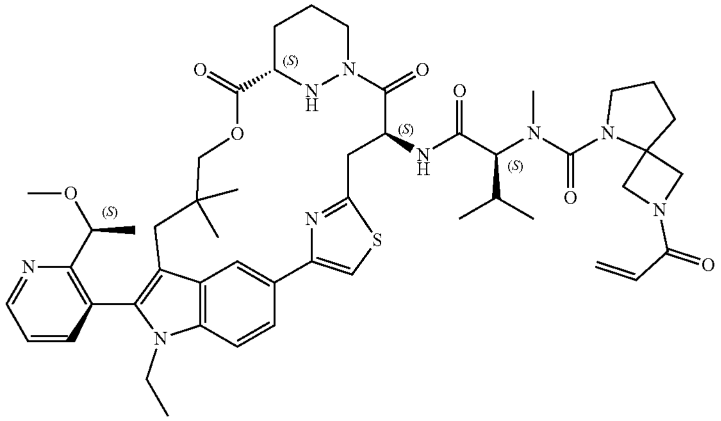 |
| B668 | 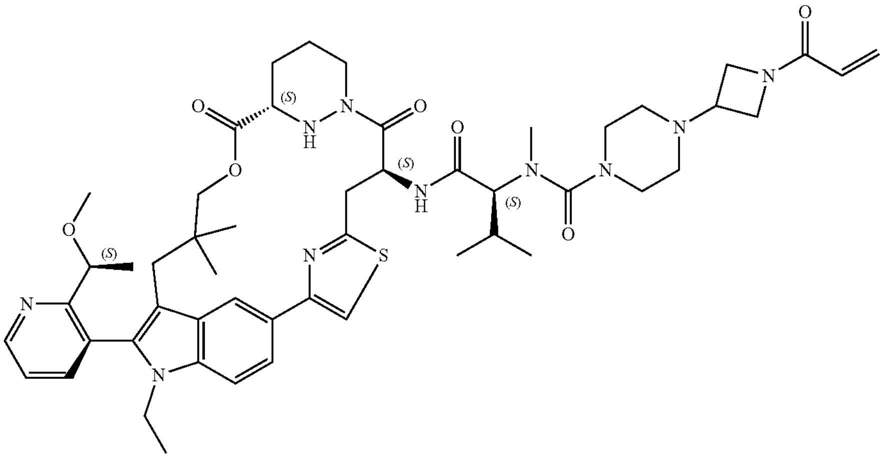 |
| B669 | 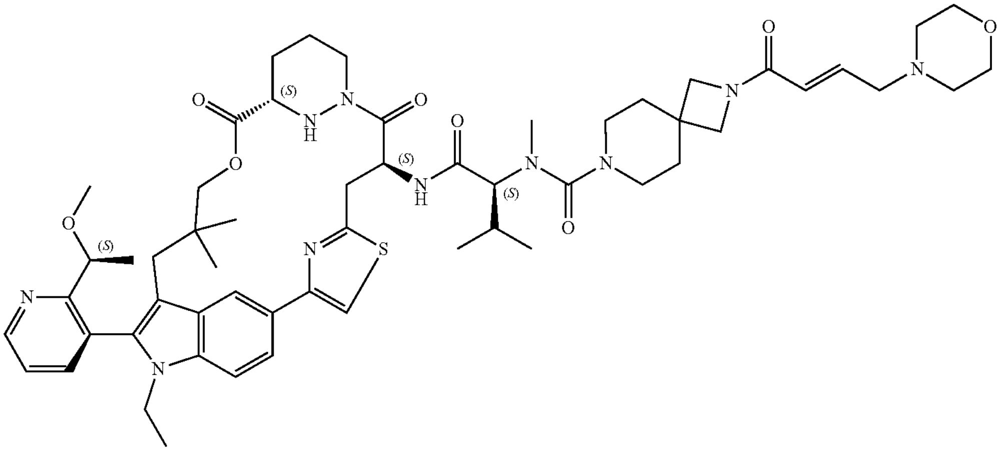 |

TABLE 2-continued
| Certain Compounds | |
|---|---|
| Ex # | Structure |
| B670 | 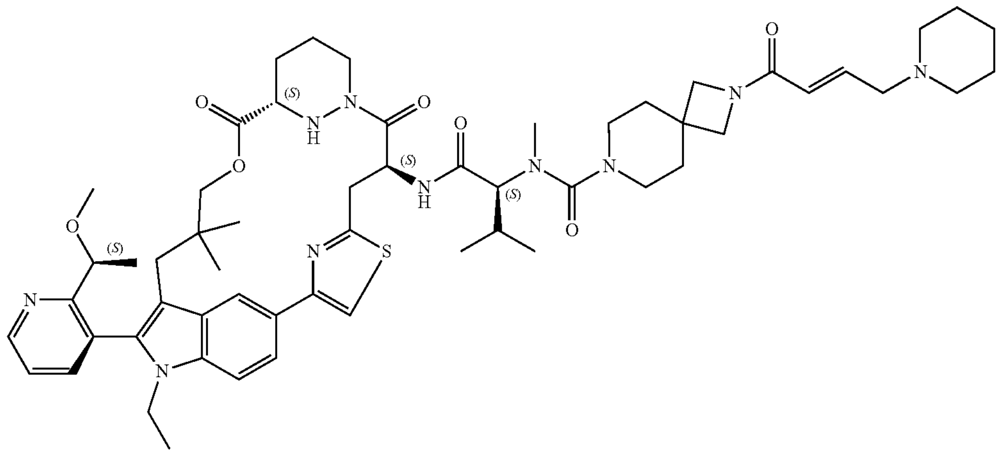 |
| B671 | 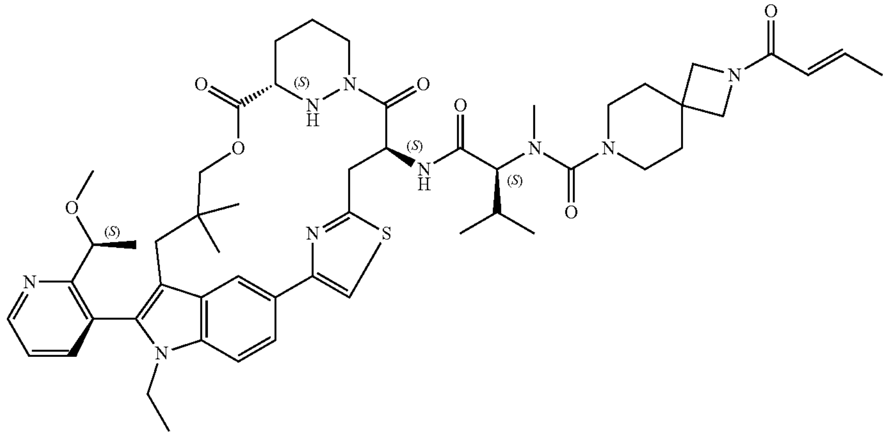 |
| B672 | 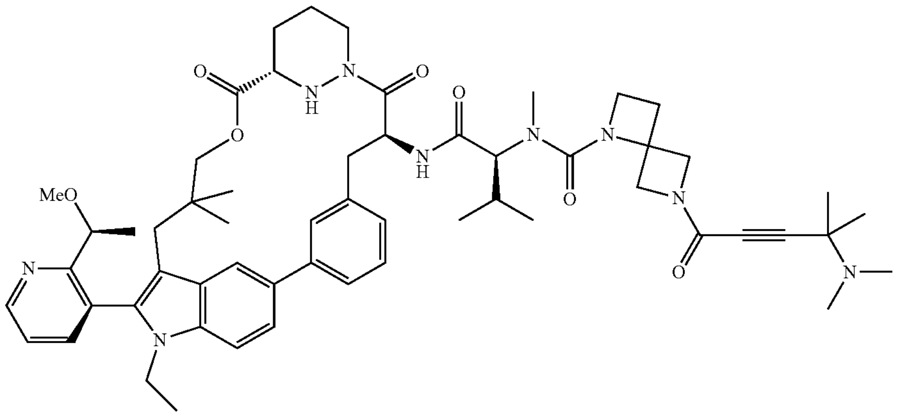 |

TABLE 2-continued
| Certain Compounds | |
|---|---|
| Ex # | Structure |
| B673 | 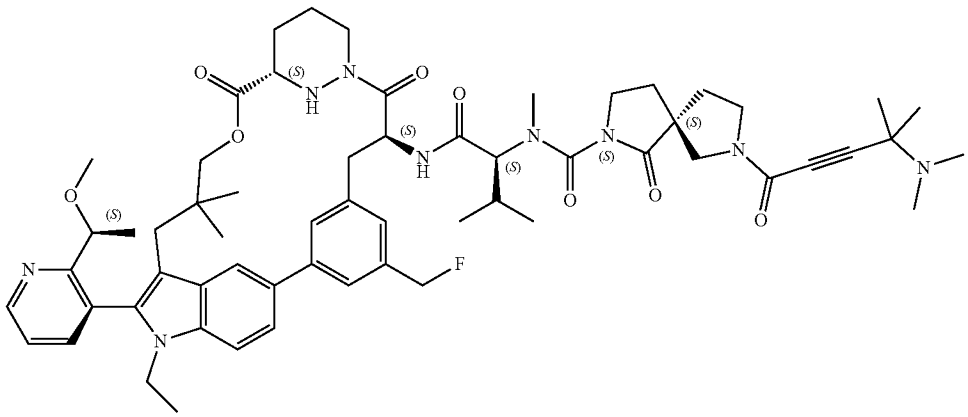 |
| B674 | 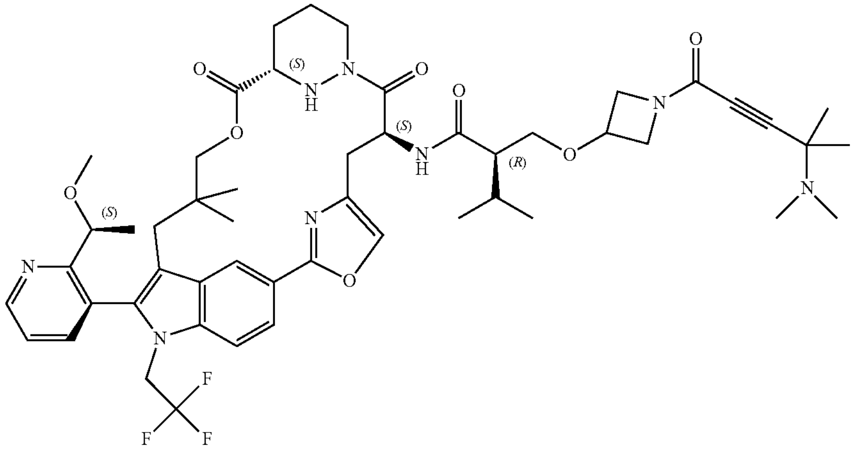 |
| B675 | 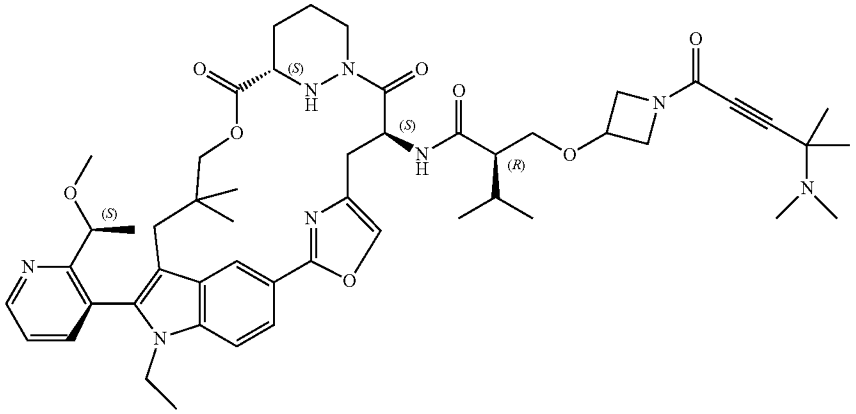 |

TABLE 2-continued
| Certain Compounds | |
|---|---|
| Ex # | Structure |
| B676 | 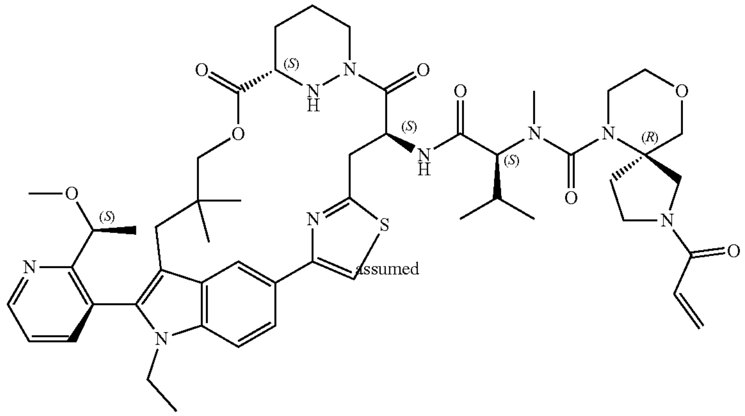 |
| B677 | 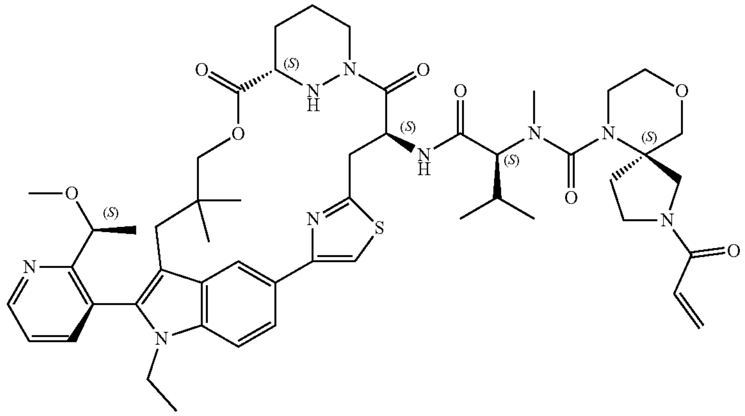 |
| B678 | 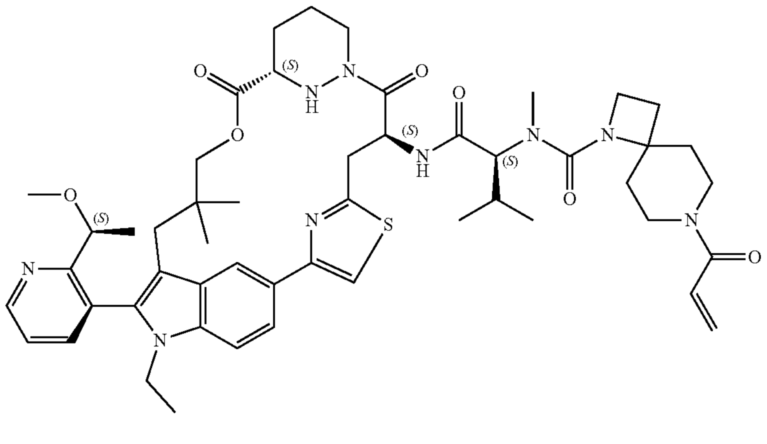 |

TABLE 2-continued
| Certain Compounds | |
|---|---|
| Ex # | Structure |
| B679 | 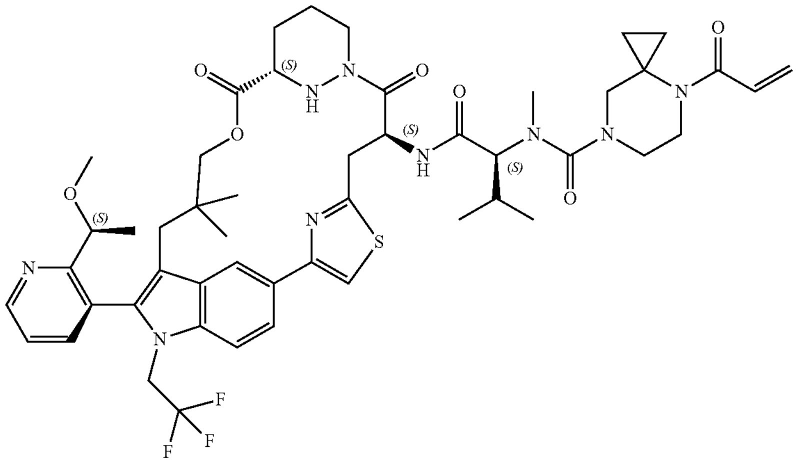 |
| B680 | 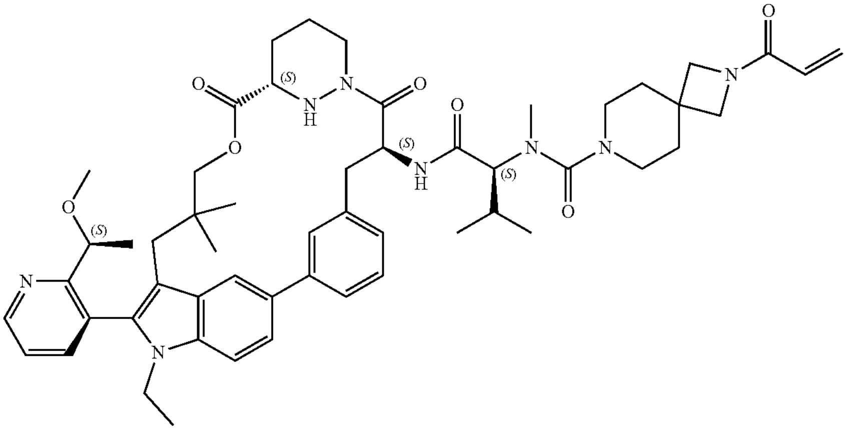 |
| B681 | 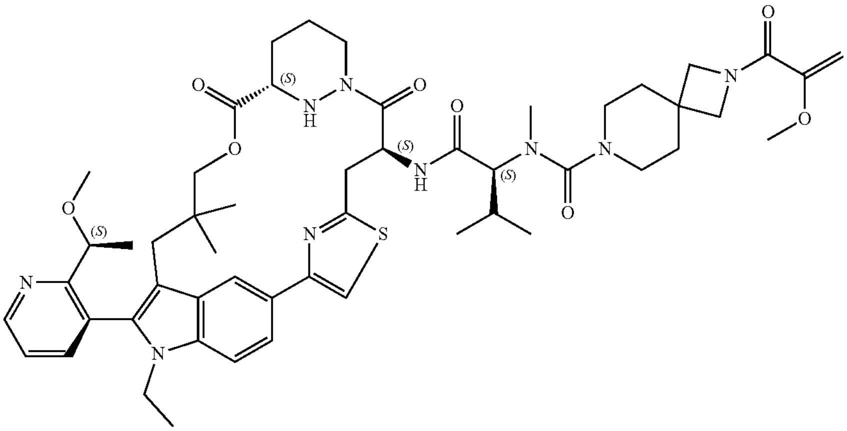 |

TABLE 2-continued
| Certain Compounds | |
|---|---|
| Ex # | Structure |
| B682 | 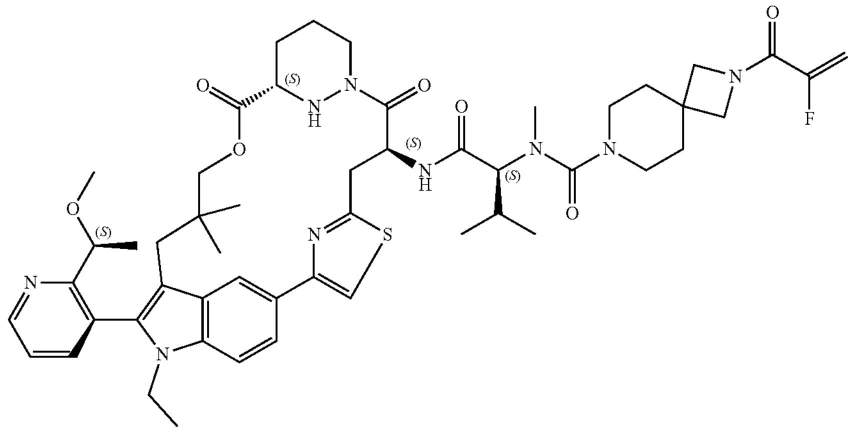 |
| B683 | 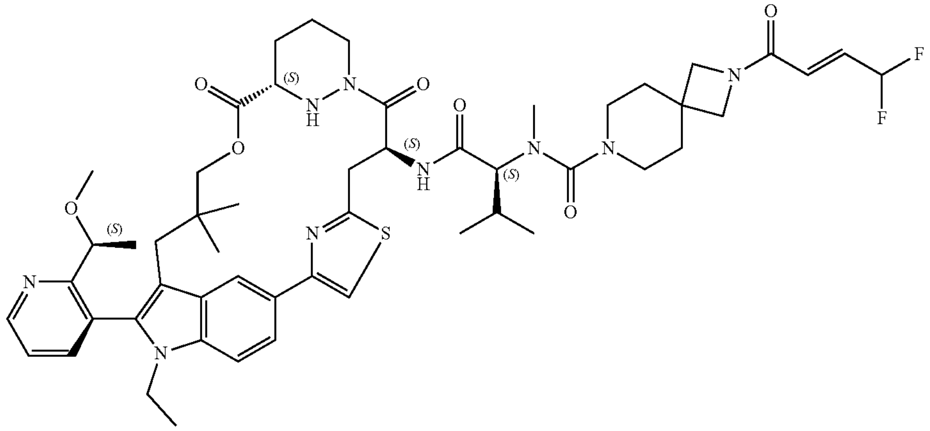 |
| B684 | 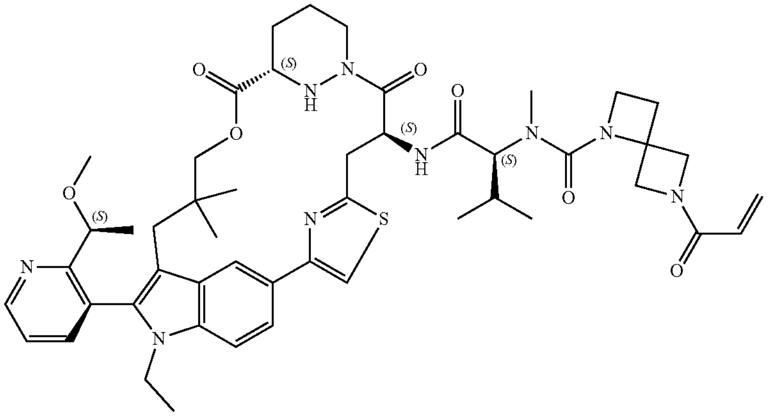 |

TABLE 2-continued
| Certain Compounds | |
|---|---|
| Ex # | Structure |
| B685 | 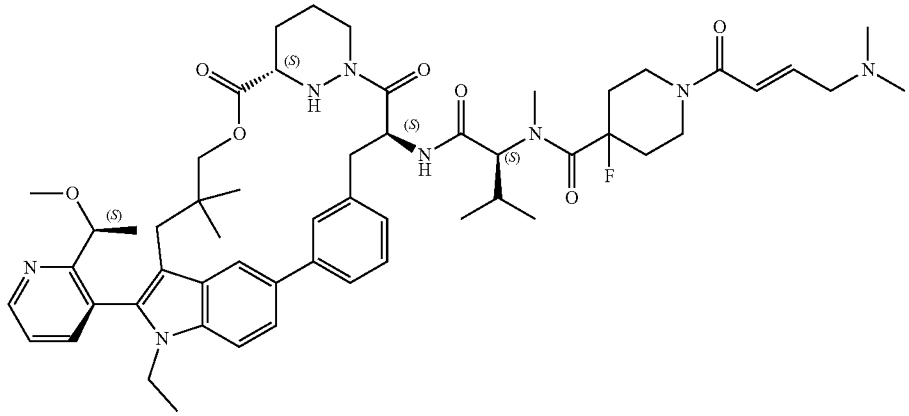 |
| B686 | 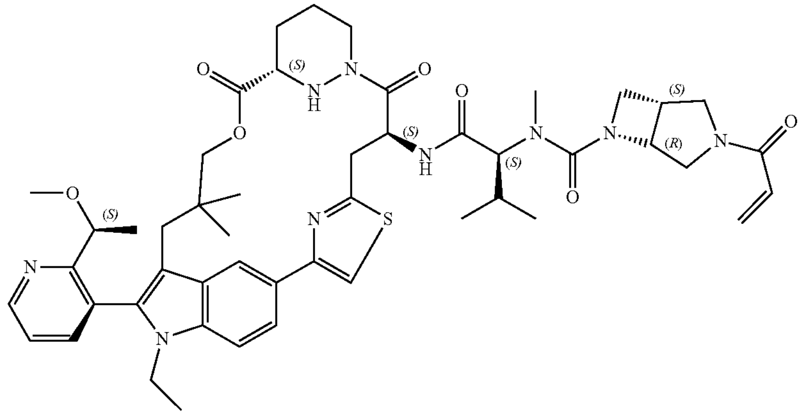 |
| B687 | 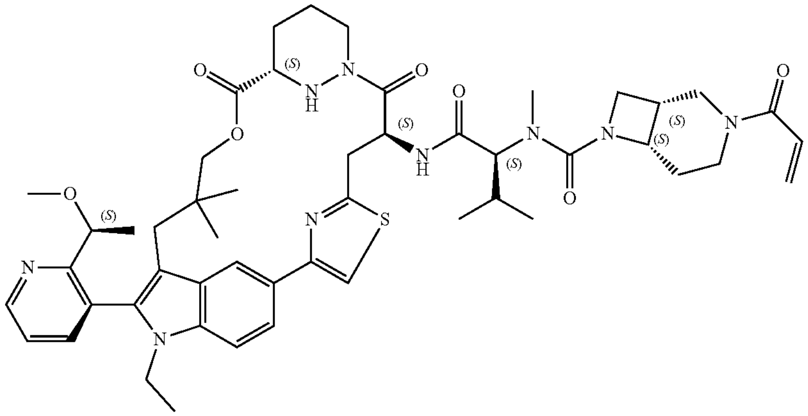 |

TABLE 2-continued
| Certain Compounds | |
|---|---|
| Ex # | Structure |
| B688 | 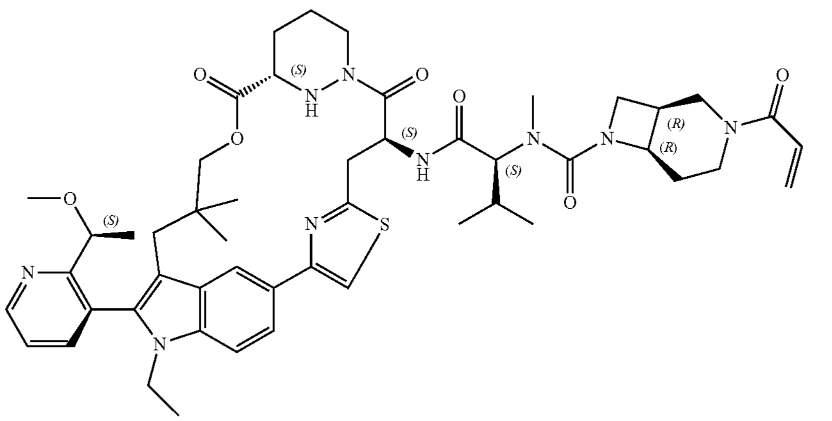 |
| B689 | 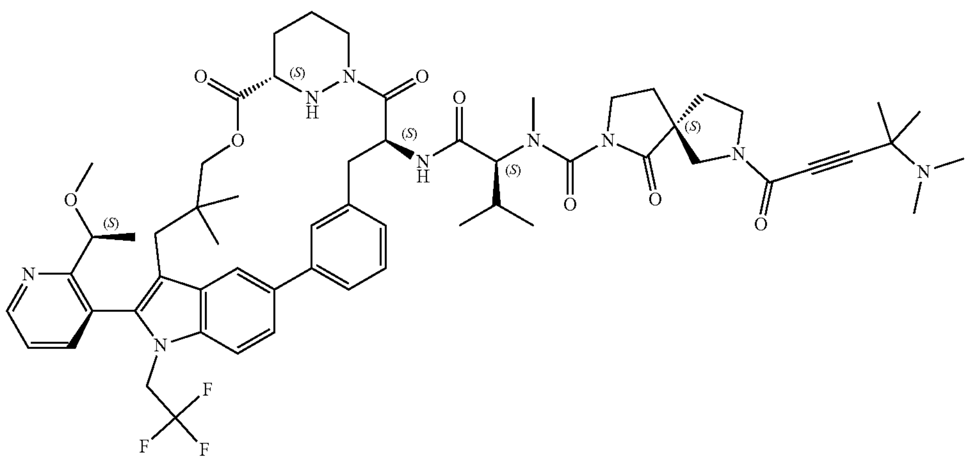 |
| B690 | 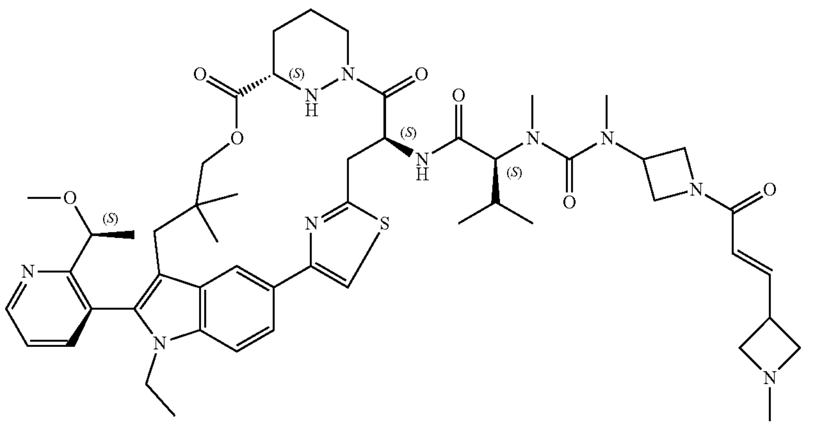 |

TABLE 2-continued
| Certain Compounds | |
|---|---|
| Ex # | Structure |
| B691 | 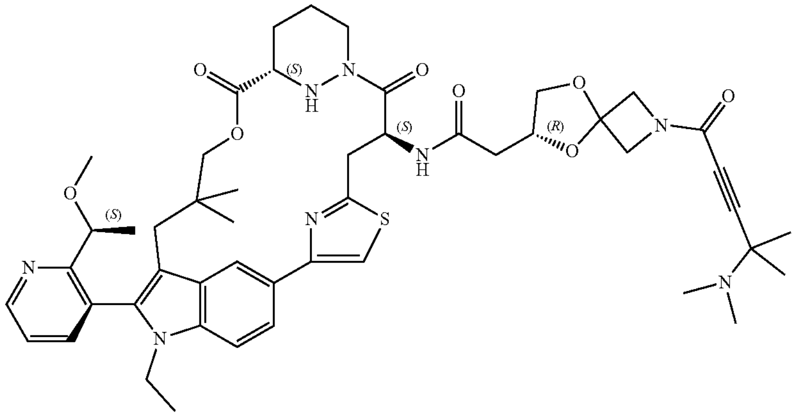 |
| B692 | 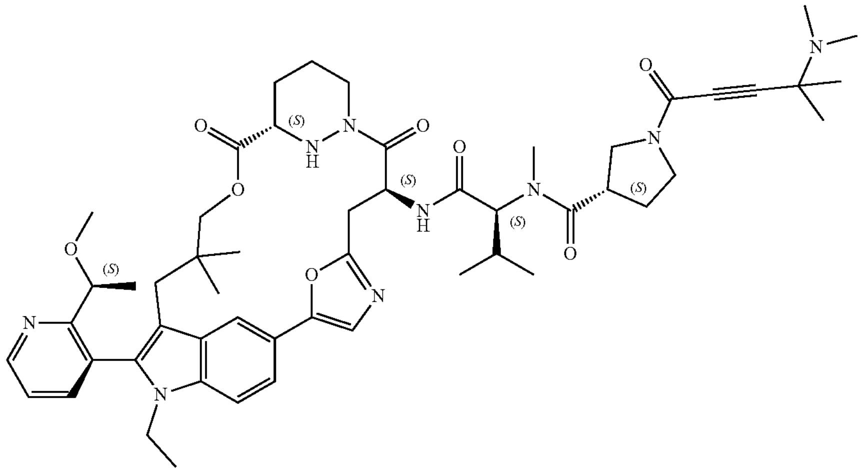 |
| B693 | 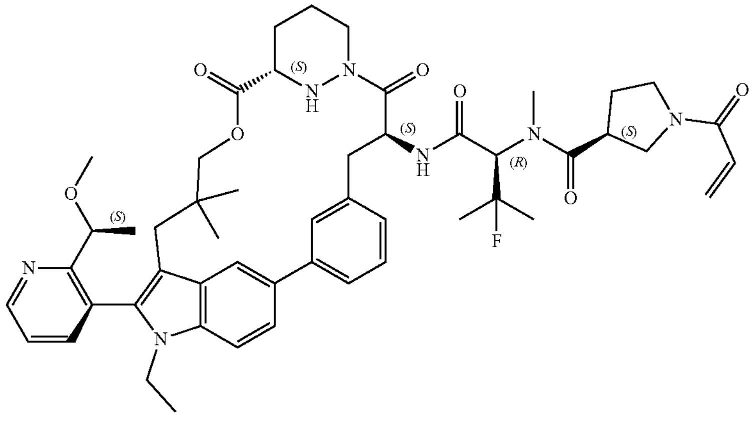 |

TABLE 2-continued
| Certain Compounds | |
|---|---|
| Ex # | Structure |
| B694 | 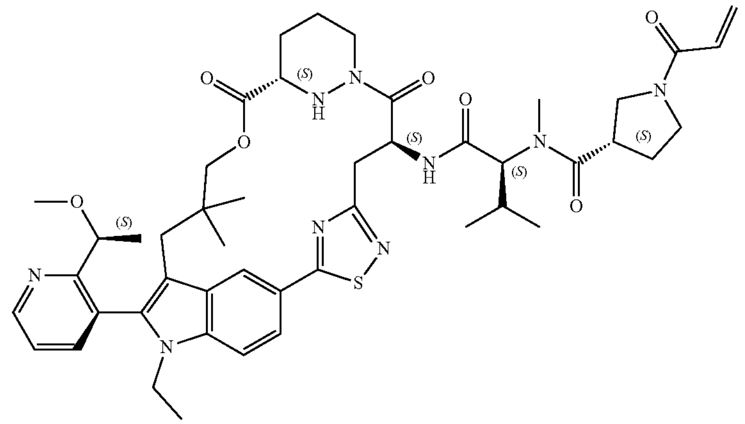 |
| B695 | 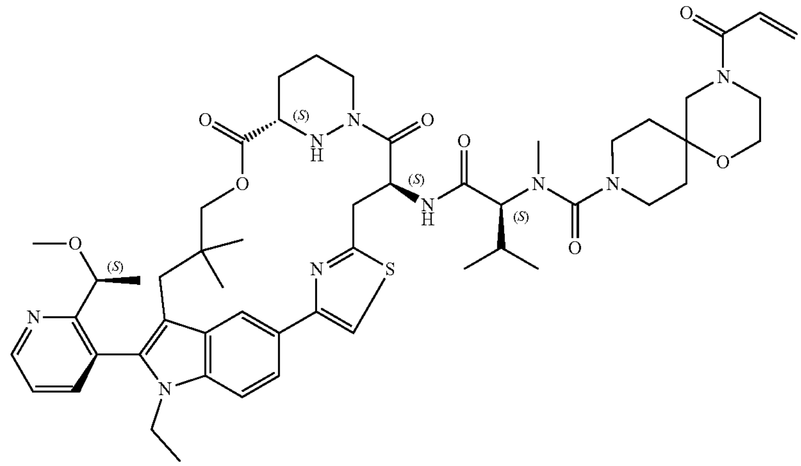 |
| B696 | 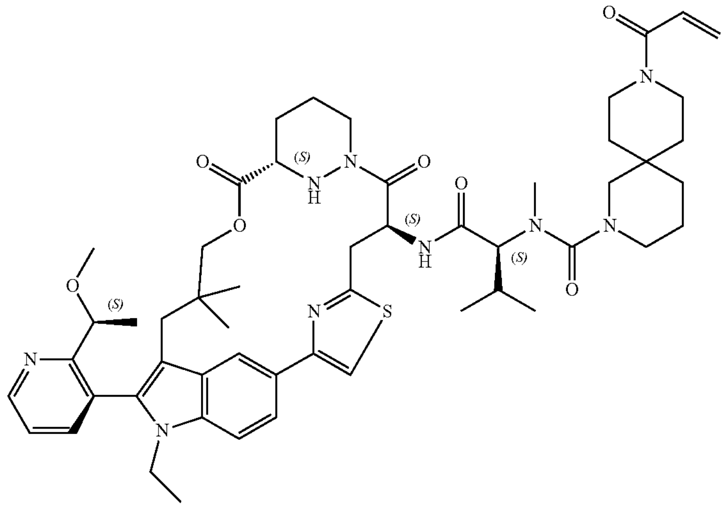 |

TABLE 2-continued
| Certain Compounds | |
|---|---|
| Ex # | Structure |
| B697 | 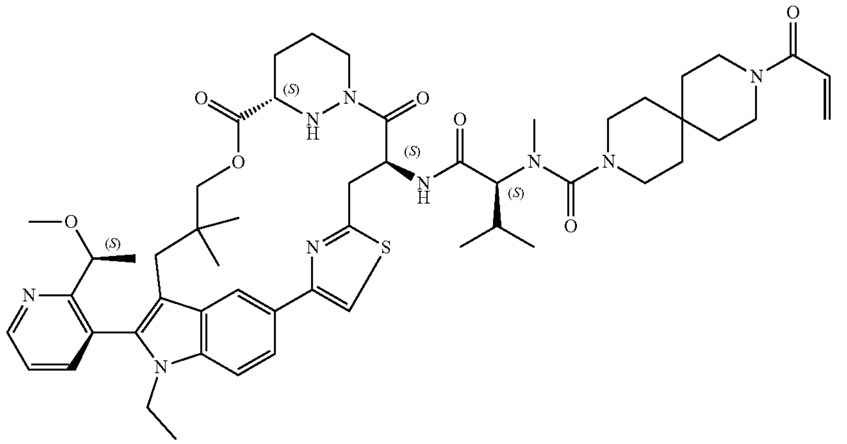 |
| B698 | 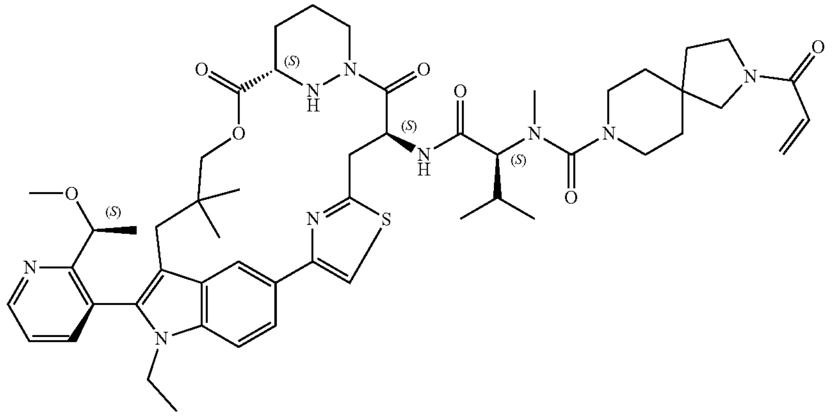 |
| B699 | 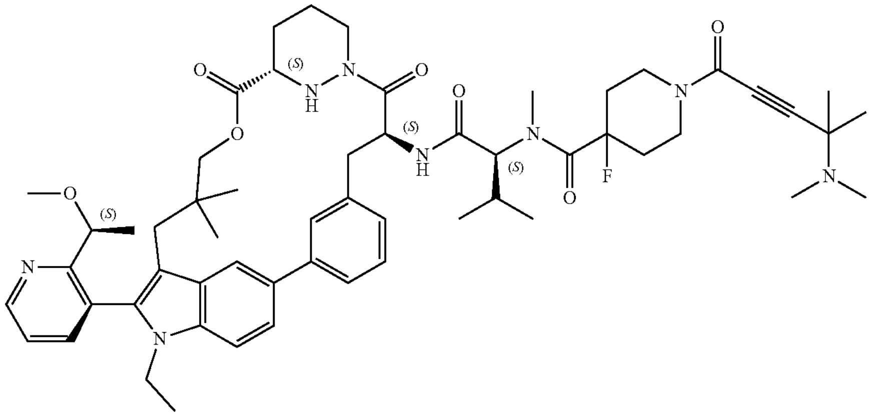 |

TABLE 2-continued
| Certain Compounds | |
|---|---|
| Ex # | Structure |
| B700 | 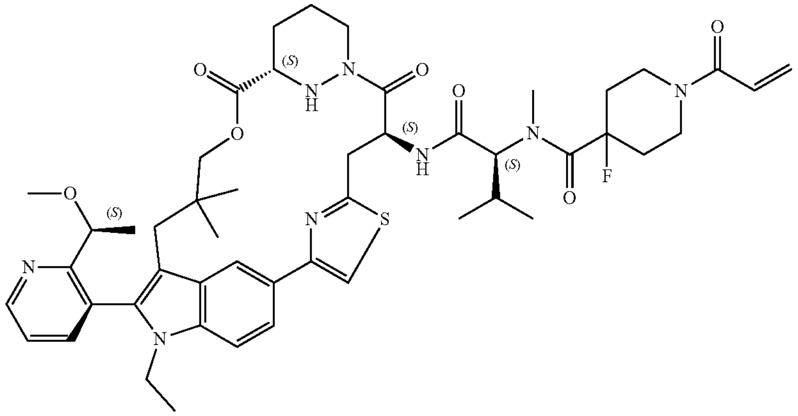 |
| B701 | 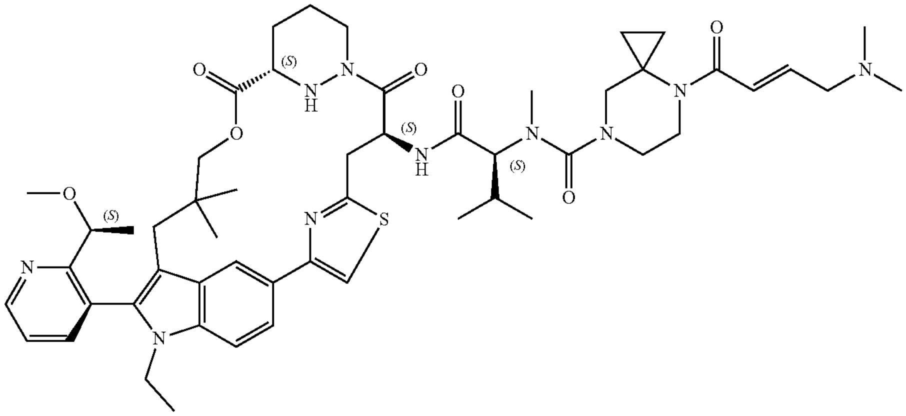 |
| B702 | 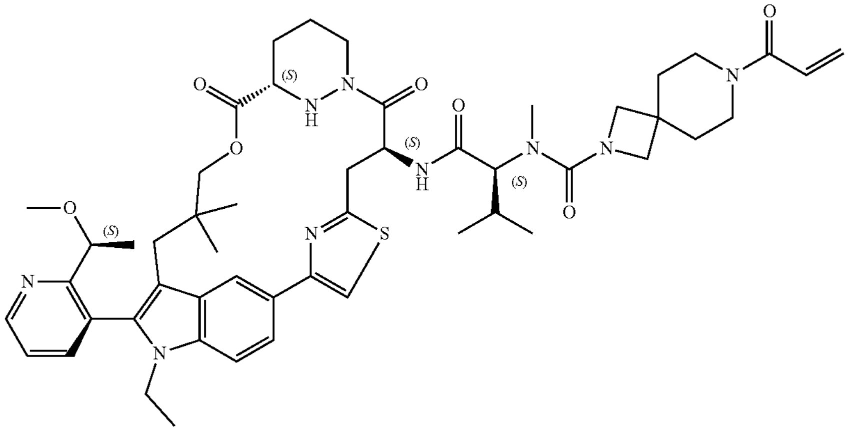 |

TABLE 2-continued
| Certain Compounds | |
|---|---|
| Ex # | Structure |
| B703 | 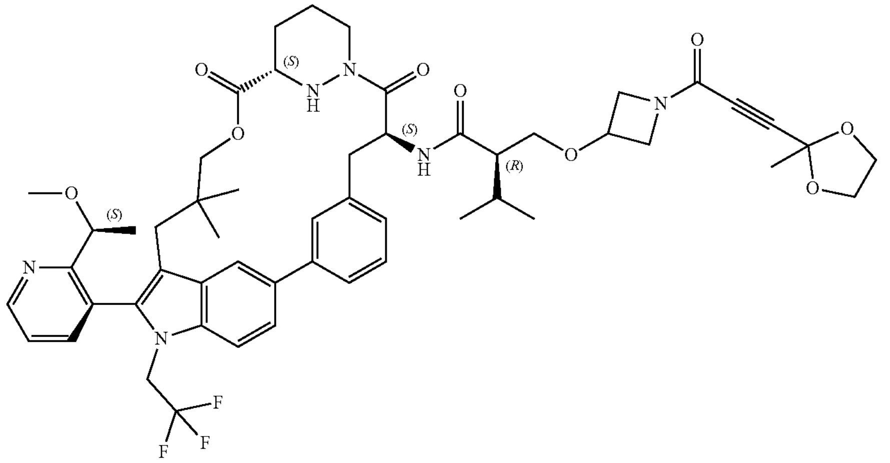 |
| B704 | 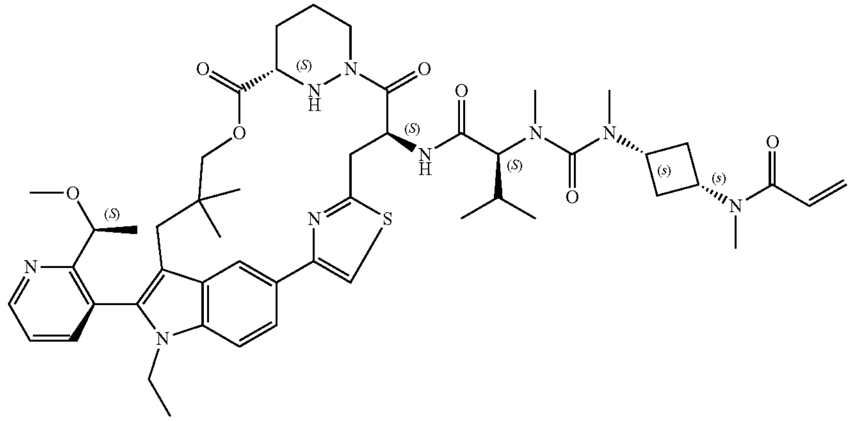 |
| B705 | 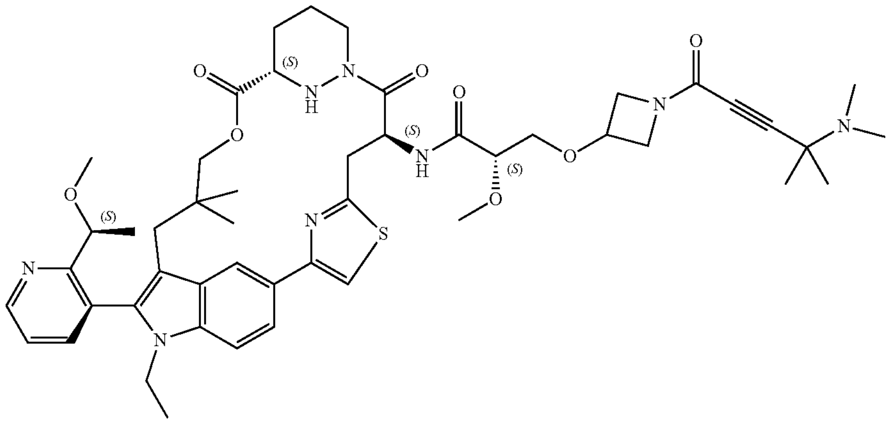 |

TABLE 2-continued
| Certain Compounds | |
|---|---|
| Ex # | Structure |
| B706 | 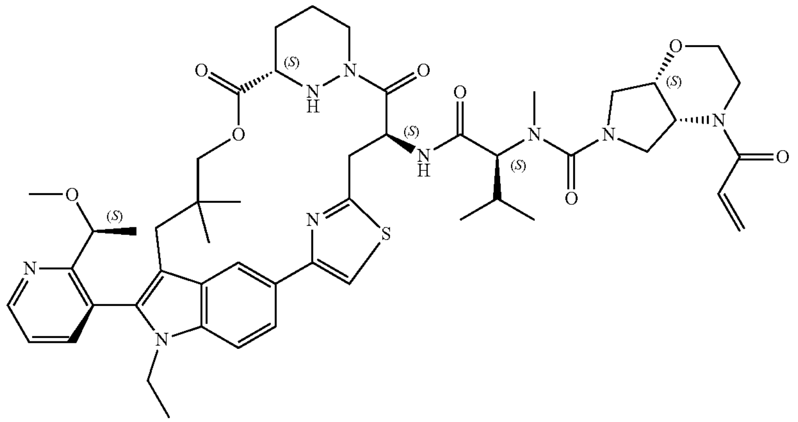 |
| B707 | 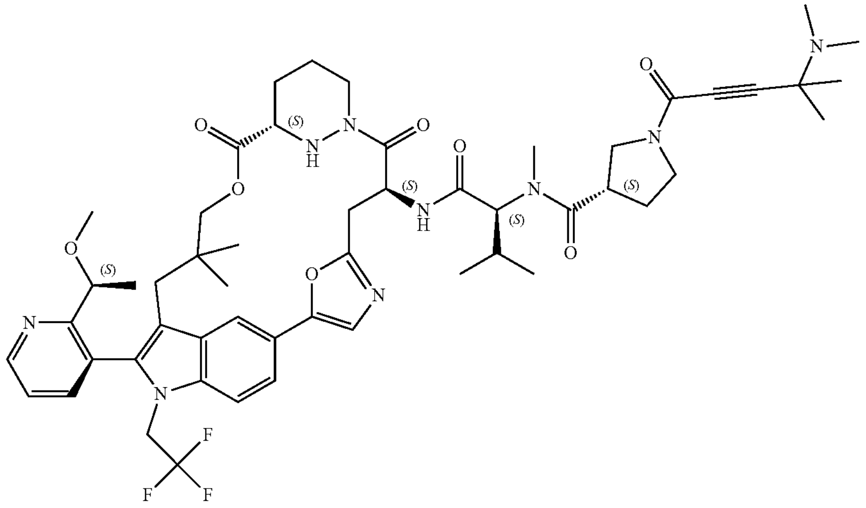 |
| B708 | 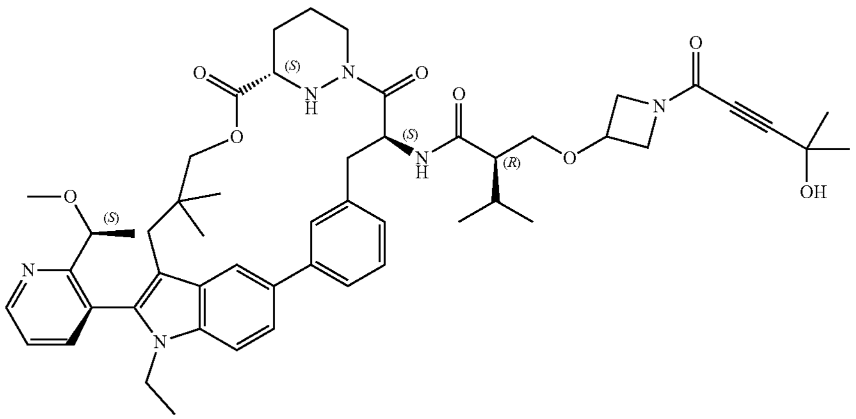 |

TABLE 2-continued
| Certain Compounds | |
|---|---|
| Ex # | Structure |
| B709 | 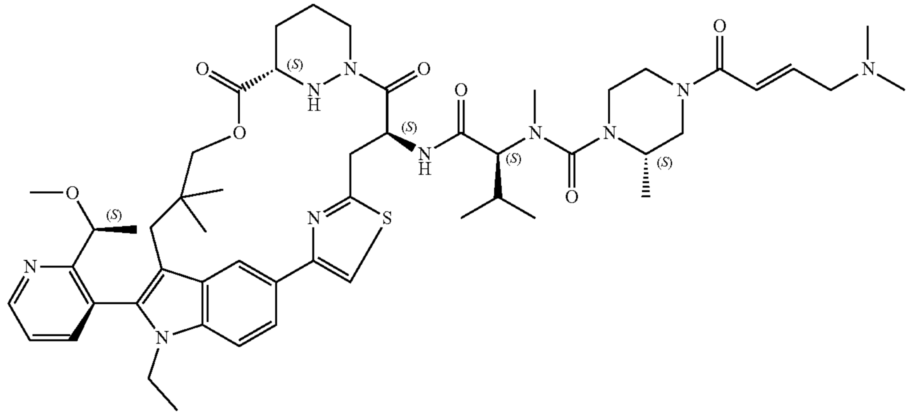 |
| B710 | 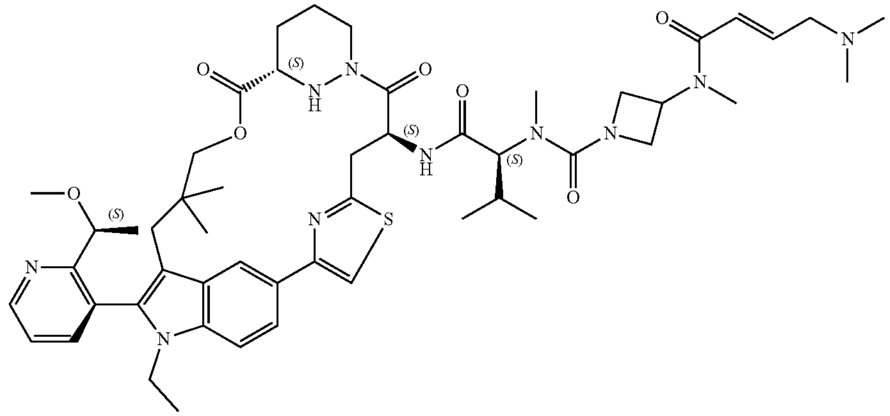 |
| B711 | 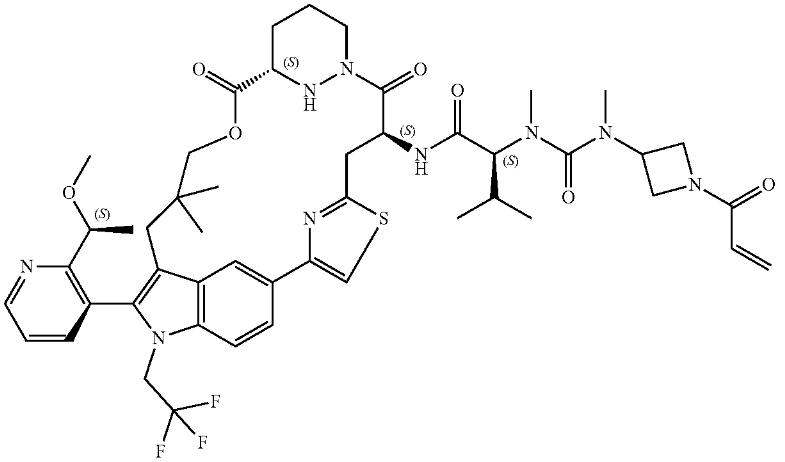 |

TABLE 2-continued
| Certain Compounds | |
|---|---|
| Ex # | Structure |
| B712 | 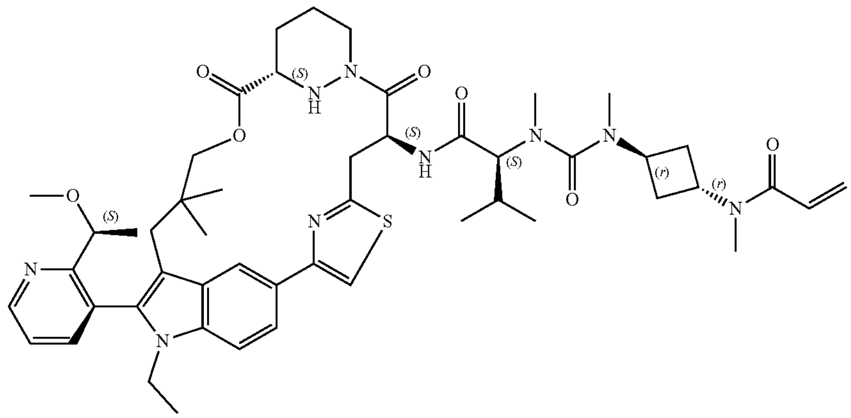 |
| B713 | 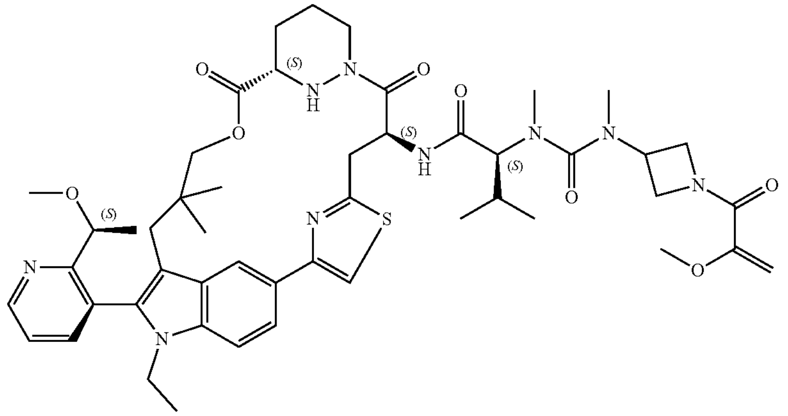 |
| B714 | 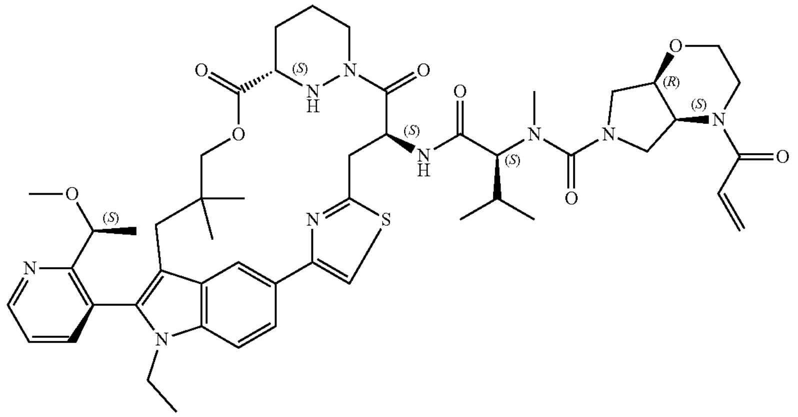 |

TABLE 2-continued
| Certain Compounds | |
|---|---|
| Ex # | Structure |
| B715 | 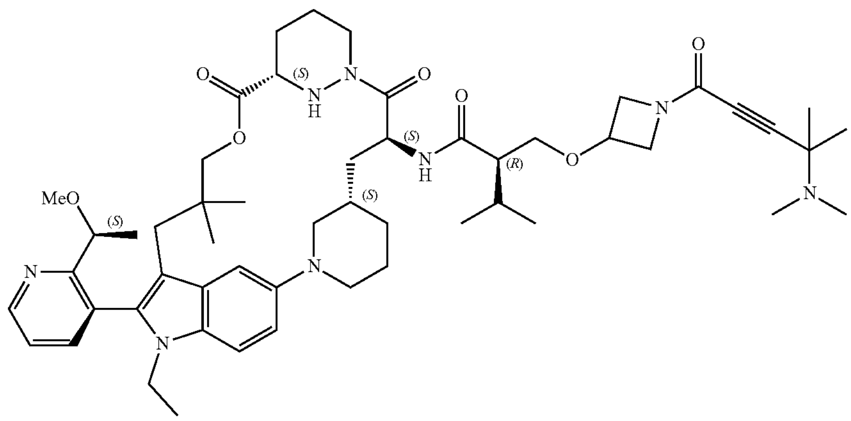 |
| B716 | 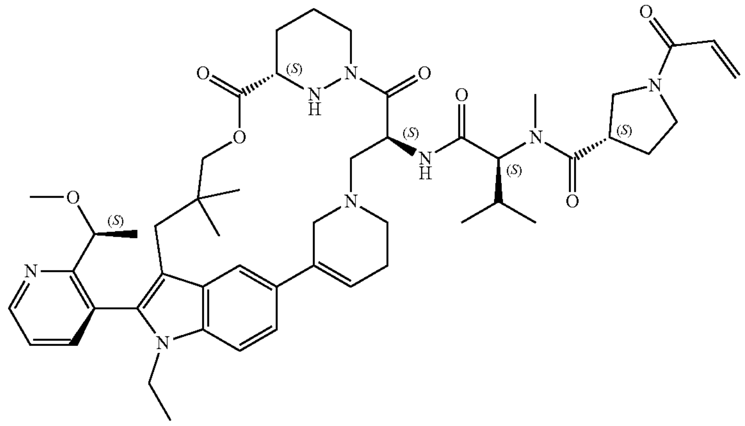 |
| B717 | 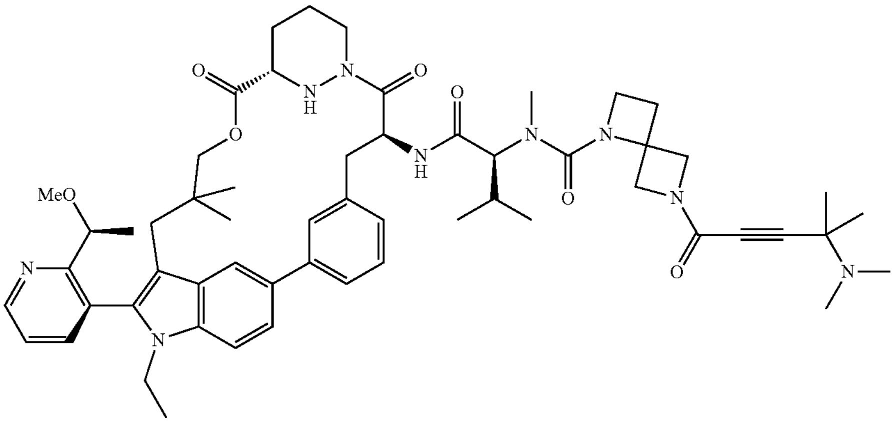 |

TABLE 2-continued
| Certain Compounds | |
|---|---|
| Ex # | Structure |
| B718 | 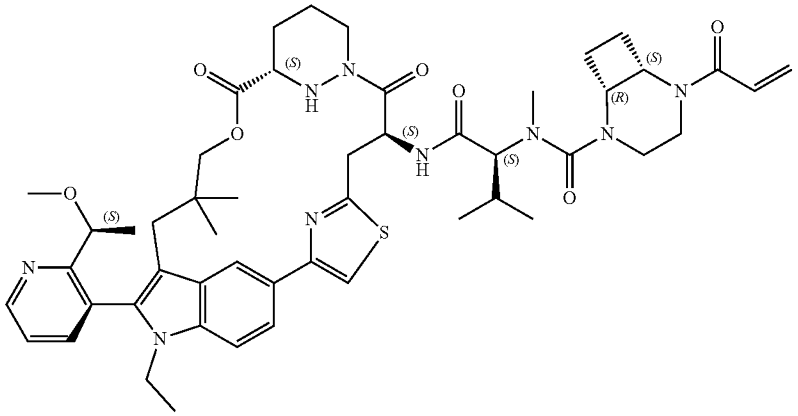 |
| B719 | 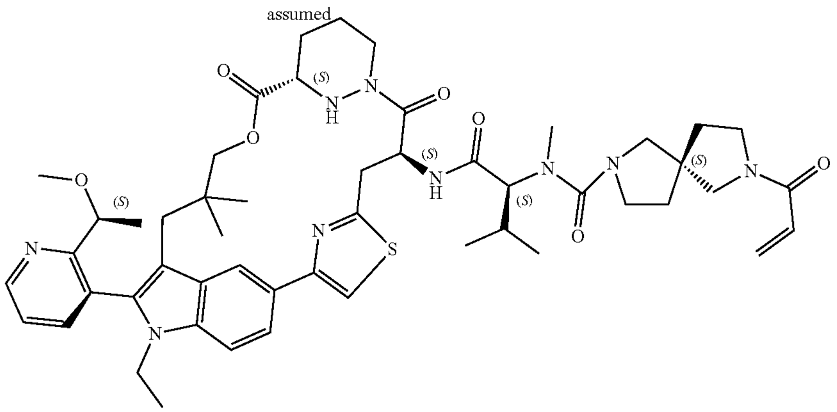 |
| B720 | 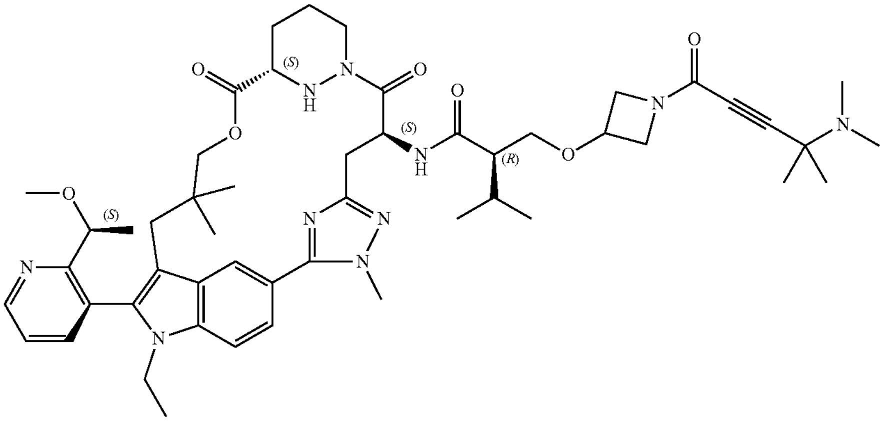 |

TABLE 2-continued
| Certain Compounds | |
|---|---|
| Ex # | Structure |
| B721 | 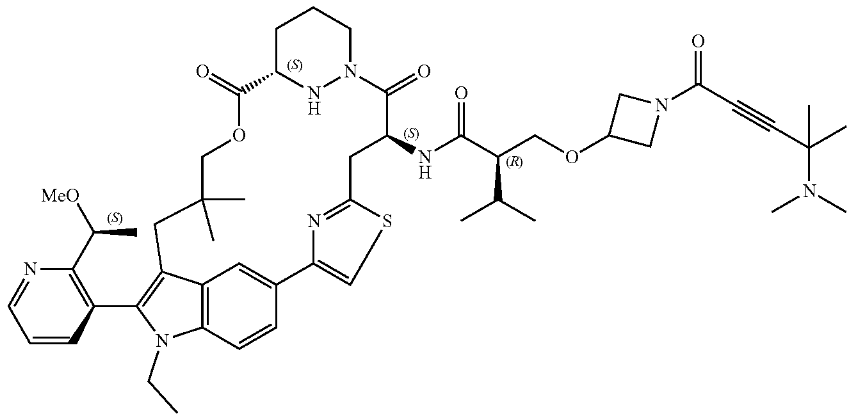 |
| B722 | 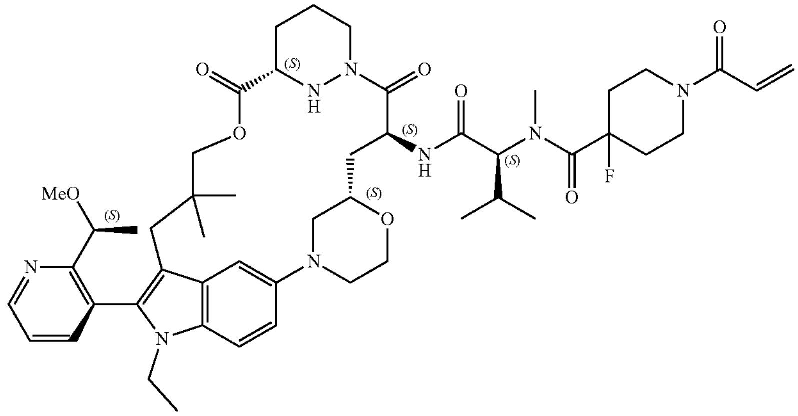 |
| B723 | 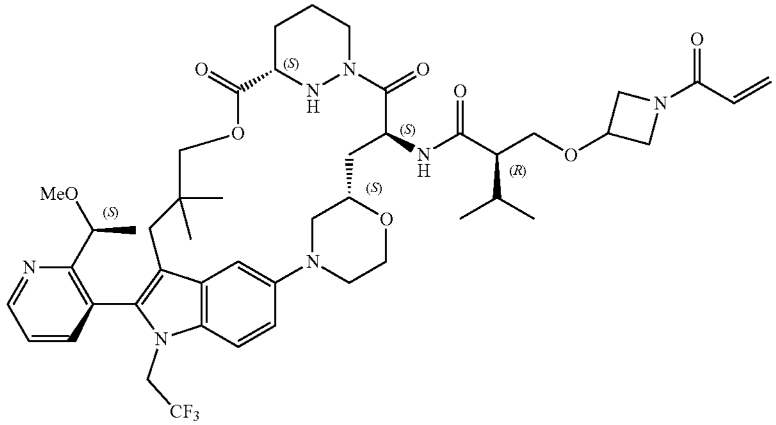 |

TABLE 2-continued
| Certain Compounds | |
|---|---|
| Ex # | Structure |
| B724 | 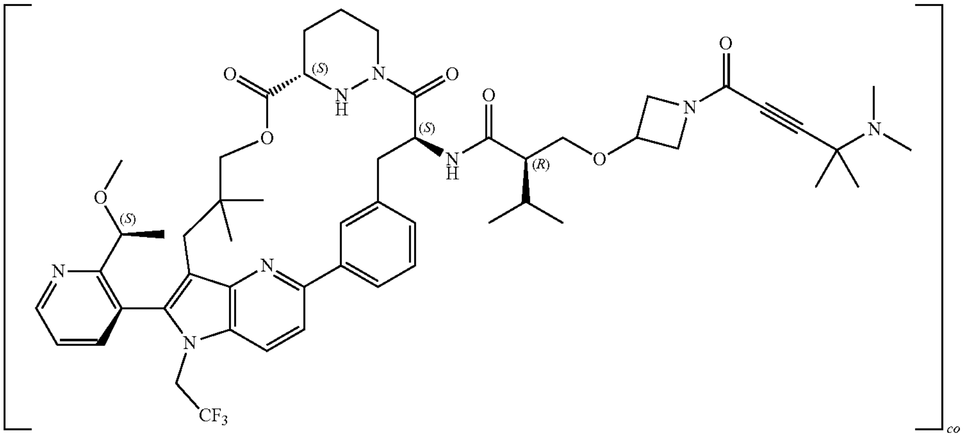 |
| B725 | 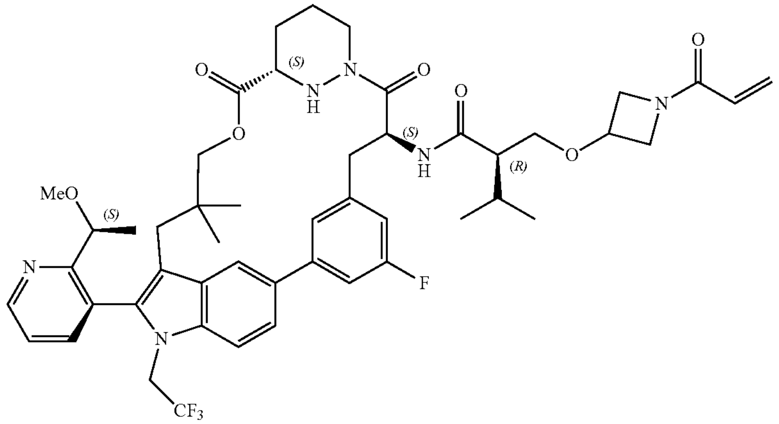 |
| B726 | 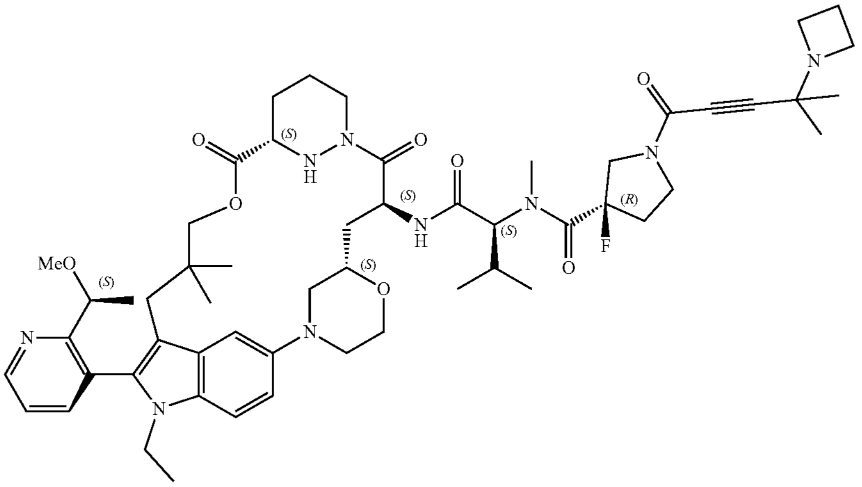 |

TABLE 2-continued
| Certain Compounds | |
|---|---|
| Ex # | Structure |
| B727 | 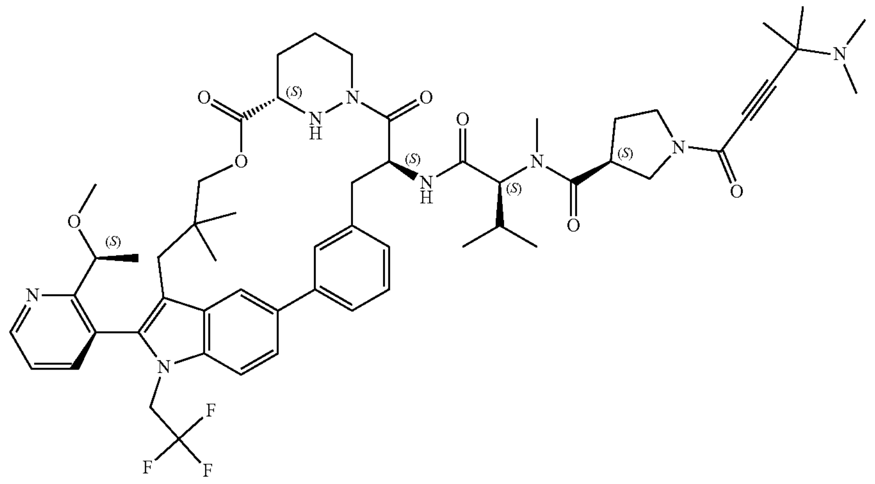 |
| B728 | 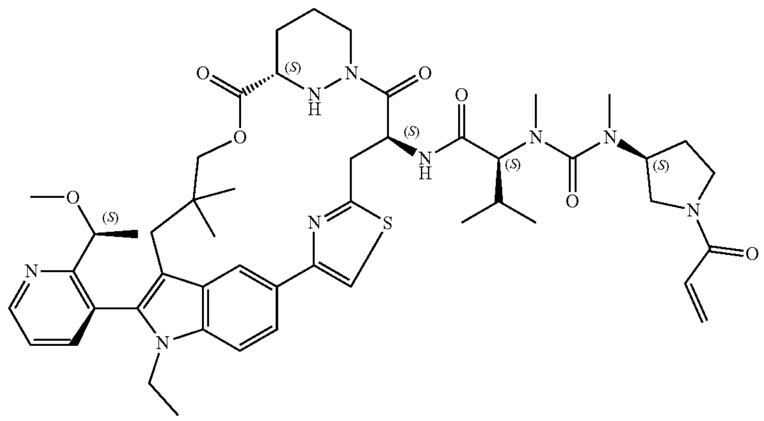 |
| B729 | 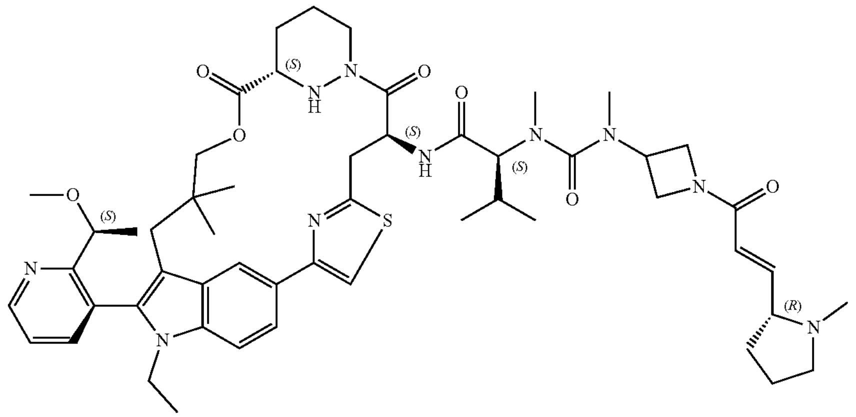 |

TABLE 2-continued
| Certain Compounds | |
|---|---|
| Ex # | Structure |
| B730 | 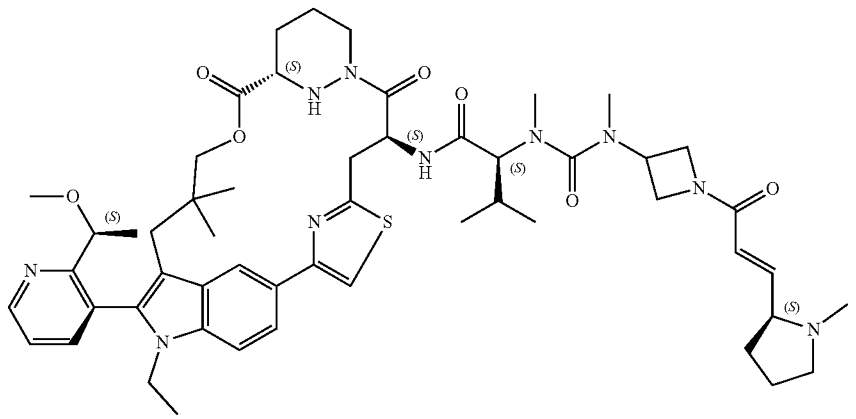 |
| B731 | 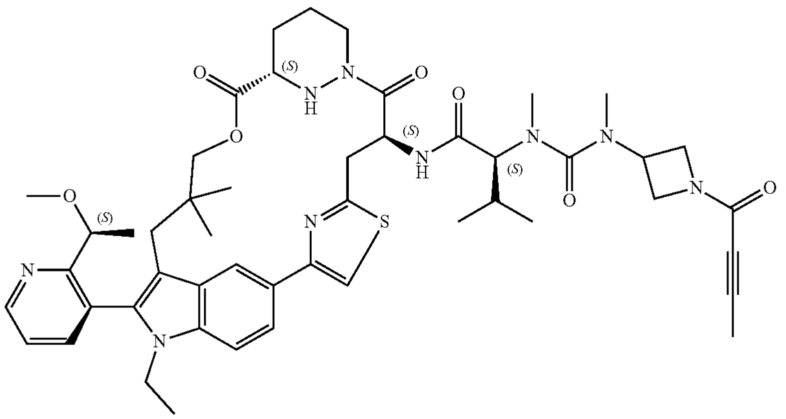 |
| B732 | 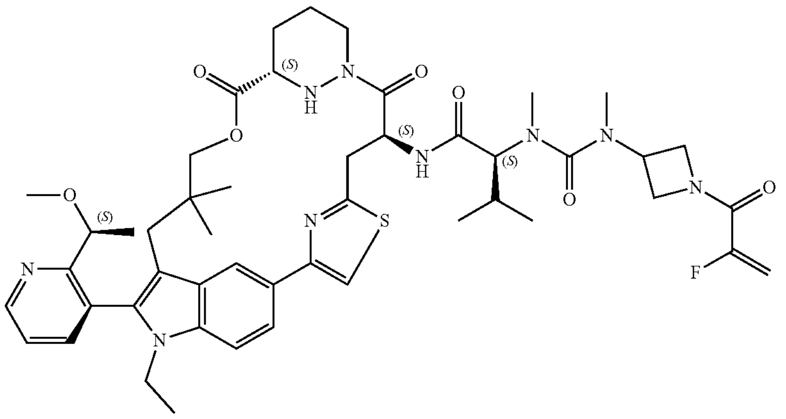 |

TABLE 2-continued
| Certain Compounds | |
|---|---|
| Ex # | Structure |
| B733 | 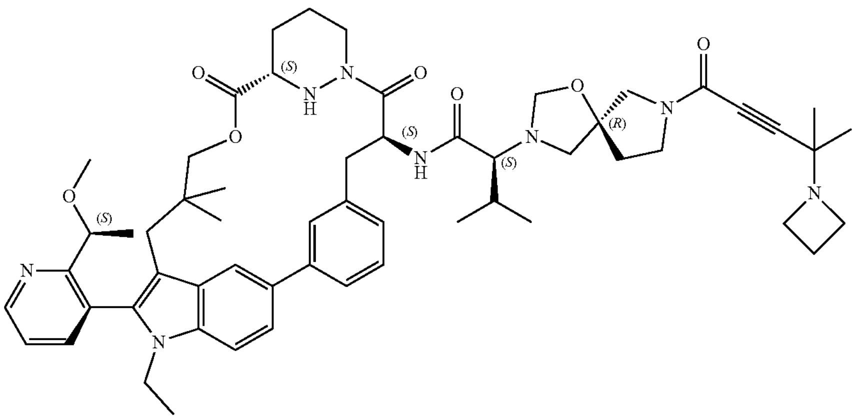 |
| B734 | 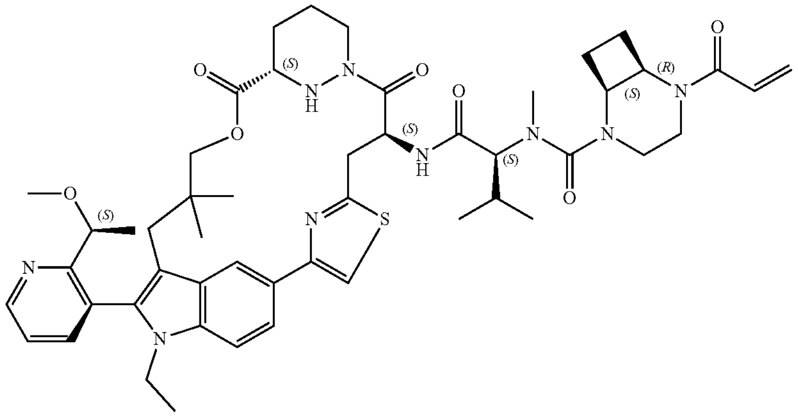 |
| B735 | 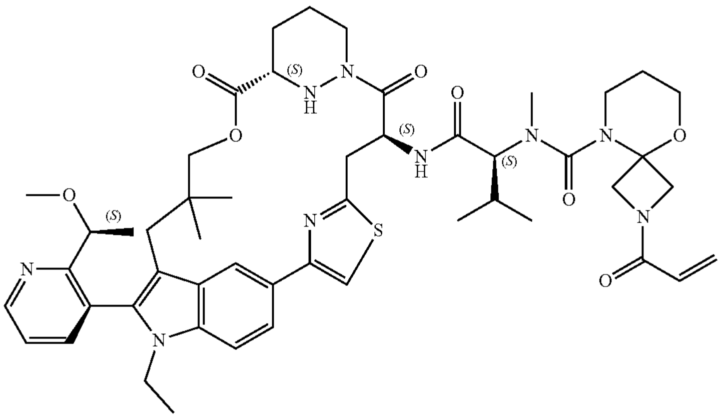 |

TABLE 2-continued
| Certain Compounds | |
|---|---|
| Ex # | Structure |
| B736 | 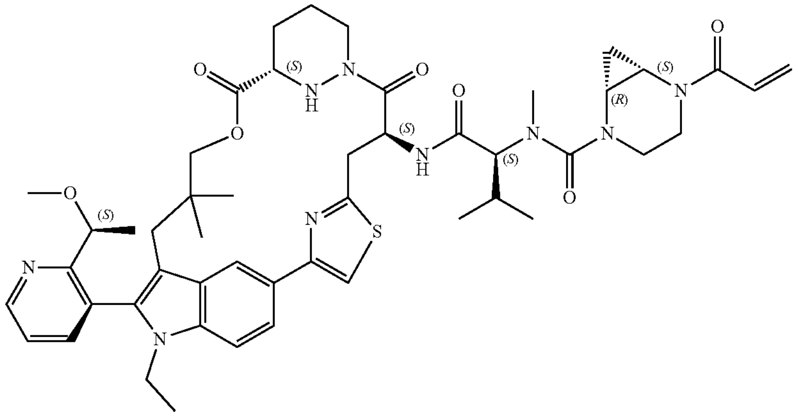 |
| B737 | 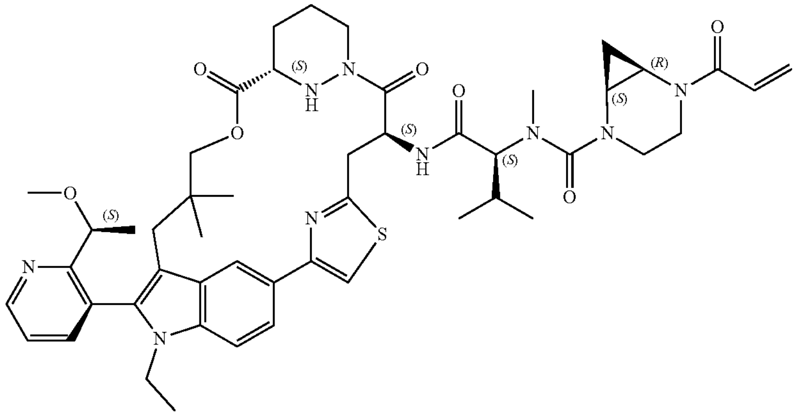 |
| B738 | 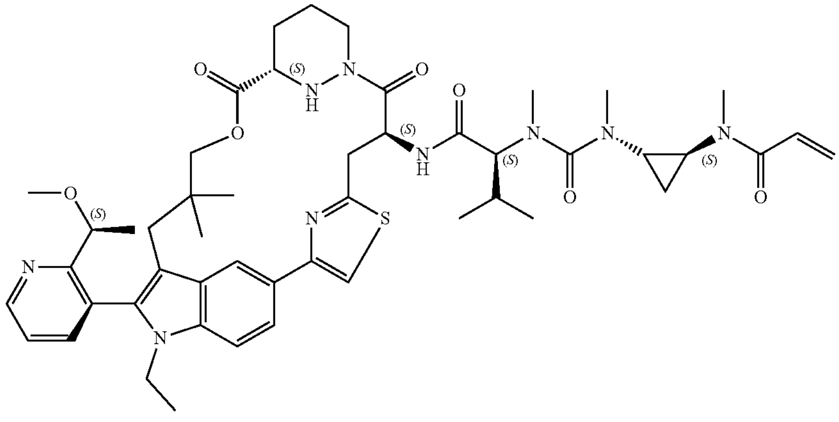 |

TABLE 2-continued
| Certain Compounds | |
|---|---|
| Ex # | Structure |
| B739 | 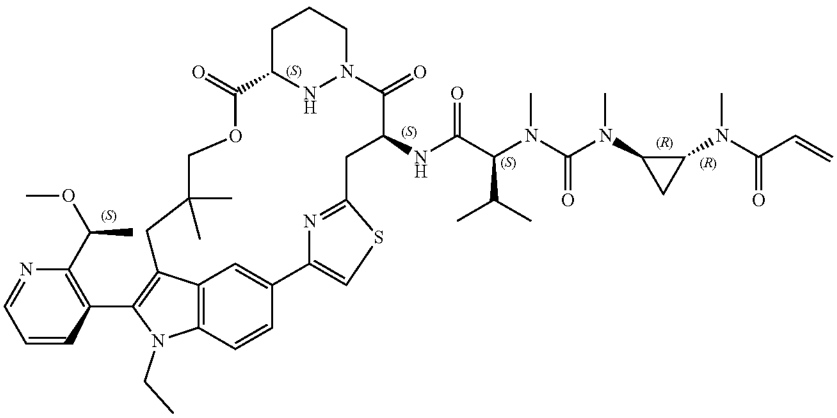 |
| B740 | 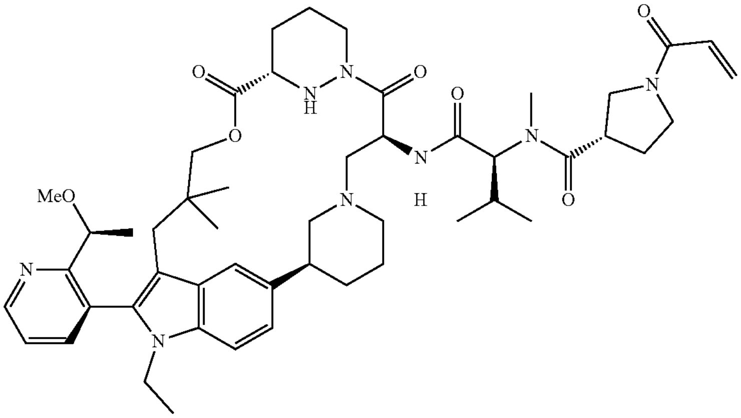 |
| B741 | 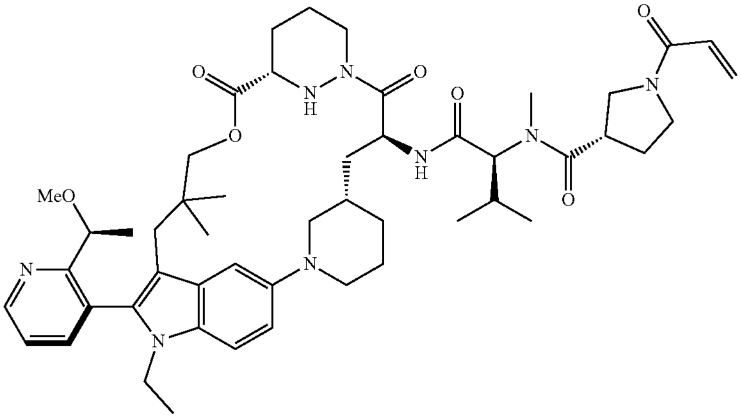 |

TABLE 2-continued
| Certain Compounds | |
|---|---|
| Ex # | Structure |
| C1 | 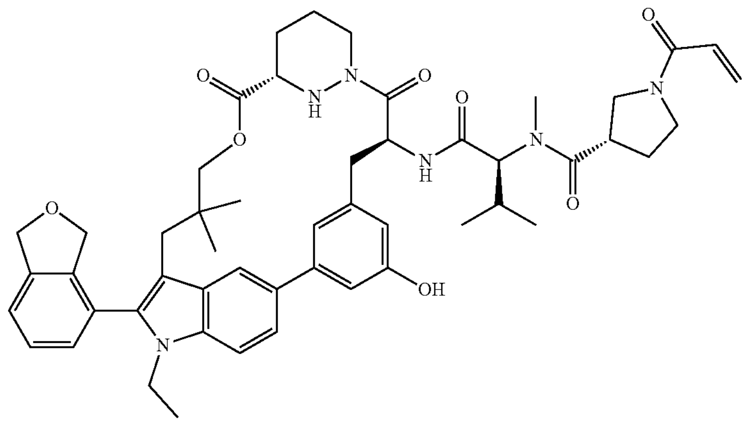 [SMILES: C=CC(=O)N1CC[C@H](C(=O)N(C)[C@H](C(=O)N[C@H]2Cc3cc(O)cc(c3)-c3ccc4c(c3)c(c(-c3cccc5c3COC5)n4CC)CC(C)(C)COC(=O)[C@@H]3CCCN(N3)C2=O)C(C)C)C1] |
| C2 | 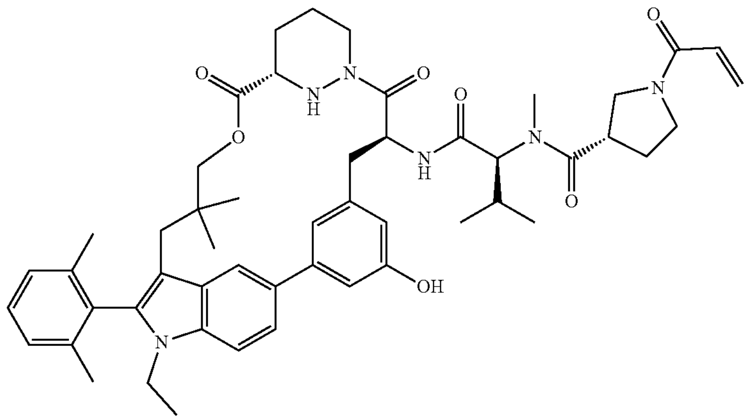 [SMILES: C=CC(=O)N1CC[C@H](C(=O)N(C)[C@H](C(=O)N[C@H]2Cc3cc(O)cc(c3)-c3ccc4c(c3)c(c(-c3c(C)cccc3C)n4CC)CC(C)(C)COC(=O)[C@@H]3CCCN(N3)C2=O)C(C)C)C1] |
| C3 | 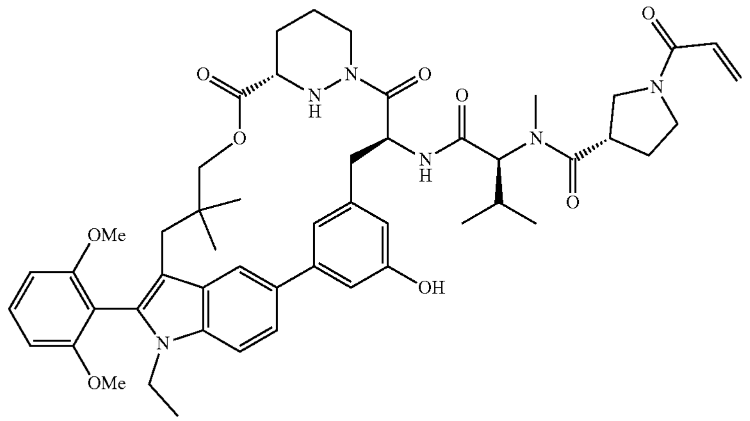 [SMILES: C=CC(=O)N1CC[C@H](C(=O)N(C)[C@H](C(=O)N[C@H]2Cc3cc(O)cc(c3)-c3ccc4c(c3)c(c(-c3c(OC)cccc3OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C4 | 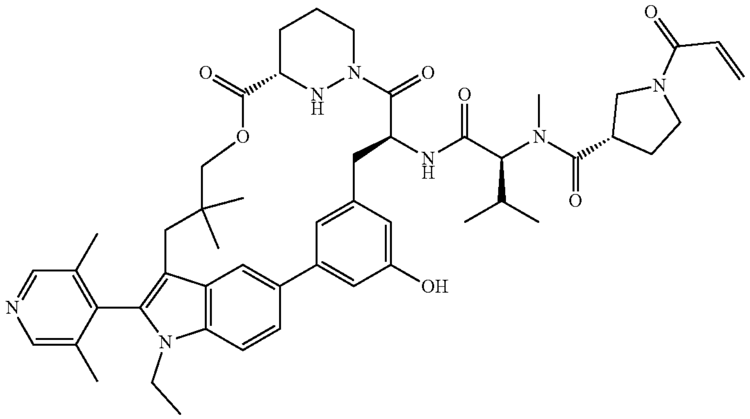 [SMILES: C=CC(=O)N1CC[C@H](C(=O)N(C)[C@H](C(=O)N[C@H]2Cc3cc(O)cc(c3)-c3ccc4c(c3)c(c(-c3c(C)cncc3C)n4CC)CC(C)(C)COC(=O)[C@@H]3CCCN(N3)C2=O)C(C)C)C1] |
| C5 | 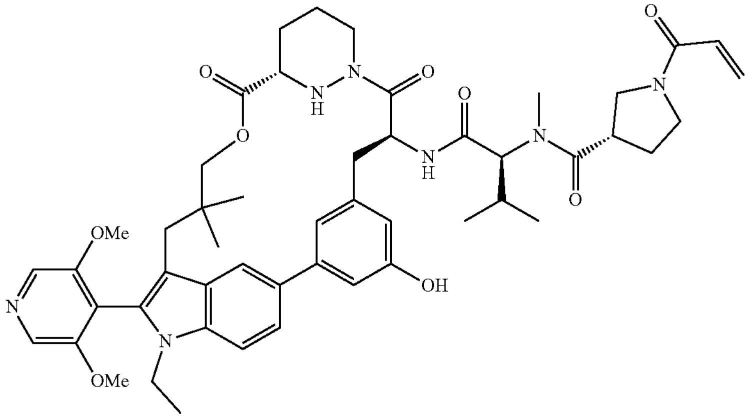 [SMILES: C=CC(=O)N1CC[C@H](C(=O)N(C)[C@H](C(=O)N[C@H]2Cc3cc(O)cc(c3)-c3ccc4c(c3)c(c(-c3c(OC)cncc3OC)n4CC)CC(C)(C)COC(=O)[C@@H]3CCCN(N3)C2=O)C(C)C)C1] |
| C6 | 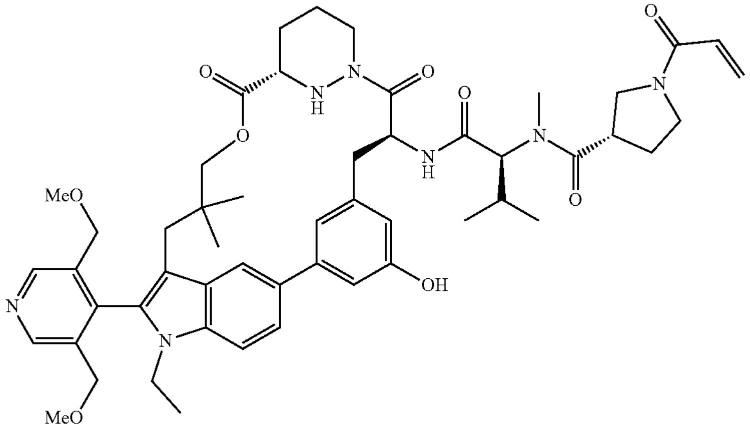 [SMILES: C=CC(=O)N1CC[C@H](C(=O)N(C)[C@H](C(=O)N[C@H]2Cc3cc(O)cc(c3)-c3ccc4c(c3)c(c(-c3c(COC)cncc3COC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C7 | 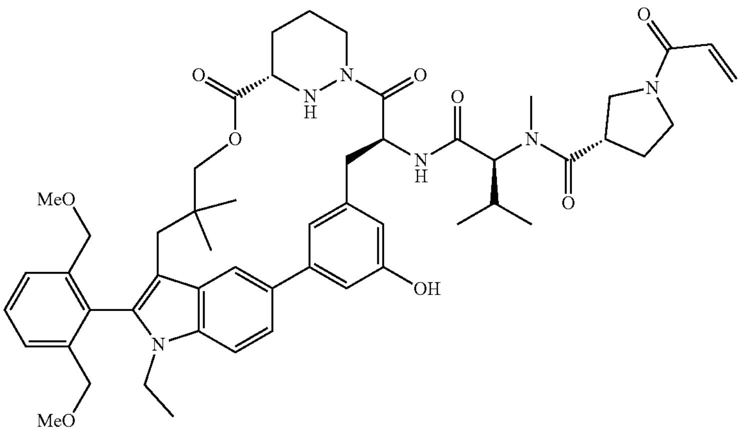 [SMILES: C=CC(=O)N1CC[C@H](C(=O)N(C)[C@H](C(=O)N[C@H]2Cc3cc(O)cc(c3)-c3ccc4c(c3)c(c(-c3c(COC)cccc3COC)n4CC)CC(C)(C)COC(=O)[C@@H]3CCCN(N3)C2=O)C(C)C)C1] |
| C11 | 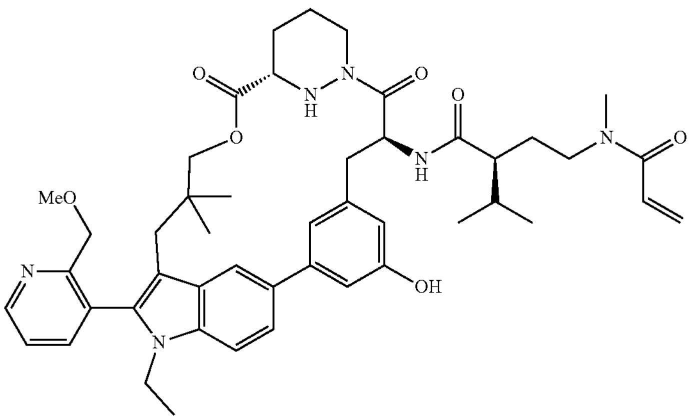 [SMILES: C=CC(=O)N(C)CC[C@H](C(=O)N[C@H]1Cc2cc(O)cc(c2)-c2ccc3c(c2)c(c(-c2cccnc2COC)n3CC)CC(C)(C)COC(=O)[C@@H]2CCCN(N2)C1=O)C(C)C] |
| C12 | 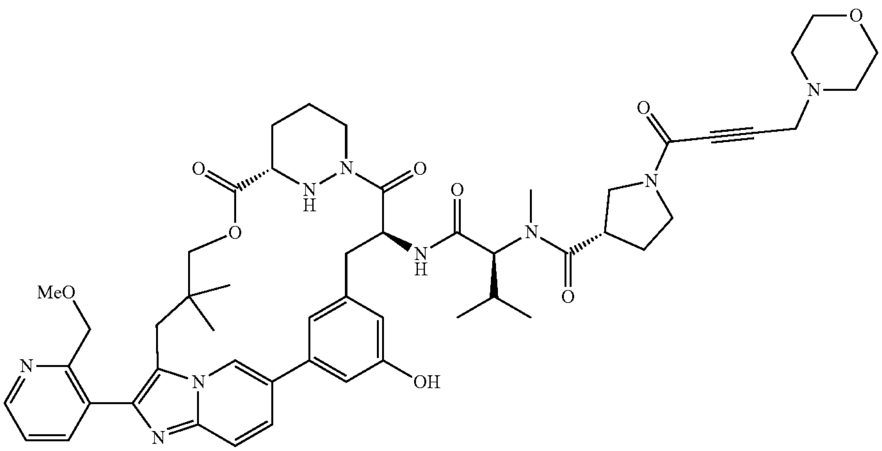 [SMILES: COCc1ncccc1-c1nc2ccc3cn2c1CC(C)(C)COC(=O)[C@@H]1CCCN(N1)C(=O)[C@@H](NC(=O)[C@H](C(C)C)N(C)C(=O)[C@H]1CCN(C(=O)C#CCN2CCOCC2)C1)Cc1cc(O)cc-3c1] |

TABLE 2-continued
| Certain Compounds | |
|---|---|
| Ex # | Structure |
| C13 | 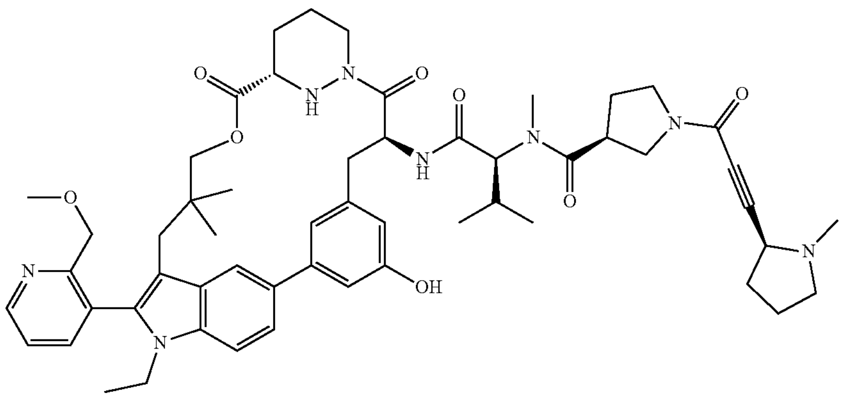 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@@H]3CCCN3C)C1)C(=O)N1CCC[C@H](N1)C(=O)OCC(C)(C)C2] |
| C18 | 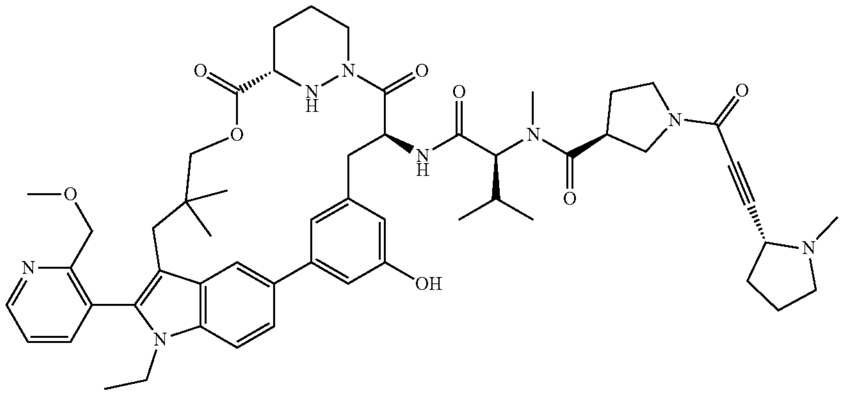 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@H]3CCCN3C)C1)C(=O)N1CCC[C@H](N1)C(=O)OCC(C)(C)C2] |
| C21 | 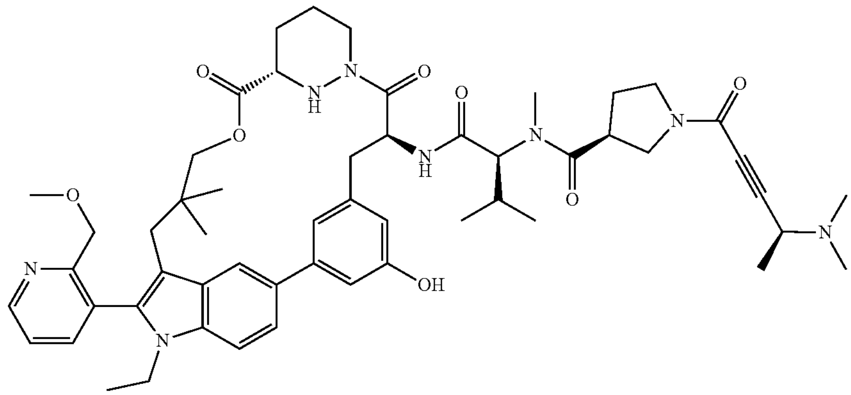 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@H](C)N(C)C)C1)C(=O)N1CCC[C@H](N1)C(=O)OCC(C)(C)C2] |

TABLE 2-continued
| Certain Compounds | |
|---|---|
| Ex # | Structure |
| C22 | 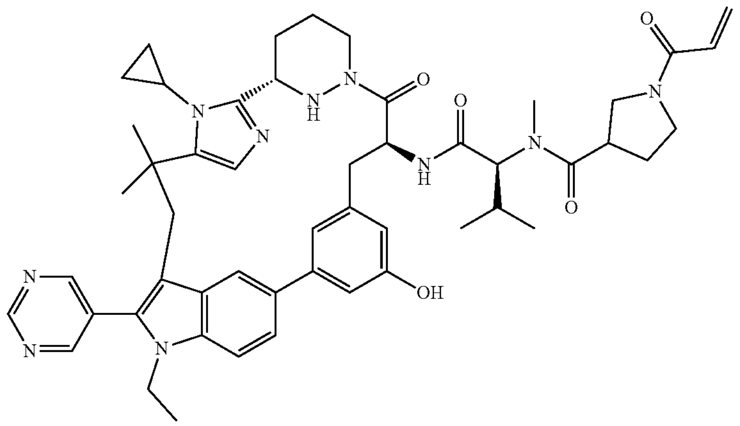 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC(C)(C)c3cnc(n3C3CC3)[C@@H]3CCCN(N3)C2=O)C(C)C)C1] |
| C25 | 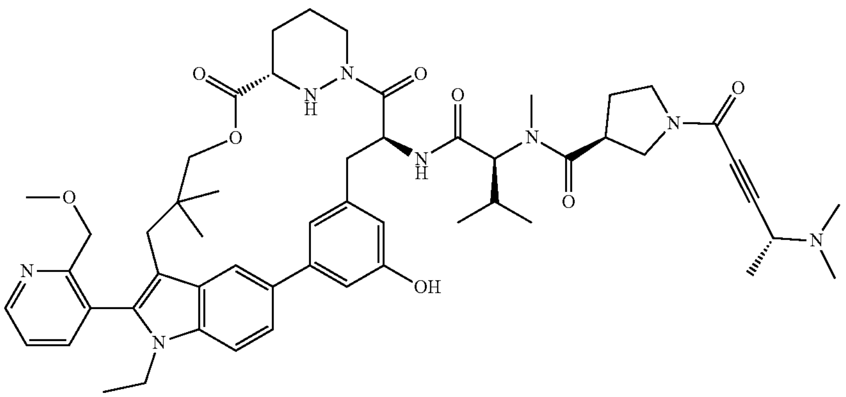 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@@H](C)N(C)C)C1)C(=O)N1CCC[C@H](N1)C(=O)OCC(C)(C)C2] |
| C27 | 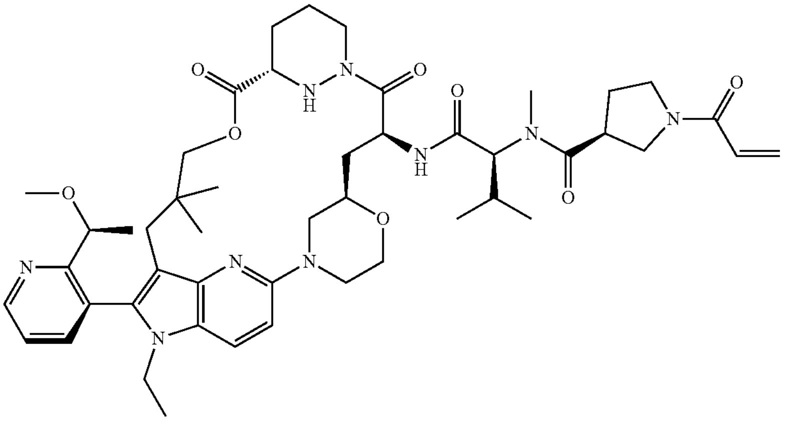 |

TABLE 2-continued
| Certain Compounds | |
|---|---|
| Ex # | Structure |
| C28 | 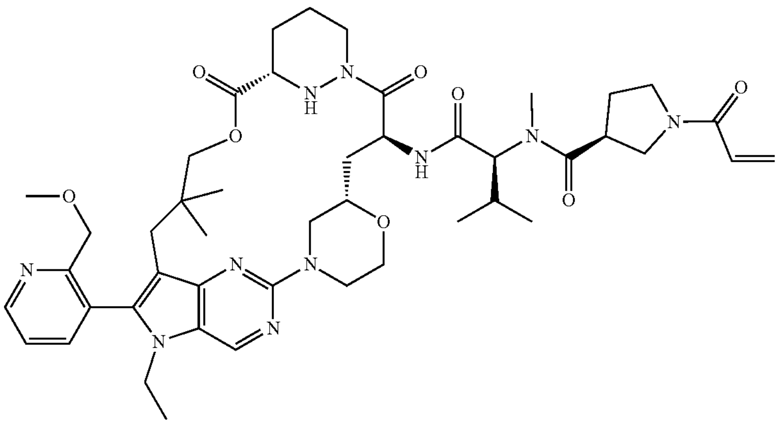 [SMILES: C=CC(=O)N1CC[C@H](C(=O)N(C)[C@H](C(=O)N[C@H]2C[C@H]3CN(CCO3)c3ncc4c(n3)c(c(-c3cccnc3COC)n4CC)CC(C)(C)COC(=O)[C@@H]3CCCN(N3)C2=O)C(C)C)C1] |
| C29 | 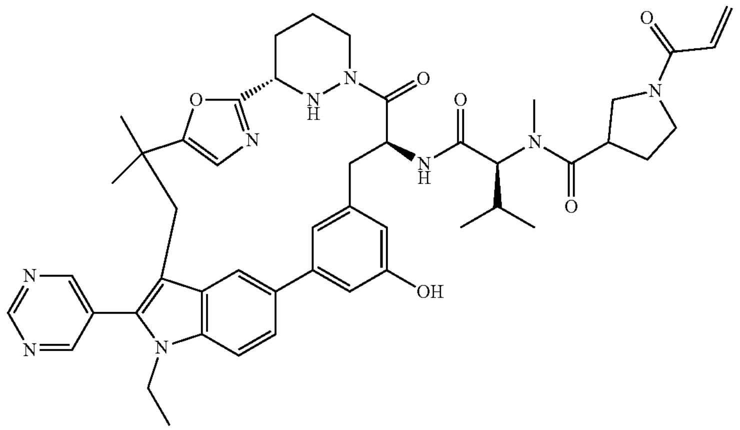 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC(C)(C)C3=CN=C(O3)[C@@H]3CCCN(N3)C2=O)C(C)C)C1] |
| C30 | 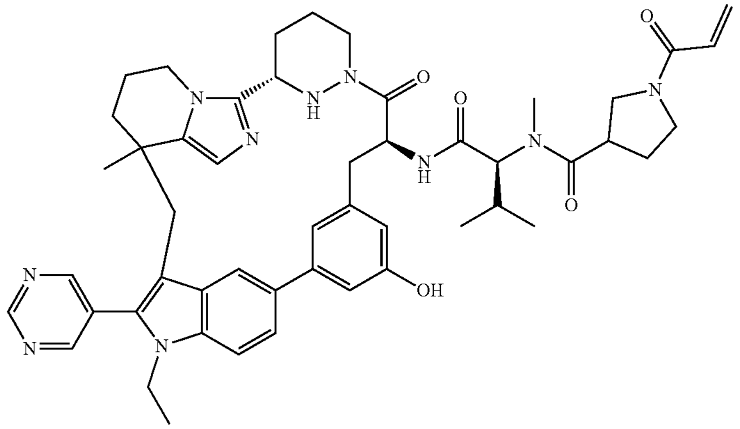 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC3(C)CCCn4c3cnc4[C@@H]3CCCN(N3)C2=O)C(C)C)C1] |

TABLE 2-continued
| Certain Compounds | |
|---|---|
| Ex # | Structure |
| C32 | 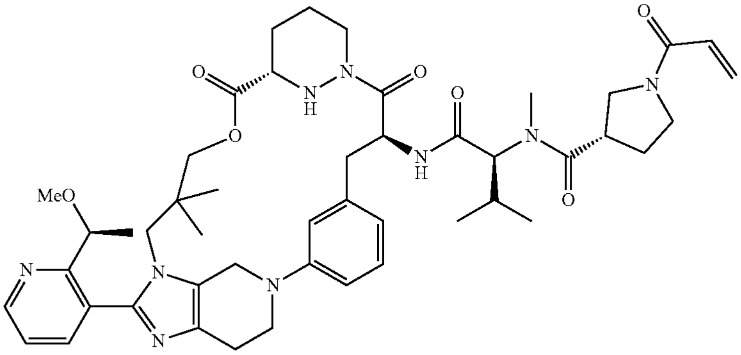 [SMILES: C=CC(=O)N1CC[C@H](C(=O)N(C)[C@H](C(=O)N[C@H]2Cc3cccc(c3)N3CCc4nc(-c5cccnc5[C@H](C)OC)n(c4C3)CC(C)(C)COC(=O)[C@@H]3CCCN(N3)C2=O)C(C)C)C1] |
| C34 | 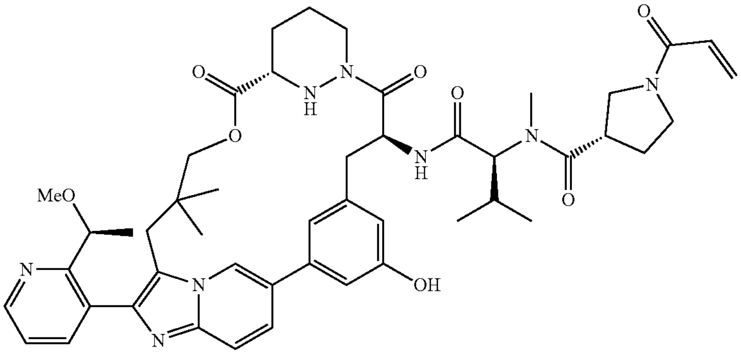 [SMILES: C=CC(=O)N1CC[C@H](C(=O)N(C)[C@H](C(=O)N[C@H]2Cc3cc(O)cc(c3)-c3ccc4nc(-c5cccnc5[C@H](C)OC)c(n4c3)CC(C)(C)COC(=O)[C@@H]3CCCN(N3)C2=O)C(C)C)C1] |
| C38 | 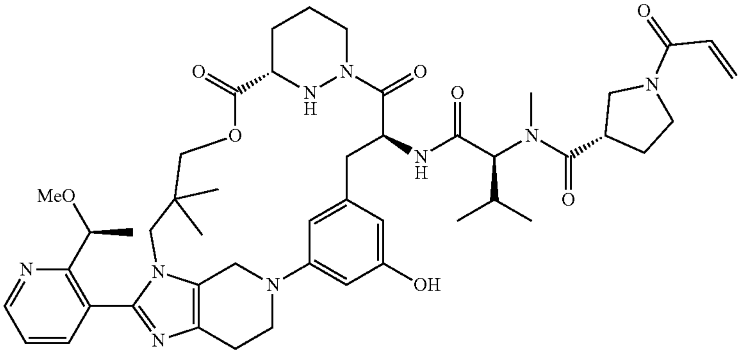 [SMILES: C=CC(=O)N1CC[C@H](C(=O)N(C)[C@H](C(=O)N[C@H]2Cc3cc(O)cc(c3)N3CCc4nc(-c5cccnc5[C@H](C)OC)n(c4C3)CC(C)(C)COC(=O)[C@@H]3CCCN(N3)C2=O)C(C)C)C1] |
| C47 | 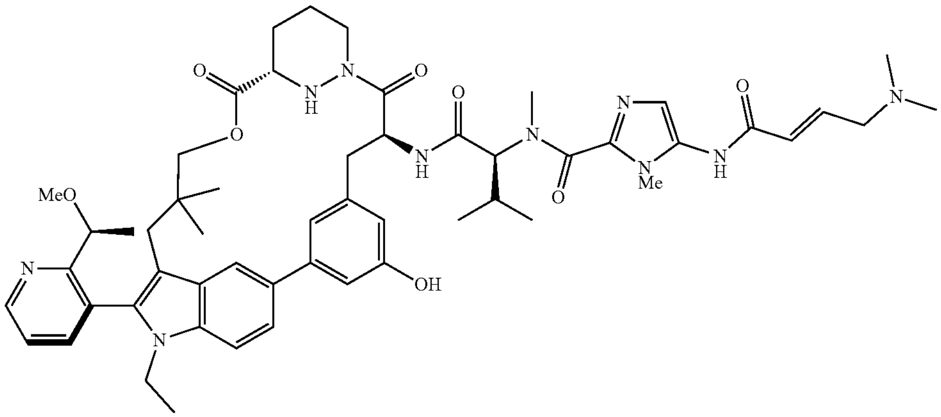 |

TABLE 2-continued
| Certain Compounds | |
|---|---|
| Ex # | Structure |
| C38 | 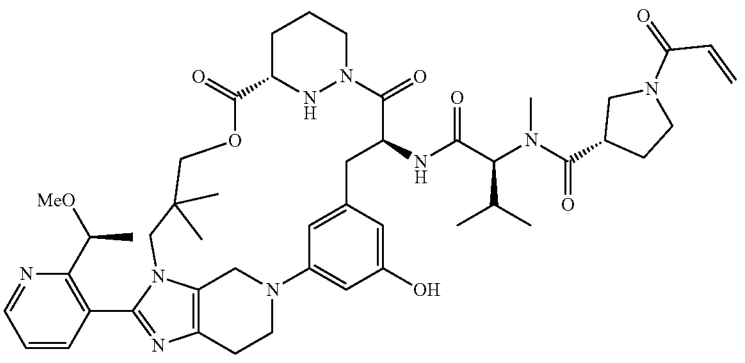 [SMILES: C=CC(=O)N1CC[C@H](C(=O)N(C)[C@H](C(=O)N[C@H]2Cc3cc(O)cc(c3)N3CCc4nc(-c5cccnc5[C@H](C)OC)n(c4C3)CC(C)(C)COC(=O)[C@@H]3CCCN(N3)C2=O)C(C)C)C1] |
| C47 | 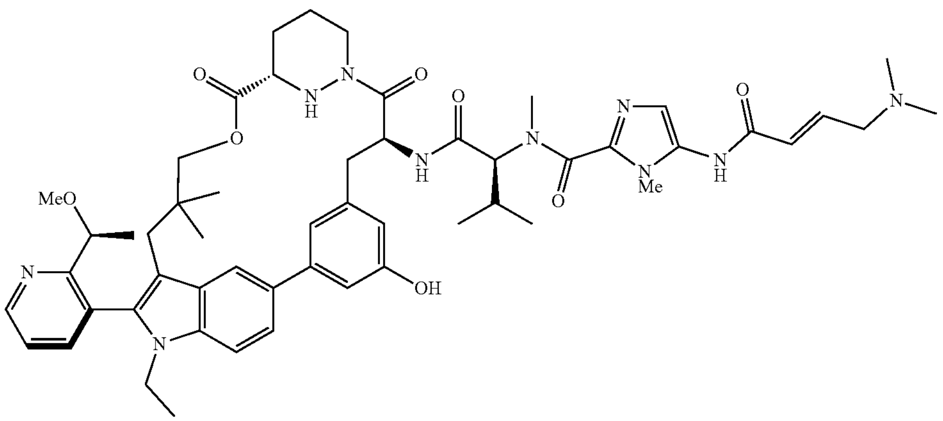 |
| C64 | 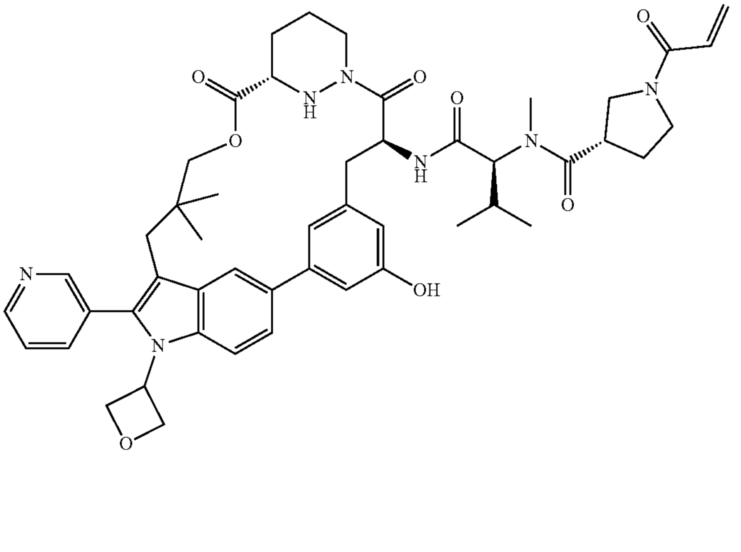 [SMILES: C=CC(=O)N1CC[C@H](C(=O)N(C)[C@H](C(=O)N[C@H]2Cc3cc(O)cc(c3)-c3ccc4c(c3)c(c(-c3cccnc3)n4C3COC3)CC(C)(C)COC(=O)[C@@H]3CCCN(N3)C2=O)C(C)C)C1] |

TABLE 2-continued
| Certain Compounds | |
|---|---|
| Ex # | Structure |
| C65 | 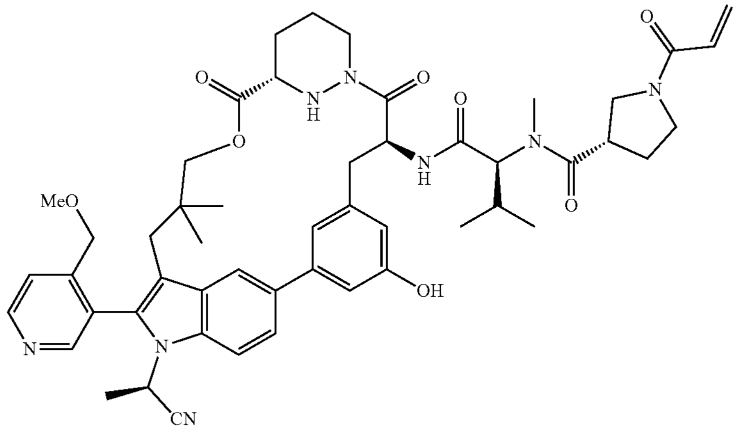 [SMILES: C=CC(=O)N1CC[C@H](C(=O)N(C)[C@H](C(=O)N[C@H]2Cc3cc(O)cc(c3)-c3ccc4c(c3)c(c(-c3cnccc3COC)n4[C@H](C)C#N)CC(C)(C)COC(=O)[C@@H]3CCCN(N3)C2=O)C(C)C)C1] |
| C66 | 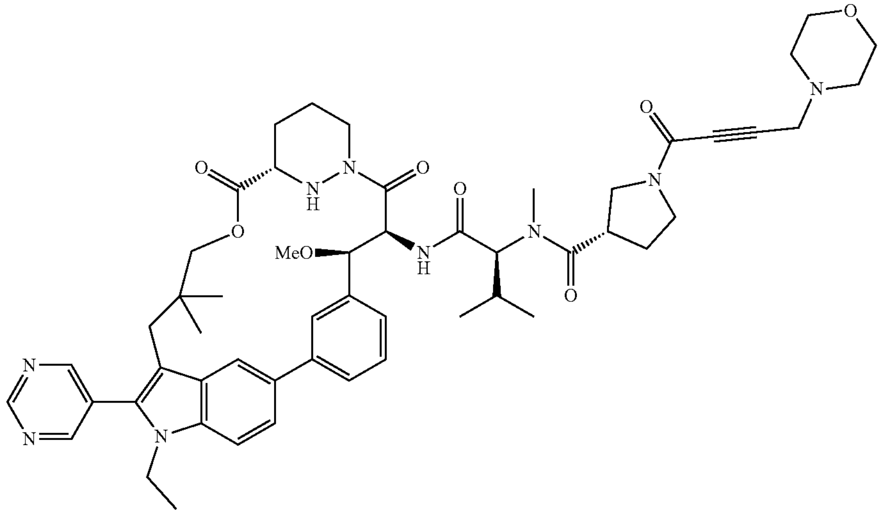 [SMILES: CCn1c(-c2cncnc2)c2c3cc(ccc31)-c1cccc(c1)[C@@H](OC)[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| C70 | 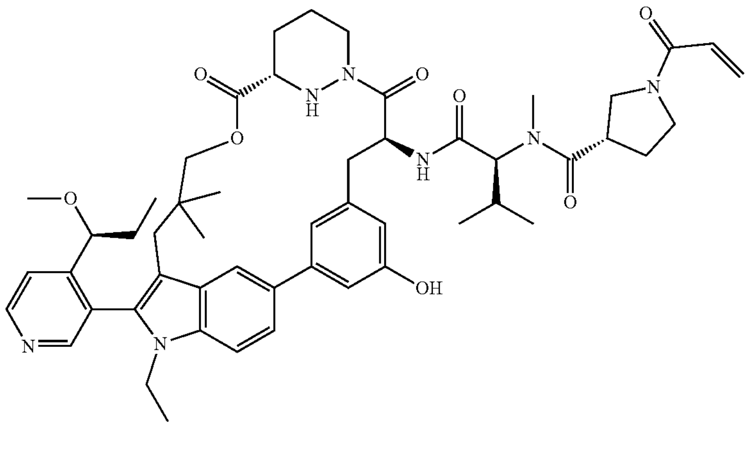 [SMILES: C=CC(=O)N1CC[C@H](C(=O)N(C)[C@H](C(=O)N[C@H]2Cc3cc(O)cc(c3)-c3ccc4c(c3)c(c(-c3cnccc3[C@H](CC)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C73 | 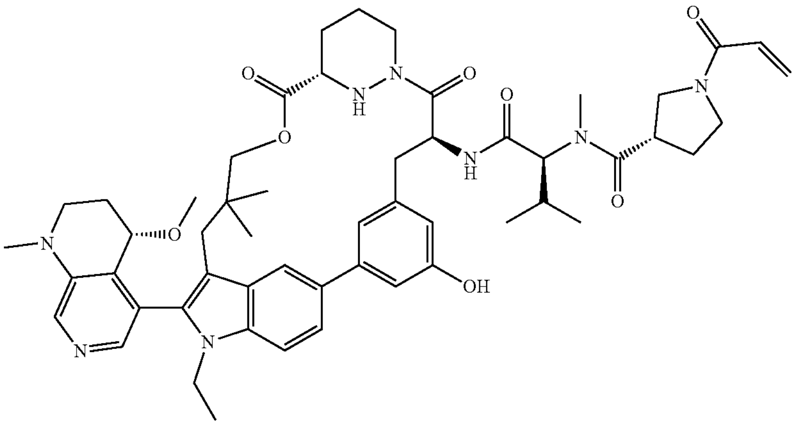 [SMILES: C=CC(=O)N1CC[C@H](C(=O)N(C)[C@H](C(=O)N[C@H]2Cc3cc(O)cc(c3)-c3ccc4c(c3)c(c(-c3cncc5c3[C@@H](OC)CCN5C)n4CC)CC(C)(C)COC(=O)[C@@H]3CCCN(N3)C2=O)C(C)C)C1] |
| C74 | 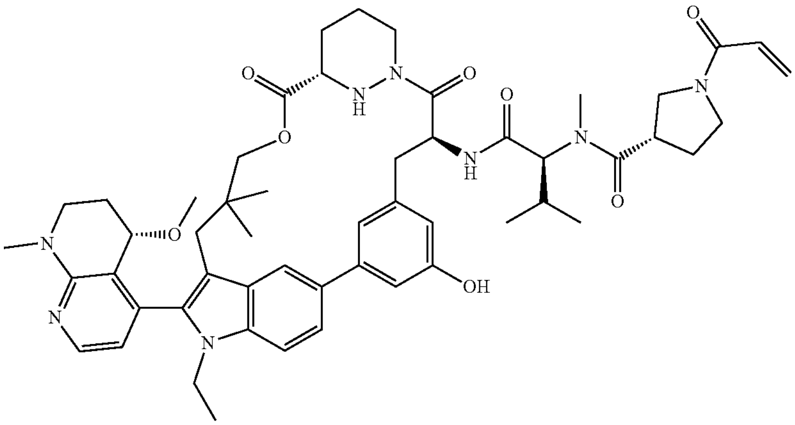 [SMILES: C=CC(=O)N1CC[C@H](C(=O)N(C)[C@H](C(=O)N[C@H]2Cc3cc(O)cc(c3)-c3ccc4c(c3)c(c(-c3ccnc5c3[C@@H](OC)CCN5C)n4CC)CC(C)(C)COC(=O)[C@@H]3CCCN(N3)C2=O)C(C)C)C1] |
| C75 | 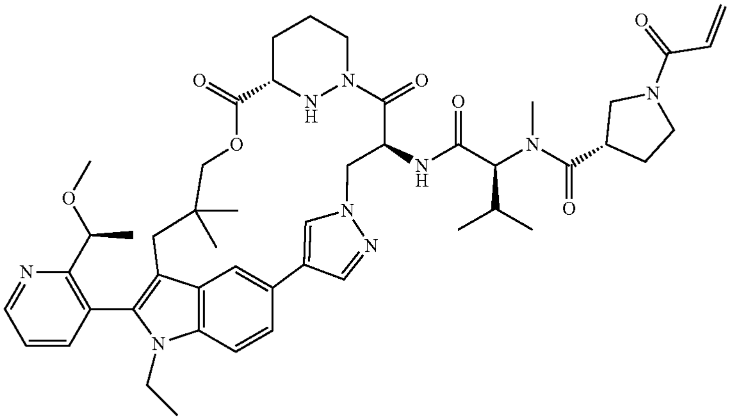 [SMILES: C=CC(=O)N1CC[C@H](C(=O)N(C)[C@H](C(=O)N[C@H]2Cn3cc(cn3)-c3ccc4c(c3)c(c(-c3cccnc3[C@H](C)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C76 | 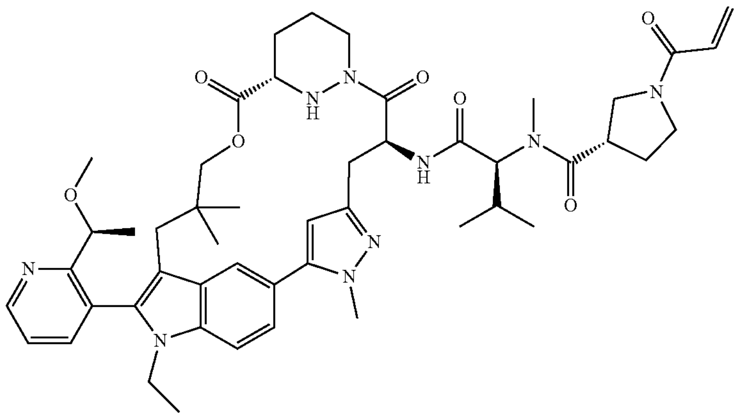 [SMILES: C=CC(=O)N1CC[C@H](C(=O)N(C)[C@H](C(=O)N[C@H]2Cc3cc(n(C)n3)-c3ccc4c(c3)c(c(-c3cccnc3[C@H](C)OC)n4CC)CC(C)(C)COC(=O)[C@@H]3CCCN(N3)C2=O)C(C)C)C1] |
| C77 | 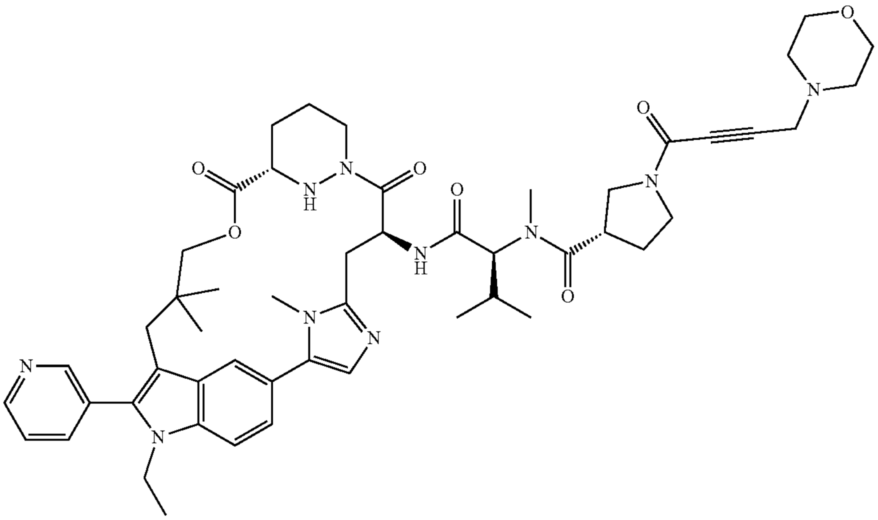 [SMILES: CCn1c(-c2cccnc2)c2c3cc(ccc31)-c1cnc(n1C)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| C81 | 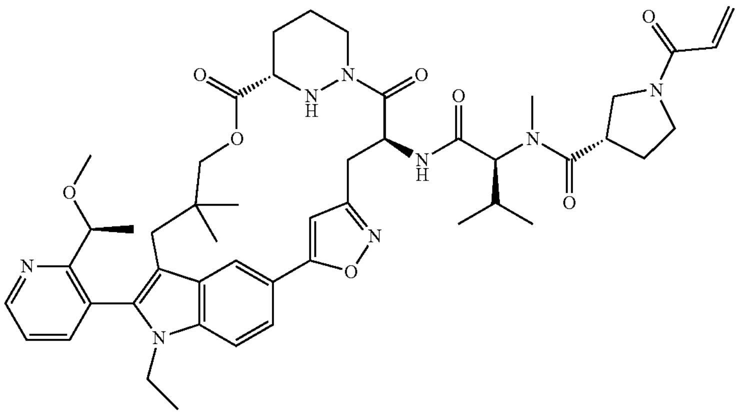 [SMILES: C=CC(=O)N1CC[C@H](C(=O)N(C)[C@H](C(=O)N[C@H]2Cc3cc(on3)-c3ccc4c(c3)c(c(-c3cccnc3[C@H](C)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C83 | 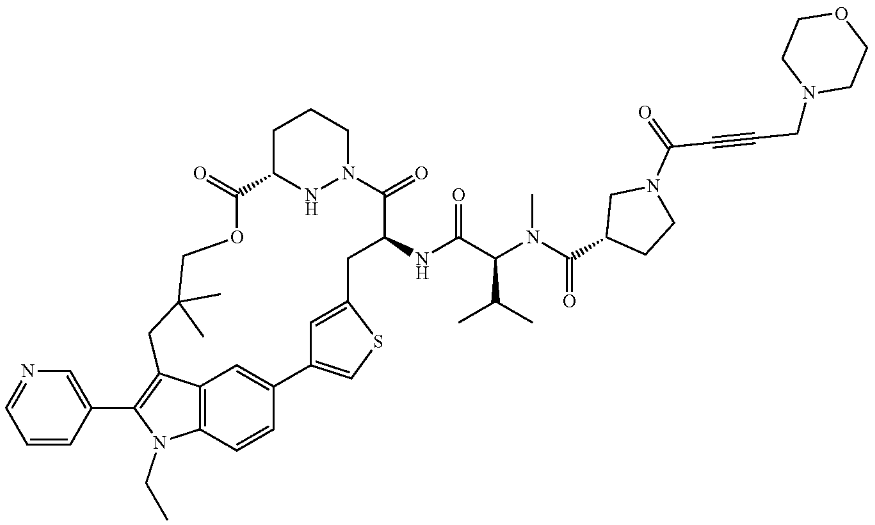 [SMILES: CCn1c(-c2cccnc2)c2c3cc(ccc31)-c1csc(c1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| C85 | 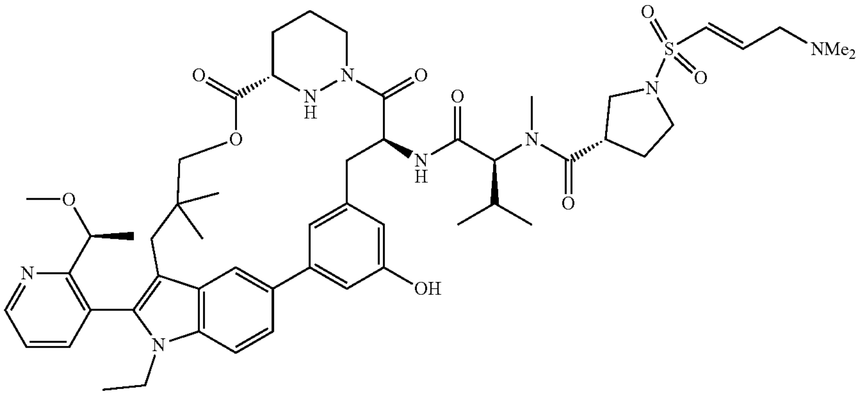 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(S(=O)(=O)/C=C/CN(C)C)C1)C(=O)N1CCC[C@H](N1)C(=O)OCC(C)(C)C2] |
| C86 | 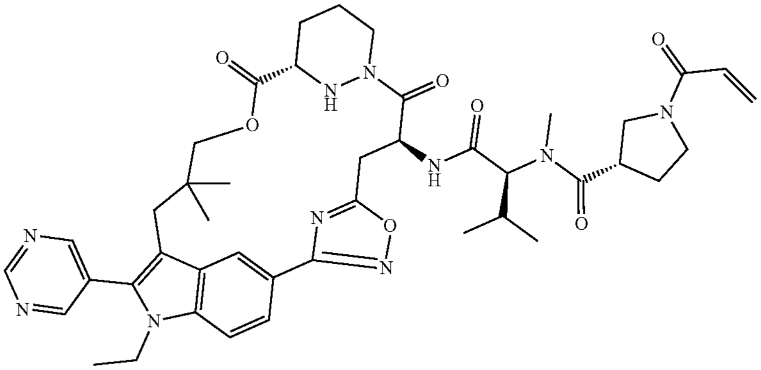 [SMILES: C=CC(=O)N1CC[C@H](C(=O)N(C)[C@H](C(=O)N[C@H]2Cc3nc(no3)-c3ccc4c(c3)c(c(-c3cncnc3)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C87 | 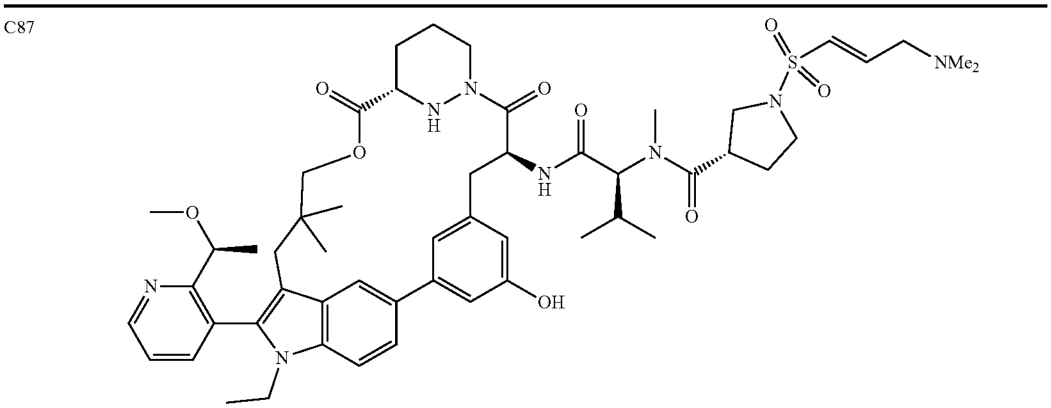 |
| C88 | 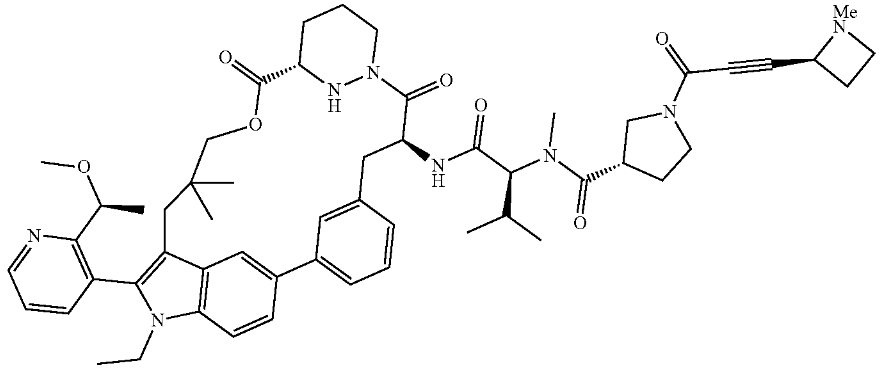 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)C#C[C@@H]3CCN3C)C1)C(=O)N1CCC[C@H](N1)C(=O)OCC(C)(C)C2] |
| C89 | 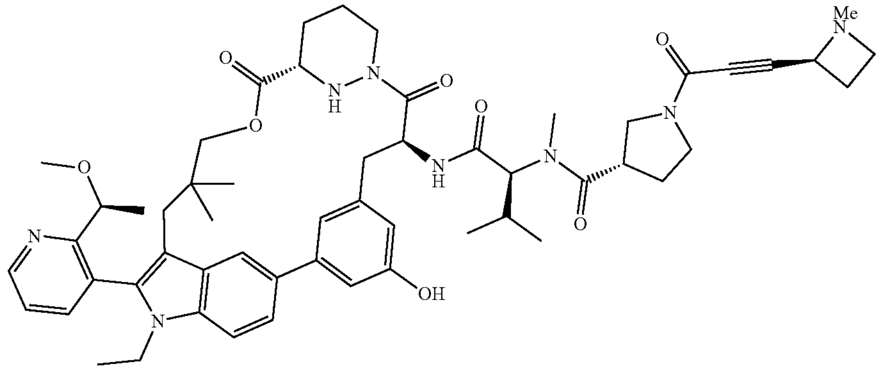 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)C#C[C@@H]3CCN3C)C1)C(=O)N1CCC[C@H](N1)C(=O)OCC(C)(C)C2] |
| C90 | 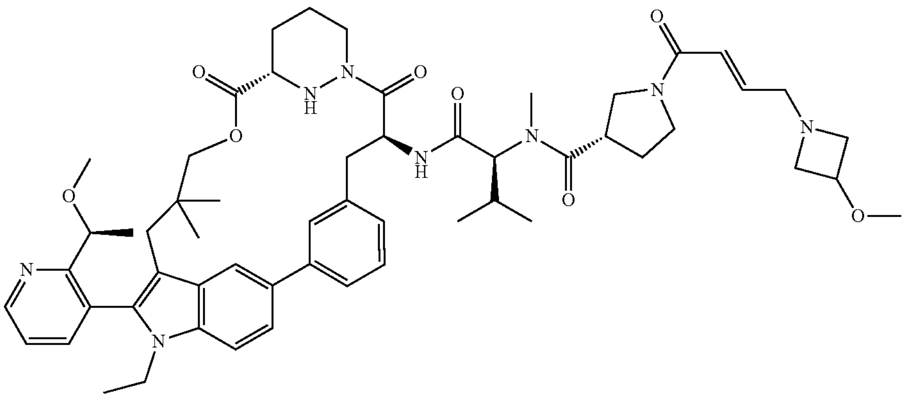 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)/C=C/CN3CC(OC)C3)C1)C(=O)N1CCC[C@H](N1)C(=O)OCC(C)(C)C2] |

TABLE 2-continued
| Certain Compounds | |
|---|---|
| Ex # | Structure |
| C91 | 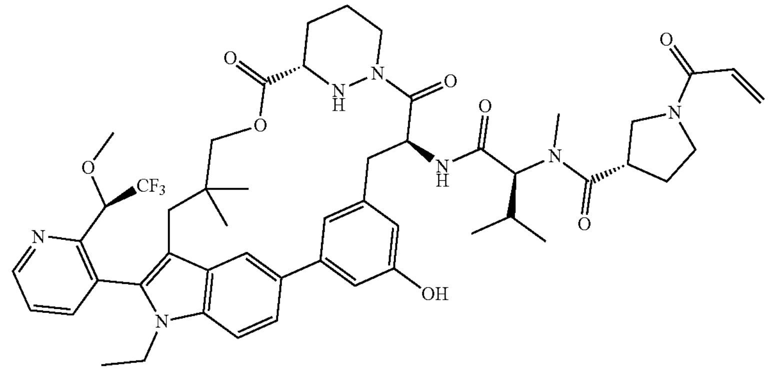 [SMILES: C=CC(=O)N1CC[C@H](C(=O)N(C)[C@H](C(=O)N[C@H]2Cc3cc(O)cc(c3)-c3ccc4c(c3)c(c(-c3cccnc3[C@@H](OC)C(F)(F)F)n4CC)CC(C)(C)COC(=O)[C@@H]3CCCN(N3)C2=O)C(C)C)C1] |
| C96 | 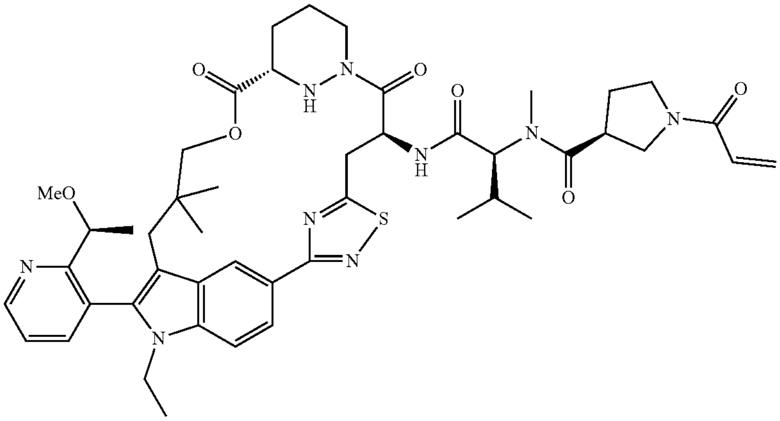 [SMILES: C=CC(=O)N1CC[C@H](C(=O)N(C)[C@H](C(=O)N[C@H]2Cc3nc(ns3)-c3ccc4c(c3)c(c(-c3cccnc3[C@H](C)OC)n4CC)CC(C)(C)COC(=O)[C@@H]3CCCN(N3)C2=O)C(C)C)C1] |
| C97 | 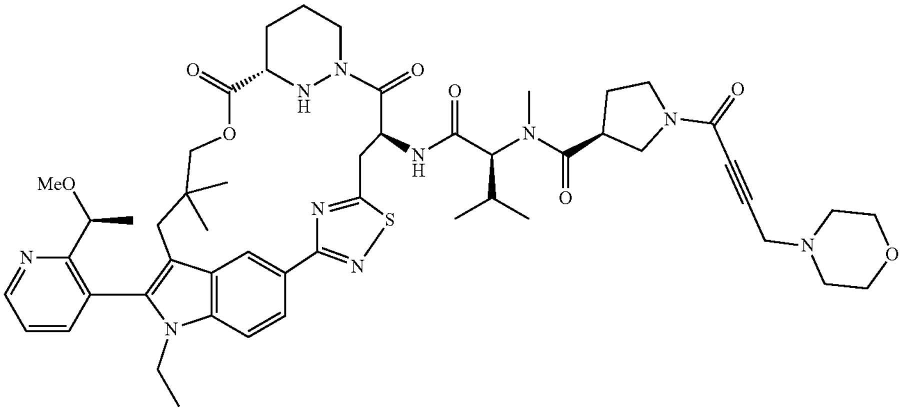 |

TABLE 2-continued
| Certain Compounds | |
|---|---|
| Ex # | Structure |
| C102 | 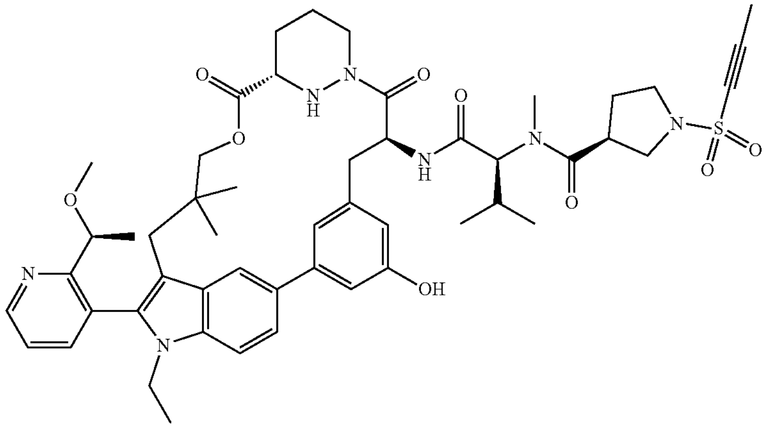 [SMILES: CC#CS(=O)(=O)N1CC[C@H](C(=O)N(C)[C@H](C(=O)N[C@H]2Cc3cc(O)cc(c3)-c3ccc4c(c3)c(c(-c3cccnc3[C@H](C)OC)n4CC)CC(C)(C)COC(=O)[C@@H]3CCCN(N3)C2=O)C(C)C)C1] |
| C103 | 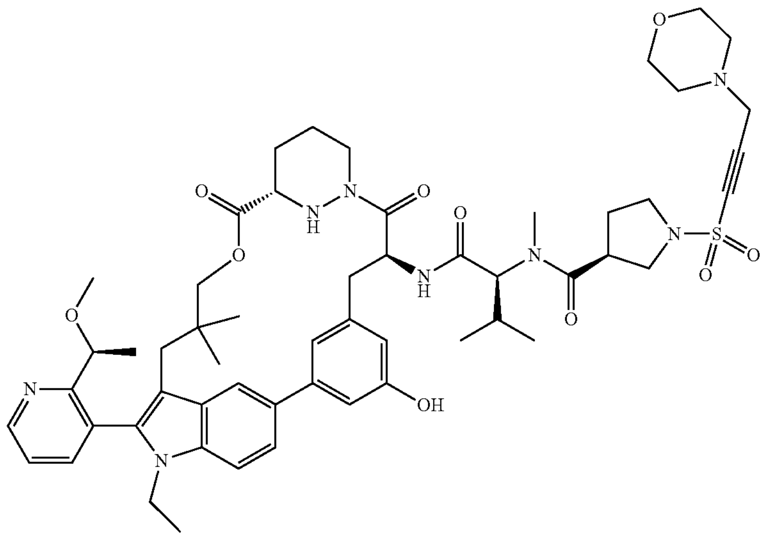 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(S(=O)(=O)C#CCN3CCOCC3)C1)C(=O)N1CCC[C@H](N1)C(=O)OCC(C)(C)C2] |
| C104 | 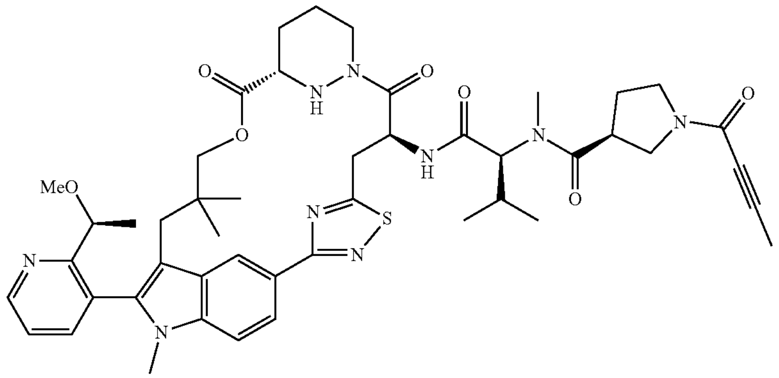 [SMILES: CC#CC(=O)N1CC[C@H](C(=O)N(C)[C@H](C(=O)N[C@H]2Cc3nc(ns3)-c3ccc4c(c3)c(c(-c3cccnc3[C@H](C)OC)n4C)CC(C)(C)COC(=O)[C@@H]3CCCN(N3)C2=O)C(C)C)C1] |

TABLE 2-continued
| Certain Compounds | |
|---|---|
| Ex # | Structure |
| C106 | 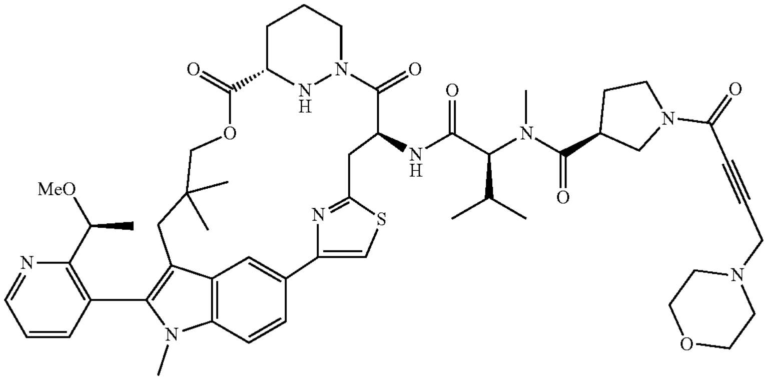 |
| C107 | 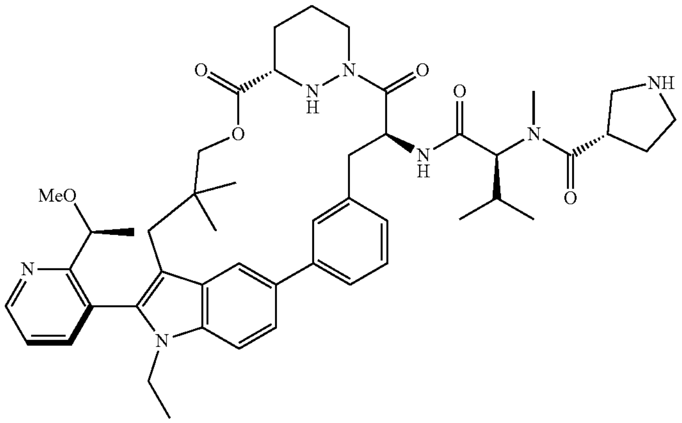 |
| C109 | 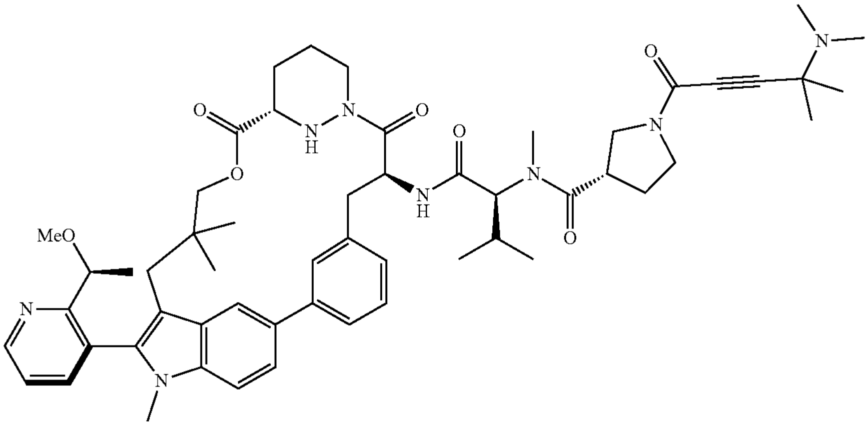 |

TABLE 2-continued
| Certain Compounds | |
|---|---|
| Ex # | Structure |
| C111 | 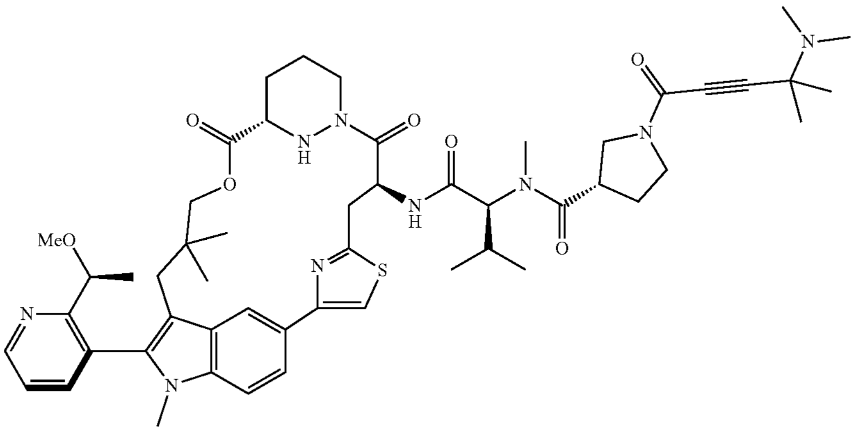 |
| C112 | 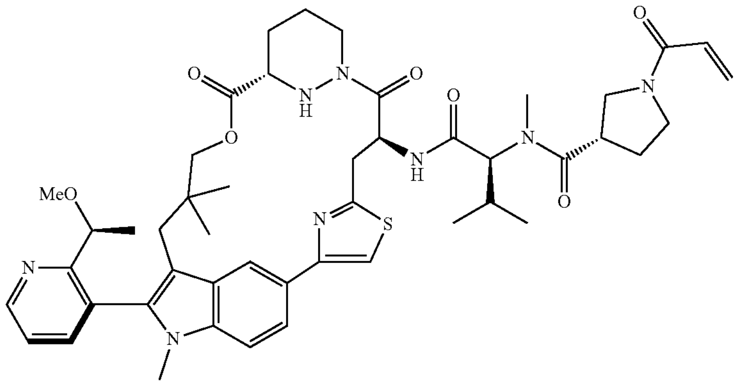 |
| C113 | 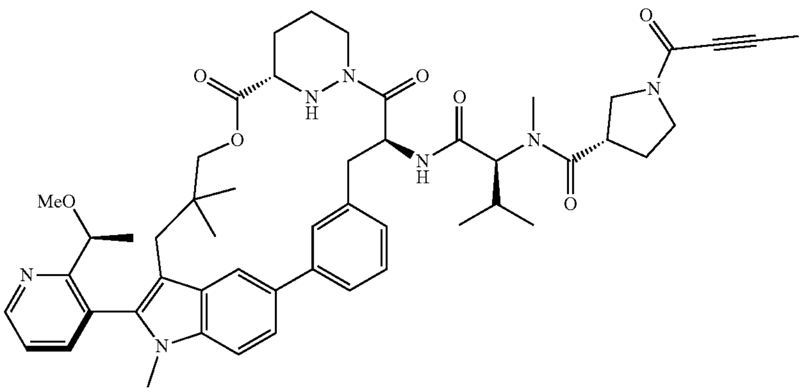 |

TABLE 2-continued
| Certain Compounds | |
|---|---|
| Ex # | Structure |
| C115 | 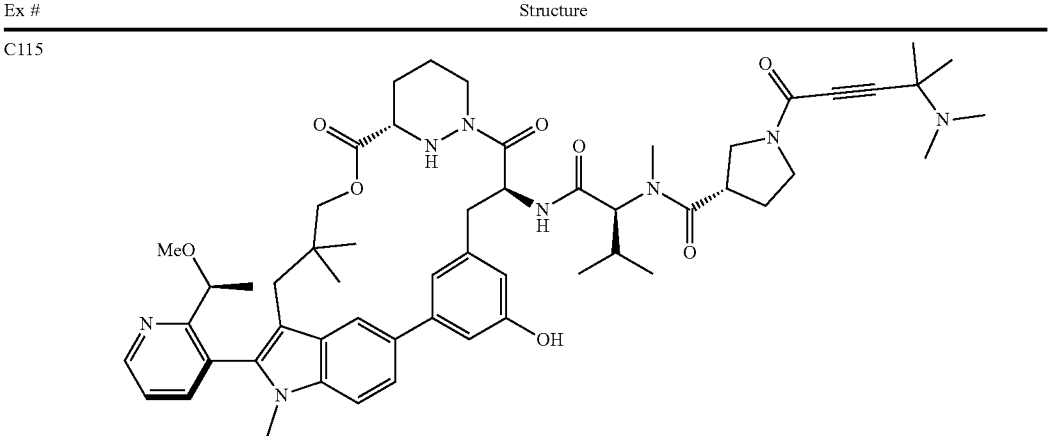 |
| C116 | 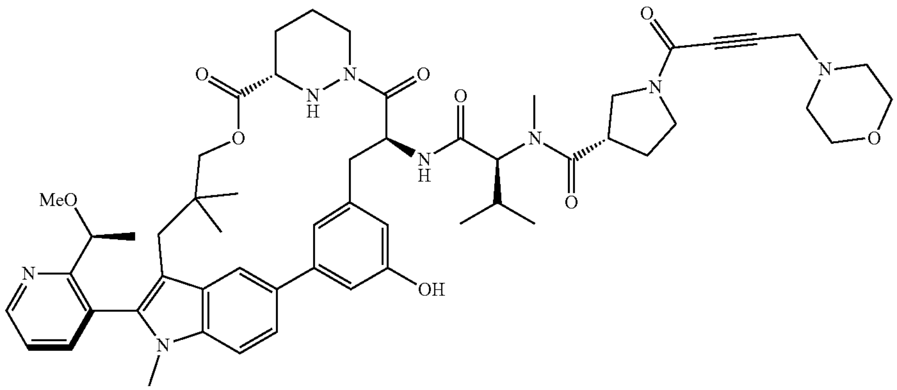 |
| C117 | 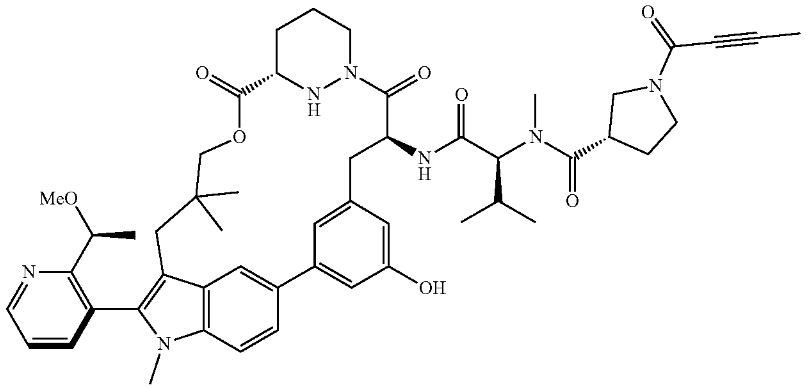 |
| C118 | 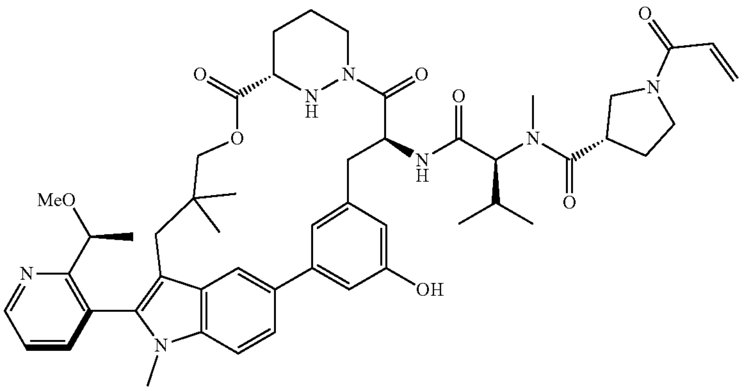 |

TABLE 2-continued
| Certain Compounds | |
|---|---|
| Ex # | Structure |
| C119 | 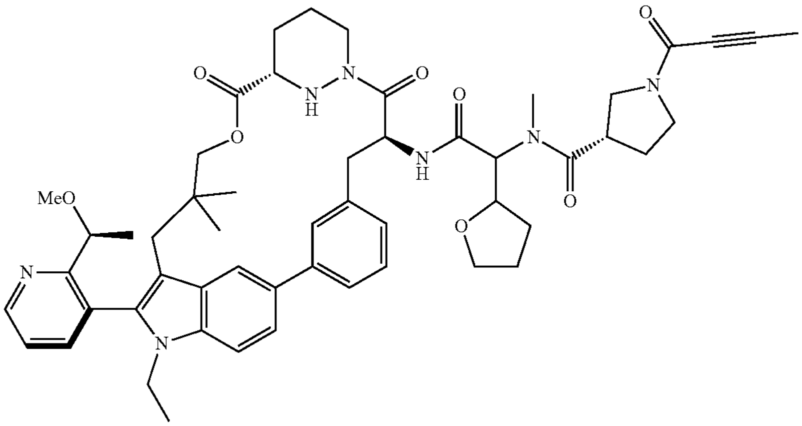 |
| C120 | 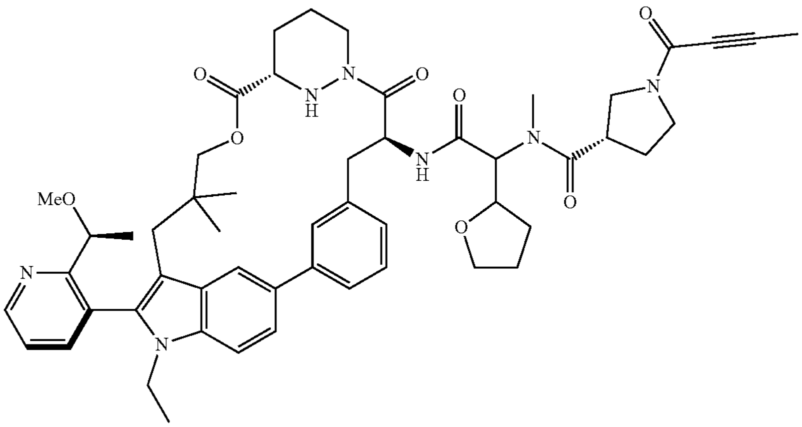 |
| C121 | 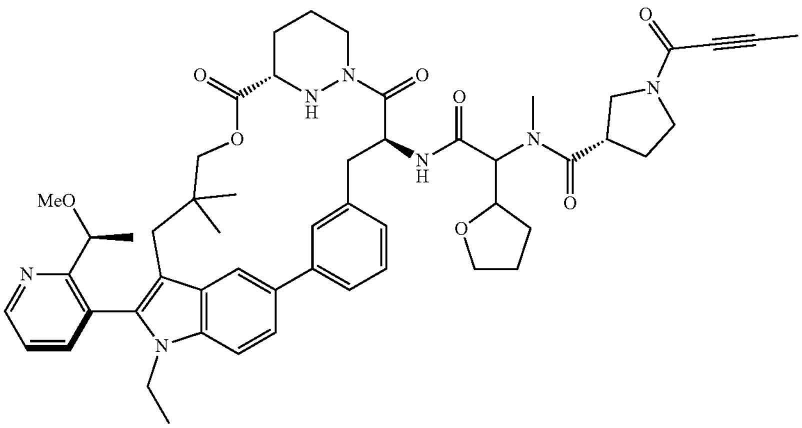 |

TABLE 2-continued
| Certain Compounds | |
|---|---|
| Ex # | Structure |
| C122 | 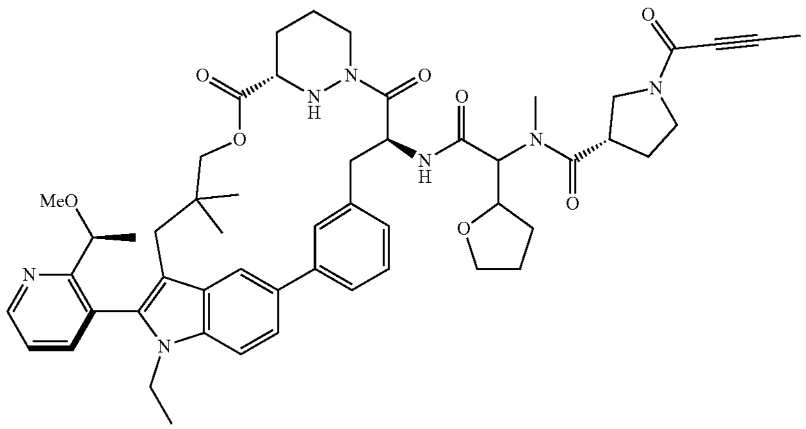 |
| C123 | 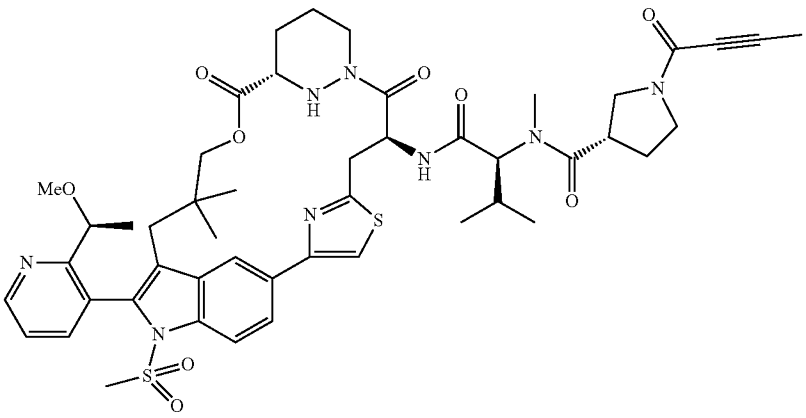 [SMILES: CC#CC(=O)N1CC[C@H](C(=O)N(C)[C@H](C(=O)N[C@H]2Cc3nc(cs3)-c3ccc4c(c3)c(c(-c3cccnc3[C@H](C)OC)n4S(C)(=O)=O)CC(C)(C)COC(=O)[C@@H]3CCCN(N3)C2=O)C(C)C)C1] |
| C124 | 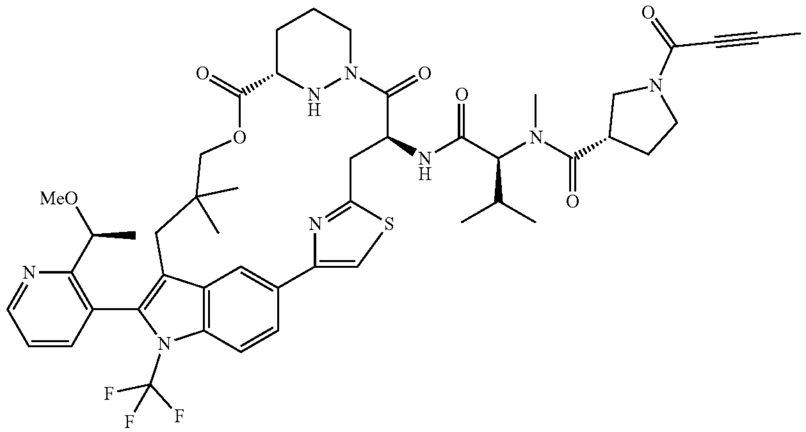 [SMILES: CC#CC(=O)N1CC[C@H](C(=O)N(C)[C@H](C(=O)N[C@H]2Cc3nc(cs3)-c3ccc4c(c3)c(c(-c3cccnc3[C@H](C)OC)n4C(F)(F)F)CC(C)(C)COC(=O)[C@@H]3CCCN(N3)C2=O)C(C)C)C1] |

TABLE 2-continued
| Certain Compounds | |
|---|---|
| Ex # | Structure |
| C126 | 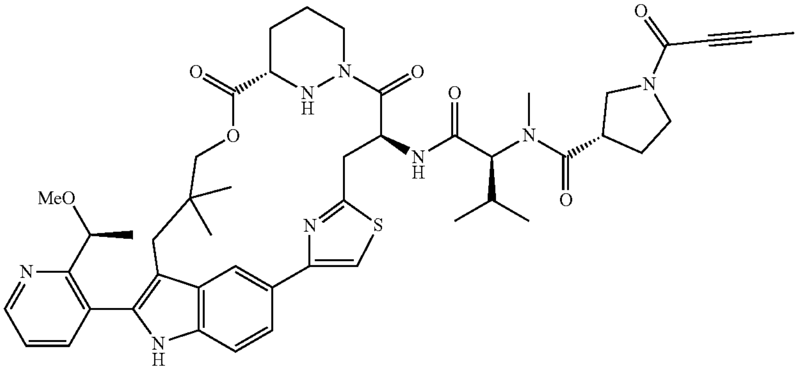 [SMILES: CC#CC(=O)N1CC[C@H](C(=O)N(C)[C@H](C(=O)N[C@H]2Cc3nc(cs3)-c3ccc4[nH]c(-c5cccnc5[C@H](C)OC)c(c4c3)CC(C)(C)COC(=O)[C@@H]3CCCN(N3)C2=O)C(C)C)C1] |
| C127 | 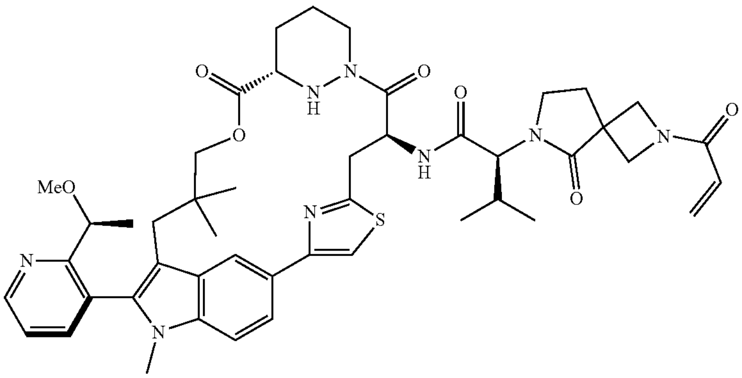 |
| C128 | 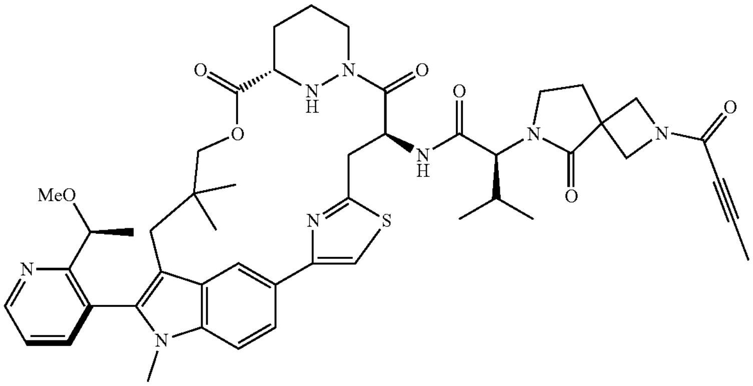 |
| C129 | 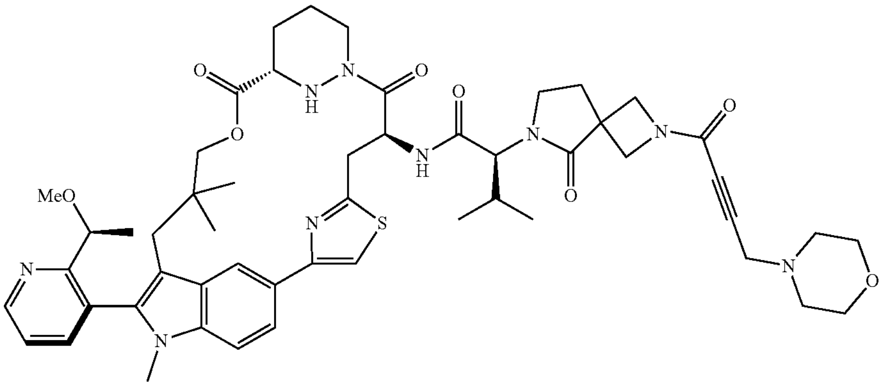 |

TABLE 2-continued
| Certain Compounds | |
| --- | --- |
| Ex # | Structure |
| C130 | 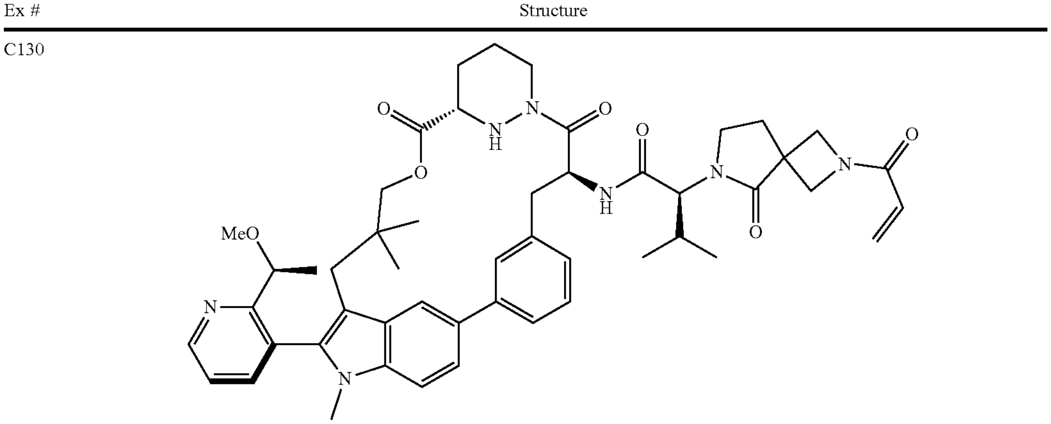 |
| C131 | 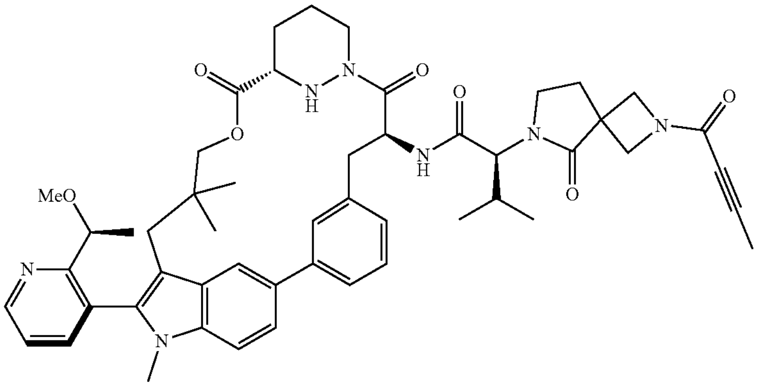 |
| C132 | 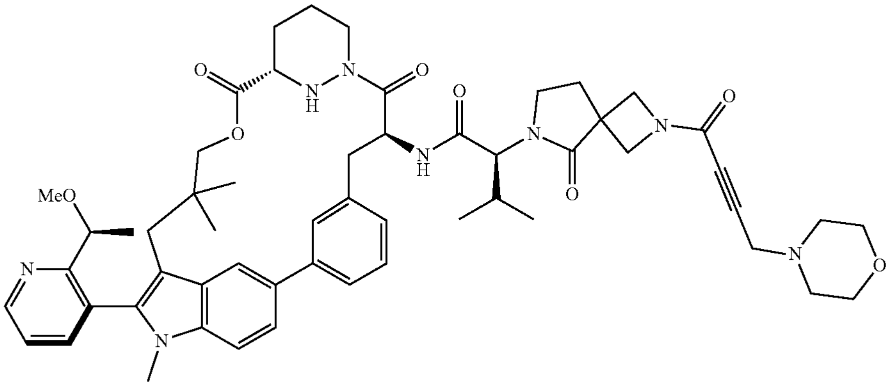 |
| C139 | 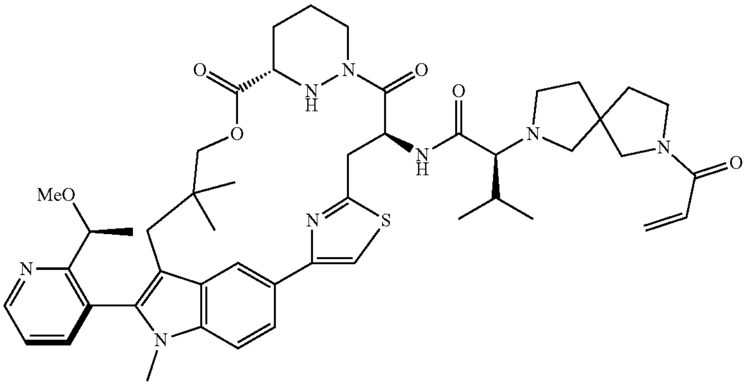 |

TABLE 2-continued
| Certain Compounds | |
|---|---|
| Ex # | Structure |
| C140 | 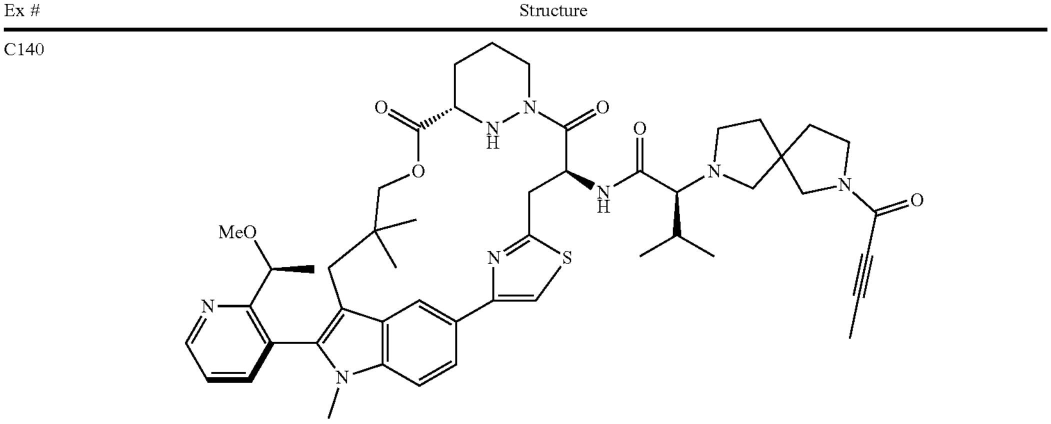 |
| C141 | 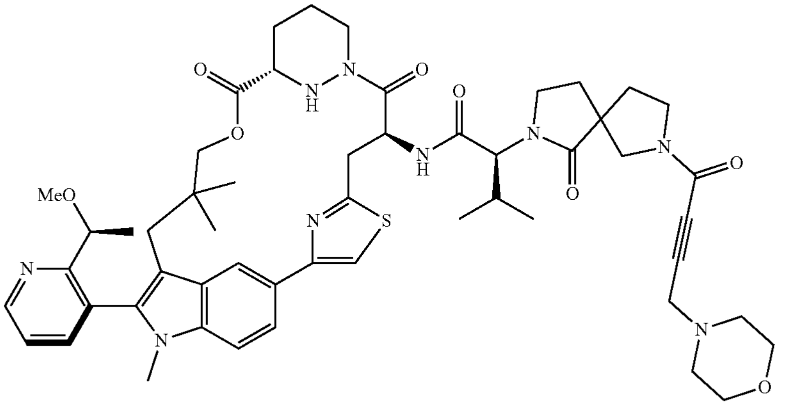 |
| C142 | 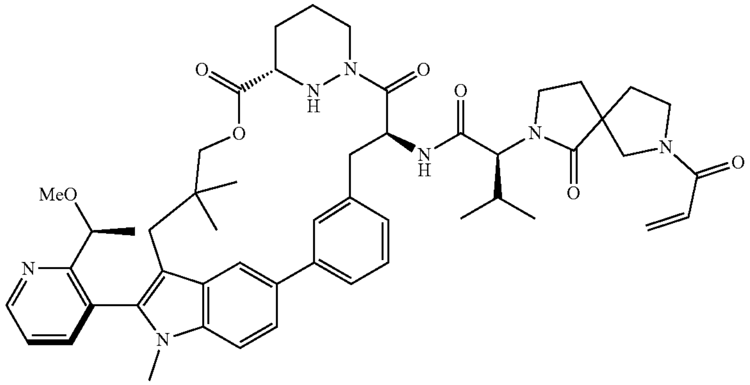 |
| C143 | 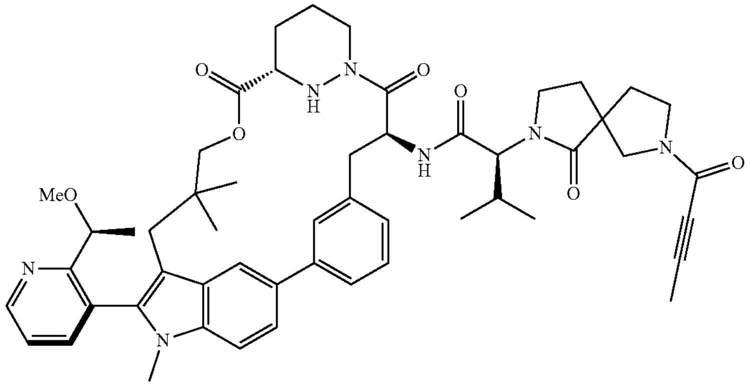 |

TABLE 2-continued
| Certain Compounds | |
|---|---|
| Ex # | Structure |
| C144 | 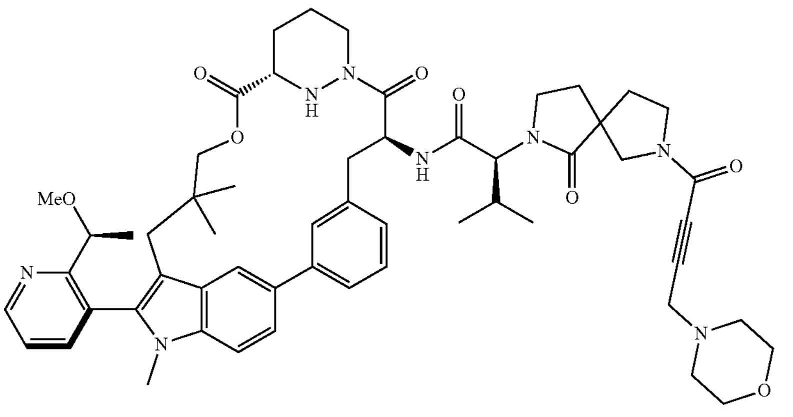 |
| C145 | 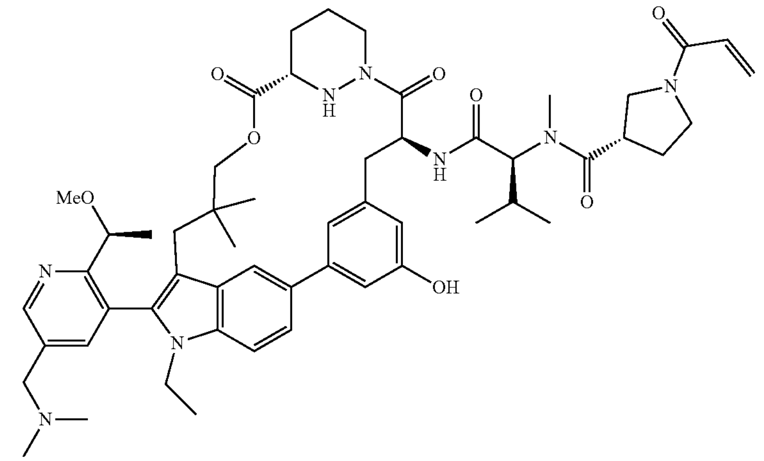 [SMILES: C=CC(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |
| C146 | 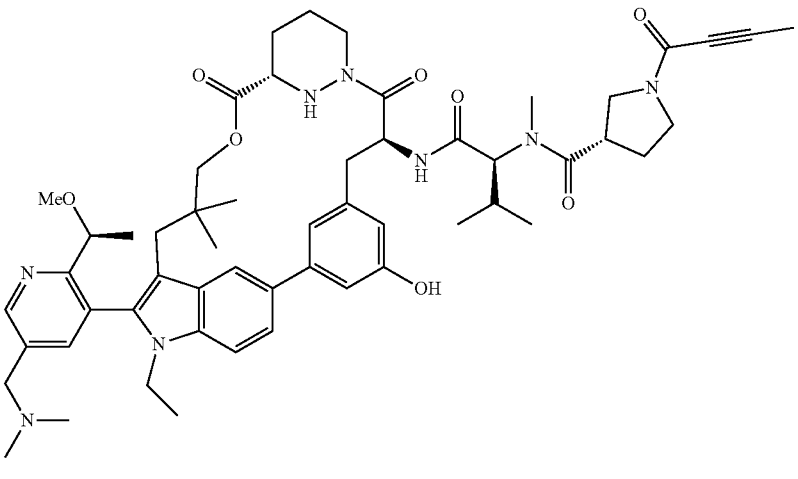 [SMILES: CC#CC(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C147 | 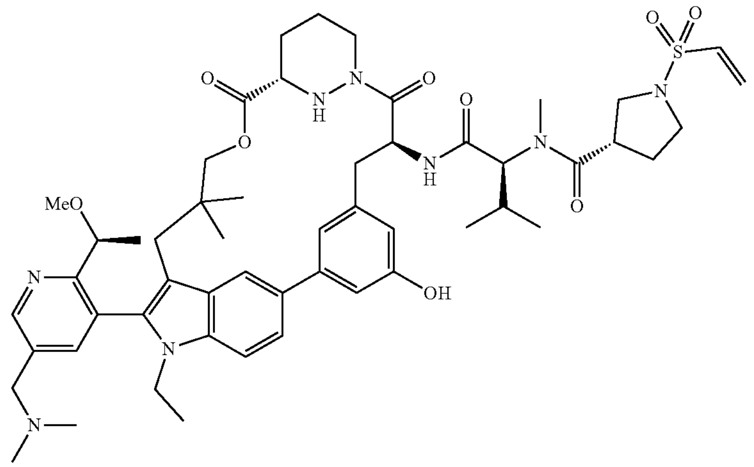 [SMILES: C=CS(=O)(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |
| C148 | 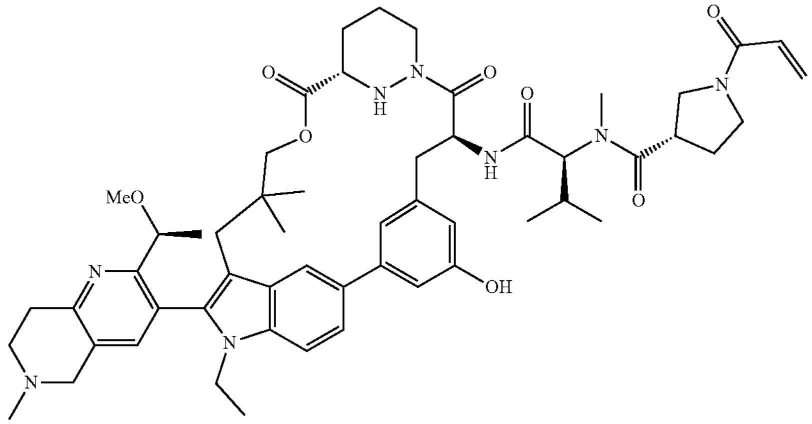 [SMILES: C=CC(=O)N1CC[C@H](C(=O)N(C)[C@H](C(=O)N[C@H]2Cc3cc(O)cc(c3)-c3ccc4c(c3)c(c(-c3cc5c(nc3[C@H](C)OC)CCN(C)C5)n4CC)CC(C)(C)COC(=O)[C@@H]3CCCN(N3)C2=O)C(C)C)C1] |
| C149 | 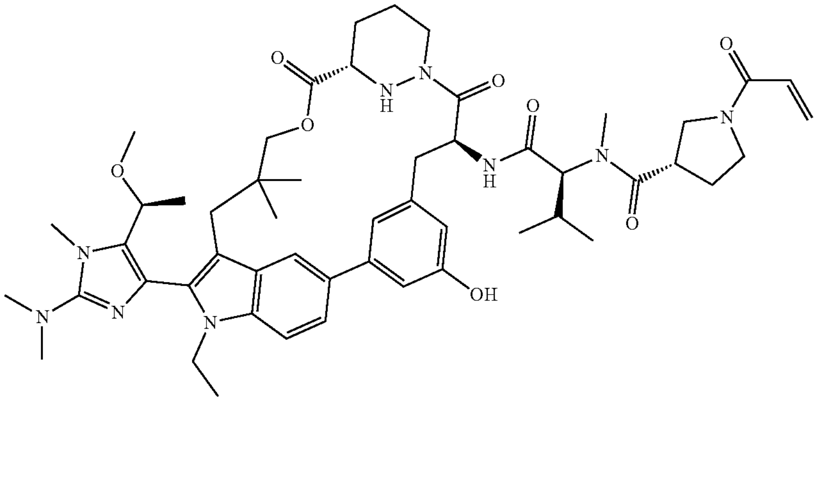 [SMILES: C=CC(=O)N1CC[C@H](C(=O)N(C)[C@H](C(=O)N[C@H]2Cc3cc(O)cc(c3)-c3ccc4c(c3)c(c(-c3nc(N(C)C)n(C)c3[C@H](C)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C150 | 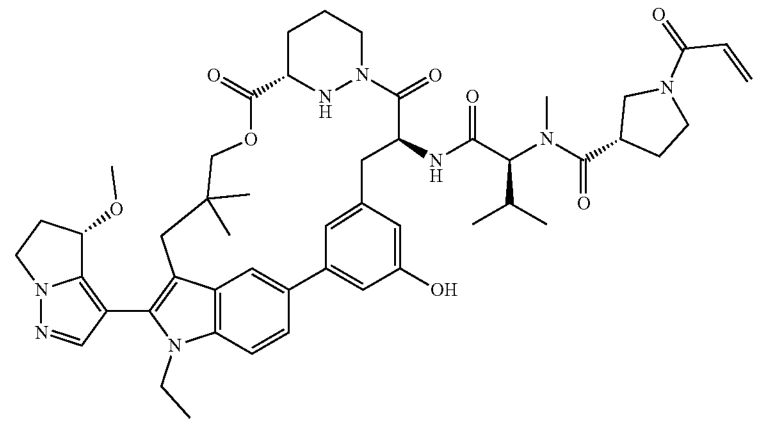 [SMILES: C=CC(=O)N1CC[C@H](C(=O)N(C)[C@H](C(=O)N[C@H]2Cc3cc(O)cc(c3)-c3ccc4c(c3)c(c(-c3cnn5c3[C@@H](OC)CC5)n4CC)CC(C)(C)COC(=O)[C@@H]3CCCN(N3)C2=O)C(C)C)C1] |
| C161 | 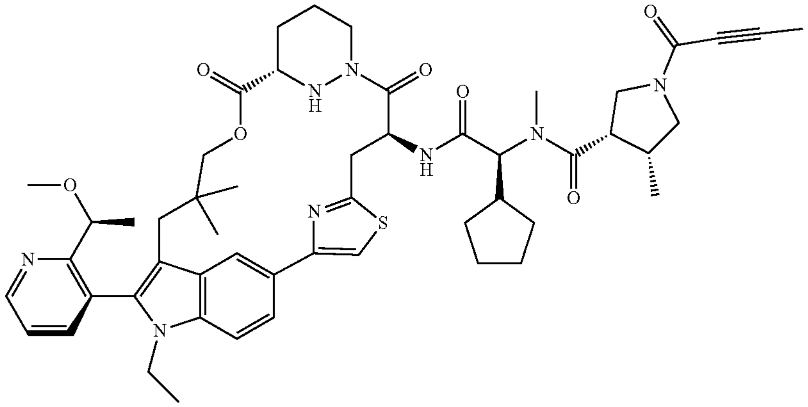 |
| C162 | 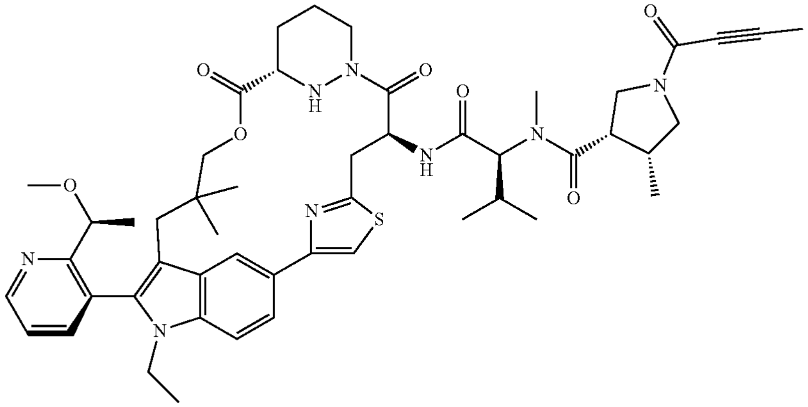 |

TABLE 2-continued
| Certain Compounds | |
|---|---|
| Ex # | Structure |
| C163 | 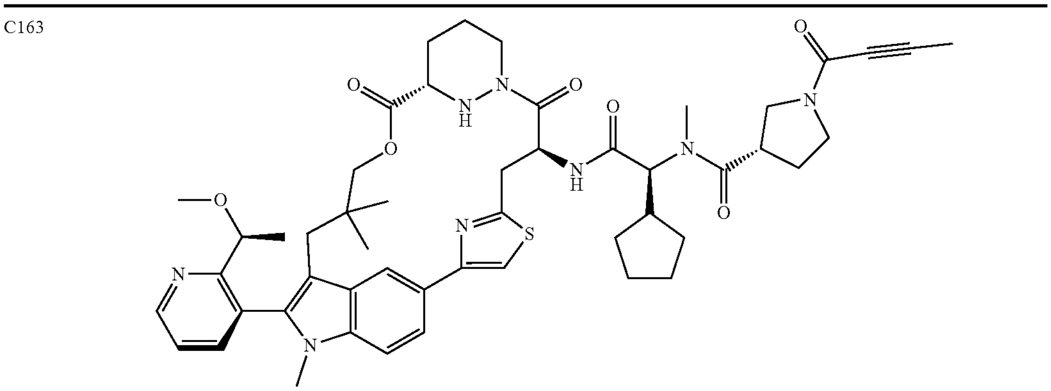 |
| C164 | 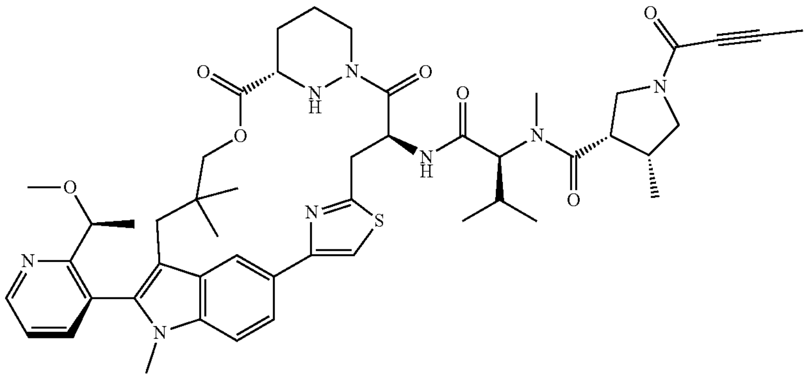 |
| C165 | 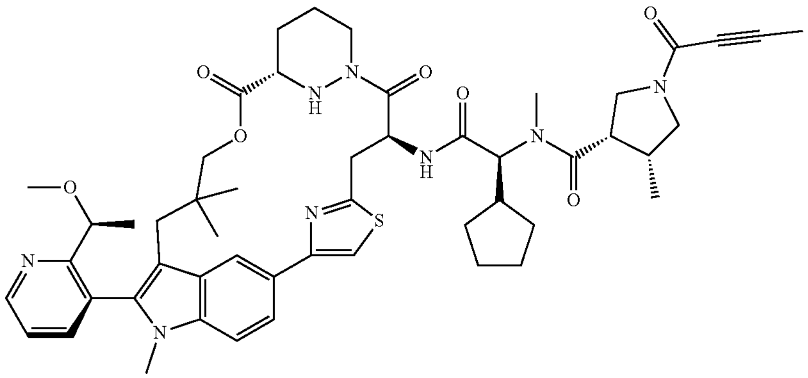 |
| C167 | 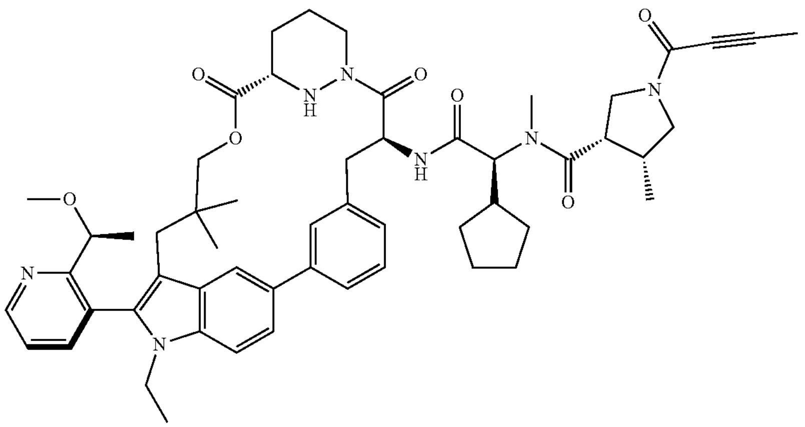 |

TABLE 2-continued
| Certain Compounds | |
|---|---|
| Ex # | Structure |
| C168 | 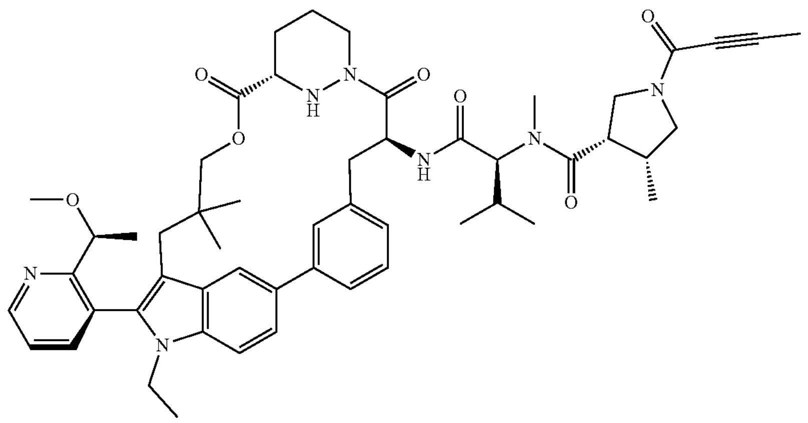 |
| C169 | 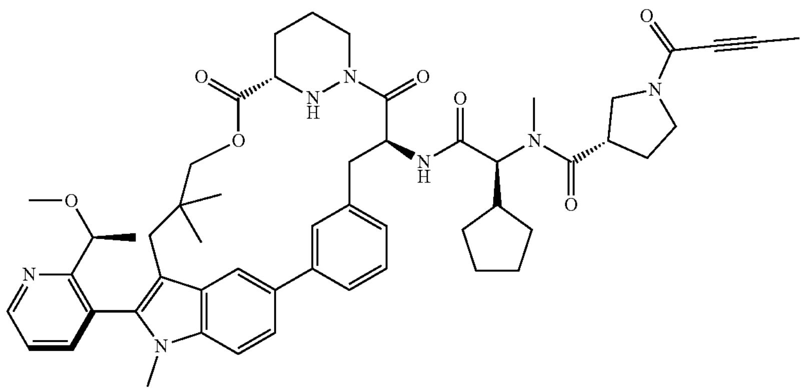 |
| C170 | 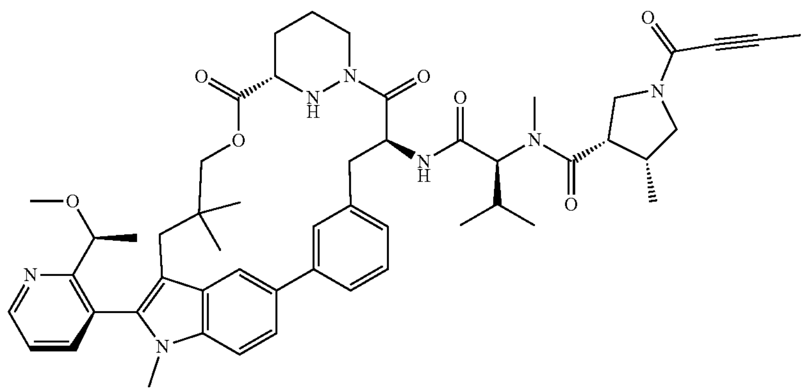 |

TABLE 2-continued
| Certain Compounds | |
|---|---|
| Ex # | Structure |
| C171 | 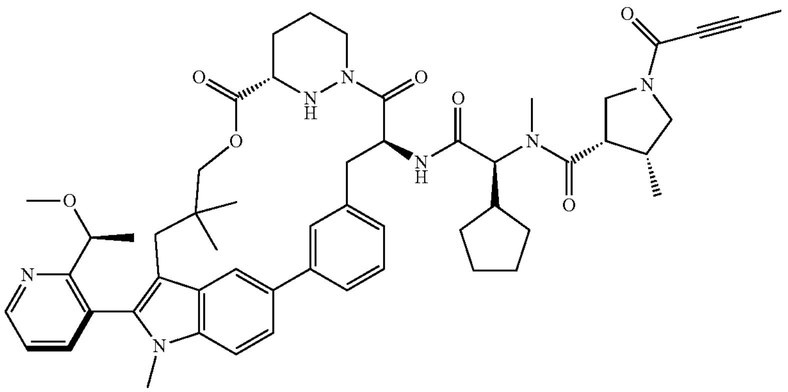 |
| C172 | 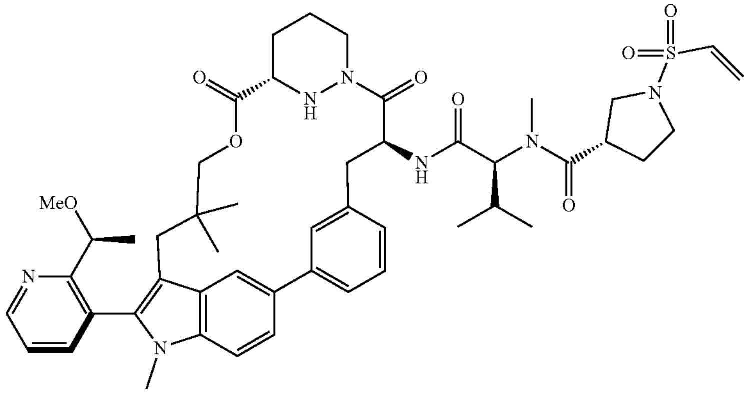 |
| C173 | 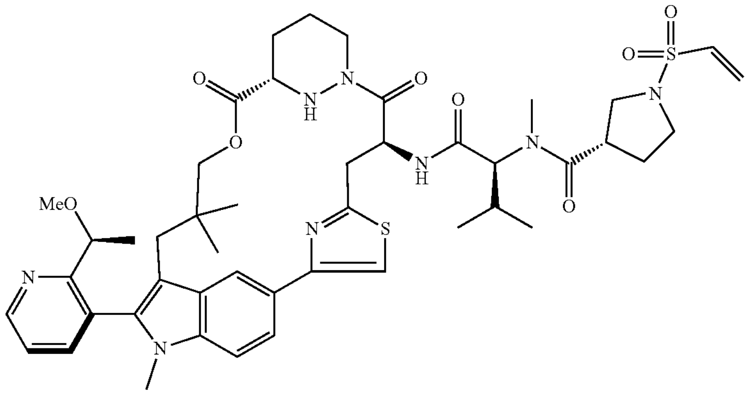 |

TABLE 2-continued
| Certain Compounds | |
|---|---|
| Ex # | Structure |
| C174 | 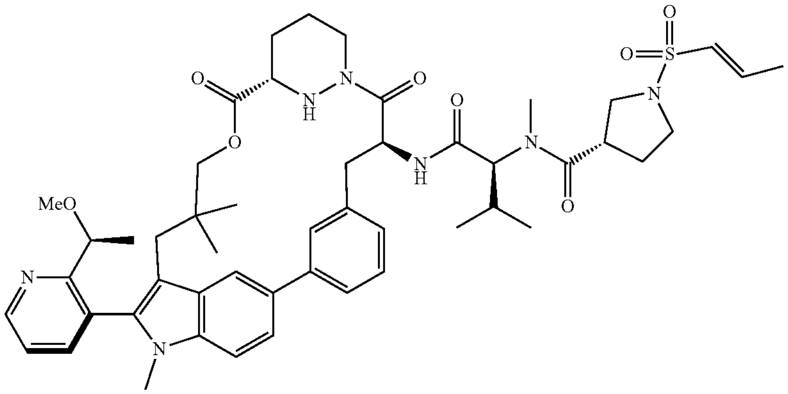 |
| C175 | 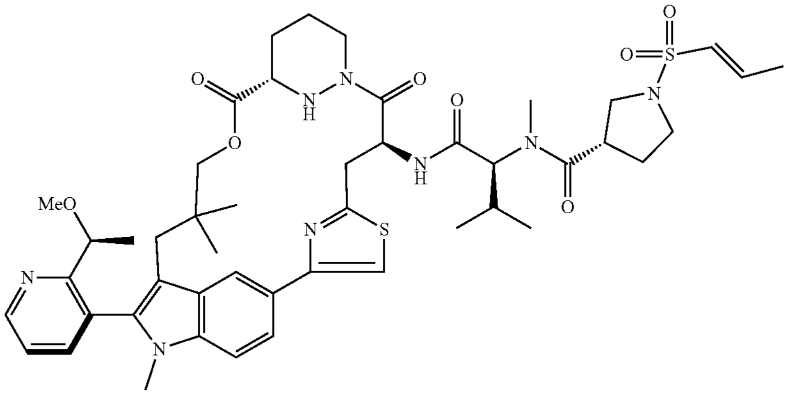 |
| C176 | 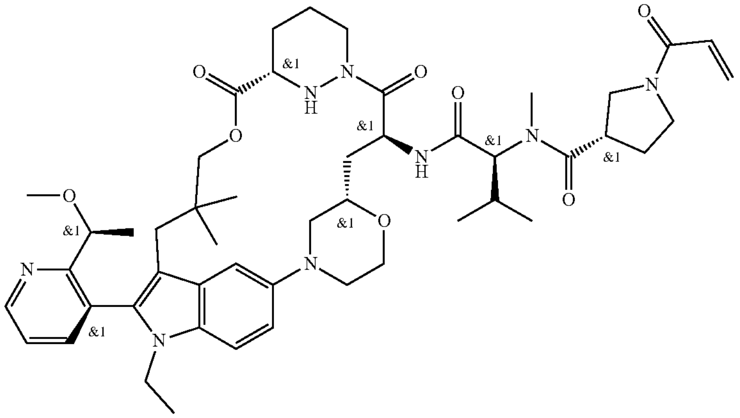 |

TABLE 2-continued
| Certain Compounds | |
|---|---|
| Ex # | Structure |
| C177 | 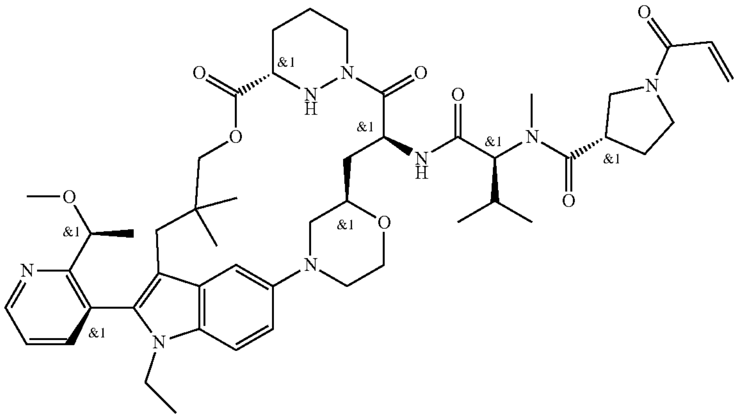 |
| C178 | 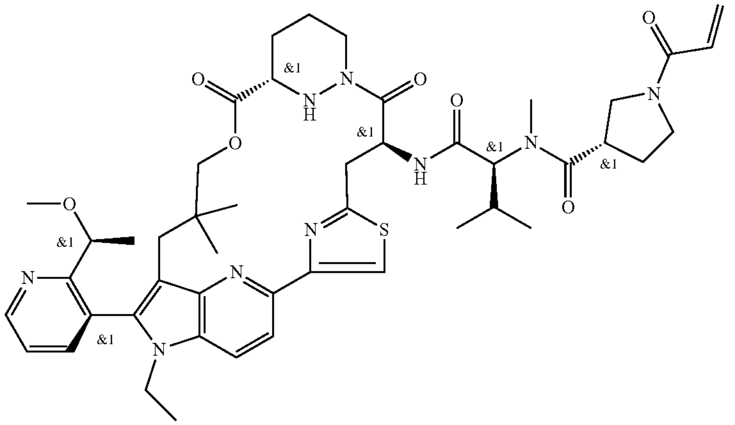 |
| C179 | 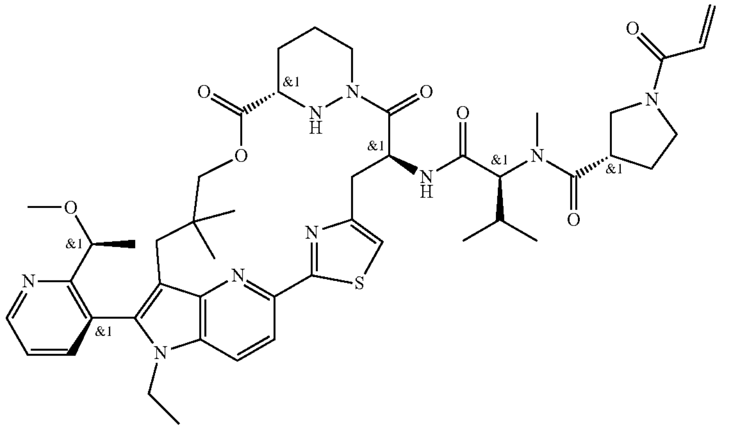 |

TABLE 2-continued
| Certain Compounds | |
|---|---|
| Ex # | Structure |
| C180 | 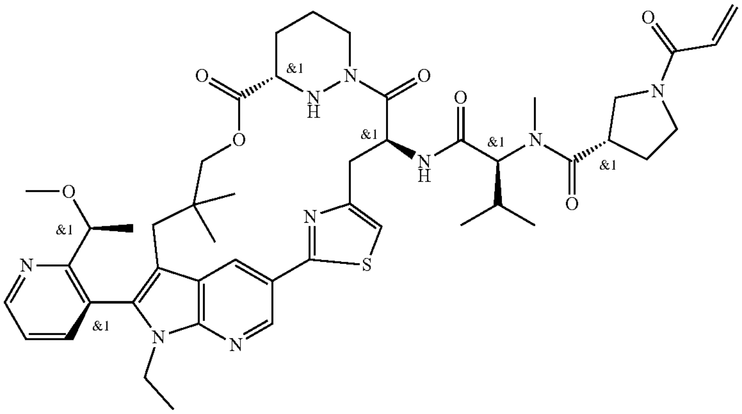 |
| C181 | 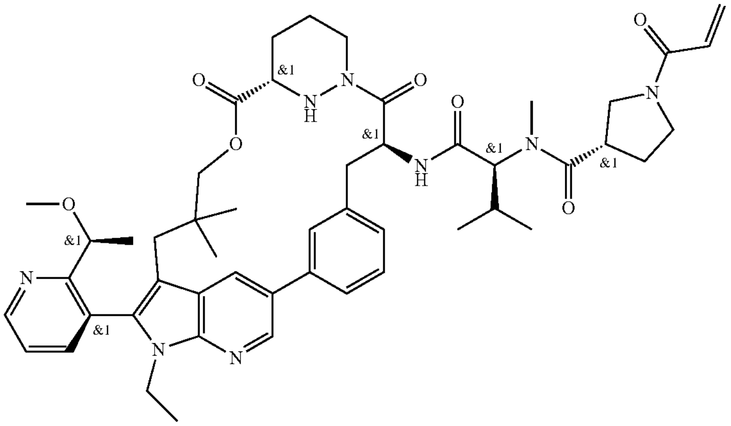 |
| C182 | 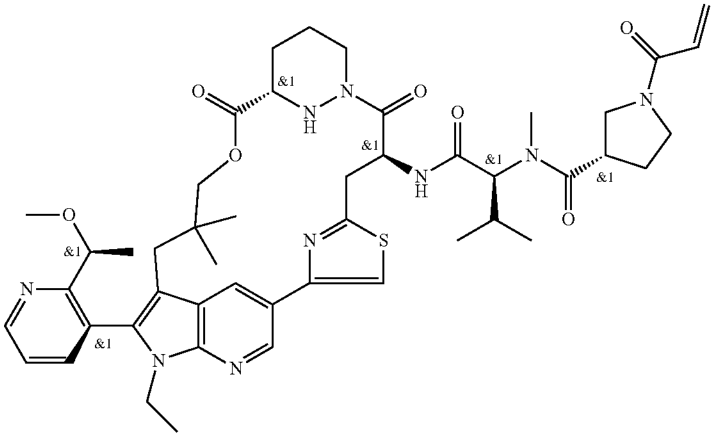 |

TABLE 2-continued
| Certain Compounds | |
|---|---|
| Ex # | Structure |
| C183 | 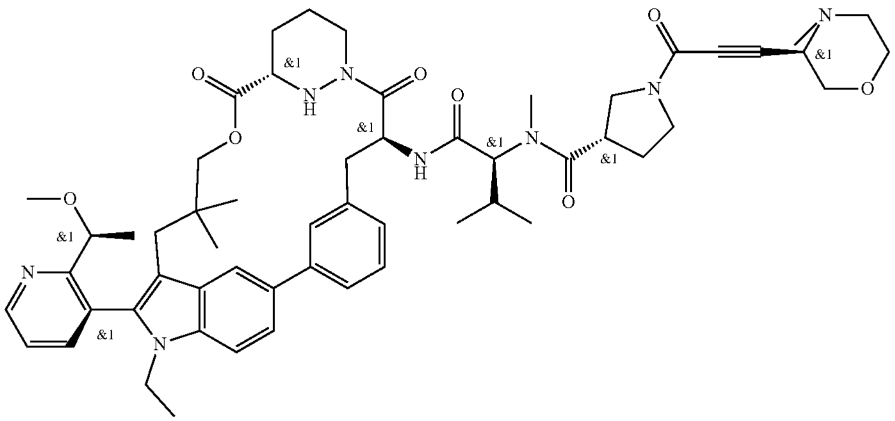 |
| C184 | 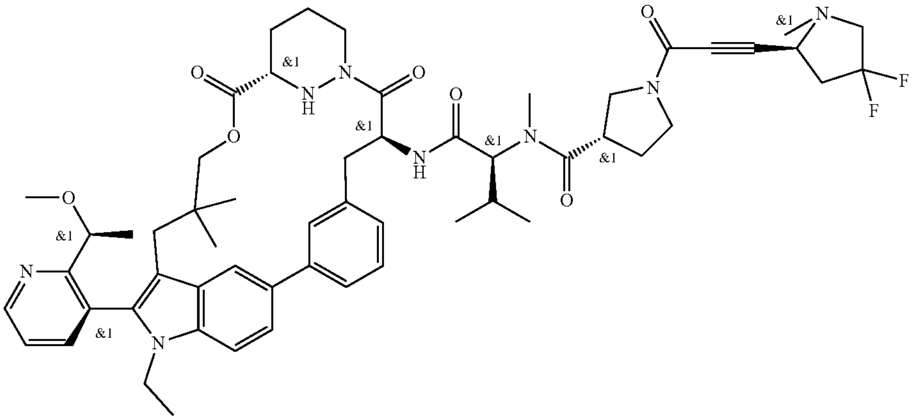 |
| C185 | 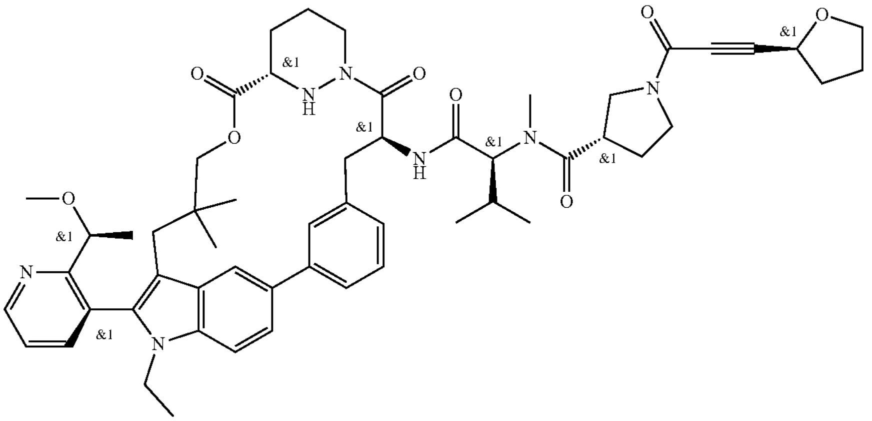 |

TABLE 2-continued
| Certain Compounds | |
|---|---|
| Ex # | Structure |
| C186 | 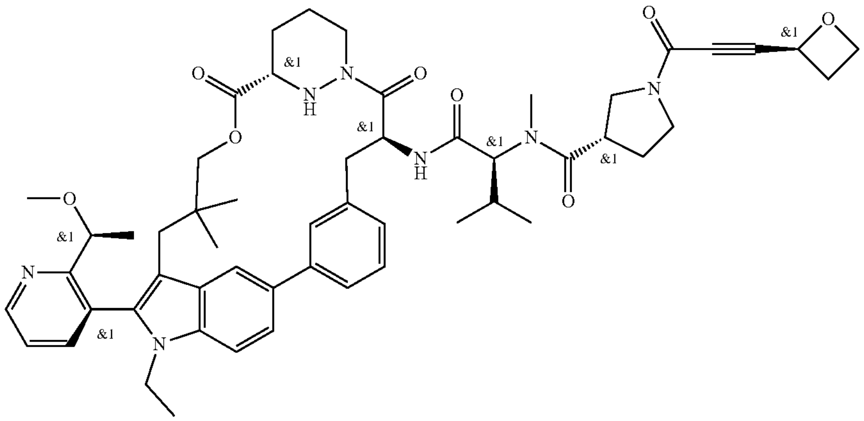 |
| C187 | 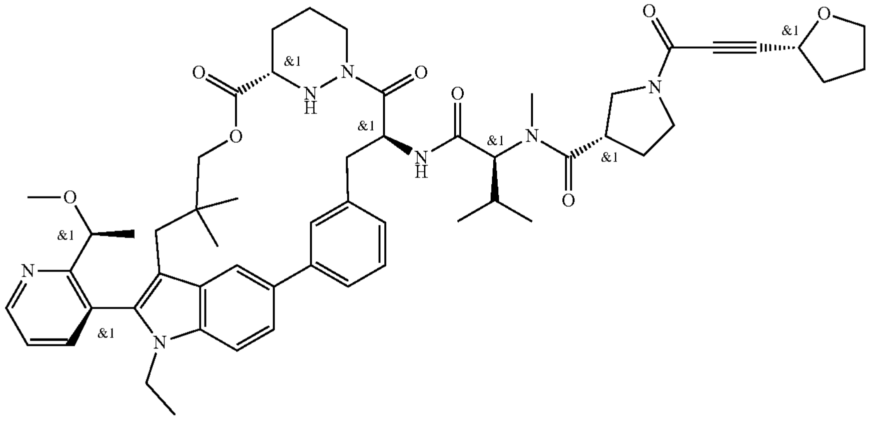 |
| C188 | 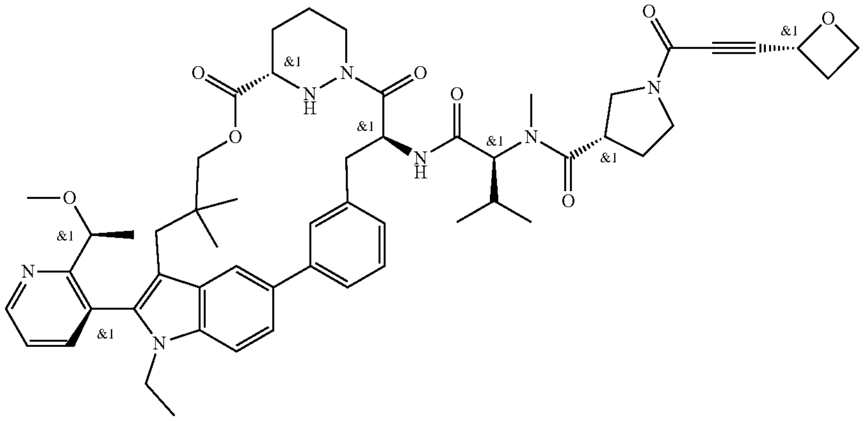 |

TABLE 2-continued
| Certain Compounds | |
|---|---|
| Ex # | Structure |
| C189 | 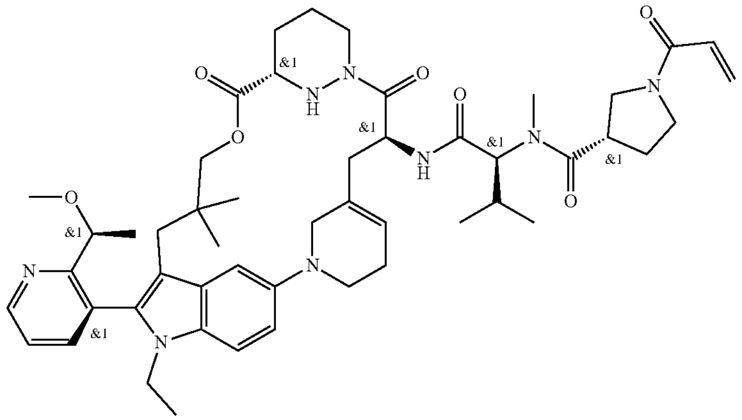 |
| C190 | 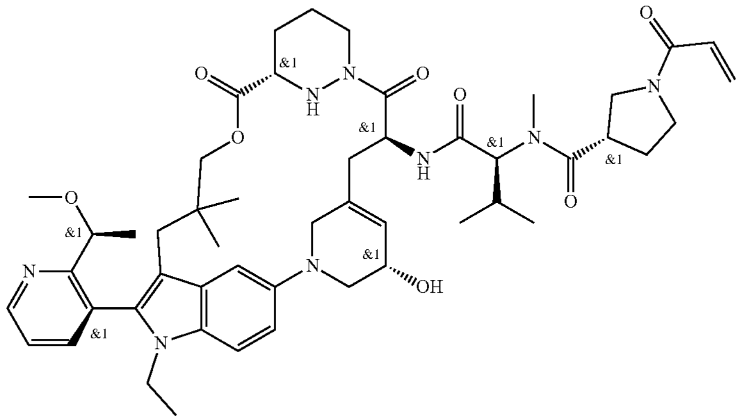 |
| C191 | 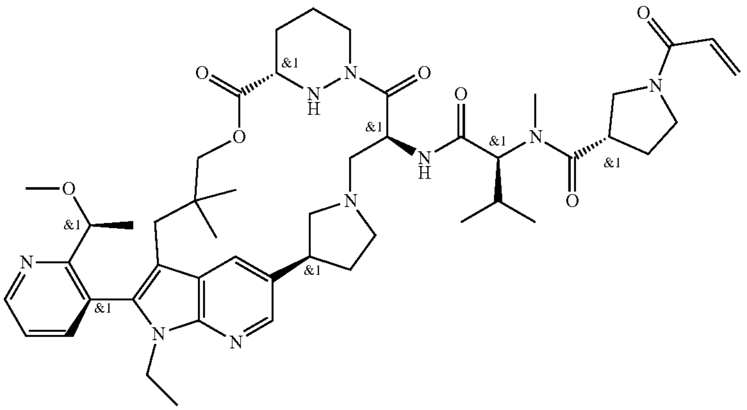 |

TABLE 2-continued
| Certain Compounds | |
|---|---|
| Ex # | Structure |
| C192 | 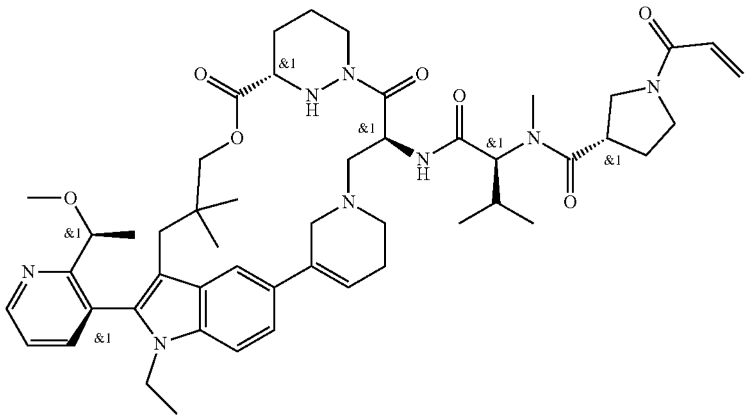 |
| C194 | 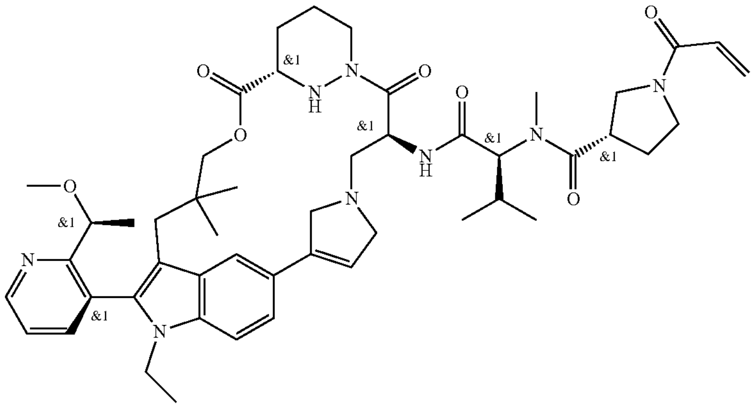 |
| C195 | 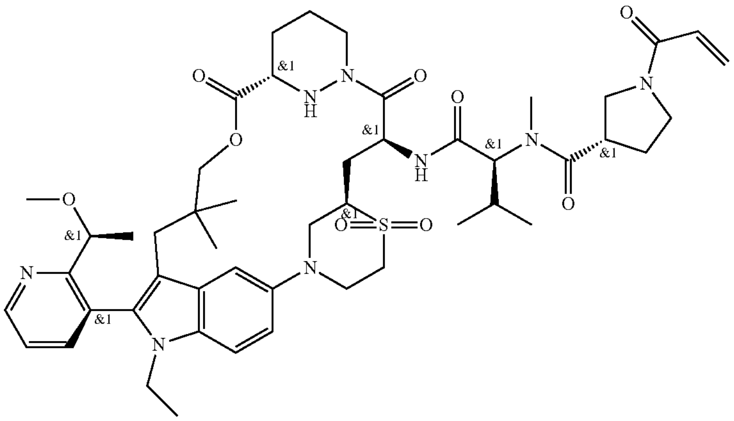 |

TABLE 2-continued
| Certain Compounds | |
|---|---|
| Ex # | Structure |
| C196 | 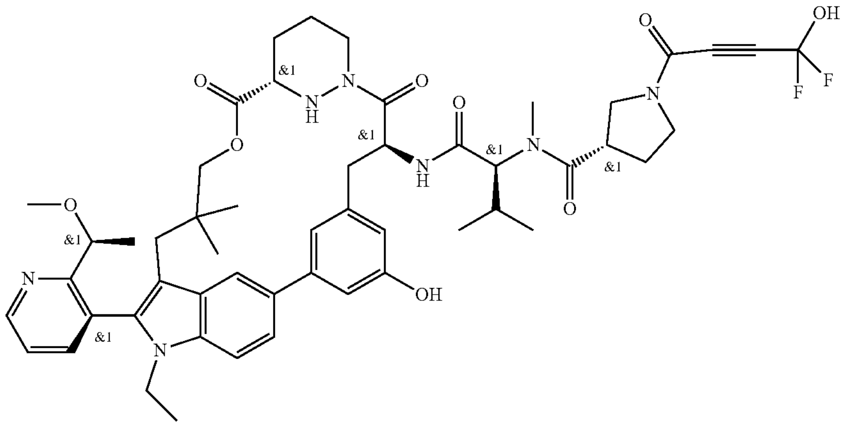 |
| C197 | 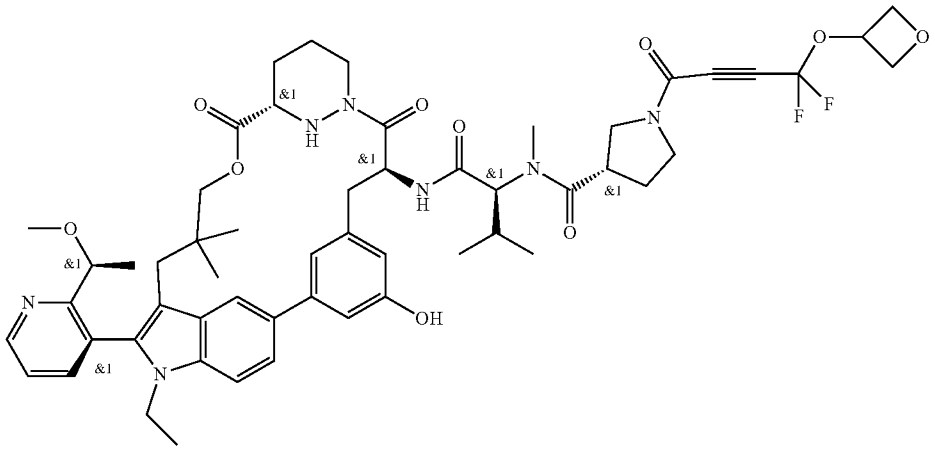 |
| C198 | 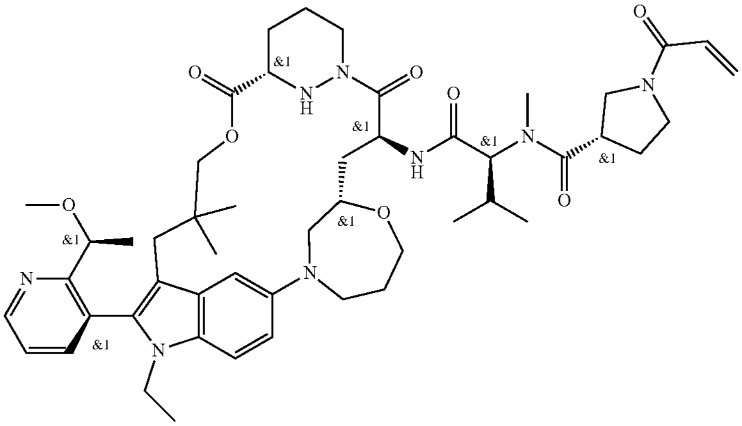 |

TABLE 2-continued
| Certain Compounds | |
|---|---|
| Ex # | Structure |
| C199 | 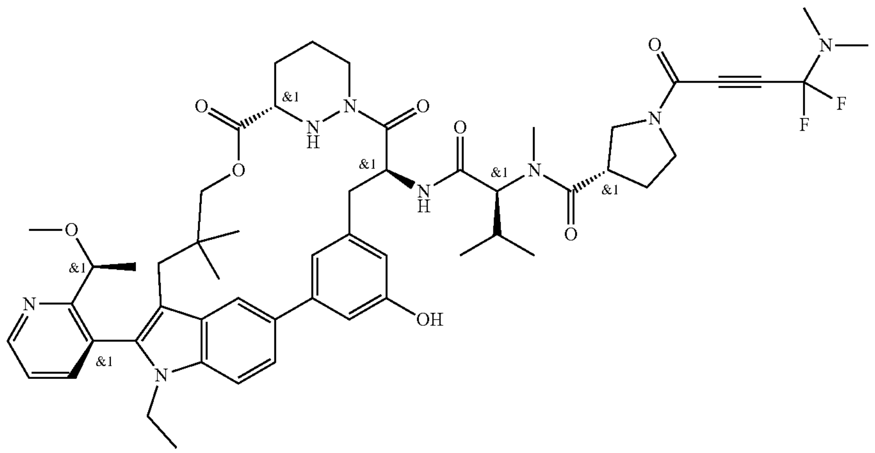 |
| C200 | 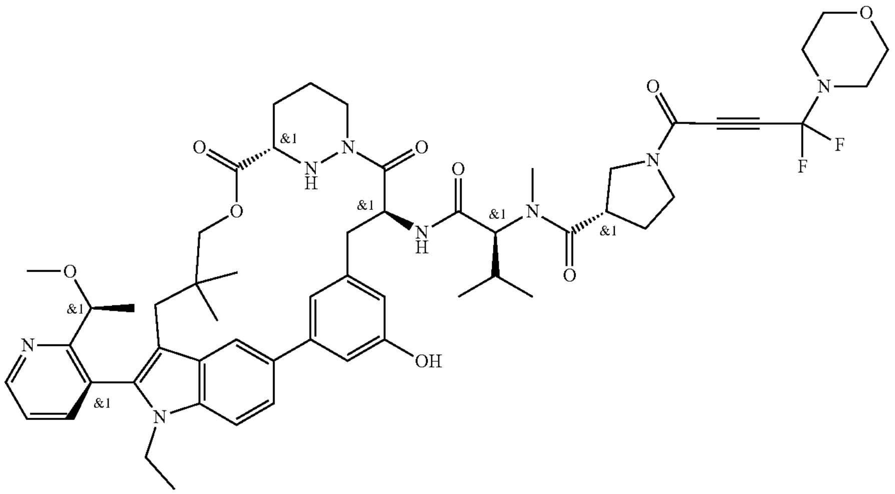 |
| C201 | 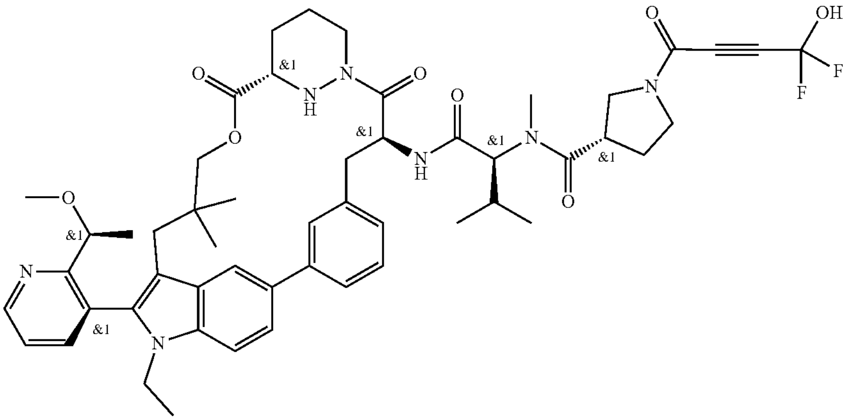 |

TABLE 2-continued
| Certain Compounds | |
|---|---|
| Ex # | Structure |
| C202 | 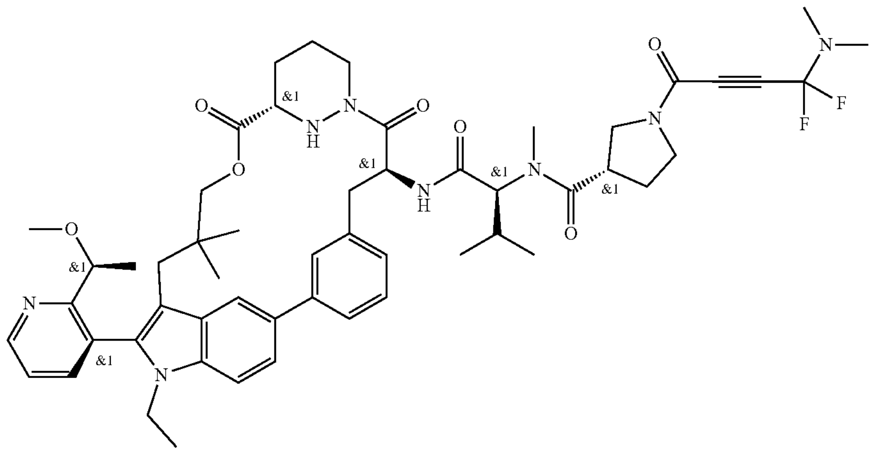 |
| C203 | 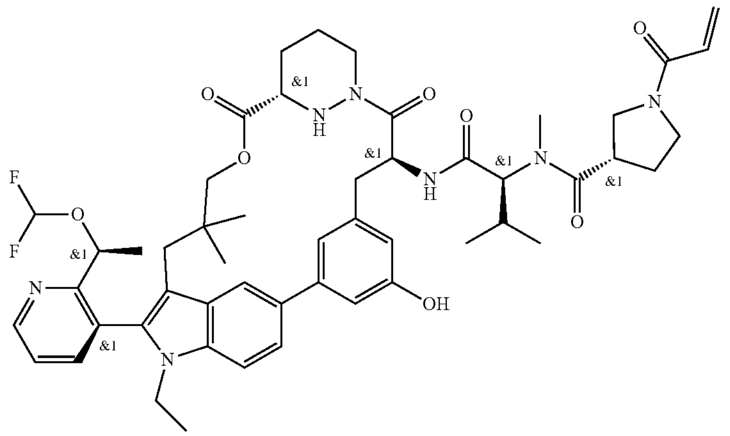 |
| C204 | 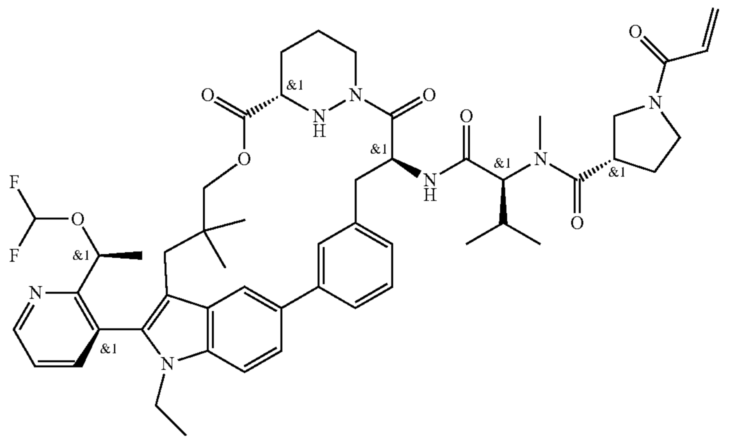 |

TABLE 2-continued
| Certain Compounds | |
|---|---|
| Ex # | Structure |
| C205 | 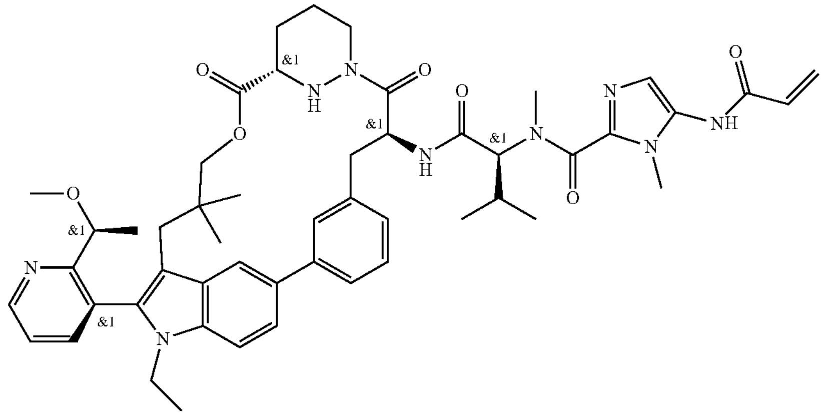 |
| C206 | 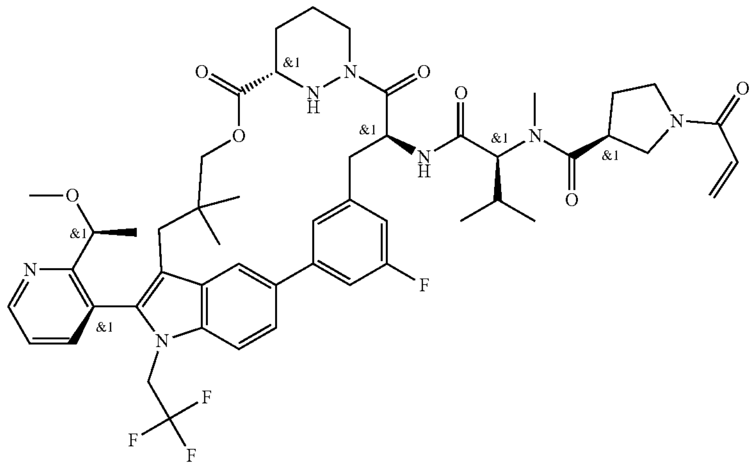 |
| C207 | 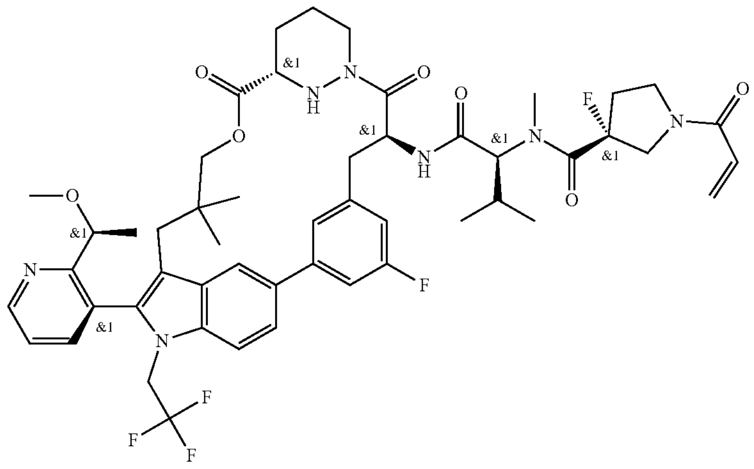 |

TABLE 2-continued
| Certain Compounds | |
|---|---|
| Ex # | Structure |
| C208 | 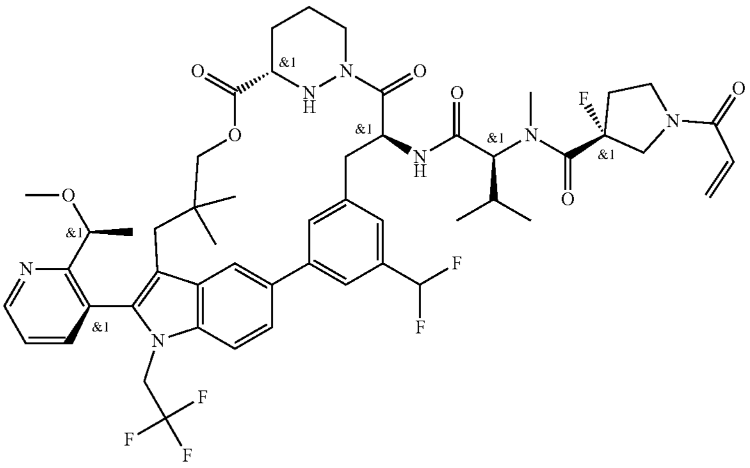 |
| C209 | 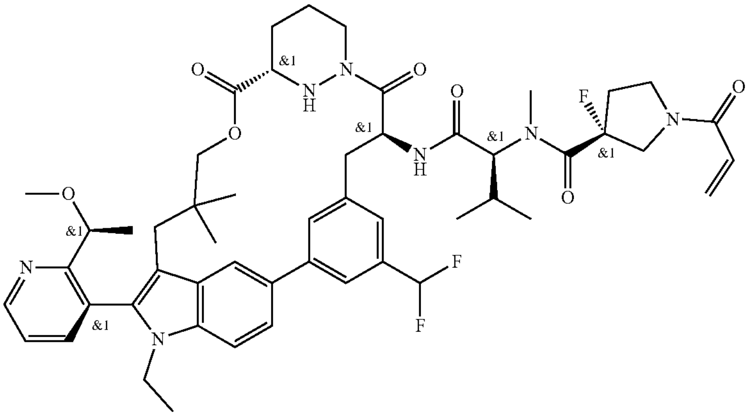 |
| C210 | 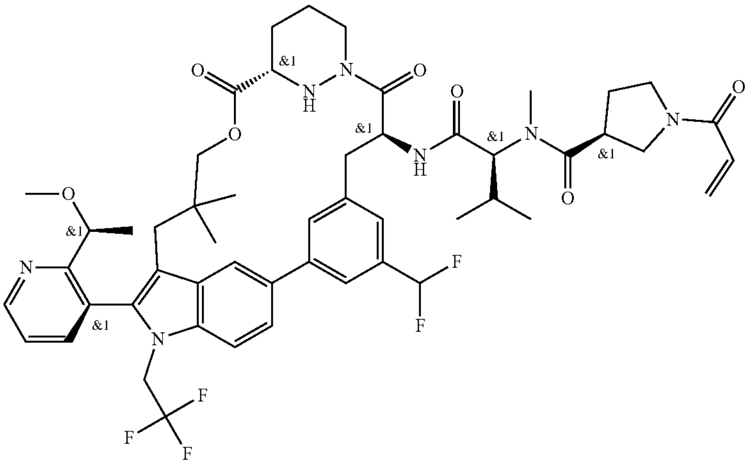 |

TABLE 2-continued
| Certain Compounds | |
|---|---|
| Ex # | Structure |
| C211 | 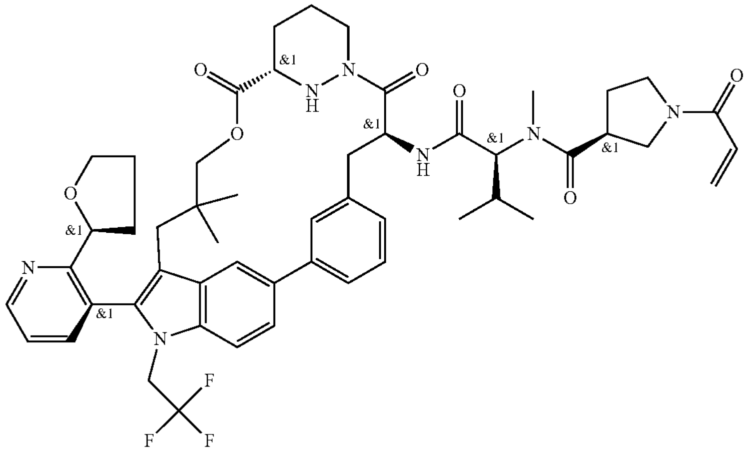 |
| C212 | 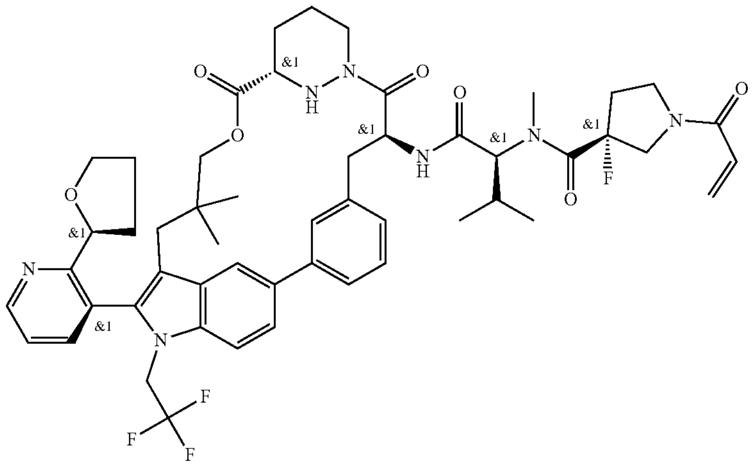 |
| C213 | 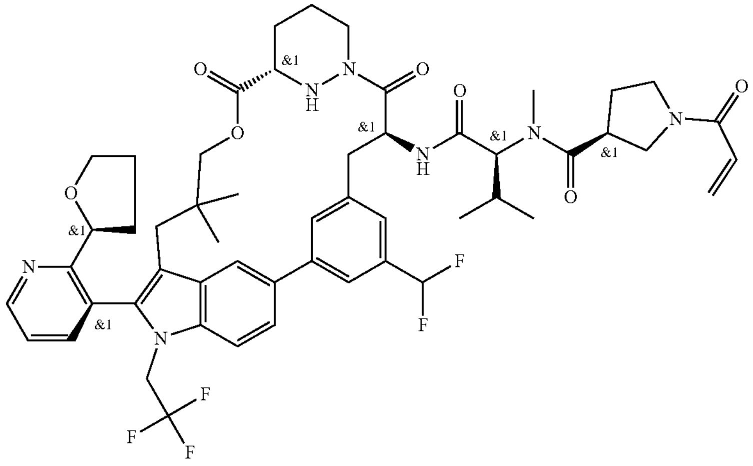 |

TABLE 2-continued
| Certain Compounds | |
|---|---|
| Ex # | Structure |
| C214 | 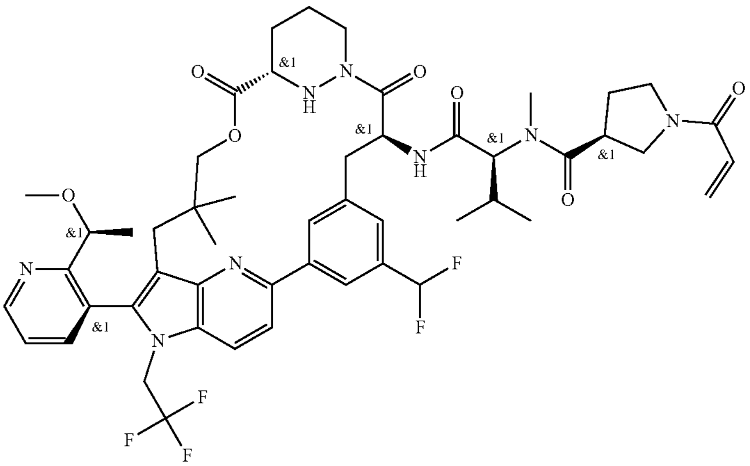 |
| C215 | 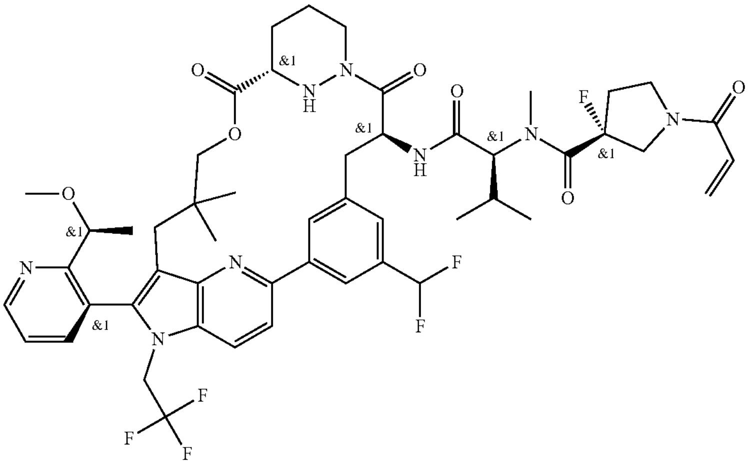 |
| C216 | 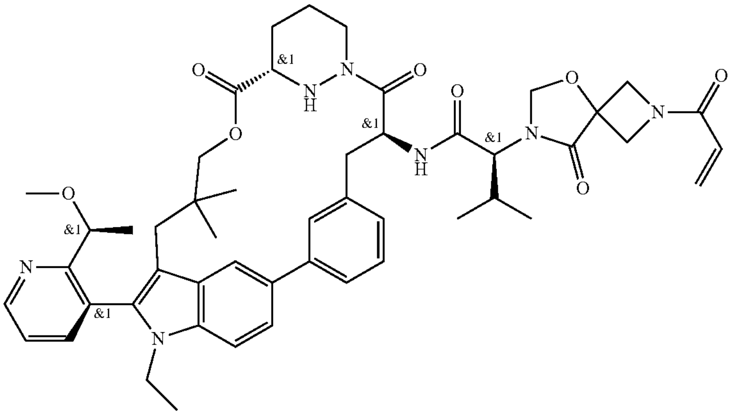 |

TABLE 2-continued
| Certain Compounds | |
|---|---|
| Ex # | Structure |
| C217 | 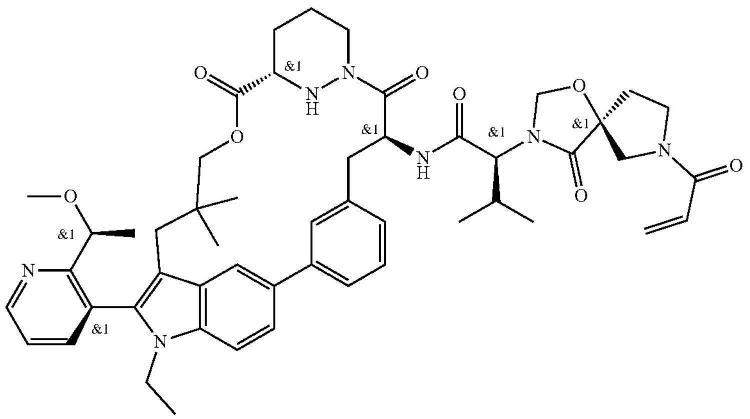 |
| C218 | 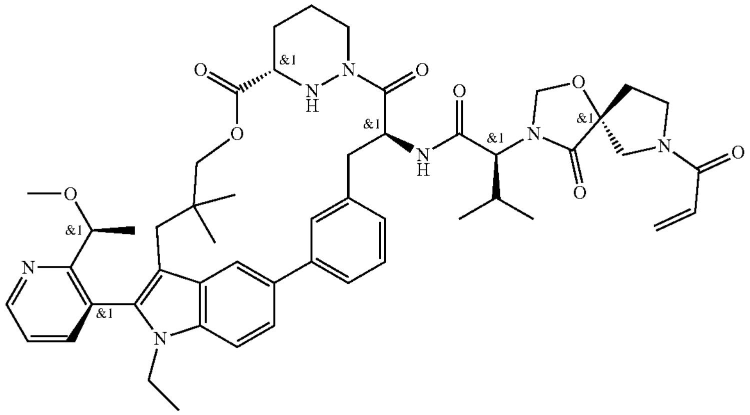 |
| C219 | 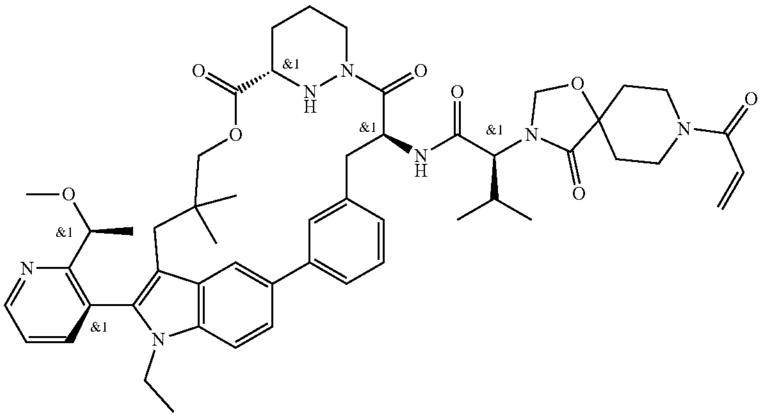 |

TABLE 2-continued
| Certain Compounds | |
|---|---|
| Ex # | Structure |
| C220 | 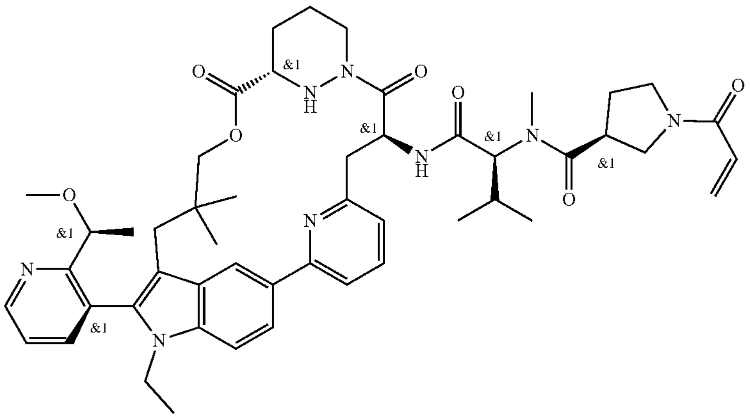 |
| C221 | 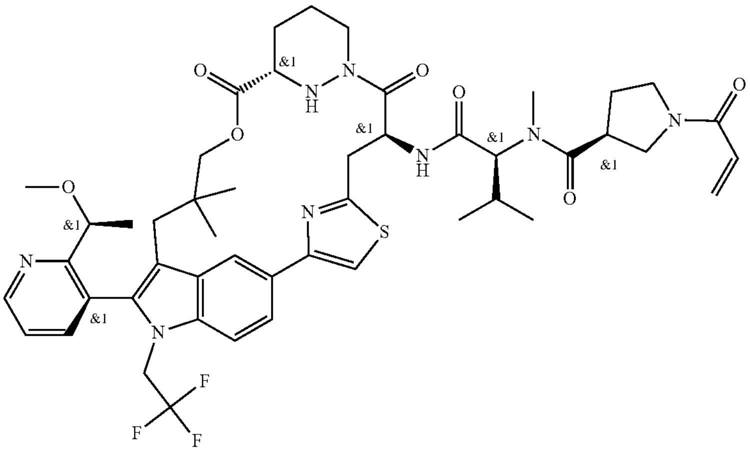 |
| C222 | 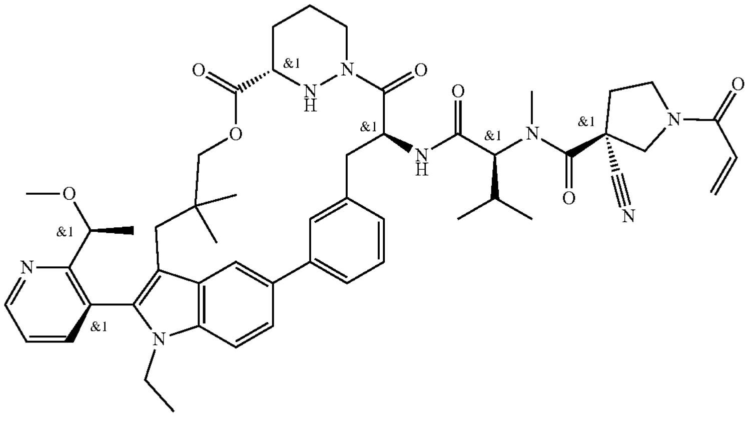 |

TABLE 2-continued
| Certain Compounds | |
|---|---|
| Ex # | Structure |
| C223 | 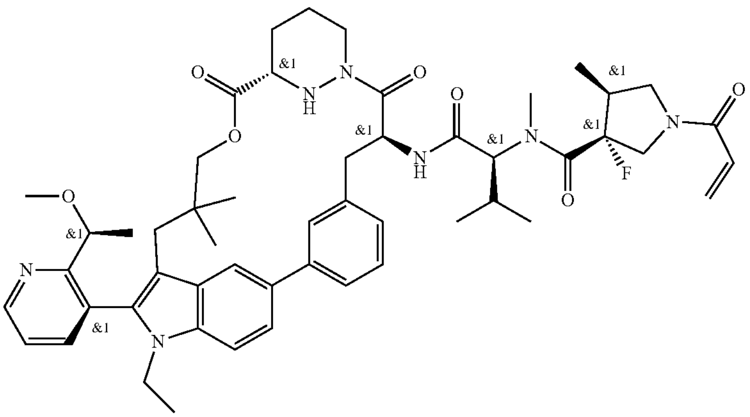 |
| C224 | 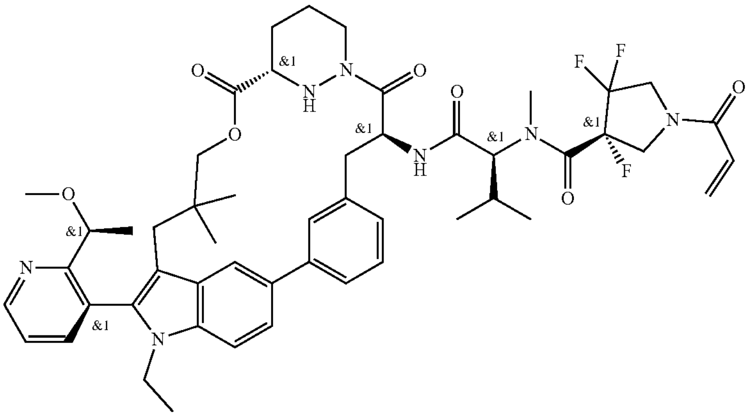 |
| C225 | 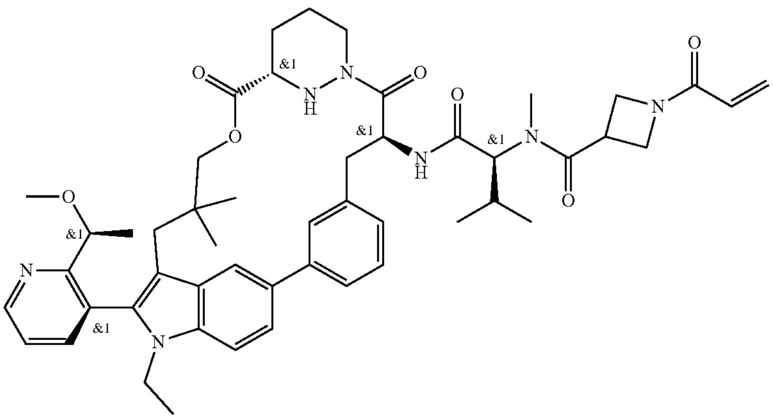 |

TABLE 2-continued
| Certain Compounds | |
|---|---|
| Ex # | Structure |
| C226 | 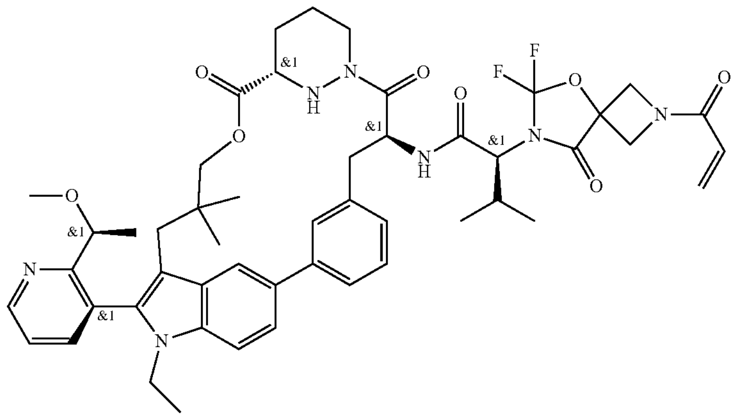 |
| C227 | 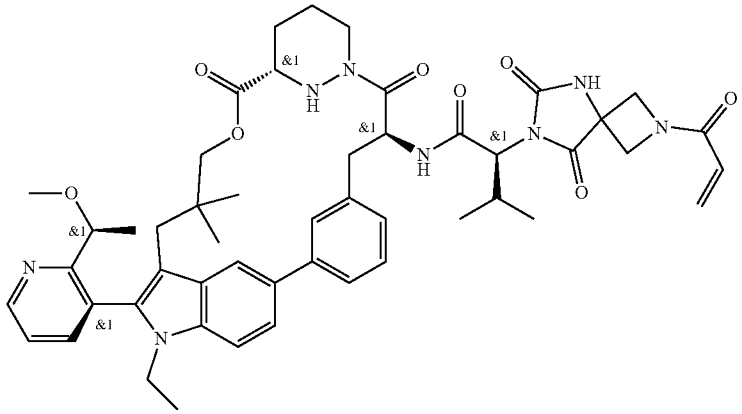 |
| C228 | 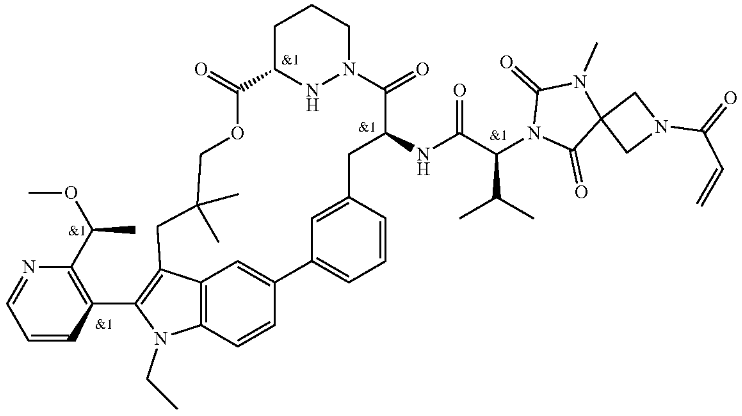 |

TABLE 2-continued
| Certain Compounds | |
|---|---|
| Ex # | Structure |
| C229 | 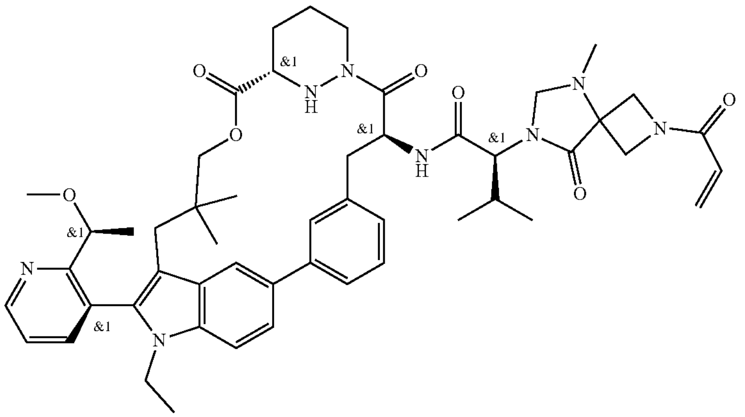 |
| C230 | 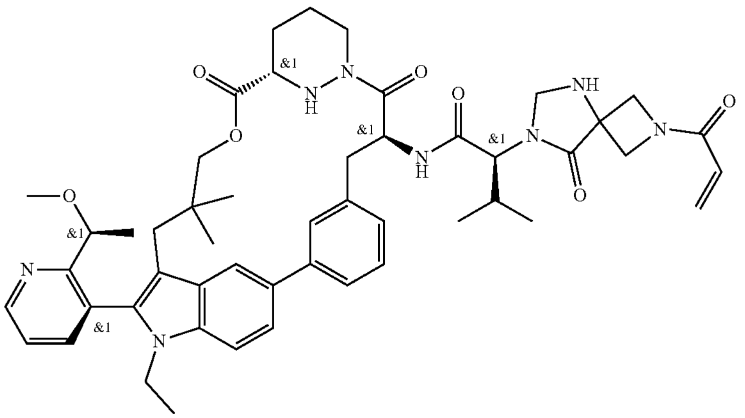 |
| C231 | 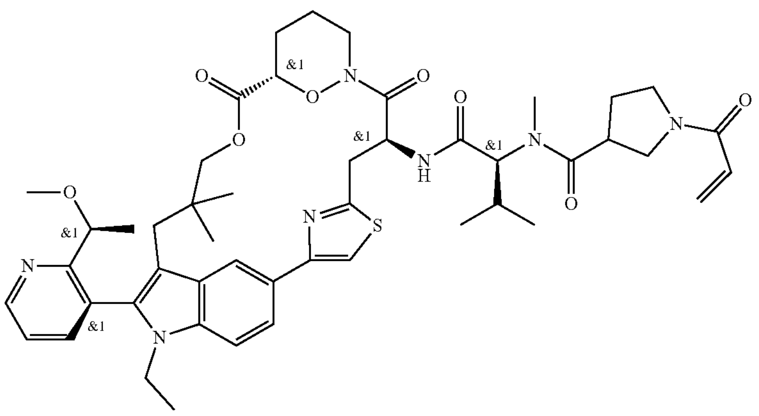 |

TABLE 2-continued
| Certain Compounds | |
|---|---|
| Ex # | Structure |
| C232 | 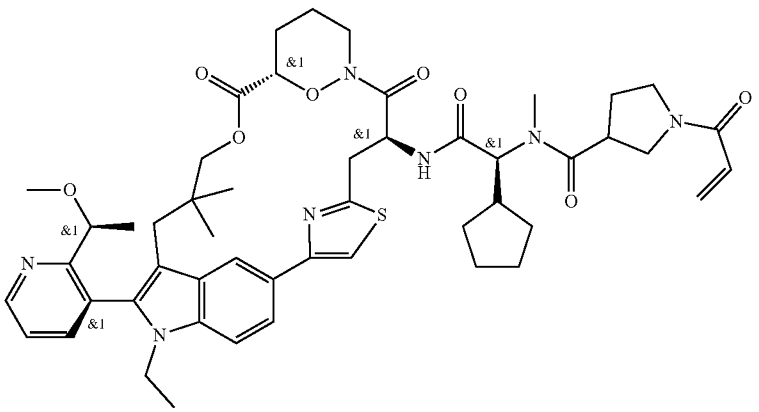 |
| C233 | 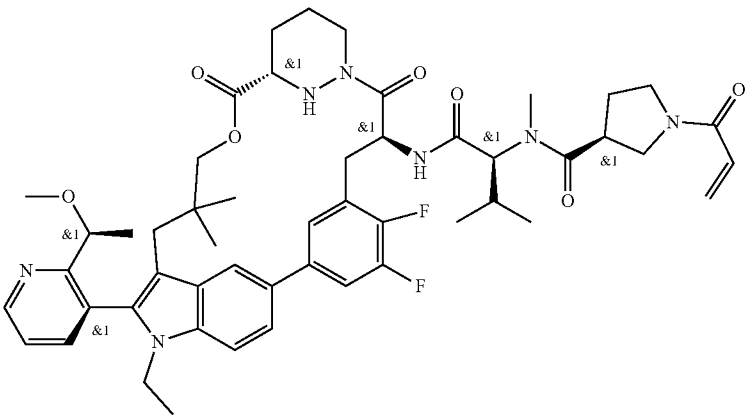 |
| C234 | 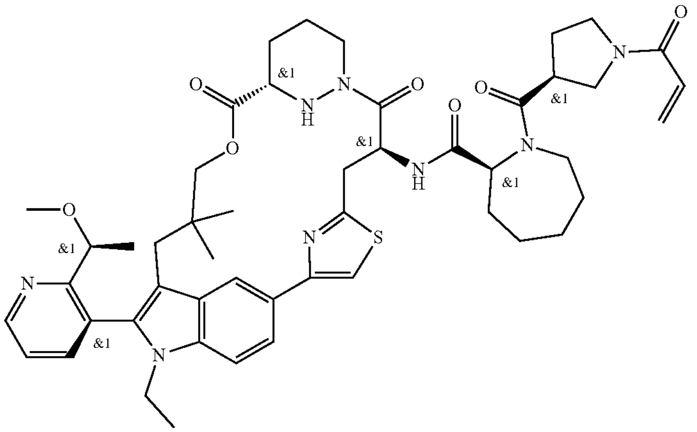 |

TABLE 2-continued
| Certain Compounds | |
|---|---|
| Ex # | Structure |
| C235 | 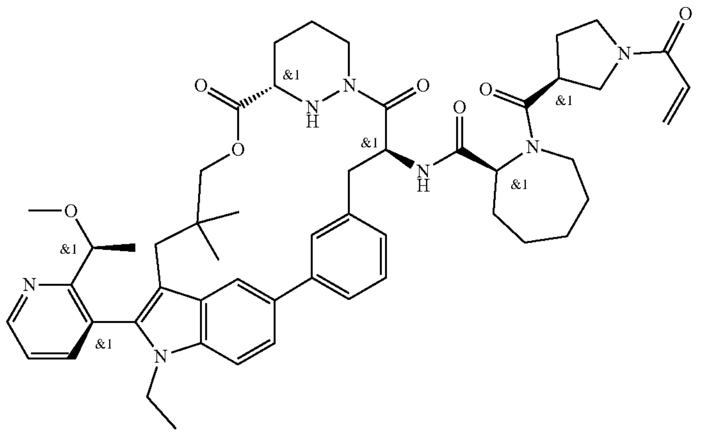 |
| C236 | 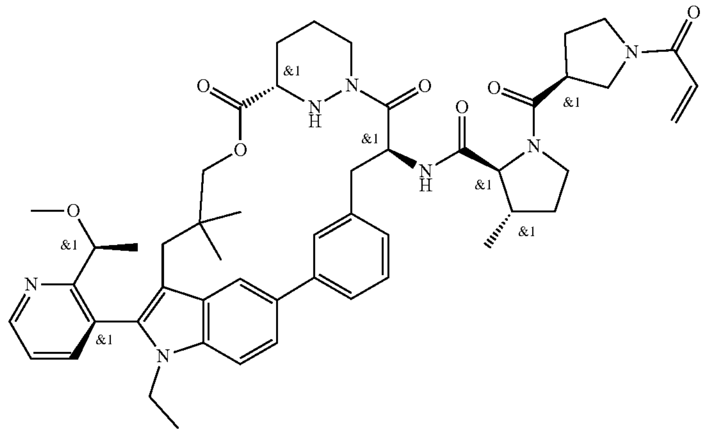 |
| C237 | 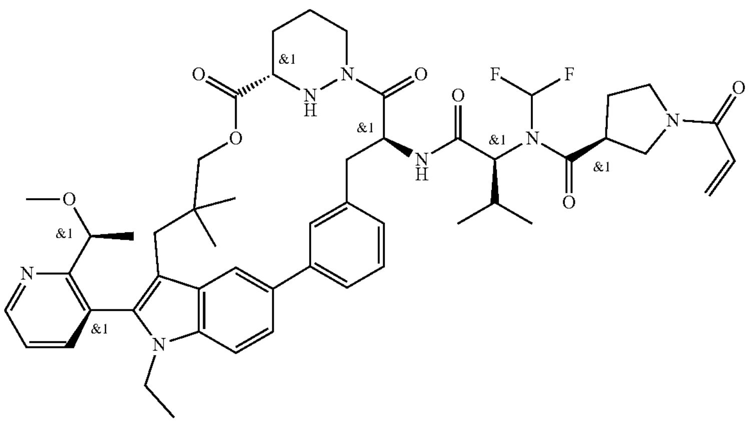 |

TABLE 2-continued
| Certain Compounds | |
|---|---|
| Ex # | Structure |
| C238 | 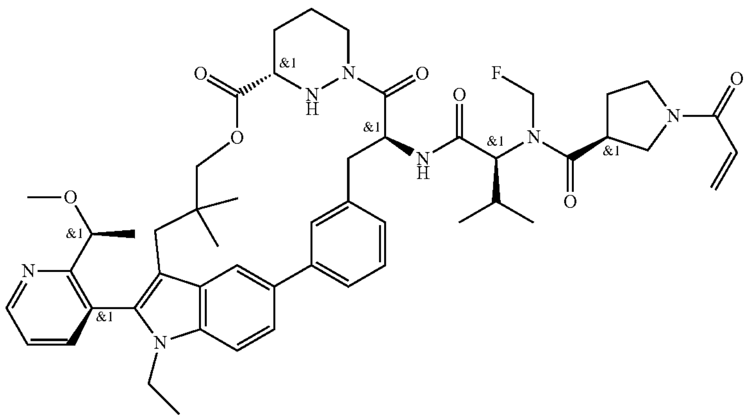 |
| C239 | 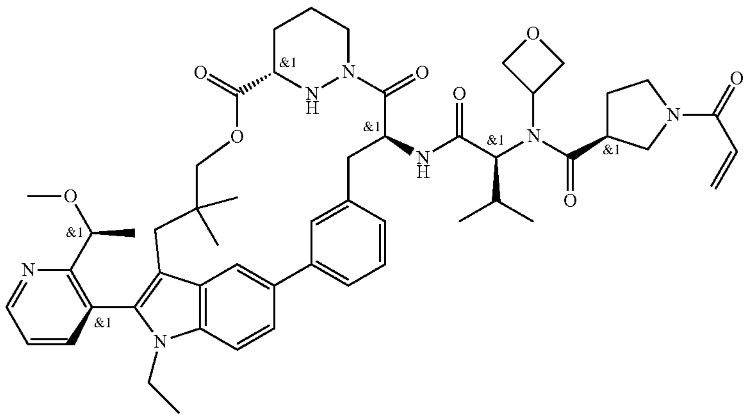 |
| C240 | 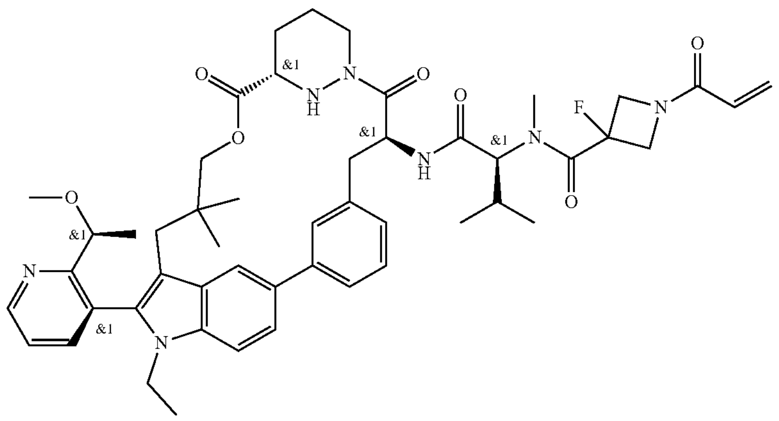 |

TABLE 2-continued
| Certain Compounds | |
|---|---|
| Ex # | Structure |
| C241 | 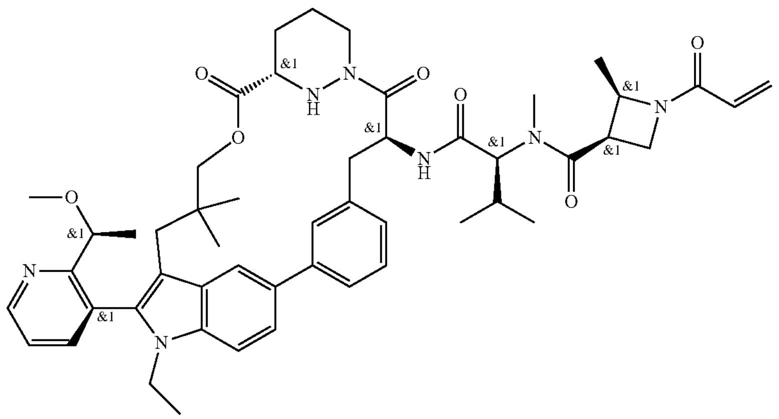 |
| C242 | 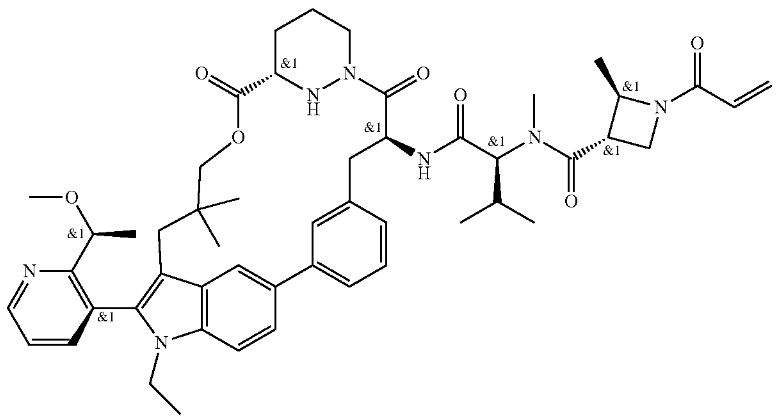 |
| C243 | 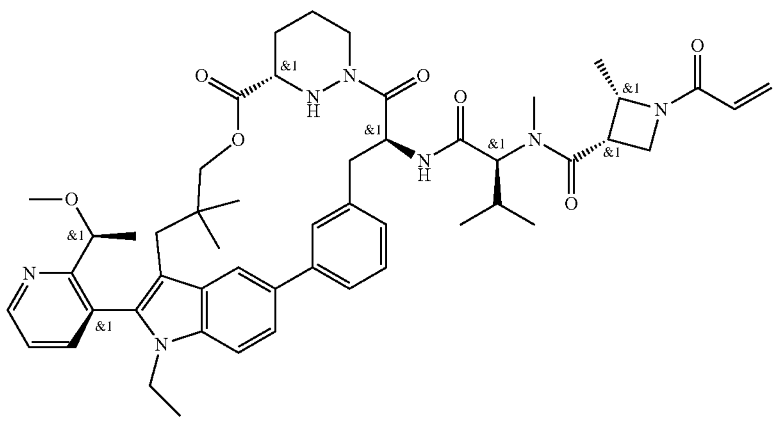 |

TABLE 2-continued
| Certain Compounds | |
|---|---|
| Ex # | Structure |
| C244 | 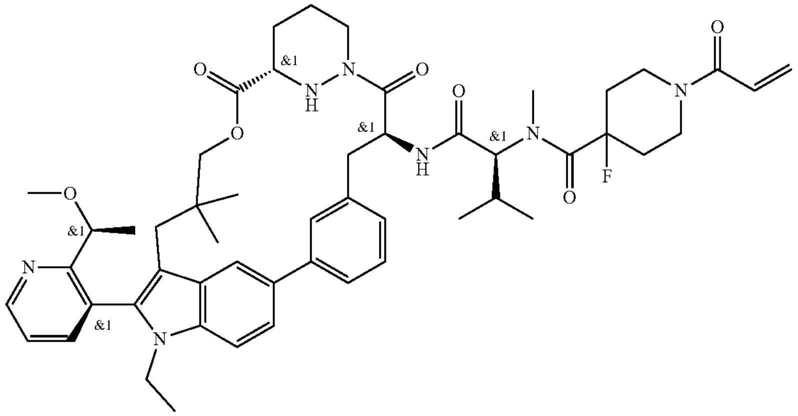 |
| C245 | 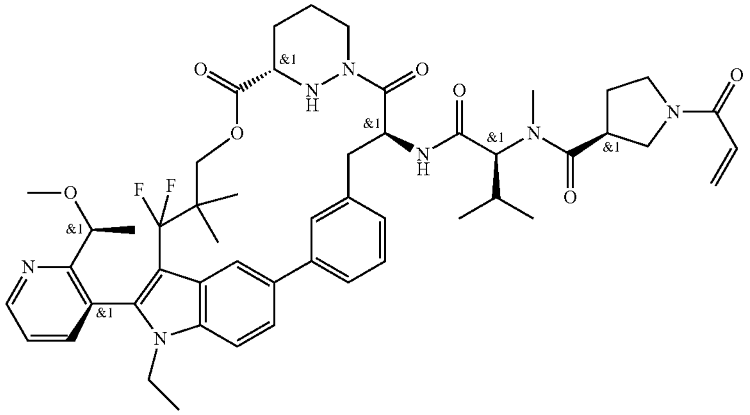 |
| C246 | 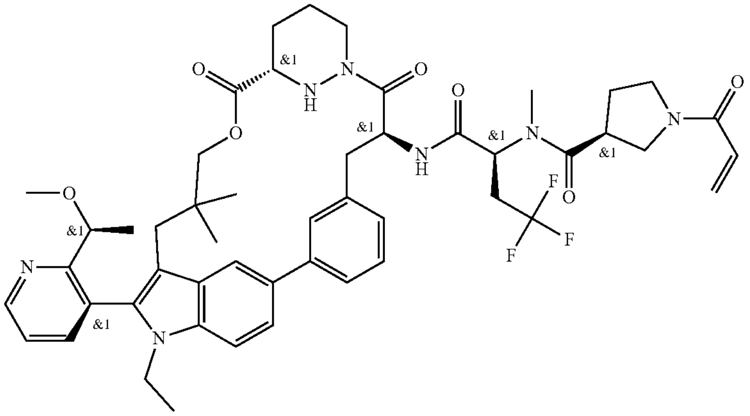 |

TABLE 2-continued
| Certain Compounds | |
|---|---|
| Ex # | Structure |
| C247 | 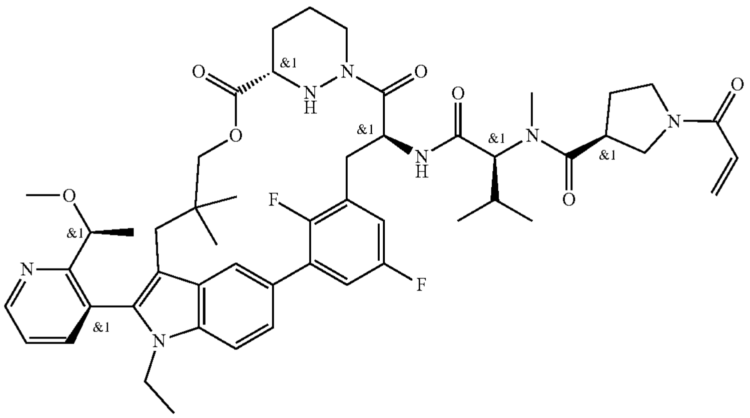 |
| C248 | 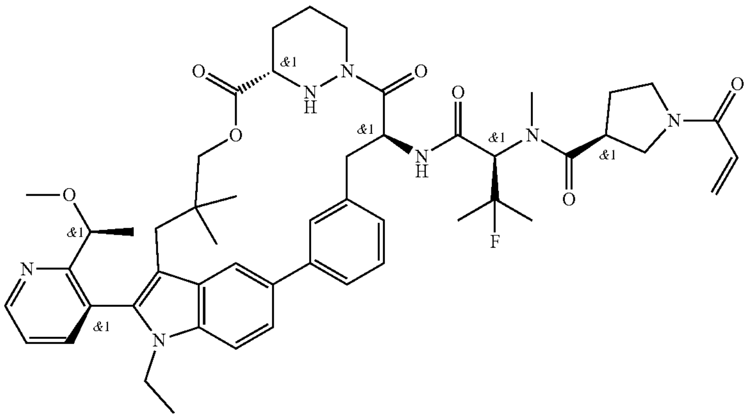 |
| C249 | 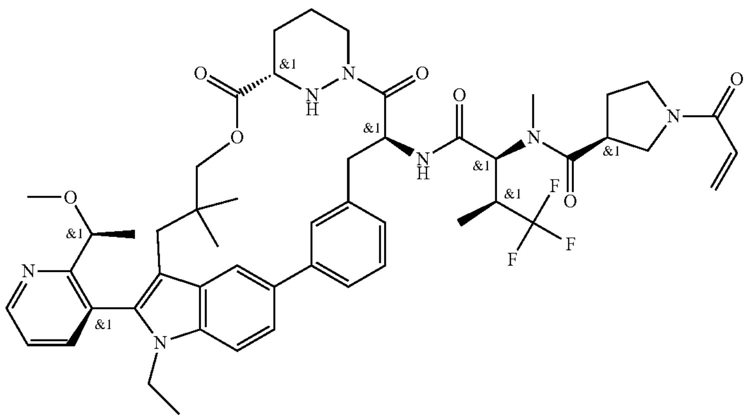 |

TABLE 2-continued
| Certain Compounds | |
|---|---|
| Ex # | Structure |
| C250 | 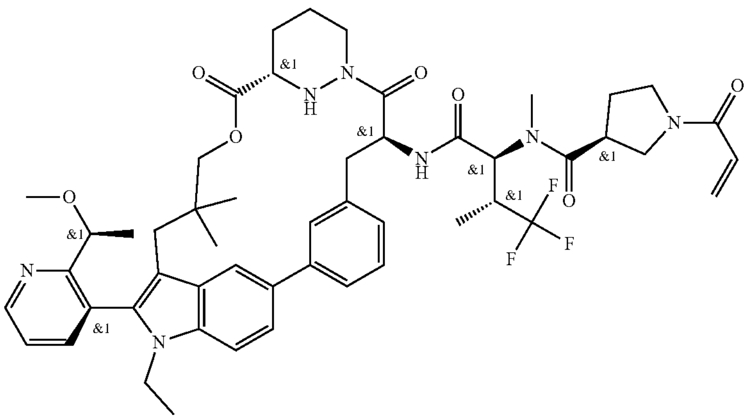 |
| C251 | 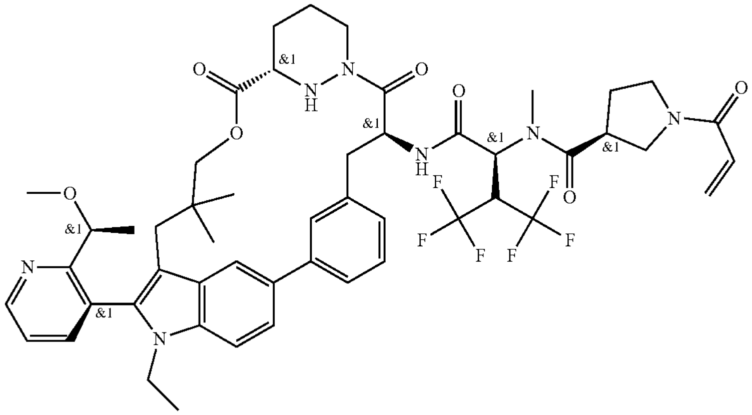 |
| C252 | 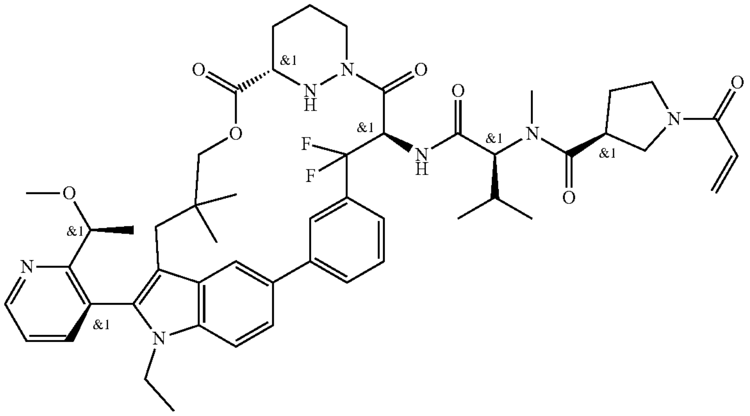 |

TABLE 2-continued
| Certain Compounds | |
|---|---|
| Ex # | Structure |
| C253 | 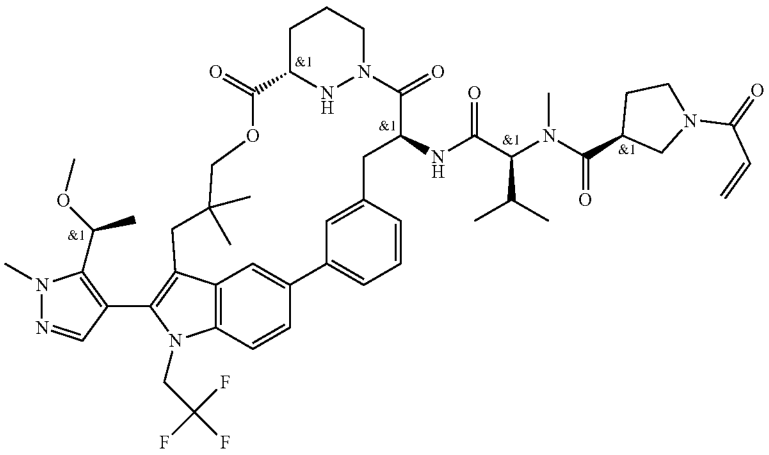 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CC(C)(C)COC(=O)[C@@H]3CCCN(N3)C2=O)C(C)C)C1] |
| C254 | 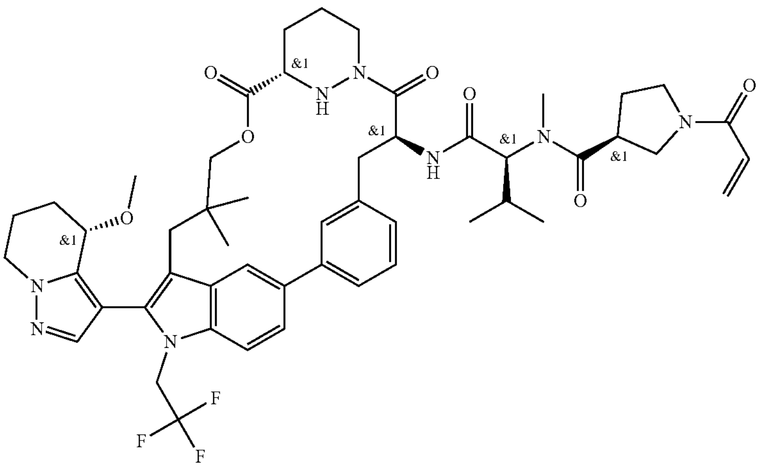 [SMILES: C=CC(=O)N1CC[C@H](C(=O)N(C)[C@H](C(=O)N[C@H]2Cc3cccc(c3)-c3ccc4c(c3)c(c(-c3cnn5c3[C@@H](OC)CCC5)n4CC(F)(F)F)CC(C)(C)COC(=O)[C@@H]3CCCN(N3)C2=O)C(C)C)C1] |
| C255 | 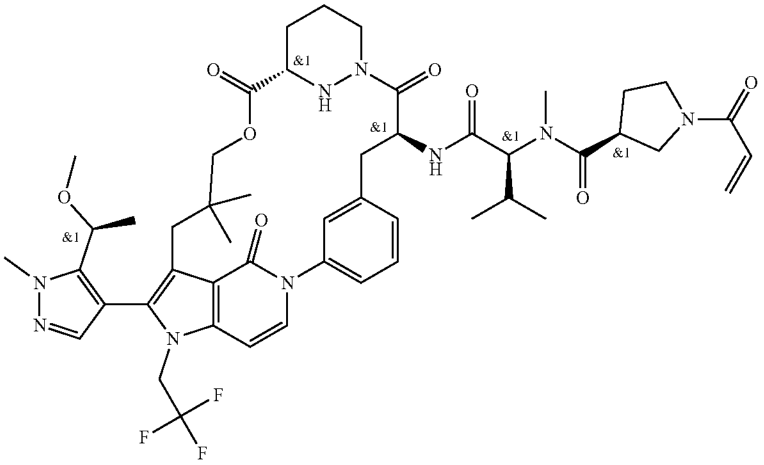 [SMILES: C=CC(=O)N1CC[C@H](C(=O)N(C)[C@H](C(=O)N[C@H]2Cc3cccc(c3)-n3ccc4c(c(c(-c5cnn(C)c5[C@H](C)OC)n4CC(F)(F)F)CC(C)(C)COC(=O)[C@@H]4CCCN(N4)C2=O)c3=O)C(C)C)C1] |

TABLE 2-continued
| Certain Compounds | |
|---|---|
| Ex # | Structure |
| C256 | 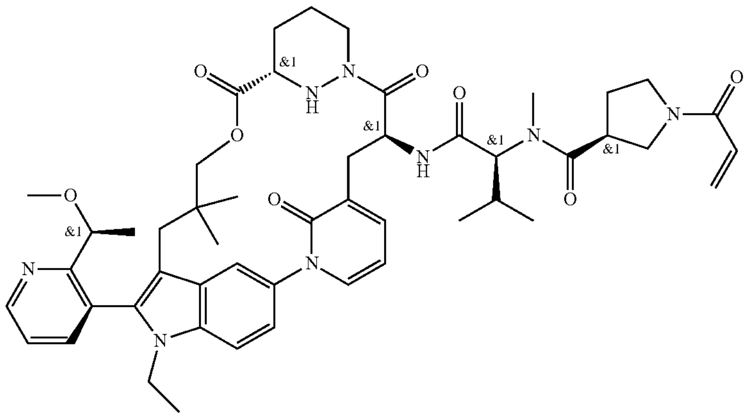 |
| C257 | 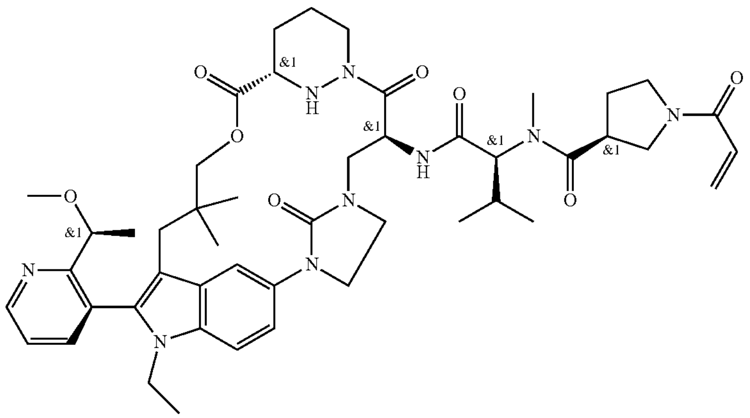 |
| C258 | 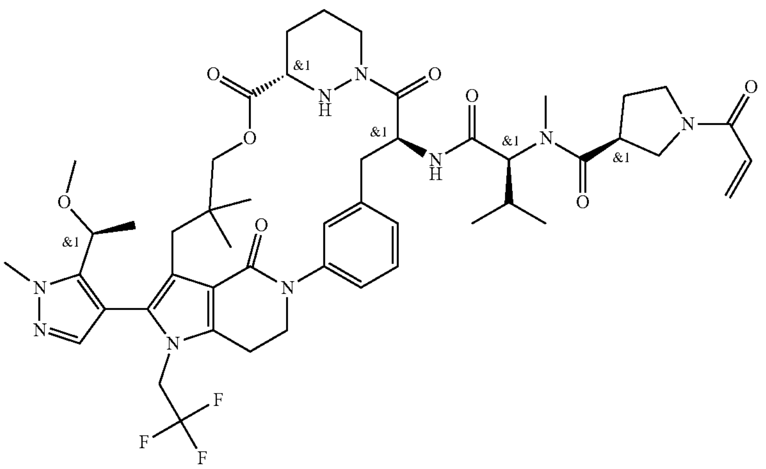 [SMILES: C=CC(=O)N1CC[C@H](C(=O)N(C)[C@H](C(=O)N[C@H]2Cc3cccc(c3)N3CCc4c(c(c(-c5cnn(C)c5[C@H](C)OC)n4CC(F)(F)F)CC(C)(C)COC(=O)[C@@H]4CCCN(N4)C2=O)C3=O)C(C)C)C1] |

TABLE 2-continued
| Certain Compounds | |
|---|---|
| Ex # | Structure |
| C259 | 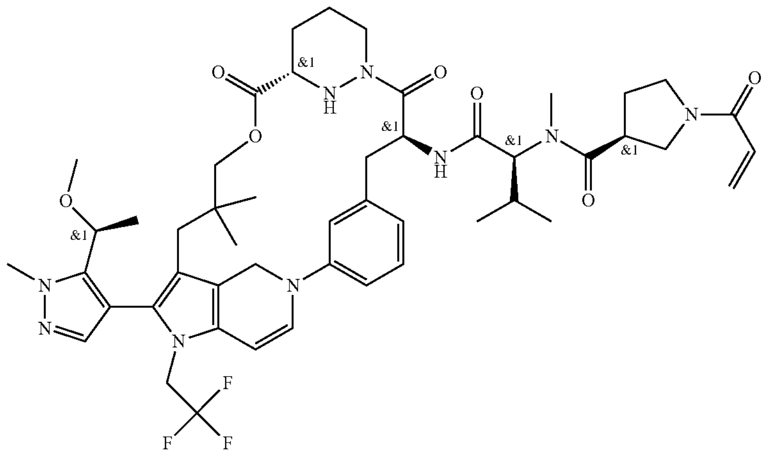 [SMILES: C=CC(=O)N1CC[C@H](C(=O)N(C)[C@H](C(=O)N[C@H]2Cc3cccc(c3)N3C=Cc4c(c(c(-c5cnn(C)c5[C@H](C)OC)n4CC(F)(F)F)CC(C)(C)COC(=O)[C@@H]4CCCN(N4)C2=O)C3)C(C)C)C1] |
| C260 | 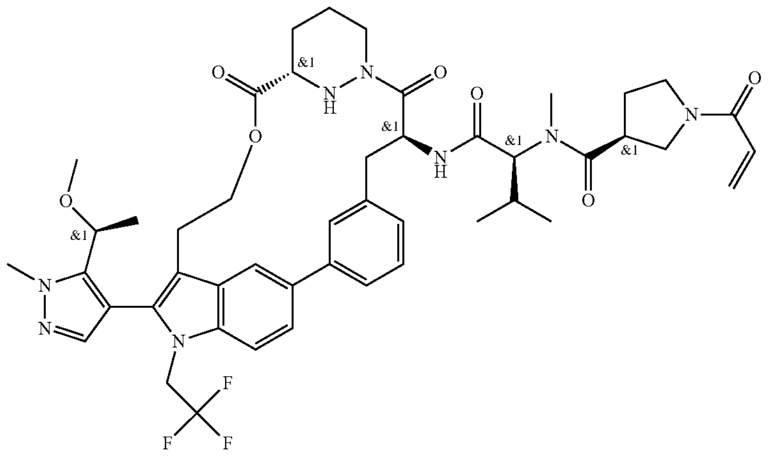 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CCOC(=O)[C@@H]3CCCN(N3)C2=O)C(C)C)C1] |
| C261 | 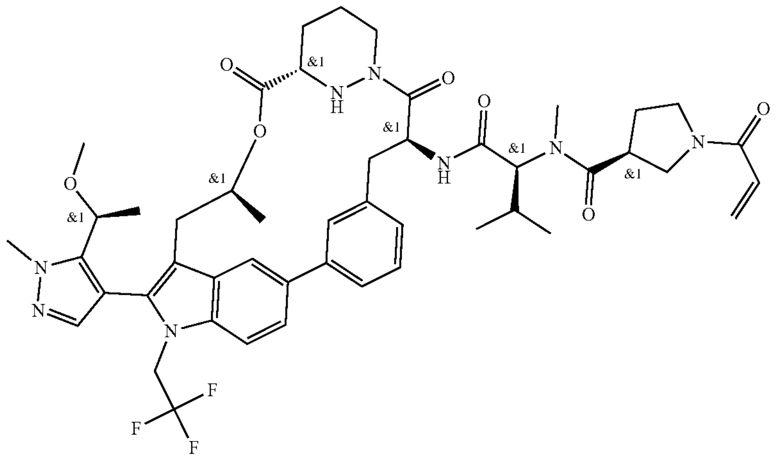 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)C[C@H](C)OC(=O)[C@@H]3CCCN(N3)C2=O)C(C)C)C1] |

TABLE 2-continued
| Certain Compounds | |
|---|---|
| Ex # | Structure |
| C262 | 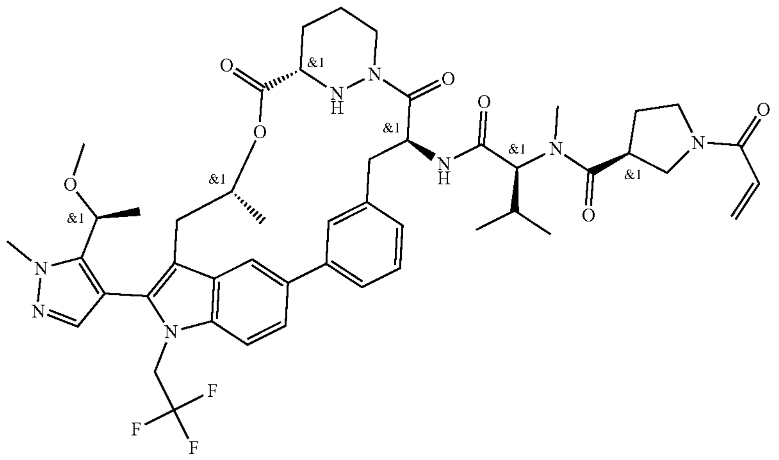 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)C[C@@H](C)OC(=O)[C@@H]3CCCN(N3)C2=O)C(C)C)C1] |
| C263 | 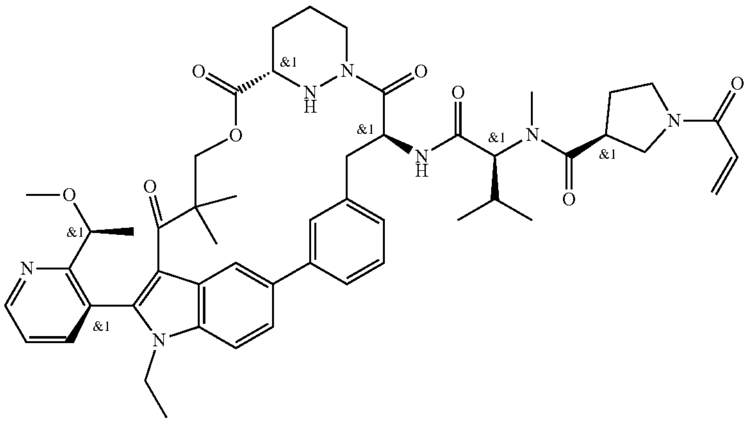 |
| C264 | 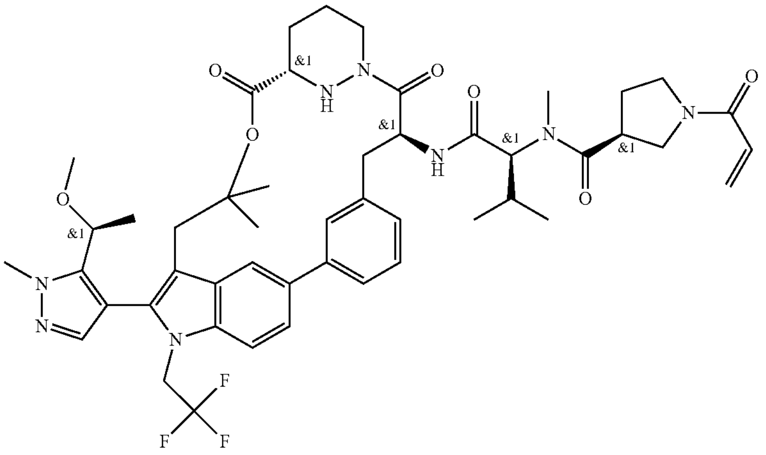 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CC(C)(C)OC(=O)[C@@H]3CCCN(N3)C2=O)C(C)C)C1] |

TABLE 2-continued
| Certain Compounds | |
|---|---|
| Ex # | Structure |
| C265 | 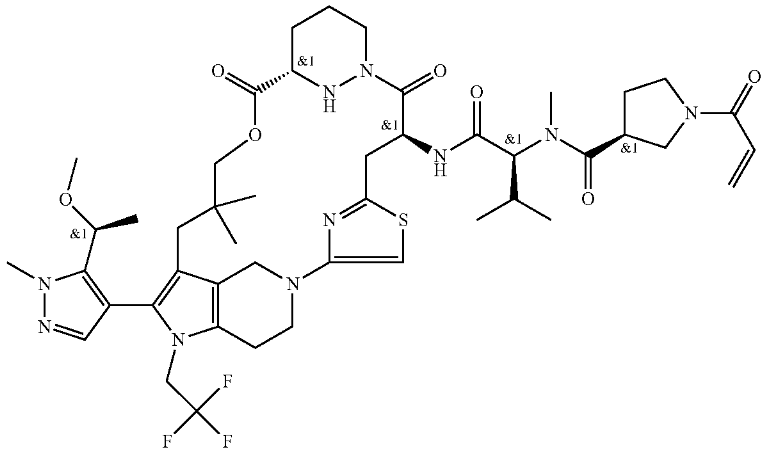 [SMILES: C=CC(=O)N1CC[C@H](C(=O)N(C)[C@H](C(=O)N[C@H]2Cc3nc(cs3)N3CCc4c(c(c(-c5cnn(C)c5[C@H](C)OC)n4CC(F)(F)F)CC(C)(C)COC(=O)[C@@H]4CCCN(N4)C2=O)C3)C(C)C)C1] |
| C266 | 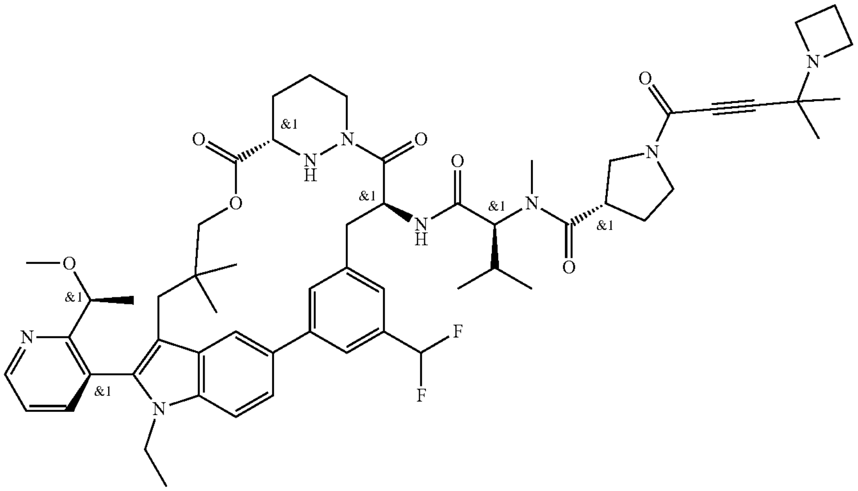 |
| C267 | 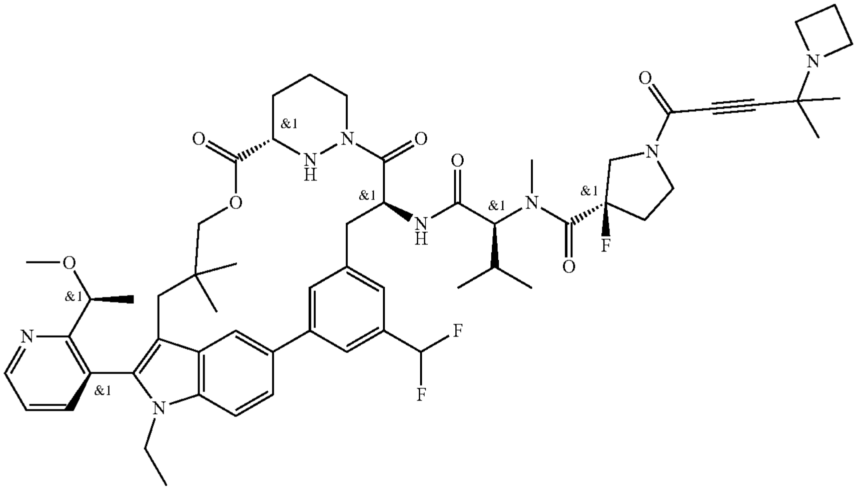 |

TABLE 2-continued
| Certain Compounds | |
|---|---|
| Ex # | Structure |
| C268 | 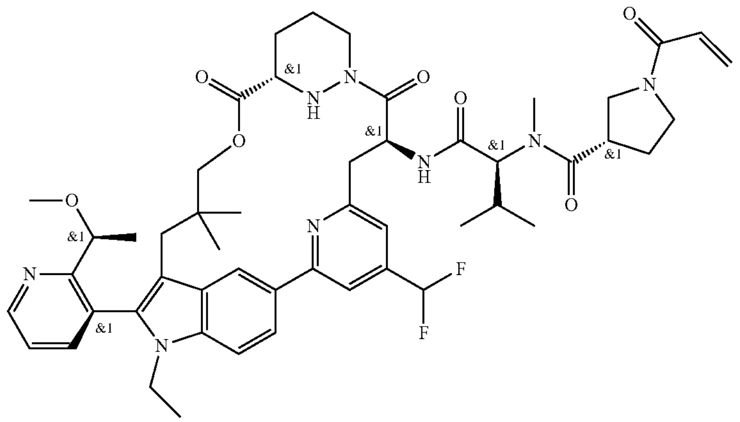 |
| C269 | 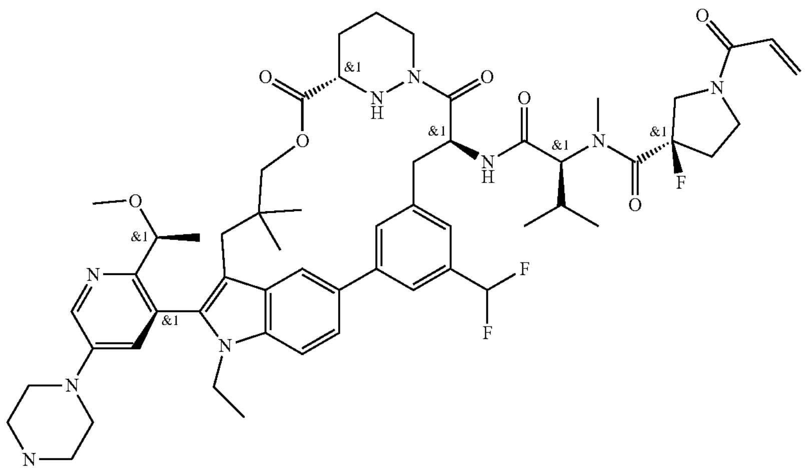 |
| C270 | 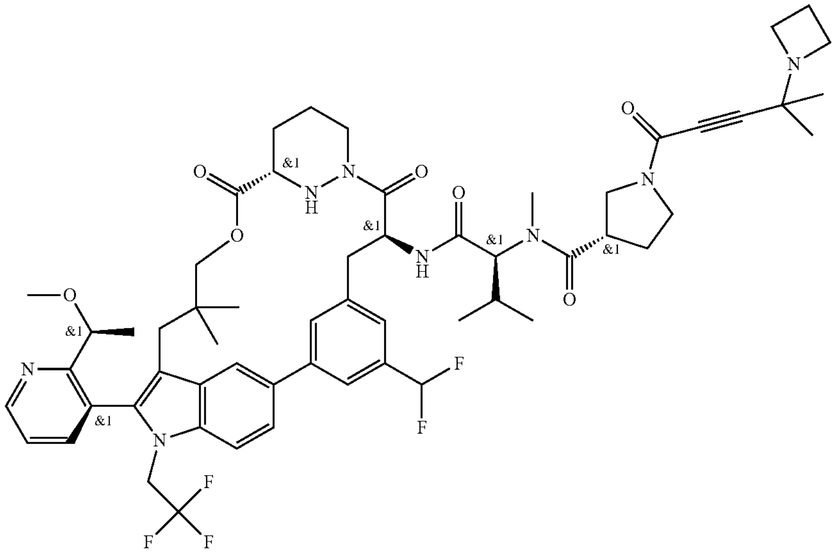 |

TABLE 2-continued
| Certain Compounds | |
|---|---|
| Ex # | Structure |
| C271 | 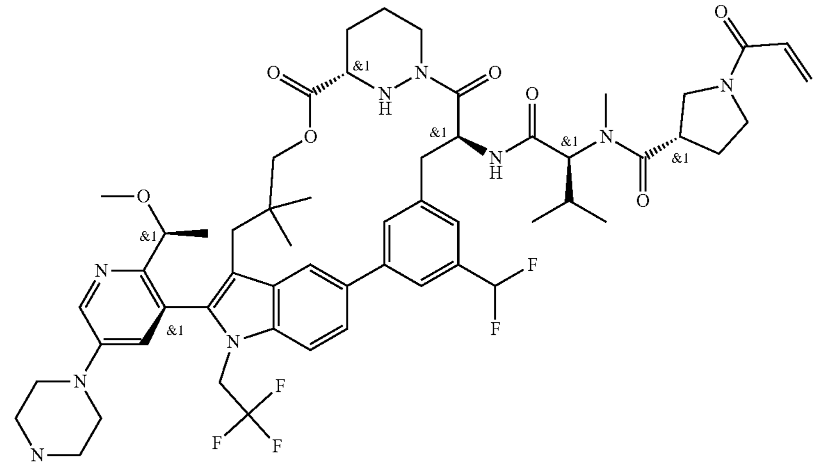 |
| C272 | 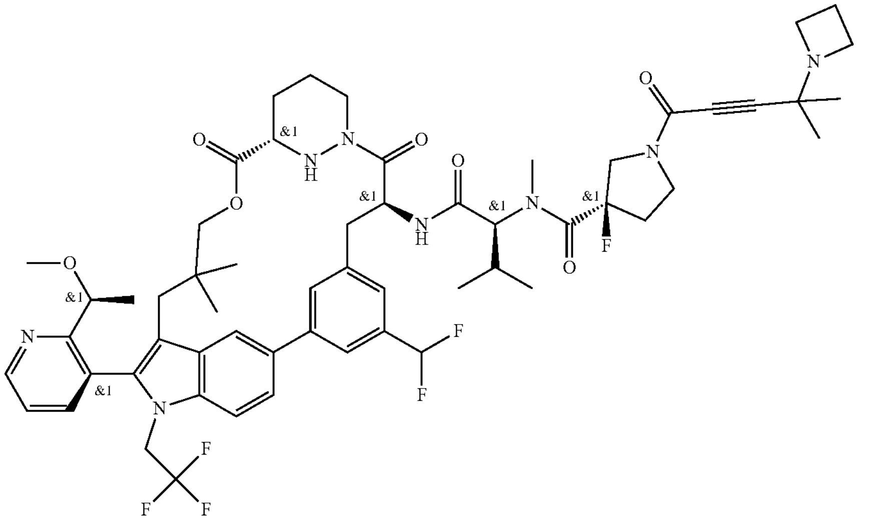 |
| C273 | 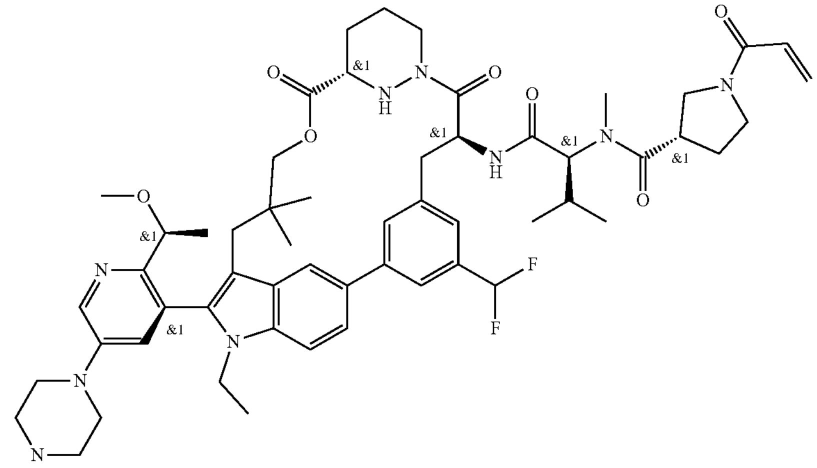 |

TABLE 2-continued
| Certain Compounds | |
|---|---|
| Ex # | Structure |
| C274 | 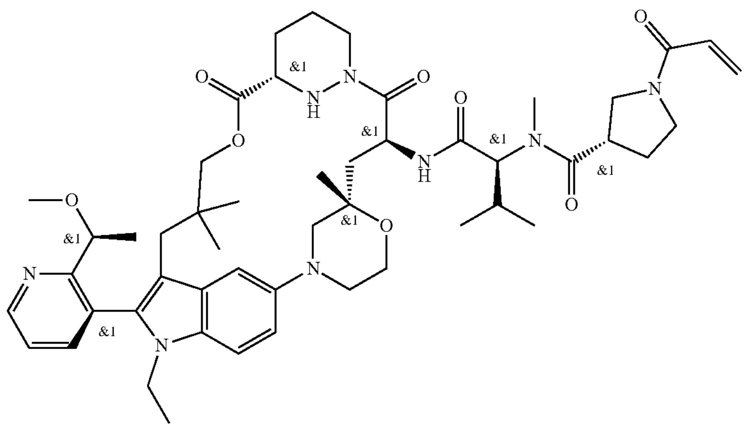 |
| C275 | 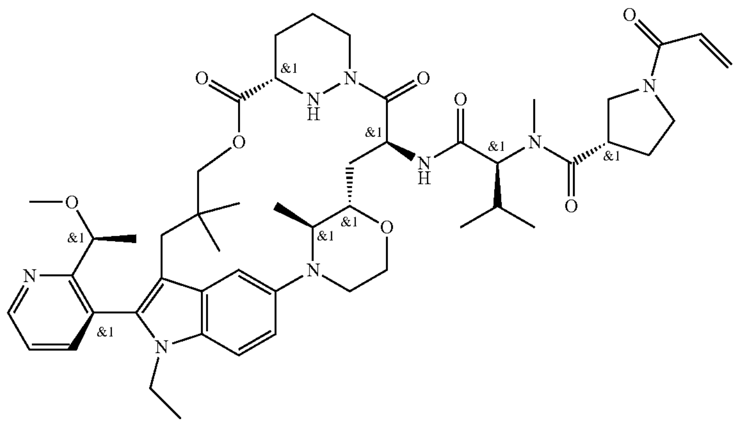 |
| C276 | 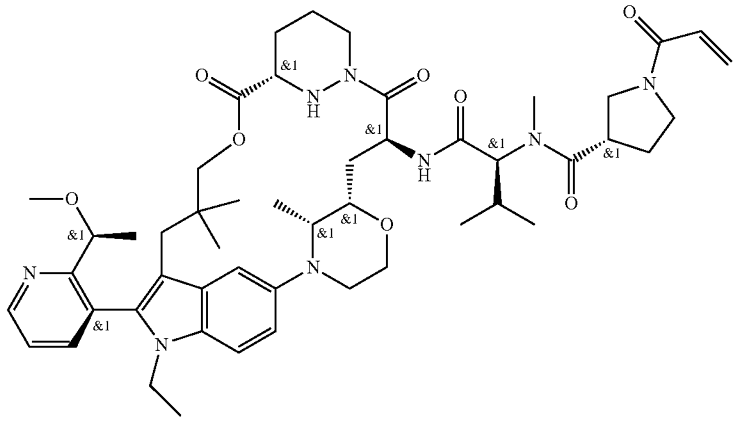 |

TABLE 2-continued
| Certain Compounds | |
|---|---|
| Ex # | Structure |
| C277 | 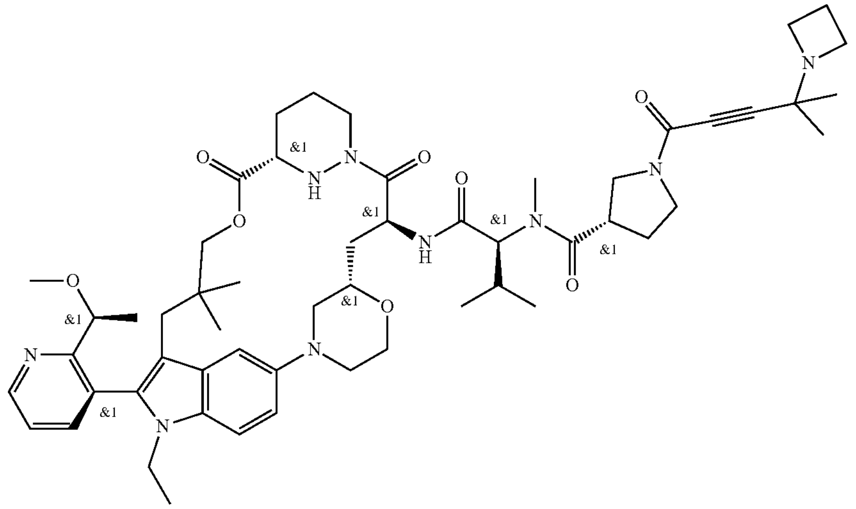 |
| C278 | 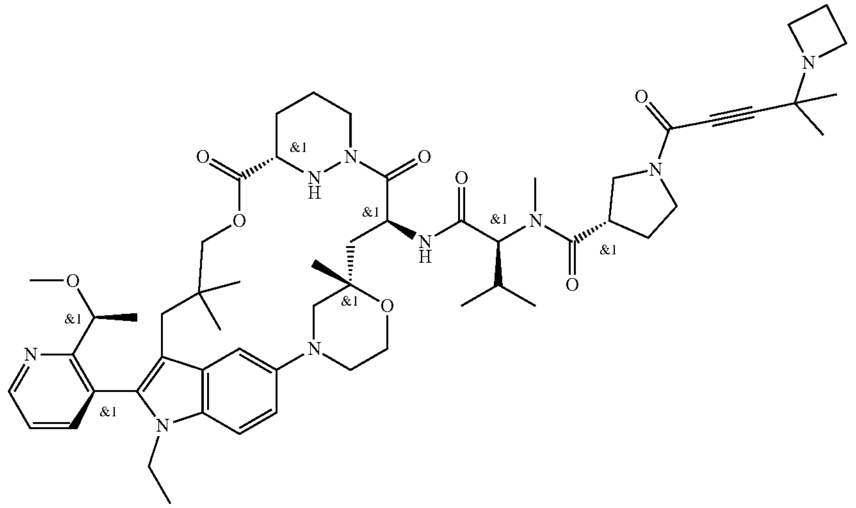 |
| C279 | 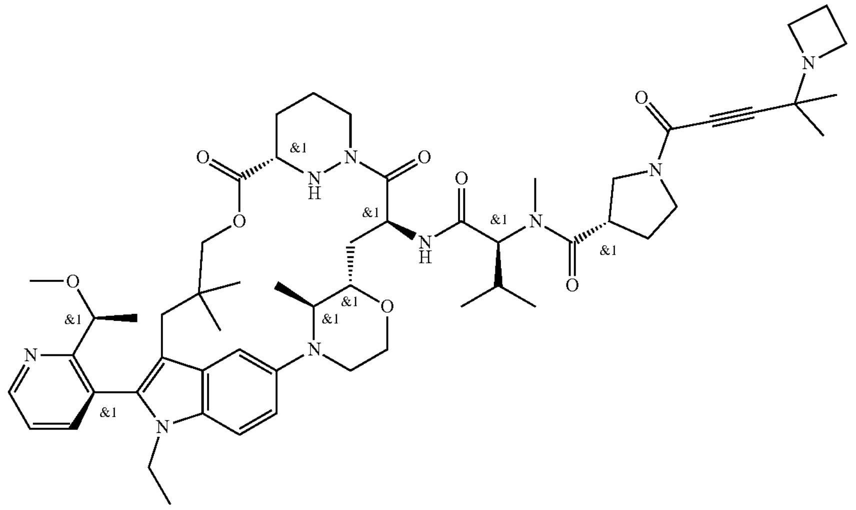 |

TABLE 2-continued
| Certain Compounds | |
|---|---|
| Ex # | Structure |
| C280 | 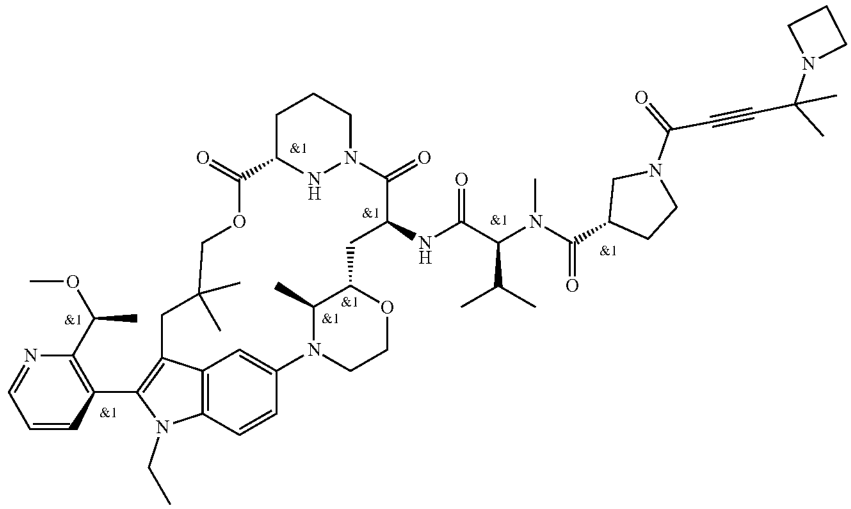 |
| C282 | 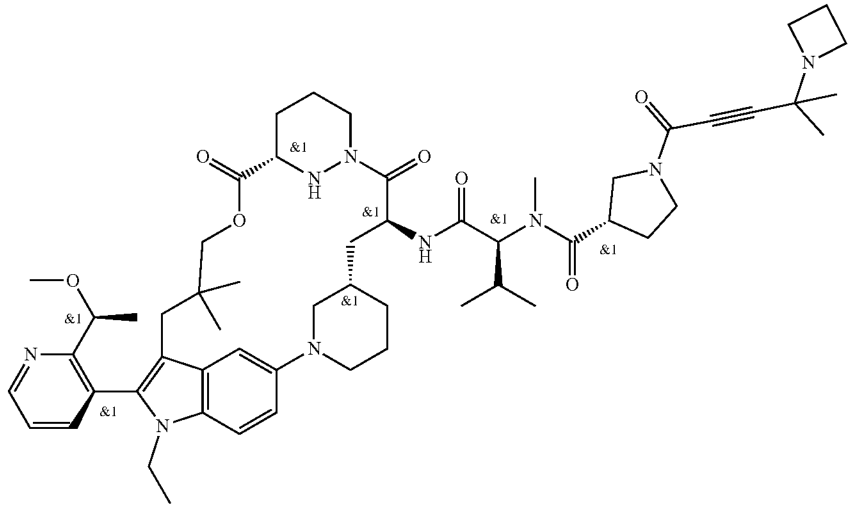 |
| C283 | 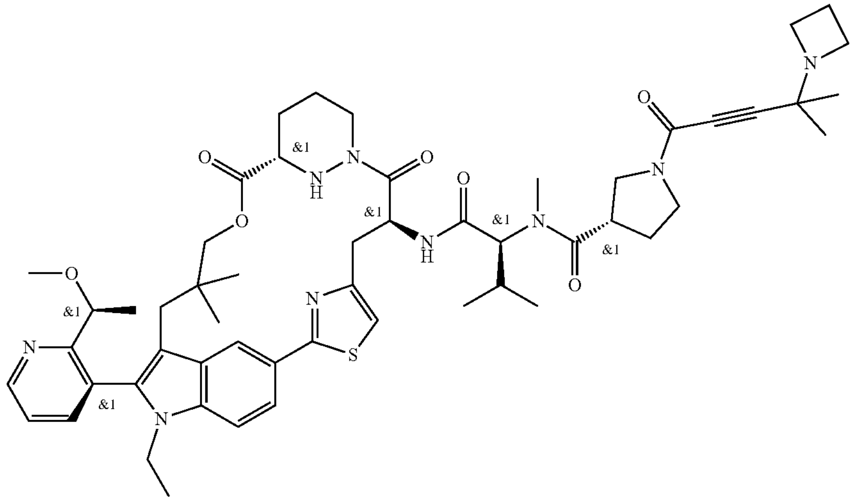 |

TABLE 2-continued
| Certain Compounds | |
|---|---|
| Ex # | Structure |
| C284 | 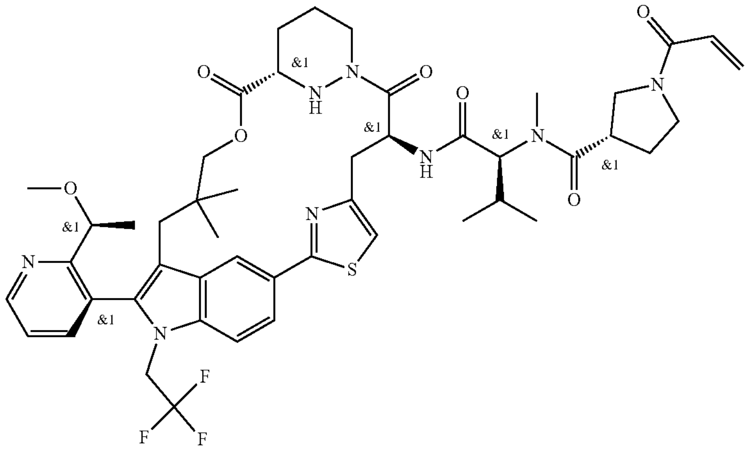 |
| C285 | 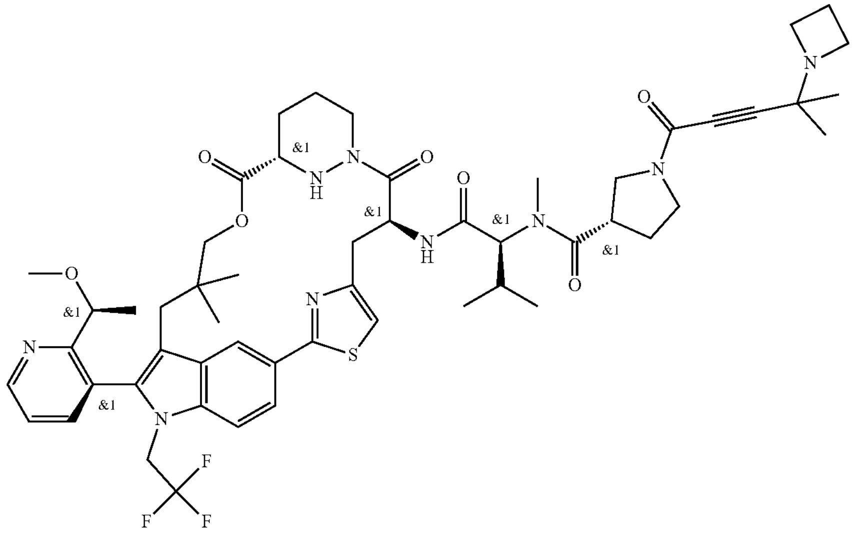 |
| C286 | 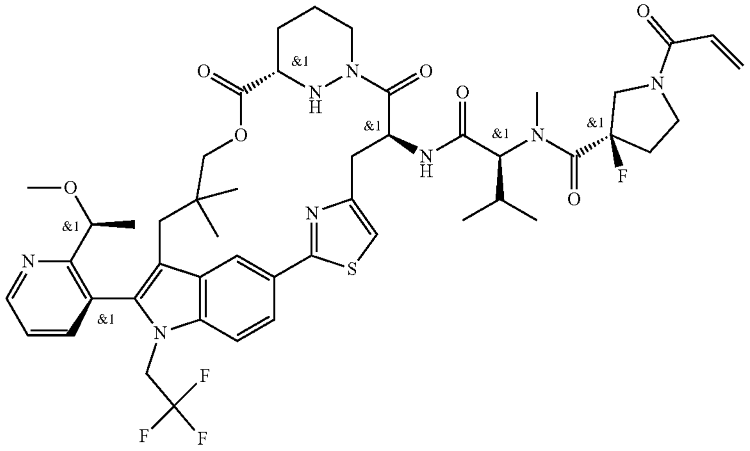 |

TABLE 2-continued
| Certain Compounds | |
|---|---|
| Ex # | Structure |
| C287 | 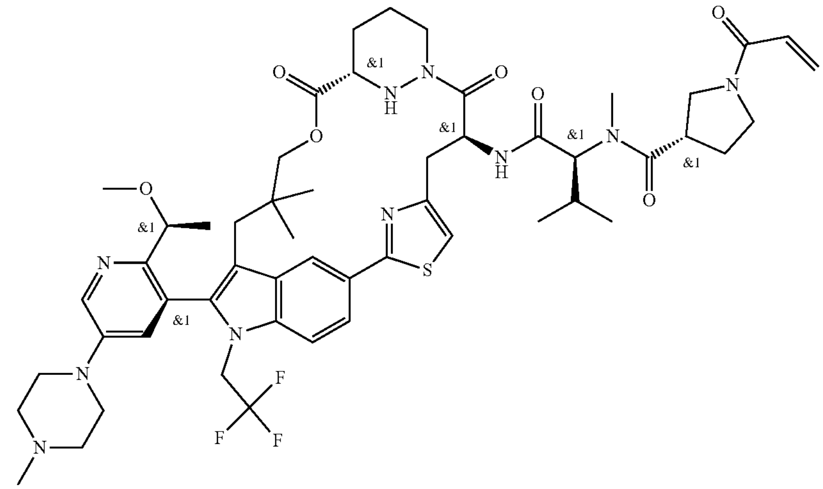 |
| C288 | 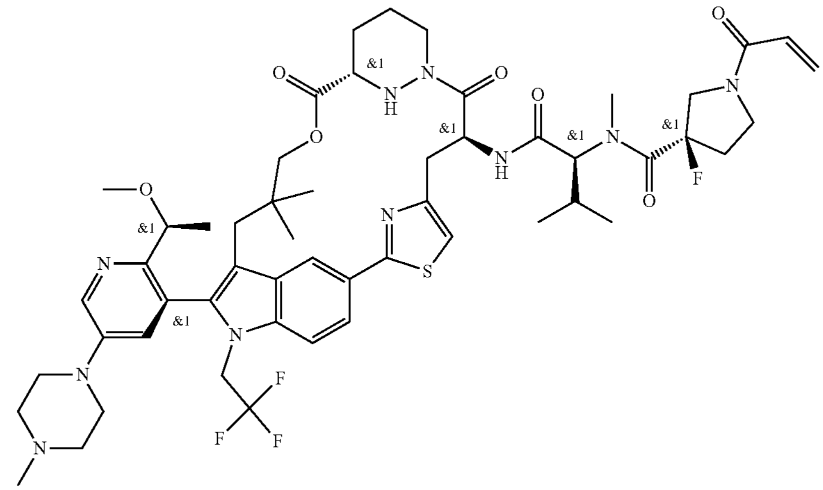 |
| C289 | 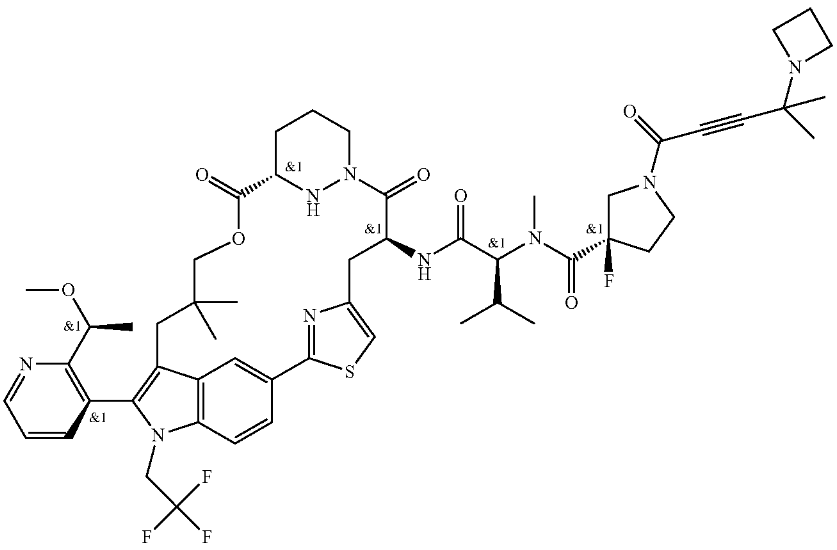 |

TABLE 2-continued
| Certain Compounds | |
|---|---|
| Ex # | Structure |
| C290 | 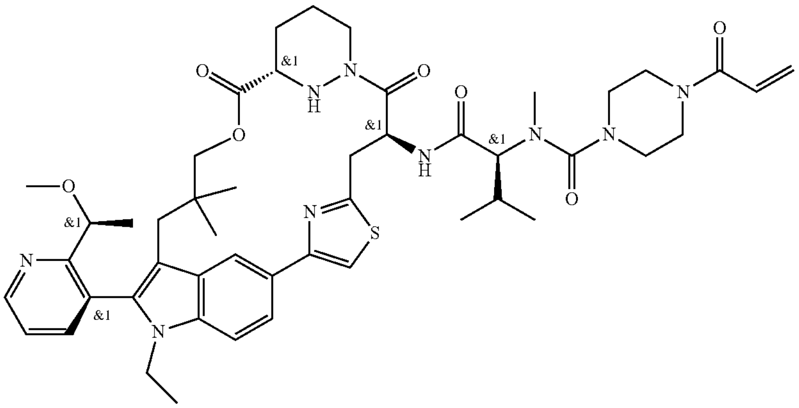 |
| C291 | 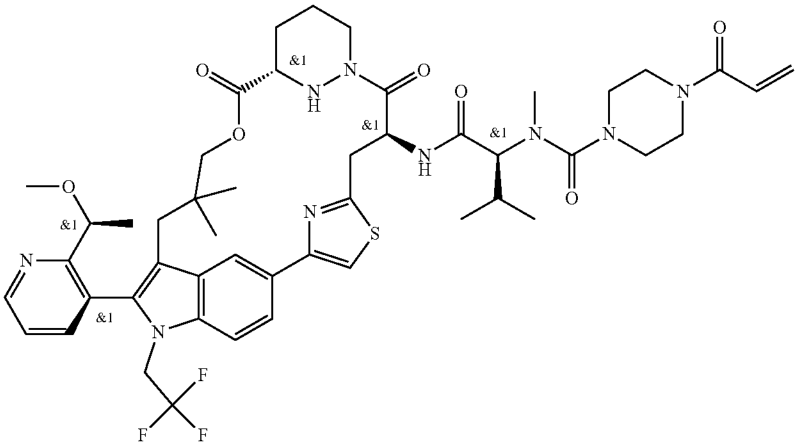 |
| C292 | 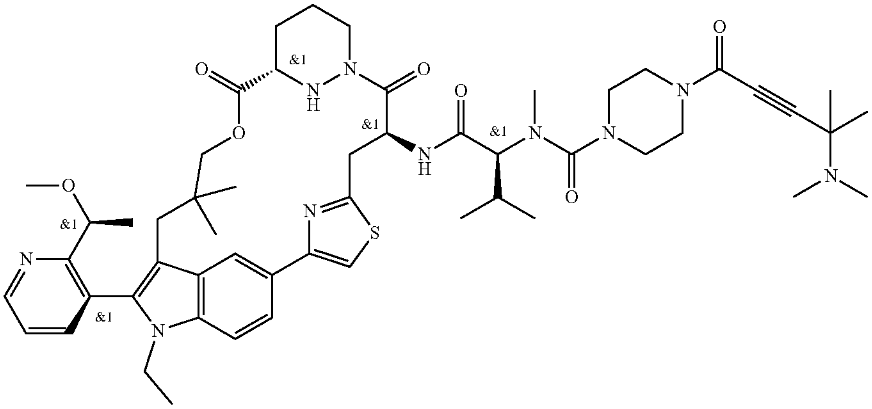 |

TABLE 2-continued
| Certain Compounds | |
|---|---|
| Ex # | Structure |
| C293 | 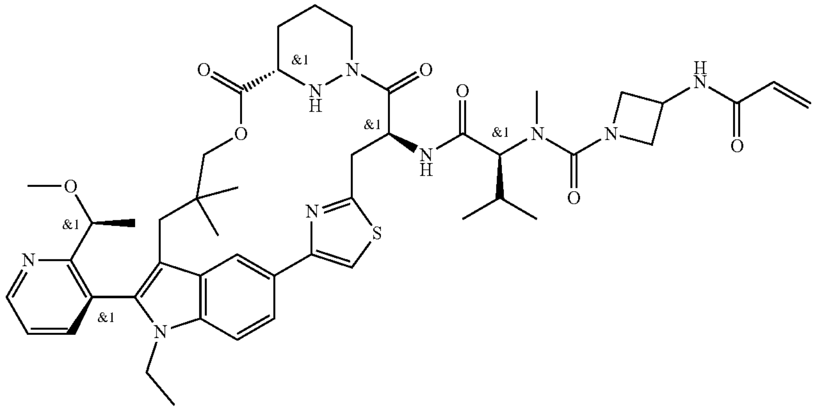 |
| C294 | 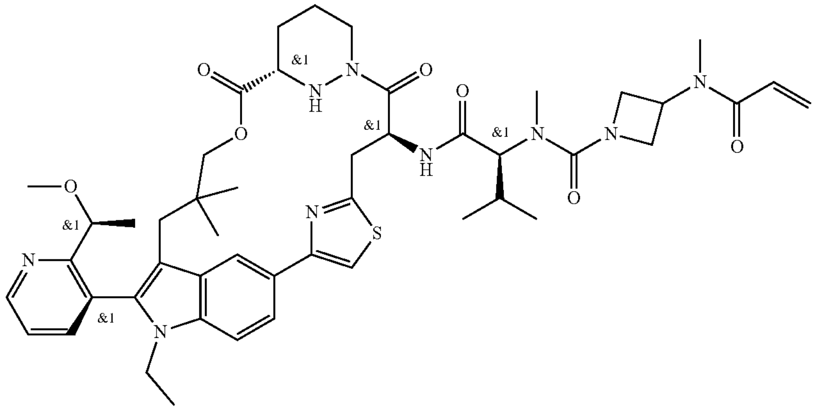 |
| C295 | 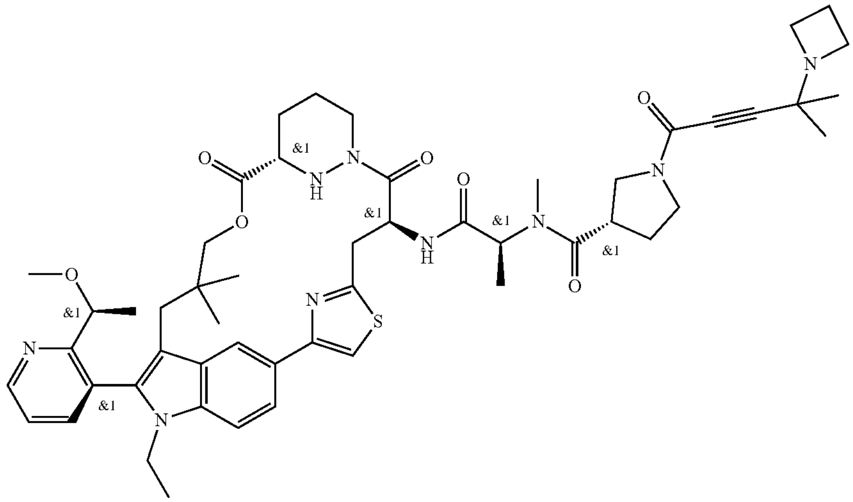 |

TABLE 2-continued
| Certain Compounds | |
|---|---|
| Ex # | Structure |
| C296 | 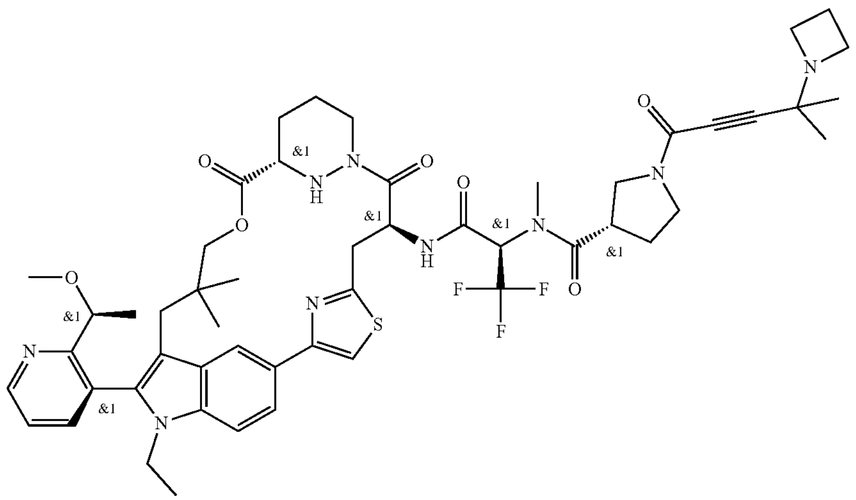 |
| C297 | 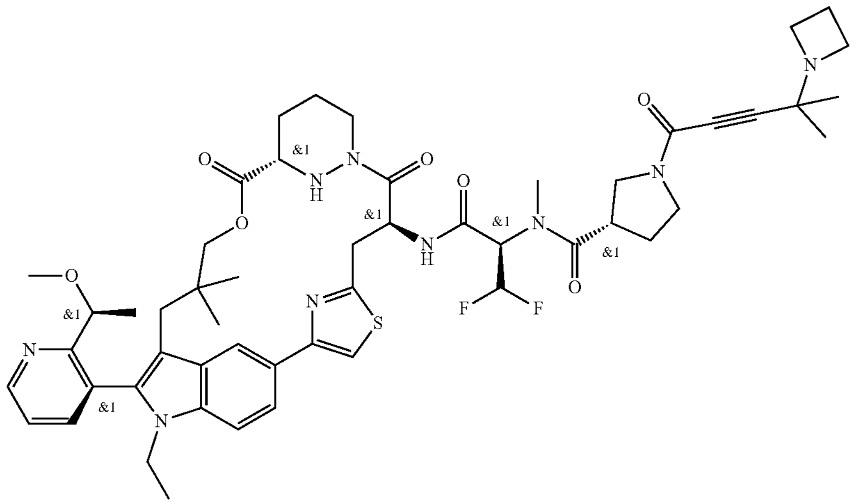 |
| C298 | 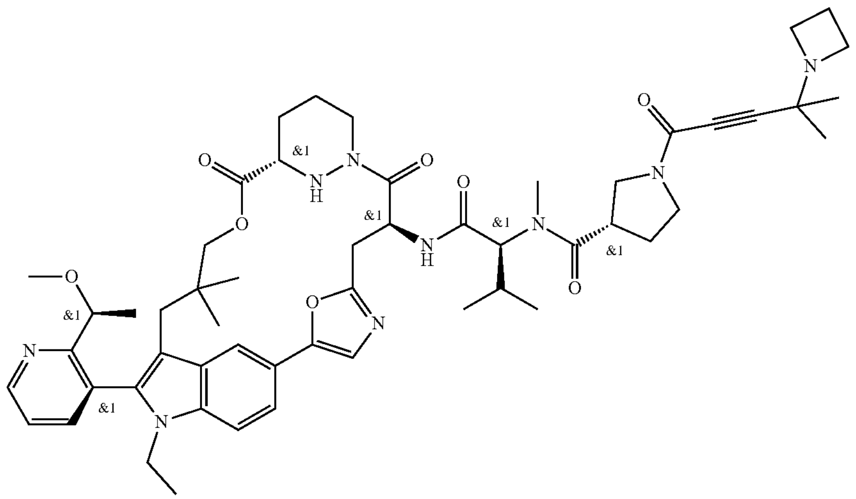 |

TABLE 2-continued
| Certain Compounds | |
|---|---|
| Ex # | Structure |
| C299 | 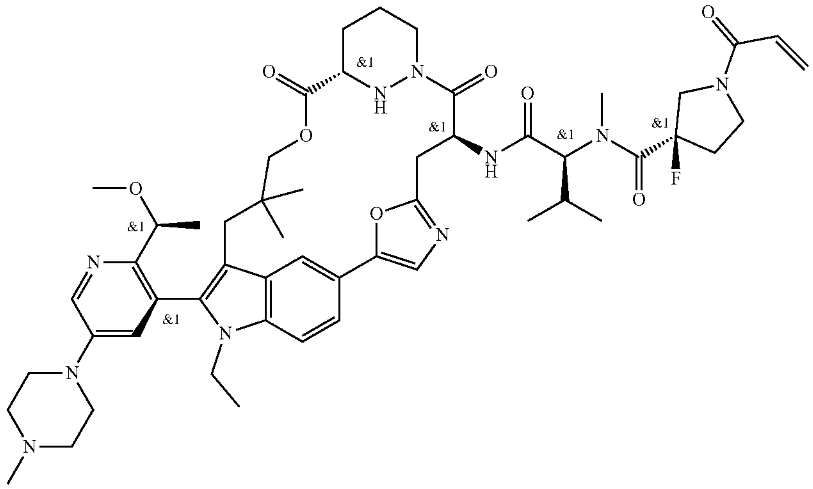 |
| C300 | 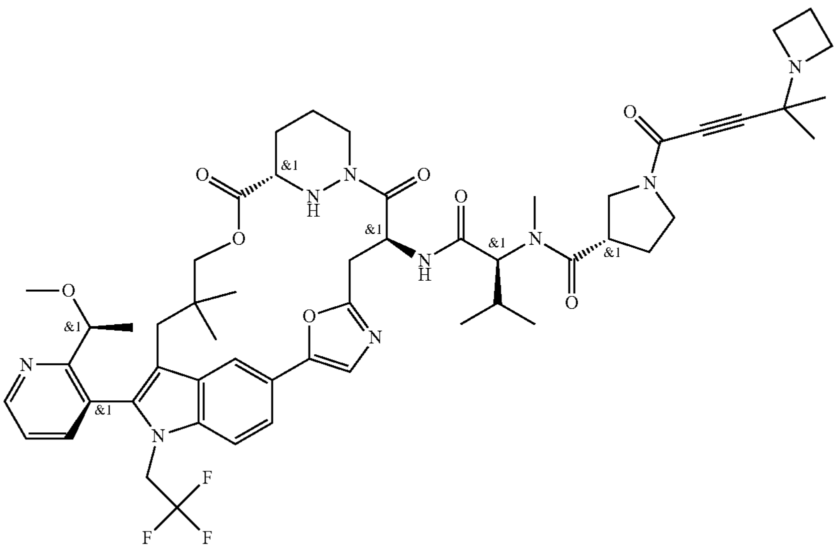 |
| C301 | 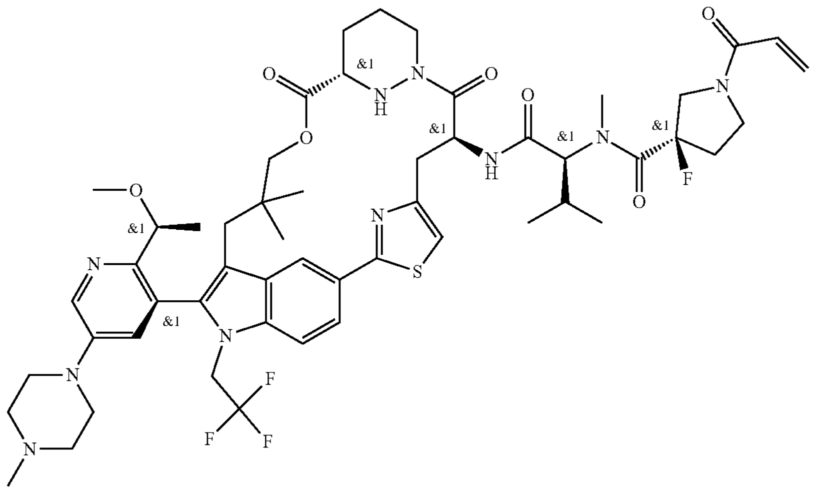 |

TABLE 2-continued
| Certain Compounds | |
|---|---|
| Ex # | Structure |
| C302 | 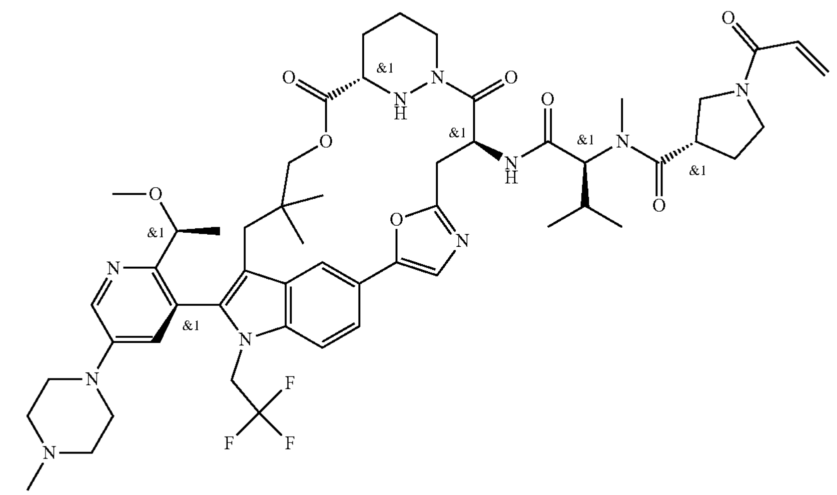 |
| C303 | 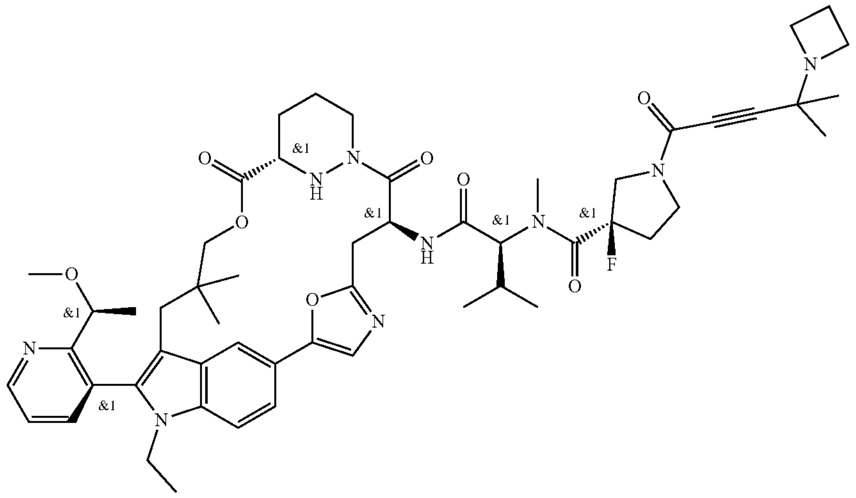 |
| C304 | 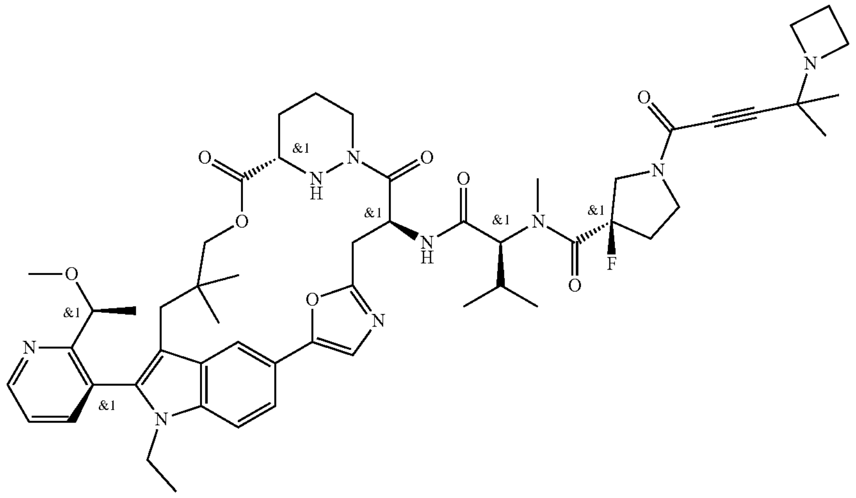 |

TABLE 2-continued
| Certain Compounds | |
|---|---|
| Ex # | Structure |
| C305 | 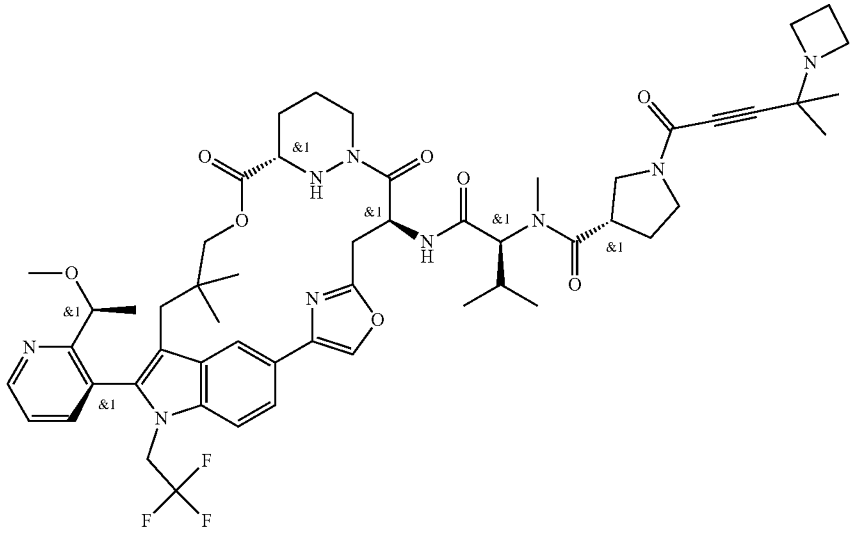 |
| C306 | 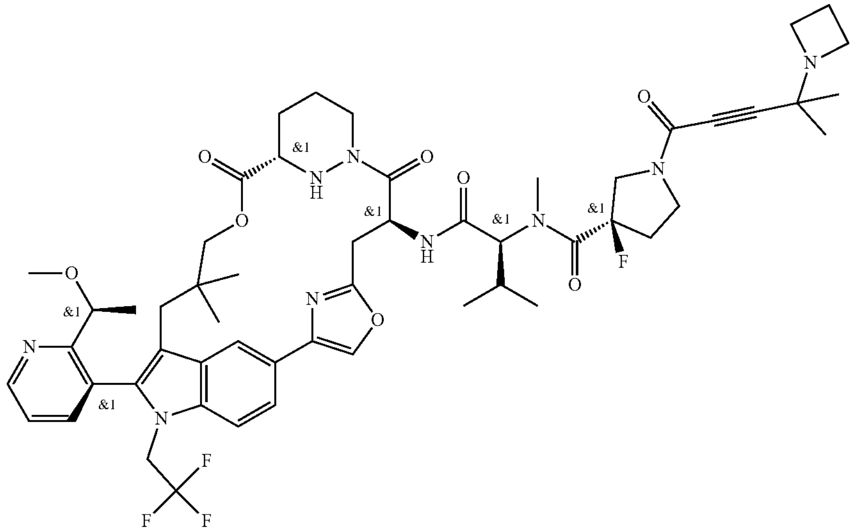 |
| C307 | 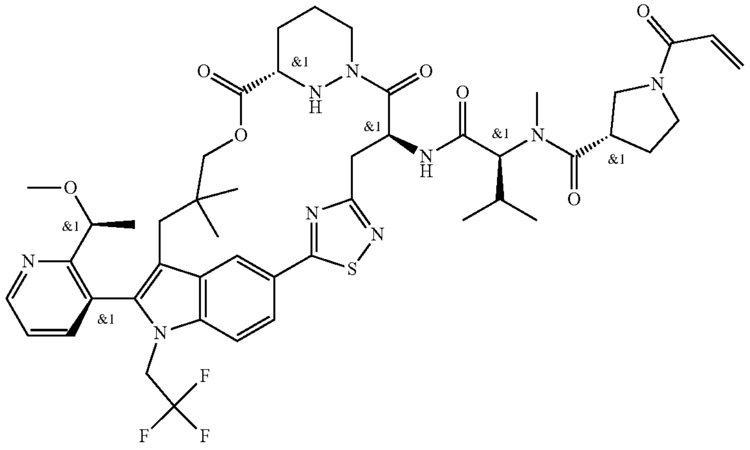 |

TABLE 2-continued
| Certain Compounds | |
|---|---|
| Ex # | Structure |
| C308 | 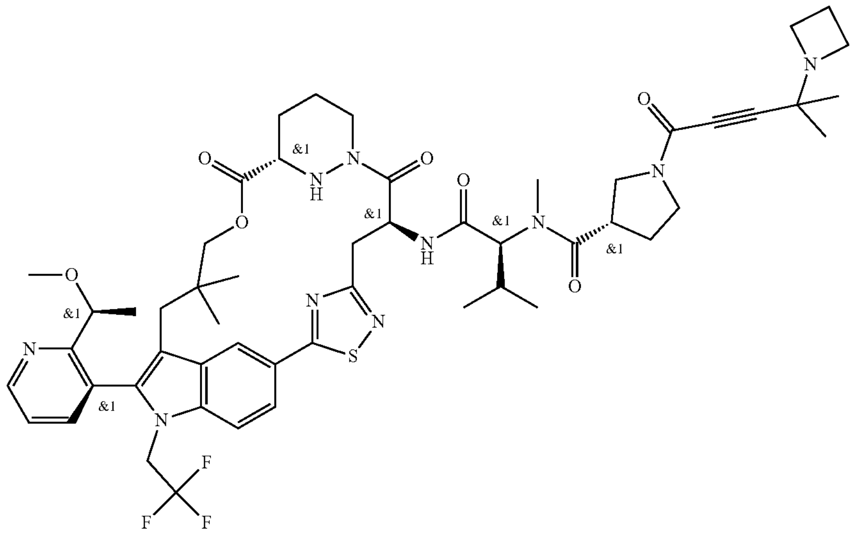 |
| C309 | 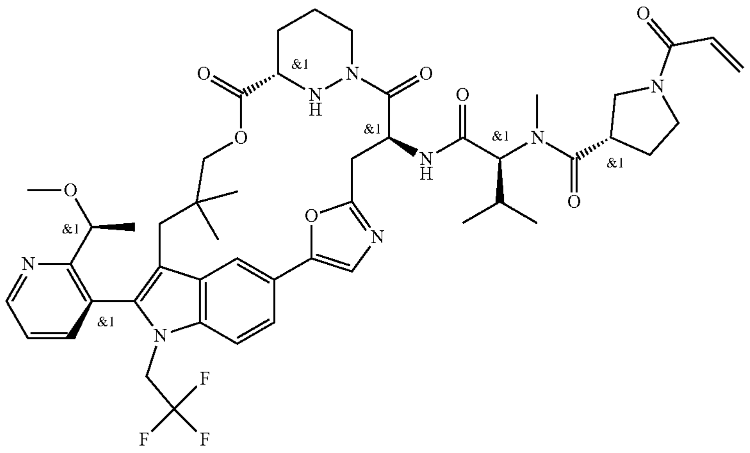 |
| C310 | 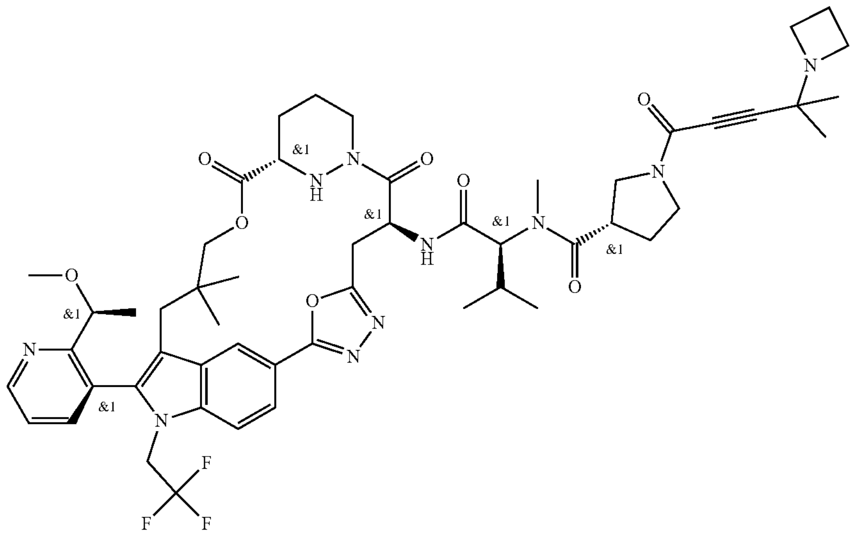 |

TABLE 2-continued
| Certain Compounds | |
|---|---|
| Ex # | Structure |
| C311 | 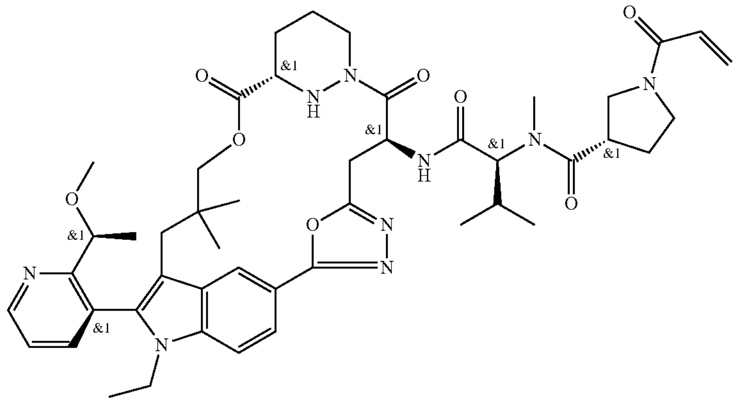 |
| C312 | 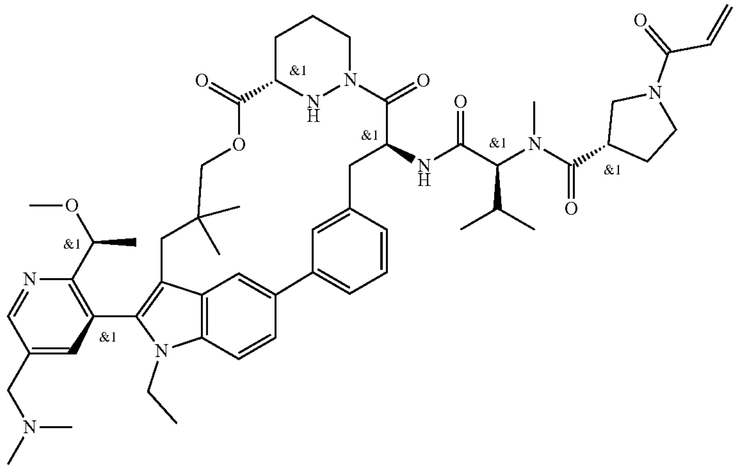 |
| C313 | 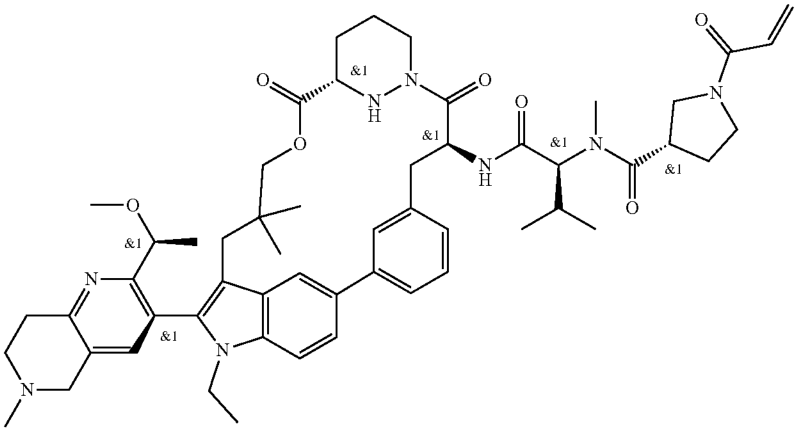 |

TABLE 2-continued
| Certain Compounds | |
|---|---|
| Ex # | Structure |
| C314 | 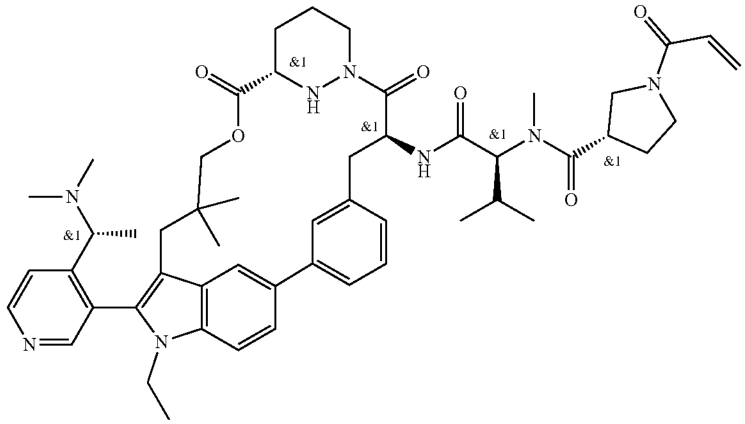 [SMILES: C=CC(=O)N1CC[C@H](C(=O)N(C)[C@H](C(=O)N[C@H]2Cc3cccc(c3)-c3ccc4c(c3)c(c(-c3cnccc3[C@@H](C)N(C)C)n4CC)CC(C)(C)COC(=O)[C@@H]3CCCN(N3)C2=O)C(C)C)C1] |
| C315 | 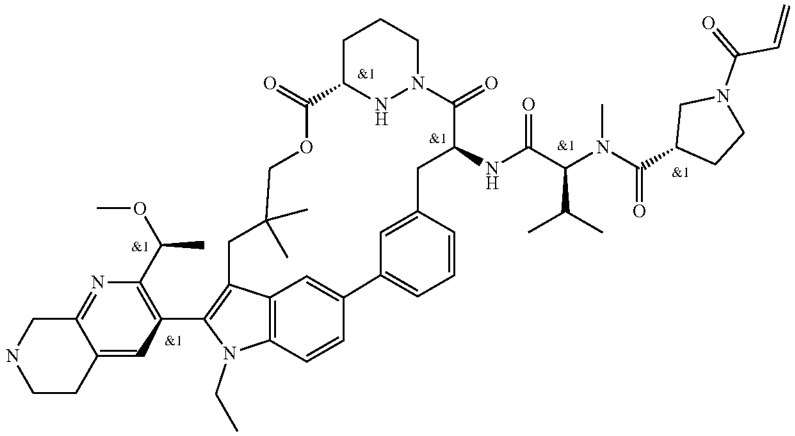 |
| C316 | 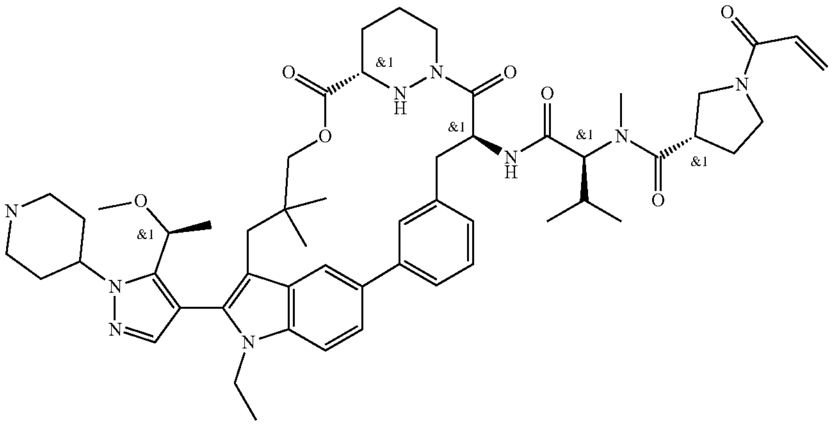 [SMILES: C=CC(=O)N1CC[C@H](C(=O)N(C)[C@H](C(=O)N[C@H]2Cc3cccc(c3)-c3ccc4c(c3)c(c(-c3cnn(C5CCNCC5)c3[C@H](C)OC)n4CC)CC(C)(C)COC(=O)[C@@H]3CCCN(N3)C2=O)C(C)C)C1] |

TABLE 2-continued
| Certain Compounds | |
|---|---|
| Ex # | Structure |
| C317 | 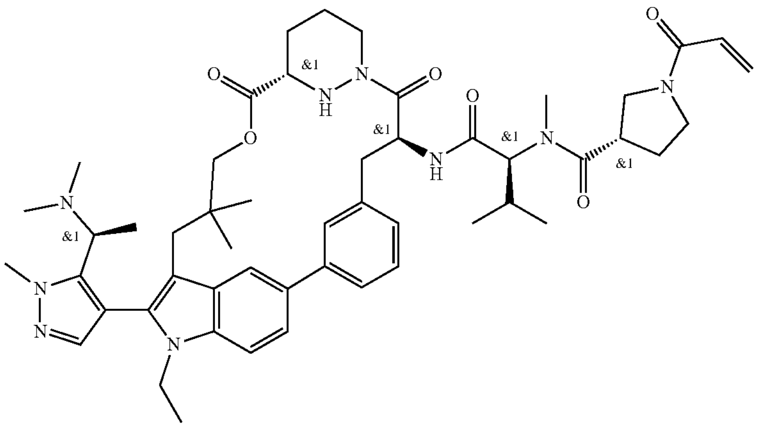 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)N(C)C)n4CC)CC(C)(C)COC(=O)[C@@H]3CCCN(N3)C2=O)C(C)C)C1] |
| C318 | 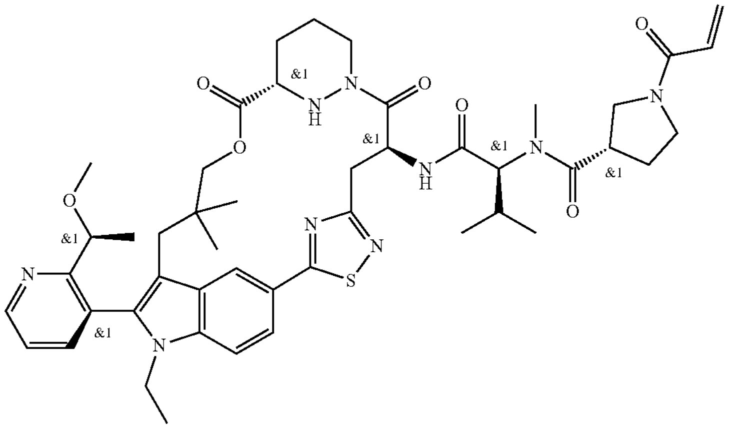 |
| C319 | 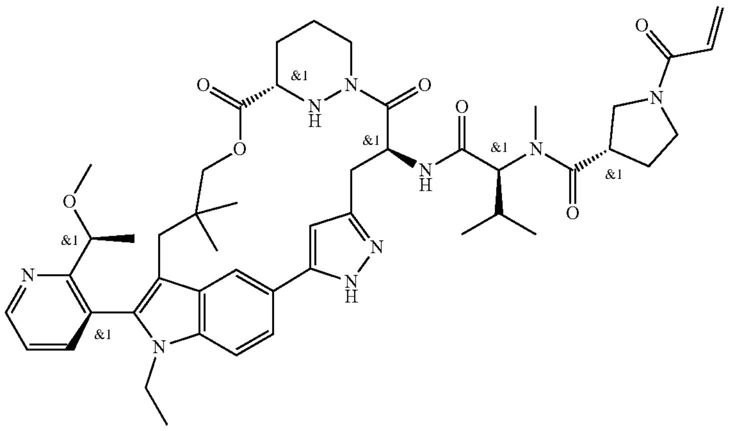 |

TABLE 2-continued
| Certain Compounds | |
|---|---|
| Ex # | Structure |
| C320 | 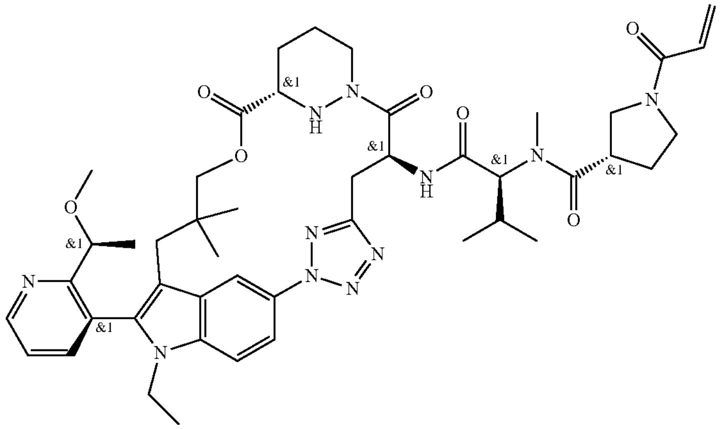 |
| C321 | 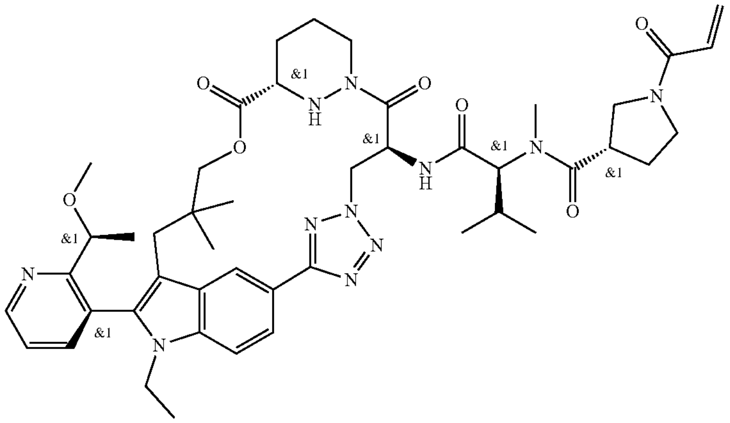 |
| C322 | 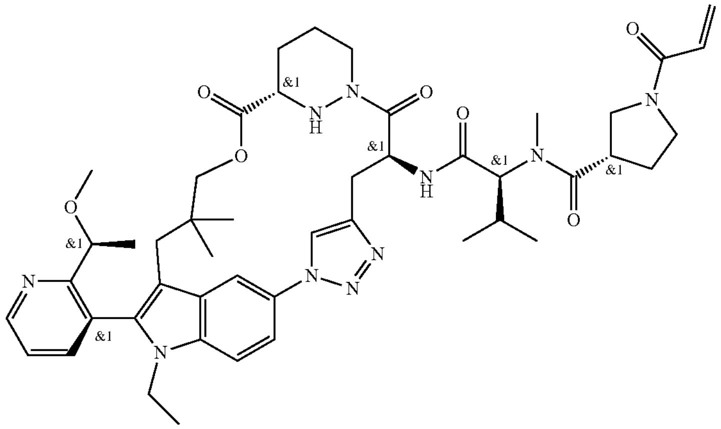 |

TABLE 2-continued
| Certain Compounds | |
|---|---|
| Ex # | Structure |
| C323 | 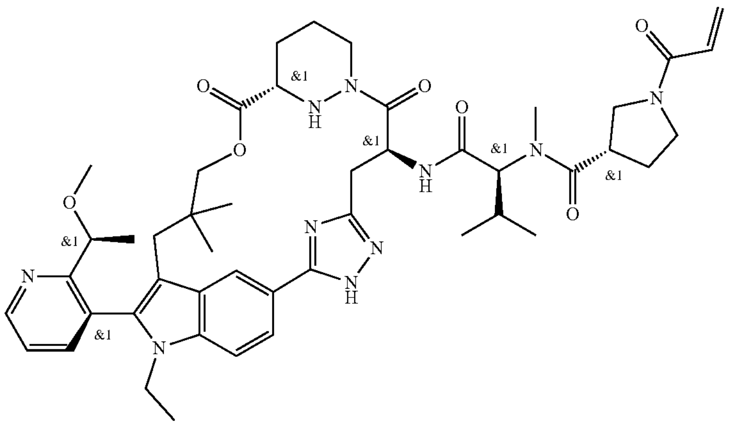 |
| C324 | 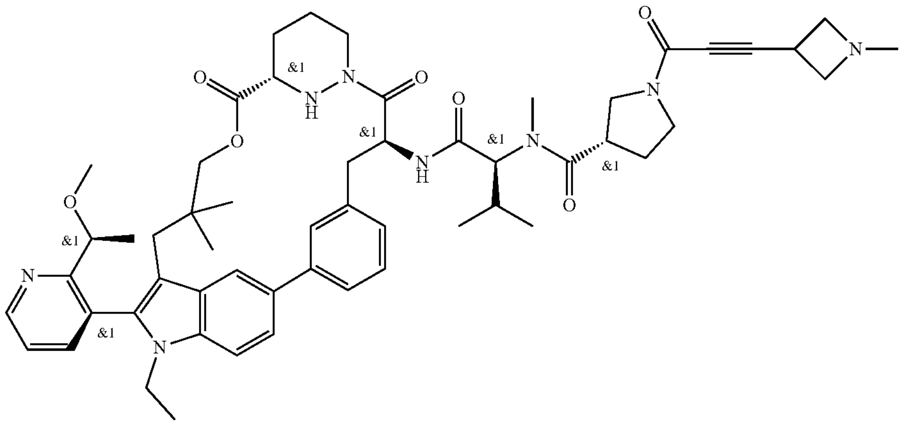 |
| C325 | 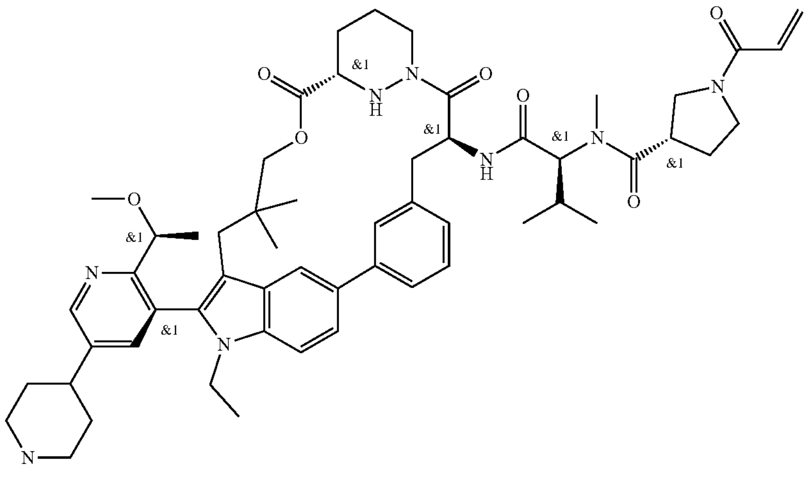 |

TABLE 2-continued
| Certain Compounds | |
|---|---|
| Ex # | Structure |
| C326 | 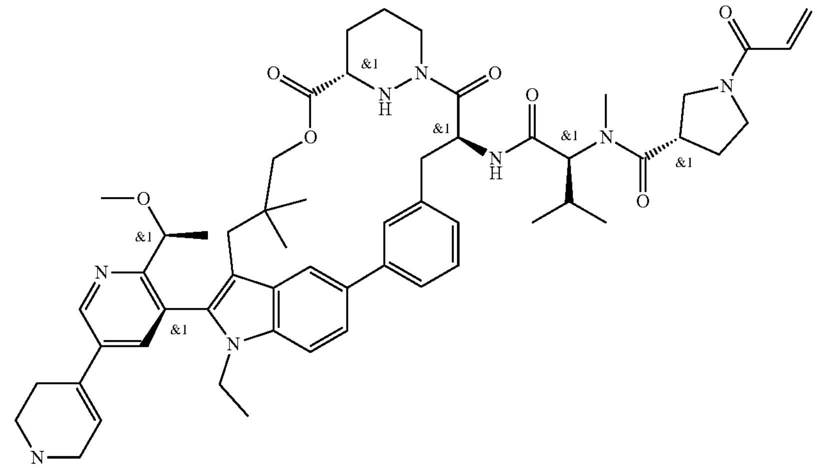 |
| C327 | 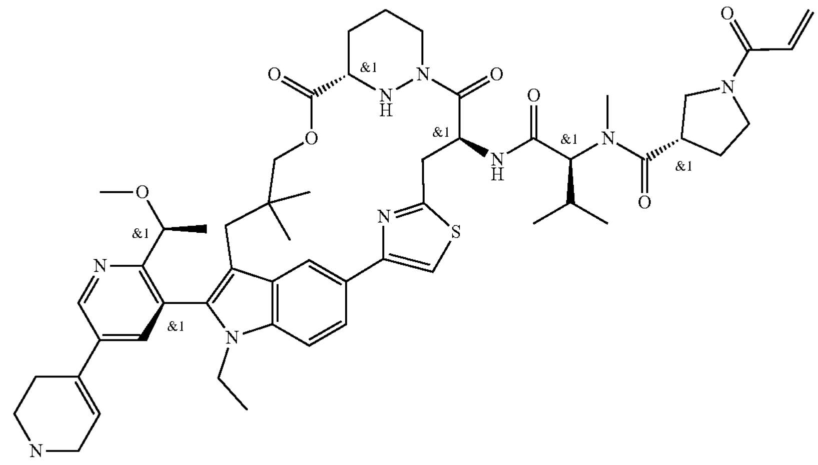 |
| C328 | 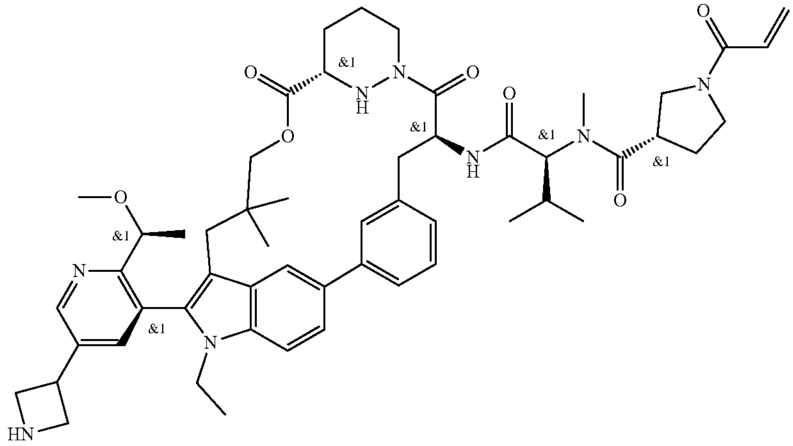 |

TABLE 2-continued
| Certain Compounds | |
|---|---|
| Ex # | Structure |
| C329 | 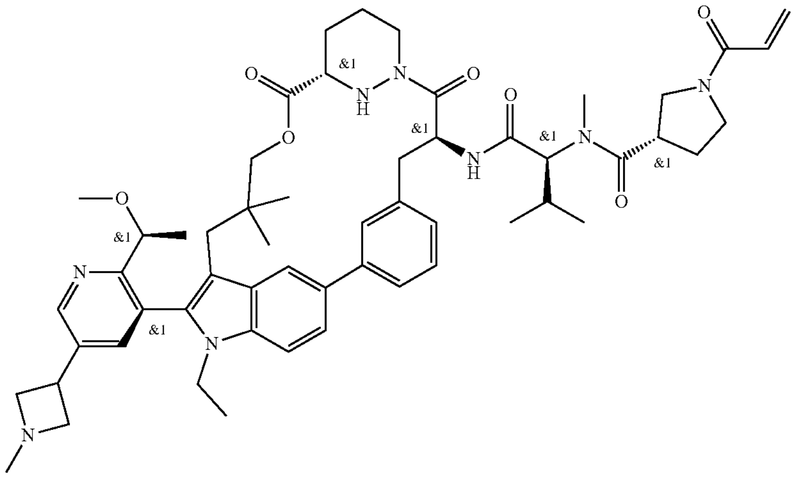 |
| C330 | 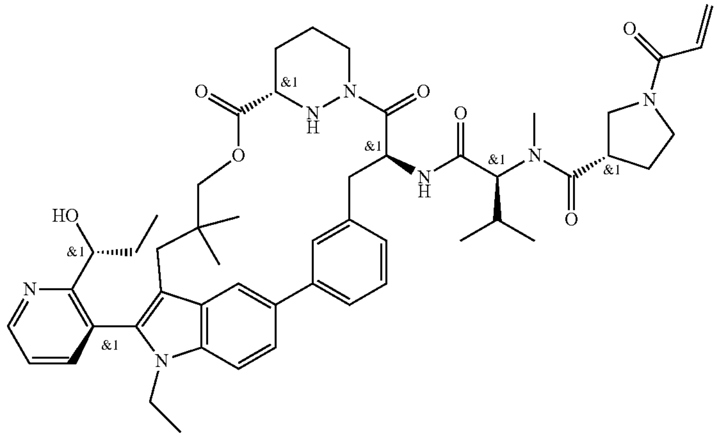 |
| C331 | 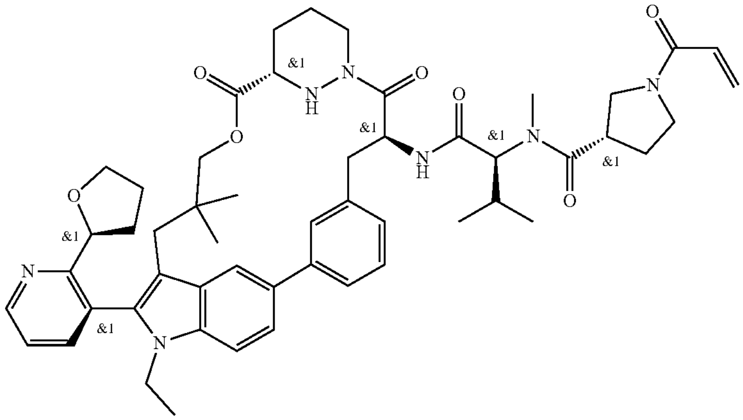 |

TABLE 2-continued
| Certain Compounds | |
|---|---|
| Ex # | Structure |
| C332 | 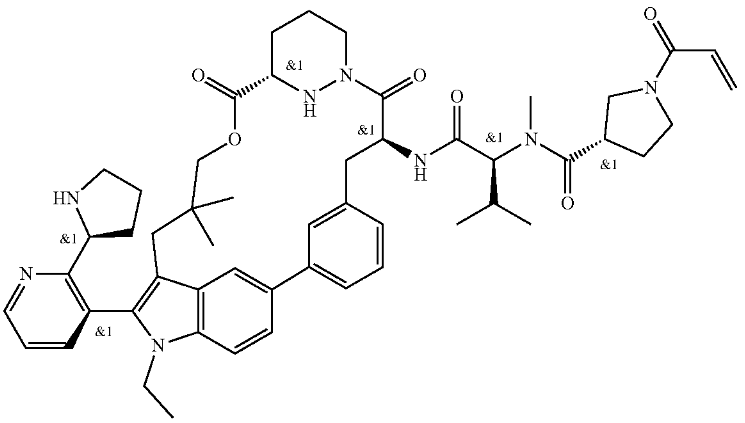 |
| C333 | 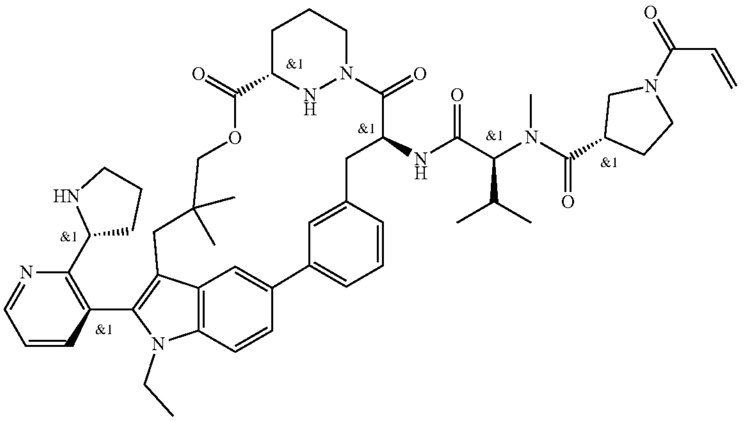 |
| C334 | 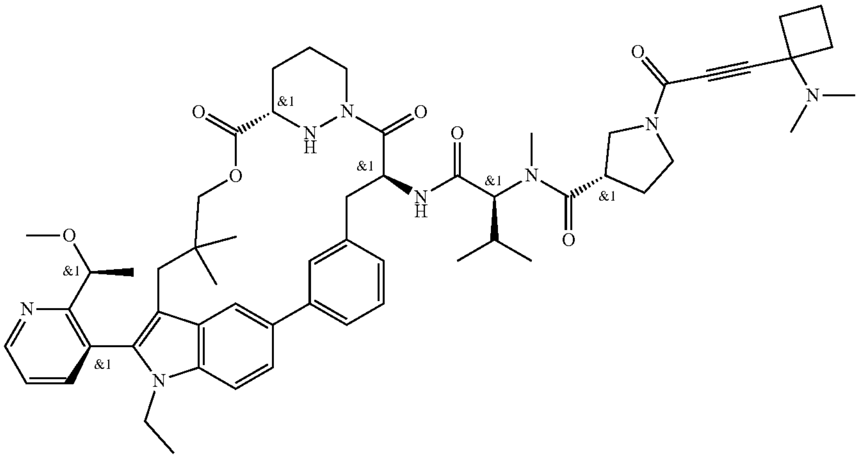 |

TABLE 2-continued
| Certain Compounds | |
|---|---|
| Ex # | Structure |
| C335 | 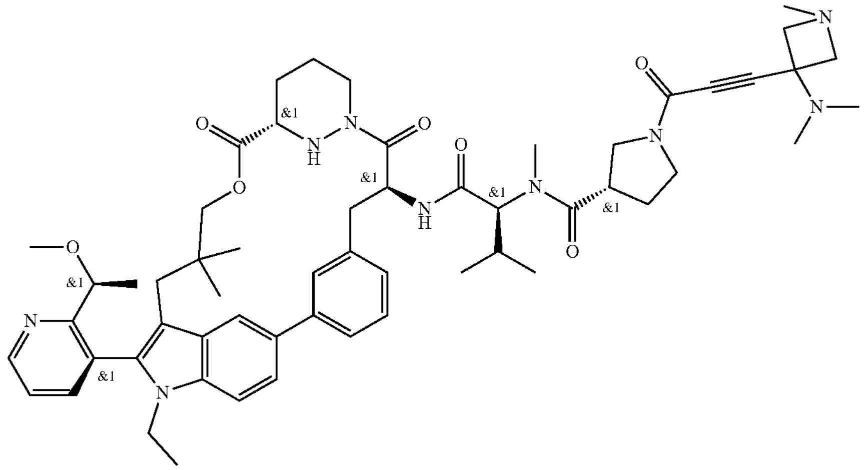 |
| C336 | 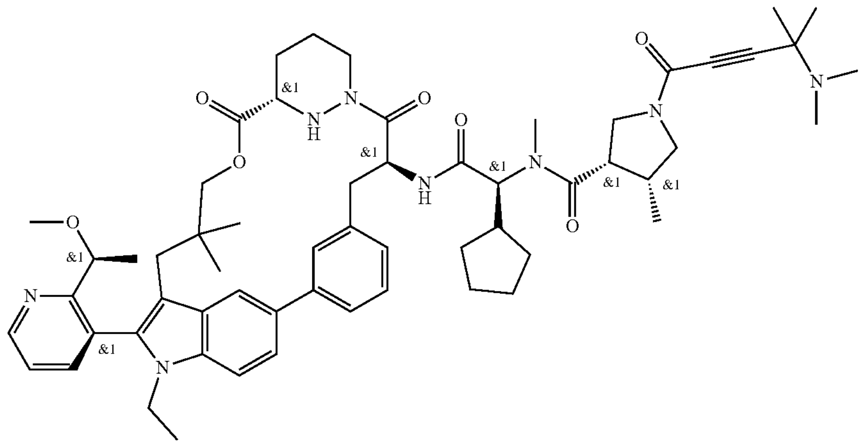 |
| C337 | 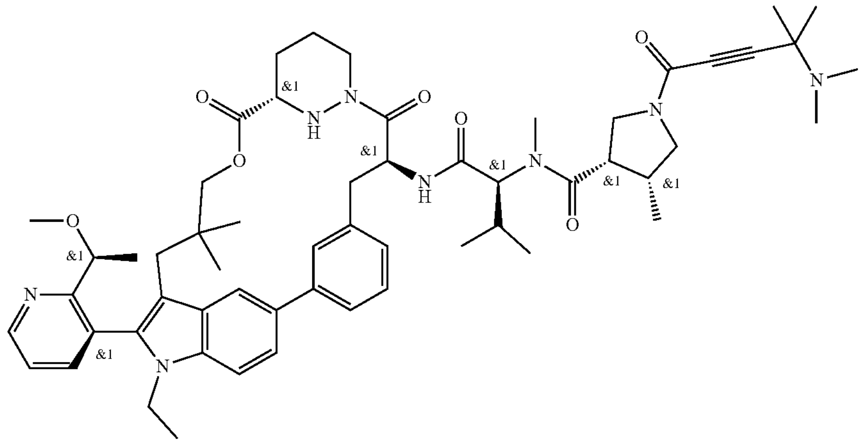 |

TABLE 2-continued
| Certain Compounds | |
|---|---|
| Ex # | Structure |
| C338 | 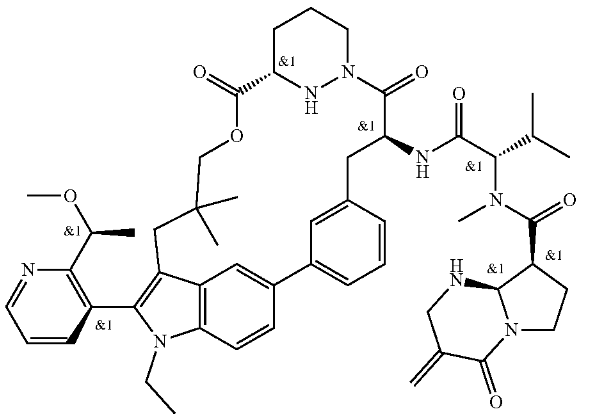 |
| C339 | 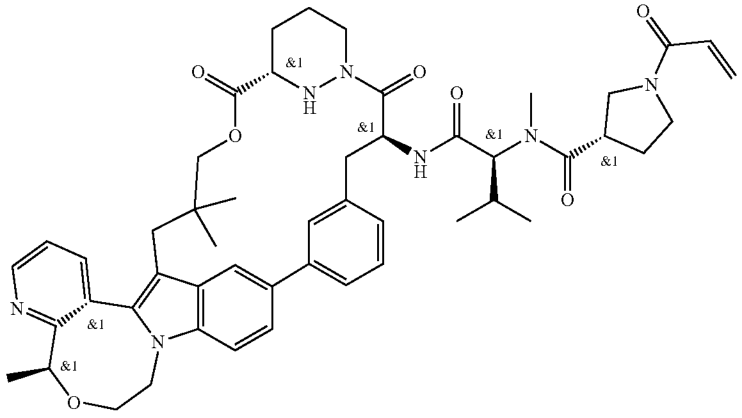 |
| C340 | 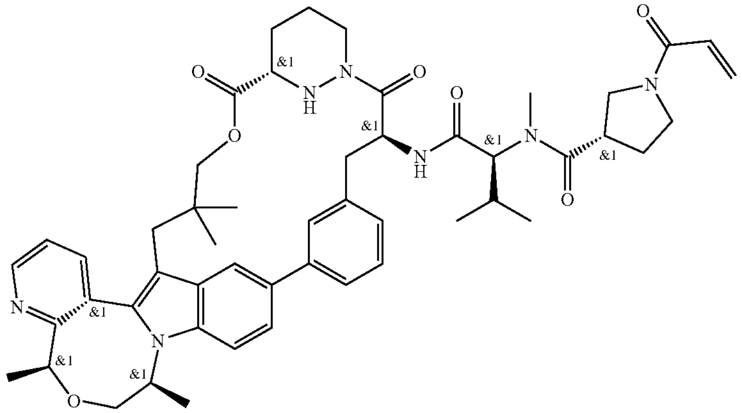 |

TABLE 2-continued
| Certain Compounds | |
|---|---|
| Ex # | Structure |
| C341 | 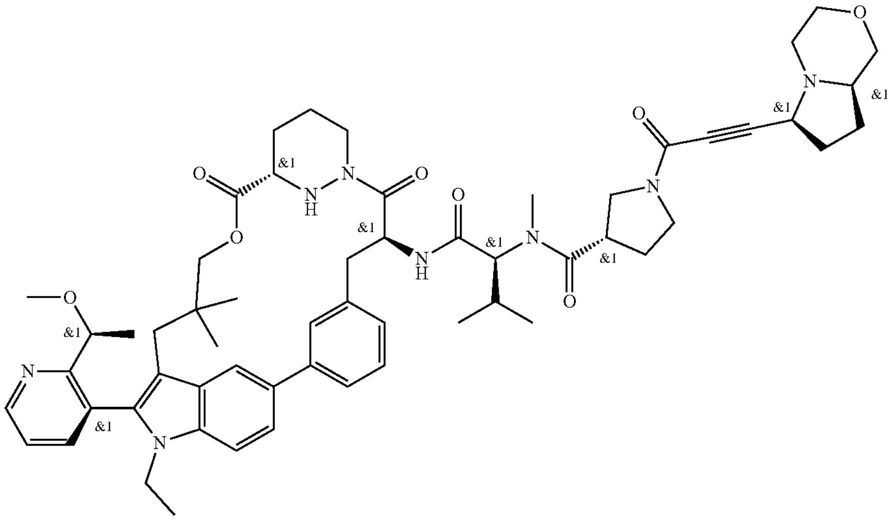 |
| C342 | 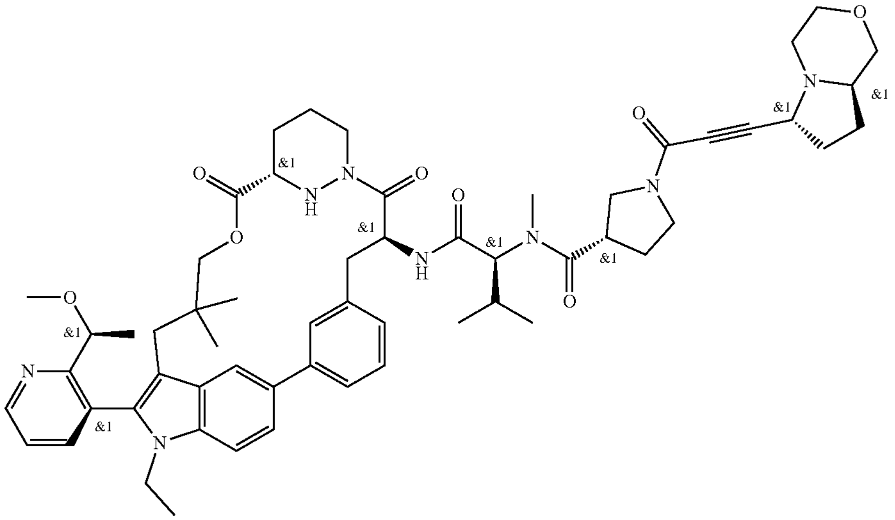 |
| C343 | 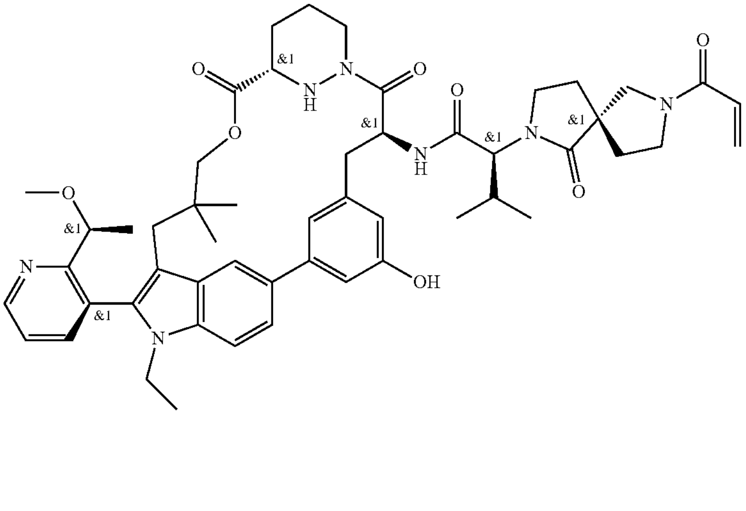 |

TABLE 2-continued
| Certain Compounds | |
|---|---|
| Ex # | Structure |
| C344 | 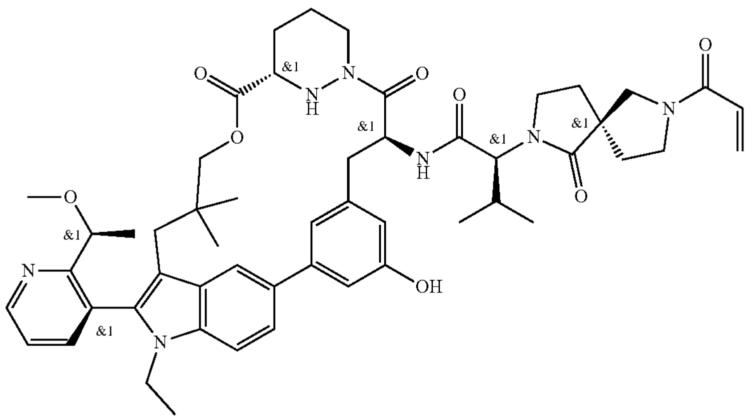 |
| C345 | 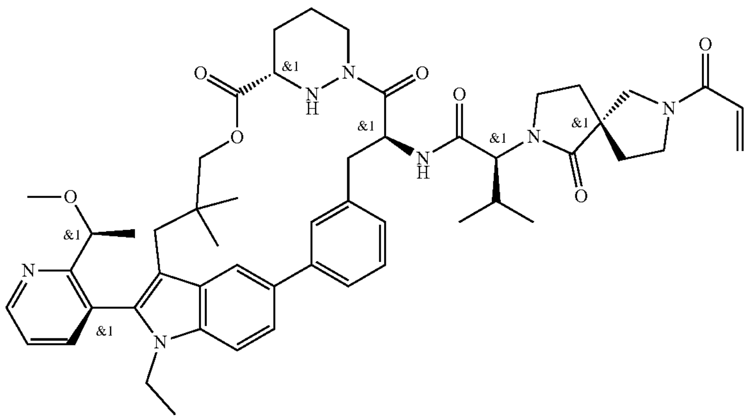 |
| C346 | 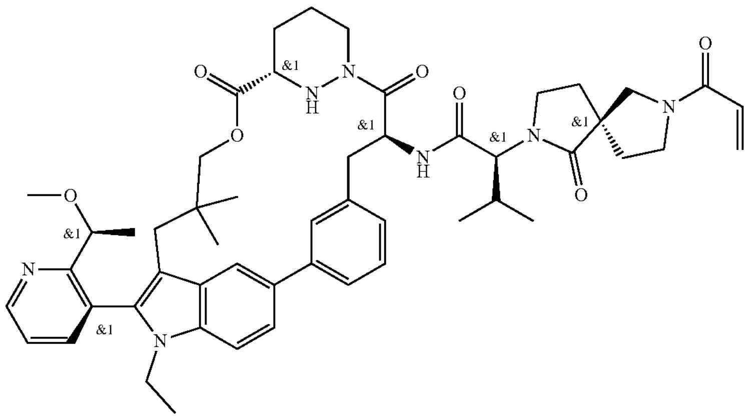 |

TABLE 2-continued
| Certain Compounds | |
|---|---|
| Ex # | Structure |
| C347 | 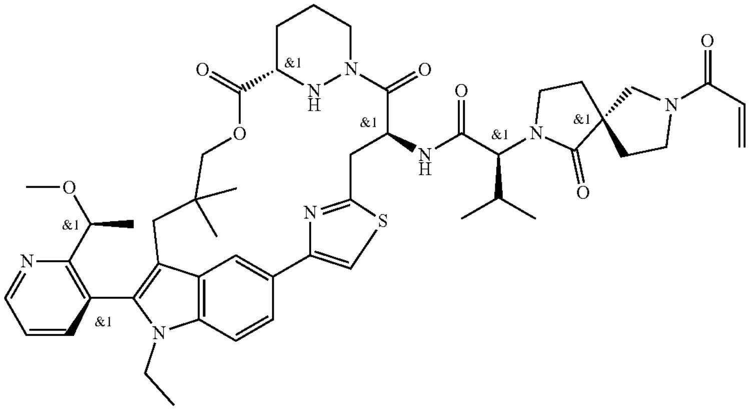 |
| C348 | 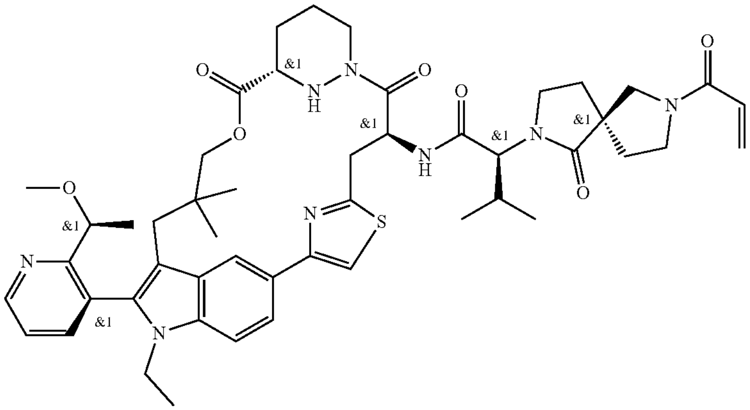 |
| C349 | 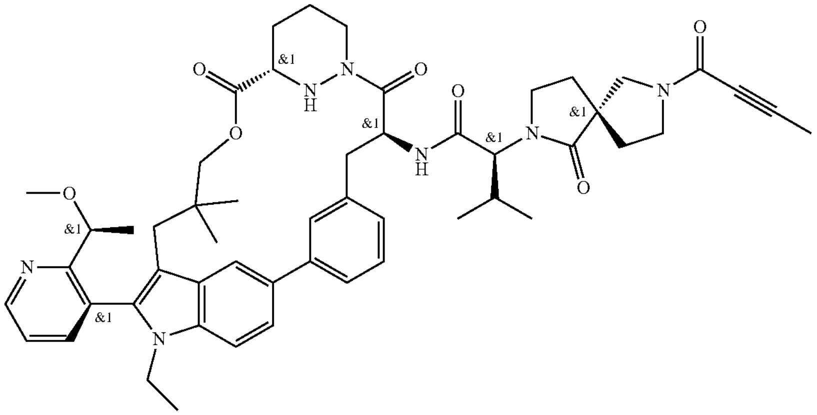 |

TABLE 2-continued
| Certain Compounds | |
|---|---|
| Ex # | Structure |
| C350 | 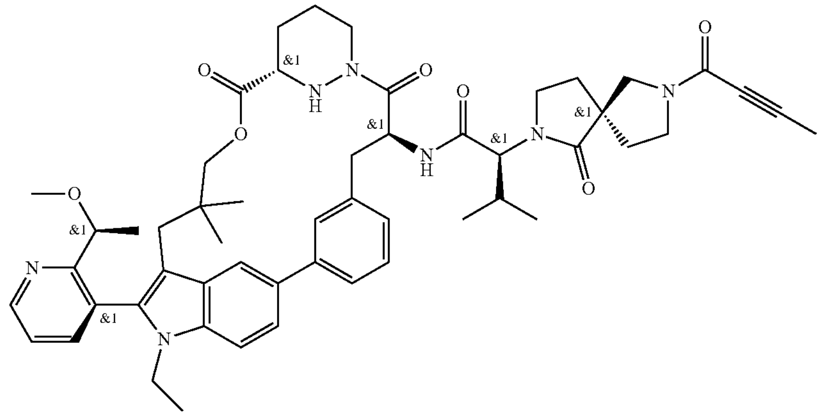 |
| C351 | 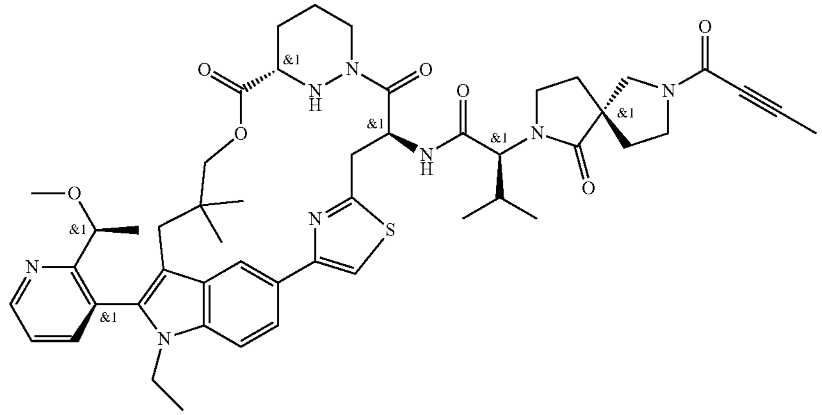 |
| C352 | 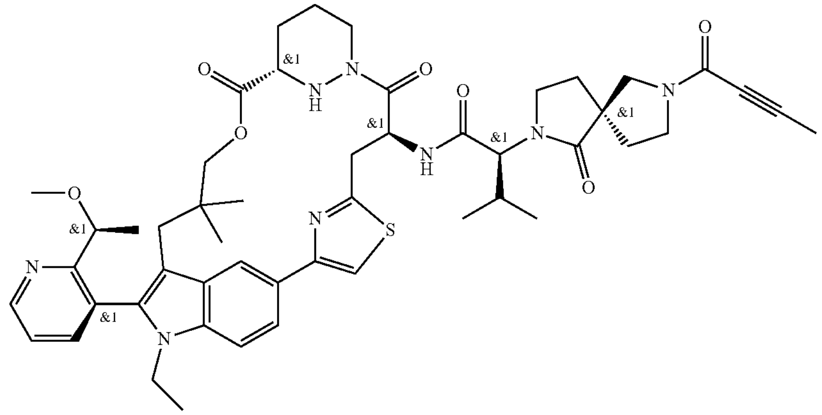 |

TABLE 2-continued
| Certain Compounds | |
|---|---|
| Ex # | Structure |
| C353 | 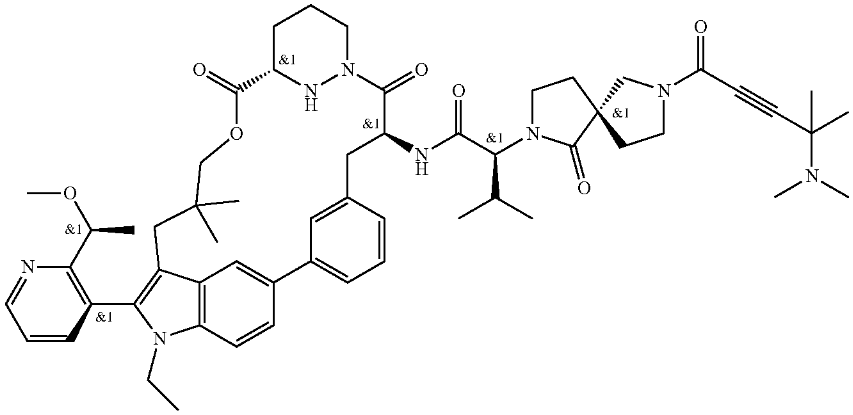 |
| C354 | 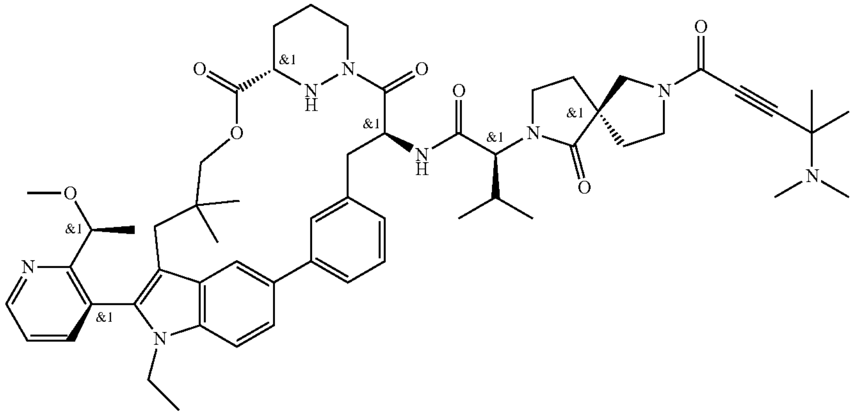 |
| C355 | 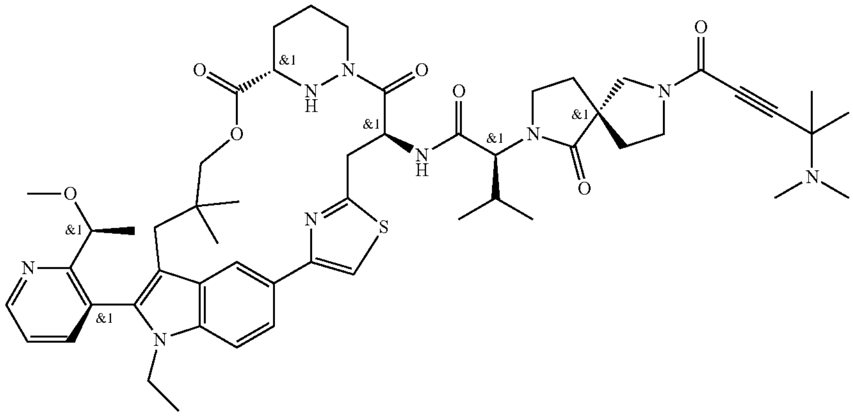 |

TABLE 2-continued
| Certain Compounds | |
|---|---|
| Ex # | Structure |
| C356 | 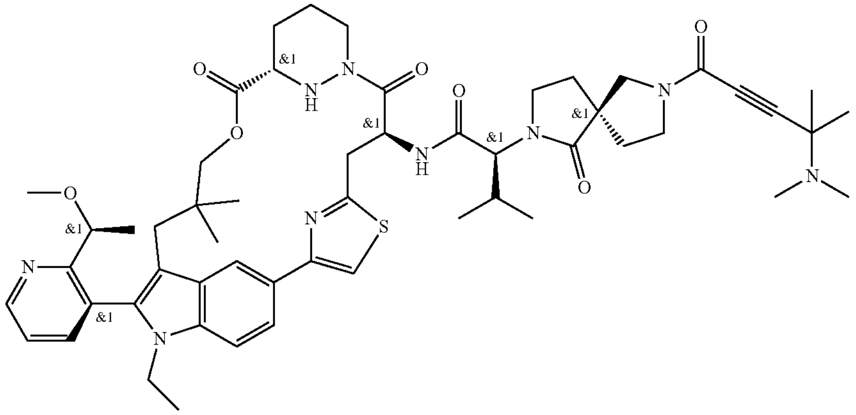 |
| C357 | 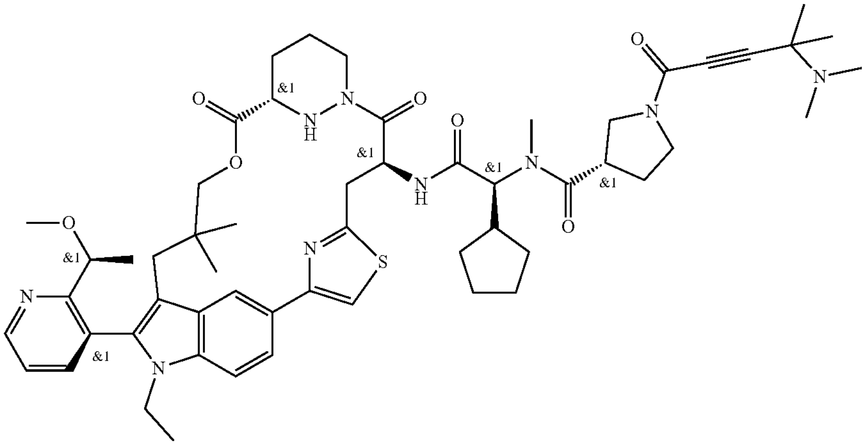 |
| C358 | 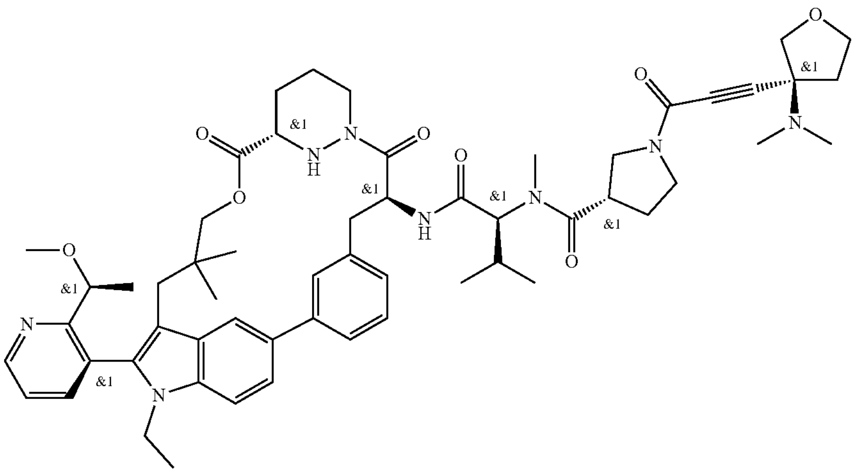 |

TABLE 2-continued
| Certain Compounds | |
|---|---|
| Ex # | Structure |
| C359 | 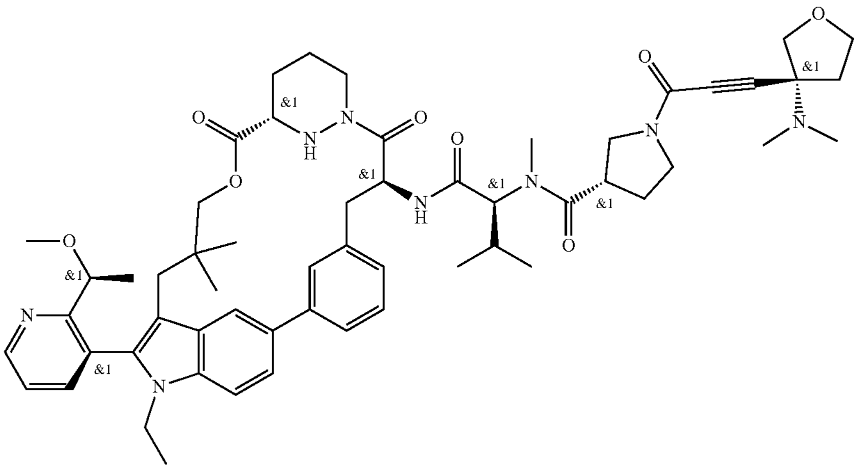 |
| C360 | 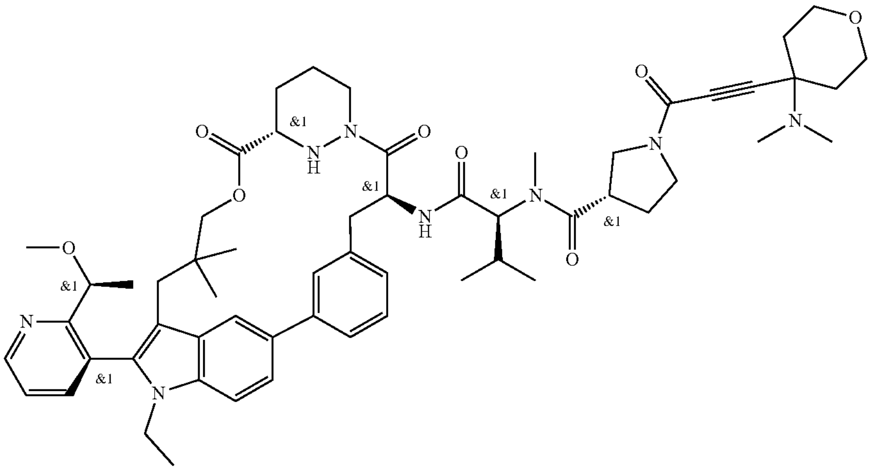 |
| C361 | 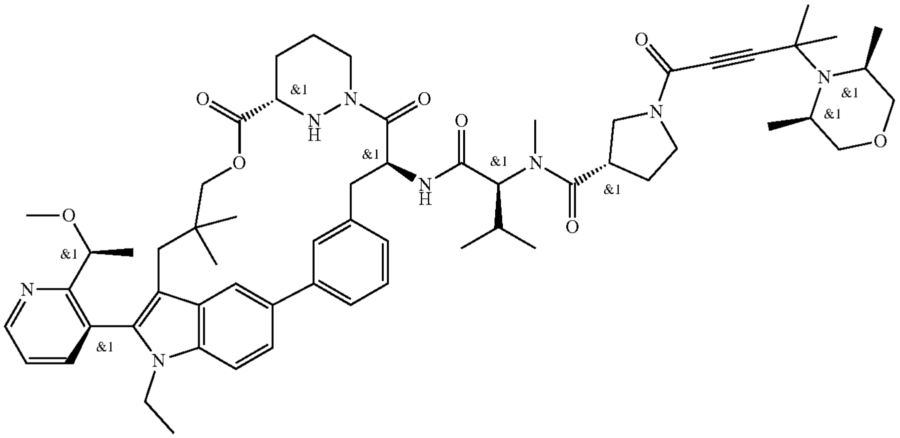 |

TABLE 2-continued
| Certain Compounds | |
|---|---|
| Ex # | Structure |
| C362 | 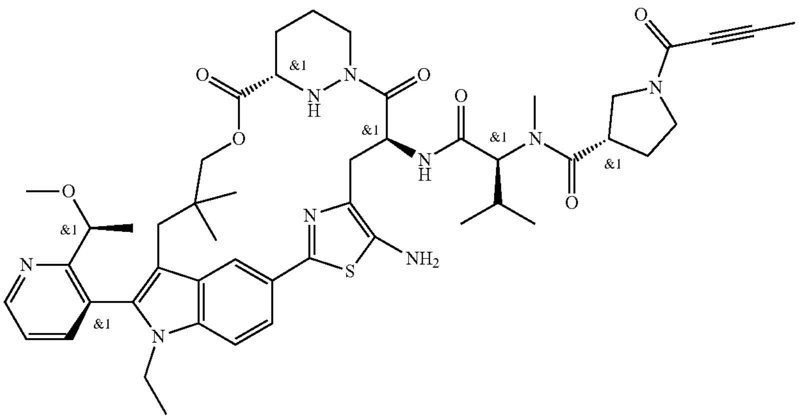 |
| C363 | 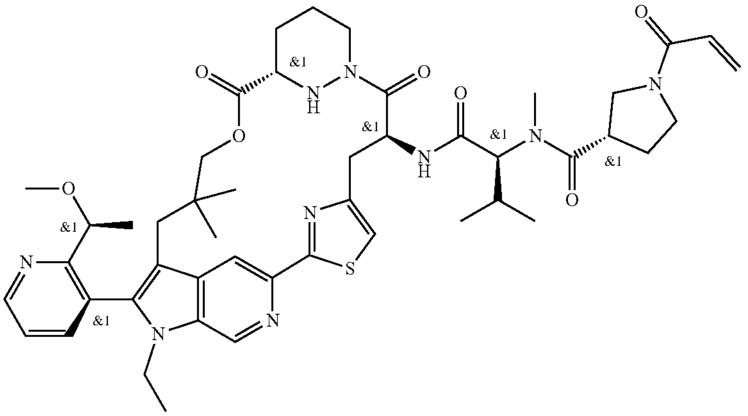 |
| C364 | 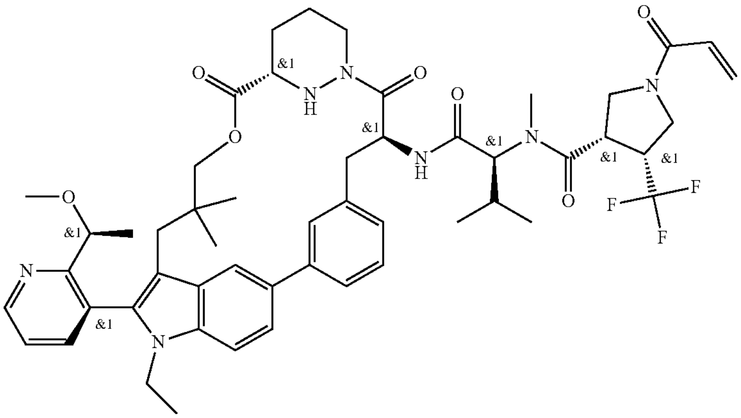 |

TABLE 2-continued
| Certain Compounds | |
|---|---|
| Ex # | Structure |
| C365 | 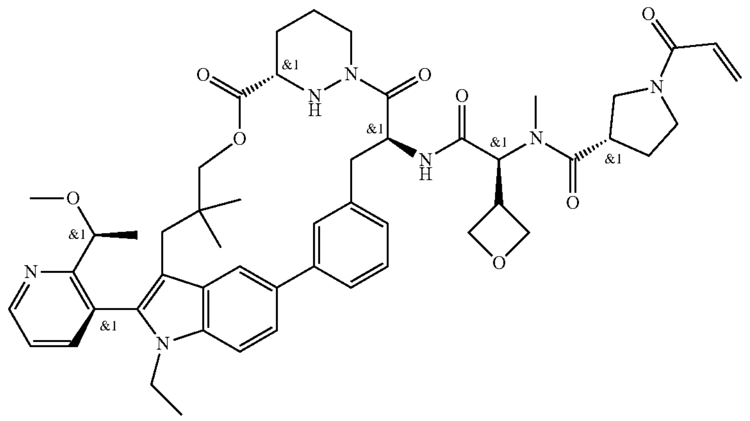 |
| C366 | 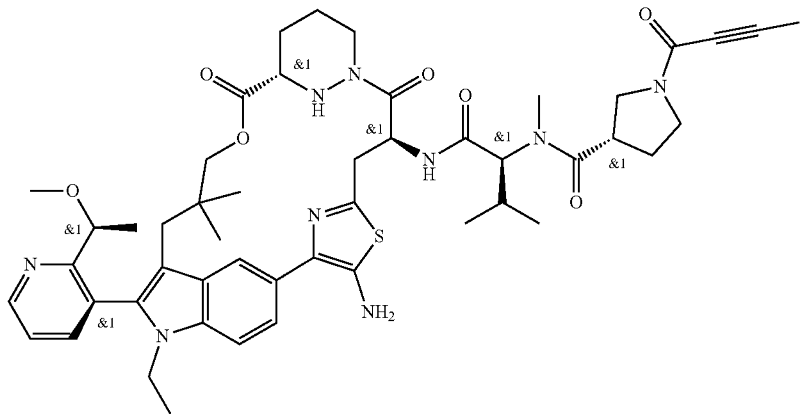 |
| C367 | 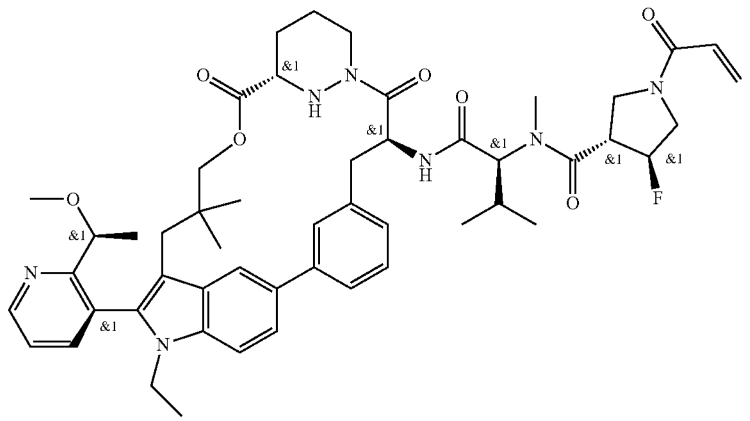 |

TABLE 2-continued
| Certain Compounds | |
|---|---|
| Ex # | Structure |
| C368 | 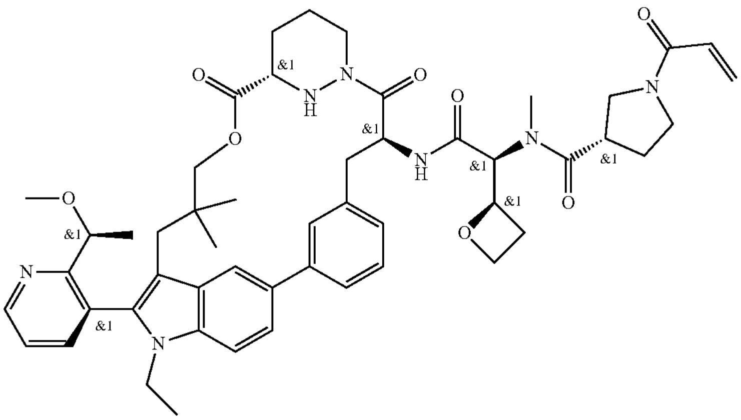 |
| C369 | 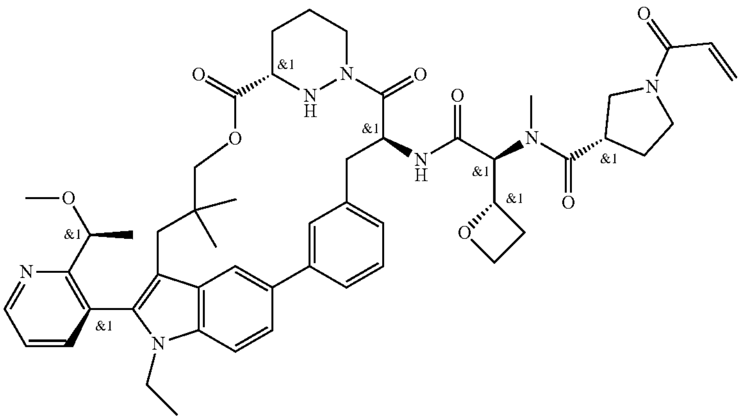 |
| C370 | 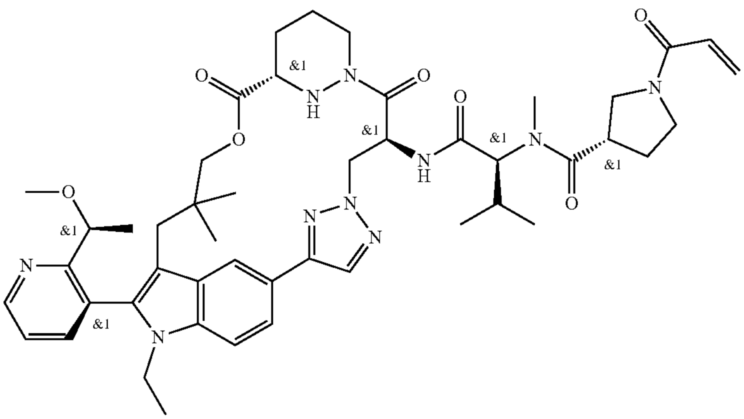 |

TABLE 2-continued
| Certain Compounds | |
|---|---|
| Ex # | Structure |
| C371 | 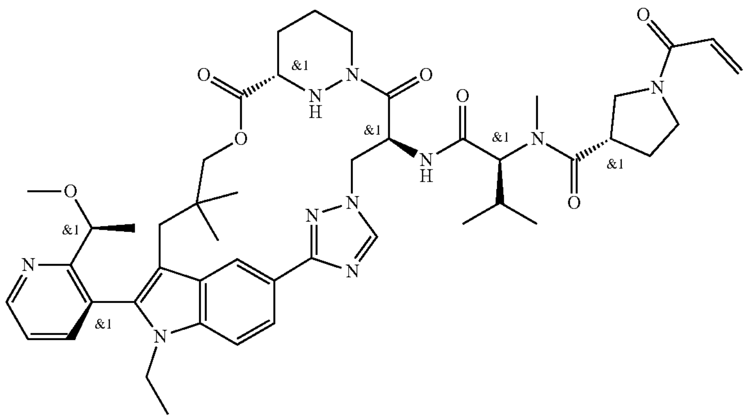 |
| C372 | 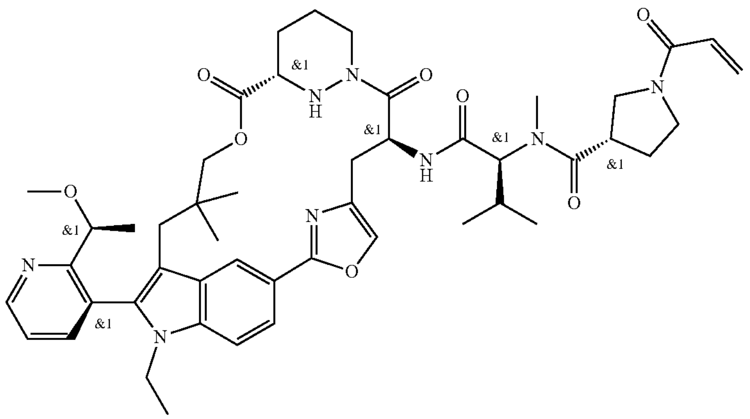 |
| C373 | 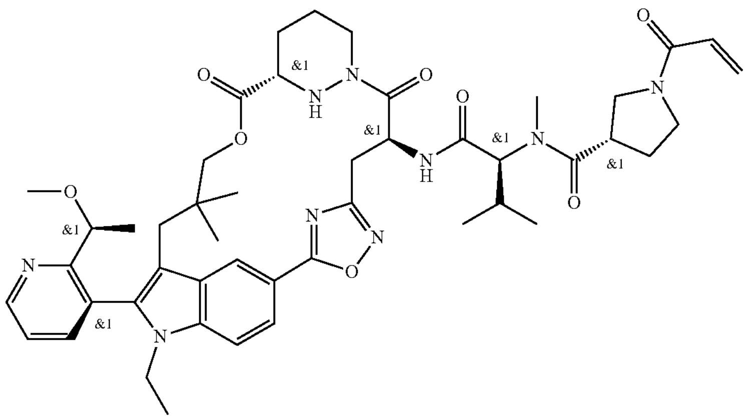 |

TABLE 2-continued
| Certain Compounds | |
|---|---|
| Ex # | Structure |
| C374 | 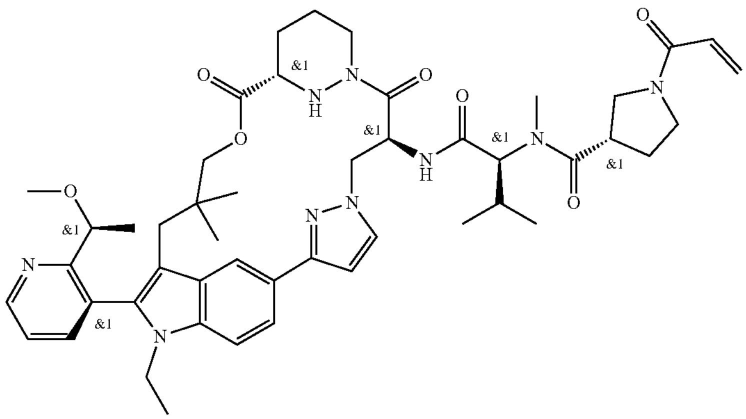 |
| C375 | 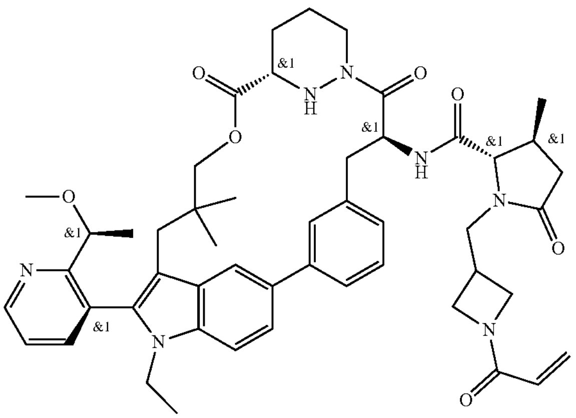 |
| C376 | 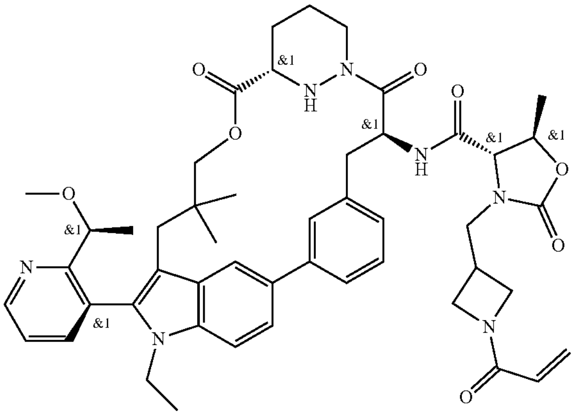 |

TABLE 2-continued
| Certain Compounds | |
|---|---|
| Ex # | Structure |
| C377 | 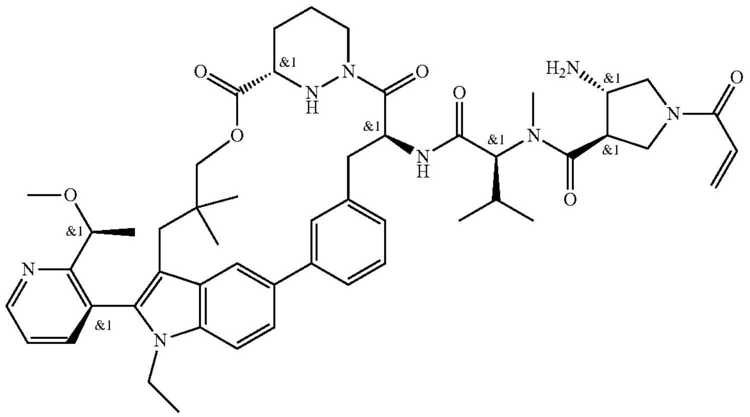 |
| C378 | 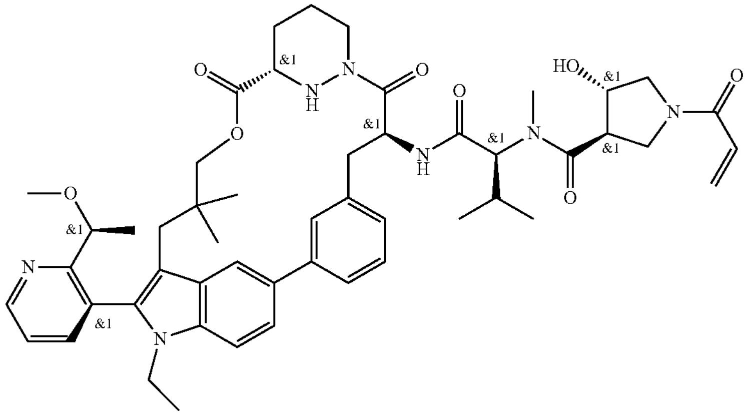 |
| C379 | 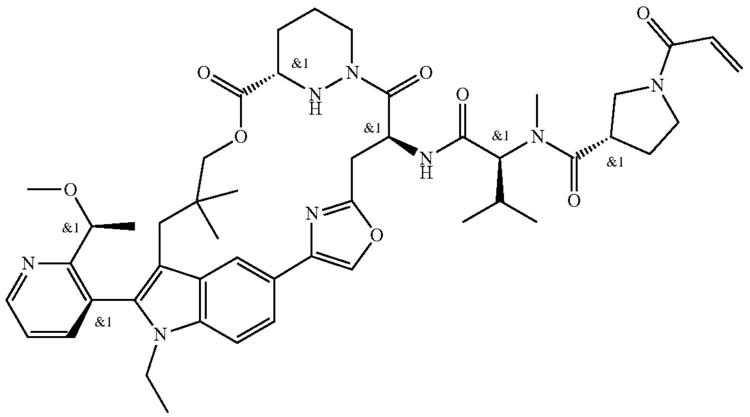 |

TABLE 2-continued
| Certain Compounds | |
|---|---|
| Ex # | Structure |
| C380 | 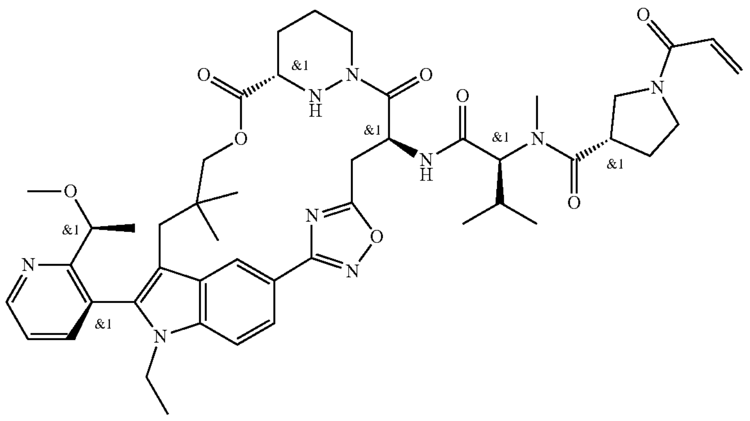 |
| C381 | 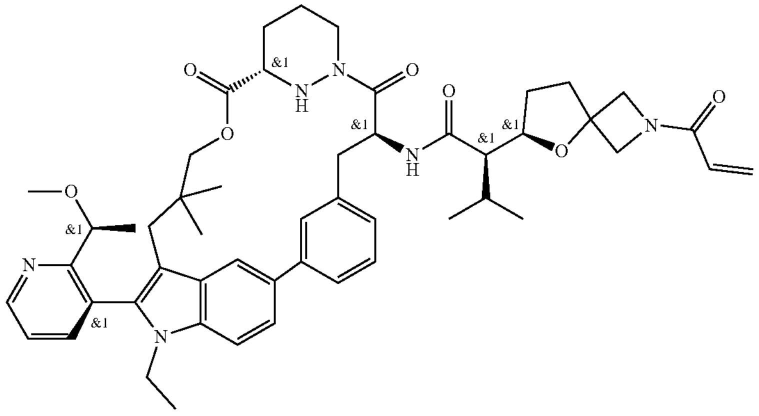 |
| C382 | 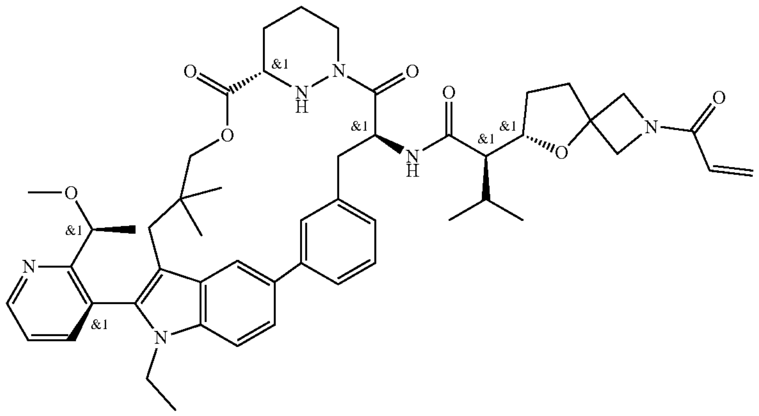 |

TABLE 2-continued
| Certain Compounds | |
|---|---|
| Ex # | Structure |
| C383 | 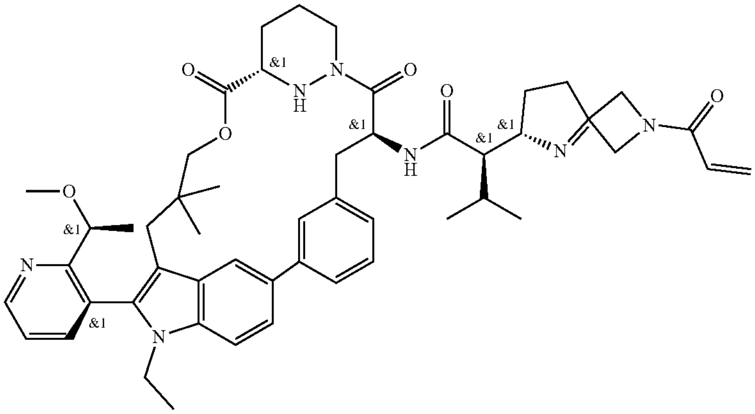 |
| C384 | 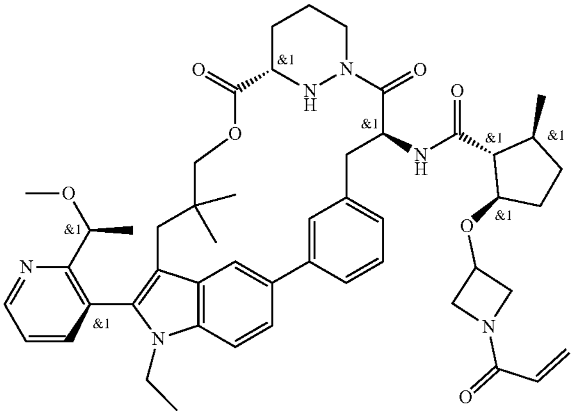 |
| C385 | 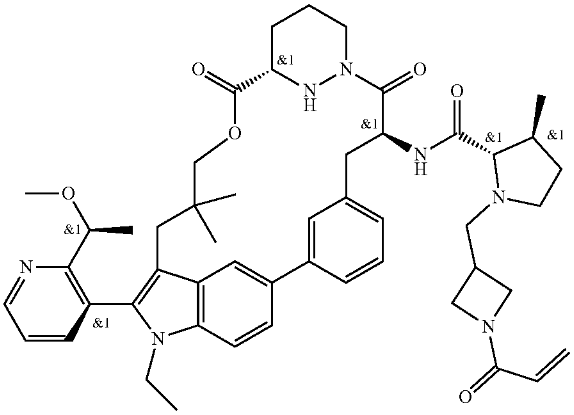 |

TABLE 2-continued
| Certain Compounds | |
|---|---|
| Ex # | Structure |
| C386 | 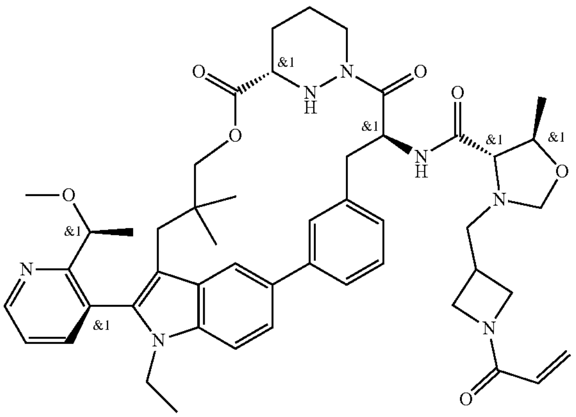 |
| C387 | 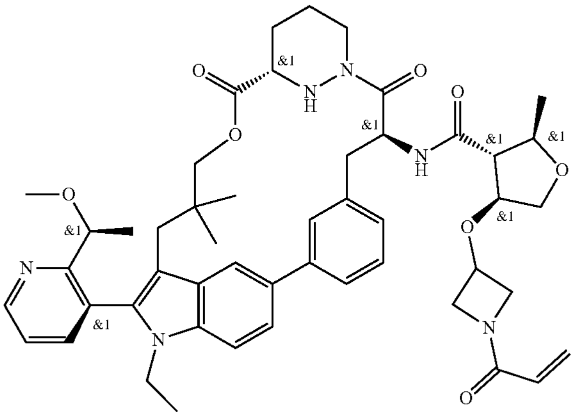 |
| C388 | 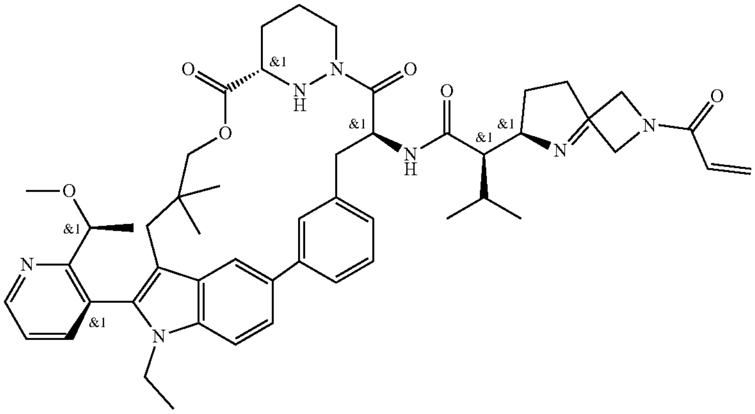 |

TABLE 2-continued
| Certain Compounds | |
|---|---|
| Ex # | Structure |
| C389 | 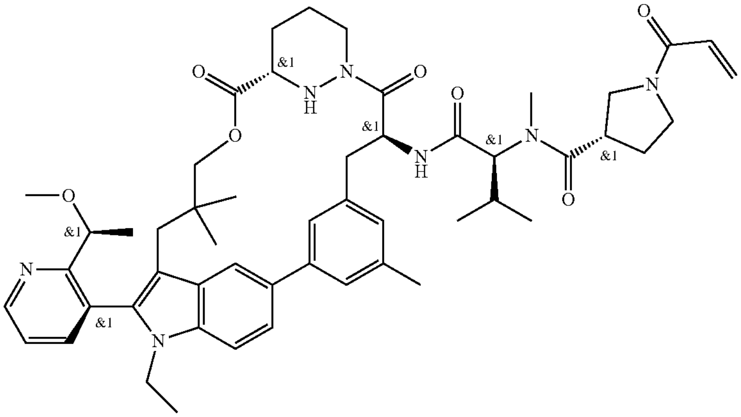 |
| C390 | 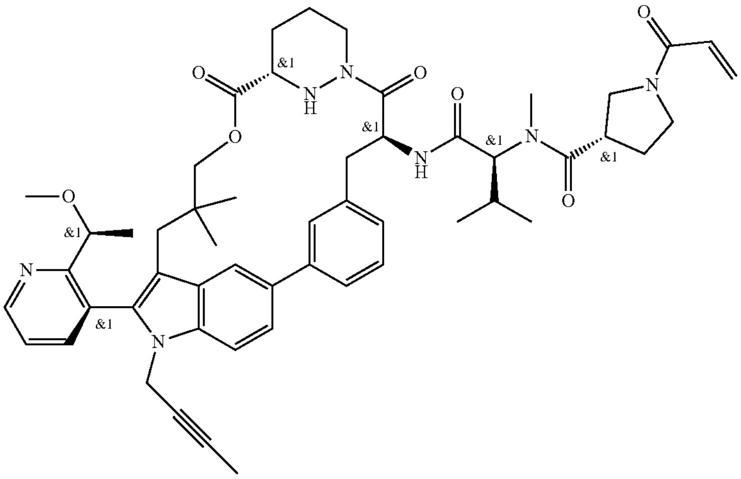 |
| C391 | 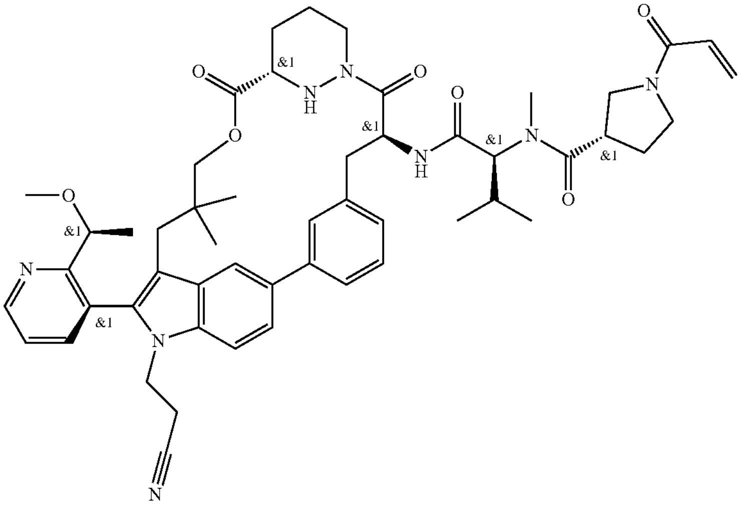 |

TABLE 2-continued
| Certain Compounds | |
|---|---|
| Ex # | Structure |
| C392 | 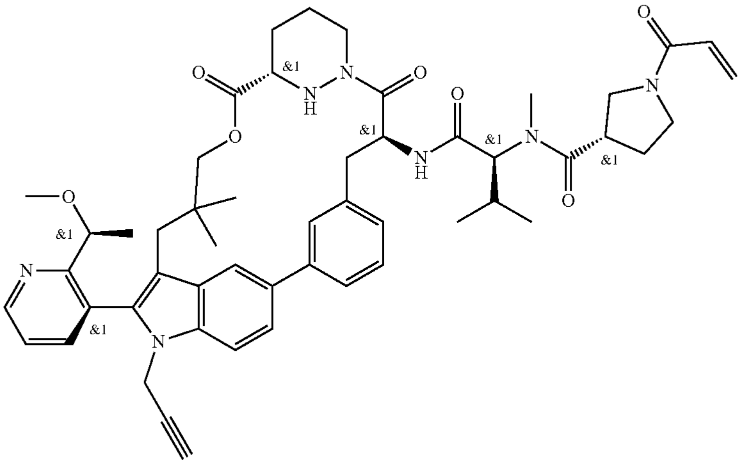 |
| C393 | 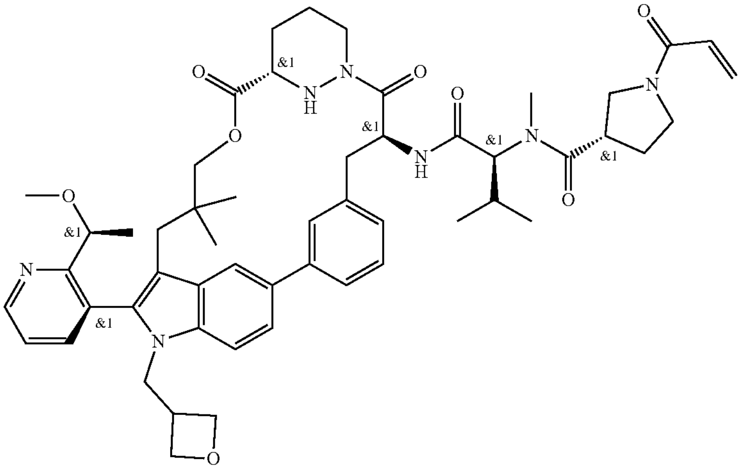 |
| C394 | 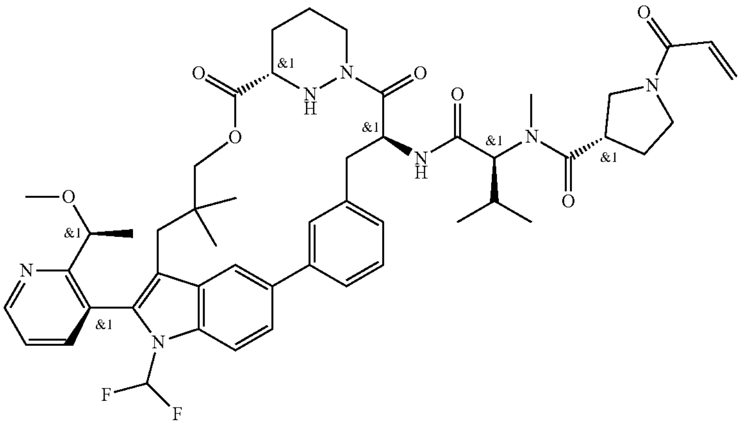 |

TABLE 2-continued
| Certain Compounds | |
|---|---|
| Ex # | Structure |
| C395 | 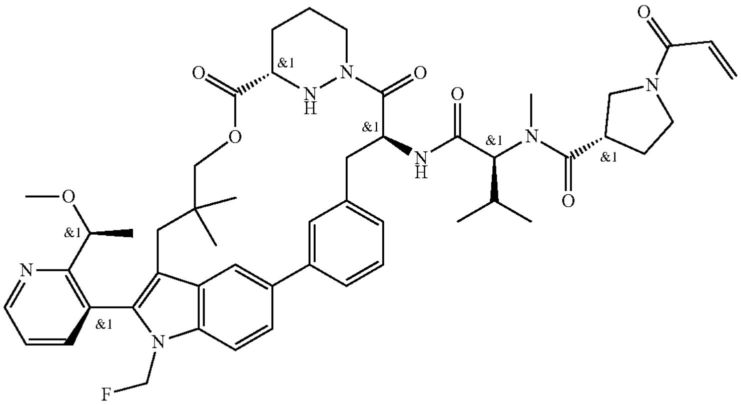 |
| C396 | 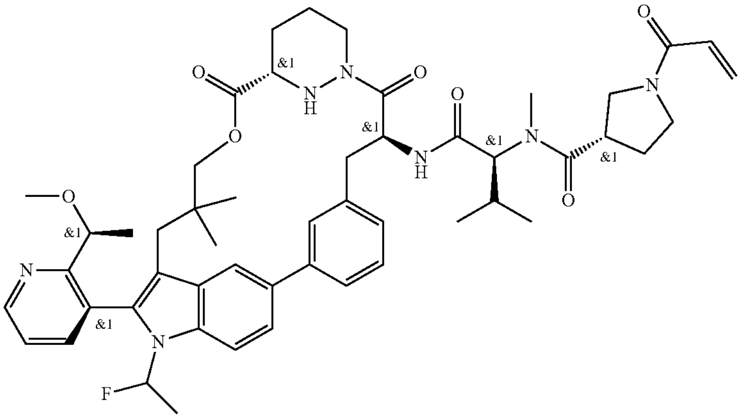 |
| C397 | 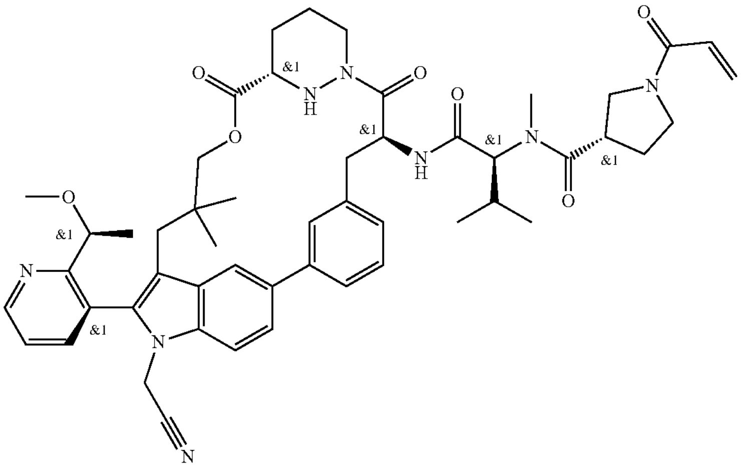 |

TABLE 2-continued
| Certain Compounds | |
|---|---|
| Ex # | Structure |
| C398 | 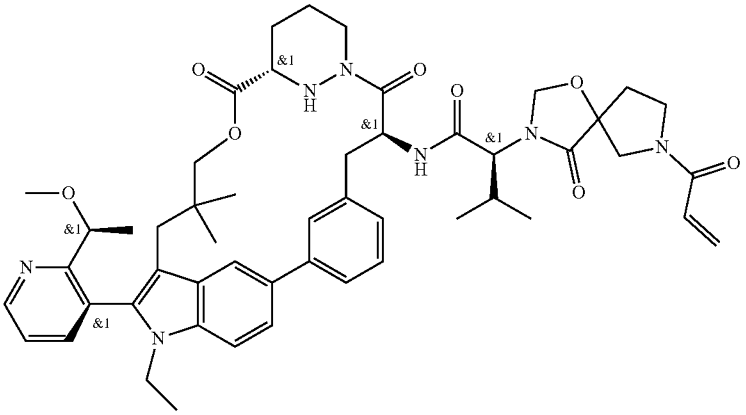 |
| C399 | 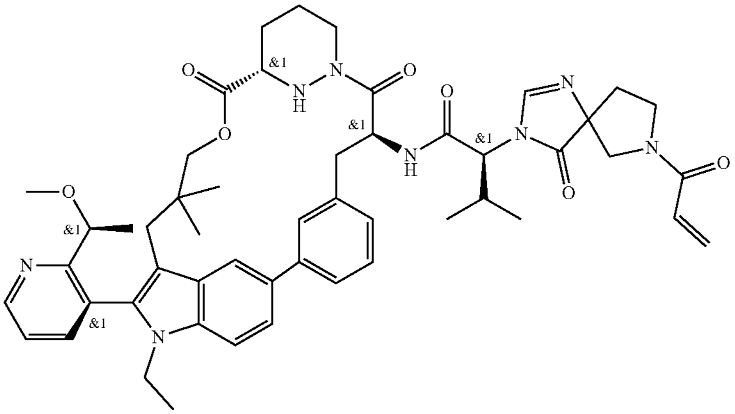 |
| C400 | 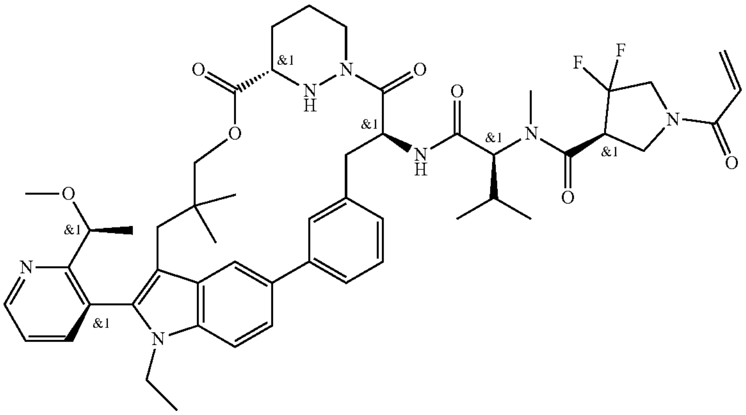 |

TABLE 2-continued
| Certain Compounds | |
| --- | --- |
| Ex # | Structure |
| C401 | 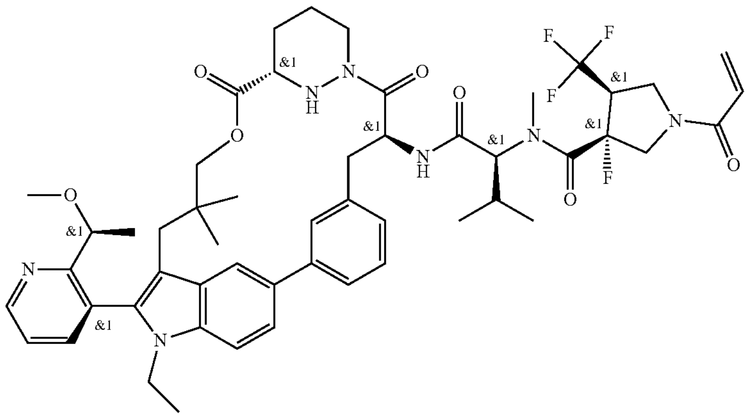 |
| C402 | 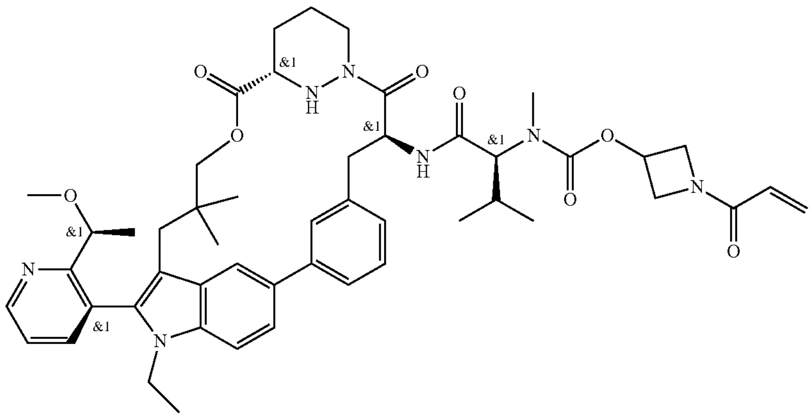 |
| C403 | 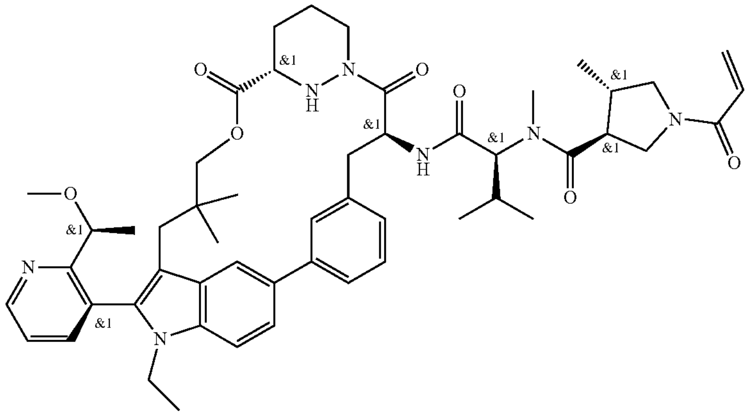 |

TABLE 2-continued
| Certain Compounds | |
|---|---|
| Ex # | Structure |
| C404 | 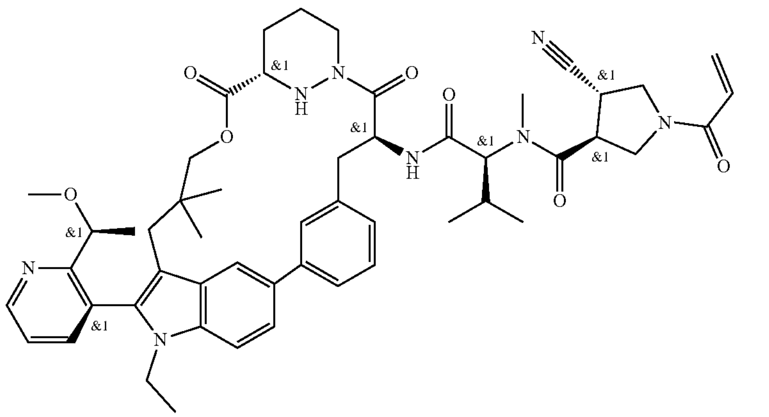 |
| C405 | 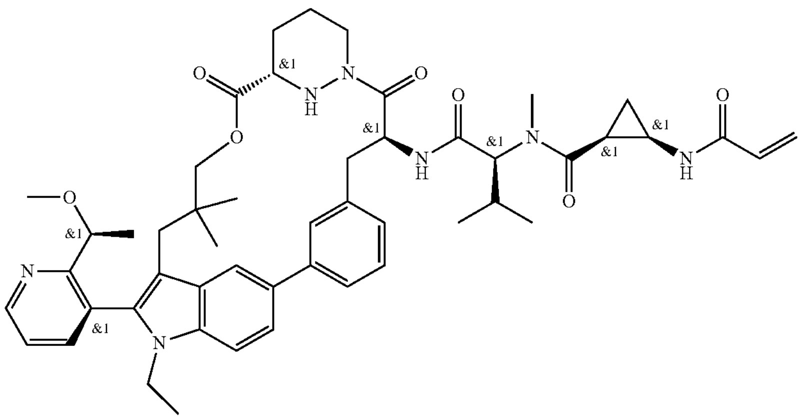 |
| C406 | 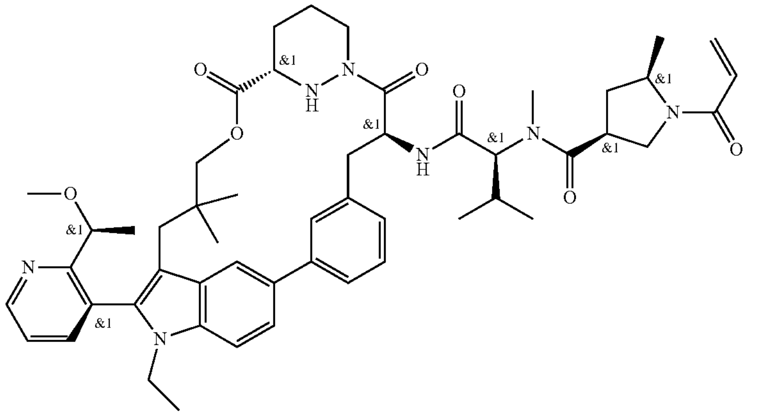 |

TABLE 2-continued
| Certain Compounds | |
|---|---|
| Ex # | Structure |
| C407 | 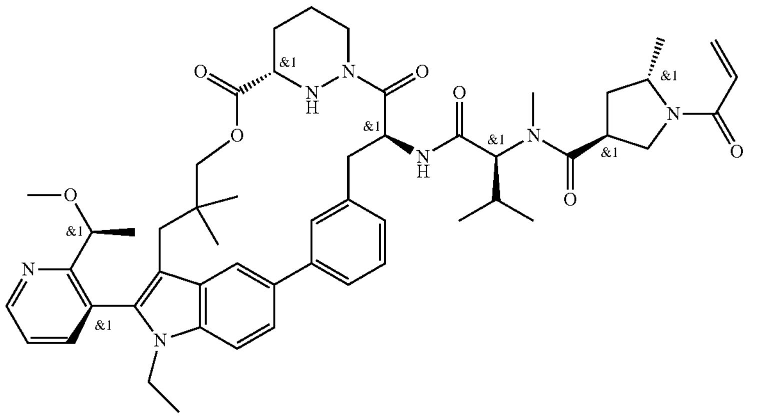 |
| C408 | 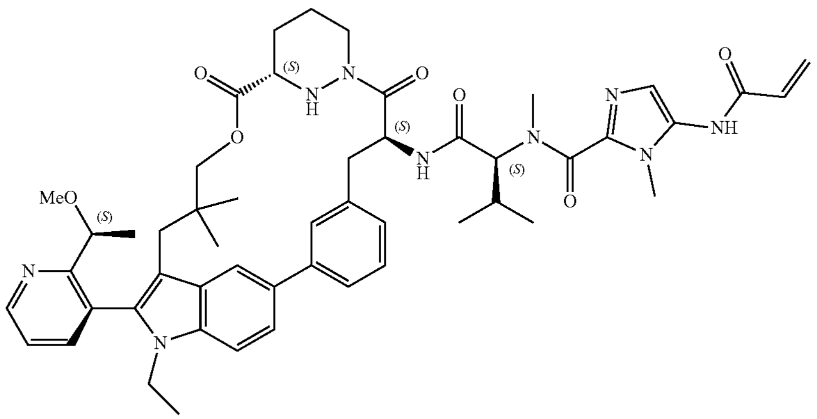 |
| C409 | 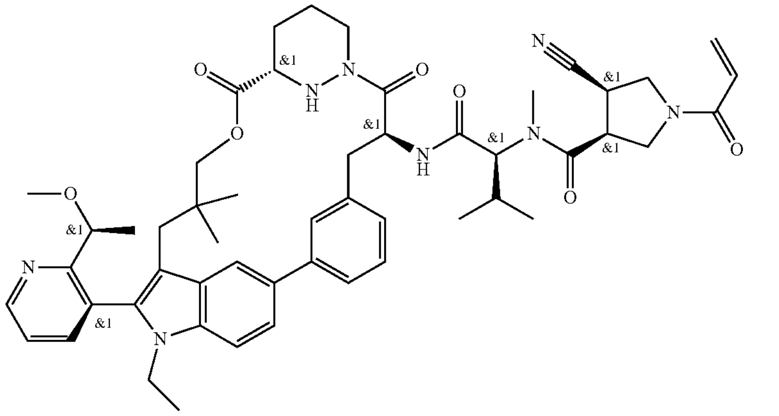 |

TABLE 2-continued
| Certain Compounds | |
|---|---|
| Ex # | Structure |
| C410 | 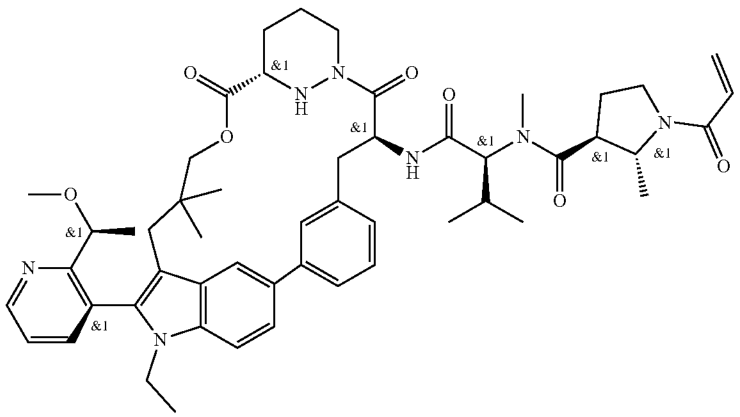 |
| C411 | 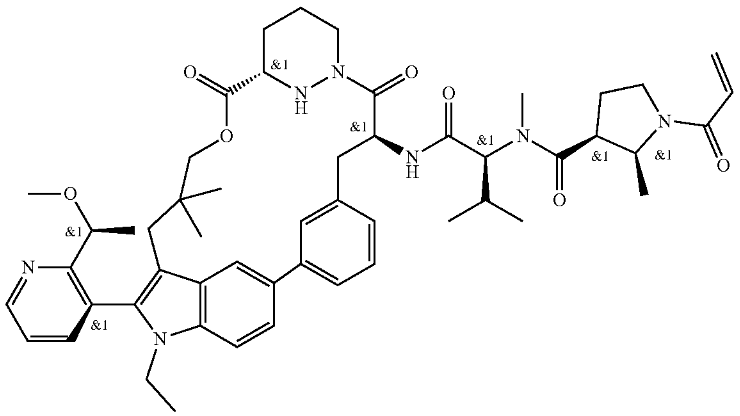 |
| C412 | 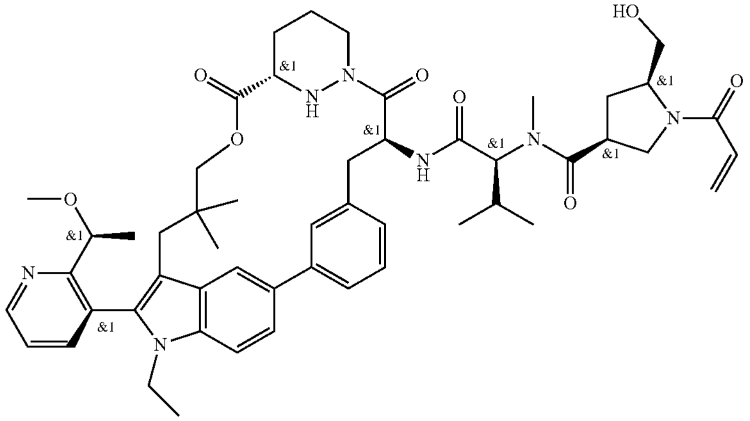 |

TABLE 2-continued
| Certain Compounds | |
|---|---|
| Ex # | Structure |
| C413 | 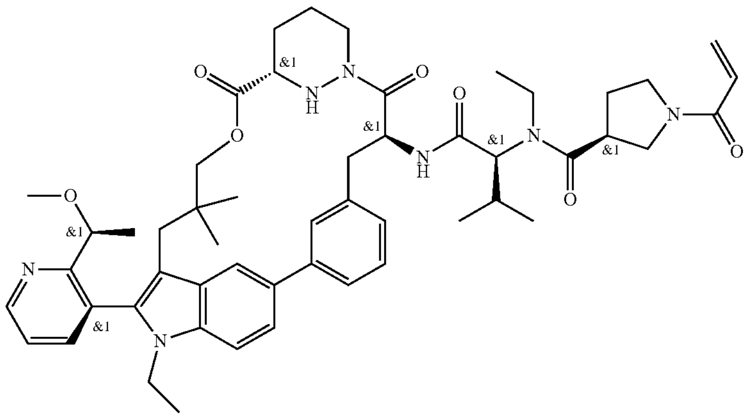 |
| C414 | 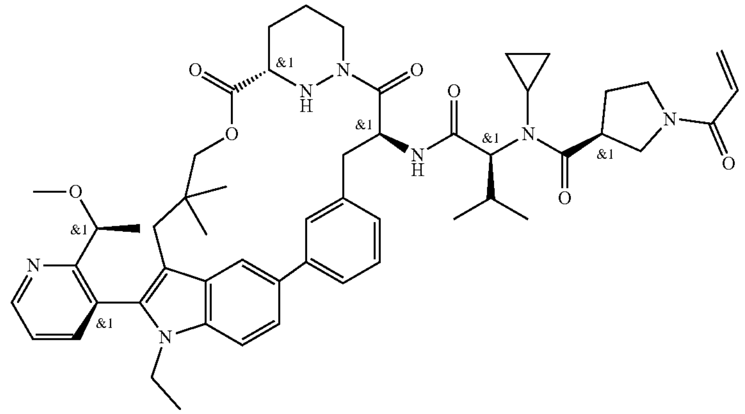 |
| C415 | 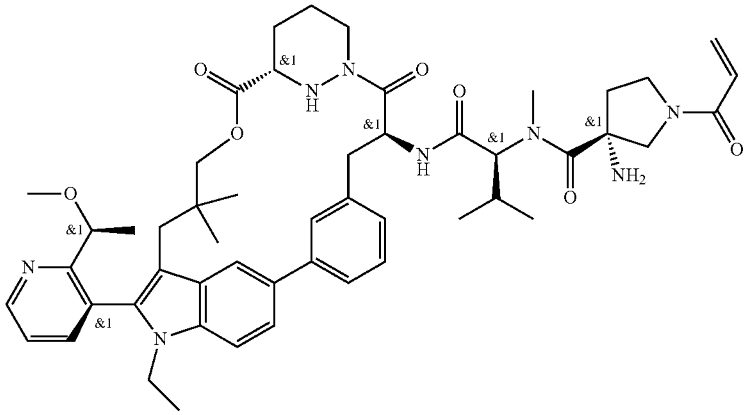 |

TABLE 2-continued
| Certain Compounds | |
|---|---|
| Ex # | Structure |
| C416 | 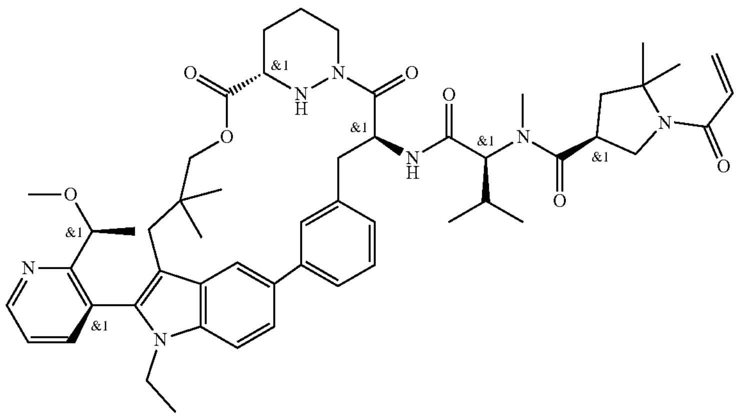 |
| C417 | 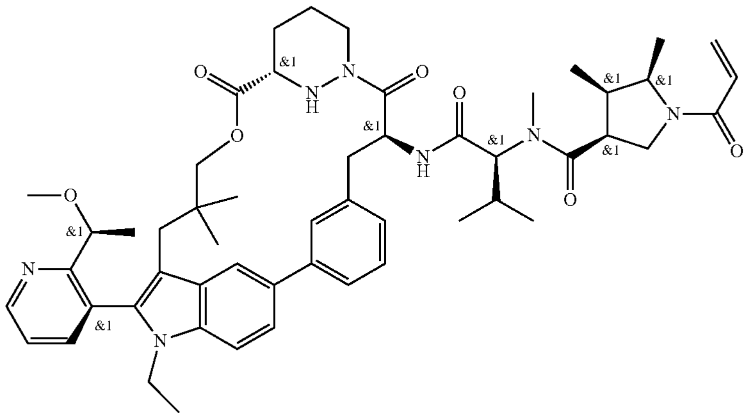 |
| C418 | 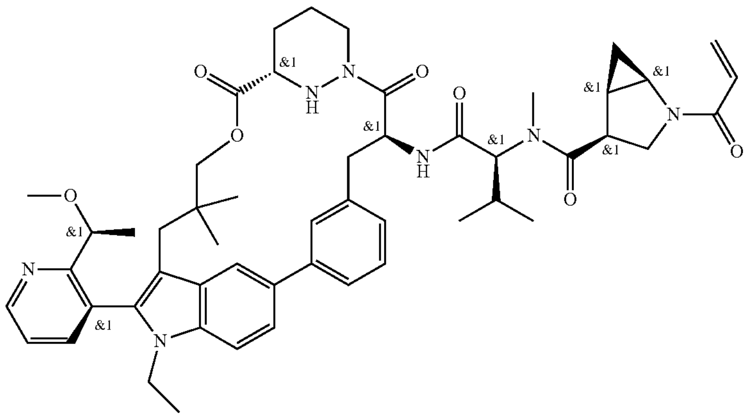 |

TABLE 2-continued
| Certain Compounds | |
|---|---|
| Ex # | Structure |
| C419 | 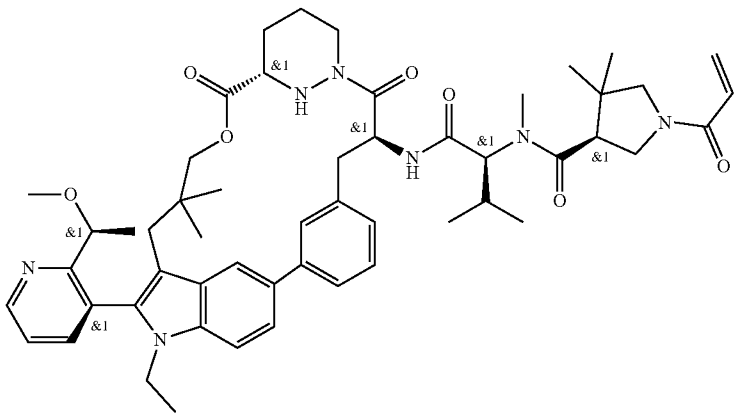 |
| C420 | 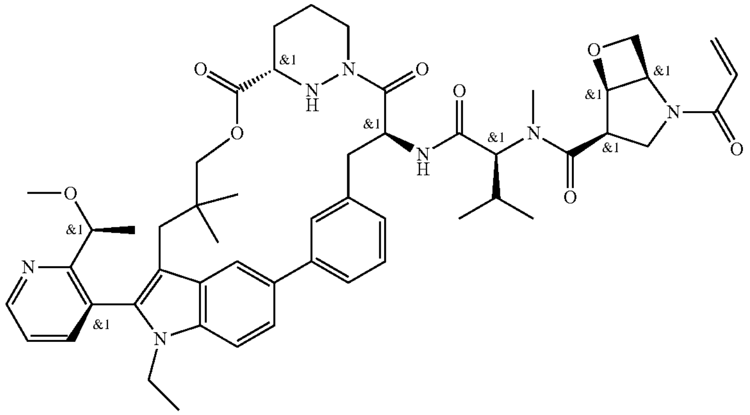 |
| C421 | 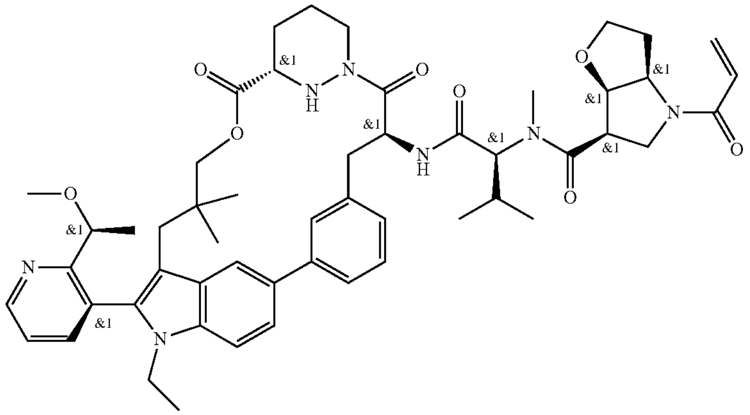 |

TABLE 2-continued
| Certain Compounds | |
|---|---|
| Ex # | Structure |
| C422 | 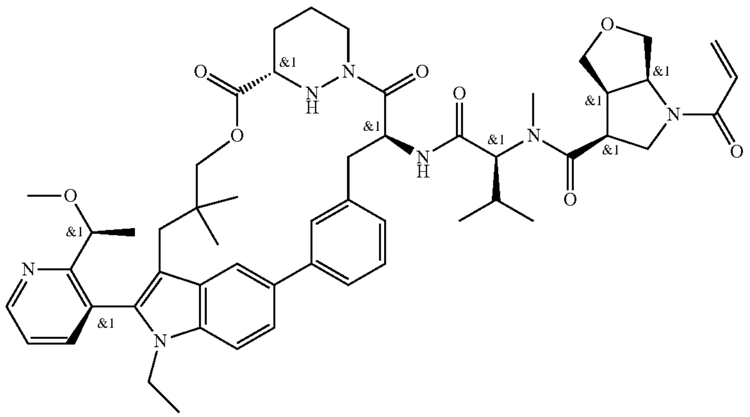 |
| C423 | 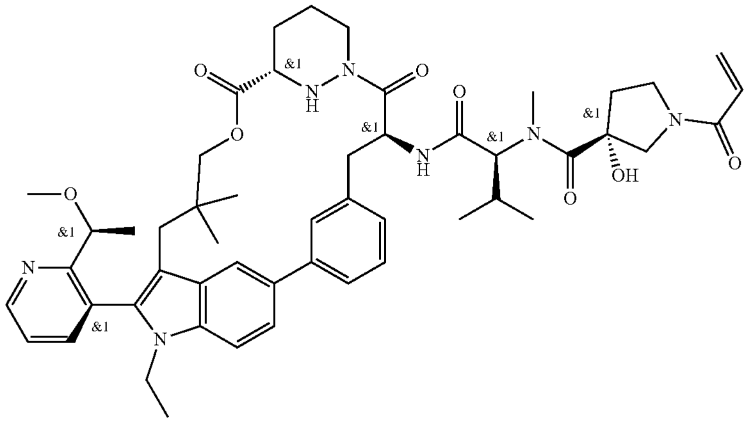 |
| C424 | 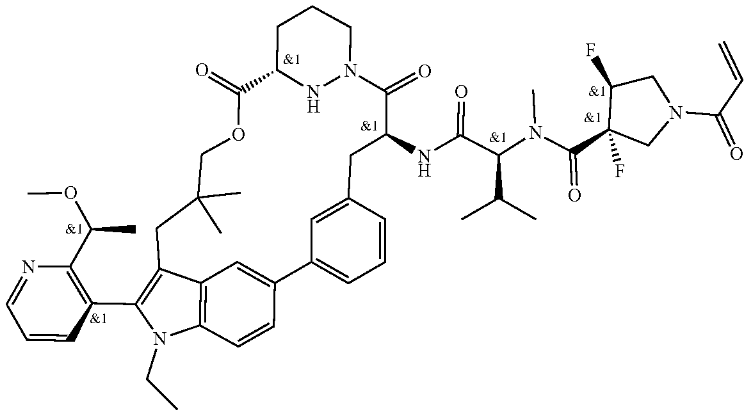 |

TABLE 2-continued

| Certain Compounds | |
|---|---|
| Ex # | Structure |
| C425 | 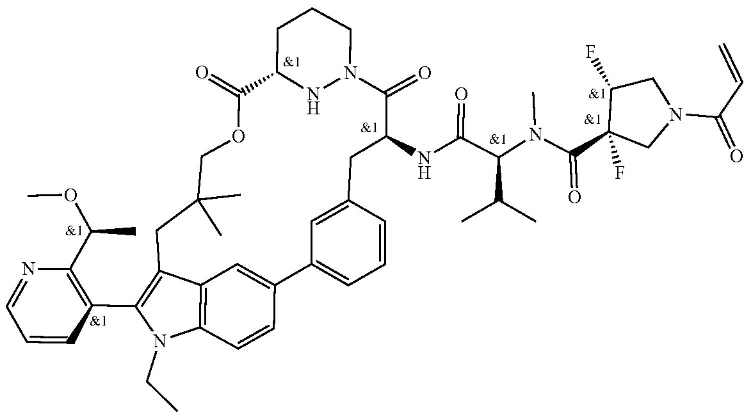 |

Note that some compounds are shown with bonds as flat or wedged. In some instances, the relative stereochemistry of stereoisomers has been determined; in some instances, the absolute stereochemistry has been determined. In some instances, a single Example number corresponds to a mixture of stereoisomers. All stereoisomers of the compounds of the foregoing table are contemplated by the present invention. In particular embodiments, an atropisomer of a compound of the foregoing table is contemplated. Brackets are to be ignored.

In some embodiments, the compound is not a compound contained in WO 2020/132597, the disclosure of which is incorporated herein by reference in its entirety. In some embodiments, the compound is not a compound contained in WO 2021/091982, the disclosure of which is incorporated herein by reference in its entirety.

Also provided is a pharmaceutical composition comprising a compound of the present invention, or a pharmaceutically acceptable salt thereof, and a pharmaceutically acceptable excipient.

Further provided is a conjugate, or salt thereof, comprising the structure of Formula V:

Formula V

M—L—P, wherein L is a linker;

P is a monovalent organic moiety; and

M has the structure of Formula VIa:

Formula VIa

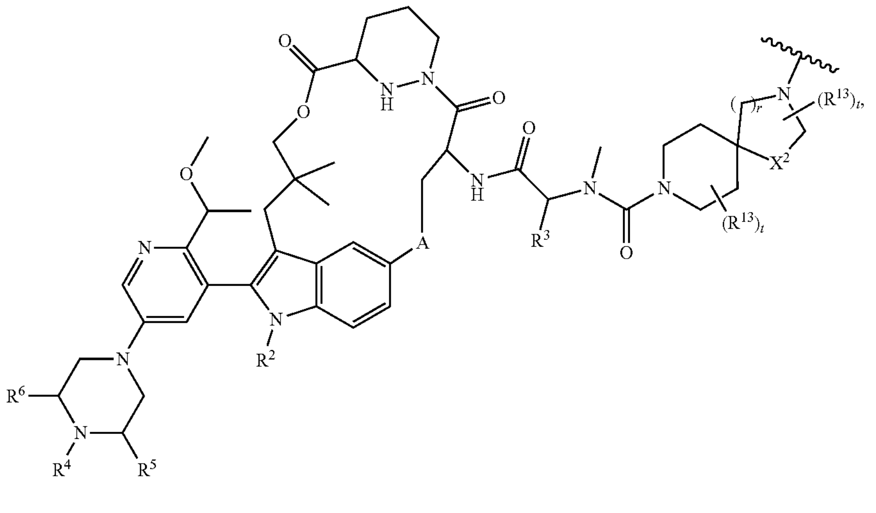

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl;

$X^2$ is O, $C(R^{11})_2$, $NR^{12}$, S, or $SO_2$;

r is 1 or 2;

each t is, independently, 0, 1, or 2;

$R^{11}$ and $R^{12}$ are each, independently, hydrogen, optionally substituted $C_1$-$C_4$ alkyl, optionally substituted $C_2$-$C_4$ heteroalkyl, or optionally substituted 3 to 5-membered cycloalkyl;

each $R^{13}$ is, independently, —$CH_3$; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

Further provided is a conjugate, or salt thereof, comprising the structure of Formula V:

Formula V

M—L—P, wherein L is a linker;

P is a monovalent organic moiety; and

M has the structure of Formula VIb:

Formula VIb

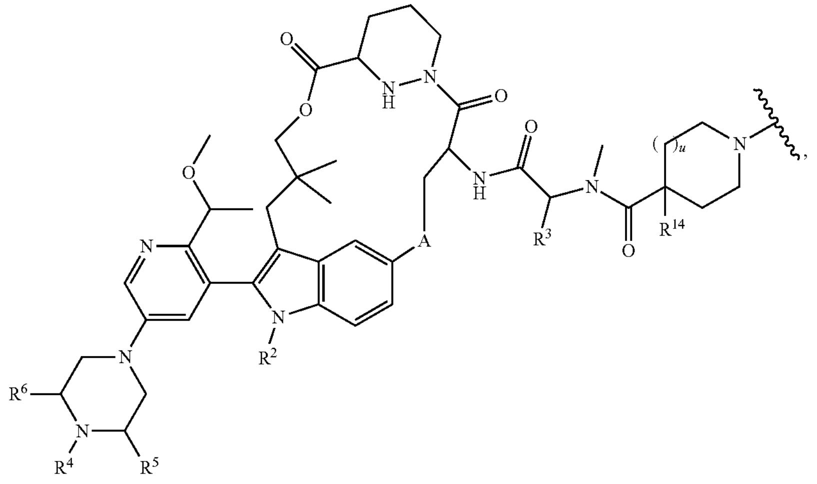

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl;

$R^{14}$ is fluoro, hydrogen, or $C_1$-$C_3$ alkyl;

u is 0 or 1; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

Further provided is a conjugate, or salt thereof, comprising the structure of Formula V:

Formula V

M—L—P, wherein L is a linker;

P is a monovalent organic moiety; and

M has the structure of Formula VIc:

Formula VIc

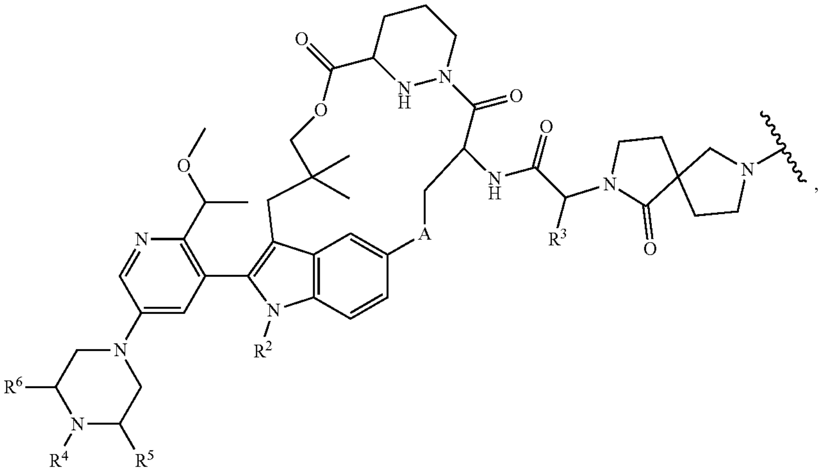

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

Further provided is a conjugate, or salt thereof, comprising the structure of Formula V:

Formula V

M—L—P, wherein L is a linker;

P is a monovalent organic moiety; and

M has the structure of Formula VId:

Formula VId

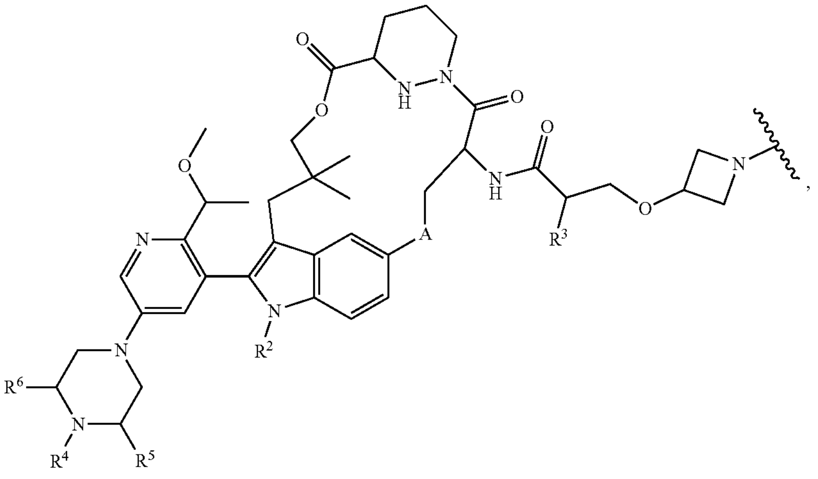

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

In some embodiments of conjugates of the present invention, the monovalent organic moiety is a protein. In some embodiments, the protein is a Ras protein. In some embodiments, the Ras protein is K-Ras G12C, K-Ras G13C, H-Ras G12C, H-Ras G13C, N-Ras G12C, or N-Ras G13C. In some embodiments of conjugates of the present invention, the linker is bound to the monovalent organic moiety through a bond to a sulfhydryl group of an amino acid residue of the monovalent organic moiety.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12C, K-Ras G13C, H-Ras G12C, H-Ras G13C, N-Ras G12C, or N-Ras G13C. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12C, K-Ras G13C, H-Ras G12C, H-Ras G13C, N-Ras G12C, or N-Ras G13C. Other Ras proteins are described herein. The cell may be a cancer cell, such as a pancreatic cancer cell, a colorectal cancer cell, a non-small cell lung cancer cell, an acute myeloid leukemia cell, a multiple myeloma cell, a thyroid gland adenocarcinoma cell, a myelodysplastic syndrome cell, or a squamous cell lung carcinoma cell. Other cancer types are described herein. The cell may be in vivo or in vitro.

Further provided is a method of treating a K-Ras G13C mutant cancer with a compound of Formula II-5.

Further provided is a method of treating a K-Ras G12C mutant cancer with a compound of Formula II-6.

With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is a HER2 inhibitor, an EGFR inhibitor, a second Ras inhibitor, a SHP2 inhibitor, an SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art. These methods include but are not limited to those methods described in the Schemes below.

Scheme 1. General synthesis of macrocyclic esters

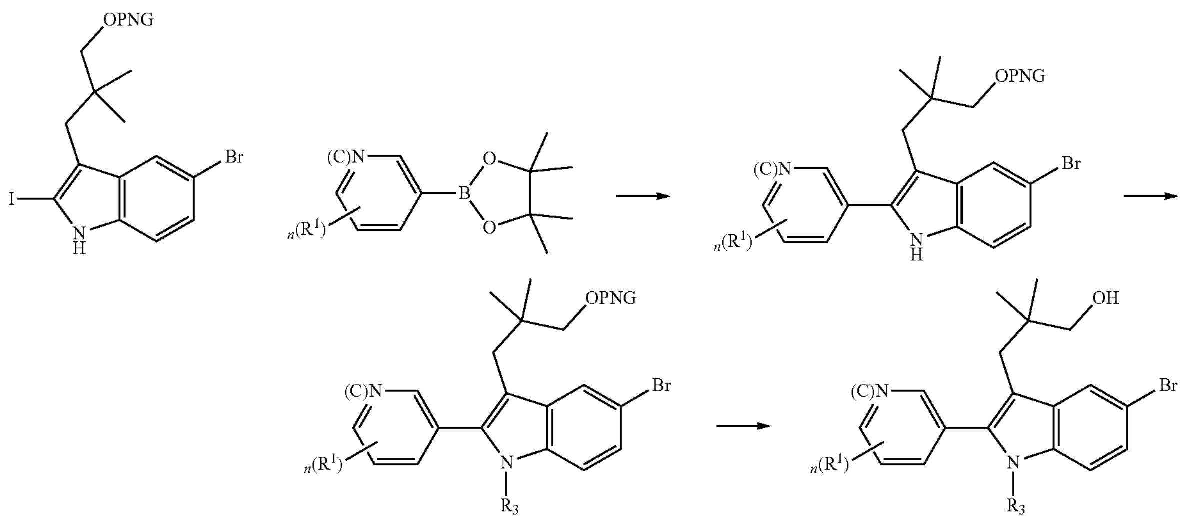

1

-continued
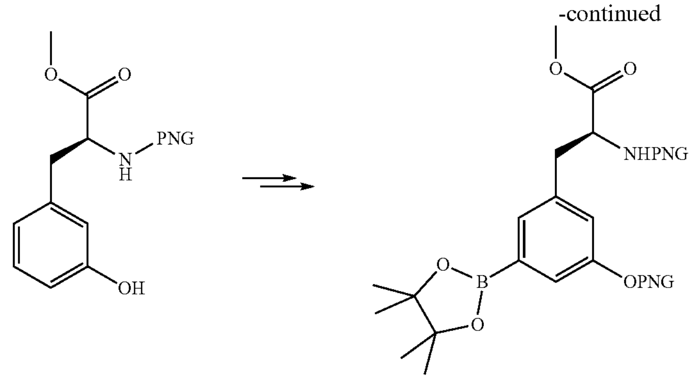
3
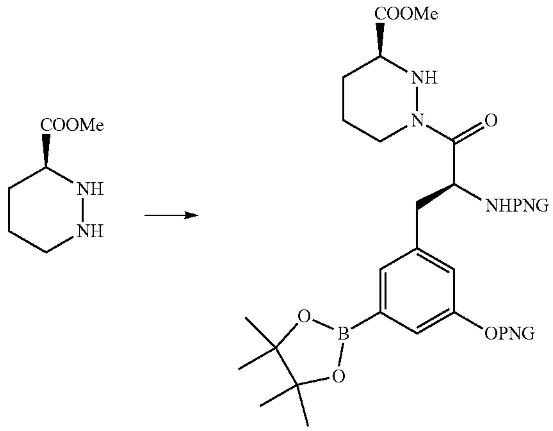
2
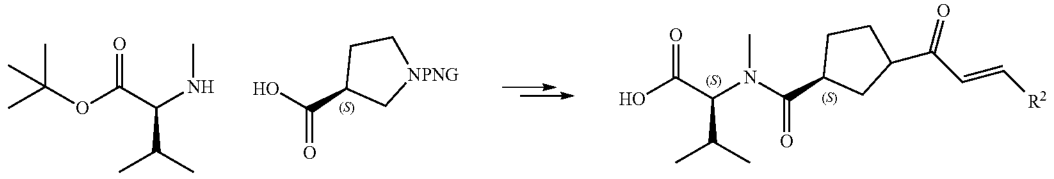
4
or
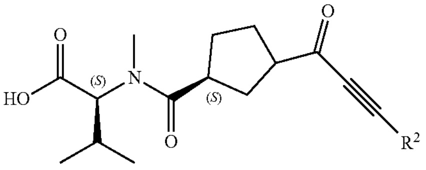
4
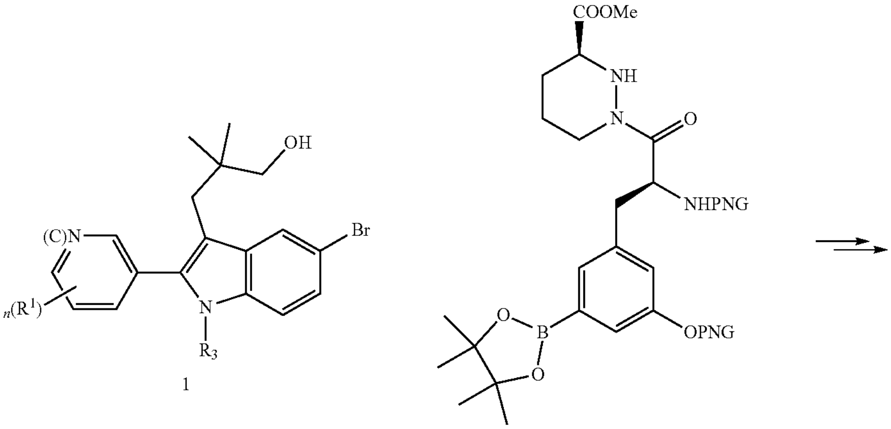
1
2

-continued

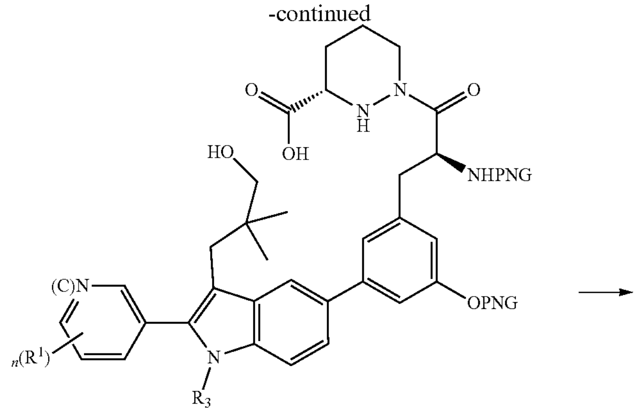

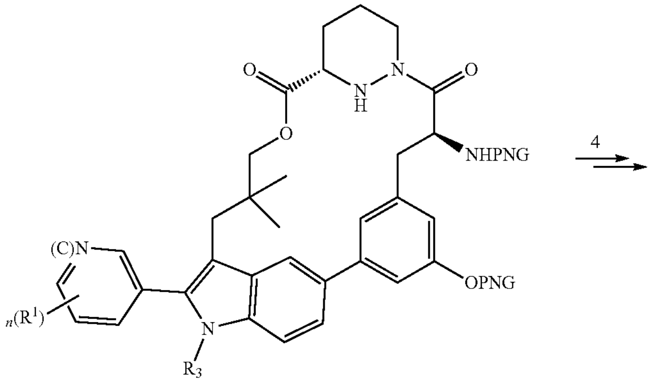

5

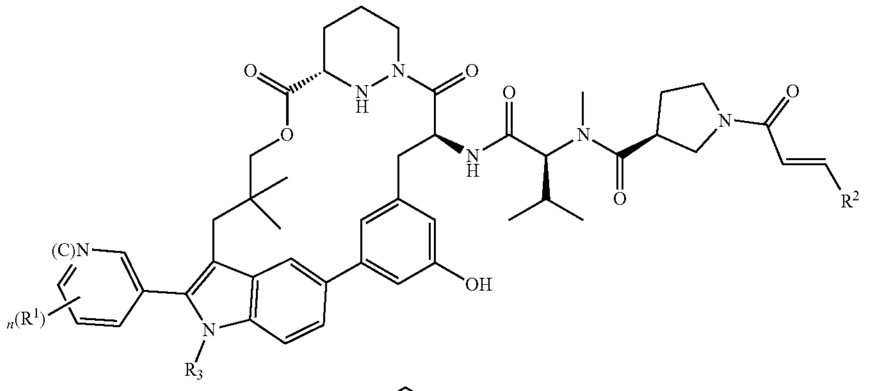

or

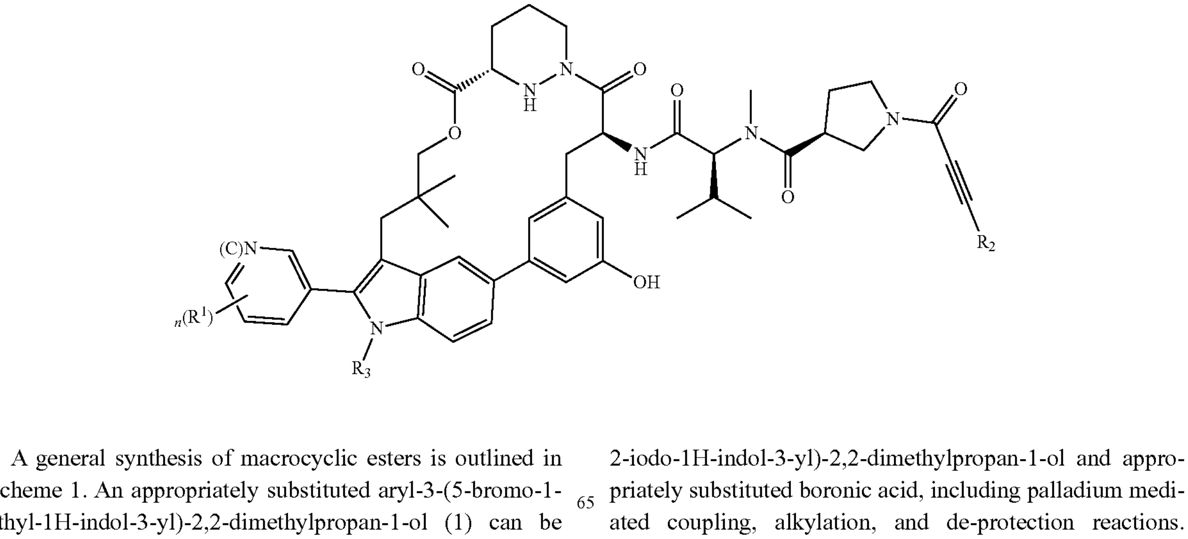

A general synthesis of macrocyclic esters is outlined in Scheme 1. An appropriately substituted aryl-3-(5-bromo-1-ethyl-1H-indol-3-yl)-2,2-dimethylpropan-1-ol (1) can be prepared in three steps starting from protected 3-(5-bromo-2-iodo-1H-indol-3-yl)-2,2-dimethylpropan-1-ol and appropriately substituted boronic acid, including palladium mediated coupling, alkylation, and de-protection reactions. Methyl-amino-hexahydropyridazine-3-carboxylate-boronic ester (2) can be prepared in three steps, including protection, iridium catalyst mediated borylation, and coupling with methyl methyl (S)-hexahydropyridazine-3-carboxylate.

An appropriately substituted acetylpyrrolidine-3-carbonyl-N-methyl-L-valine (or an alternative aminoacid derivative (4) can be made by coupling of methyl-L-valinate and protected (S)-pyrrolidine-3-carboxylic acid, followed by deprotection, coupling with a carboxylic acid containing an appropriately substituted Michael acceptor, and a hydrolysis step.

The final macrocyclic esters can be made by coupling of methyl-amino-hexahydropyridazine-3-carboxylate-boronic ester (2) and aryl-3-(5-bromo-1-ethyl-1H-indol-3-yl)-2,2-dimethylpropan-1-ol (1) in the presence of a Pd catalyst followed by hydrolysis and macrolactonization steps to result in an appropriately protected macrocyclic intermediate (5). Deprotection and coupling with an appropriately substituted intermediate 4 results in a macrocyclic product. Additional deprotection or functionalization steps can be required to produce the final compound.

Scheme 2. Alternative general synthesis of macrocyclic esters

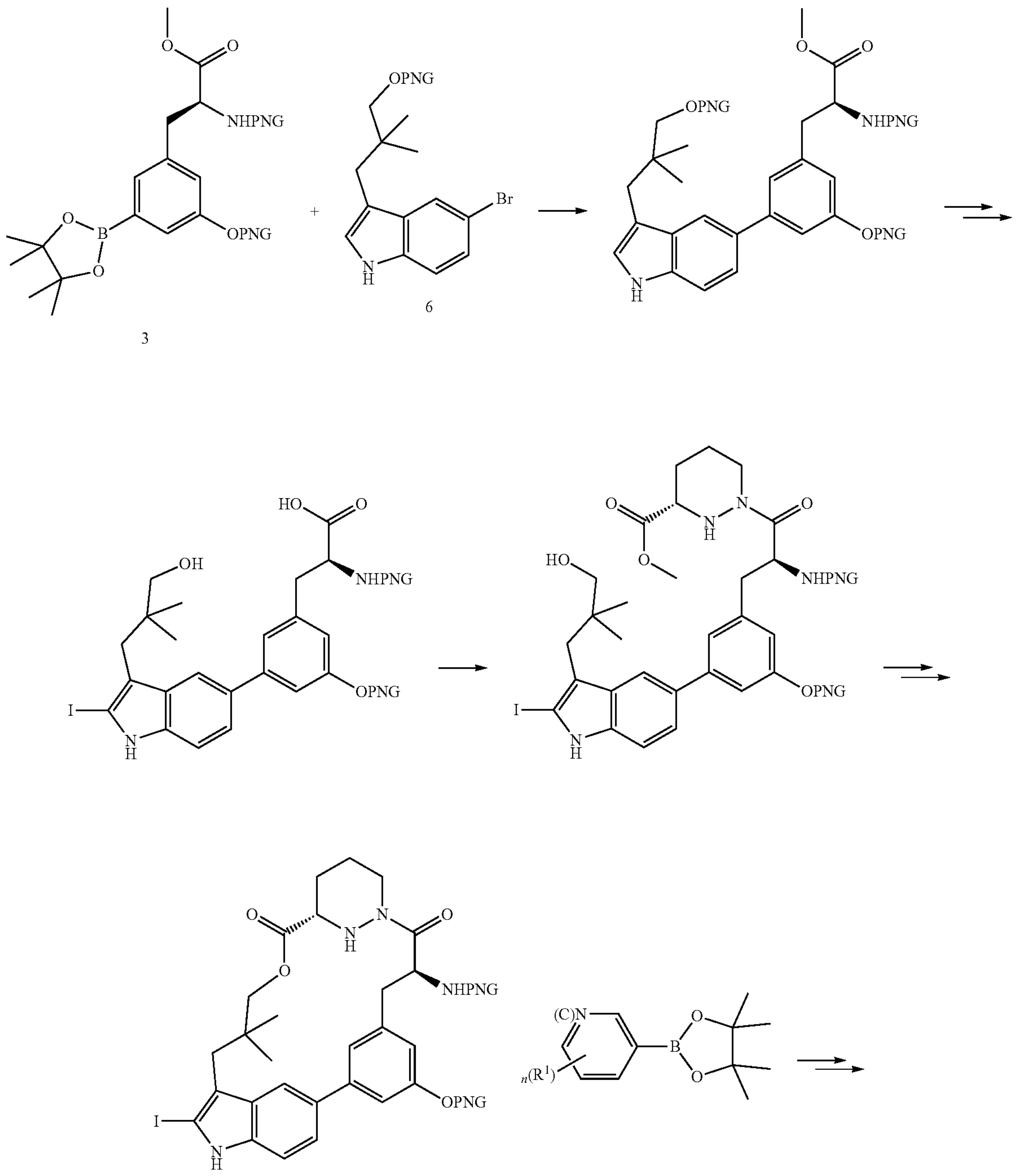

3

6

7

-continued

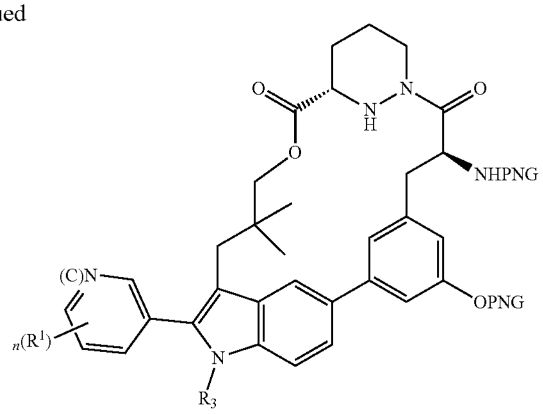

5

Alternatively, macrocyclic ester can be prepared as described in Scheme 2. An appropriately protected bromo-indolyl (6) coupled in the presence of a Pd catalyst with boronic ester (3), followed by iodination, deprotection, and ester hydrolysis. Subsequent coupling with methyl (S)-hexahydropyridazine-3-carboxylate, followed by hydrolysis and macrolactonization can result in iodo intermediate (7). Coupling in the presence of a Pd catalyst with an appropriately substituted boronic ester and alkyllation can yield fully protected macrocycle (5). Additional deprotection or functionalization steps are required to produce the final compound.

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below. For example, a person of skill in the art would be able to install into a macrocyclic ester a desired —B-L-W group of a compound of Formula (I), where B, L and W are defined herein, including by using methods exemplified in the Example section herein.

Compounds of Table 1 herein were prepared using methods disclosed herein or were prepared using methods disclosed herein combined with the knowledge of one of skill in the art. Compounds of Table 2 may be prepared using methods disclosed herein or may be prepared using methods disclosed herein combined with the knowledge of one of skill in the art.

Scheme 3. General synthesis of macrocyclic esters

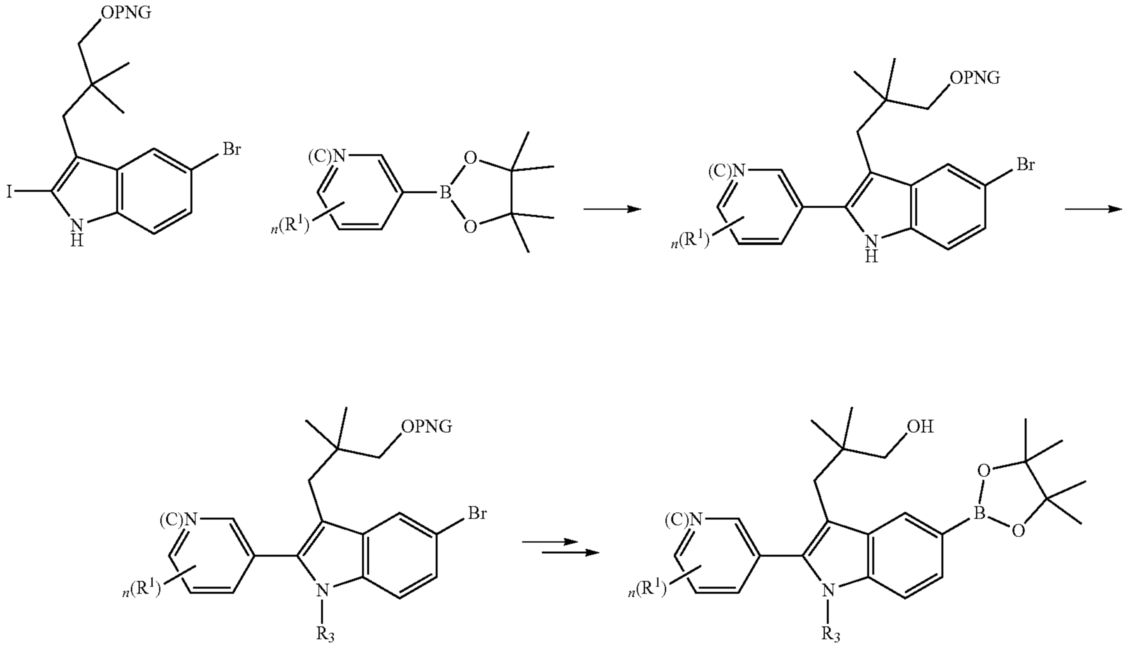

8

-continued
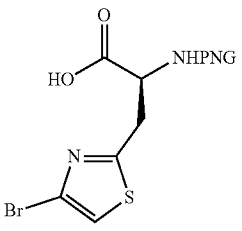
9
+
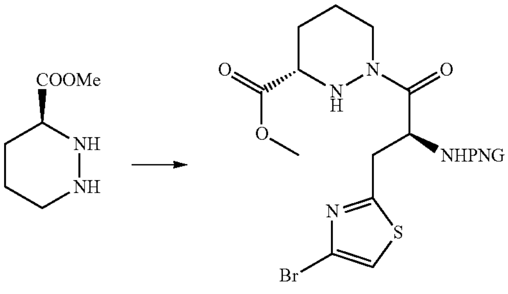
10
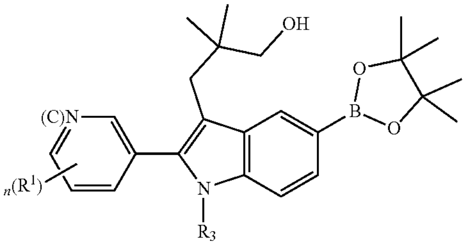
8
+
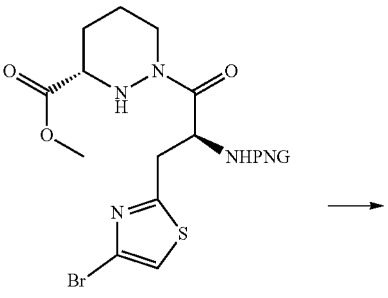
10
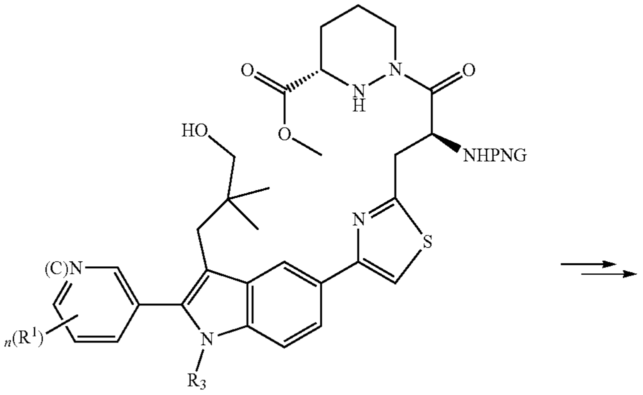
11
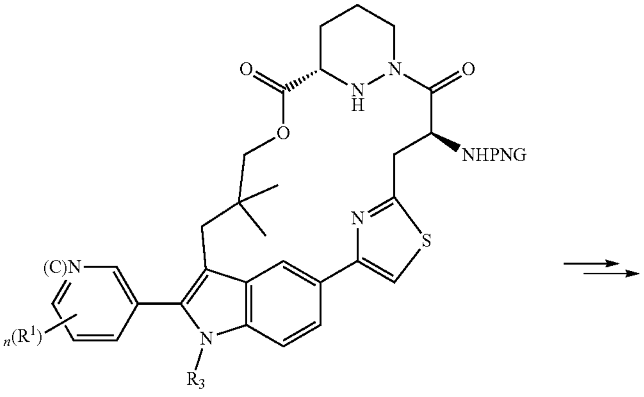
12

-continued

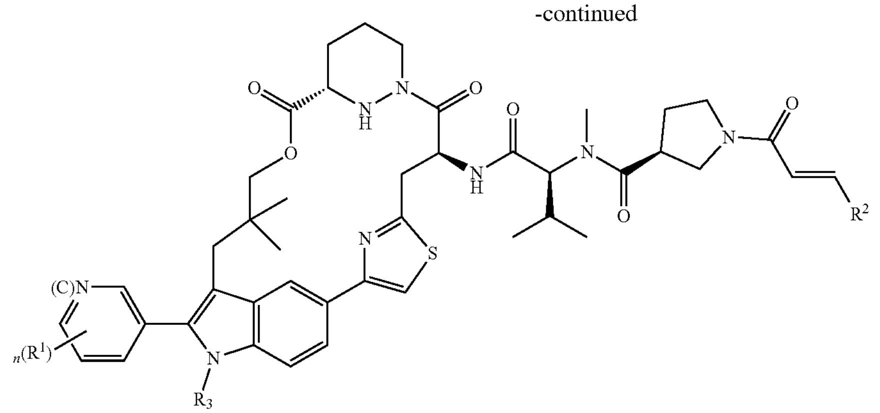

or

13

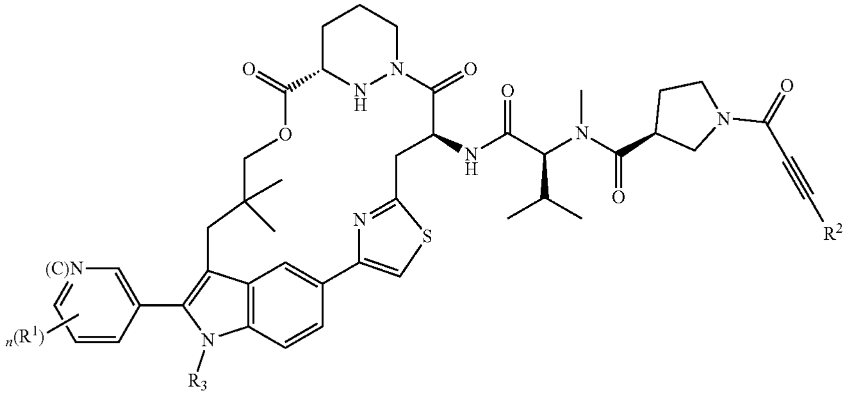

14

An alternative general synthesis of macrocyclic esters is outlined in Scheme 3. An appropriately substituted indolyl boronic ester (8) can be prepared in four steps starting from protected 3-(5-bromo-2-iodo-1H-indol-3-yl)-2,2-dimethyl-propan-1-ol and appropriately substituted boronic acid, including Palladium mediated coupling, alkylation, de-protection, and Palladium mediated borylation reactions.

Methyl-amino-3-(4-bromothiazol-2-yl)propanoyl)hexa-hydropyridazine-3-carboxylate (10) can be prepared via coupling of (S)-2-amino-3-(4-bromothiazol-2-yl)propanoic acid (9) with methyl (S)-hexahydropyridazine-3-carboxy-late.

The final macrocyclic esters can be made by coupling of Methyl-amino-3-(4-bromothiazol-2-yl)propanoyl)hexahy-dropyridazine-3-carboxylate (10) and an appropriately substituted indolyl boronic ester (8) in the presence of Pd catalyst followed by hydrolysis and macrolactonization steps to result in an appropriately protected macrocyclic intermediate (11). Deprotection and coupling with an appropriately substituted intermediate 4 can result in a macrocyclic product. Additional deprotection or functionalization steps could be required to produce a final compound 13 or 14.

Scheme 4. General synthesis of macrocyclic esters

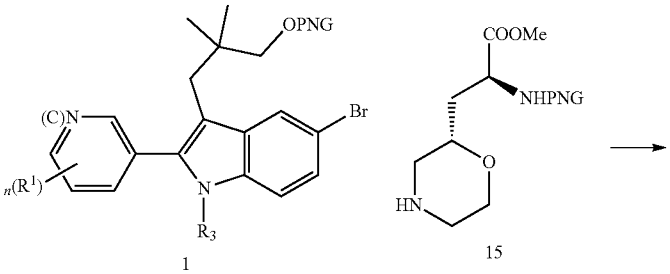

1 15

-continued
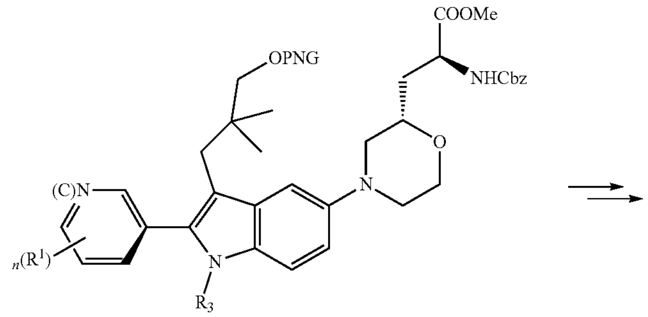
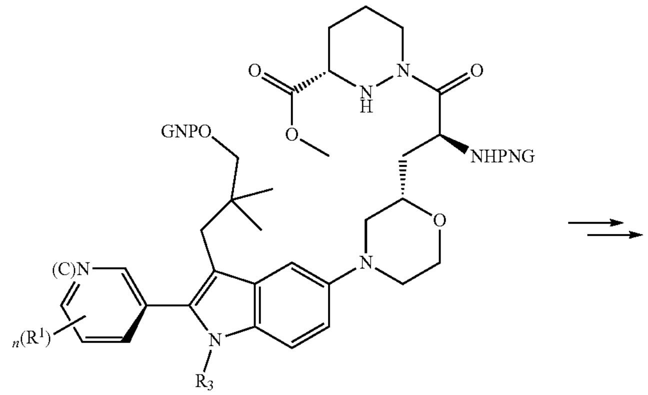
16
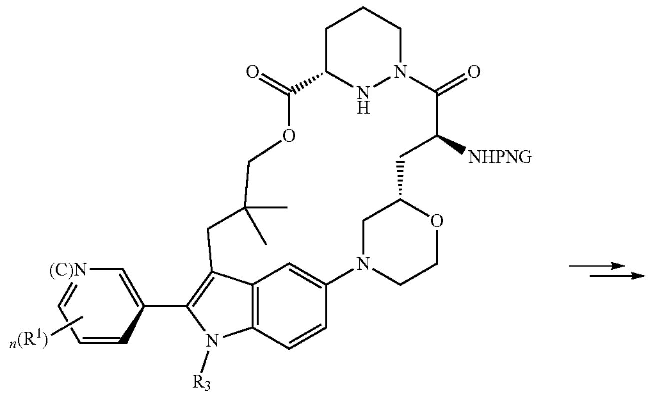
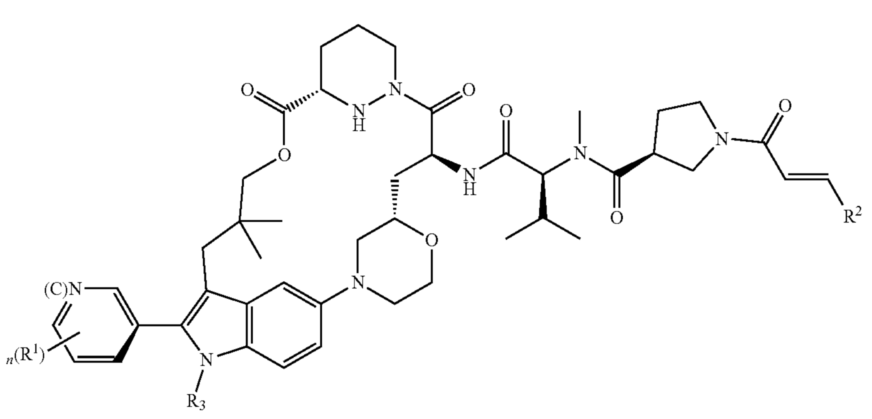
or
17

-continued

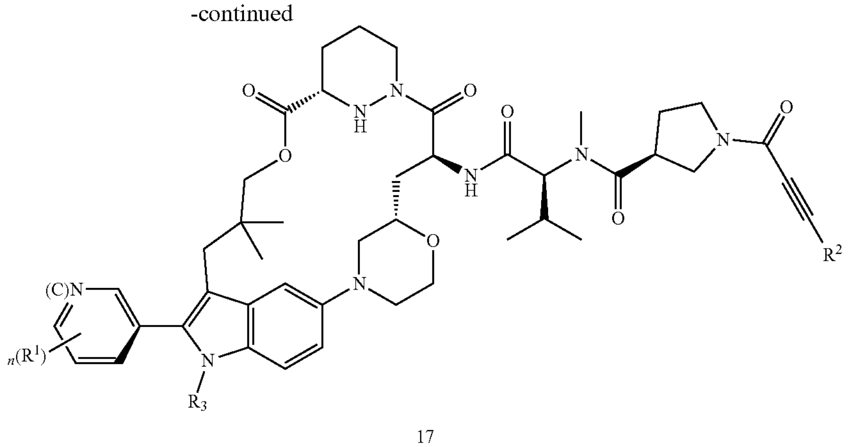

17

An alternative general synthesis of macrocyclic esters is outlined in Scheme 4. An appropriately substituted morpholine or an alternative herecyclic intermediate (15) can be coupled with appropriately protected Intermediate 1 via Palladium mediated coupling. Subsequent ester hydrolysis, and coupling with piperazoic ester results in intermediate 16.

The macrocyclic esters can be made by hydrolysis, deprotection and macrocyclization sequence. Subsequent deprotection and coupling with Intermediate 4 (or analogs) result in an appropriately substituted final macrocyclic products. Additional deprotection or functionalization steps could be required to produce a final compound 17.

Scheme 5. General synthesis of macrocyclic esters

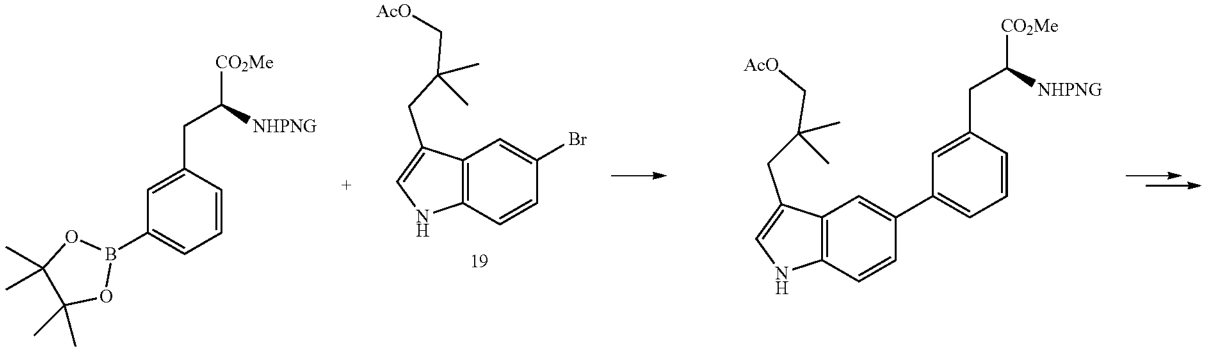

18

19

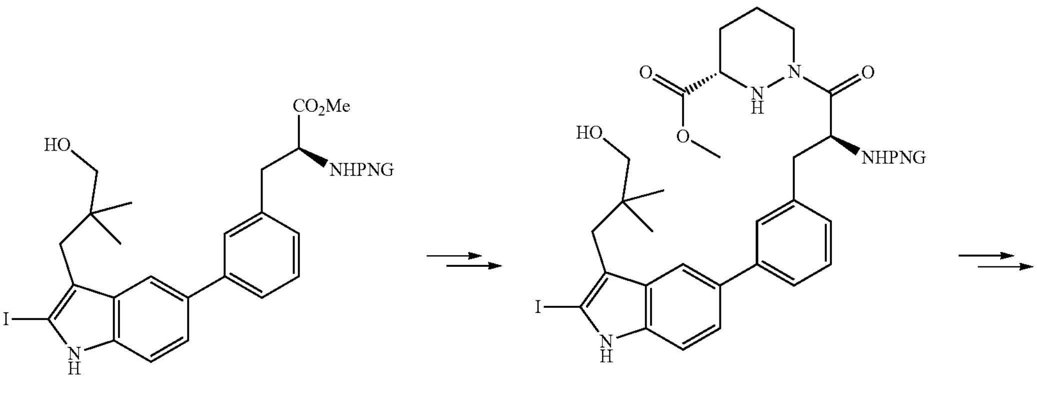

-continued
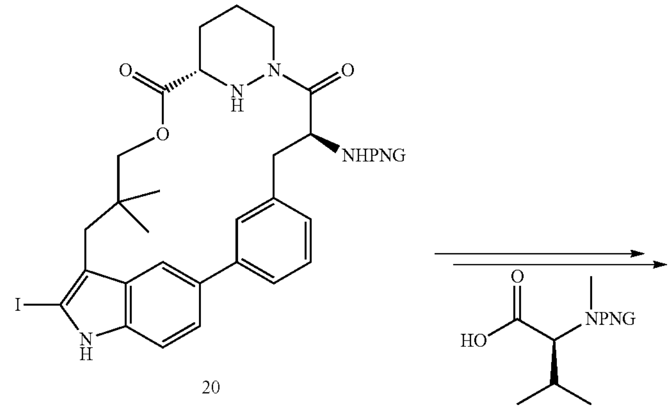
20
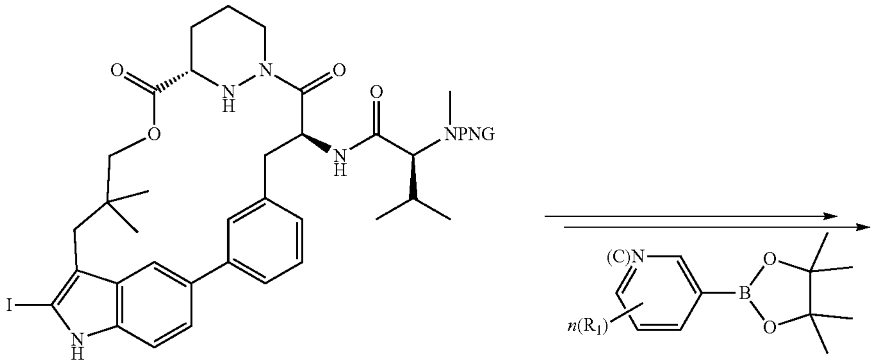
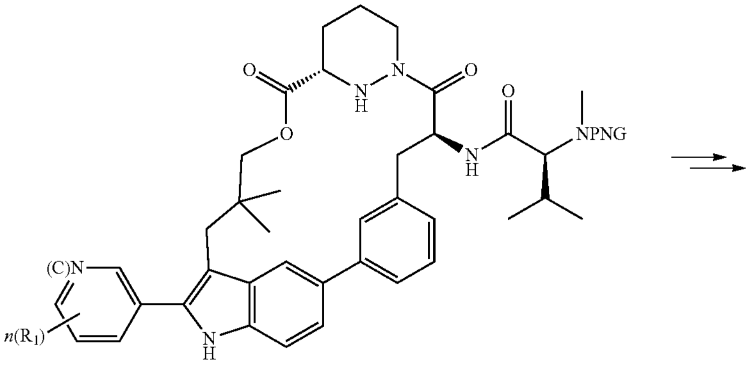
21
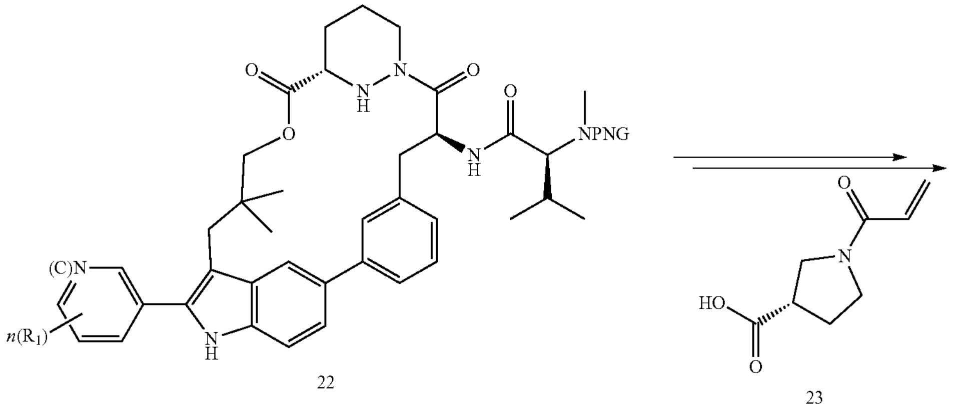
22 23

-continued

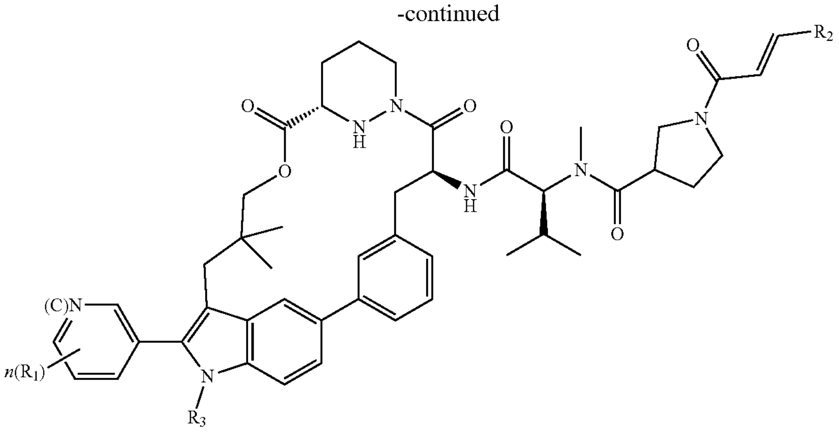

or

24

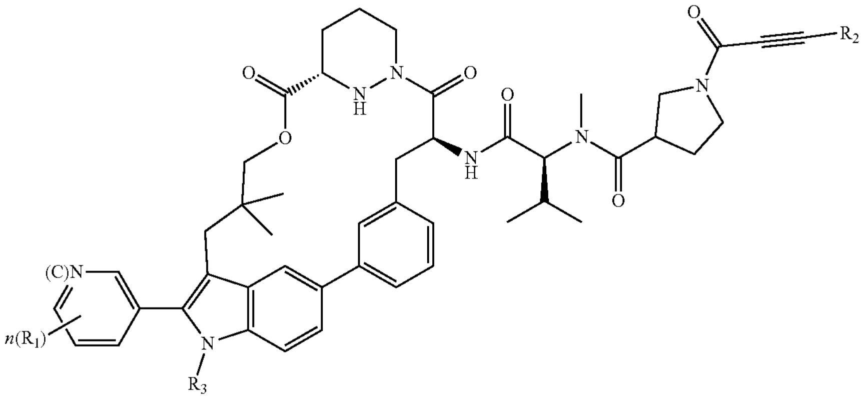

24

An alternative general synthesis of macrocyclic esters is outlined in Scheme 5. An appropriately substituted macrocycle (20) can be prepared starting from an appropriately protected boronic ester 18 and bromo indolyl intermediate (19), including Palladium mediated coupling, hydrolysis, coupling with piperazoic ester, hydrolysis, de-protection, and macrocyclizarion steps. Subsequent coupling with an appropriately substituted protected aminoacid followed by palladium mediated coupling yields intermediate 21. Additional deprotection and derivatization steps, including alkylation may be required at this point.

The final macrocyclic esters can be made by coupling of intermediate (22) and an appropriately substituted carboxylic acid intermediate (23). Additional deprotection or functionalization steps could be required to produce a final compound (24).

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below. For example, a person of skill in the art would be able to install into a macrocyclic ester a desired —B-L-W group of a compound of Formula (I), where B, L and W are defined herein, including by using methods exemplified in the Example section herein.

Pharmaceutical Compositions and Methods of Use

Pharmaceutical Compositions and Methods of Administration

The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term “pharmaceutical composition” refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients.

Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition or of a subject who exhibits only early signs of the disease, disorder, or condition. Alternatively, or additionally, in some embodiments, treatment may be administered to a subject who exhibits one or more established signs of the relevant disease, disorder, or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy*, 21*st* *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention, or a pharmaceutically acceptable salt thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein.

In some embodiments, the pharmaceutical composition may further comprise an additional compound having anti-proliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma, and teratoma;

Lung, for example: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases (e.g., myelofibrosis and myeloproliferative neoplasms), multiple myeloma, myelodysplastic syndrome), Hodgkin's disease, non-Hodgkin's lymphoma (malignant lymphoma);

Skin, for example: malignant melanoma, basal cell carcinoma, squamous cell carcinoma, Kaposi's sarcoma, moles dysplastic nevi, lipoma, angioma, dermatofibroma, keloids, psoriasis; and Adrenal glands, for example: neuroblastoma.

In some embodiments, the Ras protein is wild-type ($Ras^{WT}$). Accordingly, in some embodiments, a compound of the present invention is employed in a method of treating a patient having a cancer comprising a $Ras^{WT}$ (e.g., K-$Ras^{WT}$, H-$Ras^{WT}$ or N-$Ras^{WT}$). In some embodiments, the Ras protein is Ras amplification (e.g., K-$Ras^{amp}$). Accordingly, in some embodiments, a compound of the present invention is employed in a method of treating a patient having a cancer comprising a $Ras^{amp}$ (K-$Ras^{amp}$, H-$Ras^{amp}$ or N-$Ras^{amp}$). In some embodiments, the cancer comprises a Ras mutation, such as a Ras mutation described herein. In some embodiments, a mutation is selected from:

(a) the following K-Ras mutants: G12D, G12V, G12C, G13D, G12R, G12A, Q61H, G12S, A146T, G13C, Q61 L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;

or a combination of any of the foregoing. In some embodiments, the cancer comprises a K-Ras mutation selected from the group consisting of G12C, G12D, G13C, G12V, G13D, G12R, G12S, Q61H, Q61K and 061 L. In some embodiments, the cancer comprises an N-Ras mutation selected from the group consisting of G12C, Q61H, Q61K, Q61 L, Q61P and Q61R. In some embodiments, the cancer comprises an H-Ras mutation selected from the group consisting of Q61H and Q61 L. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V. In some embodiments, a compound of the present invention inhibits more than one Ras mutant. For example, a compound may inhibit both K-Ras G12C and K-Ras G13C. A compound may inhibit both N-Ras G12C and K-Ras G12C. In some embodiments, a compound may inhibit both K-Ras G12C and K-Ras G12D. In some embodiments, a compound may inhibit both K-Ras G12V and K-Ras G12C. In some embodiments, a compound may inhibit both K-Ras G12V and K-Ras G12S. In some embodiments, a compound of the present invention inhibits $Ras^{WT}$ in addition to one or more additional Ras mutations (e.g., K-, H- or N-$Ras^{WT}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K, H or N-$Ras^{WT}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K, H or N-$Ras^{WT}$ and N-Ras Q61R, Q61K, G12D, Q61 L, Q61H, G13R, G13D, G12S, G12C, G12V, G12A, G13V, G12R, P185S, G13C, A146T, G60E, Q61P, A59D, E132K, E49K, T50I, A146V, or A59T). In some embodiments, a compound of the present invention inhibits $Ras^{amp}$ in addition to one or more additional Ras mutations (e.g., K-, H- or N-$Ras^{amp}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K, H or N-$Ras^{amp}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K, H or N-$Ras^{amp}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNA-Clamp; RealQuality; EntroGen; LightMix; StripAssay; Hybcell plexA; Devyser; Surveyor; Cobas; and TheraScreen Pyro. See, also, e.g., WO 2020/106640.

In some embodiments, the cancer is non-small cell lung cancer and the Ras mutation comprises a K-Ras mutation, such as K-Ras G12C, K-Ras G12V or K-Ras G12D. In some embodiments, the cancer is colorectal cancer and the Ras mutation comprises a K-Ras mutation, such as K-Ras G12C, K-Ras G12V or K-Ras G12D. In some embodiments, the cancer is pancreatic cancer and the Ras mutation comprises an K-Ras mutation, such as K-Ras G12D or K-Ras G12V. In some embodiments, the cancer is pancreatic cancer and the Ras mutation comprises an N-Ras mutation, such as N-Ras G12D. In some embodiments, the cancer is melanoma and the Ras mutation comprises an N-Ras mutation, such as N-Ras Q61R or N-Ras Q61K. In some embodiments, the cancer is non-small cell lung cancer and the Ras protein is K-$Ras^{amp}$. In any of the foregoing if not already specified, a compound may inhibit $Ras^{WT}$ (e.g., K-, H- or N-$Ras^{WT}$) or $Ras^{amp}$ (e.g., K-, H- or N-$Ras^{amp}$) as well.

In some embodiments, a cancer comprises a Ras mutation and an $STK11^{LOF}$, a KEAP1, an EPHA5 or an NF1 mutation. In some embodiments, the cancer is non-small cell lung cancer and comprises a K-Ras G12C mutation. In some embodiments, the cancer is non-small cell lung cancer and comprises a K-Ras G12C mutation and an $STK11^{LOF}$ mutation. In some embodiments, the cancer is non-small cell lung cancer and comprises a K-Ras G12C mutation and an $STK11^{LOF}$ mutation. In some embodiments, a cancer comprises a K-Ras G13C Ras mutation and an $STK11^{LOF}$, a KEAP1, an EPHA5 or an NF1 mutation. In some embodiments, the cancer is non-small cell lung cancer and comprises a K-Ras G12D mutation. In some embodiments, the cancer is non-small cell lung cancer and comprises a K-Ras G12V mutation. In some embodiments, the cancer is colorectal cancer and comprises a K-Ras G12C mutation. In some embodiments, the cancer is pancreatic cancer and comprises a K-Ras G12C or K-Ras G12D mutation. In some embodiments, the cancer is pancreatic cancer and comprises a K-Ras G12V mutation. In some embodiments, the cancer is endometrial cancer, ovarian cancer, cholangiocarcinoma, or mucinous appendiceal cancer and comprises a K-Ras G12C mutation. In some embodiments, the cancer is gastric cancer and comprises a K-Ras G12C mutation. In some embodiments, the cancer is lung cancer, colorectal cancer, or pancreatic cancer and comprises a K-Ras G13C mutation. In some embodiments, the cancer is lung cancer or pancreatic cancer and comprises a K-Ras G13C mutation. In some embodiments, the cancer is lung cancer and comprises a K-Ras G13C mutation. In some embodiments, the cancer is pancreatic cancer and comprises a K-Ras G13C mutation. In some embodiments, the cancer is colorectal cancer and comprises a K-Ras G13C mutation. In any of the foregoing, a compound may inhibit $Ras^{WT}$ (e.g., K-, H- or N-$Ras^{WT}$) or $Ras^{amp}$ (e.g., K-, H- or N-$Ras^{amp}$) as well.

Also provided is a method of inhibiting a Ras protein in a cell, the method comprising contacting the cell with an effective amount of a compound of the present invention, or a pharmaceutically acceptable salt thereof. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro.

Combination Therapy

The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment. For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy, and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such cells. Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PD-L1. In some embodiments, the checkpoint inhibitor is an inhibitor or antagonist (e.g., an inhibitory antibody or Fc fusion or small molecule inhibitor) of PD-L2 (e.g., a PD-L2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MED10680, BMS936559, MED14736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., *Proc. Am. Soc. Clin. Oncol.* 18:233a (1999), and Douillard et al., Lancet 355(9209): 1041-1047 (2000). Other non-limiting examples of anti-cancer agents include Gleevec® (Imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammall and calicheamicin omegall (see, e.g., Agnew, Chem. Intl. Ed Engl. 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoles; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP(Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSI (e.g., elotuzumab), HSP90 inhibitors (e.g., 17 AAG and KOS 953), P13K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, JAB-3312, RLY-1971, ERAS-601, SH3809, PF-07284892, or BBP-398), an SOS1 inhibitor (e.g., BI-1701963, BI-3406, SDR5, MRTX0902, RMC-5845, or BAY-293), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312.

In some embodiments, an anti-cancer agent is an additional Ras inhibitor or a Ras vaccine, or another therapeutic modality designed to directly or indirectly decrease the oncogenic activity of Ras. In some embodiments, an anti-cancer agent is an additional Ras inhibitor. In some embodiments, the Ras inhibitor targets Ras in its active, or GTP-bound state (Ras(ON)). In some embodiments, the Ras(ON) inhibitor is RMC-6291, RMC-6236, RMC-9805 or RMC-8839. In some embodiments, the Ras inhibitor is a RAS(ON) inhibitor disclosed in WO 2021091956, WO 2021091967, WO 2021091982, WO 2022060836, or WO 2020132597, or a pharmaceutically acceptable salt, solvate, isomer (e.g., stereoisomer), prodrug, or tautomer thereof, incorporated herein by reference in their entireties. In some embodiments, the Ras inhibitor targets Ras in its inactive, or GDP-bound state. In some embodiments, the Ras inhibitor is, such as an inhibitor of K-Ras G12C, such as AMG 510, MRTX1257, MRTX849, JNJ-74699157 (ARS-3248), LY3499446, or ARS-1620, ARS-853, BPI-421286, LY3537982, JDQ443, ERAS-3490, JAB-21000, BPI-421286, D-1553, JAB-21822, GH-35, ICP-915, IB1351, RMC-6291, or GDC-6036. In some embodiments, the Ras inhibitor is an inhibitor of K-Ras G12D, such as ERAS-4, MRTX1133, RMC-9805, or JAB-22000. In some embodiments, the Ras inhibitor is a K-Ras G12V inhibitor, such as JAB-23000. In some embodiments, the Ras inhibitor is RMC-6236. Other examples of Ras inhibitors that may be combined with a Ras inhibitor of the present invention are provided in the following, incorporated herein by reference in their entireties: WO 2022087624, WO 2022087375, WO 2022087371, WO 2022083616, WO 2022083569, WO 2022081655, WO 2022078414, WO 2022076917, WO 2022072783, WO 2022066805, WO 2022066646, WO 2022063297, WO 2022061251, WO 2022056307, WO 2022052895, WO 2022047093, WO 2022042630, WO 2022040469, WO 2022037560, WO 2022031678, WO 2022028492, WO 2022028346, WO 2022026726, WO 2022026723, WO 2022015375, WO 2022002102, WO 2022002018, WO 2021259331, WO 2021257828, WO 2021252339, WO 2021248095, WO 2021248090, WO 2021248083, WO 2021248082, WO 2021248079, WO 2021248055, WO 2021245051, WO 2021244603, WO 2021239058, WO 2021231526, WO 2021228161, WO 2021219090, WO 2021219090, WO 2021219072, WO 2021218939, WO 2021217019, WO 2021216770, WO 2021215545, WO 2021215544, WO 2021211864, WO 2021190467, WO 2021185233, WO 2021180181, WO 2021175199, 2021173923, WO 2021169990, WO 2021169963, WO 2021168193, WO 2021158071, WO 2021155716, WO 2021152149, WO 2021150613, WO 2021147967, WO 2021147965, WO 2021143693, WO 2021142252, WO 2021141628, WO 2021139748, WO 2021139678, WO 2021129824, WO 2021129820, WO 2021127404, WO 2021126816, WO 2021126799, WO 2021124222, WO 2021121371, WO 2021121367, WO 2021121330, WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659, WO 2013155223, CN 114195804, CN 114195788, CN 114057776, CN 114057744, CN 114057743, CN 113999226, CN 113980032, CN 113980014, CN 113929676, CN 113754653, CN 113683616, CN 113563323, CN 113527299, CN 113527294, CN 113527293, CN 113493440, CN 113429405, CN 113248521, CN 113087700, CN 113024544, CN 113004269, CN 112920183, CN 112778284, CN 112390818, CN 112390788, CN 112300196, CN 112300194, CN 112300173, CN 112225734, CN 112142735, CN 112110918, CN 112094269, CN 112047937, and CN 109574871, or a pharmaceutically acceptable salt, solvate, isomer (e.g., stereoisomer), prodrug, or tautomer thereof.

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, RO4987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5): 989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8): 1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4): 565-8; and Paez et al., EGFR Mutations In Lung Cancer Correlation With Clinical Response To Gefitinib Therapy, Science 2004, 304(5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12): 1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from AE51-Q58; AF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran-4-one (available from Axon Medchem); PI 103 hydrochloride (3-[4-(4-morpholinylpyrido-[3',2':4,5]furo[3,2-d]pyrimidin-2-yl]phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[1-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a]pyrindin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Aktl) (Barnett et al., Biochem. J. 2005, 385 (Pt. 2): 399-408); Akt-1-1,2 (inhibits Akl and 2) (Barnett et al., Biochem. J. 2005, 385 (Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15): 5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010);

ridaforolimus (also known as deforolimus or AP23573); rapalogs, e.g., as disclosed in WO98/02441 and WO01/14387, e.g. AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552, having the structure

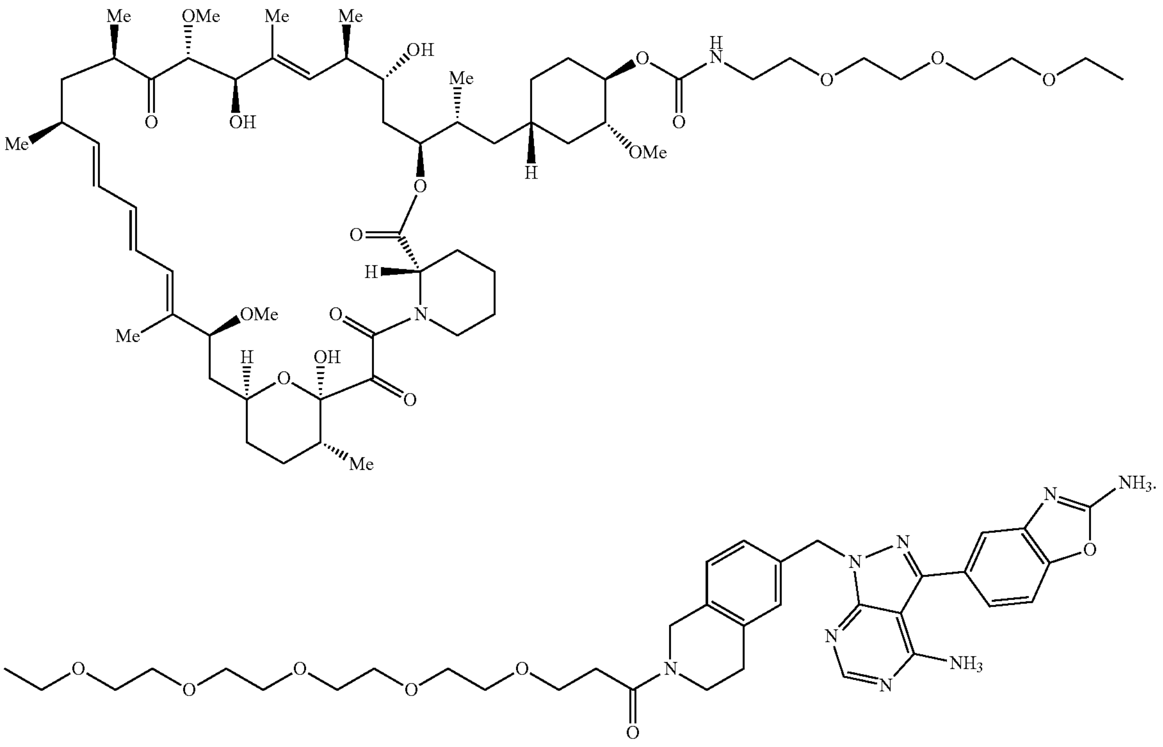

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include those found in the following publications: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget,* 2017, 8, 113734; and patent applications: WO 2022063190, WO 2022043685, WO 2022042331, WO 2022033430, WO 2022033430, WO 2022017444, WO 2022007869, WO 2021259077, WO 2021249449, WO 2021249057, WO 2021244659, WO 2021218755, WO 2021281752, WO 2021197542, WO 2021176072, WO 2021149817, WO 2021148010, WO 2021147879, WO 2021143823, WO 2021143701, WO 2021143680, WO 2021121397, WO 2021119525, WO 2021115286, WO 2021110796, WO 2021088945, WO 2021073439, WO 2021061706, WO 2021061515, WO 2021043077, WO 2021033153, WO 2021028362, WO 2021033153, WO 2021028362, WO 2021018287, WO 2020259679, WO 2020249079, WO 2020210384, WO 2020201991, WO 2020181283, WO 2020177653, WO 2020165734, WO 2020165733, WO 2020165732, WO 2020156243, WO 2020156242, WO 2020108590, WO 2020104635, WO 2020094104, WO 2020094018, WO 2020081848, WO 2020073949, WO 2020073945, WO 2020072656, WO 2020065453, WO 2020065452, WO 2020063760, WO 2020061103, WO 2020061101, WO 2020033828, WO 2020033286, WO 2020022323, WO 2019233810, WO 2019213318, WO 2019183367, WO 2019183364, WO 2019182960, WO 2019167000, WO 2019165073, WO 2019158019, WO 2019152454, WO 2019051469, WO 2019051084, WO 2018218133, WO 2018172984, WO 2018160731, WO 2018136265, WO 2018136264, WO 2018130928, WO 2018129402, WO 2018081091, WO 2018057884, WO 2018013597, WO 2017216706, WO 2017211303, WO 2017210134, WO 2017156397, WO 2017100279, WO 2017079723, WO 2017078499; WO 2016203406, WO 2016203405, WO 2016203404, WO 2016196591, WO 2016191328, WO 2015107495, WO 2015107494, WO 2015107493, WO 2014176488, WO 2014113584, US 20210085677, U.S. Ser. No. 10/858,359, U.S. Ser. No. 10/934,302, U.S. Ser. No. 10/954,243, U.S. Ser. No. 10/988,466, U.S. Ser. No. 11/001,561, U.S. Ser. No. 11/033,547, U.S. Ser. No. 11/034,705, U.S. Ser. No. 11/044,675, CN 114213417, CN 114163457, CN 113896710, CN 113248521, CN 113248449, CN 113135924, CN 113024508, CN 112920131, CN 112823796, CN 112402385, CN 111848599, CN 111704611, CN 111265529, and CN 108113848, or a pharmaceutically acceptable salt, solvate, isomer (e.g., stereoisomer), prodrug, or tautomer thereof, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RMC-4630. In some embodiments, the SHP2 inhibitor is JAB-3068. In some embodiments, the SHP2 inhibitor is JAB-3312. In some embodiments, the SHP2 inhibitor is RLY-1971. In some embodiments, the SHP2 inhibitor is ERAS-601. In some embodiments, the SHP2 inhibitor is BBP-398.

In some embodiments, the additional therapeutic agent is selected from the group consisting of a MEK inhibitor, a HER2 inhibitor, a SHP2 inhibitor, a CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PD-L1 inhibitor and a SOS1 inhibitor. In some embodiments, a Ras inhibitor of the present invention is used in combination with a PD-L1 inhibitor and a SHP2 inhibitor. In some embodiments, a Ras inhibitor of the present invention is used in combination with a MEK inhibitor and a SHP2 inhibitor. In some embodiments, the cancer is colorectal cancer and the treatment comprises administration of a Ras inhibitor of the present invention in combination with a second or third therapeutic agent.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PD-L1, anti-CTLA4, anti-LAGI, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1): 186-192; Thompson et al., Clin. Cancer Res. 2007, 13(6): 1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863, 949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Angl and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892, 112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-Ia, interferon beta-Ib, interferon gamma, natural interferon gamma-Ia, interferon gamma-Ib, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS- 663513; PF-05082566; CDX-1127; anti-OX40 (Providence Health Services); huMAbOX40L; atacicept; CP-870893; lucatumumab; dacetuzumab; muromonab-CD3; ipilumumab; MED14736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Numbered Embodiments

1. A compound, or pharmaceutically acceptable salt thereof, having the structure of Formula I:

Formula I

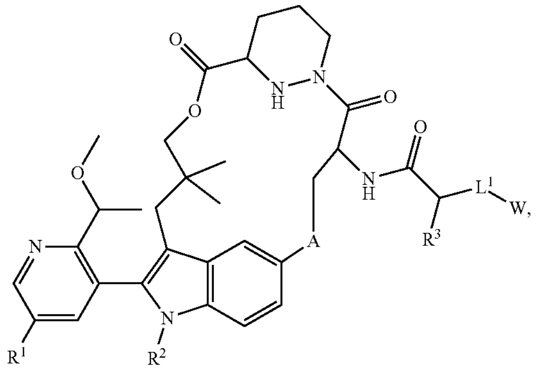

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$L^1$ is absent or a linker;

W is a cross-linking group comprising a vinyl ketone, vinyl sulfone, ynone, or an alkynyl sulfone;

$R^1$ is hydrogen, optionally substituted 3 to 10-membered heterocycloalkyl, or optionally substituted $C_1$-$C_6$ heteroalkyl;

$R^2$ is optionally substituted $C_1$-$C_6$ alkyl; and $R^3$ is optionally substituted $C_1$-$C_6$ alkyl or optionally substituted $C_1$-$C_3$ heteroalkyl.

2. The compound of embodiment 1, or pharmaceutically acceptable salt thereof, wherein A is optionally substituted thiazole, optionally substituted oxazole, optionally substituted morpholino, optionally substituted pyrrolidinyl, optionally substituted pyridyl, optionally substituted azetidinyl, optionally substituted pyrazinyl, optionally substituted pyrimidine, optionally substituted piperidinyl, optionally substituted oxadiazole, optionally substituted thiadiazole, optionally substituted triazole, optionally substituted thiomorpholino, or optionally substituted phenyl.

3. The compound of embodiment 1 or 2, or pharmaceutically acceptable salt thereof, having the structure of Formula II-1:

Formula II-1

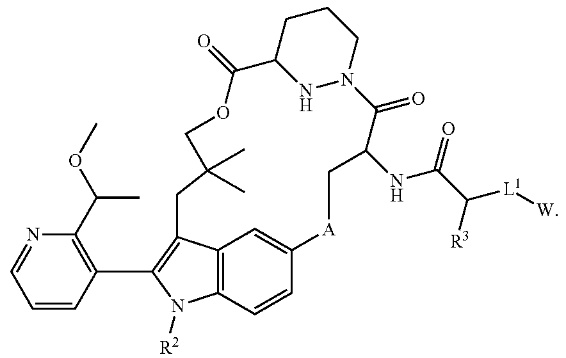

4. The compound of embodiment 1 or 2, or pharmaceutically acceptable salt thereof, having the structure of Formula II-2:

Formula II-2

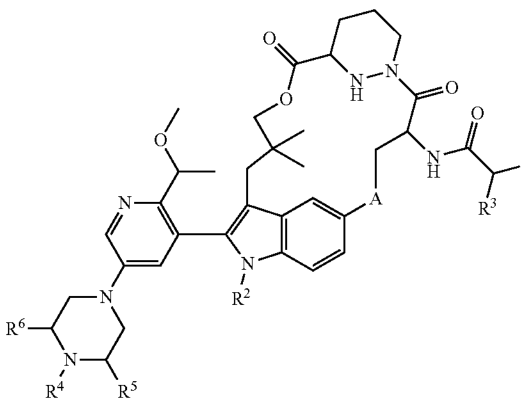

wherein $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

5. The compound of embodiment 4, or pharmaceutically acceptable salt thereof, having the structure of Formula II-3:

Formula II-3

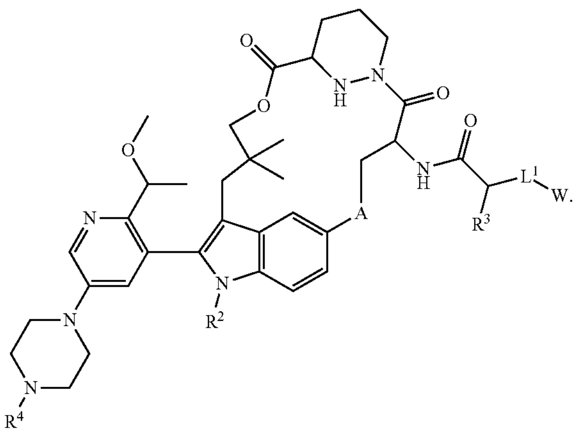

6. The compound of embodiment 4, or pharmaceutically acceptable salt thereof, having the structure of Formula II-4:

Formula II-4

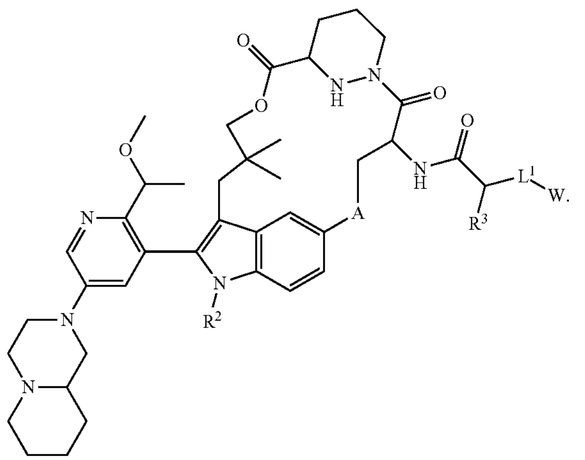

7. The compound of any one of embodiments 1 to 6, or pharmaceutically acceptable salt thereof, wherein $R^2$ is:

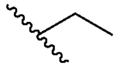

or

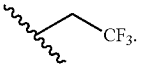

8. The compound of any one of embodiments 1 to 7, or pharmaceutically acceptable salt thereof, wherein $R^3$ is optionally substituted $C_1$-$C_6$ alkyl.

9. The compound of embodiment 8, or pharmaceutically acceptable salt thereof, wherein $R^3$ is:

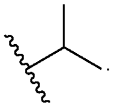 [SMILES: *C(C)C]

10. The compound of any one of embodiments 1 to 7, or pharmaceutically acceptable salt thereof, wherein $R^3$ is optionally substituted $C_1$-$C_3$ heteroalkyl.

11. The compound of embodiment 10, or pharmaceutically acceptable salt thereof, wherein $R^3$ is:

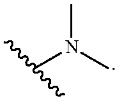 [SMILES: *N(C)C]

12. The compound of any one of embodiments 1 to 11, or pharmaceutically acceptable salt thereof, wherein A is optionally substituted 5 to 10-membered heteroarylene.

13. The compound of embodiment 12, or pharmaceutically acceptable salt thereof, wherein A is:

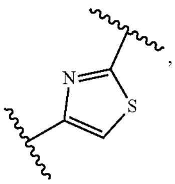,
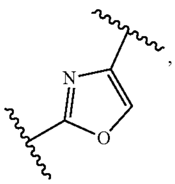,
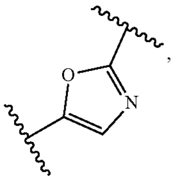,
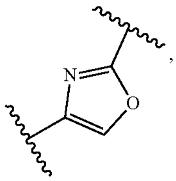,
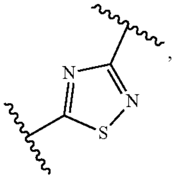,
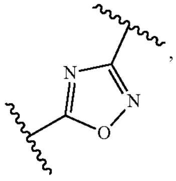,
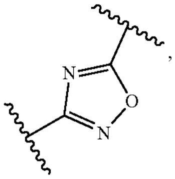,
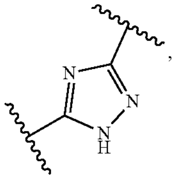,
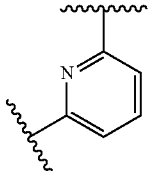,
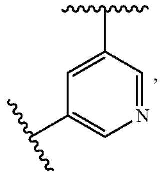,
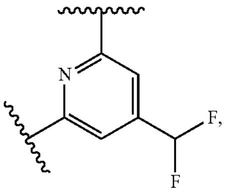,
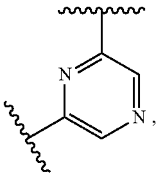, or -continued

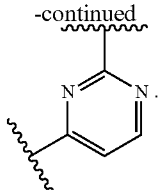.

14. The compound of any one of embodiments 1 to 11, or pharmaceutically acceptable salt thereof, wherein A is optionally substituted phenyl.

15. The compound of embodiment 14, or pharmaceutically acceptable salt thereof, wherein A is:

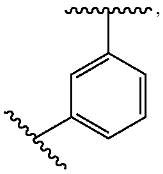,
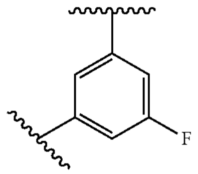,
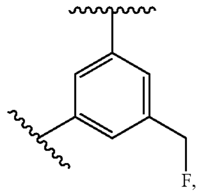, or
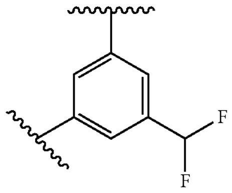.

16. The compound of any one of embodiments 1 to 11, or pharmaceutically acceptable salt thereof, wherein A is optionally substituted 3 to 6-membered heterocycloalkylene.

17. The compound of embodiment 16, or pharmaceutically acceptable salt thereof, wherein A is selected from the following, or a stereoisomer thereof:

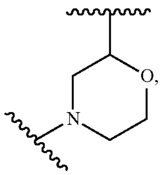,
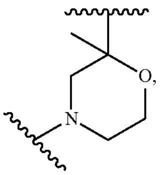,
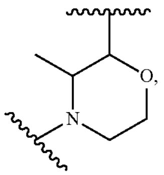,
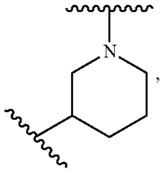,
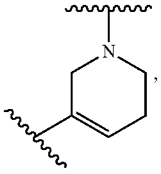,
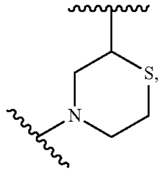,
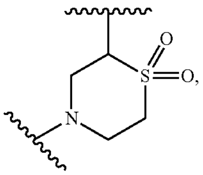,
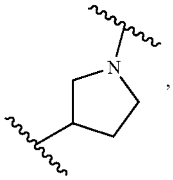, or
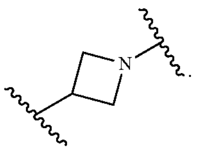.

18. The compound of any one of embodiments 1 to 17, or pharmaceutically acceptable salt thereof, wherein the linker is the structure of Formula III:

Formula III $$A^1—(B^1)_f—(C^1)_g—(B^2)_h—(D^1)—(B^3)_i—(C^2)_j—(B^4)_k—A^2,$$

wherein $A^1$ is a bond between the linker and $CH(R^3)$; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and $NR^N$; each $R^N$ is, independently, hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$— to —$(B^3)_i$—$(C^2)_j$—$(B^4)_k$—$A^2$.

19. The compound of any one of embodiments 1 to 18, or pharmaceutically acceptable salt thereof, wherein the linker is or comprises a cyclic moiety.

20. The compound of embodiment 19, or pharmaceutically acceptable salt thereof, wherein the linker has the structure of Formula IIIa:

Formula IIIa

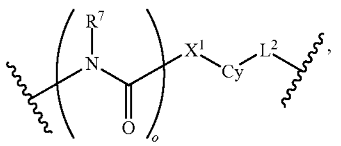

wherein o is 0 or 1;

$R^7$ is hydrogen, optionally substituted $C_1$-$C_6$ alkyl, optionally substituted 3 to 8-membered cycloalkylene, or optionally substituted 3 to 8-membered heterocycloalkylene;

$X^1$ is absent, optionally substituted $C_1$-$C_4$ alkylene, O, $NCH_3$, or optionally substituted $C_1$-$C_4$ heteroalkylene;

Cy is optionally substituted 3 to 8-membered cycloalkylene, optionally substituted 3 to 12-membered heterocycloalkylene, optionally substituted 6-10 membered arylene, or optionally substituted 5 to 10-membered heteroarylene; and $L^2$ is absent, —$SO_2$—, —NH—, optionally substituted $C_1$-$C_4$ alkylene, optionally substituted $C_1$-$C_4$ heteroalkylene, or optionally substituted 3 to 6-membered heterocycloalkylene.

21. The compound of embodiment 20, or pharmaceutically acceptable salt thereof, wherein the linker is selected from, or a stereoisomer thereof:

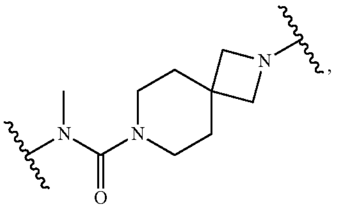

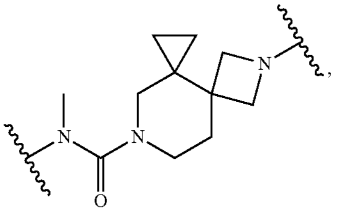

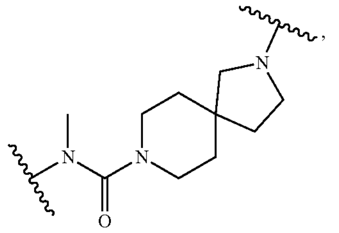

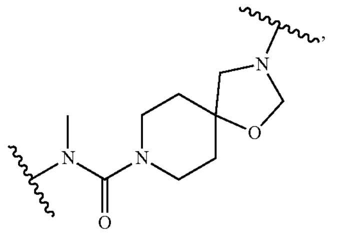

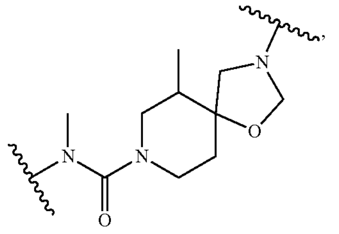

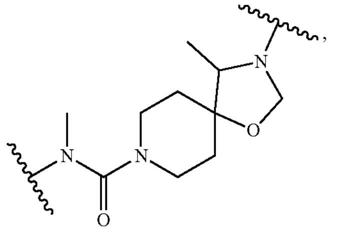

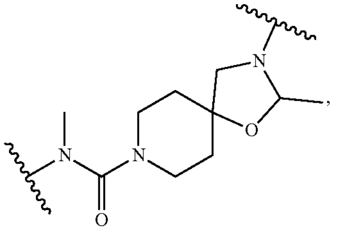

-continued
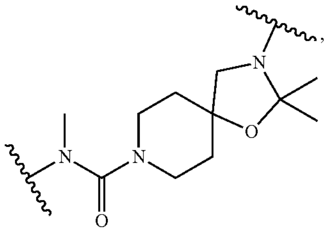
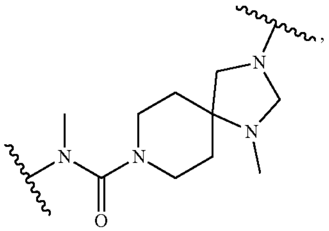
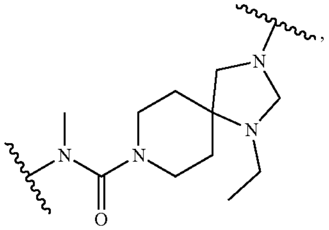
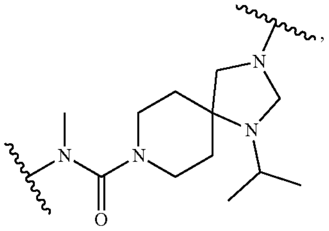
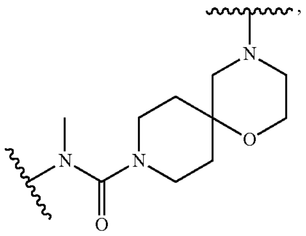
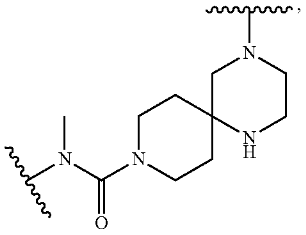
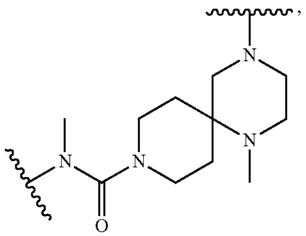
-continued
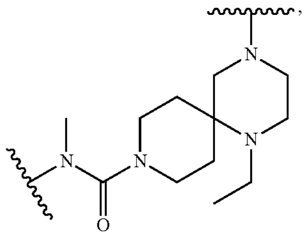
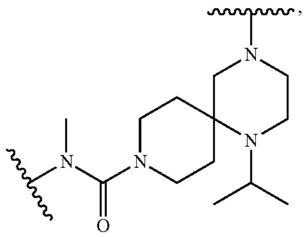
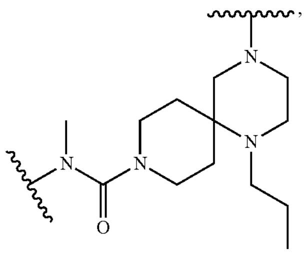
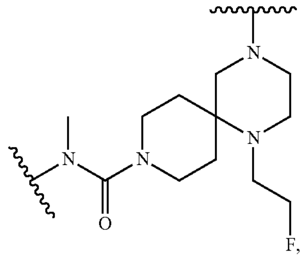
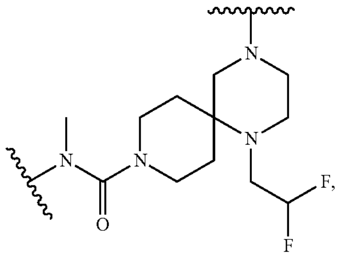
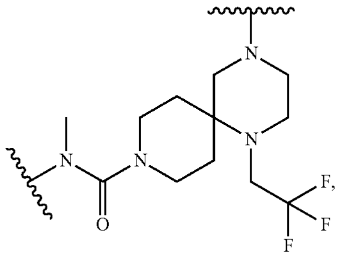

-continued
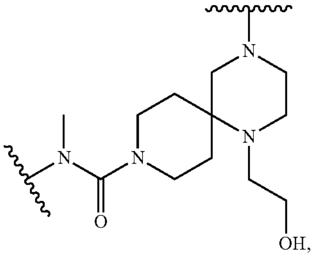
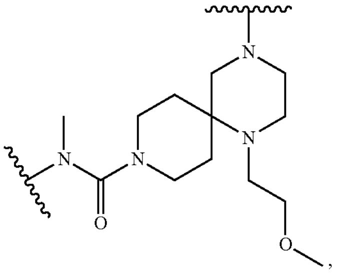
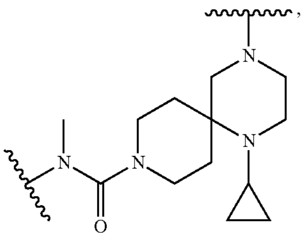
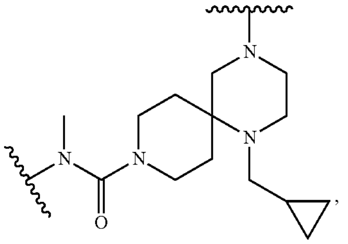
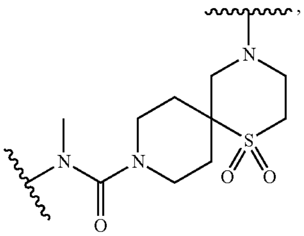
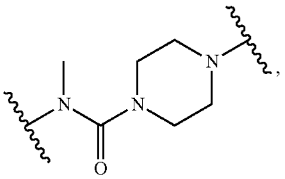
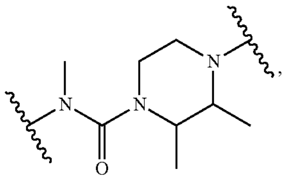
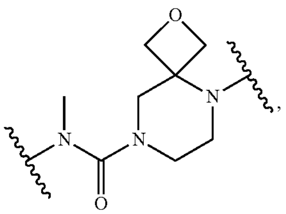
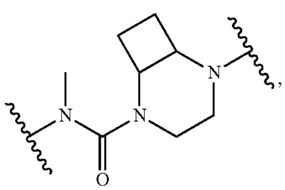
-continued
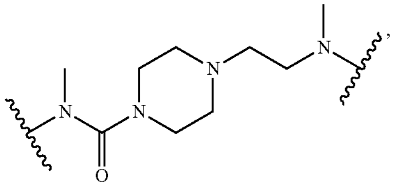
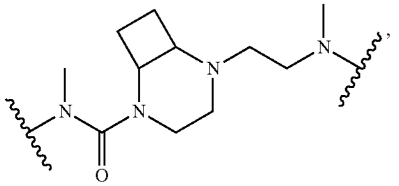
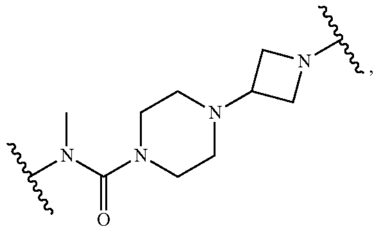
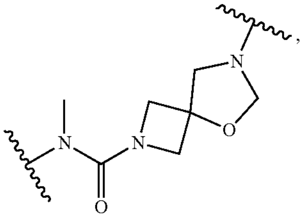
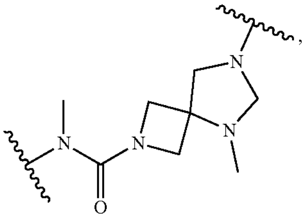
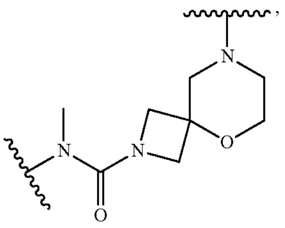
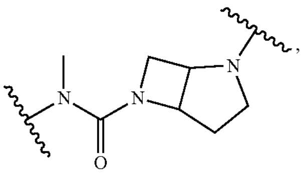
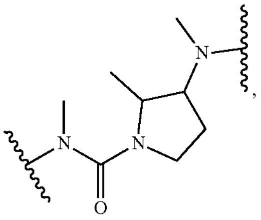
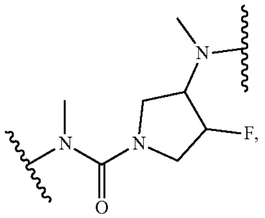

-continued

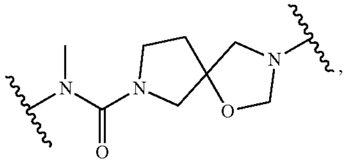

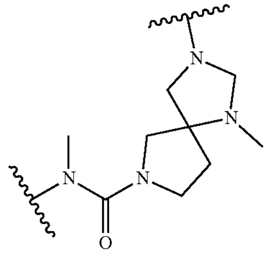

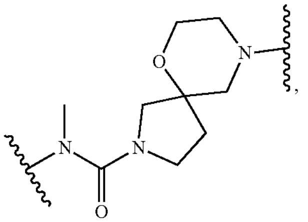

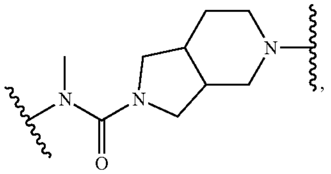

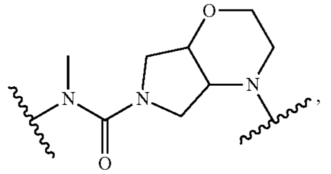

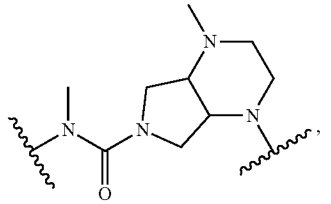

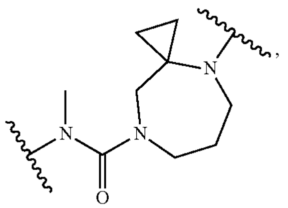

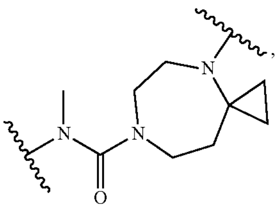

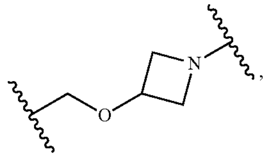

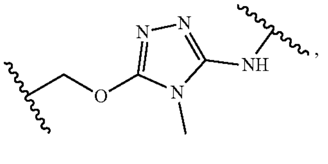

-continued

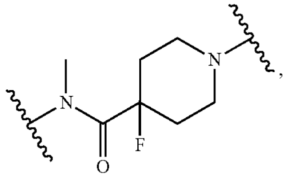

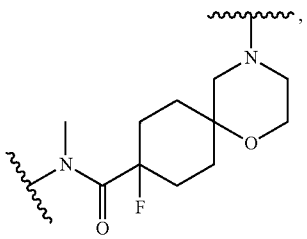

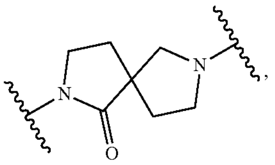

or

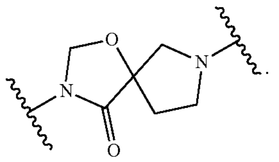

22. The compound of any one of embodiments embodiment 1 to 21, or pharmaceutically acceptable salt thereof, wherein the compound is not a compound of Table 2.

23. The compound of any one of embodiments 1 to 22, or pharmaceutically acceptable salt thereof, having the structure of Formula II-5:

Formula II-5

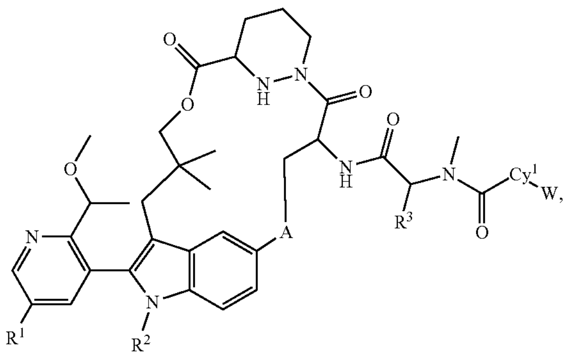

wherein $Cy^1$ is optionally substituted spirocyclic 8 to 11-membered heterocycloalkylene or optionally substituted bicyclic 7 to 9-membered heterocycloalkylene; and wherein W comprises a vinyl ketone or a vinyl sulfone.

24. The compound of embodiment 23, or pharmaceutically acceptable salt thereof, wherein $Cy^1$ is optionally substituted spirocyclic 10 to 11-membered heterocycloalkylene.

25. The compound of embodiment 24, or pharmaceutically acceptable salt thereof, having the structure of Formula II-5a:

Formula II-5a

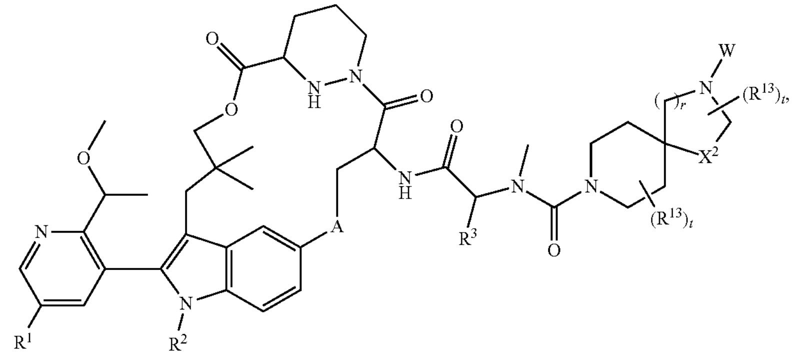

wherein $X^2$ is O, $C(R^{11})_2$, $NR^{12}$, S, or $SO_2$.

r is 1 or 2;

each t is, independently, 0, 1, or 2;

$R^{11}$ and $R^{12}$ are each, independently, hydrogen, optionally substituted $C_1$-$C_4$ alkyl, optionally substituted $C_2$-$C_4$ heteroalkyl, or optionally substituted 3 to 5-membered cycloalkyl; and each $R^{13}$ is, independently, $—CH_3$.

26. The compound of embodiment 25, or pharmaceutically acceptable salt thereof, wherein r is 1.

27. The compound of embodiment 25, or pharmaceutically acceptable salt thereof, wherein r is 2.

28. The compound of any one of embodiments 25 to 27, or pharmaceutically acceptable salt thereof, wherein $X^2$ is O.

29. The compound of any one of embodiments 25 to 27, or pharmaceutically acceptable salt thereof, wherein $X^2$ is S.

30. The compound of any one of embodiments 25 to 27, or pharmaceutically acceptable salt thereof, wherein $X^2$ is $SO_2$.

31. The compound of any one of embodiments 25 to 27, or pharmaceutically acceptable salt thereof, wherein $X^2$ is $NR^{12}$.

32. The compound of embodiment 31, or pharmaceutically acceptable salt thereof, wherein $R^{12}$ is selected from, or a stereoisomer thereof:

$—CH_3$, 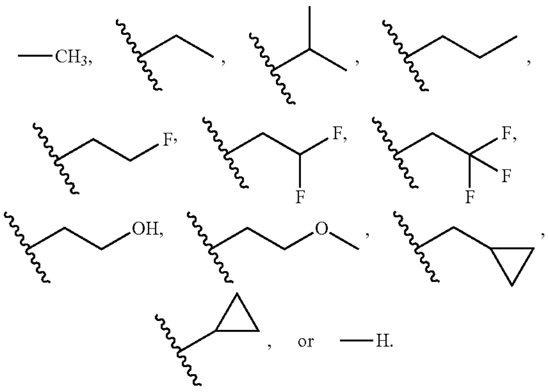 , or —H.

33. The compound of any one of embodiments 25 to 27, or pharmaceutically acceptable salt thereof, wherein $X^2$ is $C(R^{11})_2$.

34. The compound embodiment 33, or pharmaceutically acceptable salt thereof, wherein each $R^{11}$ is hydrogen.

35. The compound of any one of embodiments 1 to 34, or pharmaceutically acceptable salt thereof, wherein W is a cross-linking group comprising a vinyl ketone.

36. The compound of embodiment 35, or pharmaceutically acceptable salt thereof, wherein W has the structure of Formula IVa:

Formula IVa

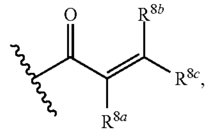

wherein $R^{8a}$, $R^{8b}$, and $R^{8c}$ are, independently, hydrogen, —CN, halogen, or $—C_1$-$C_3$ alkyl optionally substituted with one or more substituents independently selected from —OH, $—O—C_1$-$C_3$ alkyl, $—NH_2$, $—NH(C_1$-$C_3alkyl)$, $—N(C_1$-$C_3$ $alkyl)_2$, or a 4 to 7-membered saturated heterocycloalkyl.

37. The compound of embodiment 36, or pharmaceutically acceptable salt thereof, wherein W is selected from, or a stereoisomer thereof:

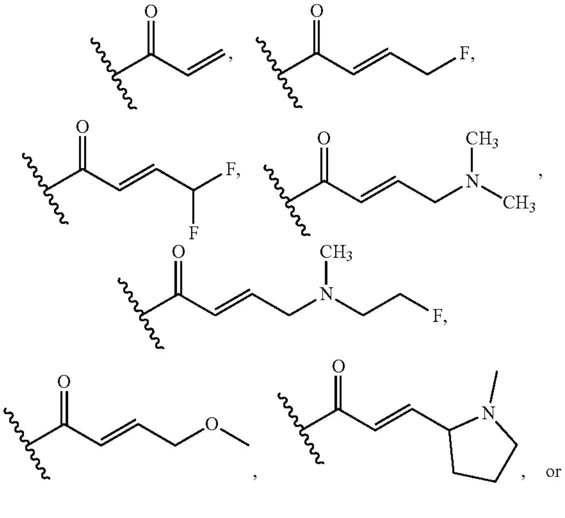 or

-continued

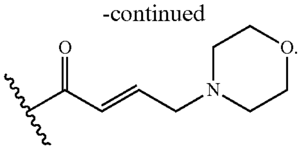

38. The compound of any one of embodiments 1 to 34, or pharmaceutically acceptable salt thereof, wherein W is a cross-linking group comprising a vinyl sulfone.

39. The compound of embodiment 38, or pharmaceutically acceptable salt thereof, wherein W has the structure of Formula IVc:

Formula IVc

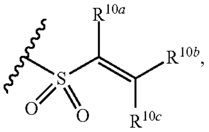

wherein $R^{10a}$, $R^{10b}$, and $R^{11c}$ are, independently, hydrogen, —CN, or —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl.

40. The compound of embodiment 39, or pharmaceutically acceptable salt thereof, wherein W is:

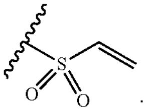 [SMILES: *S(=O)(=O)C=C]

41. The compound of any one of embodiments 1 to 34, or pharmaceutically acceptable salt thereof, wherein W is a cross-linking group comprising an ynone.

42. The compound of embodiment 41, or pharmaceutically acceptable salt thereof, wherein W has the structure of Formula IVb:

Formula IVb

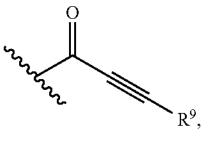

wherein $R^9$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated cycloalkyl, or a 4 to 7-membered saturated heterocycloalkyl.

43. The compound of embodiment 42, or pharmaceutically acceptable salt thereof, wherein W is selected from:

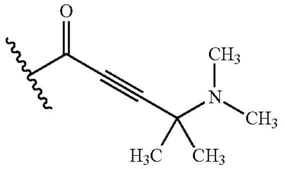

or

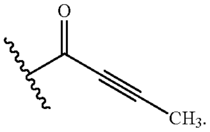

44. The compound of embodiment 42 or 43, or pharmaceutically acceptable salt thereof, having the structure of Formula II-6:

Formula II-6

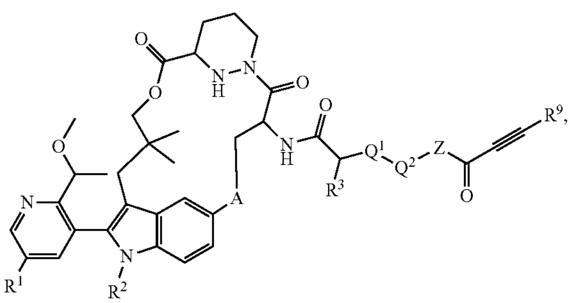

wherein $Q^1$ is $CH_2$, $NR^N$, or O;

$Q^2$ is CO, $NR^N$, or O; and

Z is optionally substituted 3 to 6-membered heterocycloalkylene or optionally substituted 5 to 10-membered heteroarylene; or wherein $Q^1$-$Q^2$-Z is an optionally substituted 9 to 10-membered spirocyclic heterocycloalkylene.

45. The compound of any one of embodiments 42 to 44, or pharmaceutically acceptable salt thereof, having the structure of Formula II-6a:

Formula II-6a

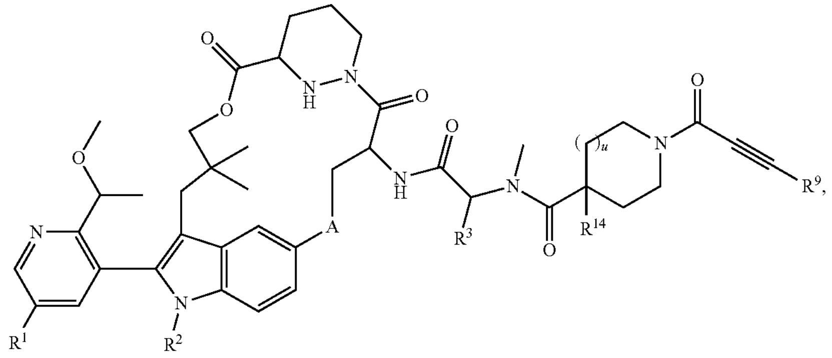

wherein $R^{14}$ is fluoro, hydrogen, or $C_1$-$C_3$ alkyl; and u is 0 or 1.

46. The compound of embodiment 45, or pharmaceutically acceptable salt thereof, wherein $R^{14}$ is fluoro and u is 1.

47. The compound of embodiment 45, or pharmaceutically acceptable salt thereof, wherein $R^{14}$ is hydrogen and u is 0.

48. The compound of any one of embodiments 42 to 44, or pharmaceutically acceptable salt thereof, having the structure of Formula II-6b:

Formula II-6b

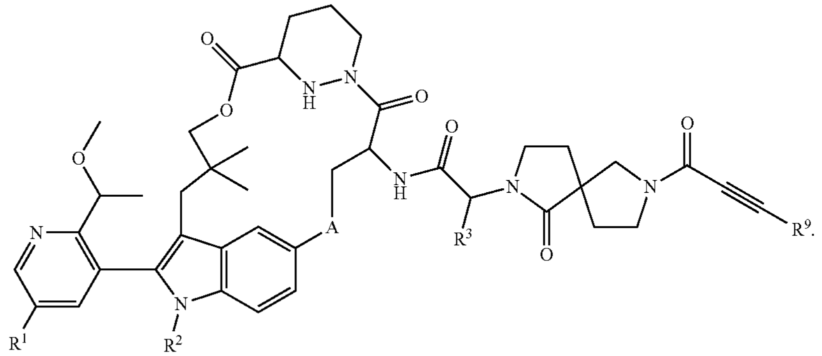

49. The compound of any one of embodiments 42 to 44, or pharmaceutically acceptable salt thereof, having the structure of Formula II-6c:

Formula II-6c

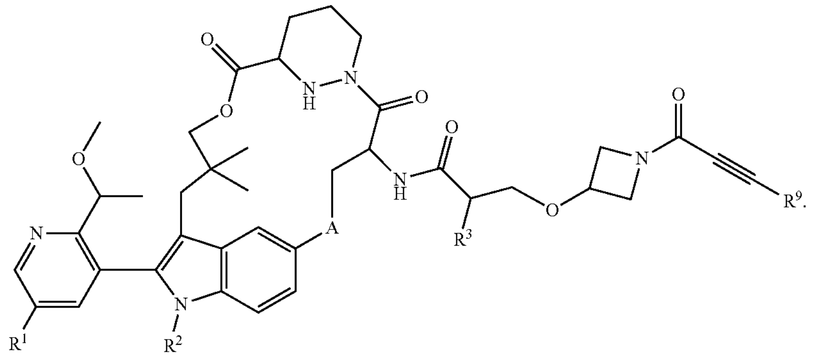

50. A compound, or a pharmaceutically acceptable salt thereof, selected from Table 1.

51. A pharmaceutical composition comprising a compound of any one of embodiments 1 to 50, or a pharmaceutically acceptable salt thereof, and a pharmaceutically acceptable excipient.

52. A conjugate, or salt thereof, comprising the structure of Formula V:

Formula V

M—L—P, wherein L is a linker;

P is a monovalent organic moiety; and

M has the structure of Formula VIa:

Formula VIa

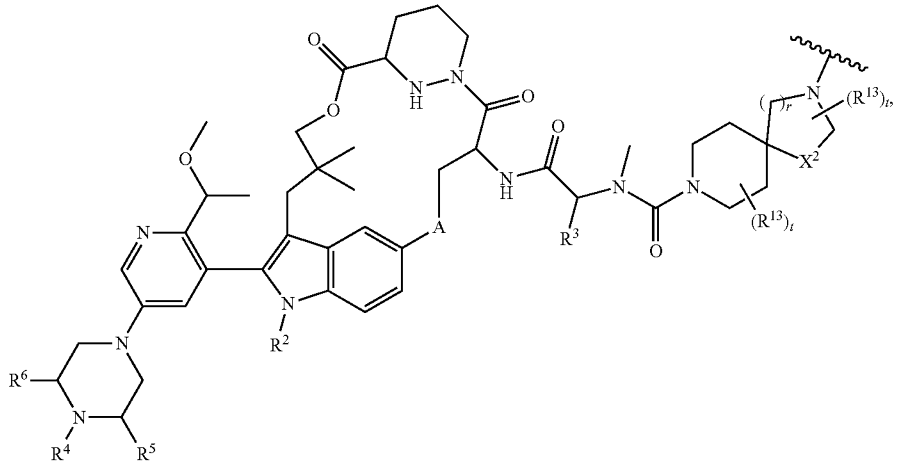

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl;

$X^2$ is O, $C(R^{11})_2$, $NR^{12}$, S, or $SO_2$;

r is 1 or 2;

each t is, independently, 0, 1, or 2;

$R^{11}$ and $R^{12}$ are each, independently, hydrogen, optionally substituted $C_1$-$C_4$ alkyl, optionally substituted $C_2$-$C_4$ heteroalkyl, or optionally substituted 3 to 5-membered cycloalkyl;

each $R^{13}$ is, independently, —$CH_3$; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

53. A conjugate, or salt thereof, comprising the structure of Formula V:

Formula V

M—L—P, wherein L is a linker;

P is a monovalent organic moiety; and

M has the structure of Formula VIb:

Formula VIb

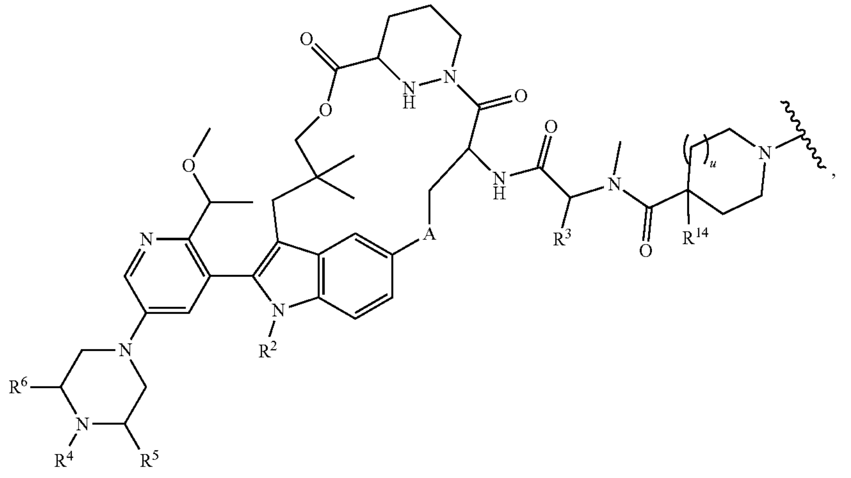

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl;

$R^{14}$ is fluoro, hydrogen, or $C_1$-$C_3$ alkyl;

u is 0 or 1; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

54. A conjugate, or salt thereof, comprising the structure of Formula V:

$$M—L—P,$$ Formula V wherein L is a linker;

P is a monovalent organic moiety; and

M has the structure of Formula VIc:

Formula VIc

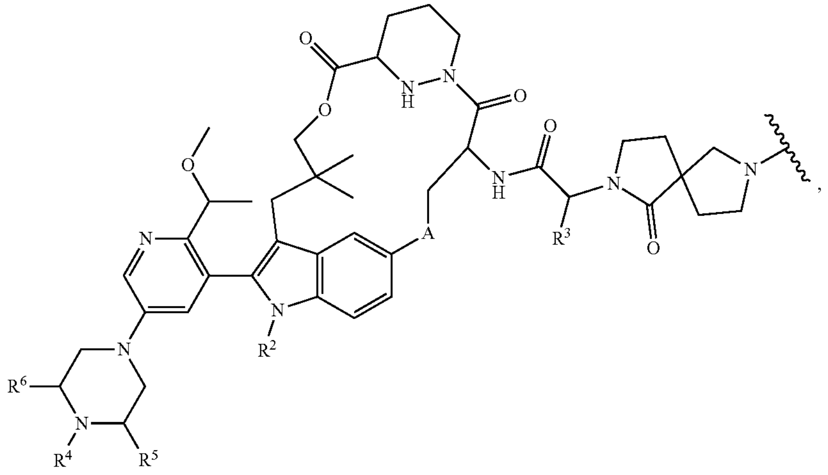

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

55. A conjugate, or salt thereof, comprising the structure of Formula V:

Formula V

M—L—P, wherein L is a linker;

P is a monovalent organic moiety; and

M has the structure of Formula Vid:

Formula VId

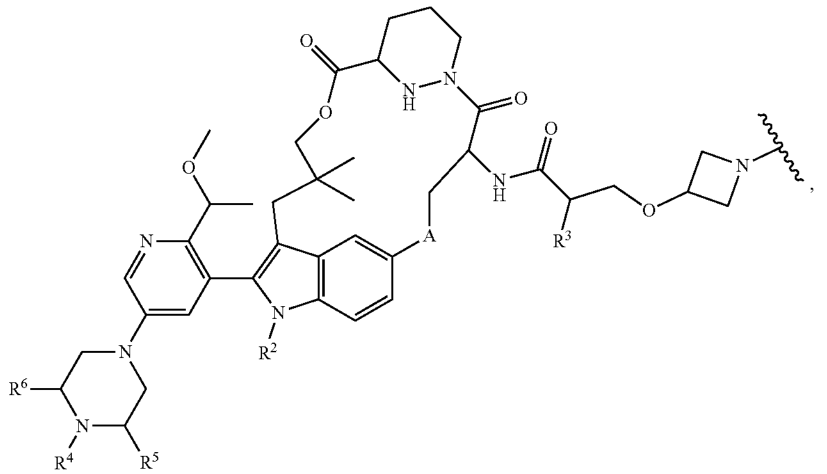

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl;

$R^3$ is optionally substituted $C_1$-$C_6$ alkyl or optionally substituted $C_1$-$C_3$ heteroalkyl; and $R^4$, $R^5$, and $R^6$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered heterocycloalkyl; or $R^4$ and $R^5$ combine with the atoms to which they are attached to form an optionally substituted 3 to 8-membered cycloalkyl or an optionally substituted 3 to 8-membered heterocycloalkyl; or $R^4$ and $R^6$ combine with the atoms to which they are attached to form an optionally substituted 3 to 8-membered cycloalkyl or an optionally substituted 3 to 8-membered heterocycloalkyl.

56. The conjugate of any one of embodiments 52 to 55, or salt thereof, wherein the monovalent organic moiety is a protein.

57. The conjugate of embodiment 56, or salt thereof, wherein the protein is a Ras protein.

58. The conjugate of embodiment 57, or salt thereof, wherein the Ras protein is K-Ras G12C, K-Ras G13C, H-Ras G12C, H-Ras G13C, N-Ras G12C, or N-Ras G13C.

59. The conjugate of any one of embodiments 52 to 58, or a salt thereof, wherein the linker is bound to the monovalent organic moiety through a bond to a sulfhydryl group of an amino acid residue of the monovalent organic moiety.

60. A method of treating cancer in a subject in need thereof, the method comprising administering to the subject a therapeutically effective amount of a compound of any one of embodiments 1 to 50, or a pharmaceutically acceptable salt thereof, or a pharmaceutical composition of embodiment 51.

61. The method of embodiment 60, wherein the cancer is pancreatic cancer, colorectal cancer, non-small cell lung cancer, or endometrial cancer.

62. The method of embodiment 60 or 61, wherein the cancer comprises a Ras mutation.

63. The method of embodiment 62, wherein the Ras mutation is K-Ras G12C, K-Ras G13C, H-Ras G12C, H-Ras G13C, N-Ras G12C, or N-Ras G13C.

64. A method of treating a Ras protein-related disorder in a subject in need thereof, the method comprising administering to the subject a therapeutically effective amount of a compound of any one of embodiments 1 to 50, or a pharmaceutically acceptable salt thereof, or a pharmaceutical composition of embodiment 51.

65. A method of inhibiting a Ras protein in a cell, the method comprising contacting the cell with an effective amount of a compound of any one of embodiments 1 to 50, or a pharmaceutically acceptable salt thereof, or a pharmaceutical composition of embodiment 51.

66. The method of embodiment 64 or 65, wherein the Ras protein is K-Ras G12C, K-Ras G13C, H-Ras G12C, H-Ras G13C, N-Ras G12C, or N-Ras G13C.

67. The method of embodiment 65 or 66, wherein the cell is a cancer cell.

68. The method of embodiment 67, wherein the cancer cell is a pancreatic cancer cell, a colorectal cancer cell, a non-small cell lung cancer cell, or an endometrial cancer cell.

69. The method or use of any one of embodiments 60 to 68, wherein the method or use further comprises administering an additional anti-cancer therapy.

70. The method of embodiment 69, wherein the additional anti-cancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

71. The method of embodiment 69 or 70, wherein the additional anti-cancer therapy is a SHP2 inhibitor.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure or scope of the appended claims.

Chemical Syntheses

Definitions used in the following examples and elsewhere herein are:

| | |
|---|---|
| $CH_2Cl_2$, DCM | Methylene chloride, Dichloromethane |
| $CH_3CN$, MeCN | Acetonitrile |
| CuI | Copper (I) iodide |
| DIPEA | Diisopropylethyl amine |
| DMF | N,N-Dimethylformamide |
| EtOAc | Ethyl acetate |
| h | hour |
| $H_2O$ | Water |
| HCl | Hydrochloric acid |
| $K_3PO_4$ | Potassium phosphate (tribasic) |
| MeOH | Methanol |
| $Na_2SO_4$ | Sodium sulfate |
| NMP | N-methyl pyrrolidone |
| Pd(dppf)$Cl_2$ | [1,1'-Bis(diphenylphosphino)ferrocene]dichloropalladium(II) |

Instrumentation

Mass spectrometry data collection took place with a Shimadzu LCMS-2020, an Agilent 1260LC-6120/6125MSD, a Shimadzu LCMS-2010EV, or a Waters Acquity UPLC, with either a QDa detector or SQ Detector 2. Samples were injected in their liquid phase onto a C-18 reverse phase. The compounds were eluted from the column using an acetonitrile gradient and fed into the mass analyzer. Initial data analysis took place with either Agilent ChemStation, Shimadzu LabSolutions, or Waters MassLynx. NMR data was collected with either a Bruker AVANCE III HD 400 MHz, a Bruker Ascend 500 MHz instrument, or a Varian 400 MHz, and the raw data was analyzed with either TopSpin or Mestrelab Mnova.

Synthesis of Intermediates

Intermediate 1. Synthesis of 3-(5-bromo-1-ethyl-2-[2-[(1S)-1-methoxyethyl]pyridin-3-yl]indol-3-yl)-2,2-dimethylpropan-1-ol

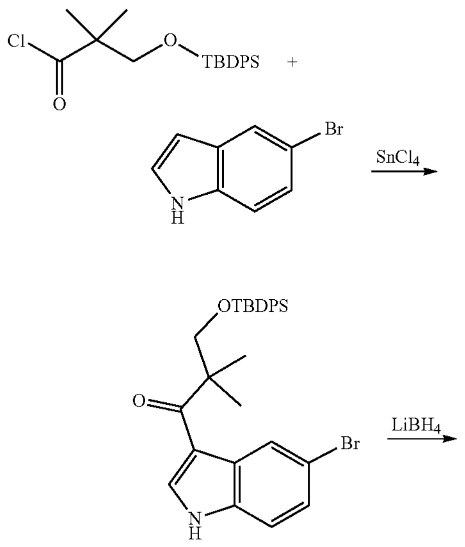

-continued

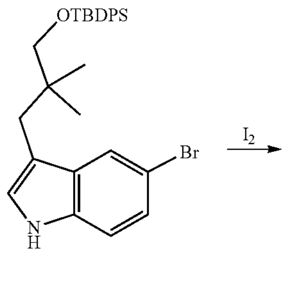

-continued

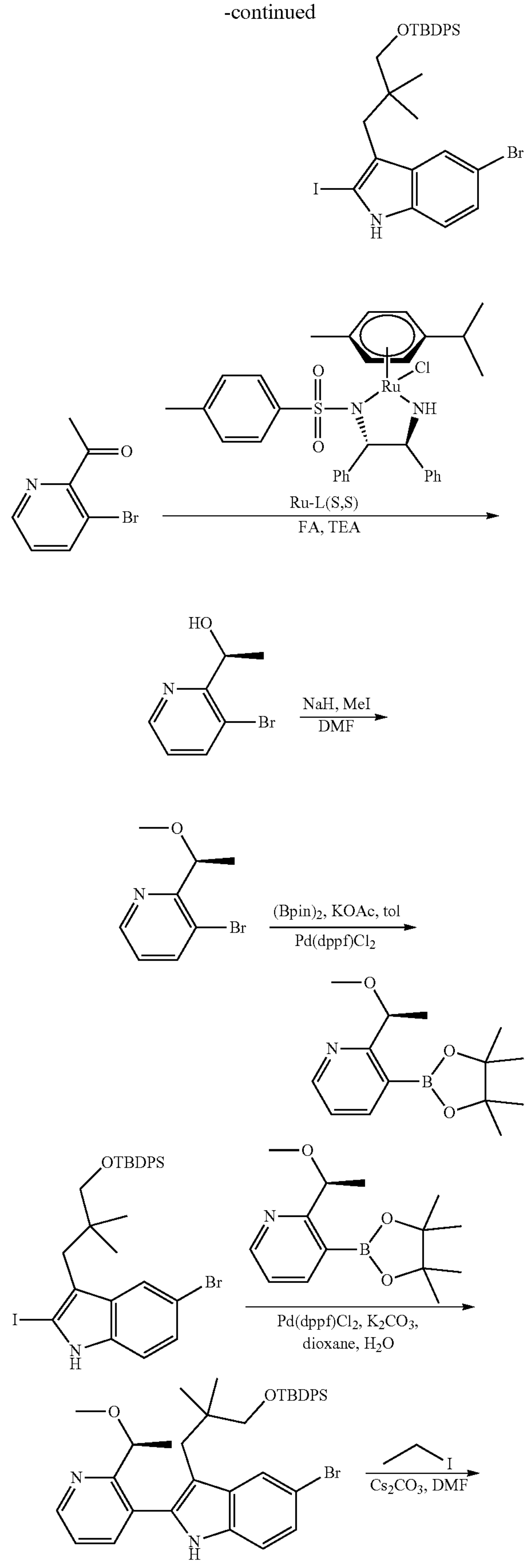

-continued

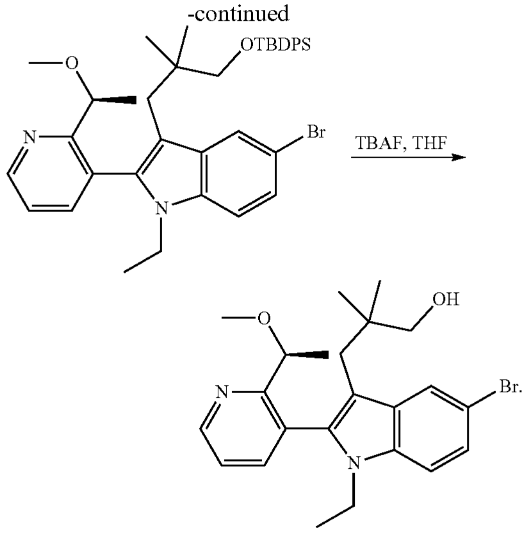

Intermediate 1

Step 1. To a mixture of 3-((tert-butyldiphenylsilyl)oxy)-2,2-dimethylpropanoyl chloride (65 g, 137 mmol, crude) in DCM (120 mL) at 0° C. under an atmosphere of $N_2$ was added 1 M $SnCl_4$ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (100 mL×4), dried over $Na_2SO_4$, and filtered. The filtrate was concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (55 g, 75% yield). LCMS (ESI): m/z [M+Na] calc'd for $C_{29}H_{32}BrNO_2SiNa$ 556.1; found 556.3.

Step 2. To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of $N_2$ was added $LiBH_4$ (6.1 g, 281 mmol). The mixture was heated to 60° C. and stirred for 20 h, then MeOH (10 mL) and EtOAc (100 mL) were added and the mixture washed with brine (50 mL), dried over $Na_2SO_4$, filtered, and the filtrate concentrated under reduced pressure. The residue was diluted with DCM (50 mL), cooled to 10° C. and diludine (9.5 g, 37.4 mmol) and TsOH·$H_2O$ (890 mg, 4.7 mmol) added. The mixture was stirred at 10° C. for 2 h, filtered, the filtrate concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (41 g, 84% yield). LCMS (ESI): m/z [M+H] calc'd for $C_{29}H_{34}BrNOSi$ 519.2; found 520.1; $^1H$ NMR (400 MHz, $CDCl_3$) δ 7.96 (s, 1H), 7.75-7.68 (m, 5H), 7.46-7.35 (m, 6H), 7.23-7.19 (m, 2H), 6.87 (d, J=2.1 Hz, 1H), 3.40 (s, 2H), 2.72 (s, 2H), 1.14 (s, 9H), 0.89 (s, 6H).

Step 3. To a mixture of 1-(5-bromo-1H-indol-3-yl)-3-((tert-butyldiphenylsilyl)oxy)-2,2-dimethylpropan-1-one (1.5 g, 2.9 mmol) and 12 (731 mg, 2.9 mmol) in THE (15 mL) at rt was added AgOTf (888 mg, 3.5 mmol). The mixture was stirred at rt for 2 h, then diluted with EtOAc (200 mL) and washed with saturated $Na_2S_2O_3$ (100 mL), dried over anhydrous $Na_2SO_4$, and filtered. The filtrate was concentrated under reduced pressure and the residue was purified by silica gel column chromatography to give 5-bromo-3-(3-((tert-butyldiphenylsilyl)oxy)-2,2-dimethylpropyl)-2-iodo-1H-indole (900 mg, 72% yield) as a solid. $^{1}H$ NMR (400 MHz, DMSO-$d_6$) δ 11.70 (s, 1H), 7.68 (d, J=1.3 Hz, 1H), 7.64-7.62 (m, 4H), 7.46-7.43 (m, 6H), 7.24-7.22 (d, 1H), 7.14-7.12 (dd, J=8.6, 1.6 Hz, 1H), 3.48 (s, 2H), 2.63 (s, 2H), 1.08 (s, 9H), 0.88 (s, 6H).

Step 4. To a stirred mixture of HCOOH (66.3 g, 1.44 mol) in TEA (728 g, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to rt and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous $Na_2SO_4$, and filtered. The filtrate was concentrated under reduced pressure and the residue was purified by silica gel column chromatography to give (1 S)-1-(3-bromopyridin-2-yl)ethanol (100 g, 74% yield) a an oil. LCMS (ESI): m/z [M+H] calc'd for $C_7H_8BrNO$ 201.1; found 201.9.

Step 5. To a stirred mixture of (1 S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was allowed to warm to rt and stirred for 2 h. The mixture was cooled to 0° C. and saturated $NH_4Cl$ (5 L) was added. The mixture was extracted with EtOAc (3×1.5 L), dried over anhydrous $Na_2SO_4$ and filtered. The filtrate was concentrated under reduced pressure and the residue was purified by silica gel column chromatography to give 3-bromo-2-[(1 S)-1-methoxyethyl]pyridine (90 g, 75% yield) as an oil. LCMS (ESI): m/z [M+H] calc'd for $C_8H_{10}BrNO$ 215.0; found 215.9.

Step 6. To a stirred mixture of 3-bromo-2-[(1 S)-1-methoxyethyl]pyridine (90 g, 417 mmol) and Pd(dppf)$Cl_2$ (30.5 g, 41.7 mmol) in toluene (900 mL) at rt under an atmosphere of Ar was added bis(pinacolato)diboron (127 g, 500 mmol) and KOAc (81.8 g, 833 mmol) in portions. The mixture was heated to 100° C. and stirred for 3 h. The filtrate was concentrated under reduced pressure and the residue was purified by $Al_2O_3$ column chromatography to give 2-[(1 S)-1-methoxyethyl]-3-(4,4,5,5-tetramethyl-1,3,2-dioxaborolan-2-yl)pyridine (100 g, 63% yield) as a semi-solid. LCMS (ESI): m/z [M+H] calc'd for $C_{14}H_{22}BNO_3$ 263.2; found 264.1.

Step 7. To a stirred mixture of 5-bromo-3-[3-[(tert-butyldiphenylsilyl)oxy]-2,2-dimethylpropyl]-2-iodo-1H-indole (140 g, 217 mmol) and 2-[(1 S)-1-methoxyethyl]-3-(4,4,5,5-tetramethyl-1,3,2-dioxaborolan-2-yl)pyridine (100 g, 380 mmol) in 1,4-dioxane (1.4 L) at rt under an atmosphere of Ar was added $K_2CO_3$ (74.8 g, 541 mmol), Pd(dppf)$Cl_2$ (15.9 g, 21.7 mmol), and $H_2O$ (280 mL) in portions. The mixture was heated to 85° C. and stirred for 4 h, then cooled, $H_2O$ (5 L) added, and the mixture extracted with EtOAc (3×2 L). The combined organic layers were washed with brine (2×1 L), dried over anhydrous $Na_2SO_4$, and filtered. The filtrate was concentrated under reduced pressure and the residue was purified by silica gel column chromatography to give 5-bromo-3-[3-[(tert-butyldiphenylsilyl)oxy]-2,2-dimethylpropyl]-2-[2-[(1 S)-1-methoxyethyl]pyridin-3-yl]-1H-indole (71 g, 45% yield) as a solid. LCMS (ESI): m/z [M+H] calc'd for $C_{37}H_{43}BrN_2O_2Si$ 654.2; found 655.1.

Step 8. To a stirred mixture of 5-bromo-3-[3-[(tert-butyldiphenylsilyl)oxy]-2,2-dimethylpropyl]-2-[2-[(1 S)-1-methoxyethyl]pyridin-3-yl]-1H-indole (71 g, 108 mmol) in DMF (0.8 L) at 0° C. under an atmosphere of $N_2$ was added $Cs_2CO_3$ (70.6 g, 217 mmol) and EtI (33.8 g, 217 mmol) in portions. The mixture was warmed to rt and stirred for 16 h then $H_2O$ (4 L) added and the mixture extracted with EtOAc (3×1.5 L). The combined organic layers were washed with brine (2×1 L), dried over anhydrous $Na_2SO_4$, and filtered. The filtrate was concentrated under reduced pressure and the residue was purified by silica gel column chromatography to give 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 80% yield) as an oil. LCMS (ESI): m/z [M+H] calc'd for $C_{39}H_{47}BrN_2O_2Si$ 682.3; found 683.3.

Step 9. To a stirred mixture of TBAF (172.6 g, 660 mmol) in THF (660 mL) at rt under an atmosphere of $N_2$ was added 5-bromo-3-[3-[(tert-butyldiphenylsilyl)oxy]-2,2-dimethylpropyl]-1-ethyl-2-[2-[(1 S)-1-methoxyethyl]pyridin-3-yl]indole (66 g, 97 mmol) in portions. The mixture was heated to 50° C. and stirred for 16 h, cooled, diluted with $H_2O$ (5 L), and extracted with EtOAc (3×1.5 L). The combined organic layers were washed with brine (2×1 L), dried over anhydrous $Na_2SO_4$, and filtered. After filtration, the filtrate was concentrated under reduced pressure. The filtrate was concentrated under reduced pressure and the residue was purified by silica gel column chromatography to give 3-(5-bromo-1-ethyl-2-[2-[(1 S)-1-methoxyethyl]pyridin-3-yl]indol-3-yl)-2,2-dimethylpropan-1-ol (30 g, 62% yield) as a solid. LCMS (ESI): m/z [M+H] calc'd for $C_{23}H_{29}BrN_2O_2$ 444.1; found 445.1.

Intermediate 1. Alternative Synthesis Through Fisher Indole Route

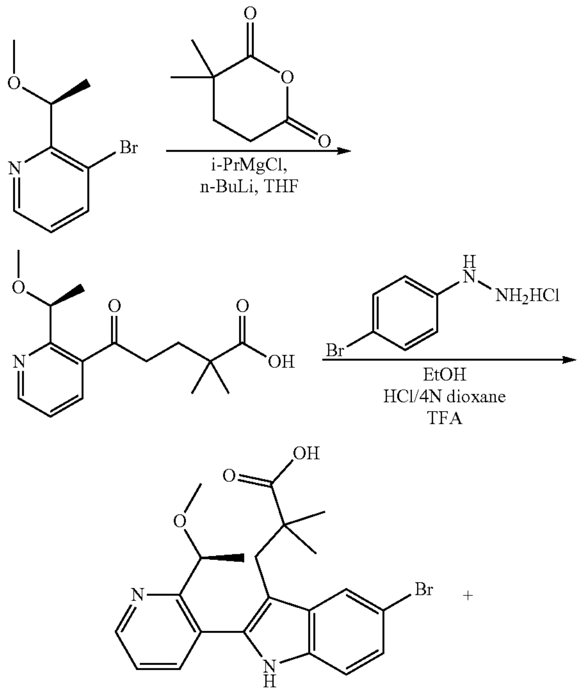

-continued

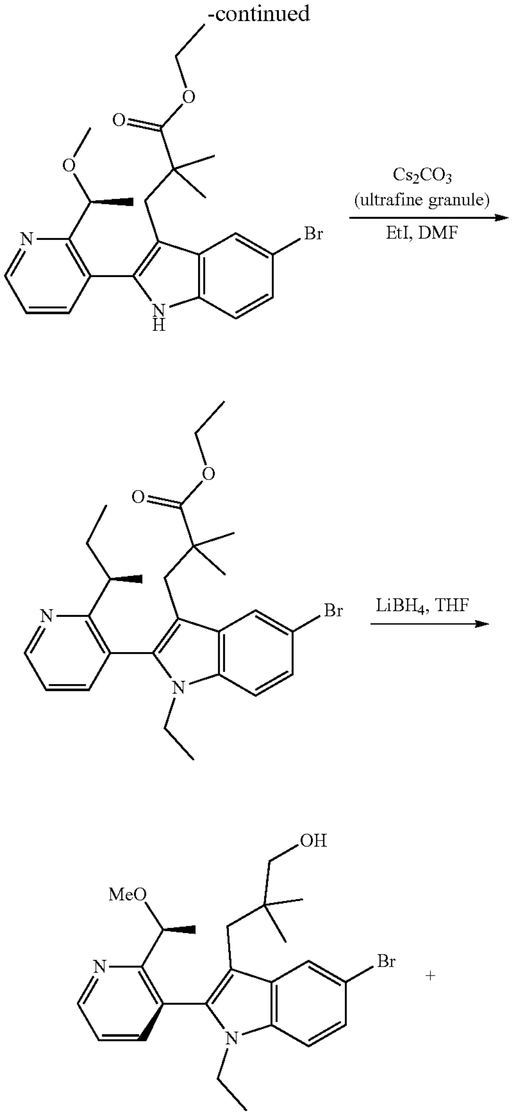

Intermediate 1

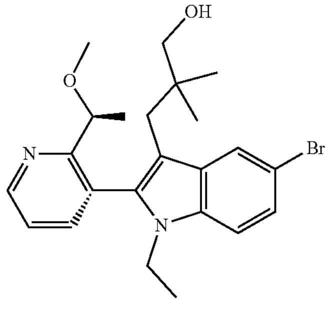

Step 1. To a mixture of i-PrMgCl (2M in in THF, 0.5 L) at −10° C. under an atmosphere of $N_2$ was added n-BuLi, 2.5 M in hexane (333 mL, 833 mmol) dropwise over 15 min. The mixture was stirred for 30 min at −10° C. then 3-bromo-2-[(1 S)-1-methoxyethyl]pyridine (180 g, 833 mmol) in THE (0.5 L) added dropwise over 30 min at −10° C. The resulting mixture was warmed to −5° C. and stirred for 1 h, then 3,3-dimethyloxane-2,6-dione (118 g, 833 mmol) in THE (1.2 L) was added dropwise over 30 min at −5° C. The mixture was warmed to 0° C. and stirred for 1.5 h, then quenched with the addition of pre-cooled 4M HCl in 1,4-dioxane (0.6 L) at 0° C. to adjust pH ~5. The mixture was diluted with ice-water (3 L) and extracted with EtOAc (3×2.5 L). The combined organic layers were dried over anhydrous $Na_2SO_4$, filtered, the filtrate was concentrated under reduced pressure, and the residue was purified by silica gel column chromatography to give 5-[2-[(1 S)-1-methoxyethyl]pyridin-3-yl]-2,2-dimethyl-5-oxopentanoic acid (87 g, 34% yield) as a solid. LCMS (ESI): m/z [M+H] calc'd for $C_{15}H_{21}NO_4$ 279.2; found 280.1.

Step 2. To a mixture of 5-[2-[(1S)-1-methoxyethyl]pyridin-3-yl]-2,2-dimethyl-5-oxopentanoic acid (78 g, 279 mmol) in EtOH (0.78 L) at rt under an atmosphere of $N_2$ was added (4-bromophenyl)hydrazine HCl salt (68.7 g, 307 mmol) in portions. The mixture was heated to 85° C. and stirred for 2 h, cooled to rt, then 4M HCl in 1,4-dioxane (69.8 mL, 279 mmol) added dropwise. The mixture was heated to 85° C. and stirred for an additional 3 h, then concentrated under reduced pressure, and the residue was dissolved in TFA (0.78 L). The mixture was heated to 60° C. and stirred for 1.5 h, concentrated under reduced pressure, and the residue adjusted to pH ~5 with saturated $NaHCO_3$, then extracted with EtOAc (3×1.5 L). The combined organic layers were dried over anhydrous $Na_2SO_4$, filtered, the filtrate concentrated under reduced pressure, and the residue was purified by silica gel column chromatography to give 3-(5-bromo-2-[2-[(1 S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (78 g, crude). LCMS (ESI): m/z [M+H] calc'd for $C_{21}H_{23}BrN_2O_3$ 430.1 and $C_{23}H_{27}BrN_2O_3$ 458.1; found 431.1 and 459.1.

Step 3. To a mixture of 3-(5-bromo-2-[2-[(1 S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of $N_2$ was added $Cs_2COS$ (449 g, 1.38 mol) in portions. EtI (215 g, 1.38 mmol) in DMF (200 mL) was then added dropwise at 0° C. The mixture was warmed to rt and stirred for 4 h then diluted with brine (5 L) and extracted with EtOAc (3×2.5 L). The combined organic layers were washed with brine (2×1.5 L), dried over anhydrous $Na_2SO_4$, and filtered. The filtrate was concentrated under reduced pressure and the residue was purified by silica gel column chromatography to give ethyl 3-(5-bromo-1-ethyl-2-[2-[(1 S)-1-methoxyethyl]pyridin-3-yl]indol-3-yl)-2,2-dimethylpropanoate (160 g, 57% yield) as a solid. LCMS (ESI): m/z [M+H] calc'd for $C_{25}H_{31}BrN_2O_3$ 486.2; found 487.2.

Step 4. To a mixture of ethyl 3-(5-bromo-1-ethyl-2-[2-[(1 S)-1-methoxyethyl]pyridin-3-yl]indol-3-yl)-2,2-dimethylpropanoate (160 g, 328 mmol) in THF (1.6 L) at 0° C. under an atmosphere of $N_2$ was added $LiBH_4$ (28.6 g, 1.3 mol). The mixture was heated to 60° C. for 16 h, cooled, and quenched with pre-cooled (0° C.) aqueous $NH_4Cl$ (5 L). The mixture was extracted with EtOAc (3×2 L) and the combined organic layers were washed with brine (2×1 L), dried over anhydrous $Na_2SO_4$, and filtered. The filtrate was concentrated under reduced pressure and the residue was purified by silica gel column chromatography to give to two atropisomers (as single atropisomers) of 3-(5-bromo-1-ethyl-2-(2-((S)-1-methoxyethyl)pyridin-3-yl)-1H-indol-3-yl)-2,2-dimethylpropan-1-ol (60 g, 38% yield) and (40 g, 26% yield) both as solids. LCMS (ESI): m/z [M+H] calc'd for $C_{23}H_{29}BrN_2O_2$ 444.1; found 445.2.

Intermediate 2. Synthesis of tert-butyl (($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate

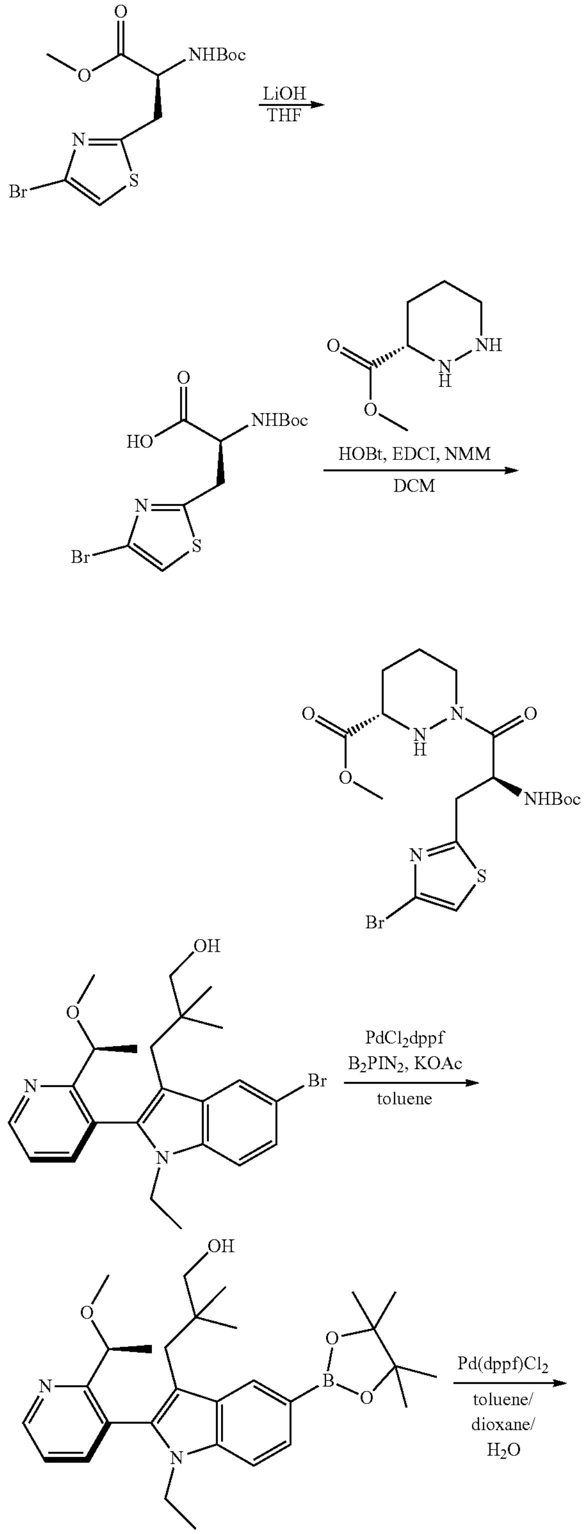

-continued

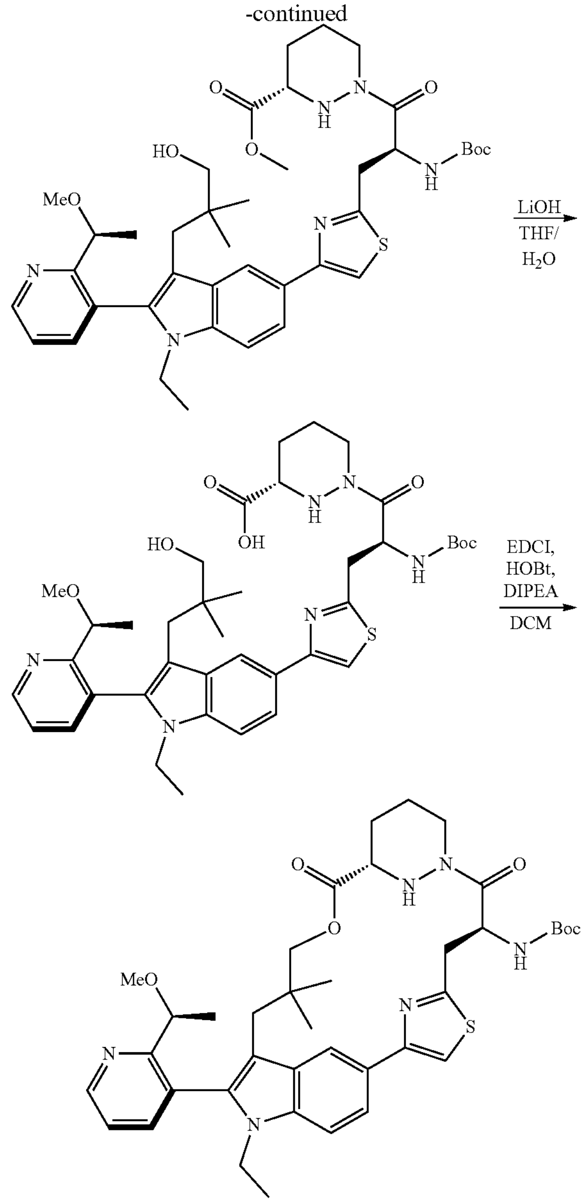

Step 1. To a solution of methyl (2S)-3-(4-bromo-1,3-thiazol-2-yl)-2-[(tert-butoxycarbonyl)amino]propanoate (110 g, 301.2 mmol) in THE (500 mL) and $H_2O$ (200 mL) at room temperature was added LiOH (21.64 g, 903.6 mmol). The resulting solution was stirred for 1 h and was then concentrated under reduced pressure. The resulting residue was adjusted to pH 6 with 1 M HCl and then extracted with DCM (3×500 mL). The combined organic layers were, dried over $Na_2SO_4$, filtered, and concentrated under reduced pressure to afford the desired product (108 g, crude). LCMS (ESI) m/z: [M+H] calcd for Cn $H_{15}BrN_2O_4S$: 351.00; found 351.0.

Step 2. To a solution of (S)-3-(4-bromothiazol-2-yl)-2-((tert-butoxycarbonyl)amino)propanoic acid (70 g, 199.3 mmol) in DCM (500 mL) at 0° C. was added methyl (3S)-1,2-diazinane-3-carboxylate bis(trifluoroacetic acid) salt (111.28 g, 298.96 mmol), NMM (219.12 mL. 1993.0 mmol), EDCI (76.41 g, 398.6 mmol) and HOBt (5.39 g, 39.89 mmol). The resulting solution was warmed to room temperature and stirred for 1 h. The reaction was then quenched with $H_2O$ (500 mL) and was extracted with EtOAc (3×500 mL). The combined organic layers were dried over $Na_2SO_4$, filtered, and concentrated under reduced pressured. The residue was purified by silica gel chromatography (0-+50% EtOAc/pet. ether) to afford the desired product (88.1 g, 92.6% yield). LCMS (ESI) m/z: [M+H] calcd for $C_{17}H_{25}BrN_4O_5S$: 477.08; found 477.1.

Step 3. To a solution of 3-(5-bromo-1-ethyl-2-(2-((S)-1-methoxyethyl)pyridin-3-yl)-1H-indol-3-yl)-2,2-dimethyl-propan-1-ol (60 g, 134.7 mmol) in toluene (500 mL) at room temperature was added bis(pinacolato)diboron (51.31 g, 202.1 mmol), Pd(dppf)$Cl_2$ (9.86 g, 13.48 mmol) and KOAc (26.44 g, 269.4 mmol). Then reaction mixture was then heated to 90° C. and stirred for 2 h. The reaction solution was then cooled to room temperature and concentrated under reduced pressure. Purification by silica gel chromatography (0→50% EtOAc/pet. ether) afforded the desired product (60.6 g, 94.0% yield). LCMS (ESI) m/z: [M+H] calcd for $C_{29}H_{41}BN_2O_4$: 493.32; found 493.3.

Step 4. To a solution of (S)-3-(1-ethyl-2-(2-(1-methoxy-ethyl)pyridin-3-yl)-5-(4,4,5,5-tetramethyl-1,3,2-dioxaborolan-2-yl)-1H-indol-3-yl)-2,2-dimethylpropan-1-ol (30 g, 60.9 mmol) in toluene (600 mL), dioxane (200 mL), and $H_2O$ (200 mL) at room temperature was added methyl (S)-1-((S)-3-(4-bromothiazol-2-yl)-2-((tert-butoxycarbonyl)amino)propanoyl)hexahydropyridazine-3-carboxylate (43.62 g, 91.4 mmol), $K_3PO_4$ (32.23 g, 152.3 mmol) and Pd(dppf)$Cl_2$ (8.91 g, 12.18 mmol). The resulting solution was heated to 70° C. and stirred overnight. The reaction mixture was then cooled to room temperature and was quenched with $H_2O$ (200 mL). The resulting mixture was extracted with EtOAc (3×1000 mL) and the combined organic layers were dried over $Na_2SO_4$, filtered, and concentrated under reduced pressure. The residue was purified by silica gel chromatography (0→90% EtOAc/pet. ether) to afford the desired product (39.7 g, 85.4% yield). LCMS (ESI) m/z: [M+H] calcd for $C_{40}H_{54}N_6O_7S$: 763.39; found 763.3.

Step 5. To a solution of methyl (S)-1-((S)-2-((tert-butoxy-carbonyl)amino)-3-(4-(1-ethyl-3-(3-hydroxy-2,2-dimethyl-propyl)-2-(2-((S)-1-methoxyethyl)pyridin-3-yl)-1H-indol-5-yl)thiazol-2-yl)propanoyl)hexahydropyridazine-3-carboxylate (39.7 g, 52.0 mmol) in THE (400 mL) and $H_2O$ (100 mL) at room temperature was added LiOH·$H_2O$ (3.74 g, 156.2 mmol). The resulting mixture was stirred for 1.5 h and was then concentrated under reduced pressure. The residue was acidified to pH 6 with 1 M HCl and extracted with DCM (3×1000 mL). The combined organic layers were dried over $Na_2SO_4$, filtered, and concentrated under reduced pressure to afford the desired product (37.9 g, crude). LCMS (ESI) m/z: [M+H] calcd for $C_{39}H_{52}N_6O_7S$: 749.37; found 749.4.

Step 6. To a solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, 50.6 mmol), HOBt (34.19 g, 253.0 mmol) and DIPEA (264.4 mL, 1518 mmol) in DCM (4 L) at 0° C. was added EDCl (271.63 g, 1416.9 mmol). The resulting mixture was warmed to room temperature and stirred overnight. The reaction mixture was then quenched with $H_2O$ and washed with 1 M HCl (4×1 L). The organic layer was separated and concentrated under reduced pressure. The residue was purified by silica gel chromatography (0→70% EtOAc/pet. ether) to afford the desired product (30 g, 81.1% yield). LCMS (ESI) m/z: [M+H] calcd for $C_{39}H_{50}N_6O_6S$: 731.36; found 731.3.

Intermediate 3. Synthesis of (S)-3-bromo-5-iodo-2-(1-methoxyethyl) pyridine

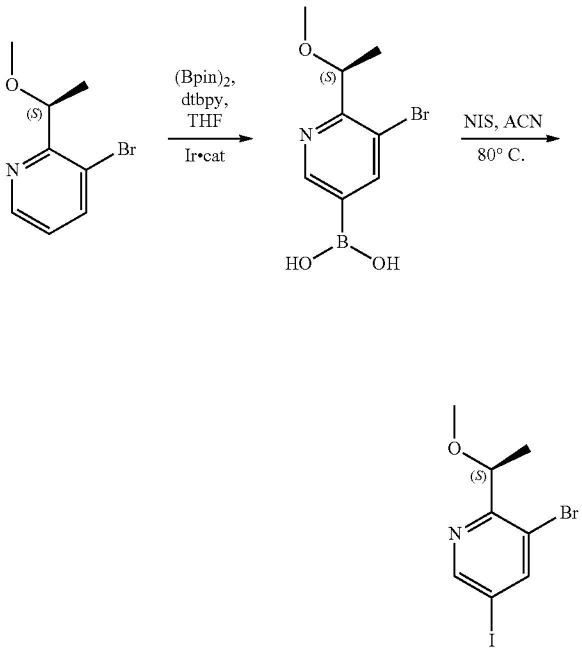

Step 1. To a stirred solution of 3-bromo-2-[(1 S)-1-methoxyethyl]pyridine (80.00 g, 370.24 mmol, 1.00 equiv) and bis(pinacolato)diboron (141.03 g, 555.3 mmol, 1.50 equiv) in THE (320 mL) was added dtbpy (14.91 g, 55.5 mmol) and Chloro(1,5-cyclooctadiene)iridium(I) dimer (7.46 g, 11.1 mmol) under argon atmosphere. The resulting mixture was stirred for 16 h at 75° C. under argon atmosphere. The mixture was concentrated under reduced pressure. The resulting mixture was dissolved in EtOAc (200 mL) and the mixture was adjusted to pH 10 with $Na_2CO_3$ (40 g) and NaOH (10 g) (mass 4:1) in water (600 mL). The aqueous layer was extracted with EtOAc (800 mL). The aqueous phase was acidified to pH=6 with HCl (6 N) to precipitate the desired solid to afford 5-bromo-6-[(1S)-1-methoxyethyl]pyridin-3-ylboronic acid (50 g, 52.0% yield) as a light-yellow solid. LCMS (ESI): m/z [M+H] calc'd for $C_8H_{11}BBrNO_3$ 259.0; found 260.0.

Step 2. To a stirred solution of 5-bromo-6-[(1 S)-1-methoxyethyl]pyridin-3-ylboronic acid (23.00 g, 88.5 mmol) in ACN (230 mL) were added NIS (49.78 g, 221.2 mmol) at room temperature under argon atmosphere. The resulting mixture was stirred for overnight at 80° C. under argon atmosphere. The resulting mixture was concentrated under reduced pressure. The resulting mixture was dissolved in DCM (2.1 L) and washed with $Na_2S_2O_3$ (3×500 mL). The organic layer was dried over anhydrous $Na_2SO_4$. After filtration, the filtrate was concentrated under reduced pressure. The residue was purified by silica gel column chromatography to afford (S)-3-bromo-5-iodo-2-(1-methoxy-ethyl)pyridine (20 g, 66.0% yield). LCMS (ESI): m/z [M+H] calc'd for $C_8H_9BrINO$ 340.9; found 341.7.

Intermediate 4. Synthesis of tert-butyl (($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate
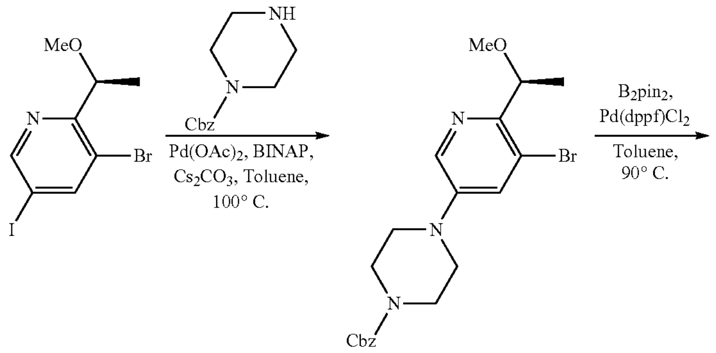
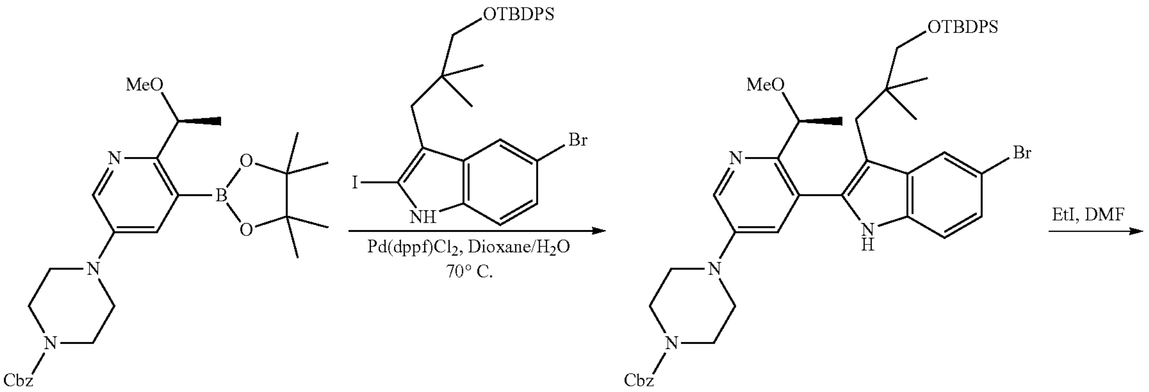
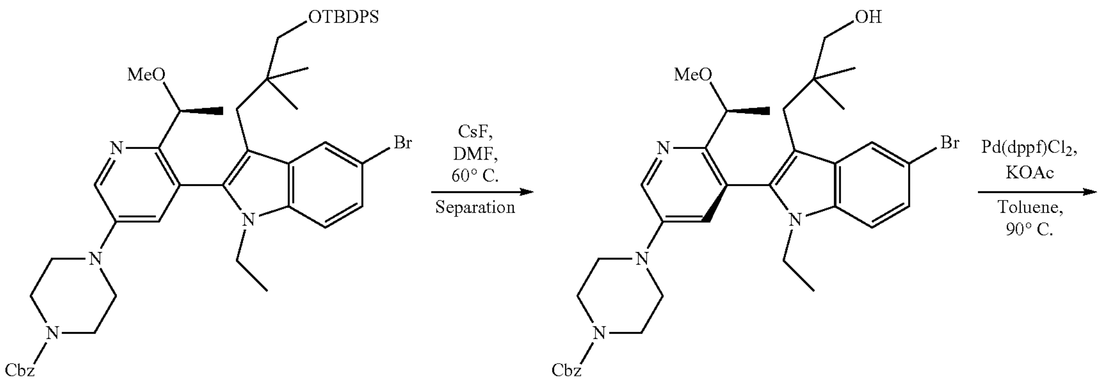

-continued
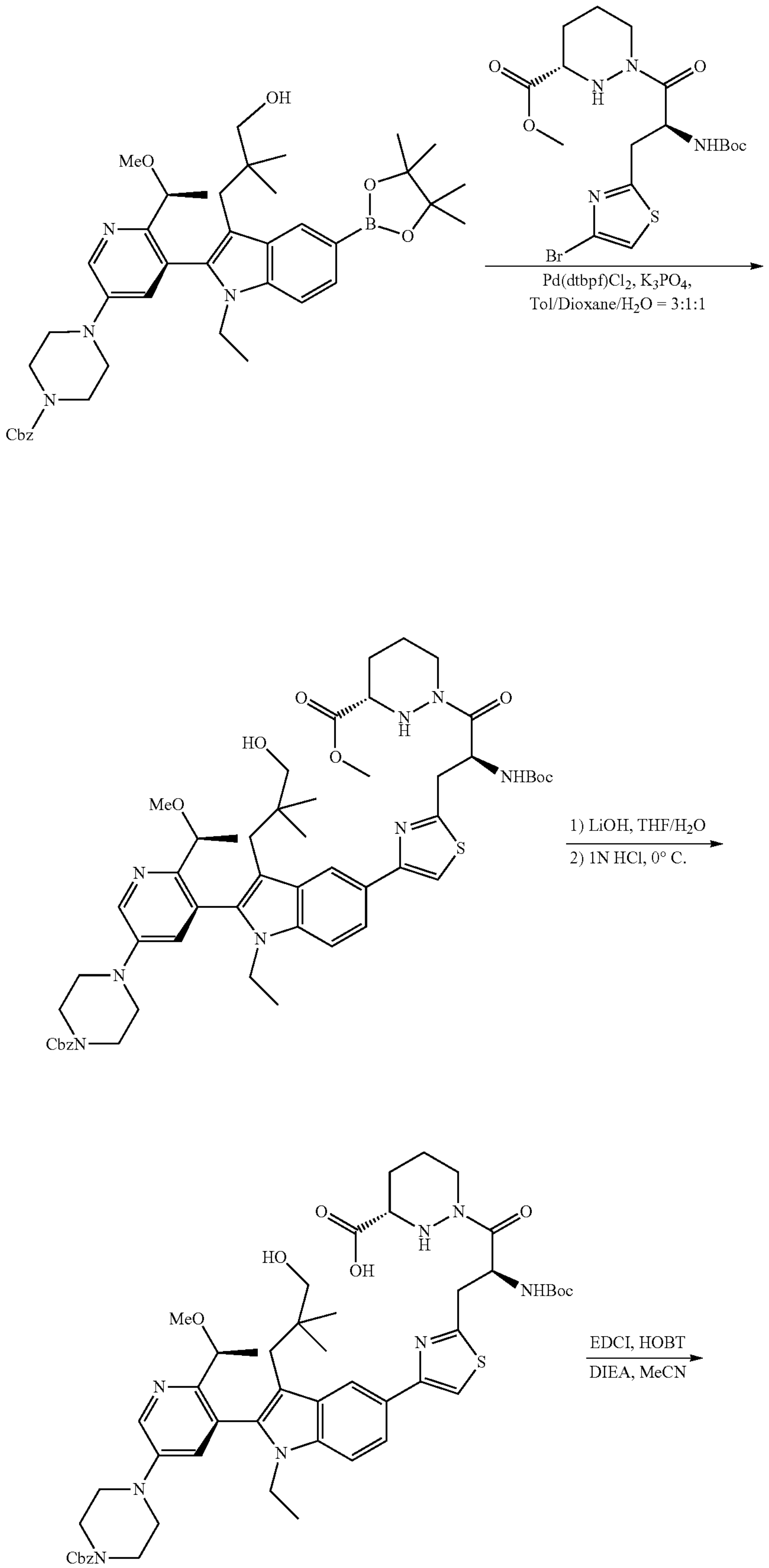

-continued

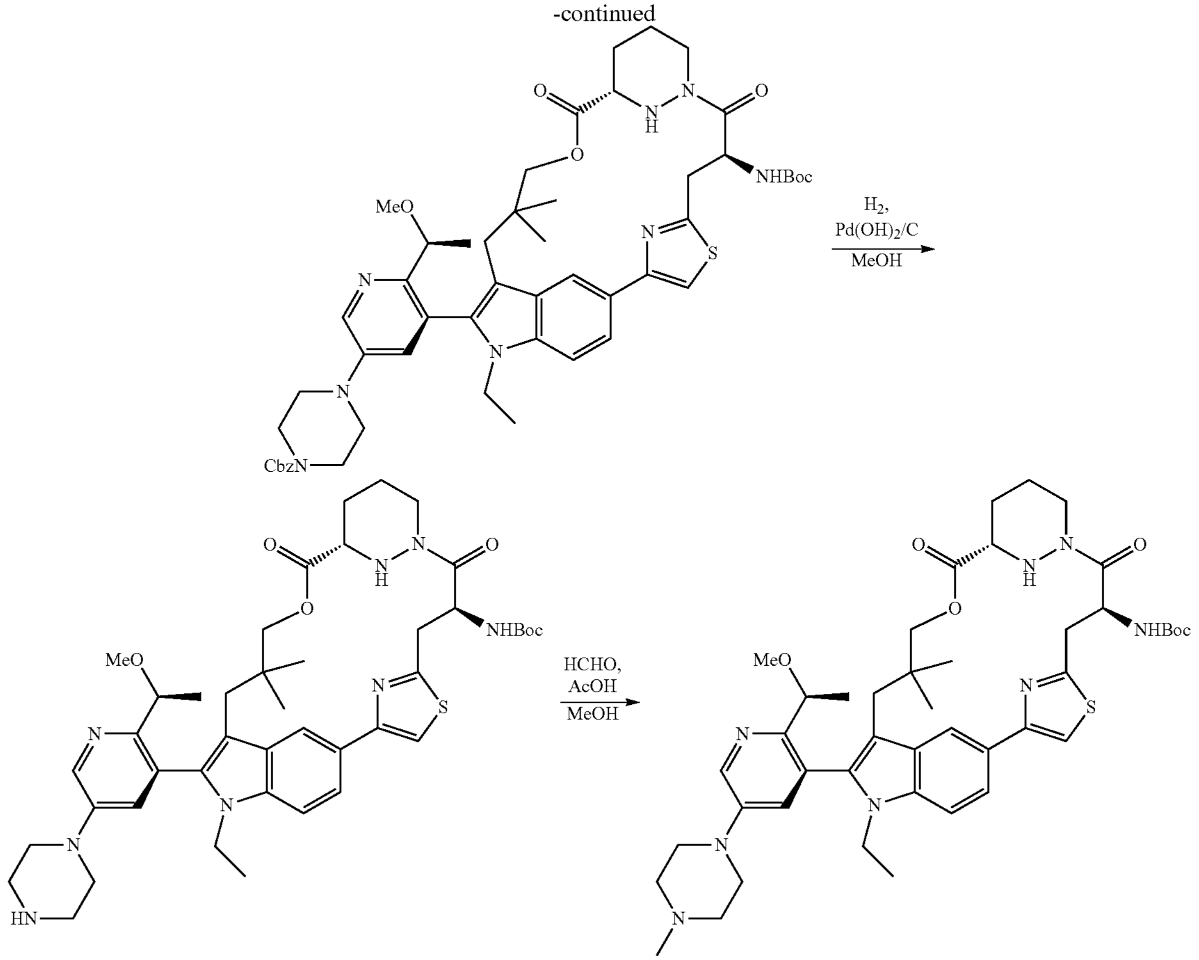

Step 1. Into a 3 L 3-necked round-bottom flask purged and maintained with an inert atmosphere of argon, was placed 3-bromo-5-iodo-2-[(1 S)-1-methoxyethyl]pyridine (147 g, 429.8 mmol) benzyl piperazine-1-carboxylate (94.69 g, 429.8 mmol), $Pd(OAc)_2$ (4.83 g, 21.4 mmol), BINAP (5.35 g, 8.6 mmol), $Cs_2CO_3$ (350.14 g, 1074.6 mmol), toluene (1 L). The resulting solution was stirred for overnight at 100° C. in an oil bath. The reaction mixture was cooled to 25° C. after reaction completed. The resulting mixture was concentrated under reduced pressure. The residue was applied onto a silica gel column with ethyl acetate/hexane (1:1). Removal of solvent under reduced pressure gave benzyl (S)-4-(5-bromo-6-(1-methoxyethyl)pyridin-3-yl)piperazine-1-carboxylate (135 g, 65.1% yield) as a dark yellow solid. LCMS (ESI): m/z [M+H] calc'd for $C_{20}H_{24}BrN_3O_3$ 433.1; found 434.1.

Step 2. Into a 3-L 3-necked round-bottom flask purged and maintained with an inert atmosphere of argon, was placed benzyl 4-[5-bromo-6-[(1 S)-1-methoxyethyl]pyridin-3-yl]piperazine-1-carboxylate (135 g, 310.8 mmol), bis(pinacolato)diboron (86.82 g, 341.9 mmol), $Pd(dppf)Cl_2$ (22.74 g, 31.0 mmol), KOAc (76.26 g, 777.5 mmol), Toluene (1 L). The resulting solution was stirred for 2 days at 90° C. in an oil bath. The reaction mixture was cooled to 25° C. The resulting mixture was concentrated under vacuum. The residue was applied onto a neutral alumina column with ethyl acetate/hexane (1:3). Removal of solvent under reduced pressure gave benzyl (S)-4-(6-(1-methoxyethyl)-5-(4,4,5,5-tetramethyl-1,3,2-dioxaborolan-2-yl)pyridin-3-yl)piperazine-1-carboxylate (167 g, crude) as a dark yellow solid. LCMS (ESI): m/z [M+H] calc'd for $C_{26}H_{36}BN_3O_5$ 481.3; found 482.1.

Step 3. Into a 3-L 3-necked round-bottom flask purged and maintained with an inert atmosphere of argon, was placed (S)-4-(6-(1-methoxyethyl)-5-(4,4,5,5-tetramethyl-1,3,2-dioxaborolan-2-yl)pyridin-3-yl)piperazine-1-carboxylate (167 g, 346.9 mmol), 5-bromo-3-[3-[(tert-butyldiphenylsilyl)oxy]-2,2-dimethylpropyl]-2-iodo-1H-indole (224.27 g, 346.9 mmol), $Pd(dppf)Cl_2$ (25.38 g, 34.6 mmol), dioxane (600 mL), $H_2O$ (200 mL), K3P04 (184.09 g, 867.2 mmol), Toluene (200 mL). The resulting solution was stirred for overnight at 70° C. in an oil bath. The reaction mixture was cooled to 25° C. after reaction completed. The resulting mixture was concentrated under vacuum. The residue was applied onto a silica gel column with ethyl acetate/hexane (1:1). Removal of solvent under reduced pressure gave benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 48.1% yield) as a yellow solid. LCMS (ESI): m/z [M+H] calc'd for $C_{49}H_{57}BrN_4O_4Si$ 872.3; found 873.3.

Step 4. To a stirred mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 167.0 mmol) and $Cs_2CO_3$ (163.28 g, 501.1 mmol) in DMF (1200 mL) was added $C_2H_{51}$ (52.11 g, 334.0 mmol) in portions at 0° C. under $N_2$ atmosphere. The final reaction mixture was stirred at 25° C. for 12 h. Desired product could be detected by LCMS. The resulting mixture was diluted with EA (1 L) and washed with brine (3×1.5 L). The organic layers were dried over anhydrous $Na_2SO_4$. After filtration, the filtrate was concentrated under reduced pressure to give benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, crude) as a yellow solid that was used directly for next step without further purification. LCMS (ESI): m/z [M+H] calc'd for $C_{51}H_{61}BrN_4O_4Si$ 900.4; found 901.4.

Step 5. To a stirred mixture of benzyl benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, 158.5 mmol) in DMF (1250 mL) was added CsF (72.24 g, 475.5 mmol). Then the reaction mixture was stirred at 60° C. for 2 days under $N_2$ atmosphere. Desired product could be detected by LCMS. The resulting mixture was diluted with EA (1 L) and washed with brine (3×1 L). Then the organic phase was concentrated under reduced pressure. The residue was purified by silica gel column chromatography, eluted with PE/EA (1/3) to afford two atropisomers of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (38 g, 36% yield, RT=1.677 min in 3 min LCMS (0.1% FA)) and B (34 g, 34% yield, RT=1.578 min in 3 min LCMS (0.1% FA)) both as yellow solid. LCMS (ESI): m/z [M+H] calc'd for $Cs_5H_{43}BrN_4O_4$ 663.2; found 662.2.

Step 6. Into a 500-mL 3-necked round-bottom flask purged and maintained with an inert atmosphere of nitrogen, was placed benzyl (S)-4-(5-(5-bromo-1-ethyl-3-(3-hydroxy-2,2-dimethylpropyl)-1H-indol-2-yl)-6-(1-methoxyethyl) pyridin-3-yl)piperazine-1-carboxylate A (14 g, 21.1 mmol), bis(pinacolato)diboron (5.89 g, 23.21 mmol), $Pd(dppf)Cl_2$ (1.54 g, 2.1 mmol), KOAc (5.18 g, 52.7 mmol), Toluene (150 mL). The resulting solution was stirred for 5 h at 90° C. in an oil bath. The reaction mixture was cooled to 25° C. The resulting mixture was concentrated under vacuum. The residue was purified by silica gel column chromatography, eluted with PE/EA (1/3) to give benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl) pyridin-3-yl)piperazine-1-carboxylate (12 g, 76.0% yield) as a yellow solid. LCMS (ESI): m/z [M+H] calc'd for $C_{41}H_{55}BN_4O_6$ 710.4; found 711.3.

Step 7. Into a 250-mL round-bottom flask purged and maintained with an inert atmosphere of argon, was placed benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (10.8 g, 15.2 mmol), methyl (3S)-1-[(2S)-3-(4-bromo-1,3-thiazol-2-yl)-2-[(tert-butoxycarbonyl)amino] propanoyl]-1,2-diazinane-3-carboxylate (7.98 g, 16.7 mmol), $Pd(dtbpf)Cl_2$ (0.99 g, 1.52 mmol), $K_3PO_4$ (8.06 g, 37.9 mmol), Toluene (60 mL), dioxane (20 mL), $H_2O$ (20 mL). The resulting solution was stirred for 3 h at 70° C. in an oil bath. The reaction mixture was cooled to 25° C. The resulting solution was extracted with EtOAc (2×50 mL) and concentrated under reduced pressure. The residue was applied onto a silica gel column with ethyl acetate/hexane (10:1). Removal of solvent to give methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (8 g, 50.9% yield) as a yellow solid. LCMS (ESI): m/z [M+H] calc'd for $C_{52}H_{68}N_8O_9S$ 980.5; found 980.9.

Step 8. To a stirred mixture of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (12 g, 12.23 mmol) in THE (100 mL)/$H_2O$ (100 mL) was added LiOH (2.45 g, 61.1 mmol) under $N_2$ atmosphere and the resulting mixture was stirred for 2 h at 25° C. Desired product could be detected by LCMS. THE was concentrated under reduced pressure. The pH of aqueous phase was acidified to 5 with HCL (1 N) at 0° C. The aqueous layer was extracted with DCM (3×100 ml). The organic phase was concentrated under reduced pressure to give (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl) hexahydropyridazine-3-carboxylic acid (10 g, 84.5% yield) as a light yellow solid. LCMS (ESI): m/z [M+H] calc'd for $C_{51}H_{66}N_8O_9S$ 966.5; found 967.0.

Step 9. Into a 3-L round-bottom flask purged and maintained with an inert atmosphere of nitrogen, was placed (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl) hexahydropyridazine-3-carboxylic acid (18 g, 18.61 mmol), ACN (1.8 L), DIEA (96.21 g, 744.4 mmol), EDCl (107.03 g, 558.3 mmol), HOBT (25.15 g, 186.1 mmol). The resulting solution was stirred for overnight at 25° C. The resulting mixture was concentrated under vacuum after reaction completed. The resulting solution was diluted with DCM (1 L). The resulting mixture was washed with HCl (3×1 L, 1 N aqueous). The resulting mixture was washed with water (3×1 L). Then the organic layer was concentrated, the residue was applied onto a silica gel column with ethyl acetate/hexane (1:1). Removal of solvent under reduced pressure gave benzyl 4-(5-(($6^3$S,4S,2)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)piperazine-1-carboxylate (10.4 g, 54.8% yields) as a light yellow solid. LCMS (ESI): m/z [M+H] calc'd for $C_{51}H_{64}N_8O_8S$ 948.5; found 949.3.

Step 10. Into a 250-mL round-bottom flask purged and maintained with an inert atmosphere of nitrogen, was placed benzyl 4-(5-(($6^3$S,4S,2)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl) pyridin-3-yl)piperazine-1-carboxylate (10.40 g, 10.9 mmol), $Pd(OH)_2/C$ (5 g, 46.9 mmol), MeOH (100 mL). The resulting solution was stirred for 3 h at 25° C. under 2 atm $H_2$ atmosphere. The solids were filtered out and the filter cake was washed with MeOH (3×100 mL). Then combined organic phase was concentrated under reduced pressure to give tert-butyl (($6^3$S,4S,Z)-11-ethyl-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (8.5 g, 90.4% yield) as a light yellow solid. LCMS (ESI): m/z [M+H] calc'd for $C_{43}H_{58}N_8O_6S$ 814.4; found 815.3.

Step 11. Into a 1000-mL round-bottom flask purged and maintained with an inert atmosphere of nitrogen, was placed tert-butyl (($6^{3}$S,4S,Z)-11-ethyl-$1^{2}$-(2-((S)-1-methoxyethyl)-5-(piperazin-1-yl)pyridin-3-yl)-10,10-dimethyl-5,7-dioxo-$6^{1}$,$6^{2}$,$6^{3}$,$6^{4}$,$6^{5}$,$6^{6}$-hexahydro-$1^{1}$H-8-oxa-2(4,2)-thiazola-1(5,3)-indola-6(1,3)- pyridazinacycloundecaphane-4-yl) carbamate (8.5 g, 10.4 mmol), MeOH (100 mL), AcOH (1.88 g, 31.2 mmol) and stirred for 15 mins. Then HCHO (1.88 g, 23.15 mmol, 37% aqueous solution) and $NaBH_3CN$ (788 mg, 12.5 mmol) was added at 25° C. The resulting solution was stirred for 3 h at 25° C. The resulting mixture was quenched with 100 mL water and concentrated under reduced pressure to remove MeOH. The resulting solution was diluted with 300 mL of DCM. The resulting mixture was washed with water (3×100 mL). Removal of solvent gave tert-butyl (($6^{3}$S,4S,Z)-$1^{1}$-ethyl-$1^{2}$-(2-((S)-1-methoxy-ethyl)-5-(4-methylpiperazin-1-yl)pyridin-3-yl)-10,10-dim-ethyl-5,7-dioxo-$6^{1}$,$6^{2}$,$6^{3}$,$6^{4}$,$6^{5}$,$6^{6}$-hexahydro-$1^{1}$H-8-oxa-2(4,2)-thiazola-1(5,3)-indola-6(1,3)-pyridazinacycloundecaphane-4-yl)carbamate (8.2 g, 90.1% yield) as a yellow solid. LCMS (ESI): m/z [M+H] calc'd for $C_{44}H_{60}N_8O_6S$ 828.4; found 829.3.

Intermediate 5. Synthesis of ($6^{3}$S,4S)-4-amino-$1^{1}$-ethyl-$1^{2}$-(2-((S)-1-methoxyethyl)pyridin-3-yl)-10,10-dimethyl-$6^{1}$,$6^{2}$,$6^{3}$,$6^{4}$,$6^{5}$,$6^{6}$-hexahydro-$1^{1}$H-8-oxa-1(5,3)-indola-6(1,3)-pyridazina-2(1,3)-benzenacycloundecaphane-5,7-dione

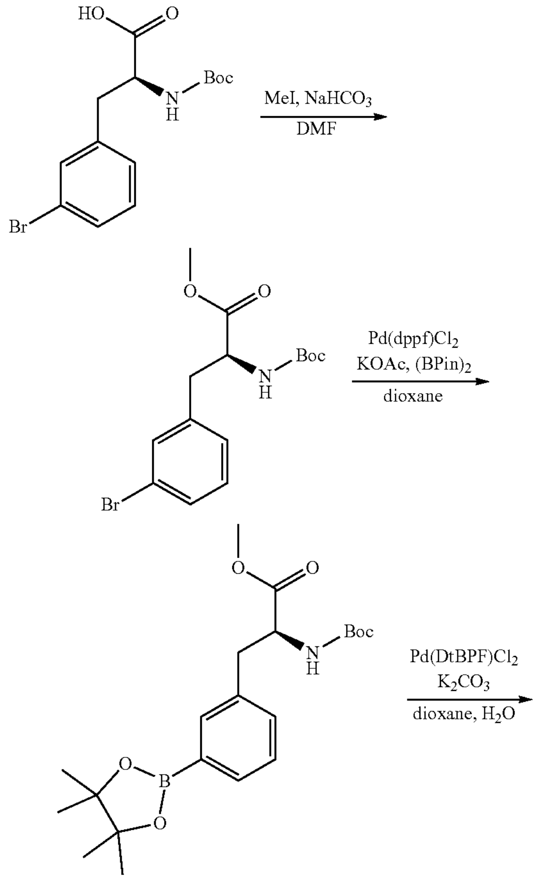

-continued

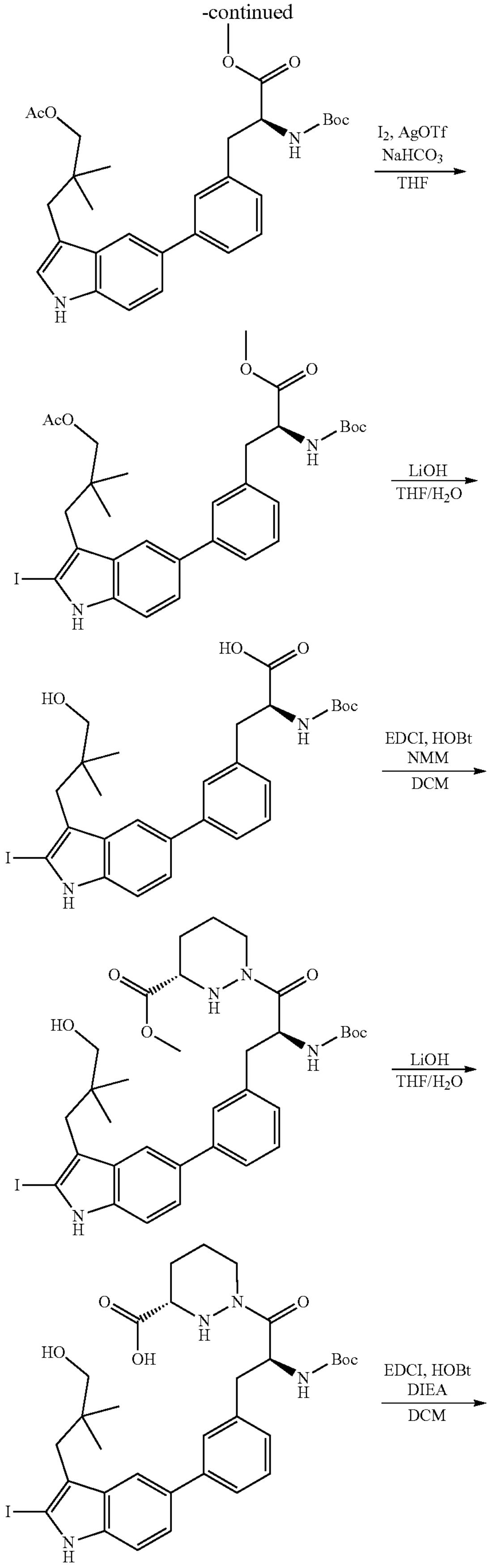

-continued

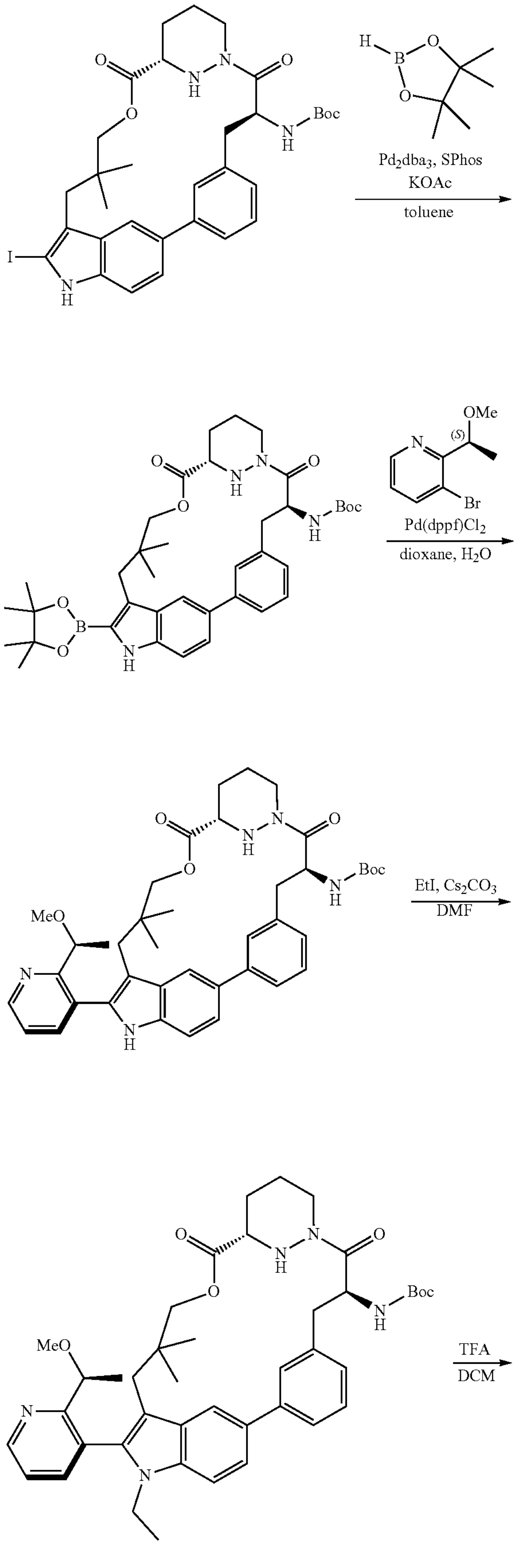

-continued

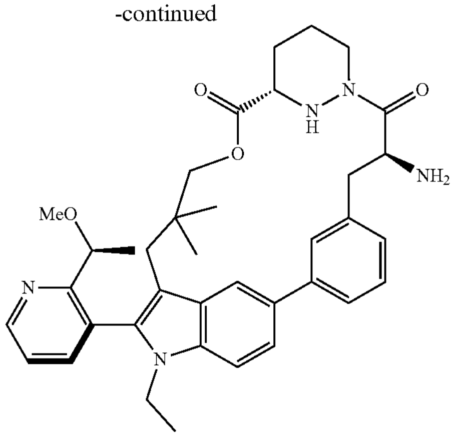

Step 1. To a solution of (2S)-3-(3-bromophenyl)-2-[(tert-butoxycarbonyl)amino]propanoic acid (100 g, 290 mmol) in DMF (1 L) at room temperature was added $NaHCO_3$ (48.8 g, 581.1 mmol) and MeI (61.9 g, 435.8 mmol). The reaction mixture was stirred for 16 h and was then quenched with $H_2O$ (1 L) and extracted with EtOAc (3×1 L). The combined organic layers were washed with brine (3×500 mL), dried over $Na_2SO_4$, filtered, and concentrated under reduced pressure. The residue was purified by silica gel column chromatography (13% EtOAc/pet. ether) to give the final product (109 g, crude). LCMS (ESI) m/z [M+Na] calcd for $C_{15}H_{20}BrNO_4$ 380.05; found: 380.0.

Step 2. To a stirred solution of methyl (2S)-3-(3-bromophenyl)-2-[(tert-butoxycarbonyl)amino]propanoate (108 g, 301.5 mmol) and bis(pinacolato)diboron (99.53 g, 391.93 mmol) in dioxane (3.2 L) was added KOAc (73.97 g, 753.70 mmol) and $Pd(dppf)Cl_2$ (22.06 g, 30.15 mmol). The reaction mixture was heated to 90° C. for 3 h and was then cooled to room temperature and extracted with EtOAc (2×3 L). The combined organic layers were washed with brine (3×800 mL), dried over $Na_2SO_4$, filtered, and concentrated under reduced pressure. The residue was purified by silica gel column chromatography (5% EtOAc/pet. ether) to afford the product (96 g, 78.6% yield). LCMS (ESI) m/z [M+Na] calcd for $C_{21}H_{32}BNO_6$ 428.22; found: 428.1.

Step 3. To a mixture of methyl (2S)-2-[(tert-butoxycarbonyl)amino]-3-[3-(4,4,5,5-tetramethyl-1,3,2-dioxaborolan-2-yl)phenyl]propanoate (94 g, 231.9 mmol) and 3-(5-bromo-1H-indol-3-yl)-2,2-dimethylpropyl acetate (75.19 g, 231.93 mmol) in dioxane (1.5 L) and $H_2O$ (300 mL) was added $K_2CO_3$ (64.11 g, 463.85 mmol) and $Pd(DtBPF)Cl_2$ (15.12 g, 23.19 mmol). The reaction mixture was heated to 70° C. and stirred for 4 h. The reaction mixture was extracted with EtOAc (2×2 L) and the combined organic layers were washed with brine (3×600 mL), dried over $Na_2SO_4$, filtered, and concentrated under reduced pressure. The residue was purified by silica gel column chromatography (20% EtOAc/pet. ether) to give the product (130 g, crude). LCMS (ESI) m/z [M+H] calcd for $C_{30}H_{38}N_2O_6$ 523.28; found: 523.1.

Step 4. To a solution of methyl (2S)-3-(3-[3-[3-(acetyloxy)-2,2-dimethylpropyl]-1H-indol-5-yl]phenyl)-2-[(tert-butoxycarbonyl)amino]propanoate (95.0 g, 181.8 mmol) and iodine (36.91 g, 145.41 mmol) in THF (1 L) at −10° C. was added AgOTf (70.0 g, 272.7 mmol) and $NaHCO_3$ (22.9 g, 272.65 mmol). The reaction mixture was stirred for 30 min and was then quenched by the addition of sat. aq. $Na_2S_2O_3$ (100 mL) at 0° C. The resulting mixture was extracted with EtOAc (3×1 L) and the combined organic layers were washed with brine (3×500 mL), dried over $Na_2SO_4$, filtered, and concentrated under reduced pressure. The residue was purified by silica gel column chromatography (50% EtOAc/pet. ether) to give methyl (S)-3-(3-(3-(3-acetoxy-2,2-dimethylpropyl)-2-iodo-1H-indol-5-yl)phenyl)-2-((tert-butoxycarbonyl)amino)propanoate (49.3 g, 41.8% yield). LCMS (ESI) m/z [M+H] calcd for $C_{30}H_{37}I_1N_2O$: 649.18; found: 649.1.

Step 5. To a solution of methyl (2S)-3-(3-[3-[3-(acetyloxy)-2,2-dimethylpropyl]-2-iodo-1H-indol-5-yl]phenyl)-2-[(tert-butoxycarbonyl)amino]propanoate (60 g, 92.5 mmol) in THE (600 mL) was added a solution of $LiOH{\cdot}H_2O$ (19.41 g, 462.5 mmol) in $H_2O$ (460 mL). The resulting solution was stirred overnight and then the pH was adjusted to 6 with HCl (1 M). The resulting solution was extracted with EtOAc (2×500 mL) and the combined organic layers was washed with brine (2×500 mL), dried over $Na_2SO_4$, filtered, and concentrated under reduced pressure to give the product (45 g, 82.1% yield). LCMS (ESI) m/z [M+Na] calcd for $C_{27}H_{33}IN_2O_6$ 615.13; found: 615.1.

Step 6. To a solution of (2S)-2-[(tert-butoxycarbonyl)amino]-3-[3-[3-(3-hydroxy-2,2-dimethylpropyl)-2-iodo-1H-indol-5-yl]phenyl]propanoic acid (30 g, 50.6 mmol) and methyl (3S)-1,2-diazinane-3-carboxylate (10.9 g, 75.9 mmol) in DCM (400 mL) was added NMM (40.97 g, 405.08 mmol), HOBt (2.05 g, 15.19 mmol), and EDCl (19.41 g, 101.27 mmol). The reaction mixture was stirred overnight and then the mixture was washed with sat. aq. $NH_4Cl$ (2×200 mL) and brine (2×200 mL), and the mixture was dried over $Na_2SO_4$, filtered, and concentrated under reduced pressure to give the product (14 g, 38.5% yield). LCMS (ESI) m/z [M+H] calcd for $C_{33}H_{43}IN_4O_6$ 718.23; found: 719.4.

Step 7. To a solution of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate (92 g, 128.0 mmol) in THF (920 mL) at 0° C. was added a solution of $LiOH{\cdot}H_2O$ (26.86 g, 640.10 mmol) in $H_2O$ (640 mL). The reaction mixture was stirred for 2 h and was then concentrated under reduced pressure to give the product (90 g, crude). LCMS (ESI) m/z [M+H] calcd for $C_{32}H_{41}IN_4O_6$ 705.22; found: 705.1.

Step 8. To a solution of (3S)-1-[(2S)-2-[(tert-butoxycarbonyl)amino]-3-[3-[3-(3-hydroxy-2,2-dimethylpropyl)-2-iodo-1H-indol-5-yl]phenyl]propanoyl]-1,2-diazinane-3-carboxylic acid (90 g, 127.73 mmol) in DCM (10 L) at 0° C. was added HOBt (34.52 g, 255.46 mmol), DIPEA (330.17 g, 2554.62 mmol) and EDCl (367.29 g, 1915.96 mmol). The reaction mixture was stirred for 16 h and was then concentrated under reduced pressure. The mixture was extracted with DCM (2×2 L) and the combined organic layers were washed with brine (3×1 L), dried over $Na_2SO_4$, filtered, and concentrated under reduced pressure. The residue was purified by silica gel column chromatography (50% EtOAc/pet. ether) to give the product (70 g, 79.8% yield). LCMS (ESI) m/z [M+H] calcd for $C_{32}H_{39}IN_4O_5$ 687.21; found: 687.1.

Step 9. A 1 L round-bottom flask was charged with tert-butyl (($6^3$S,4S)-$1^2$-iodo-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (22.0 g, 32.042 mmol), toluene (300.0 mL), $Pd_2(dba)_3$ (3.52 g, 3.845 mmol), S-Phos (3.95 g, 9.613 mmol), and KOAc (9.43 g, 96.127 mmol) at room temperature. To the mixture was added 4,4,5,5-tetramethyl-1,3,2-dioxaborolane (26.66 g, 208.275 mmol) dropwise with stirring at room temperature. The resulting solution was stirred for 3 h at 60° C. The resulting mixture was filtered, and the filter cake was washed with EtOAc. The filtrate was concentrated under reduced pressure and the remaining residue was purified by silica gel column chromatography to afford the product (22 g, 90% yield) as a solid. LCMS (ESI) m/z [M+H] calcd for $C_{38}H_{51}BN_4O_7$ 687.3; found: 687.4.

Step 10. A mixture of tert-butyl (($6^3$S,4S)-10,10-dimethyl-5,7-dioxo-$1^2$-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (2.0 g, 2.8 mmol), 3-bromo-2-[(1 S)-1-methoxyethyl]pyridine (0.60 g, 2.8 mmol), $Pd(dppf)Cl_2$ (0.39 g, 0.5 mmol), and $K_3PO_4$ (1.2 g, 6.0 mmol) in dioxane (50 mL) and $H_2O$ (10 mL) under an atmosphere of $N_2$ was heated to 70° C. and stirred for 2 h. The mixture was diluted with $H_2O$ (50 mL) and extracted with EtOAc (3×50 mL). The combined organic layers were washed with brine (3×50 mL), dried over anhydrous $Na_2SO_4$, and filtered. The filtrate was concentrated under reduced pressure and the residue was purified by silica gel column chromatography to afford the product (1.5 g, 74% yield) as a solid. LCMS (ESI) m/z [M+H] calcd for $C_{40}H_{49}N_5O_6$ 695.4; found: 696.5.

Step 11. To a solution of tert-butyl (($6^3$S,4S)-$1^2$-(2-((S)-1-methoxyethyl) pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (20 g, 28.7 mmol) and $Cs_2CO_3$ (18.7 g, 57.5 mmol) in DMF (150 mL) at 0° C. was added a solution of EtI (13.45 g, 86.22 mmol) in DMF (50 mL). The resulting mixture was stirred overnight at 35° C. and then diluted with $H_2O$ (500 mL). The mixture was extracted with EtOAc (2×300 mL) and the combined organic layers were washed with brine (3×100 mL), dried over $Na_2SO_4$, filtered, and concentrated under reduced pressure. The residue was purified by silica gel column chromatography to afford the product (4.23 g, 18.8% yield) and the atropisomer (5.78 g, 25.7% yield) as solids. LCMS (ESI) m/z [M+H] calcd for $C_{42}H_{53}N_5O_6$ 724.4; found: 724.6.

Step 12. A mixture of tert-butyl (($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (1.3 g, 1.7 mmol) in TFA (10 mL) and DCM (20 mL) was stirred at 0° C. for 2 h. The mixture was concentrated under reduced pressure to afford the product (1.30 g, crude) as a solid. LCMS (ESI) m/z [M+H] calcd for $C_{37}H_{45}N_5O_4$ 623.3; found: 624.4.

Intermediate 6: Synthesis of (S)-3-(5-bromo-1-ethyl-2-(5-iodo-2-(1-methoxyethyl)pyridin-3-yl)-1H-indol-3-yl)-2,2-dimethylpropyl acetate

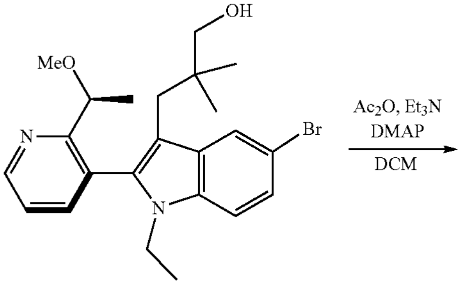

-continued

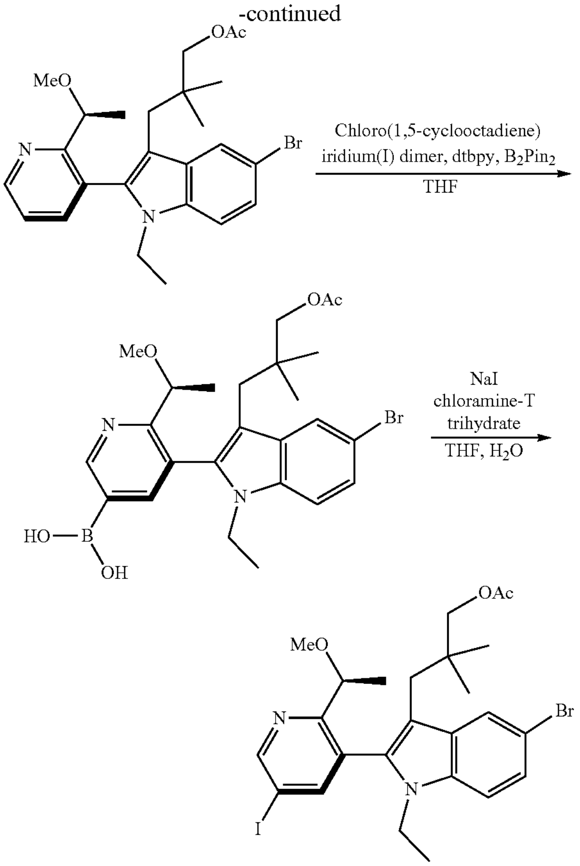

Step 1. To a stirred solution of (S)-3-(5-bromo-1-ethyl-2-(2-(1-methoxyethyl)pyridin-3-yl)-1H-indol-3-yl)-2,2-dimethylpropan-1-ol (100 g, 224.517 mmol) and $Et_3N$ (45.44 g, 449.034 mmol) in DCM (1 L) was added DMAP (2.74 g, 22.452 mmol) and $Ac_2O$ (27.50 g, 269.420 mmol) in portions at 0° C. under an argon atmosphere. The resulting mixture was stirred for 3 h at room temperature. The resulting mixture was concentrated under reduced pressure then diluted with EtOAc (1000 mL). The resulting mixture was washed with 1 M HCl (500 mL) then washed with sat. $NaHCO_3$ (500 mL) and brine (500 mL) and dried over anhydrous $Na_2SO_4$. After filtration, the filtrate was concentrated under reduced pressure. The residue was purified by trituration with pet. ether (500 mL) to afford the product (93.3 g, 85% yield) as a white solid. LCMS (ESI) m/z [M+H] calcd for $C_{25}H_{31}BrN_2O_3$: 487.16; found: 489.2.

Step 2. To a stirred solution of (S)-3-(5-bromo-1-ethyl-2-(2-(1-methoxyethyl)pyridin-3-yl)-1H-indol-3-yl)-2,2-dimethylpropyl acetate (93.3 g, 191.409 mmol) and $B_2PIN_2$ (72.91 g, 287.113 mmol) in THE (370 mL) was added dtbpy (7.71 g, 28.711 mmol) and chloro(1,5-cyclooctadiene) iridium(I) dimer (6.43 g, 9.570 mmol) in portions at room temperature under an argon atmosphere. The resulting mixture was stirred overnight at 75° C. The resulting mixture was concentrated under reduced pressure to afford the product (190 g, crude) as an oil. LCMS(ESI) m/z [M+H]; calcd for $C_{25}H_{32}BBrN_2O_5$: 531.17; found: 533.3.

Step 3. To a stirred solution of (S)-(5-(3-(3-acetoxy-2,2-dimethylpropyl)-5-bromo-1-ethyl-1H-indol-2-yl)-6-(1-methoxyethyl)pyridin-3-yl)boronic acid (110 g, 207.059 mmol) and chloramine-T trihydrate (349.96 g, 1242.354 mmol) in THE (550 mL) was added a solution of NaI (186.22 g, 1242.354 mmol) in $H_2O$ (225 mL) in portions at 0° C. under an air atmosphere. The resulting mixture was stirred overnight at 50° C. under an argon atmosphere. The resulting mixture was concentrated under reduced pressure then washed with $CHCl_3$ (500 mL). The resulting mixture was filtered, the filter cake was washed with $CHCl_3$ (3×250 mL). The filtrate was extracted with $CHCl_3$ (3×500 mL). The combined organic layers were washed with $Na_2S_2O_3$ (500 mL), washed with brine (2×200 mL) dried over anhydrous $Na_2SO_4$. After filtration, the filtrate was concentrated under reduced pressure. The residue was purified by silica gel column Intermediate 7: Synthesis of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate

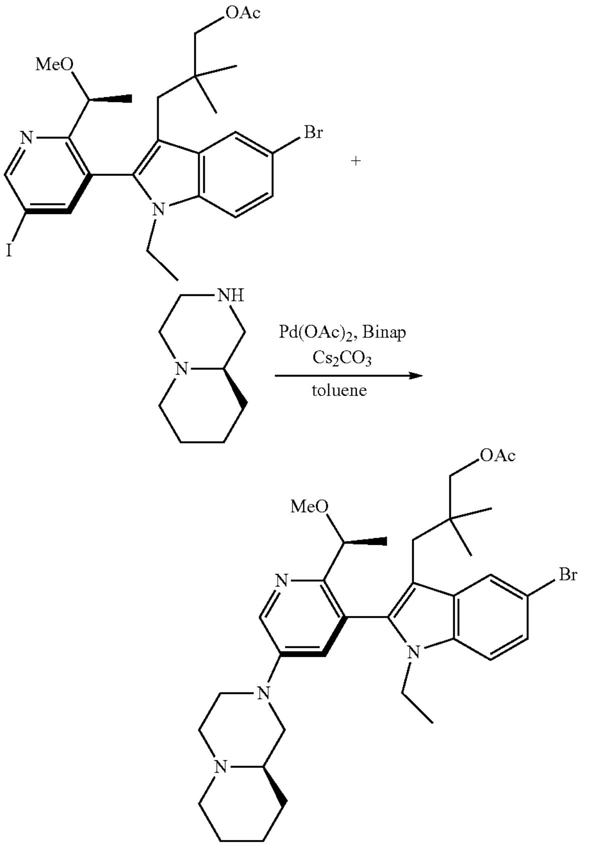

To a stirred solution of 3-(5-bromo-1-ethyl-2-{5-iodo-2-[(1 S)-1-methoxyethyl]pyridin-3-yl}indol-3-yl)-2,2-dimethylpropyl acetate (9 g, 14.674 mmol), (R)-octahydro-2H-pyrido[1,2-a]pyrazine (2.469 g, 17.609 mmol), $Cs_2CO_3$ (11.9523 g, 36.685 mmol) and BINAP (456.85 mg, 0.734 mmol) in toluene (63 mL) was added $Pd(OAc)_2$ (329.44 mg, 1.467 mmol) in portions at room temperature under an argon atmosphere. The resulting mixture was stirred for 6 h at 100° C. then the mixture was filtered, the filter cake was washed with EtOAc (100 mL). The filtrate was concentrated under reduced pressure. The residue was purified by prep-TLC (8% MeOH/DCM) to afford the product (6 g, 65% yield) as a solid. LCMS (ESI) m/z [M+H] calcd $C_{33}H_{45}BrN_4O_3$: 625.28; found: 627.4.

Intermediate 8. Synthesis of (6[3]S,4S)-4-amino-1[1]-ethyl-2[5]-(fluoromethyl)-1[2]-(2-((S)-1-methoxyethyl)pyridin-3-yl)-10,10-dimethyl-6[1],6[2],6[3],6[4],6[5],6[6]-hexahydro-1[1]H-8-oxa-1(5,3)-indola-6(1,3)-pyridazina-2(1,3)-benzenacycloundecaphane-5,7-dione

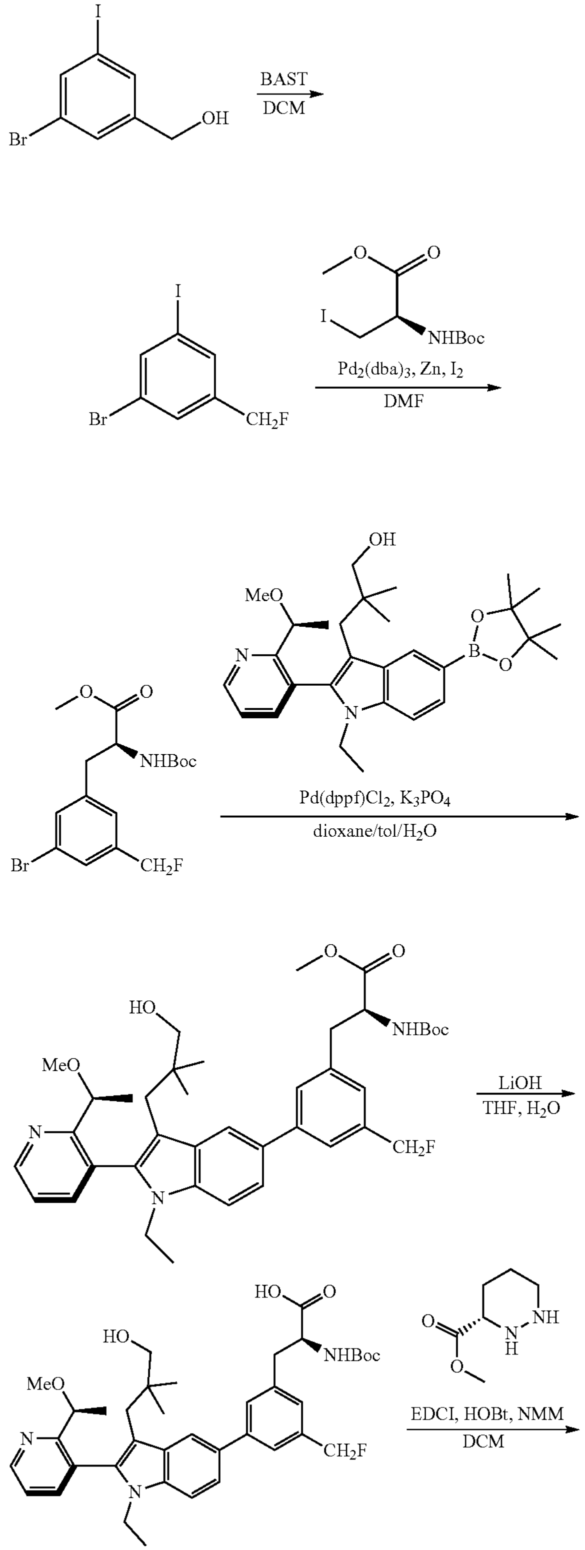

-continued

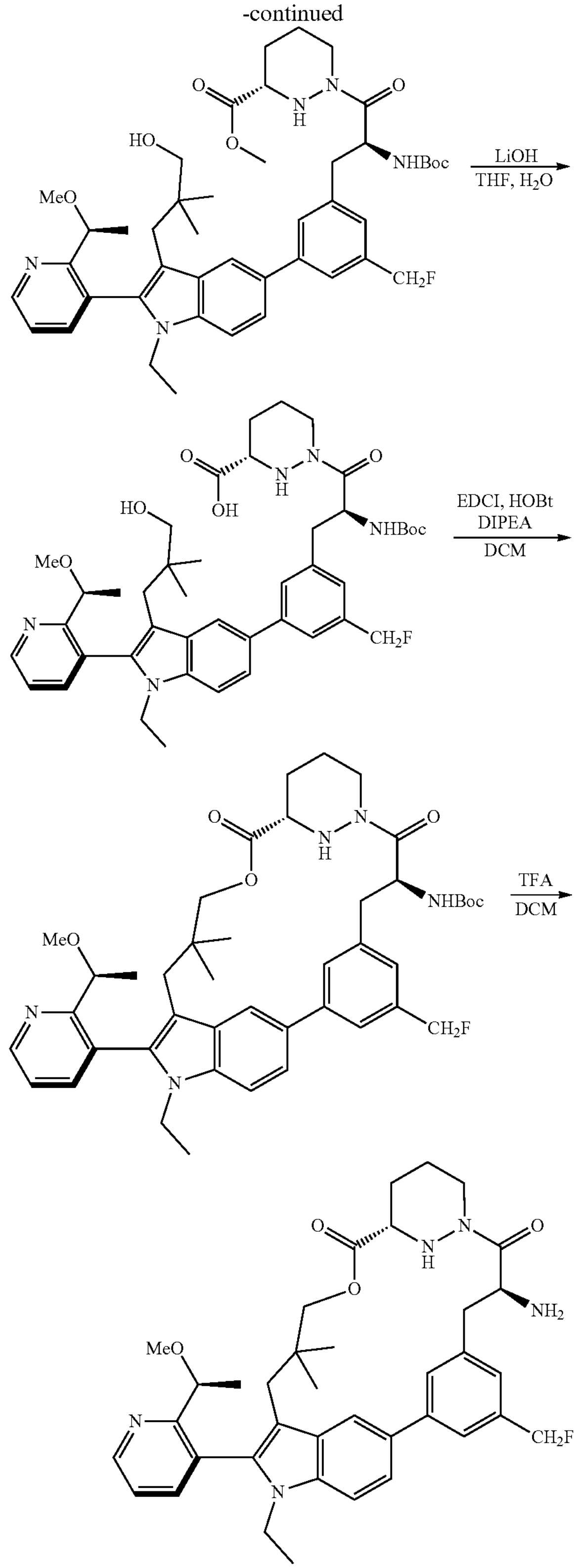

Step 1. To a solution of (3-bromo-5-iodophenyl)methanol (175.0 g, 559.227 mmol) in DCM (2 L) was added BAST (247.45 g, 1118.454 mmol) dropwise at 0° C. The resulting mixture was stirred for 16 h at room temperature. The reaction was quenched with sat. aq. $NaHCO_3$ at 0° C. The organic layers were washed with $H_2O$ (3×700 mL) and dried over anhydrous $Na_2SO_4$. After filtration, the filtrate was concentrated under reduced pressure. The residue was purified by silica gel column chromatography (3% EtOAc/pet. ether) to afford the desired product (120 g, 68% yield).

Step 2. Into a 1000 mL 3-necked round-bottom flask was added Zn powder (32.40 g, 495.358 mmol) in DMF (350.0 mL) and 12 (967.12 mg, 3.810 mmol). To the mixture was added a solution of methyl (2R)-2-[(tert-butoxycarbonyl) amino]-3-iodopropanoate (27.0 g, 82.03 mmol) in DMF (10 mL). The mixture was heated to 30° C. for 10 min. To the mixture was then added a solution of methyl (2R)-2-[(tert-butoxycarbonyl)amino]-3-iodopropanoate (54.0 g, 164.07 mmol) in DMF (20 mL). The resulting mixture was stirred for 30 min at room temperature and was filtered. The resulting solution was added to a mixture of 1-bromo-3-(fluoromethyl)-5-iodobenzene (60 g, 190.522 mmol), tris (furan-2-yl)phosphane (2.65 g, 11.431 mmol), and $Pd_2(dba)_3$ (3.49 g, 3.810 mmol) in DMF (400 mL) at room temperature under argon atmosphere and the reaction mixture was heated to 60° C. for 10 min then removed the oil bath. The resulting mixture was stirred for about 1 h until the temperature cooled down to 50° C. The reaction was quenched with aq. $NH_4Cl$ (3000 mL) and the resulting mixture was extracted with EtOAc (3×1000 mL). The combined organic layers were washed with brine (2×1000 mL) and dried over anhydrous $Na_2SO_4$. After filtration, the filtrate was concentrated under reduced pressure. The residue was purified by silica gel column chromatography (9% EtOAc/pet. ether) to afford the desired product (45 g, 60% yield).

Step 3. A mixture of methyl (2S)-3-[3-bromo-5-(fluoromethyl)phenyl]-2-[(tert-butoxycarbonyl)amino]propanoate (75.28 g, 192.905 mmol), (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (95 g, 192.905 mmol), $Pd(dppf)Cl_2$ (14.11 g, 19.291 mmol) and $K_2CO_3$ (53.32 g, 385.810 mmol) in dioxane (900 mL) and $H_2O$ (180 mL) was stirred for 2 h at 80° C. The resulting mixture was concentrated under reduced pressure and was then diluted with $H_2O$. The resulting mixture was extracted with EtOAc (3×1200 mL) and the combined organic layers were washed with $H_2O$ (3×500 mL) and dried over anhydrous $Na_2SO_4$. After filtration, the filtrate was concentrated under reduced pressure. The residue was purified by silica gel column chromatography (50% EtOAc/pet. ether) to afford the desired product (105 g, 80% yield). LCMS (ESI) m/z: [M+H] calcd for $C_{39}H_{50}FN_3O_6$: 676.38; found 676.1.

Step 4. To a stirred solution of methyl (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoate (108 g, 159.801 mmol) in THF (500 mL) was added a solution of $LiOH \cdot H_2O$ (11.48 g, 479.403 mmol) in $H_2O$ (500 mL) at 0° C. The resulting mixture was stirred for 2 h at 0° C. and was then acidified to pH 6 with 1 M HCl (aq.). The mixture was extracted with EtOAc (3×800 mL) and the combined organic layers were washed with brine (2×200 mL) and dried over anhydrous $Na_2SO_4$. After filtration, the filtrate was concentrated under reduced pressure to afford the desired product (101 g, crude). LCMS (ESI) m/z: [M+H] calcd for $C_{38}H_{48}FN_3O_6$: 662.36; found 662.1.

Step 5. To a stirred solution of (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoic acid (103 g, 155.633 mmol) and NMM (157.42 g, 1556.330 mmol) in DCM (1200 mL) was added methyl (3S)-1,2-diazinane-3-carboxylate (33.66 g, 233.449 mmol), HOBt (10.51 g, 77.816 mmol) and EDCl (59.67 g, 311.265 mmol) in portions at 0° C. The resulting mixture was stirred a t room temperature for 16 h. The organic layers were then washed with 0.5 M HCl (2×1000 mL) and brine (2×800 mL), dried over anhydrous $Na_2SO_4$, filtered, and concentrated under reduced pressure. The residue was purified by silica gel column chromatography (50% EtOAc/pet. ether) to afford the desired product (103 g, 83% yield). LCMS (ESI) m/z: [M+H] calcd for $C_{44}H_{58}FN_5O_7$: 788.44; found 788.1.

Step 6. To a stirred solution of methyl (S)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl) hexahydropyridazine-3-carboxylate (103 g, 130.715 mmol) in THE (700 mL) was added a solution of $LiOH \cdot H_2O$ (27.43 g, 653.575 mmol) in $H_2O$ (700 mL) at 0° C. The resulting mixture was stirred for 2 h at 0° C. and was then neutralized to pH 6 with 1 M HCl. The resulting mixture was extracted with EtOAc (3×800 mL) and the combined organic layers were washed with brine (2×600 mL), dried over anhydrous $Na_2SO_4$, filtered, and concentrated under reduced pressure to afford the desired product (101 g, crude). LCMS (ESI) m/z: [M+H] calcd for $C_{43}H_{56}FN_5O_7$: 774.43; found 774.1.

Step 7. To a stirred solution of (S)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl) hexahydropyridazine-3-carboxylic acid (101 g, 130.50 mmol) in DCM (5500 mL) was added DIPEA (227.31 mL, 1305.0 mmol) and HOBt (88.17 g, 652.499 mmol), and EDCl (375.26 g, 1957.498 mmol) at 0° C. The resulting mixture was stirred at room temperature overnight. The mixture was then washed with 0.5 M HCl (2×2000 mL), brine (2×2000 mL), dried over anhydrous $Na_2SO_4$, filtered, and concentrated under reduced pressure. The residue was purified by silica gel column chromatography (50% EtOAc/ pet. ether) to afford the desired product (68 g, 65% yield). LCMS (ESI) m/z: [M+H] calcd for $C_{43}H_{54}FN_5O_6$: 756.42; found 756.4.

Step 8. To a stirred solution of tert-butyl (($6^3$S,4S)-11-ethyl-$2^5$-(fluoromethyl)-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-11H-8-oxa-1(5,3)-indola-6(1,3)-pyridazina-2(1,3)-benzenacycloundecaphane-4-yl)carbamate (350 mg, 0.403 mmol) in DCM (4 mL) was added TFA (1.50 mL) at 0° C. The resulting mixture was stirred at room temperature for 1.5 h and was then concentrated under reduced pressure to afford the desired product (600 mg, crude). LCMS (ESI) m/z: [M+H] calcd for $C_{38}H_{46}FN_5O_4$: 656.36; found 656.4.

Intermediate 9. Synthesis of ($6^3$S)-4-amino-$1^1$-ethyl-$1^2$-(2-((S))-1-methoxyethyl)pyridin-3-yl)-10, 10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-5,7-dione

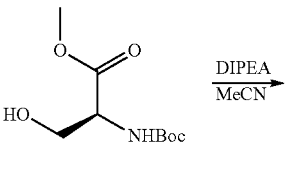

-continued

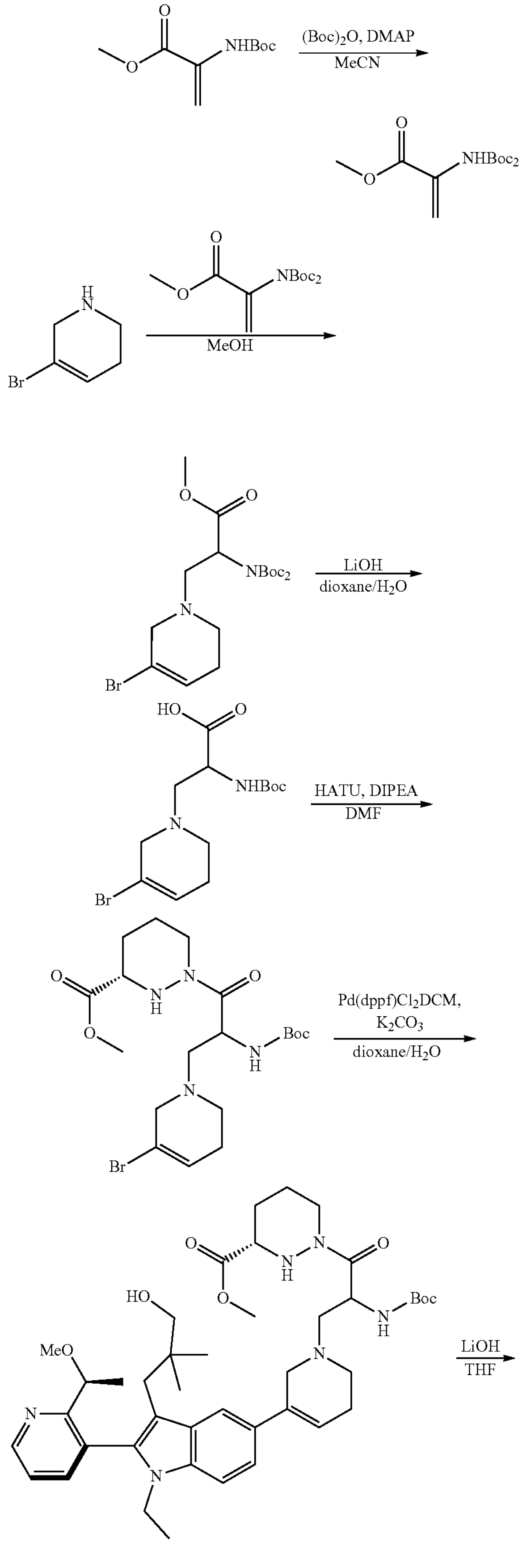

-continued

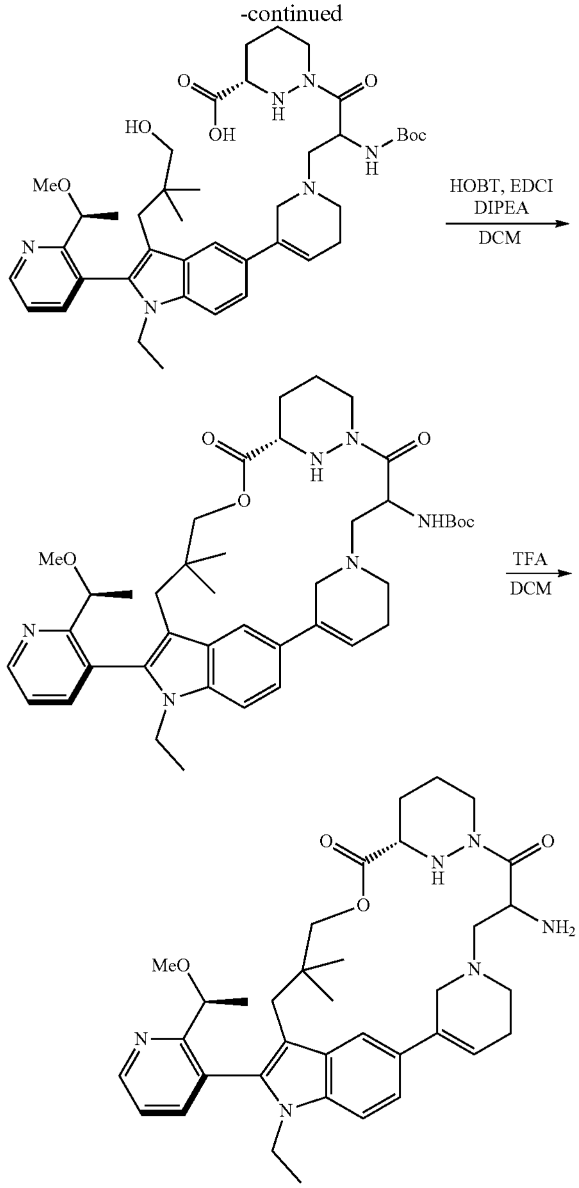

Step 1. To a solution of methyl (tert-butoxycarbonyl)-L-serinate (10 g, 45 mmol) in anhydrous MeCN (150 mL), was added DIPEA (17 g, 137 mmol). The reaction mixture was stirred at 45° C. for 2 h to give the product in solution. LCMS (ESI) m/z [M+Na] calcd for $C_9H_{15}NO_4$ 201.1; found: 224.1.

Step 2. To a solution of methyl 2-((tert-butoxycarbonyl) amino)acrylate (12 g, 60 mmol) in anhydrous MeCN (150 mL) at 0° C., was added DMAP (13 g, 90 mmol) and $(Boc)_2O$ (26 g, 120 mmol). The reaction was stirred for 6 h, then quenched with $H_2O$ (100 mL) and extracted with DCM (3×200 mL). The combined organic layers were washed with brine (150 mL), dried over anhydrous $Na_2SO_4$, filtered and concentrated under reduced pressure. The residue was purified by silica gel column chromatography to give the product (12.5 g, 65% yield) as solid. LCMS (ESI) m/z [M+Na] calcd for $C_{14}H_{23}NO_6$ 301.2; found: 324.1.

Step 3. To a mixture of 5-bromo-1,2,3,6-tetrahydropyridine (8.0 g, 49 mmol) in MeOH (120 mL) under an atmosphere of Ar was added methyl 2-{bis[(tert-butoxy)

carbonyl]amino}prop-2-enoate (22 g, 74 mmol). The mixture was stirred for 16 h, then concentrated under reduced pressure and the residue was purified by silica gel column chromatography to give the product (12 g, 47% yield) as an oil. LCMS (ESI) m/z [M+H] calcd for $C_{19}H_{31}BrN_2O_6$ 462.1; found: 463.1.

Step 4. To a mixture of methyl 2-(bis(tert-butoxycarbonyl)amino)-3-(5-bromo-3,6-dihydropyridin-1(2H)-yl)propanoate (14 g, 30 mmol) in dioxane (30 mL) and $H_2O$ (12 mL) was added LiOH (3.6 g, 151 mmol). The mixture was heated to 35° C. and stirred for 12 h, then 1 M HCl was added and the pH adjusted to ~3-4. The mixture was extracted with DCM (2×300 mL) and the combined organic layers were dried over anhydrous $Na_2SO_4$ and filtered. The filtrate was concentrated under reduced pressure to give the product (10 g, 85% yield) as a solid. LCMS (ESI) m/z [M+H] calcd for $C_{13}H_{21}BrN_2O_4$ 348.1; found: 349.0.

Step 5. To a mixture of 3-(5-bromo-3,6-dihydropyridin-1(2H)-yl)-2-((tert-butoxycarbonyl)amino)propanoic acid (10 g, 30 mmol), DIPEA (12 g, 93 mmol) and methyl (3S)-1,2-diazinane-3-carboxylate (5.4 g, 37 mmol) in DMF (100 mL) at 0° C. under an atmosphere of Ar was added HATU (13 g, 34 mmol). The mixture was stirred at 0° C. for 2 h, then $H_2O$ was added and the mixture extracted with EtOAc (2×300 mL). The combined organic layers were dried over anhydrous $Na_2SO_4$, filtered, the filtrate was concentrated under reduced pressure and the residue was purified by reverse phase chromatography to give the product (9.0 g, 55% yield) as a solid. LCMS (ESI) m/z [M+H] calcd for $C_{19}H_{31}BrN_4O$ 474.1; found: 475.1.

Step 6. A mixture of methyl (3S)-1-(3-(5-bromo-3,6-dihydropyridin-1(2H)-yl)-2-((tert-butoxycarbonyl)amino)propanoyl)hexahydropyridazine-3-carboxylate (9.0 g, 18 mmol), $K_2CO_3$ (4.5 g, 32 mmol), Pd(dppf)$Cl_2$·DCM (1.4 g, 2 mmol), 3-(1-ethyl-2-{2-[(1S)-1-methoxyethyl]pyridin-3-yl}-5-(4,4,5,5-tetramethyl-1,3,2-dioxaborolan-2-yl)indol-3-yl)-2,2-dimethylpropan-1-ol (9.8 g, 20 mmol) in dioxane (90 mL) and $H_2O$ (10 mL) under an atmosphere of Ar was heated to 75° C. and stirred for 2 h. $H_2O$ was added and the mixture was extracted with EtOAc (3×200 mL). The combined organic layers were dried over $Na_2SO_4$, filtered, the filtrate was concentrated under reduced pressure and the residue was purified by silica gel column chromatography to give the product (4.0 g, 25% yield) as a solid. LCMS (ESI) m/z [M+H] calcd for $C_{42}H_{60}N_6O_7$ 760.5; found: 761.4.

Step 7. To a mixture of methyl (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl) hexahydropyridazine-3-carboxylate (4.1 g, 5.0 mmol) in THF (35 mL) at 0° C. was added LiOH (0.60 g, 27 mmol). The mixture was stirred at 0° C. for 1.5 h, then 1 M HCl added to adjust pH to ~6-7 and the mixture was extracted with EtOAc (3×200 mL). The combined organic layers were dried over $Na_2SO_4$, filtered and the filtrate was concentrated under reduced pressure to give the product (3.6 g, 80% yield) as a solid. LCMS (ESI) m/z [M+H] calcd for $C_{41}H_{58}N_6O_7$ 746.4; found: 747.4.

Step 8. To a mixture of (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylic acid (3.6 g, 5.0 mmol) and DIPEA (24 g, 190 mmol) in DCM (700 mL) under an atmosphere of Ar was added EDCl·HCl (28 g, 140 mmol) and HOBt (6.5 g, 50 mmol). The mixture was heated to 30° C. and stirred for 16 h at 30° C., then concentrated under reduced pressure. The residue was diluted with EtOAc (200 mL) and washed with $H_2O$ (2×200 mL), brine (200 mL), dried over $Na_2SO_4$ and filtered. The filtrate was concentrated under reduced pressure and the residue was purified by silica gel column chromatography to give the product (1.45 g, 40% yield) as a solid. LCMS (ESI) m/z [M+H] calcd for $C_{41}H_{56}N_6O_6$ 728.4; found: 729.4.

Step 9, To a mixture of tert-butyl ((6$^3$S)-1$^1$-ethyl-1$^2$-(2-((S)-1-methoxyethyl)pyridin-3-yl)-10,10-dimethyl-5,7-dioxo-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (130 mg, 0.20 mmol) in DCM (1.0 mL) at 0° C. was added TFA (0.3 mL). The mixture was warmed to room temperature and stirred for 2 h, then concentrated under reduced pressure to give the product, which was used directly in the next step directly without further purification. LCMS (ESI) m/z [M+H] calcd for $C_{36}H_{48}N_6O_4$ 628.4; found: 629.4.

Intermediate 10. Synthesis of (6$^3$S,4S)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-2$^1$,2$^2$,2$^3$,2$^6$,6$^1$,6$^2$,6$^3$,6$^4$,6$^5$,6$^6$-(decahydro-1$^1$H-8-oxa-1(5,3)-indola-6(1,3)-pyridazina-2(5,1)-pyridinacycloundecaphane-5,7-dione

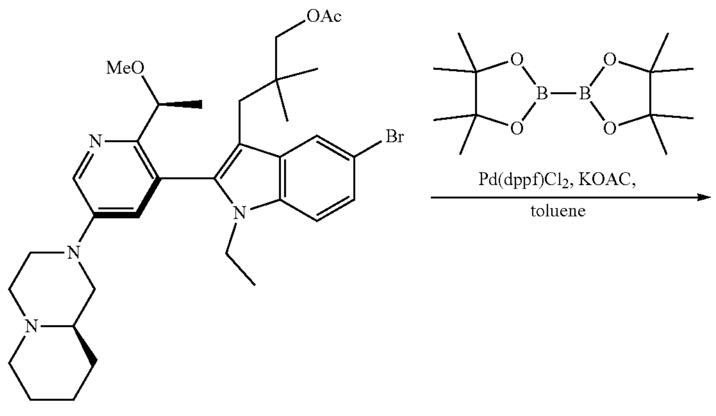

-continued
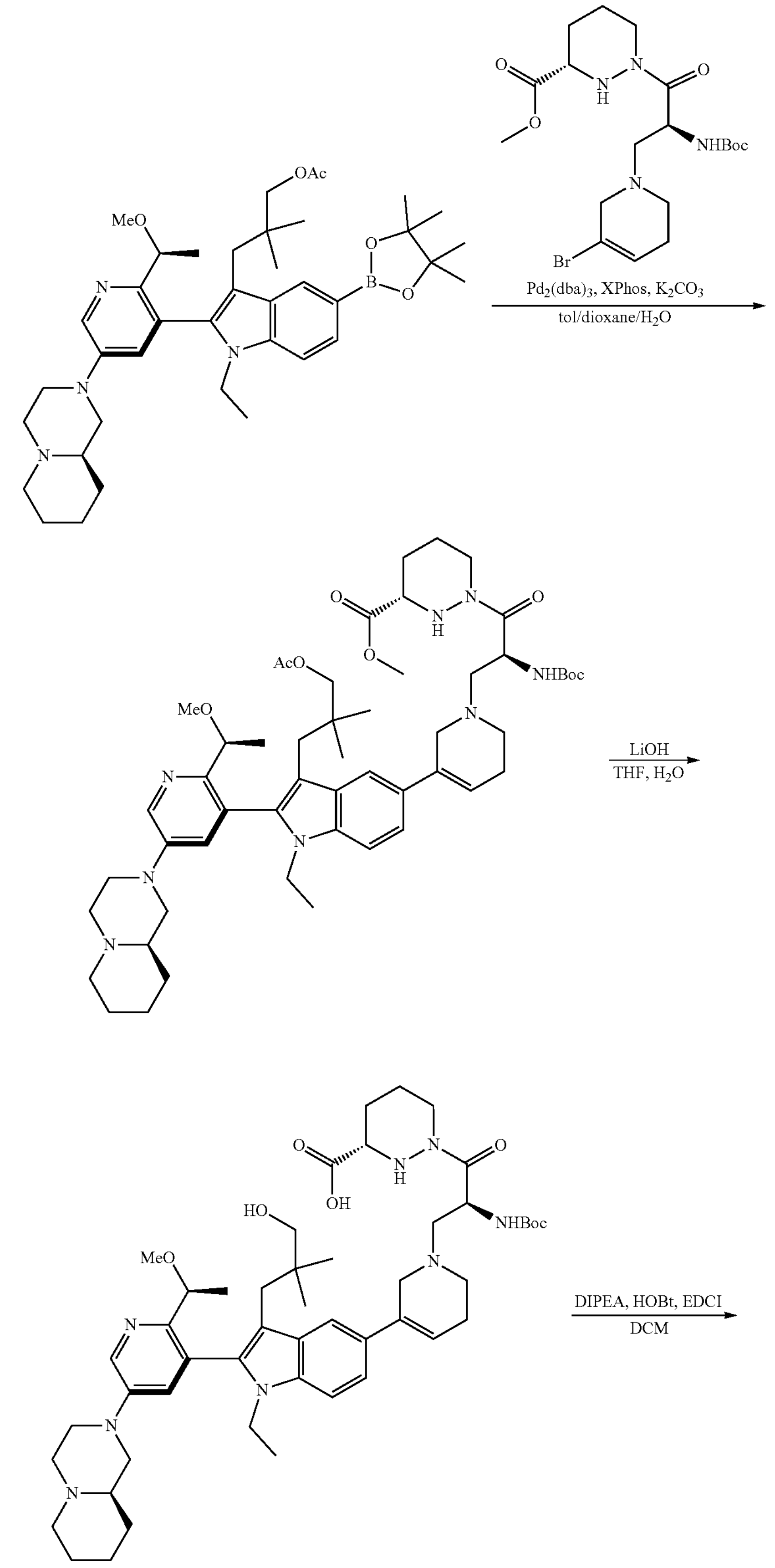

-continued

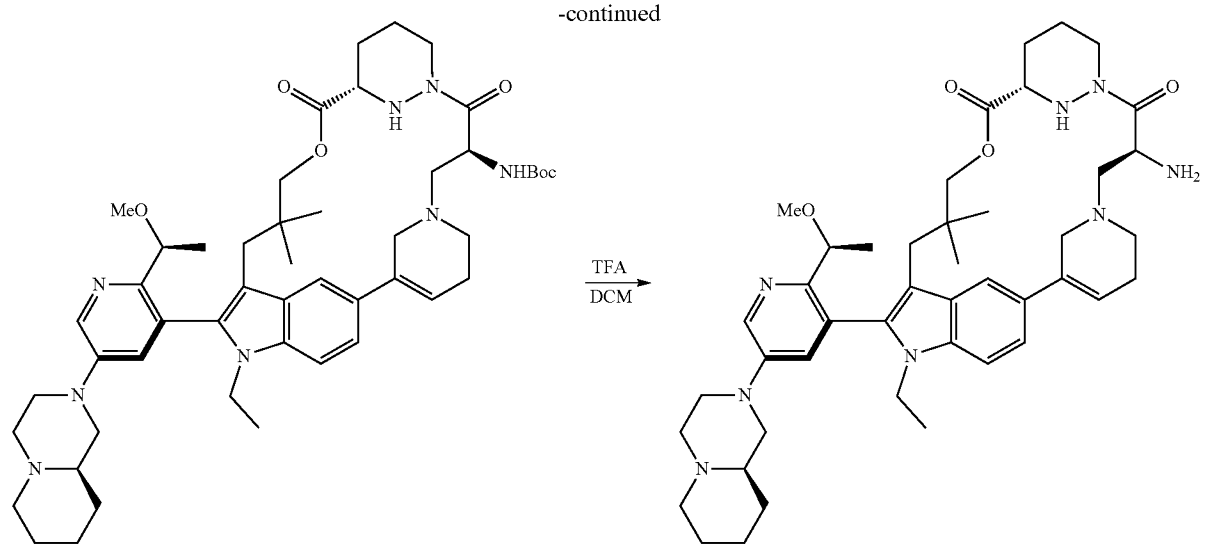

Step 1. To a stirred solution of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (1 g, 1.598 mmol) and $B_2Pin_2$ (0.81 g, 3.196 mmol) in toluene (20 mL) was added KOAc (0.39 g, 3.995 mmol) and Pd(dppf)$Cl_2$ (0.12 g, 0.16 mmol). The mixture was stirred for 2 h at 90° C. under a nitrogen atmosphere. The mixture was then basified to pH 8 with sat. aq. $NaHCO_3$. The resulting mixture was extracted with DCM (3x40 mL) and the combined organic layers were washed with brine (3x40 mL) and dried over anhydrous $Na_2SO_4$. After filtration, the filtrate was concentrated under reduced pressure. The residue was purified by silica gel column chromatography (2% MeOH/DCM) to afford the product (0.9 g, 83% yield) as a solid. LCMS (ESI) m/z [M+H] calcd for $C_{39}H_{57}BN_4O_5$: 673.45; found: 673.6.

Step 2. To a stirred solution of 3-(1-ethyl-2-(2-((S)-1-methoxyethyl)-5-((R)-octahydro-2H-pyrido[1,2-a]pyrazin-2-yl)pyridin-3-yl)-5-(4,4,5,5-tetramethyl-1,3,2-dioxaborolan-2-yl)-1H-indol-3-yl)-2,2-dimethylpropyl acetate (0.9 g, 1.338 mmol), methyl (3S)-1-[(2S)-3-(3-bromo-5,6-dihydro-2H-pyridin-1-yl)-2-[(tert-butoxycarbonyl)amino]propanoyl]-1,2-diazinane-3-carboxylate (1.02 g, 2.141 mmol), $K_2CO_3$ (0.46 g, 3.345 mmol), and X-Phos (0.26 g, 0.535 mmol) in toluene (13.5 mL), dioxane (90 mL), and $H_2O$ (4.5 mL) was added $Pd_2(dba)_3$ (0.37 g, 0.401 mmol). The mixture was stirred for 2 h at 70° C. under a nitrogen atmosphere. The mixture was then basified to pH 8 with sat. aq. $NaHCO_3$. The resulting mixture was extracted with DCM (3x100 mL) and the combined organic layers were washed with brine (3x100 mL) and dried over anhydrous $Na_2SO_4$. After filtration, the filtrate was concentrated under reduced pressure. The residue was purified by silica gel column chromatography (2% MeOH/DCM) to afford the product (1.1 g, 87% yield) as a solid. LCMS (ESI) m/z [M+H] calcd for $C_{52}H_{76}N_8O_8$: 941.59; found: 941.8.

Step 3. To a stirred solution of methyl (S)-1-((S)-3-(5-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)-3,6-dihydropyridin-1(2H)-yl)-2-((tert-butoxycarbonyl)amino)propanoyl)hexahydropyridazine-3-carboxylate (1.1 g, 1.169 mmol) in THE (8 mL) was added a solution of LiOH (0.14 g, 5.845 mmol) in $H_2O$ (8 mL) dropwise at 0° C. under a nitrogen atmosphere. The reaction mixture was stirred for 16 h. The mixture was then acidified to pH 6 with conc. HCl. The resulting mixture was extracted with DCM (3x50 mL) and dried over anhydrous $Na_2SO_4$. After filtration, the filtrate was concentrated under reduced pressure to afford the product (1.0 g, 96% yield) as a solid, which was used in the next step directly without further purification. LCMS (ESI) m/z [M+H] calcd for $C_{49}H_{72}N_8O_7$: 885.56; found: 885.5.

Step 4. To a stirred solution of (S)-1-((S)-2-((tert-butoxycarbonyl)amino)-3-(5-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)-3,6-dihydropyridin-1(2H)-yl)propanoyl)hexahydropyridazine-3-carboxylic acid (1.0 g, 1.13 mmol) and HOBt (0.76 g, 5.65 mmol) in DCM (100 mL) was added EDC·HCl (6.06 g, 31.64 mmol) and DIPEA (5.11 g, 39.55 mmol) dropwise at 0° C. under a nitrogen atmosphere. The reaction mixture was stirred for 16 h. The mixture was then basified to pH 8 with sat. aq. $NaHCO_3$. The resulting mixture was extracted with DCM (3x100 mL) and the combined organic layers were washed with brine (3x100 mL) and dried over anhydrous $Na_2SO_4$. After filtration, the filtrate was concentrated under reduced pressure. The residue was purified by silica gel column chromatography (3% MeOH/DCM) to afford the product (650 mg, 66% yield) as a solid. LCMS (ESI) m/z [M+H] calcd for $C_{49}H_{70}N_8O_6$: 867.55; found: 867.5.

Step 5. To a stirred solution of tert-butyl (($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)carbamate (300 mg, 0.346 mmol) in DCM (3 mL) was added TFA (3 mL) dropwise at 0° C. under a nitrogen atmosphere. The resulting mixture was stirred for 1 h at 0° C. The mixture was then basified to pH 8 with sat. aq. $NaHCO_3$. The resulting mixture was extracted with DCM (3x50 mL) and the combined organic layers were washed with brine (3x50 mL) and dried over anhydrous $Na_2SO_4$. After filtration, the filtrate was concentrated under reduced pressure to afford the product (260 mg, 98% yield) as a solid, which was used in the next step directly without further purification. LCMS (ESI) m/z [M+H] calcd for $C_{44}H_{62}N_8O_4$: 767.50; found: 767.2.
Intermediate 11. Synthesis of (2$^{2}$S,6$^{3}$S,4S)-4-amino-1$^{1}$-ethyl-1$^{2}$-(2-((S)-1-methoxyethyl)pyridin-3-yl)-10,10-dimethyl-6$^{1}$,6$^{2}$,6$^{3}$,6$^{4}$,6$^{5}$,6$^{6}$-hexahydro-1$^{1}$H-8-oxa-2(4,2)-morpholina-1(5,3)-indola-6(1,3)-pyridazinacycloundecaphane-5,7-dione
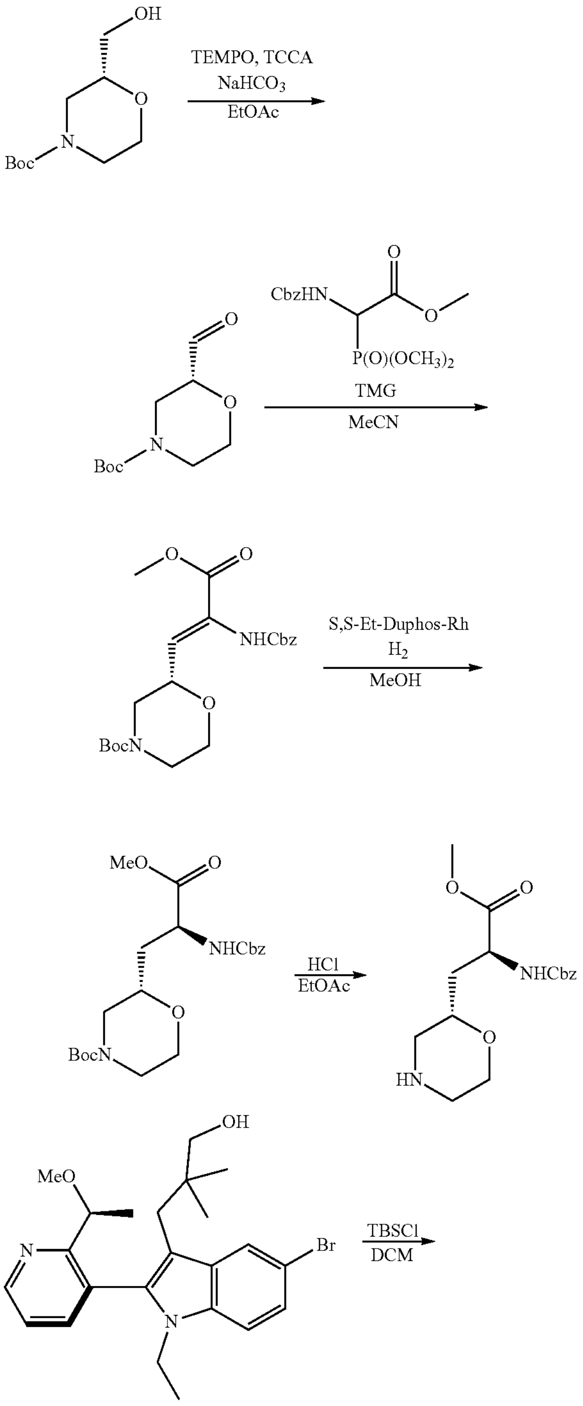
Intermediate 1
-continued
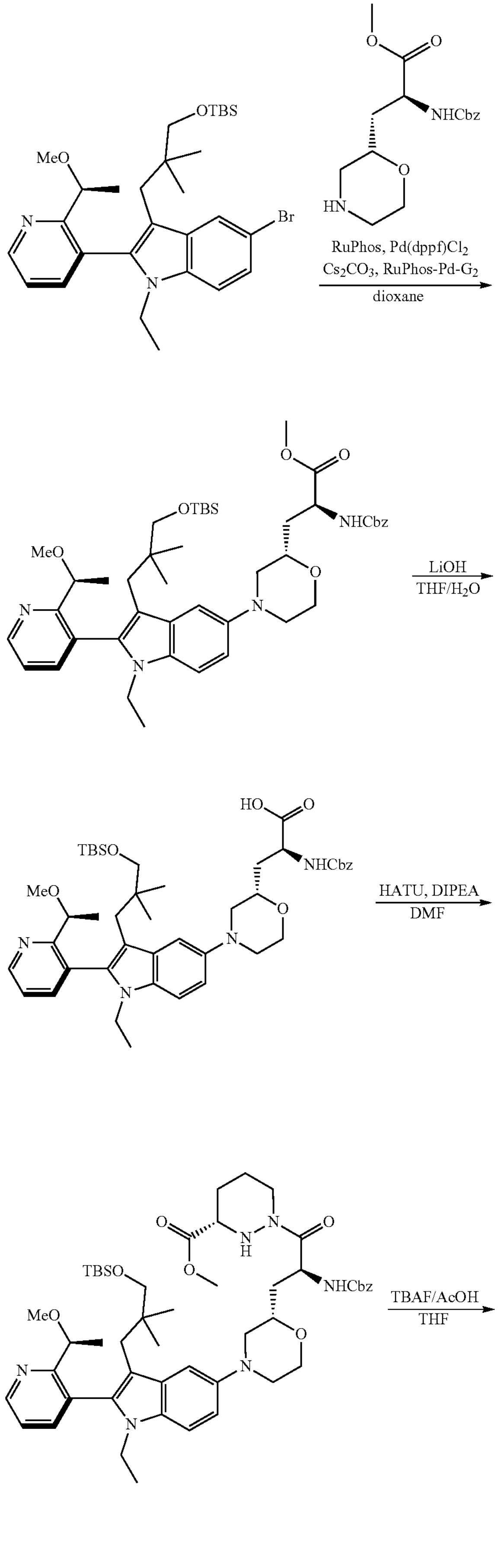

-continued

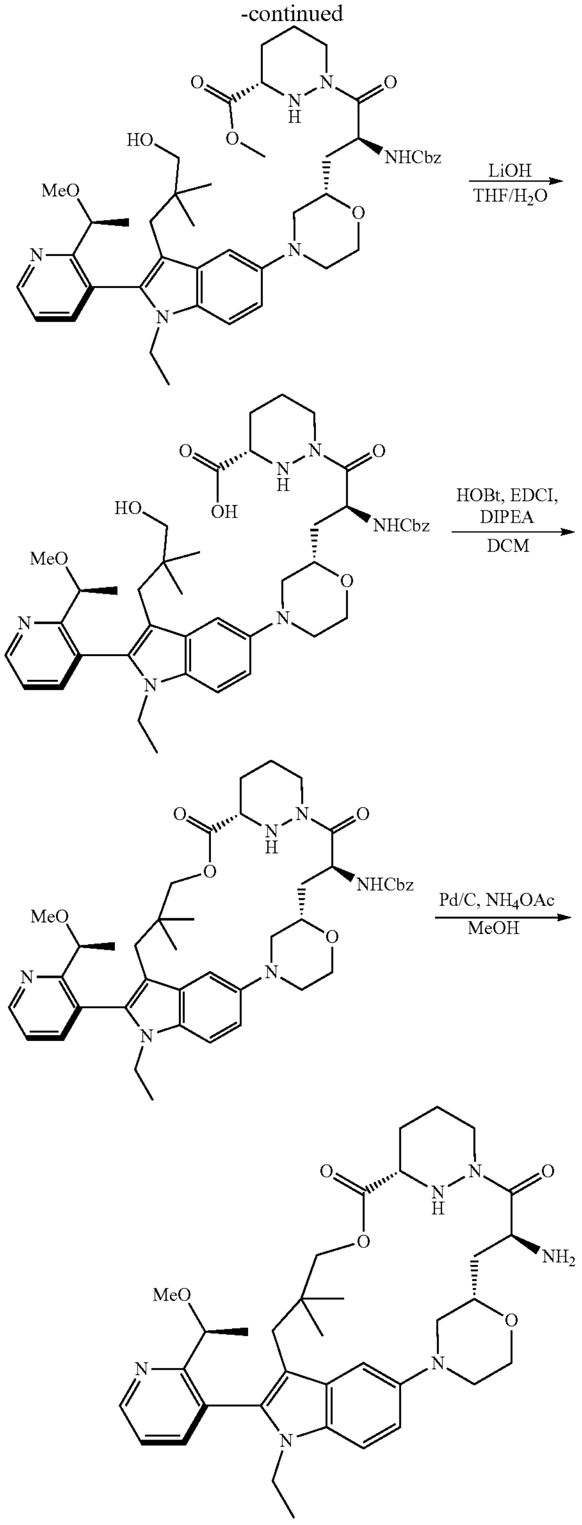

Step 1. To a solution of tert-butyl (2R)-2-(hydroxymethyl) morpholin-4-yl formate (50 g, 230 mmol) in EtOAc (1 L) was added TEMPO (715 mg, 4.6 mmol) and $NaHCO_3$ (58 g, 690 mmol) at room temperature. The mixture was cooled to −50° C., then TCCA (56 g, 241 mmol) in EtOAc (100 mL) was added dropwise over 30 min. The reaction mixture was warmed to 5° C. for 2 h, then quenched with 10% $Na_2S_2O_3$ (200 mL) and stirred for 20 min. The resulting mixture was filtered and the organic phase was separated. The aqueous phase was extracted with EtOAc (2×100 mL). The combined organic layers were washed with $H_2O$ (100 mL) and brine (100 mL), then dried over anhydrous $Na_2SO_4$. The organic layer was concentrated under reduced pressure to afford the product (50 g, crude) as an oil.

Step 2. To a solution of tert-butyl (2R)-2-formylmorpholin-4-yl formate (49 g, 153 mmol) and methyl 2-{[(benzyloxy)carbonyl]amino}-2-(dimethoxyphosphoryl)acetate (60 g, 183 mmol) in MeCN (300 mL) was added tetramethylguanidine (35 g, 306 mmol) at 0-10° C. The reaction mixture was stirred at 10° C. for 30 min then warmed to room temperature for 2 h. The reaction mixture was diluted with DCM (200 mL) and washed with 10% citric acid (200 mL) and 10% $NaHCO_3$ aq. (200 mL). The organic phase was concentrated under reduced pressure, and purified by silica gel column chromatography to afford the product (36 g, 90% yield) as solid. LCMS (ESI) m/z [M+Na] calcd for $C_{21}H_{28}N_2O_4$ 420.2; found: 443.1.

Step 3. To a solution of tert-butyl (S,Z)-2-(2-(((benzyloxy)carbonyl)amino)-3-methoxy-3-oxoprop-1-en-1-yl) morpholine-4-carboxylate (49 g, 0.12 mol) in MeOH (500 mL) was added (S,S)-Et-DUPHOS-Rh (500 mg, 0.7 mmol). The mixture was stirred at room temperature under an $H_2$ (60 psi) atmosphere for 48 h. The reaction was concentrated and purified by silica gel column chromatography to give the product (44 g, 90% yield) as solid. LCMS (ESI) m/z [M+Na] calcd for $C_{21}H_{30}N_2O_7$ 422.2; found: 445.2.

Step 4. To a stirred solution of tert-butyl (S)-2-((S)-2-(((benzyloxy)carbonyl)amino)-3-methoxy-3-oxopropyl) morpholine-4-carboxylate (2.2 g, 5.2 mmol) in EtOAc (2 mL) was added HCl/EtOAc (25 mL) at 15° C. The reaction was stirred at 15° C. for 2 h, then concentrated under reduced pressure to afford the product (1.51 g, 90% yield) as an oil. LCMS (ESI) m/z [M+H] calcd for $C_{16}H_{22}N_2O_5$ 322.1; found: 323.2.

Step 5. To a solution of 3-(5-bromo-1-ethyl-2-{2-[(1 S)-1-methoxyethyl]pyridin-3-yl}indol-3-yl)-2,2-dimethylpropan-1-ol (100 g, 0.22 mol) and imidazole (30.6 g, 0.45 mol) in DCM (800 mL) was added TBSCl (50.7 g, 0.34 mol) in DCM (200 mL) at 0° C. The reaction was stirred at room temperature for 2 h. The resulting solution was washed with $H_2O$ (3×300 mL) and brine (2×200 mL), dried over anhydrous $Na_2SO_4$, filtered and concentrated under reduced pressure. The residue was purified with silica gel column chromatography to give the product (138 g, 90% yield) as a solid. LCMS (ESI) m/z [M+H] calcd for $C_{29}H_{43}BrN_2O_2Si$ 558.2; found: 559.2.

Step 6. To a stirred solution of (S)-5-bromo-3-(3-((tert-butyldimethylsilyl)oxy)-2,2-dimethylpropyl)-1-ethyl-2-(2-(1-methoxyethyl)pyridin-3-yl)-1H-indole (50 g, 89.3 mmol) in dioxane (500 mL) was added methyl (2S)-2-{[(benzyloxy)carbonyl]amino}-3-[(2S)-morpholin-2-yl]propanoate (31.7 g, 98.2 mmol), RuPhos (16.7 g, 35.7 mmol), di-p-chlorobis(2-amino-1,1-biphenyl-2-yl-C,N)dipalladium(II) (2.8 g, 4.4 mmol) and cesium carbonate (96 g, 295 mmol) followed by RuPhos-Pd-G2 (3.5 g, 4.4 mmol) at 105° C. under an $N_2$ atmosphere. The reaction mixture was stirred for 6 h at 105° C. under an $N_2$ atmosphere. The resulting mixture was filtered, and the filtrate was concentrated under reduced pressure. The residue was purified by prep-TLC chromatography to afford the product (55 g, 73% yield) as a solid. LCMS (ESI) m/z [M+H] calcd for $C_{45}H_{64}N_4O_7Si$ 800.5; found: 801.5.

Step 7. To a solution of methyl (2S)-2-{[(benzyloxy) carbonyl]amino}-3-[(2S)-4-(3-{3-[(tert-butyldimethylsilyl) oxy]-2,2-dimethylpropyl}-1-ethyl-2-{2-[(1 S)-1-methoxyethyl]pyridin-3-yl}indol-5-yl)morpholin-2-yl]propanoate (10 g, 12 mmol) in THF (270 mL) was added LiOH (1.3 g, 31 mmol) in $H_2O$ (45 mL) at room temperature. The reaction was stirred at room temperature for 2 h, then treated with 1 N HCl to adjust pH to 4-5 at 0-5° C. The resulting mixture was extracted with EtOAc (2×50 mL). The combined organic layers were washed with brine and dried over anhydrous $Na_2SO_4$. The organic phase was then concentrated under reduced pressure to afford the product (9.5 g, 97% yield) as a solid. LCMS (ESI) m/z [M+H] calcd for $C_{44}H_{62}N_4O_7Si$ 786.4; found: 787.4.

Step 8. To a stirred solution of (2S)-2-{[(benzyloxy) carbonyl]amino}-3-[(2S)-4-(3-{3-[(tert-butyldimethylsilyl) oxy]-2,2-dimethylpropyl}-1-ethyl-2-{2-[(1 S)-1-methoxyethyl]pyridin-3-yl}indol-5-yl)morpholin-2-yl]propanoic acid (10 g, 12.7 mmol) in DMF (150 mL), was added methyl (S)-hexahydropyridazine-3-carboxylate (2 g, 14 mmol), then cooled to 0° C., DIPEA (32.8 g, 254 mmol) was added followed by HATU (9.7 g, 25.4 mmol) at 0-5° C. The reaction mixture was stirred at 0-5° C. for 1 h. The resulting mixture was diluted with EtOAc (500 mL) and $H_2O$ (200 mL). The organic layer was separated and washed with $H_2O$ (2×100 mL) and brine (100 mL), dried over anhydrous sodium sulfate. The solution was filtered and concentrated under reduced pressure, and the residue was purified by silica gel column chromatography to afford the product. LCMS (ESI) m/z [M+H] calcd for $C_{50}H_{72}N_6O_8Si$ 912.5; found: 913.4.

Step 9. A solution of methyl (S)-1-((S)-2-(((benzyloxy) carbonyl)amino)-3-((S)-4-(3-(3-((tert-butyldimethylsilyl) oxy)-2,2-dimethylpropyl)-1-ethyl-2-(2-((S)-1-methoxyethyl)pyridin-3-yl)-1H-indol-5-yl)morpholin-2-yl) propanoyl)hexahydropyridazine-3-carboxylate (8.5 g, 9 mmol) in THE (8 mL) was added a mixture of tetrabutylammonium fluoride (1M in THF, 180 mL, 180 mmol) and AcOH (11 g, 200 mmol) at room temperature. The reaction mixture was stirred at 75° C. for 3 h. The resulting mixture was diluted with EtOAc (150 mL) and washed with $H_2O$ (6×20 mL). The organic phase was concentrated under reduced pressure to give the product (7.4 g, 100% yield) as solid. LCMS (ESI) m/z [M+H] calcd for $C_{44}H_{58}N_6O_8$ 799.4; found: 798.4.

Step 10. To a solution of methyl (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl) hexahydropyridazine-3-carboxylate (8 g, 10 mmol) in THE (200 mL) was added LiOH (600 mg, 25 mmol) in $H_2O$ (30 mL). The reaction mixture was stirred at room temperature for 1 h, then treated with 1 N HCl to adjust pH to 4-5 at 0-5° C., and extracted with EtOAc (2×500 mL). The organic phase was washed with brine and concentrated under reduced pressure to afford the product (8 g, crude) as a solid. LCMS (ESI) m/z [M+H] calcd for $C_{43}H_{56}NO_8$ 784.4; found: 785.4.

Step 11. To a stirred solution of (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl) hexahydropyridazine-3-carboxylic acid (8 g, 10.2 mmol) and DIPEA (59 g, 459 mmol) in DCM (800 mL) was added EDCl (88 g, 458 mmol) and HOBt (27.6 g, 204 mmol) at room temperature under an argon atmosphere. The reaction mixture was stirred at room temperature for 16 h. The resulting mixture was concentrated under reduced pressure, and the residue was purified by silica gel column chromatography to afford the product (5 g, 66% yield) as a solid; LCMS (ESI) m/z [M+H] calcd for $C_{43}H_{54}N_6O_7$ 766.4; found: 767.4.

Step 12. To a solution of benzyl (($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)carbamate (400 mg, 0.5 mmol) in MeOH (20 mL) was added Pd/C (200 mg) and ammonium acetate (834 mg, 16 mmol) at room temperature under an $H_2$ atmosphere and the mixture was stirred for 2 h. The resulting mixture was filtered and concentrated under reduced pressure. The residue was redissolved in DCM (20 mL) and washed with $H_2O$ (5 mL×2), then concentrated under reduced pressure to afford the product (320 mg, 97% yield) as a solid. LCMS (ESI) m/z [M+H] calcd for $C_{35}H_{48}N_6O_5$ 632.4; found: 633.3.

Intermediate 12. Synthesis of (2S)-3-methyl-2-[methyl(4-(prop-2-enoyl)-1-oxa-4,9-diazaspiro[5.5] undecane-9-carbonyl)amino]butanoic acid

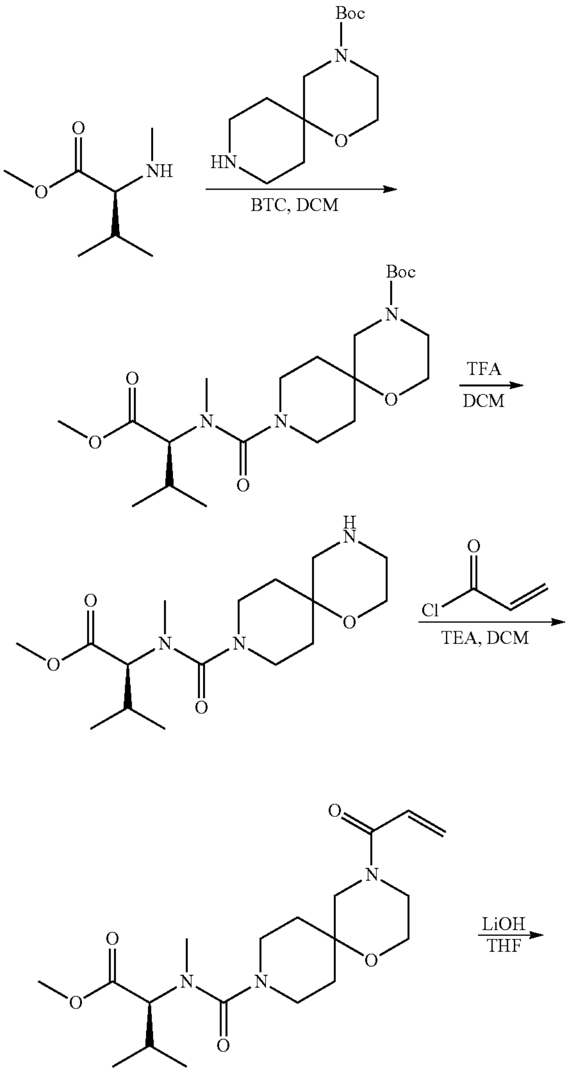

-continued

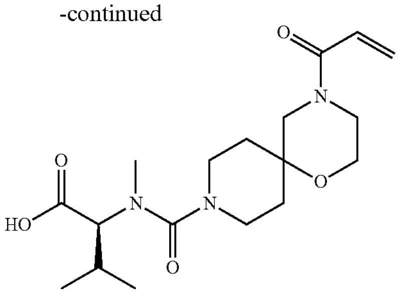

Step 1. To a mixture of ditrichloromethyl carbonate (135 mg, 0.45 mmol) and DCM (1 mL) at 0° C. was added a mixture of methyl (2S)-3-methyl-2-(methylamino)butanoate (200 mg, 1.4 mmol) and pyridine (327 mg, 4.1 mmol) in DCM (1 mL) dropwise. The mixture was stirred at 0° C. for 1 h, then tert-butyl 1-oxa-4,9-diazaspiro[5.5]undecane-4-carboxylate (353 mg, 1.4 mmol), TEA (418 mg, 4.1 mmol) in DCM (2 mL) were added dropwise at 0° C. The mixture was stirred at 0° C. for 1 h, then concentrated under reduced pressure. Brine (20 mL) was added to the residue and the mixture was extracted with DCM (3x20 mL). The combined organic layers were dried over anhydrous $Na_2SO_4$, filtered, the filtrate was concentrated under reduced pressure and the residue was purified by preparative-HPLC to give tert-butyl 9-{[(2S)-1-methoxy-3-methyl-1-oxobutan-2-yl](methyl)carbamoyl}-1-oxa-4,9-diazaspiro[5.5]undecane-4-carboxylate (335 mg, 57% yield) as a solid. LCMS (ESI): m/z $[M+H]^+$ calc'd for $C_{21}H_{37}N_3O_6$ 427.3; found 428.2.

Step 2. To a mixture of tert-butyl 9-{[(2S)-1-methoxy-3-methyl-1-oxobutan-2-yl](methyl)carbamoyl}-1-oxa-4,9-diazaspiro[5.5]undecane-4-carboxylate (330 mg, 0.77 mmol) in DCM (2.4 mL) at 0° C. was added TFA (0.8 mL). The mixture was stirred at 0° C. for h, then basified to pH ~7 with saturated $NaHCO_3$ and the mixture extracted with DCM (3x10 mL). The combined organic layers were washed with brine (3x10 mL), dried over anhydrous $Na_2SO_4$, filtered and the filtrate was concentrated under reduced pressure to give methyl (2S)-3-methyl-2-[methyl(1-oxa-4,9-diazaspiro[5.5]undecane-9-carbonyl)amino]butanoate (280 mg, crude) as a light yellow solid. LCMS (ESI): m/z $[M+H]^+$ calc'd for $C_{16}H_{29}N_3O_4$ 327.2; found 328.1.

Step 3. To a mixture of methyl (2S)-3-methyl-2-[methyl(1-oxa-4,9-diazaspiro[5.5]undecane-9-carbonyl)amino]butanoate (270 mg, 0.83 mmol) and TEA (1.67 g, 16.5 mmol) in DCM (3 mL) at 0° C. was added acryloyl chloride (75 mg, 0.83 mmol) dropwise. The mixture was stirred at 0° C. for 1 h, then concentrated under reduced pressure and the residue was purified by preparative-HPLC to give methyl (2S)-3-methyl-2-[methyl(4-(prop-2-enoyl)-1-oxa-4,9-diazaspiro[5.5]undecane-9-carbonyl)amino]butanoate (230 mg, 73% yield) as a solid. LCMS (ESI): m/z $[M+H]^+$ calc'd for $C_{19}H_{31}N_3O_5$ 381.2; found 382.2.

Step 4. To a mixture of methyl (2S)-3-methyl-2-[methyl(4-(prop-2-enoyl)-1-oxa-4,9-diazaspiro[5.5]undecane-9-carbonyl)amino]butanoate (220 mg, 0.58 mmol) in THF (1.8 mL) and $H_2O$ (0.6 mL) at 0° C. was added LiOH (21 mg, 0.87 mmol). The mixture was stirred at 0° C. for 1 day, then acidified to pH ~4 with aqueous HCl and the mixture was extracted with DCM (3x20 mL). The combined organic layers were dried over anhydrous $Na_2SO_4$, filtered and the filtrate was concentrated under reduced pressure to give (2S)-3-methyl-2-[methyl(4-(prop-2-enoyl)-1-oxa-4,9-diazaspiro[5.5]undecane-9-carbonyl)amino]butanoic acid (137 mg, 65% yield) as a solid. LCMS (ESI): m/z $[M+H]^+$ calc'd for $C_{18}H_{29}N_3O_5$ 367.2; found 368.2.

Intermediate 13. Synthesis of methyl N—((S)-3-acryloyl-2-methyl-1-oxa-3,8-diazaspiro[4.5]decane-8-carbonyl)-N-methyl-L-valinate and methyl N—((R)-3-acryloyl-2-methyl-1-oxa-3,8-diazaspiro[4.5]decane-8-carbonyl)-N-methyl-L-valinate

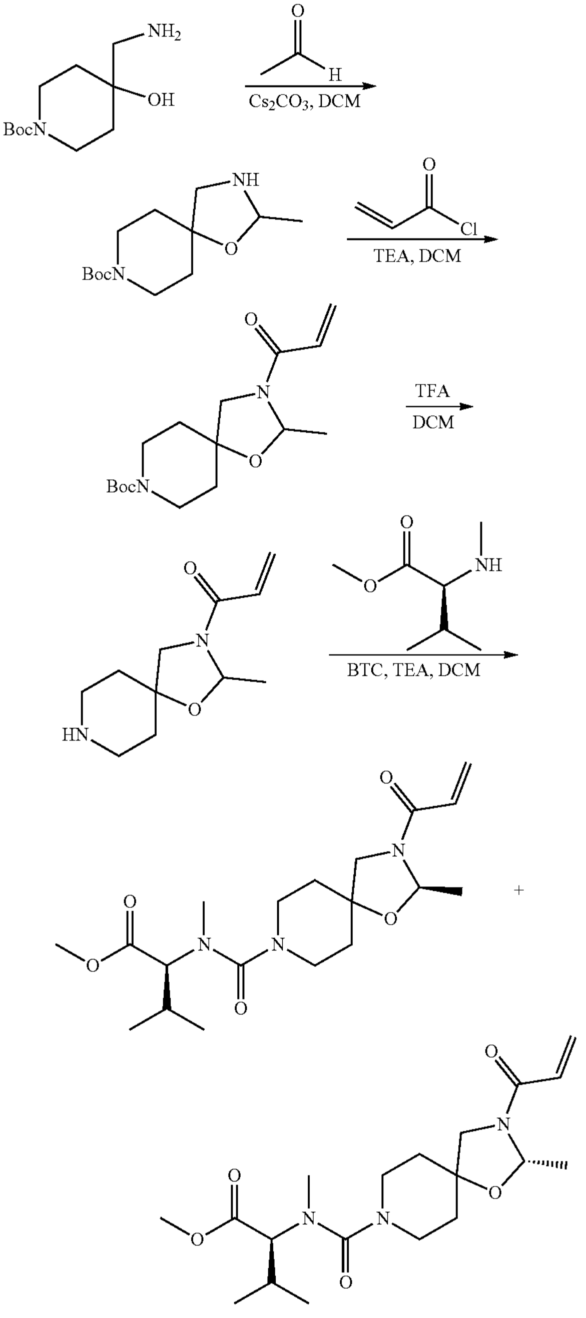

Step 1. To a mixture of tert-butyl 4-(aminomethyl)-4-hydroxypiperidine-1-carboxylate (5.0 g, 21.7 mmol) in DCM (50 mL) was added $MgSO_4$ (10 g), $Cs_2CO_3$ (7.07 g, 21.7 mmol) and acetaldehyde (0.96 g, 21.7 mmol). The mixture was stirred at rt for 2 h, then filtered and the filter cake was washed with EtOAc (5×100 mL). The filtrate was concentrated under reduced pressure to give tert-butyl 2-methyl-1-oxa-3,8-diazaspiro[4.5]decane-8-carboxylate (6 g) as an oil, which was used directly in the next step. LCMS (ESI): m/z $[M+H]^+$ calc'd for $C_{13}H_{24}N_2O_3$ 256.2; found 257.4.

Step 2. To a mixture of tert-butyl 2-methyl-1-oxa-3,8-diazaspiro[4.5]decane-8-carboxylate (5.9 g, 23.0 mmol) in DCM (50 mL) at 0° C. was added TEA (6.99 g, 69.1 mmol) and acryloyl chloride (2.08 g, 23.0 mmol). The mixture was stirred at 0° C. for 30 min, then ice/$H_2O$ was added and the mixture extracted with EtOAc (4×30 mL). The combined organic layers were dried over anhydrous $Na_2SO_4$, filtered, the filtrate was concentrated under reduced pressure and the residue was purified by silica gel column chromatography to give tert-butyl 3-acryloyl-2-methyl-1-oxa-3,8-diazaspiro[4.5]decane-8-carboxylate (2.7 g, 38%) as an oil.

Step 3. To a mixture of tert-butyl 3-acryloyl-2-methyl-1-oxa-3,8-diazaspiro[4.5]decane-8-carboxylate (2.65 g, 8.5 mmol) in DCM (26 mL) at 0° C. was added TFA (13 mL). The mixture was stirred at 0° C. for 1 h, then concentrated under reduced pressure to give 1-(2-methyl-1-oxa-3,8-diazaspiro[4.5]decan-3-yl)prop-2-en-1-one (4.8 g) as an oil. LCMS (ESI): m/z $[M+H]^+$ calc'd for $C_{11}H_{18}N_2O_2$ 210.1; found 211.2.

Step 4. To a mixture of BTC (0.40 g, 1.4 mmol) in DCM (10 mL) at 0° C. was added methyl methyl-L-valinate HCl (0.73 g, 4.1 mmol) and pyridine (1.28 g, 16.2 mmol) in DCM (7 mL). The mixture was stirred at 0° C. for 1 h, then TEA (4.10 g, 40.5 mmol) and 1-(2-methyl-1-oxa-3,8-diazaspiro[4.5]decan-3-yl)prop-2-en-1-one (1.70 g, 8.1 mmol) in DCM were added. The mixture was stirred at 0° C. for 2 h, then ice/$H_2O$ was added and the mixture extracted with EtOAc (3×20 mL). The combined organic layers were dried over anhydrous $Na_2SO_4$, filtered, and the filtrate was concentrated under reduced pressure. The residue was purified by preparative-TLC and preparative-HPLC to give methyl N—((S)-3-acryloyl-2-methyl-1-oxa-3,8-diazaspiro[4.5]decane-8-carbonyl)-N-methyl-L-valinate (750 mg) and methyl N—((R)-3-acryloyl-2-methyl-1-oxa-3,8-diazaspiro[4.5]decane-8-carbonyl)-N-methyl-L-valinate (730 mg) as an oil. LCMS (ESI): m/z $[M+H]^+$ calc'd for $C_{19}H_{31}N_3O_5$ 381.2; found 382.2.

Intermediate 14. Synthesis of (2S)-3-methyl-2-{methyl[1-methyl-3-(prop-2-enoyl)-1,3,8-triazaspiro[4.5]decan-8-yl]carbonylamino}butanoic acid, lithium salt

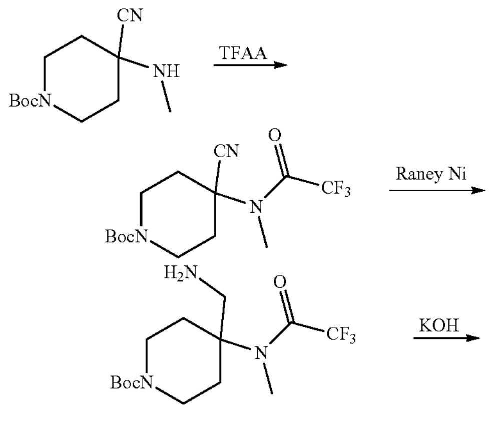

-continued

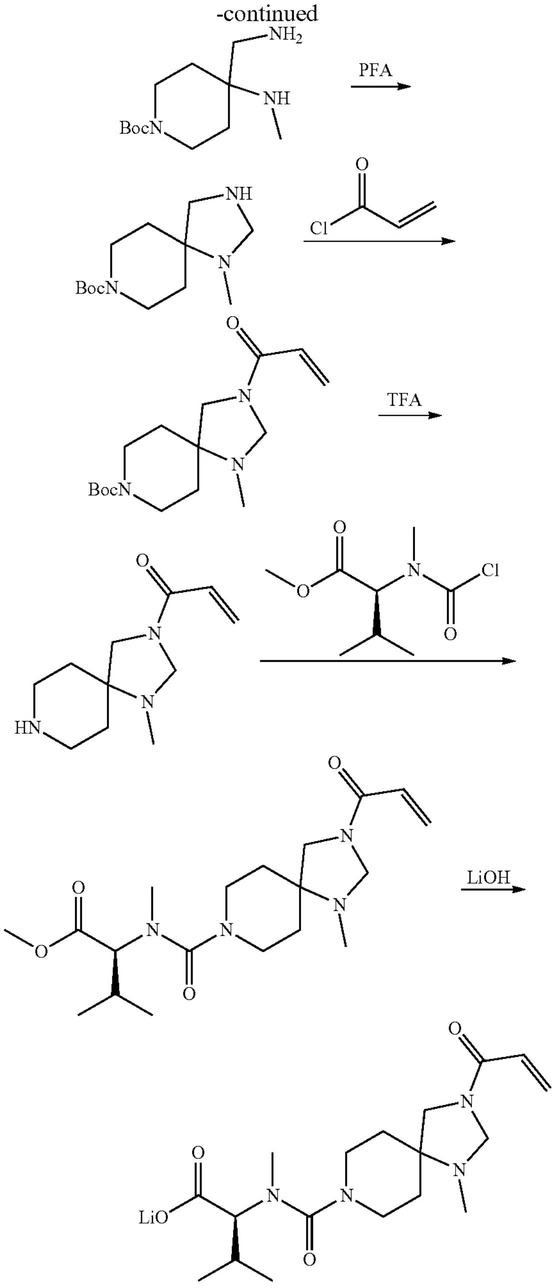

Step 1. To a mixture of tert-butyl [4-cyano-4-(methylamino)piperidin-1-yl]formate (14.4 g, 63 mmol) and pyridine (8 g, 125.6 mmol) in THF (200 mL) at 0° C. was added TFAA (15.8 g, 75.2 mmol). The mixture was warmed to rt and stirred for 1 h, then concentrated under reduced pressure. The residue was dissolved in EtOAc (100 mL), washed with 1 N HCl (100 mL), then dried over $Na_2SO_4$ and filtered. The filtrate was concentrated under reduced pressure and the crude residue was purified by silica gel column chromatography to give tert-butyl 4-cyano-4-(2,2,2-trifluoro-N-methylacetamido)piperidine-1-carboxylate (15.9 g, 71% yield) as a solid. LCMS (ESI): m/z $[M+Na]^+$ calc'd for $C_{14}H_{20}F_3N_3NaO_3$ 358.1; found 358.2.

Step 2. A mixture of tert-butyl 4-cyano-4-(2,2,2-trifluoro-N-methylacetamido)piperidine-1-carboxylate (9.6 g, 28 mmol) in EtOH (100 mL) and Raney Ni (2 g) was stirred under an atmosphere of $H_2$ (15 psi) for 16 h. The mixture was filtered, the filtrate was concentrated under reduced pressure and the crude residue was purified by silica gel column chromatography to give tert-butyl 4-(aminomethyl)-4-(2,2,2-trifluoro-1-methylacetamido)piperidine-1-carboxylate (3.9 g, 40% yield) as a solid. LCMS (ESI): m/z $[M+H]^+$ calc'd for $C_{14}H_{24}F_3N_3O_3$ 339.2; found 340.2.

Step 3. To a mixture of tert-butyl 4-(aminomethyl)-4-(2,2,2-trifluoro-1-methylacetamido)piperidine-1-carboxylate (3.9 g, 12 mmol) in MeOH (40 mL) and $H_2O$ (8 mL) was added KOH (3.45 g, 60 mmol). The mixture heated to 80° C. and stirred for 1 h, then concentrated under reduced pressure to remove MeOH. The aqueous was extracted with DCM (30 mL×3) and the combined organic layers were dried over $Na_2SO_4$ and filtered. The filtrate was concentrated under reduced pressure to give tert-butyl 4-(aminomethyl)-4-(methylamino)piperidine-1-carboxylate (2.9 g, 92% yield) as a solid. LCMS (ESI): m/z $[M+H]^+$ calc'd for $C_{12}H_{25}N_3O_2$ 243.2; found 244.2.

Step 4. To a mixture of [4-(aminomethyl)-4-(methylamino)piperidin-1-yl]tert-butyl formate (1.4 g, 5.7 mmol) in $Et_2O$ (15 mL) was added paraformaldehyde (0.77 g, 25.6 mmol). The mixture was stirred at rt for 1 h, then filtered and the filter cake washed with DCM. The filtrate was concentrated under reduced pressure to give tert-butyl {1-methyl-1,3,8-triazaspiro[4.5]decan-8-yl} formate (1.2 g, 77% yield) as an oil. LCMS (ESI): m/z $[M+H]^+$ calc'd for $C_{13}H_{25}N_3O_2$ 255.2; found 256.3.

Step 5. To a mixture of tert-butyl {1-methyl-1,3,8-triazaspiro[4.5]decan-8-yl} formate (1.4 g, 5.5 mmol), $NaHCO_3$ (1.16 g, 13.7 mmol) in $H_2O$ (15 mL) and DCM (15 mL) at 0° C. was added prop-2-enoyl chloride (0.55 g, 6 mmol). The mixture was stirred at 0° C. for 1H, then $H_2O$ (30 mL) added and the mixture was extracted with DCM (50 mL×3). The obtained organic layers were washed with brine, dried over anhydrous $Na_2SO_4$ and filtered. The filtrate was concentrated under reduced pressure and the crude residue was purified by silica gel column chromatography to give tert-butyl [1-methyl-3-(prop-2-enoyl)-1,3,8-triazaspiro[4.5]decan-8-yl]formate (0.8 g, 43% yield) as an oil. LCMS (ESI): m/z $[M+H]^+$ calc'd for $C_{16}H_{27}N_3O_3$ 309.2; found 310.3.

Step 6. To a mixture of tert-butyl [1-methyl-3-(prop-2-enoyl)-1,3,8-triazaspiro[4.5]decan-8-yl]formate (800 mg, 2.6 mmol) in DCM (6 mL) was added TFA (2 mL). The mixture was stirred at rt for 1 h then concentrated under reduced pressure to give 1-{1-methyl-1,3,8-triazaspiro[4.5]decan-3-yl}prop-2-en-1-one (540 mg), which was used directly in the next step. LCMS (ESI): m/z $[M+H]^+$ calc'd for $C_{11}H_{19}N_3O$ 209.2; found 210.3.

Step 7. To a mixture of 1-{1-methyl-1,3,8-triazaspiro[4.5]decan-3-yl}prop-2-en-1-one (540 mg, 2.6 mmol) and methyl (2S)-2-[(chlorocarbonyl)(methyl)amino]-3-methylbutanoate (589 mg, 2.83 mmol) in DCM (10 mL) at 0° C. was added TEA (781 mg, 7.74 mmol). The mixture was stirred at 0° C. for 1 h, then $H_2O$ (30 mL) added and the mixture was extracted with DCM (50 mL×3). The obtained organic layers were washed with brine, dried over anhydrous $Na_2SO_4$ and filtered. The filtrate was concentrated under reduced pressure and the crude residue was purified by silica gel column chromatography to give methyl (2S)-3-methyl-2-{methyl[1-an oil. LCMS (ESI): m/z $[M+H]^+$ calc'd for $C_{19}H_{32}N_4O_4$ 380.2; found 381.3.

Step 8. To a mixture of methyl (2S)-3-methyl-2-{methyl [1-methyl-3-(prop-2-enoyl)-1,3,8-triazaspiro[4.5]decan-8-yl]carbonylamino}butanoate (600 mg, 1.6 mmol) in THE (3 mL) was added LiOH (75.5 mg, 3.15 mmol) in $H_2O$ (2 mL). The mixture was stirred at rt for 1 h, then lyophilized to afford (2S)-3-methyl-2-{methyl[1-methyl-3-(prop-2-enoyl)-1,3,8-triazaspiro[4.5]decan-8-yl]carbonylamino}butanoic acid, lithium salt (500 mg, 78% yield) as a solid. LCMS (ESI): m/z $[M+H]^+$ calc'd for $C_{18}H_{30}N_4O_4$ 366.2; found 367.2.

Intermediate 15. Synthesis of (2S)-3-methyl-2-{methyl[3-(prop-2-enoyl)-1-oxa-3,8-diazaspiro[4.5]decan-8-yl]carbonylamino}butanoic acid

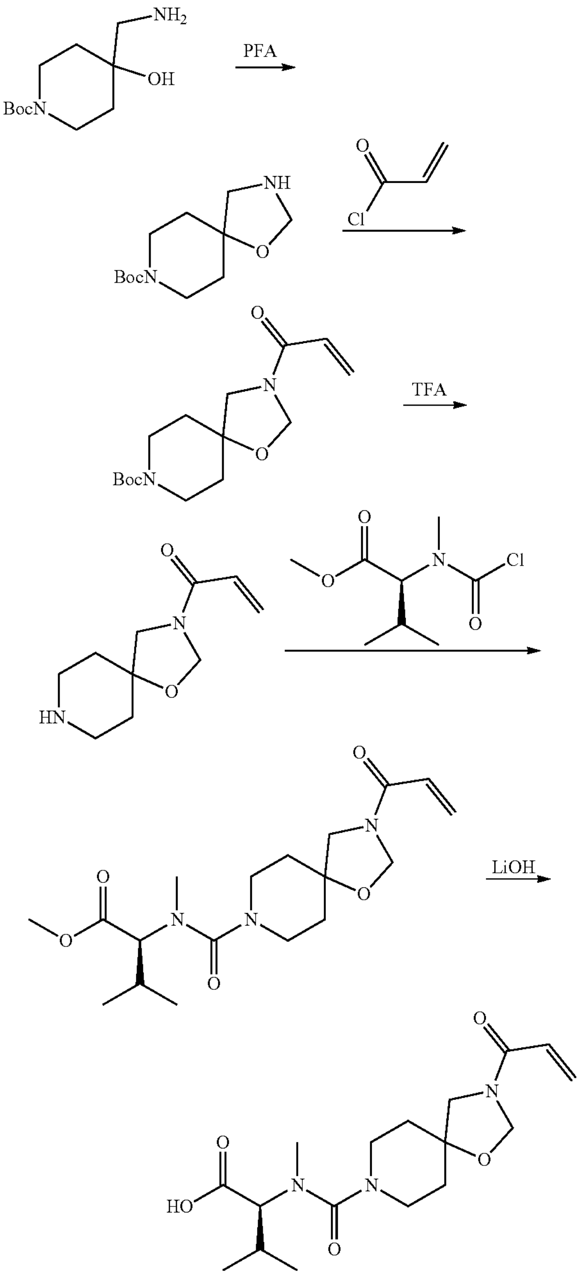

Step 1. To a mixture of tert-butyl 4-(aminomethyl)-4-hydroxypiperidine-1-carboxylate (26 g, 112.9 mmol) in MeOH (52 mL) and 3M NaOH (260 mL) was added HCHO (37 wt. % in $H_2O$; 52 mL). The mixture was stirred for stirred at rt for 16 h, then extracted with DCM (100 mL×3). The combined organic layers were dried over $Na_2SO_4$, filtered and concentrated under reduced pressure to give tert-butyl 1-oxa-3,8-diazaspiro[4.5]decane-8-carboxylate (28.8 g) as an oil. The crude product was used directly in the next step. LCMS (ESI): m/z $[M+H]^+$ calc'd for $C_{12}H_{22}N_2O_3$ 242.2; found 243.2.

Step 2. To a mixture of tert-butyl 1-oxa-3,8-diazaspiro[4.5]decane-8-carboxylate (14.4 g, 59.4 mmol) and $NaHCO_3$ (14.97 g, 178.2 mmol) in DCM (75 mL) and $H_2O$ (75 mL) at 0° C. was added prop-2-enoyl chloride (8.06 g, 89.1 mmol). The mixture was stirred at 0° C. for 1 h, then extracted with DCM (50 mL×3). The combined organic layers were concentrated under reduced pressure and the crude residue was purified by silica gel column chromatography to give tert-butyl 3-(prop-2-enoyl)-1-oxa-3,8-diazaspiro[4.5]decane-8-carboxylate (10 g, 54% yield) as an oil. LCMS (ESI): m/z $[M+H]^+$ calc'd for $C_{15}H_{24}N_2O_4$ 296.2; found 297.2.

Step 3. To a mixture of tert-butyl 3-(prop-2-enoyl)-1-oxa-3,8-diazaspiro[4.5]decane-8-carboxylate (1.0 g, 3.4 mmol) in DCM (6 mL) was added TFA (2 mL). The mixture was stirred at rt for 1 h, then concentrated under reduced pressure to give 1-{1-oxa-3,8-diazaspiro[4.5]decan-3-yl}prop-2-en-1-one (0.67 g) as an oil. The product was used to next step directly. LCMS (ESI): m/z $[M+H]^+$ calc'd for $C_{10}H_{16}N_2O_2$ 196.1; found 197.1.

Step 4. To a mixture of methyl (2S)-2-[(chlorocarbonyl)amino]-3-methylbutanoate (0.66 g, 3.4 mmol) and TEA (1.72 g, 17 mmol) in DCM (10 mL) at 0° C. was added 1-{1-oxa-3,8-diazaspiro[4.5]decan-3-yl}prop-2-en-1-one (0.67 g, 3.4 mmol). The mixture was stirred at 0° C. for 1 h, then $H_2O$ (30 mL) added and the mixture was extracted with DCM (30 mL). The combined organic layers were concentrated under reduced pressure and the crude residue was purified by silica gel column chromatography to give methyl (2S)-3-methyl-2-{methyl[3-(prop-2-enoyl)-1-oxa-3,8-diazaspiro[4.5]decan-8-yl]carbonylamino}butanoate (600 mg, 47% yield) as an oil. LCMS (ESI): m/z $[M+H]^+$ calc'd for $C_{18}H_{29}N_3O_5$ 367.2; found 368.3.

Step 5. To a mixture of methyl (2S)-3-methyl-2-{methyl[3-(prop-2-enoyl)-1-oxa-3,8-diazaspiro[4.5]decan-8-yl]carbonylamino}butanoate (600 mg, 1.63 mmol) in THF (5 mL) was added a solution of lithium hydroxide (78 mg, 3.3 mmol) in $H_2O$ (5 mL). The mixture was stirred at rt for 4 h, then adjusted to pH ~4 with 1 N HCl, and extracted with DCM (20 mL×3). The combined organic layers were concentrated under reduced pressure to give (2S)-3-methyl-2-{methyl[3-(prop-2-enoyl)-1-oxa-3,8-diazaspiro[4.5]decan-8-yl]carbonylamino}butanoic acid (500 mg) as an oil. LCMS (ESI): m/z $[M+H]^+$ calc'd for $C_{17}H_{27}N_3O_5$ 353.2; found 354.2.

Intermediate 16. Synthesis of (2S)-3-methyl-2-{methyl[4-(prop-2-enoyl)-1-propyl-1,4,9-triazaspiro[5.5]undecan-9-yl]carbonylamino}butanoic acid, lithium salt

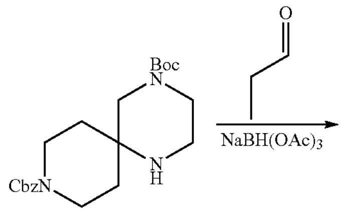

-continued

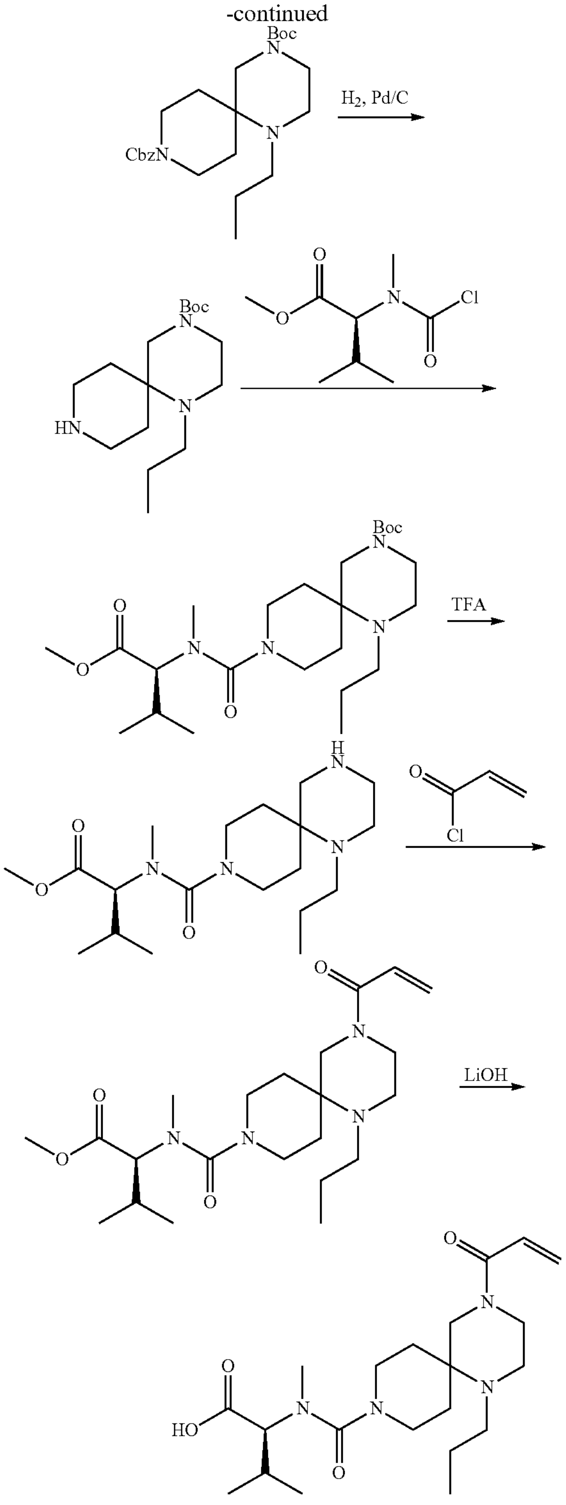

Step 1. To a mixture of tert-butyl 9-{3-[(formyloxy)methyl]phenyl}-1,4,9-triazaspiro[5.5]undecane-4-carboxylate (1.0 g, 2.6 mmol) and propanal (0.3 g, 5.2 mmol) in DCM (10 mL) was stirred at rt for 20 min. $NaBH(OAc)_3$ (1.1 g, 5.2 mmol) was added and the mixture was stirred at rt for 1 h, then $H_2O$ (20 mL) added and the mixture was extracted with DCM (20 mL×3). The combined organic layers were washed with brine (20 mL), dried over anhydrous $Na_2SO_4$ and filtered. The filtrate was concentrated under reduced pressure and the crude residue was purified by silica gel column chromatography to give tert-butyl 9-{3-[(formyloxy)methyl]phenyl}-1-propyl-1,4,9-triazaspiro[5.5]undecane-4-carboxylate (0.7 g, 62% yield) as an oil. LCMS (ESI): m/z $[M+H]^+$ calc'd for $C_{24}H_{37}N_3O_4$ 431.3; found 432.3.

Step 2. A mixture of tert-butyl 9-{3-[(formyloxy)methyl]phenyl}-1-propyl-1,4,9-triazaspiro[5.5]undecane-4-carboxylate (600 mg, 1.39 mmol) and 10% Pd/C (148 mg, 1.39 mmol) in THE (10 mL) was stirred under an atmosphere of $H_2$ (15 psi) at rt for 1 h. The mixture was filtered and the filtrate was concentrated under reduced pressure to give tert-butyl 1-propyl-1,4,9-triazaspiro[5.5]undecane-4-carboxylate (500 mg) as an oil. LCMS (ESI): m/z $[M+H]^+$ calc'd for $C_{16}H_{31}N_3O_2$ 297.2; found 298.2.

Step 3. To a mixture of methyl (2S)-2-[(chlorocarbonyl)(methyl)amino]-3-methylbutanoate (314 mg, 1.5 mmol) in DCM (5 mL) at 0° C. was added TEA (458 mg, 4.5 mmol) and tert-butyl 1-propyl-1,4,9-triazaspiro[5.5]undecane-4-carboxylate (450 mg, 1.5 mmol). The mixture was stirred at 0° C. for 1 h, then $H_2O$ (20 mL) added and the mixture was extracted with DCM (20 mL×3). The combined organic layers were washed with brine (20 mL), dried over anhydrous $Na_2SO_4$ and filtered. The filtrate was concentrated under reduced pressure and the crude residue was purified by silica gel column chromatography to give tert-butyl 9-{[(2S)-1-methoxy-3-methyl-1-oxobutan-2-yl](methyl)carbamoyl}-1-propyl-1,4,9-triazaspiro[5.5]undecane-4-carboxylate (650 mg, 83% yield) as an oil. LCMS (ESI): m/z $[M+H]^+$ calc'd for $C_{24}H_{44}N_4O_5$ 468.3; found 469.3.

Step 4. To a mixture of tert-butyl 9-{[(2S)-1-methoxy-3-methyl-1-oxobutan-2-yl](methyl)carbamoyl}-1-propyl-1,4,9-triazaspiro[5.5]undecane-4-carboxylate (550 mg, 1.17 mmol) in DCM (6 mL) at 0° C. was added TFA (2 mL). The mixture was stirred at 0° C. for 15 min, then concentrated under reduced pressure to give methyl (2S)-3-methyl-2-[methyl({1-propyl-1,4,9-triazaspiro[5.5]undecan-9-yl}carbonyl)amino]butanoate (435 mg), that was used directly in the next step. LCMS (ESI): m/z $[M+H]^+$ calc'd for $C_{19}H_{36}N_4O_3$ 368.3; found 369.3.

Step 5. To a mixture of methyl (2S)-3-methyl-2-[methyl({1-propyl-1,4,9-triazaspiro[5.5]undecan-9-yl}carbonyl)amino]butanoate (435 mg, 1.18 mmol) in DCM (5 mL) and $H_2O$ (5 mL) at 0° C. was added $NaHCO_3$ (991 mg, 11.8 mmol) and prop-2-enoyl chloride (214 mg, 2.36 mmol). The mixture was stirred at 0° C. for 1 h, then $H_2O$ (20 mL) added and the mixture was extracted with DCM (20 mL×3). The combined organic layers were washed with brine (20 mL), dried over anhydrous $Na_2SO_4$ and filtered. The filtrate was concentrated under reduced pressure and the crude residue was purified by silica gel column chromatography to give methyl (2S)-3-methyl-2-{methyl[4-(prop-2-enoyl)-1-propyl-1,4,9-triazaspiro[5.5]undecan-9-yl]carbonylamino}butanoate (460 mg, 83% yield) as an oil. LCMS (ESI): m/z $[M+H]^+$ calc'd for $C_{22}H_{38}N_4O_4$ 422.3; found 423.3.

Step 6. To a mixture of methyl (2S)-3-methyl-2-{methyl[4-(prop-2-enoyl)-1-propyl-1,4,9-triazaspiro[5.5]undecan-9-yl]carbonylamino}butanoate (100 mg, 0.24 mmol) in THE (1 mL) was added a mixture of LiOH (11.3 mg, 0.47 mmol) in $H_2O$ (1.5 mL). The mixture was stirred at rt for 4 h, then lyophilized to afford (2S)-3-methyl-2-{methyl[4-(prop-2-enoyl)-1-propyl-1,4,9-triazaspiro[5.5]undecan-9-yl]carbonylamino}butanoic acid, lithium salt (96 mg) as a solid, that was used directly in the next step. LCMS (ESI): m/z $[M+H]^+$ calc'd for $C_{21}H_{36}N_4O_4$ 408.3; found 409.3.

Intermediate 17. Synthesis of N—((S)-3-acryloyl-4-methyl-1-oxa-3,8-diazaspiro[4.5]decane-8-carbonyl)-N-methyl-L-valine methyl ester

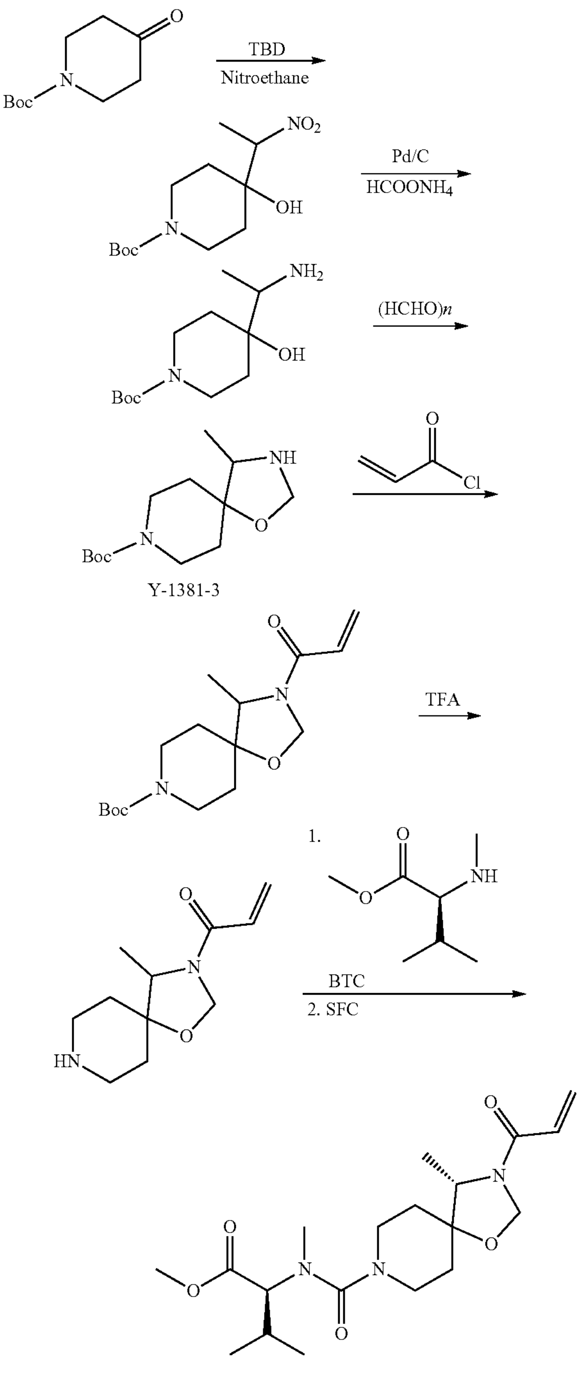

Step 1. To a solution of nitroethane (1 L) was added tert-butyl (4-oxopiperidin-1-yl) formate (200 g, 1 mol, 1 eq) and TBD (13.9 g, 0.1 mol, 0.1 eq) at 0° C. The reaction mixture was stirred at 20° C. for 16 h. The resulting mixture was concentrated under reduced pressure and the remaining residue was purified by silica gel column chromatography to afford tert-butyl 4-hydroxy-4-(1-nitroethyl)piperidine-1-carboxylate (135 g, yield 49%) as a white solid. ESI-MS m/z=299.2 [M+H]+, Calculated MW: 274.15.

Step 2. To a solution of tert-butyl 4-hydroxy-4-(1-nitroethyl)piperidine-1-carboxylate (135 g, 0.49 mol, 1 equiv) and $HCOONH_4$ (269 g, 4.3 mol, 8.7 equiv) in MeOH (1350 mL) was added Pd/C (13.6 g, 0.13 mol, 0.26 equiv) and AcOH (0.29 g, 4.9 mmol, 0.01 equiv) at room temperature. The reaction mixture was stirred for 16 h after which the mixture was adjusted to pH value of 8 with TEA (4.96 g, 0.1 equiv) and filtered. The filter cake was washed with DCM/MeOH (200 mL, 5/1). The filtrate was concentrated under reduced pressure and purified by alkaline silica gel column chromatography to afford tert-butyl 4-(1-aminoethyl)-4-hydroxypiperidine-1-carboxylate (135 g, yield 89%) as a white solid. ESI-MS m/z=189.3 $[M+H-tBu]^+$, Calculated MW: 244.34.

Step 3. To a solution of [4-(1-aminoethyl)-4-hydroxypiperidin-1-yl]tert-butyl formate (40 g, 0.16 mol, 1 eq) in ACN (800 mL) was added $MgSO_4$ (39.1 g, 0.33 mol, 2 eq), $Cs_2CO_3$ (79.7 g, 0.25 mol, 1.5 eq) and (HCHO)n (19.6 g, 0.65 mol, 4 eq). The mixture was stirred at 50° C. for 2 h under $N_2$. The reaction mixture was filtered and the filtrate was concentrated in vacuo to afford tert-butyl {4-methyl-1-oxa-3,8-diazaspiro[4.5]decan-8-yl}formate (40 g, yield 97%) as a colorless oil. ESI-MS m/z=257.3 $[M+H]^+$, Calculated MW: 256.35.

Step 4. To a mixture of tert-butyl {4-methyl-1-oxa-3,8-diazaspiro[4.5]decan-8-yl}formate (40 g, 155.4 mmol, 1 eq) and $NaHCO_3$ (52.2 g, 621.6 mmol, 3 eq) in DCM (500 mL) and $H_2O$ (500 mL) was added prop-2-enoyl chloride (15.5 g, 170.9 mmol, 1 eq) dropwise at 0° C. and stirred at 0° C. for 1 h. The resulting was filtered, and the filtrate was extracted with DCM (200 mL×2). The organic phase was washed with brine (100 mL) and concentrated under reduced pressure. The resulting residue was purified by column chromatography to afford give tert-butyl [4-methyl-3-(prop-2-enoyl)-1-oxa-3,8-diazaspiro[4.5]decan-8-yl]formate (33 g, yield 68%) as a colorless oil. ESI-MS m/z=311.1 $[M+H]^+$, Calculated MW: 310.39.

Step 5. A mixture of tert-butyl [4-methyl-3-(prop-2-enoyl)-1-oxa-3,8-diazaspiro[4.5]decan-8-yl]formate (200 g, 0.64 mol, 1 equiv) in TFA/DCM (700 ml, ⅓, 2 L) was stirred for 1 h at 0° C. The mixture was concentrated under reduced pressure at 0-10° C. to afford crude 1-(4-methyl-1-oxa-3,8-diazaspiro[4.5]decan-3-yl)prop-2-en-1-one (350 g TFA salt, purity 36%). ESI-MS m/z=211.2 $[M+H]^+$, Calculated MW: 210.28.

Step 6. To a solution of methyl (2S)-3-methyl-2-(methylamino)butanoate (63 g, 0.345 mol, 1 eq) and DIEA (360 g, 2.8 mol, 8 eq) in DCM (600 mL) was added BTC (36.5 g, 0.14 mol, 0.4 eq) in portions at 0° C., and the mixture was stirred at 0° C. for 1 h. The reaction mixture was then cooled to −40° C. and a solution of 1-{4-methyl-1-oxa-3,8-diazaspiro[4.5]decan-3-yl}prop-2-en-1-one (TFA salt, 36%, 175 g, 0.32 mol, 0.92 eq) in 300 ml DCM was added dropwise. The reaction mixture was then allowed to warm to rt and stirred for 12 h at rt. The reaction mixture was then concentrated under reduced pressure and the remaining residue was diluted with EA (0.5 L). The mixture was washed with brine (200 ml×2), dried over $Na_2SO_4$, and concentrated under reduced pressure to afford crude residue. The residue was purified by chromatography to afford methyl N-(3-acryloyl-4-methyl-1-oxa-3,8-diazaspiro[4.5]decane-8-carbonyl)-N-methyl-L-valinate as a racemic mixture (168 g, 64% yield). A portion of the racemic product (85 g) was separated using chiral SFC to afford N—((S)-3-acryloyl-4-methyl-1-oxa-3,8-diazaspiro[4.5]decane-8-carbonyl)-N-methyl-L-valine methyl ester ESI-MS m/z=382.2 $[M+H]^+$, Calculated MW: 381.2. $^1H$ NMR (400 MHz, $CD_3OD$) δ 6.72-6.24 (m, 2H), 5.85-5.70 (m, 1H), 5.22-4.99 (m, 2H), 4.01 (d, J=6.5 Hz, 1H), 3.88 (d, J=10.4 Hz, 1H), 3.69 (s, 3H), 3.51-3.40 (m, 2H), 3.25-3.06 (m, 2H), 2.96 (s, 3H), 2.26-2.15 (m, 1H), 1.82-1.63 (m, 4H), 1.19 (dd, J=6.5, 2.3 Hz, 3H), 0.95 (dd, J=12.3, 6.6 Hz, 6H).

Intermediate 18. Synthesis of methyl (2S)-2-[(3-{3-[(formyloxy)methyl]phenyl}-1-oxa-3,8-diazaspiro[4.5]decan-8-yl)carbonyl(methyl)amino]-3-methylbutanoate

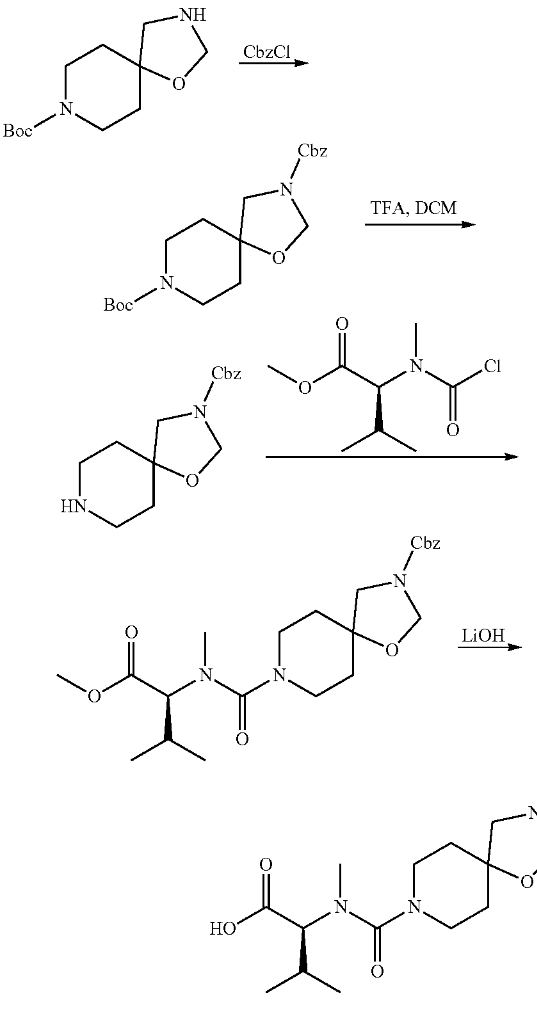

Step 1. To a solution of tert-butyl {1-oxa-3,8-diazaspiro[4.5]decan-8-yl}formate (2 g, 8.2 mmol, 1 eq) and $NaHCO_3$ (2.1 g, 25 mmol, 3 eq) in DCM/$H_2O$=1/1 (20 mL) was added CbzCl (1.7 g, 9.8 mmol, 1.2 eq). The mixture was stirred at 0° C. for 20 min. The reaction mixture was treated with $H_2O$ (20 mL), extracted with DCM (30 mL×3). The combined organic layers were washed with water (20 mL) and brine (20 mL) and then dried over $Na_2SO_4$, filtered, and concentrated under reduced pressure to afford the crude product. The crude product was purified by chromatography to afford tert-butyl (3-{3-[(formyloxy)methyl]phenyl}-1-oxa-3,8-diazaspiro[4.5]decan-8-yl) formate (2 g, 61% yield) as a colorless oil. ESI-MS m/z: 399.3 $[M+Na]^+$; Calculated MW: 376.2.

Step 2. To a solution of tert-butyl (3-{3-[(formyloxy) methyl]phenyl}-1-oxa-3,8-diazaspiro[4.5]decan-8-yl) formate (2 g, 5.3 mmol, 1 eq) in DCM (12 mL) was added TFA (6 g, 53 mmol, 10 eq) at 20° C. The reaction mixture was stirred at 20° C. for 40 min. The reaction mixture was then concentrated to afford a yellow oil. The yellow oil was dissolved in DCM (30 ml) and adjusted with saturated $NaHCO_3$ aqueous to pH=8-9. The resulting mixture was extracted with DCM (30 mL×3) and the combined organic layers were washed with water (20 mL), and brine (20 mL). The organic layer was dried over $Na_2SO_4$, filtered and concentrated under reduced pressure to afford (3-{1-oxa-3,8-diazaspiro[4.5]decan-3-yl}phenyl)methyl formate (1.5 g, 98% yield) as a white solid. ESI-MS m/z: 277.3 $[M+H]^+$; Calculated MW: 276.2.

Step 3. To a solution of methyl (2S)-2-[(chlorocarbonyl)(methyl)amino]-3-methylbutanoate (1.1 g, 5.1 mmol, 1 eq) and TEA (1.6 g, 15 mmol, 3 eq) in DCM (20 mL) was added (3-{1-oxa-3,8-diazaspiro[4.5]decan-3-yl}phenyl)methyl formate (1.4 g, 5.1 mmol, 1 eq). The mixture was stirred at 0° C. for 0.5 h. The mixture was treated with $H_2O$ (20 mL), extracted with DCM (30 mL×3) and the combined organic layers were washed with water (20 mL), and brine (20 mL). The organic layer was dried over $Na_2SO_4$, filtered and concentrated under reduced pressure to afford crude product. The crude product was purified by chromatography to afford methyl (2S)-2-[(3-{3-[(formyloxy)methyl]phenyl}-1-oxa-3,8-diazaspiro[4.5]decan-8-yl)carbonyl(methyl)amino]-3-methylbutanoate (1.7 g, 70% yield) as yellow oil. ESI-MS m/z: 448.3 $[M+H]^+$, Calculated MW: 447.2.

Step 4. To a solution of methyl (2S)-2-[(3-{3-[(formyloxy)methyl]phenyl}-1-oxa-3,8-diazaspiro[4.5]decan-8-yl)carbonyl(methyl)amino]-3-methylbutanoate (400 mg, 0.89 mmol, 1 eq) in THF (1 mL) was added a solution of LiOH (64 mg, 2.7 mmol, 3 eq) in $H_2O$ (1.5 mL). The mixture was stirred at 20° C. for 12 h. The resulting solution was adjusted pH=6 with 1 N HCl and extracted with DCM (30 mL×3). The combined organic layers were washed with water (20 mL), and brine (20 mL) and dried over $Na_2SO_4$, filtered and concentrated under reduced pressure to give (2S)-2-[(3-{3-[(formyloxy)methyl]phenyl}-1-oxa-3,8-diazaspiro[4.5]decan-8-yl)carbonyl(methyl)amino]-3-methylbutanoic acid (380 mg, 88% yield) as yellow oil. ESI-MS m/z: 434.3 $[M+H]^+$, Calculated MW: 433.2.

Intermediate 19. Synthesis of (2S)-3-methyl-2-{methyl[7-(prop-2-enoyl)-5-oxa-2,7-diazaspiro[3.4]octan-2-yl]carbonylamino}butanoic acid

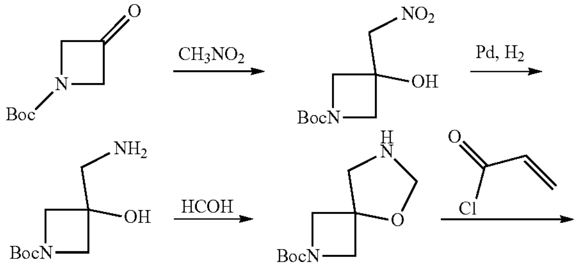

-continued

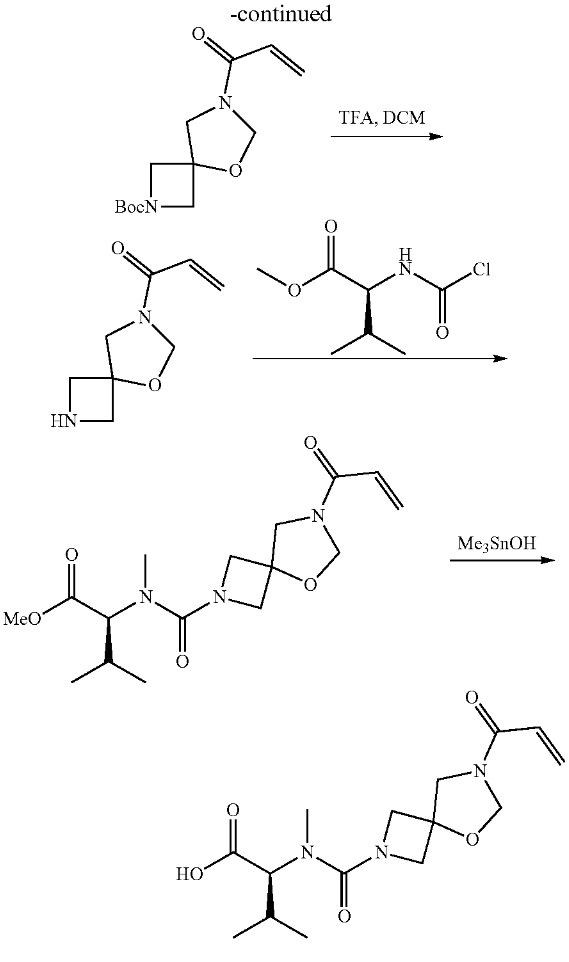

Step 1. To a solution of the tert-butyl 3-oxoazetidine-1-carboxylate (10 g, 0.058 mol, 1 eq) in EtOH (30 mL) was added $CH_2NO_2$ (12 mL) and triethylamine (0.59 g, 0.0058 mol, 0.1 eq). The resulting mixture was stirred for 16 h at 20° C. The mixture was concentrated under reduced pressure to afford tert-butyl 3-hydroxy-3-(nitromethyl)azetidine-1-carboxylate (13.5 g, 95% yield) as a yellow solid. ESI-MS m/z=255.1 $[M+Na]^+$; Calculated MW: 232.11.

Step 2. To a solution of tert-butyl 3-hydroxy-3-(nitromethyl)azetidine-1-carboxylate (13.5 g, 0.058 mol, 1.0 equiv) in MeOH (100 mL) was added Pd/C (1 g). The reaction mixture was then stirred at 20° C. for 16 hrs under hydrogen (15 psi). The resulting mixture was filtered and the filtrate was concentrated to afford tert-butyl 3-(aminomethyl)-3-hydroxyazetidine-1-carboxylate (12 g, 97% yield) as a white solid. ESI-MS m/z=103.2 $[M-Boc+H]^+$; Calculated MW: 202.13.

Step 3. To a solution of tert-butyl 3-(aminomethyl)-3-hydroxyazetidine-1-carboxylate (1.5 g, 7.4 mmol, 1.0 eq) in MeOH (3 mL) and NaOH (15 mL, 2 mol/L aqueous) was added HCHO (3 mL) (37 wt % in $H_2O$) and the reaction mixture was stirred for 16 h at 20° C. The resulting solution was extracted with DCM (3*10 mL). The combined organic layers were dried over $Na_2SO_4$ and concentrated under reduced pressure to afford tert-butyl 5-oxa-2,7-diazaspiro[3.4]octane-2-carboxylate (1 g, crude) as a yellow solid. The crude product was used directly in the next step. ESI-MS m/z=215.1 $[M+H]^+$; Calculated MW: 214.13.

Step 3. Prop-2-enoyl chloride (633 mg, 7.0 mmol, 1.5 equiv) was added to the solution of (tert-butyl 5-oxa-2,7- diazaspiro[3.4]octane-2-carboxylate (1.0 g, 4.7 mmol, 1.0 equiv) and $NaHCO_3$ (1.2 g, 14 mmol, 3.0 equiv) in DCM (5 mL) and $H_2O$ (5 mL) at 0° C. The resulting mixture was stirred at 0° C. for 1 h. The mixture was then diluted with DCM (20 mL) and washed with water (20 mL) and brine (20 mL). The organic phase was collected, dried over $Na_2SO_4$, filtered and concentrated. The resulting residue was purified by column chromatography afford tert-butyl 7-(prop-2-enoyl)-5-oxa-2,7-diazaspiro[3.4]octane-2-carboxylate (660 mg, 50% yield) as a white solid. ESI-MS m/z=269.1 $[M+H]^+$; Calculated MW: 268.14.

Step 4. To a solution of the tert-butyl 7-(prop-2-enoyl)-5-oxa-2,7-diazaspiro[3.4]octane-2-carboxylate (660 mg, 2.46 mmol, 1.0 equiv) in DCM (6 mL) was added TFA (2 mL) at 20° C. The resulting solution was stirred at 20° C. for 1 h. The solvent was removed under reduced pressure to afford 1-{5-oxa-2,7-diazaspiro[3.4]octan-7-yl}prop-2-en-1-one (510 mg, crude) as a yellow solid. This crude product was used in the next step without further purification. ESI-MS m/z=169.2 $[M+H]^+$; Calculated MW: 168.09.

Step 5. To a solution of the methyl (2S)-3-methyl-2-(methylamino)butanoate (357 mg, 2.5 mmol, 1.0 equiv) in DCM (5 mL) was added triethylamine (1492 mg, 14.7 mmol, 6 equiv) and triphosgene (365 mg, 1.23 mmol, 0.5 equiv) at 0° C. The resulting solution was stirred at 0° C. for 1 h. The mixture was used directly in the next step.

Step 6. To a solution of methyl (2S)-2-[(chlorocarbonyl)(methyl)amino]-3-methylbutanoate (509 mg, 2.46 mmol, 1 equiv) and triethylamine (1492 mg, 14.7 mmol, 6 equiv) in DCM (15 mL) was added 1-{5-oxa-2,7-diazaspiro[3.4]octan-7-yl}prop-2-en-1-one (413 mg, 2.46 mmol, 1 equiv) at 0° C. The mixture was stirred at 0° C. for 0.5 h. The mixture was then diluted with DCM (20 mL) and washed with $H_2O$ (30*2 mL). The organic layers were dried over $Na_2SO_4$ and concentrated under reduced pressure. The resulting residue was purified by chromatography to afford methyl (2S)-3-methyl-2-{methyl[7-(prop-2-enoyl)-5-oxa-2,7-diazaspiro[3.4]octan-2-yl]carbonylamino}butanoate (605 mg, 69% yield) as a white solid. ESI-MS m/z=340.2 $[M+H]^+$; Calculated MW: 339.18.

Step 7. To a solution of methyl (2S)-3-methyl-2-{methyl[7-(prop-2-enoyl)-5-oxa-2,7-diazaspiro[3.4]octan-2-yl]carbonylamino}butanoate (300 mg, 0.88 mmol, 1.0 equiv) in DCE (10 mL) was added trimethyltin hydroxide (1.9 g, 10.6 mmol, 12 eq). The reaction mixture was stirred at 85° C. for 16 h. The reaction mixture was then diluted with DCM (10 mL). The resulting mixture was washed with 1 N HCl (10 mL) and the organic layers were dried over $Na_2SO_4$ and concentrated under reduced pressure. The resulting residue was purified by chromatography to afford (2S)-3-methyl-2-{methyl[7-(prop-2-enoyl)-5-oxa-2,7-diazaspiro[3.4]octan-2-yl]carbonylamino}butanoic acid (200 mg, 66% yield) as a white solid. ESI-MS m/z=326.1 $[M+H]^+$; Calculated MW: 325.16.

Intermediate P1 and P2. Synthesis of (2S)-3-methyl-2-{methyl[3-(prop-2-enoyl)-1-oxa-3,7-diazaspiro[4.4]nonan-7-yl]carbonylamino}butanoate (P1+P2)

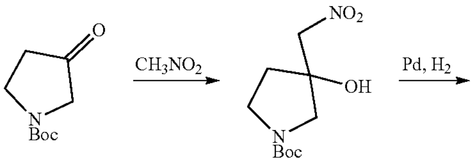

-continued

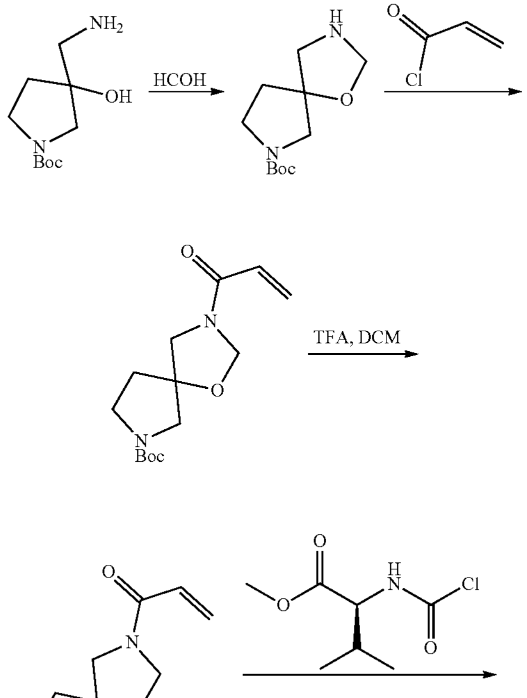

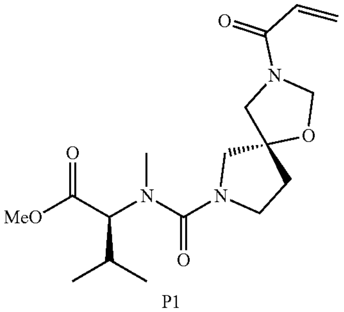

\+

P1

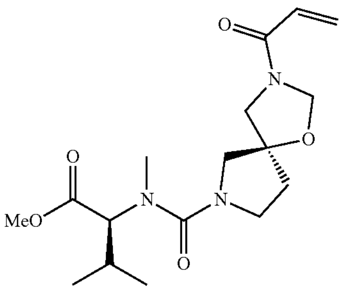

P2

Step 1. To a solution of the tert-butyl 3-oxopyrrolidine-1-carboxylate (10 g, 0.058 mol, 1 eq) in EtOH (30 mL) was added $CH_2NO_2$(12 mL) and triethylamine (0.59 g, 5.8 mol, 0.1 eq). The reaction mixture was stirred for 16 h at 20° C. After which the mixture was concentrated under reduced pressure to afford tert-butyl 3-hydroxy-3-(nitromethyl)pyrrolidine-1-carboxylate (13.3 g, 80% yield) as a yellow solid. ESI-MS m/z=269.1 $[M+Na]^+$; Calculated MW: 246.12.

Step 2. To a solution of tert-butyl 3-hydroxy-3-(nitromethyl)pyrrolidine-1-carboxylate (9.7 g, 0.039 mol, 1.0 equiv) in EtOH (100 mL) and THF (20 mL) was added raney Ni (2 g) and $NH_3H_2O$ (3 mL, purity: 28-30%). The resulting reaction mixture was stirred at 20° C. for 4 h under hydrogen (15 psi). The reaction mixture was filtered and the filtrate was concentrated to afford tert-butyl 3-(aminomethyl)-3-hydroxypyrrolidine-1-carboxylate (9.3 g, 87% yield) as a yellow oil. ESI-MS m/z=117.3 $[M-Boc+H]^+$; Calculated MW: 216.15.

Step 3. To a solution of tert-butyl 3-(aminomethyl)-3-hydroxypyrrolidine-1-carboxylate (9 g, 41.6 mmol, 1 eq) in MeOH (20 mL) and 3 N NaOH (100 mL) was added HCHO (20 mL, 37 wt % in $H_2O$). The reaction mixture was stirred for 16 h at 20° C. After which the resulting solution was extracted with DCM (3*100 mL) and the combined organic layers were dried over $Na_2SO_4$, filtered and concentrated under reduced pressure to afford tert-butyl 1-oxa-3,7-diazaspiro[4.4]nonane-7-carboxylate (6.1 g, crude) as a colorless oil. The crude product was used directly in the next step. ESI-MS m/z=129.3 $[M-Boc+H]^+$; Calculated MW: 228.15.

Step 4. Prop-2-enoyl chloride (3.6 g, 40 mmol, 1.5 equiv) was added to the solution of tert-butyl 1-oxa-3,7-diazaspiro[4.4]nonane-7-carboxylate (6.1 g, 26.7 mmol, 1.0 equiv) and $NaHCO_3$ (6.7 g, 80 mmol, 3 equiv) in DCM (60 mL) and $H_2O$ (60 mL) at 0° C. The reaction mixture was stirred at 0° C. for 1 h. The mixture was then diluted with DCM (100 mL), and washed with water (100 mL) and brine (100 mL). The organic phase was collected, dried over $Na_2SO_4$, filtered and concentrated. The resulting residue was purified by chromatography to afford tert-butyl 3-(prop-2-enoyl)-1-oxa-3,7-diazaspiro[4.4]nonane-7-carboxylate (2.4 g, 30% yield) as a white solid. ESI-MS m/z=305.1 $[M+Na]^+$; Calculated MW: 282.16.

Step 5. To a solution of the tert-butyl 3-(prop-2-enoyl)-1-oxa-3,7-diazaspiro[4.4]nonane-7-carboxylate (2.4 g, 8.5 mmol, 1.0 equiv) in DCM (30 mL) was added TFA (10 mL) at 20° C. The reaction mixture was stirred at 20° C. for 1 h. The solvent was removed under reduced pressure to give 1-{1-oxa-3,7-diazaspiro[4.4]nonan-3-yl}prop-2-en-1-one (1.6 g, crude) as a yellow solid. The crude product was used in the next step without further purification. ESI-MS m/z=183.1 $[M+H]^+$; Calculated MW: 182.22.

Step 6. To a solution of methyl (2S)-2-[(chlorocarbonyl)(methyl)amino]-3-methylbutanoate (1.75 g, 8.5 mmol, 1.0 equiv) and triethylamine (5131 mg, 51 mmol, 6.0 equiv) in DCM (20 mL) was added 1-{1-oxa-3,7-diazaspiro[4.4]nonan-3-yl}prop-2-en-1-one (1540 mg, 8.5 mmol, 1.0 equiv) at 0° C. The mixture was stirred at 0° C. for 0.5 h. The mixture was diluted with DCM (100 mL) and washed with $H_2O$ (100*2 mL). The organic layers were dried over $Na_2SO_4$ and concentrated under reduced pressure. The resulting residue was purified by chromatography to afford methyl (2S)-3-methyl-2-{methyl[3-(prop-2-enoyl)-1-oxa-3,7-diazaspiro[4.4]nonan-7-yl]carbonylamino}butanoate (1.78 g, 56% yield) as a white solid. The desired product was separated via chiral resolution (Chromatographic columns: chiralpak-ADMobile Phase:$CO_2$-MeOH (0.1% DEA)) to give methyl (2S)-3-methyl-2-{methyl[(5S)-3-(prop-2-enoyl)-1-oxa-3,7-diazaspiro[4.4]nonan-7-yl]carbonylamino}butanoate (P1, 800 mg; P2, 780 mg). ESI-MS m/z=354.2 $[M+H]^+$; Calculated MW: 353.20.

Intermediate P1-OH. Synthesis of (2S)-3-methyl-2-{methyl[(5R)-3-(prop-2-enoyl)-1-oxa-3,7-diazaspiro[4.4]nonan-7-yl]carbonylamino}butanoic acid

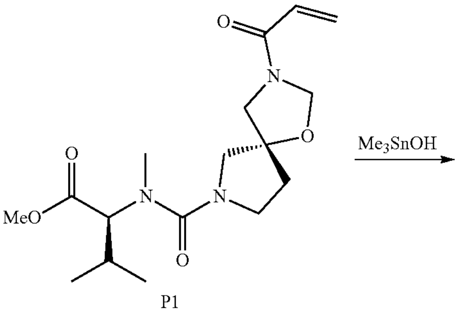

P1

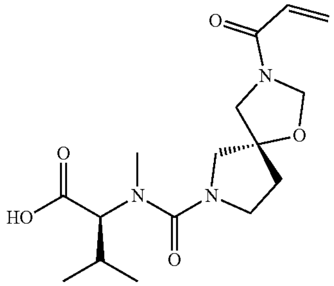

P1-OH

Step 1. To a solution of (P1) methyl (2S)-3-methyl-2-{methyl[(5S)-3-(prop-2-enoyl)-1-oxa-3,7-diazaspiro[4.4]nonan-7-yl]carbonylamino}butanoate (330 mg, 0.93 mmol, 1.0 equiv) in DCE (10 mL) was added trimethyltin hydroxide (2.5 g, 14 mmol, 15 eq). The reaction mixture was stirred at 85° C. for 16 h. The reaction mixture was then diluted with DCM (10 mL) and the resulting mixture was washed with 1 N HCl (10 mL). The organic layers were dried over $Na_2SO_4$ and concentrated under reduced pressure. The resulting residue was purified by chromatography to afford (2S)-3-methyl-2-{methyl[(5R)-3-(prop-2-enoyl)-1-oxa-3,7-diazaspiro[4.4]nonan-7-yl]carbonylamino}butanoic acid (150 mg, 45% yield) as a white solid. ESI-MS m/z=340.2 $[M+H]^+$; Calculated MW: 339.18.

Intermediate P2-OH. Synthesis of (2S)-3-methyl-2-{methyl[(5S)-3-(prop-2-enoyl)-1-oxa-3,7-diazaspiro[4.4]nonan-7-yl]carbonylamino}butanoic acid

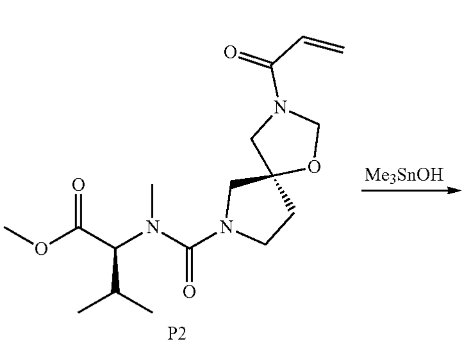

P2

-continued

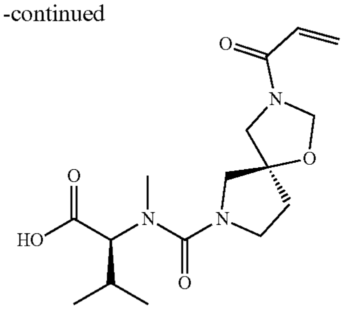

P2-OH

A mixture of (P2) methyl (2S)-3-methyl-2-{methyl[3-(prop-2-enoyl)-1-oxa-3,7-diazaspiro[4.4]nonan-7-yl]carbonylamino}butanoate (165 mg, 0.47 mmol, 1.0 equiv) and $(Me)_3SnOH$ (1.7 g, 9.3 mmol, 20 equiv) in DCE (2 mL) was stirred at 85° C. for 24 h. The mixture was diluted with DCM (20 mL), and then washed with 1 N HCl (20 mL), water (15 mL) and brine (15 mL). The organic phase was collected, dried over $Na_2SO_4$, filtered and concentrated. The resulting residue was purified by chromatography to afford (2S)-3-methyl-2-{methyl[(5S)-3-(prop-2-enoyl)-1-oxa-3,7-diazaspiro[4.4]nonan-7-yl]carbonylamino}butanoic acid (100 mg, 60% yield) as an off-white solid. ESI-MS m/z: 340.2 $[M+H]^+$. Calculated MW: 339.18

Example 1. Synthesis of 1-(4-(dimethylamino)-4-methylpent-2-ynoyl)-N-((2S)-1-((($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,3)-oxadiazola-1(5,3)-indola-6(1,3)-pyridazinacycloundecaphane-4-yl)amino)-3-methyl-1-oxobutan-2-yl)-4-fluoro-N-methylpiperidine-4-carboxamide

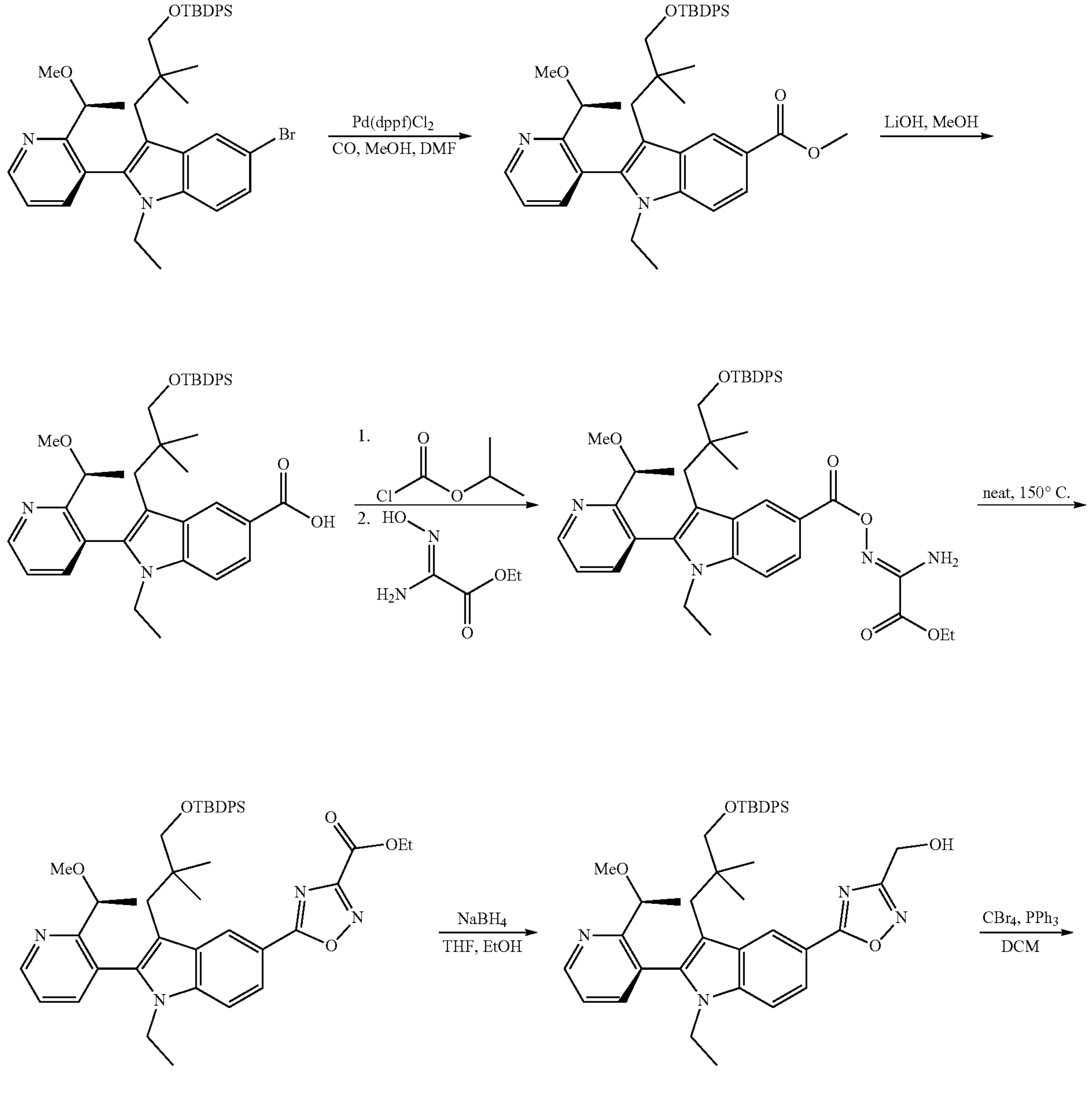

-continued
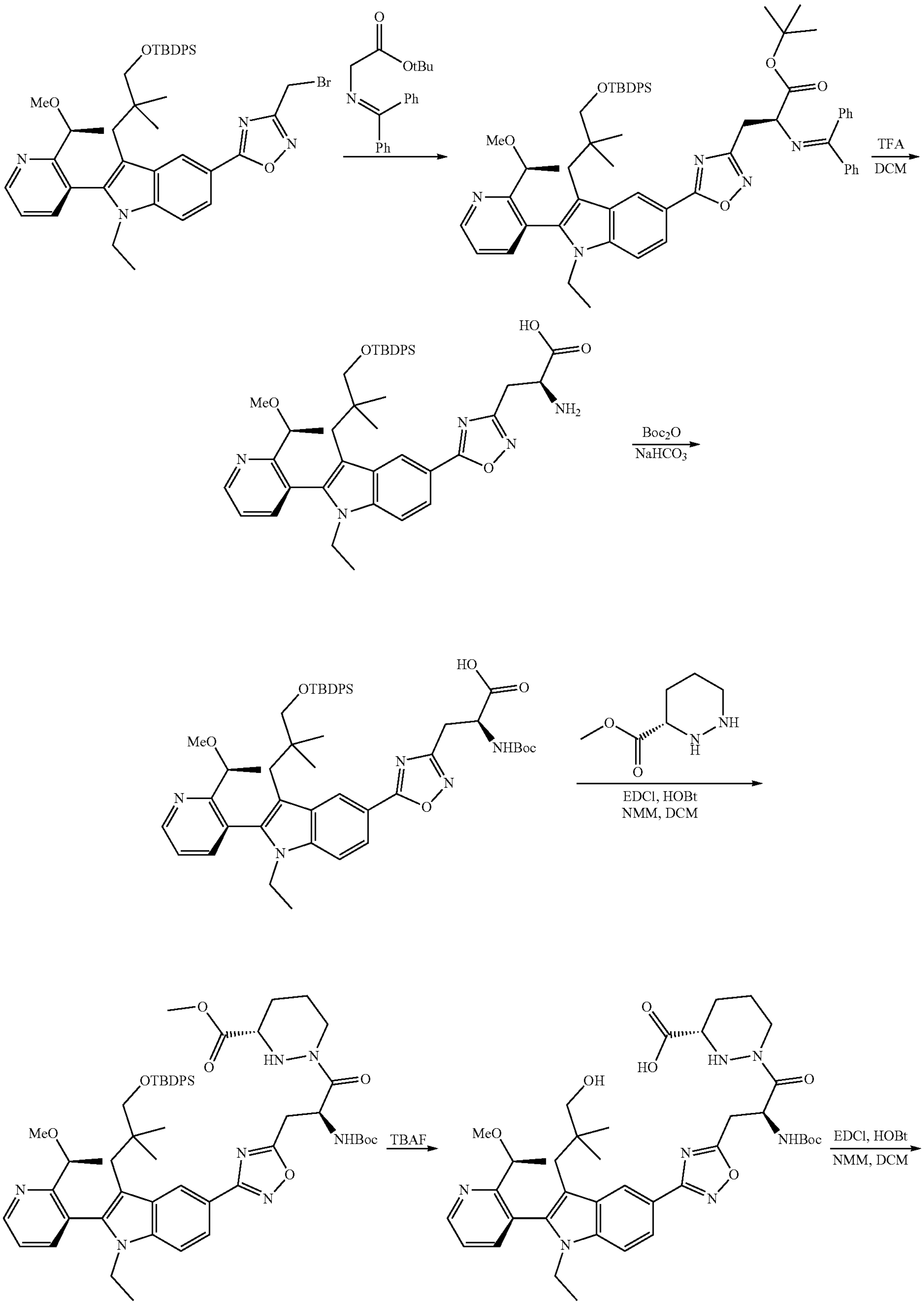

-continued

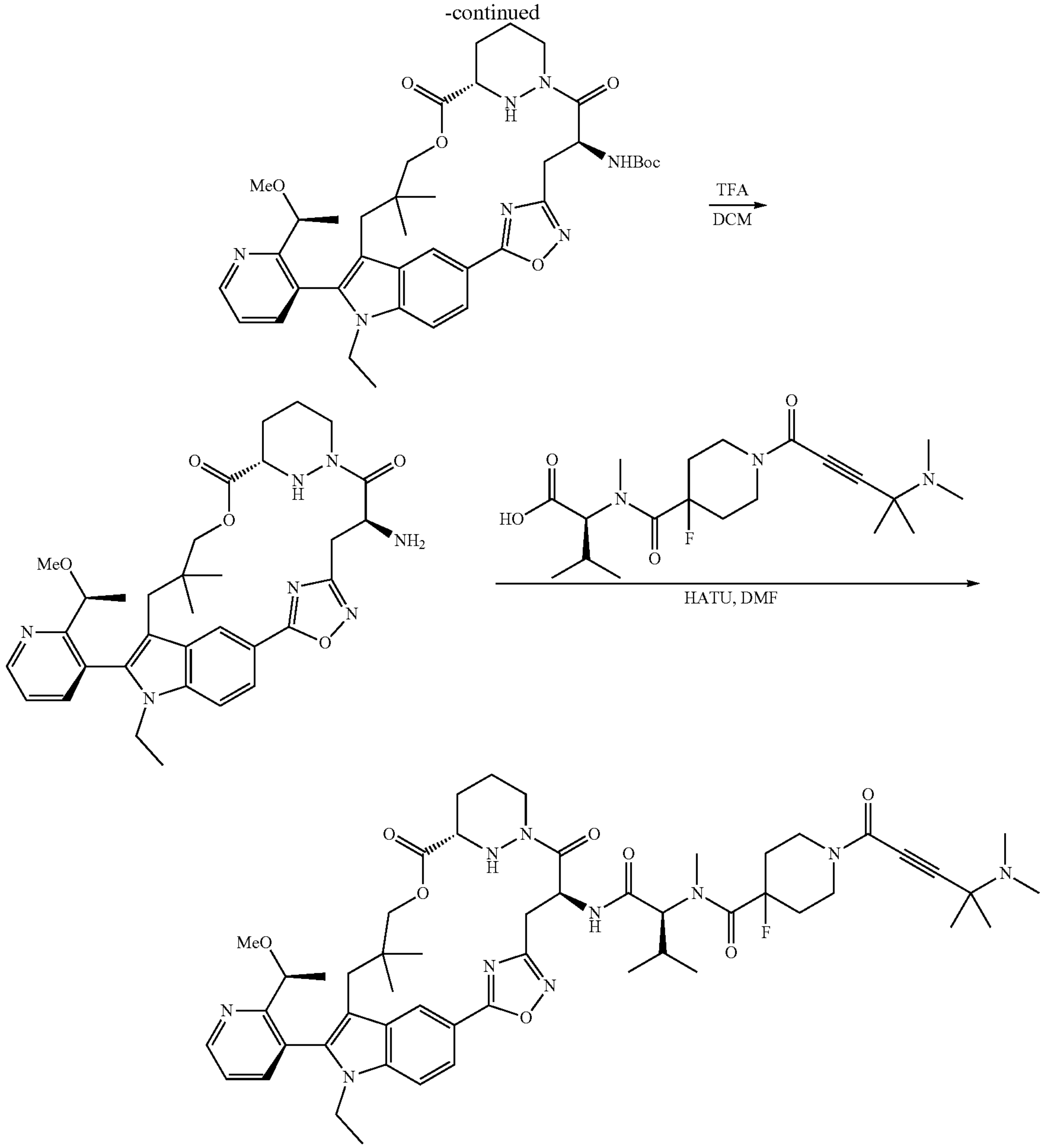

Step 1. A mixture of (2M)-5-bromo-3-[3-[(tert-butyldiphenylsilyl)oxy]-2,2-dimethylpropyl]-1-ethyl-2-[2-[(1S)-1-methoxyethyl]pyridin-3-yl]indole (10.0 g, 14.6 mmol), Pd(dppf)$Cl_2$·DCM (1.19 g, 1.46 mmol) and TEA (2.66 g, 26.3 mmol) in DMF (50 mL) and MeOH (1 mL) under an atmosphere of CO was heated too 100° C. and stirred overnight. $H_2O$ (100 mL) was added, and the mixture extracted with EtOAc (3×100 mL). The combined organic layers were dried over anhydrous $Na_2SO_4$ and filtered. The filtrate was concentrated under reduced pressure and the residue was purified by silica gel column chromatography to give (2M)-3-[3-[(tert-butyldiphenylsilyl)oxy]-2,2-dimethylpropyl]-1-ethyl-2-[2-[(1 S)-1-methoxyethyl]pyridin-3-yl]indole-5-carboxylate (8.0 g, 74% yield) as a foam. LCMS (ESI): m/z $[M+H]^+$ calc'd for $C_{41}H_{50}N_2O_4Si$ 662.4; found 663.4.

Step 2. To a mixture of (2M)-3-[3-[(tert-butyldiphenylsilyl)oxy]-2,2-dimethylpropyl]-1-ethyl-2-[2-[(1S)-1-methoxyethyl]pyridin-3-yl]indole-5-carboxylate (3.90 g, 5.9 mmol) in THE (10 mL) and MeOH (30 mL) at 0° C. was added LiOH (0.70 g, 29.2 mmol) in $H_2O$ (30 mL) dropwise. The mixture was warmed to rt and stirred for 3 h, then acidified to pH ~7 with aqueous HCl and the mixture extracted with EtOAc (3×20 mL). The combined organic layers were washed with brine (2×20 mL), dried over anhydrous $Na_2SO_4$, filtered and the filtrate was concentrated under reduced pressure to give (2M)-3-[3-[(tert-butyldiphenylsilyl)oxy]-2,2-dimethylpropyl]-1-ethyl-2-[2-[(1 S)-1-methoxyethyl]pyridin-3-yl]indole-5-carboxylic acid (2.89 g) as a solid. LCMS (ESI): m/z $[M+H]^+$ calc'd for $C_{40}H_{48}N_2O_4Si$ 648.3; found 649.3.

Step 3. To a mixture of (2M)-3-[3-[(tert-butyldiphenylsilyl)oxy]-2,2-dimethylpropyl]-1-ethyl-2-[2-[(1S)-1-methoxyethyl]pyridin-3-yl]indole-5-carboxylic acid (2.00 g, 3.1 mmol) and $K_2CO_3$ (0.85 g, 6.2 mmol) in DCM (20 mL)

at 0° C. was added isopropyl chloroformate (0.76 g, 6.2 mmol) dropwise. The mixture was stirred at rt for 45 min, then $H_2O$ was added and the mixture extracted with EtOAc (3×50 mL). The combined organic layers were dried over anhydrous $Na_2SO_4$, filtered and the filtrate was concentrated under reduced pressure. The residue was dissolved in DCM (20 mL) and ethyl [(Z)—N-hydroxycarbamimidoyl]formate (0.81 g, 6.2 mmol) and $K_2CO_3$ (0.85 g, 6.2 mmol) were added. The mixture was stirred at rt for 2 h, then $H_2O$ was added and the mixture extracted with EtOAc (3×30 mL). The combined organic layers were dried over anhydrous $Na_2SO_4$ and filtered. The filtrate was concentrated under reduced pressure and the residue was purified by preparative-HPLC to give ethyl [(Z)—N—[(Z)-(2M)-3-[3-[(tert-butyldiphenylsilyl)oxy]-2,2-dimethylpropyl]-1-ethyl-2-[2-[(1 S)-1-methoxyethyl]pyridin-3-yl]indole-5-carbonyloxy]carbamimidoyl]formate (1.23 g, 45% yield) as a solid. LCMS (ESI): m/z $[M+H]^+$ calc'd for $C_{44}H_{54}N_4O_6Si$ 762.4; found 763.3.

Step 4. Ethyl [(Z)—N—[(Z)-(2M)-3-[3-[(tert-butyldiphenylsilyl)oxy]-2,2-dimethylpropyl]-1-ethyl-2-[2-[(1 S)-1-methoxyethyl]pyridin-3-yl]indole-5-carbonyloxy]carbamimidoyl]formate (1.30 g, 1.7 mmol) was heated to 150° C. and stirred for 4 h, then purified by silica gel column chromatography to give ethyl 5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazole-3-carboxylate (600 mg, 28% yield) as a solid. LCMS (ESI): m/z $[M+H]^+$ calc'd for $C_{44}H_{52}N_4O_5Si$ 744.4; found 745.3.

Step 5. To a mixture of ethyl 5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazole-3-carboxylate (1.1 g, 1.5 mmol) in EtOH (6 mL) and THE (6 mL) at 0° C. was added $NaBH_4$ (112 mg, 3.0 mmol) in portions. The mixture was stirred at rt for 1 h, then the mixture was cooled to 0° C. and saturated $NH_4Cl$ was added and the mixture extracted with EtOAc (30 mL). The organic layer was washed with brine (20 mL), dried over anhydrous $Na_2SO_4$, filtered and the filtrate was concentrated under reduced pressure to give [5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazol-3-yl]methanol (900 mg, 78% yield) as a solid. LCMS (ESI): m/z $[M+H]^+$ calc'd for $C_{42}H_{50}N_4O_4Si$ 702.4; found 703.4.

Step 6. To a mixture of [5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazol-3-yl]methanol (900 mg, 1.3 mmol) and $Ph_3P$ (504 mg, 1.92 mmol) in DCM (9 mL) was added $CBr_4$ (637 mg, 1.92 mmol). The mixture was stirred at rt for 3 h, then $H_2O$ was added and the mixture extracted with EtOAc (10 mL). The combined organic layers were washed with brine (10 mL), dried over anhydrous $Na_2SO_4$ and filtered. The filtrate was concentrated under reduced pressure and the residue was purified by silica gel column chromatography to give (2A)-5-[3-(bromomethyl)-1,2,4-oxadiazol-5-yl]-3-[3-[(tert-butyldiphenylsilyl)oxy]-2,2-dimethylpropyl]-1-ethyl-2-[2-[(1 S)-1-methoxyethyl]pyridin-3-yl]indole (700 mg, 36% yield) as a solid. LCMS (ESI): m/z $[M+H]^+$ calc'd for $C_{42}H_{49}BrN_4O_3Si$ 764.3; found 765.2.

Step 7. To a mixture of (2M)-5-[3-(bromomethyl)-1,2,4-oxadiazol-5-yl]-3-[3-[(tert-butyldiphenylsilyl)oxy]-2,2-dimethylpropyl]-1-ethyl-2-[2-[(1 S)-1-methoxyethyl]pyridin-3-yl]indole (1.0 g, 1.3 mmol) and tert-butyl 2-[(diphenylmethylidene)amino]acetate (579 mg, 2.0 mmol) in toluene (4.2 mL) and DCM (1.8 mL) at 0° C. was added KOH (7.0 g, 124.8 mmol) in $H_2O$ (2 mL) and cinchonanium (158 mg, 0.26 mmol). The mixture was warmed to rt and stirred for 3 h, then $H_2O$ was added and the mixture extracted with EtOAc (10 mL). The combined organic layers were washed with brine (5 mL), dried over anhydrous $Na_2SO_4$ and filtered. The filtrate was concentrated under reduced pressure and the residue was purified by silica gel column chromatography to give tert-butyl 3-[5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazol-3-yl]-2-[(diphenylmethylidene)amino] propanoate (350 mg, 25% yield) as a solid. LCMS (ESI): m/z $[M+H]^+$ calc'd for $C_{61}H_{69}N_5O_5Si$ 979.5; found 980.4.

Step 8. To a mixture of tert-butyl 3-[5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazol-3-yl]-2-[(diphenylmethylidene)amino]propanoate (1.80 g, 1.8 mmol) in DCM (18 mL) at 0° C. was added TFA (18 mL) dropwise. The mixture was warmed to rt and stirred for 2 h, then concentrated under reduced pressure to give 2-amino-3-[5-[(2M)-3-[3-[(tert-butyldiphenylsilyl)oxy]-2,2-dimethylpropyl]-1-ethyl-2-[2-[(1 S)-1-methoxyethyl] pyridin-3-yl]indol-5-yl]-1,2,4-oxadiazol-3-yl]propanoic acid (4 g) as an oil. LCMS (ESI): m/z $[M+H]^+$ calc'd for $C_{44}H_{53}N_5O_5Si$ 759.4; found 760.2.

Step 9. To a mixture of 2-amino-3-[5-[(2M)-3-[3-[(tert-butyldiphenylsilyl)oxy]-2,2-dimethylpropyl]-1-ethyl-2-[2-[(1 S)-1-methoxyethyl]pyridin-3-yl]indol-5-yl]-1,2,4-oxadiazol-3-yl]propanoic acid (4.0 g, 5.3 mmol) and $NaHCO_3$ (2.65 g, 30 mmol) in THE (20 mL) and $H_2O$ (20 mL) was added $Boc_2O$ (1.72 g, 7.9 mmol) dropwise. The mixture was stirred at rt for 2 h, then $H_2O$ was added and the mixture was extracted with EtOAc (3×50 mL). The combined organic layers were dried over anhydrous $Na_2SO_4$ and filtered. The filtrate was concentrated under reduced pressure and the residue was purified by silica gel column chromatography to give 2-[(tert-butoxycarbonyl)amino]-3-[5-[(2M)-3-[3-[(tert-butyldiphenylsilyl)oxy]-2,2-dimethylpropyl]-1-ethyl-2-[2-[(1S)-1-methoxyethyl]pyridin-3-yl]indol-5-yl]-1,2,4-oxadiazol-3-yl]propanoic acid (1.2 g, 21% yield) as a solid. LCMS (ESI): m/z $[M+H]^+$ calc'd for $C_{49}H_{61}N_5O_7Si$ 859.4; found 860.2.

Step 10. To a mixture of 2-[(tert-butoxycarbonyl)amino]-3-[5-[(2M)-3-[3-[(tert-butyldiphenylsilyl)oxy]-2,2-dimethylpropyl]-1-ethyl-2-[2-[(1 S)-1-methoxyethyl]pyridin-3-yl] indol-5-yl]-1,2,4-oxadiazol-3-yl]propanoic acid (1.00 g, 1.2 mmol), methyl (3S)-1,2-diazinane-3-carboxylate (0.34 g, 2.3 mmol), HOBT (0.08 g, 0.6 mmol) and DIPEA (1.50 g, 11.6 mmol) in DCM (10 mL) at 0° C. under an atmosphere of $N_2$ was added EDCl (0.33 g, 1.7 mmol) in portions. The mixture was warmed to rt and stirred for 2 h, then $H_2O$ (50 mL) was added and the mixture extracted with EtOAc (3×50 mL). The combined organic layers were dried over anhydrous $Na_2SO_4$ and filtered. The filtrate was concentrated under reduced pressure and the residue was purified by silica gel column chromatography to give methyl (3S)-1-[(2S)-2-[(tert-butoxycarbonyl)amino]-3-[5-(3-[3-[(tert-butyldiphenylsilyl)oxy]-2,2-dimethylpropyl]-1-ethyl-2-[2-[(1 S)-1-methoxyethyl]pyridin-3-yl]indol-5-yl)-1,2,4-oxadiazol-3-yl]propanoyl]-1,2-diazinane-3-carboxylate (800 mg, 63% yield) as a solid. LCMS (ESI): m/z $[M+H]^+$ calc'd for $C_{55}H_{71}N_7O_8Si$ 985.5; found 986.6.

Step 11. To a mixture of methyl (3S)-1-[(2S)-2-[(tert-butoxycarbonyl)amino]-3-[5-(3-[3-[(tert-butyldiphenylsilyl)oxy]-2,2-dimethylpropyl]-1-ethyl-2-[2-[(1 S)-1-methoxyethyl]pyridin-3-yl]indol-5-yl)-1,2,4-oxadiazol-3-yl]propanoyl]-1,2-diazinane-3-carboxylate (800 mg, 0.8 mmol) in THF (5 mL) at 0° C. under an atmosphere of $N_2$ was added 1 M TBAF in THF (5 mL) dropwise. The mixture was heated to 60° C. and stirred overnight, then $H_2O$ (100 mL) was added and the mixture was extracted with EtOAc (3×50 mL). The combined organic layers were dried over anhydrous $Na_2SO_4$, filtered and the filtrate was concentrated under reduced pressure to give (3S)-1-[(2S)-2-[(tert-butoxycarbonyl)amino]-3-[5-[(2M)-1-ethyl-3-(3-hydroxy-2,2-dimethylpropyl)-2-[2-[(1S)-1-methoxyethyl]pyridin-3-yl]indol-5-yl]-1,2,4-oxadiazol-3-yl]propanoyl]-1,2-diazinane-3-carboxylic acid (680 mg) as a solid. LCMS (ESI): m/z $[M+H]^+$ calc'd for $C_{31}H_{51}N_7O_8$ 733.3; found 734.3.

Step 12. To a mixture of (3S)-1-[(2S)-2-[(tert-butoxycarbonyl)amino]-3-[5-[(2M)-1-ethyl-3-(3-hydroxy-2,2-dimethylpropyl)-2-[2-[(1 S)-1-methoxyethyl]pyridin-3-yl]indol-5-yl]-1,2,4-oxadiazol-3-yl]propanoyl]-1,2-diazinane-3-carboxylic acid (500 mg, 0.68 mmol), HOBT (460 mg, 3.4 mmol) and DIPEA (2.64 g, 20.4 mmol) in DCM (100 mL) at 0° C. under an atmosphere of $N_2$ was added EDCl (2.61 g, 13.6 mmol) in portions. The mixture was warmed to rt and stirred overnight, then concentrated under reduced pressure and the residue was purified by preparative-TLC to give tert-butyl ((6$^3$S,4S,Z)-1$^1$-ethyl-1$^2$-(2-((S)-1-methoxyethyl) pyridin-3-yl)-10,10-dimethyl-5,7-dioxo-6$^1$,6$^2$,6$^3$,6$^4$,6$^5$,6$^6$-hexahydro-1$^1$H-8-oxa-2(5,3)-oxadiazola-1(5,3)-indola-6(1,3)-pyridazinacycloundecaphane-4-yl)carbamate (22 mg, 18% yield) as a solid. LCMS (ESI): m/z $[M+H]^+$ calc'd for $C_{38}H_{49}N_7O_7$ 715.4; found 716.2.

Step 13. To a mixture of tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(5,3)-oxadiazola-1(5,3)-indola-6(1,3)- pyridazinacycloundecaphane-4-yl)carbamate (20 mg, 0.03 mmol) in DCM (0.30 mL) at 0° C. under an atmosphere of $N_2$ was added TFA (0.1 mL) dropwise. The mixture was warmed to rt and stirred for 1 h, then concentrated under reduced pressure to give (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-11H-8-oxa-2(5,3)-oxadiazola-1(5,3)-indola-6(1,3)-pyridazinacycloundecaphane-5,7-dione (30 mg) as an oil. LCMS (ESI): m/z $[M+H]^+$ calc'd for $C_{33}H_{41}N_7O_5$ 615.3; found 616.4.

Step 14. To a mixture of (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(5,3)-oxadiazola-1(5,3)-indola-6(1,3)-pyridazinacycloundecaphane-5,7-dione (20 mg, 0.03 mmol), DIPEA (42 mg, 0.33 mmol) and (2S)-2-(1-[1-[4-(dimethylamino)-4-methylpent-2-ynoyl]-4-fluoropiperidin-4-yl]-N-methylformamido)-3-methylbutanoic acid (19 mg, 0.05 mmol) in DMF (1 mL) at 0° C. under an atmosphere of $N_2$ was added HATU (16 mg, 0.04 mmol) in portions. The mixture was warmed to rt and stirred for 1 h, then purified by preparative-HPLC to give 1-(4-(dimethylamino)-4-methylpent-2-ynoyl)-N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(5,3)-oxadiazola-1(5,3)-indola-6(1,3)-pyridazinacycloundecaphane-4-yl)amino)-3-methyl-1-oxobutan-2-yl)-4-fluoro-N-methylpiperidine-4-carboxamide (2.4 mg, 7% yield) as a solid. LCMS (ESI): m/z $[M+H]^+$ calc'd for $C_{53}H_{71}FN_{10}O$ 994.5; found 995.4; 1H NMR (400 MHz, DMSO-$d_6$) δ 8.78 (dd, J=4.7, 1.7 Hz, 1H), 8.63 (s, 1H), 8.33 (s, 1H), 7.95-7.68 (m, 3H), 7.55 (dd, J=7.7, 4.7 Hz, 1H), 5.79 (s, 1H), 5.07 (d, J=11.7 Hz, 1H), 4.62 (d, J=10.3 Hz, 1H), 4.34-4.20 (m, 7H), 3.70-3.49 (m, 3H), 3.23 (s, 3H), 3.17-3.03 (m, 5H), 2.98-2.89 (m, 3H), 2.77 (t, J=12.2 Hz, 1H), 2.46-2.41 (m, 1H), 2.20 (dd, J=10.7, 6.6 Hz, 7H), 2.15-2.03 (m, 5H), 1.81 (d, J=12.5 Hz, 1H), 1.65 (d, J=13.0 Hz, 1H), 1.53 (d, J=11.9 Hz, 1H), 1.37 (t, J=6.3 Hz, 9H), 1.03-0.86 (m, 10H), 0.88-0.80 (m, 2H), 0.80-0.74 (m, 3H).

Example 2. Synthesis of 1-(4-(dimethylamino)-4-methylpent-2-ynoyl)-N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6',6$^2$,6$^3$,6$^4$,6$^1$,6$^1$-hexahydro-1$^1$H-8-oxa-2(3,5)-oxadiazola-1(5,3)-indola-6(1,3)-pyridazinacycloundecaphane-4-yl)amino)-3-methyl-1-oxobutan-2-yl)-4-fluoro-M-methylpiperidine-4-carboxamide

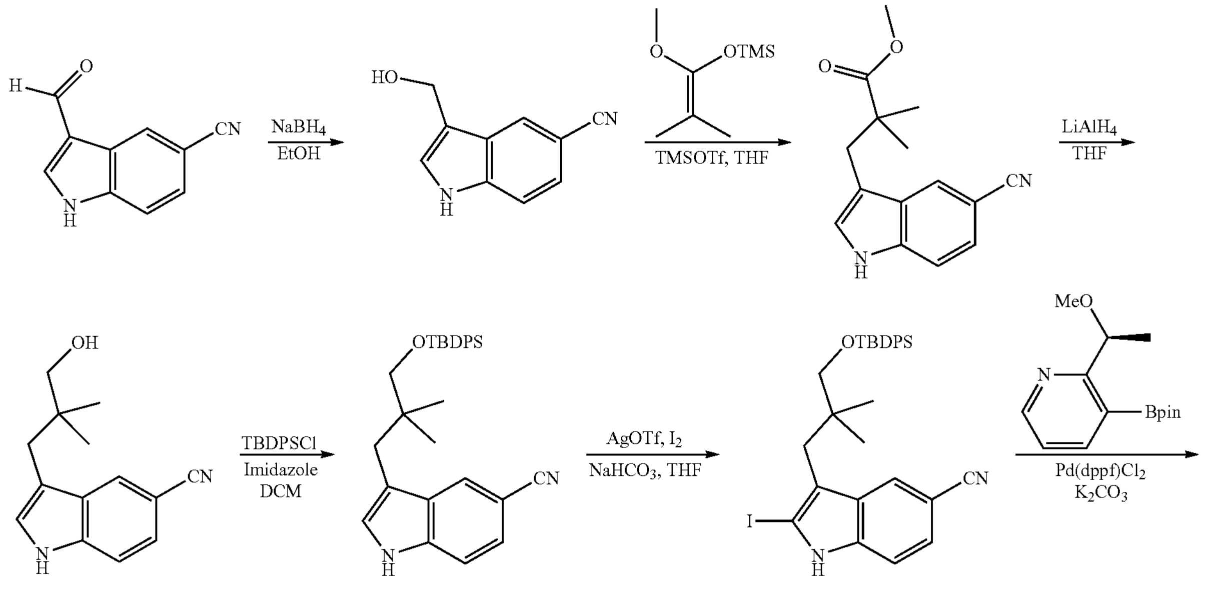

-continued
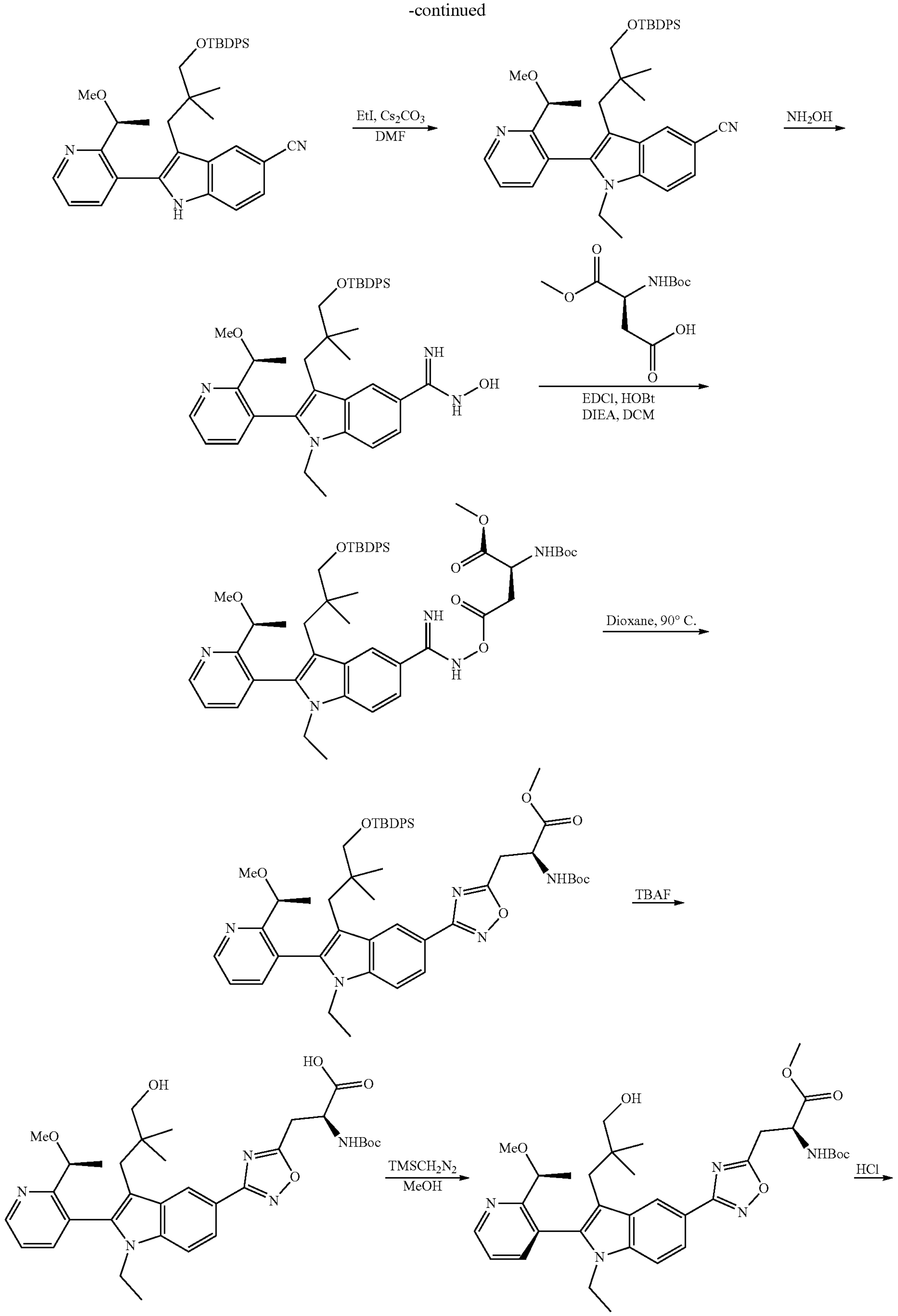

-continued
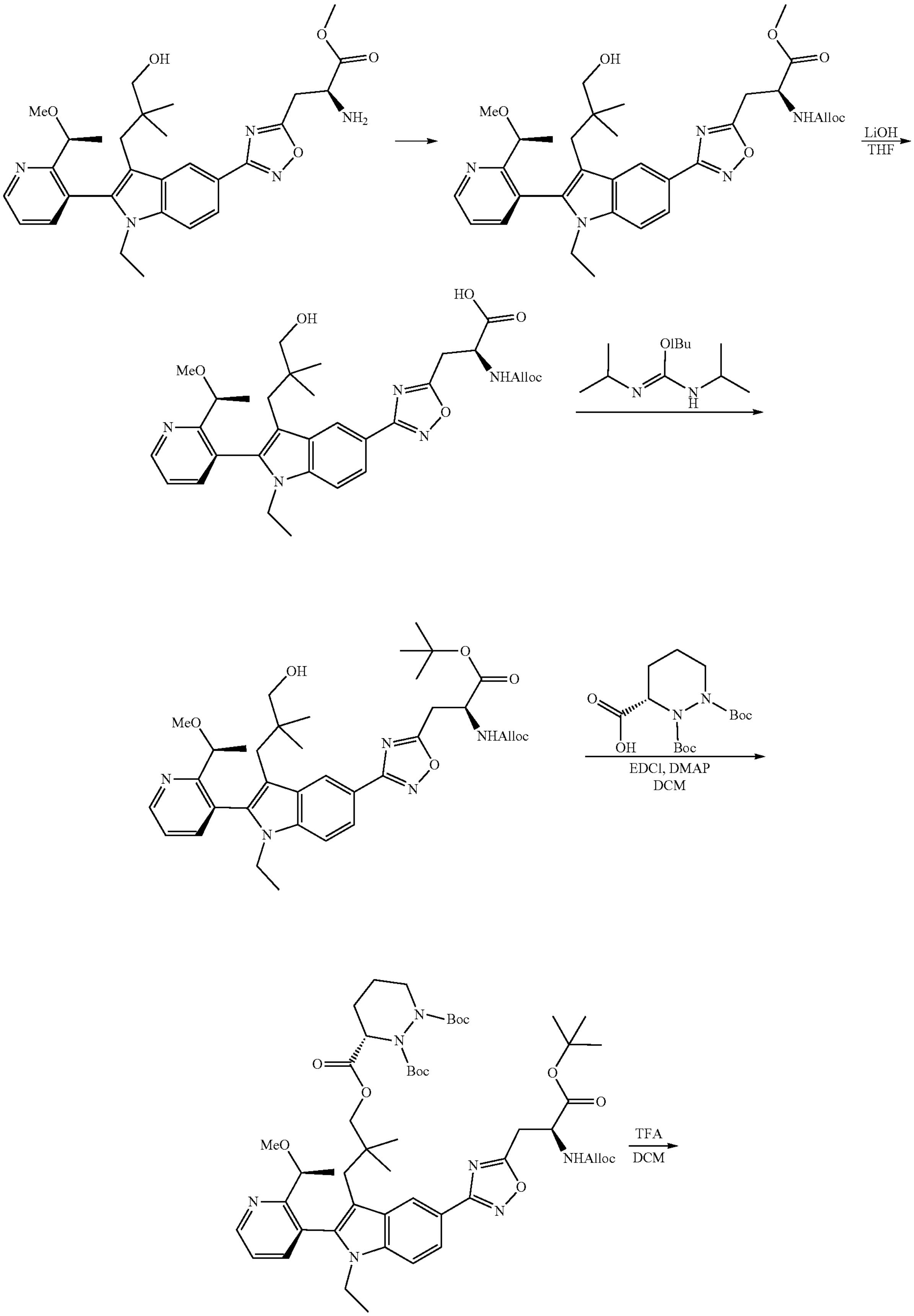

-continued
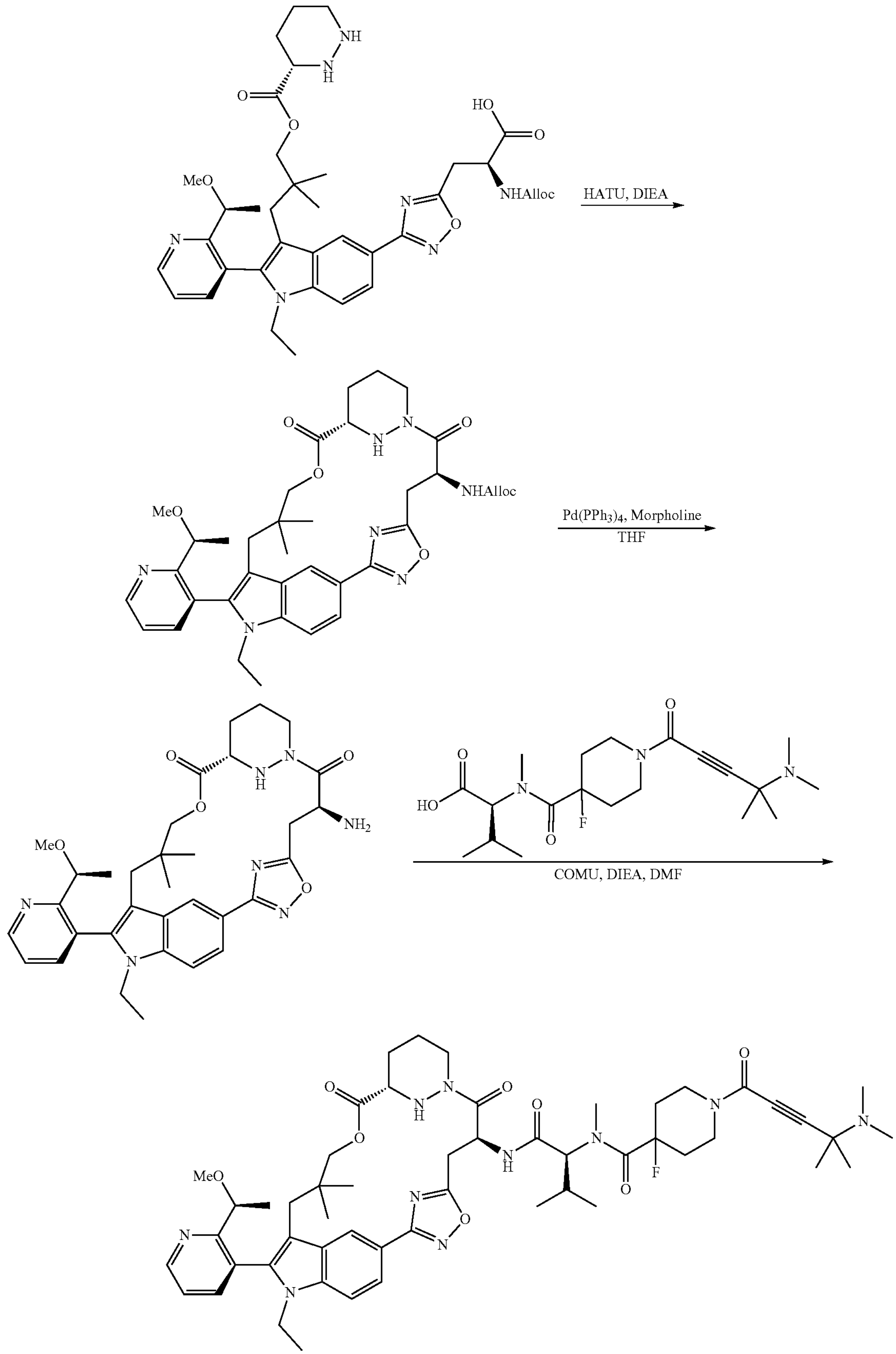

Step 1. To a mixture of 3-formyl-1H-indole-5-carbonitrile (24.8 g, 145.7 mmol) in EtOH (248 mL) at 0° C. was added $NaBH_4$ (8.05 g, 218.6 mmol) in portions. The mixture was stirred at 0° C. for 2 h then saturated $NH_4Cl$ (500 mL) was added, and the volatiles were removed under reduced pressure. The mixture was extracted with DCM (3×200 mL) and the combined organic layers were washed with water (3×200 mL), dried over anhydrous $Na_2SO_4$ and filtered. Th filtrate was concentrated under reduced pressure and the residue was purified by silica gel column chromatography to give 3-(hydroxymethyl)-1H-indole-5-carbonitrile (21 g, 84% yield) as a solid. LCMS (ESI): m/z [M−H]$^+$ calc'd for $C_{10}H_8N_2O$ 172.1; found 171.1.

Step 2. To a mixture of 3-(hydroxymethyl)-1H-indole-5-carbonitrile (20.0 g, 116.2 mmol) in THF (200 mL) at −40° C. under an atmosphere of Ar was added [(1-methoxy-2-methylprop-1-en-1-yl)oxy]trimethylsilane (50.62 g, 290.4 mmol) and TMSOTf (19.36 g, 87.1 mmol) dropwise. The mixture was stirred at −40° C. for 2 h, then brine (200 mL) was added at 0° C. The aqueous and organic layers were partitioned and the organic layer was extracted with EtOAc (3×200 mL). The combined organic layers were concentrated under reduced pressure and the residue was purified by silica gel column chromatography to give methyl 3-(5-cyano-1H-indol-3-yl)-2,2-dimethylpropanoate (22 g, 74% yield) as a solid. LCMS (ESI): m/z [M−H]$^+$ calc'd for $C_{15}H_{16}N_2O_2$ 256.1; found 255.1.

Step 3. To mixture of methyl 3-(5-cyano-1H-indol-3-yl)-2,2-dimethylpropanoate (22 g, 85.8 mmol) in THE (220 mL) at 0° C. was added 1M $LiAlH_4$ in THE (171.7 mL, 171.7 mmol) dropwise. The mixture was stirred at 0° C. for 2 h, then $Na_2SO_4·10H_2O$ was added, the mixture was filtered and the filter cake was washed with DCM (3×300 mL). The filtrate was concentrated under reduced pressure to give 3-(3-hydroxy-2,2-dimethylpropyl)-1H-indole-5-carbonitrile (12.8 g, 65% yield) as a solid. LCMS (ESI): m/z [M−H]$^+$ calc'd for $C_{14}H_{16}N_2O$ 228.1; found 255.1.

Step 4. To a mixture of 3-(3-hydroxy-2,2-dimethylpropyl)-1H-indole-5-carbonitrile (15.0 g, 65.7 mmol) in DCM (150 mL) at 0° C. was added imidazole (11.18 g, 164.3 mmol) and TBDPSCl (23.48 g, 85.4 mmol). The mixture was warmed to rt and stirred overnight, then concentrated under reduced pressure and the residue was purified by silica gel column chromatography to give 3-[3-[(tert-butyldiphenylsilyl)oxy]-2,2-dimethylpropyl]-1H-indole-5-carbonitrile (30 g, 97% yield) as an oil. LCMS (ESI): m/z [M−H]$^+$ calc'd for $C_{30}H_{34}N_2OSi$ 466.2; found 465.2.

Step 5. To a mixture of 3-[3-[(tert-butyldiphenylsilyl)oxy]-2,2-dimethylpropyl]-1H-indole-5-carbonitrile (18.0 g, 38.6 mmol) in THE (180 mL) at 0° C. under an atmosphere of $N_2$ was added $NaHCO_3$ (3.89 g, 46.3 mmol), AgOTf (10.9 g, 42.4 mmol) and 12 (8.81 g, 34.7 mmol). The mixture was stirred at 0° C. for 2 h, then 5% aqueous $Na_2S_2O_3$ was added and the mixture was extracted with EtOAc (3×200 mL). The combined organic layers were washed with water (3×200 mL), dried over anhydrous $Na_2SO_4$ and filtered. The filtrate was concentrated under reduced pressure and the residue was purified by silica gel column chromatography to give 3-[3-[(tert-butyldiphenylsilyl)oxy]-2,2-dimethylpropyl]-2-iodo-1H-indole-5-carbonitrile (18.2 g, 80% yield) as a solid. LCMS (ESI): m/z [M+Na]$^+$ calc'd for $C_{30}H_{33}IN_2NaOSi$ 615.1; found 615.0.

Step 6. To a mixture of 3-[3-[(tert-butyldiphenylsilyl)oxy]-2,2-dimethylpropyl]-2-iodo-1H-indole-5-carbonitrile (18.2 g, 30.7 mmol) and 2-[(1 S)-1-methoxyethyl]-3-(4,4,5,5-tetramethyl-1,3,2-dioxaborolan-2-yl)pyridine (32.33 g, 122.9 mmol) in 1,4-dioxane (150 mL) and $H_2O$ (30 mL) under an atmosphere of Ar was added $K_2CO_3$ (10.60 g, 76.8 mmol), Pd(dppf)$Cl_2$ (4.49 g, 6.1 mmol). The mixture was heated to 50° C. and stirred for 3 h, then concentrated under reduced pressure and the residue was purified by silica gel column chromatography to give 3-[3-[(tert-butyldiphenylsilyl)oxy]-2,2-dimethylpropyl]-2-[2-[(1 S)-1-methoxyethyl]pyridin-3-yl]-1H-indole-5-carbonitrile (20 g) as an oil. LCMS (ESI): m/z [M+H]$^+$ calc'd for $C_{38}H_{43}N_3O_2Si$ 601.3; found 602.3.

Step 7. To a mixture of 3-[3-[(tert-butyldiphenylsilyl)oxy]-2,2-dimethylpropyl]-2-[2-[(1 S)-1-methoxyethyl]pyridin-3-yl]-1H-indole-5-carbonitrile (22.0 g, 36.6 mmol) in DMF (220 mL) at 0° C. was added $Cs_2CO_3$ (35.73 g, 109.7 mmol) and EtI (34.21 g, 219.3 mmol). The mixture was stirred at 0° C. for 2 h, then $H_2O$ was added and the mixture extracted with EtOAc (300 mL). The organic layer was washed with $H_2O$ (3×300 mL), dried over anhydrous $Na_2SO_4$ and filtered. The filtrate was concentrated under reduced pressure and the residue was purified by silica gel column chromatography to give 3-[3-[(tert-butyldiphenylsilyl)oxy]-2,2-dimethylpropyl]-1-ethyl-2-[2-[(1 S)-1-methoxyethyl]pyridin-3-yl]indole-5-carbonitrile (15.6 g, 63% yield) as an oil. LCMS (ESI): m/z [M+H]$^+$ calc'd for $C_{40}H_{47}N_3O_2Si$ 629.3; found 630.0.

Step 8. To a mixture of 3-[3-[(tert-butyldiphenylsilyl)oxy]-2,2-dimethylpropyl]-1-ethyl-2-[2-[(1 S)-1-methoxyethyl]pyridin-3-yl]indole-5-carbonitrile (15.60 g, 24.8 mmol) in MeOH (156 mL) was added $NH_2OH$, 50% in $H_2O$ (9.81 g, 296.9 mmol). The mixture was heated to 50° C. and stirred for 3 h, then concentrated under reduced pressure and the residue was purified by silica gel column chromatography to give 3-[3-[(tert-butyldiphenylsilyl)oxy]-2,2-dimethylpropyl]-1-ethyl-N-hydroxy-2-[2-[(1 S)-1-methoxyethyl]pyridin-3-yl]indole-5-carboximidamide (14.6 g, 89% yield) as an oil. LCMS (ESI): m/z [M+H]$^+$ calc'd for $C_{40}H_{50}N_4O_3Si$ 662.4; found 663.2.

Step 9. To a mixture of 3-[3-[(tert-butyldiphenylsilyl)oxy]-2,2-dimethylpropyl]-1-ethyl-N-hydroxy-2-[2-[(1 S)-1-methoxyethyl]pyridin-3-yl]indole-5-carboximidamide (14.60 g, 22.0 mmol) in DCM (146 mL) at −5° C. was added DIPEA (14.23 g, 110.1 mmol), HOBt (0.60 g, 4.4 mmol), followed by EDC·HCl (5.07 g, 26.4 mmol) in portions over 2 min. The mixture was allowed to warm to rt and stirred for 2 h, then concentrated under reduced pressure and the residue was purified by silica gel column chromatography to give 4-(3-[3-[(tert-butyldiphenylsilyl)oxy]-2,2-dimethylpropyl]-1-ethyl-2-[2-[(1 S)-1-methoxyethyl]pyridin-3-yl]indol-5-yl)methanimidamido 1-methyl (2S)-2-[(tert-butoxycarbonyl)amino]butanedioate (18.1 g, 92% yield) as an oil. LCMS (ESI): m/z [M+H]$^+$ calc'd for $C_{50}H_{65}N_5O_8Si$ 891.5; found 892.3.

Step 10. A mixture of 4-(3-[3-[(tert-butyldiphenylsilyl)oxy]-2,2-dimethylpropyl]-1-ethyl-2-[2-[(1 S)-1-methoxyethyl]pyridin-3-yl]indol-5-yl)methanimidamido 1-methyl (2S)-2-[(tert-butoxycarbonyl)amino]butanedioate (18 g, 20.2 mmol) in 1,4-dioxane (900 mL) was heated to 90° C. and stirred for 3 h. The mixture was concentrated under reduced pressure and the residue was purified by silica gel column chromatography to give methyl 2-[(tert-butoxycarbonyl)amino]-3-[3-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)-1,2,4-oxadiazol-5-yl]propanoate (16.5 g, 94% yield) as an oil. LCMS (ESI): m/z [M+H]$^+$ calc'd for $C_{50}H_{63}N_5O_7Si$ 873.4; found 874.4.

Step 11. To a mixture of methyl 2-[(tert-butoxycarbonyl)amino]-3-[3-(3-{3-[(tert-butyldiphenylsilyl)oxy]-2,2-dimethylpropyl}-1-ethyl-2-{2-[(1 S)-1-methoxyethyl]pyridin- 3-yl}indol-5-yl)-1,2,4-oxadiazol-5-yl]propanoate (18 g, 20.6 mmol) in THE (180 mL) was added 1 M TBAF in THE (180 mL) dropwise. The mixture was heated to 60° C. and stirred overnight, then $H_2O$ was added and the mixture extracted with DCM (3×300 mL). The combined organic layers were washed with brine (6×300 mL), dried over anhydrous $Na_2SO_4$, filtered and the filtrate was concentrated under reduced pressure to give 2-[(tert-butoxycarbonyl)amino]-3-{3-[(2M4)-1-ethyl-3-(3-hydroxy-2,2-dimethyl-propyl)-2-{2-[(1 S)-1-methoxyethyl]pyridin-3-yl}indol-5-yl]-1,2,4-oxadiazol-5-yl}propanoic acid (14 g) as an oil. LCMS (ESI): m/z $[M-H]^+$ calc'd for $C_{33}H_{43}N_5O_7$ 621.3; found 620.3.

Step 12. To a mixture of 2-[(tert-butoxycarbonyl)amino]-3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}propanoic acid (14 g, 22.5 mmol) in MeOH (140 mL) at 0° C. was added $TMSCHN_2$ (12.86 g, 112.6 mmol). The mixture was stirred at 0° C. for 2 h, then concentrated under reduced pressure and the residue was purified by silica gel column chromatography to give methyl (2R)-2-[(tert-butoxycarbonyl)amino]-3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}propanoate (3.5 g, 25% yield) as an oil. LCMS (ESI): m/z $[M+H]^+$ calc'd for $C_{34}H_{45}N_5O_7$ 635.3; found 636.4.

Step 13. To a mixture of methyl (2R)-2-[(tert-butoxycarbonyl)amino]-3-{3-[(2M)-1-ethyl-3-(3-hydroxy-2,2-dimethylpropyl)-2-{2-[(1S)-1-methoxyethyl]pyridin-3-yl}indol-5-yl]-1,2,4-oxadiazol-5-yl}propanoate (2.0 g, 3.2 mmol) in 1,4-dioxane (20 mL) was added HCl in 1,4-dioxane (20 mL). The mixture was stirred at rt for 1 h, then concentrated under reduced pressure to give methyl (2R)-2-amino-3-{3-[(2M)-1-ethyl-3-(3-hydroxy-2,2-dimethyl-propyl)-2-{2-[(1 S)-1-methoxyethyl]pyridin-3-yl}indol-5-yl]-1,2,4-oxadiazol-5-yl}propanoate (1.5 g, 89% yield) as a solid. LCMS (ESI): m/z $[M+H]^+$ calc'd for $C_{29}H_{37}N_5O_5$ 535.3; found 536.4.

Step 14. To a mixture of methyl (2R)-2-amino-3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}propanoate (3.0 g, 5.6 mmol) in THE (30 mL) and $H_2O$ (6 mL) at 0° C. was added $NaHCO_3$ (1.18 g, 14.0 mmol) and allyl chlorocarbonate (1.01 g, 8.4 mmol). The mixture was stirred at 0° C. for 2 h, then concentrated under reduced pressure and the residue was purified by silica gel column chromatography to give methyl 3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}-2-{[(prop-2-en-1-yloxy)carbonyl]amino}propanoate (1.5 g, 43% yield) as a solid. LCMS (ESI): m/z $[M+H]^+$ calc'd for $C_{33}H_{41}N_5O_7$ 619.3; found 620.4.

Step 15. To a mixture of methyl 3-{3-[(2M)-1-ethyl-3-(3-hydroxy-2,2-dimethylpropyl)-2-{2-[(1S)-1-methoxyethyl]pyridin-3-yl}indol-5-yl]-1,2,4-oxadiazol-5-yl}-2-{[(prop-2-en-1-yloxy)carbonyl]amino}propanoate (1.5 g, 2.1 mmol) in THE (15 mL) at 0° C. was added LiOH (16 mg, 6.8 mmol) in $H_2O$ (15 mL). The mixture was stirred at 0° C. for 1 h, then acidified to pH ~4 with aqueous HCl and extracted with DCM (3×30 mL). The combined organic layers were washed with brine (3×30 mL), dried over anhydrous $Na_2SO_4$, filtered and the filtrate was concentrated under reduced pressure to give (2R)-3-[3-[(2M)-1-ethyl-3-(3-hydroxy-2,2-dimethylpropyl)-2-[2-[(1 S)-1-methoxyethyl]pyridin-3-yl]indol-5-yl]-1,2,4-oxadiazol-5-yl]-2-[[(prop-2-en-1-yloxy)carbonyl]amino]propanoic acid (1.46 g) as a solid. LCMS (ESI): m/z $[M+H]^+$ calc'd for $C_{32}H_{39}N_5O_7$ 605.3; found 606.3.

Step 16. To a mixture of (2R)-3-[3-[(2M)-1-ethyl-3-(3-hydroxy-2,2-dimethylpropyl)-2-[2-[(1S)-1-methoxyethyl]pyridin-3-yl]indol-5-yl]-1,2,4-oxadiazol-5-yl]-2-[[(prop-2-en-1-yloxy)carbonyl]amino]propanoic acid (1.46 g, 2.4 mmol) in DCM (15 mL) at 0° C. was added (Z)—N,N-diisopropyltert-butoxymethanimidamide (2.41 g, 12.1 mmol). The mixture was heated to 40° C. and stirred overnight, then $H_2O$ was added and the mixture extracted with DCM (3×20 mL). The combined organic layers were washed with aqueous $NH_4Cl$ (3×40 mL), dried over anhydrous $Na_2SO_4$, filtered and the filtrate was concentrated under reduced pressure to give tert-butyl 3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}-2-{[(prop-2-en-1-yloxy)carbonyl]amino}propanoate (2.3 g) as a solid. LCMS (ESI): m/z $[M+H]^+$ calc'd for $C_{36}H_{47}N_5O_7$ 661.4; found 662.4.

Step 17. To a mixture of tert-butyl 3-{3-[(2M)-1-ethyl-3-(3-hydroxy-2,2-dimethylpropyl)-2-{2-[(1 S)-1-methoxyethyl]pyridin-3-yl}indol-5-yl]-1,2,4-oxadiazol-5-yl}-2-{[(prop-2-en-1-yloxy)carbonyl]amino}propanoate (2.30 g, 3.5 mmol) in DCM (23 mL) at −5° C. was added DMAP (85 mg, 0.7 mmol), (3S)-1,2-bis(tert-butoxycarbonyl)-1,2-diazinane-3-carboxylic acid (3.44 g, 10.4 mmol) and EDCl (0.87 g, 4.5 mmol) in portions. The mixture was warmed to rt and stirred for 2 h, then concentrated under reduced pressure and the residue was purified by silica gel column chromatography to give 3-(2-[[(2M)-5-[5-[(2R)-3-(tert-butoxy)-3-oxo-2-[[(prop-2-en-1-yloxy)carbonyl]amino]propyl]-1,2,4-oxadiazol-3-yl]-1-ethyl-2-[2-[(1S)-1-methoxyethyl]pyridin-3-yl]indol-3-yl]methyl]-2-methylpropyl)1,2-di-tert-butyl (3S)-1,2-diazinane-1,2,3-tricarboxylate (2.29 g, 68% yield) as a solid. LCMS (ESI): m/z $[M+H]^+$ calc'd for $C_{51}H_{71}N_7O_{12}$ 973.5; found 974.4.

Step 18. To a mixture of 3-(2-[[(2M)-5-[5-[(2R)-3-(tert-butoxy)-3-oxo-2-[[(prop-2-en-1-yloxy)carbonyl]amino]propyl]-1,2,4-oxadiazol-3-yl]-1-ethyl-2-[2-[(1 S)-1-methoxyethyl]pyridin-3-yl]indol-3-yl]methyl]-2-methylpropyl)1,2-di-tert-butyl (3S)-1,2-diazinane-1,2,3-tricarboxylate (2.29 g, 2.4 mmol) in DCM (30 mL) at 0° C. was added TFA (10 mL) dropwise. The mixture was stirred at 0° C. for 5 h, then concentrated under reduced pressure. The mixture was basified to pH ~7 with saturated $NaHCO_3$ and extracted with DCM (3×300 mL). The combined organic layers were washed with $H_2O$ (3×60 mL), dried over anhydrous $Na_2SO_4$, filtered and the filtrate was concentrated under reduced pressure to give 3-{3-[(2M)-3-{3-[(3S)-1,2-diazinane-3-carbonyloxy]-2,2-dimethylpropyl}-1-ethyl-2-{2-[(1 S)-1-methoxyethyl]pyridin-3-yl}indol-5-yl]-1,2,4-oxadiazol-5-yl}-2-{[(prop-2-en-1-yloxy)carbonyl]amino}propanoic acid (1.4 g, 83% yield) as a solid. LCMS (ESI): m/z $[M-H]^+$ calc'd for $C_{37}H_{47}N_7O_8$ 717.4; found 716.5.

Step 19. To a mixture of 3-{3-[(2M)-3-{3-[(3S)-1,2-diazinane-3-carbonyloxy]-2,2-dimethylpropyl}-1-ethyl-2-{2-[(1 S)-1-methoxyethyl]pyridin-3-yl}indol-5-yl]-1,2,4-oxadiazol-5-yl}-2-{[(prop-2-en-1-yloxy)carbonyl]amino}propanoic acid (720 mg, 1.0 mmol) in DCM (7.2 mL) at 0° C. was added DIPEA (3.89 g, 30.1 mmol) and HATU (4.58 g, 12.0 mmol). The mixture was warmed to rt and stirred overnight, then concentrated under reduced pressure and the residue was purified by silica gel column chromatography to give prop-2-en-1-yl N-[(7S,13S,19M)-21-ethyl-20-[2-[(1 S)-1-methoxyethyl]pyridin-3-yl]-17,17-dimethyl-8,14-dioxo-4,15-dioxa-3,9,21,27,28-pentaazapentacyclo[17.5.2.1^[2,5].1^[9,13].0^[22,26]]octacosa-1(25),2,5(28),19,22(26),23-hexaen-7-yl]carbamate (230 mg, 33% yield) as a solid. LCMS (ESI): m/z $[M-H]^+$ calc'd for $C_{37}H_{45}N_7O_7$ 699.3; found 699.9.

Step 20. To a mixture of allyl ((6$^3$S,4S,Z)-1$^1$-ethyl-1$^2$-(2-((S)-1-methoxyethyl)pyridin-3-yl)-10,10-dimethyl-5,7-dioxo-6',6$^2$,6$^3$,6$^4$,6$^5$,6$^6$-hexahydro-1'H-8-oxa-2(3,5)-oxadiazola-1(5,3)-indola-6(1,3)-pyridazinacycloundecaphane-4-yl)carbamate (135 mg, 0.19 mmol) in THF (1.35 mL) under an atmosphere of Ar was added morpholine (50 mg, 0.58 mmol) and $Pd(PPh_3)_4$ (22.29 mg, 0.019 mmol). The mixture was heated to 35° C. and stirred for 4 h, then directly purified by silica gel column chromatography to give (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1'H-8-oxa-2(3,5)-oxadiazola-1(5,3)-indola-6(1,3)-pyridazinacycloundecaphane-5,7-dione (120 mg) as a solid. LCMS (ESI): m/z $[M+H]^+$ calc'd for $C_{33}H_{41}N_7O_5$ 615.3; found 616.4.

Step 21. To a mixture of (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1'H-8-oxa-2(3,5)-oxadiazola-1(5,3)-indola-6(1,3)-pyridazinacycloundecaphane-5,7-dione (100 mg, 0.16 mmol) in DMF (1 mL) at 0° C. was added DIPEA (315 mg, 2.44 mmol), (2S)-2-(1-[1-[4-(dimethylamino)-4-methylpent-2-ynoyl]-4-fluoropiperidin-4-yl]-N-methylformamido)-3-methylbutanoic acid (129 mg, 0.32 mmol) and COMU (104 mg, 0.24 mmol). The mixture was stirred at 0° C. for 1 h, then-purified by preparative-HPLC 1-(4-(dimethylamino)-4-methylpent-2-ynoyl)-N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1'H-8-oxa-2(3,5)-oxadiazola-1(5,3)-indola-6(1,3)-pyridazinacycloundecaphane-4-yl)amino)-3-methyl-1-oxobutan-2-yl)-4-fluoro-N-methylpiperidine-4-carboxamide (25 mg, 15% yield) as a solid. LCMS (ESI): m/z $[M-H]^+$ calc'd for $C_{53}H_{71}FN_{10}O_8$ 994.5; found 995.8; $^1$H NMR (400 MHz, DMSO-$d_6$) δ 8.78 (dd, J=4.8, 1.8 Hz, 1H), 8.45 (d, J=17.0 Hz, 2H), 7.86-7.75 (m, 2H), 7.71 (d, J=8.7 Hz, 1H), 7.54 (dd, J=7.7, 4.7 Hz, 1H), 5.69 (s, 1H), 5.16 (d, J=11.8 Hz, 1H), 4.71-4.49 (m, 1H), 4.41-4.06 (m, 7H), 3.68-3.47 (m, 3H), 3.23 (s, 4H), 3.15-3.05 (m, 3H), 2.94 (d, J=11.1 Hz, 2H), 2.79-2.61 (m, 1H), 2.45-2.37 (m, 1H), 2.26-1.95 (m, 12H), 1.85-1.63 (m, 2H), 1.57-1.42 (m, 1H), 1.39-1.24 (m, 9H), 1.03-0.71 (m, 12H), 0.34 (s, 3H).

Example 3. Synthesis of (4aR,7aS)-4-acryloyl-N-((2S)-1-(((2$^3$R,6$^3$S,4S)-1$^2$-(2-((S)-1-methoxyethyl)pyridin-3-yl)-10,10-dimethyl-5,7-dioxo-1-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4]oxazine-6(2H)-carboxamide

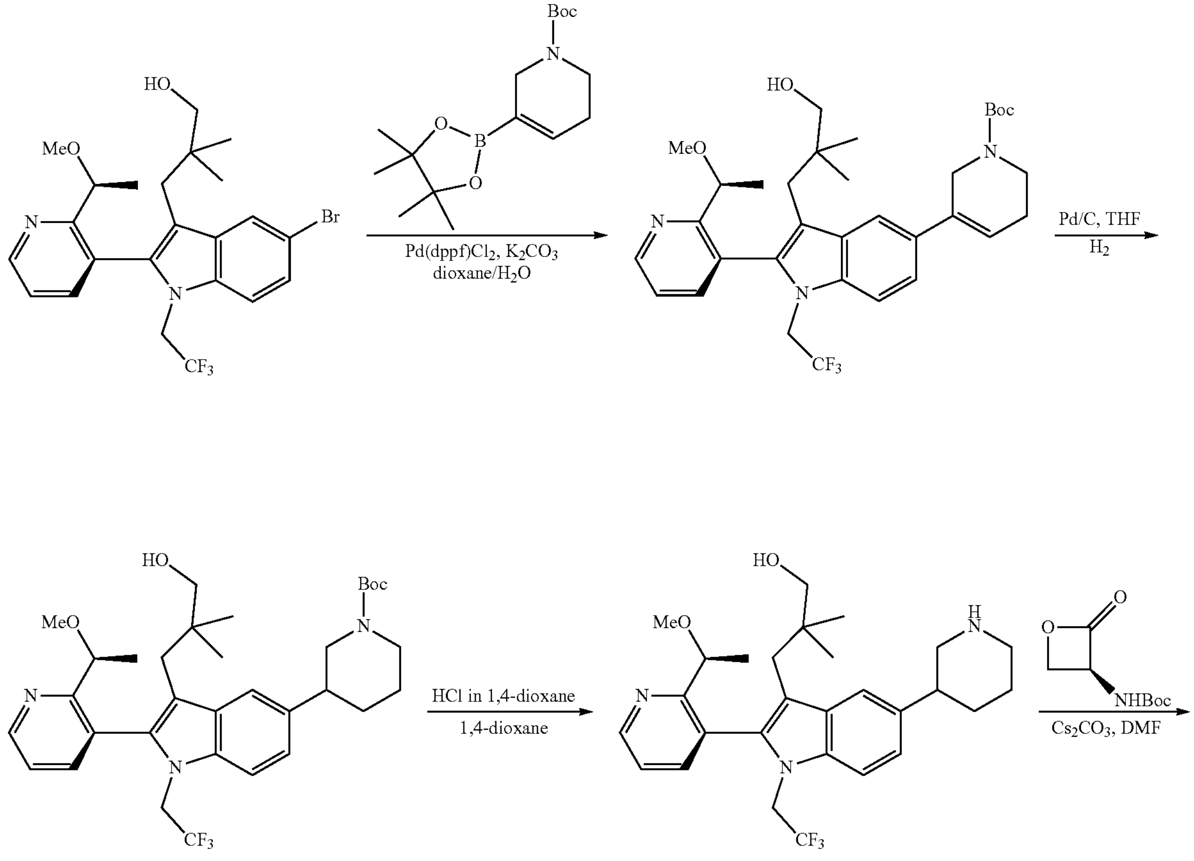

-continued
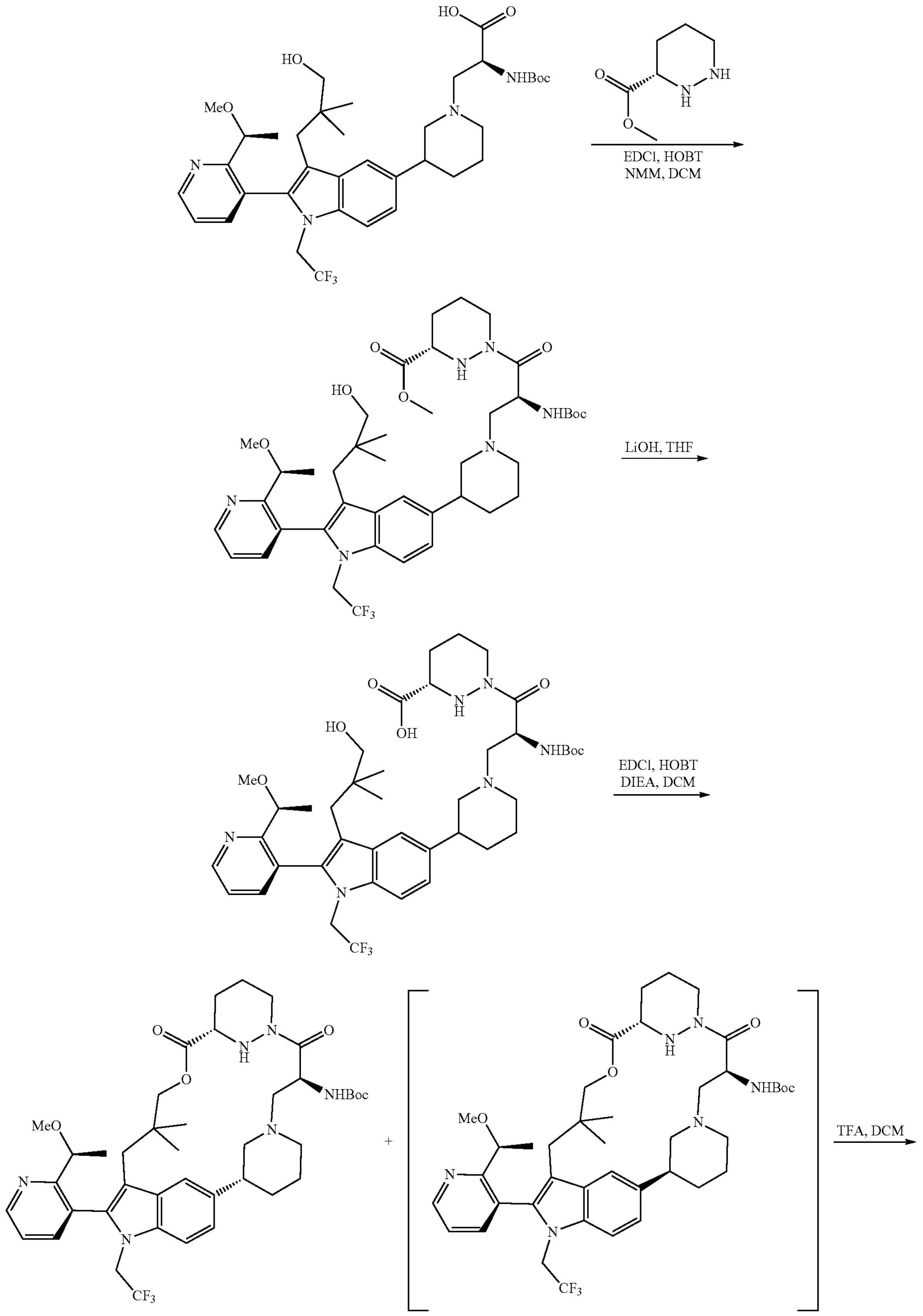

-continued
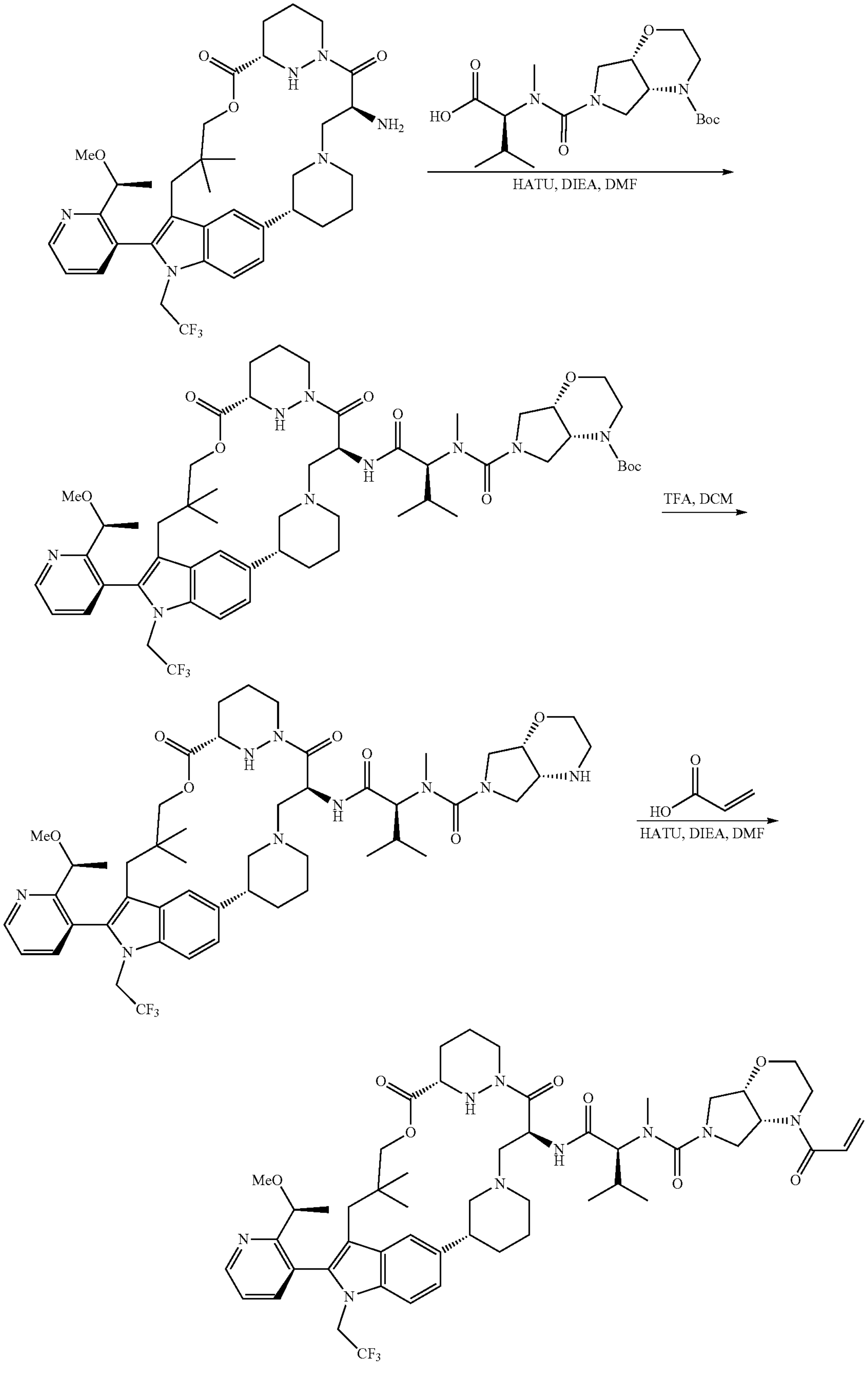

Step 1. To a mixture of 3-[(2M)-5-bromo-2-[2-[(1 S)-1-methoxyethyl]pyridin-3-yl]-1-(2,2,2-trifluoroethyl) indol-3-yl]-2,2-dimethylpropan-1-ol (10.0 g, 20.0 mmol) and tert-butyl 3-(4,4,5,5-tetramethyl-1,3,2-dioxaborolan-2-yl)-5,6-dihydro-2H-pyridine-1-carboxylate (9.29 g, 30.0 mmol) in 1,4-dioxane (85 mL) and $H_2O$ (17 mL) under an atmosphere of $N_2$ was added Pd(dppf)$Cl_2$ (0.73 g, 1.0 mmol) and $K_2CO_3$ (6.92 g, 50.1 mmol) in portions. The mixture was heated to 80° C. and stirred for 3 h, then the mixture extracted with EtOAc (3×100 mL). The combined organic layers were washed with brine (3×100 mL), dried over anhydrous $Na_2SO_4$ and filtered. The filtrate was concentrated under reduced pressure and the residue was purified by silica gel column chromatography to give tert-butyl 3-[(2M)-3-(3-hydroxy-2,2-dimethylpropyl)-2-[2-[(1 S)-1-methoxyethyl] pyridin-3-yl]-1-(2,2,2-trifluoroethyl)indol-5-yl]-5,6-dihydro-2H-pyridine-1-carboxylate (9.0 g, 67% yield) as a solid. LCMS (ESI): m/z $[M+H]^+$ calc'd for $C_{33}H_{42}F_3N_3O_4$ 601.3; found 602.3.

Step 2. A mixture of tert-butyl 3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]-5,6-dihydro-2H-pyridine-1-carboxylate (6.00 g, 10.0 mmol) and Pd/C (605 mg, 5.7 mmol) in THF (60 mL) was stirred under an atmosphere of $H_2$ overnight. The mixture was filtered and the filtrate was concentrated under reduced pressure to give tert-butyl 3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidine-1-carboxylate (5.8 g) as an oil. LCMS (ESI): m/z $[M+H]^+$ calc'd for $C_{33}H_{44}F_3N_3O_4$ 603.3; found 604.3.

Step 3. To a mixture of tert-butyl 3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidine-1-carboxylate (5.70 g, 9.4 mmol) in 1,4-dioxane (30 mL) at 0° C. under an atmosphere of $N_2$ was added HCl in 1,4-dioxane (30 mL). The mixture was stirred at 0° C. for 2 h, then aqueous $NaHCO_3$ was added and the mixture was extracted with EtOAc (3×20 mL). The combined organic layers were washed with brine (3×20 mL), dried over anhydrous $Na_2SO_4$, filtered and the filtrate was concentrated under reduced pressure to give 3-[(2M)-2-[2-[(1 S)-1-methoxyethyl]pyridin-3-yl]-5-(piperidin-3-yl)-1-(2,2,2-trifluoroethyl) indol-3-yl]-2,2-dimethylpropan-1-ol (4.8 g) as an oil. LCMS (ESI): m/z $[M+H]^+$ calc'd for $C_{28}H_{36}F_3N_3O_2$ 503.3; found 504.3.

Step 4. To a mixture of 3-[(2M)-2-[2-[(1 S)-1-methoxyethyl]pyridin-3-yl]-5-(piperidin-3-yl)-1-(2,2,2-trifluoroethyl) indol-3-yl]-2,2-dimethylpropan-1-ol (4.6 g, 9.1 mmol) in DMF (46 mL) under an atmosphere of $N_2$ was added tert-butyl N-[(3S)-2-oxooxetan-3-yl]carbamate (3.46 g, 18.3 mmol) and $Cs_2CO_3$ (7.44 g, 22.8 mmol). The mixture was heated to 40° C. and stirred for 2 h, then $H_2O$ was added and the mixture was extracted with EtOAc (3×50 mL). The combined organic layers were washed with brine (3×50 mL), dried over anhydrous $Na_2SO_4$ and filtered. The filtrate was concentrated under reduced pressure and the residue was purified by preparative-HPLC to give (2S)-2-[(tert-butoxycarbonyl) amino]-3-[3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoic acid (2.7 g, 39% yield) as a solid. LCMS (ESI): m/z $[M+H]^+$ calc'd for $C_{36}H_{49}F_3N_4O_6$ 690.4; found 691.1.

Step 5. To a mixture of methyl (3S)-1,2-diazinane-3-carboxylate (835 mg, 5.79 mmol) in DCM (20 mL) at 0° C. under an atmosphere of $N_2$ was added NMM (2.93 g, 29.0 mmol), (2S)-2-[(tert-butoxycarbonyl)amino]-3-[3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoic acid (2.00 g, 2.9 mmol), EDCl (833 mg, 4.3 mmol) and HOBT (196 mg, 1.5 mmol) in portions. The mixture was stirred at rt for h, then $H_2O$ was added and the mixture extracted with DCM (3×10 mL). The combined organic layers were washed with brine (3×10 mL), dried over anhydrous $Na_2SO_4$ and filtered. The filtrate was concentrated under reduced pressure and the residue was purified by silica gel column chromatography to give methyl (3S)-1-[(2S)-2-[(tert-butoxycarbonyl)amino]-3-[3-[(2)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoyl]-1,2-diazinane-3-carboxylate (2.0 g, 72% yield) as a solid. LCMS (ESI): m/z $[M+H]^+$ calc'd for $C_{42}H_{59}F_3N_6O_7$ 816.4; found 817.5.

Step 6. To a mixture of methyl (3S)-1-[(2S)-2-[(tert-butoxycarbonyl)amino]-3-[3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoyl]-1,2-diazinane-3-carboxylate (2.0 g, 2.5 mmol) in THE (20 mL) under an atmosphere of $N_2$ was added 1 M LiOH (12.24 mL, 12.24 mmol). The mixture was stirred at rt, then acidified to pH ~6 with 1M HCl and the mixture extracted with EtOAc (3×10 mL). The combined organic layers were washed with brine (3×10 mL), dried over anhydrous $Na_2SO_4$, filtered and the filtrate was concentrated under reduced pressure to give (3S)-1-[(2S)-2-[(tert-butoxycarbonyl)amino]-3-[3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoyl]-1,2-diazinane-3-carboxylic acid (1.8 g) as a solid. LCMS (ESI): m/z $[M+H]^+$ calc'd for $C_{41}H_{57}F_3N_6O_7$ 802.4; found 803.5.

Step 7. To a mixture of (3S)-1-[(2S)-2-[(tert-butoxycarbonyl)amino]-3-[3-[(2M)-3-(3-hydroxy-2,2-dimethylpropyl)-2-[2-[(1 S)-1-methoxyethyl]pyridin-3-yl]-1-(2,2,2-trifluoroethyl)indol-5-yl]piperidin-1-yl]propanoyl]-1,2-diazinane-3-carboxylic acid (1.80 g, 2.2 mmol) in DCM (360 mL) at 0° C. under an atmosphere of $N_2$ was added DIPEA (8.69 g, 67.3 mmol), HOBT (1.51 g, 11.2 mmol) and EDCl (8.60 g, 44.8 mmol) in portions. The mixture was stirred at rt for h, $H_2O$ was added, and the mixture was extracted with DCM (3×10 mL) The combined organic layers were washed with brine (3×10 mL), dried over anhydrous $Na_2SO_4$ and filtered. The filtrate was concentrated under reduced pressure and the residue was purified by preparative-TLC to give two diastereomers of tert-butyl (($6^3$S, 4S)-$1^2$-(2-((S)-1-methoxyethyl) pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl)carbamate (160 mg, 9% yield) and (140 mg, 8% yield) both as solid. LCMS (ESI): m/z $[M+H]^+$ calc'd for $C_{41}H_{55}F_3N_6O_6$ 784.4; found 785.7.

Step 8. To a mixture of tert-butyl (($6^3$S, 4S)-$1^2$-(2-((S)-1-methoxyethyl) pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl)carbamate (170 mg, 0.21 mmol) in DCM (2 mL) at 0° C. under an atmosphere of $N_2$ was added TFA (0.6 mL). The mixture was stirred at 0° C. for 2 h, then acidified to pH ~8 with saturated aqueous $NaHCO_3$ and extracted with DCM (3×10 mL). The combined organic layers were washed with brine (3×10 mL), dried over anhydrous $Na_2SO_4$, filtered and the filtrate was concentrated under reduced pressure to give ($2^3$R,$6^3$S,4S)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-5,7-dione (160 mg) as an oil. LCMS (ESI): m/z $[M+H]^+$ calc'd for $C_{36}H_{47}F_3N_6O_4$ 684.4; found 685.4.

Step 9. To mixture of ($2^3$R,$6^3$S,4S)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-5,7-dione (150 mg, 0.22 mmol) in DMF (2 mL) at 0° C. under an atmosphere of $N_2$ was added DIPEA (283 mg, 2.2 mmol), (2S)-2-[(4aR,7aS)-4-(tert-butoxycarbonyl)-hexahydropyrrolo[3,4-b][1,4]oxazine-6-carbonyl(methyl)amino]-3-methylbutanoic acid (127 mg, 0.33 mmol) and HATU (100 mg, 0.26 mmol) in portions. The mixture was warmed to rt and stirred for 2 h, then $H_2O$ was added and the mixture was extracted with EtOAc (3×10 mL). The combined organic layers were washed with brine (3×10 mL), dried over anhydrous $Na_2SO_4$ and filtered. The filtrate was concentrated under reduced pressure and the residue was purified by preparative-TLC to give tert-butyl (4aR,7aS)-6-(((2S)-1-(((2$^3$R,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(3,1)-piperidinacycloundecaphane-4-yl)amino)-3-methyl-1-oxobutan-2-yl)(methyl)carbamoyl)hexahydropyrrolo[3,4-b][1,4]oxazine-4(4aH)-carboxylate (150 mg, 52% yield) as a solid. LCMS (ESI): m/z $[M+H]^+$ calc'd for $C_{54}H_{76}F_3N_9O_9$ 1051.6; found 1052.5.

Step 10. To mixture of tert-butyl (4aR,7aS)-6-(((2S)-1-(((2$^3$R,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(3,1)-piperidinacycloundecaphane-4-yl)amino)-3-methyl-1-oxobutan-2-yl)(methyl)carbamoyl)hexahydropyrrolo[3,4-b][1,4]oxazine-4(4aH)-carboxylate (150 mg, 0.14 mmol) in DCM (2 mL) at 0° C. under an atmosphere of $N_2$ was added TFA (0.70 mL). The mixture was warmed to rt and stirred for 2 h, then acidified to pH ~8 with saturated $NaHCO_3$ and the mixture extracted with DCM (3×10 mL). The combined organic layers were washed with brine (3×10 mL), dried over anhydrous $Na_2SO_4$, filtered and the filtrate was concentrated under reduced pressure to give (4aR,7aS)—N-((2S)-1-(((2$^3$R,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1'$^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4]oxazine-6(2H)-carboxamide (130 mg) as an oil. LCMS (ESI): m/z $[M+H]^+$ calc'd for $C_{49}H_{68}F_3N_9O_7$ 951.5; found 952.6.

Step 11. To a mixture of (4aR,7aS)—N-((2S)-1-(((2$^3$R,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1 $^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4]oxazine-6(2H)-carboxamide (120 mg, 0.13 mmol) in DMF (2 mL) at 0° C. under an atmosphere of $N_2$ was added DIPEA (163 mg, 1.26 mmol), acrylic acid (13.6 mg, 0.19 mmol) and HATU (57.5 mg, 0.15 mmol) in portions. The mixture was allowed to warm to rt and stirred for 2 h, then $H_2O$ was added and the mixture extracted with EtOAc (3×10 mL). The combined organic layers were washed with brine (3×10 mL), dried over anhydrous $Na_2SO_4$ and filtered. The filtrate was concentrated under reduced pressure and the residue was purified by preparative-HPLC to give (4aR,7aS)-4-acryloyl-N-((2S)-1-(((2$^3$R,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4]oxazine-6(2H)-carboxamide (16 mg, 12% yield) as a solid. LCMS (ESI): m/z $[M+H]^+$ calc'd for $C_{52}H_{70}F_3N_9O_8$ 1005.5; found 1006.9; $^1$H NMR (300 MHz, DMSO-$d_6$) δ 8.83 (dd, J=4.7, 1.7 Hz, 1H), 7.84 (t, J=7.4 Hz, 2H), 7.71 (d, J=8.5 Hz, 1H), 7.60 (dd, J=7.8, 4.7 Hz, 1H), 7.40 (s, 1H), 7.24 (d, J=8.5 Hz, 1H), 6.94-6.79 (m, 1H), 6.25 (d, J=16.7 Hz, 1H), 5.87-5.77 (m, 2H), 5.77 (s, 1H), 5.59-5.42 (m, 1H), 5.34 (d, J=12.0 Hz, 1H), 4.83 (s, 2H), 4.31 (d, J=12.9 Hz, 1H), 4.22 (d, J=6.8 Hz, 1H), 4.10-4.01 (m, 2H), 3.93 (d, J=11.3 Hz, 5H), 3.82-3.62 (m, 4H), 3.67-3.56 (m, 4H), 3.59-3.44 (m, 5H), 3.44-3.31 (m, 1H), 3.23 (d, J=5.7 Hz, 4H), 3.09 (s, 1H), 2.88-2.69 (m, 7H), 2.73-2.59 (m, 3H), 2.35 (m, 2H), 2.29 (s, 1H), 2.12 (s, 4H), 2.06 (s, 1H), 1.84 (s, 1H), 1.74-1.56 (m, 4H), 1.45 (d, J=6.1 Hz, 3H), 1.35-1.04 (m, 1H), 1.05-0.91 (m, 2H), 0.92-0.63 (m, 8H), 0.43 (s, 3H).

Example 4. Synthesis of (4aR,7aS)-4-acryloyl-N-((2S)-1-(((2$^3$S,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4]oxazine-6(2H)-carboxamide

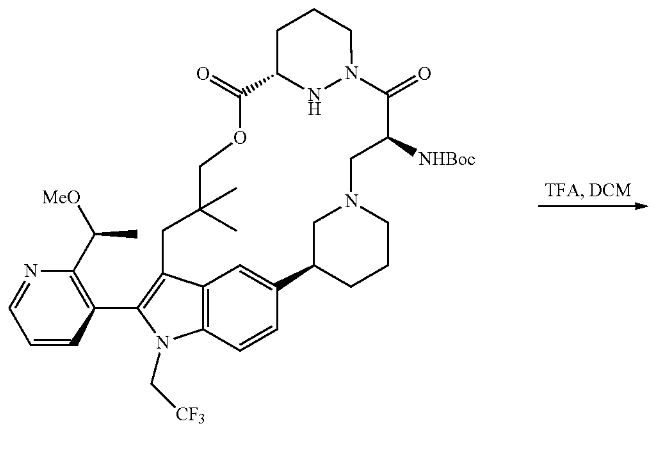

-continued
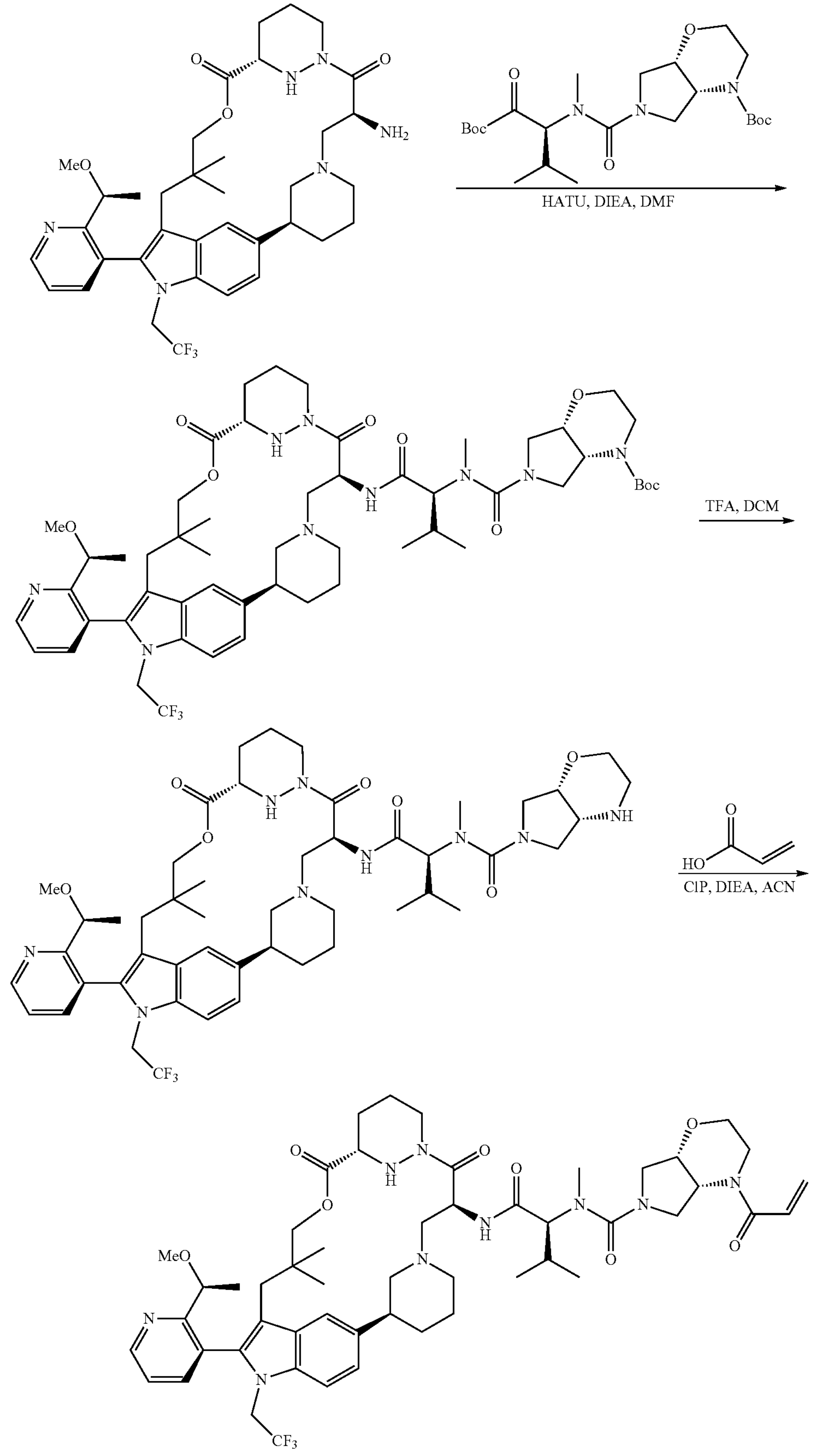

Step 1. To a mixture of tert-butyl (($2^3$S,$6^3$S,4S)-$1^2$-(2-((S)-1-methoxyethyl) pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl) carbamate (200 mg, 0.26 mmol) in DCM (2 mL) at 0° C. was added TFA (0.7 mL). The mixture was stirred at 0° C. for 2 h, then acidified to pH ~8 with saturated $NaHCO_3$ and extracted with DCM (3×10 mL). The combined organic layers were washed with brine (3×10 mL), dried over anhydrous $Na_2SO_4$, filtered and the filtrate was concentrated under reduced pressure to give ($2^3$S,$6^3$S,4S)-4-amino-$1^2$-(2-((S)-1-methoxyethyl) pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-5,7-dione (200 mg) as an oil. LCMS (ESI): m/z $[M+H]^+$ calc'd for $C_{36}H_{47}F_3N_6O_4$ 684.4; found 985.4.

Step 2. To a mixture of ($2^3$S,$6^3$S,4S)-4-amino-$1^2$-(2-((S)-1-methoxyethyl) pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-5,7-dione (200 mg, 0.29 mmol) in DMF (2 mL) at 0° C. under an atmosphere of $N_2$ was added DIPEA (378 mg, 2.9 mmol), (2S)-2-[(4aR,7aS)-4-(tert-butoxycarbonyl)-hexahydropyrrolo[3,4-b][1,4] oxazine-6-carbonyl (methyl) amino]-3-methylbutanoic acid (169 mg, 0.44 mmol) and HATU (133 mg, 0.35 mmol). The mixture was warmed to rt and stirred for 2 h, then $H_2O$ added and the mixture was extracted with EtOAc (3×10 mL). The combined organic layers were washed with brine (3×10 mL), dried over anhydrous $Na_2SO_4$ and filtered. The filtrate was concentrated under reduced pressure and the crude residue was purified by preparative-TLC to give tert-butyl (4aR,7aS)-6-(((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1 $^1$H-8-oxa-1(5,3)-indola-6(1,3)-pyridazina-2(3,1)-piperidinacycloundecaphane-4-yl)amino)-3-methyl-1-oxobutan-2-yl)(methyl) carbamoyl)hexahydropyrrolo[3,4-b][1,4]oxazine-4(4aH)-carboxylate (230 mg, 67% yield) as a solid. LCMS (ESI): m/z $[M+H]^+$ calc'd for $C_{54}H_{76}F_3N_9O_9$ 1051.6; found 1052.6.

Step 3. To a mixture of tert-butyl (4aR,7aS)-6-(((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl) amino)-3-methyl-1-oxobutan-2-yl)(methyl) carbamoyl) hexahydropyrrolo[3,4-b][1,4]oxazine-4(4aH)-carboxylate (230 mg, 0.22 mmol) in DCM (3 mL) at 0° C. under an atmosphere of $N_2$ was added TFA. The mixture was warmed to rt and stirred for 2 h, then $H_2O$ added and the mixture extracted with DCM (3×10 mL). The combined organic layers were washed with brine (3×10 mL), dried over anhydrous $Na_2SO_4$, filtered and the filtrate was concentrated under reduced pressure to give (4aR,7aS)—N-((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl) amino)-3-methyl-1-oxobutan-2-yl)-N-methylhexahydropyrrolo[3,4-b][1,4]oxazine-6(2H)-carboxamide (220 mg) as a solid. LCMS (ESI): m/z $[M+H]^+$ calc'd for $C_{49}H_{68}F_3N_9O_7$ 951.5; found 952.5.

Step 4. To a mixture of (4aR,7aS)—N-((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4] oxazine-6(2H)-carboxamide (220 mg, 0.23 mmol) in ACN (3 mL) at 0° C. under an atmosphere of $N_2$ was added DIPEA (299 mg, 2.3 mmol), acrylic acid (25 mg, 0.35 mmol) and CIP (77 mg, 0.28 mmol). The mixture was warmed to rt and stirred for 2 h, then $H_2O$ added and the mixture extracted with EtOAc (3×10 mL). The combined organic layers were washed with brine (3×10 mL), dried over anhydrous $Na_2SO_4$ and filtered. The filtrate was concentrated under reduced pressure and the crude residue was purified by preparative-HPLC to give (4aR,7aS)-4-acryloyl-N-((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1'H-8-oxa-1(5,3)-indola-6(1,3)-pyridazina-2(3,1)-piperidinacycloundecaphane-4-yl)amino)-3-methyl-1-oxobutan-2-yl)-N-methylhexahydropyrrolo[3,4-b][1,4] oxazine-6(2H)-carboxamide (20 mg, 8% yield) as a solid. LCMS (ESI): m/z $[M+H]^+$ calc'd for $C_{52}H_{70}F_3N_9O_8$ 1005.5; found 1006.9; $^1$H NMR (300 MHz, DMSO-$d_6$) δ 8.75 (dd, J=4.7, 1.8 Hz, 1H), 7.77 (d, J=7.9 Hz, 1H), 7.67 (t, J=9.2 Hz, 2H), 7.58-7.48 (m, 2H), 7.17 (d, J=8.6 Hz, 1H), 6.86 (dd, J=17.2, 10.6 Hz, 1H), 6.20 (d, J=16.5 Hz, 1H), 5.80-5.59 (m, 2H), 5.48 (s, 1H), 5.11 (d, J=11.7 Hz, 1H), 4.73 (d, J=15.3 Hz, 2H), 4.35 (d, J=12.8 Hz, 1H), 4.21-4.04 (m, 2H), 3.99-3.71 (m, 6H), 3.67-3.49 (m, 3H), 3.30-3.05 (m, 7H), 3.04-2.91 (m, 3H), 2.77-2.60 (m, 9H), 2.09 (d, J=42.2 Hz, 5H), 1.81 (d, J=28.6 Hz, 2H), 1.64-1.56 (m, 5H), 1.40 (d, J=6.1 Hz, 3H), 0.95 (s, 3H), 0.82 (t, J=6.4 Hz, 6H), 0.21 (s, 3H).

Example 5. Synthesis of 4-acryloyl-N-((2S)-1-((($6^3$S,4S,Z)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-oxazola-1(5,3)-indola-6(1,3)-pyridazinacycloundecaphane-4-yl)amino)-3-methyl-1-oxobutan-2-yl)-N-methyl-1-oxa-4,9-diazaspiro[5.5]undecane-9-carboxamide

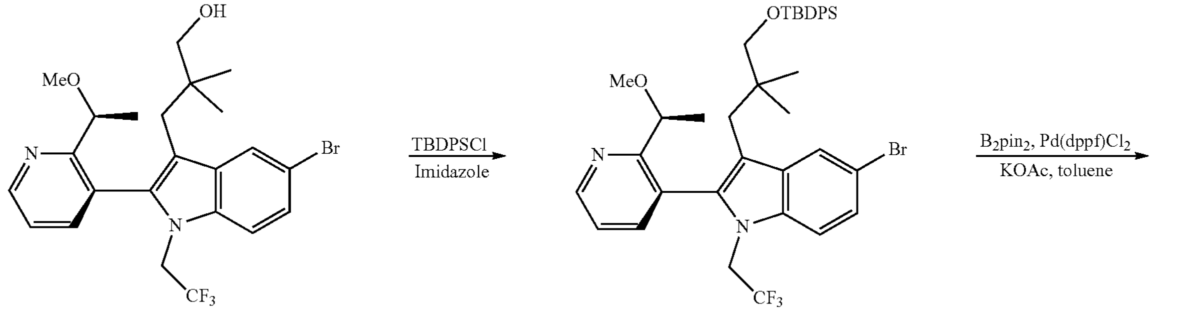

-continued
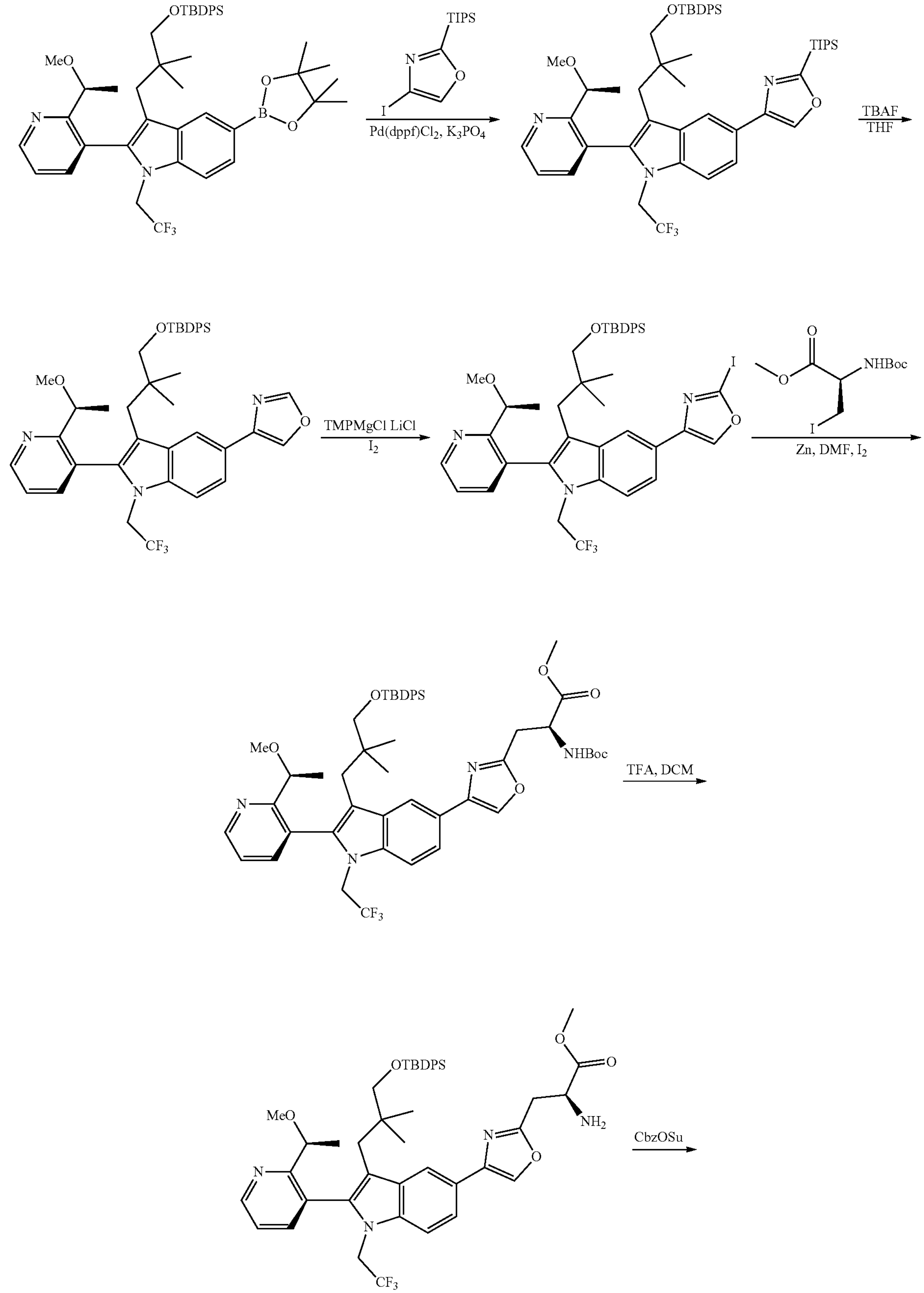

-continued
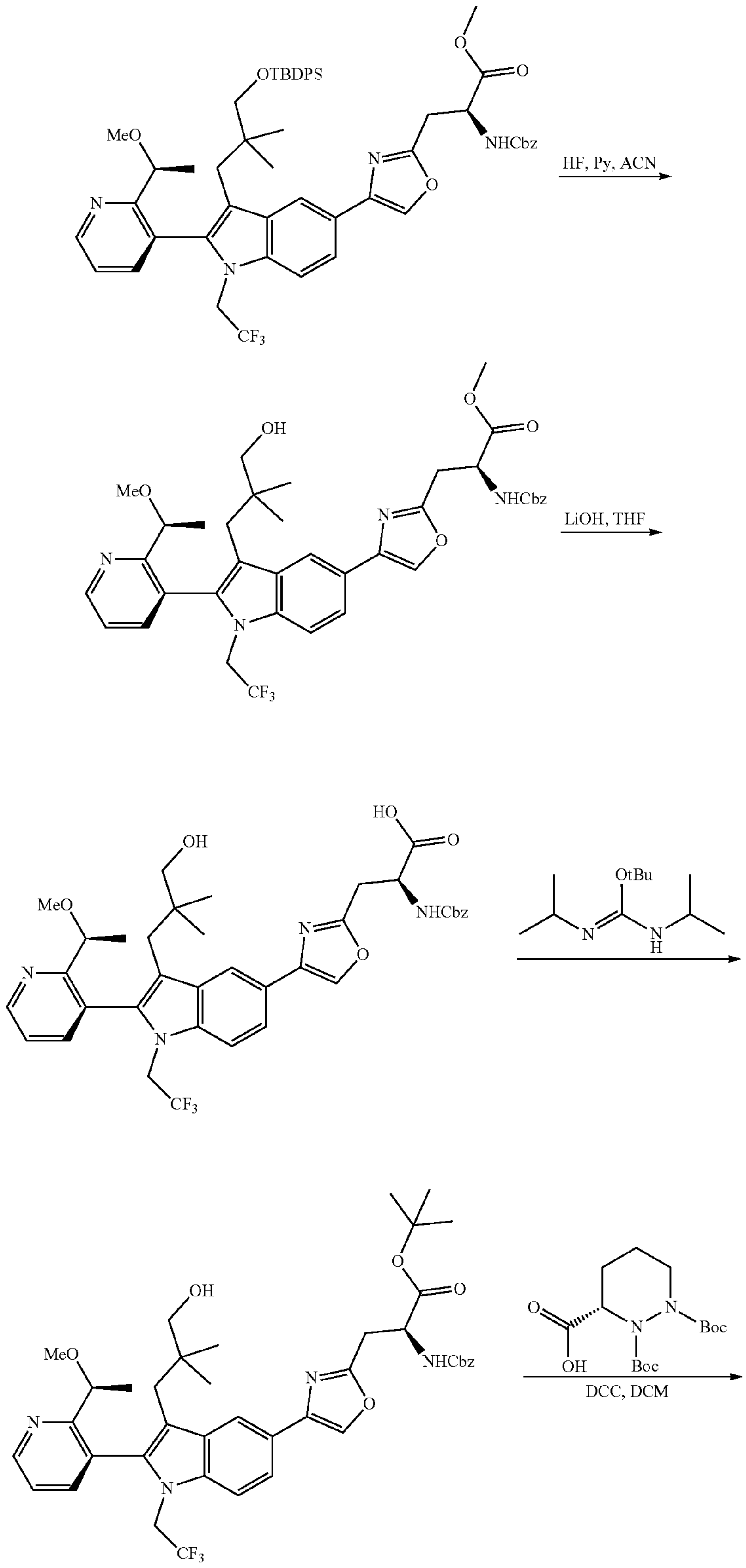

-continued
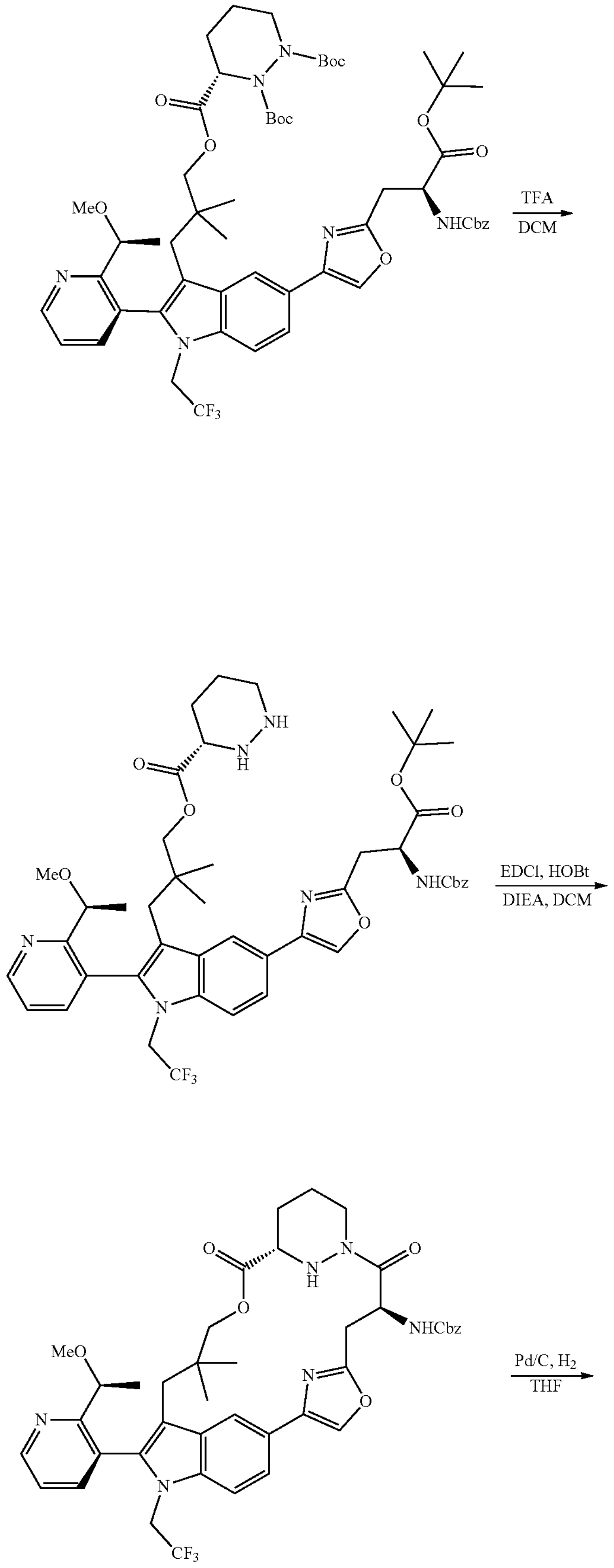

-continued

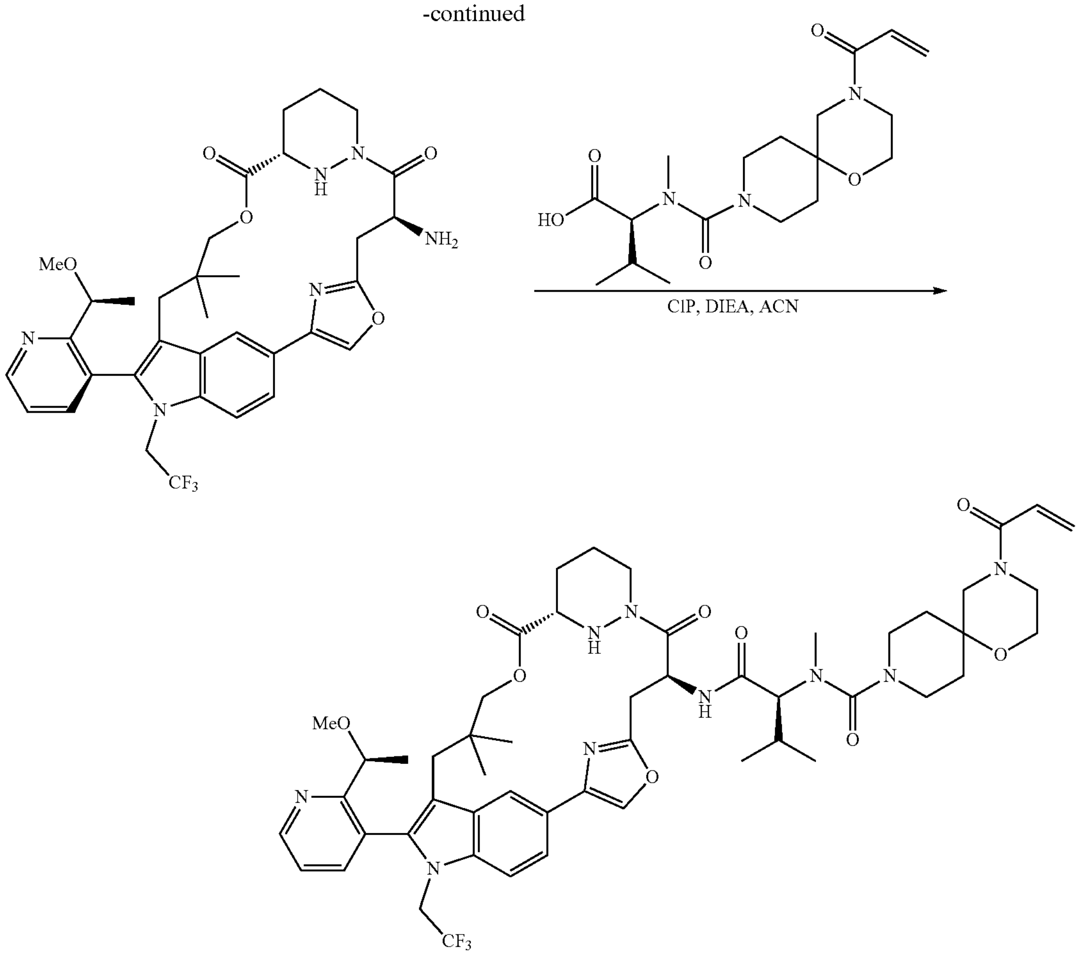

Step 1. To a mixture of (S)-3-(3-((tert-butyldiphenyisilyl)oxy)-2,2-dimethylpropyl)-2-(2-(1-methoxyethyl)pyridin-3-yl)-5-(4,4,5,5-tetramethyl-1,3,2-dioxaborolan-2-yl)-1-(2,2,2-trifluoroethyl)-1H-indole (6.3 g, 8.0 mmol) and 4-iodo-2-(triisopropylsilyl)-1,3-oxazole (8.46 g, 24.1 mmol) in 1,4-dioxane (60 mL) and $H_2O$ (12 mL) under an atmosphere of Ar was added $K_3PO_4$ (4.26 g, 20.1 mmol) and Pd(dppf)$Cl_2$ (0.59 g, 0.80 mmol). The mixture was heated to 70° C. and stirred for 2 h, then concentrated under reduced pressure and the residue was purified by silica gel column chromatography to give (S)-4-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-2-(triisopropylsilyl)oxazole (8.84 g) as an oil. LCMS (ESI): m/z $[M+H]^+$ calc'd for $C_{51}H_{66}F_3N_3O_3Si_2$ 881.5; found 882.5.

Step 2. To a mixture of (2M)-3-[3-[(tert-butyldiphenylsilyl)oxy]-2,2-dimethylpropyl]-2-[2-[(1 S)-1-methoxyethyl]pyridin-3-yl]-1-(2,2,2-trifluoroethyl)-5-[2-(triisopropylsilyl)-1,3-oxazol-4-yl]indole (8.84 g, 10.0 mmol) in THE (90 mL) at 0° C. was added 1M TBAF in THF (10.0 mL, 10.0 mmol). The mixture was stirred at 0° C. for 1 h, then washed with saturated $NH_4Cl$ (3×100 mL). The combined aqueous layers were extracted with EtOAc (3×100 mL) and the combined organic layers were dried over anhydrous $Na_2SO_4$ and filtered. The filtrate was concentrated under reduced pressure to give (2M)-3-[3-[(tert-butyldiphenylsilyl)oxy]-2,2-dimethylpropyl]-2-[2-[(1 S)-1-methoxyethyl]pyridin-3-yl]-5-(1,3-oxazol-4-yl)-1-(2,2,2-trifluoroethyl)indole (8.4 g) as an oil. LCMS (ESI): m/z $[M+H]^+$ calc'd for $C_{42}H_{46}F_3N_3O_3Si$ 725.3; found 726.4.

Step 3. To a mixture of (2M)-3-[3-[(tert-butyldiphenylsilyl)oxy]-2,2-dimethylpropyl]-2-[2-[(1 S)-1-methoxyethyl]pyridin-3-yl]-5-(1,3-oxazol-4-yl)-1-(2,2,2-trifluoroethyl)indole (4.5 g, 6.2 mmol) in THE (45 mL) at 0° C. under an atmosphere of $N_2$ was added 1 M TMPMgCl·LiCl (12.2 mL, 12.2 mmol) dropwise. The mixture was warmed to rt and stirred for 1 h, then a mixture of 12 (1.89 g, 7.4 mmol) in THE (10 mL) was added dropwise. The mixture was stirred at rt for 1 h, then re-cooled to 0° C. and saturated $NH_4Cl$ added and the mixture extracted with EtOAc (3×10 mL). The combined organic layers were washed with brine (2×10 mL), dried over anhydrous $Na_2SO_4$ and filtered. The filtrate was concentrated under reduced pressure and the residue was purified by preparative-TLC to give (S)-4-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-2-iodooxazole (3.0 g, 57% yield) as a solid. LCMS (ESI): m/z $[M+H]^+$ calc'd for $C_{42}H_{45}F_3IN_3O_3Si$ 851.2; found 852.3.

Step 4. To a mixture of Zn (645 mg, 9.9 mmol) in DMF (10 mL) under an atmosphere of Ar was added $I_2$ (125 mg, 0.49 mmol). The mixture was heated to 45° C. and stirred for 30 min, then methyl (2R)-2-[(tert-butoxycarbonyl)amino]-3-iodopropanoate (1.22 g, 3.7 mmol) in DMF (5 mL) was added dropwise at 45° C. The mixture was stirred at 45° C. for 2 h then cooled to 0° C. and (S)-4-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-2-iodooxazole (2.1 g, 2.5 mmol), then $Pd(PPh_3)_2C_{12}$ (173 mg, 0.25 mmol) in DMF (20 mL) added dropwise. The mixture was heated to 75° C. and stirred for 2 h, then brine (20 mL) added and the mixture extracted with EtOAc (3×50 mL). The combined organic layers were washed with brine (3×10 mL), dried over anhydrous $Na_2SO_4$ and filtered. The filtrate was concentrated under reduced pressure and the residue was purified by silica gel column chromatography to give methyl (S)-2-((tert-butoxycarbonyl)amino)-3-(4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (1.6 g, 70% yield) as an oil. LCMS (ESI): m/z $[M+H]^+$ calc'd for $C_{51}H_{61}F_3N_4O_7Si$ 926.4; found 927.5.

Step 5. To a mixture of (S)-2-((tert-butoxycarbonyl)amino)-3-(4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (2.4 g, 2.6 mmol) in DCM (1.8 mL) at 0° C. was added TFA (0.6 mL). The mixture was stirred at 0° C. for 1 h, then saturated $NaHCO_3$ was added and the mixture was extracted with DCM/MeOH (10:1; 3×50 mL). The combined organic layers were washed with brine (3×20 mL), dried over anhydrous $Na_2SO_4$, filtered and the filtrate was concentrated under reduced pressure to give methyl (S)-2-amino-3-(4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (2.1 g, 98% yield) as a solid. LCMS (ESI): m/z $[M+H]^+$ calc'd for $C_{46}H_{53}F_3N_4O_5Si$ 826.4; found 827.5.

Step 6. To a mixture of (S)-2-amino-3-(4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (2.1 g, 2.5 mmol) in THF (15 mL) and $H_2O$ (5 mL) at 0° C. was added $NaHCO_3$ (0.64 g, 7.6 mmol) and benzyl 2,5-dioxopyrrolidin-1-yl carbonate (0.95 g, 3.8 mmol). The mixture was stirred at 0° C. for 1 h then EtOAc (20 mL) added and the mixture was washed with brine (3×10 mL). The organic layer was concentrated under reduced pressure and the residue was purified by silica gel column chromatography to give methyl (S)-2-(((benzyloxy)carbonyl) amino)-3-(4-(3-(3-((tert-butyidiphenylsilyl)oxy)-2,2-dimethyl propyl)-2-(2-((S)-1-methoxyethyl)pyridin-3-yl)-1-(2,2,2-trifluoroethyl)-1H-indol-5-yl)oxazol-2-yl)propanoate (2.2 g, 90% yield) as a solid. LCMS (ESI): m/z $[M+H]^+$ calc'd for $C_{54}H_{59}F_3N_4O_7Si$ 960.4; found 961.4.

Step 7. To a mixture of methyl (S)-2-(((benzyloxy)carbonyl)amino)-3-(4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (2.2 g, 2.3 mmol) in ACN (11 mL) at 0° C. was added HF-pyridine (11 mL, 122 mmol). The mixture was warmed to rt and stirred for 1 h, then basified to pH ~7 with saturated $NaHCO_3$. The aqueous and organic layers were partitioned and the organic layer was concentrated under reduced pressure to give methyl (S)-2-(((benzyloxy)carbonyl)amino)-3-(4-(3-(3-hydroxy-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (1.7 g) as a solid. LCMS (ESI): m/z $[M+H]^+$ calc'd for $C_{31}H_{41}F_3N_4O_7$ 722.3; found 723.3.

Step 8. To a mixture of methyl (S)-2-(((benzyloxy)carbonyl)amino)-3-(4-(3-(3-hydroxy-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (1.7 g, 2.4 mmol) in THF (1.2 mL) and $H_2O$ (0.4 mL) at 0° C. was added LiOH (0.08 g, 3.5 mmol). The mixture was stirred at 0° C. overnight, then acidified to pH ~4 with aqueous HCl. The mixture was extracted with DCM/MeOH (10:1; 3×20 mL). The combined organic layers were dried over anhydrous $Na_2SO_4$, filtered and the filtrate was concentrated under reduced pressure to give (2S)-2-{[(benzyloxy)carbonyl]amino}-3-{4-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]-1,3-oxazol-2-yl}propanoic acid (1.5 g, 90% yield) as an oil. LCMS (ESI): m/z $[M+H]^+$ calc'd for $C_{37}H_{39}F_3N_4O_7$ 708.3; found 709.3.

Step 9. To a mixture of (2S)-2-{[(benzyloxy)carbonyl]amino}-3-{4-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]-1,3-oxazol-2-yl}propanoic acid (1.5 g, 2.1 mmol) in DCM (15 mL) and (Z)—N,N'-diisopropyl tert-butoxymethanimidamide (2.12 mL, 10.6 mmol). The mixture was heated to 40° C. and stirred for 3 h, then concentrated under reduced pressure and the residue was purified by silica gel column chromatography to give tert-butyl (S)-2-(((benzyloxy)carbonyl)amino)-3-(4-(3-(3-hydroxy-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (1.6 g, 99% yield) as a solid. LCMS (ESI): m/z $[M+H]^+$ calc'd for $C_{41}H_{47}F_3N_4O_7$ 764.3; found 765.3.

Step 10. To a mixture of tert-butyl (S)-2-(((benzyloxy)carbonyl)amino)-3-(4-(3-(3-hydroxy-2,2-dimethylpropyl)-2-(2-((S)-1-methoxyethyl)pyridin-3-yl)-1-(2,2,2-trifluoroethyl)-1H-indol-5-yl)oxazol-2-yl)propanoate (1.8 g, 2.4 mmol) in DCM (16 mL) at 0° C. was added (3S)-1,2-bis(tert-butoxycarbonyl)-1,2-diazinane-3-carboxylic acid (1.04 g, 3.1 mmol) and DCC (0.65 g, 3.1 mmol). The mixture was stirred at 0° C. for 1 h, then concentrated under reduced pressure and the residue was purified by silica gel column chromatography to give 3-(3-(5-(2-((S)-2-(((benzyloxy)carbonyl)amino)-3-(tert-butoxy)-3-oxopropyl)oxazol-4-yl)-2-(2-((S)-1-methoxyethyl)pyridin-3-yl)-1-(2,2,2-trifluoroethyl)-1H-indol-3-yl)-2,2-dimethylpropyl) 1,2-di-tert-butyl (S)-tetrahydropyridazine-1,2,3-tricarboxylate (1.8 g, 80% yield) as a solid. LCMS (ESI): m/z $[M+H]^+$ calc'd for $C_{56}H_{71}F_3N_6O_{12}$ 1076.5; found 1077.4.

Step 11. To a mixture of 3-(3-(5-(2-((S)-2-(((benzyloxy)carbonyl)amino)-3-(tert-butoxy)-3-oxopropyl)oxazol-4-yl)-2-(2-((S)-1-methoxyethyl)pyridin-3-yl)-1-(2,2,2-trifluoroethyl)-1H-indol-3-yl)-2,2-dimethylpropyl) 1,2-di-tert-butyl (S)-tetrahydropyridazine-1,2,3-tricarboxylate (1.8 g, 1.7 mmol) in DCM (15 mL) at 0° C. was added TFA (5 mL). The mixture was stirred at 0° C. for 1 h, then saturated $NaHCO_3$ was added and the mixture extracted with EtOAc (3×100 mL). The combined organic layers were washed with brine (3×10 mL), dried over anhydrous $Na_2SO_4$, filtered and the filtrate was concentrated under reduced pressure to give (S)-2-(((benzyloxy)carbonyl)amino)-3-(4-(3-(3-(((S)-hexahydropyridazine-3-carbonyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoic acid (1.27 g, 93% yield) as a solid. LCMS (ESI): m/z $[M+H]^+$ calc'd for $C_{42}H_{47}F_3N_6O$ 820.3; found 821.4.

Step 12. To a mixture of (S)-2-(((benzyloxy)carbonyl)amino)-3-(4-(3-(3-(((S)-hexahydropyridazine-3-carbonyl)oxy)-2,2-dimethylpropyl)-2-(2-((S)-1-methoxyethyl)pyridin-3-yl)-1-(2,2,2-trifluoroethyl)-1H-indol-5-yl)oxazol-2-yl)propanoic acid (870 mg, 1.1 mmol) and DIPEA (4.1 g, 31.8 mmol) in DCM (175 mL) at 0° C. was added HOBt (1.15 g, 8.5 mmol) and EDCl (8.13 g, 42.4 mmol) in portions over 15 min. The mixture was allowed to warm to rt and stirred overnight then concentrated under reduced pressure and the residue was purified by silica gel column chromatography to give benzyl (($6^3$S,4S,Z)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1 $^1$H-8-oxa-2(4,2)-oxazola-1(5,3)-indola-6(1,3)-pyridazinacycloundecaphane-4-yl)carbamate (180 mg, 21% yield) as a solid. LCMS (ESI): m/z $[M+H]^+$ calc'd for $C_{42}H_{45}F_3N_6O_7$ 802.3; found 803.4.

Step 13. A mixture of benzyl (($6^3$S,4S,Z)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-oxazola-1(5,3)-indola-6(1,3)-pyridazinacycloundecaphane-4-yl)carbamate (150 mg, 0.19 mmol) and 10% Pd/C (0.1 g) in THF (2 mL) was stirred at 35° C. under an atmosphere of $H_2$ (balloon) for 1 h. The mixture was filtered through a pad of Celite and the filtrate was concentrated under reduced pressure to give ($6^3$S,4S,Z)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-2(4,2)-oxazola-1(5,3)-indola-6(1,3)-pyridazinacycloundecaphane-5,7-dione (112 mg, 90% yield) as a solid. LCMS (ESI): m/z $[M+H]^+$ calc'd for $C_{34}H_3F_3N_6O_5$ 668.3; found 669.3.

Step 14. To a mixture of ($6^3$S,4S,Z)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-2(4,2)-oxazola-1(5,3)-indola-6(1,3)-pyridazinacycloundecaphane-5,7-dione (91 mg, 0.14 mmol) in ACN (1 mL) at 0° C. was added DIPEA (352 mg, 2.7 mmol) and (2S)-3-methyl-2-[methyl(4-(prop-2-enoyl)-1-oxa-4,9-diazaspiro[5.5]undecane-9-carbonyl)amino]butanoic acid (75 mg, 0.20 mmol) and 2-chloro-1,3-dimethyl-4,5-dihydro-1H-imidazol-3-ium; hexafluorophosphate(V) (46 mg, 0.16 mmol). The mixture was stirred at 0° C. for 1 h, then concentrated under reduced pressure and the residue was purified by preparative-HPLC to give 4-acryloyl-N-((2S)-1-((($6^3$S,4S,Z)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-oxazola-1(5,3)-indola-6(1,3)-pyridazinacycloundecaphane-4-yl)amino)-3-methyl-1-oxobutan-2-yl)-N-methyl-1-oxa-4,9-diazaspiro[5.5]undecane-9-carboxamide (29.6 mg, 21% yield) as a solid. LCMS (ESI): m/z $[M+H]^+$ calc'd for $C_{52}H_{66}F_3N_9O_9$ 1017.5; found 1018.7; $^1$H NMR (400 MHz, DMSO-$d_6$) δ 8.77 (dd, J=4.7, 1.8 Hz, 1H), 8.45-8.21 (m, 3H), 7.94-7.70 (m, 2H), 7.63 (d, J=7.6 Hz, 1H), 7.54 (m, 1H), 6.84 (t, J=13.8 Hz, 1H), 6.16 (d, J=16.5 Hz, 1H), 5.70 (d, J=10.5 Hz, 1H), 5.62-5.50 (m, 2H), 5.08 (d, J=11.9 Hz, 1H), 4.94-4.75 (m, 1H), 4.35 (td, J=12.1, 3.2 Hz, 1H), 4.34-4.15 (m, 2H), 3.94-3.80 (m, 1H), 3.65 (d, J=5.0 Hz, 2H), 3.57-3.48 (m, 6H), 3.28 (s, 4H), 3.19-2.93 (m, 4H), 2.93-2.62 (m, 5H), 2.40 (d, J=14.4 Hz, 1H), 2.20-2.04 (m, 2H), 1.86-1.57 (m, 5H), 1.58-1.40 (m, 2H), 1.37 (d, J=6.1 Hz, 3H), 0.98-0.77 (m, 9H), 0.28 (s, 3H).

Example 6. Synthesis of 4-acryloyl-N-((2S)-1-((($6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-azetidinacycloundecaphane-4-yl)amino)-3-methyl-1-oxobutan-2-yl)-N-methyl-1-oxa-4,9-diazaspiro[5.5] undecane-9-carboxamide

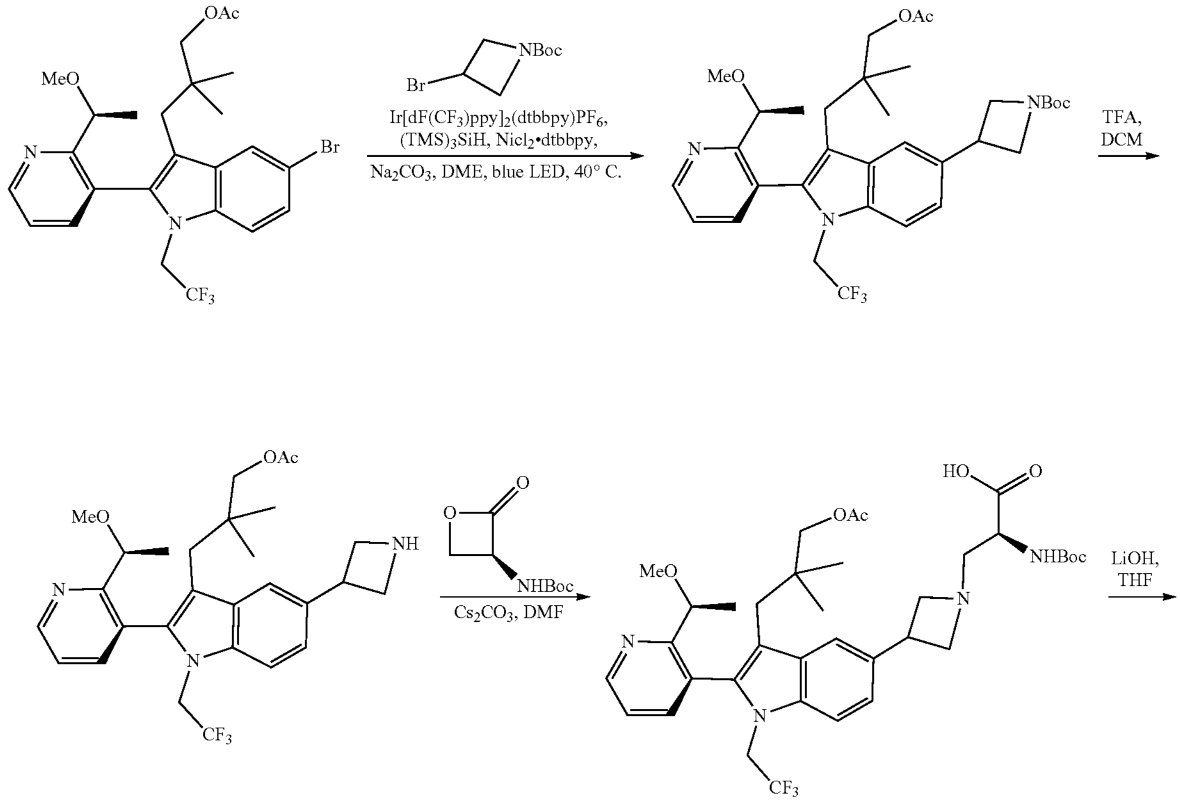

-continued
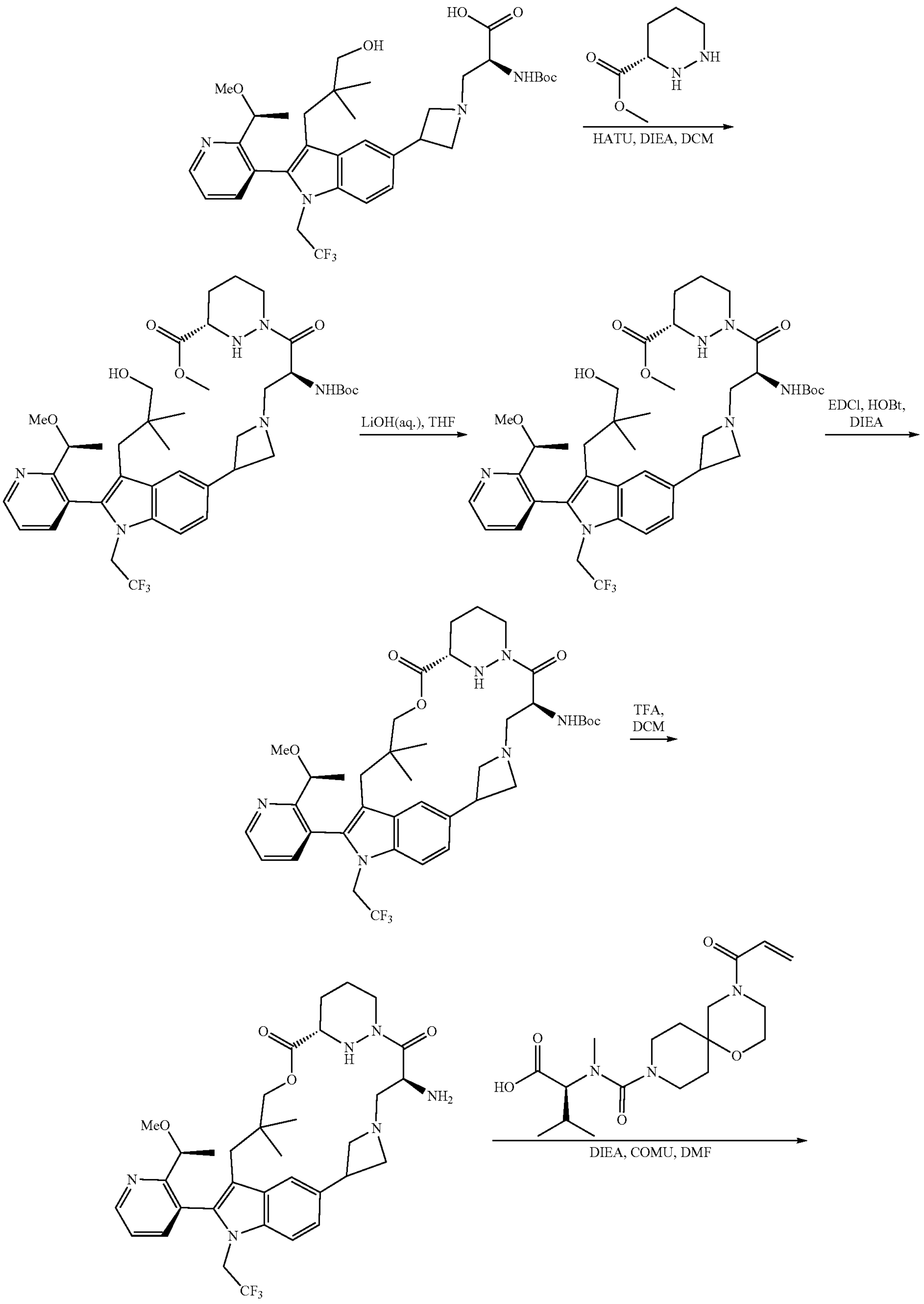

-continued

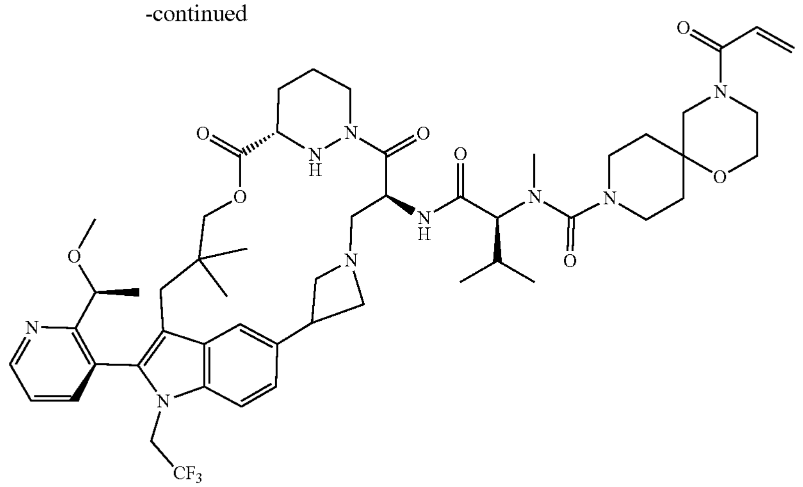

Step 1. To a 40 mL vial equipped with a stir bar was added photocatalyst Ir[dF($CF_3$)ppy]$_2$(dtbbpy)$PF_6$ (62 mg, 0.055 mmol), methyl 4-bromobenzoate (1.5 g, 2.8 mmol), 4-bromotetrahydropyran (981 mg, 4.2 mmol) tris(trimethylsilyl) silane (689 mg, 2.8 mmol), and anhydrous sodium carbonate (587 mg, 5.54 mmol). The vial was sealed and placed under an atmosphere of $N_2$ then DME (15 mL) added. To a separate vial was added $NiCl_2$·glyme (6.1 mg, 0.028 mmol) and 4,4'-di-tert-butyl-2,2'-bipyridine (7.4 mg, 0.028 mmol). The catalyst vial was sealed, purged with $N_2$ and DME (2 mL) was added, then this mixture was sonicated 5 min, after which, the mixture was added to the photocalatyst. The mixture was degassed with $N_2$ for 10 min, then the mixture was sealed and stirred under irradiation from a 34 W blue LED lamp (7 cm away, with a cooling fan to keep the reaction temperature at rt. The mixture was stirred at rt for 6 h, then $H_2O$ was added and the mixture extracted with EtOAc (3x30 mL). The combined organic layers were washed with brine (30 mL), dried over anhydrous $Na_2SO_4$ and filtered. The filtrate was concentrated under reduced pressure and the crude residue was purified by silica gel column chromatography to give tert-butyl 3-[(2M)-3-[3-(acetyloxy)-2,2-dimethylpropyl]-2-{2-[(1 S)-1-methoxyethyl]pyridin-3-yl}-1-(2,2,2-trifluoroethyl)indol-5-yl]azetidine-1-carboxylate (700 mg, 41% yield) as a solid. LCMS (ESI): m/z [M+H]$^+$ calc'd for $C_{33}H_{42}F_3N_3O_5$ 617.3; found 618.4.

Step 2. To a mixture of tert-butyl 3-[(2M)-3-[3-(acetyloxy)-2,2-dimethylpropyl]-2-{2-[(1 S)-1-methoxyethyl] pyridin-3-yl}-1-(2,2,2-trifluoroethyl)indol-5-yl]azetidine-1-carboxylate (800 mg, 1.3 mmol) in DCM (8 mL) at 0° C. was added TFA (2.95 g, 25.9 mmol). The mixture was warmed to rt and stirred for 2 h, then concentrated under reduced pressure and the residue was basified to pH ~8 with saturated $NaHCO_3$ and extracted with EtOAc (3x30 mL). The combined organic layers were washed with brine (30 mL), dried over anhydrous $Na_2SO_4$, filtered and the filtrate was concentrated under reduced pressure to give 3-[(2M)-5-(azetidin-3-yl)-2-{2-[(1 S)-1-methoxyethyl]pyridin-3-yl}-1-(2,2,2-trifluoroethyl)indol-3-yl]-2,2-dimethylpropyl acetate (650 mg, 97%) as a solid. LCMS (ESI): m/z [M+H]$^+$ calc'd for $C_{28}H_{34}F_3N_3O_3$ 517.3; found 518.3.

Step 3. To a mixture of 3-[(2M)-5-(azetidin-3-yl)-2-{2-[(1 S)-1-methoxyethyl]pyridin-3-yl}-1-(2,2,2-trifluoroethyl)indol-3-yl]-2,2-dimethylpropyl acetate (900 mg, 1.7 mmol) in DMF (9 mL) was added tert-butyl N-[(3S)-2-oxooxetan-3-yl]carbamate (488 mg, 2.6 mmol) and $Cs_2CO_3$ (567 mg, 1.7 mmol). The mixture was heated to 40° C. and stirred for 2 h, then $H_2O$ was added and the mixture extracted with EtOAc (3x30 mL). The combined organic layers were washed with brine (30 mL), dried over anhydrous $Na_2SO_4$ and filtered. After filtration, the filtrate was concentrated under reduced pressure. The filtrate was concentrated under reduced pressure and the crude residue was purified by preparative-HPLC to give (2S)-3-{3-[(2M)-3-[3-(acetyloxy)-2,2-dimethylpropyl]-2-{2-[(1 S)-1-methoxyethyl] pyridin-3-yl}-1-(2,2,2-trifluoroethyl)indol-5-yl]azetidin-1-yl}-2-[(tert-butoxycarbonyl)amino]propanoic acid (400 mg, 33% yield) as a solid. LCMS (ESI): m/z [M+H]$^+$ calc'd for $C_{36}H_{47}F_3N_4O_7$ 704.3; found 705.4.

Step 4. To a mixture of (2S)-3-{3-[(2M)-3-[3-(acetyloxy)-2,2-dimethylpropyl]-2-{2-[(1 S)-1-methoxyethyl]pyridin-3-yl}-1-(2,2,2-trifluoroethyl)indol-5-yl]azetidin-1-yl}-2-[(tert-butoxycarbonyl)amino]propanoic acid (400 mg, 0.57 mmol) in THF (2.8 mL) at 0° C. was added 1M LiOH (2.84 mL, 2.84 mmol). The mixture was stirred at 0° C. for 2 h, then diluted with DCM (30 mL). The organic layer was washed with $H_2O$ (3x30 mL) and the combined aqueous layers were acidified to pH ~5 with 1 M HCl, then extracted with EtOAc (3x40 mL). The combined organic layers were washed with brine (40 mL), dried over anhydrous $Na_2SO_4$, filtered and the filtrate was concentrated under reduced pressure to give (2S)-2-[(tert-butoxycarbonyl)amino]-3-{3-[(2M)-3-(3-hydroxy-2,2-dimethylpropyl)-2-{2-[(1S)-1-methoxyethyl]pyridin-3-yl}-1-(2,2,2-trifluoroethyl)indol-5-yl]azetidin-1-yl}propanoic acid (300 mg, 80%) as a solid. LCMS (ESI): m/z [M+H]$^+$ calc'd for $C_{34}H_{45}F_3N_4O_6$ 662.3; found 663.4.

Step 5. To a mixture of (2S)-2-[(tert-butoxycarbonyl) amino]-3-{3-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]azetidin-1-yl}propanoic acid (300 mg, 0.45 mmol) in DCM (3 mL) at 0° C. was added DIPEA (351 mg, 2.7 mmol), methyl (3S)-1,2-diazinane-3-carboxylate (131 mg, 0.91 mmol) and HATU (258 mg, 0.68 mmol). The mixture was stirred at 0° C. for 3 h, then $H_2O$ was added and the mixture extracted with DCM (3x30 mL). The combined organic layers were dried over anhydrous $Na_2SO_4$, filtered, the filtrate was concentrated under reduced pressure and the crude residue was purified by preparative-TLC to give methyl (3S)-1-[(2S)-2-[(tert-butoxycarbonyl)amino]-3-{3-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]azetidin-1-yl}propanoyl]-1,2-diazinane-3-carboxylate (290 mg, 81%) as a solid. LCMS (ESI): m/z [M+H]$^+$ calc'd for $C_{40}H_{55}F_3N_6O_7$ 788.4; found 789.5.

Step 6. To a mixture of methyl (3S)-1-[(2S)-2-[(tert-butoxycarbonyl)amino]-3-{3-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]azetidin-1-yl}propanoyl]-1,2-diazinane-3-carboxylate (290 mg, 0.37 mmol) in THE (1.8 mL) at 0° C. was added 1 M LiOH (1.84 mL, 1.84 mmol). The mixture was stirred at 0° C. for 1 h, then DCM (20 mL) was added and the mixture washed with $H_2O$ (3x30 mL). The combined aqueous layers were acidified to pH ~5 with 1M HCl and the mixture was extracted with EtOAc (3x60 mL). The combined organic layers were dried over anhydrous $Na_2SO_4$, filtered and the filtrate was concentrated under reduced pressure to give (3S)-1-[(2S)-2-[(tert-butoxycarbonyl)amino]-3-{3-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]azetidin-1-yl}propanoyl]-1,2-diazinane-3-carboxylic acid (230 mg, 81% yield) as a solid. LCMS (ESI): m/z $[M+H]^+$ calc'd for $C_{39}H_{53}F_3N_6O_7$ 774.4; found 775.5.

Step 7. To a mixture of (3S)-1-[(2S)-2-[(tert-butoxycarbonyl)amino]-3-{3-[(2M)-3-(3-hydroxy-2,2-dimethylpropyl)-2-{2-[(1 S)-1-methoxyethyl]pyridin-3-yl}-1-(2,2,2-trifluoroethyl)indol-5-yl]azetidin-1-yl}propanoyl]-1,2-diazinane-3-carboxylic acid (280 mg, 0.36 mmol) in DCM (56 mL) was added DIPEA (1.4 g, 10.8 mmol), HOBT (293 mg, 2.2 mmol) and EDCl (2.1 g, 10.8 mmol). The mixture was warmed to 30° C. and stirred overnight the $H_2O$ was added and the mixture extracted with DCM (3x50 mL). The combined organic layers were dried over anhydrous $Na_2SO_4$, filtered, the filtrate was concentrated under reduced pressure and the residue was purified by preparative-TLC to give tert-butyl (($6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-azetidinacycloundecaphane-4-yl)carbamate (100 mg, 37% yield) as a solid. LCMS (ESI): m/z $[M+H]^+$ calc'd for $C_{39}H_{51}F_3N_6O_6$ 756.4; found 757.4.

Step 8. To a mixture of tert-butyl (($6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-azetidinacycloundecaphane-4-yl)carbamate (100 mg, 0.13 mmol) in DCM (2 mL) at 0° C. was added TFA (301 mg, 2.64 mmol). The mixture was stirred at 0° C. for 4 h, then concentrated under reduced pressure to give ($6^3$S,4S)-4-amino-$1^2$-(2-((S)-1-methoxyethyl)pyridin-3-yl)-10,10-dimethyl-11-(2,2,2-trifluoroethyl)-$6^1$,$6^2$,$6^3$,$6^4$,$6^5$,$6^6$-hexahydro-$1^1$H-8-oxa-1 (5,3)-indola-6(1,3)-pyridazina-2(3,1)-azetidinacycloundecaphane-5,7-dione (80 mg, 92% yield) as a solid. LCMS (ESI): m/z $[M+H]^+$ calc'd for $C_{34}H_{43}F_3N_6O_4$ 656.3; found 657.5.

Step 9. To a mixture of ($6^3$S,4S)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-azetidinacycloundecaphane-5,7-dione (90 mg, 0.14 mmol) in DMF (2 mL) at 0° C. was added DIPEA (106 mg, 0.82 mmol), (2S)-3-methyl-2-[methyl(4-(prop-2-enoyl)-1-oxa-4,9-diazaspiro[5.5]undecane-9-carbonyl)amino]butanoic acid (76 mg, 0.21 mmol) and COMU (88 mg, 0.21 mmol). The mixture was stirred at 0° C. for 1 h, then $H_2O$ was added and the mixture was extracted with EtOAc (3x20 mL). The combined organic layers were washed with brine (20 mL), dried over anhydrous $Na_2SO_4$ and filtered. The filtrate was concentrated under reduced pressure and the residue was purified by preparative-HPLC to give 4-acryloyl-N-((2S)-1-((($6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1 $^1$H-8-oxa-1(5,3)-indola-6(1,3)-pyridazina-2(3,1)- azetidinacycloundecaphane-4-yl)amino)-3-methyl-1-oxobutan-2-yl)-N-methyl-1-oxa-4,9-diazaspiro[5.5]undecane-9-carboxamide (37 mg, 27% yield) as a solid. LCMS (ESI): m/z $[M+H]^+$ calc'd for $C_{52}H_{70}F_3N_9O_8$ 1005.5; found 1006.8; 1H NMR (400 MHz, DMSO-$d_6$) δ 8.73 (dd, J=4.7, 1.8 Hz, 1H), 7.80 (s, 1H), 7.71-7.69 (m, 2H), 7.58-7.46 (m, 2H), 7.10 (d, J=8.4 Hz, 1H), 6.86-6.71 (m, 1H), 6.11 (dd, J=16.3, 9.7 Hz, 1H), 5.65 (t, J=8.3 Hz, 1H), 5.46 (dq, J=17.2, 8.8 Hz, 1H), 5.29-5.15 (m, 2H), 4.87-4.74 (m, 1H), 4.23 (d, J=12.3 Hz, 1H), 4.11 (q, J=6.0 Hz, 1H), 4.07-3.97 (m, 1H), 3.86-3.71 (m, 2H), 3.61-3.47 (m, 12H), 3.23 (m, 5H), 3.07-2.87 (m, 5H), 2.78 (s, 3H), 2.76-2.66 (m, 1H), 2.32 (d, J=14.4 Hz, 1H), 2.18-2.05 (m, 1H), 2.04-1.94 (m, 1H), 1.78 (d, J=10.0 Hz, 1H), 1.71 (d, J=13.3 Hz, 1H), 1.58 (dd, J=16.6, 6.9 Hz, 4H), 1.48-1.38 (m, 1H), 1.32 (d, J=6.0 Hz, 3H), 0.88-0.75 (m, 9H), 0.24 (s, 3H).

Example 7. Synthesis of (2R)-3-acryloyl-N-((2S)-1-((($6^3$S,4S)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,66-decahydro-1'1H-8-oxa-1(5,3)-indola-6(1,3)-pyridazina-2(5,1)-pyridinacycloundecaphane-4-yl)amino)-3-methyl-1-oxobutan-2-yl)-N,2-dimethyl-1-oxa-3,8-diazaspiro[4.5]decane-8-carboxamide

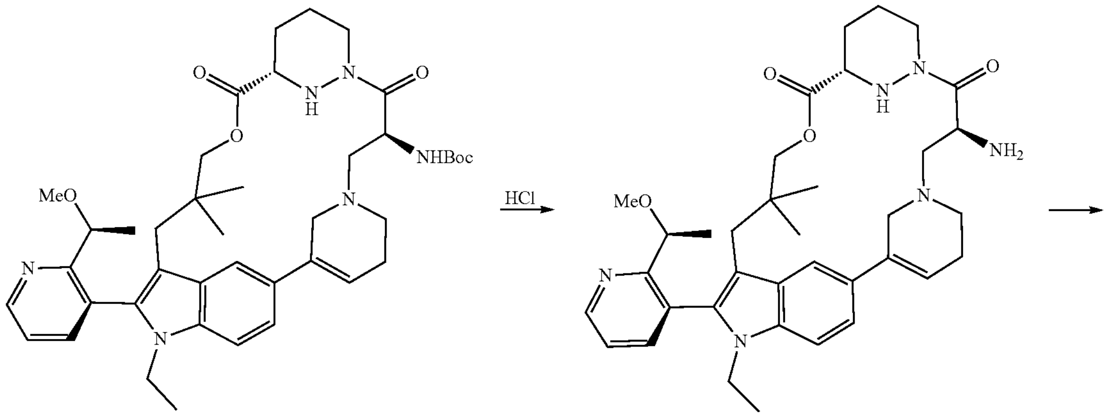

-continued

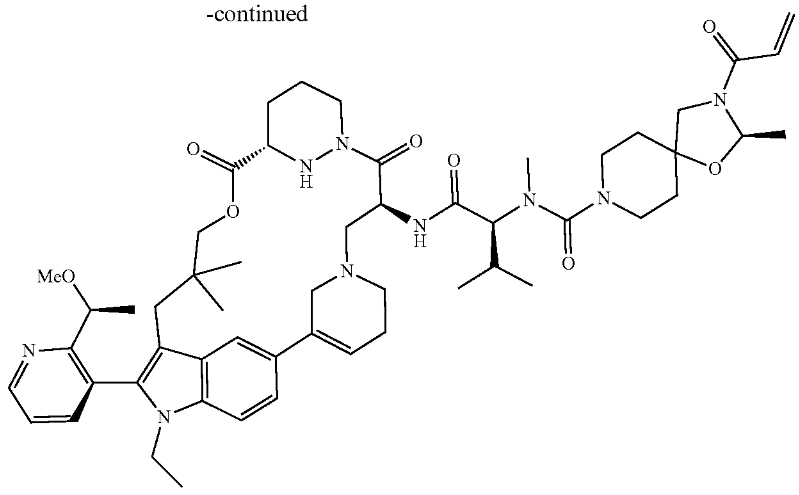

Step 1. To a mixture of methyl N—((R)-3-acryloyl-2-methyl-1-oxa-3,8-diazaspiro[4.5]decane-8-carbonyl)-N-methyl-L-valinate (430 mg, 1.127 mmol, 1.00 equiv) in THE (4 mL) and $H_2O$ (4 mL) was added NaOH (225 mg, 5.6 mmol). The mixture was stirred at rt for 16 hours at rt, then acidified to pH ~5 with 1 M HCl and the mixture was extracted with EtOAc (4×10 mL). The combined organic layers were washed with brine (3 mL), dried over anhydrous $Na_2SO_4$, filtered and the filtrate was concentrated under reduced pressure to give N—((R)-3-acryloyl-2-methyl-1-oxa-3,8-diazaspiro[4.5]decane-8-carbonyl)-N-methyl-L-valine (300 mg) as a solid. LCMS (ESI): m/z $[M+H]^+$ calc'd for $C_{18}H_{29}N_3O_5$ 367.2; found 368.3.

Step 2. To a mixture of tert-butyl (($6^3$S,4S)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-1'H-8-oxa-1(5,3)-indola-6(1,3)-pyridazina-2(5,1)-pyridinacycloundecaphane-4-yl)carbamate (1.0 g, 1.4 mmol) in DCM (10 mL) at 0° C. was added HCl in 1,4-dioxane (5 mL). The mixture was stirred at 0° C. for 2 h, then concentrated under reduced pressure to give ($6^3$S, 4S)-4-amino-11-ethyl-2-(2-((S)-1-methoxyethyl)pyridin-3-yl)-10,10-dimethyl-$2^1$,$2^2$,$2^3$,$2^6$,$6^1$,$6^2$,$6^3$,$6^4$,$6^5$,$6^6$-decahydro-11H-8-oxa-1(5,3)-indola-6(1,3)-pyridazina-2(5,1)-pyridinacycloundecaphane-5,7-dione HCl (1.0 g) as a solid. LCMS (ESI): m/z $[M+H]^+$ calc'd for $C_{36}H_{48}N_6O_4$ 628.4; found 629.6.

Step 3. To a mixture of ($6^3$S,4S)-4-amino-$1^1$-ethyl-$1^2$-(2-((S)-1-methoxyethyl)pyridin-3-yl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)- pyridinacycloundecaphane-5,7-dione HCl (460 mg, 0.73 mmol) and N—((R)-3-acryloyl-2-methyl-1-oxa-3,8-diazaspiro[4.5]decane-8-carbonyl)-N-methyl-L-valine (269 mg, 0.73 mmol) in DMF (5 mL) at 0° C. was added DIPEA (2.84 g, 22.0 mmol) and COMU (282 mg, 0.66 mmol). The mixture was stirred at 0° C. for 1 h, then $H_2O$ was added and the mixture extracted with EtOAc (5×10 mL). The combined organic layers were washed with brine (3×6 mL), dried over anhydrous $Na_2SO_4$ and filtered. The filtrate was concentrated under reduced pressure and the residue was purified by preparative-HPLC to give (2R)-3-acryloyl-N-((2S)-1-((($6^3$S,4S)-$1^1$-ethyl-$1^2$-(2-((S)-1-methoxyethyl)pyridin-3-yl)-10,10-dimethyl-5,7-dioxo-$2^1$, $2^2$,$2^3$,$2^6$,$6^1$,$6^2$,$6^3$,$6^4$,$6^5$,$6^6$-decahydro-1'H-8-oxa-1(5,3)-indola-6(1,3)-pyridazina-2(5,1)-pyridinacycloundecaphane-4-yl)amino)-3-methyl-1-oxobutan-2-yl)-N,2-dimethyl-1-oxa-3,8-diazaspiro[4.5]decane-8-carboxamide (50 mg, 7% yield) as a solid. LCMS (ESI): m/z $[M+H]^+$ calc'd for $C_{54}H_{75}N_9O_8$ 977.6; found 978.6; $^1$H NMR (400 MHz, DMSO-$d_6$) δ 8.83-8.67 (m, 1H), 7.89 (dd, J=18.7, 8.2 Hz, 2H), 7.62-7.33 (m, 4H), 6.57 (dd, J=16.7, 10.3 Hz, 1H), 6.38-6.11 (m, 2H), 5.75 (d, J=9.8 Hz, 2H), 5.61 (d, J=11.8 Hz, 1H), 5.35 (d, J=5.5 Hz, 1H), 4.30 (d, J=12.7 Hz, 1H), 4.16 (q, J=6.2 Hz, 1H), 4.04 (s, 2H), 3.92-3.68 (m, 4H), 3.63 (s, 2H), 3.18 (d, J=61.5 Hz, 6H), 2.95 (d, J=33.8 Hz, 5H), 2.78 (t, J=11.8 Hz, 1H), 2.64 (d, J=24.7 Hz, 7H), 2.42-1.83 (m, 7H), 1.89-1.45 (m, 7H), 1.40 (dd, J=11.9, 5.7 Hz, 6H), 1.10 (t, J=7.0 Hz, 3H), 0.94-0.64 (m, 9H), 0.52 (s, 3H).

Example 8. Synthesis of 3-acryloyl-N-((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-pyrrolidinacycloundecaphane-4-yl)amino)-3-methyl-1-oxobutan-2-yl)-N-methyl-1-oxa-3,8-diazaspiro[4.5]decane-8-carboxamide

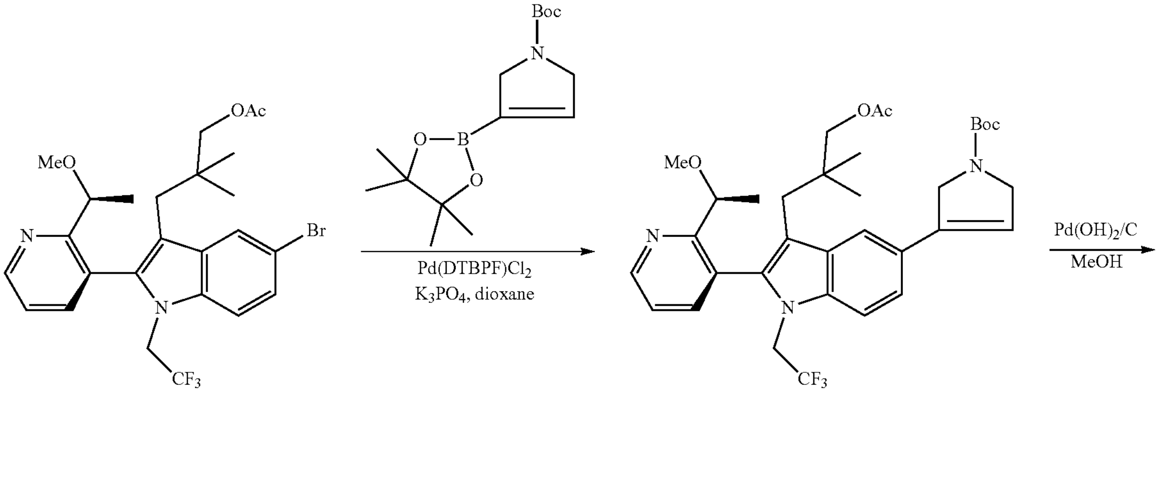

-continued
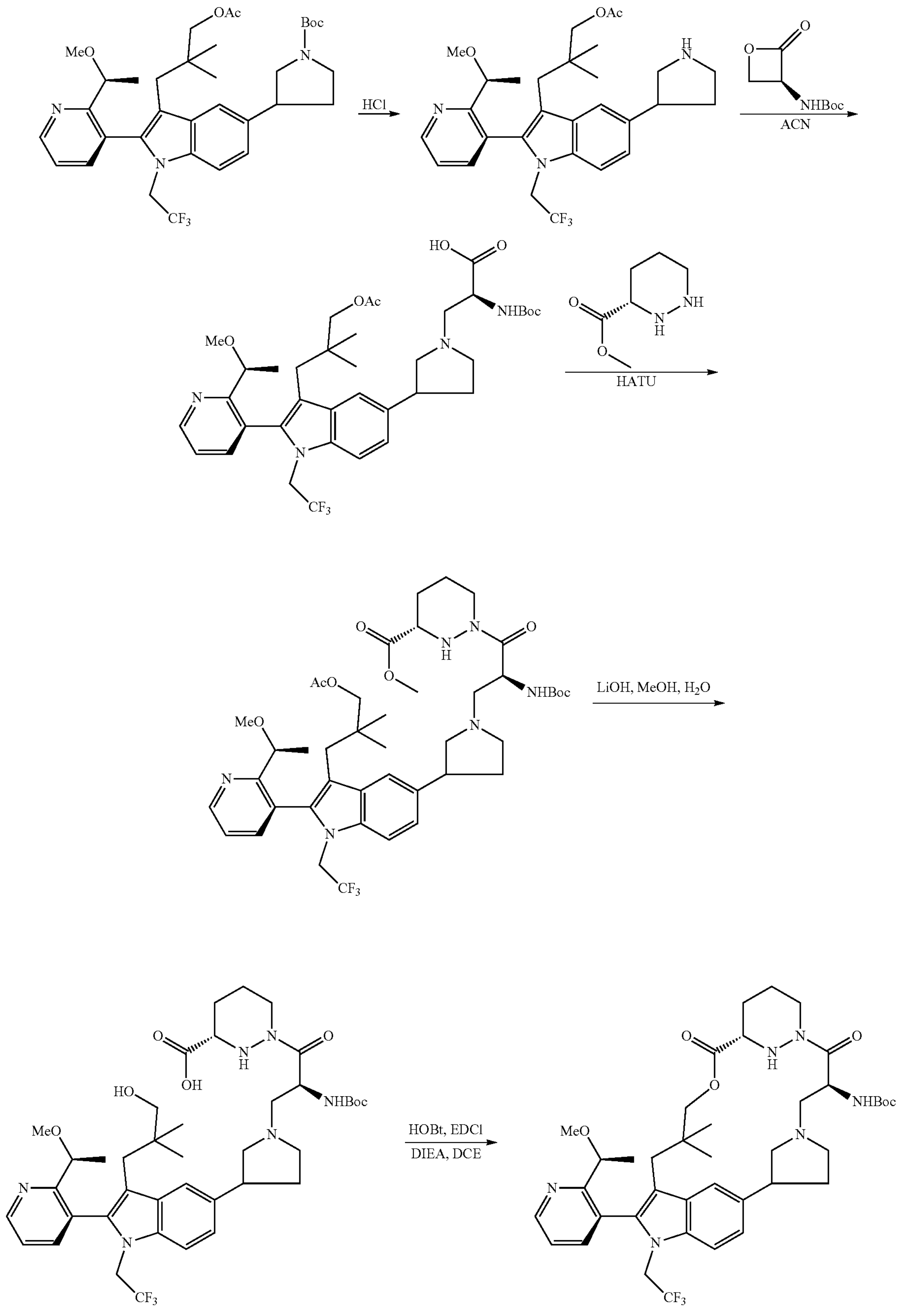

-continued
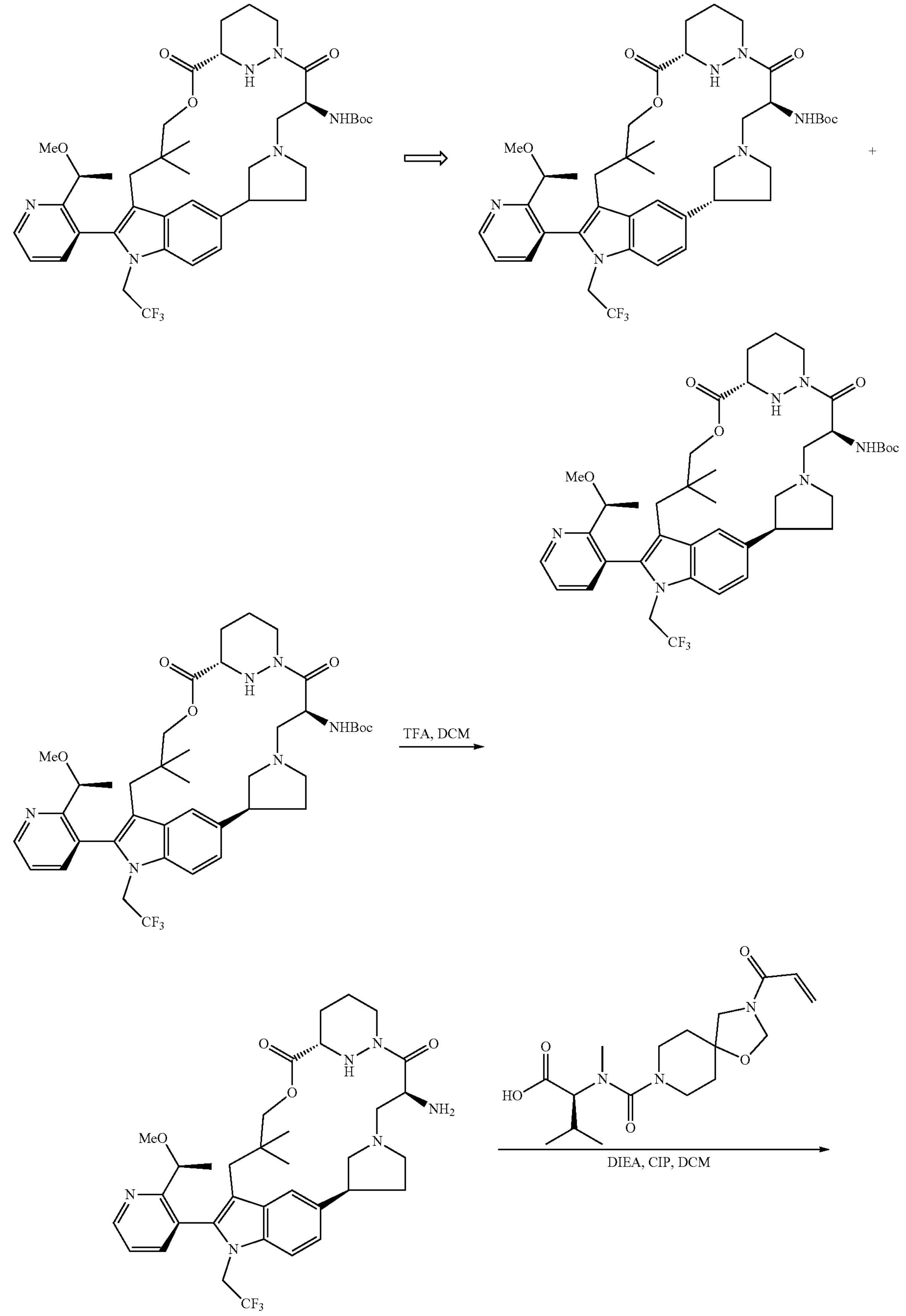

-continued

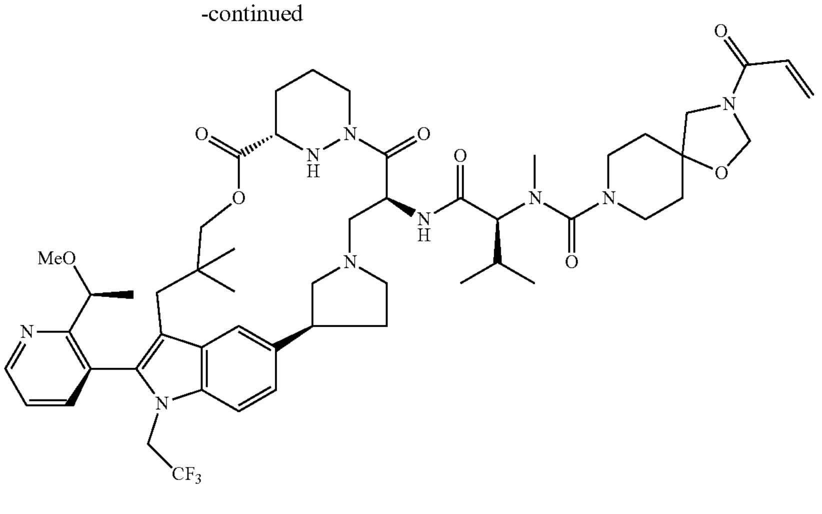

Step 1. To a mixture of (S)-3-(5-bromo-2-(2-(1-methoxyethyl) pyridin-3-yl)-1-(2,2,2-trifluoroethyl)-1H-indol-3-yl)-2,2-dimethylpropyl acetate (10 g, 18.5 mmol) and tert-butyl 3-(4,4,5,5-tetramethyl-1,3,2-dioxaborolan-2-yl)-2,5-dihydro-1H-pyrrole-1-carboxylate (8.18 g, 27.7 mmol) in dioxane (100 mL) and $H_2O$ (20 mL) under an atmosphere of Ar was added Pd(DTBPF)$Cl_2$ (1.20 g, 1.85 mmol) and $K_3P04$ (9.80 g, 46.2 mmol). The mixture was heated to 85° C. and stirred for 1 h, then extracted with EtOAc (10 mL). The combined organic layers were washed with brine (8×5 mL), dried over anhydrous $Na_2SO_4$ and filtered. The filtrate was concentrated under reduced pressure and the residue was purified by silica gel column chromatography to give tert-butyl (S)-3-(3-(3-acetoxy-2,2-dimethylpropyl)-2-(2-(1-methoxyethyl) pyridin-3-yl)-1-(2,2,2-trifluoroethyl)-1H-indol-5-yl)-2,5-dihydro-1H-pyrrole-1-carboxylate (13 g, 89% yield) as an oil. LCMS (ESI): m/z $[M+H]^+$ calc'd for $C_{34}H_{42}F_3N_3O_5$ 629.3; found 630.4.

Step 2. A mixture of tert-butyl (S)-3-(3-(3-acetoxy-2,2-dimethylpropyl)-2-(2-(1-methoxyethyl) pyridin-3-yl)-1-(2,2,2-trifluoroethyl)-1H-indol-5-yl)-2,5-dihydro-1H-pyrrole-1-carboxylate (10.75 g, 17.1 mmol) and $Pd(OH)_2/C$ (3.2 g, 22.8 mmol) in MeOH (100 mL) was heated to 40° C. and under an atmosphere of $H_2$ for 2 h. The mixture was filtered and the filter cake was washed with DCM (10×10 mL). The filtrate was concentrated under reduced pressure and the residue was purified by preparative-HPLC to give tert-butyl 3-(3-(3-acetoxy-2,2-dimethylpropyl)-2-(2-((S)-1-methoxyethyl)pyridin-3-yl)-1-(2,2,2-trifluoroethyl)-1H-indol-5-yl) pyrrolidine-1-carboxylate (6.4 g, 56% yield) as an oil. LCMS (ESI): m/z $[M+H]^+$ calc'd for $C_{34}H_{44}F_3N_3O_5$ 631.3; found 632.4.

Step 3. To a mixture of tert-butyl 3-(3-(3-acetoxy-2,2-dimethylpropyl)-2-(2-((S)-1-methoxyethyl)pyridin-3-yl)-1-(2,2,2-trifluoroethyl)-1H-indol-5-yl)pyrrolidine-1-carboxylate (7.0 g, 11.1 mmol) in dioxane (70 mL) was added HCl in 1,4-dioxane (17.5 mL). The mixture was stirred at rt for 1 h, then concentrated under reduced pressure to give 3-(2-(2-((S)-1-methoxyethyl)pyridin-3-yl)-5-(pyrrolidin-3-yl)-1-(2,2,2-trifluoroethyl)-1H-indol-3-yl)-2,2-dimethylpropyl acetate (7.6 g) as an oil. LCMS (ESI): m/z $[M+H]^+$ calc'd for $C_{29}H_{36}F_3N_3O_3$ 531.3; found 532.5.

Step 4. To a mixture of 3-(2-(2-((S)-1-methoxyethyl) pyridin-3-yl)-5-(pyrrolidin-3-yl)-1-(2,2,2-trifluoroethyl)-1H-indol-3-yl)-2,2-dimethylpropyl acetate (7.7 g, 14.5 mmol) in ACN (80 mL) was added tert-butyl (S)-(2-oxooxetan-3-yl)carbamate (4.07 g, 21.7 mmol) and $CS_2CO_3$ (11.80 g, 36.2 mmol). The mixture was heated to 40° C. and stirred for 2 h, then acidified to pH ~7 with conc. HCl and the mixture was extracted with EtOAc (500 mL). The combined organic layers were washed with brine (3×100 mL), dried over anhydrous $Na_2SO_4$ and filtered. The filtrate was concentrated under reduced pressure and the residue was purified by preparative-HPLC to give (2S)-3-(3-(3-(3-acetoxy-2,2-dimethylpropyl)-2-(2-((S)-1-methoxyethyl) pyridin-3-yl)-1-(2,2,2-trifluoroethyl)-1H-indol-5-yl)pyrrolidin-1-yl)-2-((tert-butoxycarbonyl)amino)propanoic acid (2.3 g, 19% yield) as an oil. LCMS (ESI): m/z $[M+H]^+$ calc'd for $C_{37}H_{49}F_3N_4O_7$ 718.4; found 719.5.

Step 5. To a mixture of methyl (S)-hexahydropyridazine-3-carboxylate (0.69 g, 4.8 mmol), DIPEA (16.54 g, 128 mmol) and (2S)-3-(3-(3-(3-acetoxy-2,2-dimethylpropyl)-2-(2-((S)-1-methoxyethyl)pyridin-3-yl)-1-(2,2,2-trifluoroethyl)-1H-indol-5-yl)pyrrolidin-1-yl)-2-((tert-butoxycarbonyl)amino)propanoic acid (2.3 g, 3.2 mmol) in DCM (60 mL) at 0° C. under an atmosphere of $N_2$ was added HATU (1.46 g, 3.84 mmol) in portions. The resulting mixture was warmed to rt and stirred for 1 h, the $H_2O$ was added and the mixture extracted with EtOAc (200 mL). The combined organic layers were washed with brine (3×400 mL), dried over anhydrous $Na_2SO_4$ and filtered. The filtrate was concentrated under reduced pressure and the residue was purified by preparative-HPLC to give methyl (3S)-1-((2S)-3-(3-(3-(3-acetoxy-2,2-dimethylpropyl)-2-(2-((S)-1-methoxyethyl)pyridin-3-yl)-1-(2,2,2-trifluoroethyl)-1H-indol-5-yl)pyrrolidin-1-yl)-2-((tert-butoxycarbonyl)amino) propanoyl)hexahydropyridazine-3-carboxylate (2 g, 70% yield) as an oil. LCMS (ESI): m/z $[M+H]^+$ calc'd for $C_{43}H_{59}F_3N_6O$ 844.4; found 845.6.

Step 6. A mixture of methyl (3S)-1-((2S)-3-(3-(3-(3-acetoxy-2,2-dimethylpropyl)-2-(2-((S)-1-methoxyethyl) pyridin-3-yl)-1-(2,2,2-trifluoroethyl)-1H-indol-5-yl)pyrrolidin-1-yl)-2-((tert-butoxycarbonyl)amino)propanoyl) hexahydropyridazine-3-carboxylate (2.0 g, 2.4 mmol) and LiOH (0.28 g, 11.8 mmol) in $H_2O$ (10 mL) and MeOH (20 mL) was stirred at rt. The mixture was acidified to pH ~6 with aqueous HCl and the mixture extracted with DCM (4×mL). The combined organic layers were washed with brine (6×4 mL), dried over anhydrous $Na_2SO_4$, filtered and the filtrate was concentrated under reduced pressure to give (3S)-1-((2S)-2-((tert-butoxycarbonyl)amino)-3-(3-(3-(3-hydroxy-2,2-dimethylpropyl)-2-(2-((S)-1-methoxyethyl)pyridin-3-yl)-1-(2,2,2-trifluoroethyl)-1H-indol-5-yl)pyrrolidin-1-yl)propanoyl)hexahydropyridazine-3-carboxylic acid (1.9 g) as an oil. LCMS (ESI): m/z $[M+H]^+$ calc'd for $C_{40}H_{55}F_3N_6O_7$ 788.4; found 789.4.

Step 7. To a mixture of (3S)-1-((2S)-2-((tert-butoxycarbonyl)amino)-3-(3-(3-(3-hydroxy-2,2-dimethylpropyl)-2-(2-((S)-1-methoxyethyl)pyridin-3-yl)-1-(2,2,2-trifluoroethyl)-1H-indol-5-yl)pyrrolidin-1-yl)propanoyl) hexahydropyridazine-3-carboxylic acid (1.87 g, 2.4 mmol) in DCM (340 mL) under an atmosphere of $N_2$ was added DIPEA (9.19 g, 71.1 mmol), HOBt (1.60 g, 11.9 mmol) and EDCl (9.09 g, 47.4 mmol). The mixture was stirred at rt overnight, then $H_2O$ was added and the mixture extracted with DCM (2×mL). The combined organic layers were washed with brine (3×3 mL) dried over anhydrous $Na_2SO_4$ and filtered. The filtrate was concentrated under reduced pressure and the residue was purified by silica gel column chromatography to give tert-butyl (($6^3$S,4S)-12-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-pyrrolidinacycloundecaphane-4-yl)carbamate (410 mg, 21% yield) as a solid.

Step 8. Diastereomers were separated by use of silica gel column chromatography to give each respective isomer.

Data for Isomer 1 ($R_f$=0.4 in 1:1 petroleum ether/EtOAc): LCMS (ESI): m/z $[M+H]^+$ calc'd for $C_{40}H_{53}F_3N_6O_6$ 770.4; found 771.4.

Data for Isomer 2 ($R_f$=0.7 in 1:1 petroleum ether/EtOAc): LCMS (ESI): m/z $[M+H]^+$ calc'd for $C_{40}H_{53}F_3N_6O_6$ 770.4; found 771.4.

Step 9. To a mixture of tert-butyl (($6^3$S,4S)-12-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1'H-8-oxa-1(5,3)-indola-6(1,3)-pyridazina-2(3,1)-pyrrolidinacycloundecaphane-4-yl)carbamate (410 mg, 0.53 mmol) in DCM (5 mL) at 0° C. was added TFA (1.7 mL, 22.9 mmol). The mixture was warmed to rt and stirred for 1 h, then basified to pH ~6 with saturated $NaHCO_3$ and the mixture was extracted with EtOAc (6×3 mL). The combined organic layers were washed with brine (5×3 mL), dried over anhydrous $Na_2SO_4$, filtered and the filtrate was concentrated under reduced pressure to give ($2^3$S,$6^3$S,4S)-4-amino-12-(2-((S)-1-methoxyethyl) pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(3,1)-pyrrolidinacycloundecaphane-5,7-dione (390 mg) as a solid. LCMS (ESI): m/z $[M+H]^+$ calc'd for $C_{35}H_{45}F_3N_6O_4$ 670.4; found 671.7.

Step 10. To a mixture of ($2^3$S,$6^3$S,4S)-4-amino-12-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-1 $^1$H-8-oxa-1(5,3)-indola-6(1,3)-pyridazina-2(3,1)-pyrrolidinacycloundecaphane-5,7-dione (270 mg, 0.4 mmol) and DIPEA (2.1 g, 16.1 mmol) in DCM (3 mL) at 0° C. under an atmosphere of $N_2$ was added (2S)-3-methyl-2-[methyl(3-(prop-2-enoyl)-1-oxa-3,8-diazaspiro[4.5]decane-8-carbonyl)amino]butanoic acid (142 mg, 0.4 mmol) and CIP (227 mg, 0.81 mmol). The mixture was stirred at rt for 30 min, then $H_2O$ was added and the mixture extracted with EtOAc (4×30 mL). The combined organic layers were washed with brine (5×30 mL), dried over anhydrous $Na_2SO_4$ and filtered. The filtrate was concentrated under reduced pressure and the residue was purified by preparative-HPLC to give 3-acryloyl-N-((2S)-1-((($2^3$S,$6^3$S,4S)-$1^2$-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-1 $^1$H-8-oxa-1(5,3)-indola-6(1,3)-pyridazina-2(3,1)-pyrrolidinacycloundecaphane-4-yl)amino)-3-methyl-1-oxobutan-2-yl)-N-methyl-1-oxa-3,8-diazaspiro[4.5]decane-8-carboxamide (45 mg, 10% yield) as a solid. LCMS (ESI): m/z $[M+H]^+$ calc'd for $C_{52}H_{70}F_3N_9O_8$ 1005.5; found 1006.9; $^1$H NMR (400 MHz, DMSO-$d_6$) δ 8.76 (dd, J=4.7, 1.8 Hz, 1H), 7.81 (d, J=8.8 Hz, 1H), 7.74 (d, J=7.7 Hz, 1H), 7.60 (d, J=8.4 Hz, 1H), 7.58-7.50 (m, 2H), 7.13 (d, J=8.2 Hz, 1H), 6.54 (dd, J=16.8, 10.3 Hz, 1H), 6.24-6.14 (m, 1H), 5.74 (td, J=10.2, 2.3 Hz, 1H), 5.58 (q, J=6.9 Hz, 1H), 5.46 (dt, J=17.2, 8.7 Hz, 1H), 5.13 (d, J=13.2 Hz, 2H), 5.01 (s, 1H), 4.81 (dt, J=18.2, 9.0 Hz, 1H), 4.31 (d, J=12.4 Hz, 1H), 4.20 (q, J=6.0 Hz, 1H), 3.87 (s, 1H), 3.80 (d, J=11.0 Hz, 1H), 3.67 (s, 2H), 3.60-3.55 (m, 1H), 3.45 (s, 1H), 3.12 (dt, J=17.2, 9.6 Hz, 3H), 2.76 (d, J=13.0 Hz, 5H), 2.61 (q, J=7.8, 6.9 Hz, 2H), 2.42 (d, J=14.4 Hz, 1H), 2.29-1.87 (m, 4H), 1.80 (t, J=12.5 Hz, 3H), 1.65 (dt, J=22.2, 8.9 Hz, 3H), 1.58-1.48 (m, 2H), 1.38 (d, J=6.0 Hz, 3H), 0.98-0.83 (m, 6H), 0.81 (d, J=6.6 Hz, 3H), 0.26 (s, 3H).

Example 9. Synthesis of 4-acryloyl-N-((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) amino)-3-methyl-1-oxobutan-2-yl)-N-methyl-1-oxa-4,9-diazaspiro[5.5]undecane-9-carboxamide

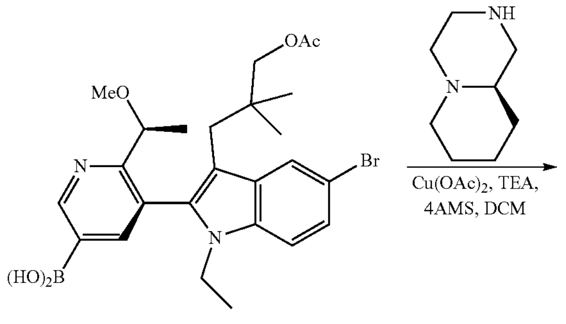

-continued
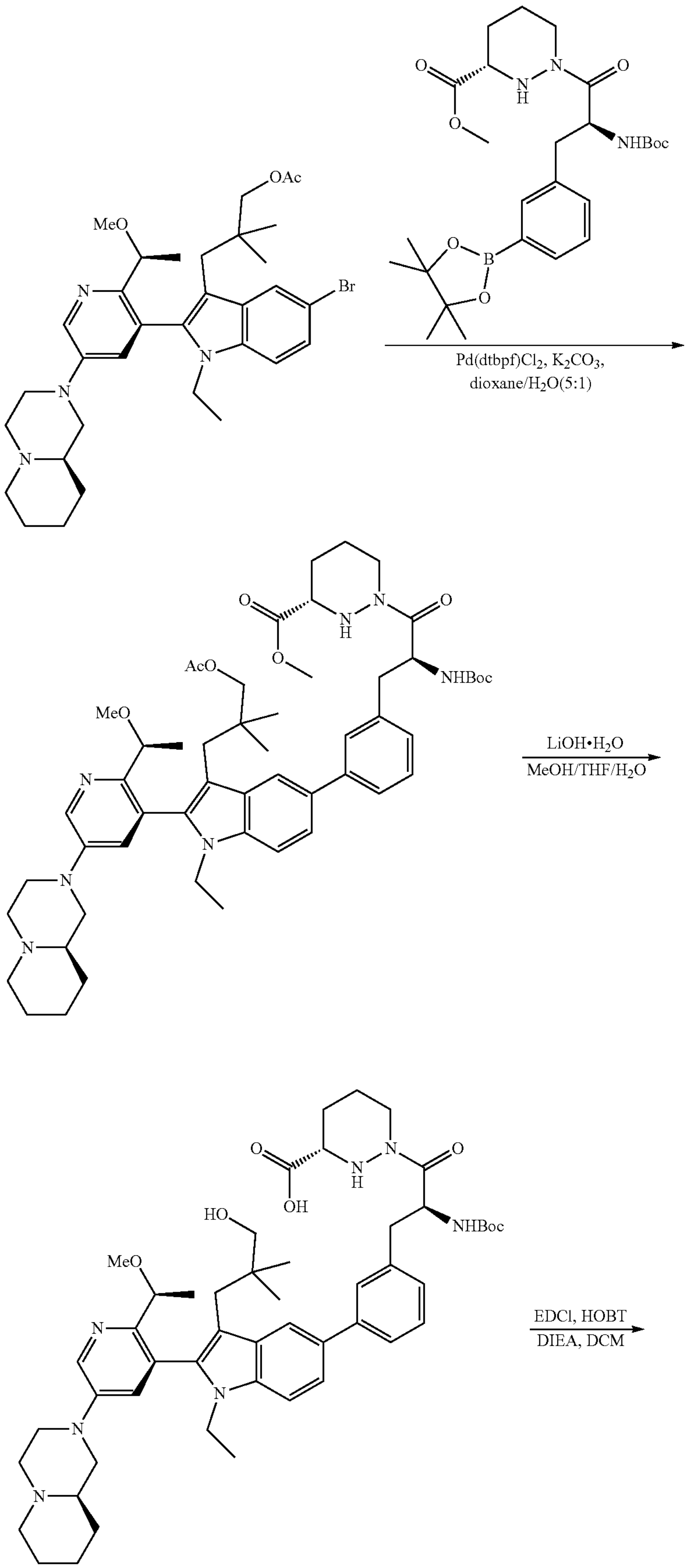

-continued
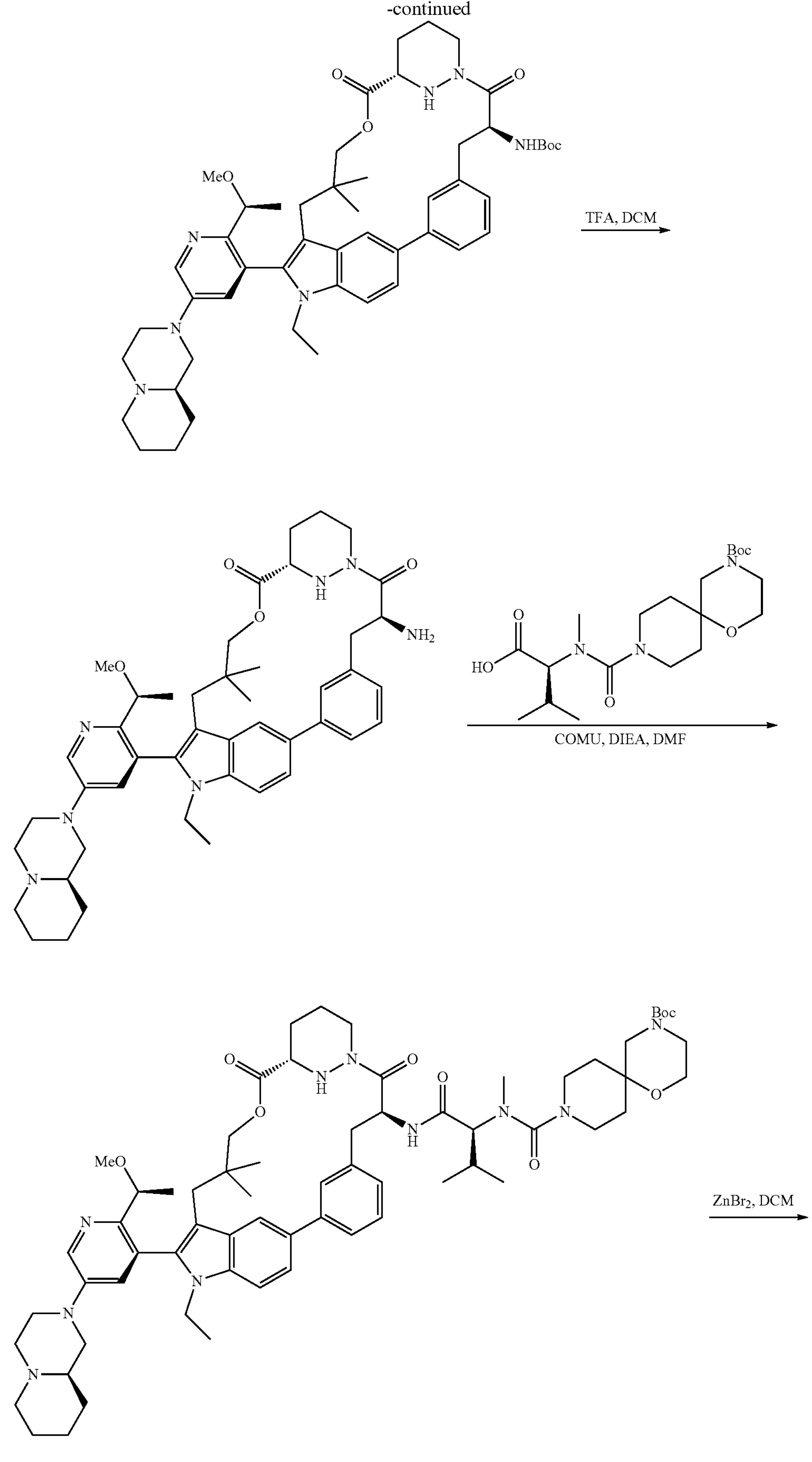

-continued

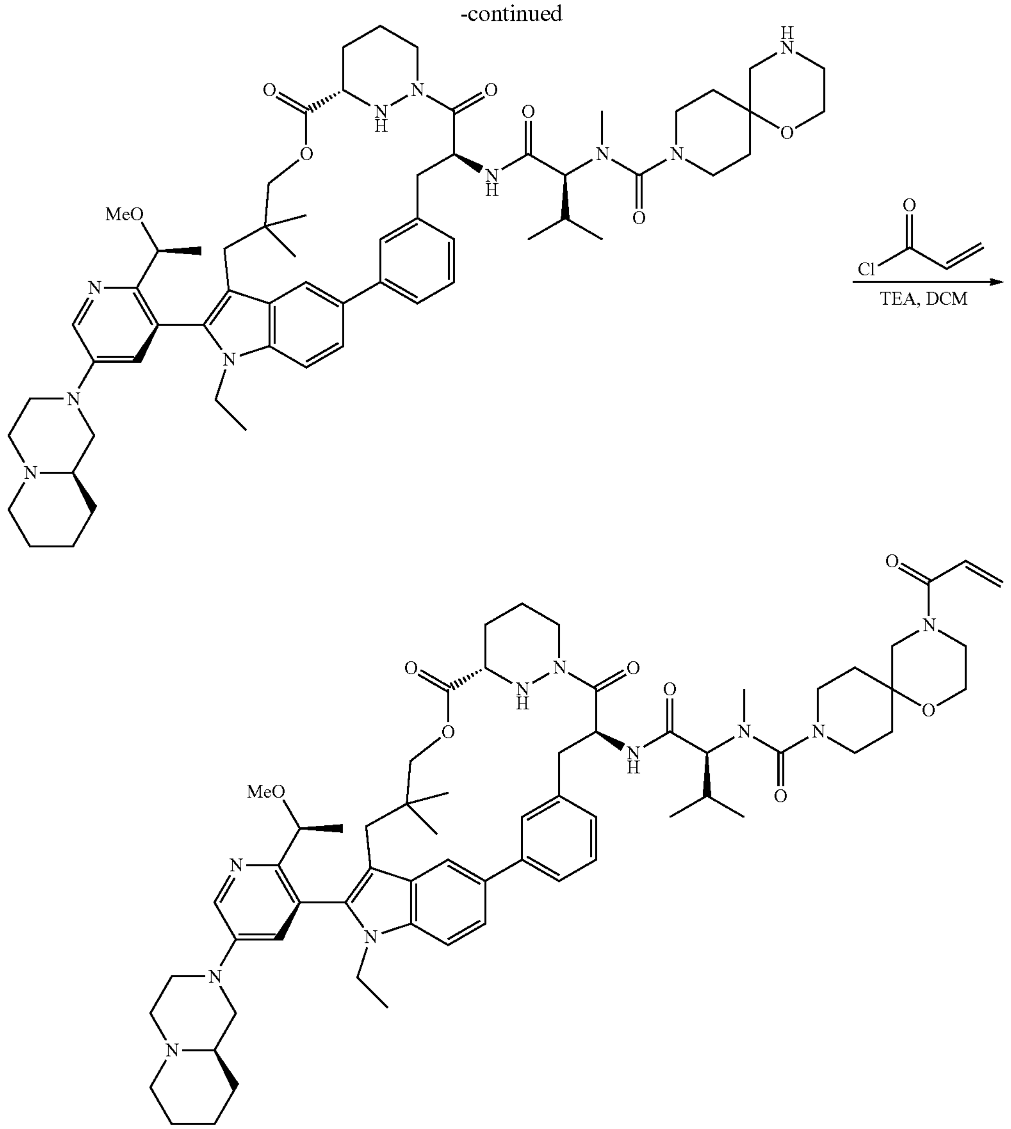

Step 1. To a mixture of (S)-(5-(3-(3-acetoxy-2,2-dimethylpropyl)-5-bromo-1-ethyl-1H-indol-2-yl)-6-(1-methoxyethyl)pyridin-3-yl)boronic acid (7.7 g, 14.5 mmol) and (R)-octahydro-2H-pyrido[1,2-a]pyrazine (3.9 g, 27.8 mmol) in DCM (230 mL) under an atmosphere of 02 was added TEA (14.7 g, 145.3 mmol) and 4 Å molecular sieves (26 g). The mixture was stirred at rt for 30 min, then $Cu(OAc)_2$ (2.4 g, 13.2 mmol) was added, the mixture heated to 40° C. and stirred overnight. Ice/$H_2O$ was added and the mixture was extracted with EtOAc (5×200 mL). The combined organic layers were washed with brine, dried over anhydrous $Na_2SO_4$ and filtered. The filtrate was concentrated under reduced pressure and the residue was purified to give 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (3.5 g, 27% yield) as a solid. LCMS (ESI): m/z $[M+H]^+$ calc'd for $C_{33}H_{45}BrN_4O_3$ 624.3; found 625.5.

Step 2. To a mixture of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (1.9 g, 3.0 mmol) and methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (1.89 g, 3.6 mmol) in dioxane (19 mL) and $H_2O$ (3.8 mL) was added $K_2CO_3$ (1.05 g, 7.6 mmol) and $Pd(dtbpf)Cl_2$ (395 mg, 0.61 mmol). The mixture was heated to 70° C. and stirred for 3 h, then diluted with EtOAc (40 mL), ice/$H_2O$ added, and the mixture was extracted with EtOAc (3×10 mL). The combined organic layers were washed with brine, dried over anhydrous $Na_2SO_4$ and filtered. The filtrate was concentrated under reduced pressure and the residue was purified to give methyl (S)-1-((S)-3-(3-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)phenyl)-2-((tert-butoxycarbonyl)amino)propanoyl)hexahydropyridazine-3-carboxylate (1.1 g, 29% yield) as a solid. LCMS (ESI): m/z $[M+H]^+$ calc'd for $C_{53}H_{73}N_7O_8$ 935.6; found 936.8.

Step 3. To a mixture of methyl (S)-1-((S)-3-(3-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)phenyl)-2-((tert-butoxycarbonyl)amino)propanoyl)hexahydropyridazine-3-carboxylate (900 mg, 0.92 mmol) in THE (4.5 mL), MeOH (4.5 mL) and $H_2O$ (4.5 mL) at 0° C. was added LiOH·$H_2O$ (89 mg, 3.7 mmol). The mixture was warmed to rt and stirred for 3 h, then ice/$H_2O$ (10 mL) added, the mixture acidified to pH ~5 with citric acid and the mixture was extracted with EtOAc (3×20 mL). The combined organic layers were washed with brine, dried over anhydrous $Na_2SO_4$, filtered and the filtrate was concentrated under reduced pressure to give (S)-1-((S)-2-((tert-butoxycarbonyl)amino)-3-(3-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)phenyl)propanoyl)hexahydropyridazine-3-carboxylic acid (900 mg) as a solid. LCMS (ESI): m/z $[M+H]^+$ calc'd for $C_{50}H_{69}N_7O_7$ 879.5; found 880.6.

Step 4. To a mixture of (S)-1-((S)-2-((tert-butoxycarbonyl)amino)-3-(3-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)phenyl)propanoyl)hexahydropyridazine-3-carboxylic acid (670 mg, 0.76 mmol) in DCM (67 mL) at 0° C. was added DIPEA (3.94 g, 30.4 mmol), EDCl (4.4 g, 22.8 mmol) and HOBT (514 mg, 3.8 mmol). The mixture was warmed to rt and stirred overnight, then ice/$H_2O$ (100 mL) was added and the mixture extracted with EtOAc (3×100 mL). The combined organic layers were washed with saturated $NH_4Cl$ (3×100 mL), dried over anhydrous $Na_2SO_4$ and filtered. The filtrate was concentrated under reduced pressure and the residue was purified to give tert-butyl (($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (450 mg, 62% yield) as a solid. LCMS (ESI): m/z $[M+H]^+$ calc'd for $C_{50}H_{67}N_7O_6$ 861.5; found 862.7.

Step 5. To a mixture of tert-butyl (($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (230 mg, 0.27 mmol) in DCM (2 mL) at 0° C. was added TFA (1 mL) dropwise. The mixture was stirred at 0° C. for 1 h, then basified to pH ~8 with saturated $NaHCO_3$ at 0° C. and the mixture extracted with EtOAc (3×30 mL). The combined organic layers were washed with brine (3×30 mL), dried over anhydrous $Na_2SO_4$, filtered and the filtrate was concentrated under reduced pressure to give ($6^3$S,4S)-4-amino-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-$6^1$,$6^2$,$6^3$,$6^4$,$6^5$,66-hexahydro-$1^1$H-8-oxa-1(5,3)-indola-6(1,3)-pyridazina-2(1,3)-benzenacycloundecaphane-5,7-dione (300 mg) as a solid, that was used in the next step without further purification. LCMS (ESI): m/z $[M+H]^+$ calc'd for $C_{45}H_{59}N_7O_4$ 761.5; found 762.8.

Step 6. To a mixture of ($6^3$S,4S)-4-amino-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione (300 mg, 0.39 mmol) and (2S)-2-[4-(tert-butoxycarbonyl)-1-oxa-4,9-diazaspiro[5.5]undecane-9-carbonyl(methyl)amino]-3-methylbutanoic acid (211 mg, 0.51 mmol) in DMF (3 mL) at 0° C. under an atmosphere of Ar was added DIPEA (1.53 g, 11.8 mmol) and COMU (168 mg, 0.39 mmol) in DMF (0.1 mL) dropwise. The mixture was stirred at 0° C. for 1 h, then ice/$H_2O$ (3 mL) was added and the mixture extracted with EtOAc (3×30 mL). The combined organic layers were washed with brine (3×30 mL), dried over anhydrous $Na_2SO_4$ and filtered. The filtrate was concentrated under reduced pressure and the residue was purified to give tert-butyl 9-(((2S)-1-((($6^3$S,4S)_$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^{\prime 1}$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)-1-oxa-4,9-diazaspiro[5.5]undecane-4-carboxylate (200 mg, 59% yield) as a solid. LCMS (ESI): m/z $[M+H]^+$ calc'd for $C_{65}H_{92}N_{10}O_9$ 1156.7; found 1158.2.

Step 7. A mixture of tert-butyl 9-(((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)-1-oxa-4,9-diazaspiro[5.5]undecane-4-carboxylate (200 mg, 0.17 mmol) and $ZnBr_2$ (195 mg, 0.87 mmol) in DCM (4 mL) was heated to 35° C. and stirred overnight. Ice/$H_2O$ (5 mL) was added and the mixture was basified to pH ~8 with saturated $NaHCO_3$ at 0° C., then extracted with EtOAc (3×30 mL). The combined organic layers were washed with brine (3×30 mL), dried over anhydrous $Na_2SO_4$, filtered and the filtrate was concentrated under reduced pressure to give N-((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methyl-1-oxa-4,9-diazaspiro[5.5]undecane-9-carboxamide (200 mg) as a solid. LCMS (ESI): m/z $[M+H]^+$ calc'd for $C_{60}H_{84}N_{10}O_7$ 1056.7; found 1058.1.

Step 8. To a mixture of N-((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methyl-1-oxa-4,9-diazaspiro[5.5]undecane-9-carboxamide (200 mg, 0.19 mmol) and TEA (57 mg, 0.57 mmol) in DCM (2 mL) at 0° C. under an atmosphere of Ar was added acryloyl chloride (12 mg, 0.13 mmol) dropwise. The mixture was stirred at 0° C. for additional 1 h, then concentrated under reduced pressure and the crude residue was purified by preparative-HPLC to give 4-acryloyl-N-((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1 (5,3)-indola-6(1,3)-pyridazina-2(1,3)-benzenacycloundecaphane-4-yl)amino)-3-methyl-1-oxobutan-2-yl)-N-methyl-1-oxa-4,9-diazaspiro[5.5]undecane-9-carboxamide (40 mg, 19% yield) as a solid. LCMS (ESI): m/z $[M+H]^+$ calc'd for $C_{63}H_{86}N_{10}O_8$ 1110.7; found 1112.1; $^1$H NMR (400 MHz, DMSO-$d_6$) δ 8.46 (d, J=2.8 Hz, 1H), 8.17-8.05 (m, 1H), 7.98 (s, 1H), 7.86 (s, 1H), 7.74-7.54 (m, 3H), 7.27-7.19 (m, 2H), 7.01-6.81 (m, 2H), 6.28-6.11 (m, 1H), 5.73 (d, J=10.3 Hz, 1H), 5.43 (d, J=9.4 Hz, 2H), 4.40-4.17 (m, 2H), 4.10 (dq, J=21.9, 7.1, 6.5 Hz, 2H), 3.95 (t, J=12.0 Hz, 1H), 3.77 (dt, J=25.3, 13.0 Hz, 3H), 3.69-3.64 (m, 3H), 3.64-3.55 (m, 3H), 3.54-3.48 (m, 2H), 3.15 (d, J=11.7 Hz, 2H), 3.07 (s, 3H), 2.97-2.89 (m, 1H), 2.79 (m, 4H), 2.66 (s, 1H), 2.56 (s, 3H), 2.42 (d, J=11.1 Hz, 1H), 2.23 (td, J=11.6, 3.2 Hz, 1H), 2.07-1.89 (m, 4H), 1.82 (d, J=12.2 Hz, 1H), 1.77-1.63 (m, 4H), 1.59 (d, J=12.6 Hz, 3H), 1.47 (d, J=13.1 Hz, 2H), 1.36 (d, J=6.1 Hz, 3H), 1.19 (m, 3H), 1.00 (t, J=7.1 Hz, 3H), 0.90-0.70 (m, 9H), 0.57 (s, 3H).

Example 10. Synthesis of (3S)-1-acryloyl-N-((2S)-1-((($6^3$S)-$1^1$-ethyl-$1^2$-(2-((S)-1-methoxyethyl)pyridin-3-yl)-10,10-dimethyl-21,21-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)-N-methylpyrrolidine-3-carboxamide
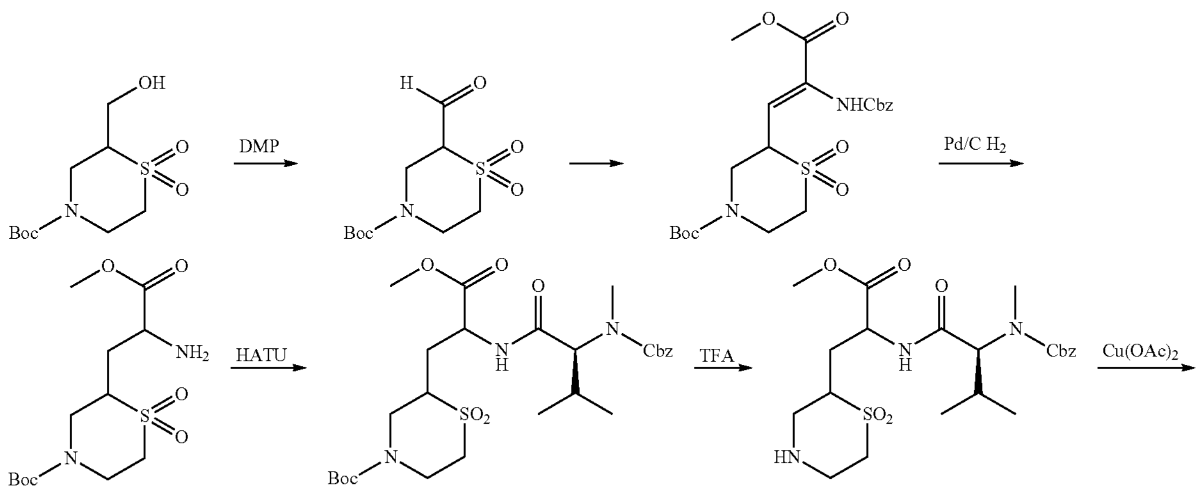
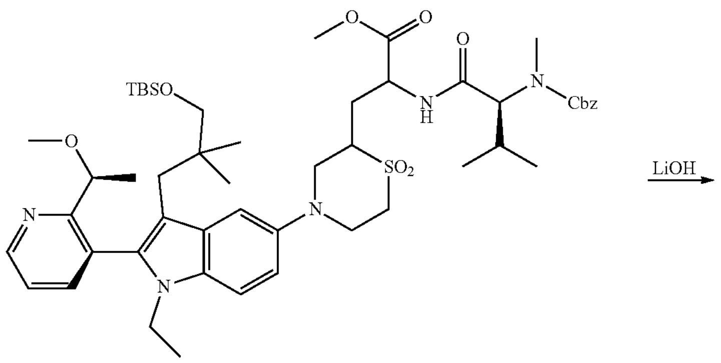
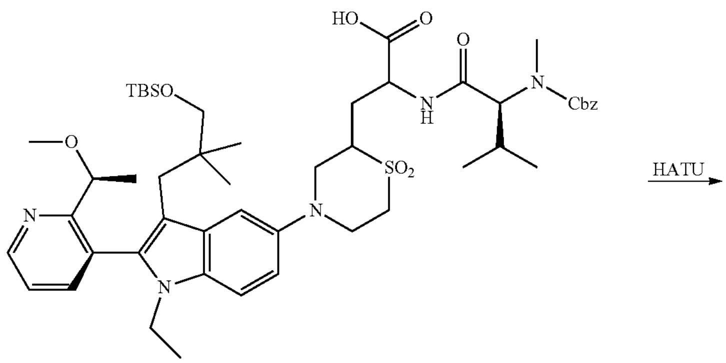

-continued
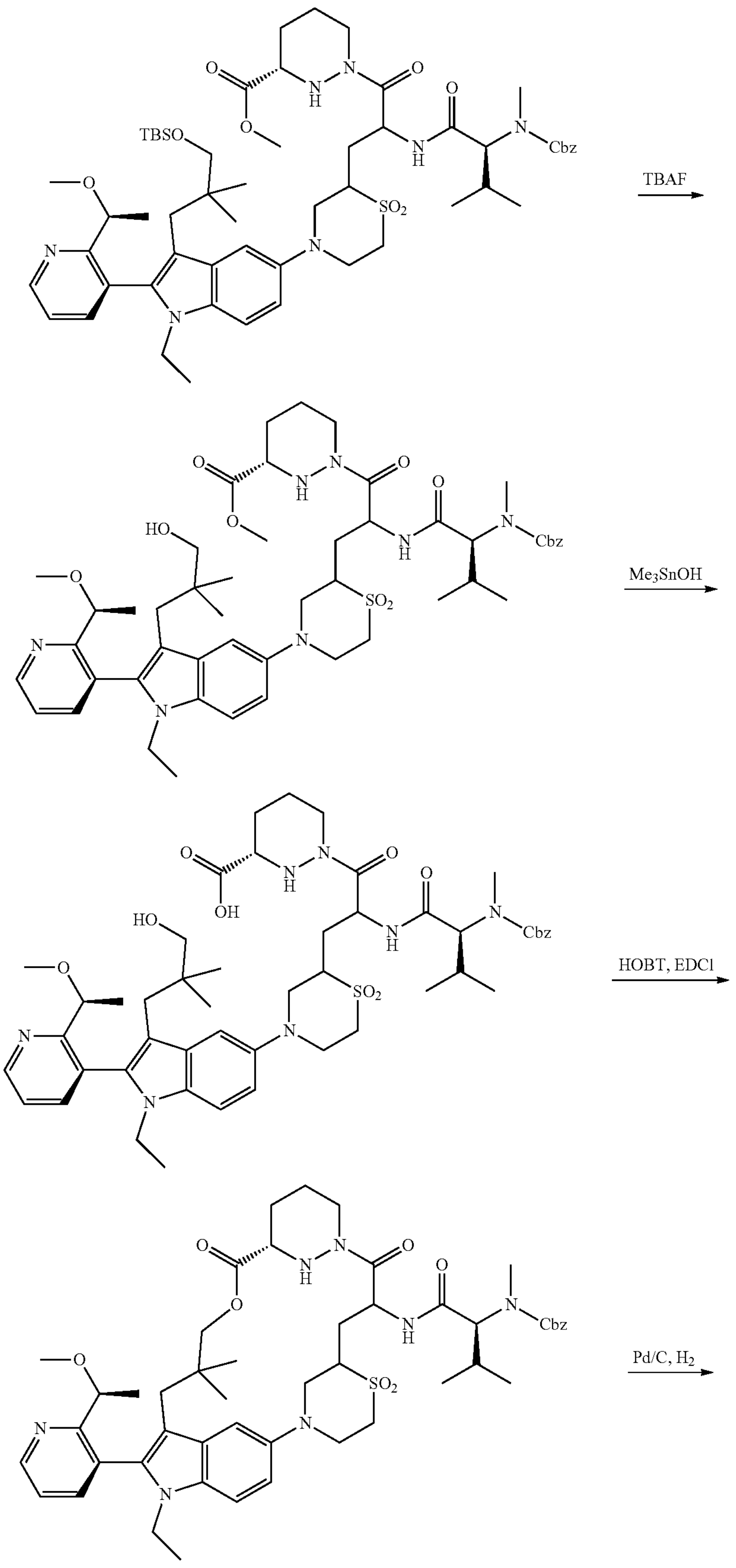

-continued
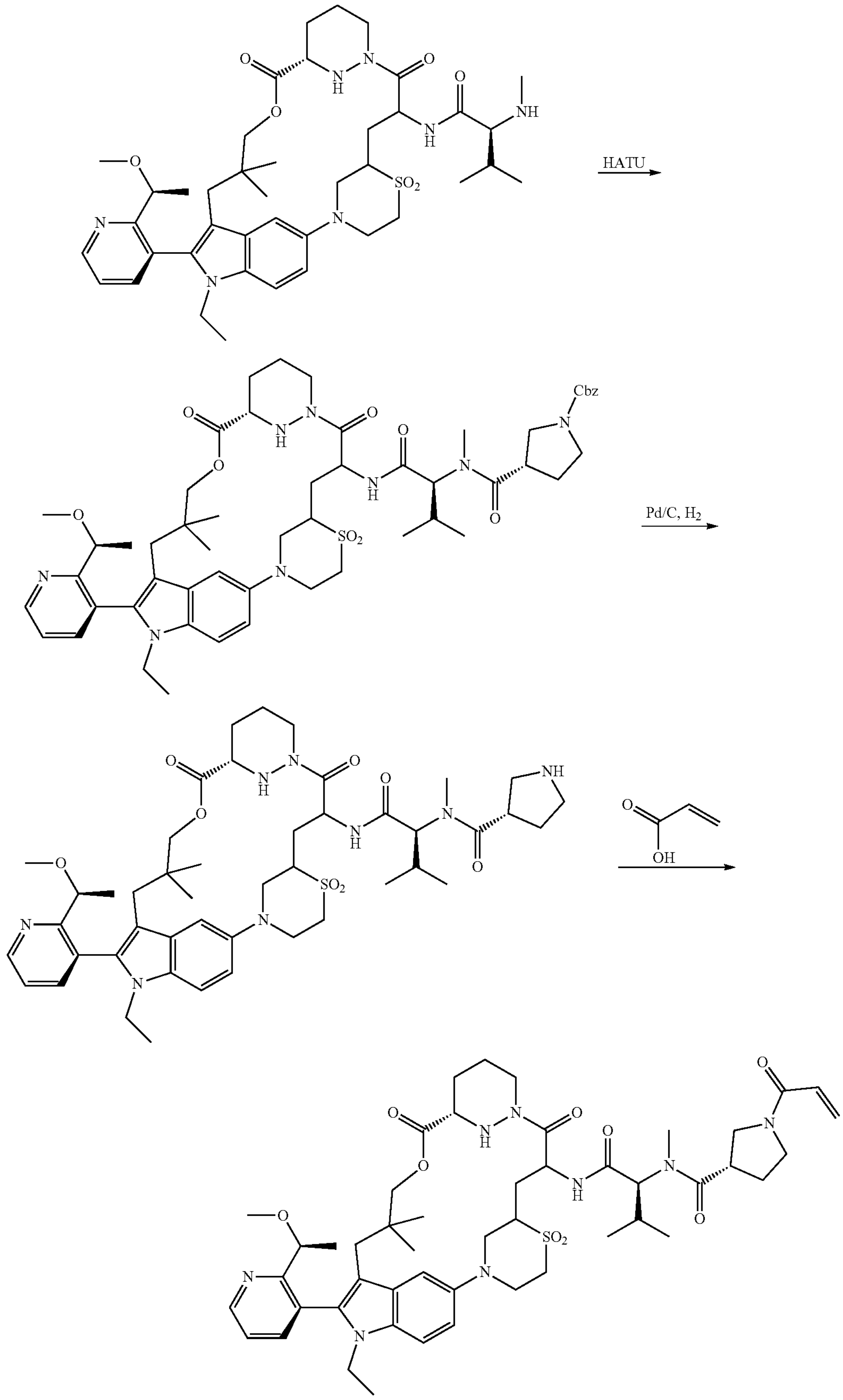

Step 1. To a mixture of tert-butyl 2-(hydroxymethyl) thiomorpholine-4-carboxylate 1,1-dioxide (17.8 g, 60 mmol) in DCM (200 mL) was added Dess-Martin periodinane (56.6 g, 130 mmol). The mixture was stirred at rt for 2 h, then filtered and the filtrate was concentrated under reduced pressure to give tert-butyl 2-formylthiomorpholine-4-carboxylate 1,1-dioxide (30 g) as a syrup, which was used in the next step without further purification. LCMS (ESI): m/z $[M-^tBu+H]^+$ calc'd for $C_6H_9NO_5S$ 207.2; found 208.0; $^1H$ NMR (400 MHz, $CDCl_3$) δ 9.88 (s, 1H), 4.17 (d, J=39.4, 33.7 Hz, 4H), 3.15 (d, J=34.2 Hz, 3H), 1.48 (s, 10H).

Step 2. To a mixture of tert-butyl 2-formylthiomorpholine-4-carboxylate 1,1-dioxide (58 g, 60 mmol) in ACN (400 mL) at 0° C. was added 1,1,3,3-tetramethylguanidine (30.5 g, 200 mmol) and methyl 2-{[(benzyloxy)carbonyl]amino}-2-(dimethoxyphosphoryl)acetate (43.8 g, 130 mmol). The mixture was warmed to rt and stirred for 2 h then concentrated under reduced pressure. The residue was diluted with EtOAc (200 mL) and washed with $H_2O$ (150 mL×3), then dried and filtered. The filtrate was concentrated under reduced pressure and the residue was purified by silica gel column chromatography to give tert-butyl 2-(2-(((benzyloxy)carbonyl)amino)-3-methoxy-3-oxoprop-1-en-1-yl) thiomorpholine-4-carboxylate 1,1-dioxide (8 g, 25% yield over 2 steps) as a syrup. LCMS (ESI): m/z $[M+Na]^+$ calc'd for $C_{21}H_{28}N_2NaO_8S$ 491.2; found 491.2.

Step 3. A mixture of tert-butyl 2-(2-(((benzyloxy)carbonyl)amino)-3-methoxy-3-oxoprop-1-en-1-yl)thiomorpholine-4-carboxylate (8 g, 17.0 mmol), 10% Pd/C (4 g) and $NH_4Cl$ (9.1 g, 170 mmol) in MeOH (200 mL) was stirred at rt under an atmosphere of $H_2$ for 48 h. The mixture was filtered and the filtrate was concentrated under reduced pressure to give tert-butyl 2-(2-amino-3-methoxy-3-oxopropyl)thiomorpholine-4-carboxylate 1,1-dioxide (6.3 g) as an oil, which was used in next step without further purification. LCMS (ESI): m/z $[M+H]^+$ calc'd for $C_{13}H_{24}N_2O_6S$ 336.1; found 337.1.

Step 4. To a mixture of tert-butyl 2-(2-amino-3-methoxy-3-oxopropyl)thiomorpholine-4-carboxylate 1,1-dioxide (6.3 g, 10 mmol) and (2S)-2-({3-[(formyloxy)methyl]phenyl}(methyl)amino)-3-methylbutanoic acid (5 g, 10 mmol) in dry DMF (20 mL) at 0° C. was added DIPEA (49.2 g, 30 mmol) and HATU (7.2 g, 10 mmol). The mixture was stirred at 0° C. for 1 h, then diluted with EtOAc (100 mL) and washed with $H_2O$ (50 mL×3). The combined organic layers were concentrated under reduced pressure and the residue was purified by silica gel column chromatography to give tert-butyl 2-(2-((S)-2-(((benzyloxy)carbonyl)(methyl)amino)-3-methylbutanamido)-3-methoxy-3-oxopropyl)thiomorpholine-4-carboxylate 1,1-dioxide (5 g, 57% yield over 2 steps) as an oil. LCMS (ESI): m/z $[M+H]^+$ calc'd for $C_{27}H_{41}N_3O_9S$ 583.3; found 584.3.

Step 5. To a mixture of tert-butyl 2-(2-((S)-2-(((benzyloxy)carbonyl)(methyl)amino)-3-methylbutanamido)-3-methoxy-3-oxopropyl)thiomorpholine-4-carboxylate 1,1-dioxide (12 g, 20 mmol) in DCM (80 mL) at 0° C. was added TFA (20 mL). The mixture was warmed to rt and stirred for 1.5 h, then concentrated under reduced pressure. The residue was diluted with EtOAc (50 mL) and adjusted to pH ~9 with saturated $Na_2CO_3$. The organic layer was concentrated under reduced pressure to give methyl 2-((S)-2-(((benzyloxy)carbonyl)(methyl)amino)-3-methylbutanamido)-3-(1,1-dioxidothiomorpholin-2-yl)propanoate (9.1 g, yield 94%) as a syrup, which was used in the next step without further purification. LCMS (ESI): m/z $[M+H]^+$ calc'd for $C_{22}H_{33}N_3O_7S$ 483.2; found 484.2.

Step 6. To a mixture of methyl 2-((S)-2-(((benzyloxy)carbonyl)(methyl)amino)-3-methylbutanamido)-3-(1,1-dioxidothiomorpholin-2-yl)propanoate (5.9 g, 12 mmol) in DCM (50 mL) at rt was added (3-{3-[(tert-butyldimethylsilyl)oxy]-2,2-dimethylpropyl}-1-ethyl-2-{2-[(1 S)-1-methoxyethyl]pyridin-3-yl}indol-5-yl)boranediol (6.4 g, 12 mmol), $Cu(OAc)_2$ (2.2 g, 12 mmol) and pyridine (2.8 g, 36 mmol). The mixture was stirred at rt for 48 h, then the mixture was filtered, the filtrate was diluted with EtOAc (30 mL) and washed with $H_2O$ (80 mL×3). The organic layer was concentrated under reduced pressure and the residue was purified by silica gel column chromatography to give methyl 2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoate (7.59 g, 66% yield) as an oil. LCMS (ESI): m/z $[M+H]^+$ calc'd for $C_{51}H_{75}N_5O_9SSi$ 961.5; found 962.3.

Step 7. To a mixture of methyl 2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoate (7.59 g, 7.9 mmol) in THE (40 mL) at 0° C. was added LiOH (0.38 g, 16 mmol) in $H_2O$ (8 mL). The mixture was stirred at 0° C. for 1.5 h, then the pH adjusted to pH ~7 with 3M HCl (5 mL), the mixture diluted with brine (15 mL) and extracted with EtOAc (50 mL×3). The combined organic layers were concentrated under reduced pressure to give 2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoic acid (7.4 g, 98% yield) as a syrup. LCMS (ESI): m/z $[M+H]^+$ calc'd for $C_{50}H_{73}N_5O_9SSi$ 947.5; found 948.4.

Step 8. To a mixture of 2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoic acid (7.4 g, 7.8 mmol) in DMF (50 mL) at 0° C. was added methyl (3S)-1,2-diazinane-3-carboxylate dihydrochloride (2.6 g, 12 mmol), DIPEA (20 g, 160 mmol) and HATU (4.6 g, 12 mmol). The mixture was stirred at 0° C. for 2 h, then diluted with EtOAc (300 mL) and washed with $H_2O$ (100 mL×2). The combined organic layers were concentrated under reduced pressure and the residue was purified by silica gel column chromatography to give (3S)-methyl 1-(2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoyl) hexahydropyridazine-3-carboxylate (8.08 g, 96% yield) as a syrup. LCMS (ESI): m/z $[M+H]^+$ calc'd for $C_{56}H_{83}N_7O_{10}SSi$ 1073.6; found 1074.5.

Step 9. To a mixture of 1 M TBAF in THE (38 mL, 38 mmol) and AcOH (2.3 g, 38 mmol) was added (3S)-methyl 1-(2-((S)-2-(((benzyloxy)carbonyl)(methyl)amino)-3-methylbutanamido)-3-(4-((R)-3-(3-((tert-butyldimethylsilyl)oxy)-2,2-dimethylpropyl)-1-ethyl-2-(2-((S)-1-methoxyethyl)pyridin-3-yl)-1H-indol-5-yl)-1,1-dioxidothiomorpholin-2-yl)propanoyl) hexahydropyridazine-3-carboxylate (8.08 g, 7.5 mmol). The mixture was heated to 55° C. and stirred for 16 h, then diluted with EtOAc (200 mL) and washed with $H_2O$ (150 mL×2). The combined organic layers were concentrated under reduce pressure to give (3S)-methyl 1-(2-((S)-2-(((benzyloxy)carbonyl)(methyl)amino)-3-methylbutanamido)-3-(4-((R)-1-ethyl-3-(3-hydroxy-2,2-dimethylpropyl)-2-(2-((S)-1-methoxyethyl)pyridin-3-yl)-1H-indol-5-yl)-1,1-dioxidothiomorpholin-2-yl)propanoyl) hexahydropyridazine-3-carboxylate (7.2 g, 99% yield) as a syrup. LCMS (ESI): m/z $[M+H]^+$ calc'd for $C_{50}H_{69}N_7O_{10}S$ 959.5; found 960.3.

Step 10. To a mixture of (3S)-methyl 1-(2-((S)-2-(((benzyloxy)carbonyl)(methyl)amino)-3-methylbutanamido)-3-(4-((R)-1-ethyl-3-(3-hydroxy-2,2-dimethylpropyl)-2-(2-((S)-1-methoxyethyl)pyridin-3-yl)-1H-indol-5-yl)-1,1-dioxidothiomorpholin-2-yl)propanoyl) hexahydropyridazine-3-carboxylate (7.2 g, 7.5 mol) in DCE (30 mL) was added $Me_3SnOH$ (6.7 g, 38 mmol). The mixture was heated to 65° C. and stirred for 16 h, then filtered and the filtrate was concentrated under reduced pressure to give (3S)-1-(2-((S)-2-(((benzyloxy)carbonyl)(methyl)amino)-3-methylbutanamido)-3-(4-((R)-1-ethyl-3-(3-hydroxy-2,2-dimethylpropyl)-2-(2-((S)-1-methoxyethyl)pyridin-3-yl)-1H-indol-5-yl)-1,1-dioxidothiomorpholin-2-yl)propanoyl)hexahydropyridazine-3-carboxylic acid (13 g) as an oil. LCMS (ESI): m/z $[M+H]^+$ calc'd for $C_{49}H_{67}N_7O_{10}S$ 945.5; found 946.4.

Step 11. To a mixture of (3S)-1-(2-((S)-2-(((benzyloxy)carbonyl)(methyl)amino)-3-methylbutanamido)-3-(4-((R)-1-ethyl-3-(3-hydroxy-2,2-dimethylpropyl)-2-(2-((S)-1-methoxyethyl)pyridin-3-yl)-1H-indol-5-yl)-1,1-dioxidothiomorpholin-2-yl)propanoyl) hexahydropyridazine-3-carboxylic acid (13 g, 7.4 mmol; ca. 55% purity) in DCM (400 mL) at 0° C. was added DIPEA (38 g, 300 mmol), HOBT (10 g, 74 mmol) and EDCl (42 g, 220 mmol). The mixture was warmed to rt and stirred for 48 h, then concentrated under reduced pressure, the residue diluted with EtOAc (200 mL) and washed with $H_2O$ (100 mL×2). The organic layer was concentrated under reduced pressure and the residue was purified by silica gel chromatography to give benzyl ((2S)-1-((($6^3$S)-$1^1$-ethyl-$1^2$-(2-((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)(methyl)carbamate [four isomers; a mixture of Isomer 1 and Isomer 2, 1.6 g; Isomer 3 (651 mg, 9.5% yield); Isomer 4 (332 mg, 4.8% yield)]. The mixture of Isomer 1 and Isomer 2 was purified further by preparative-HPLC to give Isomer 1 (470 mg, 6.8% yield) and Isomer 2 (797 mg, 12% yield).

Data for Isomer 1: LCMS (ESI): m/z $[M+H]^+$ calc'd for $C_{49}H_{65}N_7O_9S$ 927.5; found 928.4; $^1H$ NMR (400 MHz, $CD_3OD$) δ 8.74 (dd, J=4.8, 1.6 Hz, 1H), 8.36-8.13 (m, 1H), 7.91 (dd, J=7.8, 1.7 Hz, 1H), 7.52 (dd, J=7.8, 4.8 Hz, 1H), 7.45-7.25 (m, 6H), 7.21-7.07 (m, J=8.8 Hz, 1H), 5.59-5.40 (m, 2H), 5.28-5.05 (m, 2H), 4.45 (d, 1H), 4.17 (d, J=11.0 Hz, 1H), 4.13-3.97 (m, 2H), 3.97-3.62 (m, 6H), 3.50-3.34 (m, 2H), 3.27-3.04 (m, 4H), 3.01-2.83 (m, 4H), 2.78 (s, 2H), 2.64-2.32 (m, 2H), 2.24-1.90 (m, 5H), 1.84-1.65 (m, 2H), 1.46 (dd, J=16.6, 6.6 Hz, 3H), 1.36-1.17 (m, 4H), 1.02 (s, 2H), 0.94-0.70 (m, 6H), 0.58 (s, 3H).

Data for Isomer 2: LCMS (ESI): m/z $[M+H]^+$ calc'd for $C_{49}H_{65}N_7O_9S$ 927.5; found 928.4; $^1H$ NMR (400 MHz, $CD_3OD$) δ 8.71 (dd, J=4.8, 1.6 Hz, 1H), 8.18-8.01 (m, 1H), 7.83 (dd, J=7.7, 1.6 Hz, 1H), 7.52 (dd, J=7.7, 4.9 Hz, 1H), 7.45-7.23 (m, 6H), 7.20 (s, 1H), 7.06 (dd, J=8.9, 2.1 Hz, 1H), 5.66-5.50 (m, 1H), 5.29-5.05 (m, 2H), 4.36-4.18 (m, 3H), 4.17-4.09 (m, 2H), 4.05-3.86 (m, 5H), 3.75 (d, J=16.6 Hz, 1H), 3.54-3.36 (m, 2H), 3.27 (s, 1H), 3.21-3.06 (m, 4H), 3.03-2.91 (m, 1H), 2.88 (s, 3H), 2.81-2.63 (m, 2H), 2.47-2.35 (m, 1H), 2.34-2.09 (m, 3H), 2.00-1.93 (m, 1H), 1.86 (d, J=10.2 Hz, 1H), 1.79-1.63 (m, 2H), 1.43 (d, J=6.2 Hz, 3H), 1.28 (s, 1H), 1.01 (d, J=5.7 Hz, 3H), 0.91-0.77 (m, 10H), 0.57 (s, 3H).

Data for Isomer 3: LCMS (ESI): m/z $[M+H]^+$ calc'd for $C_{49}H_{65}N_7O_9S$ 927.5; found 928.4; $^1H$ NMR (400 MHz, CD30D) δ 8.79-8.66 (m, 1H), 8.17-8.04 (m, 1H), 7.88 (dd, J=19.8, 5.4 Hz, 1H), 7.52 (dd, J=7.7, 4.8 Hz, 1H), 7.45-7.16 (m, 7H), 7.15-6.98 (m, 1H), 5.50-5.38 (m, 1H), 5.16 (d, J=8.2 Hz, 2H), 4.32 (d, J=12.0 Hz, 1H), 4.24-4.16 (m, 1H), 4.14-4.02 (m, 2H), 4.00-3.72 (m, 5H), 3.62 (dd, J=30.7, 6.5 Hz, 2H), 3.28-3.14 (m, 2H), 3.11-2.92 (m, 5H), 2.88 (d, J=6.7 Hz, 3H), 2.74-2.54 (m, 1H), 2.52-2.12 (m, 4H), 1.94-1.65 (m, 2H), 1.61-1.47 (m, 1H), 1.43 (d, J=6.3 Hz, 3H), 1.38-1.25 (m, 2H), 1.18 (t, J=6.9 Hz, 3H), 0.98-0.73 (m, 9H), 0.68 (s, 3H).

Data for Isomer 4: LCMS (ESI): m/z $[M+H]^+$ calc'd for $C_{49}H_{65}N_7O_9S$ 927.5; found 928.4; $^1H$ NMR (400 MHz, $CD_3OD$) δ 8.79-8.61 (m, 1H), 8.21 (d, J=47.9 Hz, 1H), 7.92 (dd, J=7.7, 1.6 Hz, 1H), 7.64-7.46 (m, 2H), 7.44-7.20 (m, 5H), 7.07 (d, J=8.7 Hz, 1H), 5.84-5.45 (m, 1H), 5.26-5.02 (m, 2H), 4.42-3.38 (m, 11H), 3.27-3.06 (m, 4H), 3.05-2.94 (m, 3H), 2.93-2.70 (m, 4H), 2.53 (t, 1H), 2.27-2.09 (m, 2H), 2.01 (d, J=3.8 Hz, 1H), 1.87-1.54 (m, 3H), 1.52-1.26 (m, 3H), 1.26-0.98 (m, 4H), 0.97-0.40 (m, 12H).

Step 12. A mixture of benzyl ((2S)-1-((($6^3$S)-$1^1$-ethyl-$1^2$-(2-((S)-1-methoxyethyl)pyridin-3-yl)-10,10-dimethyl-$2^1$, $2^1$-dioxido-5,7-dioxo-$6^1$,$6^2$,$6^3$,$6^4$,$6^5$,$6^6$-hexahydro-1 $^1$H-8-oxa-2(4,2)-thiomorpholina-1(5,3)-indola-6(1,3)-pyridazinacycloundecaphane-4-yl)amino)-3-methyl-1-oxobutan-2-yl)(methyl)carbamate (Isomer 1; 380 mg, 0.41 mmol), Pd/C, 50% wt with $H_2O$ (100 mg) and $NH_4Cl$ (220 mg, 4.1 mmol) in MeOH (10 mL), was stirred at 15° C. for 10 h. The mixture was filtered, the filtrate was concentrated under reduced pressure, the residue was diluted with sat. $NaHCO_3$ (20 mL) and extracted with DCM (20 mL×5). The combined organic layers was dried over $Na_2SO_4$, filtered and the filtrate was concentrated under reduced pressure to give (2S)—N-(($6^3$S)-11-ethyl-12-(2-((S)-1-methoxyethyl)pyridin-3-yl)-10,10-dimethyl-$2^1$,$2^1$-dioxido-5,7-dioxo-$6^1$, $6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)-3-methyl-2-(methylamino)butanamide (300 mg, 92% yield) as a solid, and used in the next step without further purification. LCMS (ESI): m/z $[M+H]^+$ calc'd for $C_{41}H_{59}N_7O_7S$ 793.4; found 794.4.

A similar reaction was undertaken using Isomers 2, 3 and 4 as starting material to give the respective products.

Data for Isomer 2: Starting from (170 mg, 0.18 mmol) to give (140 mg, 98% yield). LCMS (ESI): m/z $[M+H]^+$ calc'd for $C_{41}H_{59}N_7O_7S$ 793.4; found 794.4.

Data for Isomer 3: Starting from (390 mg, 0.42 mmol) to give (300 mg, 90% yield). LCMS (ESI): m/z $[M+H]^+$ calc'd for $C_{41}H_{59}N_7O_7S$ 793.4; found 794.3.

Data for Isomer 4: Starting from (240 mg, 0.26 mmol) to give (200 mg, 96% yield). LCMS (ESI): m/z $[M+H]^+$ calc'd for $C_{41}H_{59}N_7O_7S$ 793.4; found 794.3.

Step 13. To a mixture of (2S)—N-(($6^3$S)-11-ethyl-12-(2-((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)-3-methyl-2-(methylamino)butanamide (Isomer 1; 120 mg, 0.15 mmol) and (3S)-1-{3-[(formyloxy)methyl]phenyl}pyrrolidine-3-carboxylic acid (56 mg, 0.23 mmol) in DMF (5 mL) at 0° C. was added DIPEA (390 mg, 3 mmol) and HATU (87 mg, 0.23 mmol). The mixture was stirred at 0° C. for 1 h, then diluted with EtOAc (20 mL) and washed with $H_2O$ (20 mL×2). The organic layer was dried over $Na_2SO_4$, filtered, the filtrate was concentrated under reduced pressure and the residue was purified by silica gel chromatography to give benzyl (3S)-3-(((2S)-1-((($6^3$S)-$1^1$-ethyl-$1^2$-(2—((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)(methyl)carbamoyl)pyrrolidine-1-carboxylate (111 mg, 72% yield) as a solid. LCMS (ESI): m/z [M+H]$^+$ calc'd for $C_{54}H_{72}N_8O_{10}S$ 1024.5; found 1025.3.

A similar reaction was undertaken using Isomers 2, 3 and 4 as starting material to give the respective products.

Data Isomer 2: Starting from (150 mg, 0.19 mmol) to give (120 mg, 62% yield). LCMS (ESI): m/z [M+H]$^+$ calc'd for $C_{54}H_{72}N_8O_{10}S$ 1024.5; found 1025.4.

Data for Isomer 3: Starting from (300 mg, 0.38 mmol) to give (300 mg, 77% yield). LCMS (ESI): m/z [M+H]$^+$ calc'd for $C_{54}H_{72}N_8O_{10}S$ 1024.5; found 1025.5.

Data for Isomer 4: Starting from (199 mg, 0.25 mmol) to give (220 mg, 85% yield). LCMS (ESI): m/z [M+H]$^+$ calc'd for $C_{54}H_{72}N_8O_{10}S$ 1024.5; found 1025.4.

Step 14. A mixture of benzyl (3S)-3-(((2S)-1-((($6^3$S)-$1^1$-ethyl-$1^2$-(2-((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)(methyl)carbamoyl)pyrrolidine-1-carboxylate (Isomer 1; 111 mg, 0.11 mmol), Pd/C, 50% wt. with $H_2O$ (30 mg) and $NH_4Cl$ (60 mg, 1.1 mmol) in MeOH (20 mL) was stirred at 15° C. for 10 h. The mixture was filtered, the filtrate was concentrated under reduced pressure and the residue was diluted with DCM (20 mL) and washed with sat. $NaHCO_3$. The organic layer was dried over $Na_2SO_4$, filtered and the filtrate was concentrated under reduced pressure to give (3S)—N-((2S)-1-((($6^3$S)-$1^1$-ethyl-$1^2$-(2-((S)-1-methoxyethyl)pyridin-3-yl)-10,10-dimethyl-21,21-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)-N-methylpyrrolidine-3-carboxamide (77 mg, 79% yield) as a solid, which was used in the next step without further purification. LCMS (ESI): m/z [M+H]$^+$ calc'd for $C_{46}H_{66}N_8O_8S$ 890.5; found 891.4.

A similar reaction was undertaken using Isomers 2, 3 and 4 as starting material to give the respective products.

Data for Isomer 2: Starting from (120 mg, 0.12 mmol) to give (85 mg, 89% yield). LCMS (ESI): m/z [M+H]$^+$ calc'd for $C_{46}H_{66}N_8O_8S$ 890.5; found 891.4.

Data for Isomer 3: Starting from (300 mg, 0.34 mmol) to give (220 mg, 73% yield). LCMS (ESI): m/z [M+H]$^+$ calc'd for $C_{46}H_{66}N_8O_8S$ 890.5; found 891.5.

Data for Isomer 4: Starting from (220 mg, 0.21 mmol) to give (147 mg, 71% yield). LCMS (ESI): m/z [M+H]$^+$ calc'd for $C_{46}H_{66}N_8O_8S$ 890.5; found 891.4.

Step 15. To a mixture of (3S)—N-((2S)-1-((($6^3$S)-$1^1$-ethyl-$1^2$-(2-((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,66-hexahydro-11H-8-oxa-2(4,2)-thiomorpholina-1(5,3)-indola-6(1,3)-pyridazinacycloundecaphane-4-yl)amino)-3-methyl-1-oxobutan-2-yl)-N-methylpyrrolidine-3-carboxamide (Isomer 1; 77 mg, 0.086 mmol) in DCM (2 mL) at 0° C. was added sat. $NaHCO_3$ (2 mL) and prop-2-enoyl chloride (7 mg, 0.077 mmol) in DCM (1 mL). The mixture was stirred at 0° C. for 30 min, then $H_2O$ added and the mixture extracted with DCM (10 mL×3). The combined organic layers were dried over $Na_2SO_4$, filtered, the filtrate was concentrated under reduced pressure and the residue was purified by preparative-TLC to give (3S)-1-acryloyl-N-((2S)-1-((($6^3$S)-$1^1$-ethyl-$1^2$-(2-((S)-1-methoxyethyl)pyridin-3-yl)-10,10-dimethyl-$2^1$,$2^1$-dioxido-5,7-dioxo-$6^1$,$6^2$,$6^3$,$6^4$,$6^5$,$6^6$-hexahydro-$1^1$H-8-oxa-2(4,2)-thiomorpholina-1(5,3)-indola-6(1,3)-pyridazinacycloundecaphane-4-yl)amino)-3-methyl-1-oxobutan-2-yl)-N-methylpyrrolidine-3-carboxamide (23 mg, 28% yield) as a solid. LCMS (ESI): m/z [M+H]$^+$ calc'd for $C_{49}H_{68}N_8O_9S$ 944.5; found 945.4; $^1$H NMR (400 MHz, CD30D) δ 8.75-8.74 (m, 1H), 7.92-7.90 (m, 1H), 7.54-7.51 (m, 1H), 7.43 (dd, J=8.8, 2.2 Hz, 1H), 7.34 (d, J=3.2 Hz, 1H), 7.25-7.15 (m, 1H), 6.71-6.60 (m, 1H), 6.32-6.25 (m, 1H), 5.77 (dd, J=10.5, 1.9 Hz, 1H), 5.53-5.48 (m, 1H), 4.62 (dd, J=24.9, 11.1 Hz, 1H), 4.45 (s, 1H), 4.13-4.03 (m, 3H), 3.89-3.76 (m, 6H), 3.69-3.63 (m, 2H), 3.60-3.35 (m, 3H), 3.25-3.21 (m, 3H), 3.13-3.11 (m, 1H), 3.00 (d, J=2.3 Hz, 5H), 2.90 (d, J=3.5 Hz, 2H), 2.25-2.20 (m, 2H), 2.16-2.09 (m, 3H), 2.04-1.94 (m, 2H), 1.80-1.72 (m, 2H), 1.46-1.43 (m, 3H), 1.29 (m, 3H), 1.26-1.22 (m, 3H), 1.01-0.98 (m, 3H), 0.95-0.88 (m, 3H), 0.84-0.81 (m, 3H), 0.62-0.59 (m, 2H).

A similar reaction was undertaken using Isomers 2, 3 and 4 as starting material to give the respective products.

Data for Isomer 2: Starting from (110 mg, 0.12 mmol) to give (24.5 mg, 21% yield). LCMS (ESI): m/z [M+H]$^+$ calc'd for $C_{49}H_{68}N_8O_9S$ 944.5; found 945.3; $^1$H NMR (400 MHz, $CD_3OD$) δ 8.71 (dd, J=4.8, 1.7 Hz, 1H), 7.91-7.78 (m, 1H), 7.52 (dd, J=7.7, 4.9 Hz, 1H), 7.45-7.36 (m, 1H), 7.25-7.03 (m, 2H), 6.65-6.56 (m, 1H), 6.30-6.22 (m, 1H), 5.76-5.70 (m, 1H), 5.67-5.48 (m, 1H), 5.27 (dd, J=11.7, 8.2 Hz, 1H), 4.69 (dd, J=10.9, 3.3 Hz, 1H), 4.37-4.28 (m, 1H), 4.26-4.18 (m, 1H), 4.18-3.98 (m, 3H), 3.97-3.83 (m, 4H), 3.82-3.62 (m, 4H), 3.60-3.41 (m, 3H), 3.28-3.20 (m, 2H), 3.14 (d, J=10.4 Hz, 3H), 3.06 (d, J=4.8 Hz, 3H), 2.96 (s, 1H), 2.89-2.77 (m, 1H), 2.73-2.55 (m, 1H), 2.48-2.34 (m, 1H), 2.33-2.18 (m, 3H), 2.13-1.95 (m, 2H), 1.90-1.84 (m, 1H), 1.80-1.67 (m, 2H), 1.43 (m, 3H), 1.27 (s, 1H), 1.14-0.95 (m, 4H), 0.94-0.85 (m, 4H), 0.82 (d, J=6.2 Hz, 5H), 0.56 (d, J=8.7 Hz, 3H).

Data for Isomer 3: Starting from (120 mg, 0.13 mmol) to give (32 mg, 11% yield). LCMS (ESI): m/z [M+H]$^+$ calc'd for $C_{49}H_{68}N_8O_9S$ 944.5; found 945.5; $^1$H NMR (400 MHz, $CD_3OD$) δ 8.73 (dt, J=3.8, 1.9 Hz, 1H), 7.93-7.86 (m, 1H), 7.53 (dd, J=7.7, 4.9 Hz, 1H), 7.40 (dd, J=8.8, 2.3 Hz, 1H), 7.28 (d, J=9.6 Hz, 1H), 7.13-6.99 (m, 1H), 6.65 (ddd, J=35.6, 16.8, 10.5 Hz, 1H), 6.28 (ddd, J=16.8, 4.9, 1.9 Hz, 1H), 5.75 (td, J=10.4, 1.9 Hz, 1H), 5.53-5.34 (m, 1H), 4.63 (dd, J=13.4, 11.3 Hz, 1H), 4.26 (d, J=11.1 Hz, 1H), 4.12-4.01 (m, 2H), 4.00-3.82 (m, 5H), 3.82-3.45 (m, 7H), 3.41-3.33 (m, 1H), 3.14-3.02 (m, 4H), 3.02-2.87 (m, 5H), 2.62-2.34 (m, 3H), 2.33-2.17 (m, 3H), 2.10-1.94 (m, 1H), 1.69-1.52 (m, 1H), 1.46-1.39 (m, 3H), 1.27 (s, 2H), 1.23-1.16 (m, 3H), 1.16-1.01 (m, 2H), 0.96-0.90 (m, 3H), 0.88-0.74 (m, 6H), 0.73-0.63 (m, 3H).

Data for Isomer 4: Starting from (147 mg, 0.16 mmol) to give (47.2 mg, 31% yield). LCMS (ESI): m/z [M+H]$^+$ calc'd for $C_{49}H_{68}N_8O_9S$ 944.5; found 945.3; $^1$H NMR (400 MHz, $CD_3OD$) δ 8.73-8.72 (m, 1H), 7.92 (dd, J=7.8, 1.6 Hz, 1H), 7.53-7.50 (m, 1H), 7.49-7.46 (m, 1H), 7.41-7.38 (m, 1H), 7.07 (d, J=8.8 Hz, 1H), 6.65-6.56 (m, 1H), 6.28-6.23 (m, 1H), 5.76-5.71 (m, 2H), 4.59-4.55 (m, 1H), 4.34-4.30 (m, 1H), 4.13-4.03 (m, 4H), 3.88-3.72 (m, 6H), 3.68-3.48 (m, 5H), 3.30-3.20 (m, 4H), 3.08-3.07 (m, 3H), 3.02 (d, J=4.1 Hz, 4H), 2.55-2.53 (m, 1H), 2.34-2.19 (m, 3H), 2.11-2.00 (m, 3H), 1.90-1.88 (m, 1H), 1.76-1.74 (m, 2H), 1.44 (d, J=6.3 Hz, 3H), 1.29 (s, 1H), 1.23-1.20 (m, 3H), 0.91-0.86 (m, 3H), 0.78-0.75 (m, 5H), 0.69-0.66 (m, 3H).

Example 11. Synthesis of 3-acryloyl-N-((2S)-1-(((2$^2$S,6$^3$S,4S)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)amino)-3-methyl-1-oxobutan-2-yl)-N,1-dimethyl-1,3,8-triazaspiro[4.5]decane-8-carboxamide

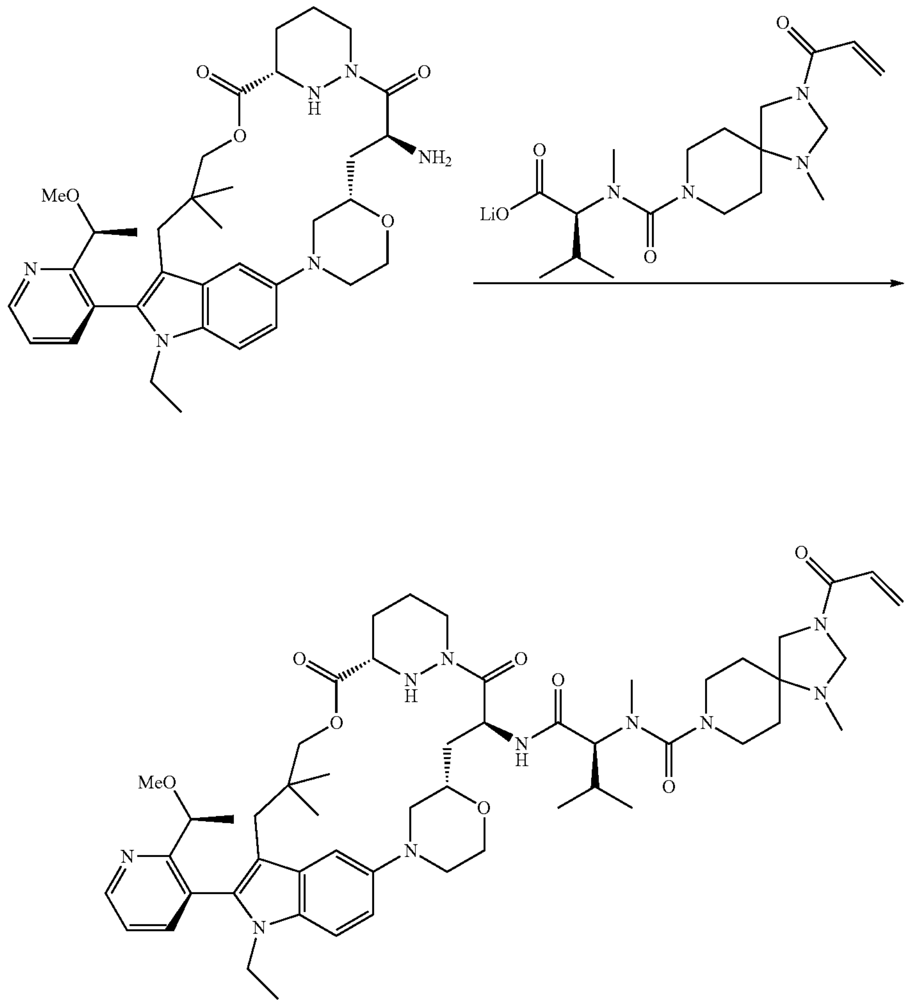

To a mixture of (2$^2$S,6$^3$S,4S)-4-amino-11-ethyl-12-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione (150 mg, 0.24 mmol) and (2S)-3-methyl-2-{methyl[1-methyl-3-(prop-2-enoyl)-1,3,8-triazaspiro[4.5]decan-8-yl]carbonylamino}butanoate, lithium salt (132 mg, 0.36 mmol) in DMF (5 mL) at 0° C. was added HATU (108 mg, 0.28 mmol) and DIPEA (459 mg, 3.5 mmol). The mixture was stirred at 0° C. for 1 h, then diluted with EtOAc (30 mL), washed with $H_2O$ (10 mL×2) and brine (10 mL). The organic layer was dried over $Na_2SO_4$ and filtered. The filtrate was concentrated under reduced pressure and the crude residue was purified by silica gel column chromatography and preparative-HPLC to give 3-acryloyl-N-((2S)-1-(((2$^2$S,6$^3$S,4S)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1'H-8-oxa-2(4,2)-morpholina-1(5,3)-indola-6(1,3)-pyridazinacycloundecaphane-4-yl)amino)-3-methyl-1-oxobutan-2-yl)-N,1-dimethyl-1,3,8-triazaspiro[4.5]decane-8-carboxamide (6.9 mg, 3% yield) as a solid. LCMS (ESI): m/z $[M+H]^+$ calc'd for $C_{53}H_{76}N_{10}O_8$ 980.6; found 367.2; $^1$H NMR (400 MHz, $CD_3OD$) δ 8.71 (dd, J=4.8, 1.6 Hz, 1H), 7.86 (dd, J=7.8, 1.6 Hz, 1H), 7.51 (dd, J=7.8, 4.8 Hz, 1H), 7.39 (d, J=8.8 Hz, 1H), 7.14-7.04 (m, 2H), 6.67-6.44 (m, 1H), 6.31 (d, J=16.8 Hz, 1H), 5.81-5.75 (m, 1H), 5.65 (d, J=9.0 Hz, 1H), 4.51-4.13 (m, 2H), 4.33 (s, 1H), 4.27-4.18 (m, 1H), 4.17-4.08 (m, 1H), 3.96-3.87 (m, 3H), 3.87-3.77 (m, 3H), 3.76-3.65 (m, 4H), 3.64-3.51 (m, 3H), 3.28-3.24 (m, 1H), 3.16 (s, 3H), 3.10-3.02 (m, 1H), 2.99-2.90 (m, 2H), 2.87-2.74 (m, 5H), 2.70-2.53 (m, 2H), 2.40-2.30 (m, 3H), 2.27-2.18 (m, 1H), 2.14-2.05 (m, 2H), 1.98-1.88 (m, 3H), 1.79-1.68 (m, 2H), 1.65-1.47 (m, 3H), 1.44 (d, J=6.4 Hz, 3H), 1.04 (t, J=6.8 Hz, 3H), 0.95 (d, J=6.4 Hz, 3H), 0.88 (d, J=6.4 Hz, 3H), 0.80-0.60 (m, 6H).

Example 12. Synthesis 2-acryloyl-N-((2S)-1-((($6^3$S, 4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-1'H-8-oxa-1(5,3)-indola-6(1,3)-pyridazina-2(5,1)- pyridinacycloundecaphane-4-yl) amino)-3-methyl-1-oxobutan-2-yl)-N-methyl-2,8-diazaspiro[4.5]decane-8-carboxamide
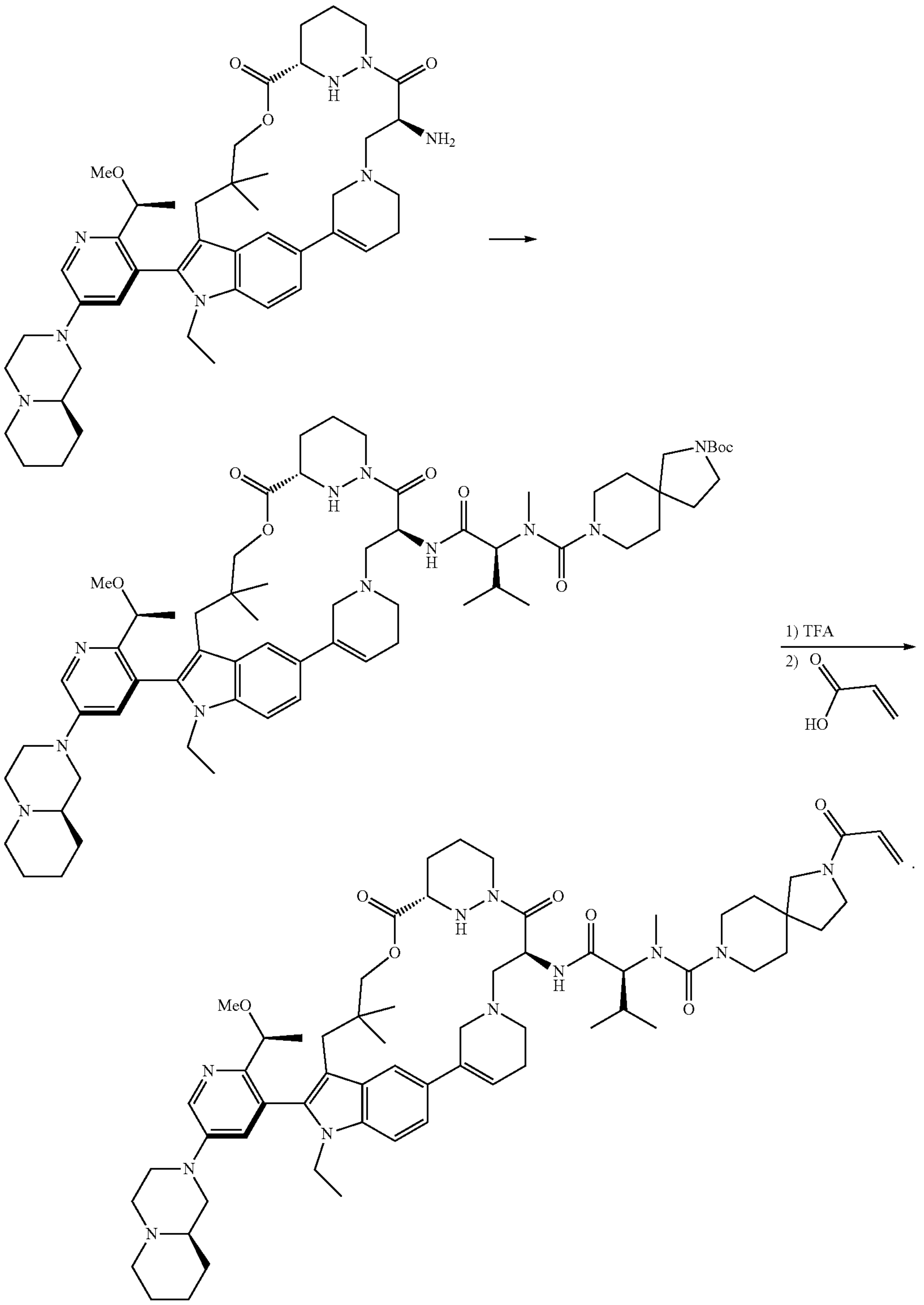

Step 1. To a mixture of ($6^3$S,4S)-4-amino-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-5,7-dione (150 mg, 0.23 mmol) in DMF (2 mL) at 0° C. was added (2S)-2-({2-[(tert-butoxy)carbonyl]-2,8-diazaspiro[4.5]decan-8-yl}carbonyl(methyl)amino)-3-methylbutanoic acid (125 mg, 0.30 mmol), DIPEA (310 mg, 2.34 mmol) and HATU (134 mg, 0.35 mmol). The mixture was stirred at 0° C. for 1 h, then $H_2O$ (150 mL) and extracted with EtOAc (150 mL×2). The combined organic layers were washed with $H_2O$ (50 mL), brine (50 mL), dried over anhydrous $Na_2SO_4$ and filtered. The filtrate was concentrated under reduced pressure and the crude residue was purified by preparative-TLC to give tert-butyl 8-(((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-2',$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)amino)-3-methyl-1-oxobutan-2-yl)(methyl)carbamoyl)-2,8-diazaspiro[4.5]decane-2-carboxylate (130 mg, 40% yield) as a solid. LCMS (ESI): m/z $[M+H]^+$ calc'd for $C_{64}H_{95}N_{11}O_8$ 1145.7; found 1146.7.

Step 2. To a mixture of tert-butyl 8-(((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)amino)-3-methyl-1-oxobutan-2-yl)(methyl)carbamoyl)-2,8-diazaspiro[4.5]decane-2-carboxylate (130 mg, 0.12 mmol) in DCM (1.0 mL) at 0° C. was added TFA (0.5 mL). The mixture was stirred at 0° C. for 1 h, then diluted with DCM (5 mL) and saturated $NaHCO_3$ added to adjust pH ~9. Prop-2-enoyl chloride (10 mg, 0.11 mmol) in DCM was added at 0° C., and the mixture was stirred at 0° C. for 15 min. The mixture was poured into $H_2O$ (50 mL) and extracted with DCM (150 mL×2). The combined organic layers were washed with $H_2O$ (50 mL), brine (50 mL), dried over anhydrous $Na_2SO_4$ and filtered. The filtrate was concentrated under reduced pressure and the crude residue was purified by preparative-TLC to give 2-acryloyl-N-((2S)-1-((($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-1'H-8-oxa-1(5,3)-indola-6(1,3)-pyridazina-2(5,1)-pyridinacycloundecaphane-4-yl)amino)-3-methyl-1-oxobutan-2-yl)-N-methyl-2,8-diazaspiro[4.5]decane-8-carboxamide as a solid. LCMS (ESI): m/z $[M+H]^+$ calc'd for $C_{62}H_{89}N_{11}O_7$ 1099.7; found 1100.6; $^1$H NMR (400 MHz, $CD_3OD$) δ 8.45 (d, J=2.8 Hz, 1H), 7.54 (d, J=9.2 Hz, 2H), 7.42 (d, J=8.4 Hz, 2H), 6.65 (m, 1H), 6.41-6.21 (m, 2H), 5.93 (dd, J=7.6, 3.8 Hz, 1H), 5.81-5.75 (m, 1H), 4.50 (d, J=12.8 Hz, 1H), 4.20-4.04 (m, 3H), 3.98-3.71 (m, 8H), 3.63-3.48 (m, 2H), 3.46-3.36 (m, 2H), 3.30-3.15 (m, 3H), 3.12-2.97 (m, 6H), 2.93-2.76 (m, 6H), 2.64 (t, J=11.2 Hz, 2H), 2.55 (d, J=11.6 Hz, 9H), 2.45-2.12 (m, 4H), 1.99-1.83 (m, 2H), 1.80-1.55 (m, 10H), 1.48-1.29 (m, 6H), 1.22 (t, J=7.0 Hz, 3H), 0.93 (dd, J=22.8, 6.4 Hz, 9H), 0.72 (s, 3H).

Example 13. Synthesis of 3-acryloyl-N-((2S)-1-((($2^2$S,$6^3$S,4S)-11-ethyl-$1^2$-(2-((S)-1-methoxyethyl)pyridin-3-yl)-10,10-dimethyl-5,7-dioxo-$6^1$,$6^2$,$6^3$,$6^4$,$6^5$,66-hexahydro-1'H-8-oxa-2(4,2)-morpholina-1(5,3)-indola-6(1,3)-pyridazinacycloundecaphane-4-yl)amino)-3-methyl-1-oxobutan-2-yl)-N-methyl-1-oxa-3,8-diazaspiro[4.5]decane-8-carboxamide

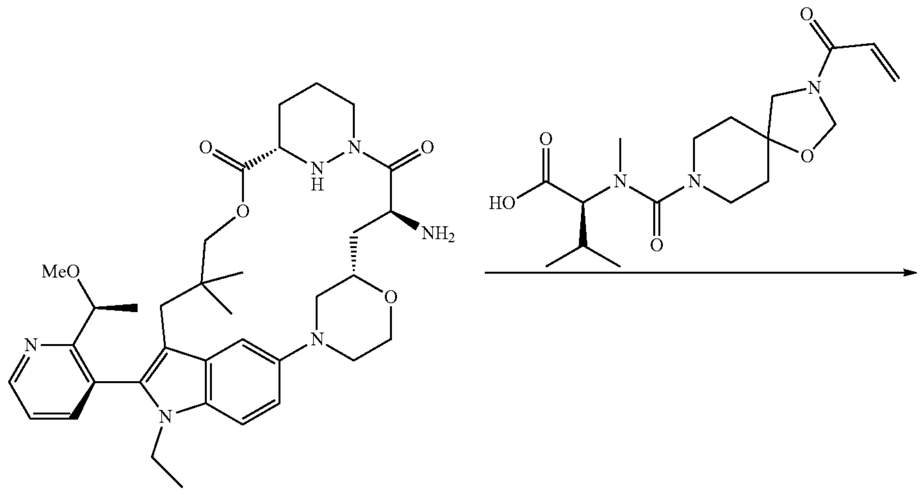

-continued

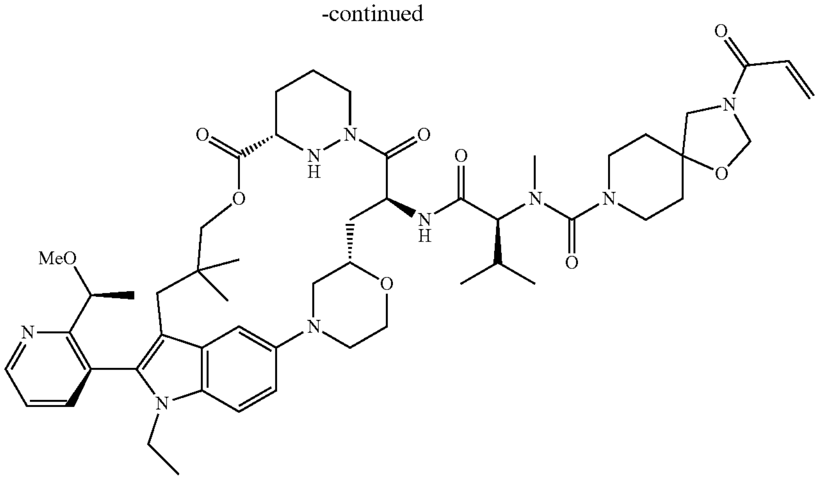

To a mixture of ($2^2$S,$6^3$S,4S)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-1'H-8-oxa-2(4,2)-morpholina-1(5,3)-indola-6(1,3)-pyridazinacycloundecaphane-5,7-dione (450 mg, 0.7 mmol). The mixture was stirred at 0° C. for 1 h, then $H_2O$ (20 mL) was added and the mixture was extracted with EtOAc (30 mL×3). The combined organic layers were washed with brine (20 mL), dried over anhydrous $Na_2SO_4$ and filtered. The filtrate was concentrated under reduced pressure and the crude residue was purified by silica gel column chromatography and preparative-HPLC to give 3-acryloyl-N-((2S)-1-((($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)amino)-3-methyl-1-oxobutan-2-yl)-N-methyl-1-oxa-3,8-diazaspiro[4.5]decane-8-carboxamide (297 mg, 40% yield) as a solid. LCMS (ESI): m/z $[M+H]^+$ calc'd for $C_{52}H_{73}N_9O_9$ 967.6; found 968.6; $^1$H NMR (400 MHz, $CD_3OD$) δ 8.72-8.69 (m, 1H), 8.10 (d, J=6.4 Hz, 1H), 7.89-7.80 (m, 1H), 7.56-7.47 (m, 1H), 7.45-7.35 (m, 1H), 7.17-7.01 (m, 2H), 6.62-6.45 (m, 1H), 6.32 (s, 1H), 5.85-5.71 (m, 1H), 5.64 (d, J=8.8 Hz, 1H), 5.19 (s, 1H), 5.10 (s, 1H), 4.46 (d, J=12.4 Hz, 1H), 4.25-4.03 (m, 2H), 3.99-3.61 (m, 8H), 3.61-3.33 (m, 6H), 3.29-3.18 (m, 2H), 3.15 (s, 3H), 2.99-2.71 (m, 6H), 2.68-2.46 (m, 2H), 2.30-2.17 (m, 1H), 2.12-2.02 (m, 2H), 1.96-1.54 (m, 8H), 1.43 (d, J=6.4 Hz, 3H), 1.15-0.97 (m, 3H), 0.96-0.79 (m, 6H), 0.77-0.53 (m, 6H).

Example 14. Synthesis of 4-acryloyl-N-((2S)-1-((($6^3$S,4S)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)amino)-3-methyl-1-oxobutan-2-yl)-N-methyl-1-propyl-1,4,9-triazaspiro[5.5]undecane-9-carboxamide

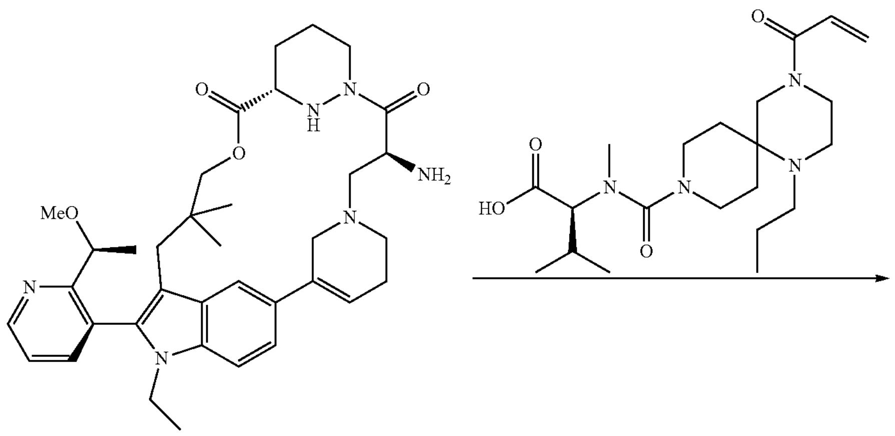

-continued

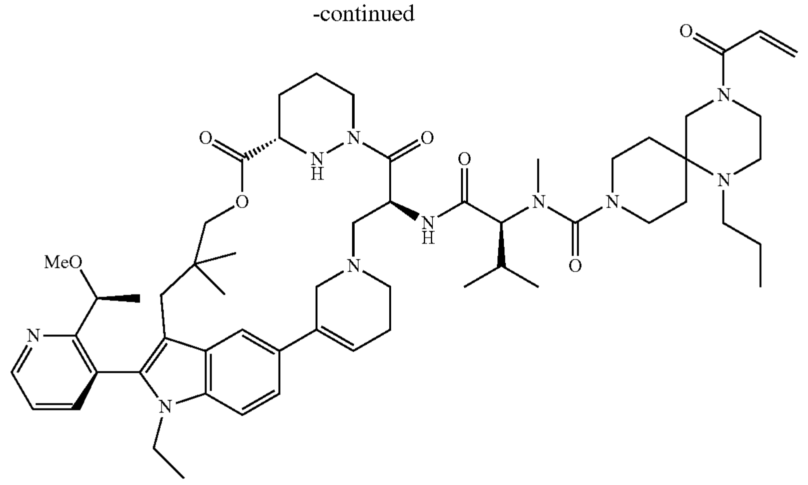

To a mixture of ($6^3$S,4S)-4-amino-$1^1$-ethyl-$1^2$-(2-((S)-1-methoxyethyl)pyridin-3-yl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)- pyridinacycloundecaphane-5,7-dione (113 mg, 0.18 mmol) and (2S)-3-methyl-2-{methyl[4-(prop-2-enoyl)-1-propyl-1,4,9-triazaspiro[5.5]undecan-9-yl] carbonylamino}butanoic acid, lithium salt (88 mg, 0.22 mmol) in DMF (2 mL) at 0° C. was added DIPEA (464 mg, 3.6 mmol) and HATU (82 mg, 0.23 mmol). The mixture was stirred at 0° C. for 1 h, then $H_2O$ (20 mL) was added and the mixture was extracted with DCM (20 mL×3). The combined organic layers were washed with brine (20 mL), dried over anhydrous $Na_2SO_4$ and filtered. The filtrate was concentrated under reduced pressure and the crude residue was purified by preparative-HPLC to give 4-acryloyl-N-((2S)-1-((($6^3$S,4S)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-1'H-8-oxa-1(5,3)-indola-6(1,3)-pyridazina- 2(5, 1)-pyridinacycloundecaphane-4-yl)amino)-3-methyl-1-oxobutan-2-yl)-N-methyl-1-propyl-1,4,9-triazaspiro[5.5] undecane-9-carboxamide (26 mg, 14% yield) as a solid. LCMS (ESI): m/z $[M+H]^+$ calc'd for $C_{57}H_{82}N_{10}O_7$ 1018.6; found 1019.6; $^1H$ NMR (400 MHz, $CD_3OD$) δ 8.73 (dd, J=8.0, 4.0 Hz, 1H), 7.90 (dd, J=8.0, 4.0 Hz, 1H), 7.54-7.51 (m, 3H), 7.41-7.38 (m, 1H), 6.90-6.74 (m, 1H), 6.30-6.18 (m, 2H), 5.91-5.88 (m, 1H), 5.80-5.75 (m, 1H), 4.59-4.46 (m, 1H), 4.10-3.47 (m, 15H), 3.19-2.72 (m, 17H), 2.42-2.15 (m, 8H), 2.08-1.63 (m, 7H), 1.48-1.44 (m, 6H), 1.16 (t, J=6.4 Hz, 3H), 0.93-0.86 (m, 9H), 0.66 (s, 3H).

Example 15. Synthesis of (2S)—N-[(6S,8S,14S, 20M)-21-[5-(4-cyclopropylpiperazin-1-yl)-2-[(1S)-1-methoxyethyl]pyridin-3-yl]-22-ethyl-18,18-dimethyl-9,15-dioxo-5,16-dioxa-2,10,22,28-tetraazapentacyclo[18.5.2.$1^{2,6}$.$1^{10,14}$.$0^{23,27}$] nonacosa-1(26),20,23(27),24-tetraen-8-yl]-3-methyl-2-{methyl[3-(prop-2-enoyl)-1-oxa-3,8-diazaspiro [4.5]decane-8-carbonyl]amino}butanamide

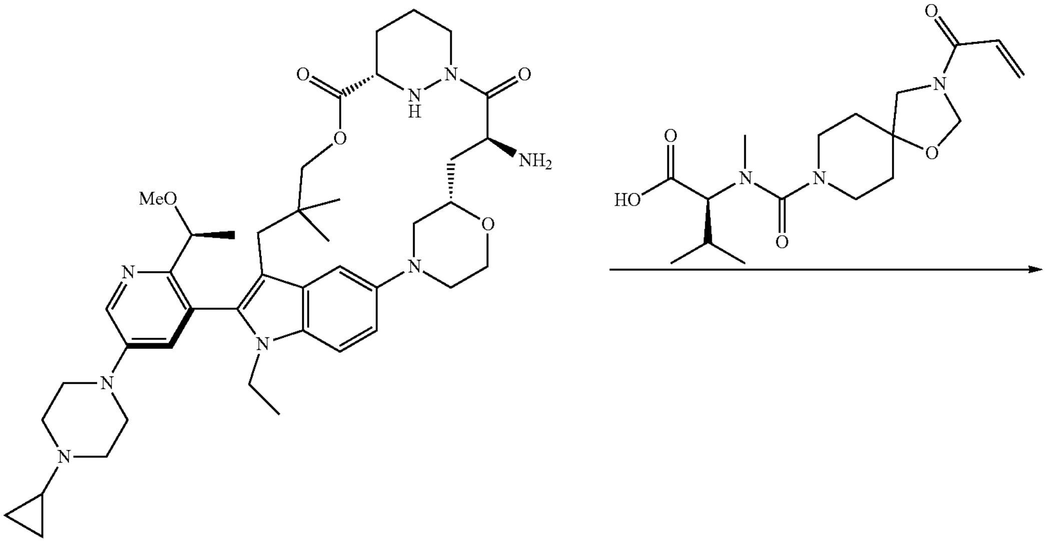

-continued

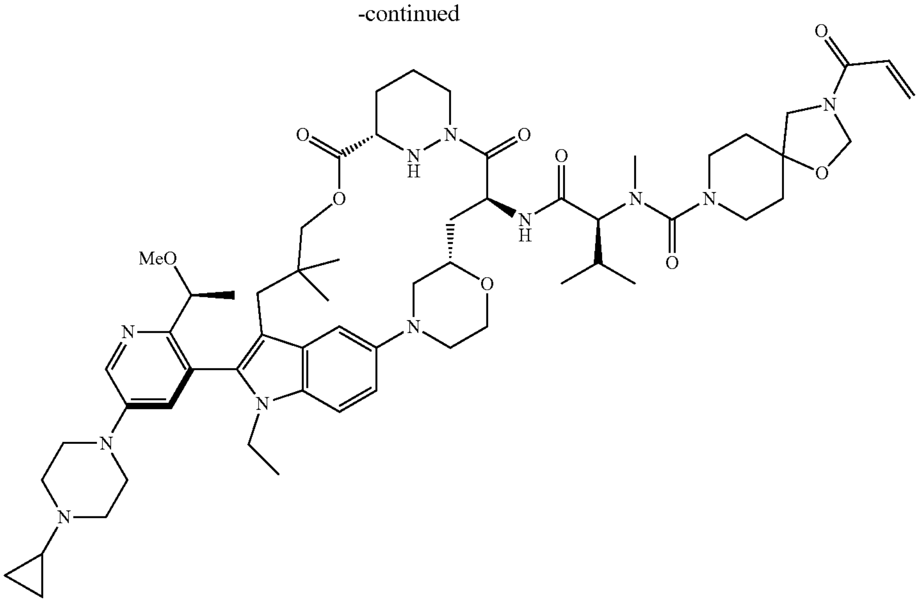

To a solution of ((6S,8S,14S)-8-amino-21-[5-(4-cyclopropylpiperazin-1-yl)-2-[(1S)-1-methoxyethyl]pyridin-3-yl]-22-ethyl-18,18-dimethyl-5,16-dioxa-2,10,22,28-tetraazapentacyclo[18.5.2.1^{2,6}.1^{10,14}.0^{23,27}]nonacosa-1(26),20,23(27),24-tetraene-9,15-dione (60 mg, 0.08 mmol, 1 equiv) and (2S)-3-methyl-2-{methyl[3-(prop-2-enoyl)-1-oxa-3,8-diazaspiro[4.5]decan-8-yl]carbonylamino}butanoic acid (42 mg, 0.119 mmol, 1.5 equiv,) in DMF (3 mL) was added N,N-Diisopropylethylamine (205 mg, 1.59 mmol, 20 equiv) followed by HATU (60 mg, 0.159 mmol, 2 equiv) at −5~0° C. This reaction was stirred at −5~0° C. for 1 h. The reaction mixture was quenched with water (5 mL) and extracted with EA (10 mL×3). The combined organic phase was washed with water (10 mL×1) and brine (10 mL×1). The organic phase was concentrated to dryness and the resulting residue was purified by chromatography to afford (2S)—N-[(6S,8S,14S,20M)-21-[5-(4-cyclopropylpiperazin-1-yl)-2-[(1S)-1-methoxyethyl]pyridin-3-yl]-22-ethyl-18,18-dimethyl-9,15-dioxo-5,16-dioxa-2,10,22,28-tetraazapentacyclo[18.5.2.$1^{2,6}$.$1^{10,14}$.$0^{23,27}$]nonacosa-1(26),20,23(27),24-tetraen-8-yl]-3-methyl-2-{methyl[3-(prop-2-enoyl)-1-oxa-3,8-diazaspiro[4.5]decane-8-carbonyl]amino}butanamide (16 mg, 18% yield) as a white solid. ESI-MS m/z=1092.6[M+H]$^+$; Calculated MW: 1091.7; $^1$H NMR (400 MHz, $CD_3OD$) δ 8.29 (d, J=2.9 Hz, 1H), 7.25 (dd, J=22.5, 5.9 Hz, 2H), 7.06-6.91 (m, 2H), 6.51-6.16 (m, 2H), 5.75-5.63 (m, 1H), 5.55 (d, J=8.9 Hz, 1H), 5.09 (d, J=5.0 Hz, 1H), 5.00 (s, 1H), 4.57-4.32 (m, 2H), 4.09-3.95 (m, 2H), 3.98-3.50 (m, 9H), 3.52-3.21 (m, 7H), 3.23-3.03 (m, 8H), 3.03 (s, 3H), 2.85 (dd, J=26.6, 15.7 Hz, 2H), 2.69 (d, J=14.8 Hz, 2H), 2.61-2.41 (m, 2H), 2.22-2.07 (m, 1H), 1.99 (dd, J=18.3, 12.0 Hz, 2H), 1.94-1.09 (m, 13H), 0.98 (t, J=6.9 Hz, 3H), 0.81 (dd, J=27.0, 6.5 Hz, 6H), 0.64 (d, J=28.9 Hz, 6H), 0.50-0.32 (m, 4H).

Example 16. Synthesis of (2S)—N-[(8S,14S,20M)-22-ethyl-21-{2-[(1S)-1-methoxyethyl]-5-(4-methylpiperazin-1-yl)pyridin-3-yl}-18,18-dimethyl-9,15-dioxo-16-oxa-6,10,22,28-tetraazapentacyclo[18.5.2.$1^{2,6}$.$1^{10,14}$.$0^{23,27}$]nonacosa-1(26),2,20,23(27),24-pentaen-8-yl]-3-methyl-2-{methyl[3-(prop-2-enoyl)-1-oxa-3,8-diazaspiro[4.5]decane-8-carbonyl]amino}butanamide

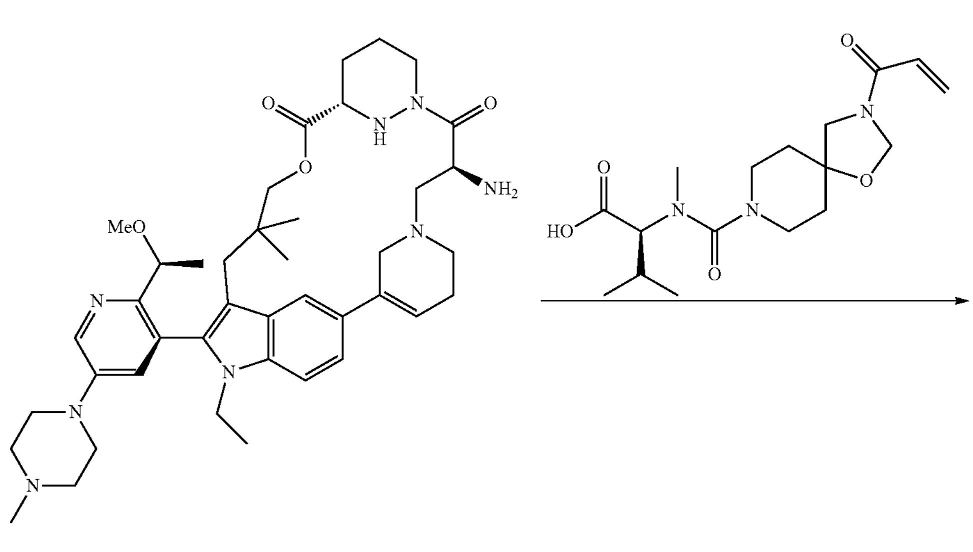

-continued

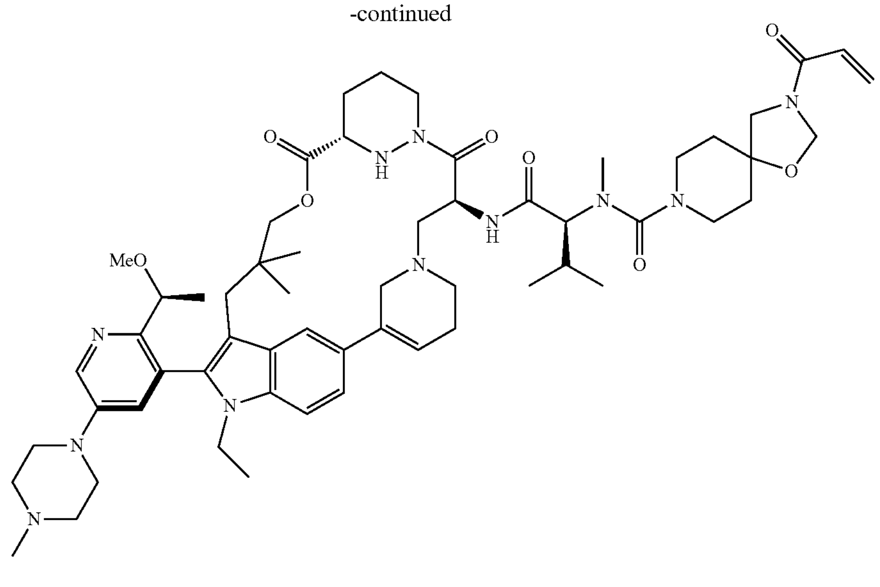

To a solution of (8S)-8-amino-22-ethyl-21-{2-[(1S)-1-methoxyethyl]-5-(4-methylpiperazin-1-yl)pyridin-3-yl}-18,18-dimethyl-16-oxa-6,10,22,28-tetraazapentacyclo [18.5.2.1^{2,6}.1^{10,14}.0^{23,27}]nonacosa-1(26),2,20,23(27),24-pentaene-9,15-dione (70 mg, 0.10 mmol, 1.0 equiv) and (2S)-3-methyl-2-{methyl[3-(prop-2-enoyl)-1-oxa-3,8-diazaspiro[4.5]decan-8-yl]carbonylamino}butanoic acid (40 mg, 0.12 mmol, 1.2 equiv) in DMF (2 mL) was added HATU (44 mg, 0.12 mmol, 1.2 equiv) and DIEA (187 mg, 1.44 mmol, 15.0 equiv) at 0° C. The reaction mixture was stirred at 0° C. for 1 h. The solution was purified by chromatography to afford (2S)—N-[(8S,14S,20M)-22-ethyl-21-{2-[(1S)-1-methoxyethyl]-5-(4-methylpiperazin-1-yl)pyridin-3-yl}-18,18-dimethyl-9,15-dioxo-16-oxa-6,10,22,28-tetraazapentacyclo[18.5.2.1$^{2,6}$.1$^{10,14}$.0$^{23,27}$]nonacosa-1(26),2,20,23(27),24-pentaen-8-yl]-3-methyl-2-{methyl[3-(prop-2-enoyl)-1-oxa-3,8-diazaspiro[4.5]decane-8-carbonyl]amino}butanamide (20.5 mg, 18% yield) as a white solid. ESI-MS m/z=1062.5[M+H]$^+$; Calculated MW: 1061.64. $^1$H NMR (400 MHz, $CD_3OD$) δ 8.43 (d, J=2.8 Hz, 1H), 7.58-7.49 (m, 2H), 7.45-7.35 (m, 2H), 6.65-6.41 (m, 1H), 6.38-6.32 (m, 1H), 6.29 (s, 1H), 5.91 (dd, J=8.8, 2.6 Hz, 1H), 5.84-5.78 (m, 1H), 5.21 (dd, J=7.6, 4.0 Hz, 1H), 5.12 (q, J=6.0 Hz, 1H), 4.50 (d, J=13.2 Hz, 1H), 4.18-3.02 (m, 3H), 3.00-3.81 (m, 4H), 3.76-3.70 (m, 1H), 3.59 (s, 1H), 3.52-3.42 (m, 2H), 3.42-3.34 (m, 6H), 3.28-3.20 (m, 2H), 3.14-3.07 (m, 1H), 3.06-2.98 (m, 3H), 2.90-2.74 (m, 7H), 2.70-2.62 (m, 4H), 2.62-2.56 (m, 1H), 2.44-2.29 (m, 6H), 2.26-2.17 (m, 1H), 2.16-2.09 (m, 1H), 2.00-1.90 (m, 1H), 1.89-1.78 (m, 3H), 1.76-1.64 (m, 3H), 1.44 (d, J=6.4 Hz, 3H), 1.21 (t, J=7.2 Hz, 2H), 0.95 (d, J=6.4 Hz, 3H), 0.92-0.82 (m, 6H), 0.71 (s, 3H).

Example 17. Synthesis of (2S)—N-[(6S,8S,14S,20P)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1$^{2,6}$.1$^{10,14}$.0$^{23,27}$]nonacosa-1(26),20,23(27),24-tetraen-8-yl]-2-({3-[(2E)-4-fluorobut-2-enoyl]-1-oxa-3,8-diazaspiro[4.5]decane-8-carbonyl}(methyl)amino)-3-methylbutanamide

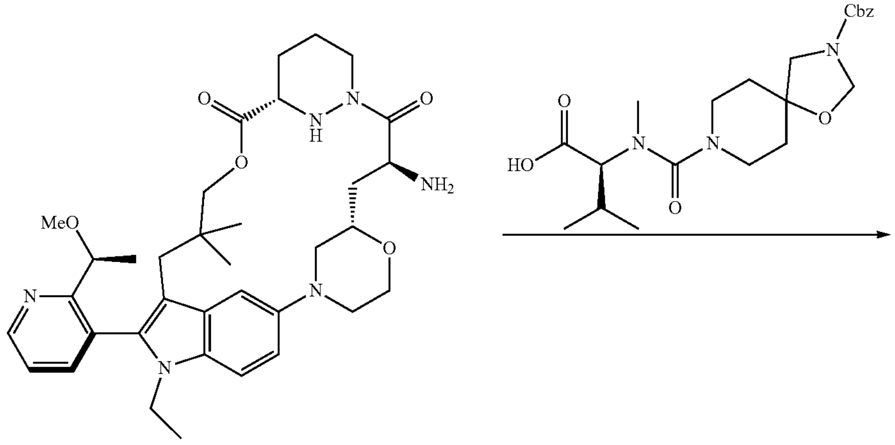

-continued

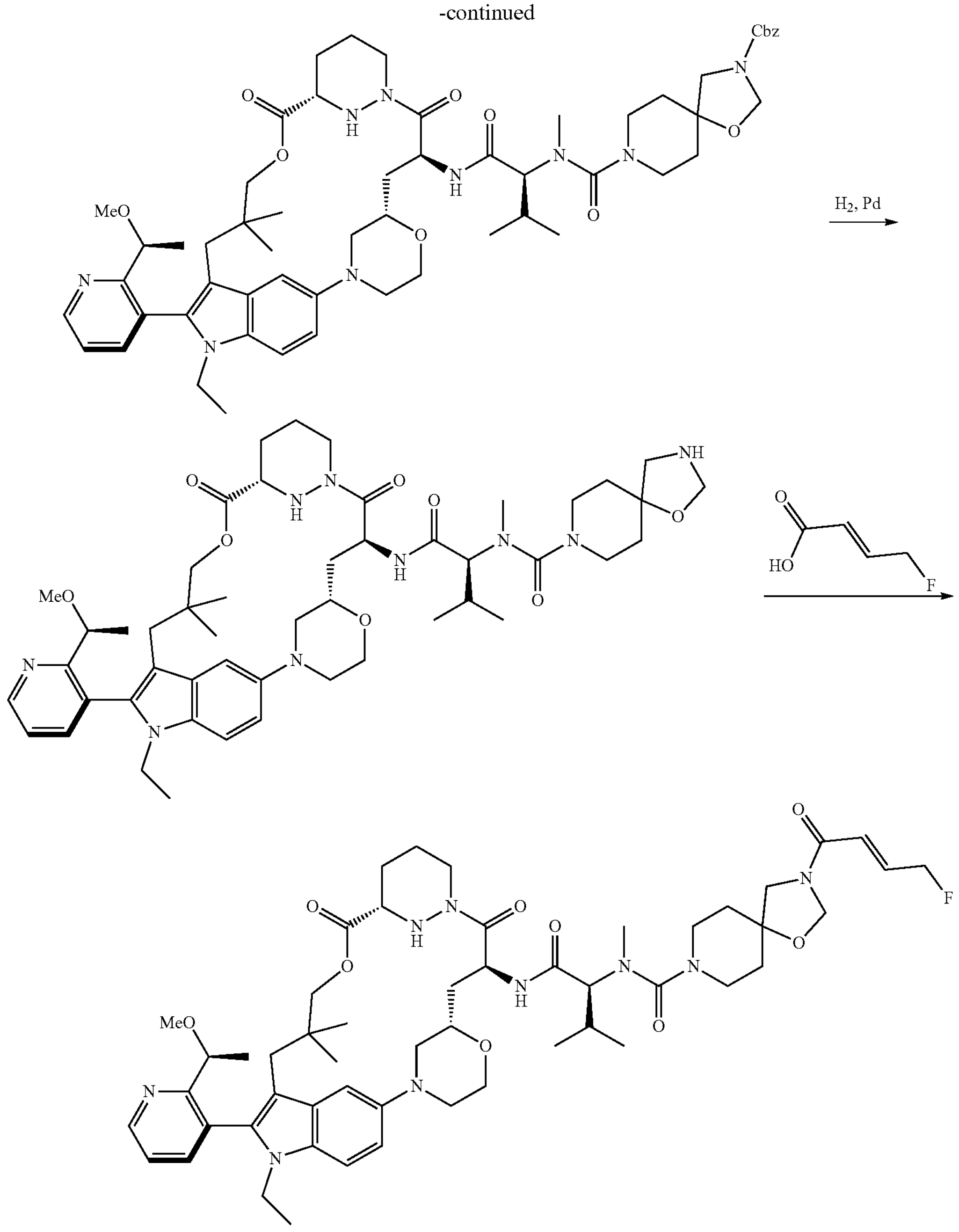

Step 1. To a solution of (2S)-2-[(3-{3-[(formyloxy)methyl]phenyl}-1-oxa-3,8-diazaspiro[4.5]decan-8-yl)carbonyl(methyl)amino]-3-methylbutanoic acid (308 mg, 0.71 mmol, 1.5 eq) and (6S,8S,14S)-8-amino-22-ethyl-21-{2-[(1S)-1-methoxyethyl]pyridin-3-yl}-18,18-dimethyl-5,16-dioxa-2,10,22,28-tetraazapentacyclo[18.5.2.1^{2,6}.1^{10,14}.0^{23,27}]nonacosa-1(26),20,23(27),24-tetraene-9,15-dione (300 mg, 0.47 mmol, 1 eq) in DMF (3 mL) was added DIEA (184 mg, 1.4 mmol, 3 eq) and HATU (216 mg, 0.57 mmol, 1.2 eq) at 0° C. The mixture was stirred at 0° C. for 0.5 h. The reaction mixture was quenched with $H_2O$ (30 mL), extracted with EtOAc (20 mL×3), and the combined organic layers were washed with water (20 mL), brine (20 mL), dried over $Na_2SO_4$. The mixture was filtered and concentrated under reduced pressure. The resulting residue was purified by chromatography to afford [3-(8-{[(1S)-1-{[(6S,8S,14S)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1^{2,6}.1^{10,14}.0^{23,27}]nonacosa-1(26),20,23(27),24-tetraen-8-yl]carbamoyl}-2-methylpropyl](methyl)carbamoyl}-1-oxa-3,8-diazaspiro[4.5]decan-3-yl)phenyl]methyl formate (300 mg, 60% yield) as a white solid. ESI-MS m/z: 1048.5 $[M+H]^+$, Calculated MW: 1047.6.

Step 2. To a solution of [3-(8-{[(1S)-1-{[(6S,8S,14S)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1^{2,6}.1^{10,14}.0^{23,27}]nonacosa-1(26),20,23(27),24-tetraen-8-yl]carbamoyl}-2-methylpropyl](methyl)carbamoyl}-1-oxa-3,8-diazaspiro[4.5]decan-3-yl)

phenyl]methyl formate (300 mg, 0.29 mmol, 1 eq) in i-PrOH (10 mL) was added 20% $Pd(OH)_2/C$ (30 mg, 60% water). The mixture was stirred at 20° C. for 20 min under $H_2$ (15 psi) atmosphere. The mixture was filtered and the filtrate was concentrated under reduced pressure to afford (2S)—N-[(6S,8S,14S)-22-ethyl-21-{2-[(1 S)-1-methoxyethyl]pyridin-3-yl}-18,18-dimethyl-9,15-dioxo-5,16-dioxa-2,10,22,28-tetraazapentacyclo[18.5.2.1^{2,6}.1^{10,14}.0^{23,27}]nonacosa-1(26),20,23(27),24-tetraen-8-yl]-3-methyl-2-[methyl({1-oxa-3,8-diazaspiro[4.5]decan-8-yl}carbonyl)amino]butanamide (200 mg, 61% yield) as brown oil. ESI-MS m/z: 914.4 $[M+H]^+$, Calculated MW: 913.5

Step 3. To a solution of (2S)—N-[(6S,8S,14S)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1^{2,6}.1^{10,14}.0^{23,27}]nonacosa-1(26),20,23(27),24-tetraen-8-yl]-3-methyl-2-[methyl({1-oxa-3,8-diazaspiro[4.5]decan-8-yl}carbonyl)amino]butanamide (200 mg, 0.22 mmol, 1 eq), (2E)-4-fluorobut-2-enoic acid (23 mg, 0.22 mmol, 1 eq) and TEA (111 mg, 0.11 mmol, 5 eq) in DMF (3 mL) was added $T_3P$ (278 mg, 0.44 mmol, 2 eq, 50% EtOAc) at 0° C. The reaction mixture was stirred at 0° C. for 0.5 h. The reaction mixture was then quenched with water (20 mL) and the resulting mixture was extracted with EtOAc (15 mL×4). The combined organic phases were washed with brine (10 mL×4), dried over anhydrous sodium sulfate, filtered, and concentrated under reduced pressure. The resulting residue was purified by chromatography to afford (2S)—N-[(6S,8S,14S,20P)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.$1^{2,6}$.$1^{10,14}$.$0^{23}$,$2^1$]nonacosa-1(26),20,23(27),24-tetraen-8-yl]-2-({3-[(2E)-4-fluorobut-2-enoyl]-1-oxa-3,8-diazaspiro[4.5]decane-8-carbonyl}(methyl)amino)-3-methylbutanamide (56.7 mg, 26% yield) as a white solid. ESI-MS m/z: 1000.6 $[M+H]^+$, Calculated MW: 999.6. $^1$H NMR (400 MHz, $CD_3OD$) δ 8.74 (dd, J=4.8, 1.6 Hz, 1H), 8.15 (d, J=6.0 Hz, 1H), 7.89 (dd, J=8.0, 1.6 Hz, 1H), 7.54 (dd, J=8.0, 4.8 Hz, 1H), 7.41 (d, J=9.2 Hz, 1H), 7.13-7.09 (m, 2H), 7.02-6.88 (m, 1H), 6.51-6.26 (m, 1H), 5.73-5.60 (m, 1H), 5.29-5.01 (m, 4H), 4.49 (d, J=12.8 Hz, 1H), 4.30-4.21 (m, 1H), 4.17-4.11 (m, 1H), 4.02-3.78 (m, 6H), 3.72-3.67 (m, 2H), 3.64-3.56 (m, 2H), 3.54-3.45 (m, 2H), 3.44-3.36 (m, 2H), 3.31-3.24 (m, 2H), 3.19 (s, 3H), 3.00-2.91 (m, 1H), 2.90-2.74 (m, 5H), 2.71-2.54 (m, 2H), 2.29-2.21 (m, 1H), 2.17-2.05 (m, 2H), 1.98-1.85 (m, 4H), 1.77-1.72 (m, 3H), 1.69-1.60 (m, 1H), 1.46 (d, J=6.0 Hz, 3H), 1.07 (t, J=6.4 Hz, 3H), 0.96 (d, J=6.4 Hz, 3H), 0.91 (d, J=7.6 Hz, 3H), 0.83-0.58 (m, 6H).

Example 18. Synthesis of (2S)—N-[(6S,8S,14S,20M)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.$1^{2,6}$.$1^{10,14}$.$0^{23,27}$]nonacosa-1(26),20,23(27),24-tetraen-8-yl]-3-methyl-2-{methyl[7-(prop-2-enoyl)-5-oxa-2,7-diazaspiro[3.4]octane-2-carbonyl]amino}butanamide

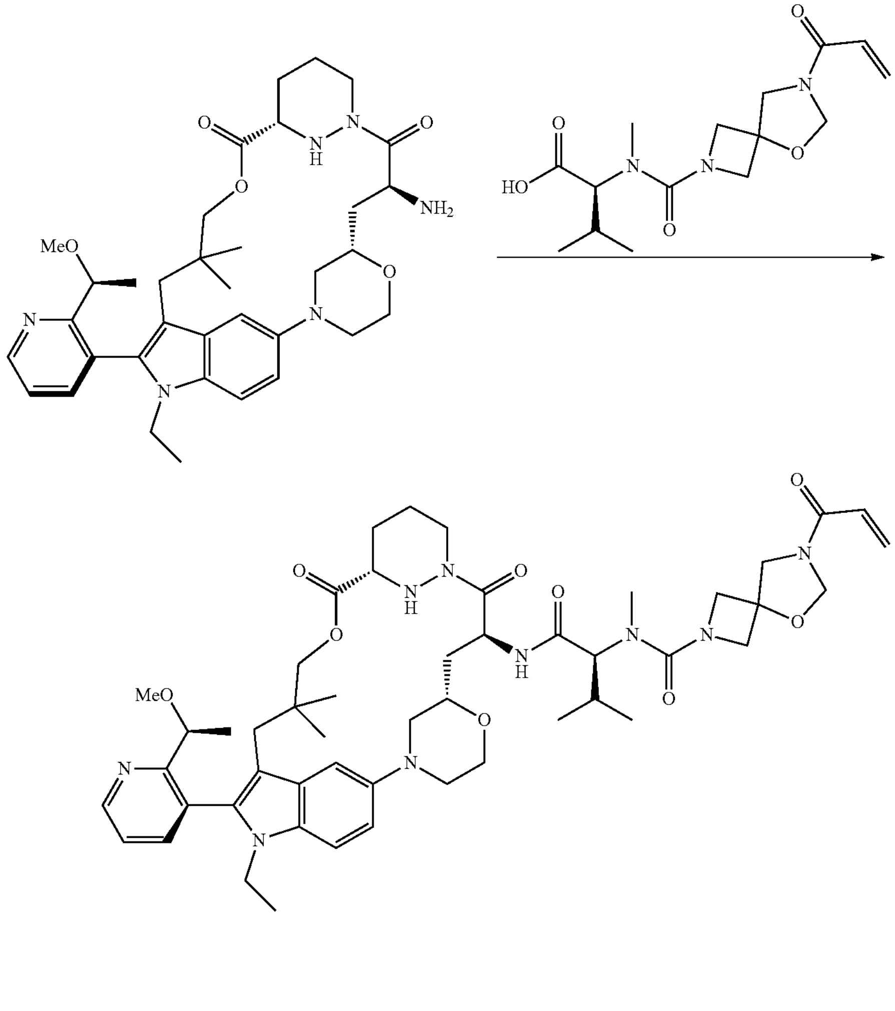

To a solution of the (6S,8S,14S)-8-amino-22-ethyl-21-{2-[(1S)-1-methoxyethyl]pyridin-3-yl}-18,18-dimethyl-5,16-dioxa-2,10,22,28-tetraazapentacyclo[18.5.2.1^{2,6}.1^{10,14}.0^{23,27}]nonacosa-1(26),20,23(27),24-tetraene-9,15-dione (250 mg, 0.40 mmol, 1.0 equiv) and (2S)-3-methyl-2-{methyl[7-(prop-2-enoyl)-5-oxa-2,7-diazaspiro[3.4]octan-2-yl]carbonylamino}butanoic acid (200 mg, 0.60 mmol, 1.5 equiv) in DMF (4 mL) was added HATU (180 mg, 0.47 mmol, 1.2 equiv) and DIEA (766 mg, 5.2 mmol, 15 equiv) dropwise at 0° C. The reaction mixture was stirred at 0° C. for 1 h. The solution was purified by chromatography to afford (2S)—N-[(6S,8S,14S,20M)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.$1^{2,6}$.$1^{10,14}$.$0^{23,27}$]nonacosa-1(26),20,23(27),24-tetraen-8-yl]-3-methyl-2-{methyl[7-(prop-2-enoyl)-5-oxa-2,7-diazaspiro[3.4]octane-2-carbonyl]amino}butanamide (124.3 mg, yield: 33%) as a white solid. ESI-MS m/z=940.5[M+H]$^+$; Calculated MW: 939.52 $^1$H NMR (400 MHz, $CD_3OD$) δ 8.71 (dd, J=4.8, 1.6 Hz, 1H), 7.86 (dd, J=7.6, 1.6 Hz, 1H), 7.51 (dd, J=7.6, 4.8 Hz, 1H), 7.39 (d, J=8.8 Hz, 1H), 7.16-7.05 (m, 2H), 6.61-6.27 (m, 2H), 5.86-5.76 (m, 1H), 5.67-5.58 (m, 1H), 5.18 (s, 1H), 5.09 (s, 1H), 4.46 (d, J=11.6 Hz, 1H), 4.29-4.19 (m, 3H), 4.18-4.10 (m, 3H), 4.07 (d, J=9.6 Hz, 1H), 3.99-3.90 (m, 3H), 3.89-3.82 (m, 1H), 3.82-3.78 (m, 2H), 3.77-3.66 (m, 2H), 3.54 (d, J=11.6 Hz, 1H), 3.16 (s, 3H), 2.94 (t, J=10.8 Hz, 1H), 2.85-2.74 (m, 5H), 2.71-2.64 (m, 1H), 2.63-2.49 (m, 1H), 2.26-2.16 (m, 1H), 2.15-2.05 (m, 2H), 1.92 (d, J=14.8 Hz, 2H), 1.81-1.69 (m, 1H), 1.68-1.56 (m, 1H), 1.44 (d, J=6.4 Hz, 3H), 1.33 (d, J=6.4 Hz, 2H), 1.04 (t, J=6.8 Hz, 3H), 0.95 (d, J=6.4 Hz, 3H), 0.88 (d, J=6.4 Hz, 3H), 0.76 (s, 3H), 0.68 (s, 3H).

Example 19. Synthesis of (2S)—N-[(6S,8S,14S,20M)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.$1^{2,6}$.$1^{10,14}$.$0^{23,27}$]nonacosa-1(26),20,23(27),24-tetraen-8-yl]-3-methyl-2-{methyl[(5S)-3-(prop-2-enoyl)-1-oxa-3,7-diazaspiro[4.4]nonane-7-carbonyl]amino}butanamide

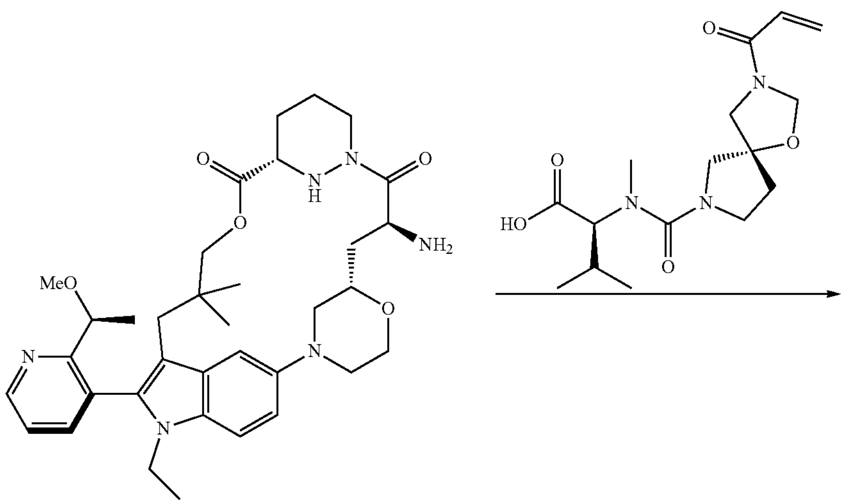

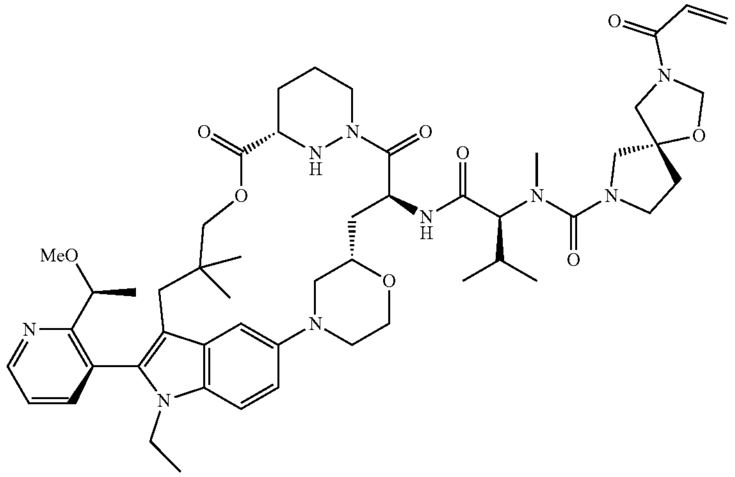

To a solution of the (6S,8S,14S)-8-amino-22-ethyl-21-{2-[(1S)-1-methoxyethyl]pyridin-3-yl}-18,18-dimethyl-5,16-dioxa-2,10,22,28-tetraazapentacyclo[18.5.2.1^{2,6}.1^{10,14}.0{23,27}]nonacosa-1(26),20,23(27),24-tetraene-9,15-dione (160 mg, 0.25 mmol, 1.0 equiv) and (2S)-3-methyl-2-{methyl[(5S)-3-(prop-2-enoyl)-1-oxa-3,7-diazaspiro[4.4]nonan-7-yl]carbonylamino}butanoic acid (137 mg, 0.4 mmol, 1.6 equiv) in DMF (4 mL) was added HATU (115 mg, 0.3 mmol, 1.2 equiv) and DIEA (490 mg, 3.7 mmol, 15.0 equiv) dropwise at 0° C. The reaction mixture was stirred at 0° C. for 1 h. The solution was purified by chromatography to afford (2S)—N-[(6S,8S,14S,20M)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1$^{2,6}$.1$^{10,14}$.0$^{23,27}$]nonacosa-1(26),20,23(27),24-tetraen-8-yl]-3-methyl-2-{methyl[(5S)-3-(prop-2-enoyl)-1-oxa-3,7-diazaspiro[4.4]nonane-7-carbonyl]amino}butanamide (65.5 mg, yield: 27%) as white solid. ESI-MS m/z=954.5[M+H]$^+$; Calculated MW: 953.54. $^1$H NMR (400 MHz, $CD_3OD$ δ 8.71 (dd, J=4.8, 1.6 Hz, 1H), 7.86 (dd, J=7.6, 1.6 Hz, 1H), 7.51 (dd, J=7.6, 4.8 Hz, 1H), 7.39 (d, J=8.8 Hz, 1H), 7.16-7.02 (m, 2H), 6.61-6.36 (m, 1H), 6.36-6.27 (m, 1H), 5.83-5.76 (m, 1H), 5.64 (d, J=7.6 Hz, 1H), 5.21 (dd, J=11.2, 4.0 Hz, 1H), 5.11 (q, J=6.0 Hz, 1H), 4.47 (d, J=12.0 Hz, 1H), 4.25-4.18 (m, 1H), 4.17-4.12 (m, 1H), 4.04 (d, J=11.2 Hz, 1H), 3.97-3.64 (m, 11H), 3.55 (d, J=11.6 Hz, 1H), 3.50-3.40 (m, 2H), 3.26 (s, 1H), 3.15 (s, 3H), 2.98-2.75 (m, 6H), 2.68-2.49 (m, 2H), 2.25-2.15 (m, 2H), 2.15-2.01 (m, 3H), 1.92 (d, J=14.8 Hz, 2H), 1.81-1.59 (m, 2H), 1.44 (d, J=6.0 Hz, 3H), 1.05 (t, J=6.4 Hz, 3H), 1.00-0.85 (m, 6H), 0.80-0.60 (m, 6H).

Example 20. Synthesis of Synthesis of (2S)—N-[(6S,8S,14S,20M)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1$^{2,6}$.1$^{10,14}$.0$^{23,27}$]nonacosa-1(26),20,23(27),24-tetraen-8-yl]-3-methyl-2-{methyl[(5R)-3-(prop-2-enoyl)-1-oxa-3,7-diazaspiro[4.4]nonane-7-carbonyl]amino}butanamide

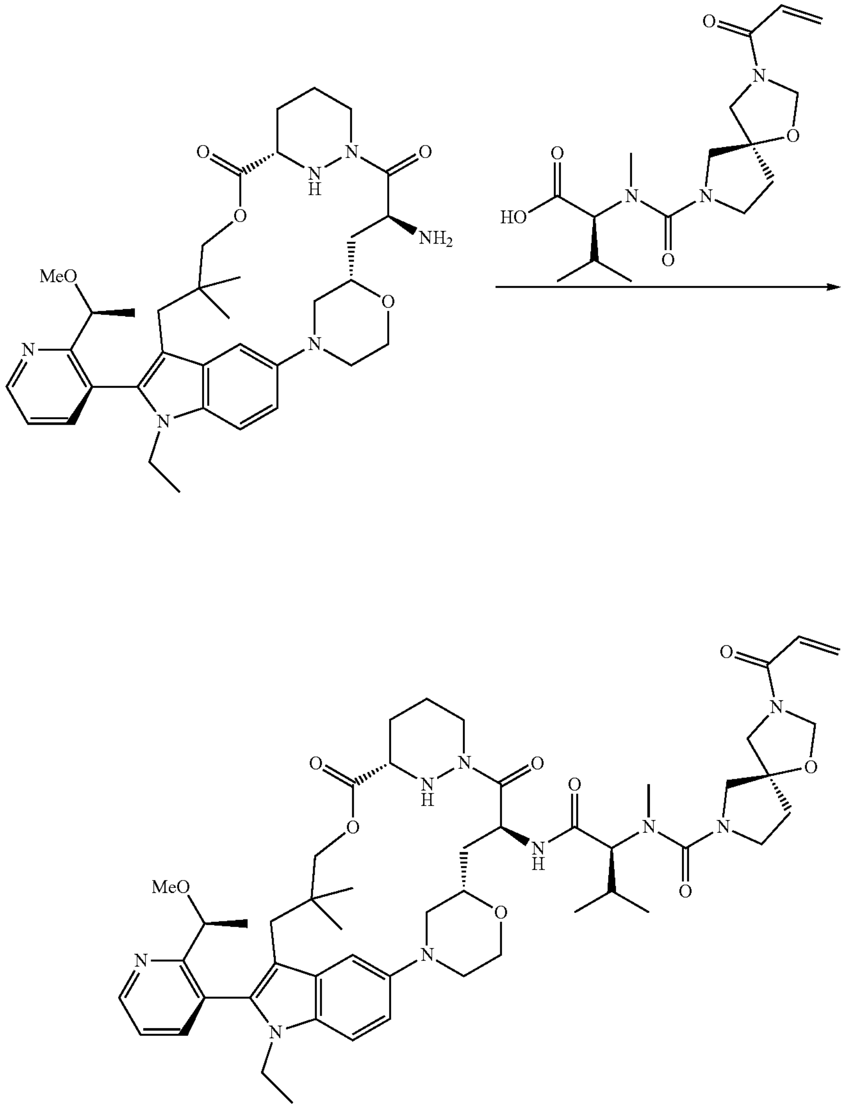

To a solution of (6S,8S,14S)-8-amino-22-ethyl-21-{2-[(1S)-1-methoxyethyl]pyridin-3-yl}-18,18-dimethyl-5,16-dioxa-2,10,22,28-tetraazapentacyclo[18.5.2.1^{2,6}.1^{10,14}.0^{23,27}]nonacosa-1(26),20,23(27),24-tetraene-9,15-dione (160 mg, 0.25 mmol, 1.0 equiv) and (2S)-3-methyl-2-{methyl[3-(prop-2-enoyl)-1-oxa-3,7-diazaspiro[4.4]nonan-7-yl]carbonylamino}butanoic acid (103 mg, 0.30 mmol, 1.2 equiv) and DIPEA (653 mg, 5.1 mmol, 20 equiv) in DMF (1 mL) was added HATU (96 mg, 0.25 mmol, 1.0 equiv) at 0° C., then the mixture was stirred at 0-5° C. for 1 h. The mixture was diluted with EA (20 mL), then washed with water (20 mL*2) and brine (20 mL). The organic phase was collected, dried over $Na_2SO_4$, filtered and concentrated. The resulting residue was purified by chromatography to afford (2S)—N-[(6S,8S,14S)-22-ethyl-21-{2-[(1S)-1-methoxyethyl]pyridin-3-yl}-18,18-dimethyl-9,15-dioxo-5,16-dioxa-2,10,22,28-tetraazapentacyclo[18.5.2.1{2,6}.1^{10,14}.0^{23,27}]nonacosa-1(26),20,23(27),24-tetraen-8-yl]-3-methyl-2-{methyl[(5R)-3-(prop-2-enoyl)-1-oxa-3,7-diazaspiro[4.4]nonan-7-yl]carbonylamino}butanamide (92 mg, 38% yield) as an off-white solid. ESI-MS m/z: 954.4 $[M+H]^+$. Calculated MW: 953.54. 1H NMR (400 MHz, MeOD) δ 8.72-8.70 (m, 1H), 7.85-7.82 (m, 1H), 7.51-7.51 (m, 1H), 7.38 (d, J=8.8 Hz, 1H), 7.15-7.01 (m, 2H), 6.59-6.41 (m, 1H), 6.35-6.27 (m, 1H), 5.85-5.73 (m, 1H), 5.64 (d, J=8.8 Hz, 1H), 5.19-5.10 (m, 1H), 5.10 (s, 1H), 4.46 (d, J=12.0 Hz, 1H), 4.23-4.11 (m, 2H), 3.92-3.82 (m, 7H), 3.76-3.63 (m, 4H), 3.50-3.49 (m, 4H), 3.26 (s, 1H), 3.15 (s, 3H), 2.95-2.74 (m, 1H), 2.88-2.73 (m, 5H), 2.65-2.54 (m, 2H), 2.29-2.18 (m, 1H), 2.23-2.02 (m, 4H), 1.92 (d, J=14.8 Hz, 2H), 1.73-1.62 (m, 2H), 1.43 (d, J=6.4 Hz, 3H), 1.10-1.02 (m, 3H), 0.94 (d, J=6.4 Hz, 3H), 0.88 (d, J=6.8 Hz, 3H), 0.60-0.50 (m, 6H).

TABLE 3

Exemplary Compounds Prepared by Methods of the Present Invention

| Ex# | Molecular weight (g/mol) | LCMS (ESI) m/z Found |
|---|---|---|
| A1 | 938.2 | 938.7 |
| A2 | 1080.38 | 1081.1 |
| A3 | 1078.39 | 1078.7 |
| A4 | 1071.378 | 1071.5 |
| A5 | 1109.35 | 1109.8 |
| A6 | 1087.396 | 1087.9 |
| A7 | 1031.164 | 1031.9 |
| A8 | 1055.379 | 1056.7 |
| A9 | 1040.31 | 1040.9 |
| A10 | 966.21 | 966.2 |
| A11 | 1000.29 | 1000.7 |
| A12 | 1006.182 | 1006.9 |
| A13 | 991.219 | 991.9 |
| A14 | 1087.396 | 1087.8 |
| A15 | 1073.369 | 1073.4 |
| A16 | 954.18 | 954.4 |
| A17 | 1047.25 | 1047.6 |
| A18 | 1014.161 | 1014.8 |
| A19 | 959.202 | 959.1 |
| A20 | 968.21 | 968.3 |
| A21 | 940.156 | 940.5 |
| A22 | 1066.306 | 1066.8 |
| A23 | 990.095 | 990.5 |
| A24 | 1010.198 | 1010.8 |
| A25 | 1000.134 | 1000.7 |
| A26 | 1006.182 | 1006.9 |
| A27 | 950.195 | 950.7 |
| A28 | 1033.35 | 1033.4 |
| A29 | 1018.149 | 1018.9 |
| A30 | 1100.315 | 1100.8 |
| A31 | 1016.298 | 1016.8 |
| A32 | 1069.285 | 1069.6 |

TABLE 3-continued

Exemplary Compounds Prepared by Methods of the Present Invention

| Ex# | Molecular weight (g/mol) | LCMS (ESI) m/z Found |
|---|---|---|
| A33 | 1018.149 | 1018.7 |
| A34 | 1064.334 | 1065.1 |
| A35 | 1014.326 | 1014.4 |
| A36 | 975.205 | 975.6 |
| A37 | 950.151 | 950.5 |
| A38 | 1009.307 | 1009.2 |
| A39 | 1065.322 | 1065.6 |
| A40 | 945.175 | 945.8 |
| A41 | 982.237 | 982.8 |
| A42 | 982.237 | 982.3 |
| A43 | 1092.397 | 1092.6 |
| A44 | 1066.359 | 1065.6 |
| A45 | 931.148 | 931.7 |
| A46 | 996.264 | 996.8 |
| A47 | 978.249 | 978.2 |
| A48 | 982.237 | 982.8 |
| A49 | 977.192 | 977.5 |
| A50 | 1083.389 | 1083.9 |
| A51 | 1031.357 | 1031.5 |
| A52 | 1062.371 | 1062.5 |
| A53 | 1097.416 | 1098.0 |
| A54 | 1019.346 | 1019.6 |
| A55 | 977.265 | 977.5 |
| A56 | 1019.346 | 1019.5 |
| A57 | 972.245 | 972.7 |
| A58 | 978.249 | 978.8 |
| A59 | 1049.251 | 1049.5 |
| A60 | 1111.443 | 1112.1 |
| A61 | 949.211 | 949.5 |
| A62 | 1097.416 | 1097.9 |
| A63 | 978.249 | 978.8 |
| A64 | 978.249 | 978.8 |
| A65 | 963.238 | 963.45 |
| A66 | 1006.182 | 1006.8 |
| A67 | 991.292 | 991.6 |
| A68 | 1000.227 | 1000.6 |
| A69 | 1021.318 | 1021.5 |
| A70 | 963.238 | 963.4 |
| A71 | 952.211 | 952.6 |
| A72 | 1023.309 | 1023.6 |
| A73 | 995.28 | 995.5 |
| A74 | 1017.33 | 1017.6 |
| A75 | 1060.399 | 1060.6 |
| A76 | 1041.3 | 1041.6 |
| A77 | 1035.345 | 1035.5 |
| A78 | 950.151 | 950.7 |
| A79 | 1018.149 | 1018.7 |
| A80 | 1023.334 | 1023.6 |
| A81 | 1005.319 | 1005.5 |
| A82 | 1023.334 | 1023.6 |
| A83 | 1100.464 | 1100.6 |
| A84 | 1009.307 | 1009.5 |
| A85 | 1114.37 | 1114.6 |
| A86 | 1032.316 | 1032.9 |
| A87 | 1027.297 | 1027.5 |
| A88 | 992.276 | 992.8 |
| A89 | 1057.323 | 1057.8 |
| A90 | 1008.275 | 1008.8 |
| A91 | 945.175 | 945.9 |
| A92 | 1037.34 | 1037.9 |
| A93 | 978.249 | 978.8 |
| A94 | 1006.182 | 1006.8 |
| A95 | 1034.288 | 1034.9 |
| A96 | 1059.29 | 1059.6 |
| A97 | 1063.38 | 1063.9 |
| A98 | 1012.263 | 1012.8 |
| A99 | 1064.36 | 1064.8 |
| A100 | 1050.33 | 1050.8 |
| A101 | 1062.39 | 1062.9 |
| A102 | 1064.36 | 1064.8 |
| A103 | 1034.34 | 1034.8 |
| A104 | 929.176 | 929.8 |

TABLE 3-continued

| Exemplary Compounds Prepared by Methods of the Present Invention | | |
|---|---|---|
| Ex# | Molecular weight (g/mol) | LCMS (ESI) m/z Found |
| A105 | 952.19 | 952.3 |
| A106 | 1002.219 | 1002.5 |
| A107 | 1029.192 | 1029.6 |
| A108 | 954.183 | 954.4 |
| A109 | 1004.166 | 1004.8 |
| A110 | 1062.342 | 1062.9 |
| A111 | 1030.325 | 1030.9 |
| A112 | 1104.452 | 1104.5 |
| A113 | 888.083 | 888.4 |
| A114 | 954.183 | 954.5 |
| A115 | 1081.321 | 1081.9 |
| A116 | 992.155 | 992.7 |
| A117 | 1061.28 | 1062.7 |
| A118 | 995.211 | 995.4 |
| A119 | 979.26 | 979.9 |
| A120 | 1080.333 | 1080.8 |
| A121 | 952.211 | 952.4 |
| A122 | 1065.39 | 1065.8 |
| A123 | 938.115 | 938.8 |
| A124 | 974.217 | 974.7 |
| A125 | 1096.404 | 1097.0 |
| A126 | 1090.425 | 1090.7 |
| A127 | 995.211 | 995.8 |
| A128 | 984.228 | 984.5 |
| A129 | 1045.288 | 1045.6 |
| A130 | 996.264 | 996.5 |
| A131 | 1021.34 | 1021.3 |
| A132 | 955.16 | 955.4 |
| A133 | 986.272 | 986.8 |
| A134 | 1085.284 | 1085.8 |
| A135 | 935.155 | 935.5 |
| A136 | 954.183 | 954.7 |
| A137 | 1101.35 | 1101.9 |
| A138 | 1048.315 | 1048.9 |
| A139 | 994.227 | 994.7 |
| A140 | 992.155 | 992.7 |
| A141 | 1028.34 | 1029.5 |
| A142 | 977.192 | 977.7 |
| A143 | 1058.3 | 1058.7 |
| A144 | 1047.37 | 1047.9 |
| A145 | 1026.309 | 1026.5 |
| A146 | 938.2 | 938.4 |
| A147 | 1010.291 | 1010.5 |
| A148 | 1060.34 | 1060.4 |
| A149 | 934.123 | 934.7 |
| A150 | 1094.41 | 1095.0 |
| A151 | 976.25 | 976.5 |
| A152 | 1047.37 | 1047.8 |
| A153 | 938.2 | 938.4 |
| A154 | 997.24 | 997.5 |
| A155 | 1068.334 | 1068.9 |
| A156 | 1063.278 | 1063.5 |
| A157 | 1148.38 | 1148.5 |
| A158 | 1116.36 | 1116.6 |
| A159 | 992.276 | 992.5 |
| A160 | 950.21 | 950.5 |
| A161 | 1103.32 | 1104.0 |
| A162 | 1047.37 | 1047.6 |
| A163 | 1038.223 | 1038.8 |
| A164 | 938.2 | 938.5 |
| A165 | 1069.241 | 1069.6 |
| A166 | 1019.2 | 1019.7 |
| A167 | 1060.34 | 1060.4 |
| A168 | 950.21 | 950.9 |
| A169 | 931.192 | 931.5 |
| A170 | 950.21 | 950.8 |
| A171 | 955.27 | 955.5 |
| A172 | 1103.395 | 1103.6 |
| A173 | 1118.358 | 1118.4 |
| A174 | 1118.358 | 1118.4 |
| A175 | 955.27 | 955.5 |
| A176 | 1082.27 | 1082.4 |

TABLE 3-continued

| Exemplary Compounds Prepared by Methods of the Present Invention | | |
|---|---|---|
| Ex# | Molecular weight (g/mol) | LCMS (ESI) m/z Found |
| A177 | 964.222 | 964.4 |
| A178 | 964.222 | 964.4 |
| A179 | 1080.386 | 1080.4 |
| A180 | 1064.387 | 1064.4 |
| A181 | 1064.387 | 1064.4 |
| A182 | 979.184 | 979.5 |
| A183 | 1048.315 | 1048.8 |
| A184 | 950.21 | 950.7 |
| A185 | 986.272 | 986.9 |
| A186 | 996.264 | 996.3 |
| A187 | 1037.268 | 1037.7 |
| A188 | 1041.231 | 1041.7 |
| A189 | 995.28 | 995.9 |
| A190 | 1037.316 | 1037.8 |
| A191 | 975.205 | 975.8 |
| A192 | 1019.346 | 1019.8 |
| A193 | 978.249 | 978.7 |
| A194 | 1005.319 | 1005.6 |
| A195 | 977.265 | 977.6 |
| A196 | 978.249 | 978.7 |
| A197 | 991.292 | 991.4 |
| A198 | 1018.289 | 1018.9 |
| A199 | 981.253 | 981.5 |
| A200 | 1036.28 | 1036.9 |
| A201 | 1035.345 | 1035.5 |
| A202 | 1004.262 | 1004.5 |
| A203 | 981.253 | 981.5 |
| A204 | 1119.414 | 1119.9 |
| A205 | 980.265 | 980.5 |
| A206 | 1021.318 | 1021.6 |
| A207 | 1039.333 | 1039.5 |
| A208 | 993.28 | 993.8 |
| A209 | 1141.368 | 1141.8 |

Matched Pair Analysis

Figure 1B:
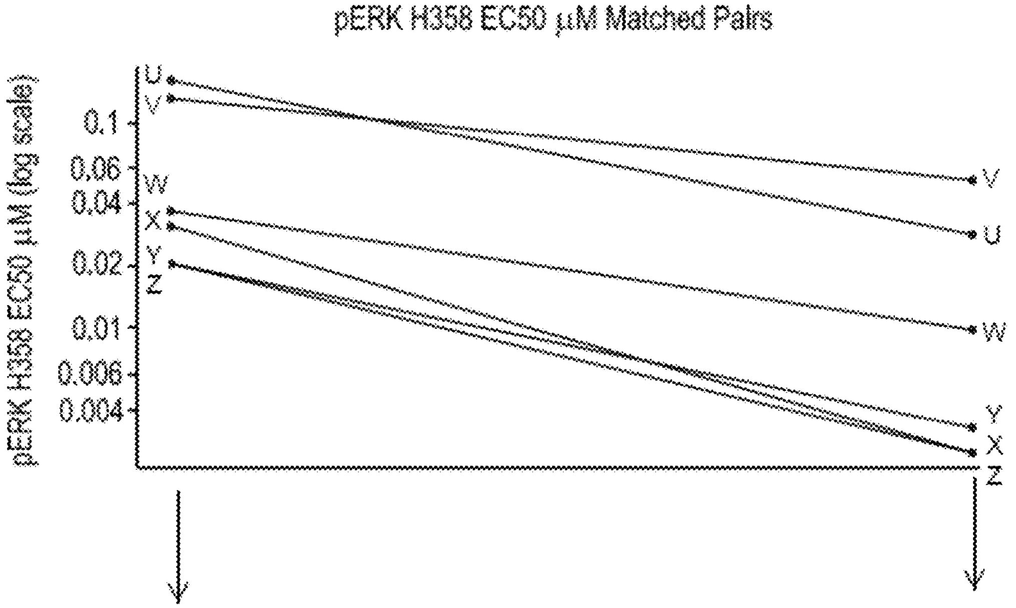
Figure 1B:
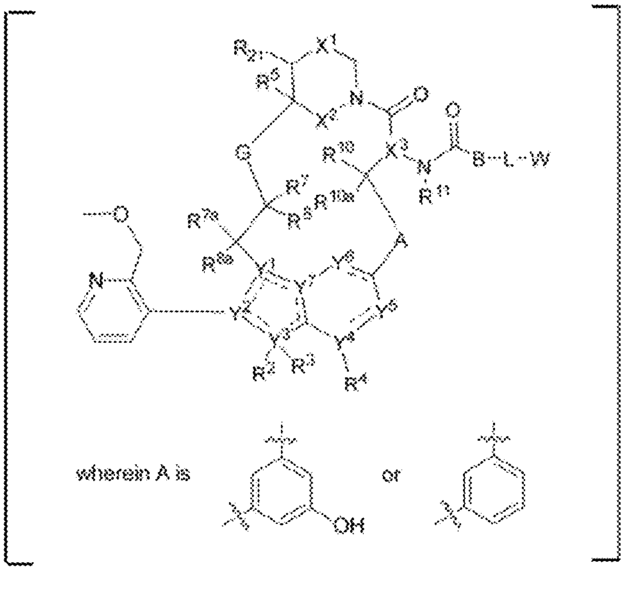
Figure 1B:
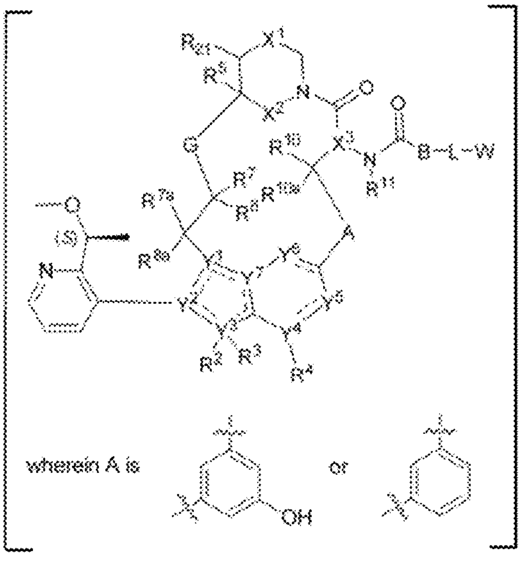

FIGS. 1A-1B compare the potency in two different cell-based assays of compounds of Formula BB (points on the right) and corresponding compounds of Formula AA (points on the left) wherein a hydrogen (in Formula AA) is replaced with (S)Me (in Formula BB). The y axes represent pERK EC50 (FIG. 1A) or CTG IC50 (FIG. 1B) as measured in an H358 cell line. Assay protocols are below. The linked points represent a matched pair that differs only between H and (S)Me substitution. Unexpectedly, each compound of Formula BB demonstrated increased potency in cell assays compared to the corresponding compound of Formula AA.

Stereoisomers

Compounds of Formula I of the present invention may form stereoisomers (e.g., enantiomers, diastereomers, or atropisomers). Certain stereoisomers of compounds of the present invention (e.g., compounds of Formula Ia) may have improved biological activity (e.g., a lower IC50 in a K-Ras G12C or K-Ras G13C pERK potency assay, a lower IC50 in a cell viability assay, a lower IC50 in a Raf-Ras binding assay, a greater cross-linking percent in a K-Ras G12C or K-Ras G13C cross-linking assay, any improved activity as measured by the biological assays described herein, or a combination of such properties) over other isomers. It is therefore desirable to produce preparations having increased stereochemical purity.

Atropisomer Separation

Figure 2A:
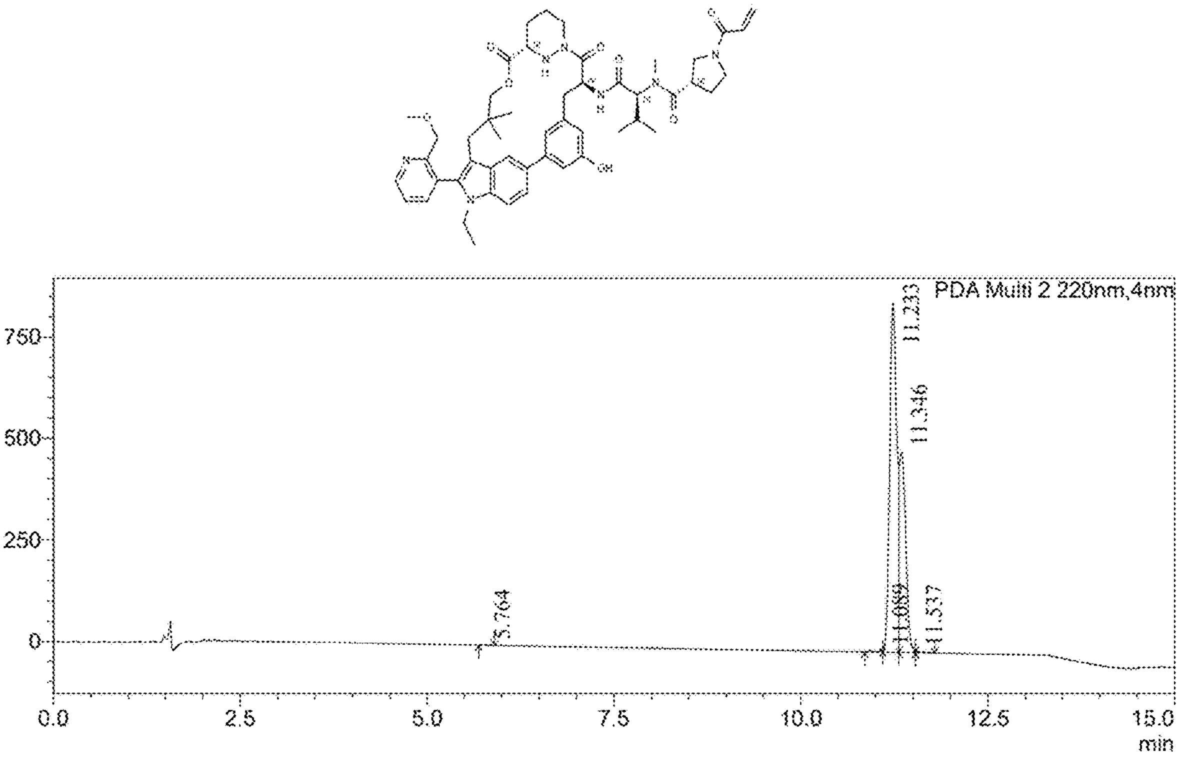
FIGS. 2A-2C: HPLC traces showing that a compound of Formula AA gives inseparable diastereomers having retention times of 11.233 minutes and 11.346 minutes (FIG. 2A). By contrast, addition of a methyl group to form a compound of Formula BB allows for facile separation of the diastereomers, with one diastereomer having a retention time of 11.364 minutes (FIG. 2B) and the other diastereomer having a retention time of 10.045 minutes (FIG. 2C). The structure of the compounds are shown above each HPLC trace.
Figure 2B:
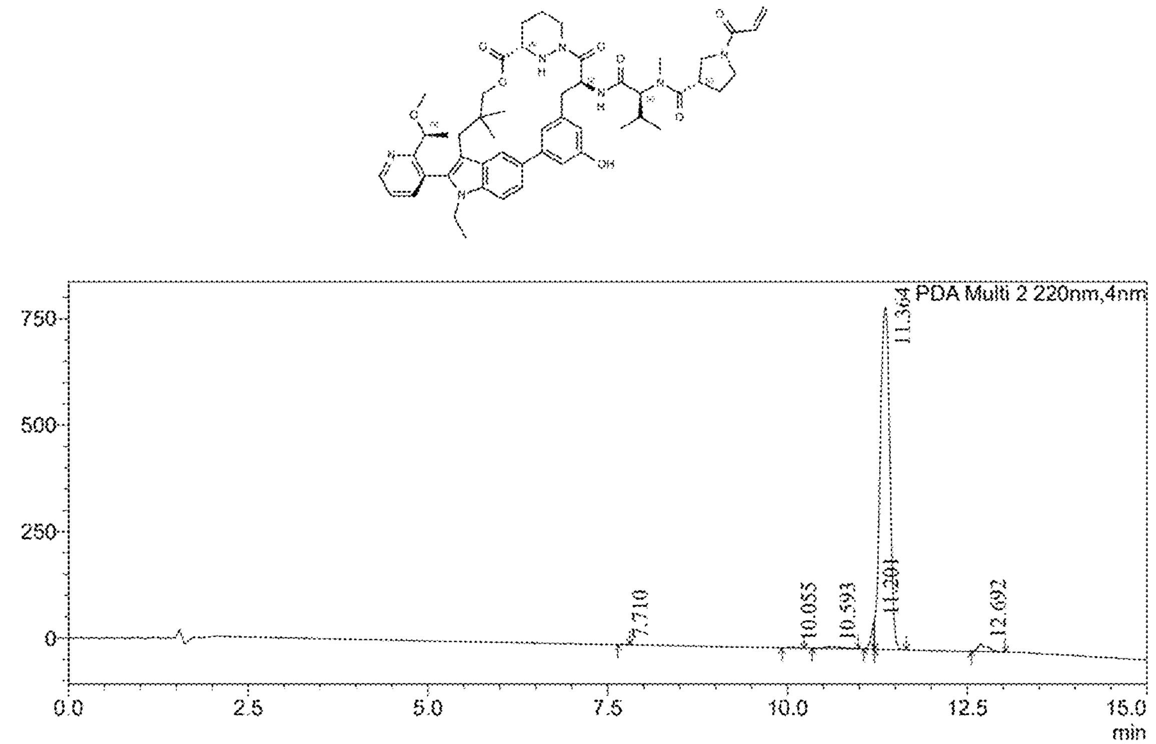
Figure 2C:
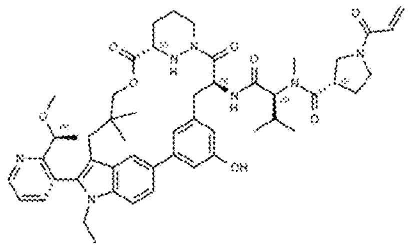
Figure 2C:
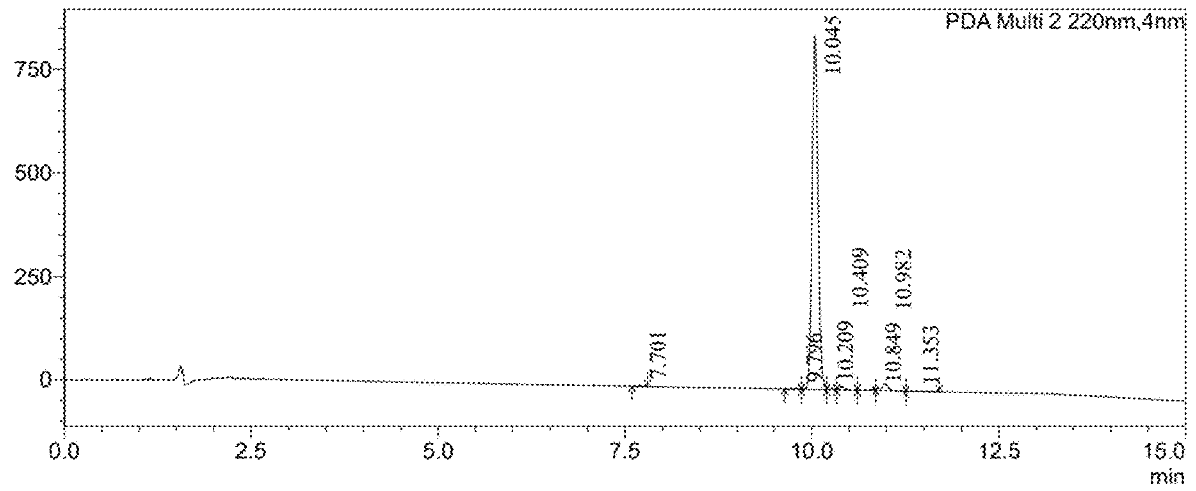

Addition of a methyl group (e.g., a compound of Formula BB in FIG. 1A or FIG. 1B) produced the unexpected benefit of allowing for atropisomer separation. As shown in FIG. 2A, a compound of Formula AA (containing a hydrogen only) shows 2 overlapping, inseparable atropisomers. Addition of a methyl group to form a compound of Formula BB allows for the atropisomers to be readily separated by conventional chromatography methods (FIG. 2B). Given that the compounds were already diastereomeric, it was unexpected that the addition of another stereogenic carbon (by addition of the methyl group) allowed for facile separation.

Furthermore, the presence of the methyl group in Formula BB allowed for atropisomer separation of Intermediate 1. Intermediate 1 contains diastereomeric atropisomers, which can be separated by conventional means, whereas des-methyl-Intermediate 1 would require arduous separation of enantiomers (e.g., using chiral chromatography).

Intermediate 1

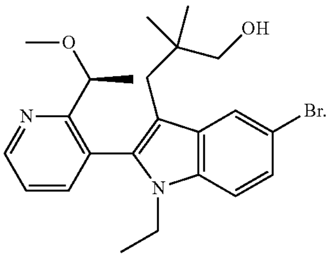

Intermediate 1

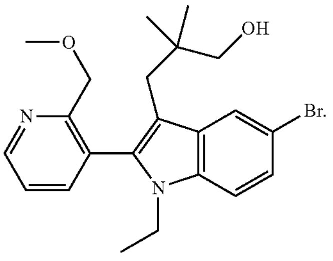

Des-methyl

Activity of Stereoisomers

Compounds of Formula I may form atropisomers that differ in the stereochemistry of the pyridyl group, as shown in Formula CC and Formula DD.

Formula CC

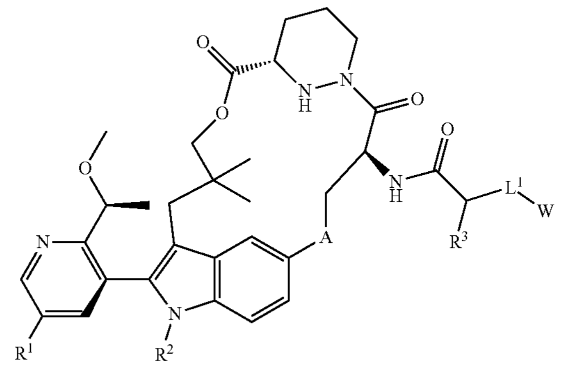

Formula DD

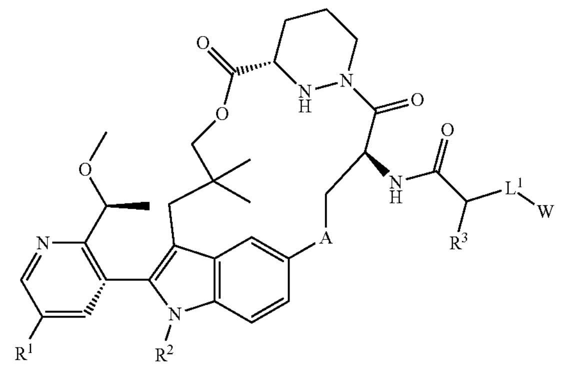

Atropisomers of Formula CC and Formula DD exhibit different potencies. In general, atropisomers having the pyridyl stereochemistry of Formula CC demonstrate increased potency over the corresponding compounds of Formula DD, as shown in Table 4. All assays in Table 4 are performed in a K-Ras G12C cell line as described herein.

TABLE 4

Atropisomer activity
++ Cmpd of Formula CC is more than 10-fold more potent than Cmpd of Formula DD
+ Cmpd of Formula CC is 1.1-fold to 10-fold more potent than Cmpd of Formula DD
− Cmpd of Formula DD is more potent than Cmpd of Formula CC

| Ex # | Compound of Formula DD |
|---|---|
| 1 | 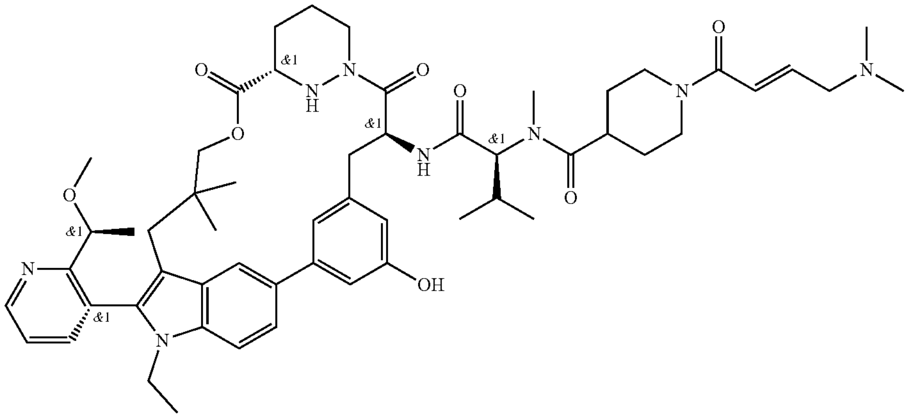 |

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>– Cmpd of Formula DD is more potent than Cmpd of Formula CC |
|---|
| 2 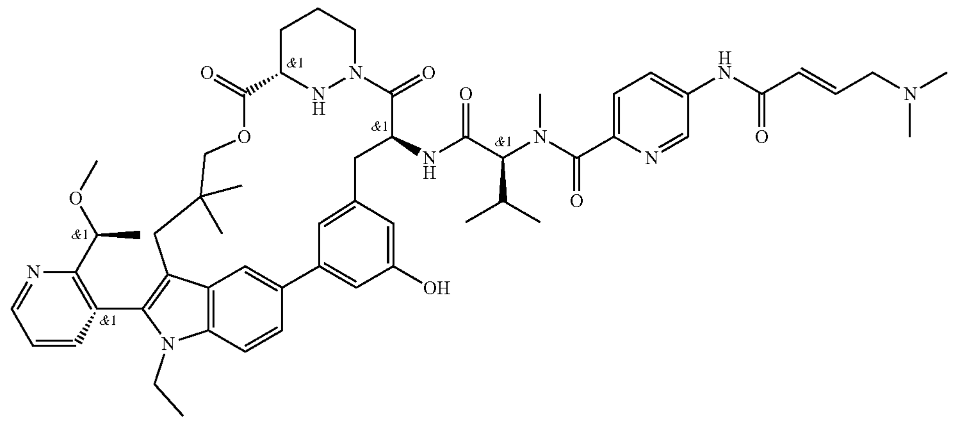 |
| 3 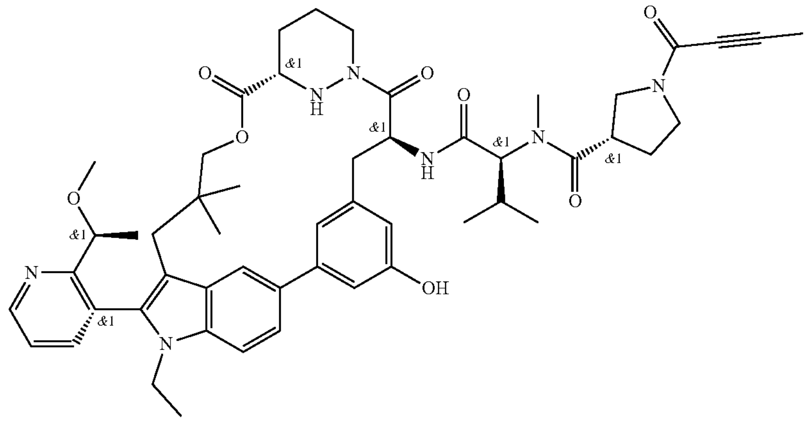 |
| 4 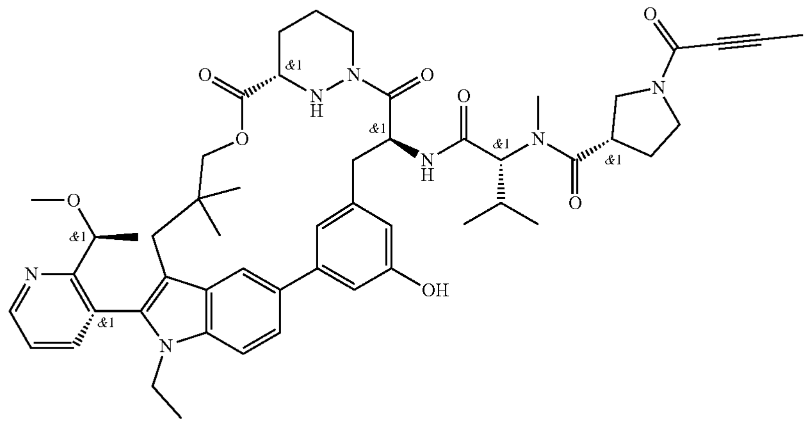 |

TABLE 4-continued
| | Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>– Cmpd of Formula DD is more potent than Cmpd of Formula CC |
|---|---|
| 5 | 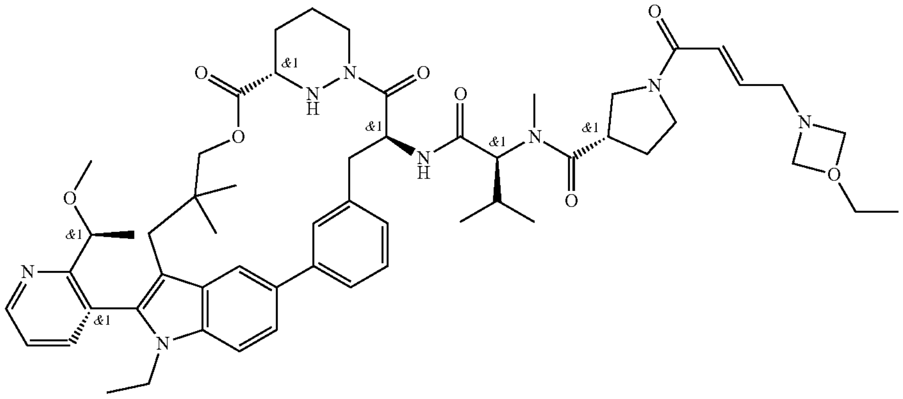 |
| 6 | 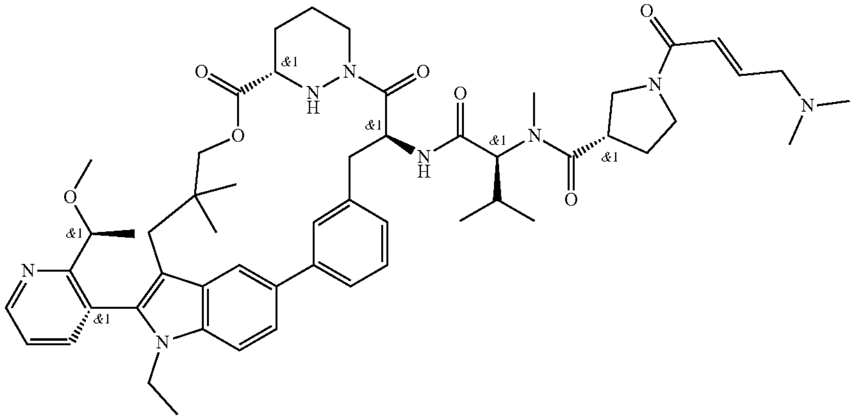 |
| 7 | 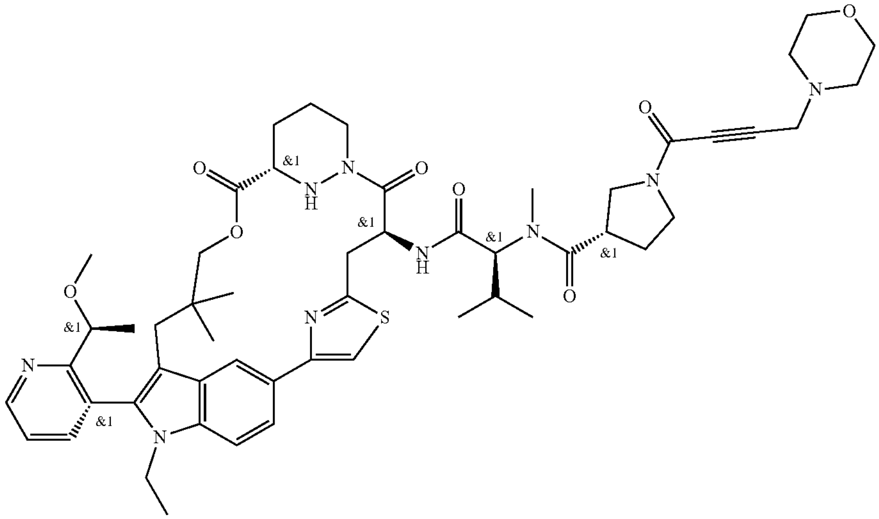 |

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>− Cmpd of Formula DD is more potent than Cmpd of Formula CC |
|---|
8
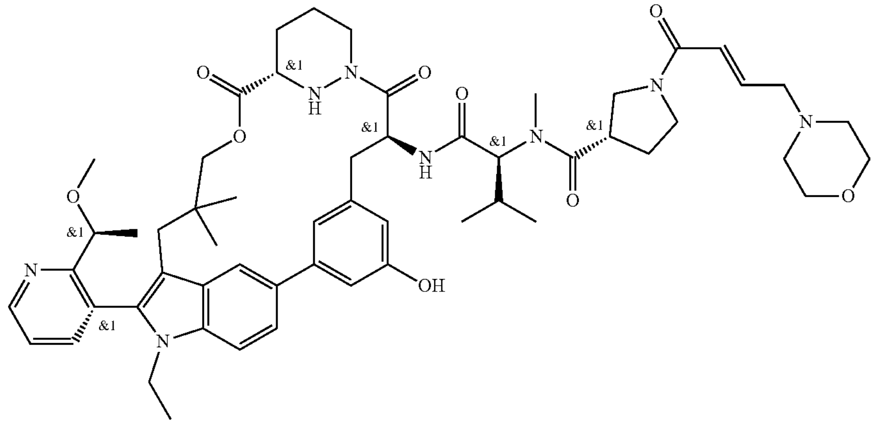
9
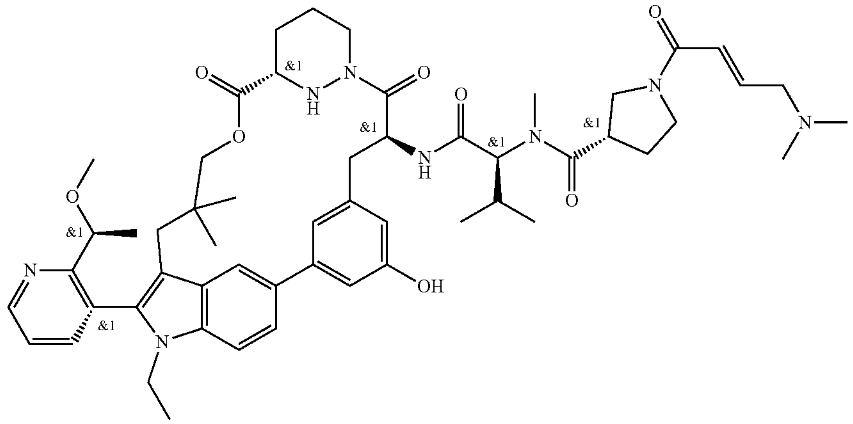
14
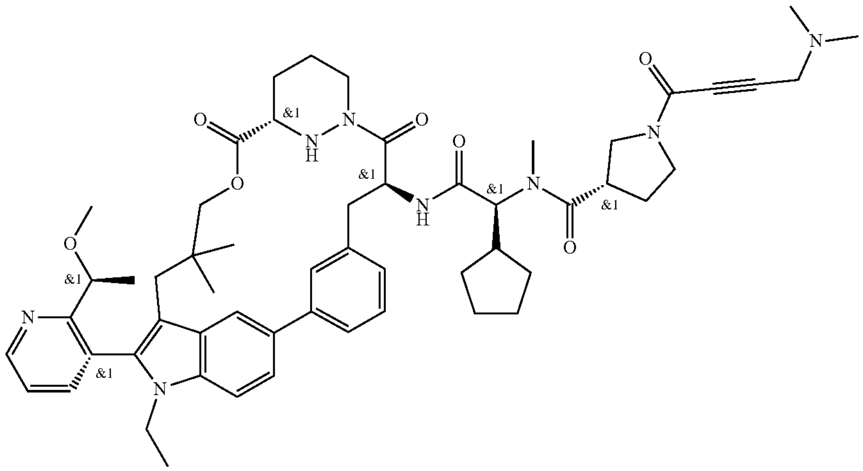

TABLE 4-continued
| Atropisomer activity |
|---|
| ++ Cmpd of Formula CC is more than 10-fold more potent than Cmpd of Formula DD |
| + Cmpd of Formula CC is 1.1-fold to 10-fold more potent than Cmpd of Formula DD |
| – Cmpd of Formula DD is more potent than Cmpd of Formula CC |
15
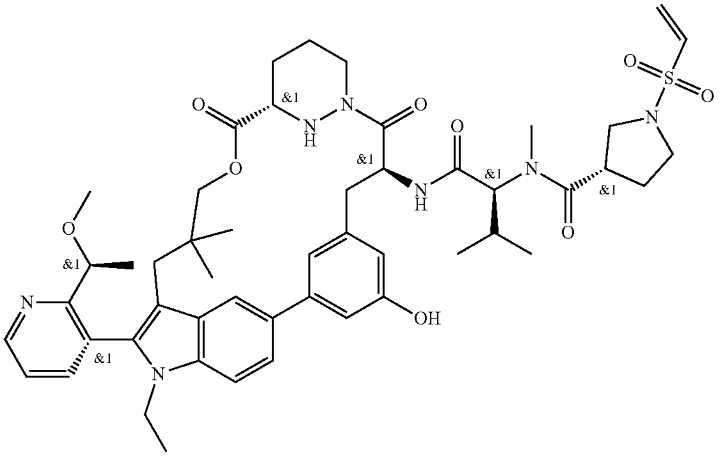
16
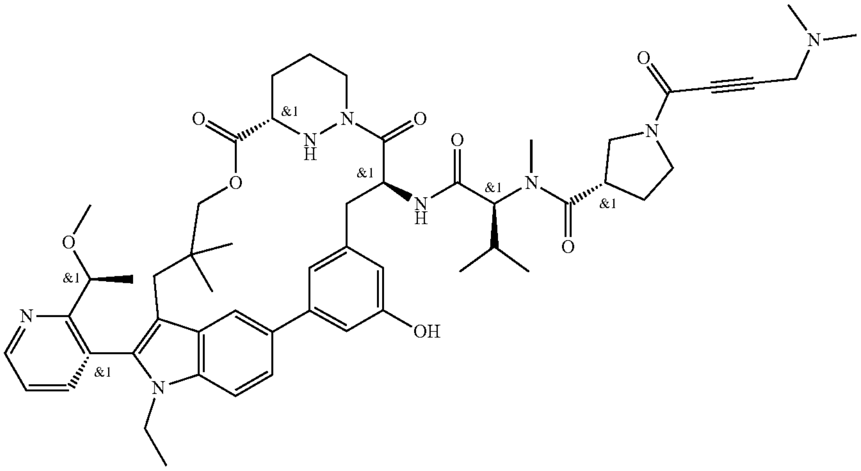
17
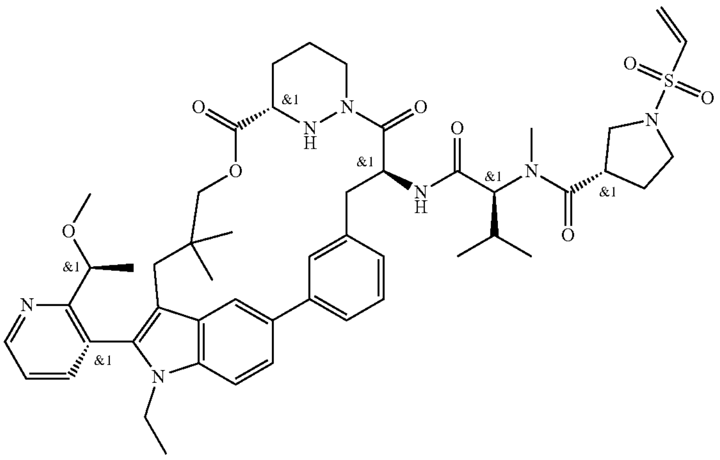

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>− Cmpd of Formula DD is more potent than Cmpd of Formula CC |
|---|
| 18 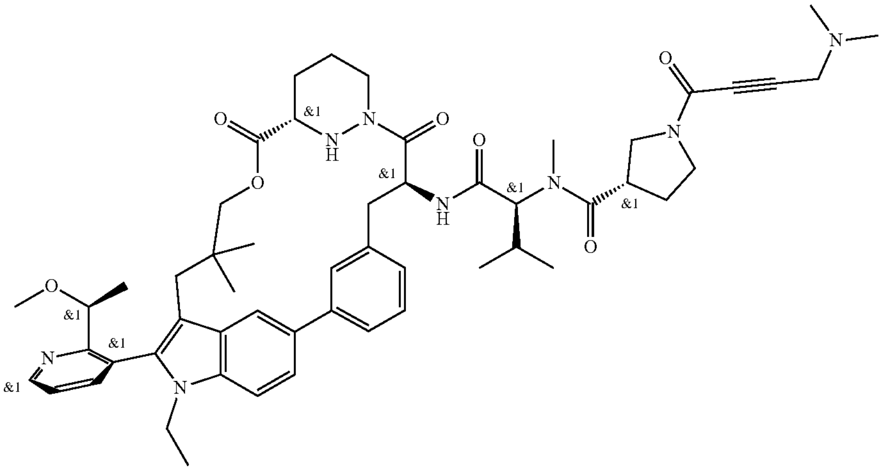 |
| 19 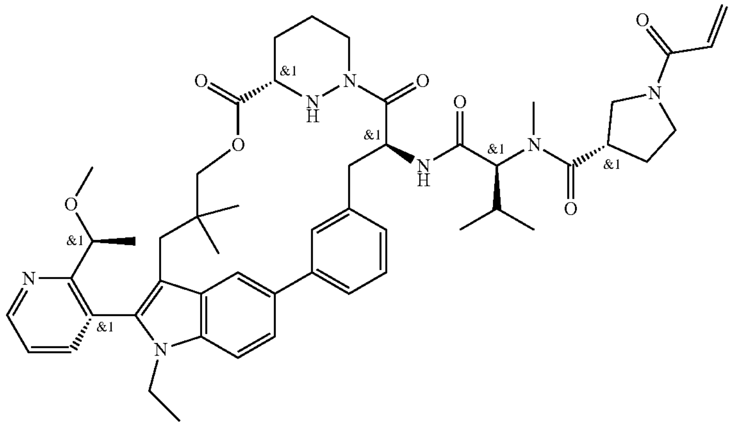 |
| 20 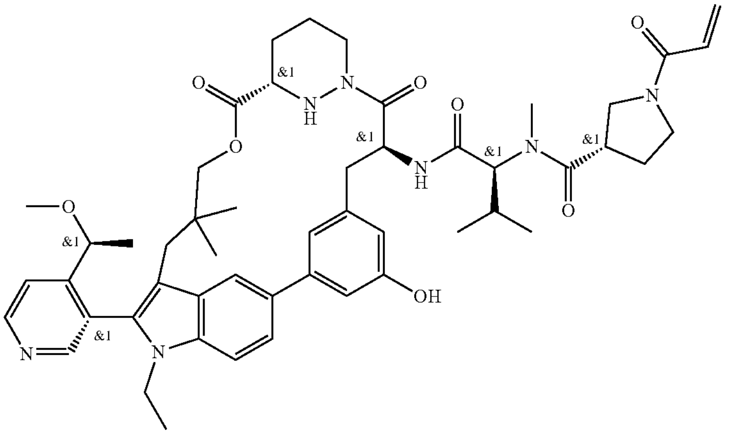 |

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>− Cmpd of Formula DD is more potent than Cmpd of Formula CC |
|---|
17
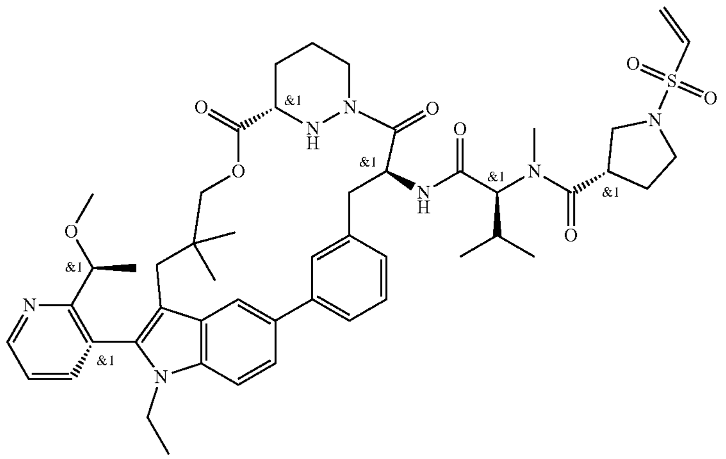
18
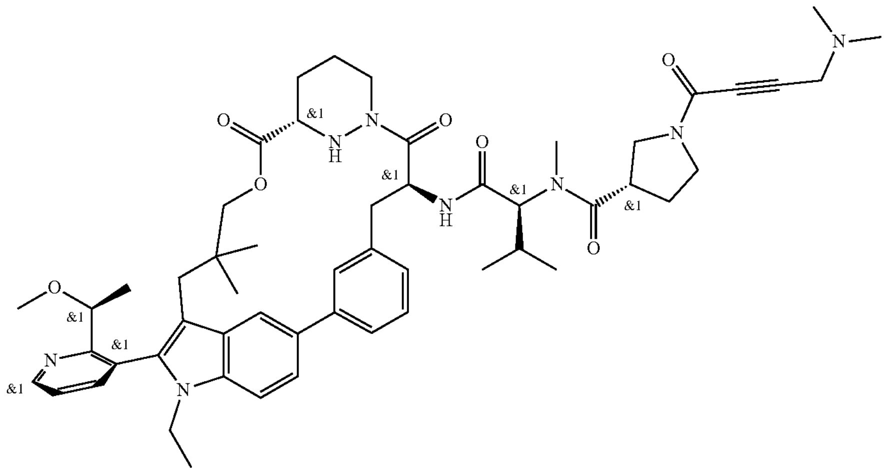
19
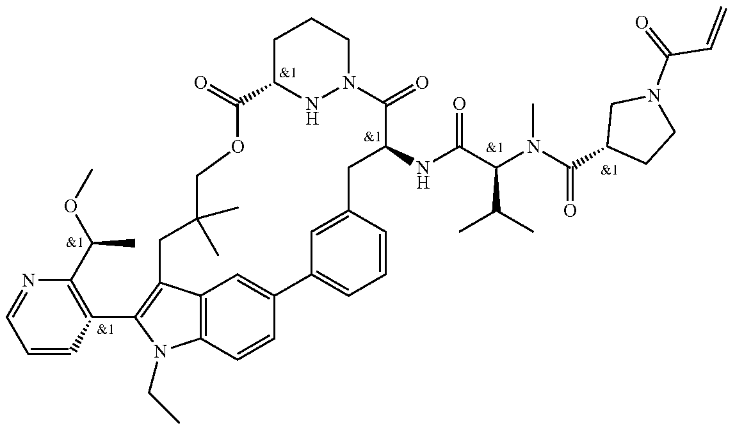

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>– Cmpd of Formula DD is more potent than Cmpd of Formula CC |
|---|
| 20 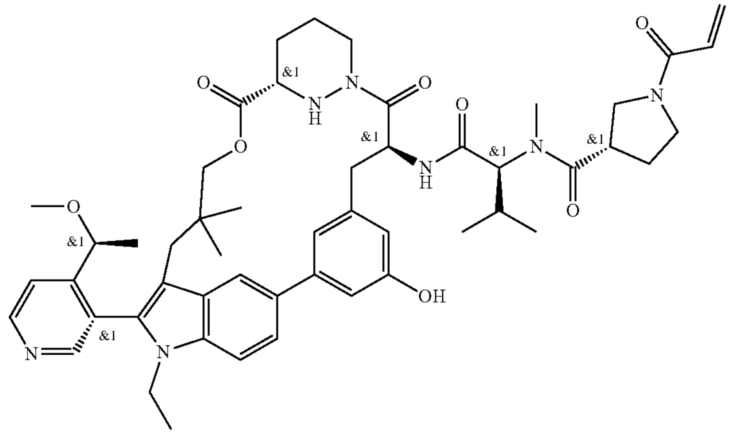 |
| 21 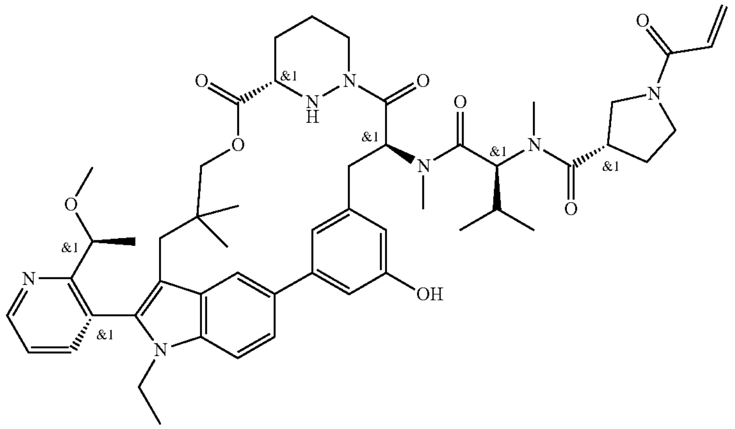 |
| Ex # | Compound of Formula CC |
|---|---|
| 1 | 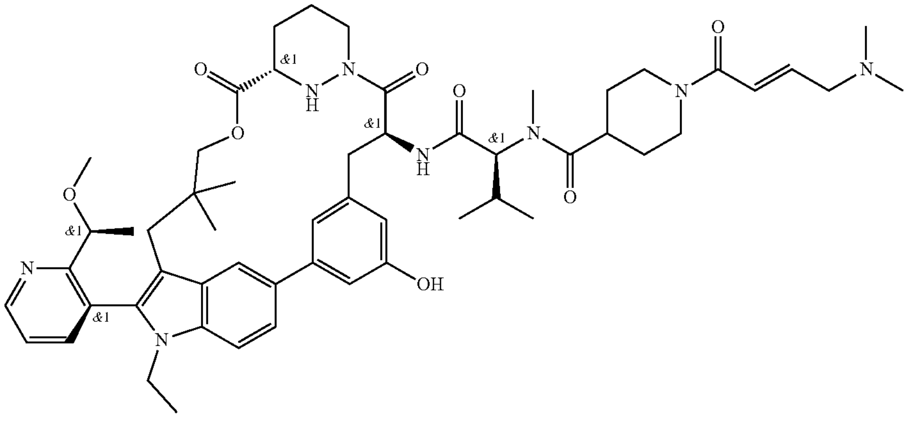 |

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>− Cmpd of Formula DD is more potent than Cmpd of Formula CC |
|---|
| 2 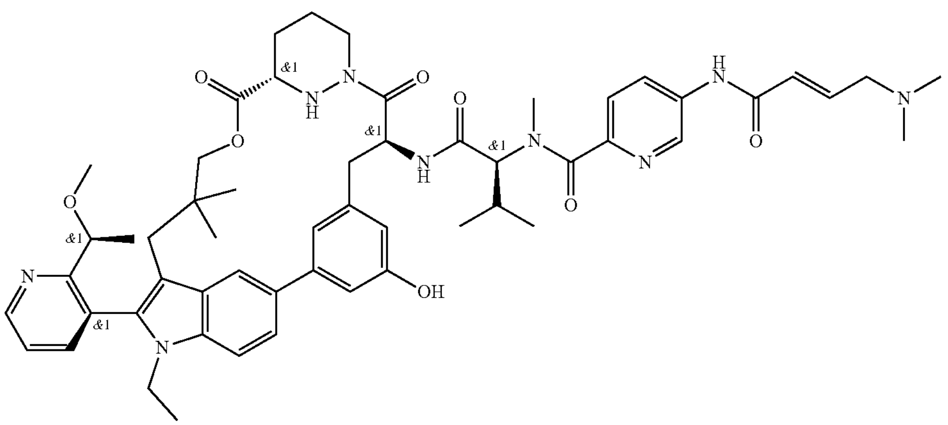 |
| 3 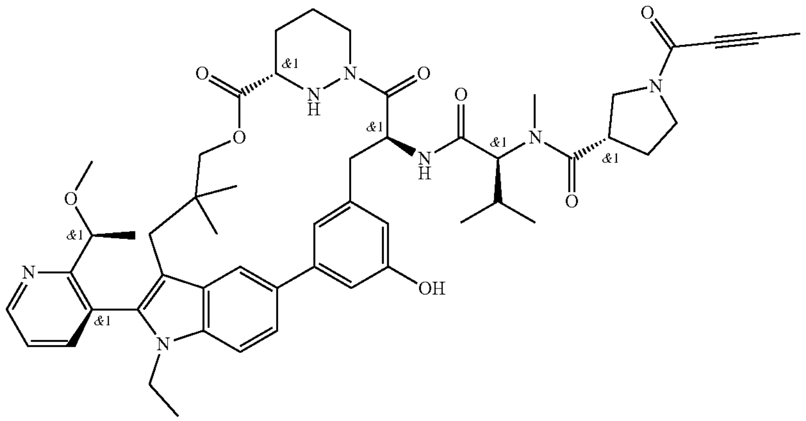 |
| 4 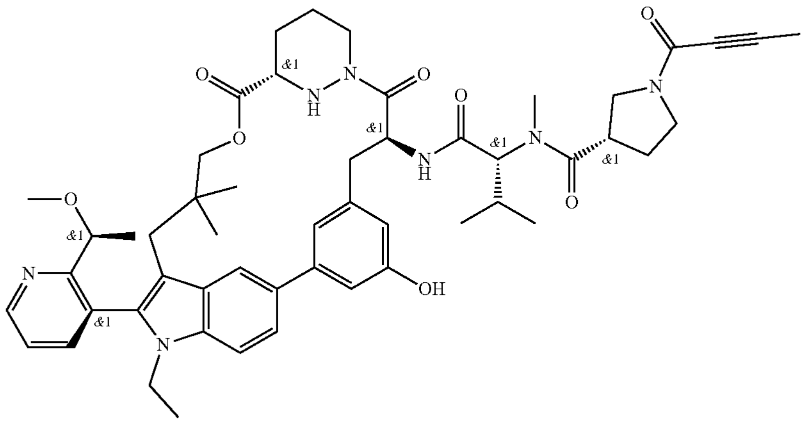 |

TABLE 4-continued
| Atropisomer activity |
| --- |
| ++ Cmpd of Formula CC is more than 10-fold more potent than Cmpd of Formula DD |
| + Cmpd of Formula CC is 1.1-fold to 10-fold more potent than Cmpd of Formula DD |
| − Cmpd of Formula DD is more potent than Cmpd of Formula CC |
5
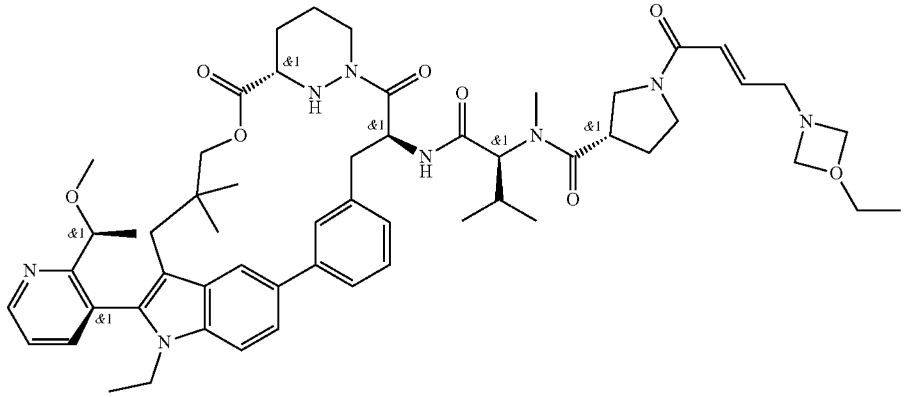
6
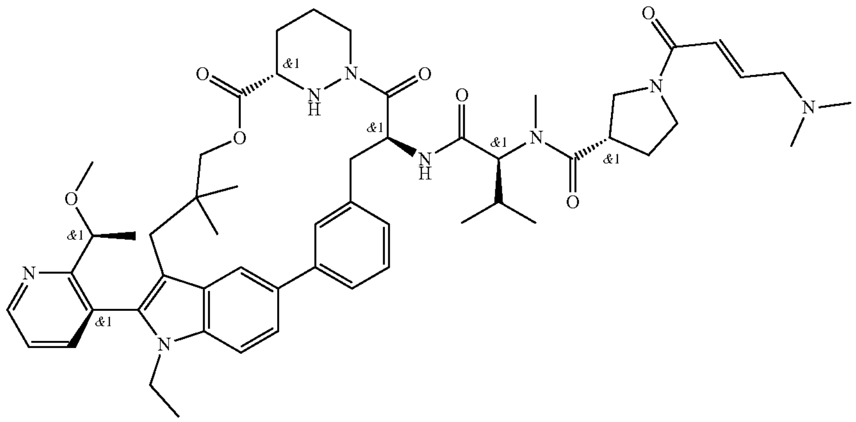
7
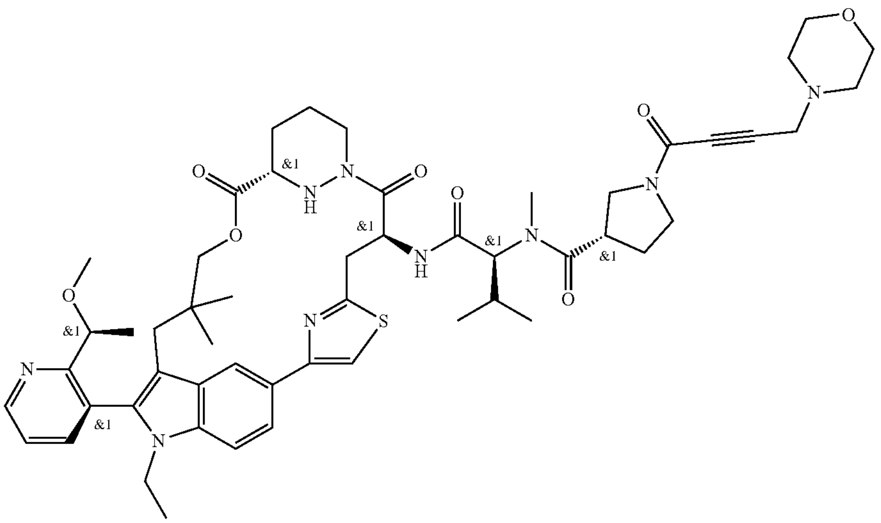

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>− Cmpd of Formula DD is more potent than Cmpd of Formula CC |
|---|
8
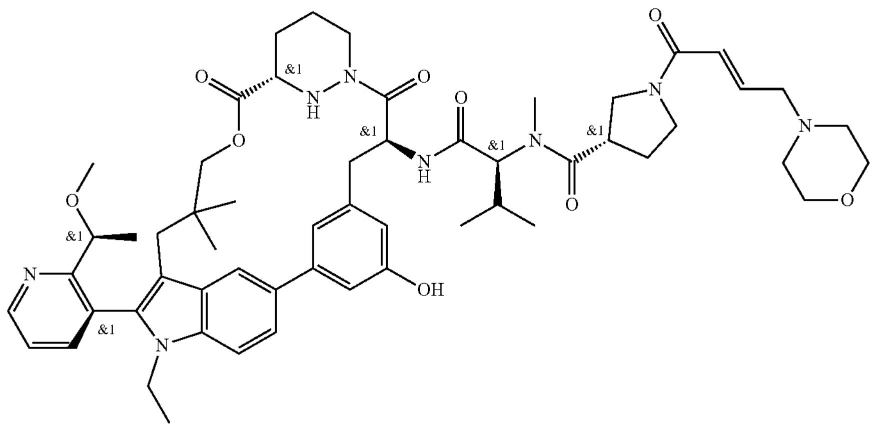
9
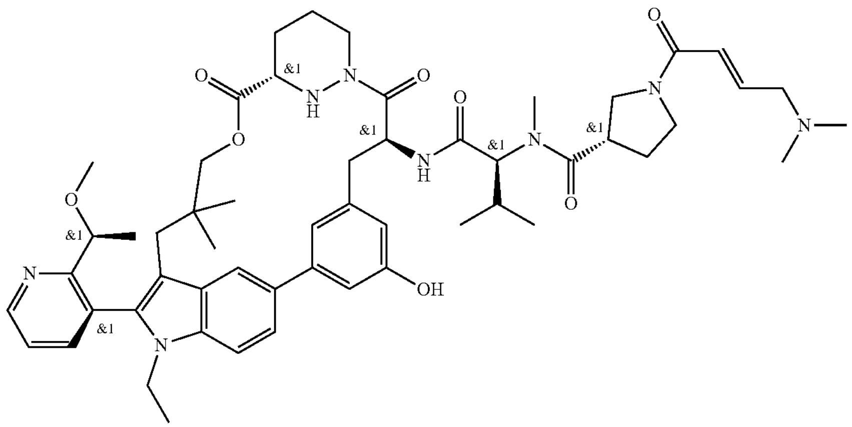
14
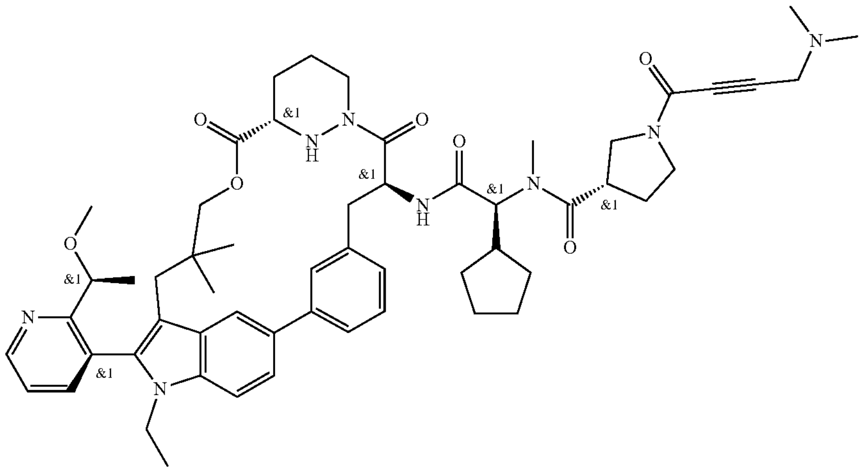

TABLE 4-continued
| Atropisomer activity |
|---|
| ++ Cmpd of Formula CC is more than 10-fold more potent than Cmpd of Formula DD |
| + Cmpd of Formula CC is 1.1-fold to 10-fold more potent than Cmpd of Formula DD |
| − Cmpd of Formula DD is more potent than Cmpd of Formula CC |
15
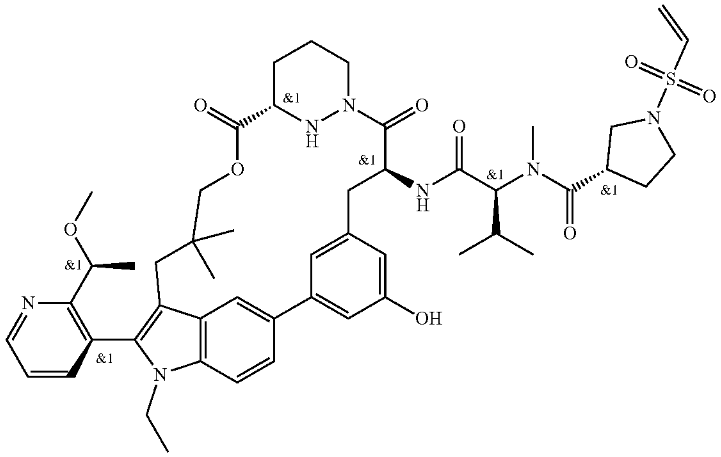
16
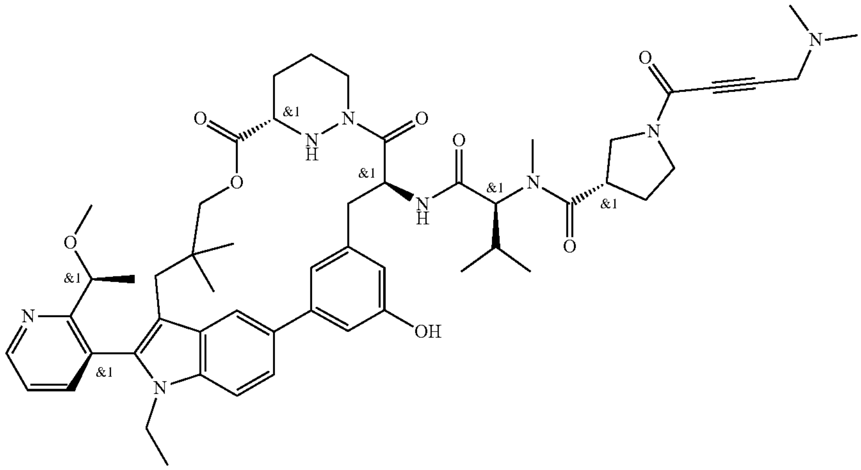
17
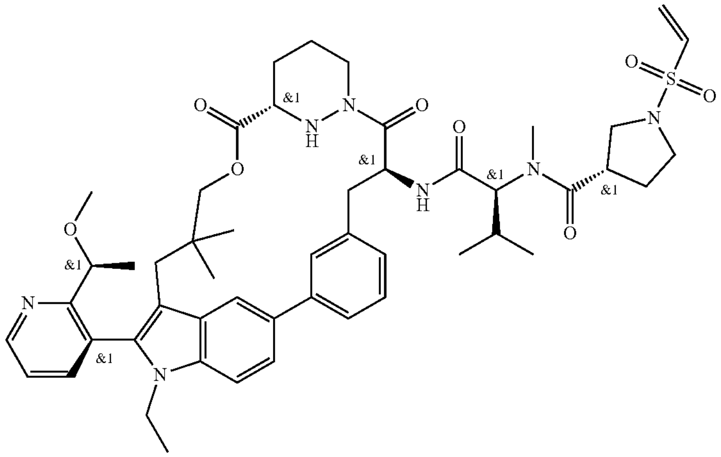

TABLE 4-continued
| Atropisomer activity<br>++ Cmpd of Formula CC is more than 10-fold more potent than Cmpd of Formula DD<br>+ Cmpd of Formula CC is 1.1-fold to 10-fold more potent than Cmpd of Formula DD<br>– Cmpd of Formula DD is more potent than Cmpd of Formula CC |
|---|
18
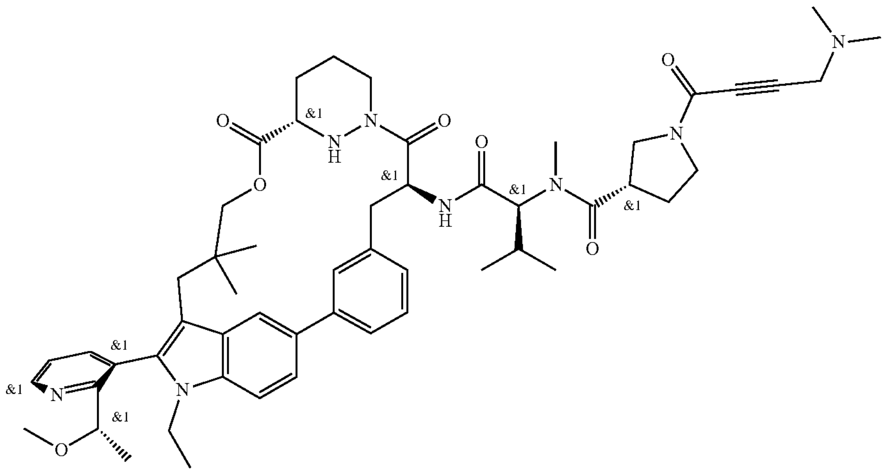
19
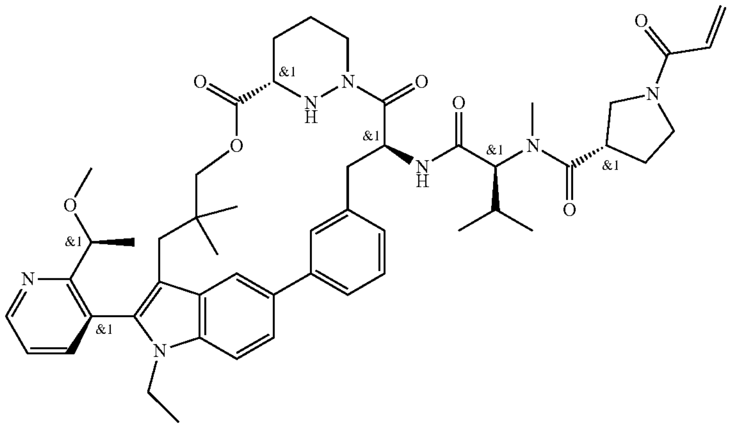
20
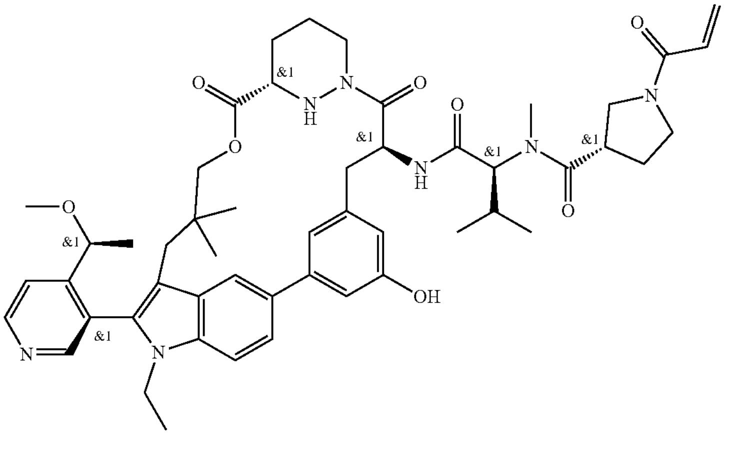

TABLE 4-continued
| Atropisomer activity |
| --- |
| ++ Cmpd of Formula CC is more than 10-fold more potent than Cmpd of Formula DD |
| + Cmpd of Formula CC is 1.1-fold to 10-fold more potent than Cmpd of Formula DD |
| − Cmpd of Formula DD is more potent than Cmpd of Formula CC |
17
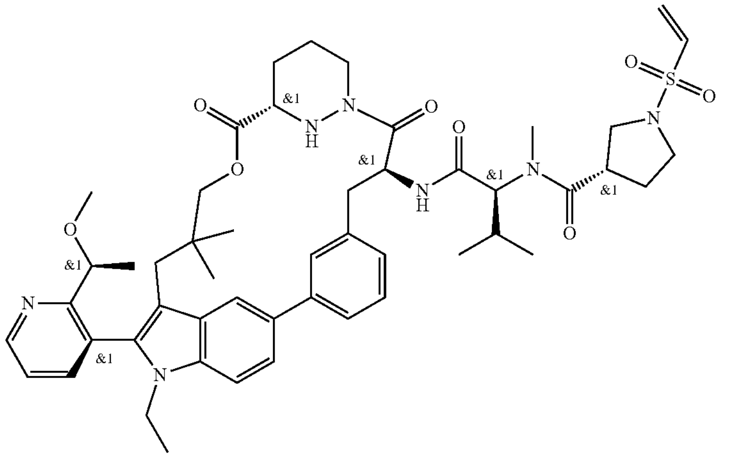
18
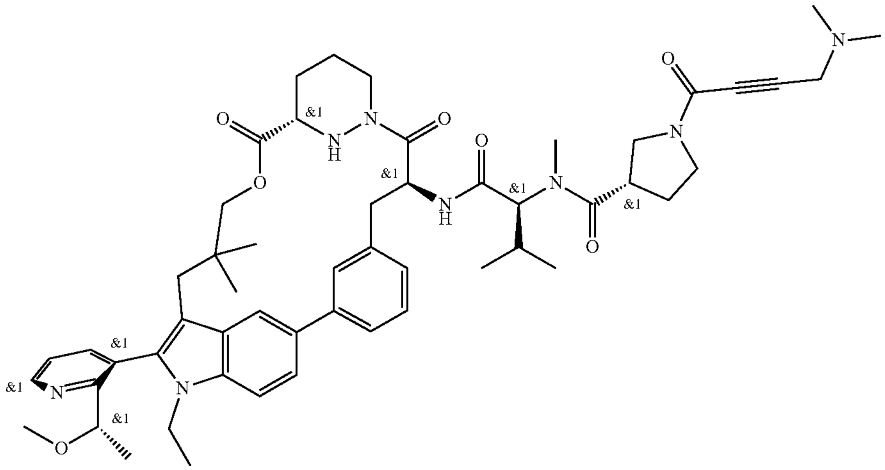
19
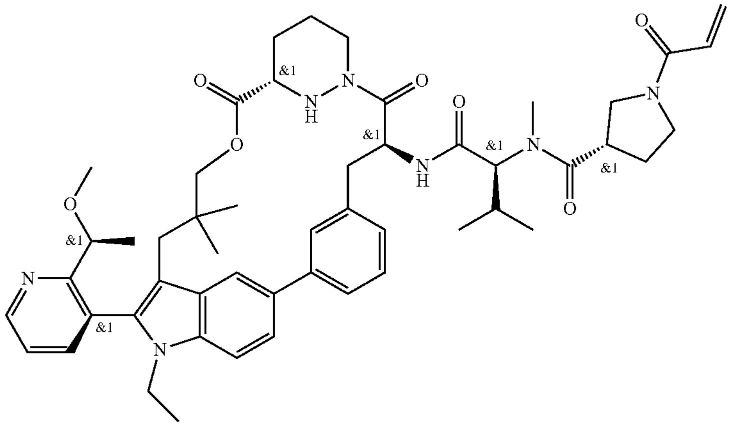

TABLE 4-continued

Atropisomer activity
++ Cmpd of Formula CC is more than 10-fold more potent than Cmpd of Formula DD
+ Cmpd of Formula CC is 1.1-fold to 10-fold more potent than Cmpd of Formula DD
− Cmpd of Formula DD is more potent than Cmpd of Formula CC

20

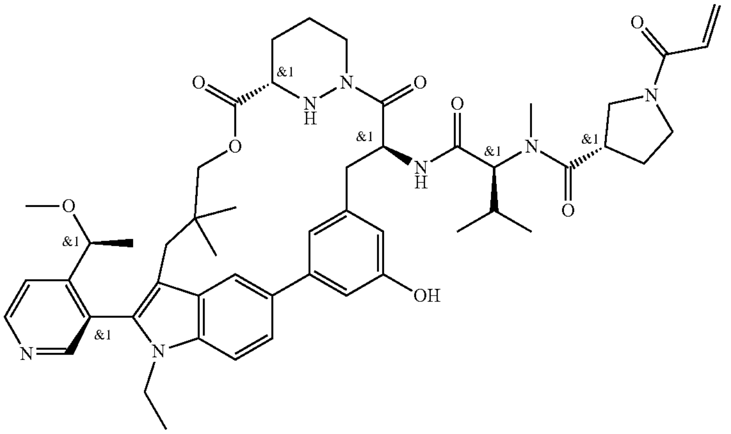

21

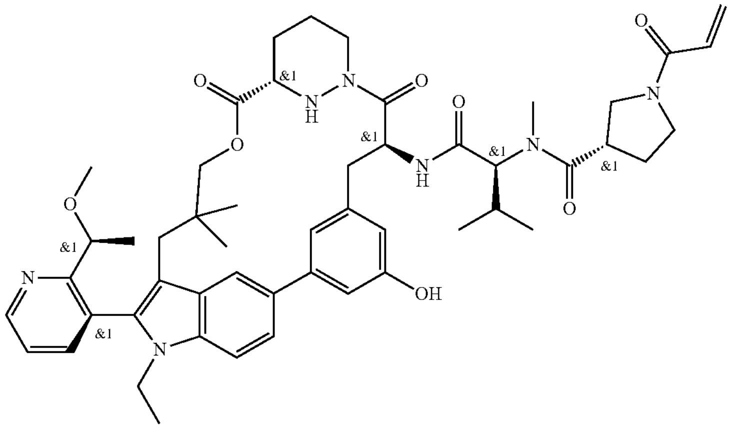

| Ex # | MOA IC50 | PERK IC50 | 2D Cell Viability IC50 |
|---|---|---|---|
| 1 | ++ | + | ++ |
| 2 | + | + | + |
| 3 | ++ | ++ | ++ |
| 4 | ++ | ++ | ++ |
| 5 | ++ | ++ | ++ |
| 6 | ++ | ++ | ++ |
| 7 | ++ | ++ | ++ |
| 8 | ++ | ++ | ++ |
| 9 | ++ | + | ++ |
| 14 | − | − | − |
| 15 | + | + | ++ |
| 16 | ++ | − | − |
| 17 | ++ | + | + |
| 18 | + | ++ | + |
| 19 | ++ | ++ | ++ |
| 20 | ++ | + | ++ |
| 17 | ++ | + | + |
| 18 | + | ++ | + |
| 19 | ++ | ++ | ++ |
| 20 | ++ | + | ++ |
| 21 | ++ | + | ++ |

Biological Assays

All but 10 Compounds of Table 1 herein exhibited an $IC_{50}$ of 1 μM or less in the H358 (K-Ras G12C) pERK potency assay described below. Ten compounds exceeded 1 μM (A36, A37, A38, A121, A124, A128, A136, A189, A191, A192). Compound A130 had an $IC_{50}$ greater than 0.89 μM. Compounds of Table 1 herein exhibited an $IC_{50}$ of 3 μM or less in the MiaPaCa-2 (K-Ras G13C) pERK potency assay described below.

All but 5 compounds in Table 1 exhibited an $IC_{50}$ less than 1 μM in a cell viability assay described below (NCI-H358 (K-Ras G12C)). Five compounds exceeded 1 μM (A38, A39, A128, A191, A192). All compounds in Table 1 exhibited an $IC_{50}$ less than 3.5 μM in the Raf-Ras (FRET or MOA) binding assay described below re: K-Ras G12C. All but 3 compounds in Table 1 exhibited an $IC_{50}$ less than 1.5 μM in the Raf-Ras (FRET or MOA) binding assay described below re: K-Ras G13C. Three compounds exceeded 1.5 μM (A169, A171, A175).

All compounds in Table 1 except A168 and A170 exhibited a cross-linking percent of greater than 0 under an incubation timeframe of 4 hours in the cross-linking assay described below with respect to K-Ras G12C or K-Ras G13C.

Potency Assay: pERK

The purpose of this assay was to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in NCI-H358 cells is applicable to K-Ras G12C.

Note: This protocol may be executed substituting other cell lines to characterize inhibitors of other RAS variants, including, for example, AsPC-1 (K-Ras G12D), Capan-1 (K-Ras G12V), or NCI-H1355 (K-Ras G13C).

NCI-H358 cells were grown and maintained using media and procedures recommended by the ATCC. On the day prior to compound addition, cells were plated in 384-well cell culture plates (40 μl/well) and grown overnight in a 37° C., 5% CO2 incubator. Test compounds were prepared in 10, 3-fold dilutions in DMSO, with a high concentration of 10 mM. On the day of assay, 40 nL of test compound was added to each well of cell culture plate using an Echo550 liquid handler (LabCyte®). Concentrations of test compound were tested in duplicate. After compound addition, cells were incubated 4 hours at 37° C., 5% CO2. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 μL lysis buffer, with shaking at 600 RPM at room temperature. Lysate (10 μL) was transferred to a 384-well Opti-plate (PerkinElmer) and 5 μL acceptor mix was added. After a 2-hour incubation in the dark, 5 μL donor mix was added, the plate was sealed, and incubated 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and IC50 was determined by fitting a 4-parameter sigmoidal concentration response model.

In other experiments, cellular pERK was determined by In-Cell Western. Following compound treatment, cells were washed twice with 200 μL tris buffered saline (TBS) and fixed for 15 minutes with 150 μL 4% paraformaldehyde in TBS. Fixed cells were washed 4 times for 5 minutes with TBS containing 0.1% Triton X-100 (TBST) and then blocked with 100 μL Odyssey blocking buffer (LI-COR) for 60 minutes at room temperature. Primary antibody (pERK, CST-4370, Cell Signaling Technology) was diluted 1:200 in blocking buffer, and 50 μL were added to each well and incubated overnight at 4° C. Cells were washed 4 times for 5 minutes with TBST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li—COR Odyssey CLx Imager. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

Regarding G13C, another pERK assay protocol is as follows.

Note: This protocol may be executed substituting other cell lines to characterize inhibitors of other RAS variants, including, for example, AsPC-1 (K-Ras G12D), Capan-1 (K-Ras G12V), or NCI-H358 (K-Ras G12C).

MIA PaCa-2 KRAS G13C A12 cells were grown and maintained using media and procedures recommended by the ATCC. On the day prior to compound addition, cells were plated in 384-well cell culture plates (8,000 cells/40 μl/well) and grown overnight in a 37° C., 5% CO2 incubator. Test compounds were prepared in 10, 3-fold dilutions in DMSO, with a high concentration of 10, 1 or 0.1 mM. On the day of assay, 40 nL of test compound were added to each well of cell culture plate using an Echo550 liquid handler (LabCyte®). Concentrations of test compound were tested in duplicate. After compound addition, cells were incubated 4 hours at 37° C., 5% CO2. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 μL lysis buffer, with shaking at 600 RPM at room temperature. Lysate (10 μL) was transferred to a 384-well Opti-plate (PerkinElmer) and 5 μL acceptor mix was added. After a 2-hour incubation in the dark, 5 μL donor mix was added, the plate was sealed, and incubated 2 hours at room temperature. Signal was read on an Envision plate reader (PerkinElmer) using standard AlphaLISA settings. Analysis of raw data was carried out in Genedata Screener and Prism (GraphPad). Data were normalized by the following calculation: ((sample signal−average low control)/(average DMSO−average low control)) *100. Signal was plotted vs. the decadal logarithm of compound concentration, and $IC_{50}$ was determined by fitting a 4-parameter sigmoidal concentration response model.

In other experiments, cellular pERK was determined by In-Cell Western. Following compound treatment, cells were washed twice with 200 μL tris buffered saline (TBS) and fixed for 15 minutes with 150 μL 4% paraformaldehyde in TBS. Fixed cells were washed 4 times for 5 minutes with TBS containing 0.1% Triton X-100 (TBST) and then blocked with 100 μL Odyssey blocking buffer (LI-COR) for 60 minutes at room temperature. Primary antibody (pERK, CST-4370, Cell Signaling Technology) was diluted 1:200 in blocking buffer, and 50 μL were added to each well and incubated overnight at 4° C. Cells were washed 4 times for 5 minutes with TBST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li—COR Odyssey CLx Imager. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

Determination of Cell Viability in RAS Mutant Cancer Cell Lines

Protocol: CellTiter-Glo® Cell Viability Assay

Note—The following protocol describes a procedure for monitoring cell viability of K-Ras mutant cancer cell lines in response to a compound of the invention. Other RAS isoforms may be employed, though the number of cells to be seeded will vary based on cell line used.

The purpose of this cellular assay was to determine the effects of test compounds on the proliferation of three human cancer cell lines (NCI-H358 (K-Ras G12C), AsPC-1 (K-Ras G12D), and Capan-1 (K-Ras G12V)) over a 5-day treatment period by quantifying the amount of ATP present at endpoint using the CellTiter-Glo® 2.0 Reagent (Promega).

Cells were seeded at 250 cells/well in 40 μL of growth medium in 384-well assay plates and incubated overnight in a humidified atmosphere of 5% $CO_2$ at 37° C. On the day of the assay, 10 mM stock solutions of test compounds were first diluted into 3 mM solutions with 100% DMSO. Well-mixed compound solutions (15 μL) were transferred to the next wells containing 30 μL of 100% DMSO, and repeated until a 9-concentration 3-fold serial dilution was made (starting assay concentration of 10 μM). Test compounds (132.5 nL) were directly dispensed into the assay plates containing cells. The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-Glo® 2.0 Reagent (25 μL) was added, and plate contents were mixed for 2 minutes on an orbital shaker before incubation at room temperature for 10 minutes. Luminescence was measured using the PerkinElmer Enspire. Data were normalized by the following: (Sample signal/Avg. DMSO)*100. The data were fit using a four-parameter logistic fit.

Another CTG assay protocol employed with respect to MIA PaCa-2 KRAS G13C A12 (K-Ras G13C, in particular, is as follows, Note: other RAS isoforms may be employed (e.g., NCI-H358 (K-Ras G12C), AsPC-1 (K-Ras G12D), and Capan-1 (K-Ras G12V)), though the number of cells to be seeded will vary based on cell line used).

The purpose of this cellular assay was to determine the effects of test compounds on the proliferation of human cancer cell lines over a 5-day treatment period by quantifying the amount of ATP present at endpoint using the CellTiter-Glo® 2.0 Reagent (Promega).

Cells were seeded at 250 cells/well in 40 μL of growth medium in 384-well assay plates and incubated overnight in a humidified atmosphere of 5% $CO_2$ at 37° C. Test compounds were prepared in 9 point, 3-fold dilutions in DMSO, with a high concentration of 10, 1 or 0.1 mM. On the day of the assay, test compounds (40 nL) were directly dispensed into the assay plates containing cells. The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-Glo® 2.0 Reagent (25 μL) was added, and plate contents were mixed for 2 minutes on an orbital shaker before incubation at room temperature for 10 minutes. Luminescence was measured using the PerkinElmer Enspire. Data were normalized by the following: (Sample signal/Avg. DMSO)*100. The data were fit using a four-parameter logistic fit.

Disruption of B-Raf Ras-Binding Domain ($BRAF^{RBD}$) Interaction with K-Ras by Compounds of the Invention (Also Called a FRET Assay or an MOA Assay)

Note—The following protocol describes a procedure for monitoring disruption of K-Ras G12C (GMP-PNP) binding to $BRAF^{RBD}$ by a compound of the invention. This protocol may also be executed substituting other Ras proteins or nucleotides.

The purpose of this biochemical assay was to measure the ability of test compounds to facilitate ternary complex formation between a nucleotide-loaded K-Ras isoform and Cyclophilin A; the resulting ternary complex disrupts binding to a $BRAF^{RBD}$ construct, inhibiting K-Ras signaling through a RAF effector. Data was reported as IC50 values.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP, and GST-$BRAF^{RBD}$ were combined in a 384-well assay plate at final concentrations of 25 μM, 12.5 nM and 50 nM, respectively. Compound was present in plate wells as a 10-point 3-fold dilution series starting at a final concentration of 30 μM. After incubation at 25° C. for 3 hours, a mixture of Anti-His Eu—W1024 and anti-GST allophycocyanin was then added to assay sample wells at final concentrations of 10 nM and 50 nM, respectively, and the reaction incubated for an additional 1.5 hours. TR-FRET signal was read on a microplate reader (Ex 320 nm, Em 665/615 nm). Compounds that facilitate disruption of a K-Ras:RAF complex were identified as those eliciting a decrease in the TR-FRET ratio relative to DMSO control wells.

Cross-Linking of Ras Proteins with Compounds of the Invention to Form Conjugates The following cross-linking assay describes a method of determining covalent adduct formation by a compound of the present invention with a Ras protein.

(Note—the following protocol describes a procedure for monitoring cross-linking of K-Ras G12C (GMP-PNP) to a compound of the invention. This protocol may also be executed substituting other Ras proteins or nucleotides).

The purpose of this biochemical assay was to measure the ability of test compounds to covalently label nucleotide-loaded K-Ras isoforms. In assay buffer containing 12.5 mM HEPES pH 7.4, 75 mM NaCl, 1 mM $MgCl_2$, 1 mM BME, 5 μM Cyclophilin A and 2 μM test compound, a 5 μM stock of GMP-PNP-loaded K-Ras (1-169) G12C was diluted 10-fold to yield a final concentration of 0.5 μM; with final sample volume being 100 μL.

The sample was incubated at 25° C. for a time period of up to 24 hours prior to quenching by the addition of 10 μL of 5% Formic Acid. Quenched samples were centrifuged at 15000 rpm for 15 minutes in a benchtop centrifuge before injecting a 10 μL aliquot onto a reverse phase $C_4$ column and eluting into a mass spectrometer with an increasing acetonitrile gradient in the mobile phase. Analysis of raw data was carried out using Waters MassLynx MS software, with % bound calculated from the deconvoluted protein peaks for labeled and unlabeled K-Ras.

In Vitro Cell Proliferation Panels

Potency for inhibition of cell growth may be assessed at CrownBio using standard methods. Briefly, cell lines are cultured in appropriate medium, and then plated in 3D methylcellulose. Inhibition of cell growth is determined by CellTiter-Glo® after 5 days of culture with increasing concentrations of compounds. Compound potency is reported as the 50% inhibition concentration (absolute IC50). The assay took place over 7 days. On day 1, cells in 2D culture are harvested during logarithmic growth and suspended in culture medium at 1×105 cells/mi. Higher or lower cell densities are used for some cell lines based on prior optimization. 3.5 ml of cell suspension is mixed with 6.5% growth medium with 1% methylcellulose, resulting in a cell suspension in 0.65% methylcellulose. 90 μl of this suspension is distributed in the wells of 2 96-well plates. One plate is used for day 0 reading and 1 plate is used for the end-point experiment. Plates are incubated overnight at 37 C with 5% CO2. On day 2, one plate (for t0 reading) is removed and 10 μl growth medium plus 100 μl CellTiter-Glo® Reagent is added to each well. After mixing and a 10 minute incubation, luminescence is recorded on an EnVision Multi-Label Reader (Perkin Elmer). Compounds in DMSO are diluted in growth medium such that the final, maximum concentration of compound is 10 μM, and serial 4-fold dilutions are performed to generate a 9-point concentration series. 10 μl of compound solution at 10 times final concentration is added to wells of the second plate. Plate is then incubated for 120 hours at 37 C and 5% CO2. On day 7 the plates are removed, 100 μl CellTiter-Glo® Reagent is added to each well, and after mixing and a 10 minute incubation, luminescence is recorded on an EnVision Multi-Label Reader (Perkin Elmer). Data is exported to GeneData Screener and modeled with a sigmoidal concentration response model in order to determine the IC50 for compound response.

Not all cell lines with a given RAS mutation may be equally sensitive to a RAS inhibitor targeting that mutation, due to differential expression of efflux transporters, varying dependencies on RAS pathway activation for growth, or other reasons. This has been exemplified by the cell line KYSE-410 which, despite8 having a KRAS G12C mutation, is insensitive to the KRAS G12C (OFF) inhibitor MRTX-849 (Hallin et al., Cancer Discovery 10:54-71 (2020)), and the cell line SW1573, which is insensitive to the KRAS G12C (OFF) inhibitor AMG510 (Canon et al., Nature 575: 217-223 (2019)).

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications, including priority application U.S. Application No. 63/184,599, are herein incorporated by reference in their entirety to the same extent as if each individual publication, patent or patent application was specifically and individually indicated to be incorporated by reference in its entirety.

The invention claimed is:

1. A compound selected from the group of compounds consisting of:

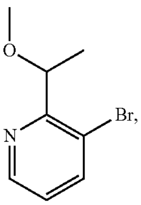
,

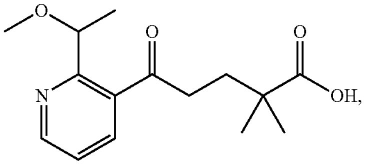
,

-continued

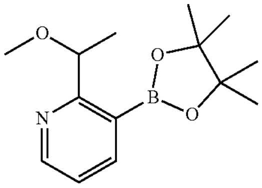
,

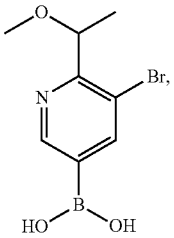
, and

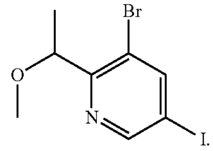
.

2. The compound of claim 1, wherein the compound has the structure:

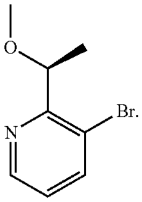
.

3. The compound of claim 1, wherein the compound has the structure:

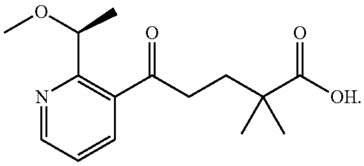 [SMILES: CO[C@@H](C)c1ncccc1C(=O)CCC(C)(C)C(=O)O]
.

4. The compound of claim 1, wherein the compound has the structure:

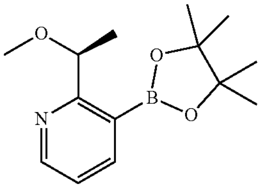
.

5. The compound of claim 1, wherein the compound has the structure:

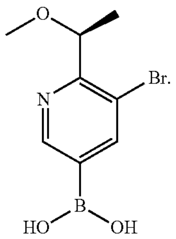
6. The compound of claim 1, wherein the compound has the structure:
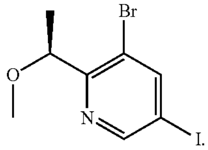
* * * * *